(12) United States Patent
Phillips et al.

(10) Patent No.: US 10,849,982 B2
(45) Date of Patent: Dec. 1, 2020

(54) C3-CARBON LINKED GLUTARIMIDE DEGRONIMERS FOR TARGET PROTEIN DEGRADATION

(71) Applicant: C4 Therapeutics, Inc., Watertown, MA (US)

(72) Inventors: Andrew J. Phillips, Arlington, VA (US); Chris G. Nasveschuk, Stoneham, MA (US); James A. Henderson, Weston, MA (US); Yanke Liang, Brookline, MA (US); Minsheng He, Watertown, MA (US); Kiel Lazarski, Watertown, MA (US); Gesine Kerstin Veits, Watertown, MA (US); Harit U. Vora, Watertown, MA (US)

(73) Assignee: C4 Therapeutics, Inc., Watertown, MA (US)

(*) Notice: Subject to any disclaimer, the term of this patent is extended or adjusted under 35 U.S.C. 154(b) by 0 days.

(21) Appl. No.: 16/186,341

(22) Filed: Nov. 9, 2018

(65) Prior Publication Data
US 2019/0076542 A1    Mar. 14, 2019

Related U.S. Application Data

(63) Continuation of application No. PCT/US2017/032041, filed on May 10, 2017.
(Continued)

(51) Int. Cl.
| | | |
|---|---|---|
| A61K 47/54 | (2017.01) |
| A61K 31/4545 | (2006.01) |
| A61K 31/506 | (2006.01) |
| A61K 31/519 | (2006.01) |
| C07D 401/14 | (2006.01) |
| C07D 413/04 | (2006.01) |
| C07D 221/22 | (2006.01) |
| C07D 401/12 | (2006.01) |
| C07D 401/06 | (2006.01) |
| C07D 401/04 | (2006.01) |
| C07D 495/04 | (2006.01) |
| C07D 471/08 | (2006.01) |
| C07D 487/04 | (2006.01) |
| C07D 211/86 | (2006.01) |
| C07D 495/14 | (2006.01) |
| C07D 413/14 | (2006.01) |
| C07D 417/14 | (2006.01) |
| C07D 211/90 | (2006.01) |
| C07D 519/00 | (2006.01) |
| C07D 405/14 | (2006.01) |
| C07D 417/04 | (2006.01) |
| C07D 471/04 | (2006.01) |

(Continued)

(52) U.S. Cl.
CPC ............ *A61K 47/545* (2017.08); *A61K 31/45* (2013.01); *A61K 31/451* (2013.01); *A61K 31/454* (2013.01); *A61K 31/4545* (2013.01); *C07D 211/86* (2013.01); *C07D 211/88* (2013.01); *C07D 211/90* (2013.01); *C07D 221/22* (2013.01); *C07D 401/04* (2013.01); *C07D 401/06* (2013.01); *C07D 401/12* (2013.01); *C07D 401/14* (2013.01); *C07D 405/14* (2013.01); *C07D 413/04* (2013.01); *C07D 413/14* (2013.01); *C07D 417/04* (2013.01); *C07D 417/14* (2013.01); *C07D 471/04* (2013.01); *C07D 471/08* (2013.01); *C07D 487/04* (2013.01); *C07D 495/04* (2013.01); *C07D 495/14* (2013.01); *C07D 519/00* (2013.01); *C07K 14/47* (2013.01); *C07K 14/72* (2013.01)

(58) Field of Classification Search
CPC ....... C07F 5/02; C07D 211/88; C07D 211/86; C07D 211/90; C07D 221/22; C07D 405/14; C07D 487/04; C07D 401/04; C07D 401/12; C07D 401/14; C07D 401/06; C07D 471/04; C07D 471/08; C07D 495/14; C07D 495/04; C07D 519/00; C07D 417/04; C07D 413/14; A61K 31/45; A61K 47/545; A61K 31/451; A61K 31/4545; A61K 31/454
See application file for complete search history.

(56) References Cited

U.S. PATENT DOCUMENTS

| | | | |
|---|---|---|---|
| 5,635,517 A | 6/1997 | Muller et al. | |
| 6,306,663 B1 * | 10/2001 | Kenten ................. | C07K 14/00 436/501 |

(Continued)

FOREIGN PATENT DOCUMENTS

| | | |
|---|---|---|
| BR | PI1100318 A2 | 5/2013 |
| CN | 103421061 A | 12/2013 |

(Continued)

OTHER PUBLICATIONS

Bartlett, et al. "The evolution of thalidomide and its IMiD derivatives as anticancer agents." Nat Rev Cancer 2004, 4(4):312-322.
(Continued)

*Primary Examiner* — Mark L Shibuya
*Assistant Examiner* — Ebenezer O Sackey
(74) *Attorney, Agent, or Firm* — Knowles Intellectual Property Strategies, LLC

(57) ABSTRACT

This invention provides Degronimers that have carbon-linked E3 Ubiquitin Ligase targeting moieties (Degrons), which can be linked to a targeting ligand for a protein that has been selected for in vivo degradation, and methods of use and compositions thereof as well as methods for their preparation.

17 Claims, 389 Drawing Sheets

Related U.S. Application Data

(60) Provisional application No. 62/334,362, filed on May 10, 2016.

(51) Int. Cl.
*C07D 211/88* (2006.01)
*A61K 31/45* (2006.01)
*A61K 31/451* (2006.01)
*A61K 31/454* (2006.01)
*C07K 14/47* (2006.01)
*C07K 14/72* (2006.01)

(56) References Cited

U.S. PATENT DOCUMENTS

| | | | |
|---|---|---|---|
| 7,041,298 B2 | 5/2006 | Deshaies et al. | |
| 7,208,157 B2 | 4/2007 | Deshaies et al. | |
| 9,125,915 B2 | 9/2015 | Miyoshi et al. | |
| 9,249,161 B2 | 2/2016 | Albrecht et al. | |
| 2013/0190340 A1 | 7/2013 | Hedstrom et al. | |
| 2014/0302523 A1 | 10/2014 | Crews et al. | |
| 2014/0356322 A1 | 12/2014 | Crews et al. | |
| 2015/0119435 A1 | 4/2015 | Crews et al. | |
| 2015/0274738 A1 | 10/2015 | Gray et al. | |
| 2015/0291562 A1 | 10/2015 | Crew et al. | |
| 2016/0016966 A1 | 1/2016 | Amans et al. | |
| 2016/0022642 A1 | 1/2016 | Crews et al. | |
| 2016/0045607 A1 | 2/2016 | Crew et al. | |
| 2016/0046661 A1 | 2/2016 | Gray et al. | |
| 2016/0058872 A1 | 3/2016 | Crew et al. | |
| 2016/0176916 A1 | 6/2016 | Bradner et al. | |
| 2016/0214972 A1 | 7/2016 | Jin et al. | |
| 2016/0272639 A1 | 9/2016 | Crew et al. | |
| 2017/0008904 A1 | 1/2017 | Crew et al. | |
| 2017/0037004 A1 | 2/2017 | Crew et al. | |
| 2017/0065719 A1 | 3/2017 | Qian et al. | |
| 2018/0015087 A1 | 1/2018 | Liu et al. | |
| 2018/0085465 A1 | 3/2018 | Bradner et al. | |

FOREIGN PATENT DOCUMENTS

| | | |
|---|---|---|
| WO | WO 1998/011111 A1 | 3/1998 |
| WO | WO 2002/059106 A1 | 8/2002 |
| WO | WO 2006/102557 A2 | 9/2006 |
| WO | WO 2007/031791 A1 | 3/2007 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/143669 A2 | 11/2011 |
| WO | WO 2012/079022 A1 | 6/2012 |
| WO | WO 2012/178208 A2 | 12/2012 |
| WO | WO 2013/059215 A1 | 4/2013 |
| WO | WO 2013/089278 A1 | 6/2013 |
| WO | WO 2013/106646 A2 | 7/2013 |
| WO | WO 2013/170147 A1 | 11/2013 |
| WO | WO 2014/023081 A1 | 2/2014 |
| WO | WO 2014/145887 A1 | 9/2014 |
| WO | WO 2015/173764 A1 | 11/2015 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |

OTHER PUBLICATIONS

Berndsen et al. "New insights into ubiquitin E3 ligase mechanism" Nat. Struct. Mol. Biol. 2014, 21:301-307.

Buckley et al. "HaloPROTACS: Use of Small Molecule PROTACS to Induce Degradation of HaloTag Fusion Proteins" ACS Chemical Biology 2015, 10:1831-1837.

Buckley et al. "Small-Molecule Control of Intracellular Protein Levels through Modulation of the Ubiquitin Proteasome System" Angewandte Reviews, 2014, 53:2312-2330.

Buckley et al. "Targeting the Von Hippel-Lindau E3 Ubiquitin Ligase Using Small Molecules to Disrupt the Vhl/Hif-1alpha Interaction" J. Am. Chem. Soc. 2012, 134:4465-4468.

Bondeson et al. "Catalytic in vivo protein knockdown by small-molecule PROTACs" Nature Chemical Biology 2015, 11:611-617.

Burkhard et al. "Synthesis and Stability of Oxetane Analogs of Thalidomide and Lenalidomide" Organic Letters 2013, 15(7):4312-4315.

Chamberlain et al. "Structure of the human cereblon-DDB1-lenalidomide complex reveals basis for responsiveness to thalidomide analogs" Nature Structural and Molecule Biology, 2014, 21(9):803-809.

Chang, X. and Stewart, K. A. "What is the functional role of the thalidomide binding protein cereblon?" Int J Biochem Mol Bio. 2011, 2(3):287-294.

Corson et al. "Design and applications of bifunctional small molecules: Why two heads are better than one" ACS Chemical Biology 2008, 3(11): 677-692.

Crew, C. M. "Targeting the undruggable proteome: the small molecules of my dreams" Chemistry and Biology 2010, 17(6):551-555.

Deshaies et al. "Ring domain E3 ubiquitin ligases." Ann. Rev. Biochem. 2009, 78:399-434.

Faden et al. "Generic tools for conditionally altering protein abundance and phenotypes on demain" Biol. Chem. 2014, 395(7-8):737-762.

Fischer et al. "Structure of the DDB1-CRBN E3 ubiquitin ligase in complex with thalidomide" Nature 2014, 512:49-53.

Fischer et al. "The Molecular Basis of CRL4DDB2/CSA Ubiquitin Ligase Architecture, Targeting, and Activation," Cell 2011, 147:1024-1039.

Gosink et al. "Redirecting the Specificity of Ubiquitination by Modifying Ubiquitin-Conjugating Enzymes" Proc. Natl. Acad. Sci. USA 1995, 92:9117-9121.

(56) References Cited

OTHER PUBLICATIONS

Gustafson et al. "Small-Molecule-Mediated Degradation of the Androgen Receptor through Hydrophobic Tagging" Angewandte Chemie 2015, 54:9659-9662.
Hines et al. "Posttranslational protein knockdown couple to receptor tyrosine kinase activation with phosphoPROTACs" PNAS 2013, 110(22):8942-8947.
International Search Report and Written Opinion for PCT/US17/32041 dated Aug. 4, 2017.
Ito et al. "Identification of a Primary Target of Thalidomide Teratogenicity" Science 2010, 327(5971):1345-1350.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16):5820-5826.
Jacques et al. "Differentiation of antiinflammatory and antitumorigenic properties of stabilized enantiomers of thalidomide analogs" PNAS 2015, 112:E1471-E1479.
Kronke et al. "Lenalidomide induces ubiquitination and degradation of CDK1[alpha] in del(5q) MDS" Nature 2015, 523(7559):183-188.
Kronke et al. "Lenalidomide Causes Selective Degradation of IKZF1 and IKZF3 in Multiple Myeloma Cells" Science 2014, 343(6168):301-305.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Li et al. "Genome-wide and functional annotation of human E3 ubiquitin ligases identifies MULAN, a mitochondrial E3 that regulates the organelle's dynamics and signaling" PLOS One 2008, 3:1487.
Liu et al. "Design and biological characterization of hybrid compounds of curcumin and thalidomide for multiple myeloma" Organic and Biomolecular Chemistry 2013, 11:4757.
Lu et al. "The myeloma drug lenalidomide promotes the cereblon-dependent destruction of Ikaros proteins" Science 2014, 343:305-309.
Lu et al. "Hijacking the E3 Ubiquitin Ligase Cereblon to Efficiently Target BRD4" Chemistry and Biology 2015, 22(6):755-763.
Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Protacs: chimeric molecules that target proteins to the Skp1-Cullin-F box complex for ubiquitination and degradation" PNAS 2001, 98(15):8554-8559.
Sakamoto et al. "Development of Protacs to Target Cancer-Promoting Proteins for Ubiquitination and Degradation" Molecular and Cellular Proteomics 2003, 2(12):1350-1357.
Schneekloth et al. "Targeted Intracellular Protein Degradation Induced by a Small Molecule: En Route to Chemical Proteomics" Bioorganic and Medicinal Chemisty Letters 2008, 18:5904-5908.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Smith et al. "Targeted Intracellular Protein Degradation Induced by a Small Molecule: En Route to Chemical Proteomics" Bioorg. Med. Chem. Lett. 2008, 18(22):5904-5908.
Spratt et al. "RBR E3 ubiquitin ligases: new structures, new insights, new questions." Biochem. 2014, 458:421-437.
Toure et al. "Small-Molecule PROTACs: New Approaches to Protein Degradation" Angewandte Chemie International Edition 2016, 55:1966-1973.
Vassilev et al. "In Vivo Activation of the P53 Pathway by Small-Molecule Antagonists of MDM2" Science 2004, 303:844-848.
Wang et al. "Roles of F-box proteins in cancer." Nat. Rev. Cancer 2014, 14:233-347.
Winter et al. "Phthalimide conjugation as a strategy for in vivo target protein degradation" Science 2015, 348(6241):1376-1381.
Zengerle et al. "Selective Small Molecule Induced Degradation of the BET Bromodomain Protein BRD4" ACS Chem. Biol. 2015, 10:1770-1777.
Zhou et al. "Harnessng the Ubiquitination Machinery to Target the Degradation of Specific Cellular Proteins" Molecular Cell 2000, 6:751-756.
Contino-Pepin, et al., "Preliminary biological evaluations of new thalidomide analogus for multiple sclerosis application", Bioorganic & Medicinal Chemistry Letters, 2009, 19, 878-881.
Jarman, M. et al., "Selective inhibition of cholesterol side-chain cleavage by potential pro-drug forms of aminoglutethimide", Anti-Cancer Drug Design, vol. 3, 1988, pp. 185-190, XPOO9517051.
Jonathan W. Grant et al., "Toward the Development of a Cephalosporin-Based Dual-Release Prodrug for Use in ADEPT", Journal of Organic Chemistry, vol. 69, No. 23, Nov. 1, 2004, pp. 7965-7970. XP55639681, US ISSN: 0022-3263, DOI: 10.1021/jo048970i.
Shoji, et al., "Modified DNA Aptamer That Binds the (R)-Isomer of a Thalidomide Derivative with High Enantioselectivity", J. Am. Chem. Soc., 2007, 129, 1456-1464.

\* cited by examiner

FIG. 1Q
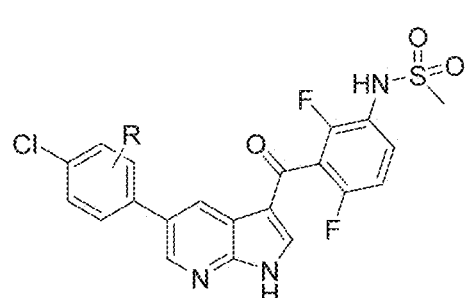
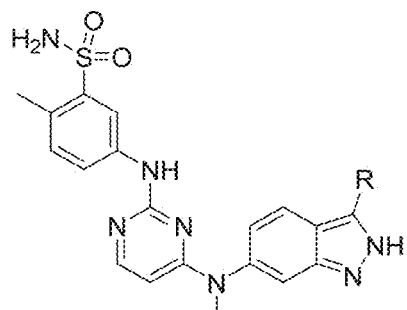
FIG. 1R
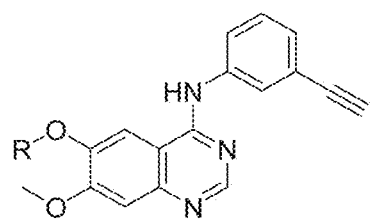
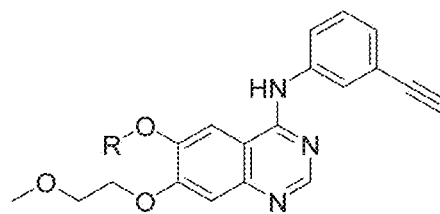
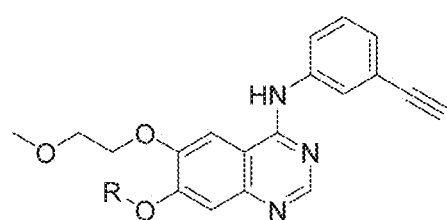
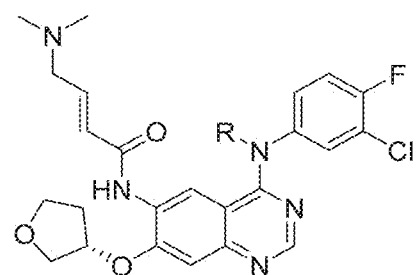
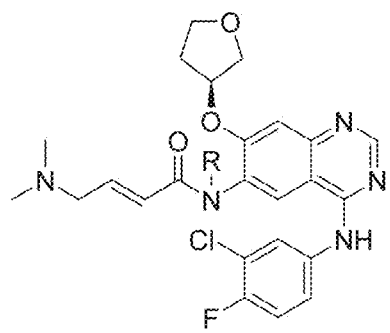
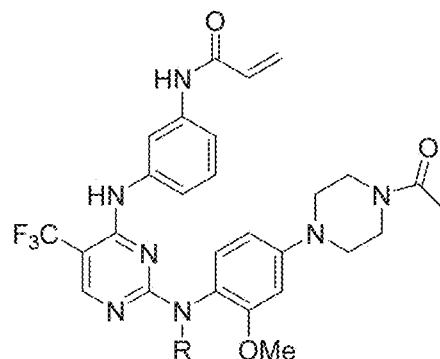

FIG. 1S
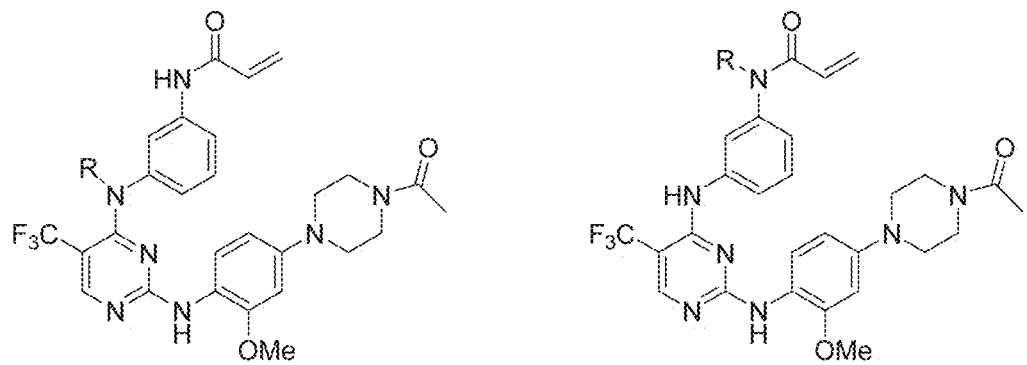
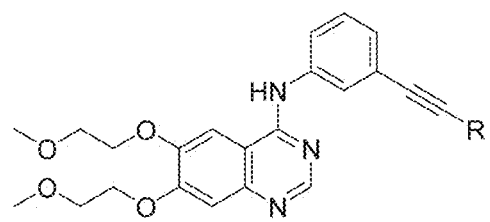
FIG. 1T
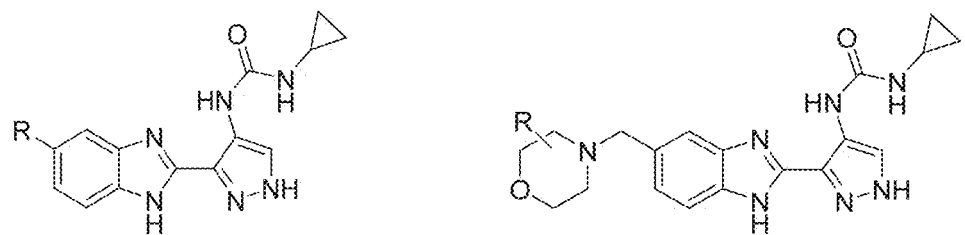
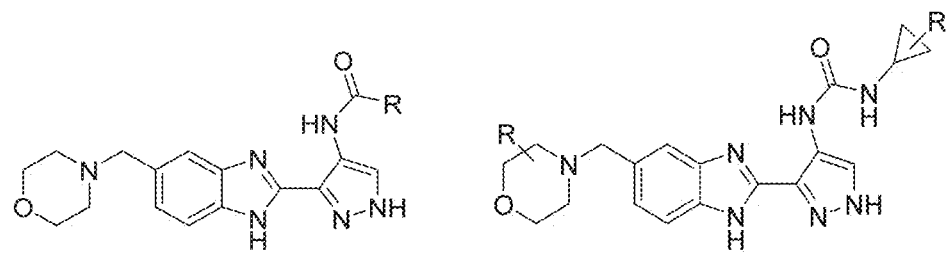

FIG. 1EE
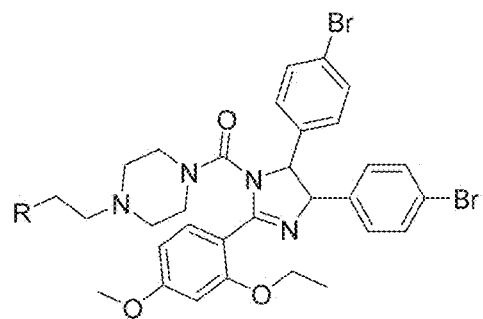
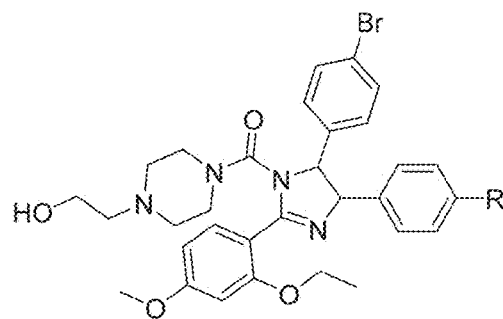
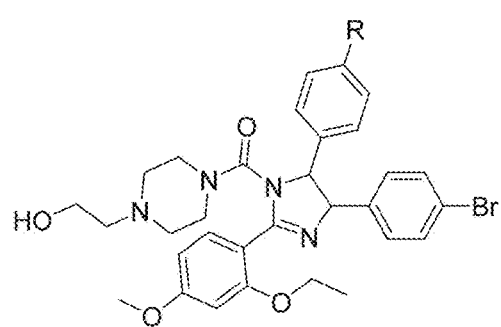
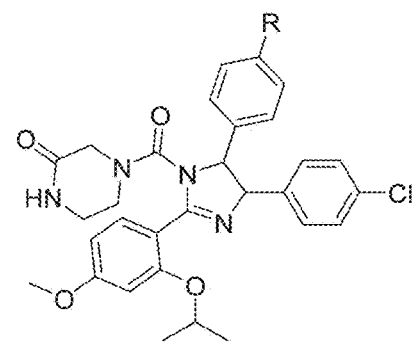
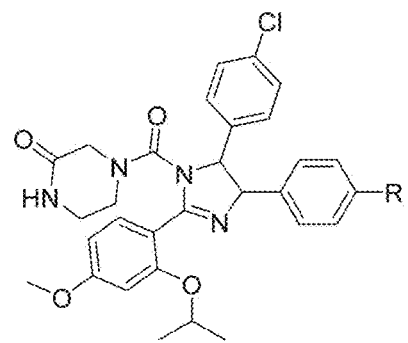
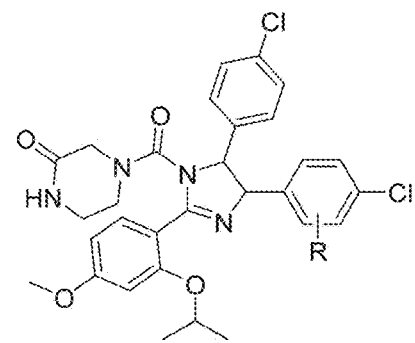
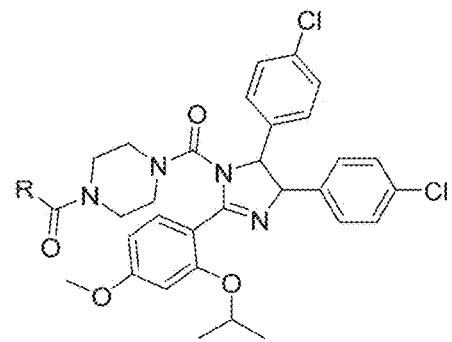
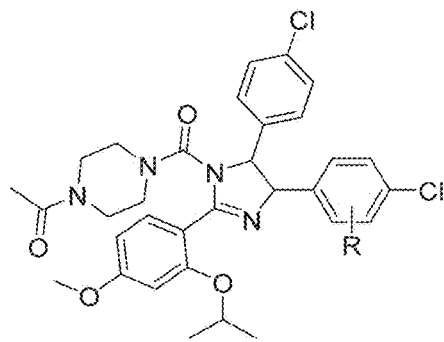

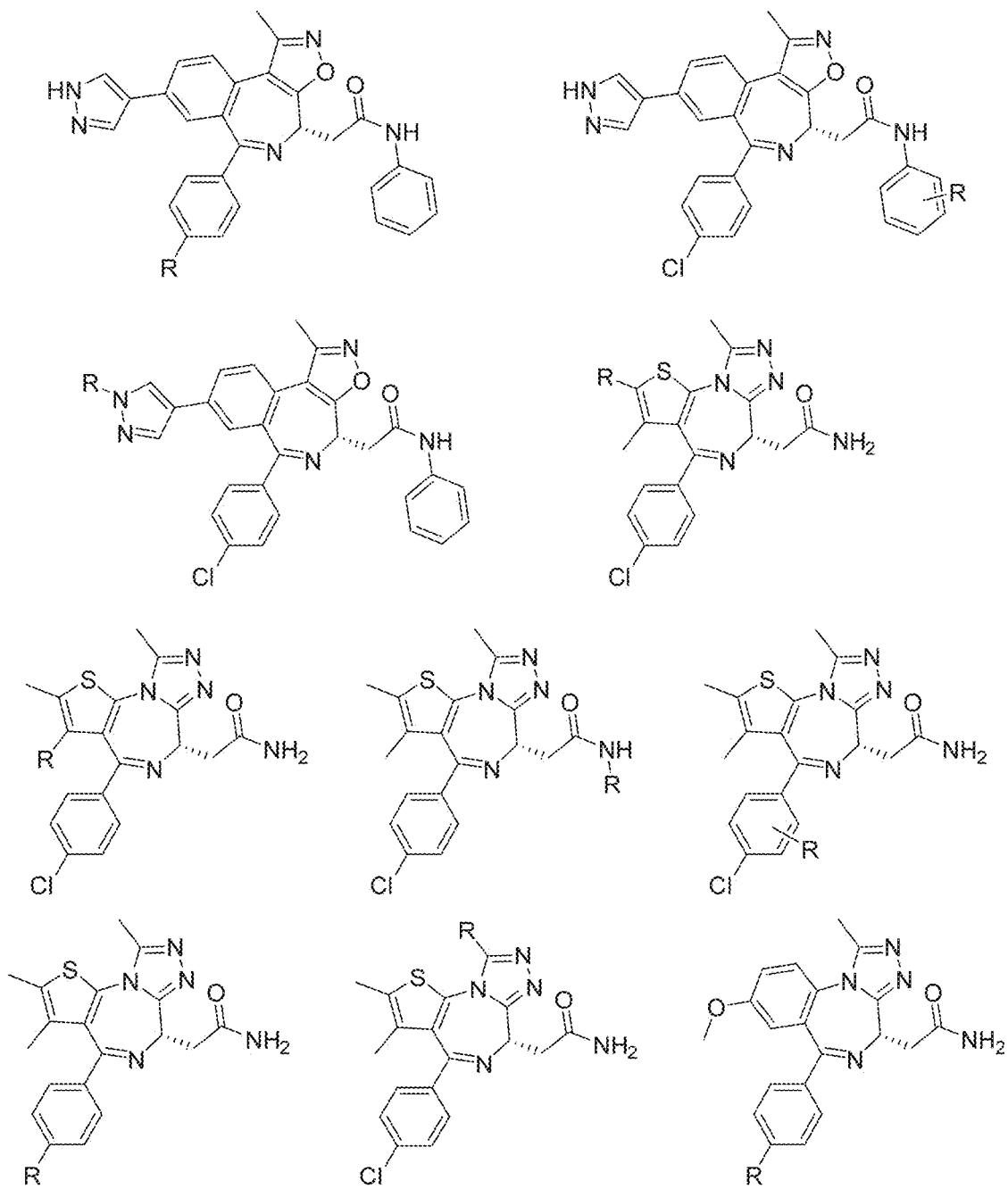
FIG. III

FIG. 1PP
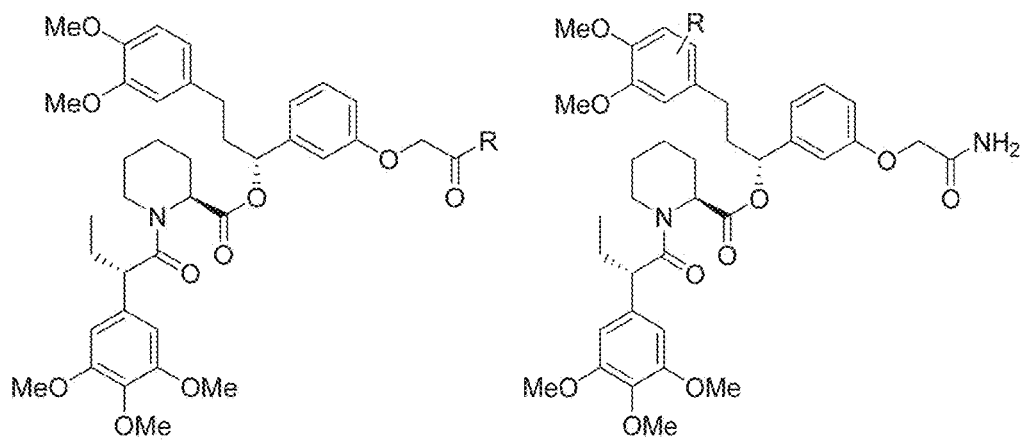
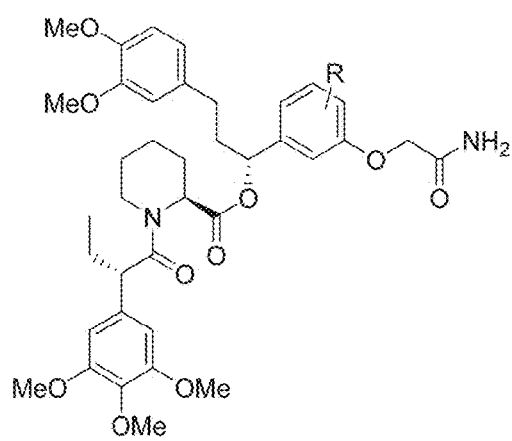
FIG. 1QQ
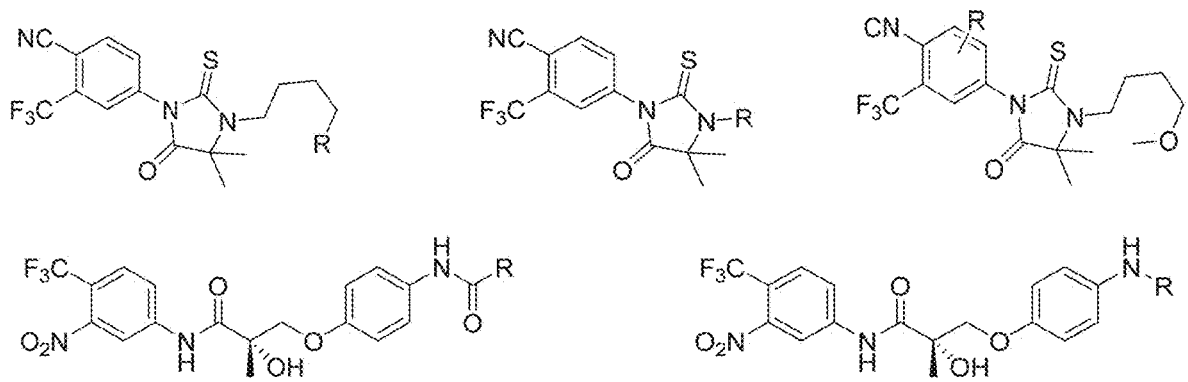

FIG. 1RR
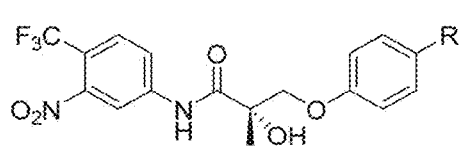
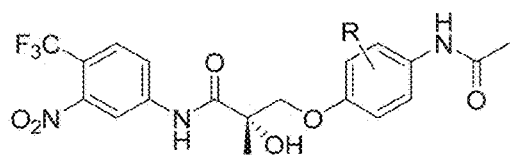
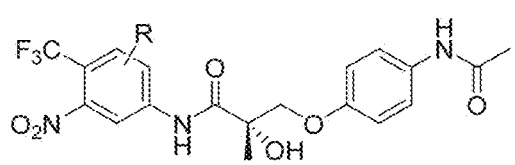
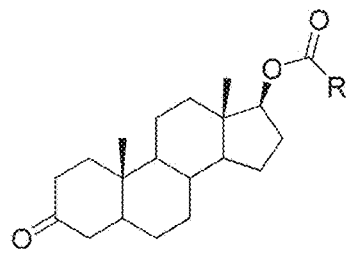
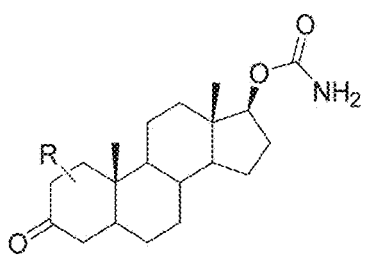
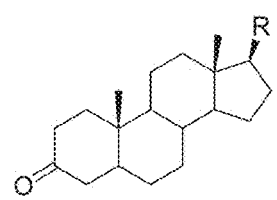
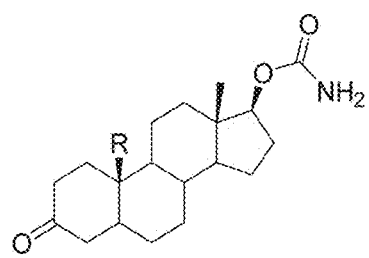
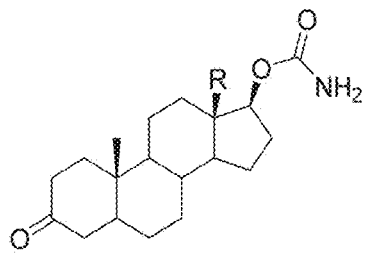
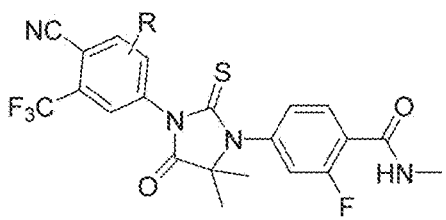
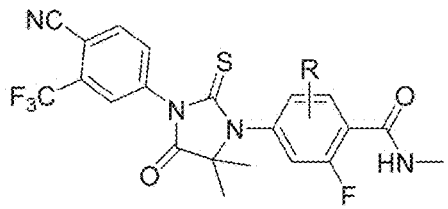
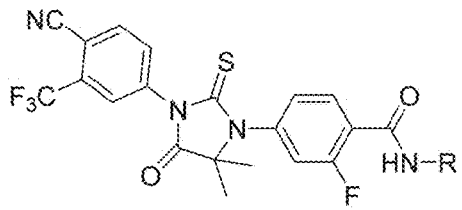
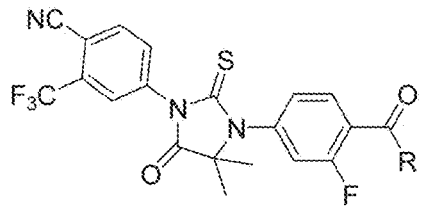
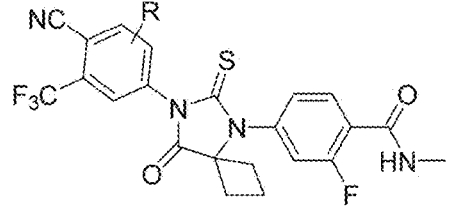

FIG. 1TT
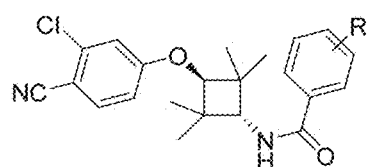 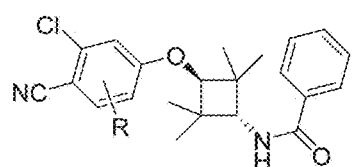
FIG. 1UU
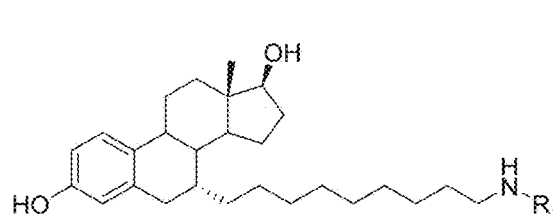 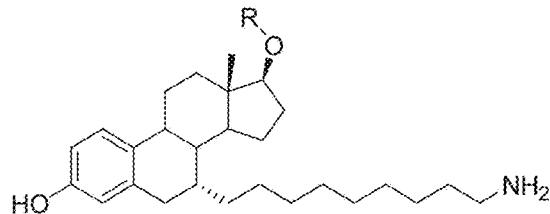
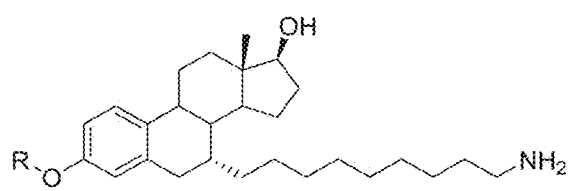 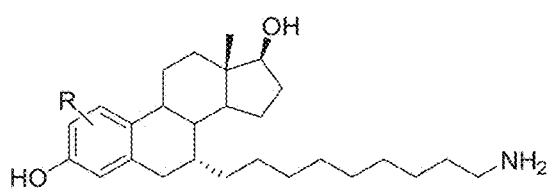
FIG. 1VV
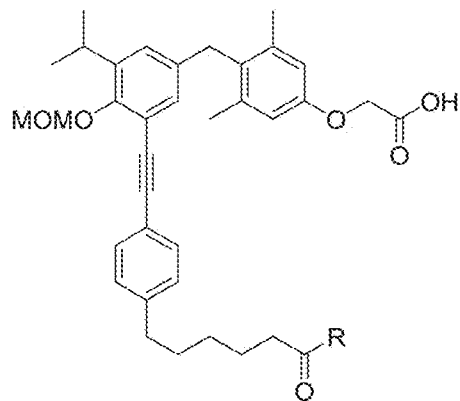 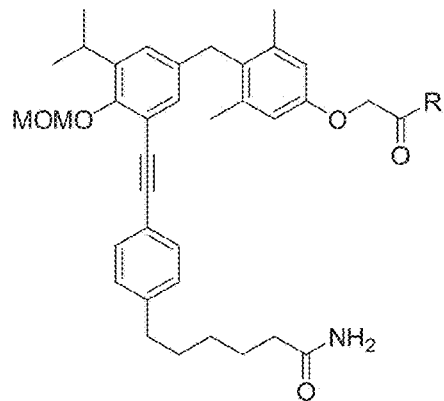

FIG. 1WW
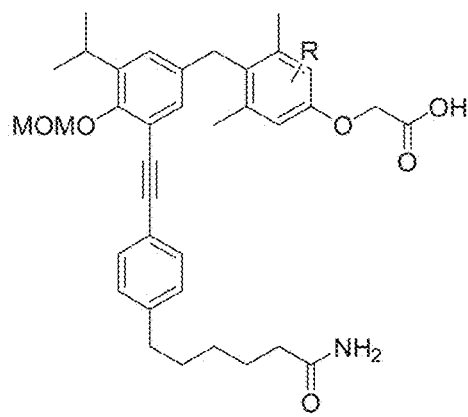
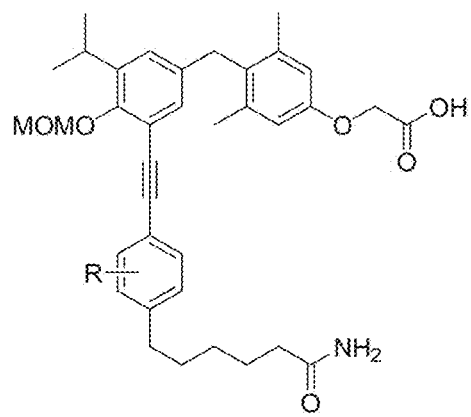
FIG. 1XX
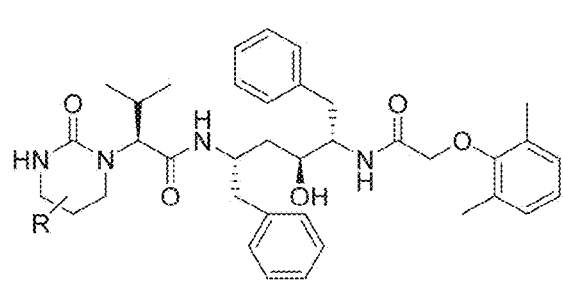
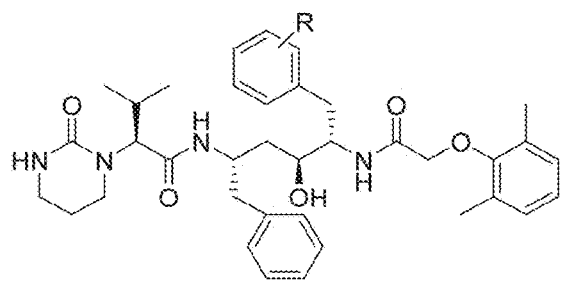
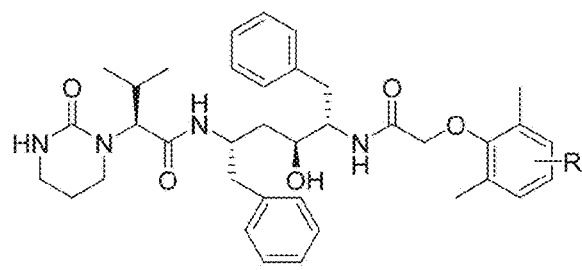
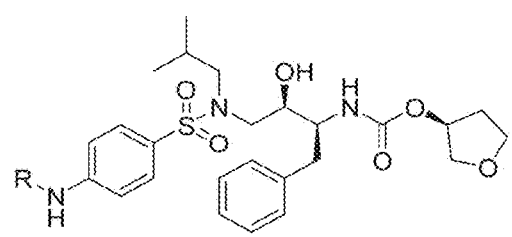
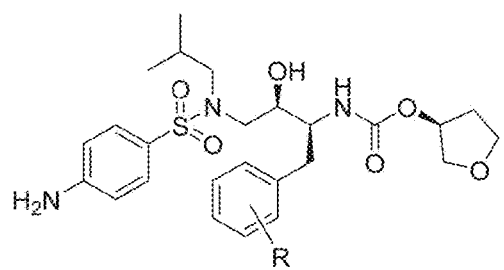
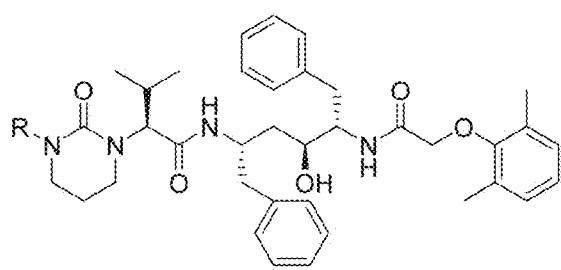

FIG. 1AAA
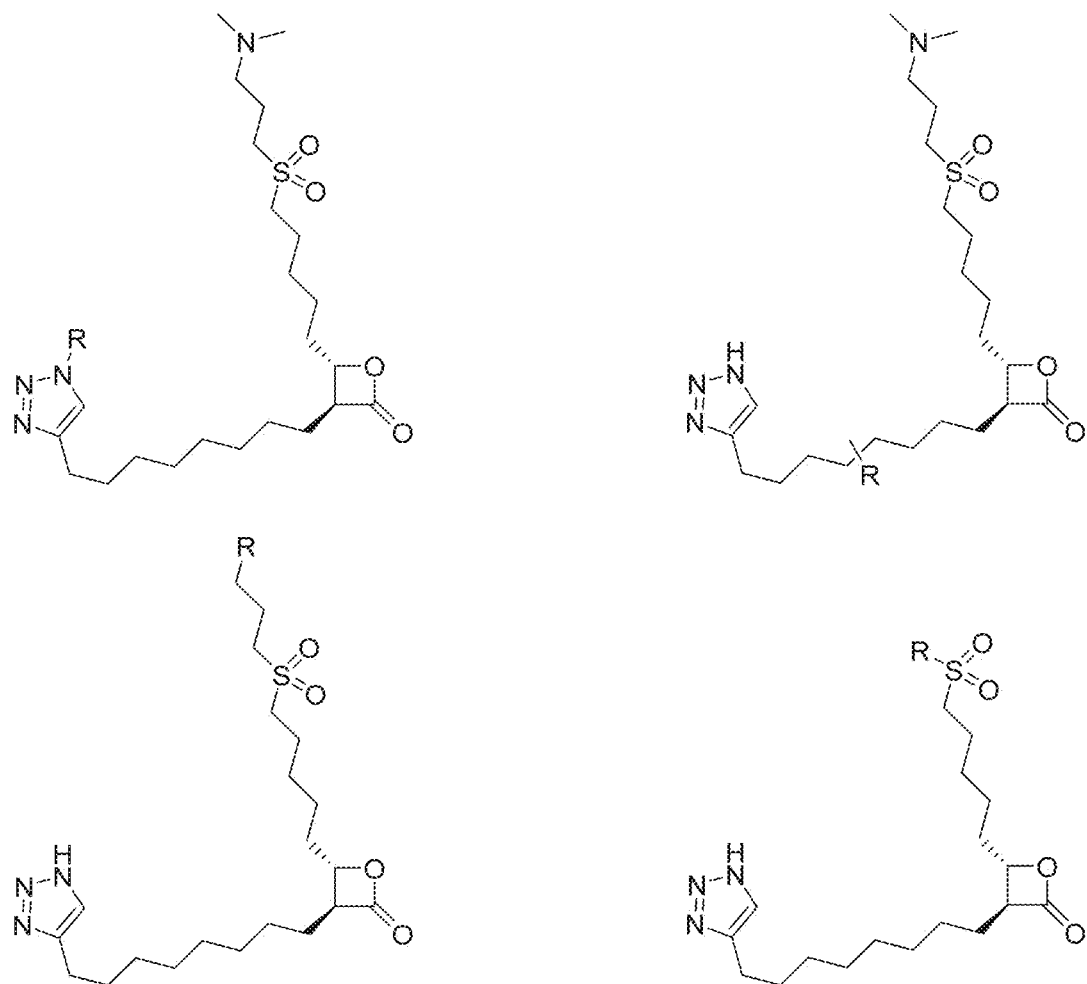
FIG. 1BBB
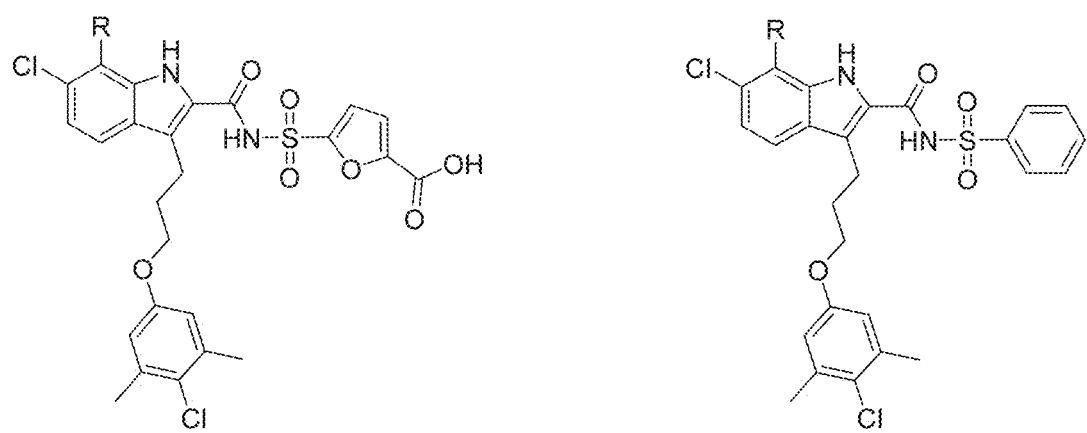

FIG. 1CCC
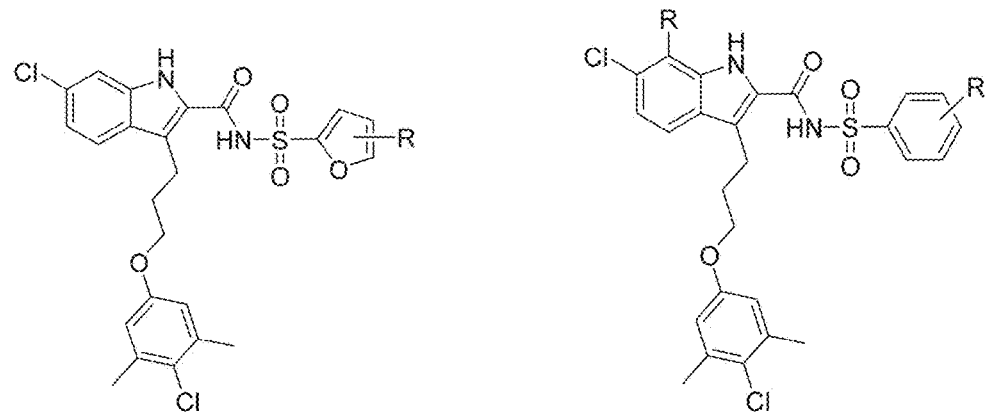
FIG. 1DDD
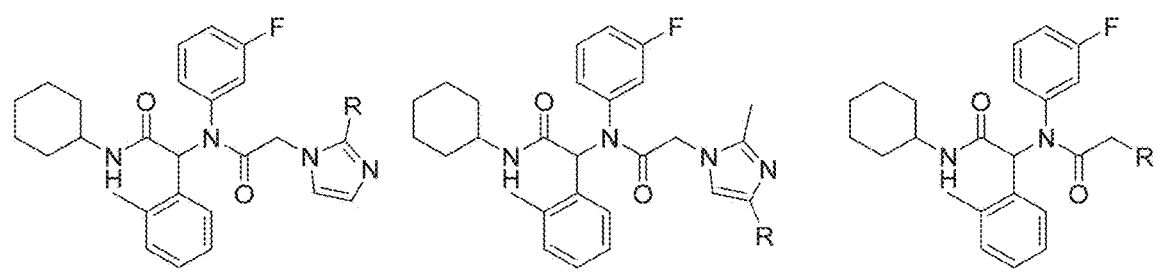
FIG. 1EEE
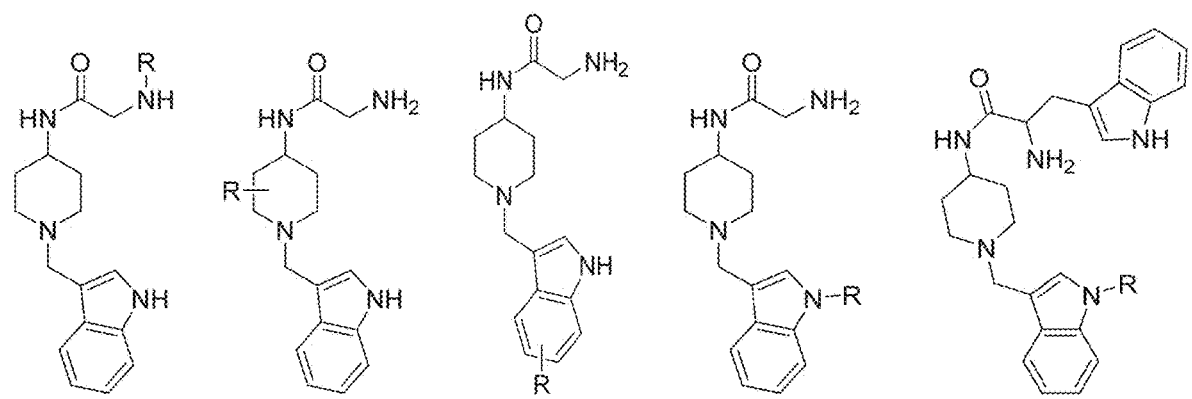

FIG. 1FFF
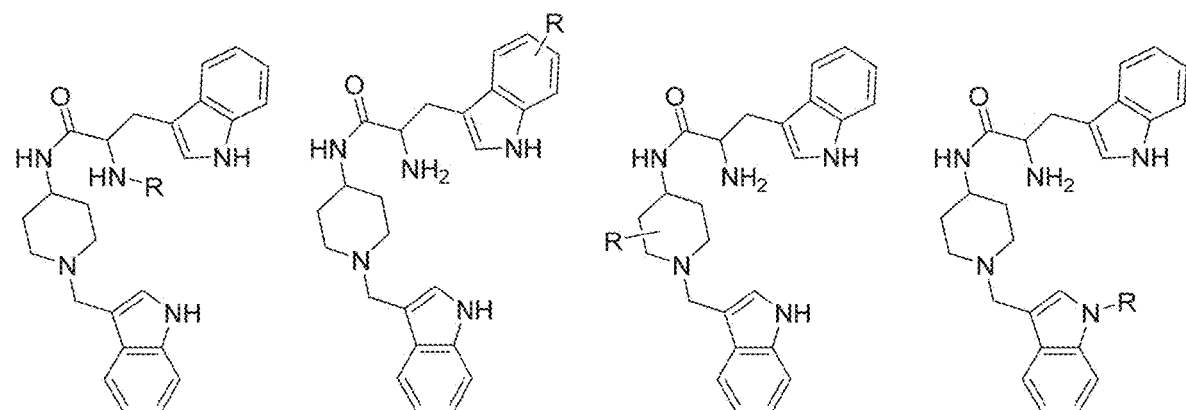
FIG. 1GGG
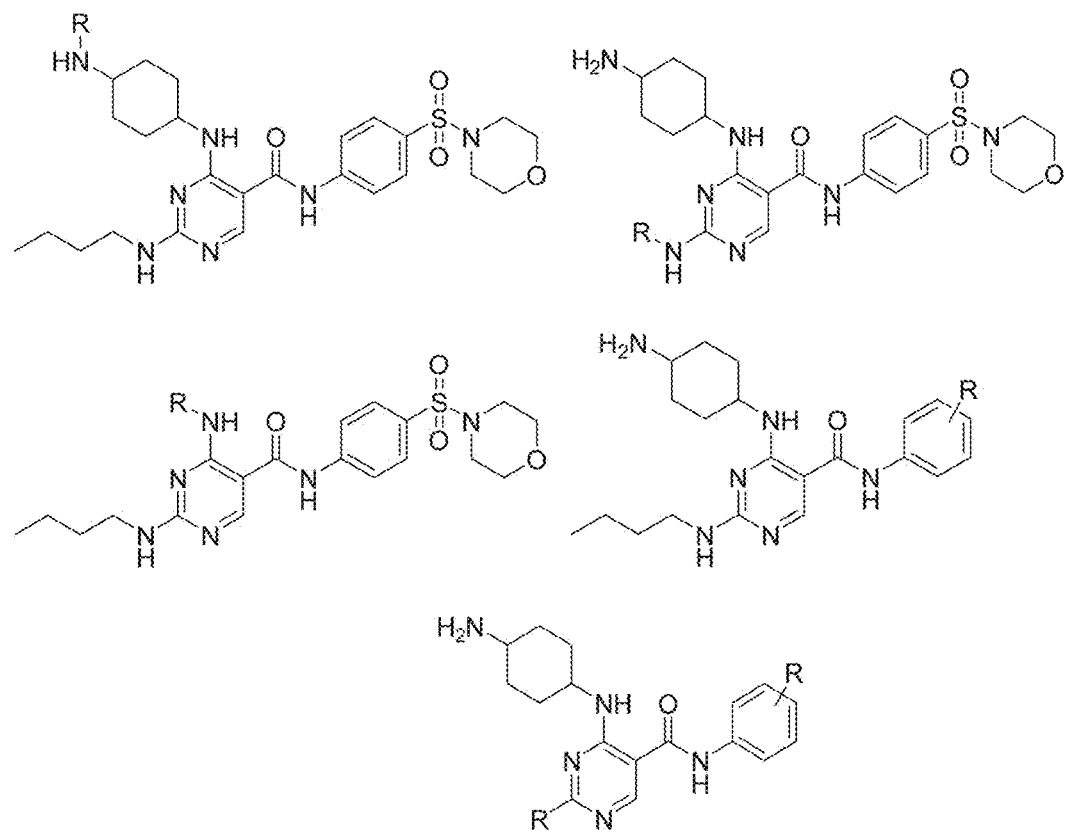

FIG. 1HHH
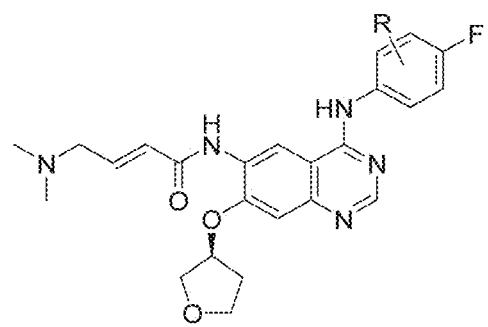
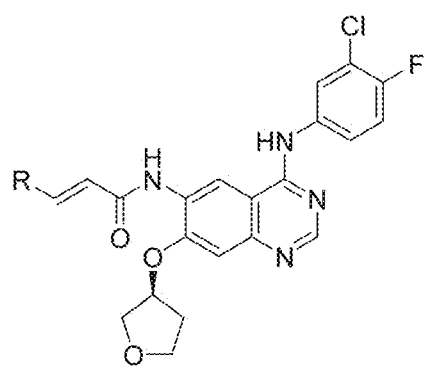
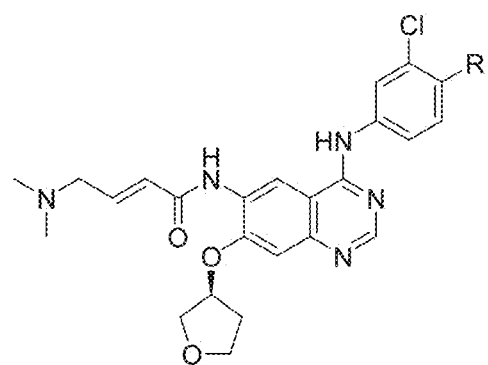
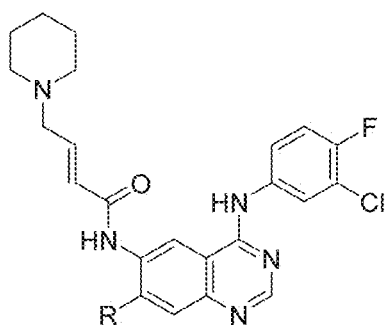
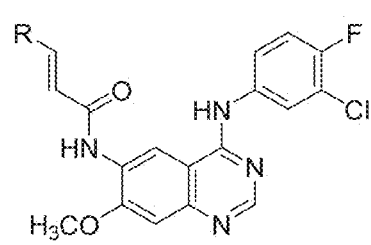
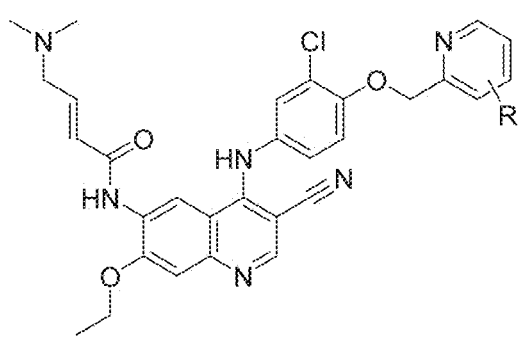
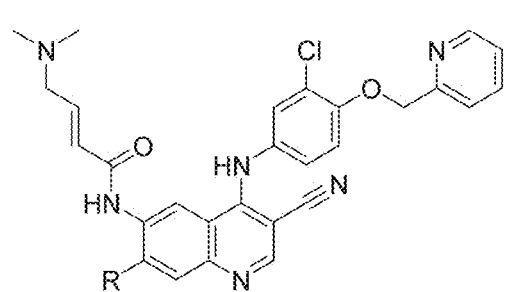
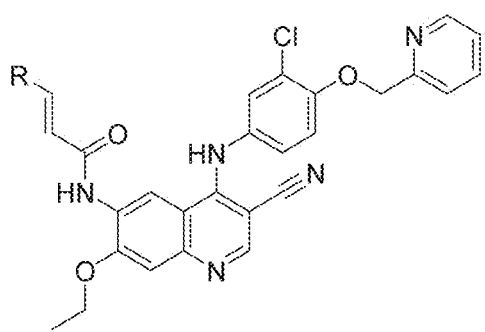

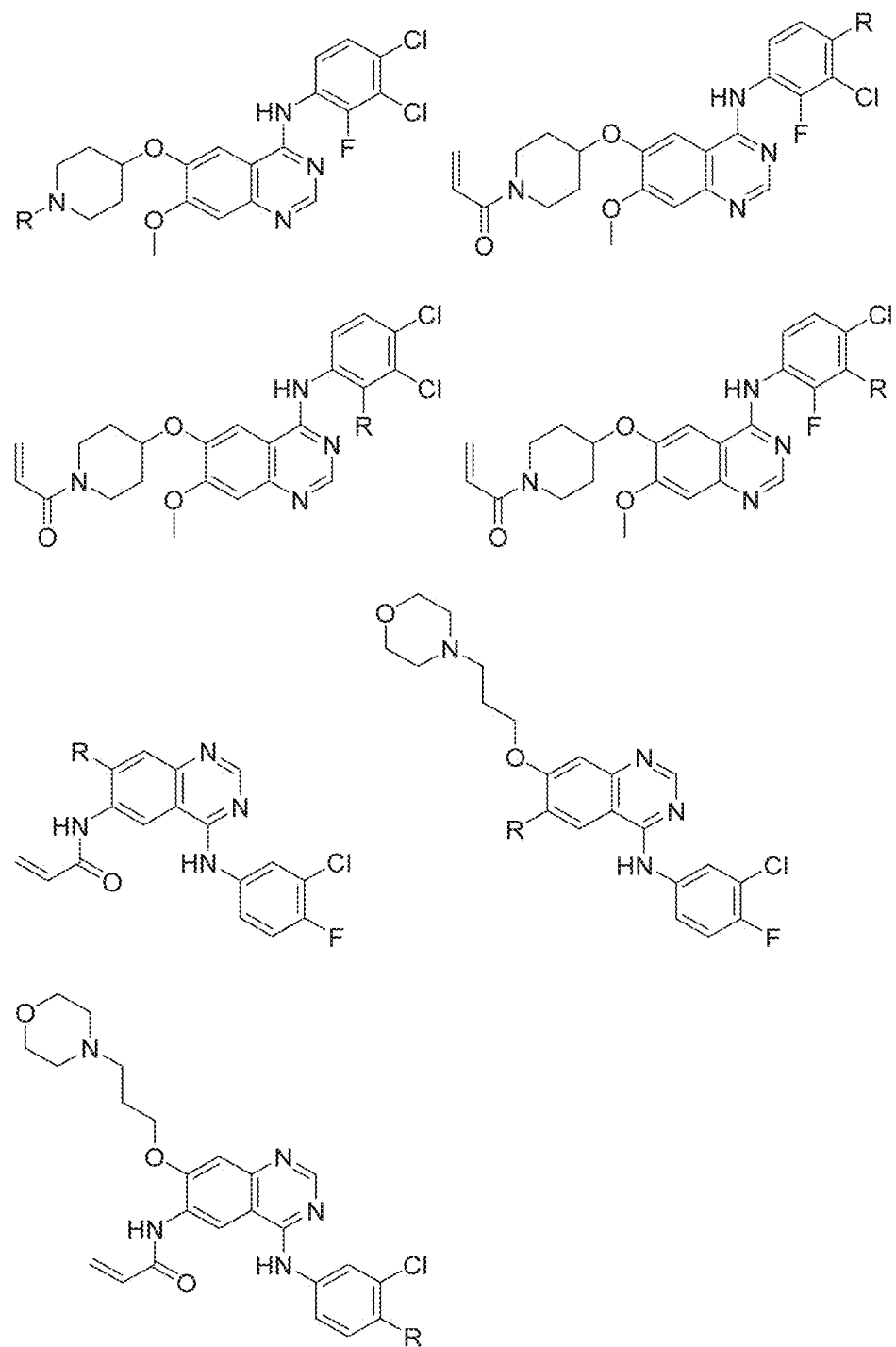
FIG. 1III

FIG. 1JJJ
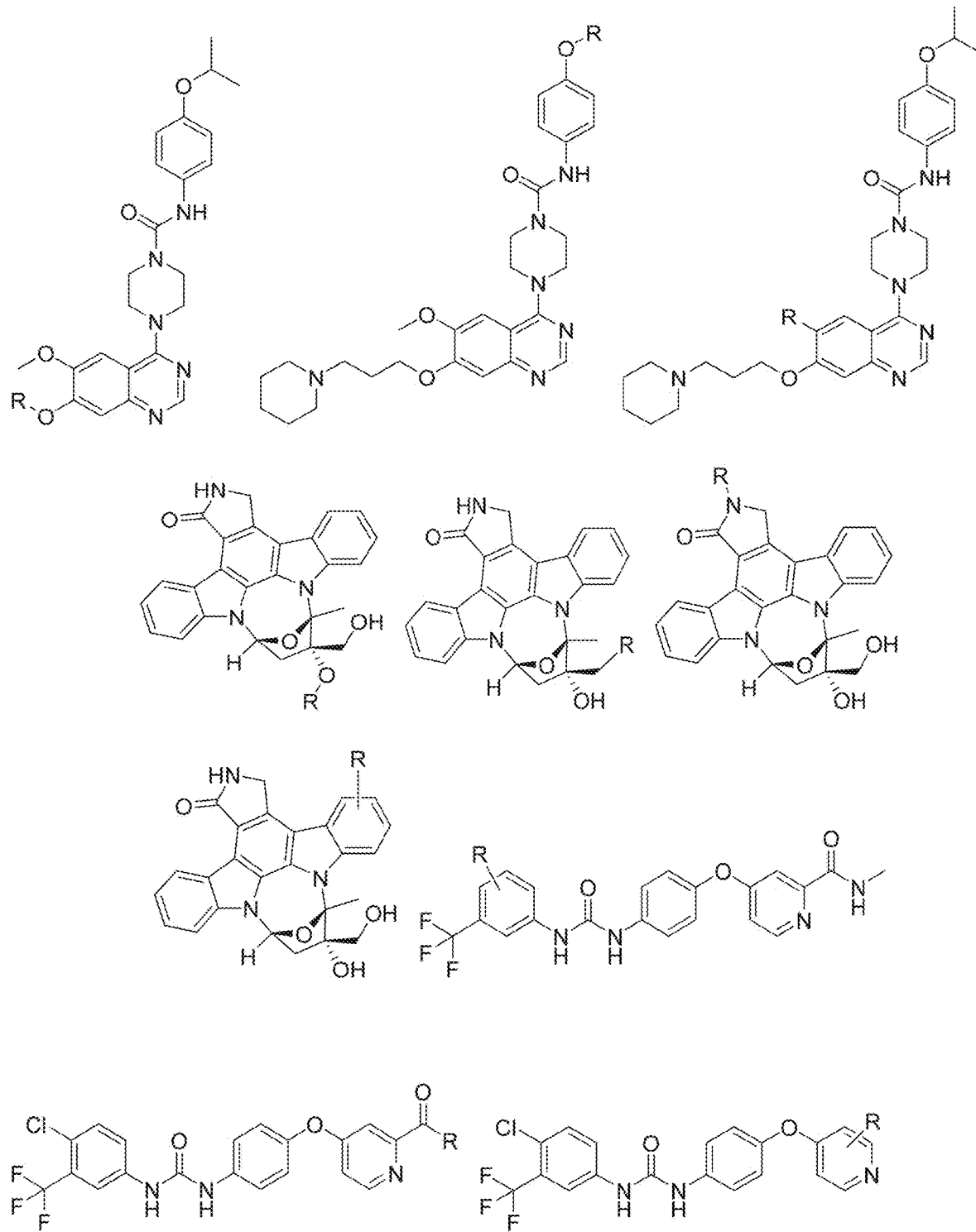

FIG. 1KKK
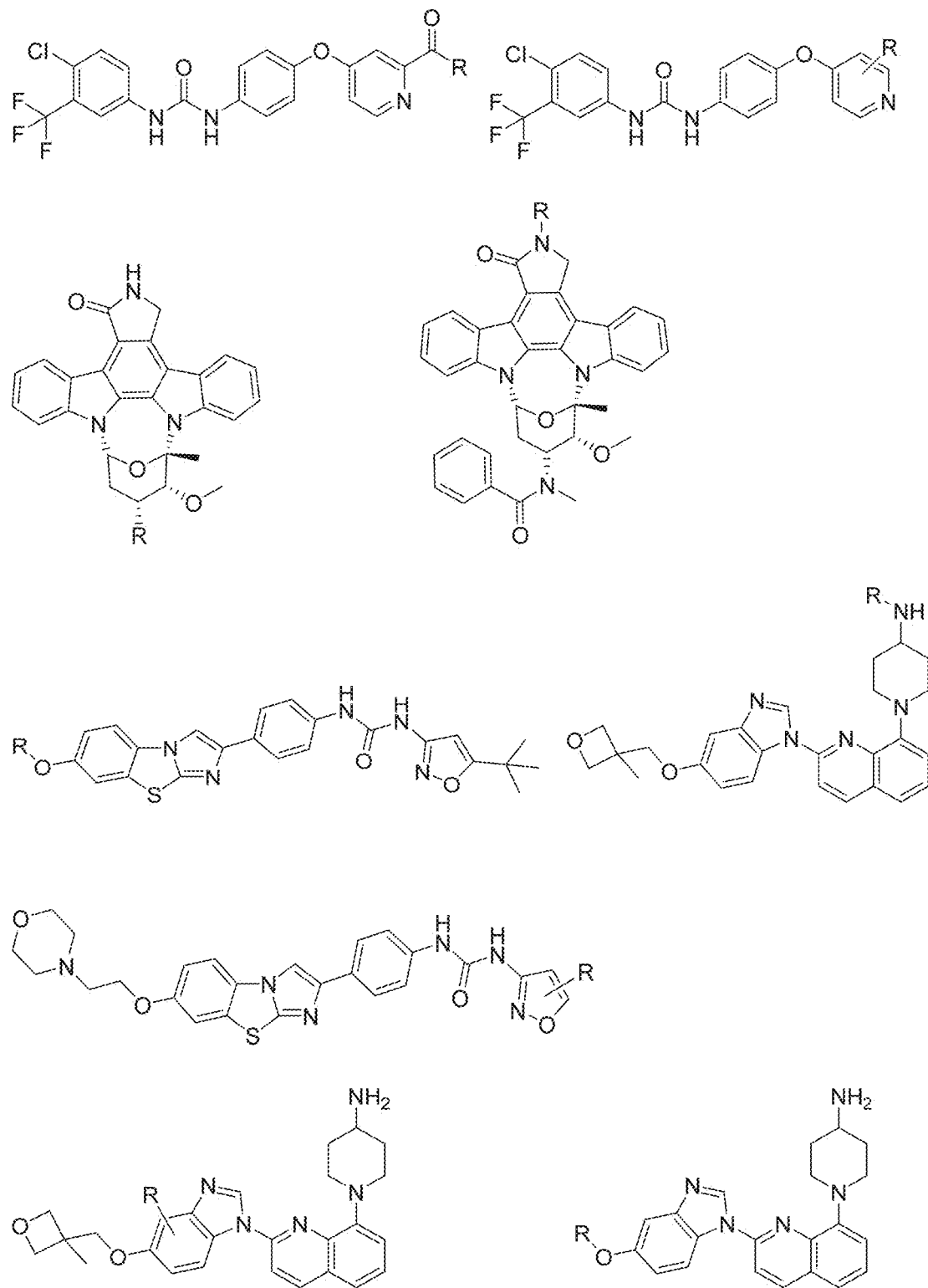

FIG. 1LLL
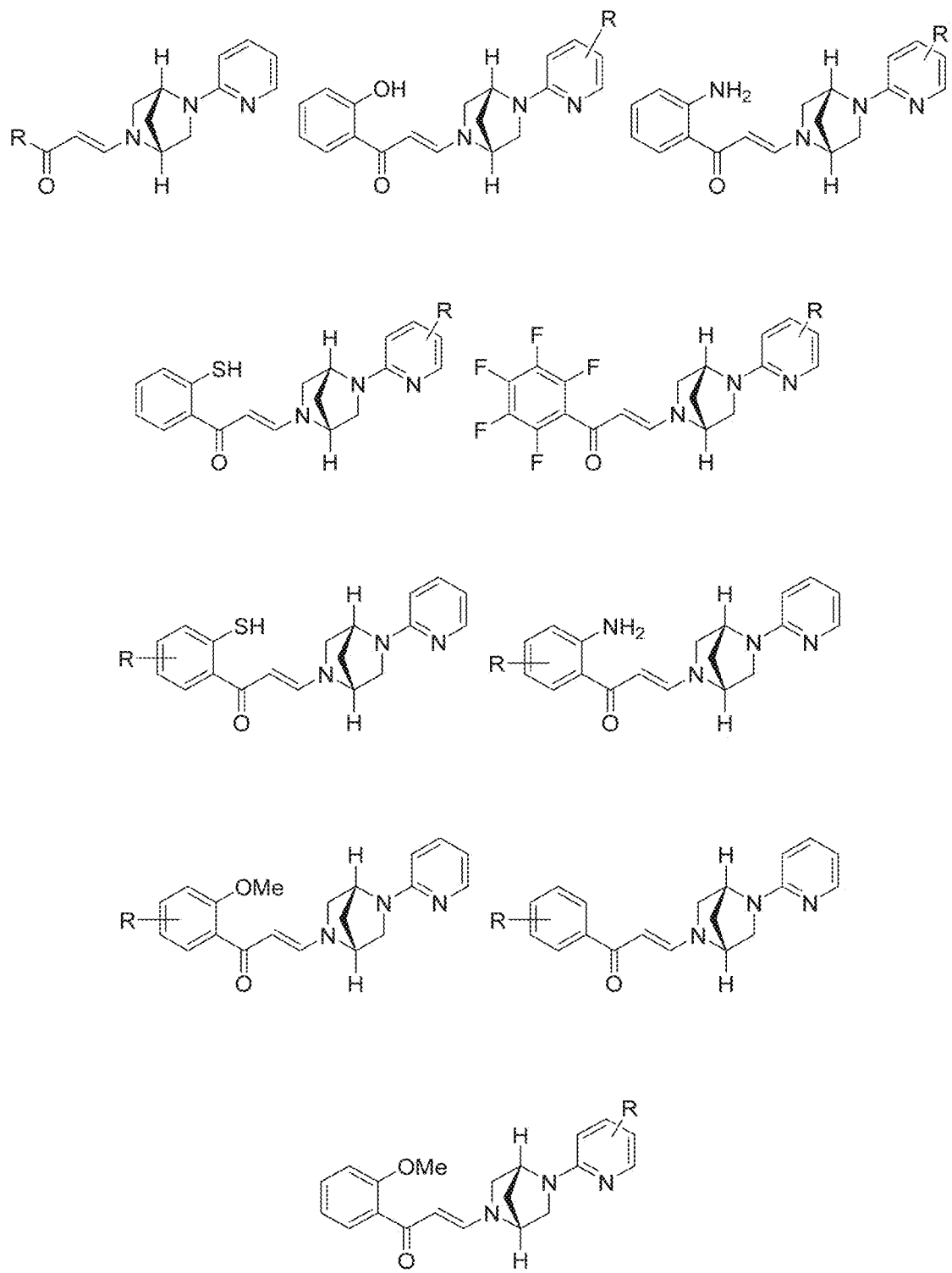

FIG. 2F
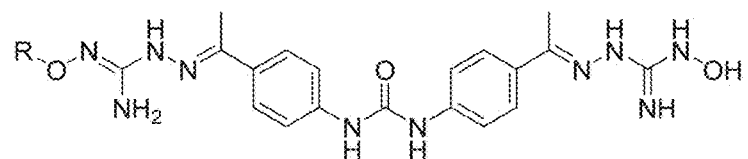
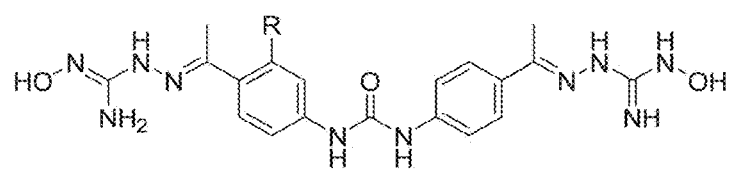
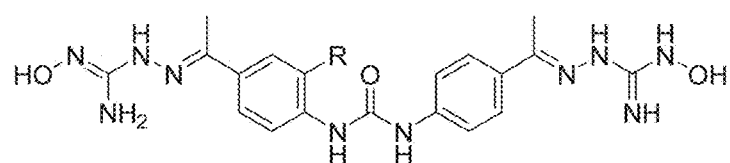
FIG. 2G
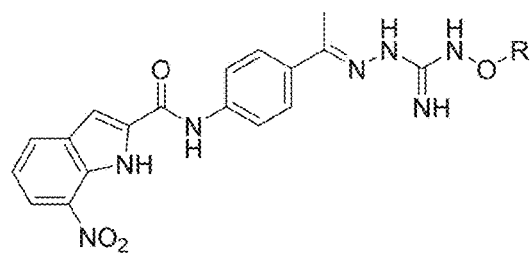
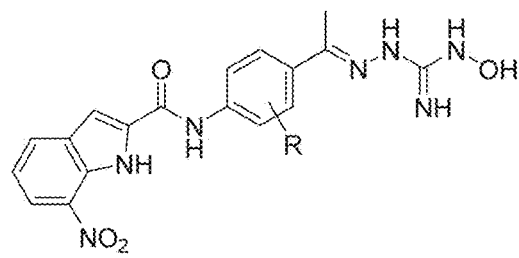
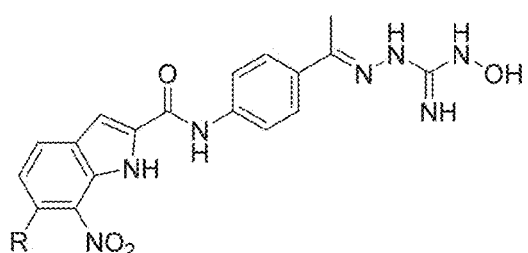
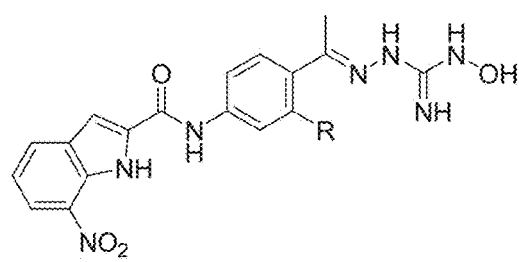

FIG. 2I
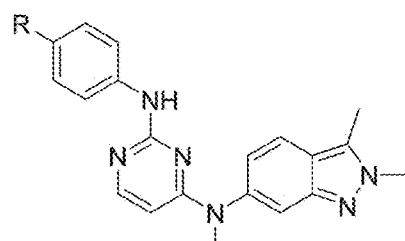
derivatized pazopanib
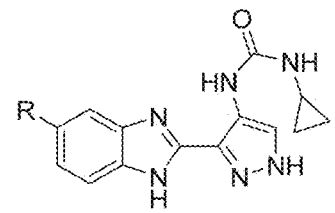
derivatized AT-9283
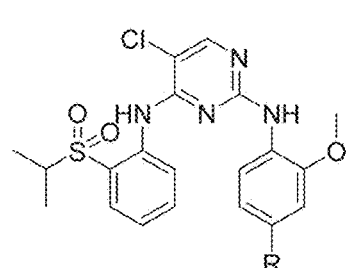
derivatized TAE684
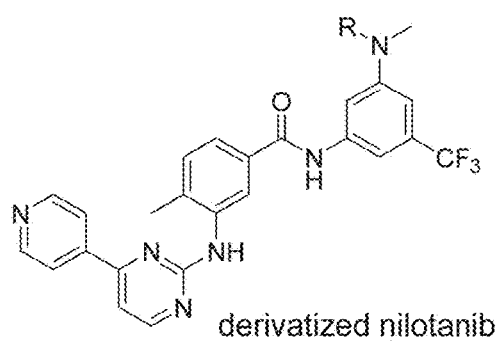
derivatized nilotanib
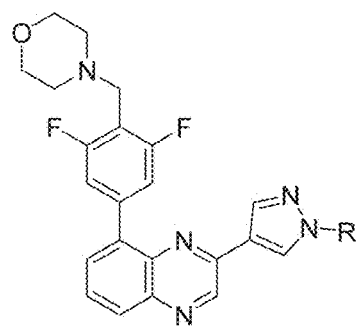
derivatized NVP-BSK805
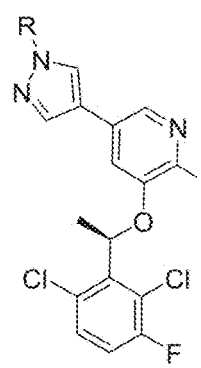
derivatized Crizotinib
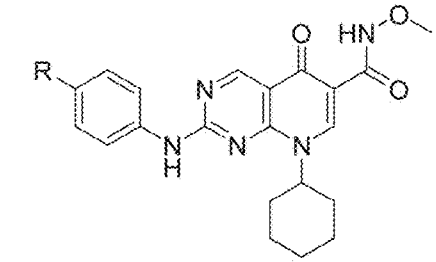
derivatized JNJ FMS
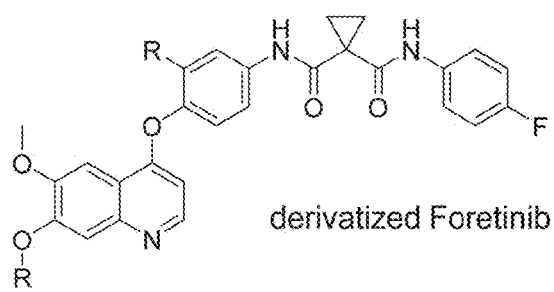
derivatized Foretinib
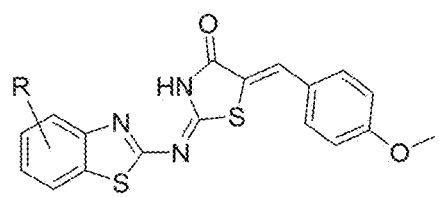
derivatized inhibitor of SHP-2 Domain of Tyrosine Phosphatase FIG. 2W
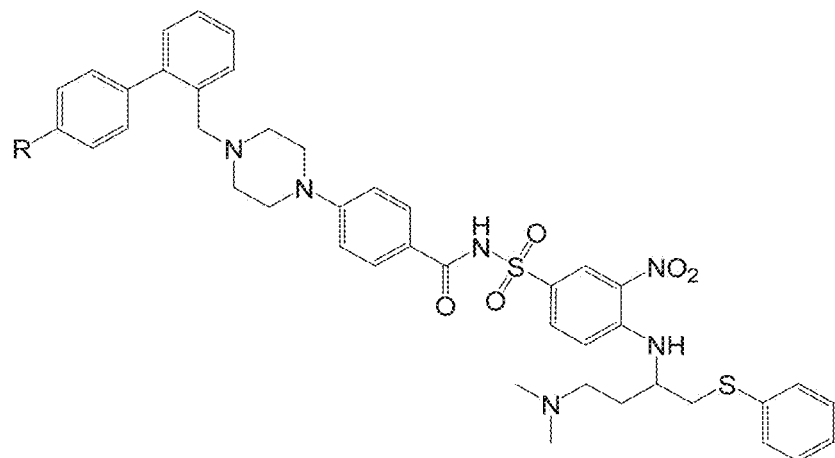
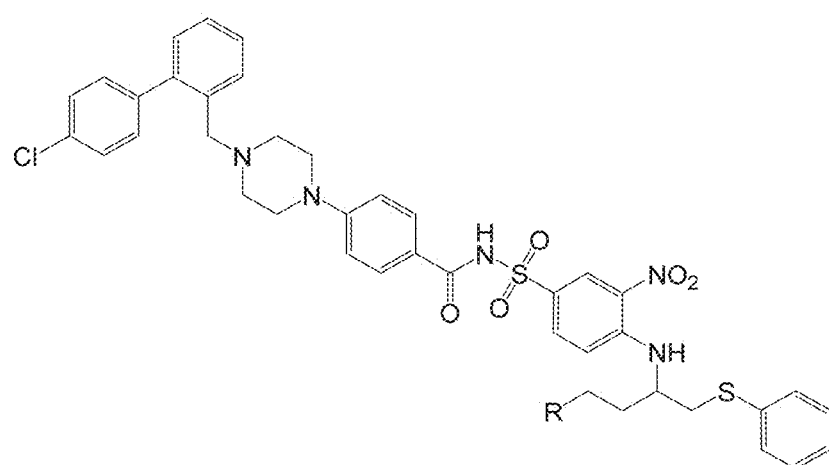
FIG. 2X
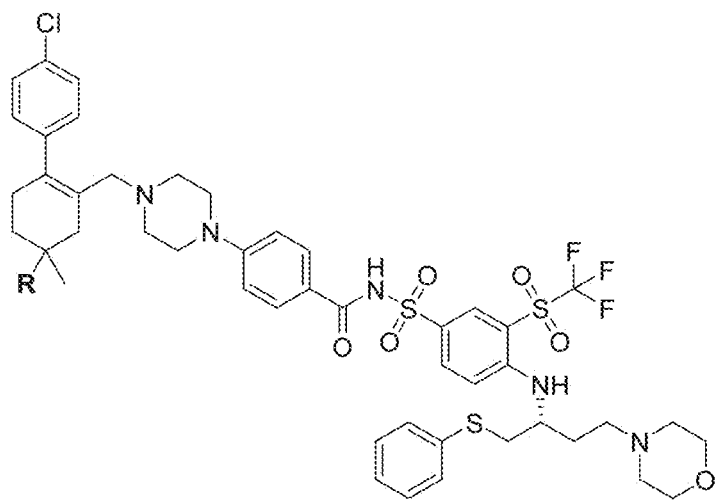
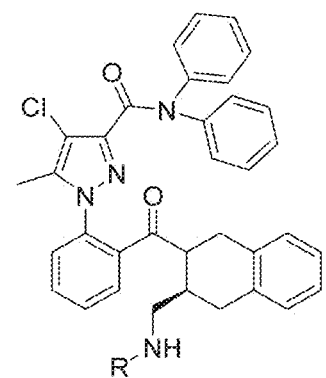

FIG. 2Y
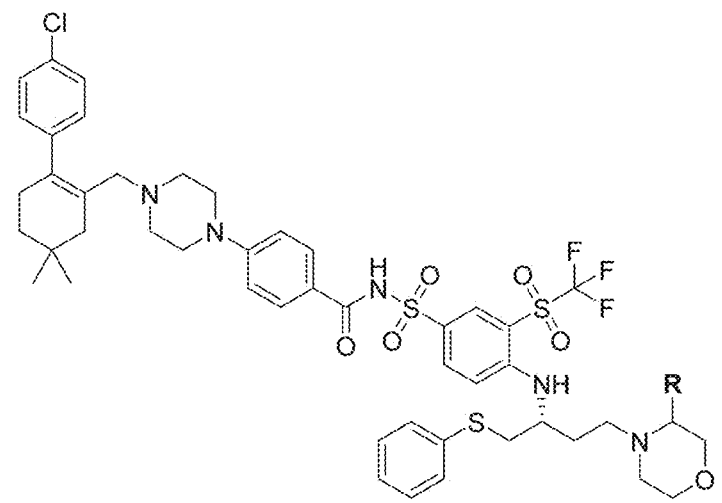
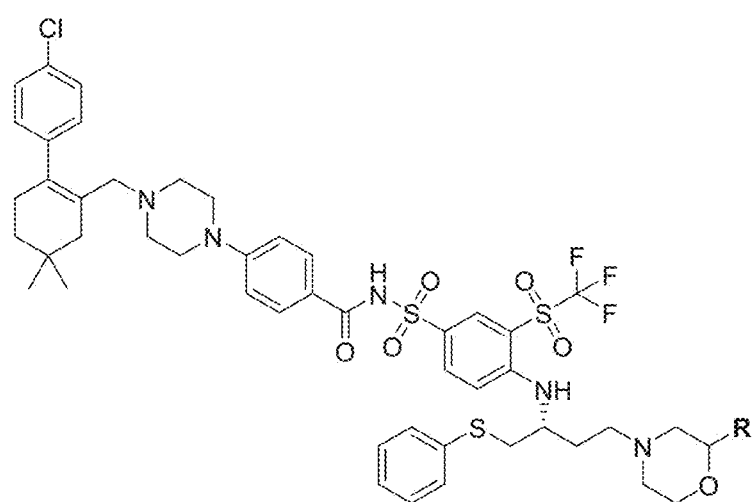
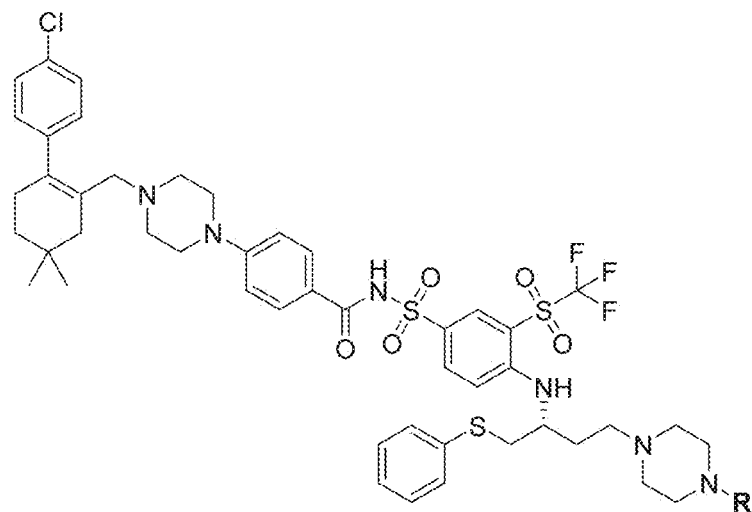

FIG. 2UU
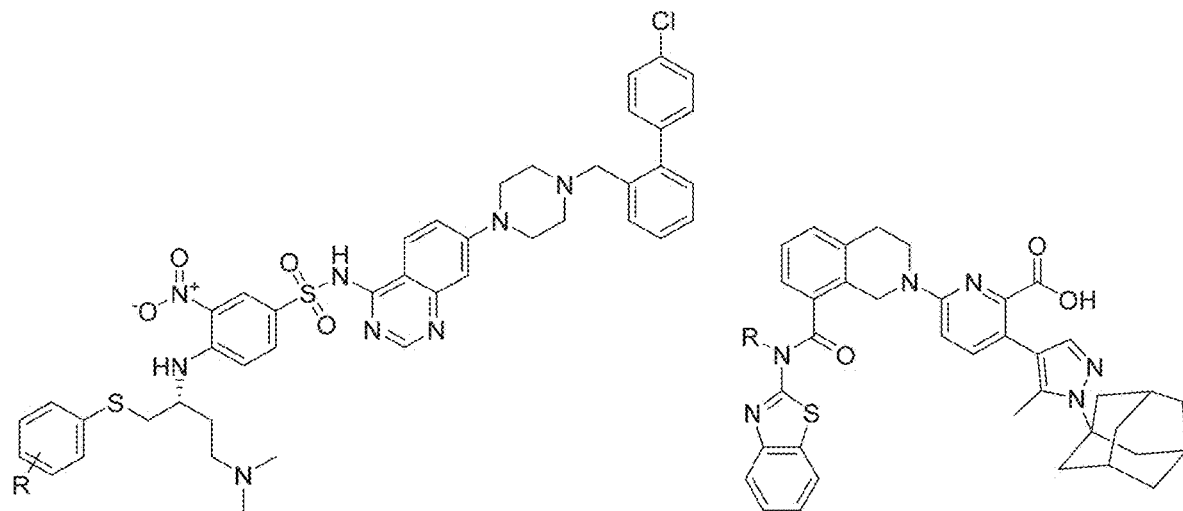
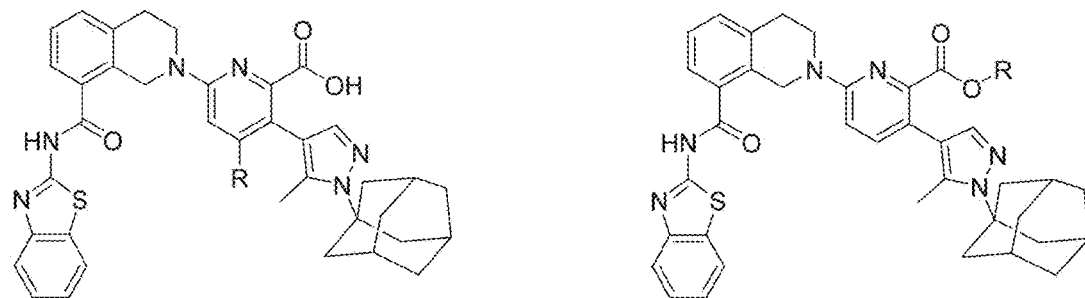
FIG. 2VV
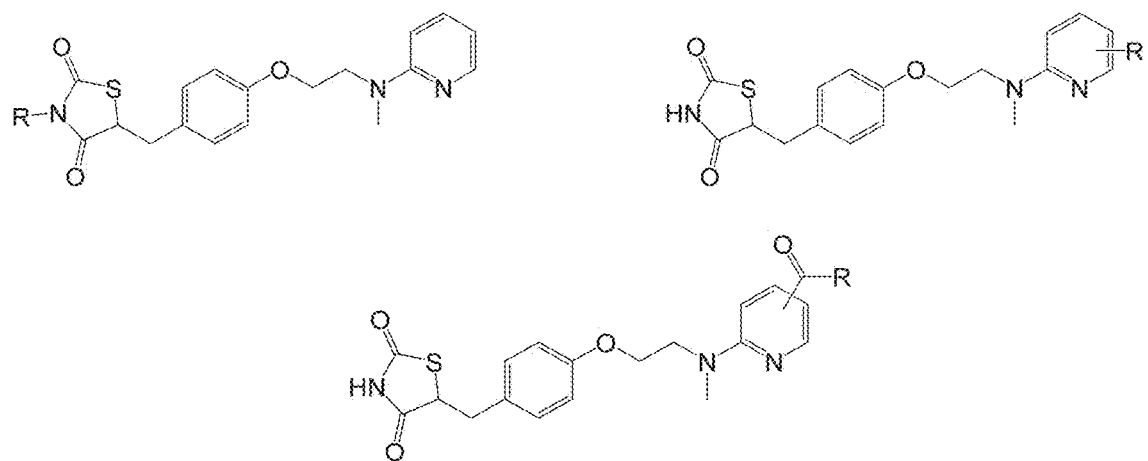

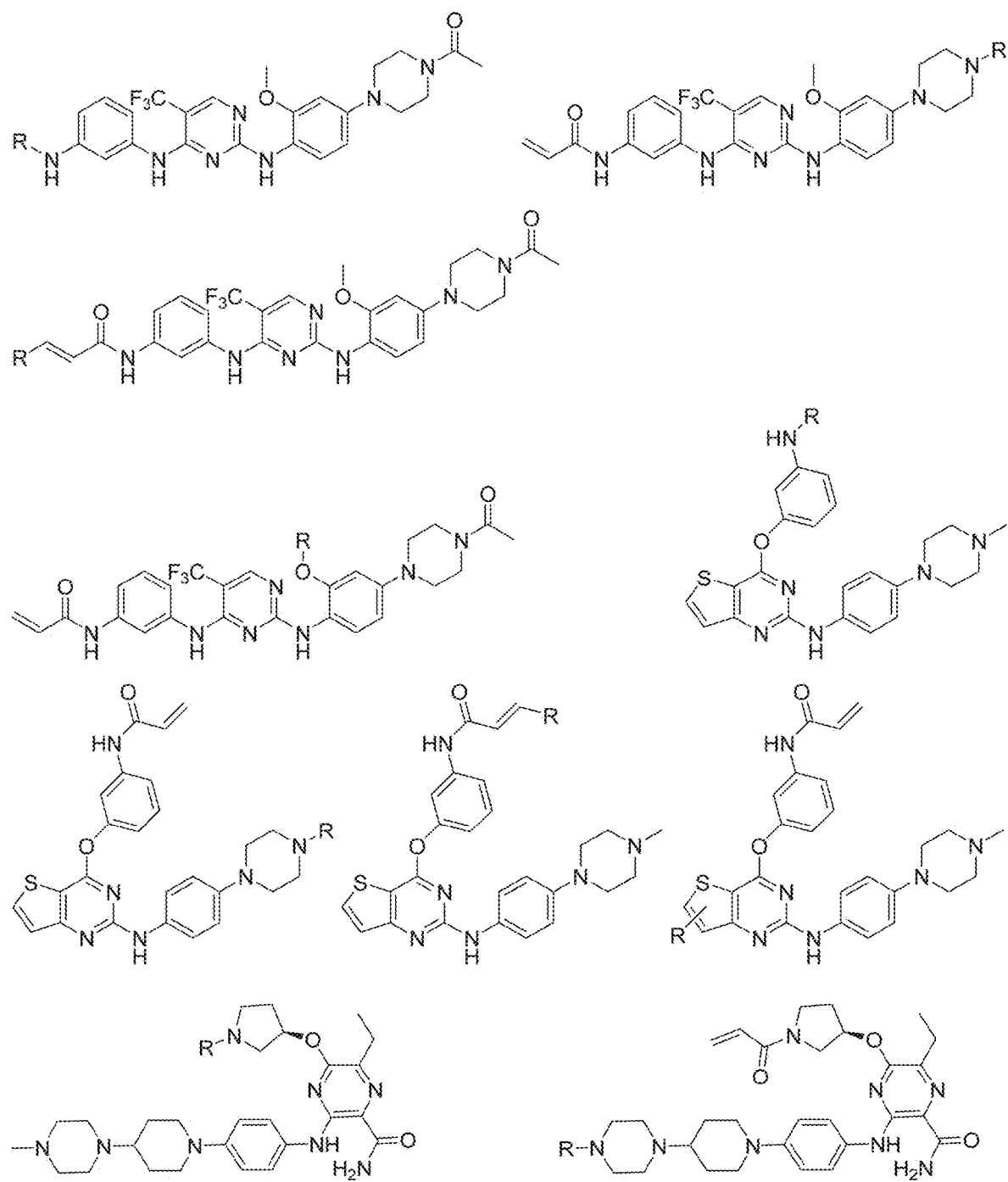
FIG. 2AAA

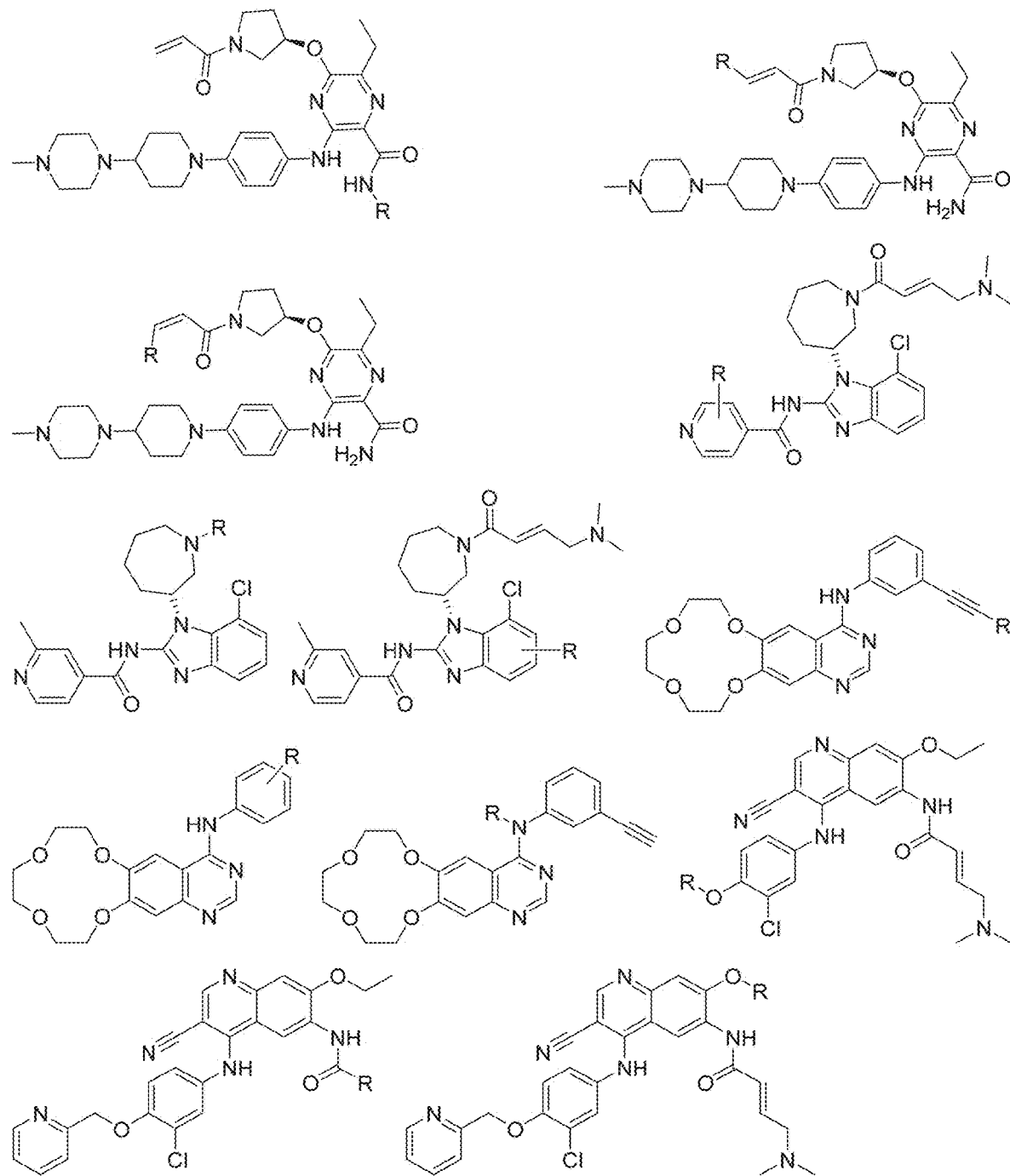
FIG. 2BBB

FIG. 2CCC
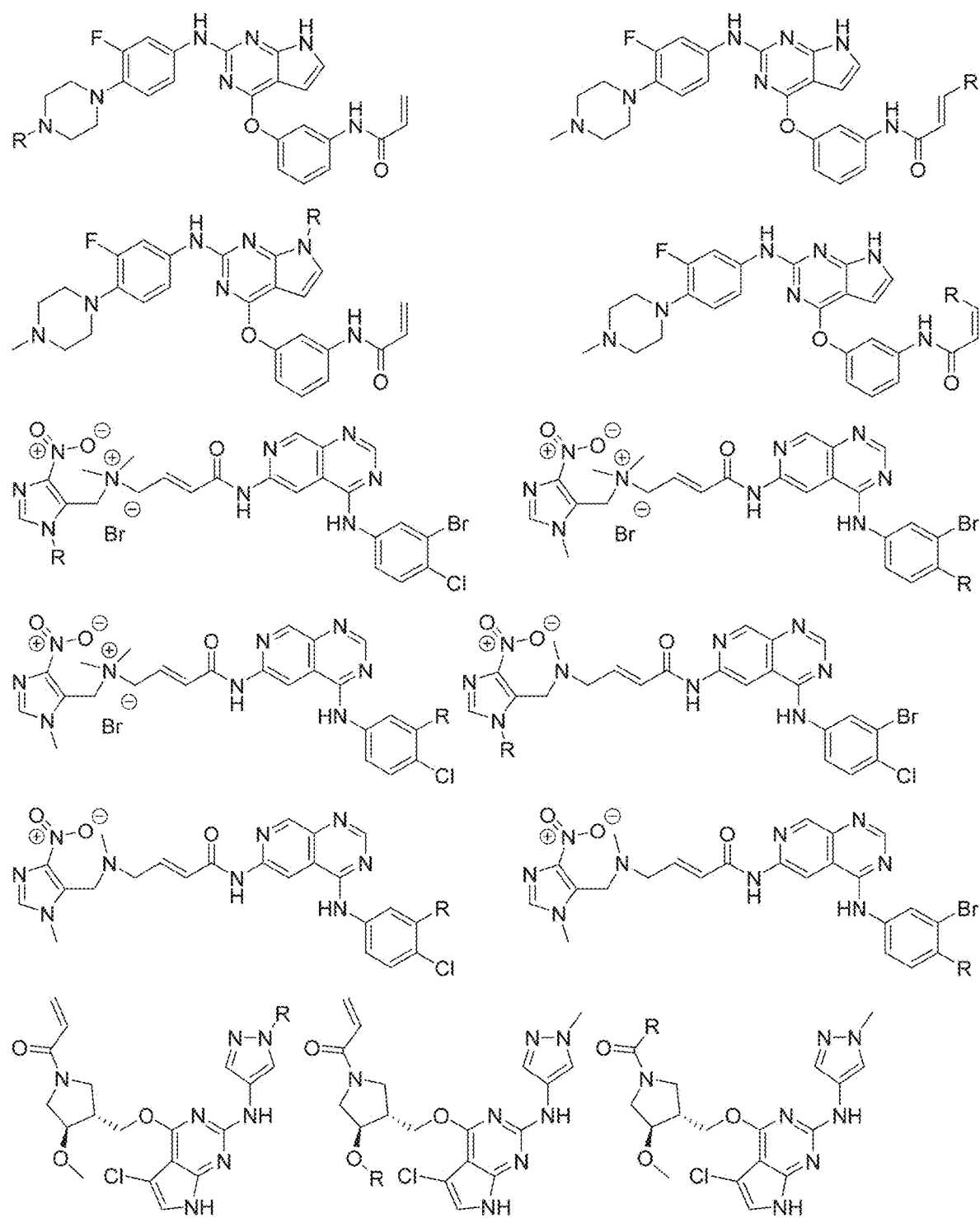

FIG. 2DDD
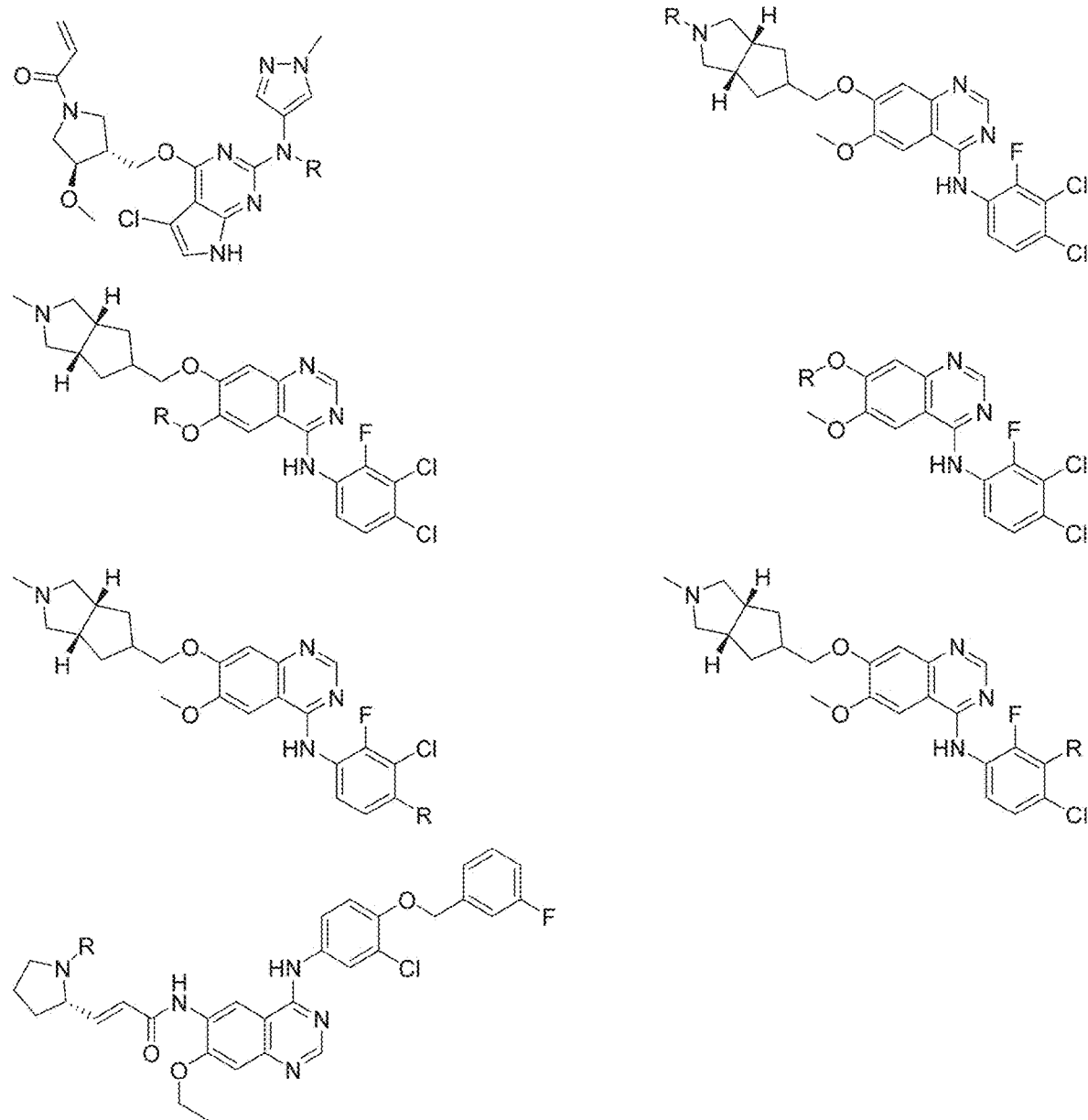

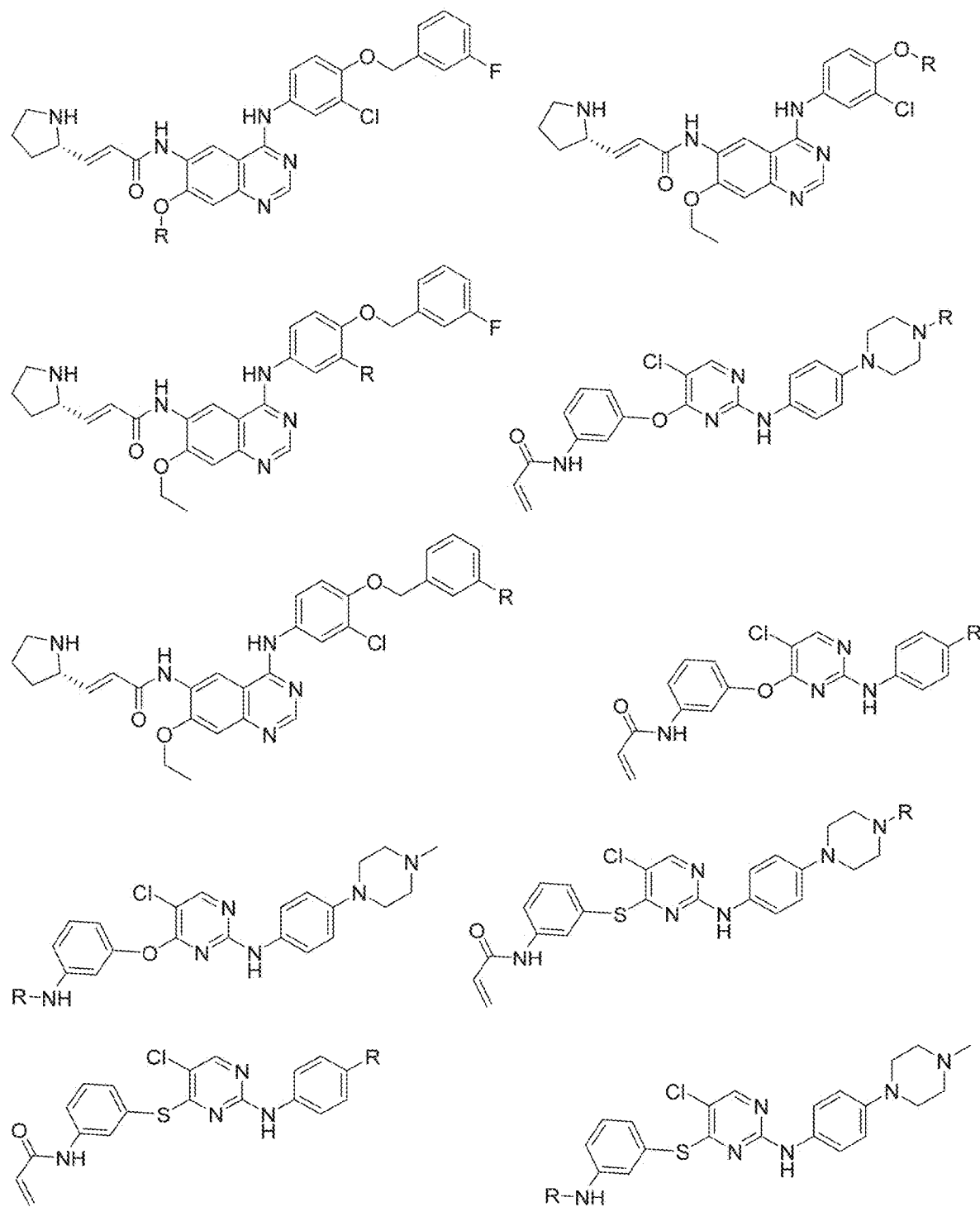
FIG. 2EEE

FIG. 2FFF
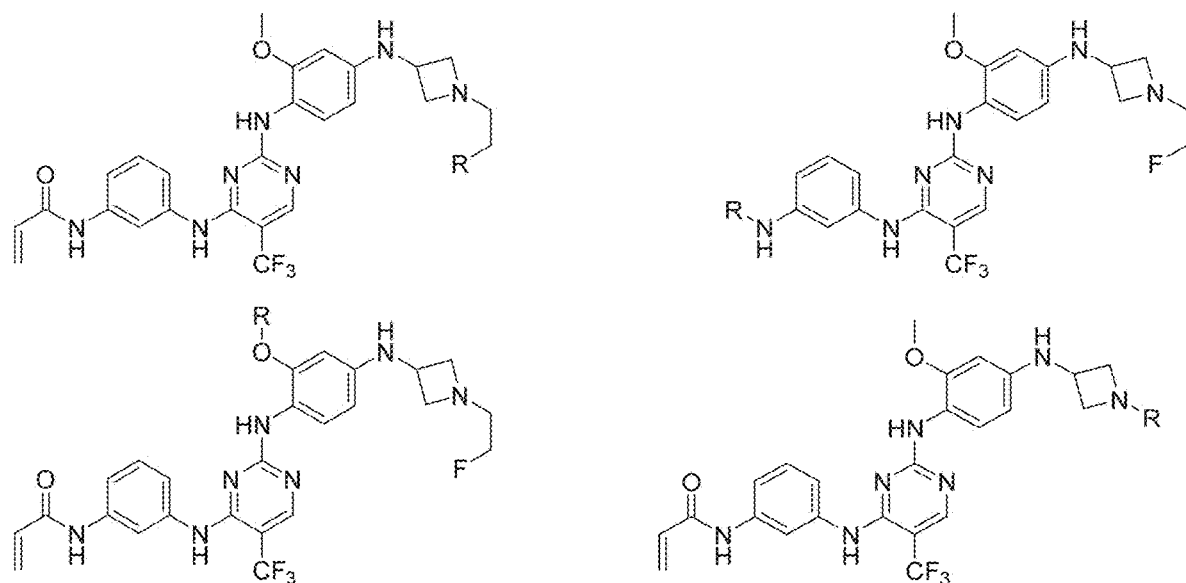
FIG. 2GGG
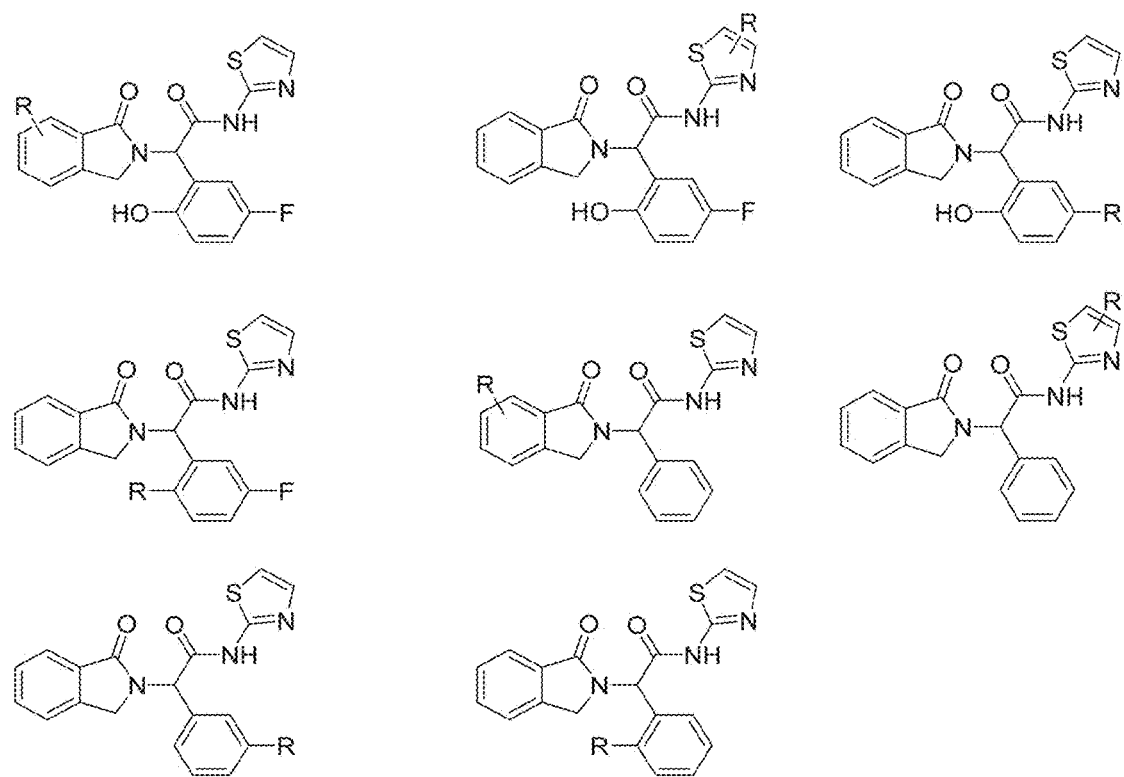

FIG. 2HHH
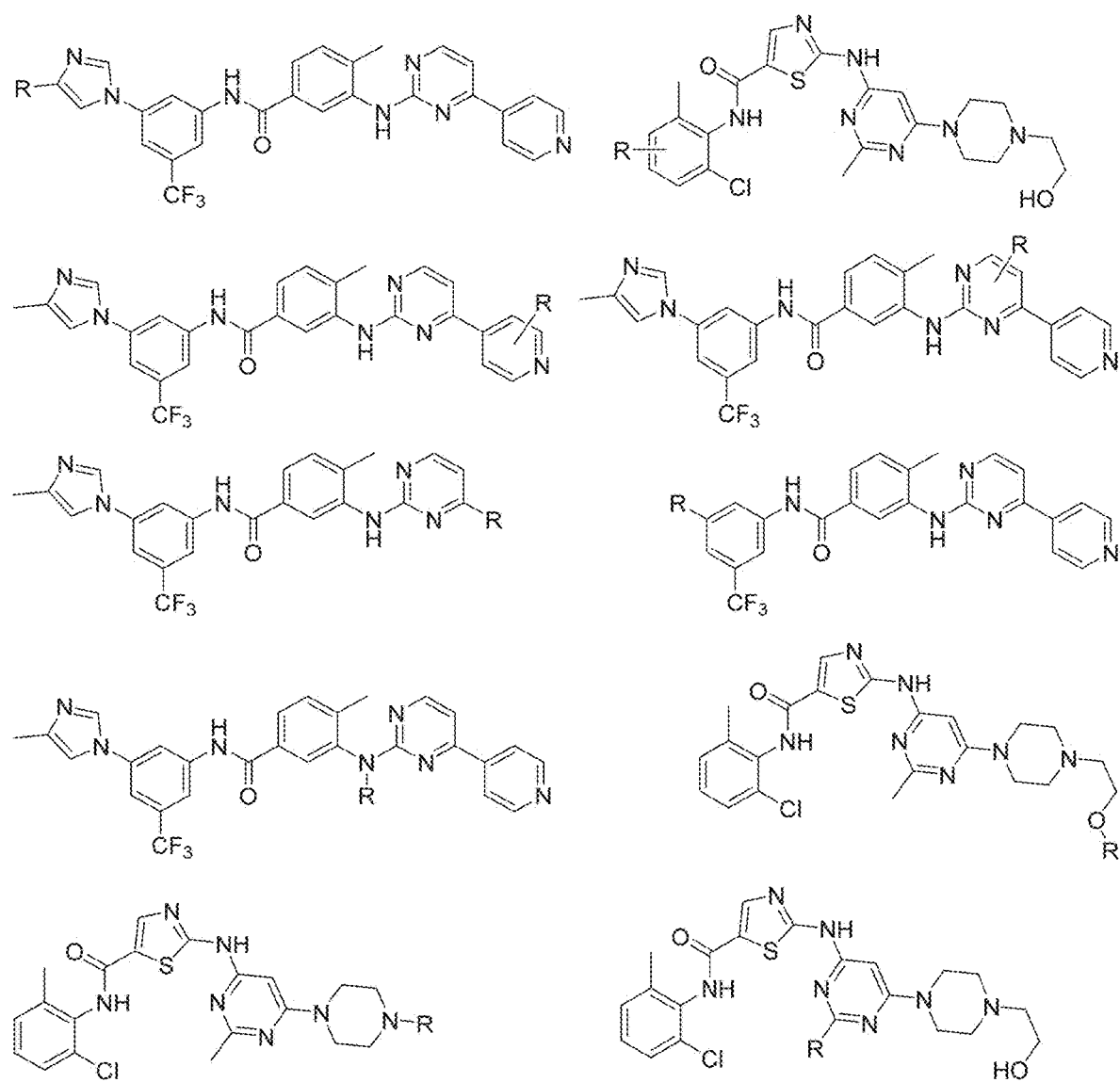

FIG. 2III
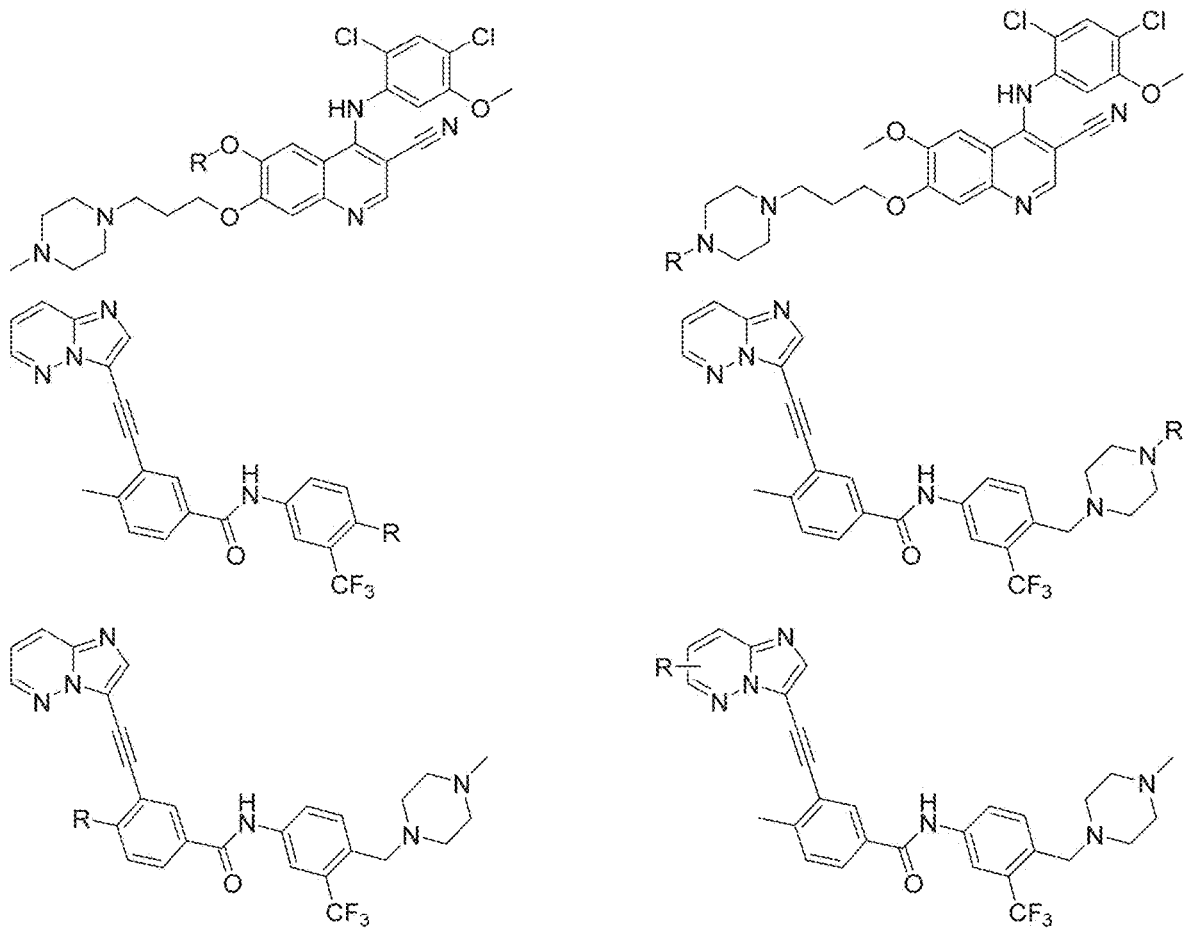
FIG. 2JJJ
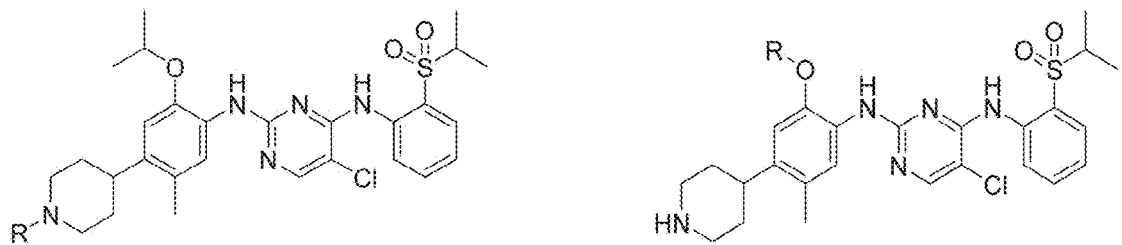

FIG. 2KKK
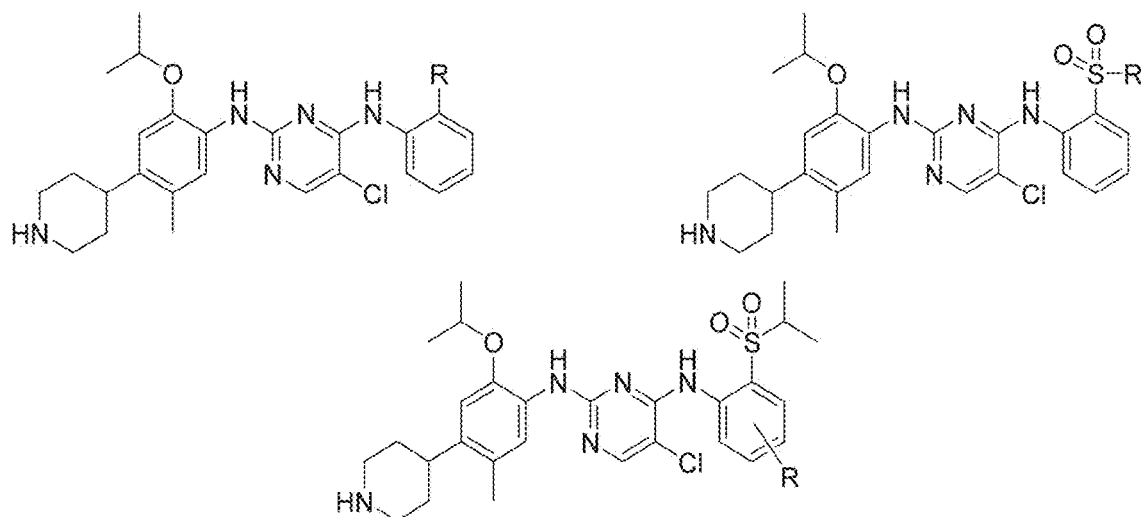
FIG. 2LLL
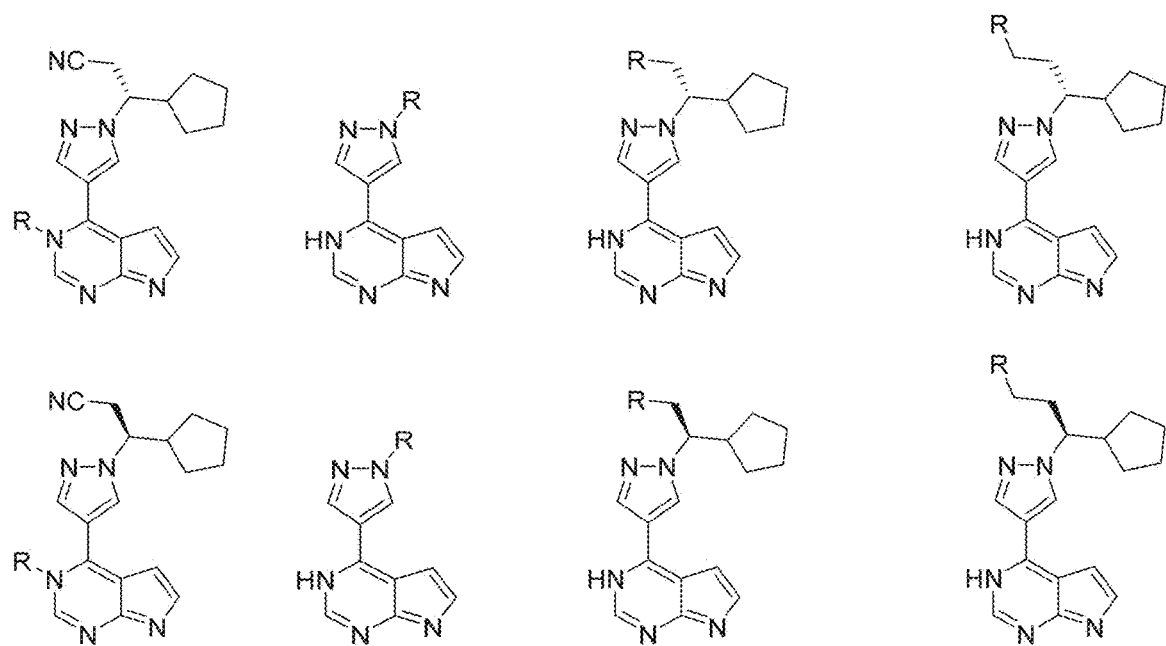

FIG. 2MMM
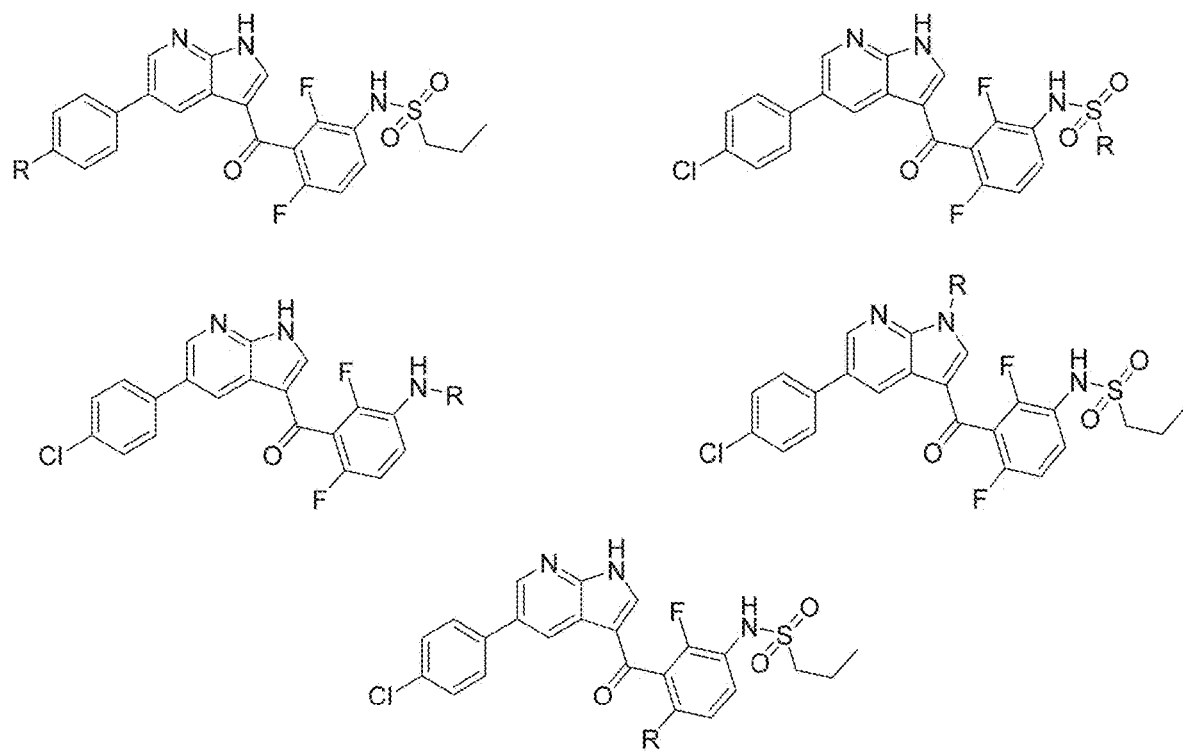
FIG. 2NNN
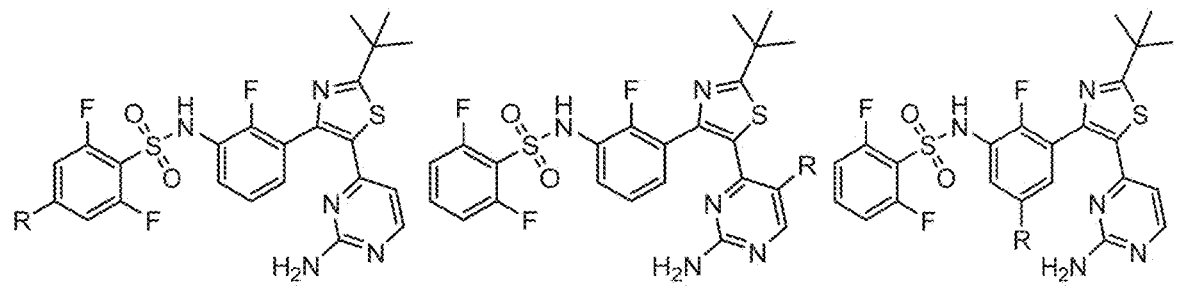

FIG. 2OOO
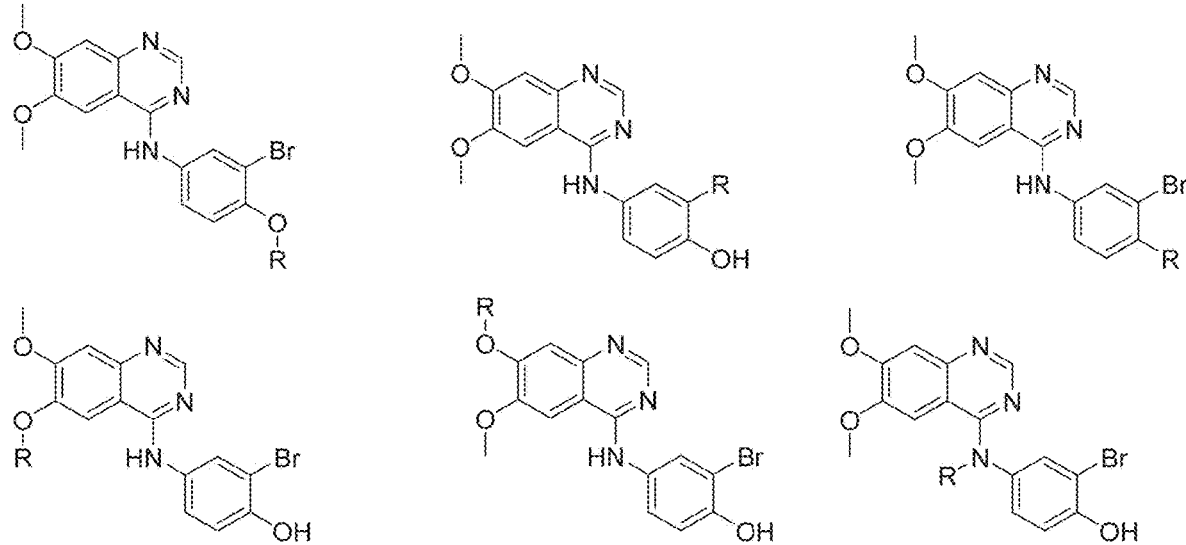
FIG. 2PPP
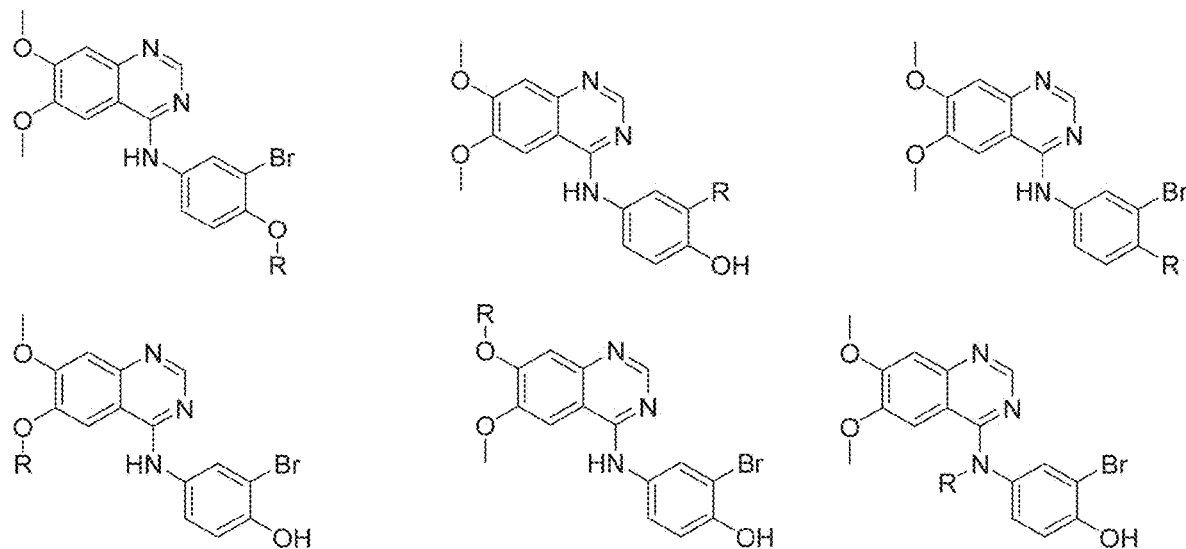

FIG. 2QQQ
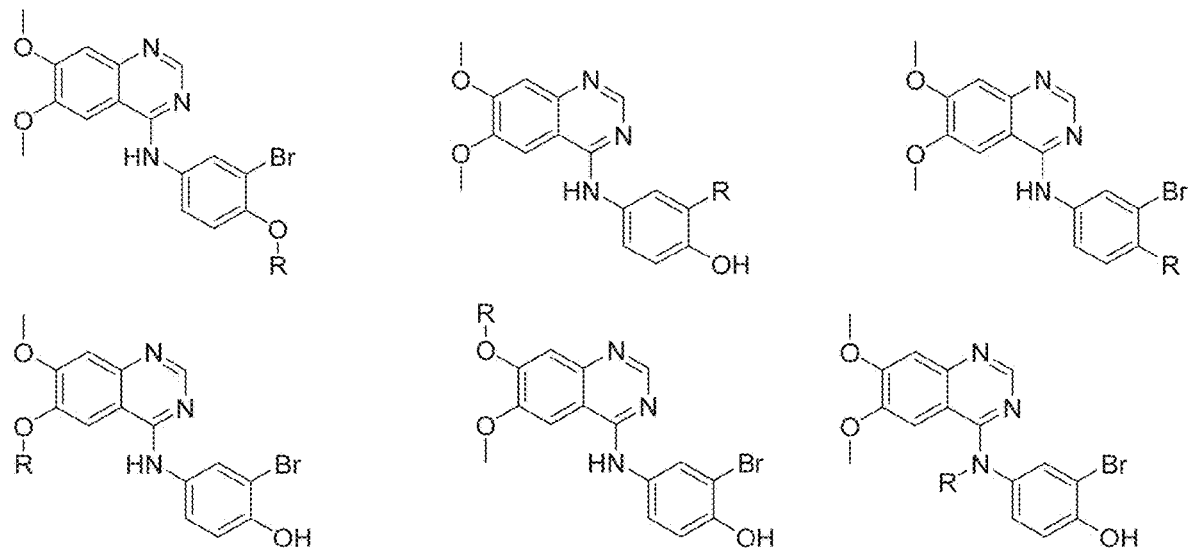
FIG. 2RRR
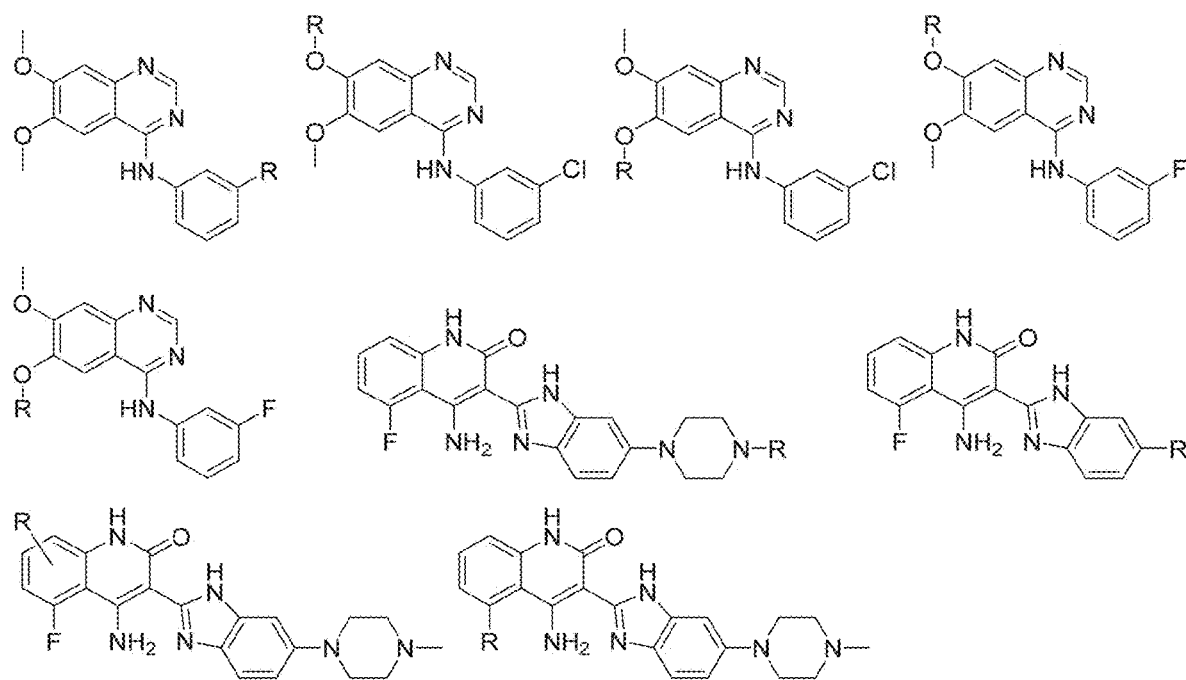

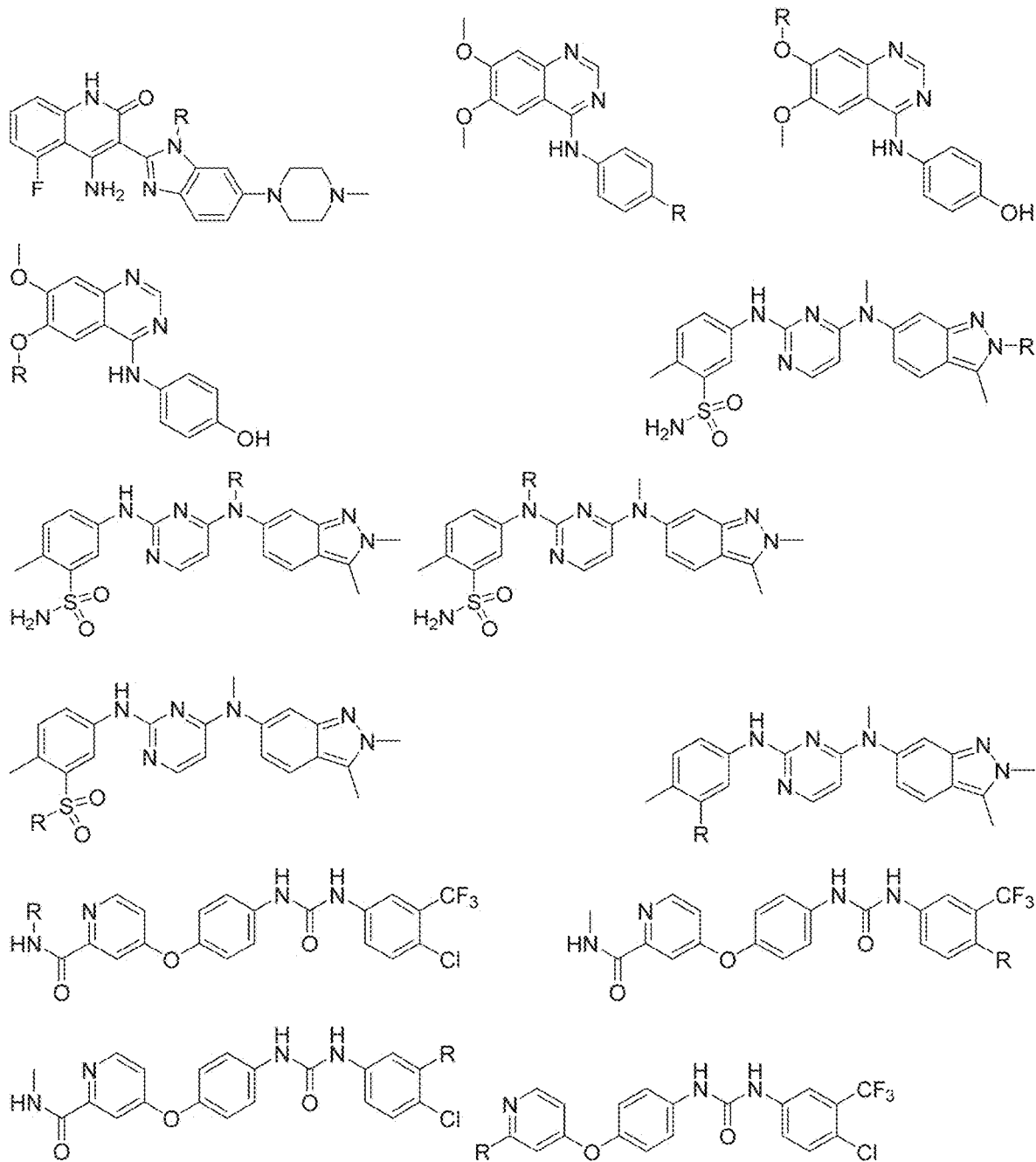
FIG. 2SSS

FIG. 2TTT
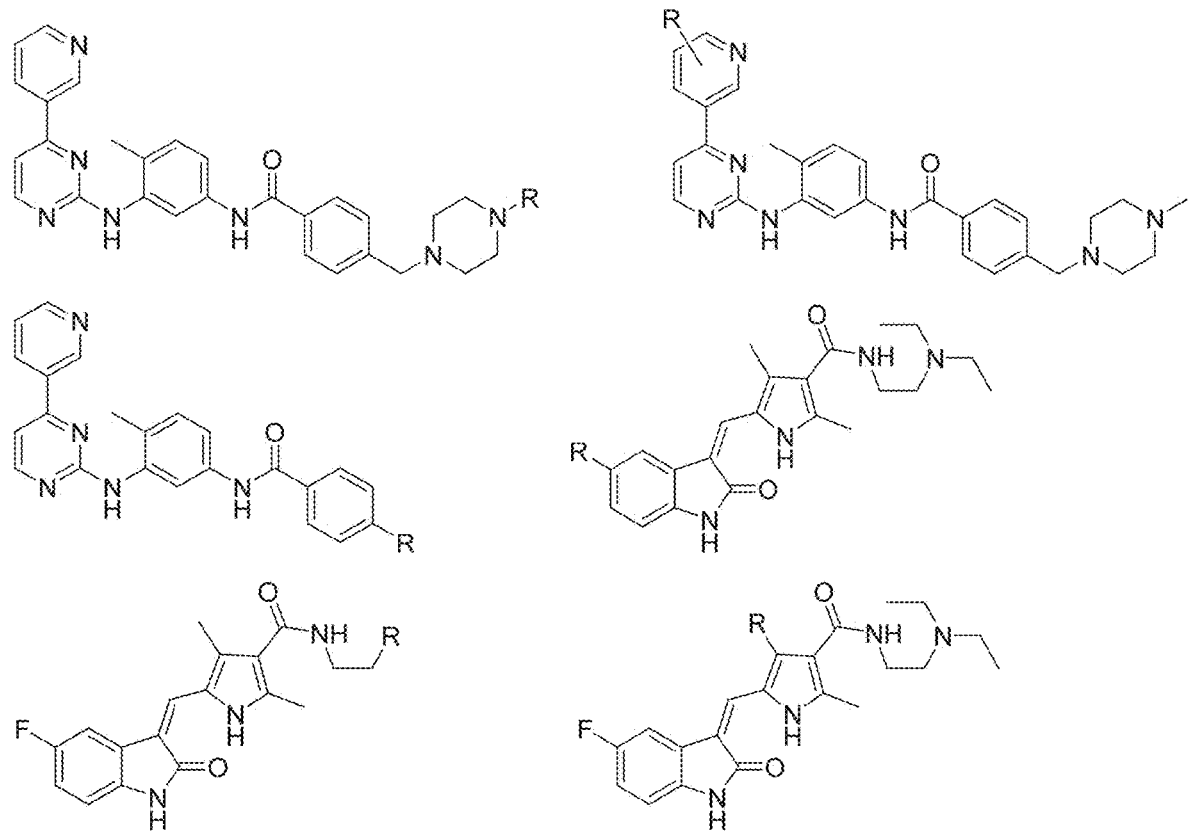
FIG. 2UUU
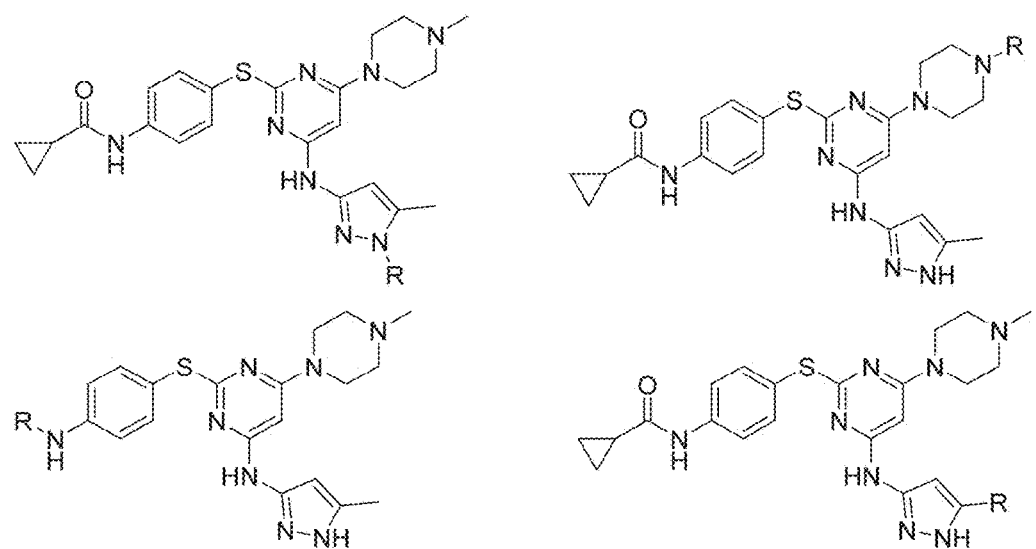

FIG. 2VVV
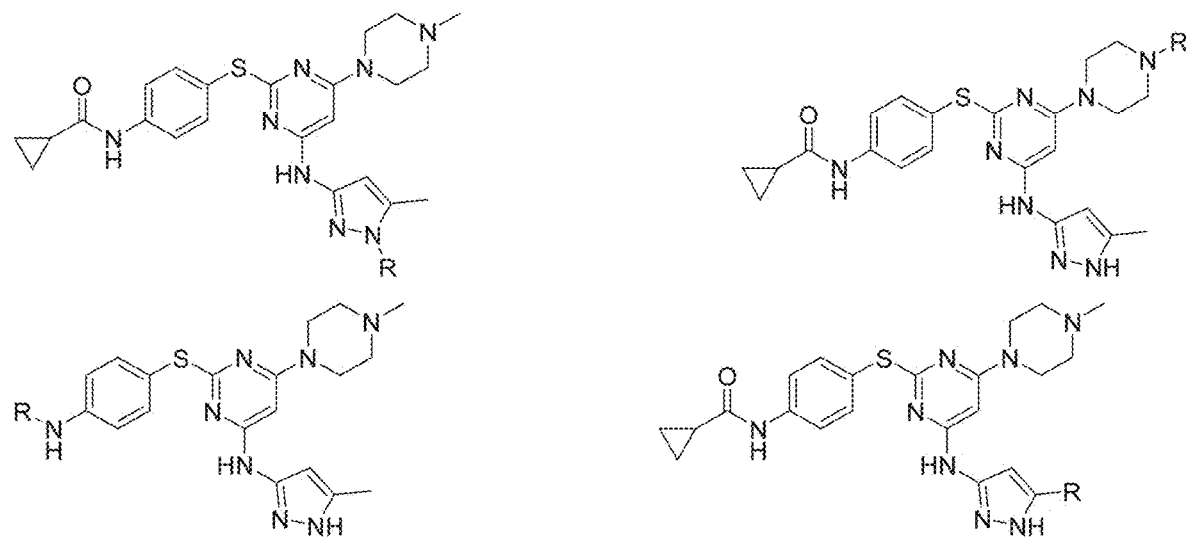
FIG. 2WWW
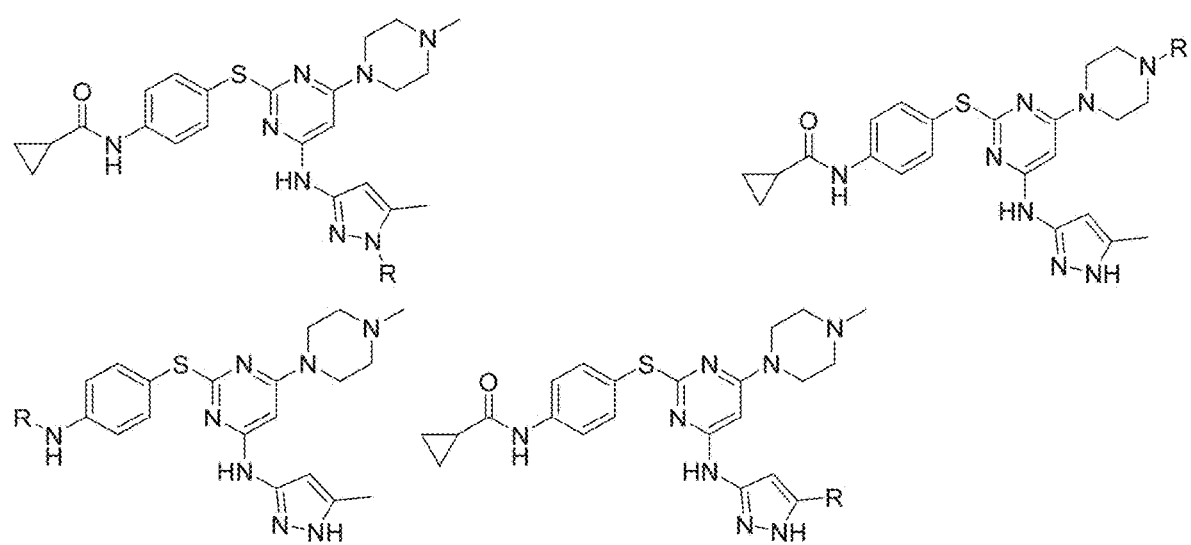

FIG. 2XXX
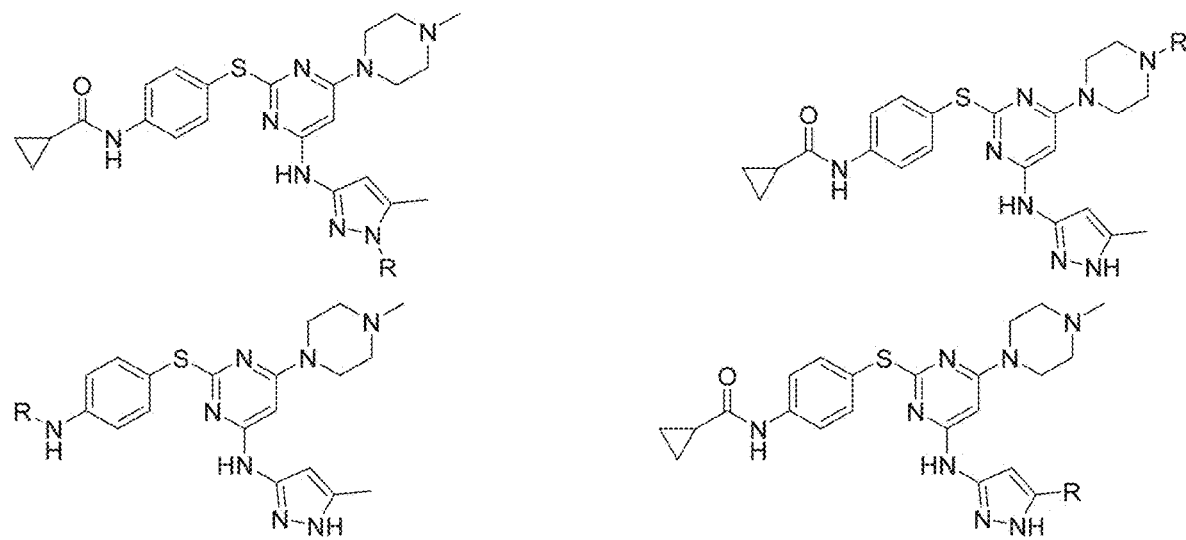
FIG. 2YYY
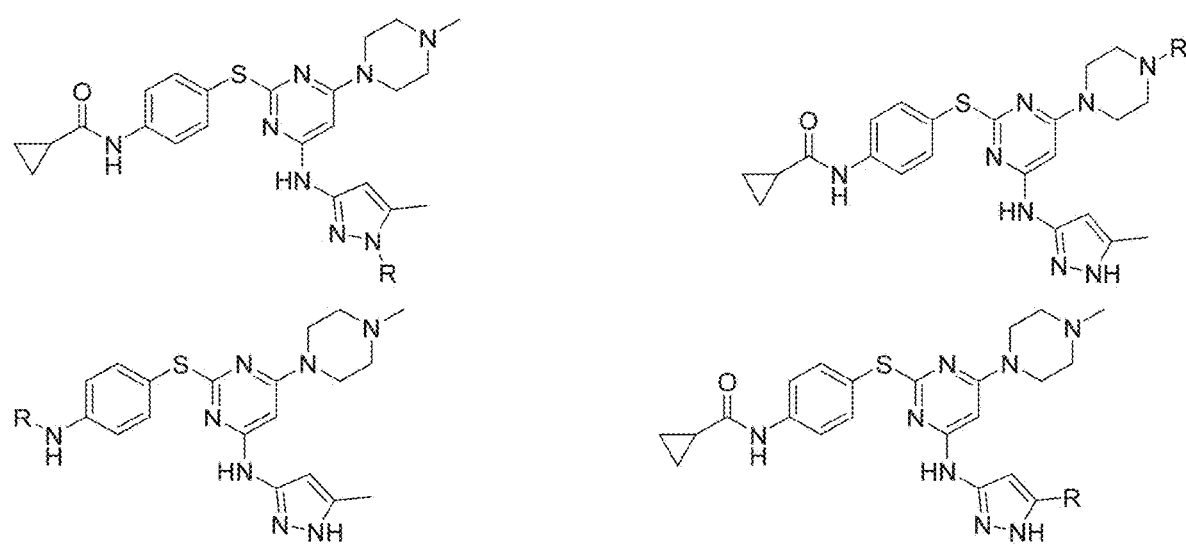

FIG. 2ZZZ
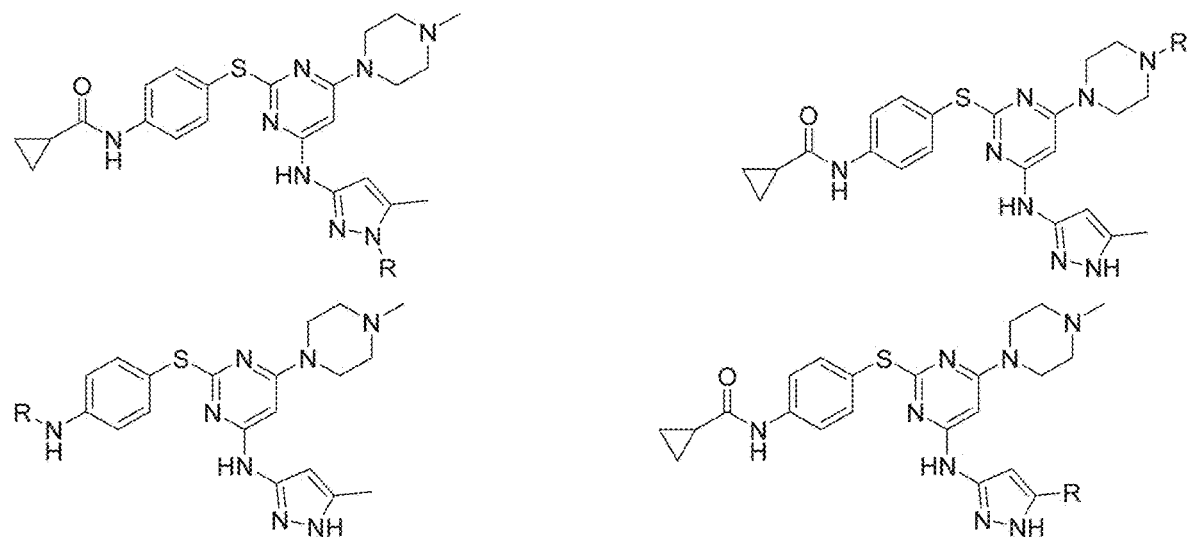
FIG. 2AAAA
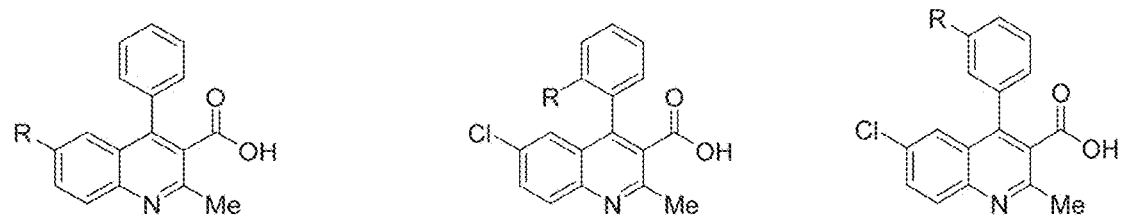
FIG. 2BBBB
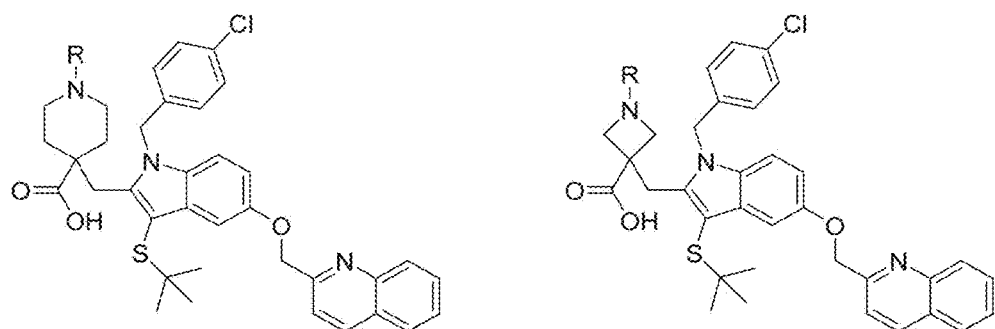

FIG. 2CCCC
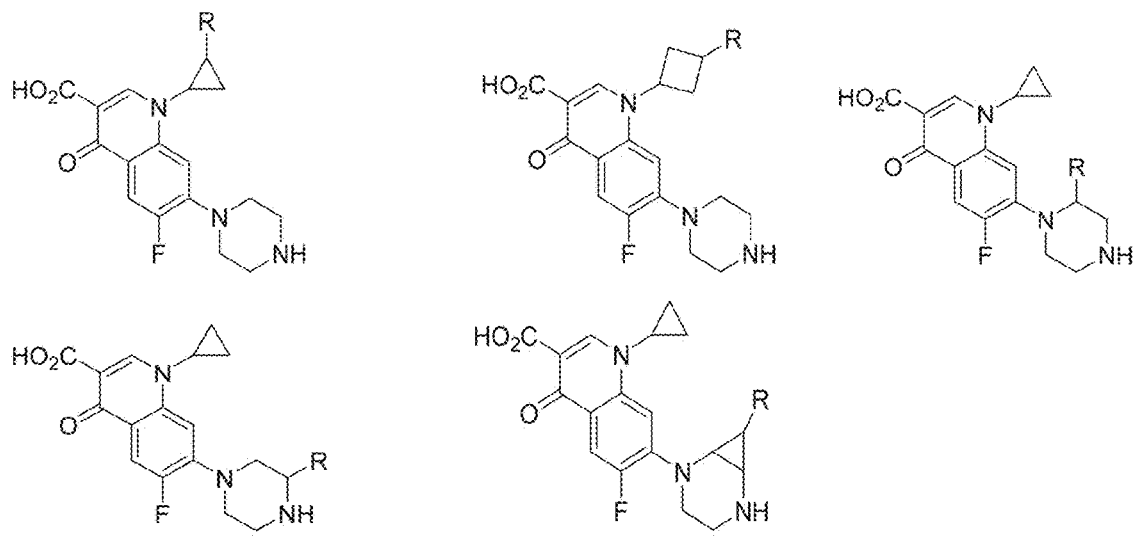
FIG. 2DDDD
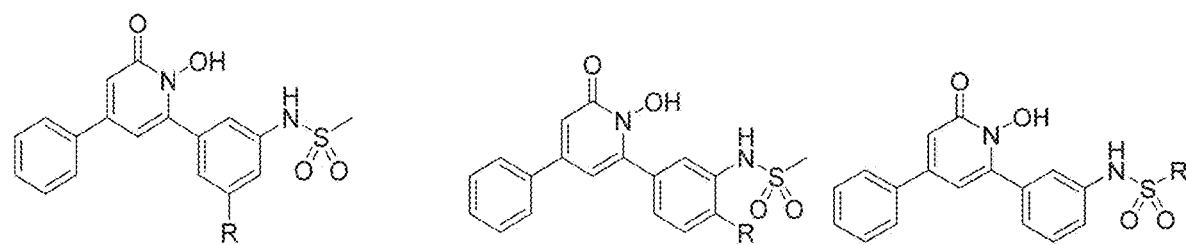
FIG. 2EEEE
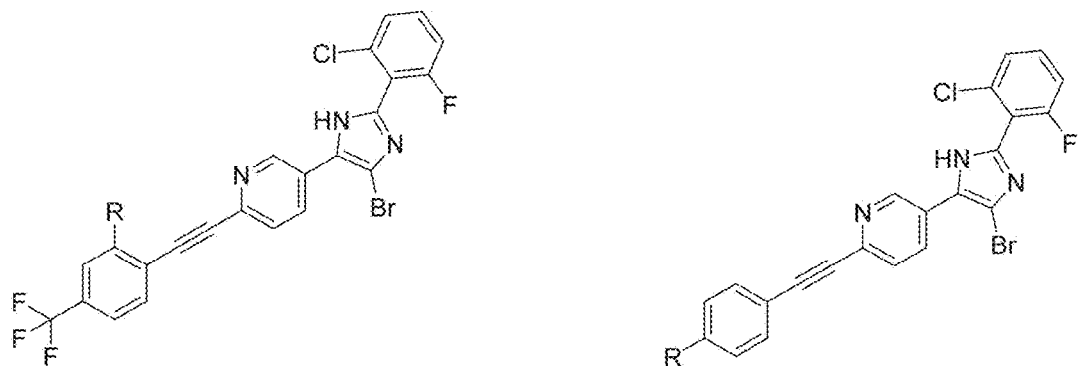

FIG. 2FFFF
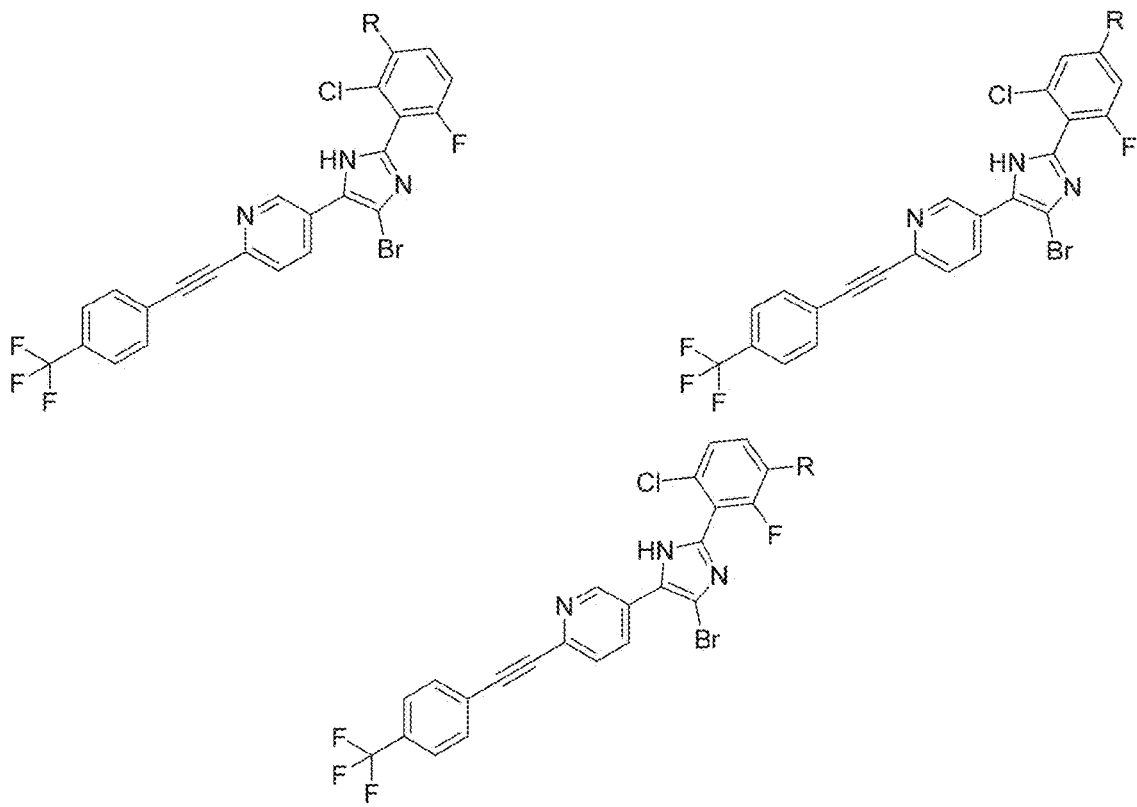
FIG. 2GGGG
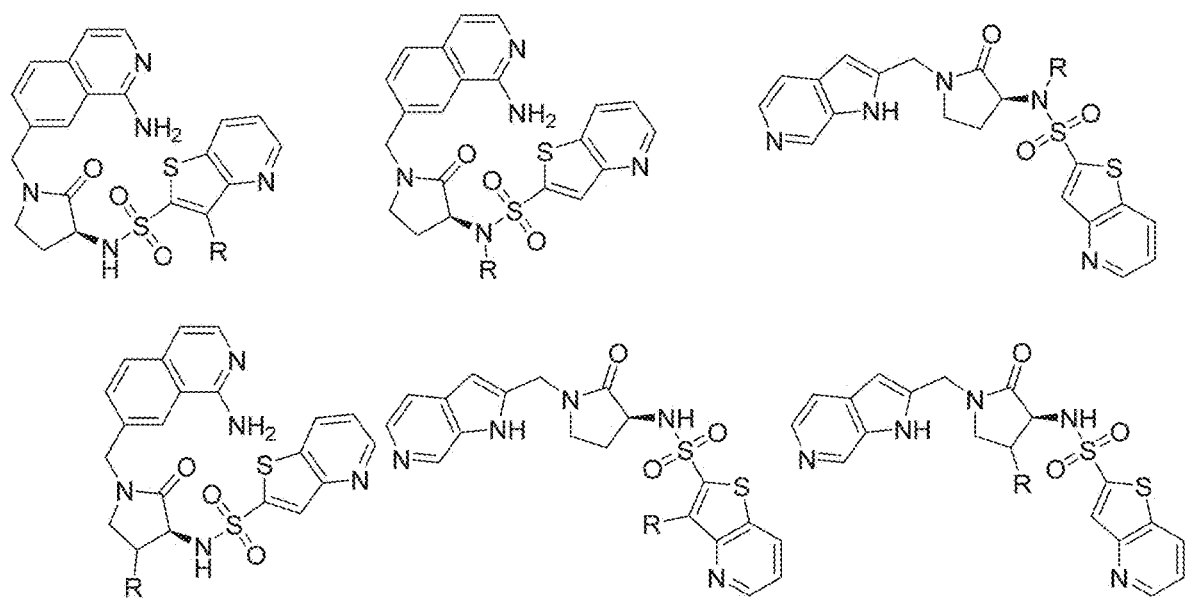

FIG. 2HHHH
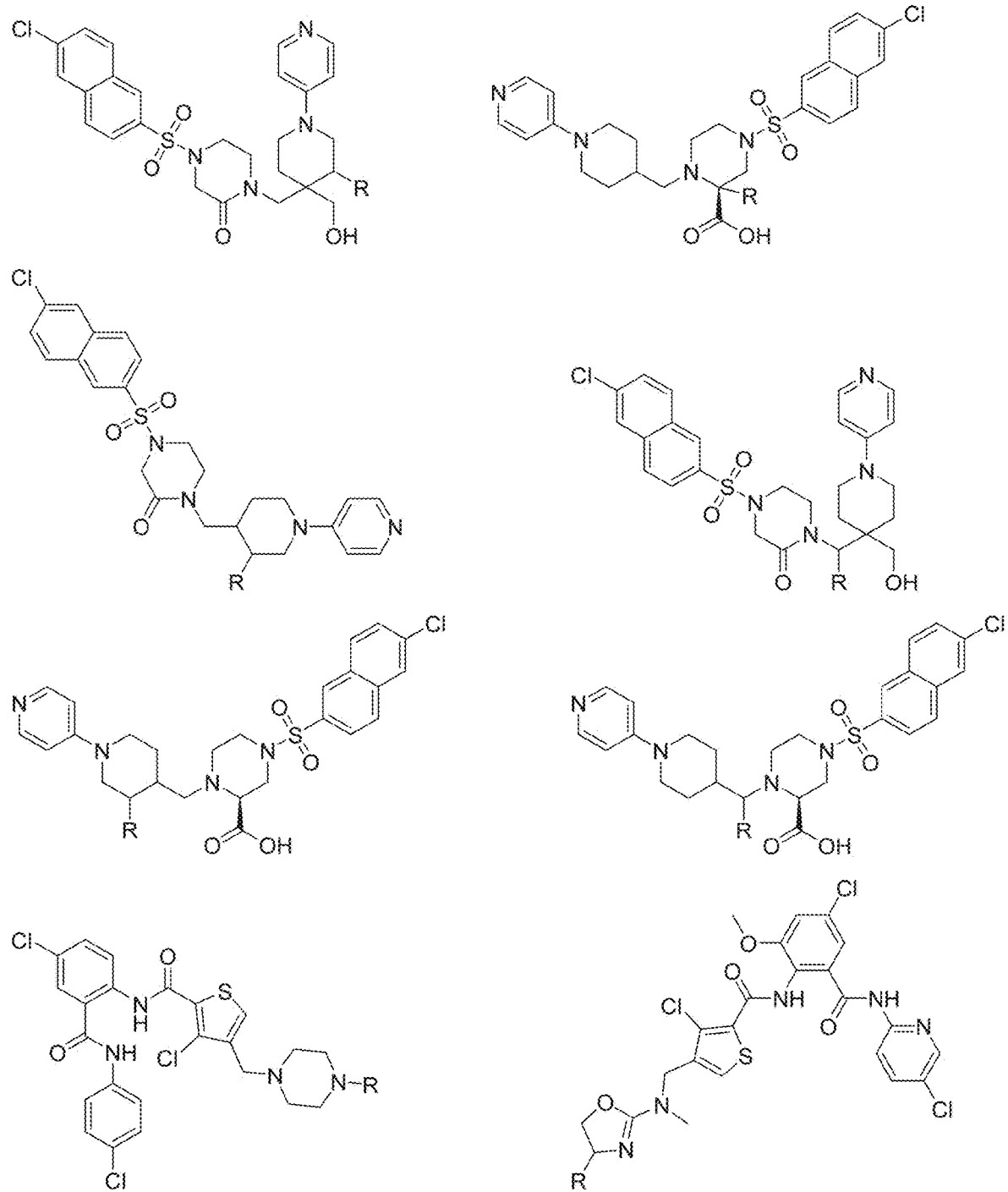

FIG. 2IIII
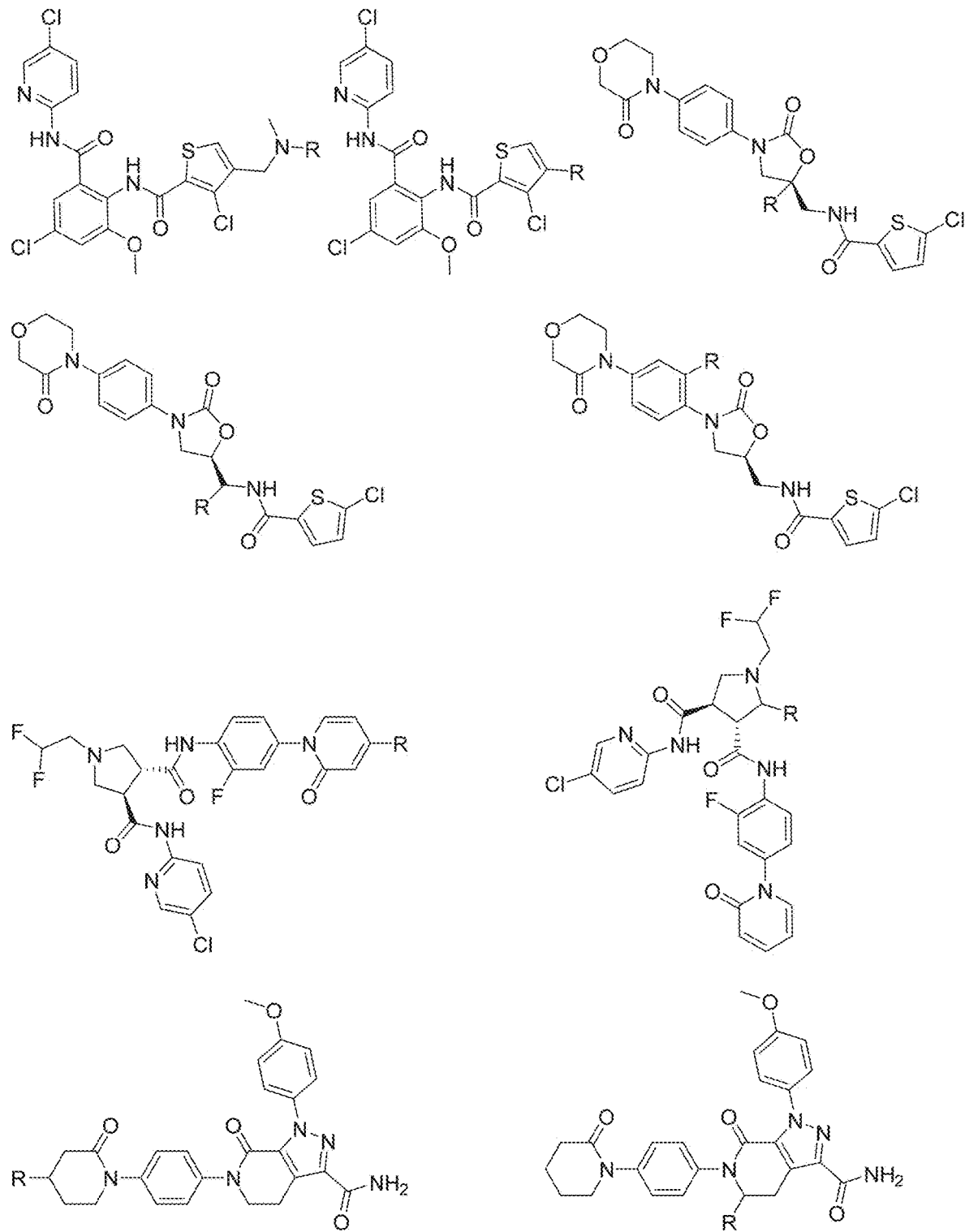

FIG. 2JJJJ
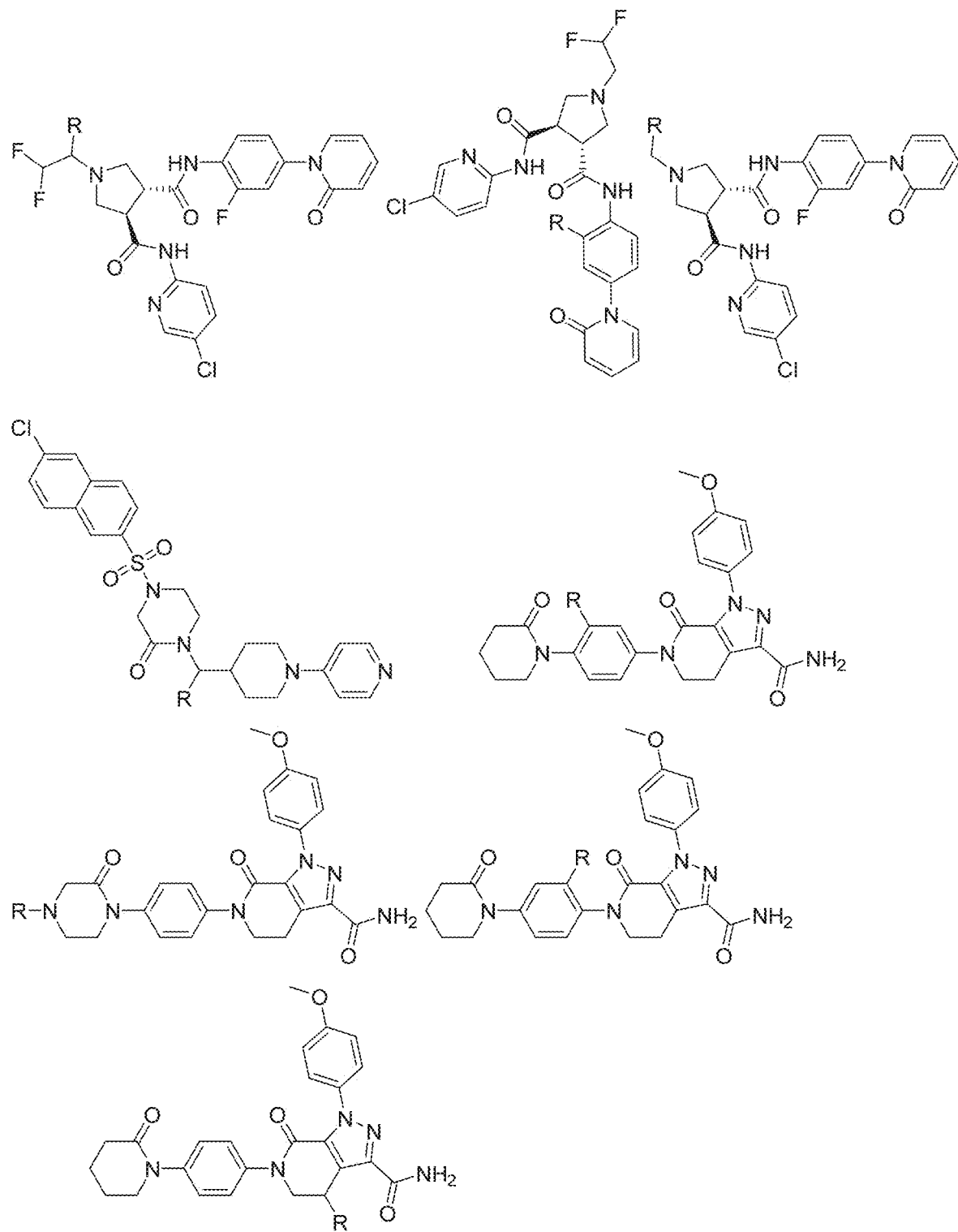

FIG. 2KKKK
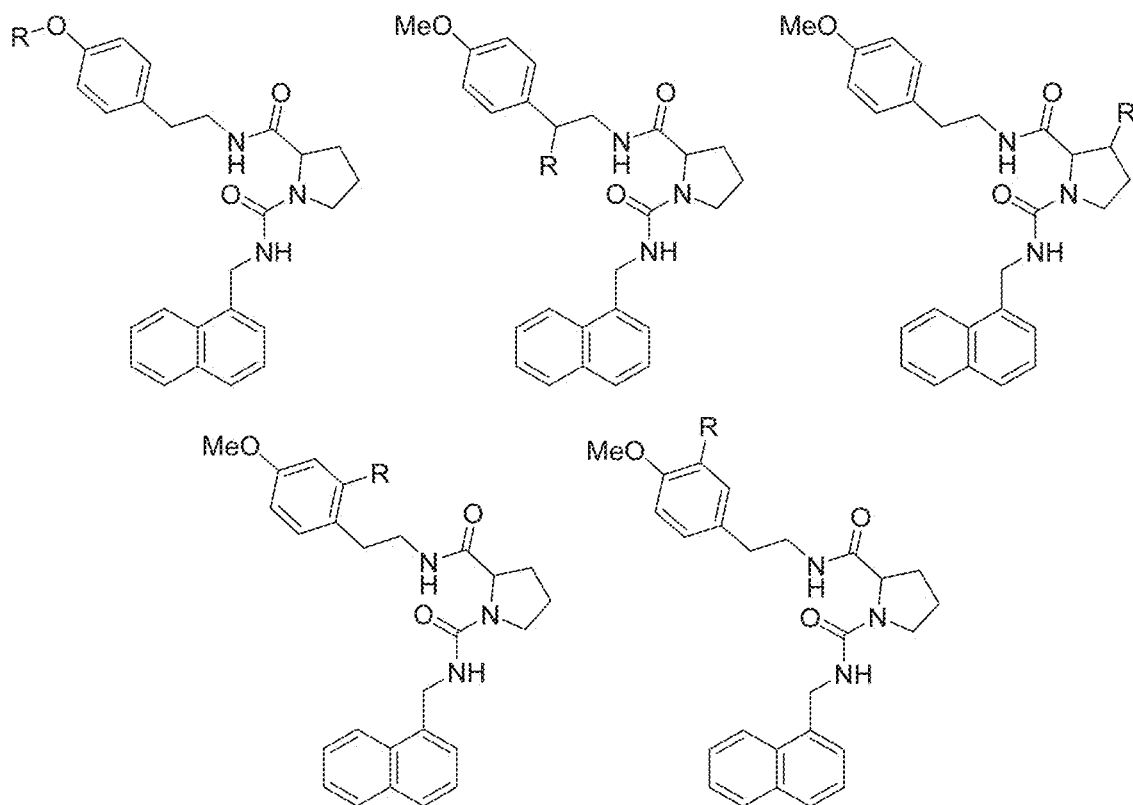
FIG. 2LLLL
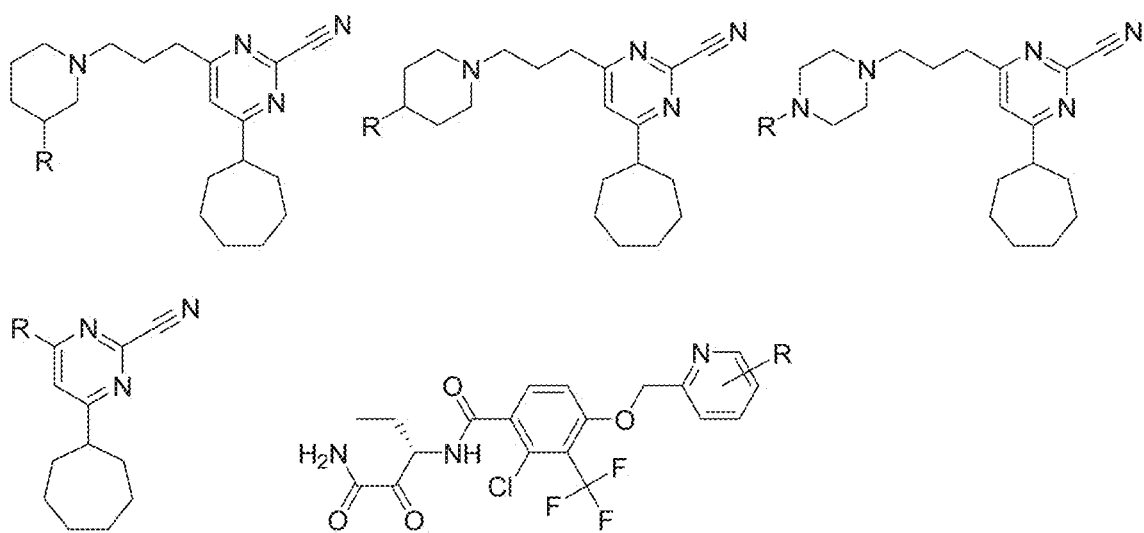

FIG. 2MMMM
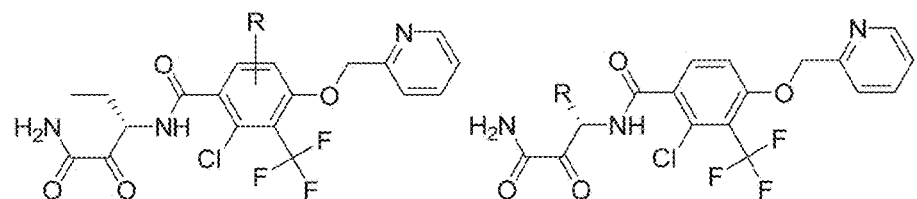
FIG. 2NNNN
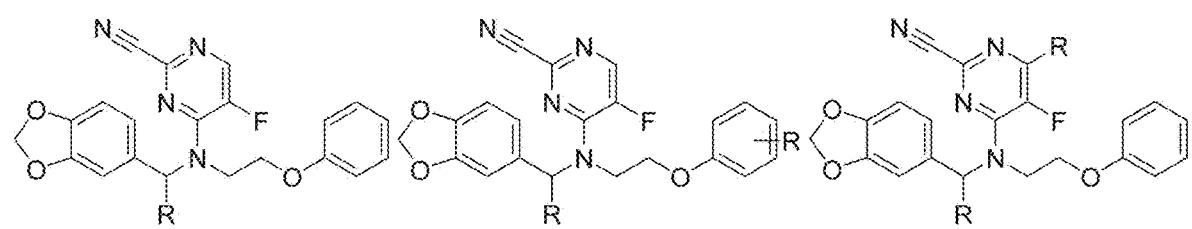
FIG. 2OOOO
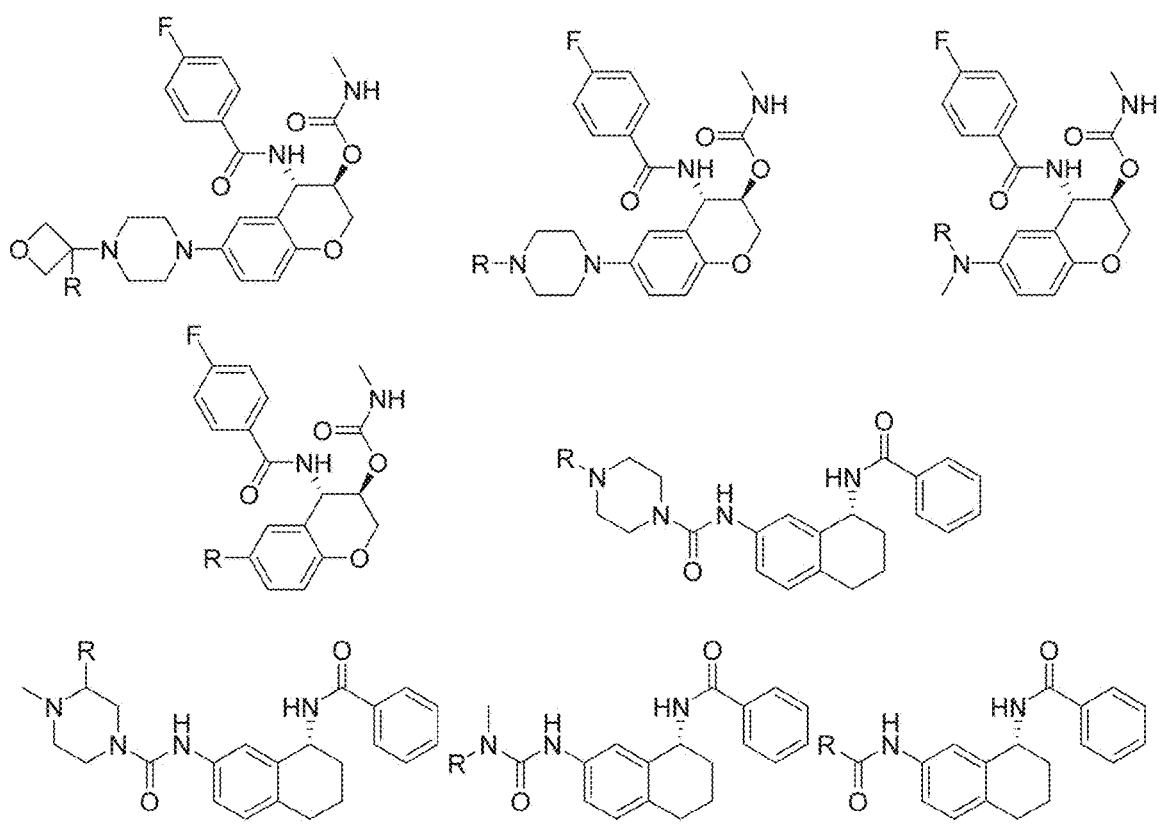

FIG. 2PPPP
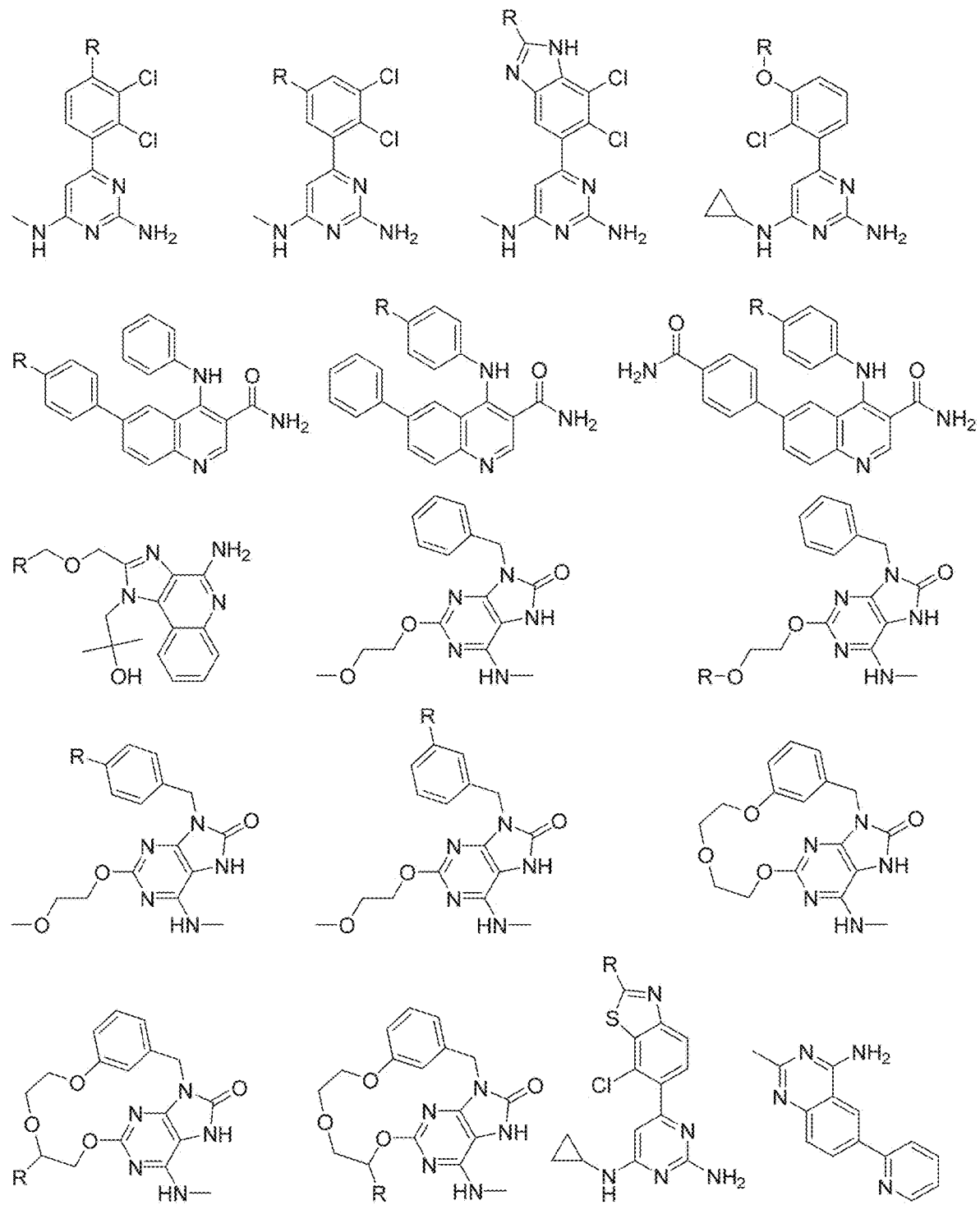

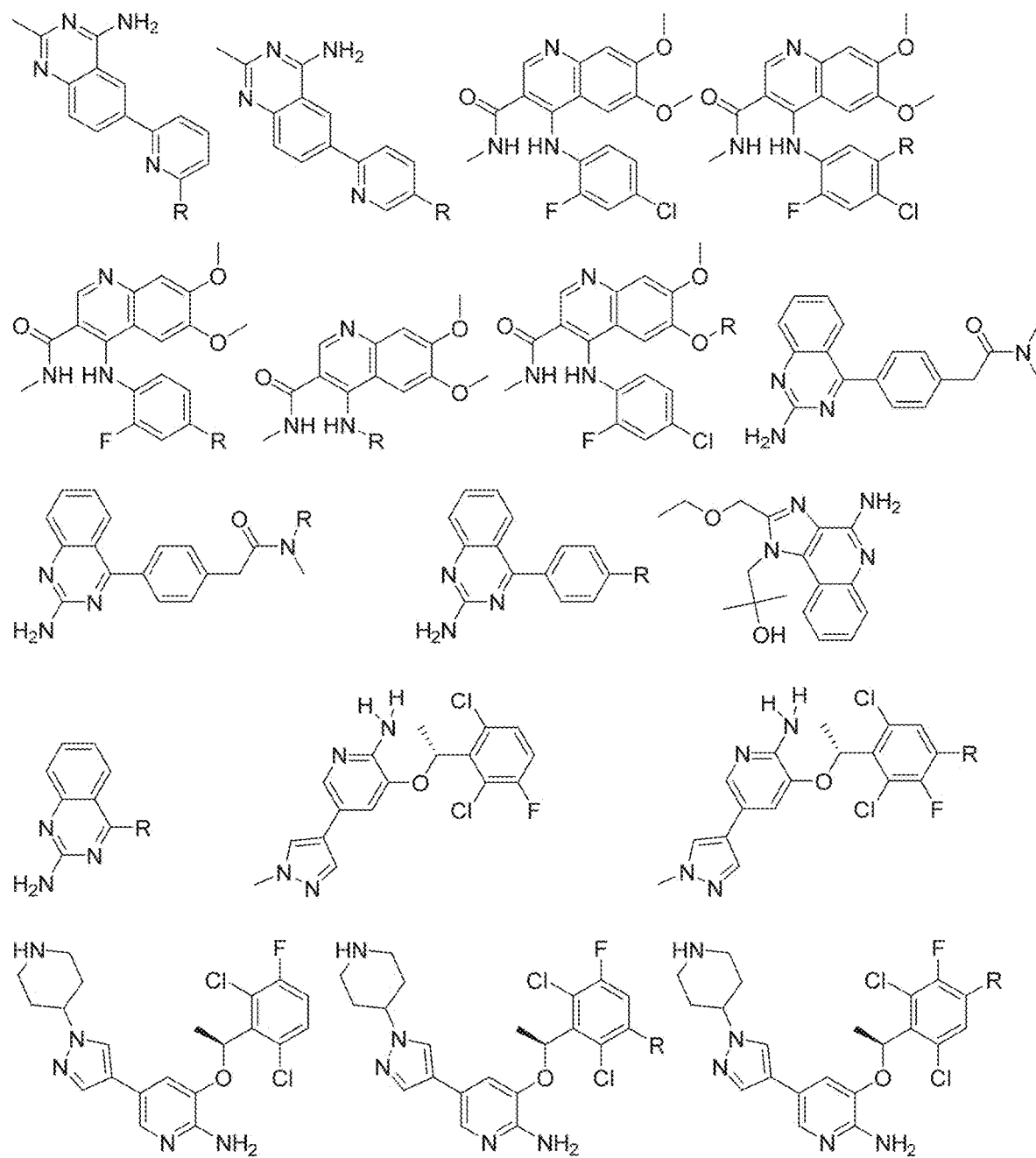
FIG. 2QQQQ

FIG. 2RRRR
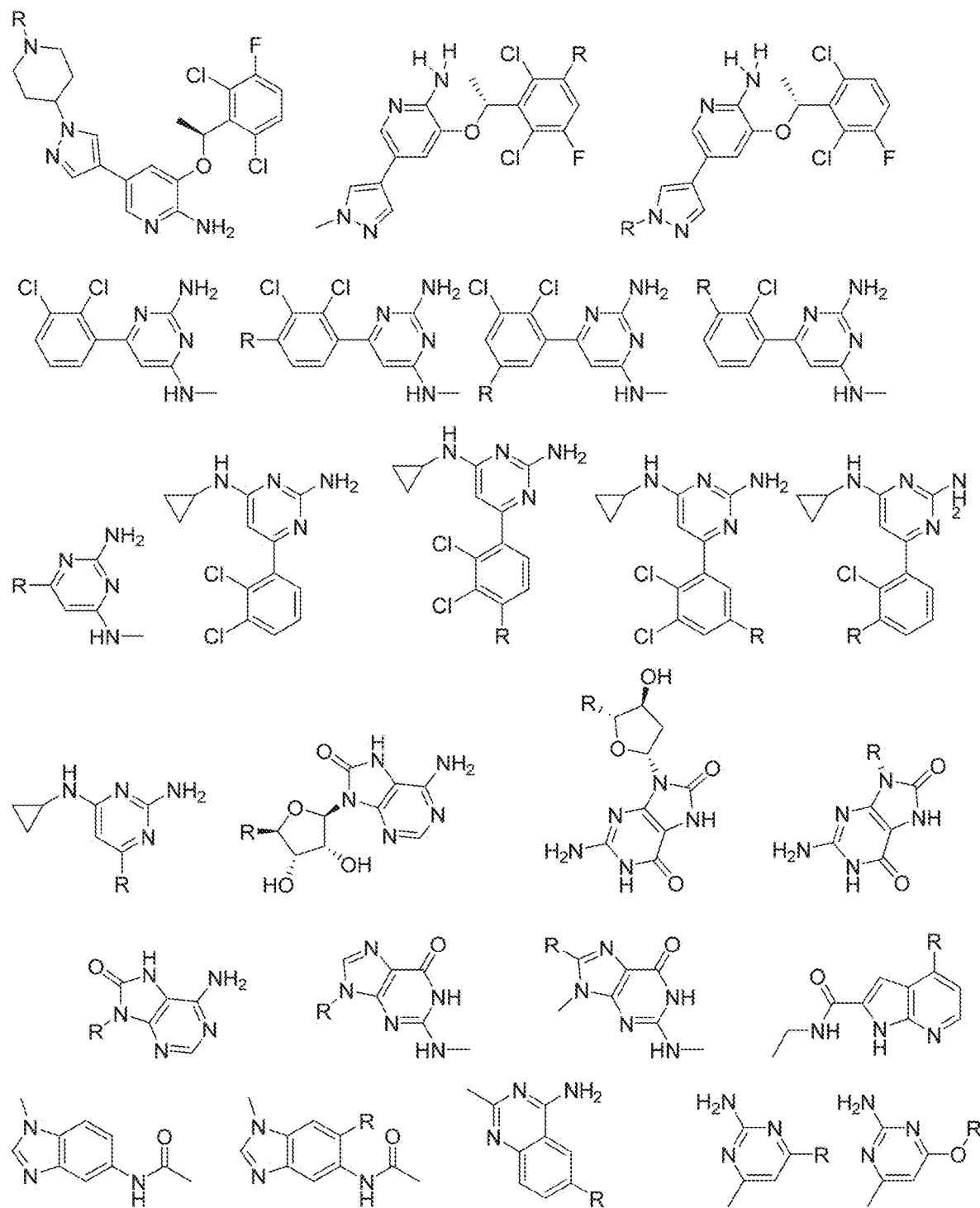

FIG. 2SSSS
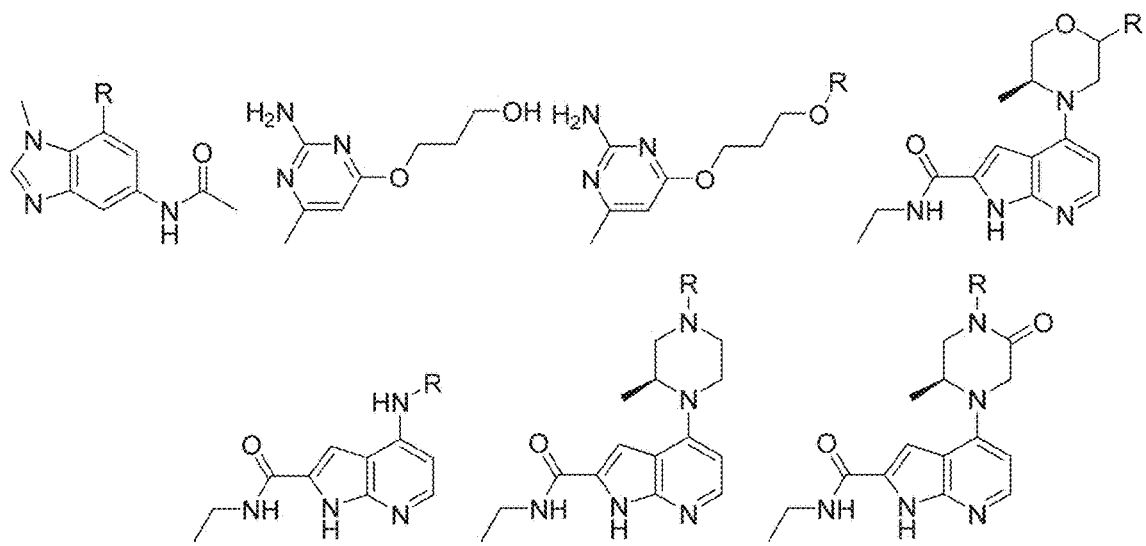
FIG. 2TTTT
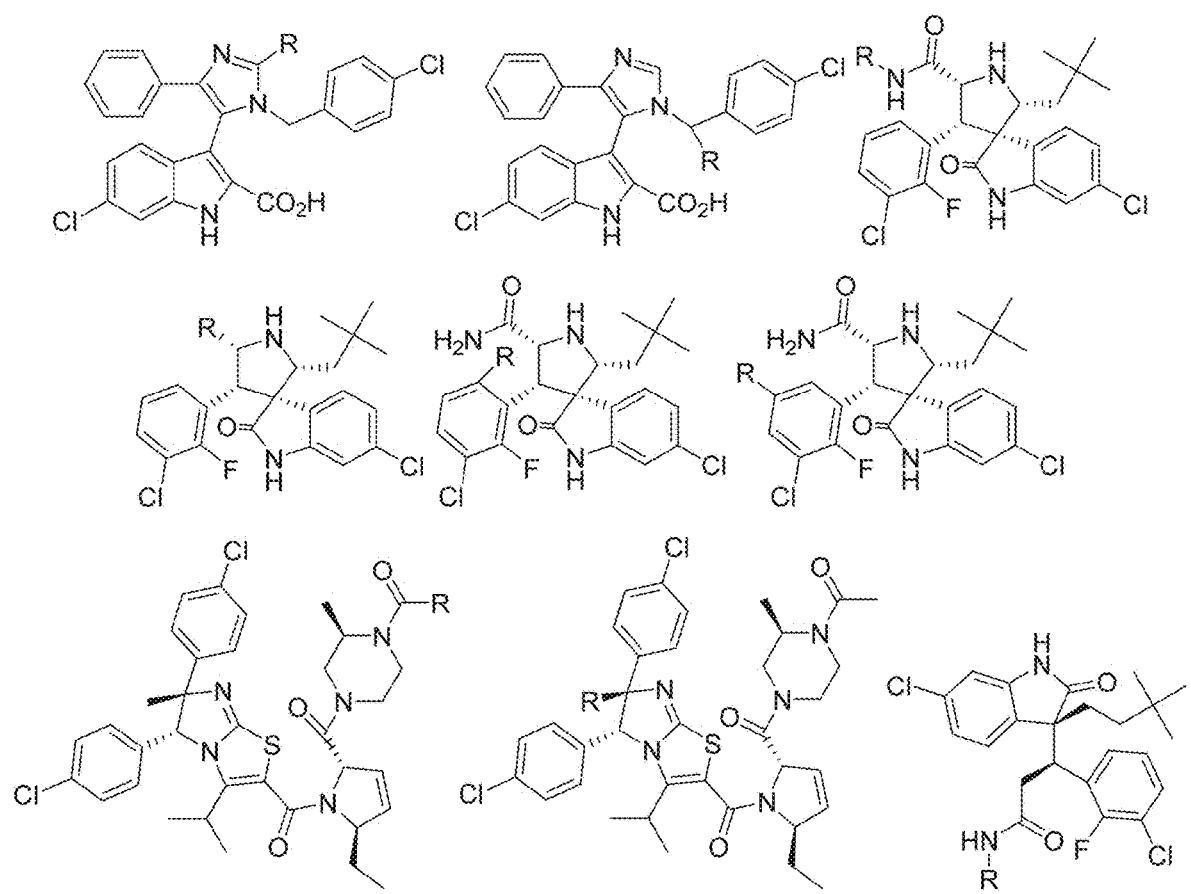

FIG. 2UUUU
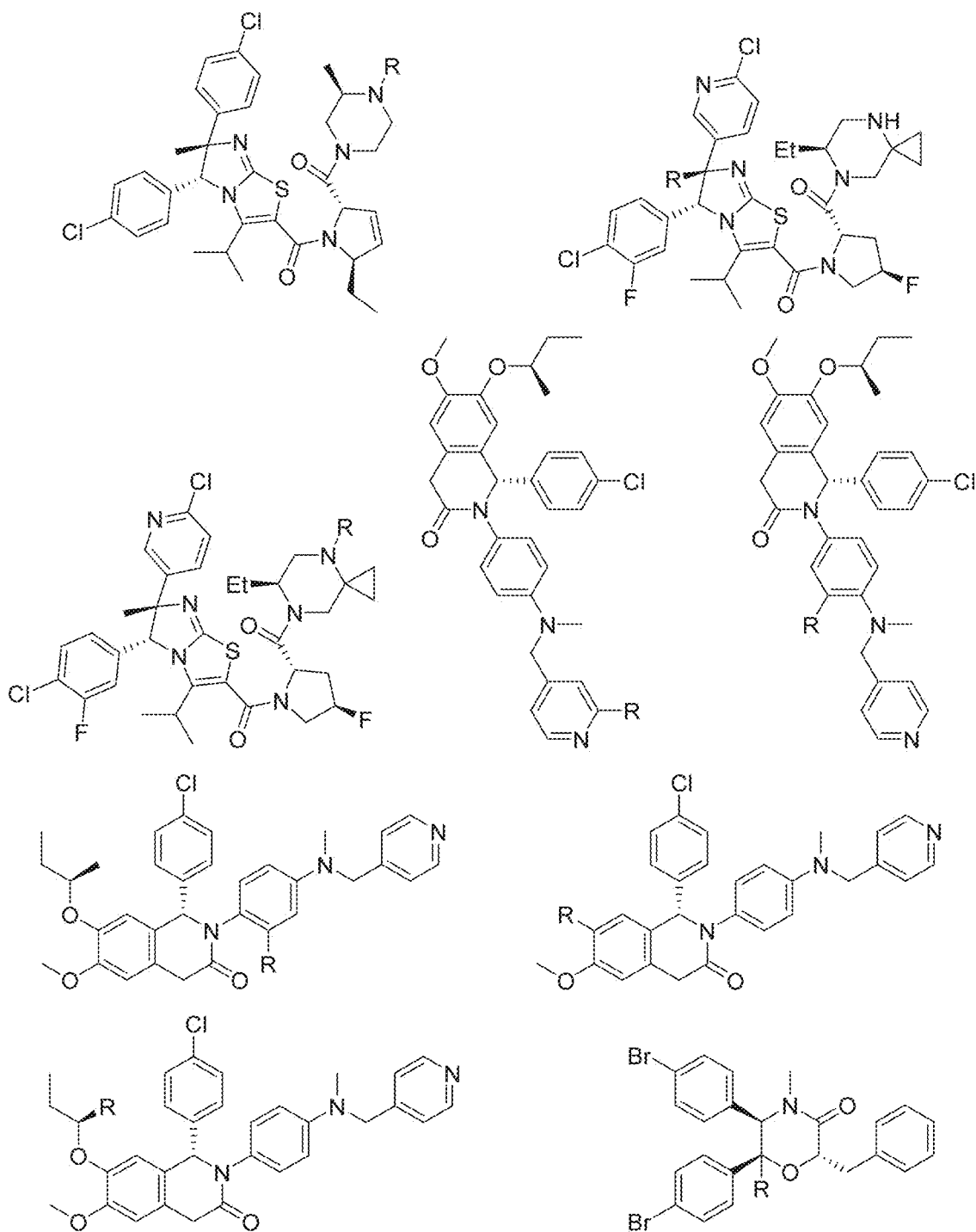

FIG. 2VVVV
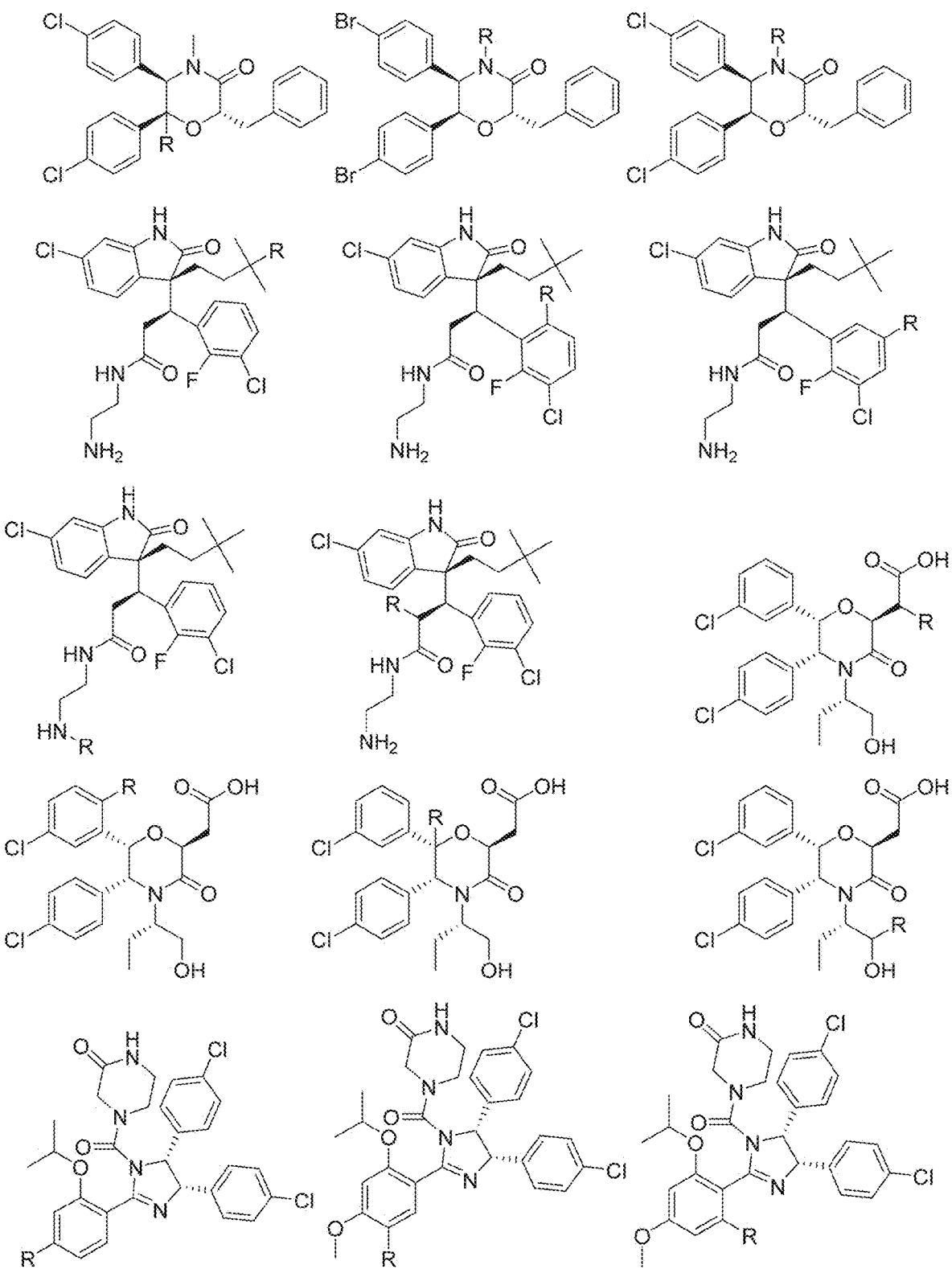

FIG. 2WWWW
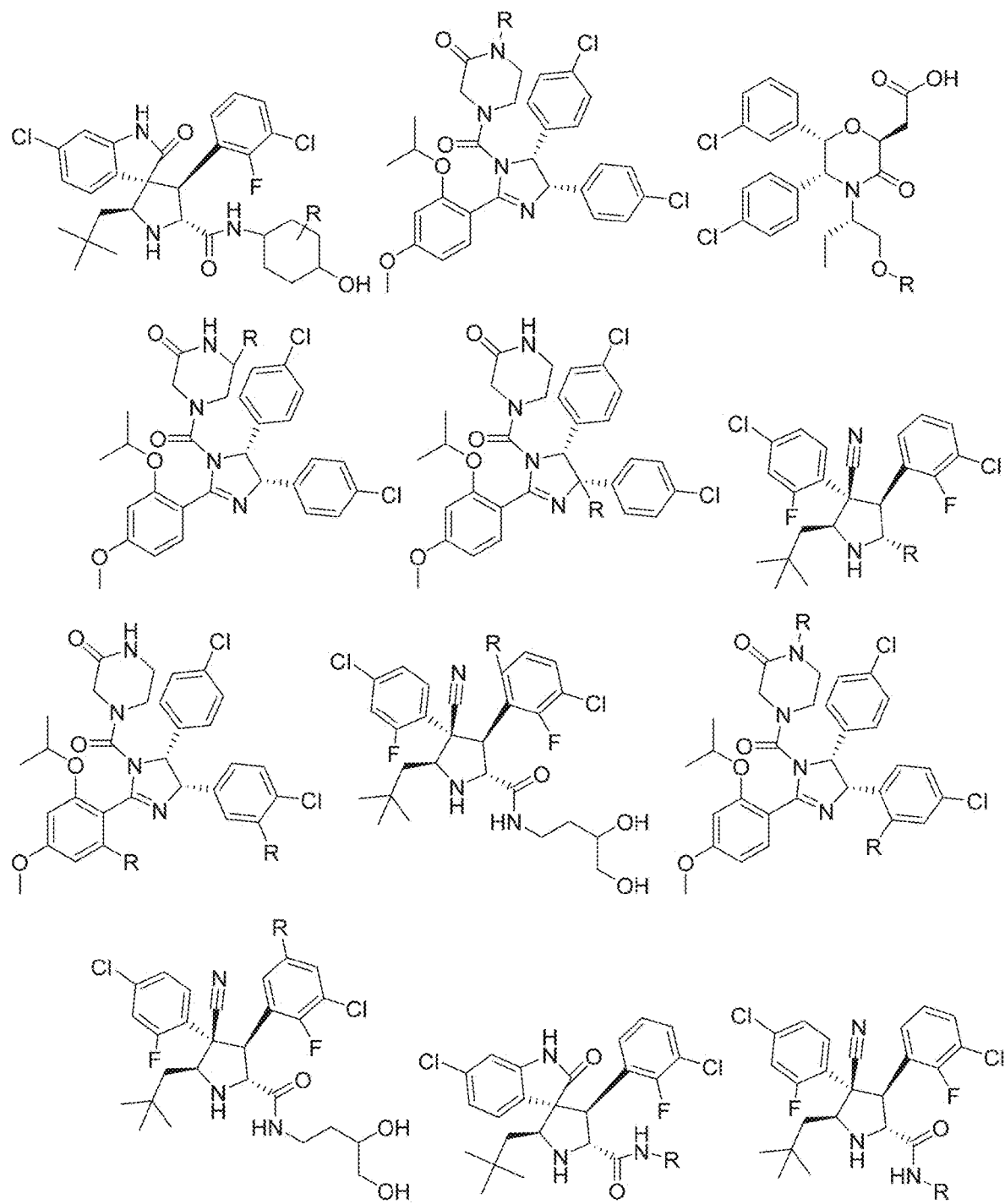

FIG. 2XXXX
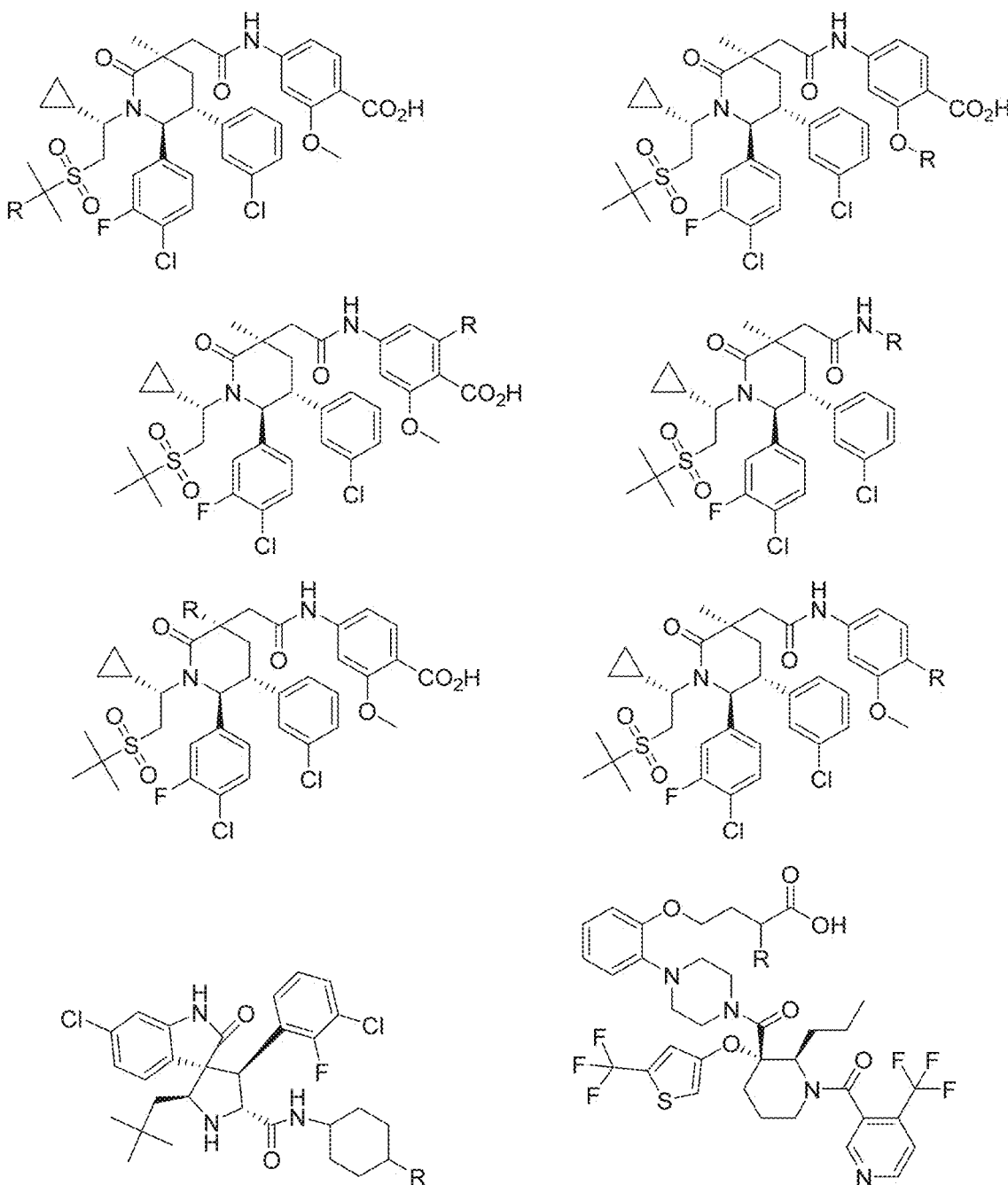

FIG. 2YYYY
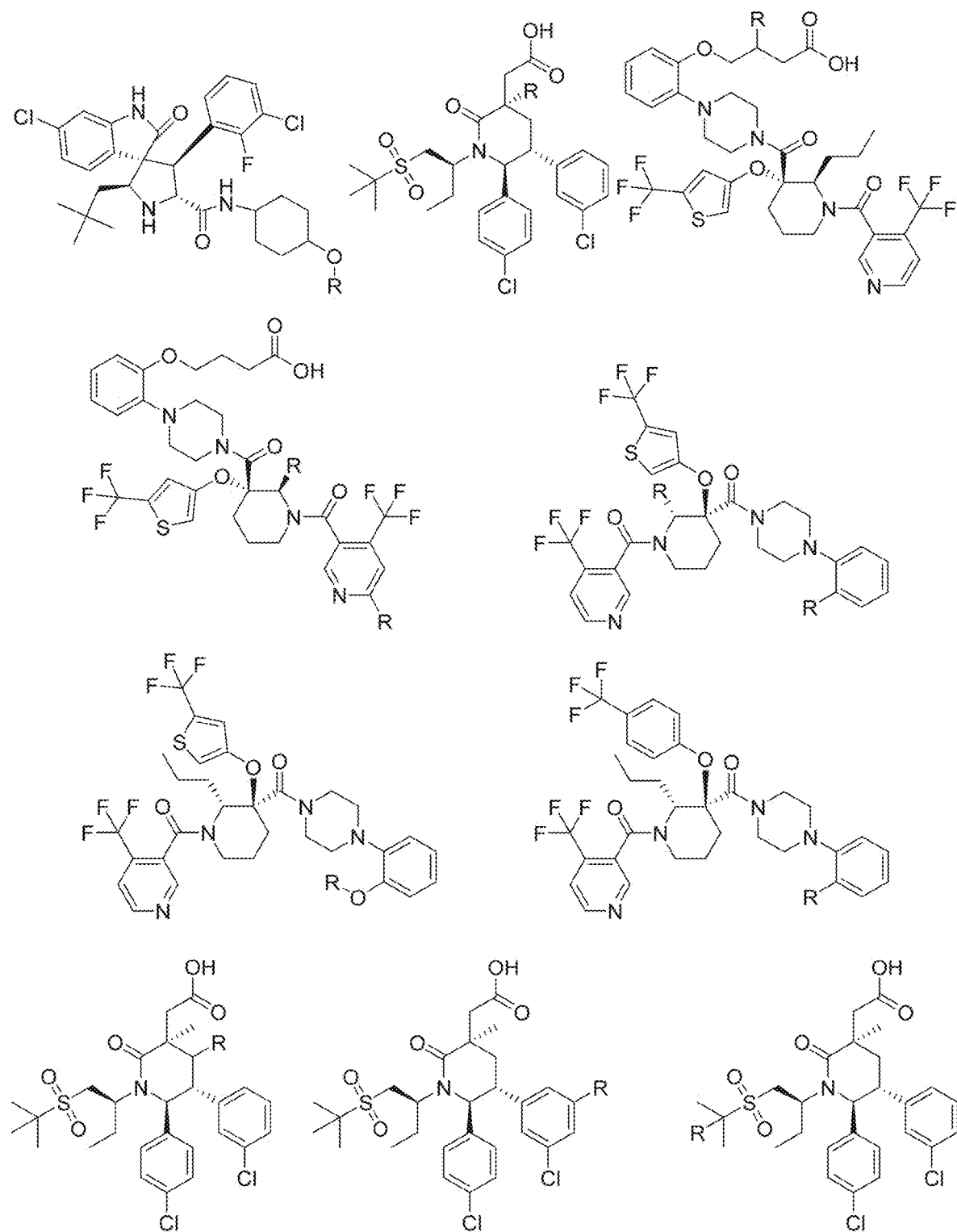

FIG. 2ZZZZ
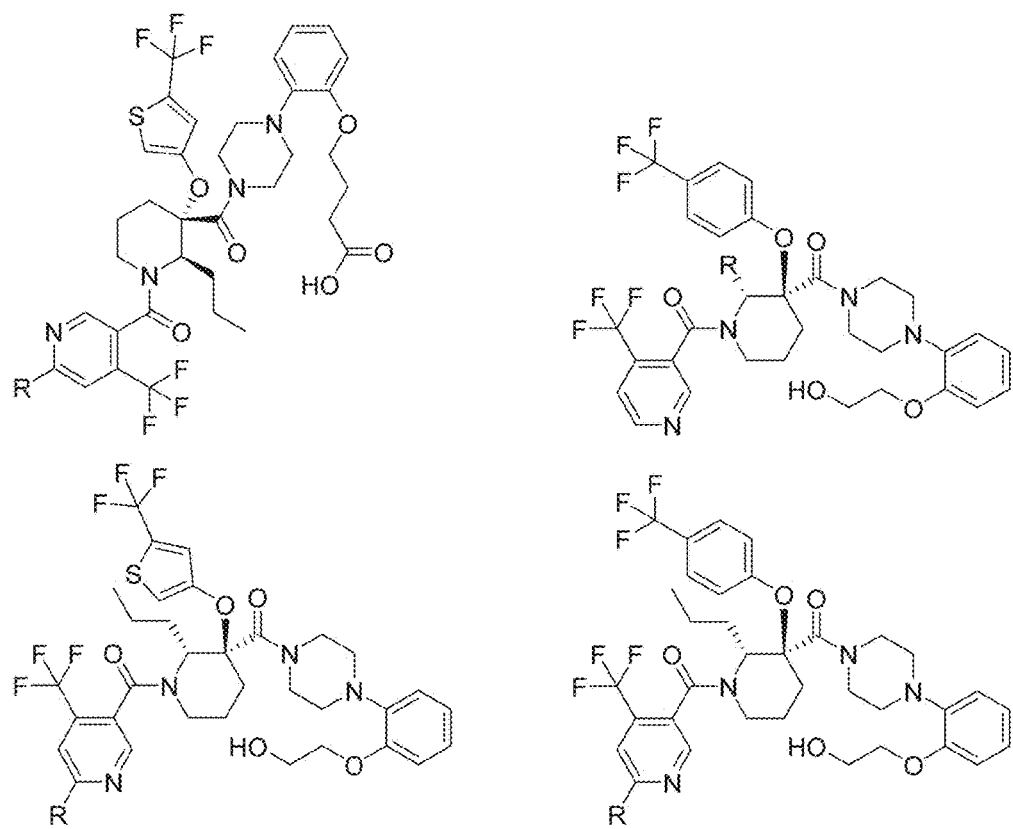
FIG. 2AAAAA
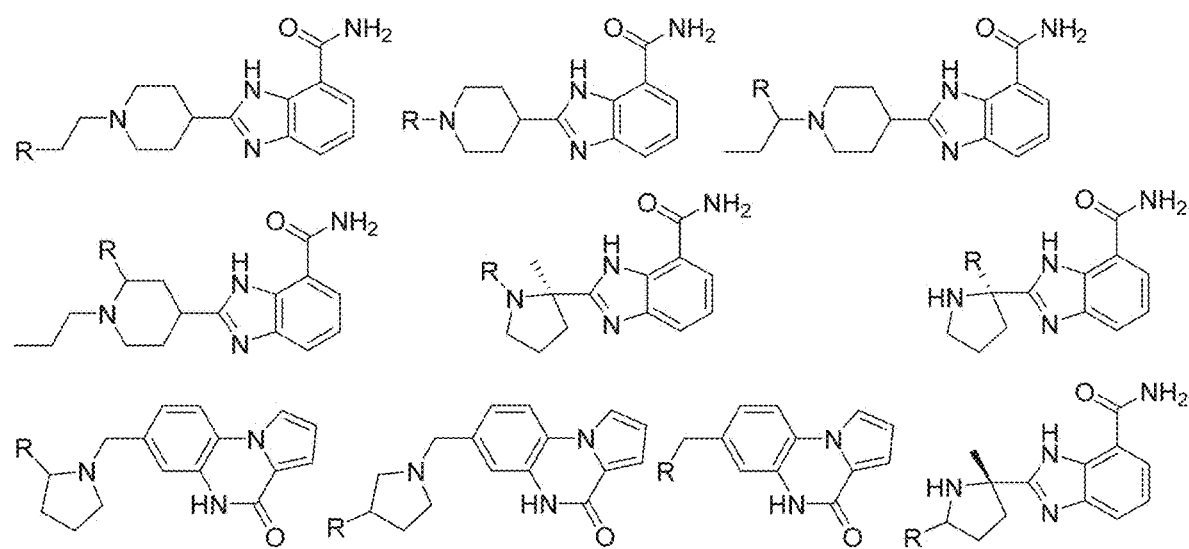

FIG. 2BBBBB
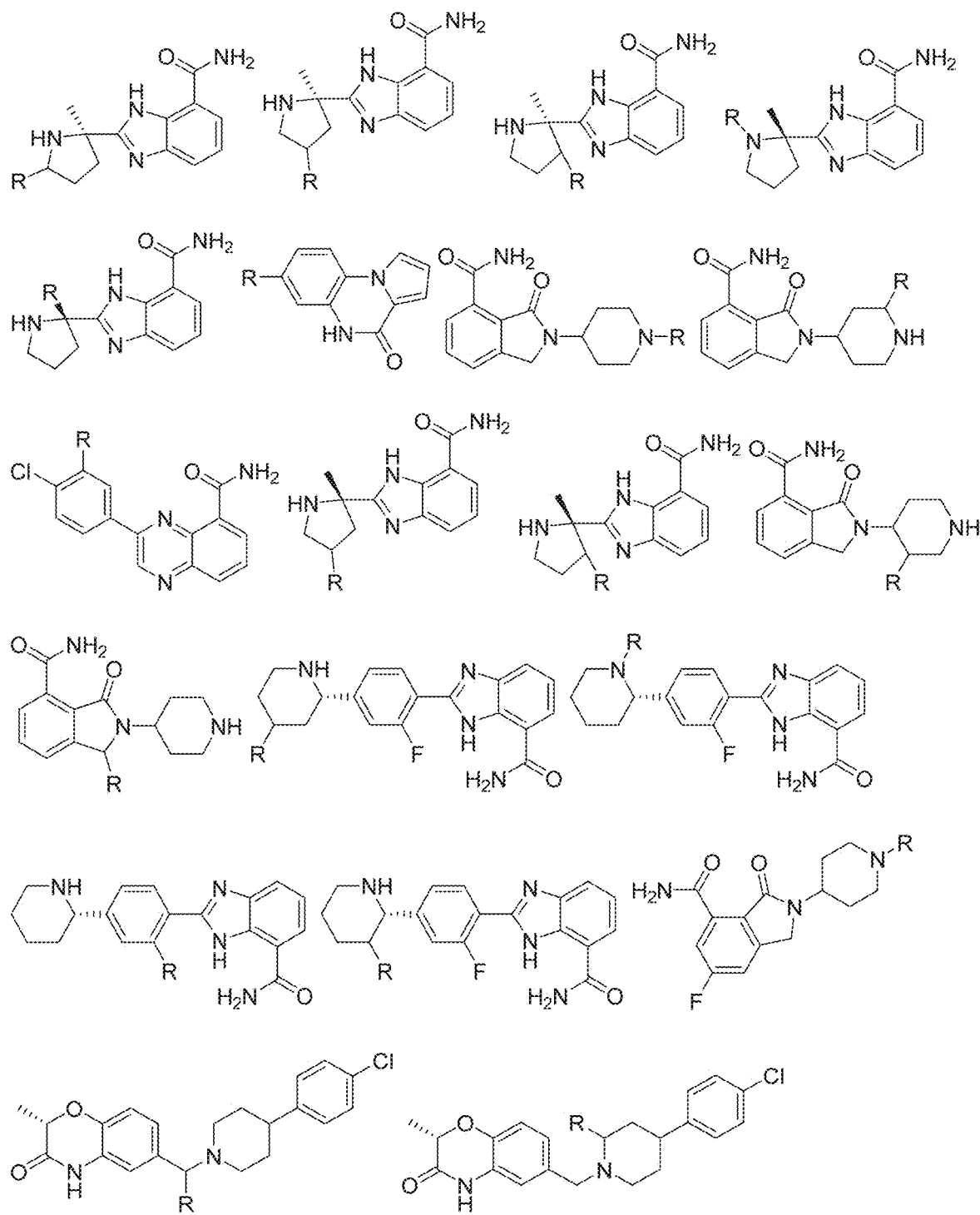

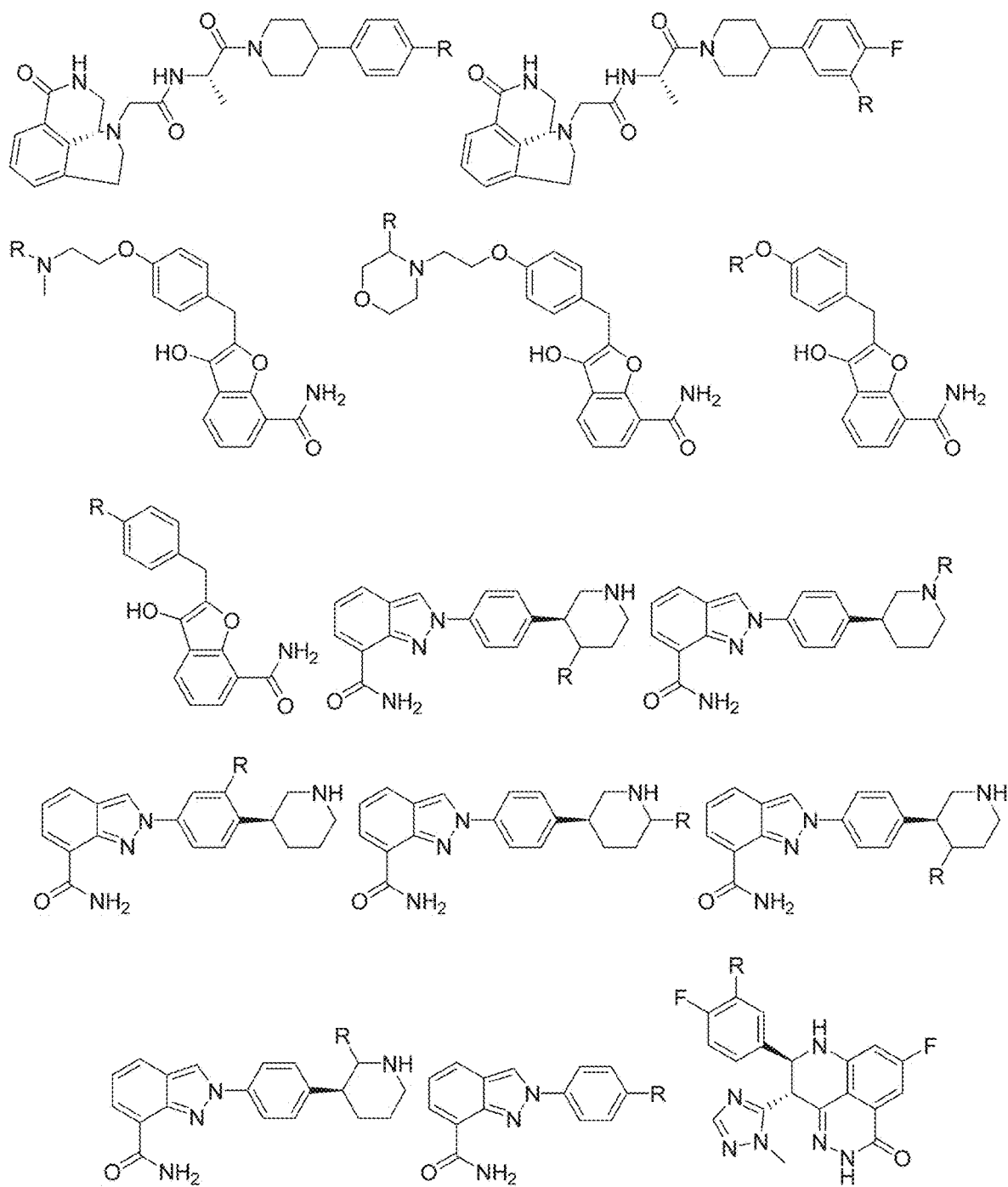
FIG. 2CCCCC

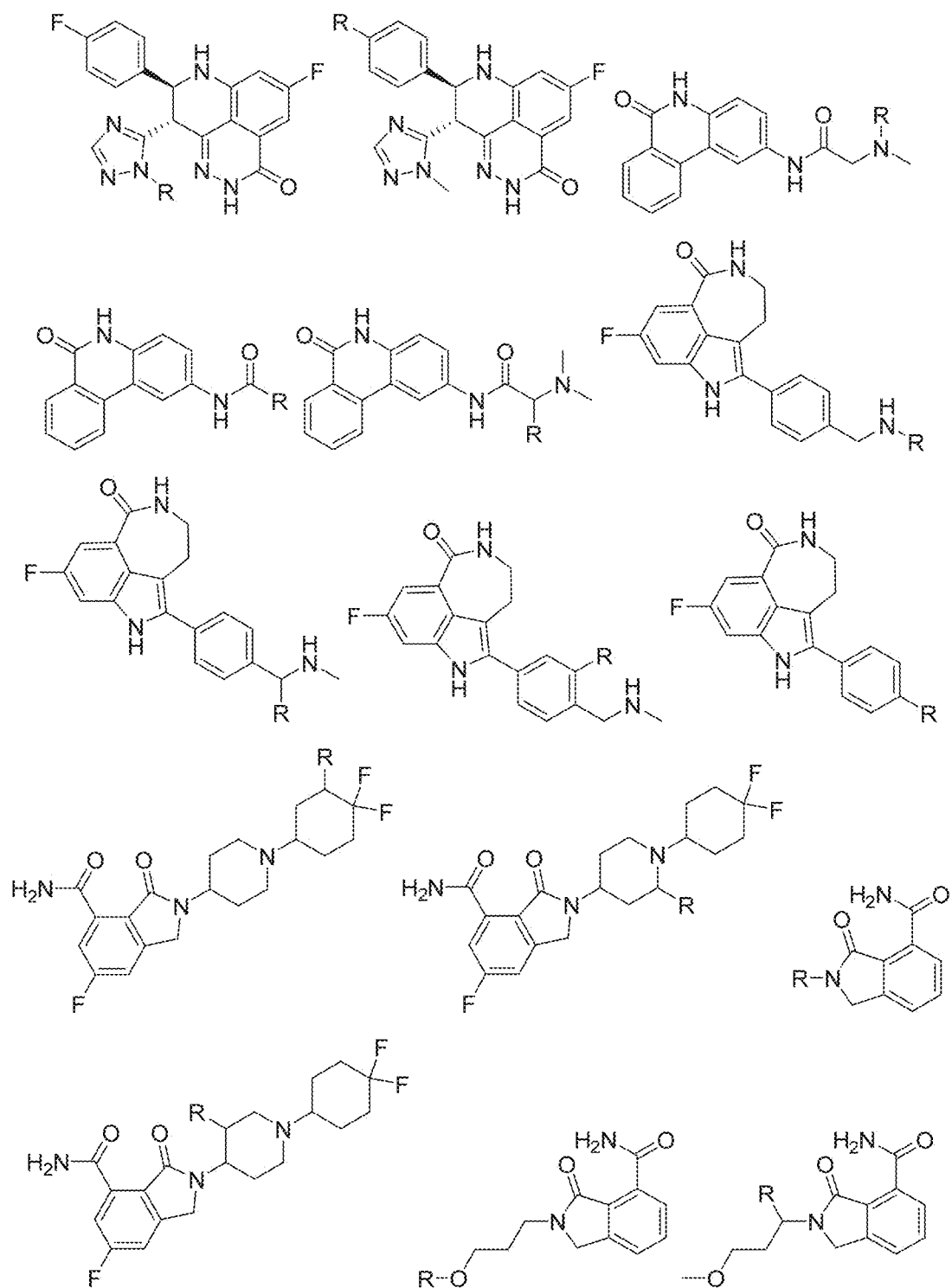
FIG. 2DDDDD

FIG. 2EEEEE
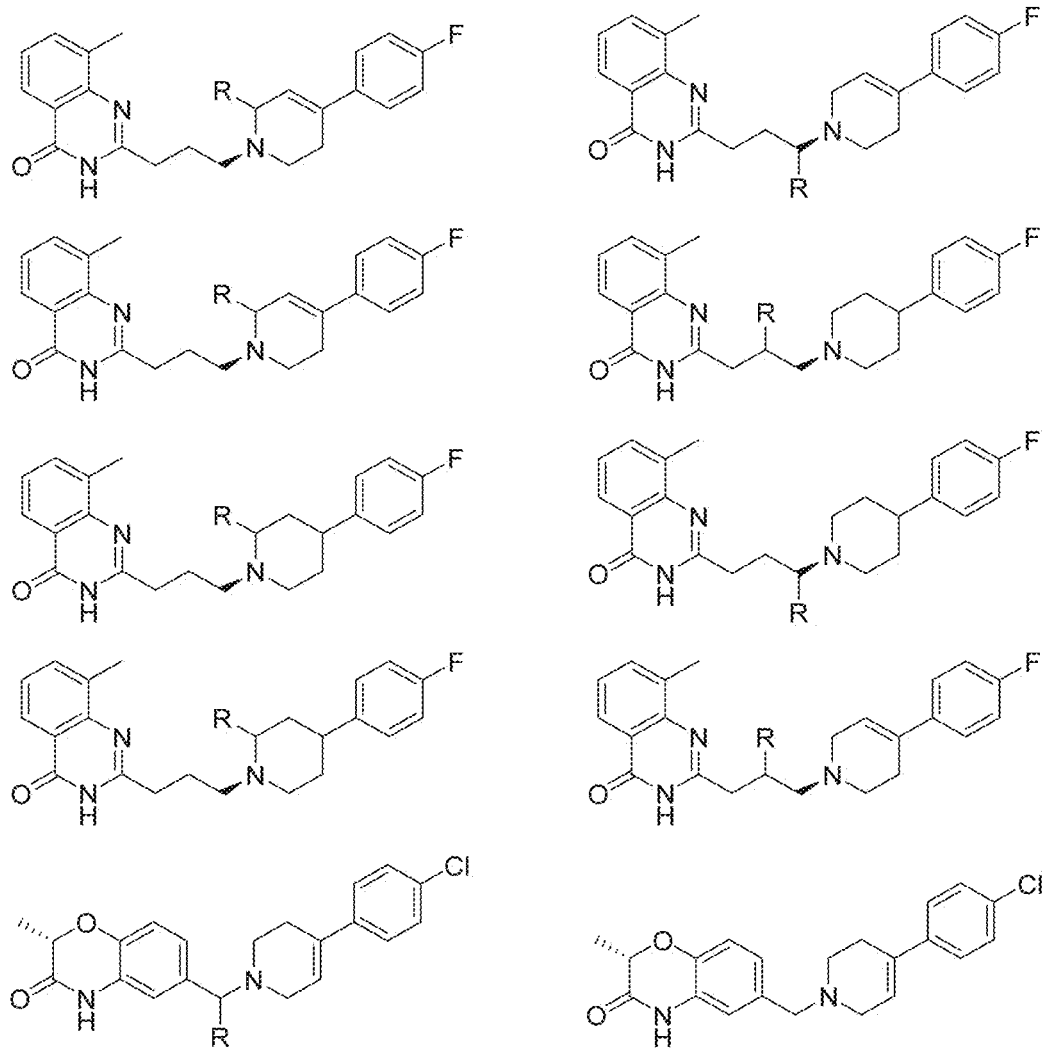
FIG. 2FFFFF
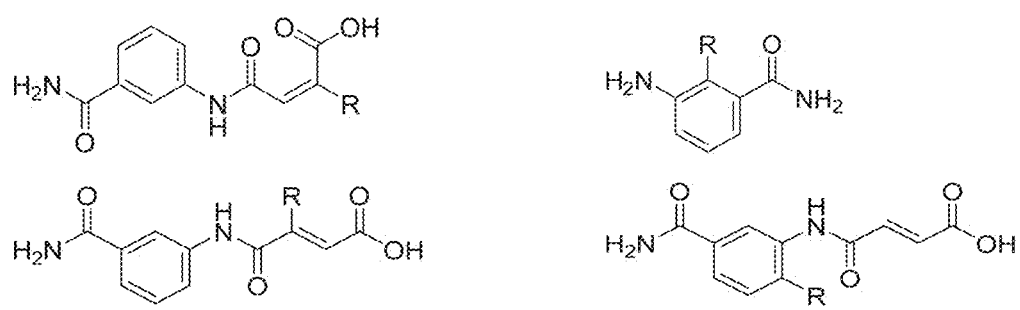

FIG. 2GGGGG
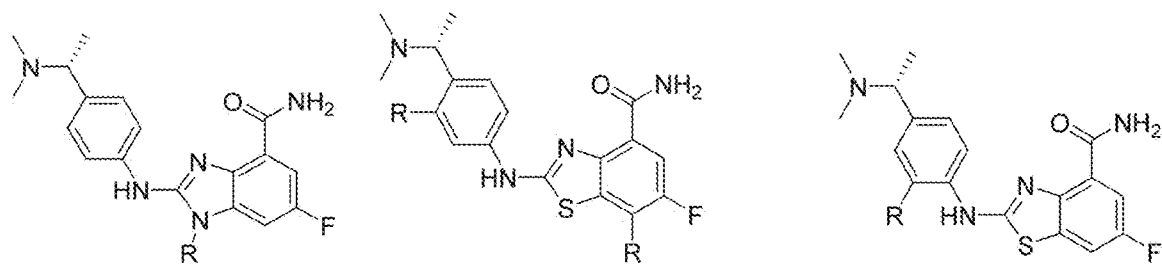
FIG. 2HHHHH
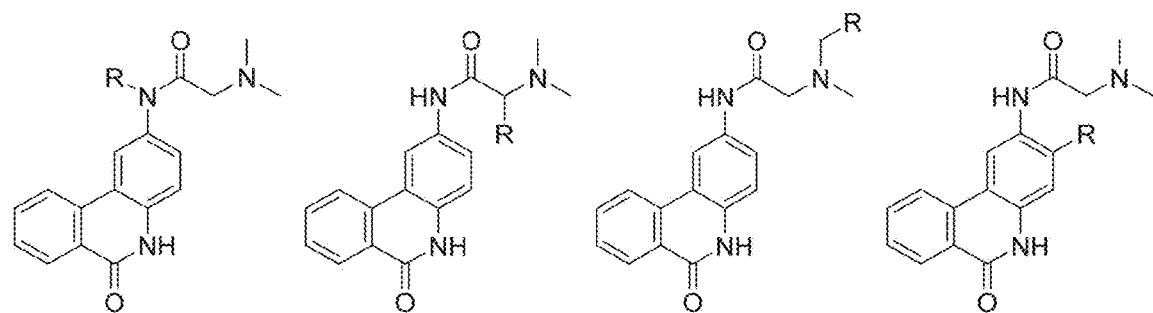
FIG. 2IIIII
FIG. 2JJJJJ
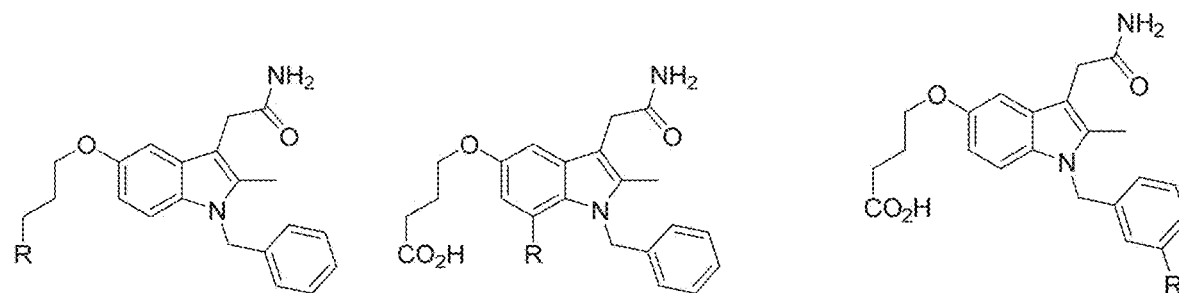

FIG. 2KKKKK
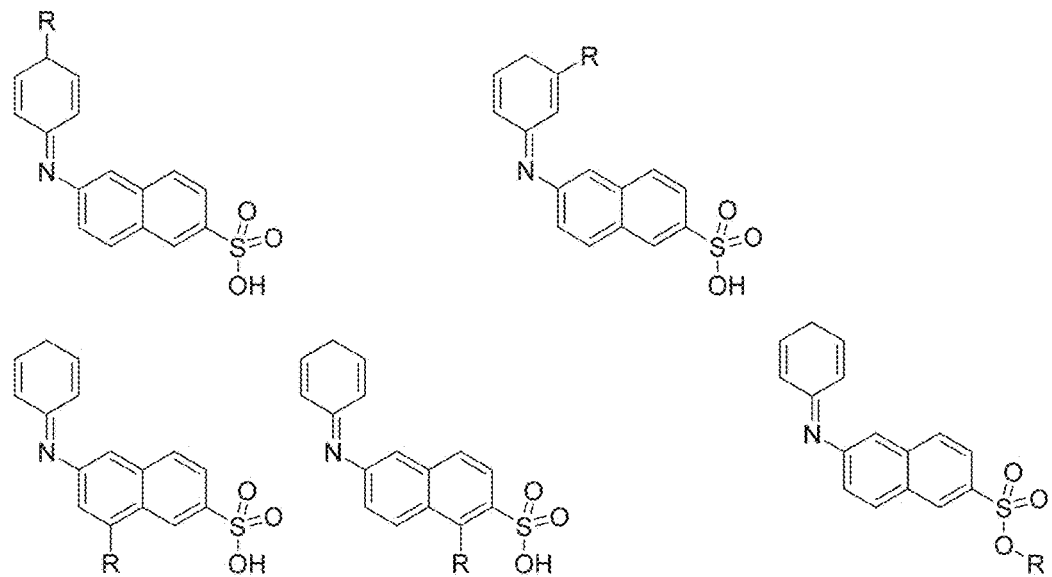
FIG. 2LLLLL
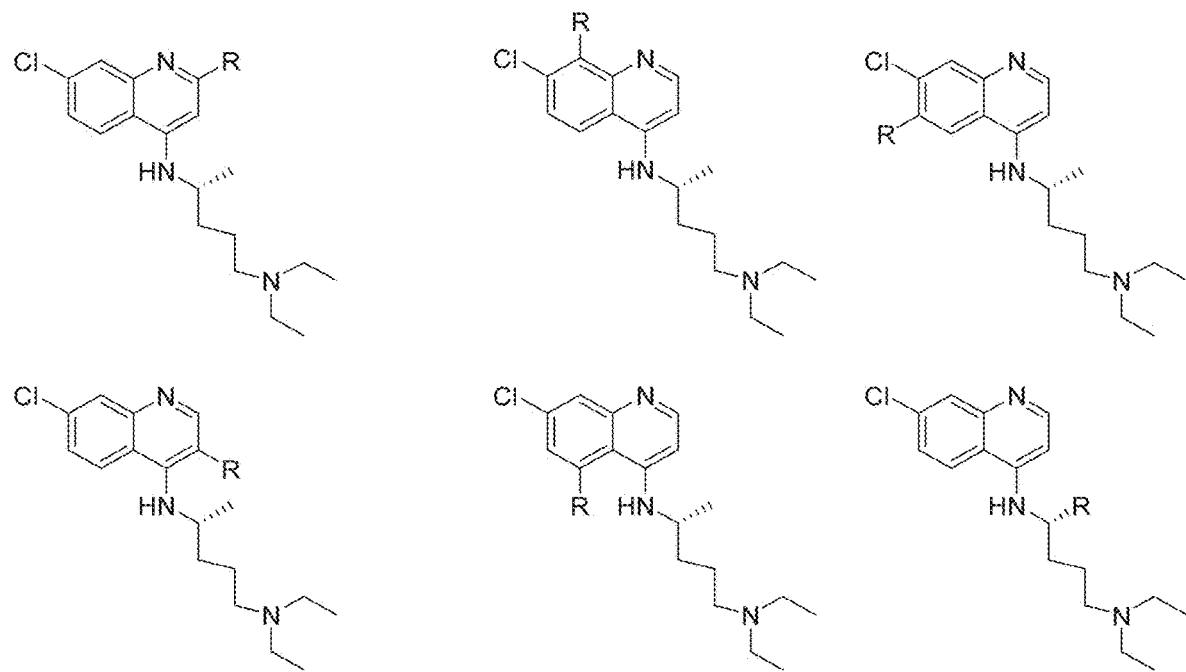

FIG. 2MMMMM
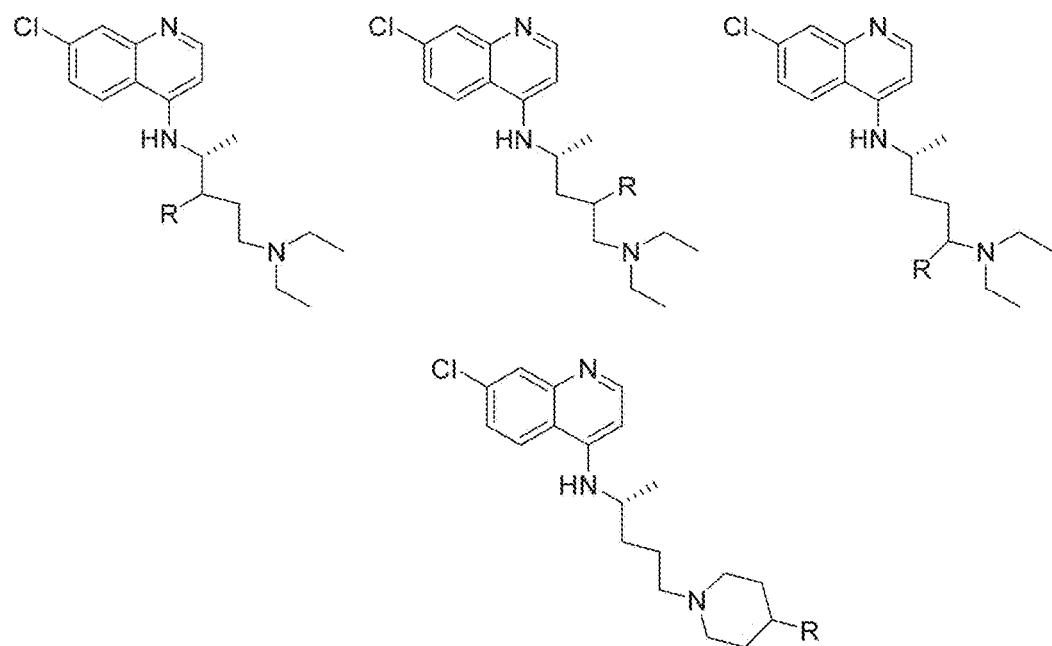
FIG. 2NNNNN
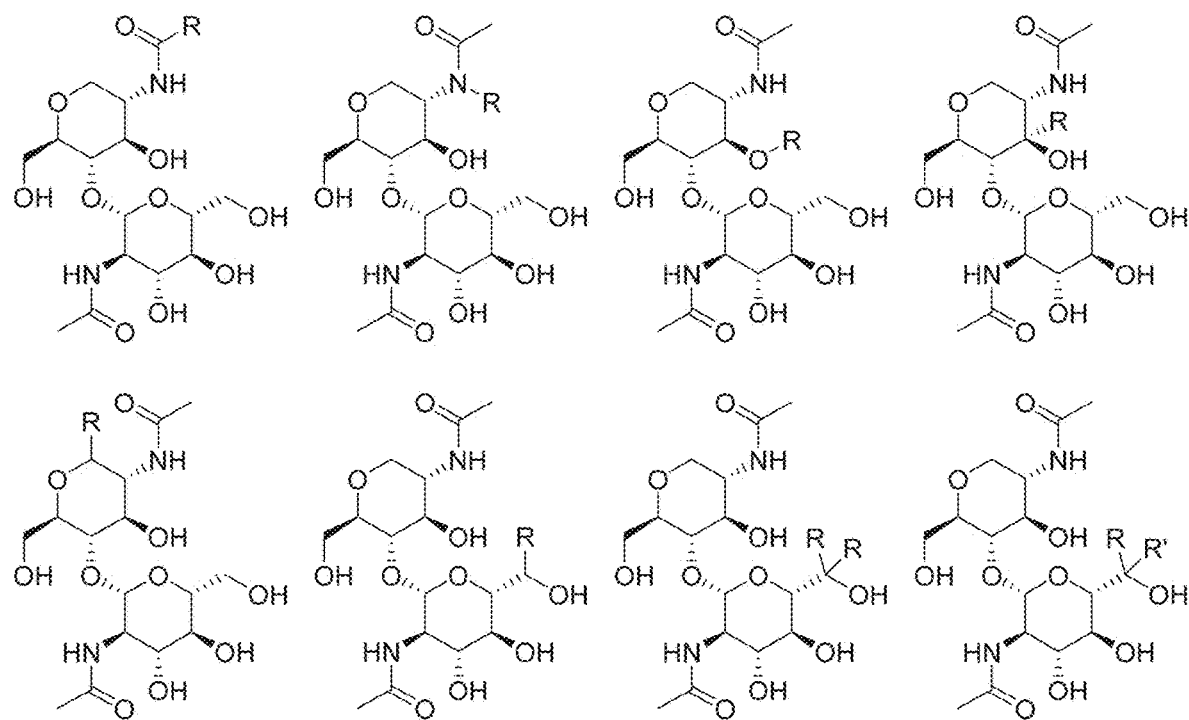

FIG. 200000
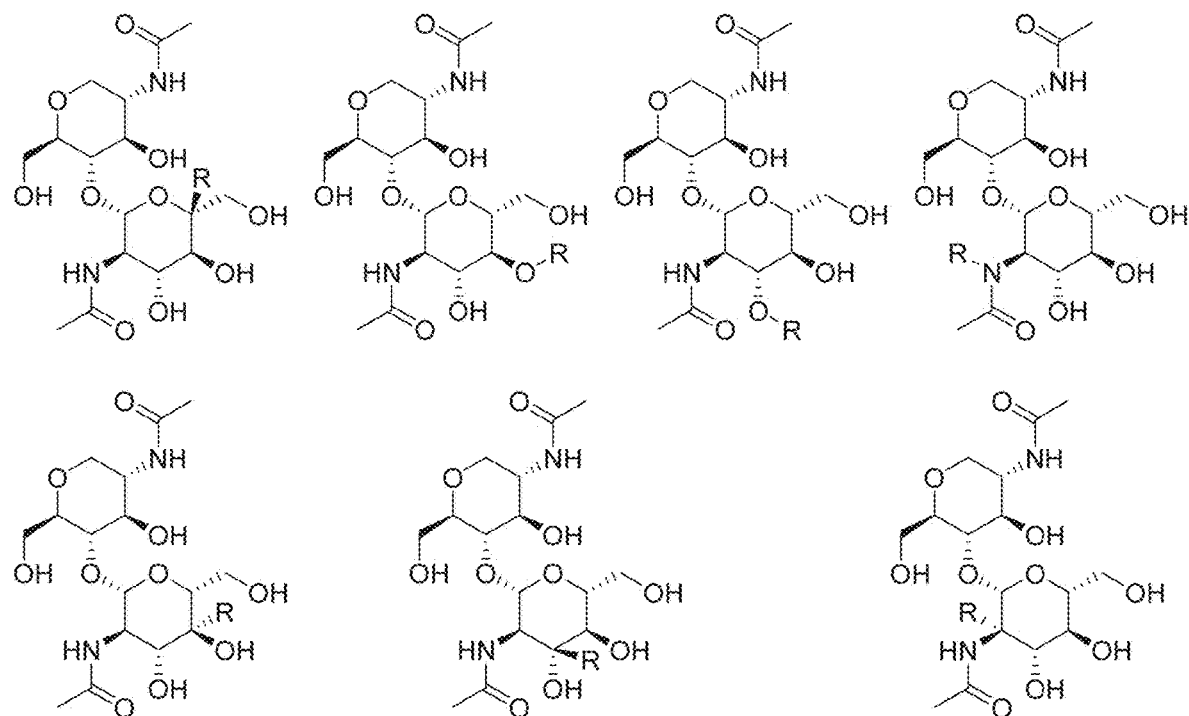
FIG. 2PPPPP
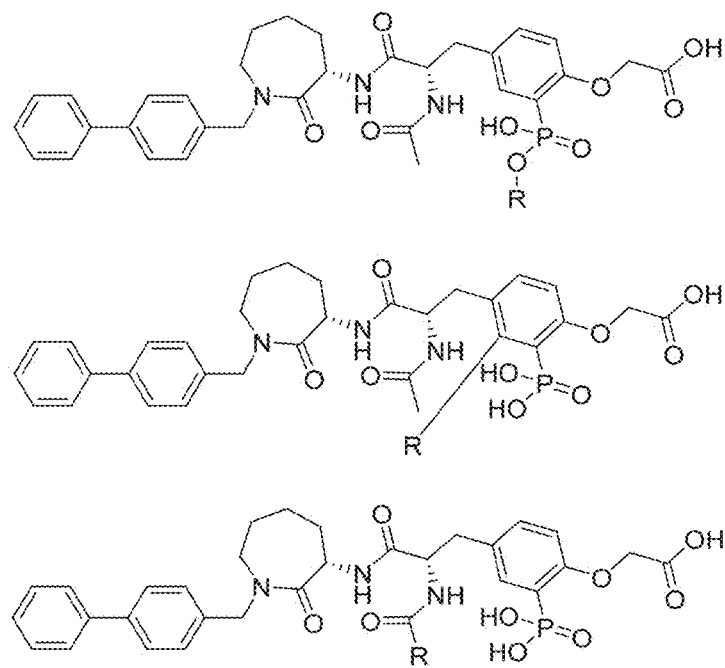

FIG. 2QQQQQ
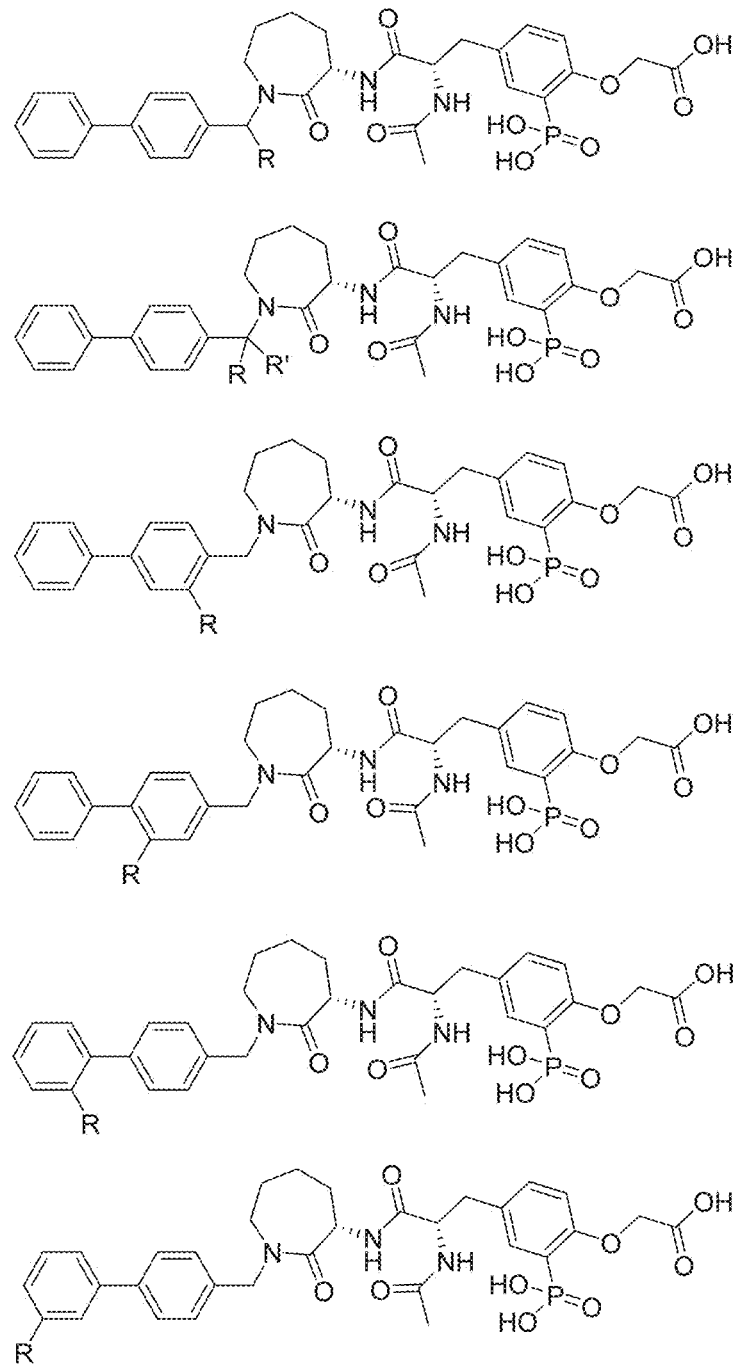

FIG. 2RRRRR
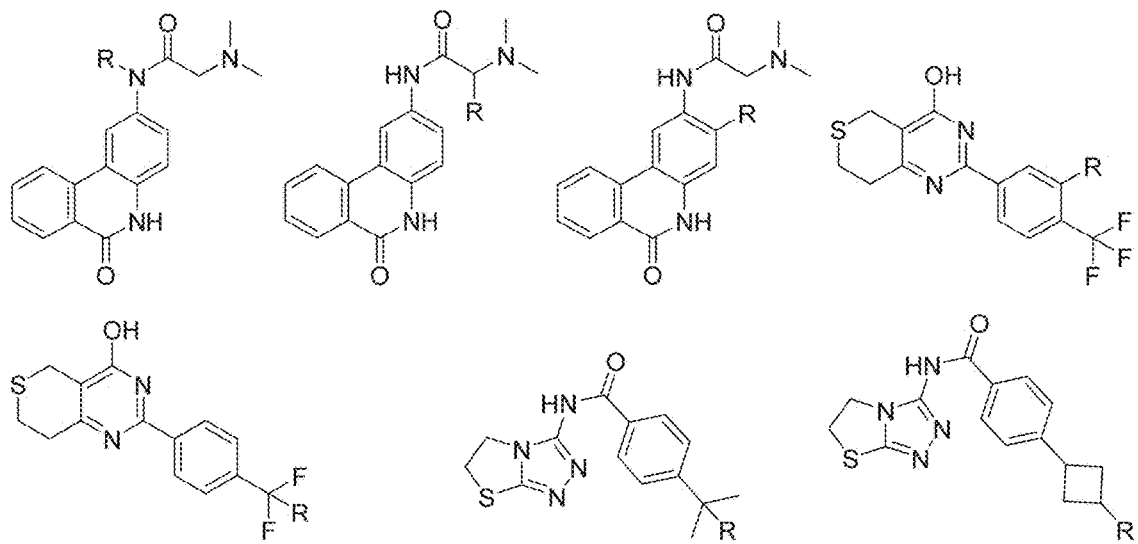
FIG. 2SSSSS
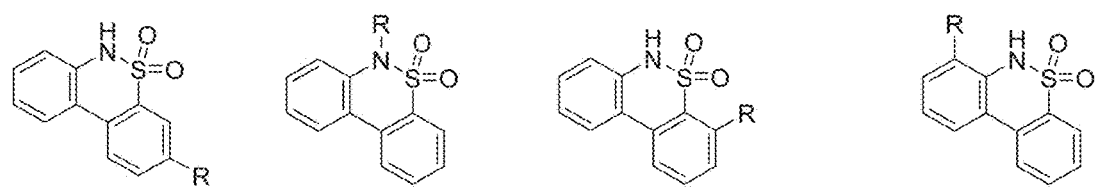
FIG. 2TTTTT
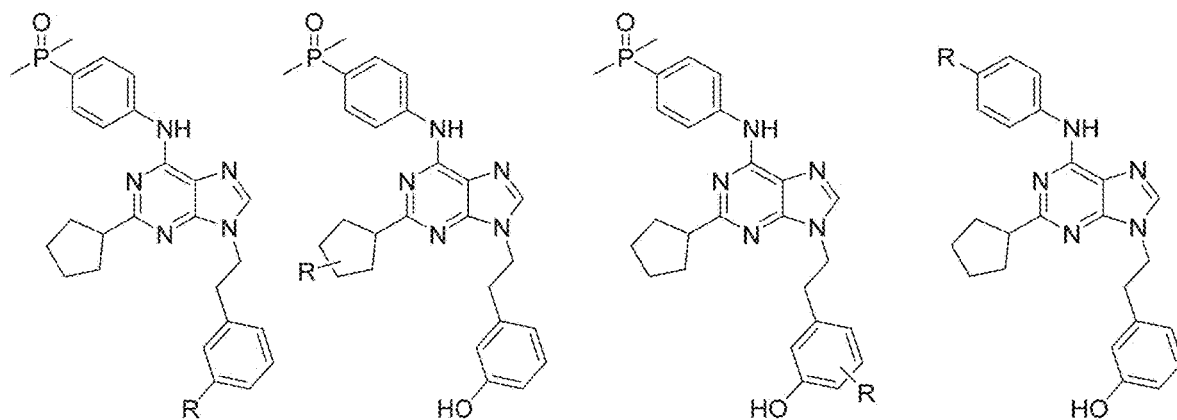

FIG. 2UUUUU
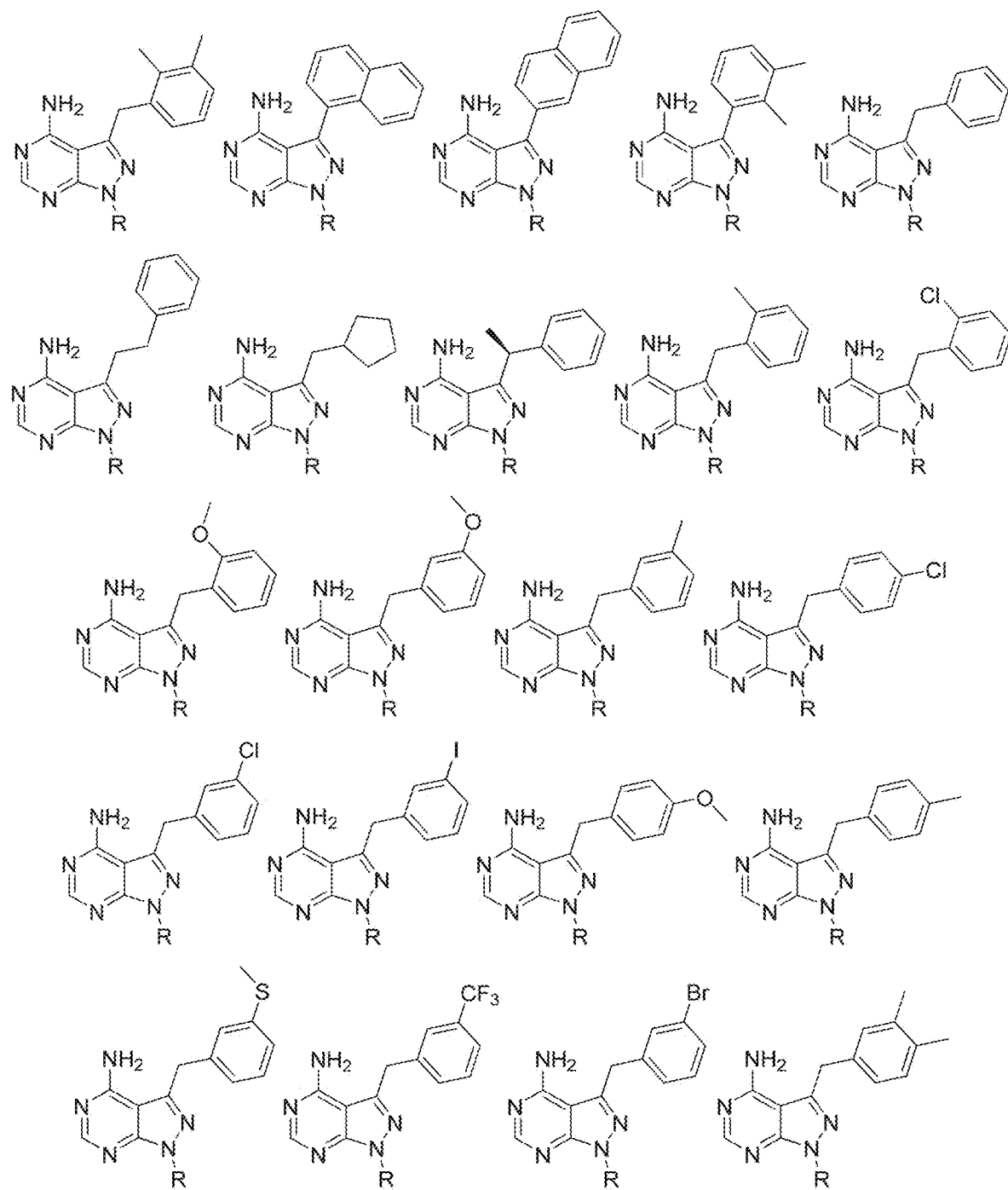

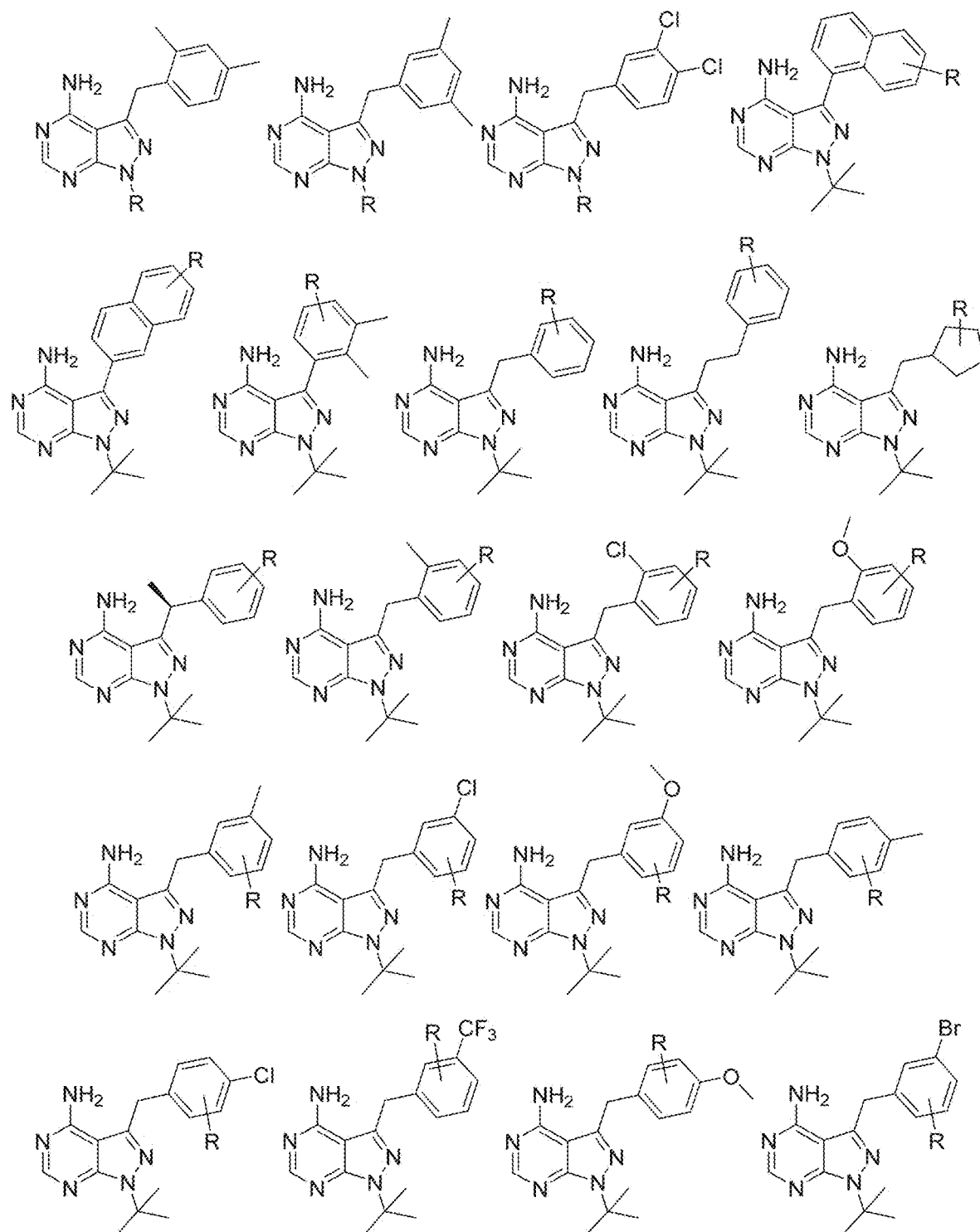
FIG. 2VVVVV

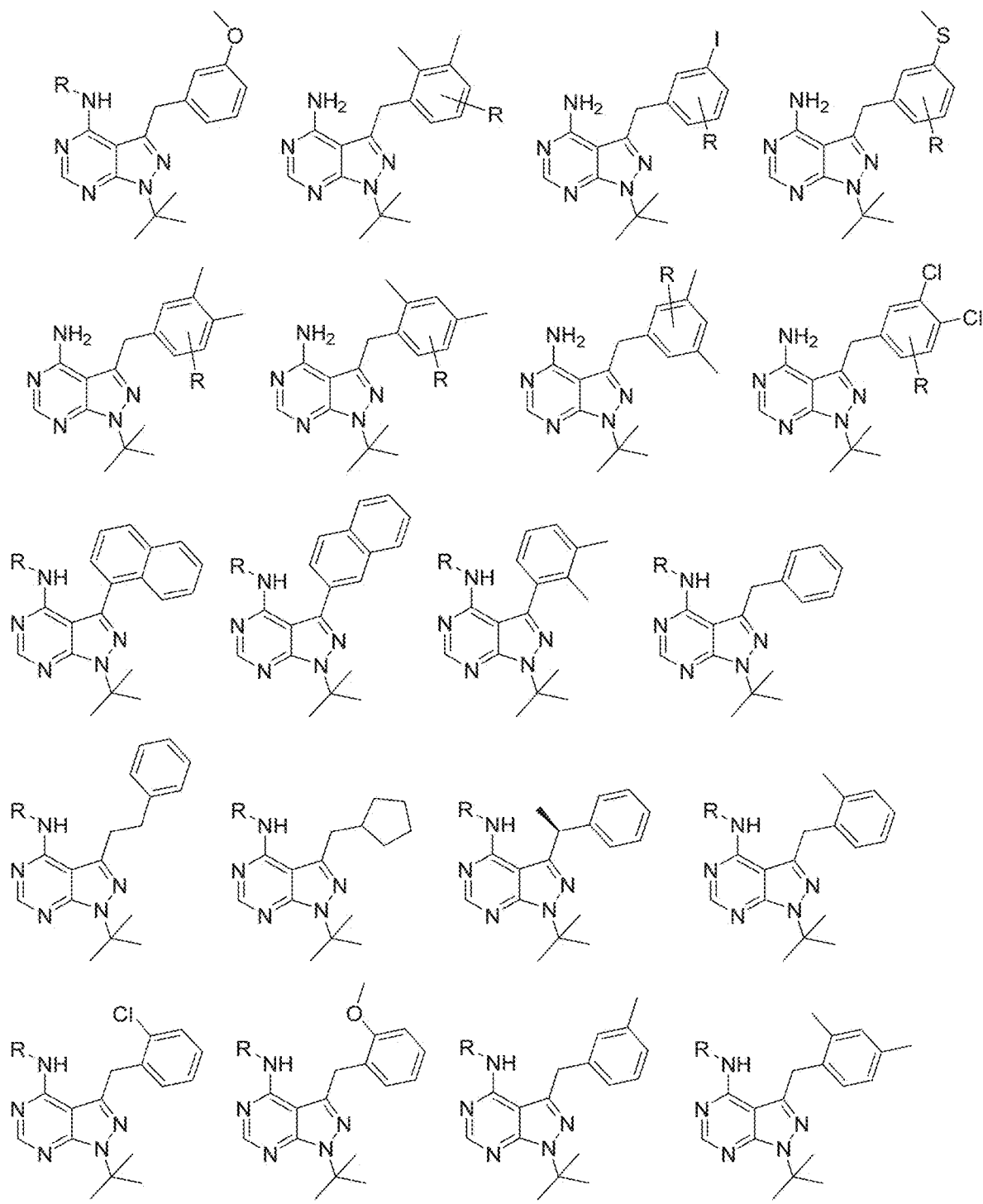
FIG. 2WWWWW

FIG. 2XXXXX
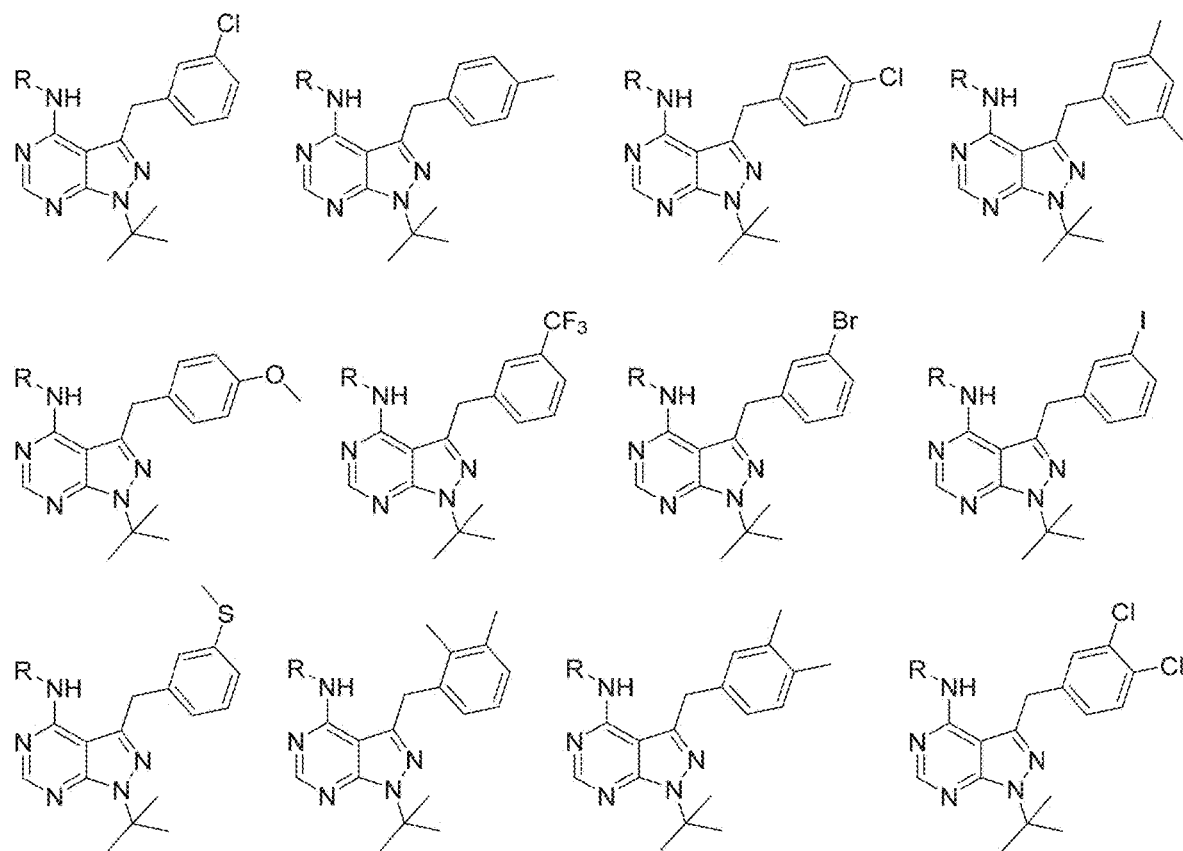
FIG. 2YYYYY
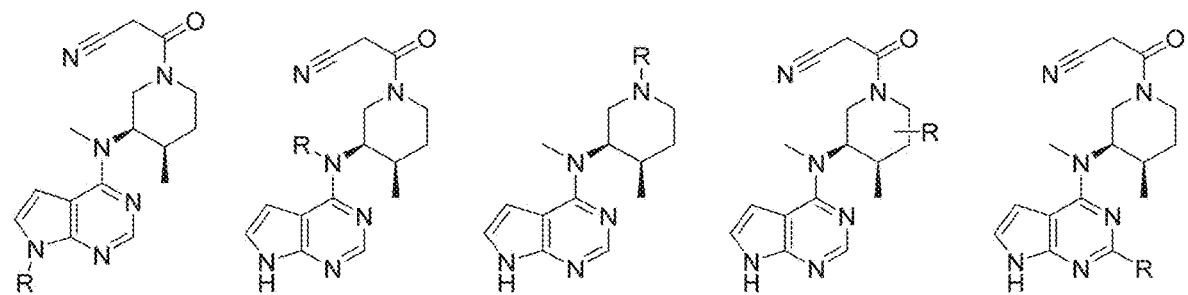

FIG. 2ZZZZZ
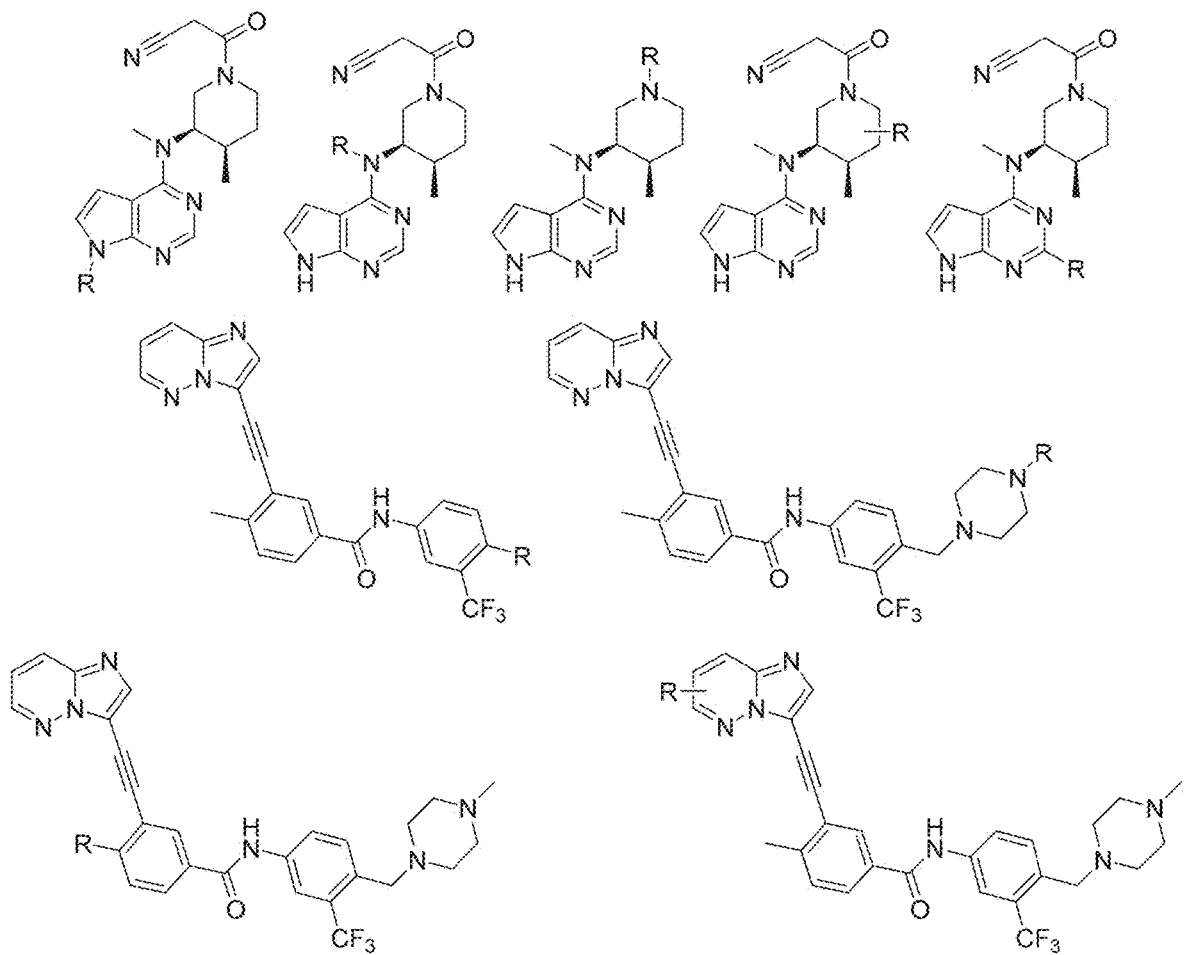
FIG. 3A
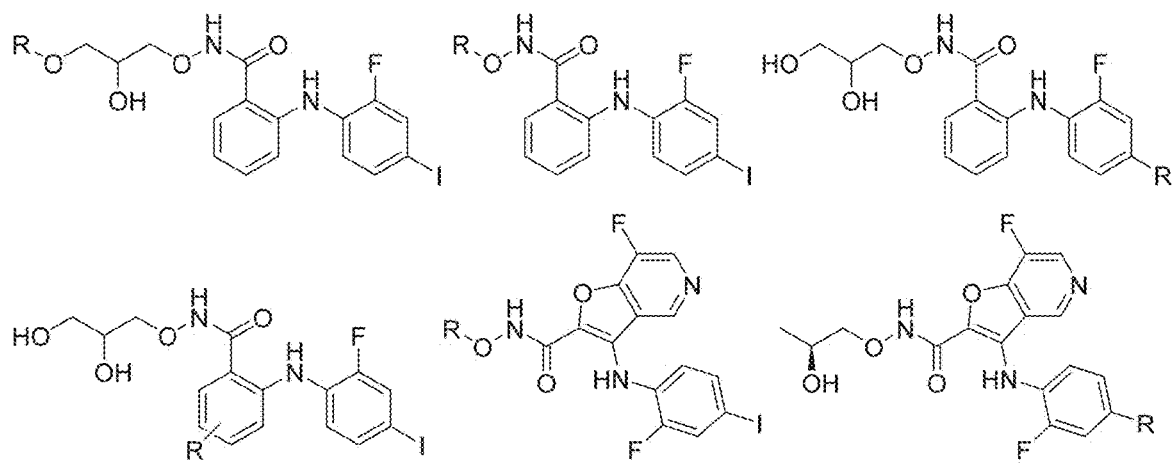

FIG. 3I
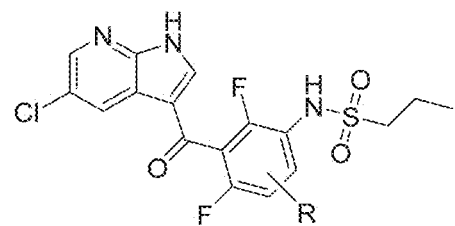 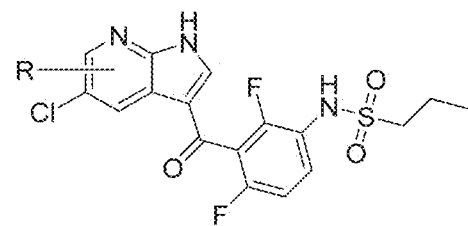
FIG. 3J
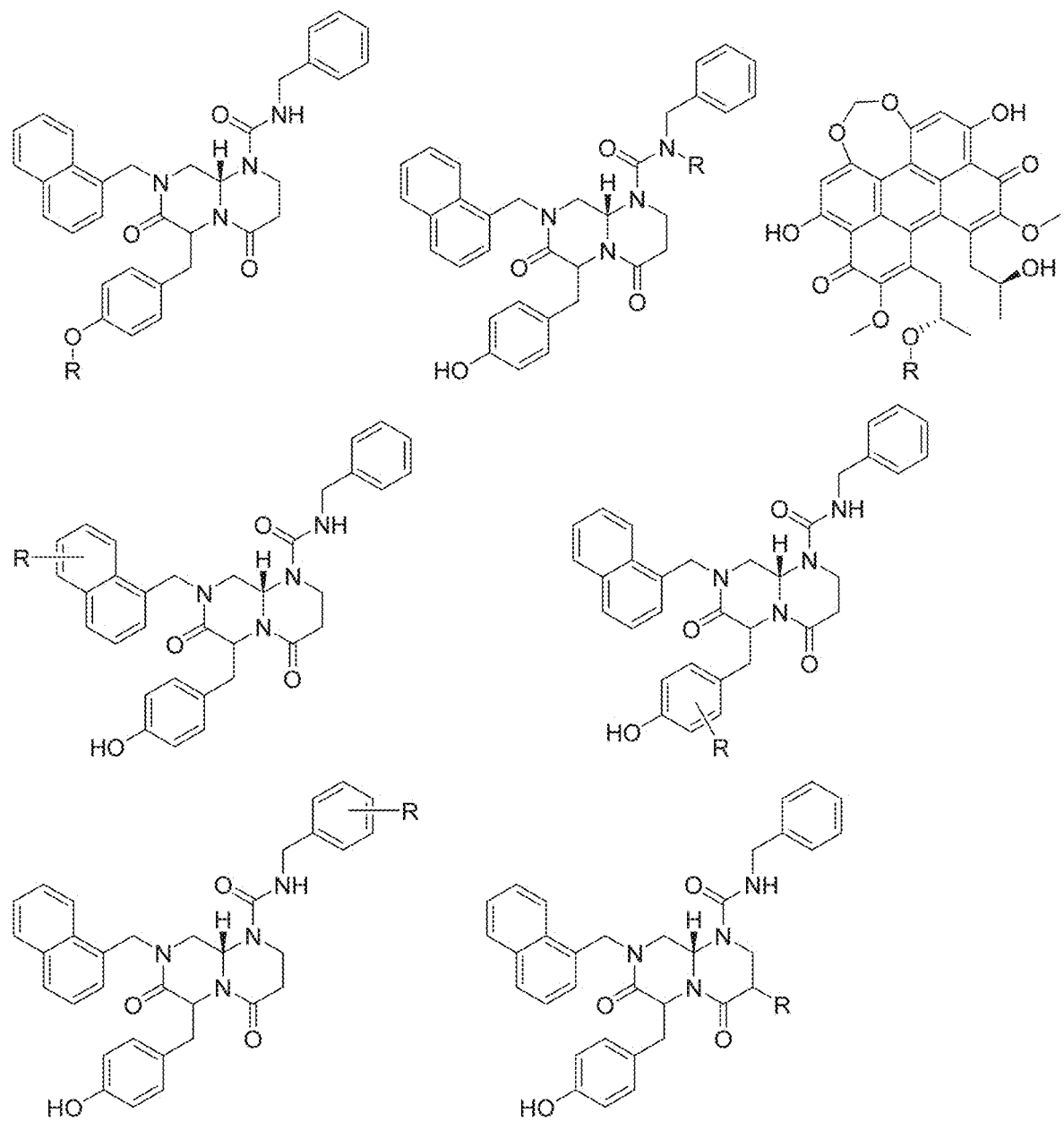

FIG. 3CC
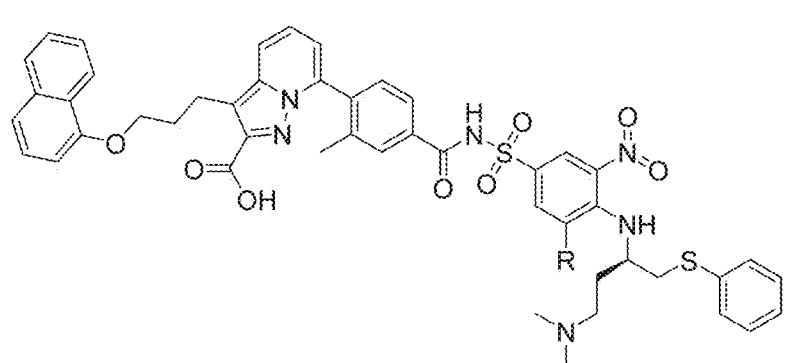
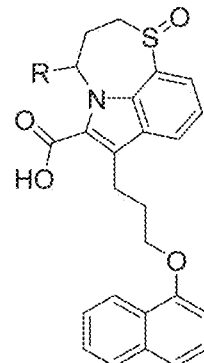
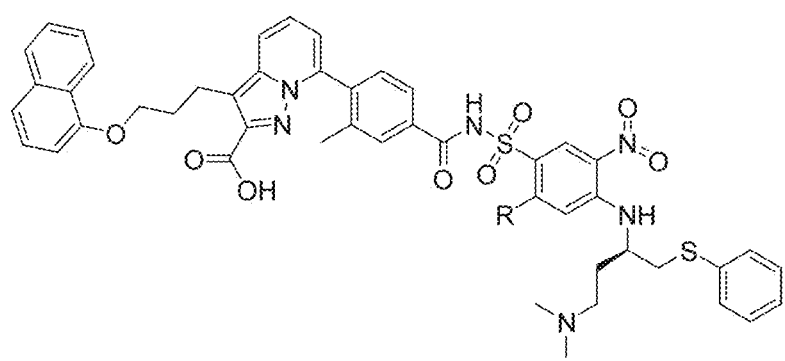
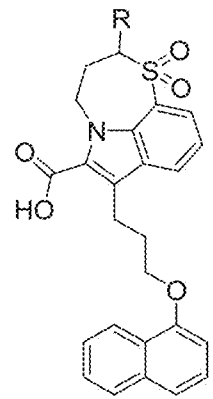
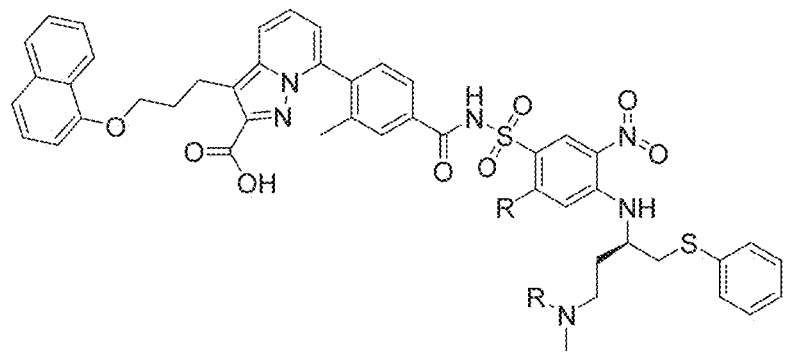
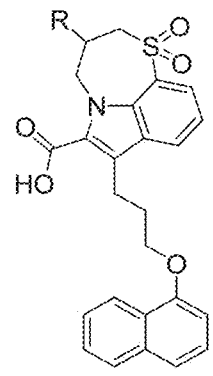
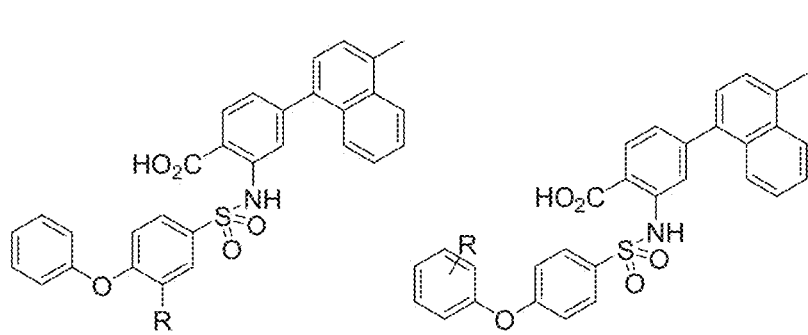
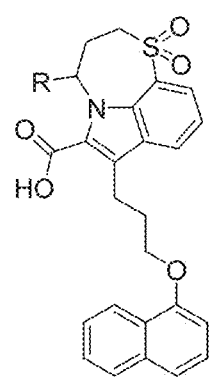

FIG. 3FF
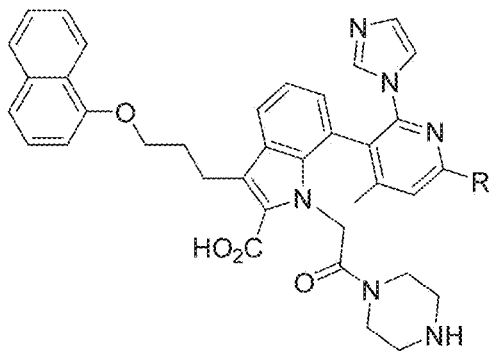
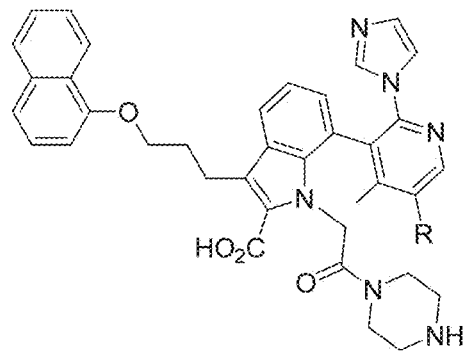
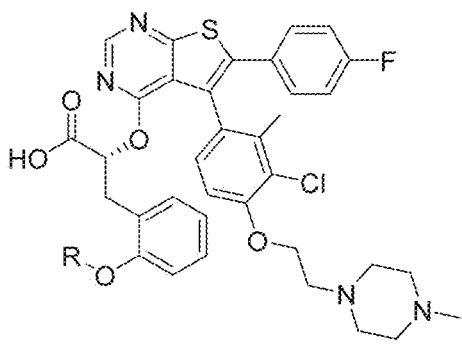
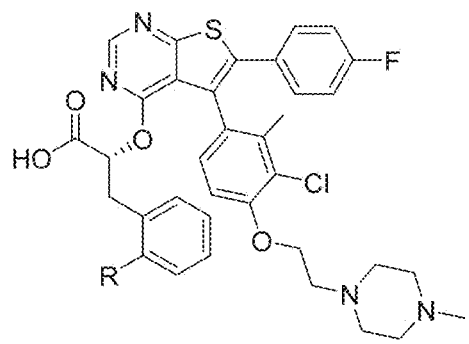
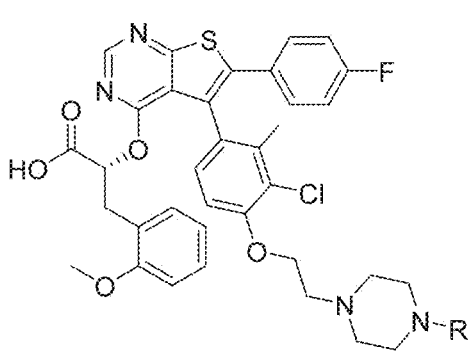
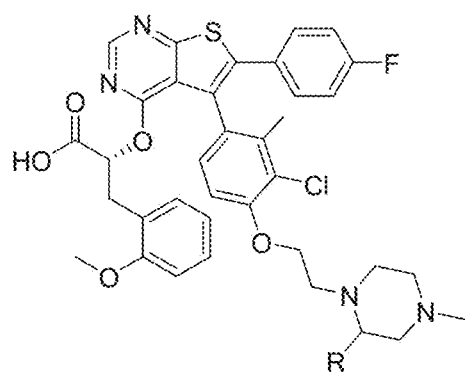
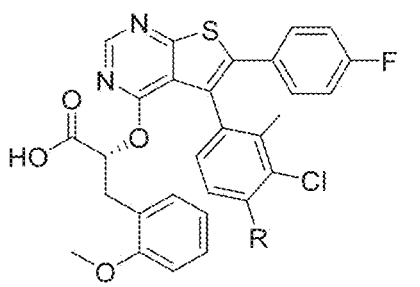
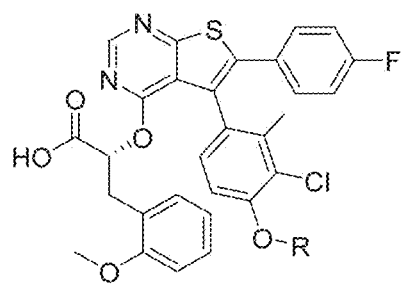

FIG. 3GG
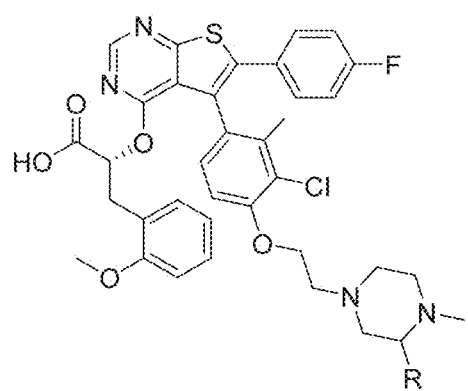
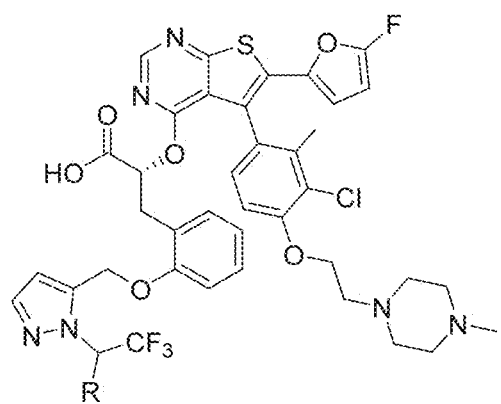
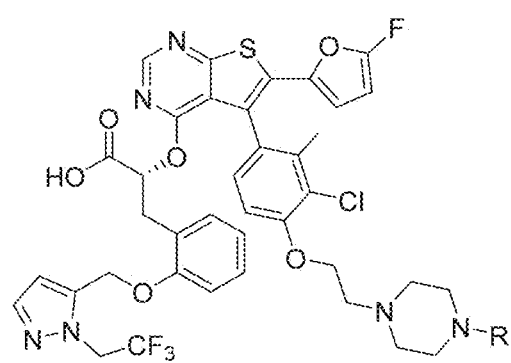
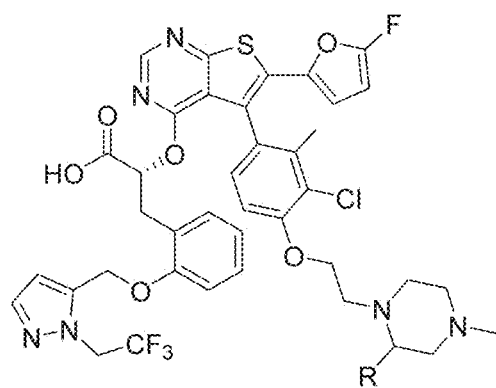
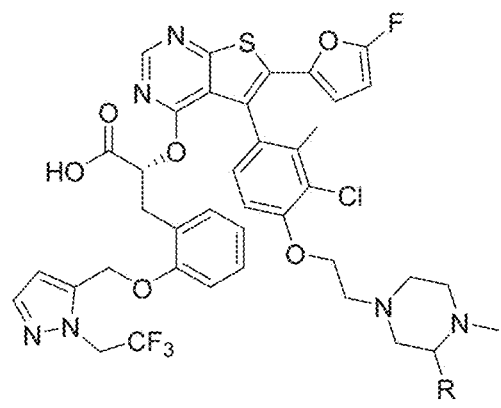
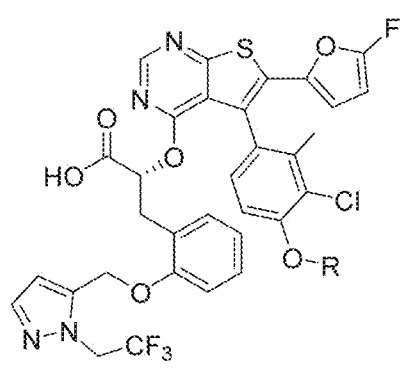

FIG. 3JJ
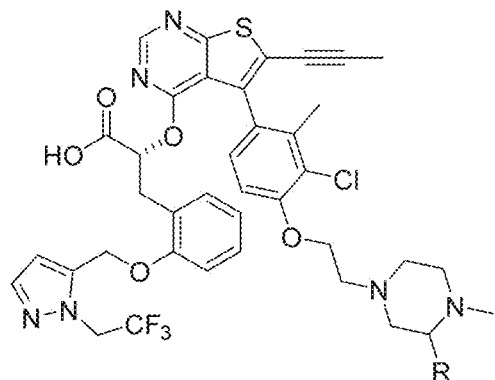
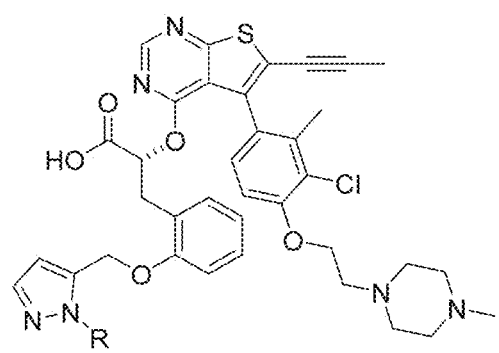
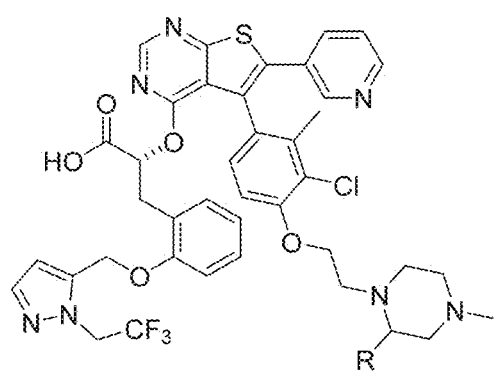
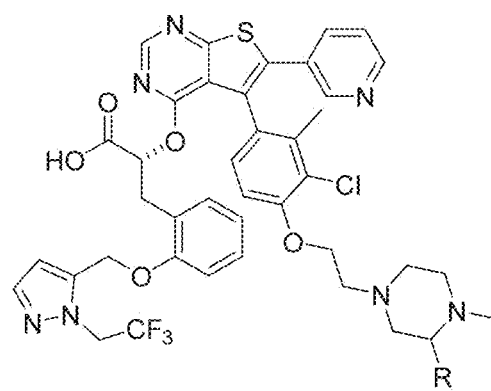
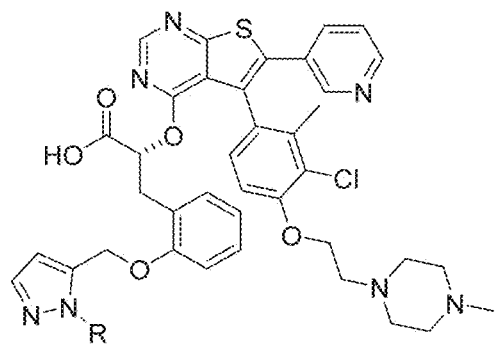
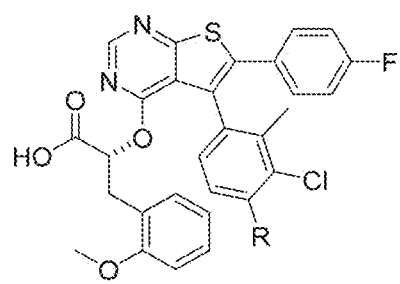
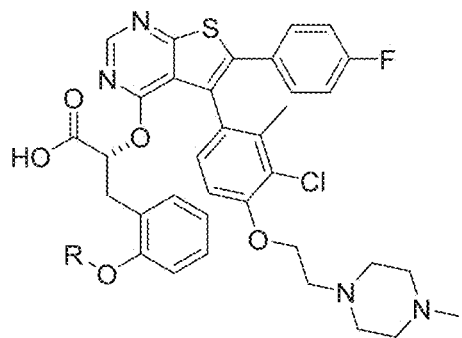
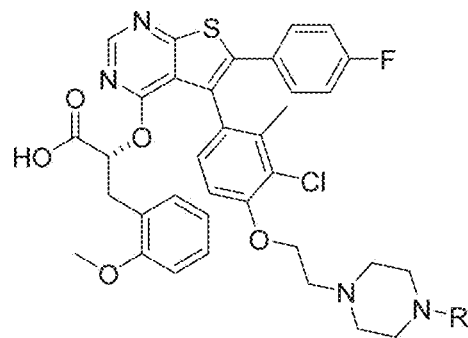

FIG. 3KK
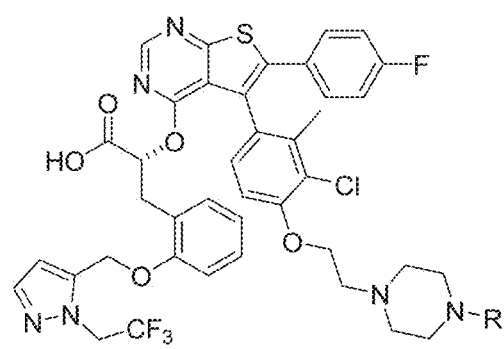
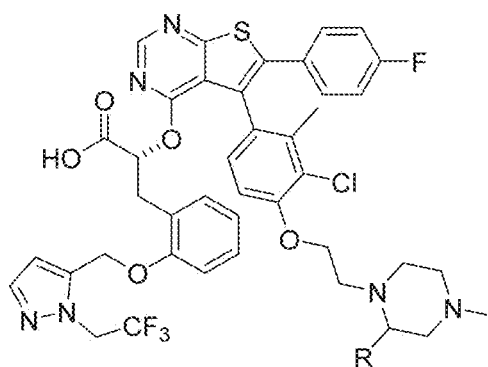
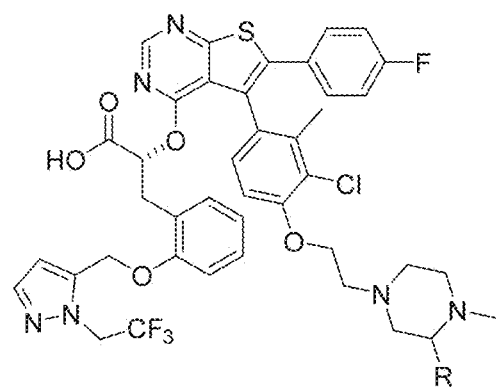
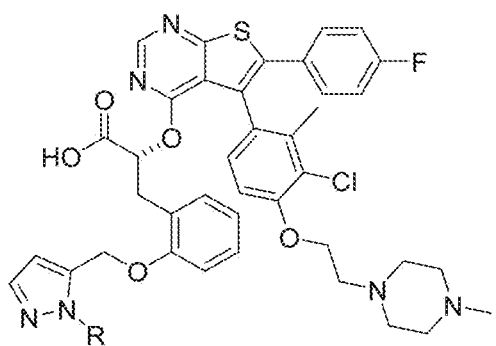
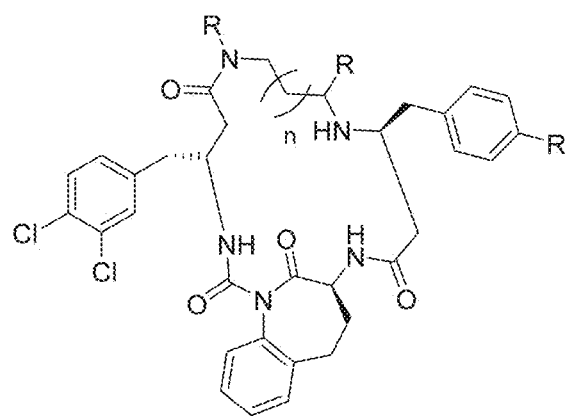
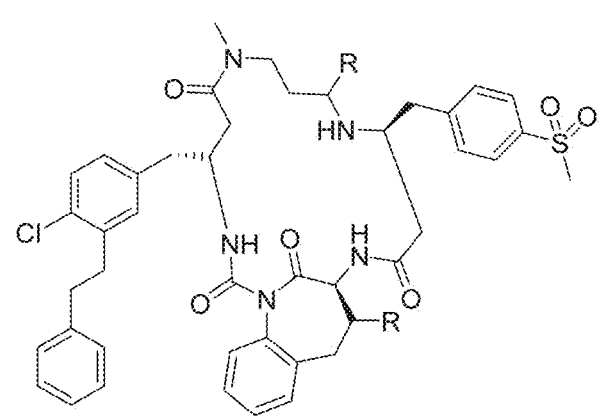

FIG. 3NN
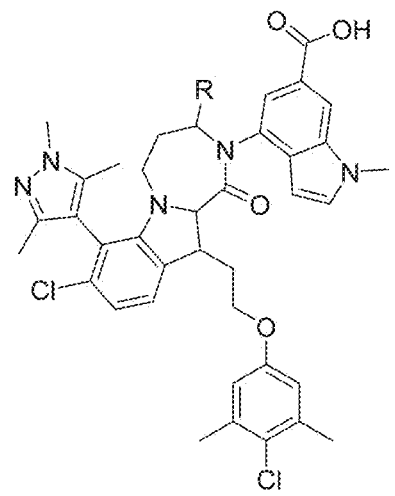
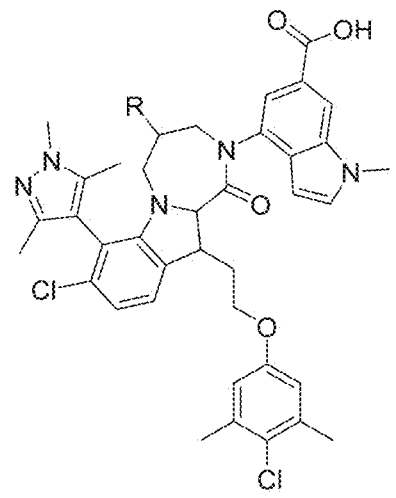
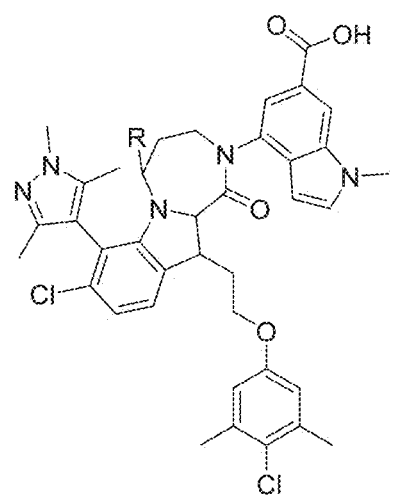
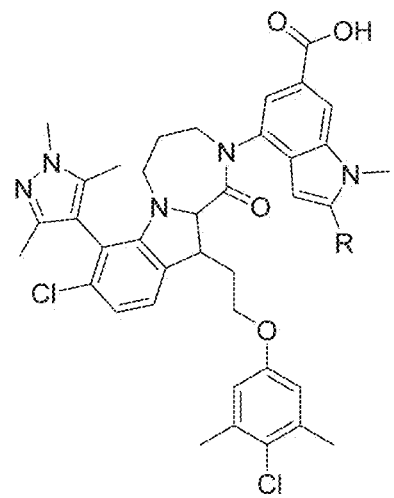
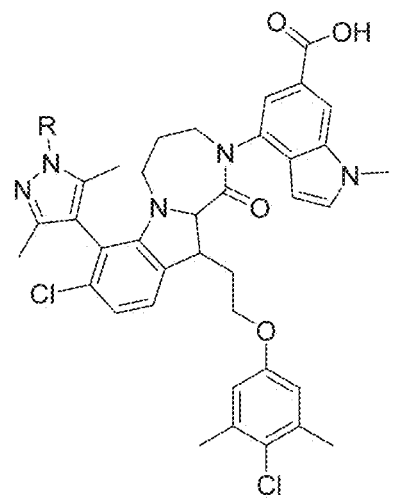
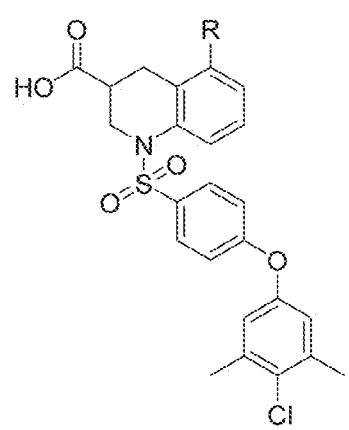

FIG. 3AAA
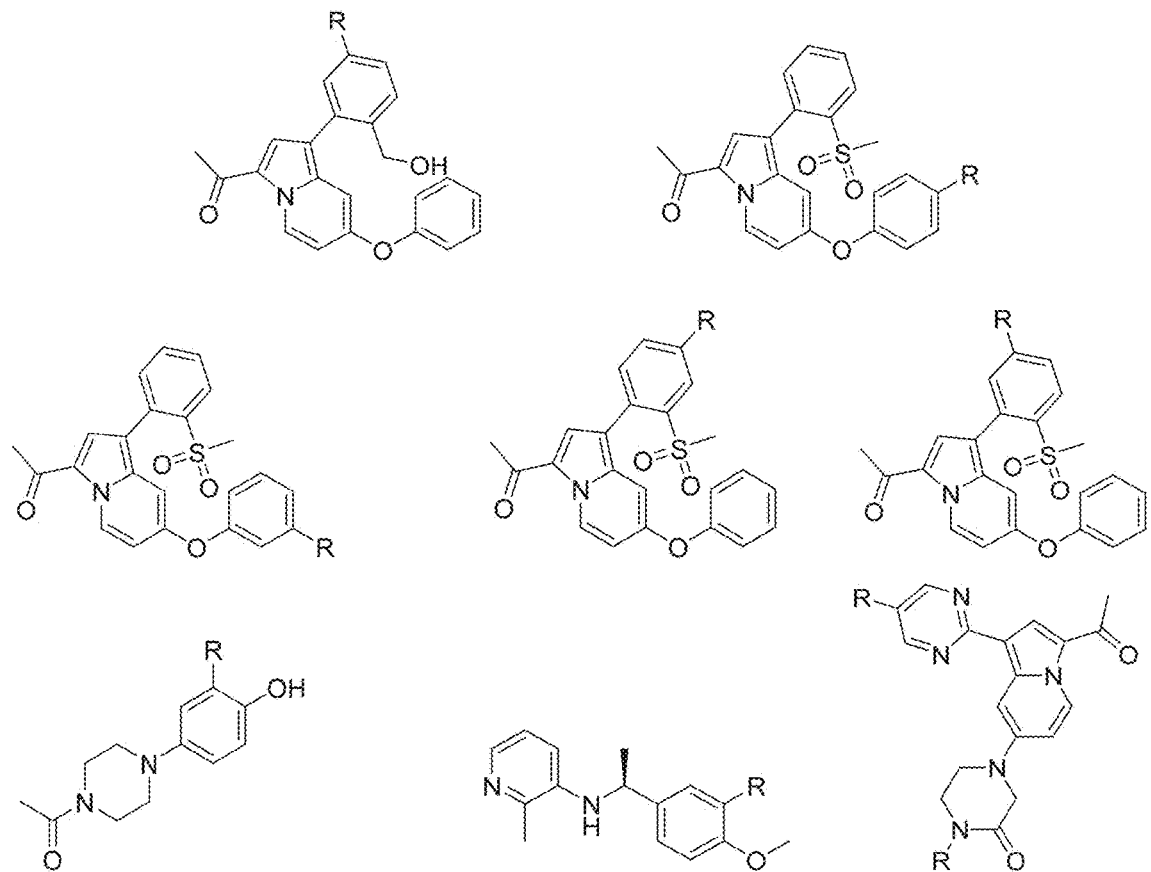
FIG. 3BBB
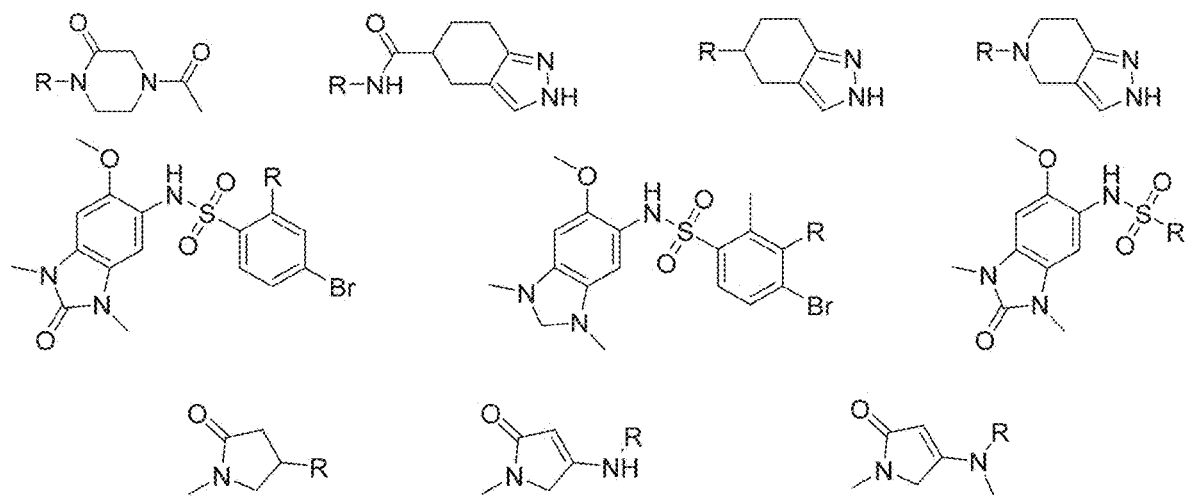

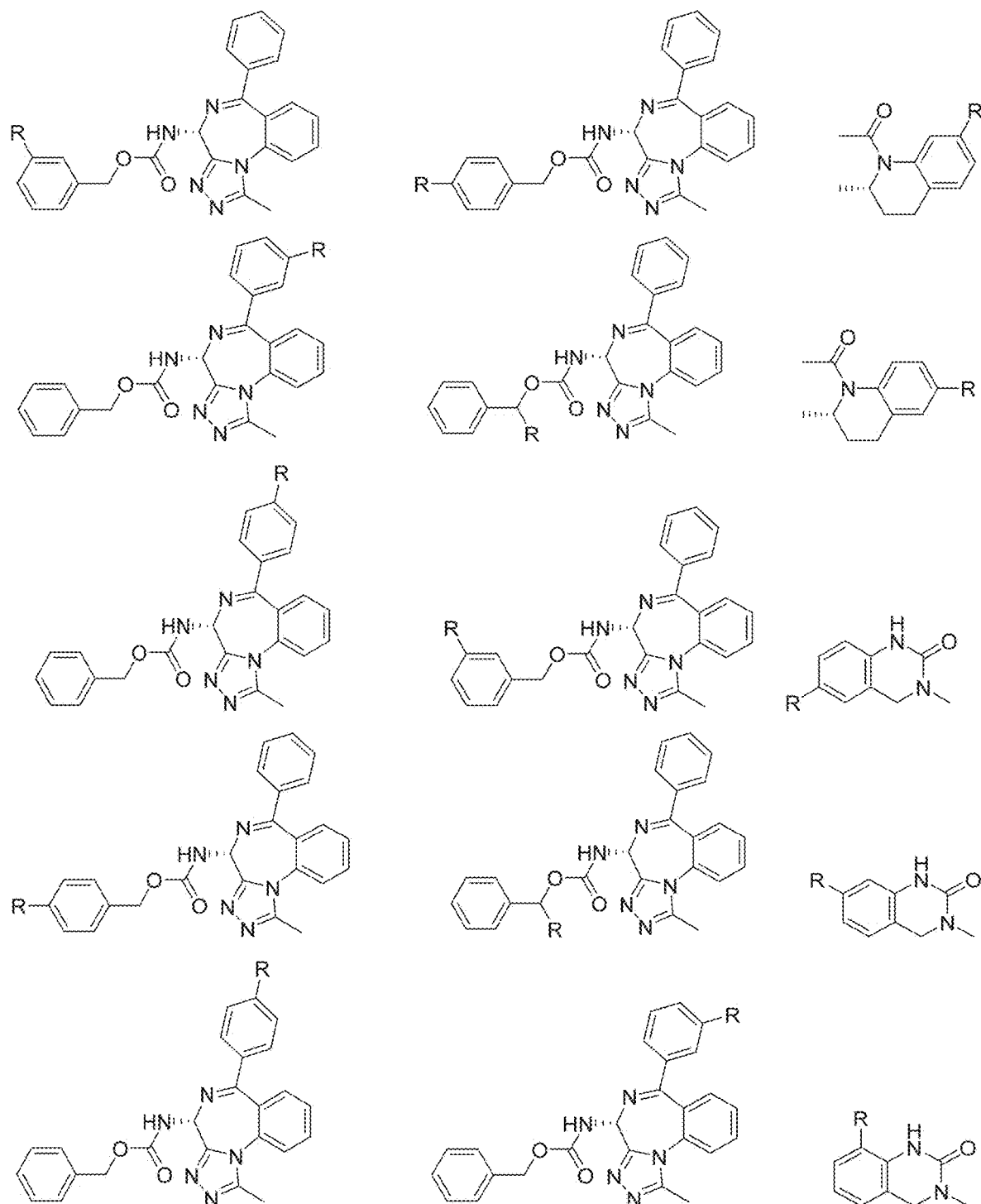
FIG. 3CCC

FIG. 3DDD

FIG. 3EEE
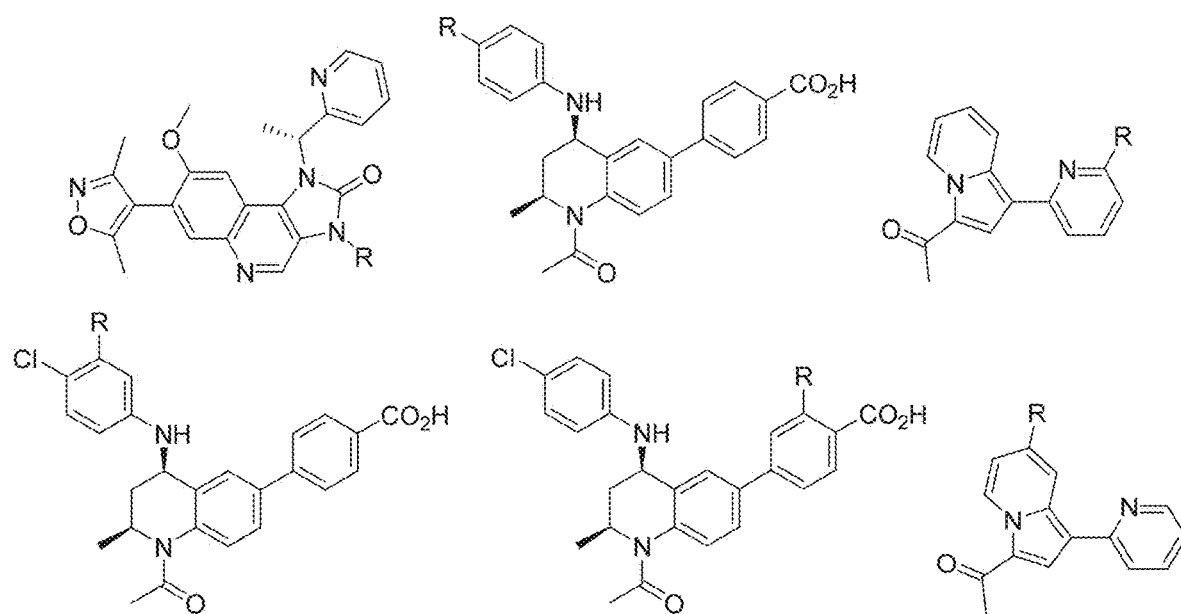
FIG. 3FFF
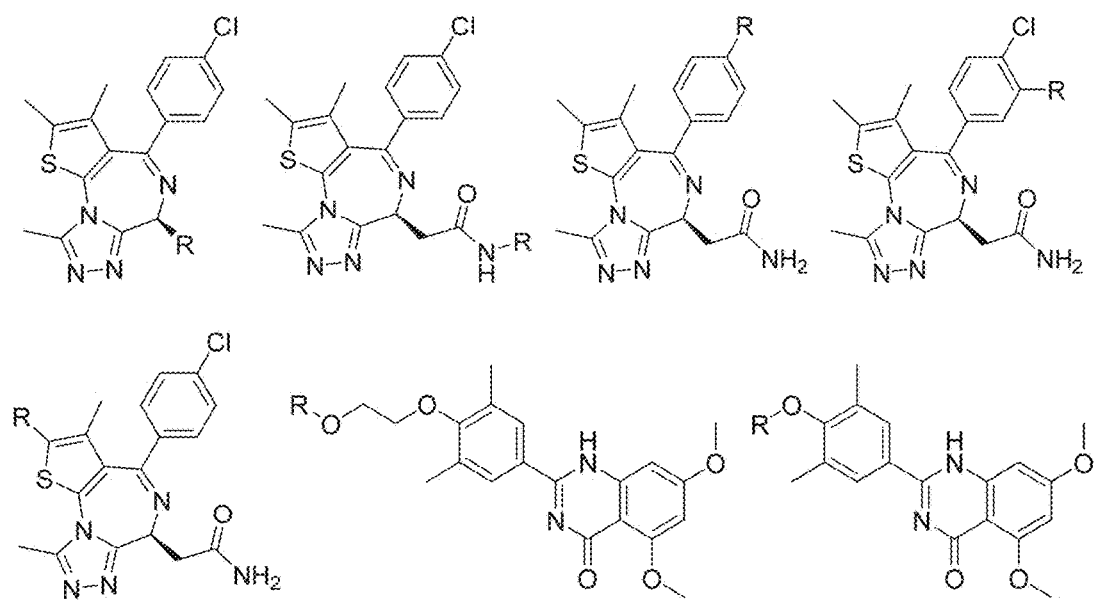

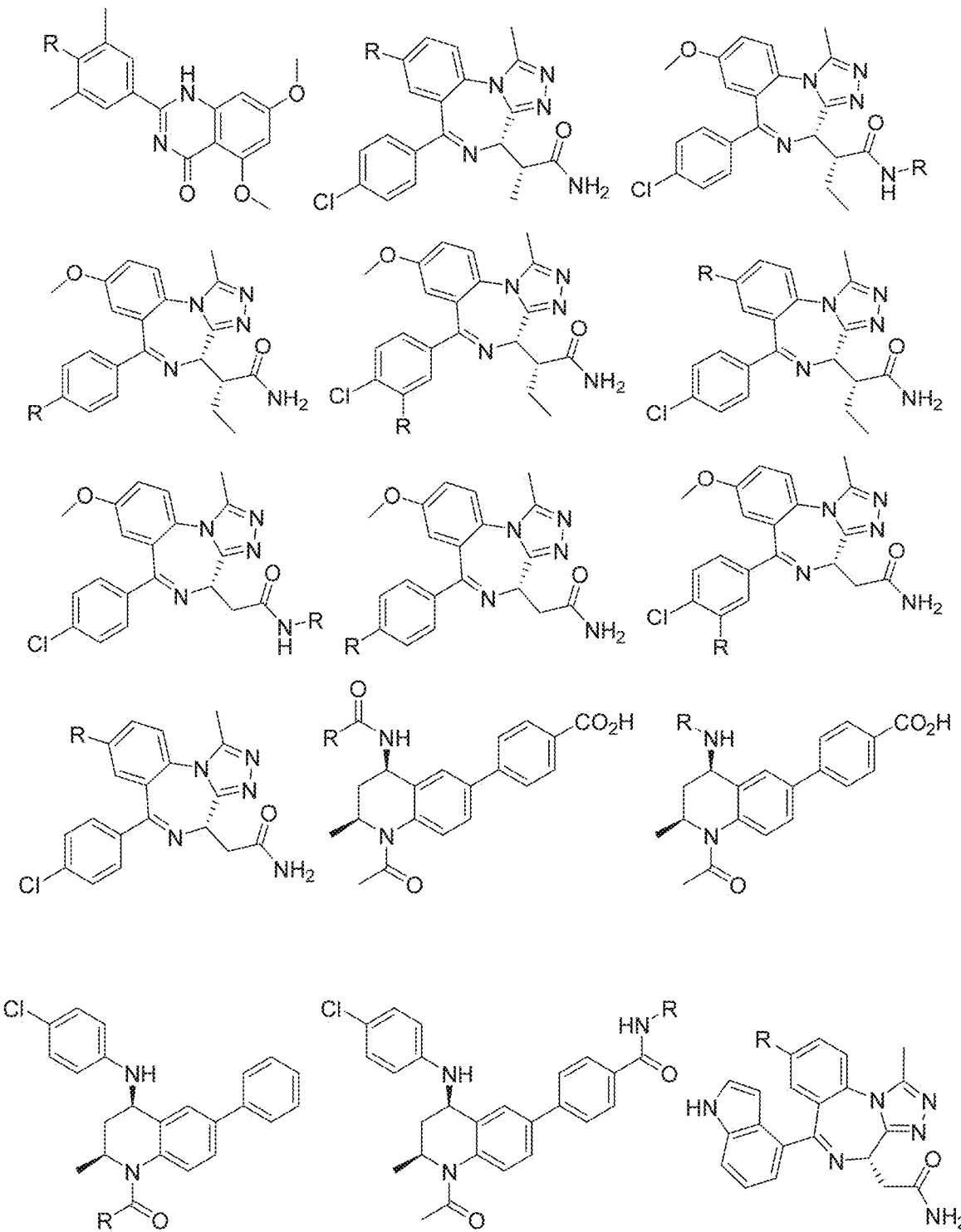
FIG. 3GGG

FIG. 3HHH
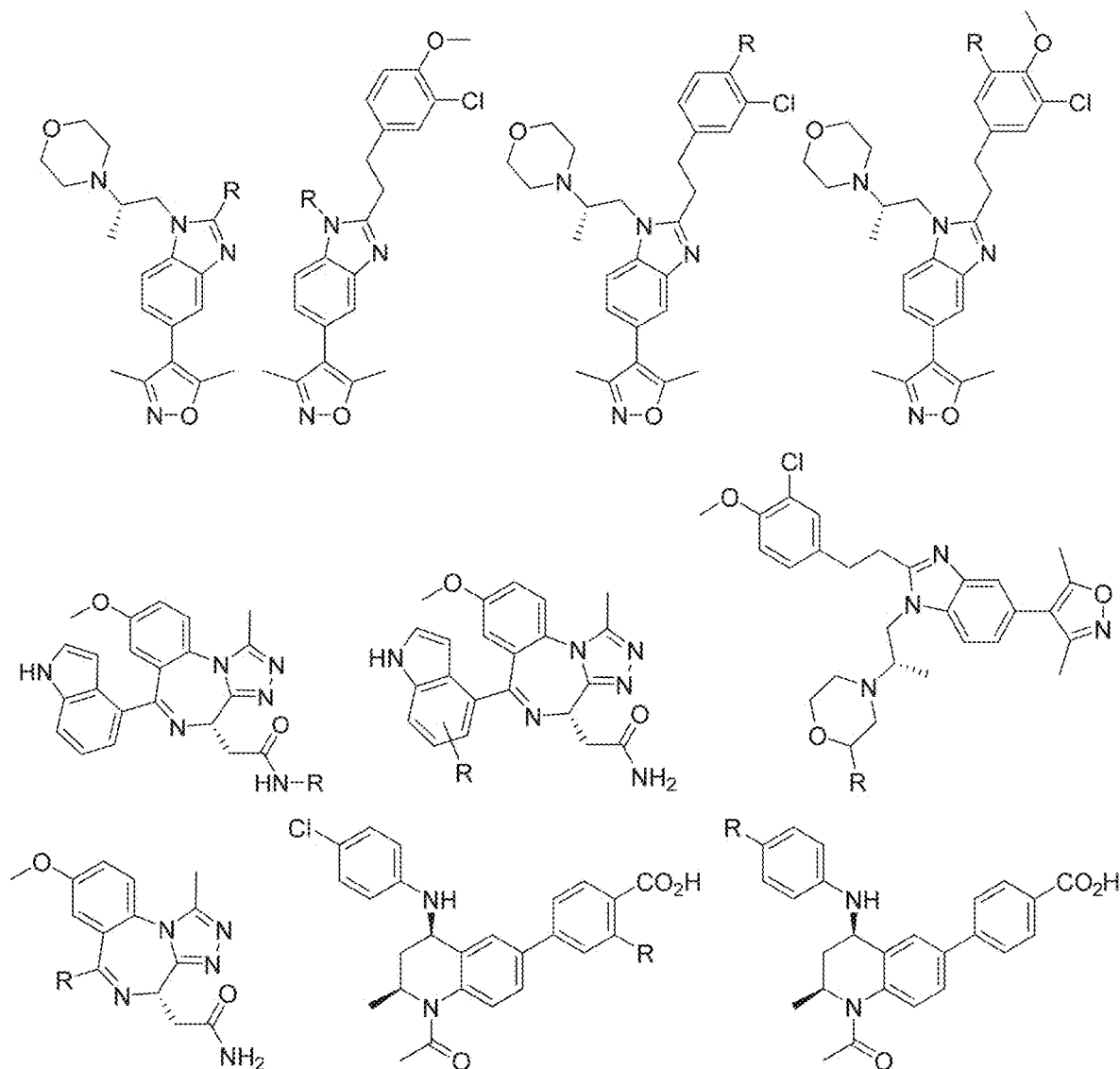
FIG. 3III
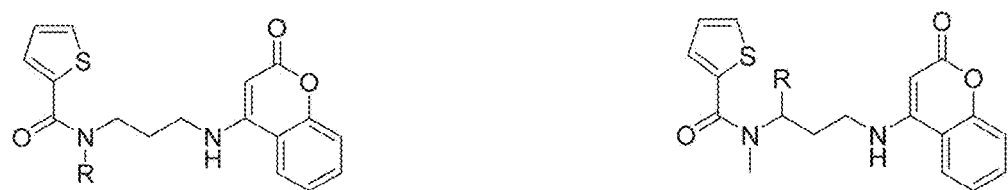

FIG. 3JJJ
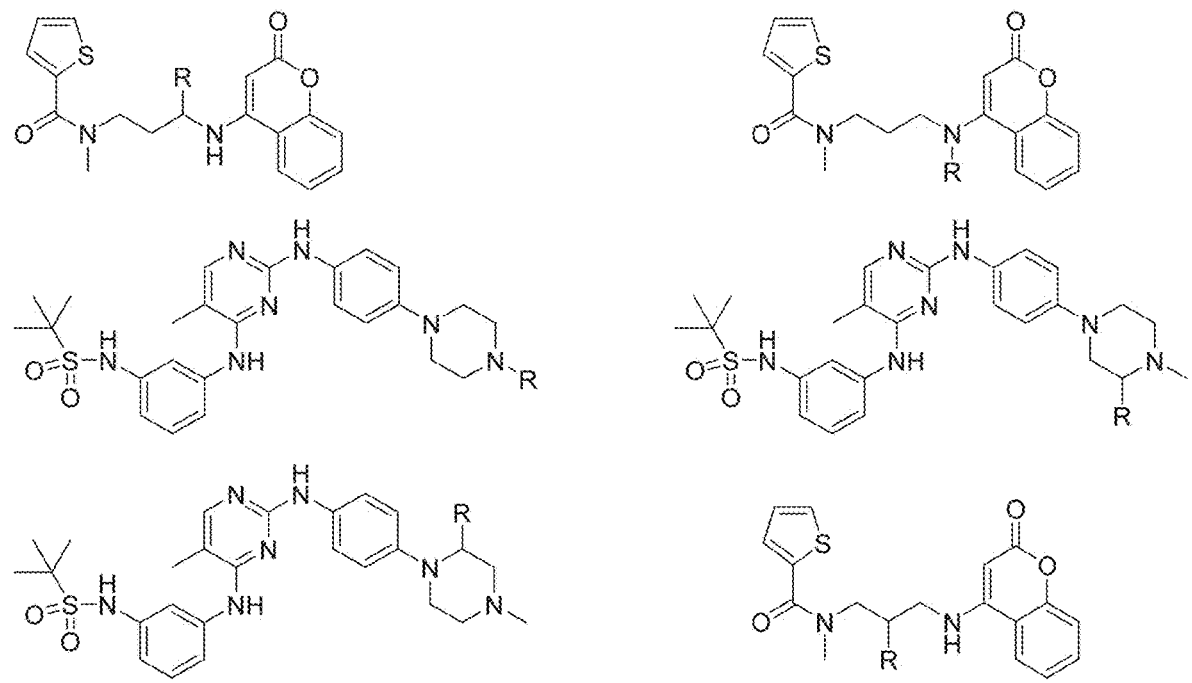
FIG. 3KKK
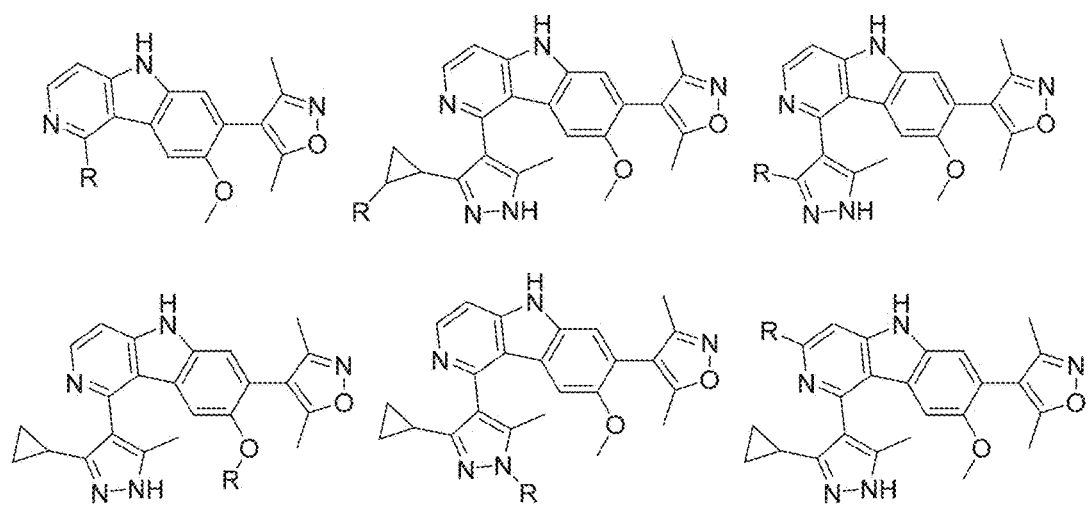

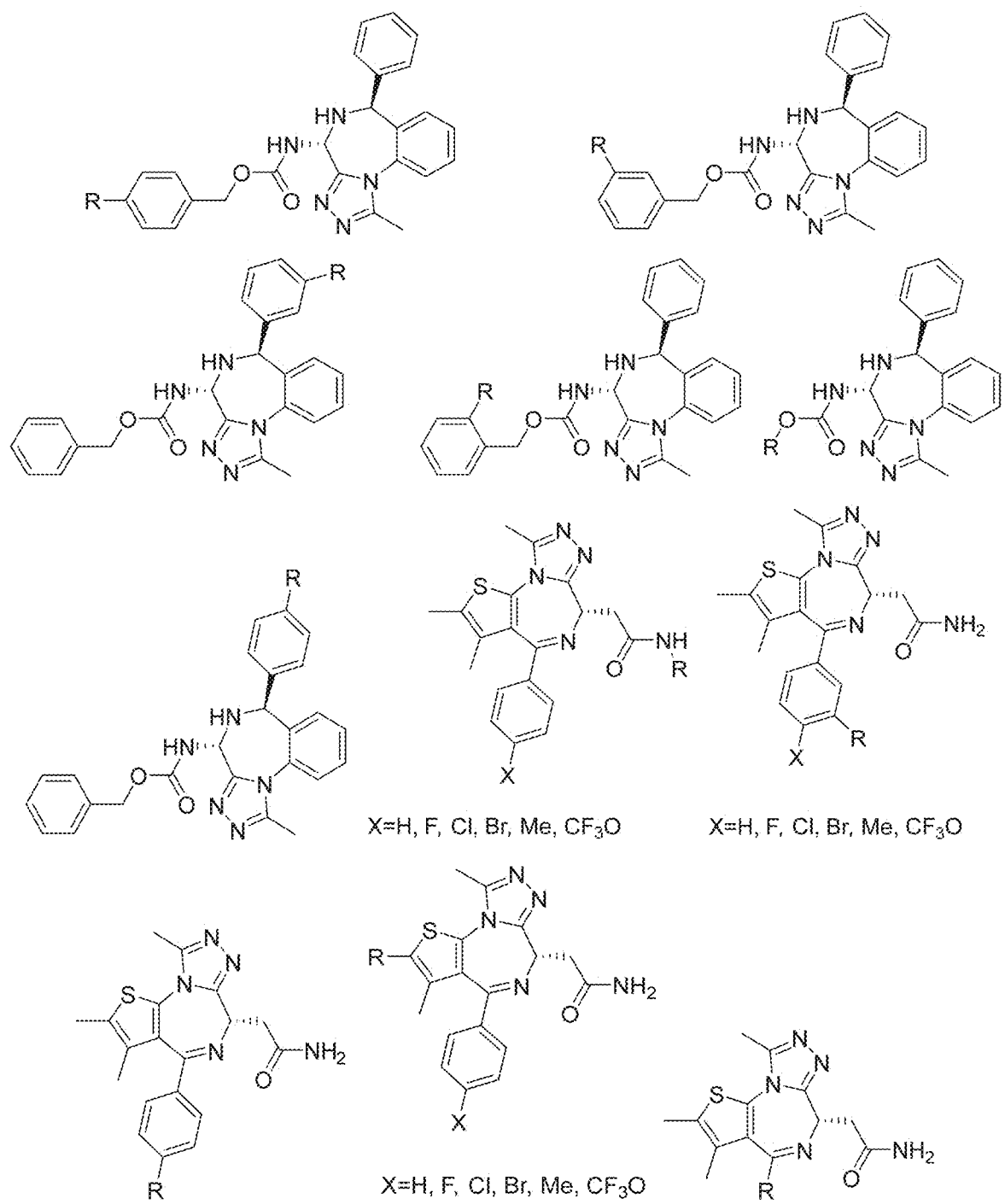
FIG. 3LLL

FIG. 3MMM
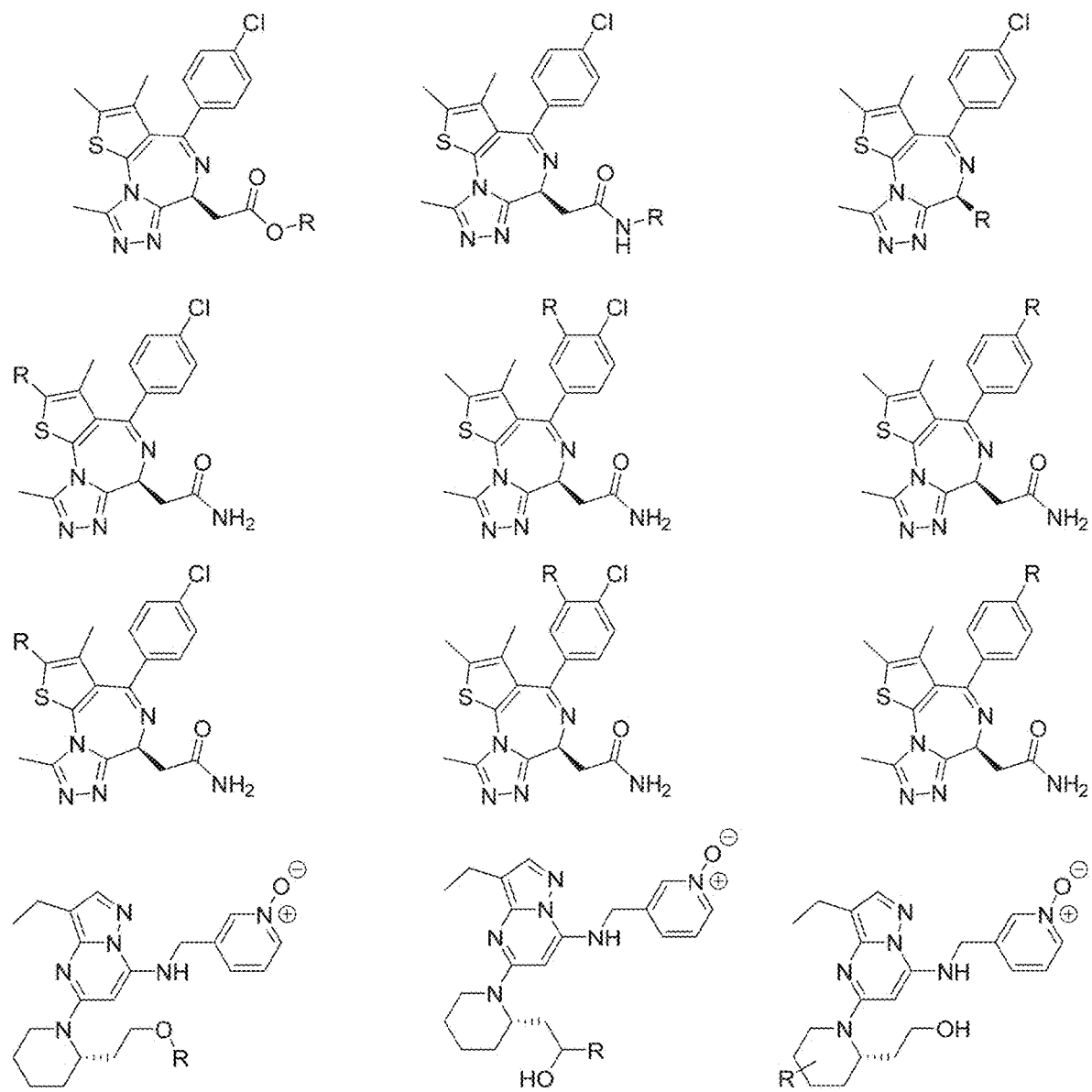
FIG. 3NNN
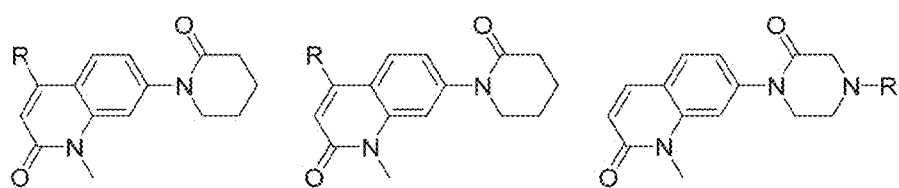

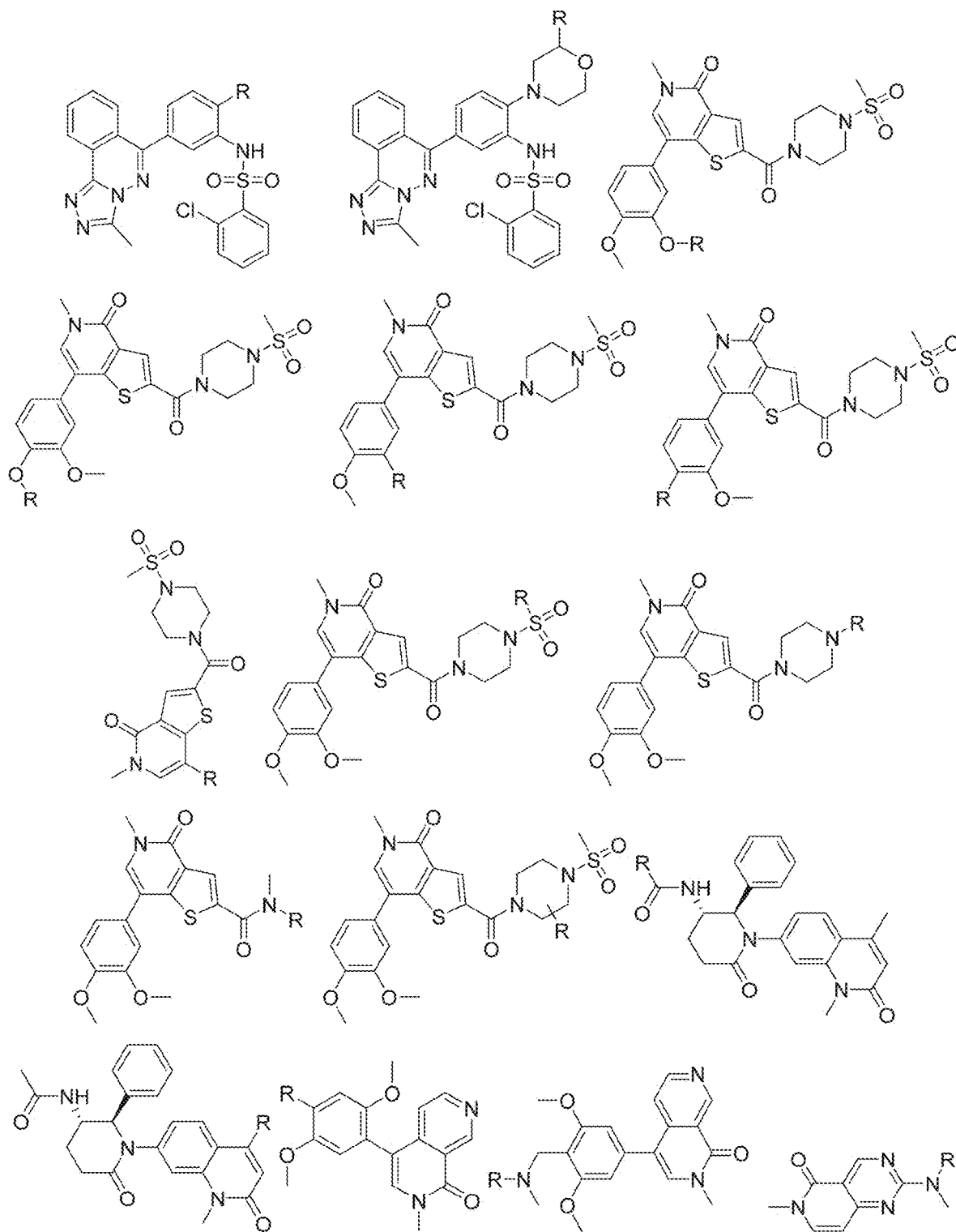
FIG. 3000

FIG. 3PPP
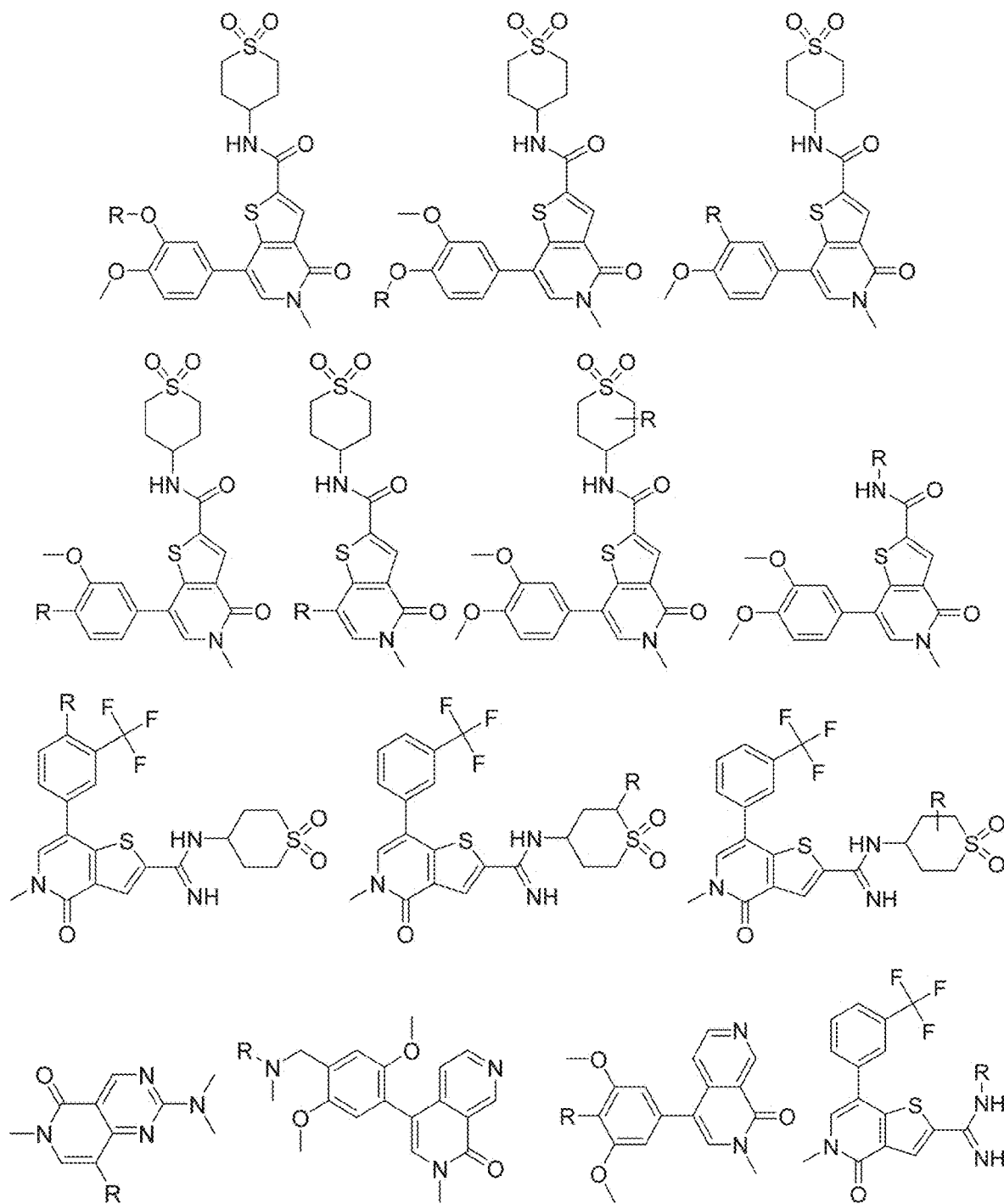

FIG. 3QQQ
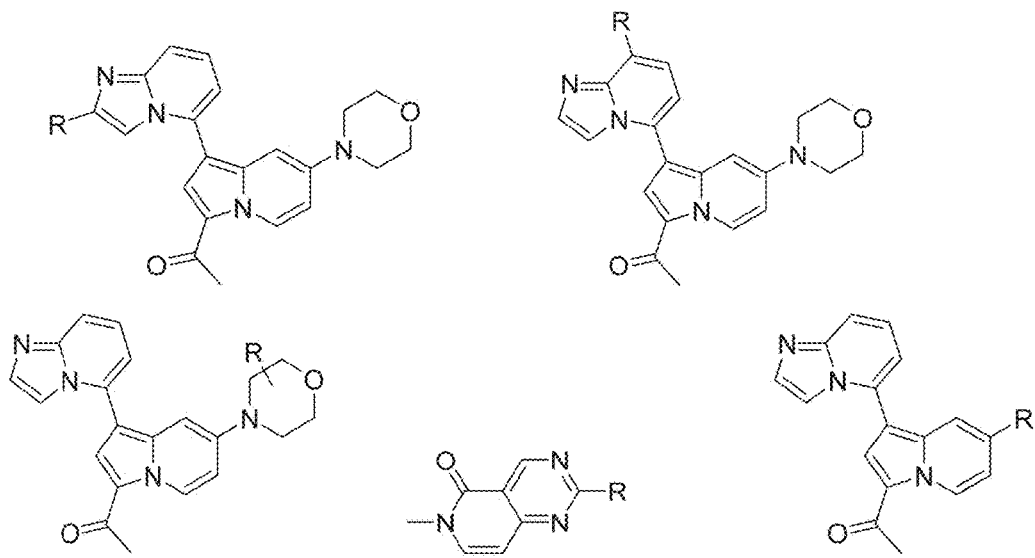
FIG. 3RRR
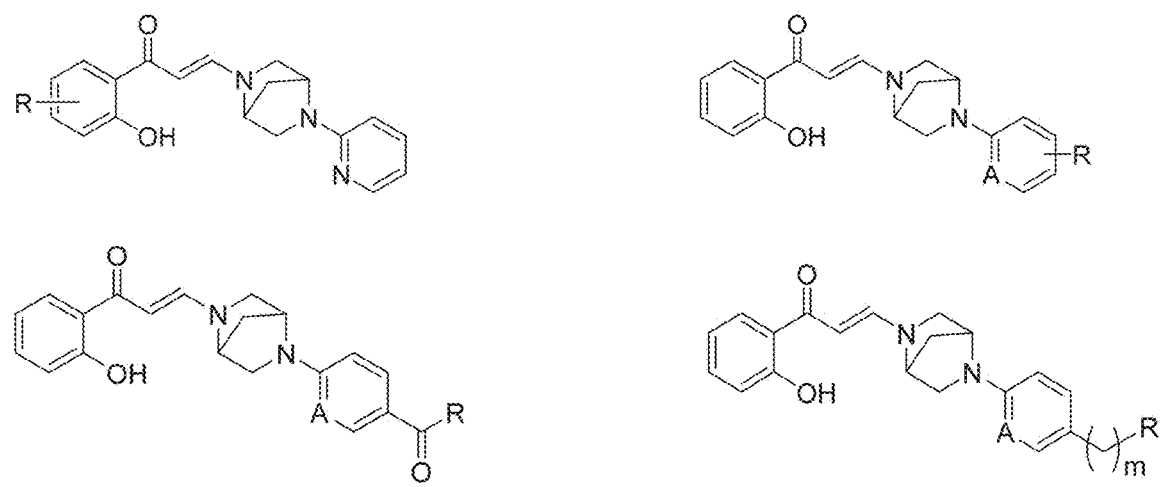
FIG. 3SSS

FIG. 3TTT
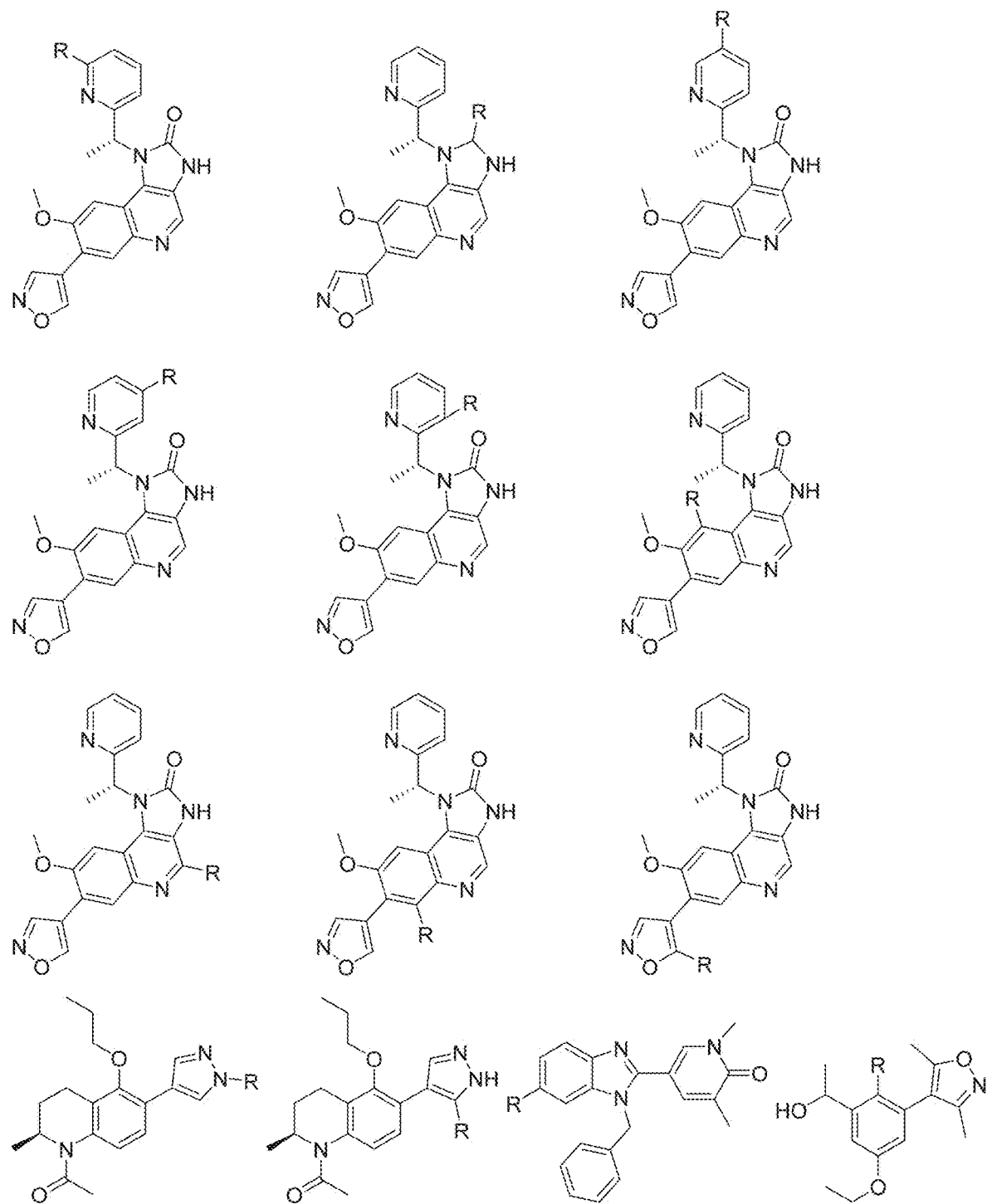

FIG. 3UUU
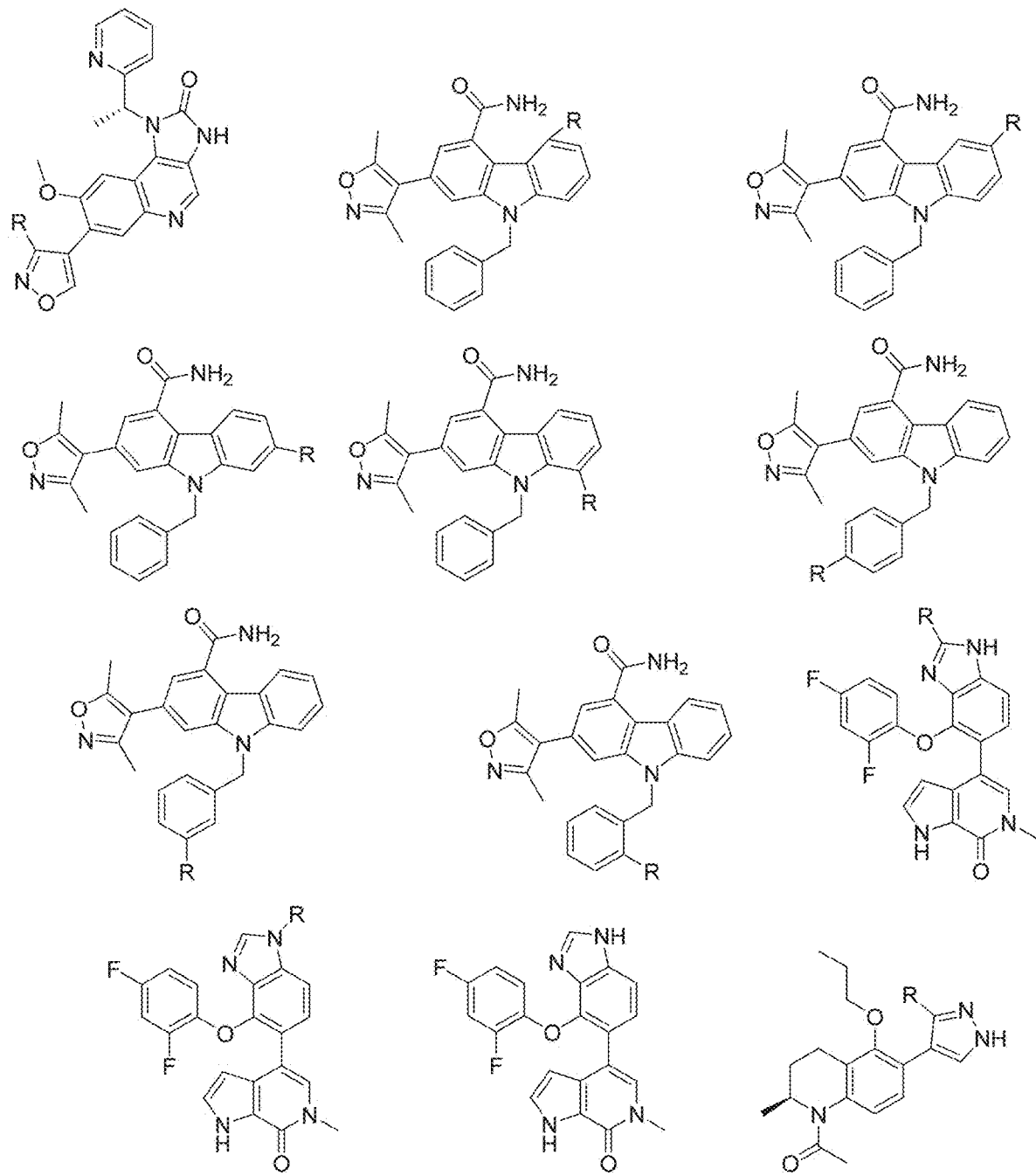

FIG. 3VVV
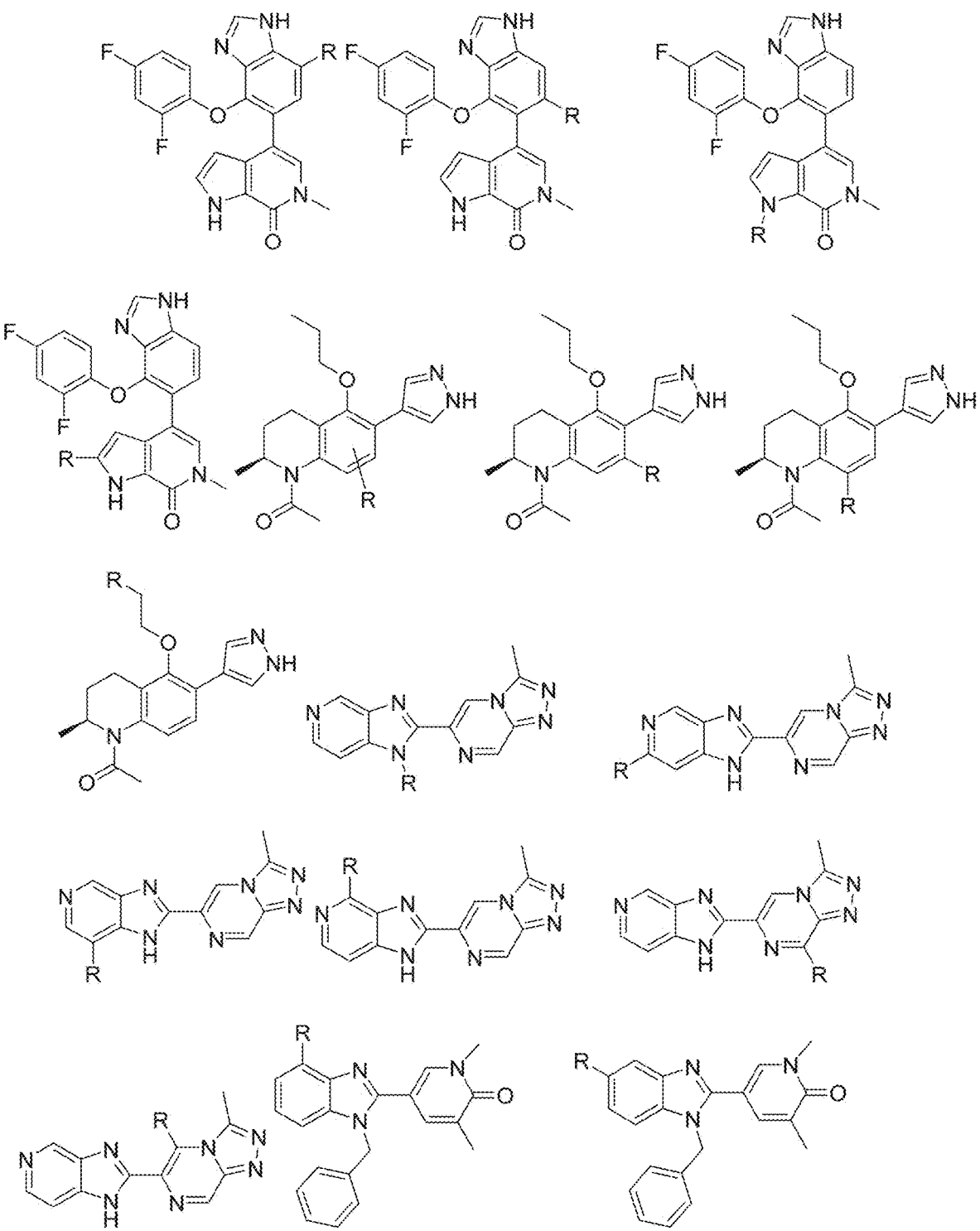

FIG. 3WWW
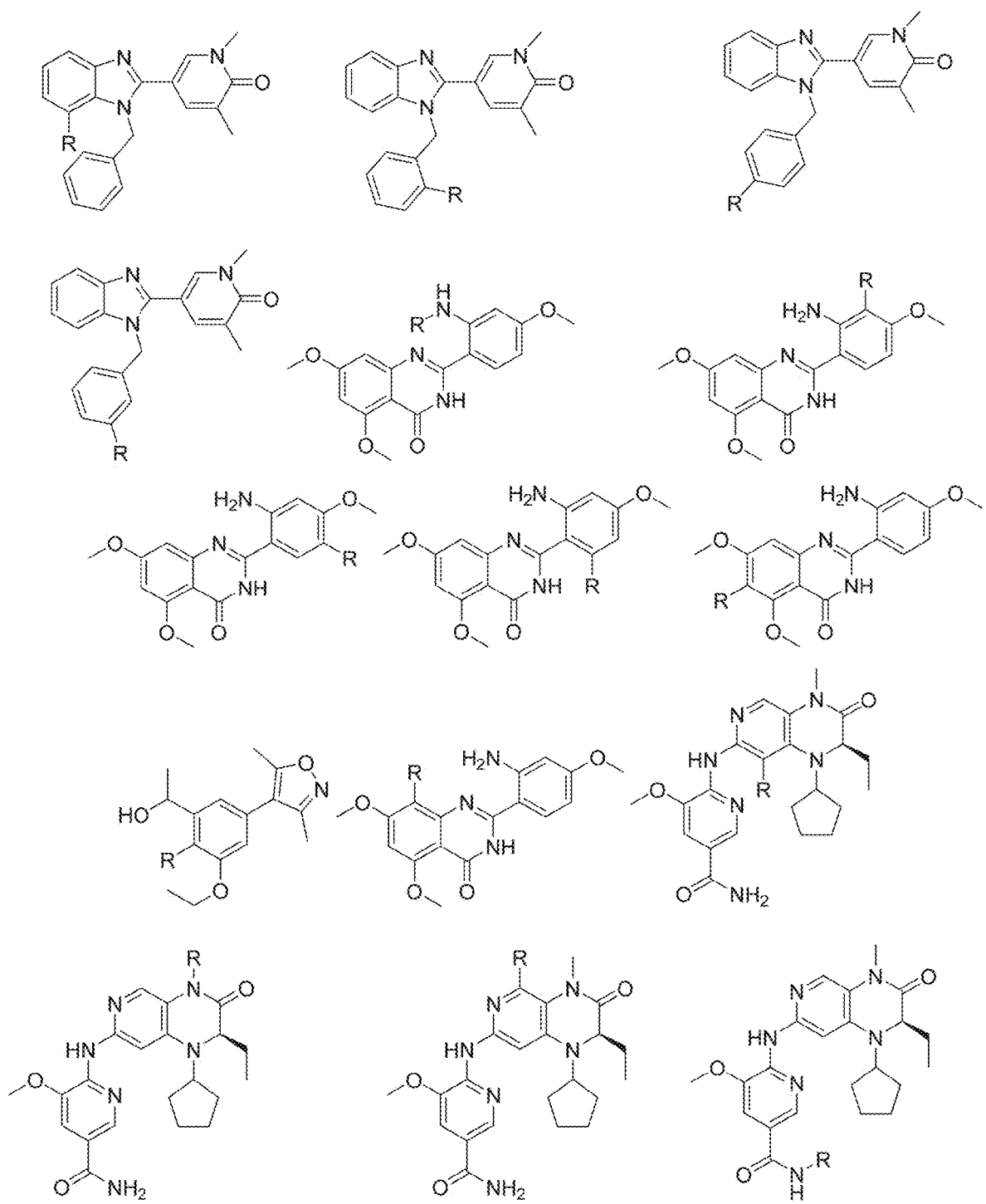

FIG. 3XXX
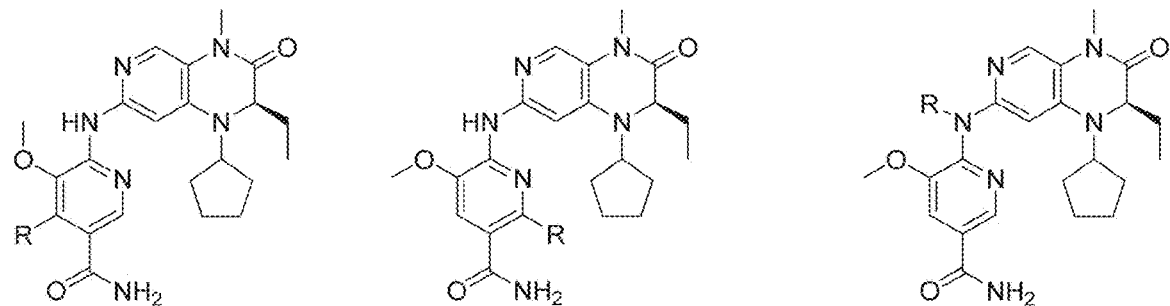
FIG. 3YYY
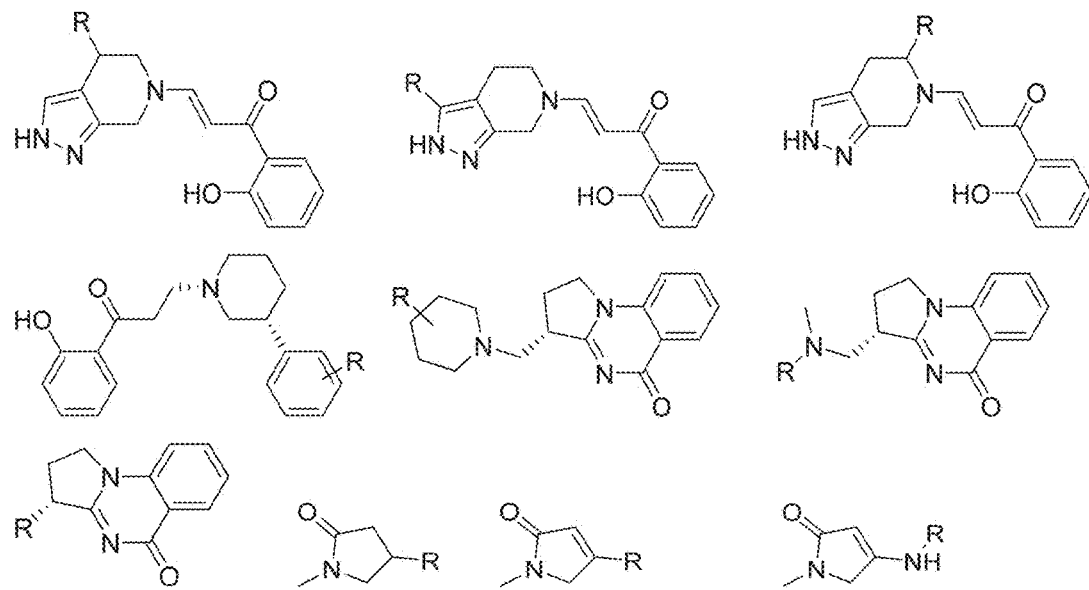
FIG. 3ZZZ
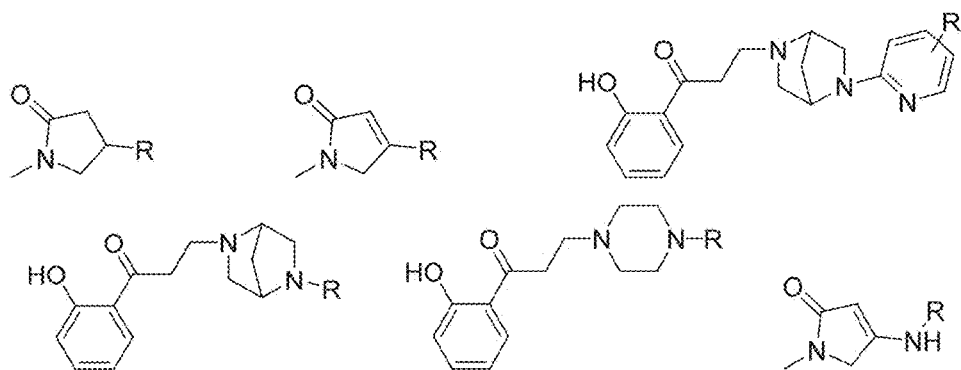

FIG. 3AAAA
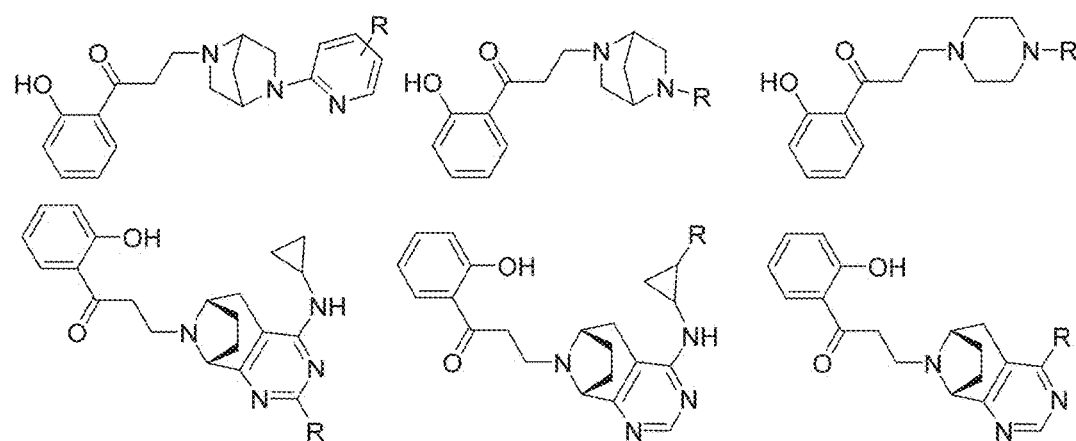
FIG. 3BBBB
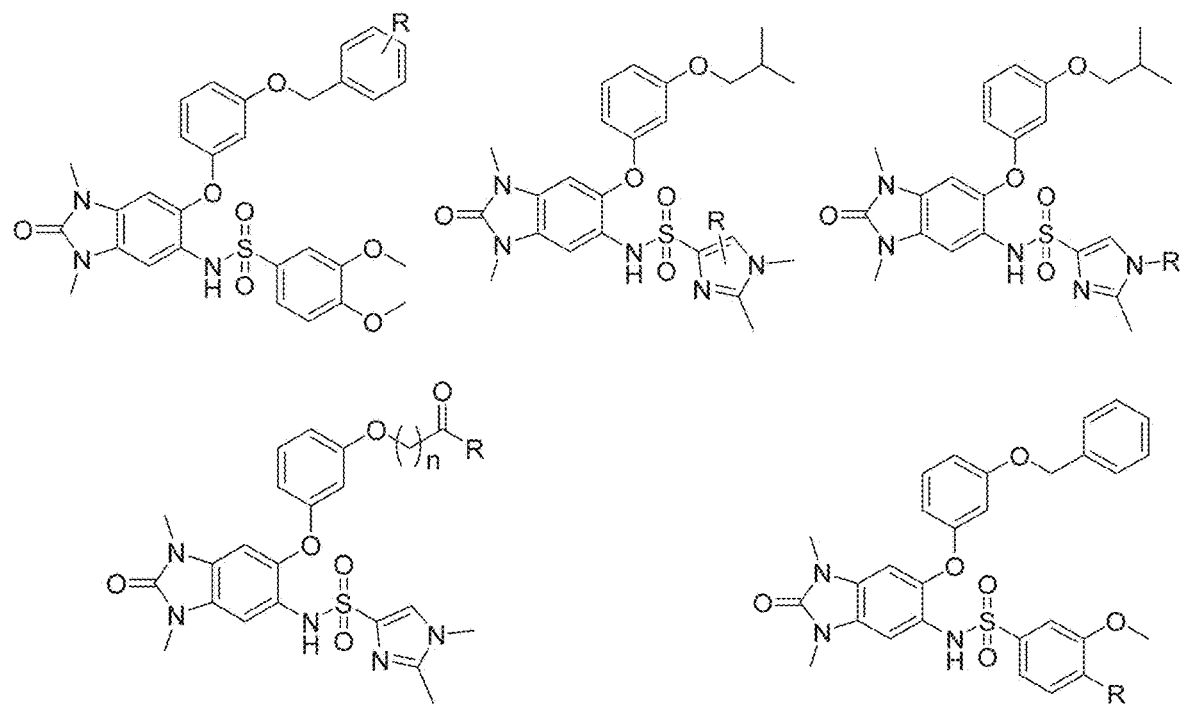

FIG. 3CCCC
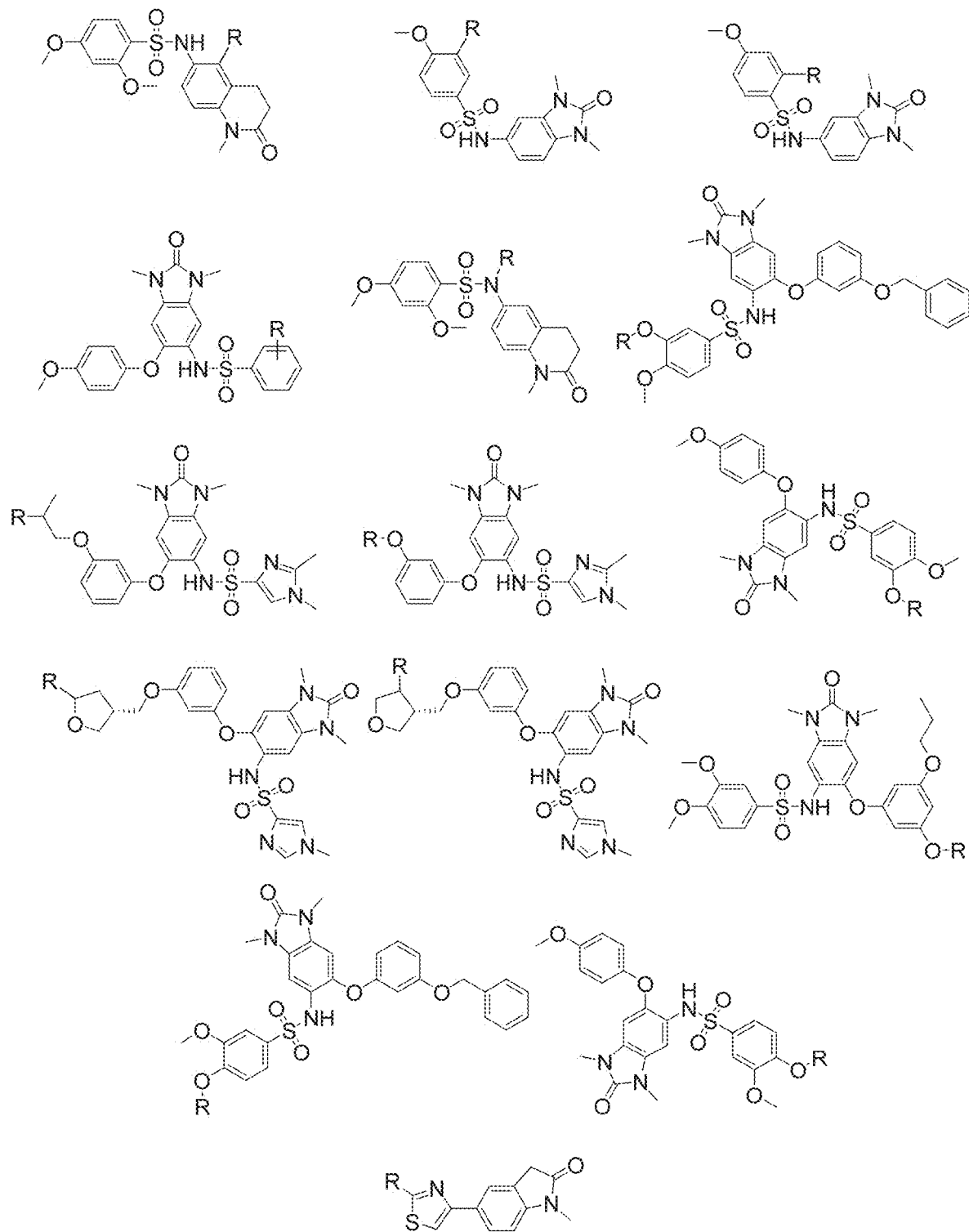

FIG. 3DDDD
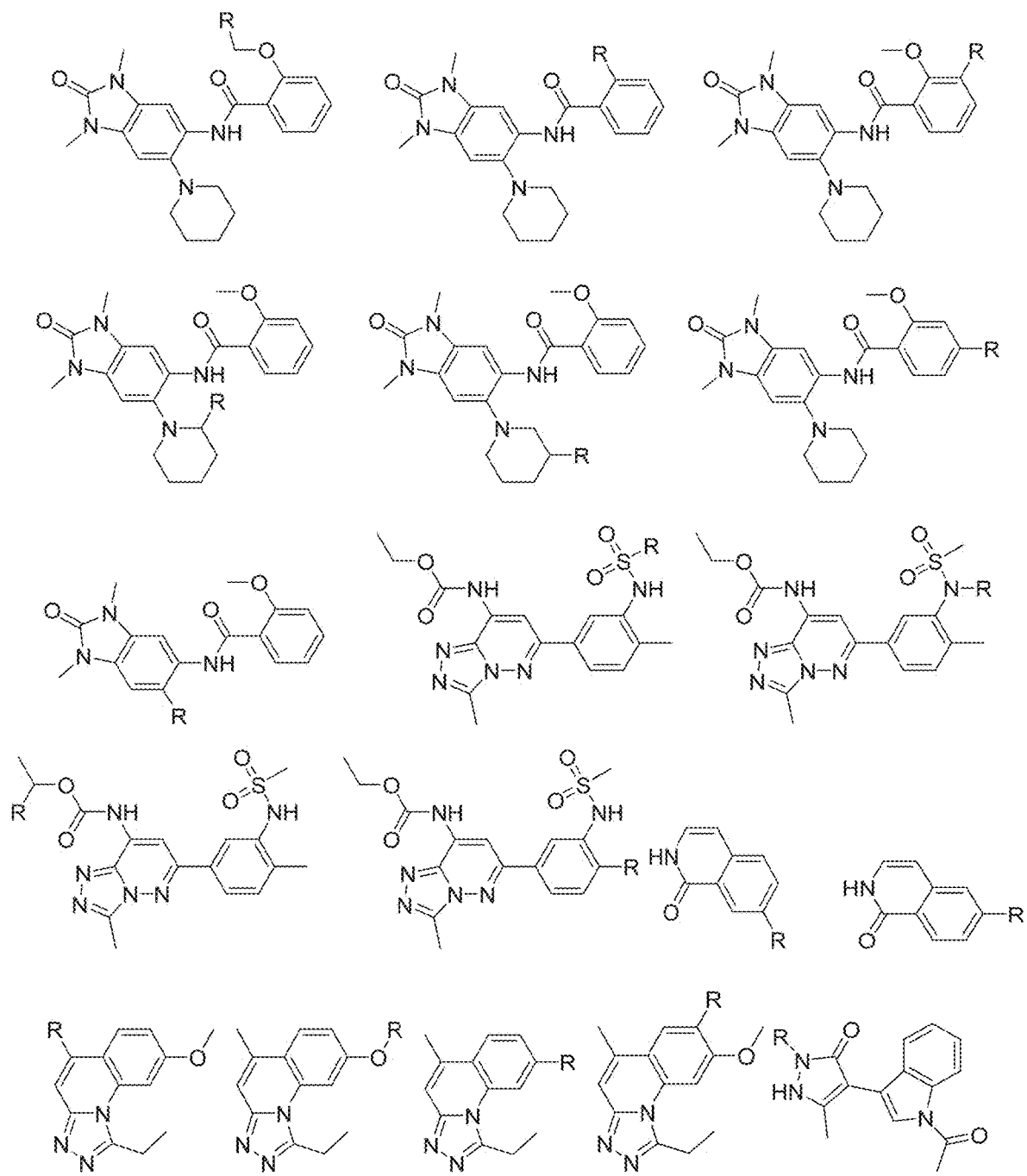

FIG. 3EEEE
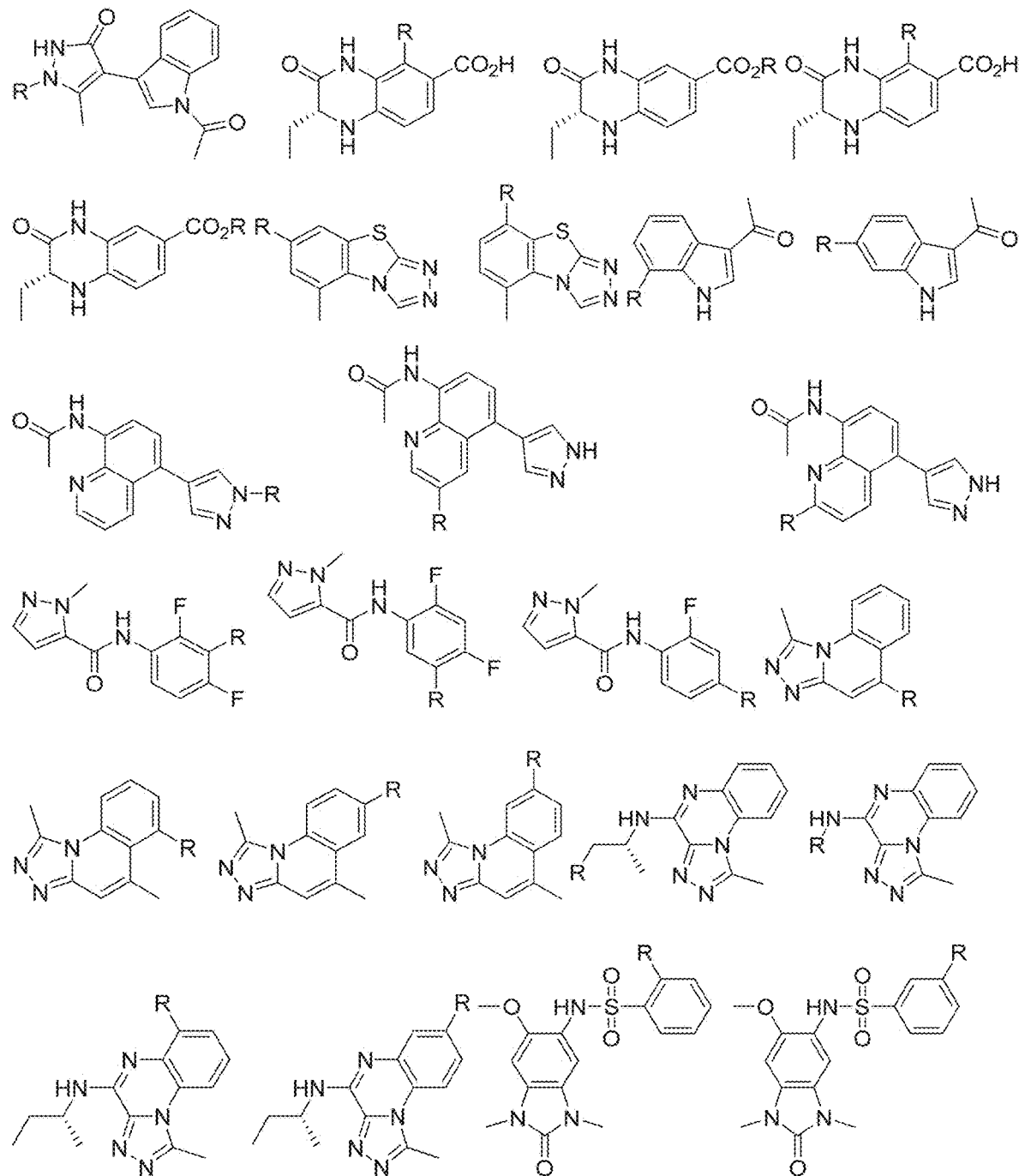

FIG. 3FFFF
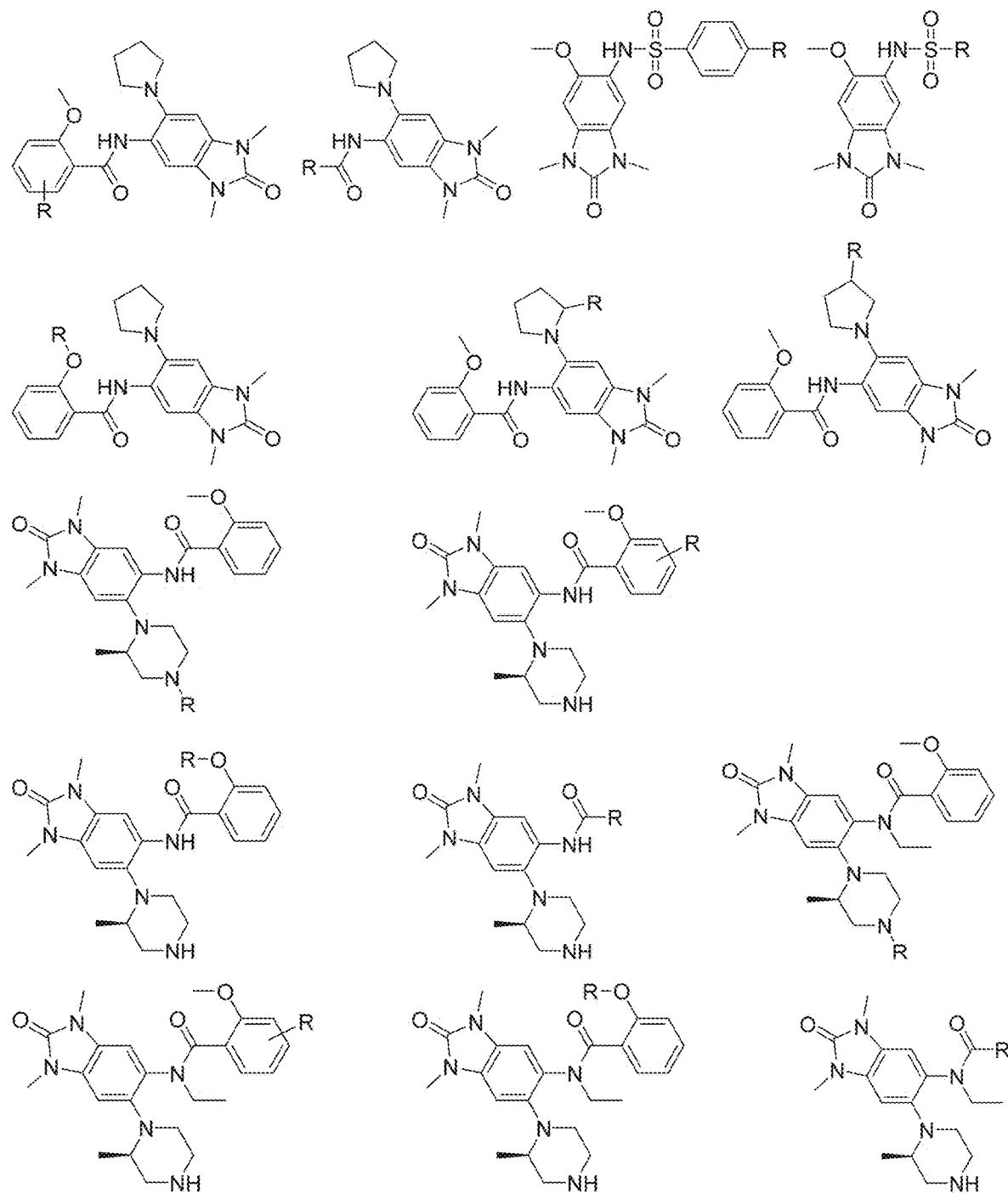

FIG. 3GGGG
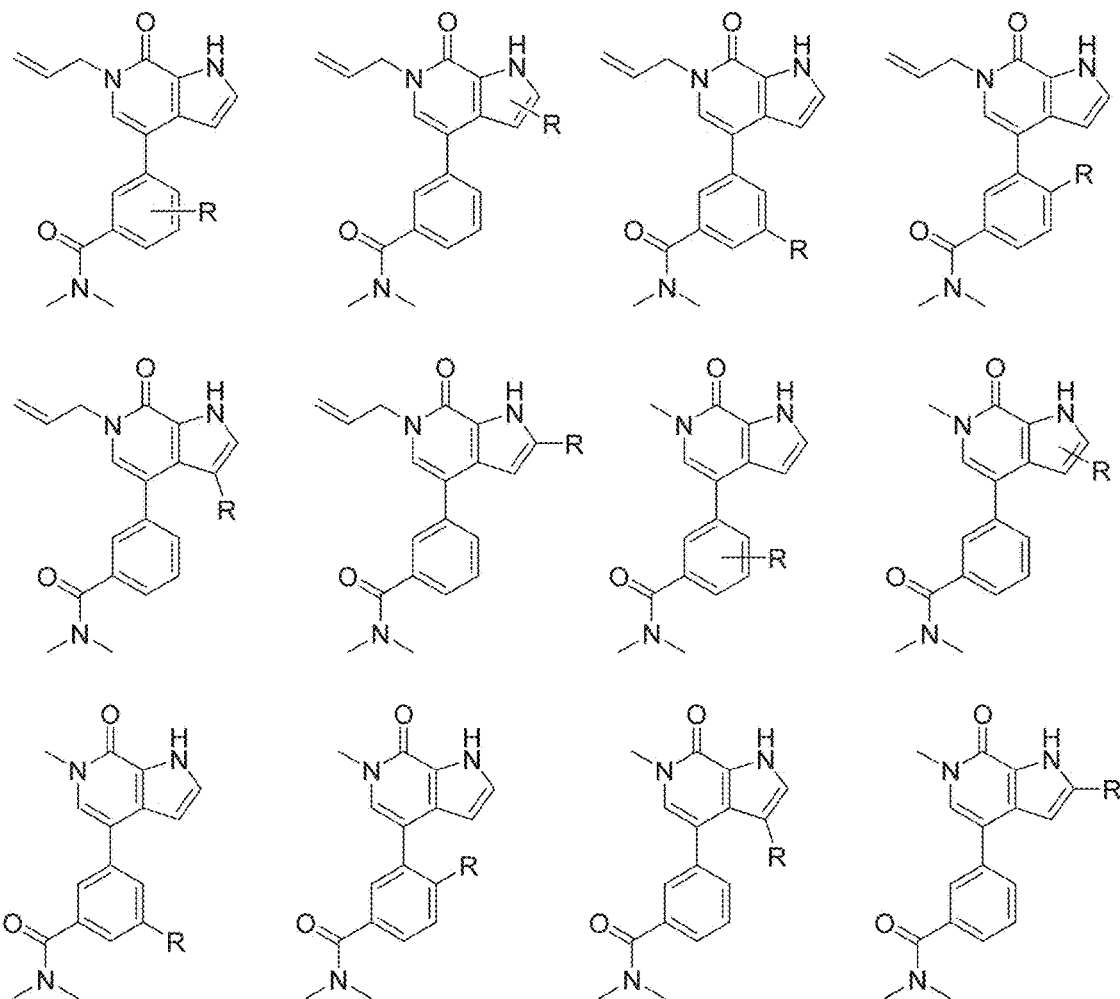
FIG. 3HHHH
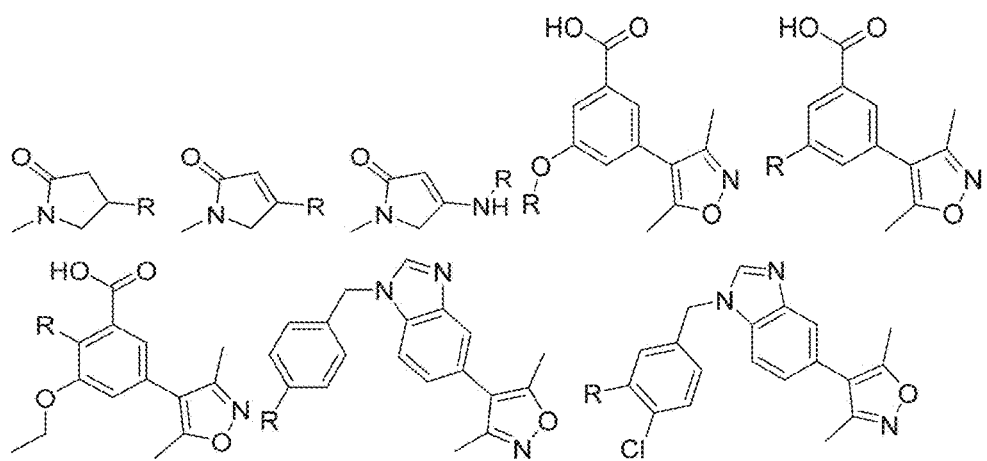

FIG. 3IIII
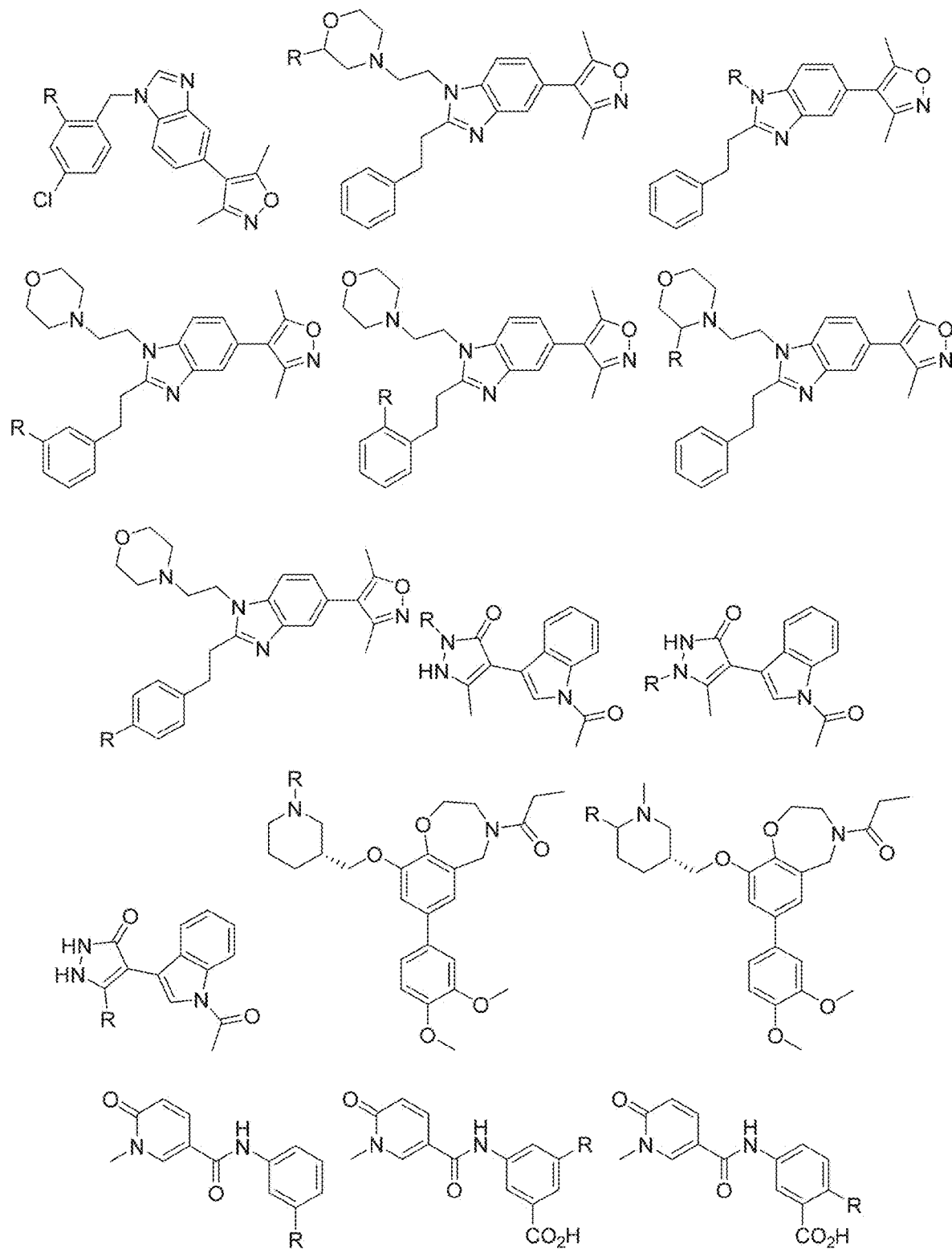

FIG. 3JJJJ
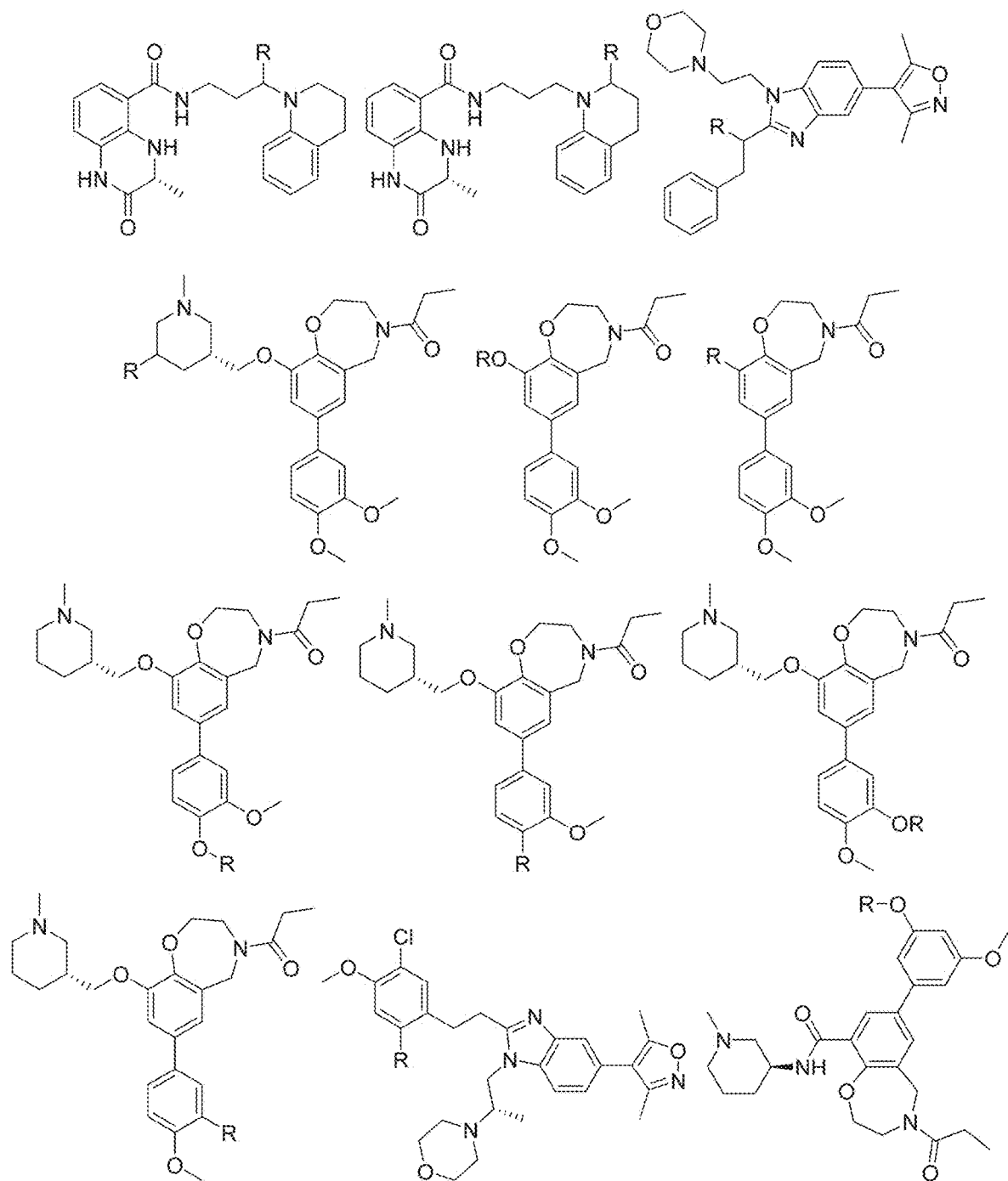

FIG. 3KKKK
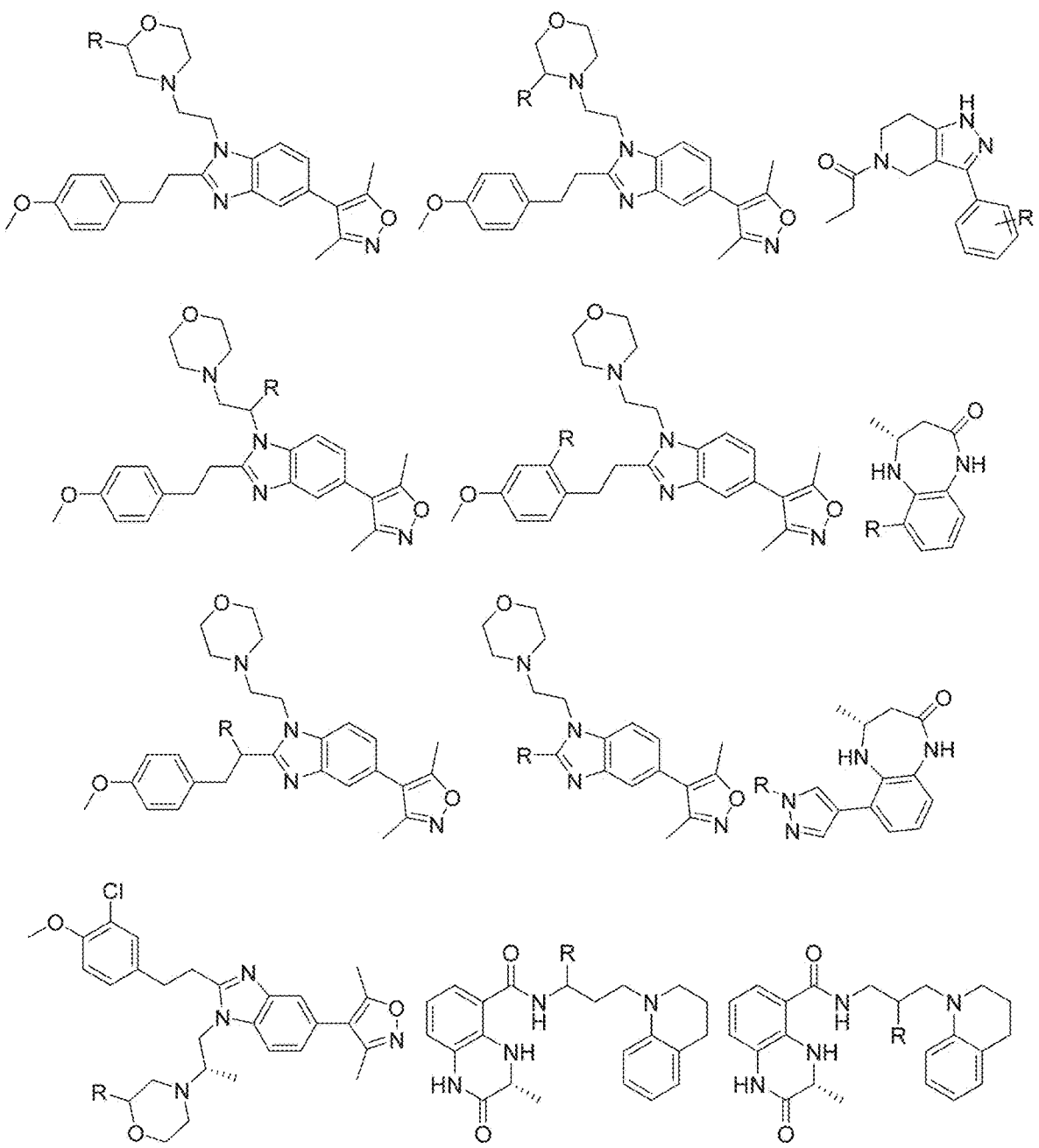

FIG. 3LLLL
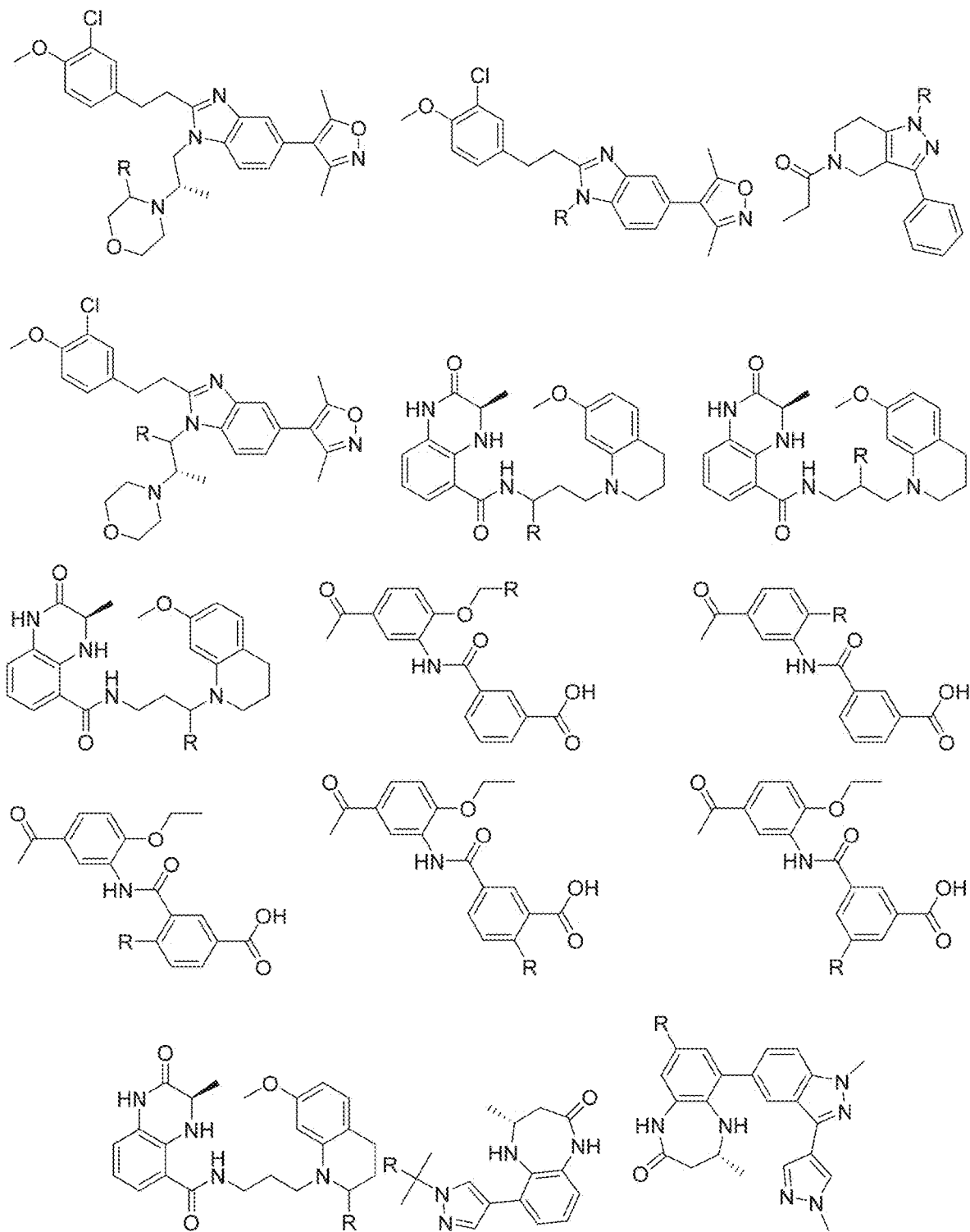

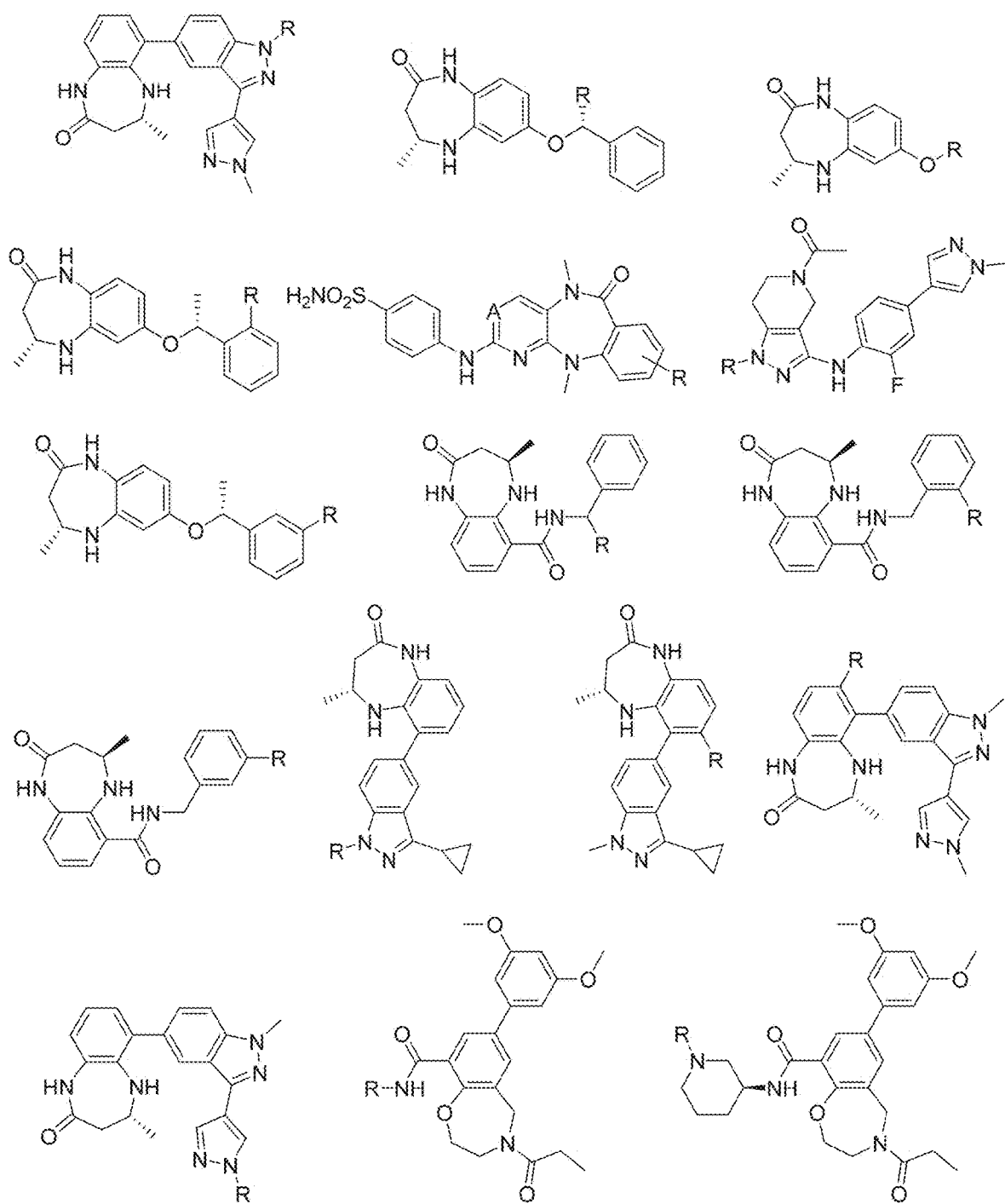
FIG. 3MMMM

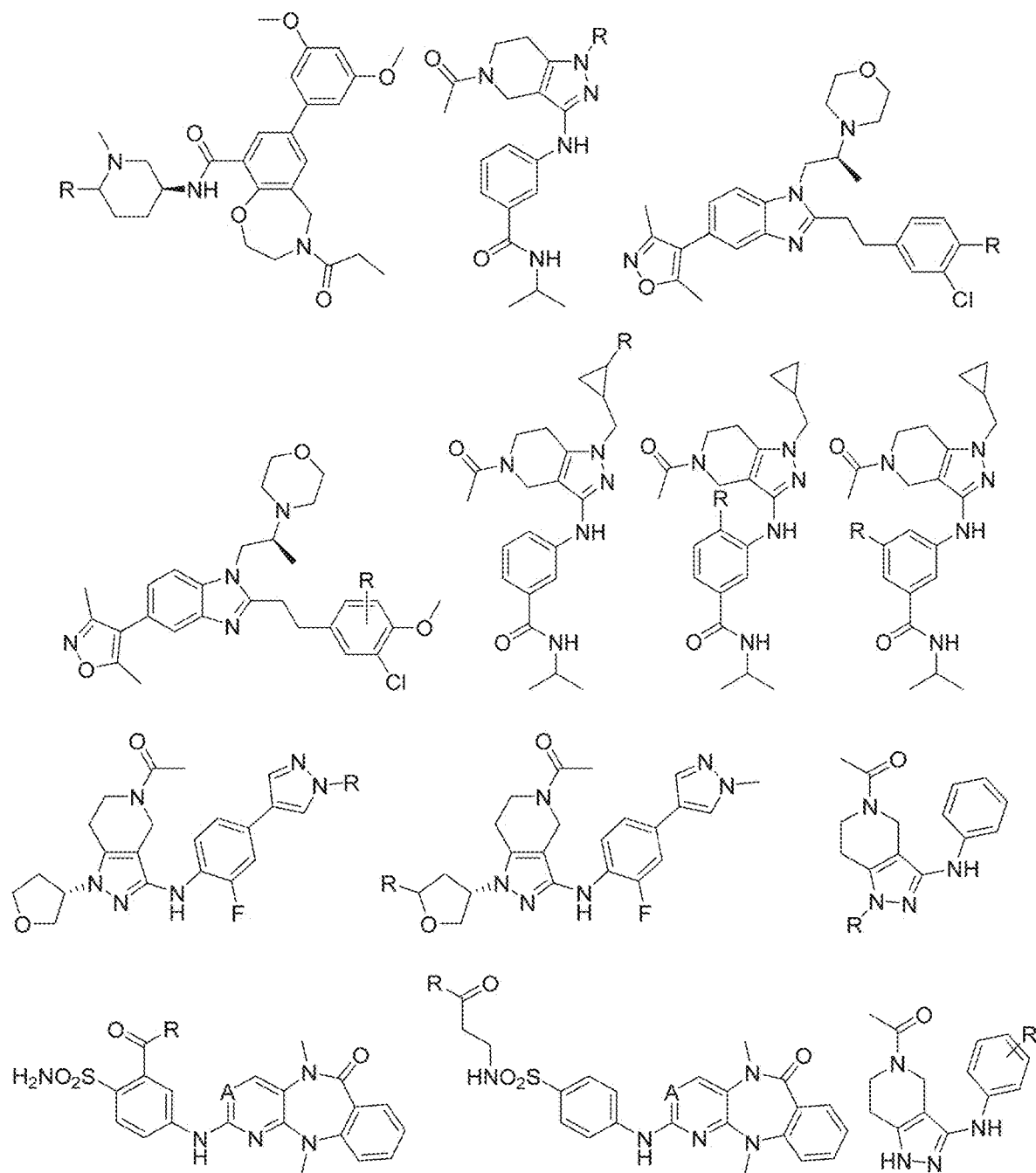
FIG. 3NNNN

FIG. 3OOOO
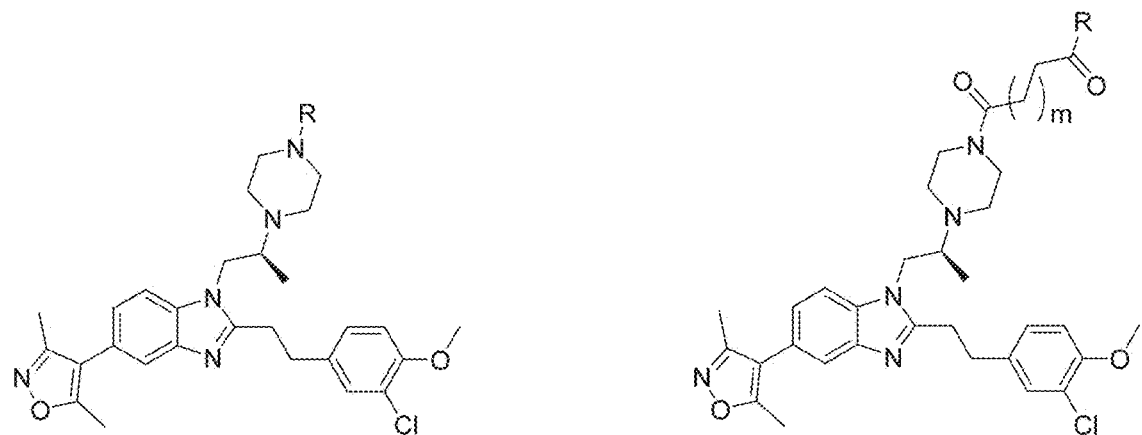
FIG. 3PPPP
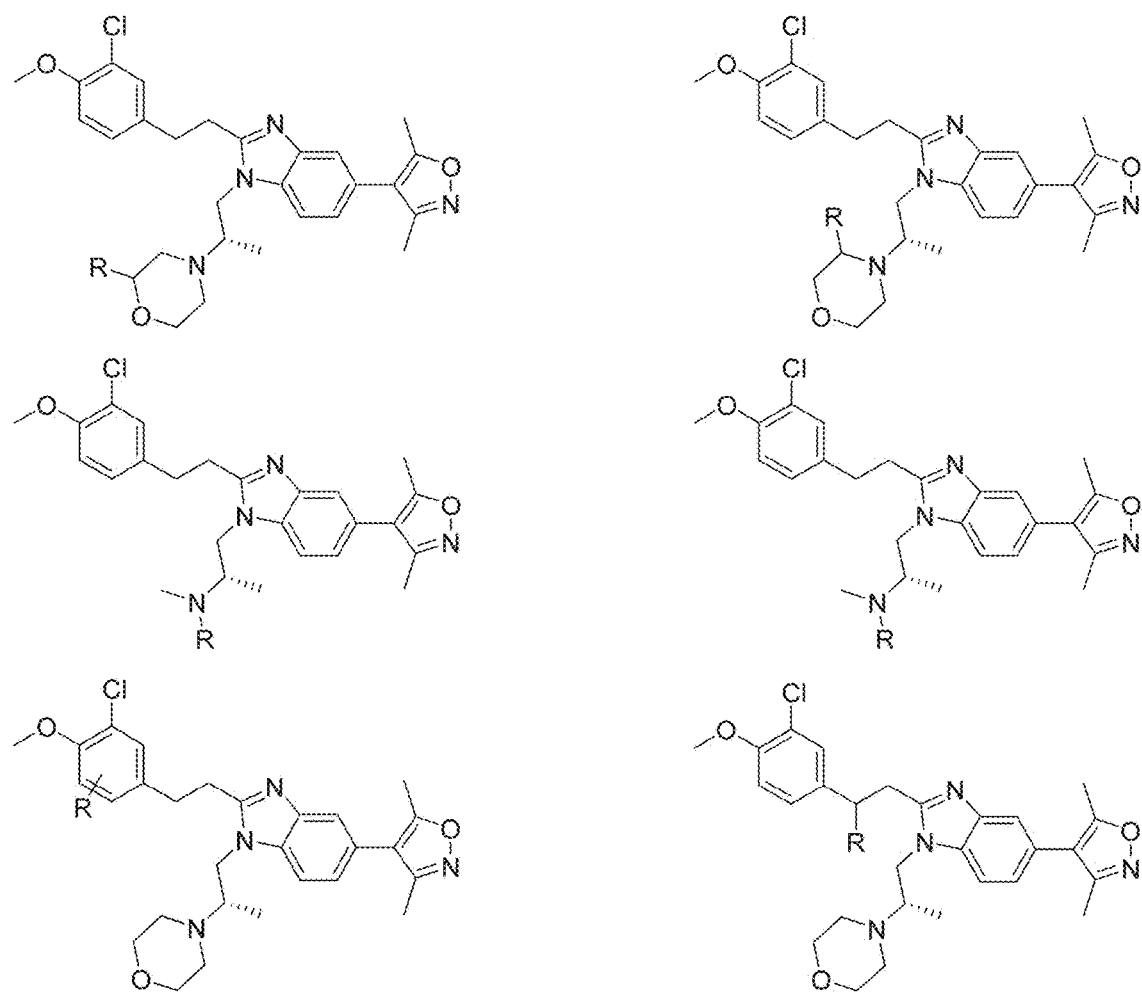

FIG. 3QQQQ
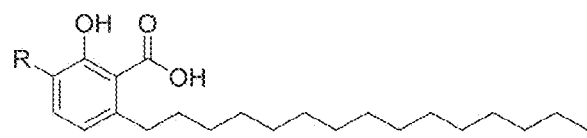
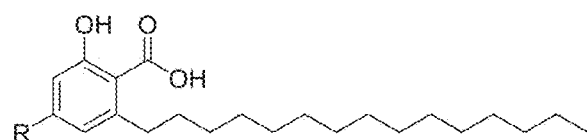
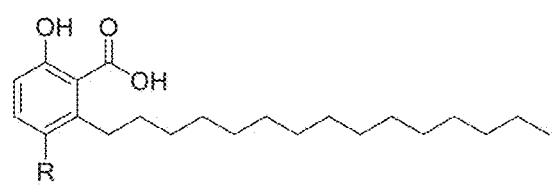
FIG. 3RRRR
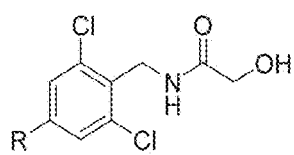 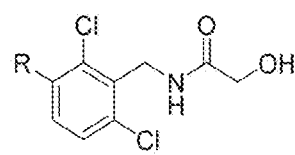 
 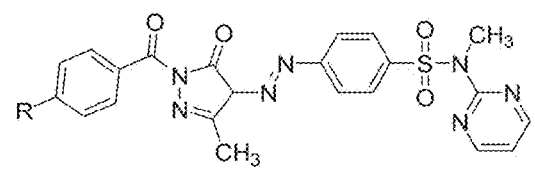
FIG. 3SSSS
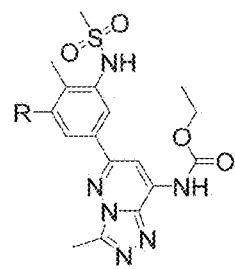 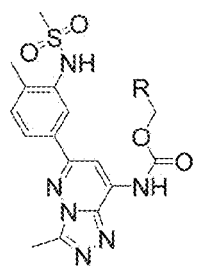 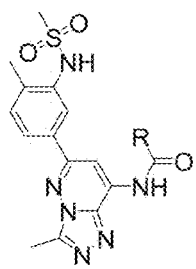 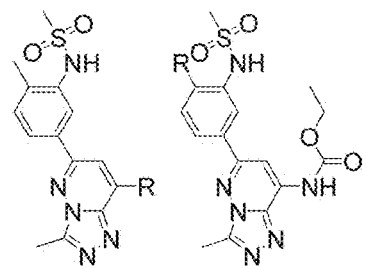

FIG. 3TTTT
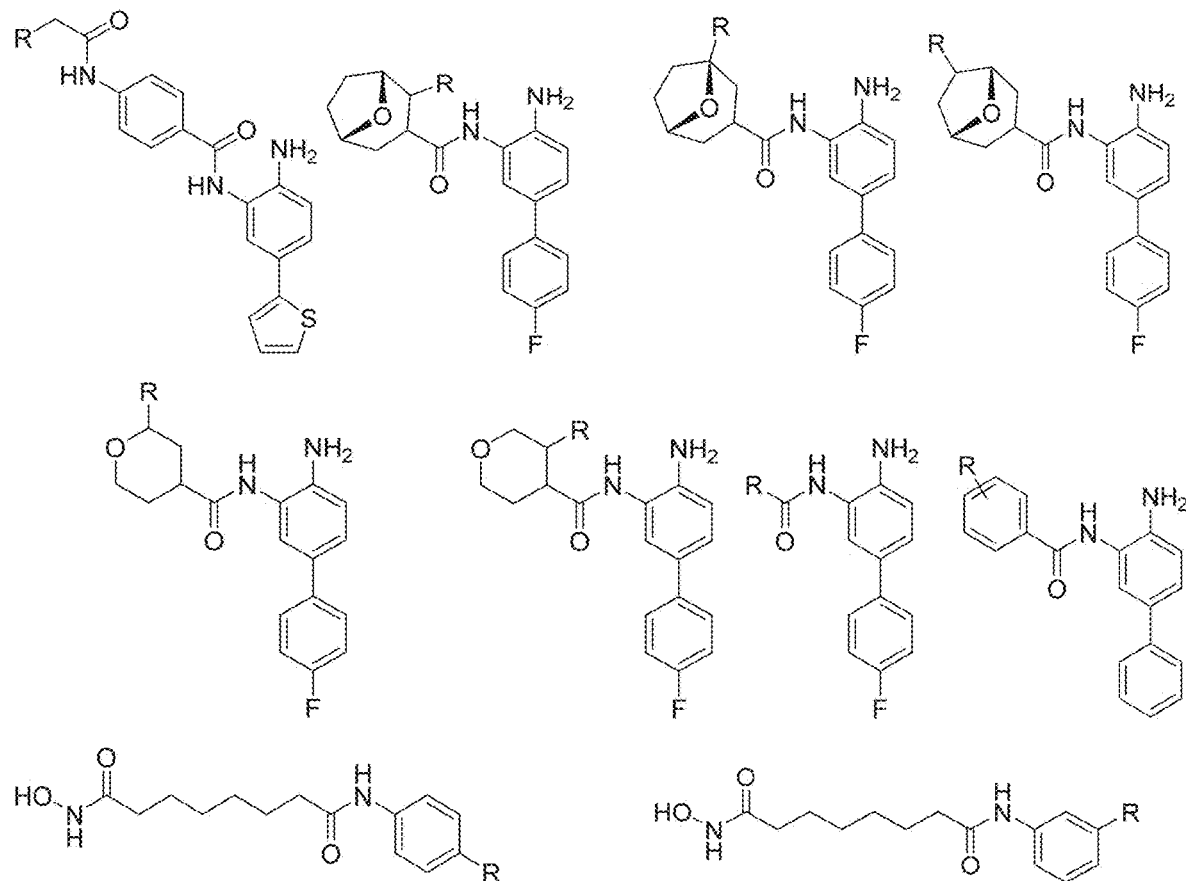
FIG. 3UUUU
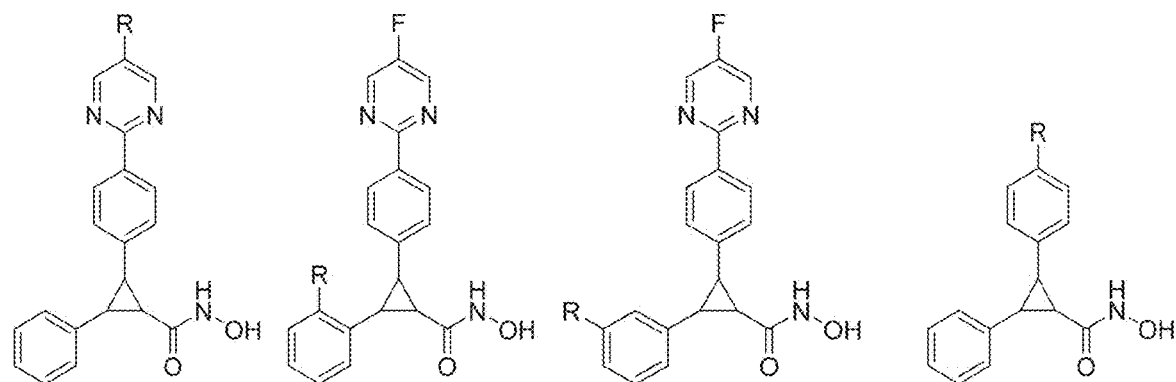

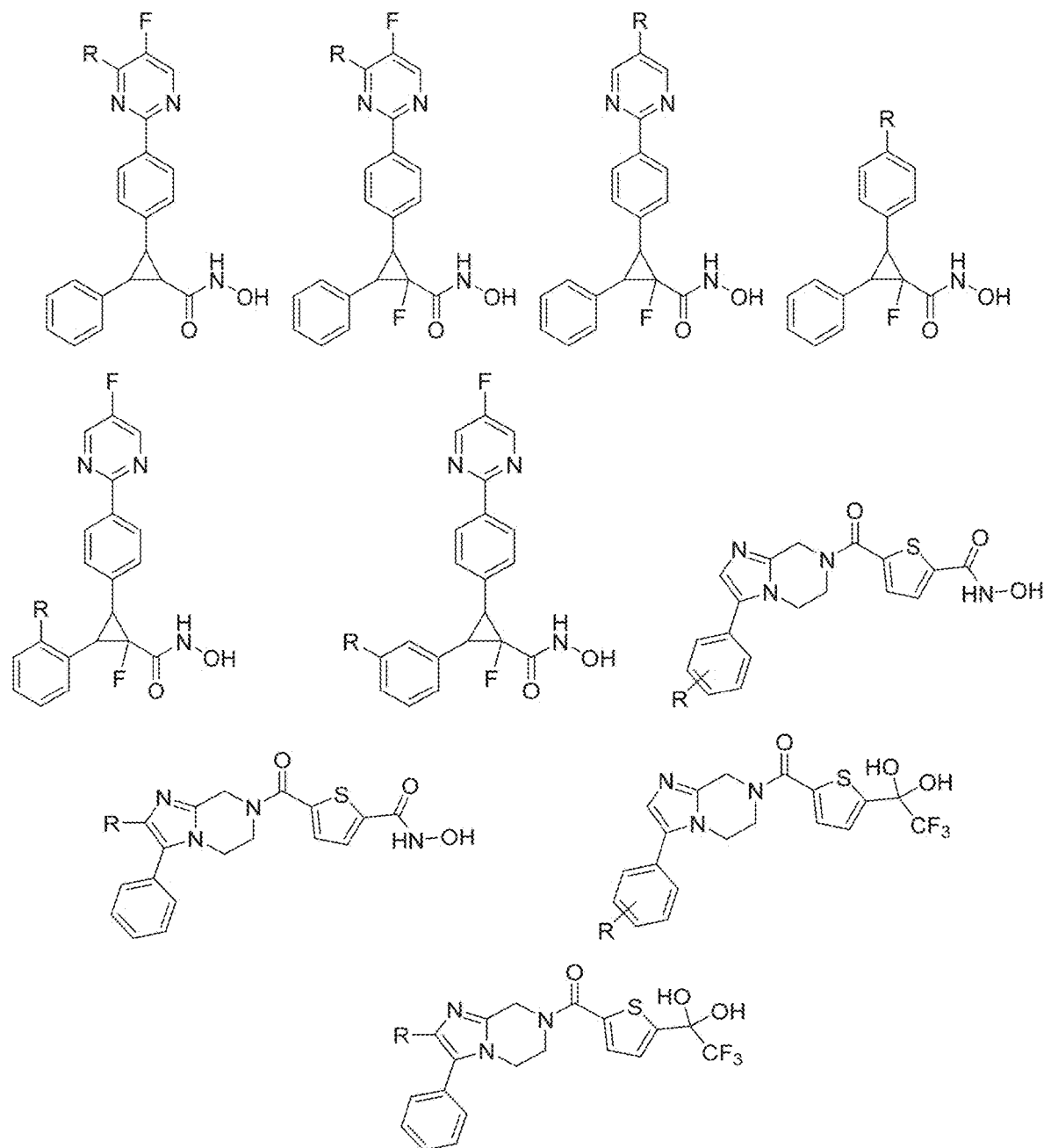
FIG. 3VVVV

FIG. 3WWWW
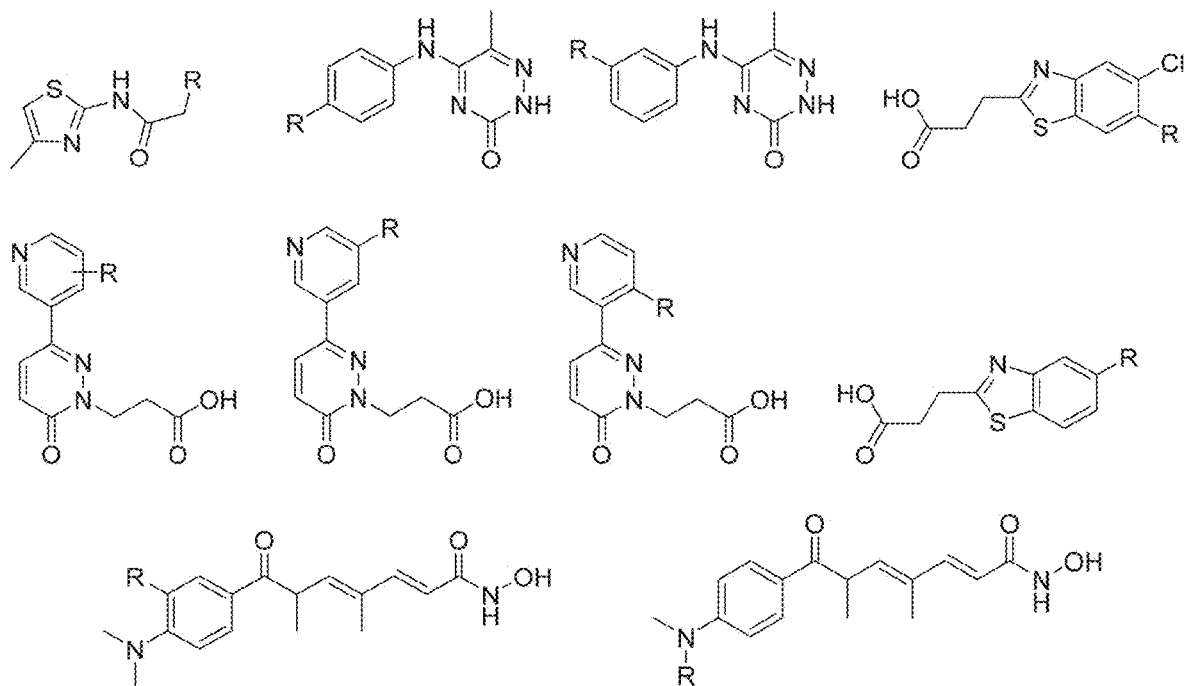
FIG. 3XXXX
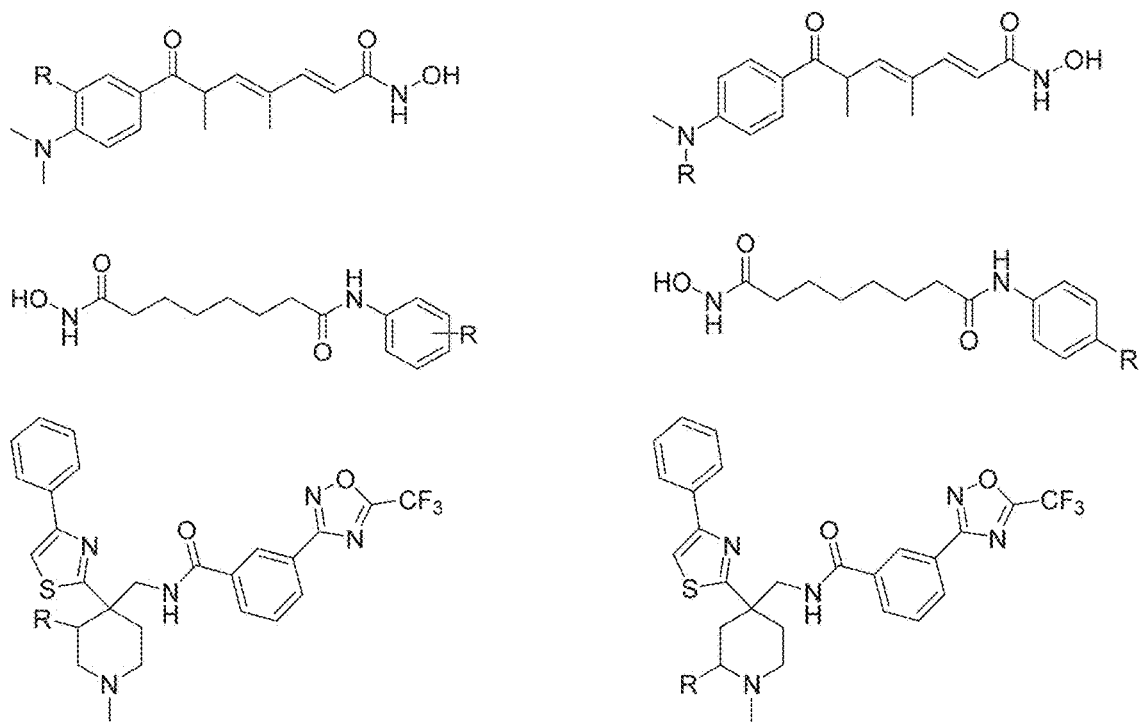

FIG. 3YYYY
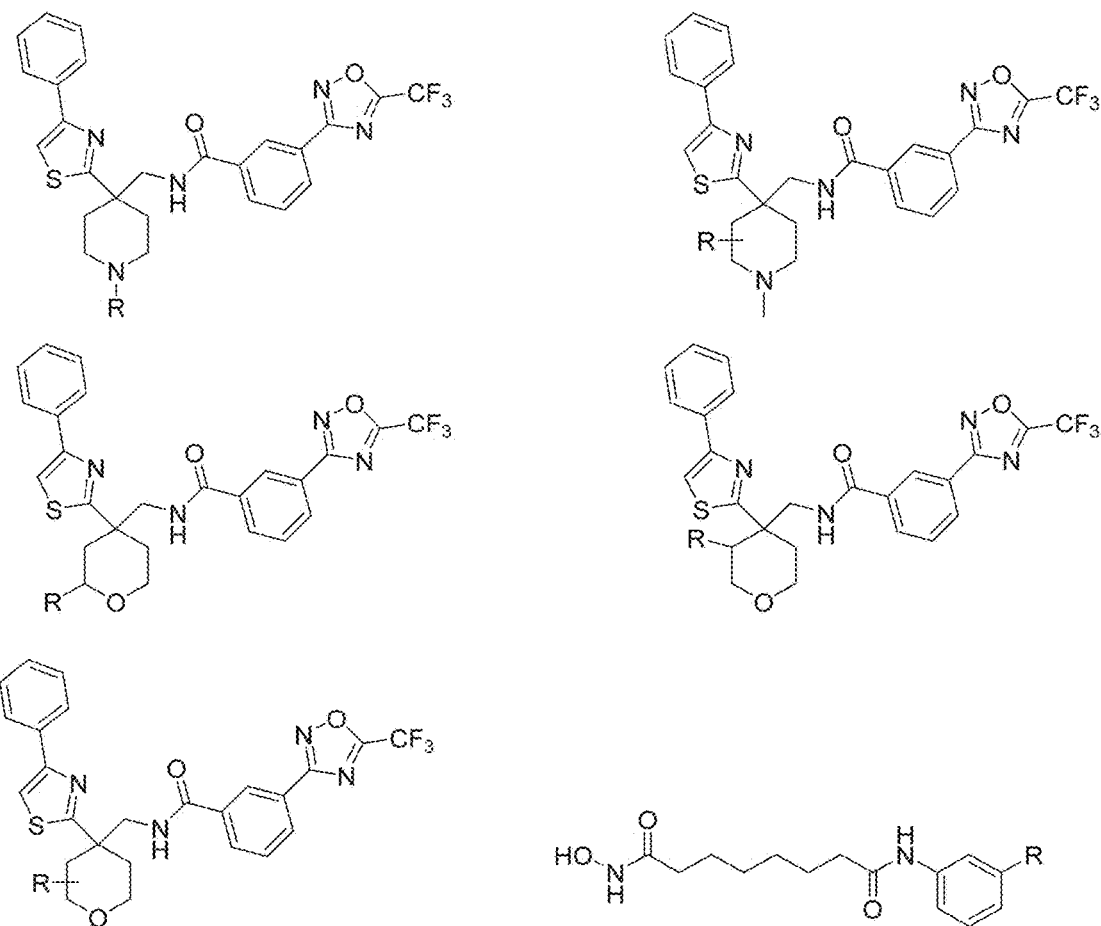
FIG. 3ZZZZ
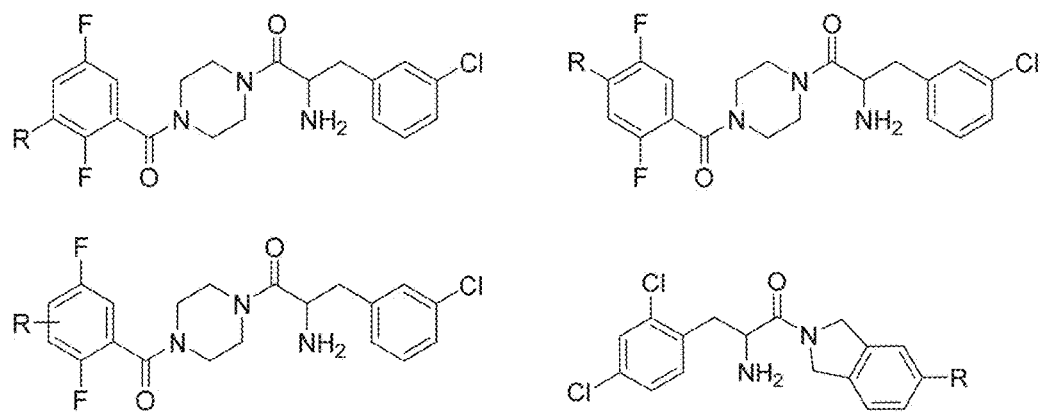

FIG. 3AAAAA
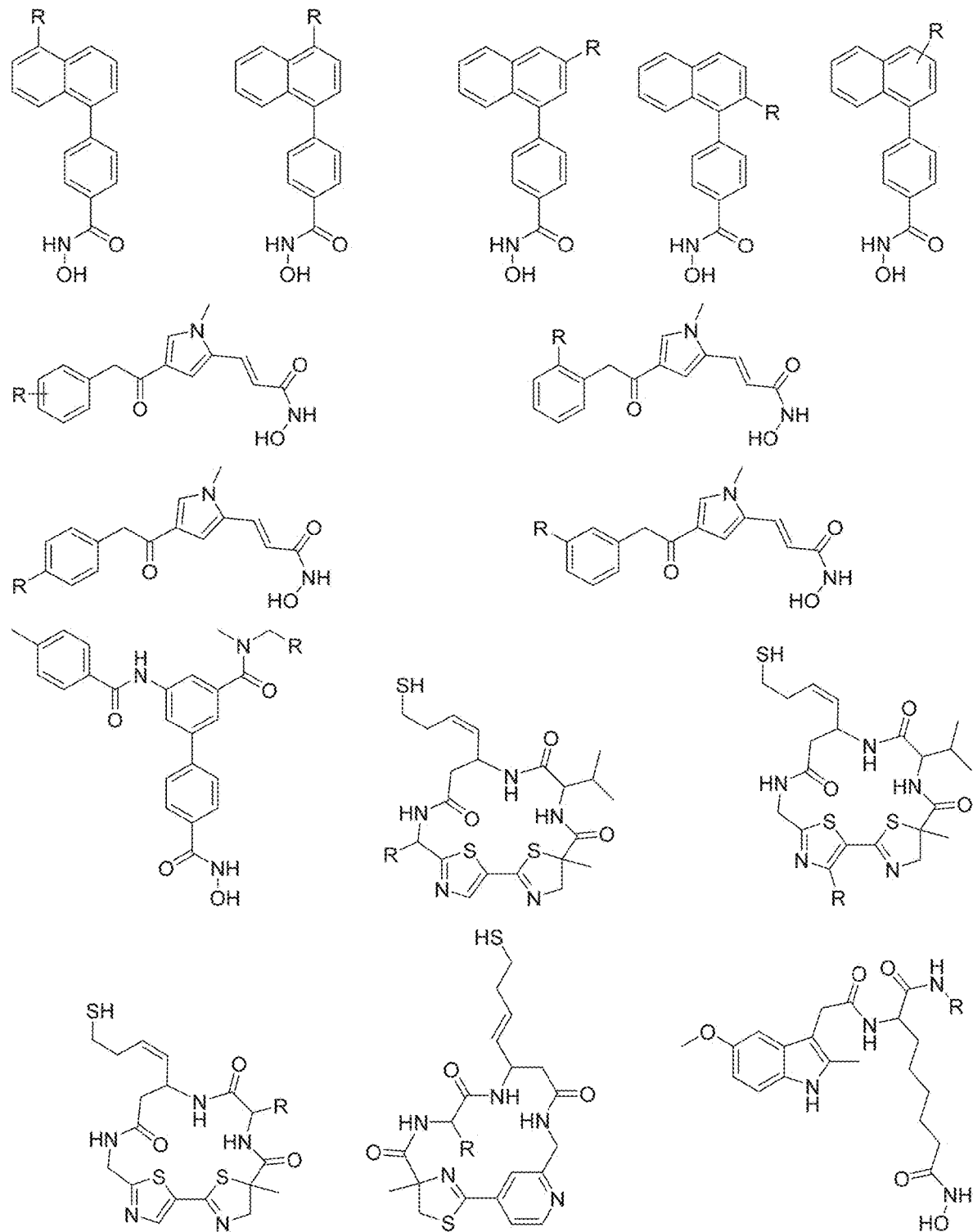

FIG. 3BBBBB
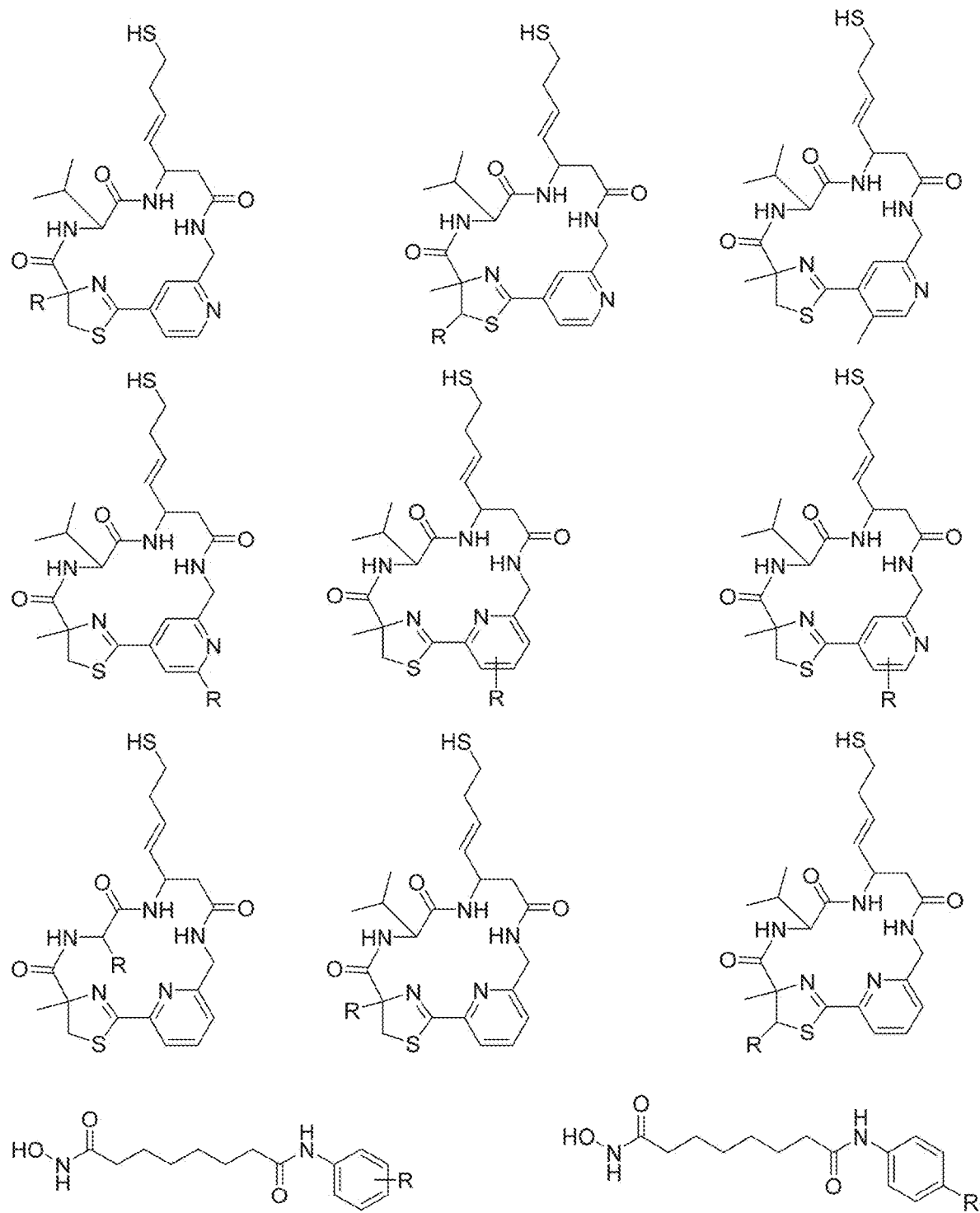

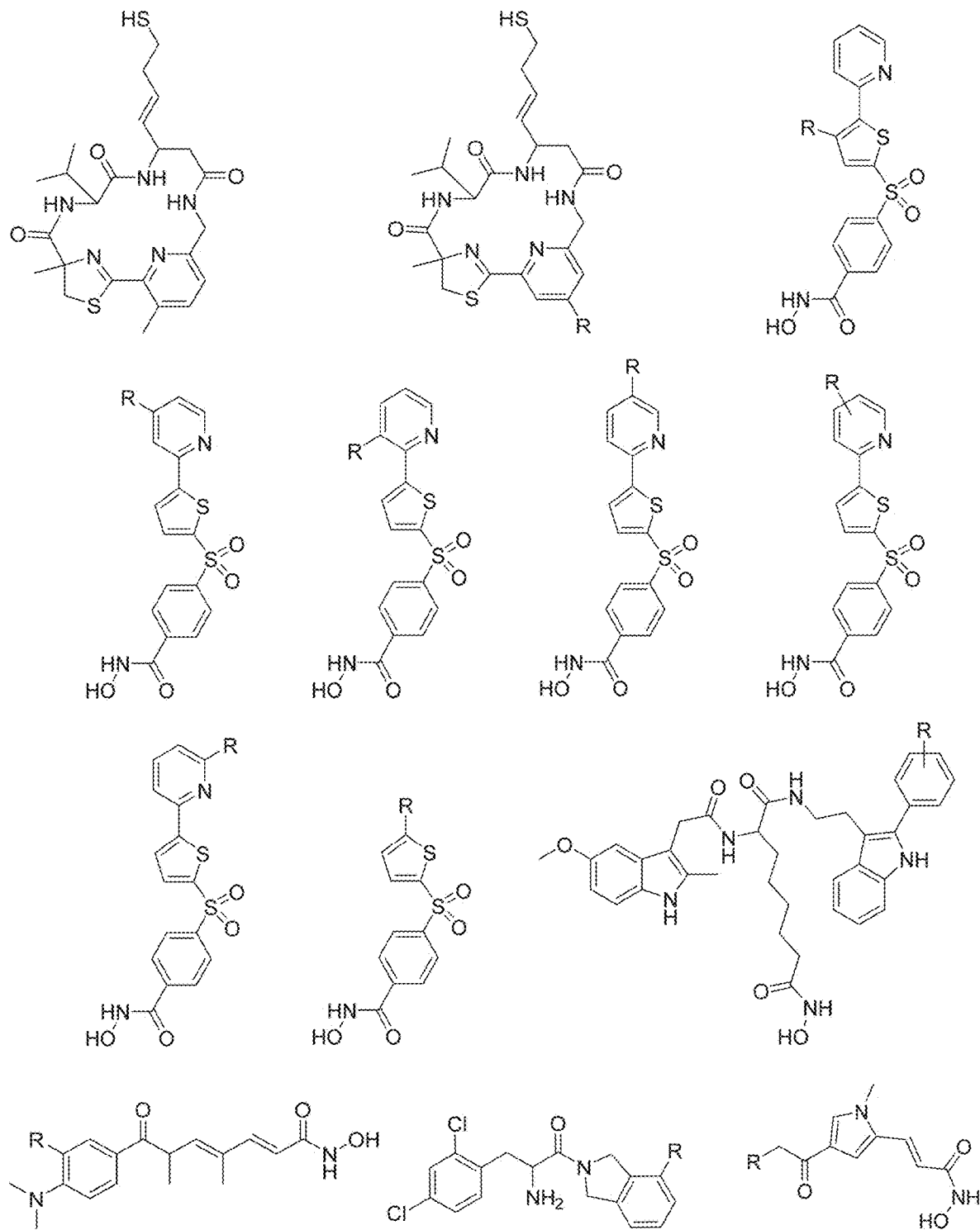
FIG. 3CCCCC

FIG. 3DDDDD
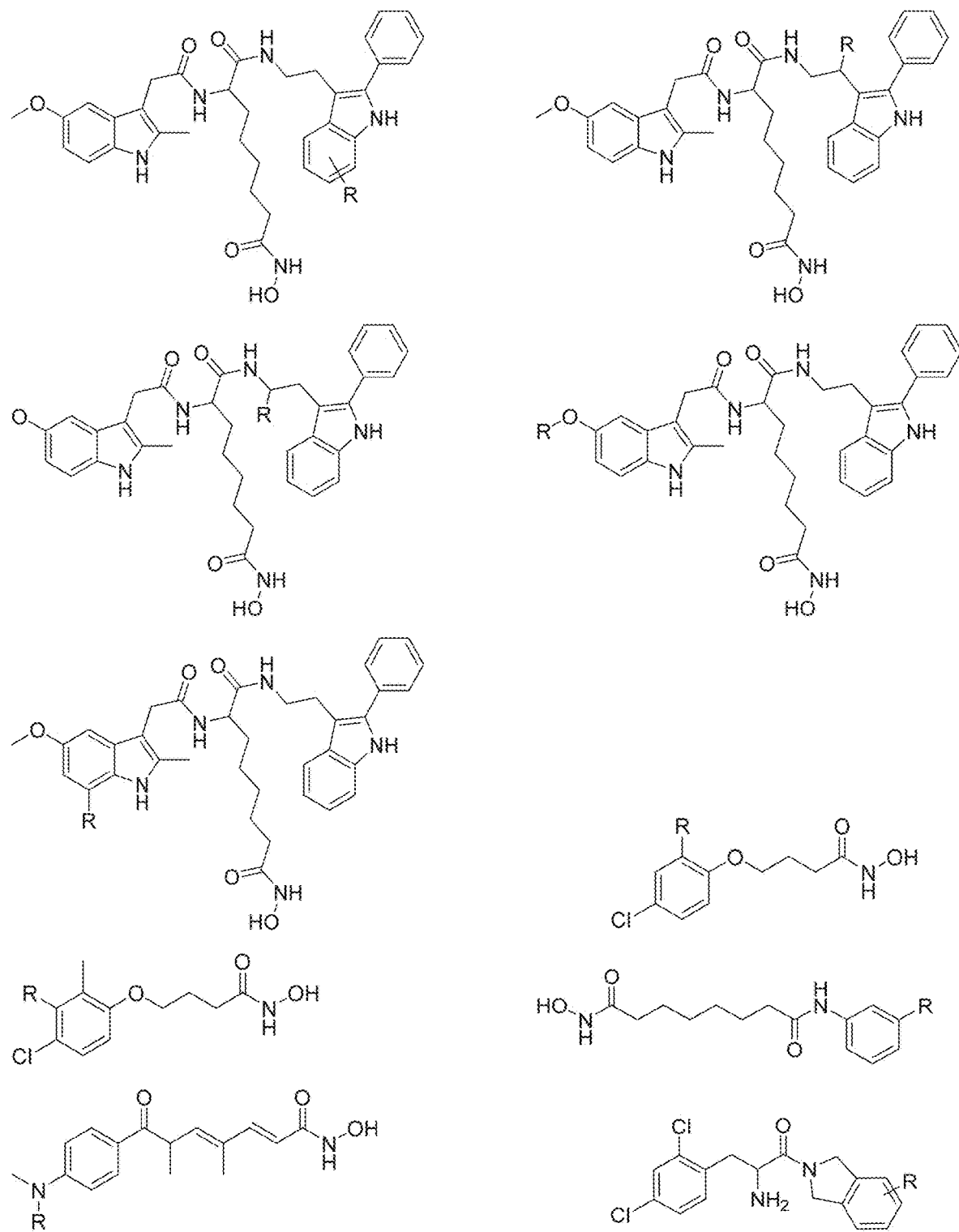

FIG. 3EEEEE
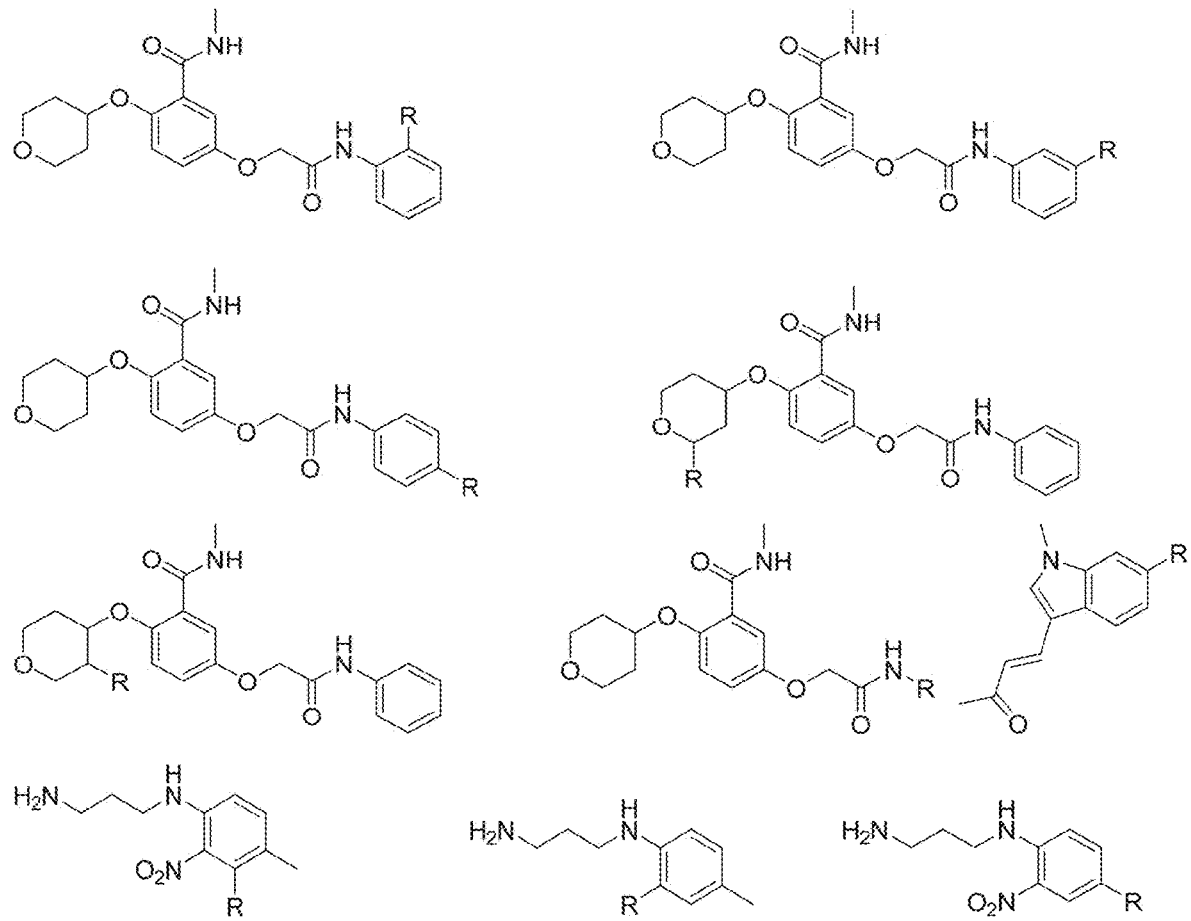
FIG. 3FFFFF
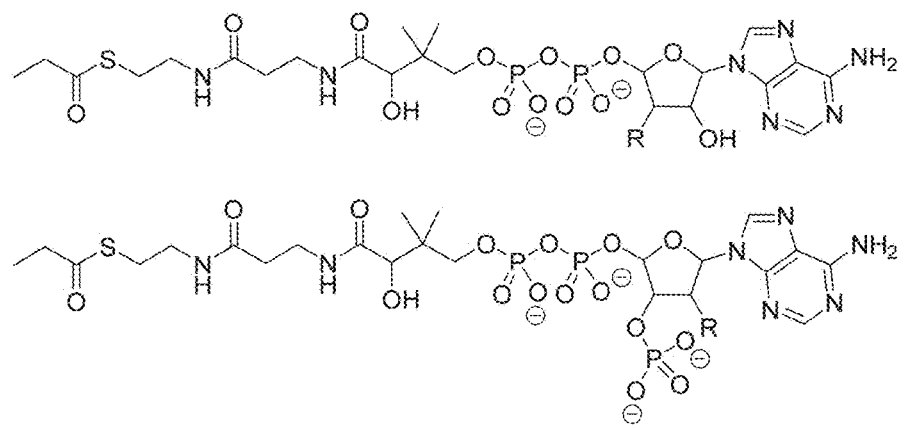

FIG. 3GGGGG
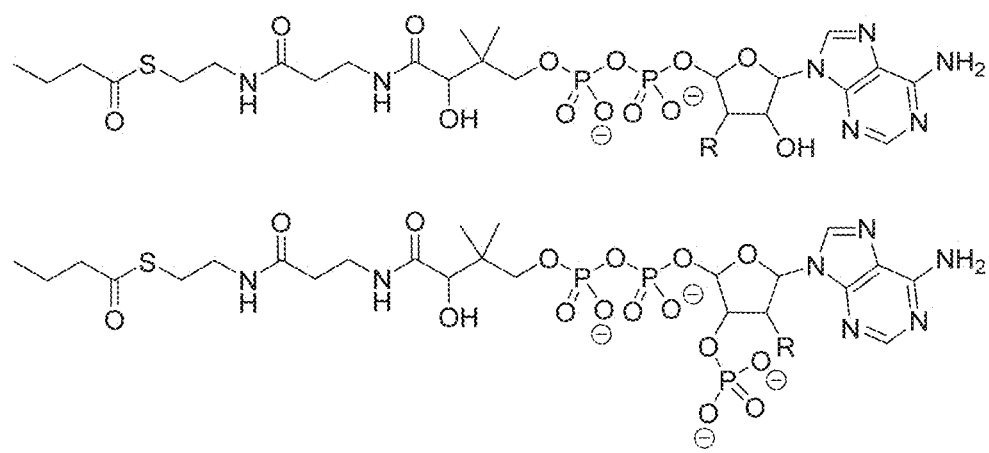
FIG. 3HHHHH
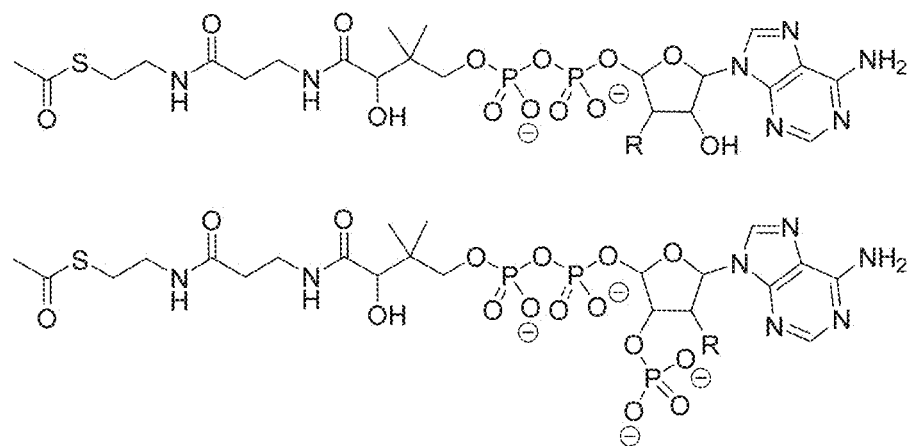
FIG. 3IIIII
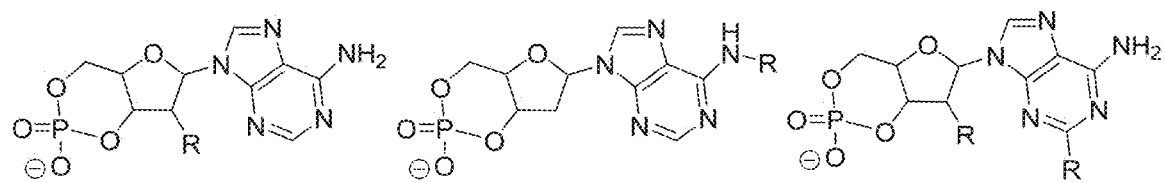

FIG. 3JJJJJ
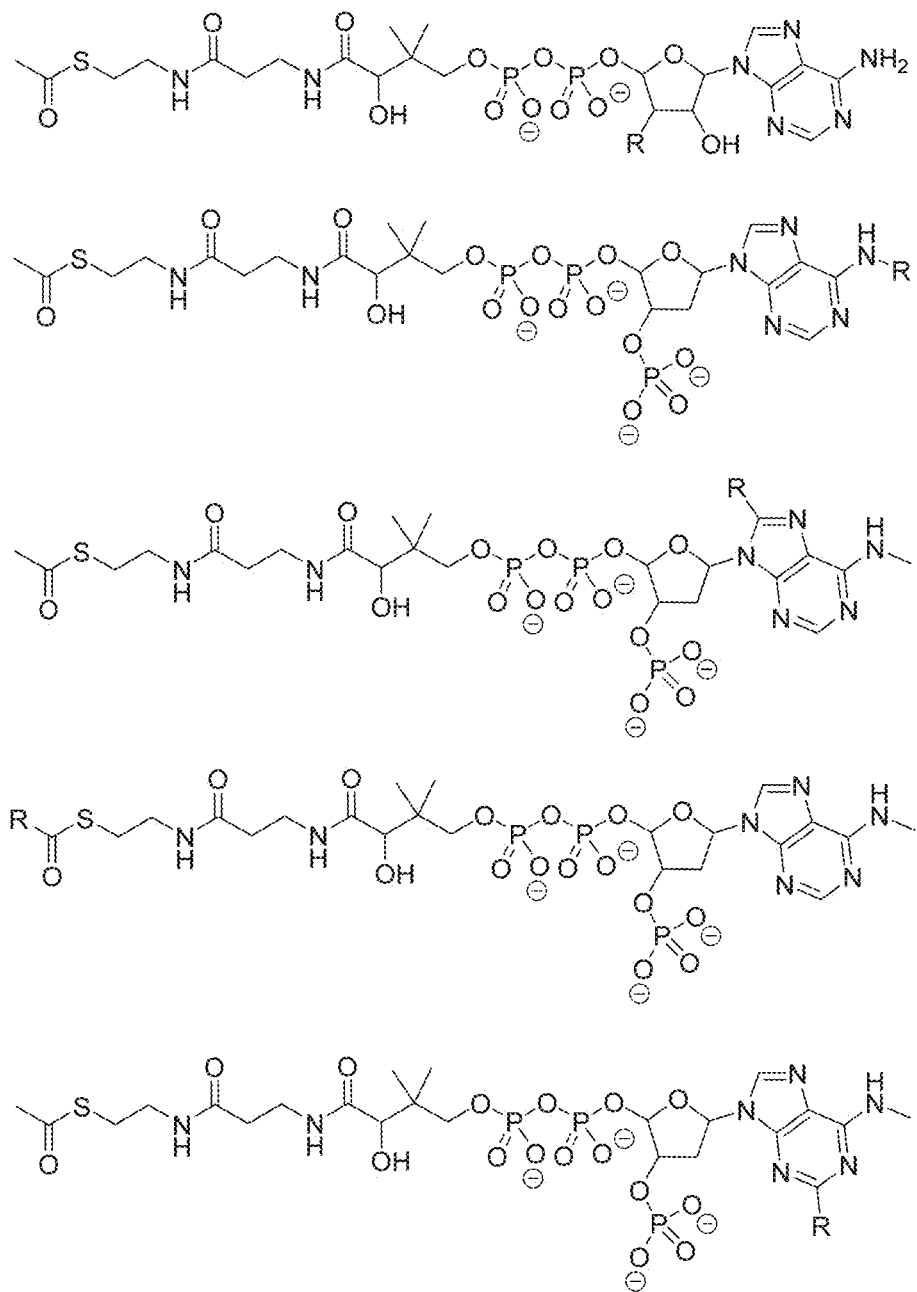

FIG. 3KKKKK
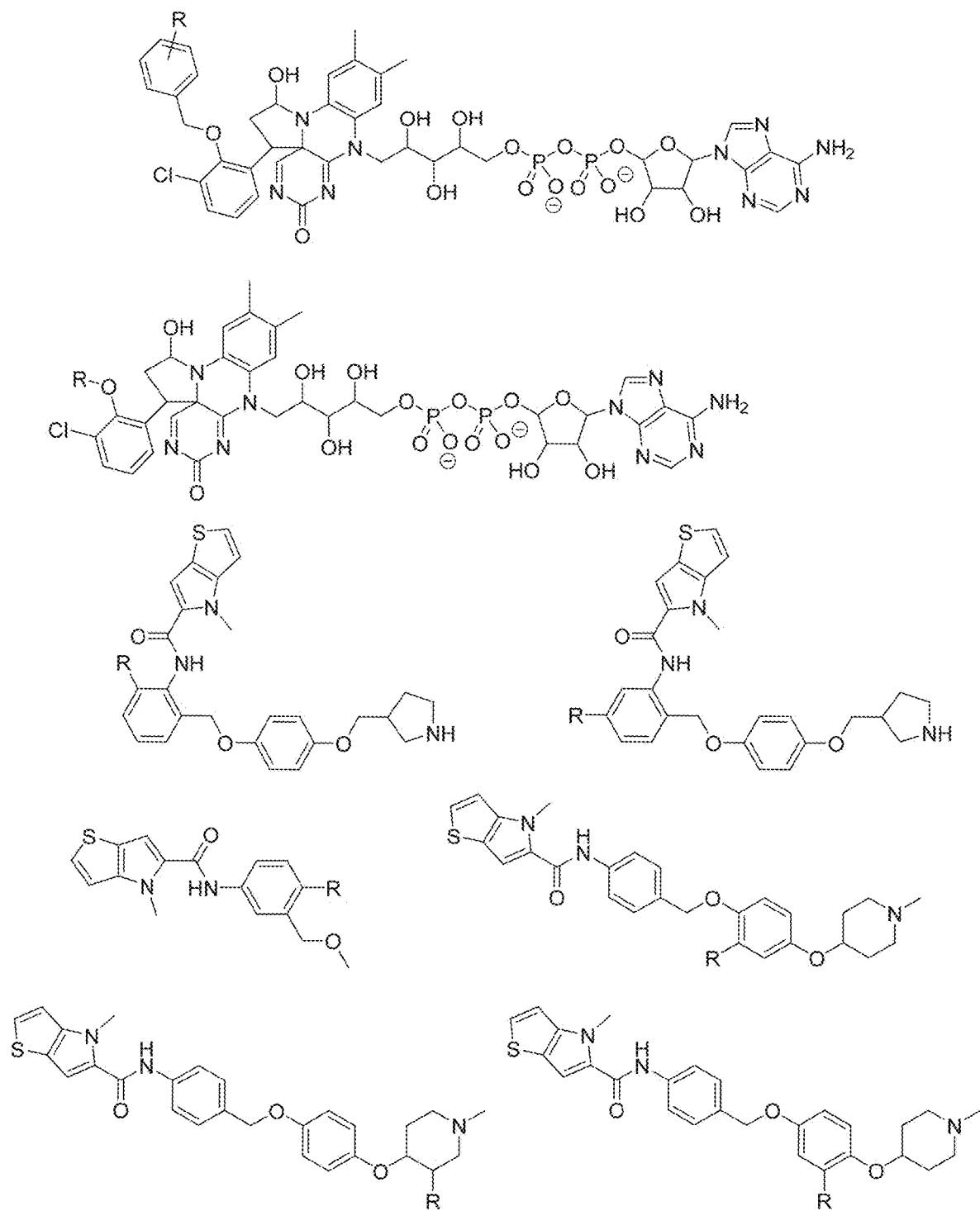

FIG. 3LLLLL
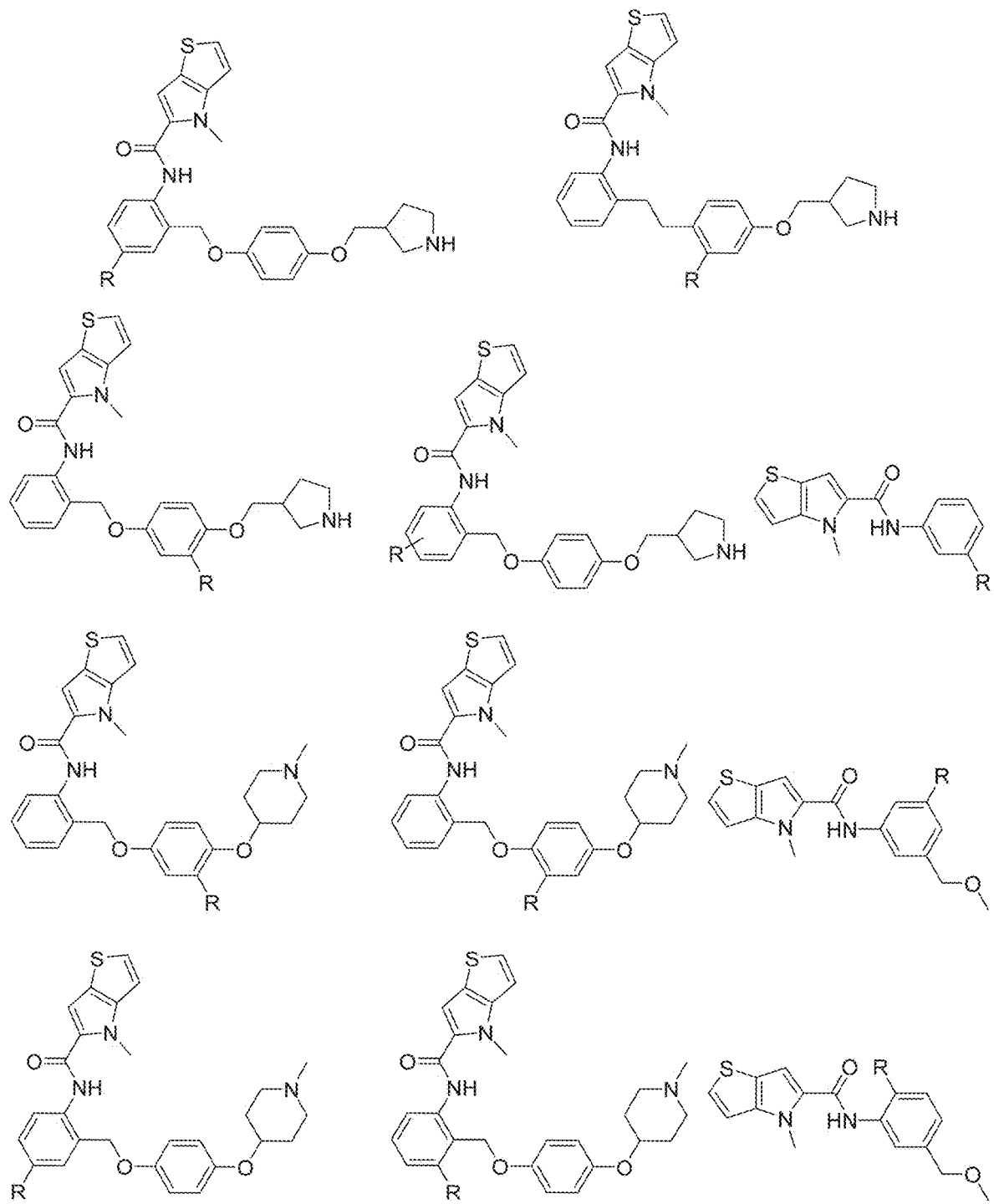

FIG. 3MMMMM
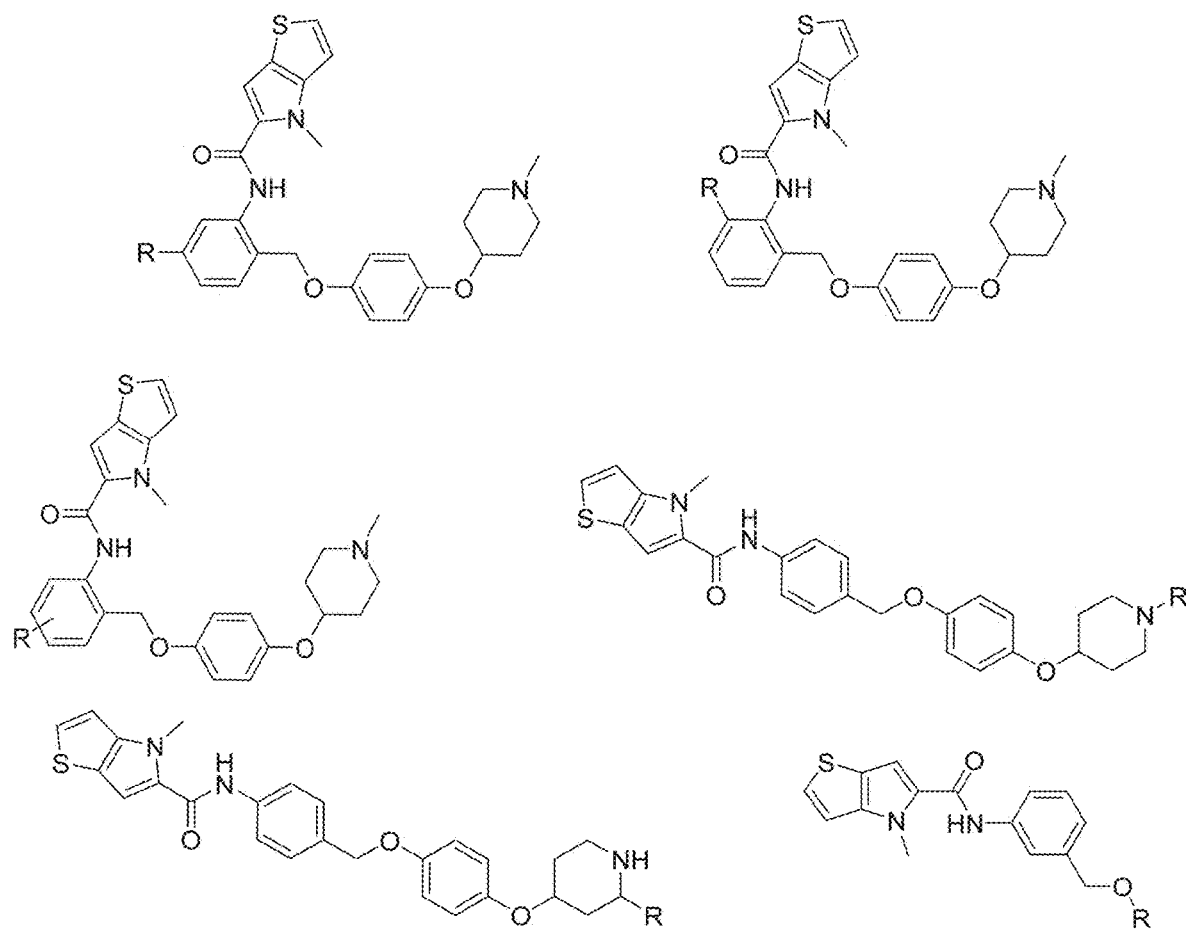
FIG. 3NNNNN
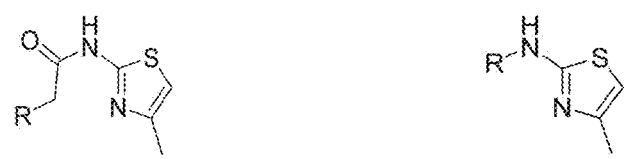

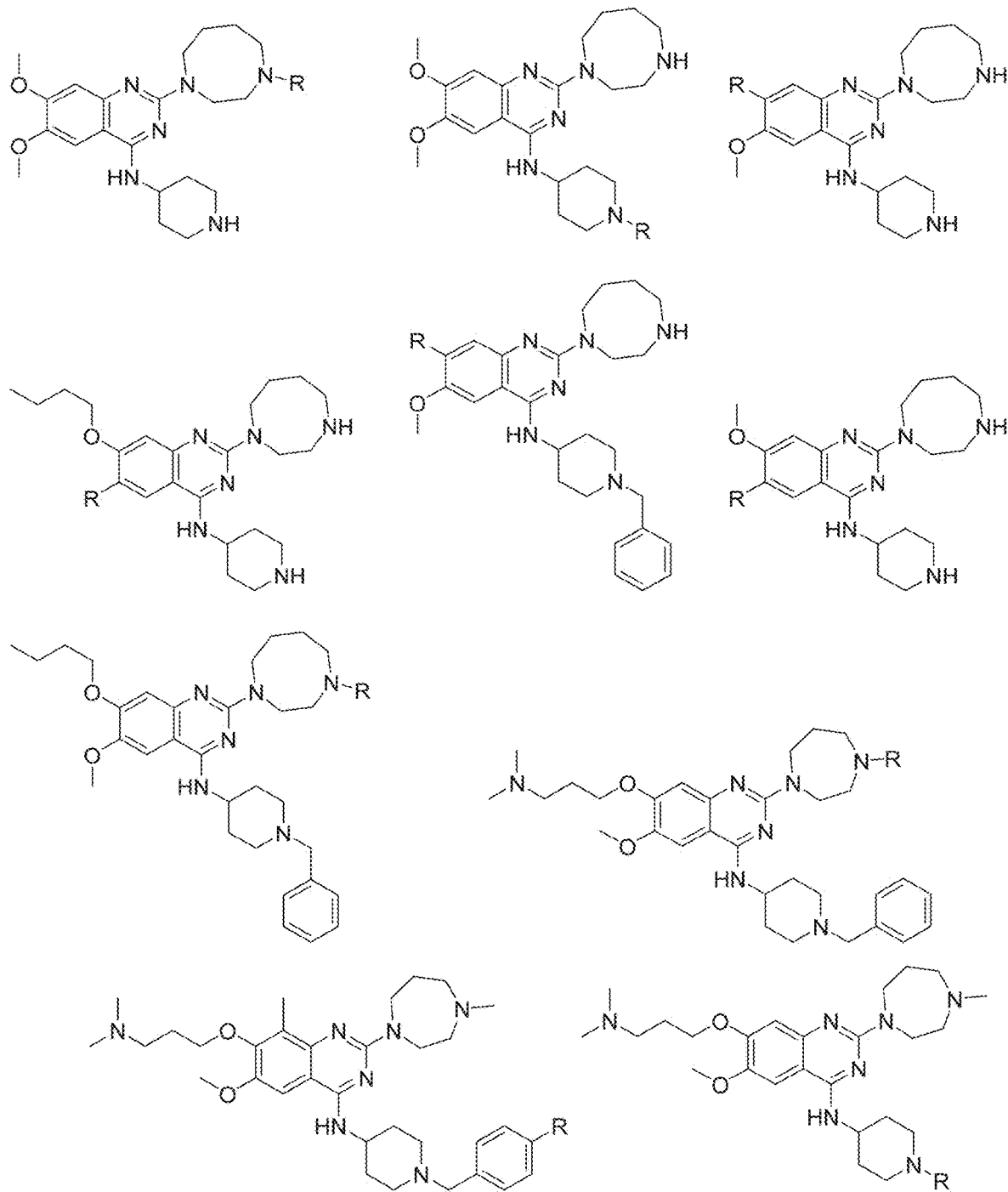
FIG. 300000

FIG. 3PPPPP
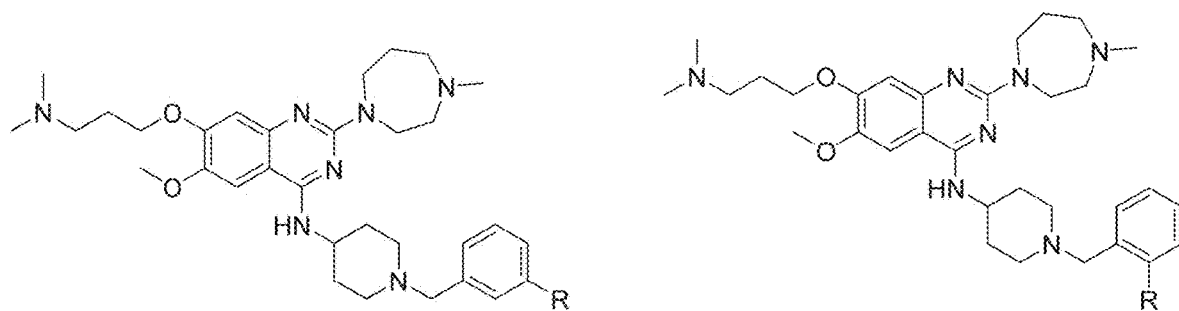
FIG. 3QQQQQ
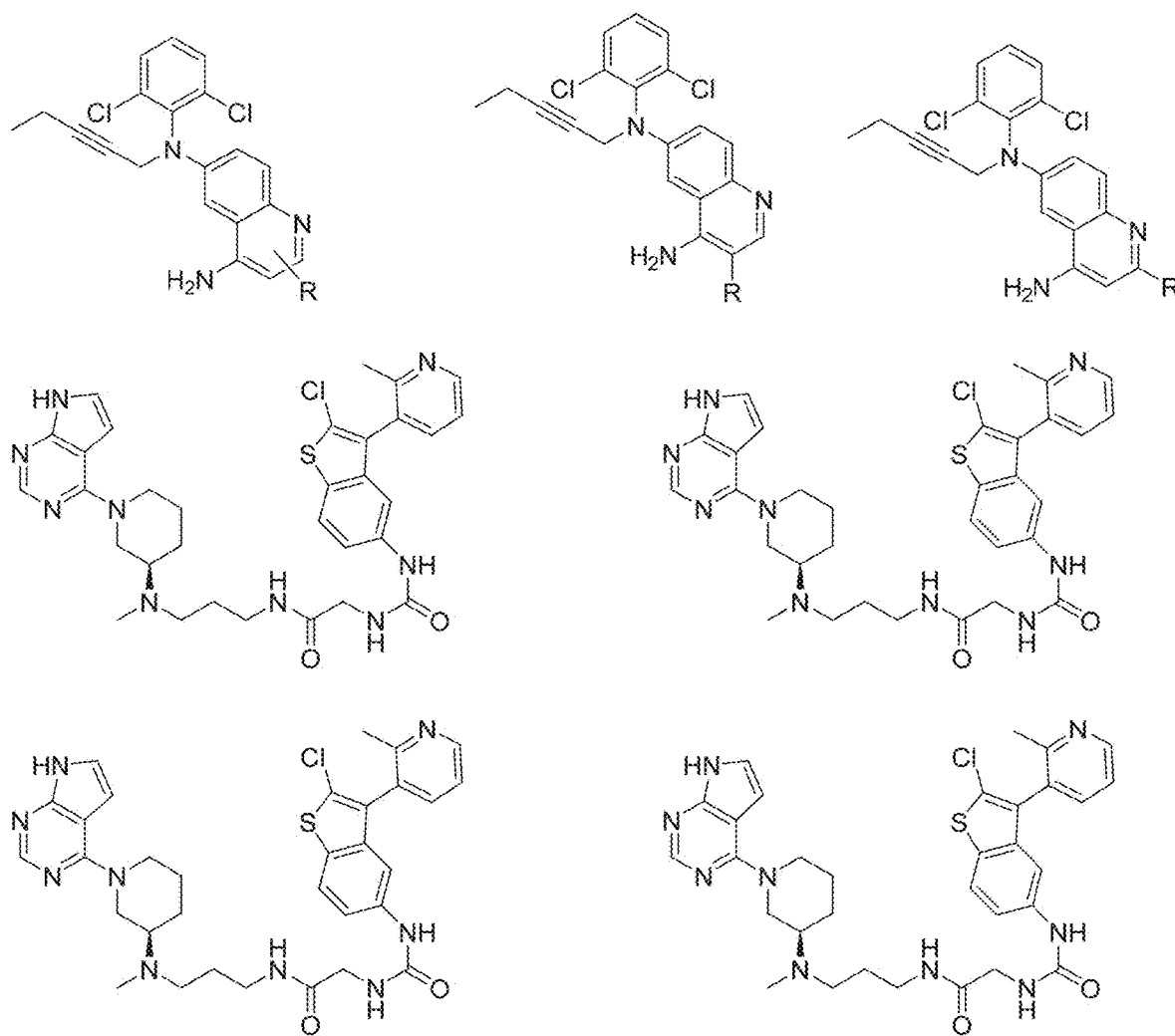

FIG. 3RRRRR
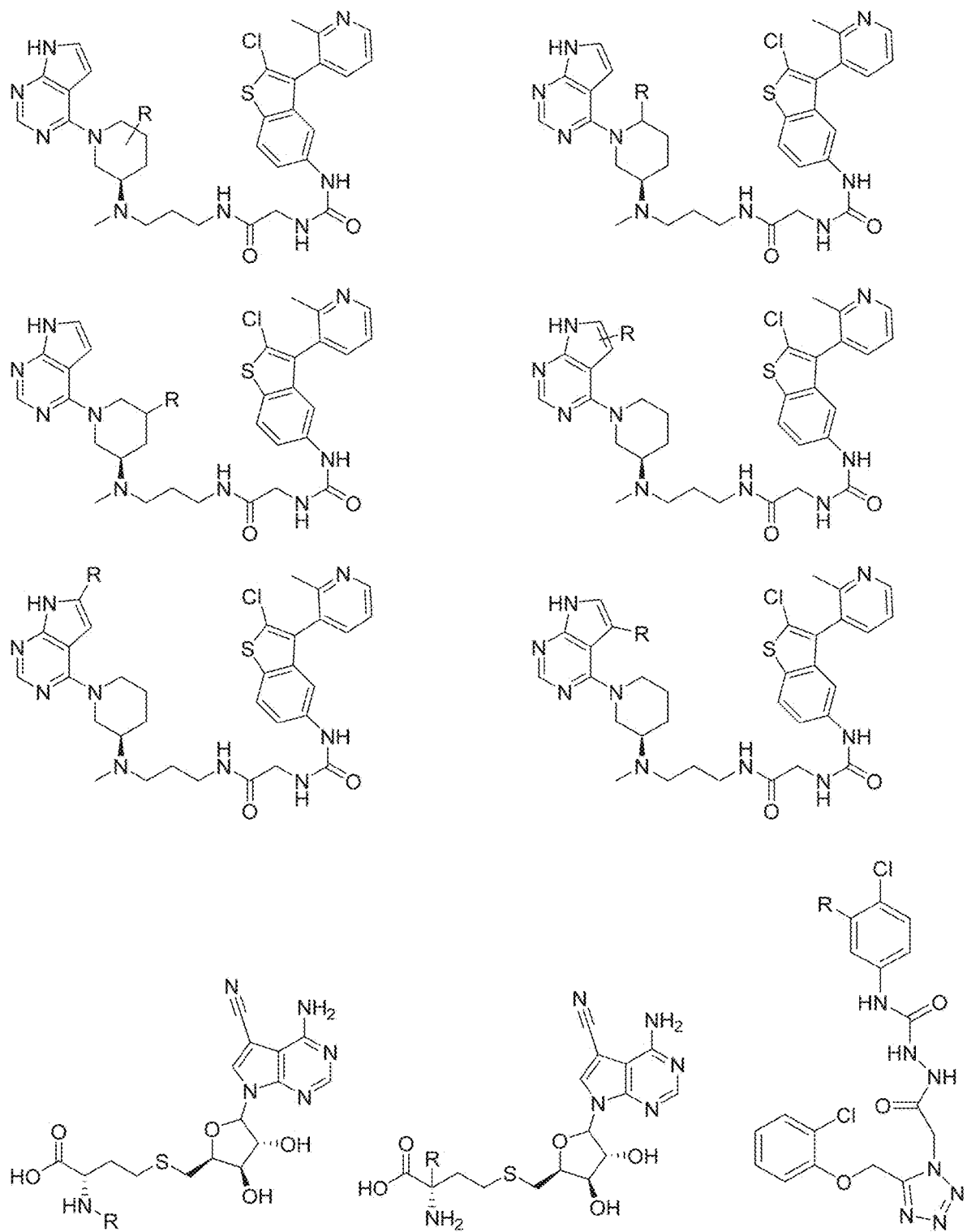

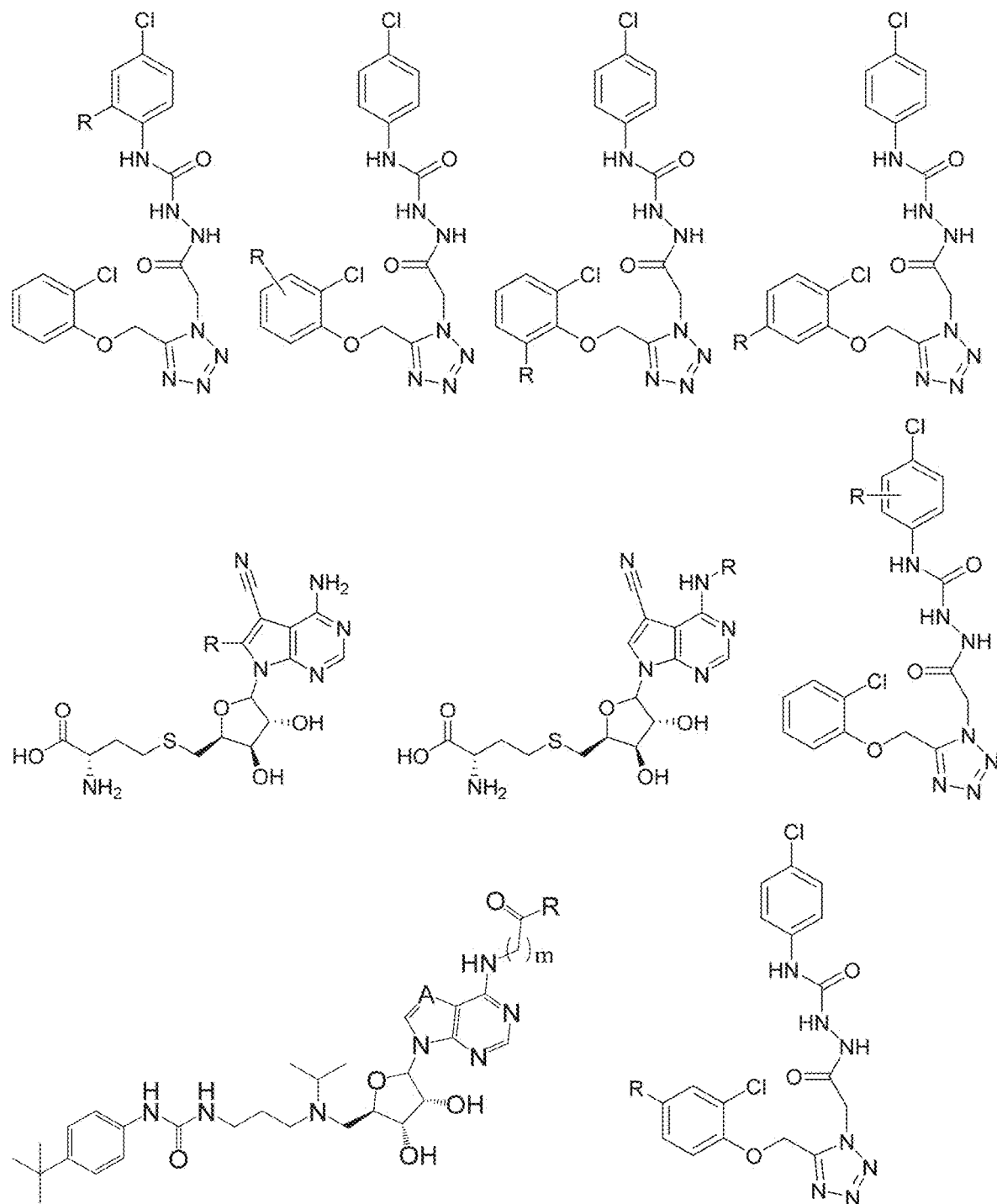
FIG. 3SSSSS

FIG. 3TTTTT
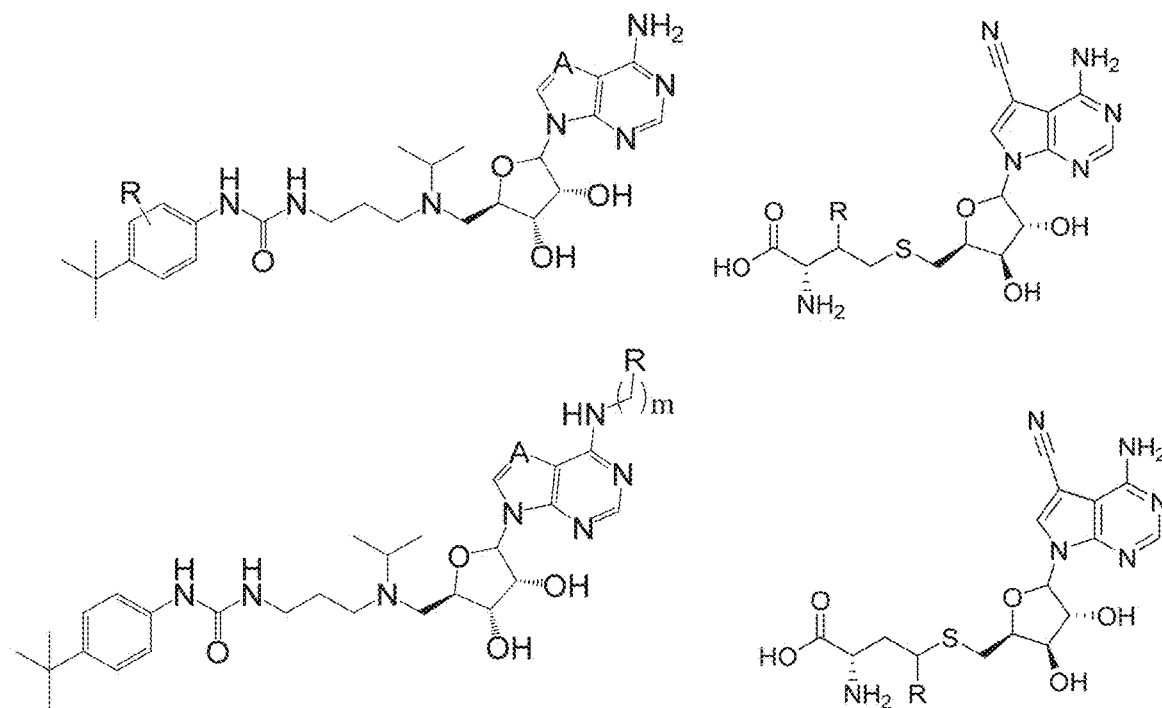
FIG. 3UUUUU
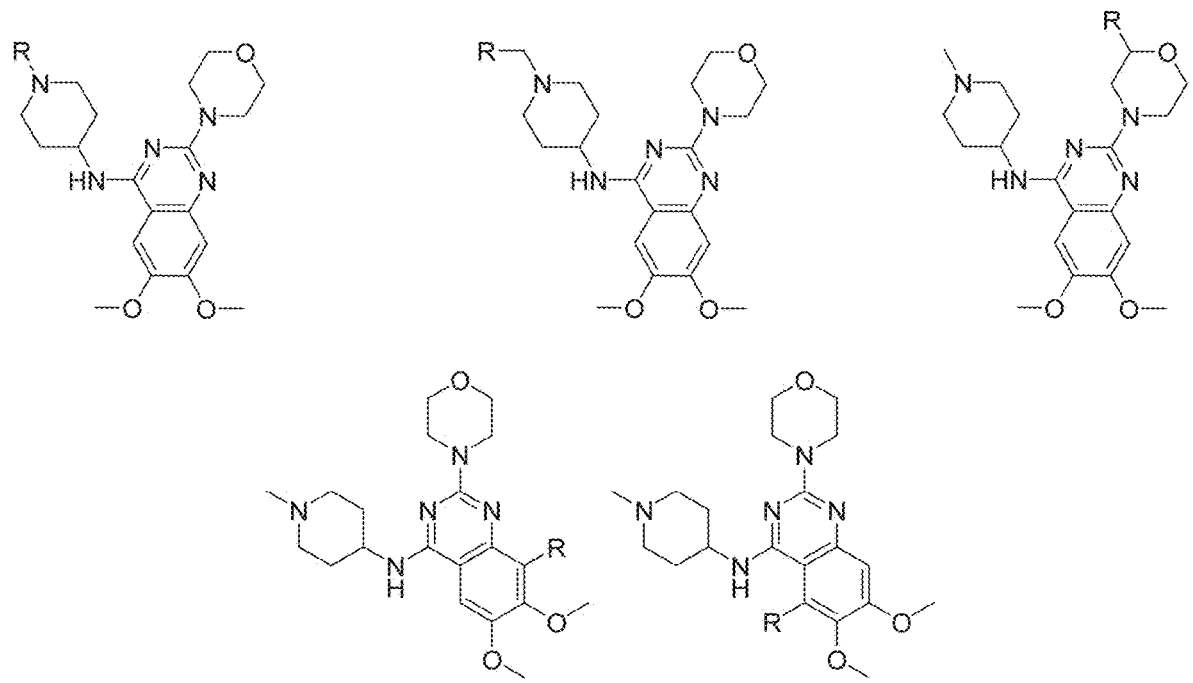

FIG. 3VVVVV
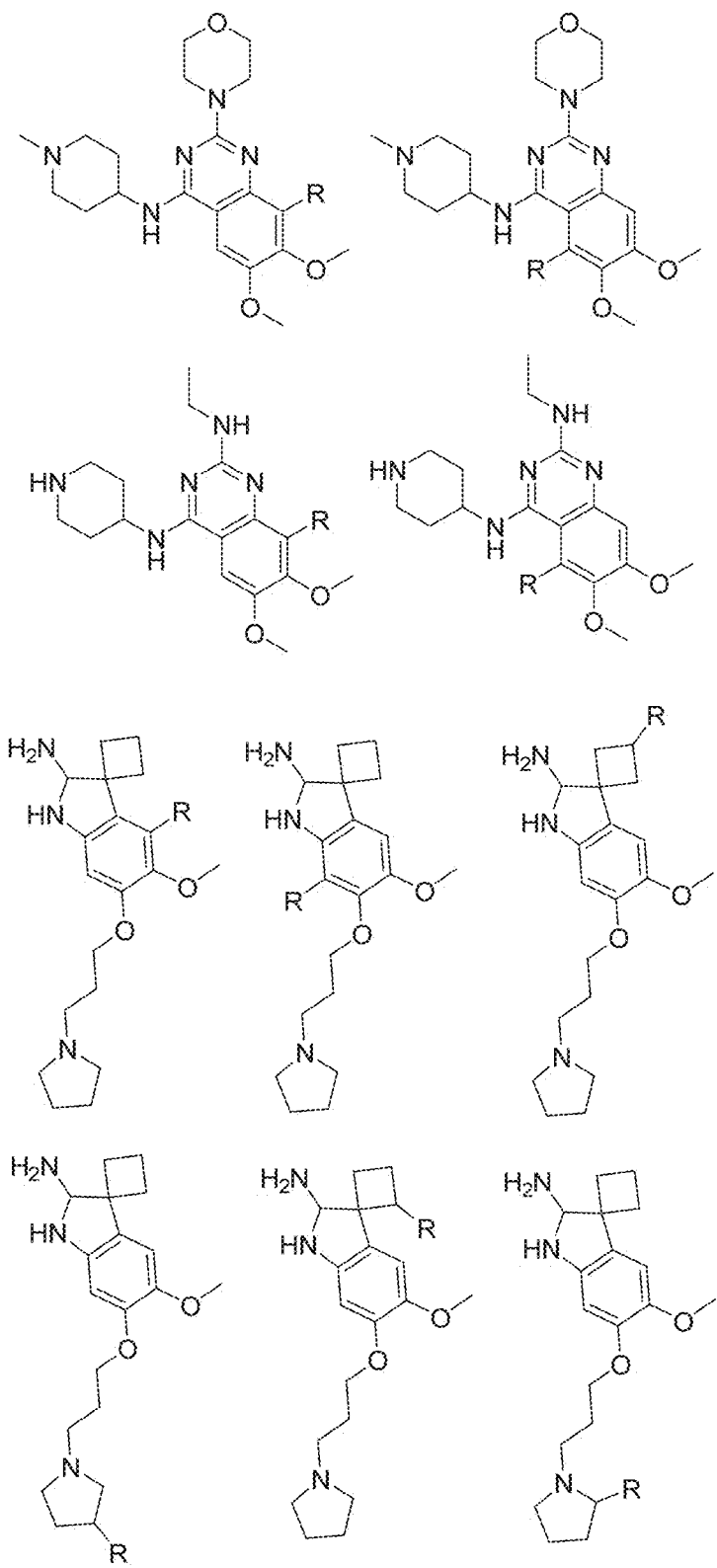

FIG. 3WWWWW
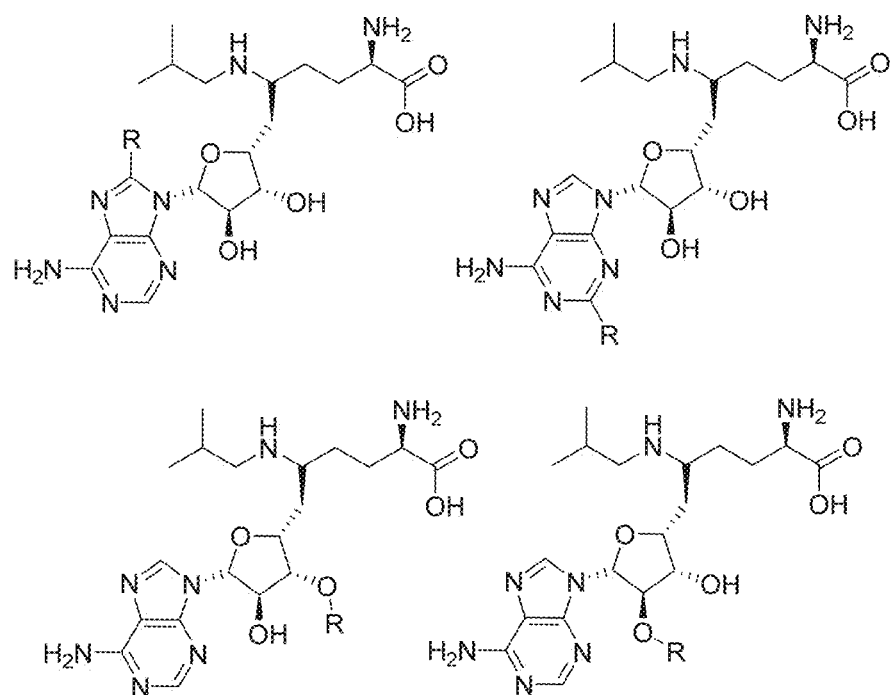
FIG. 3XXXXX
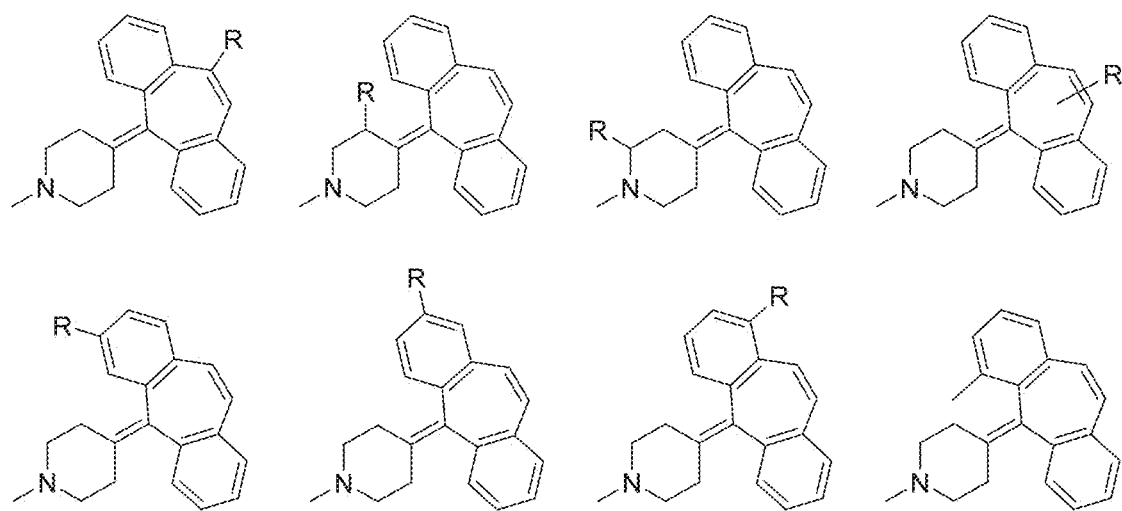

FIG. 3YYYYY
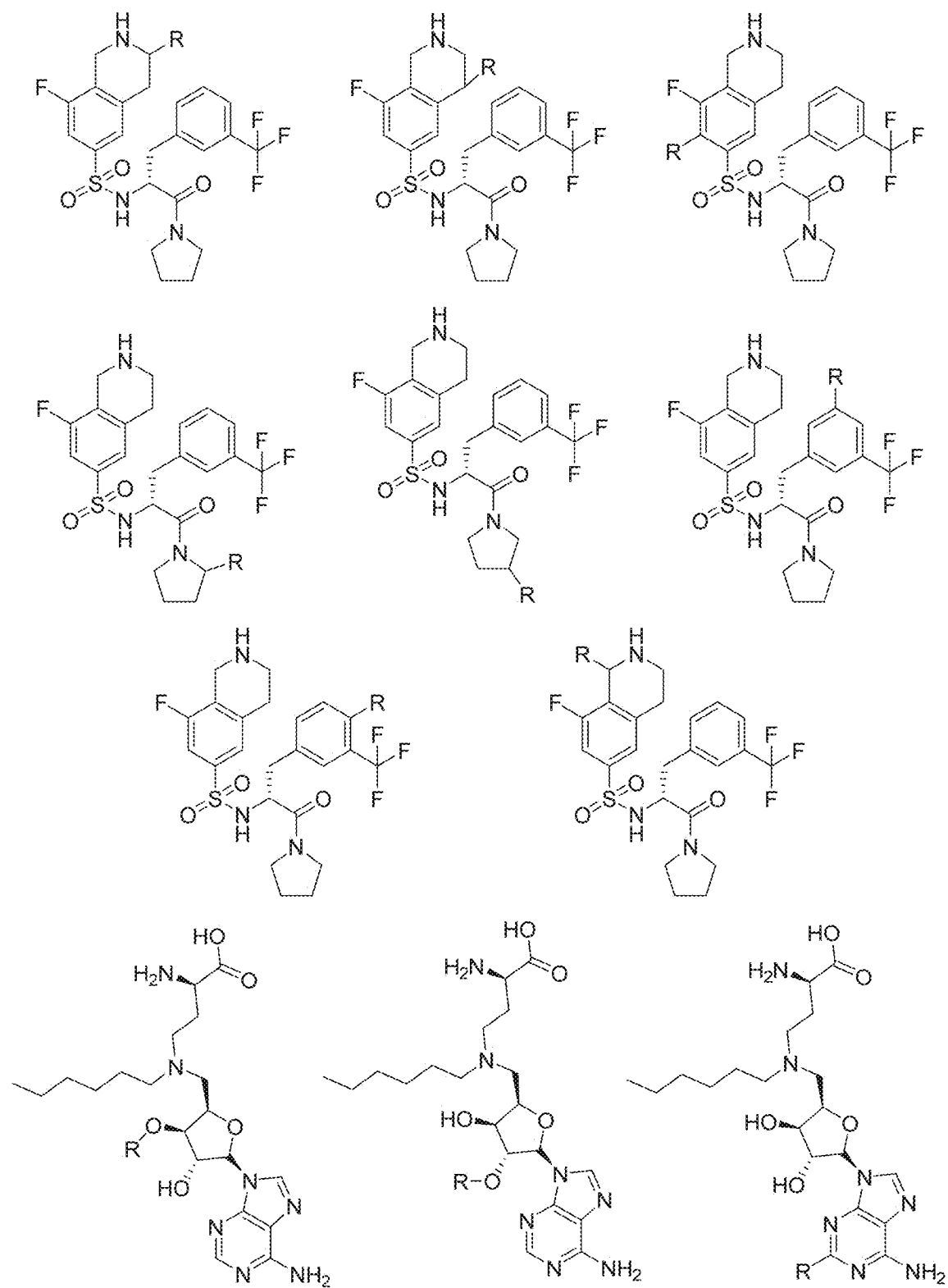

FIG. 3ZZZZZ
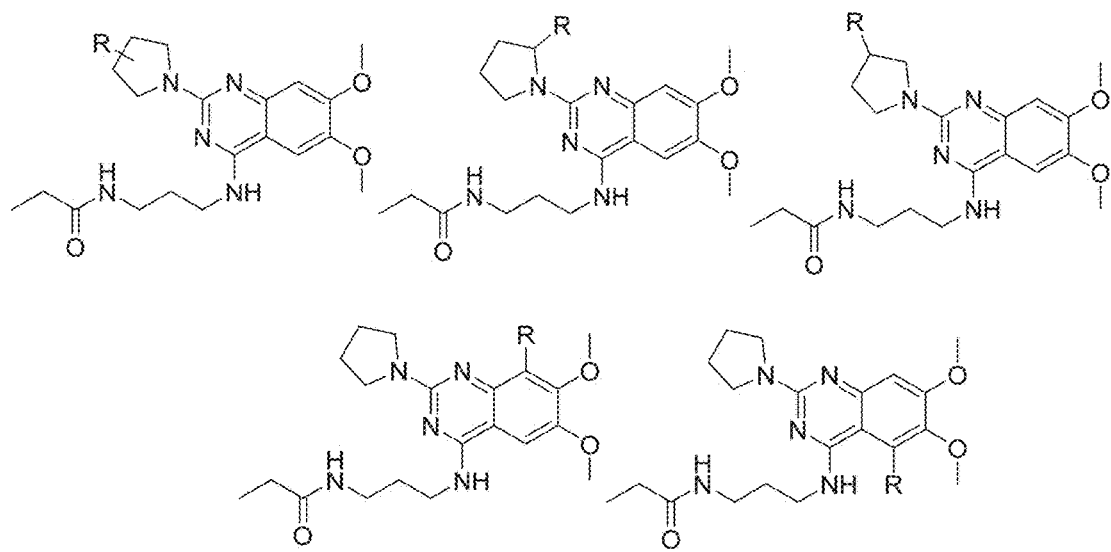
FIG. 4A
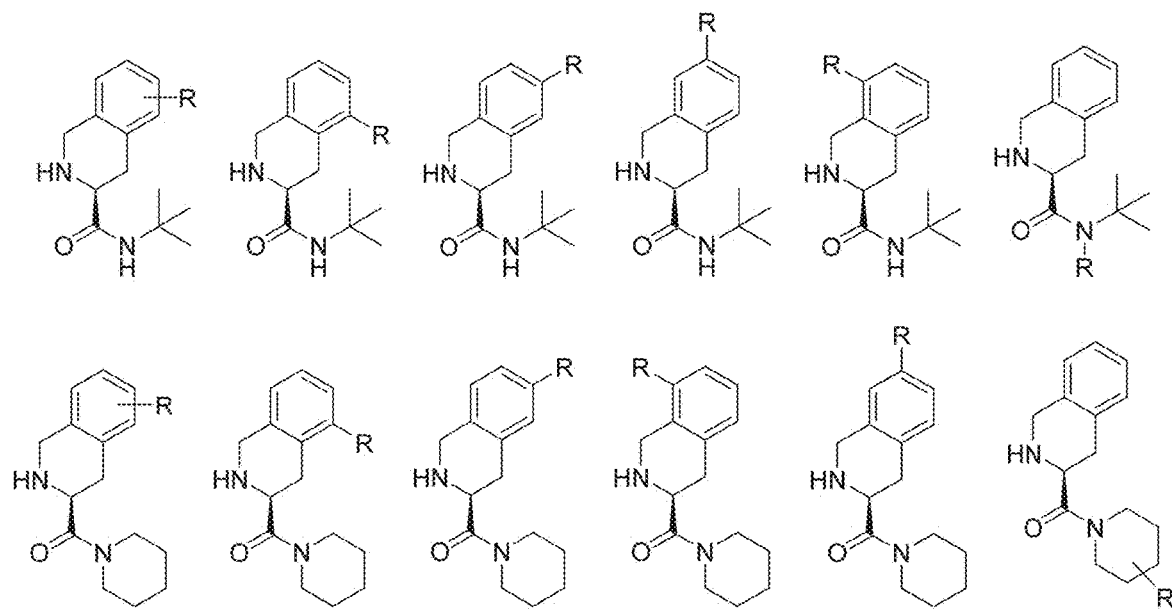

FIG. 5L
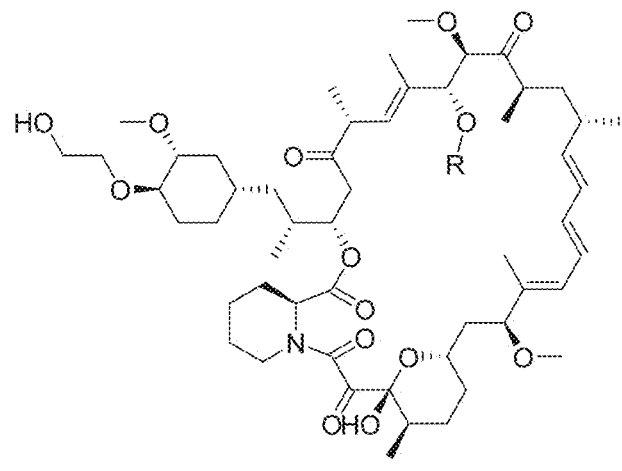
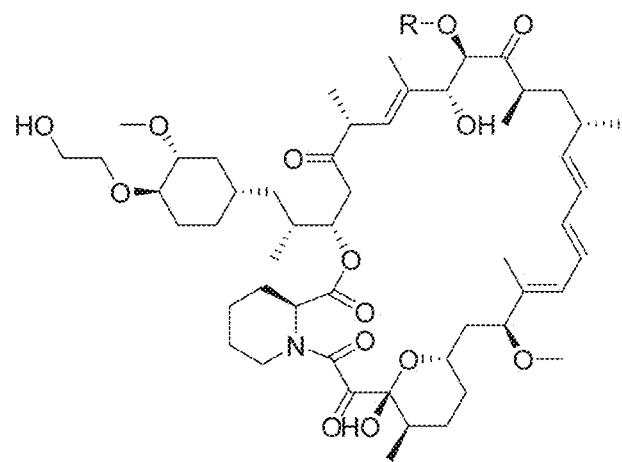
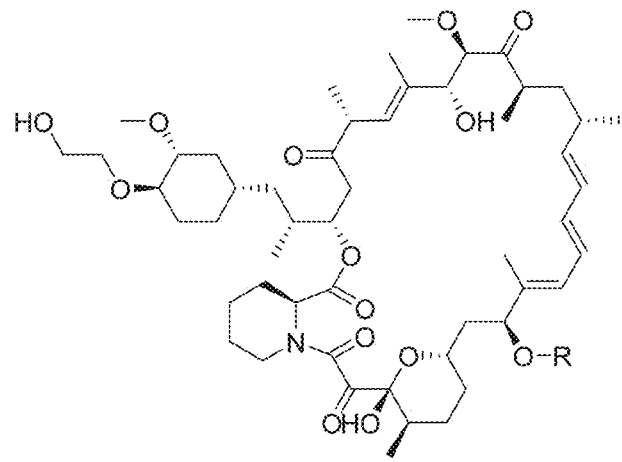

FIG. 5Z
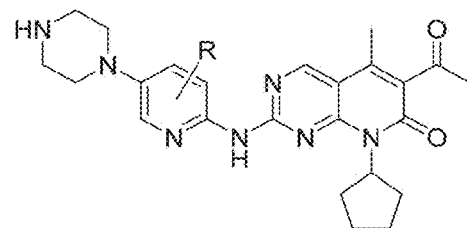
FIG. 5AA
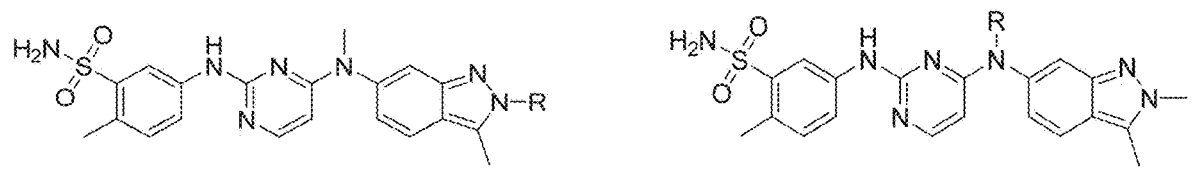
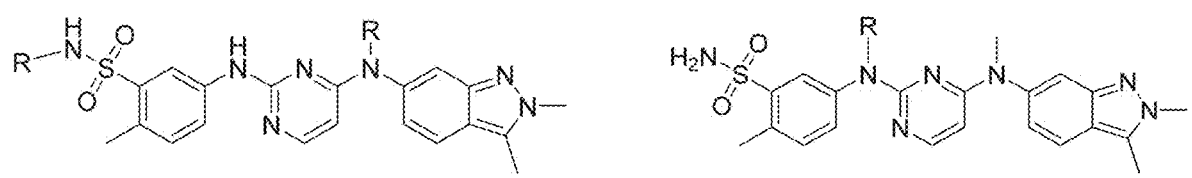
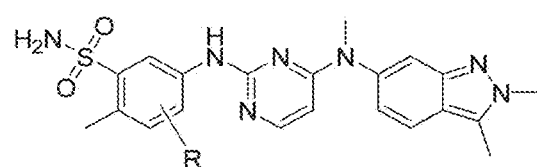
FIG. 5BB
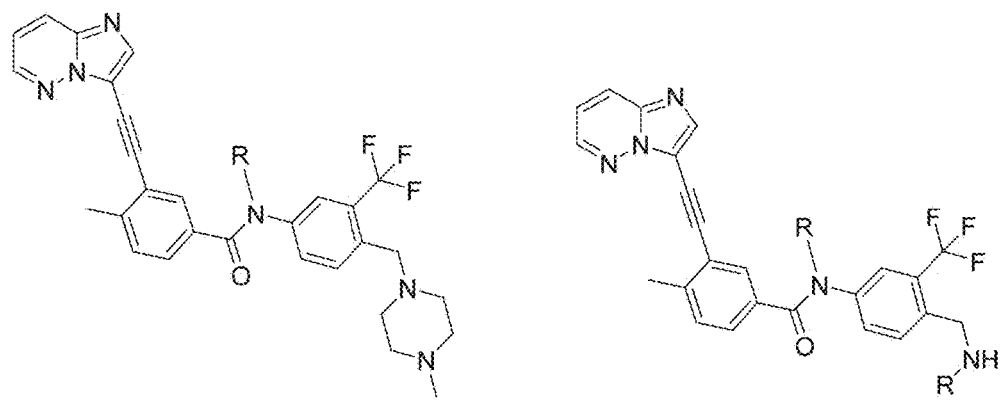

FIG. 5JJ
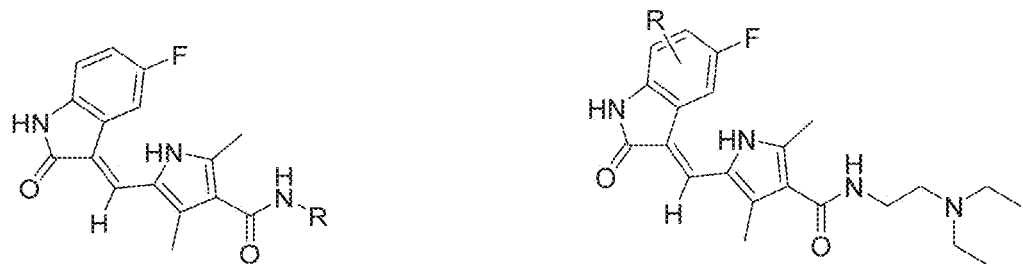
FIG. 5KK
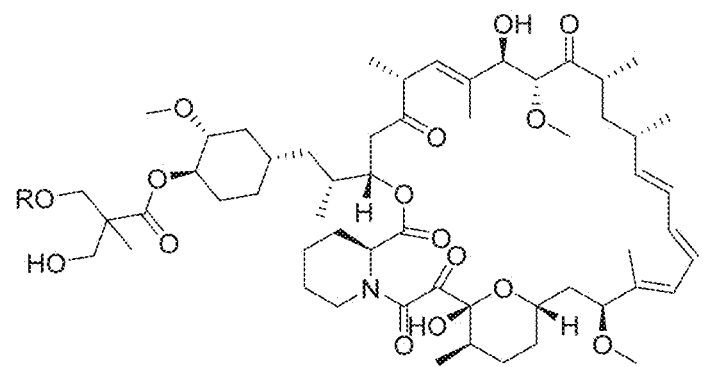
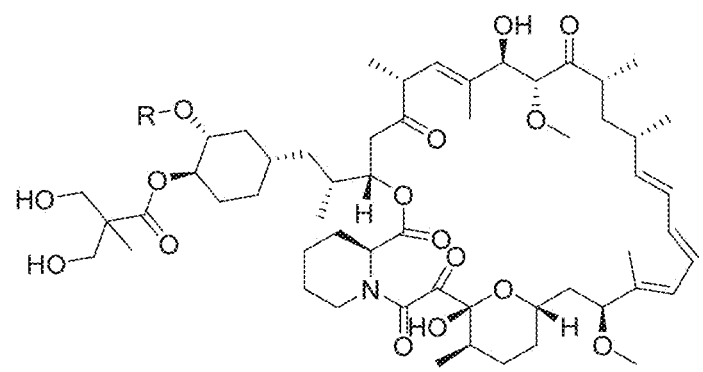

FIG. 6AA
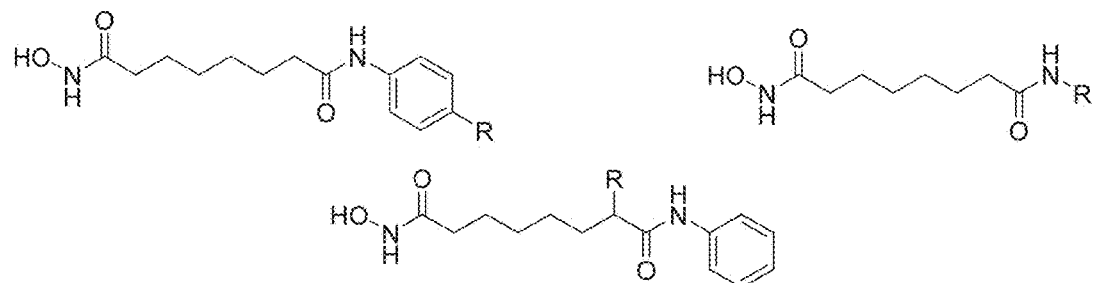
FIG. 6BB
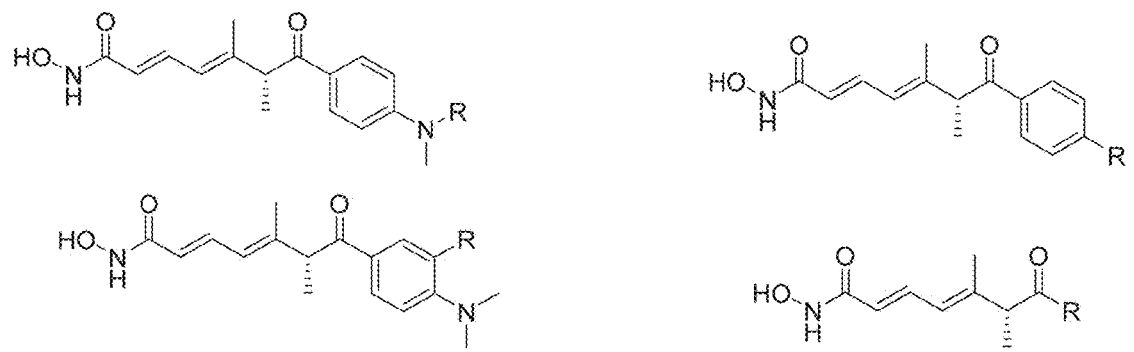
FIG. 7A
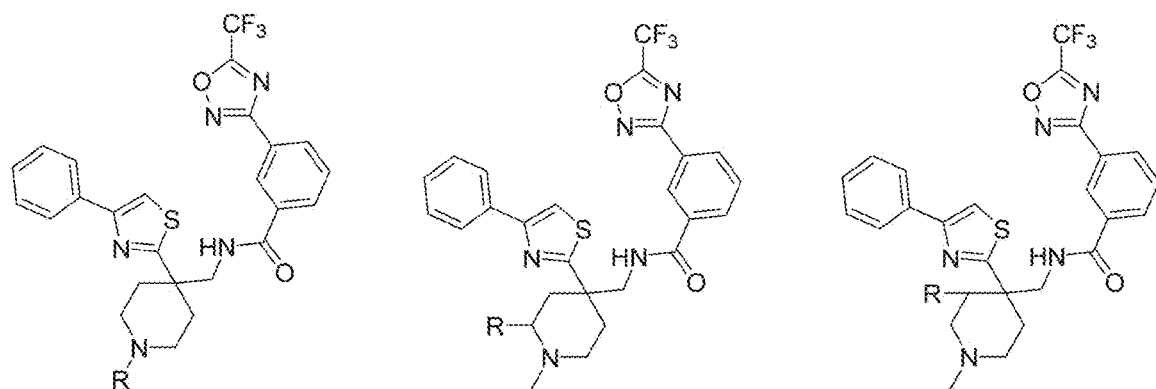
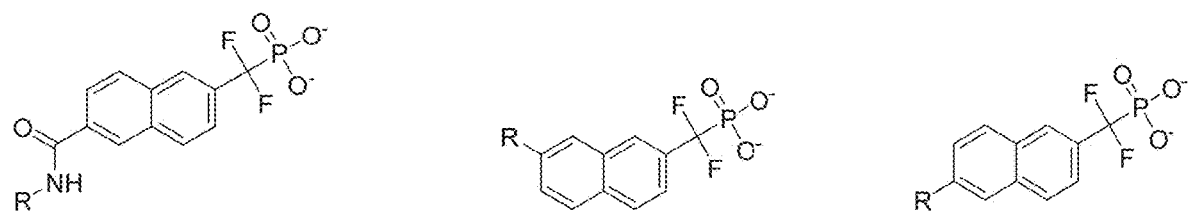

X=H, F, Cl, Br, Me, CF₃O

FIG. 8S
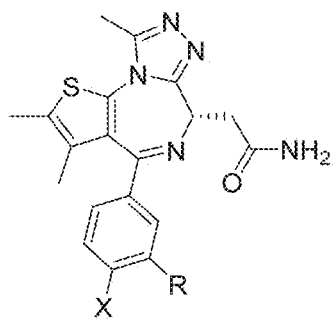
X=H, F, Cl, Br, Me, CF₃O
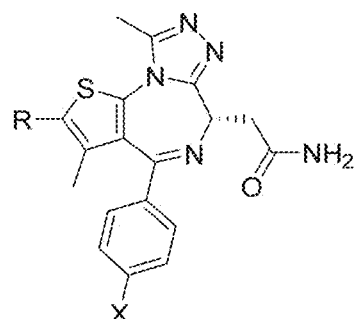
X=H, F, Cl, Br, Me, CF₃O
FIG. 8T
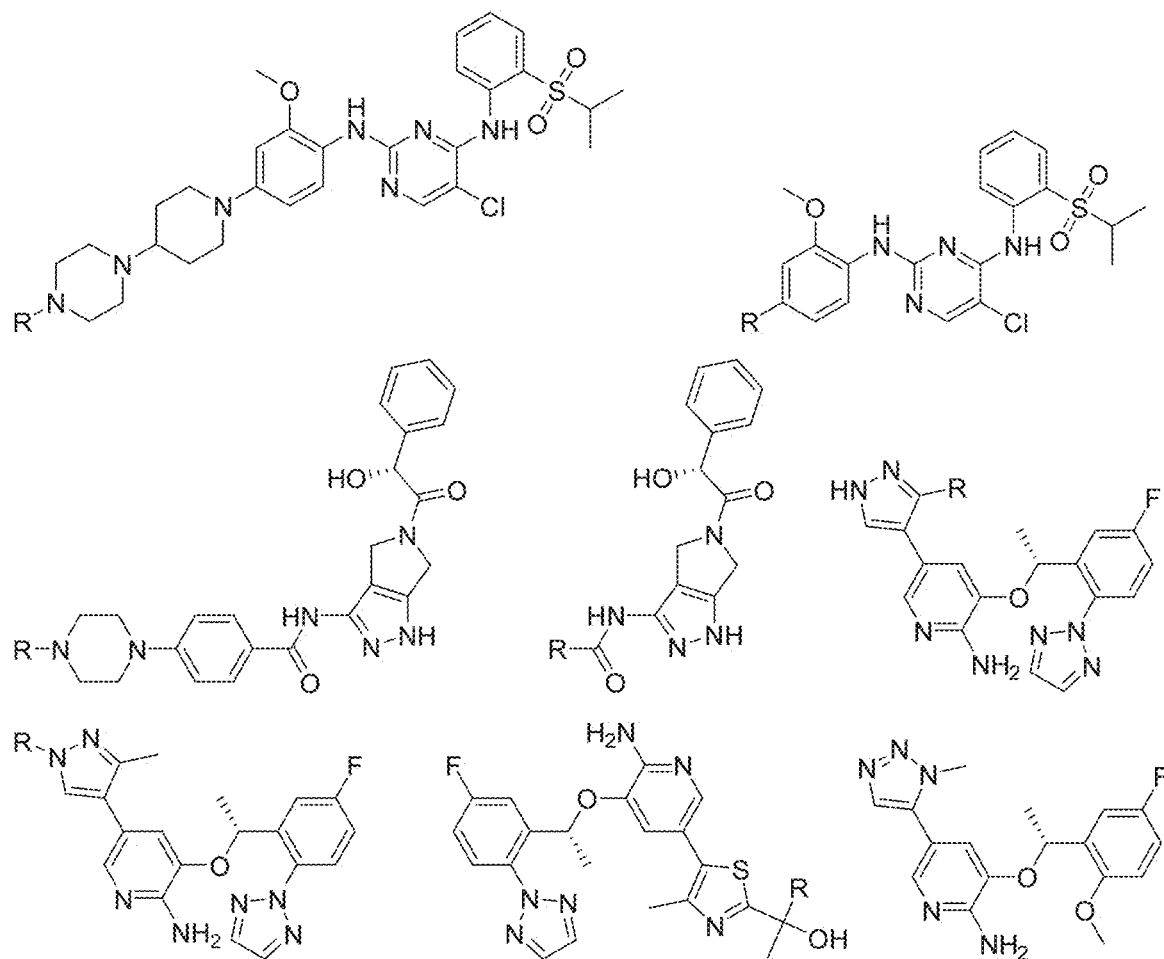

FIG. 8AAA
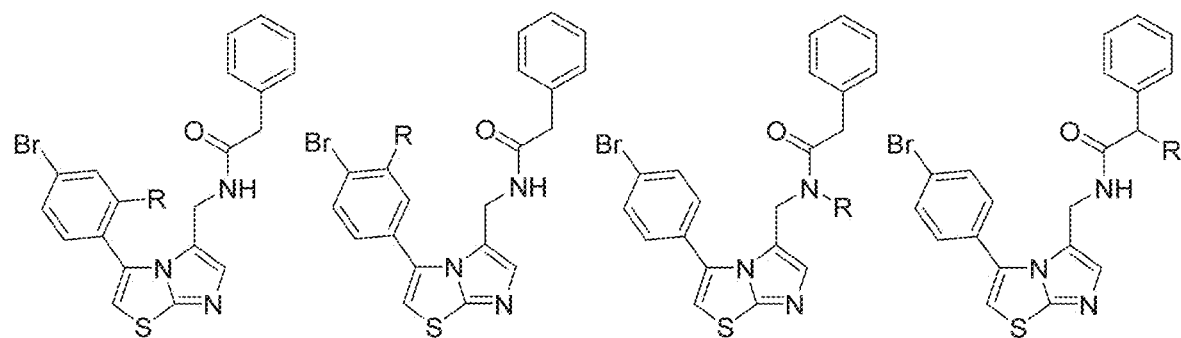
FIG. 8BBB
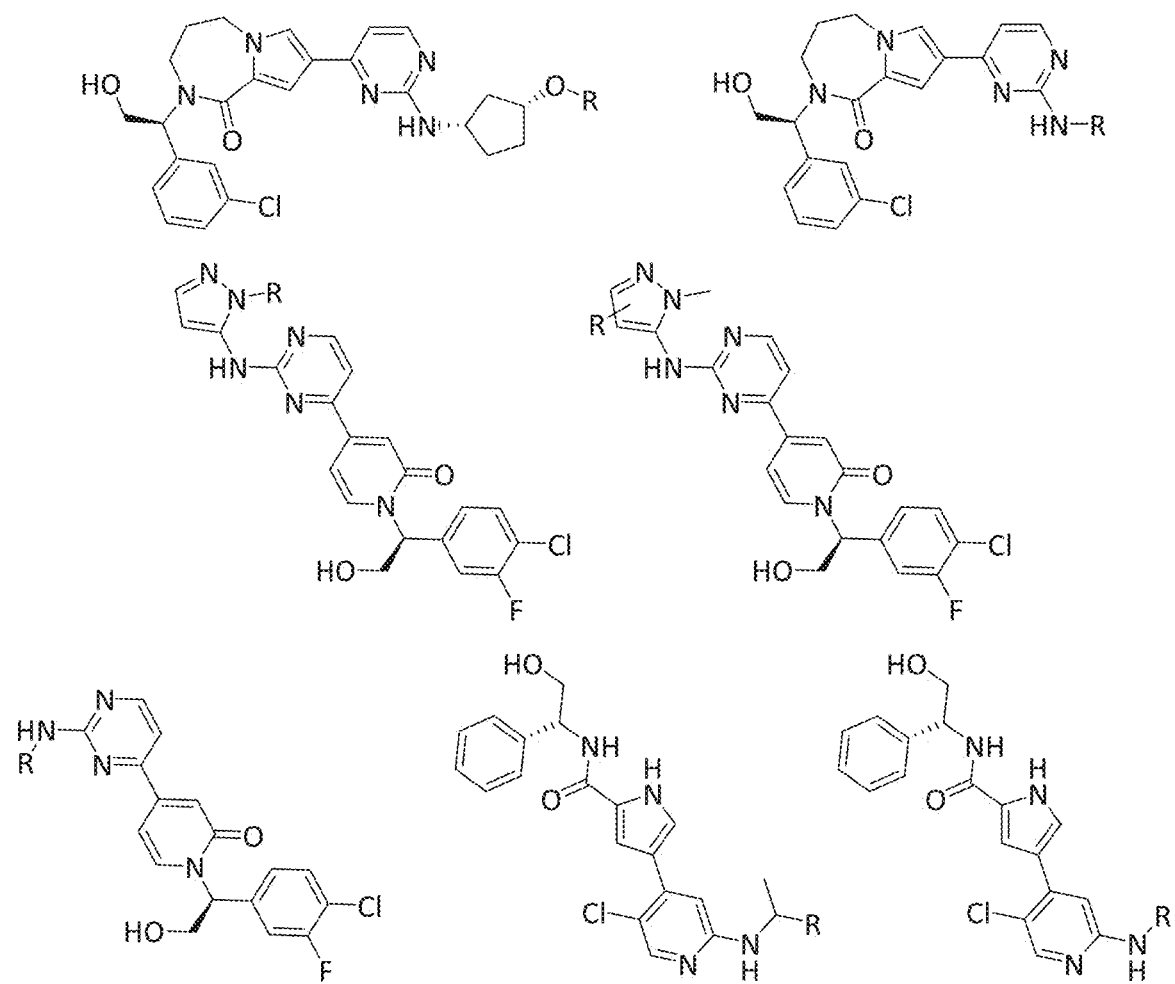

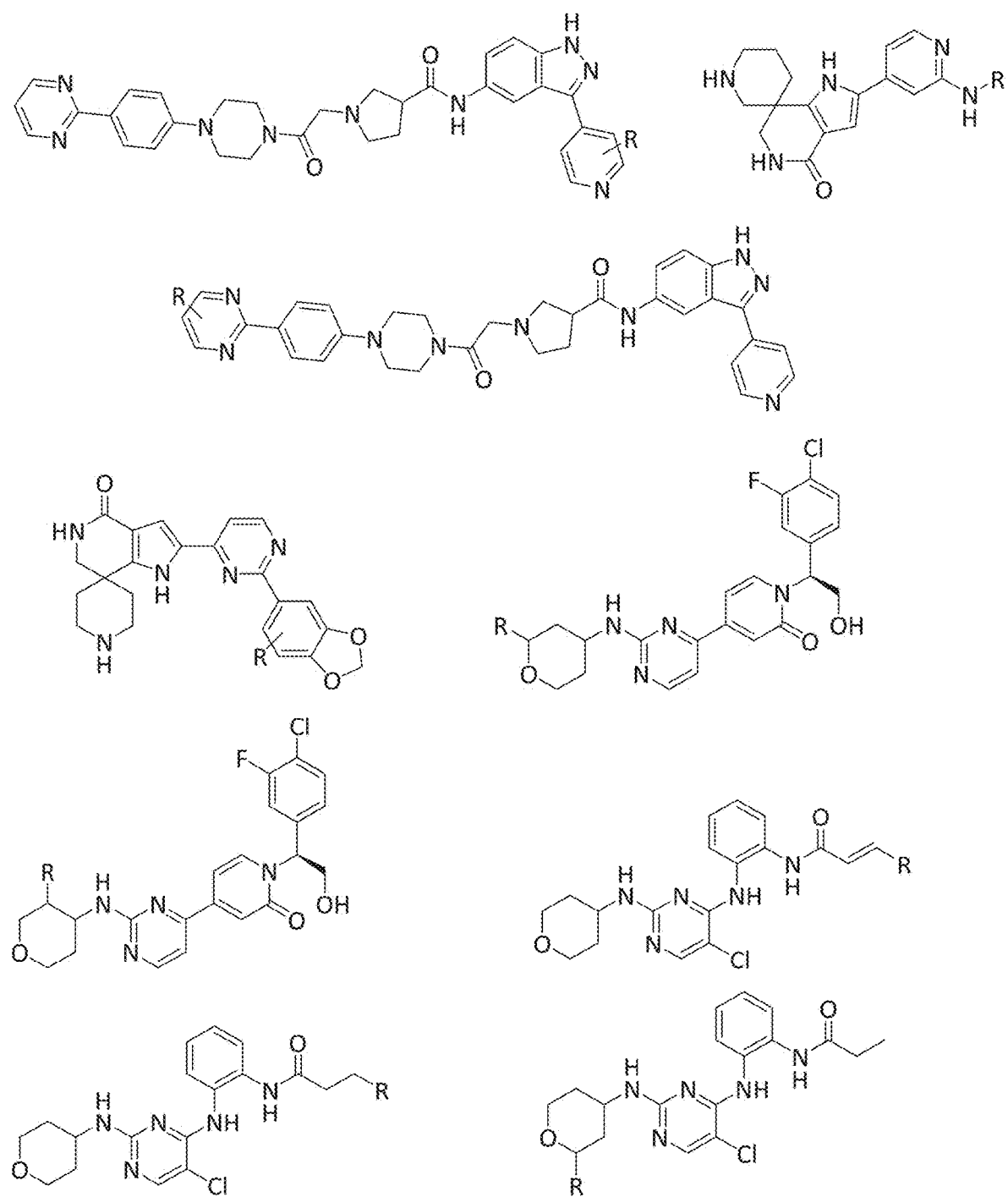
FIG. 8CCC

FIG. 8DDD
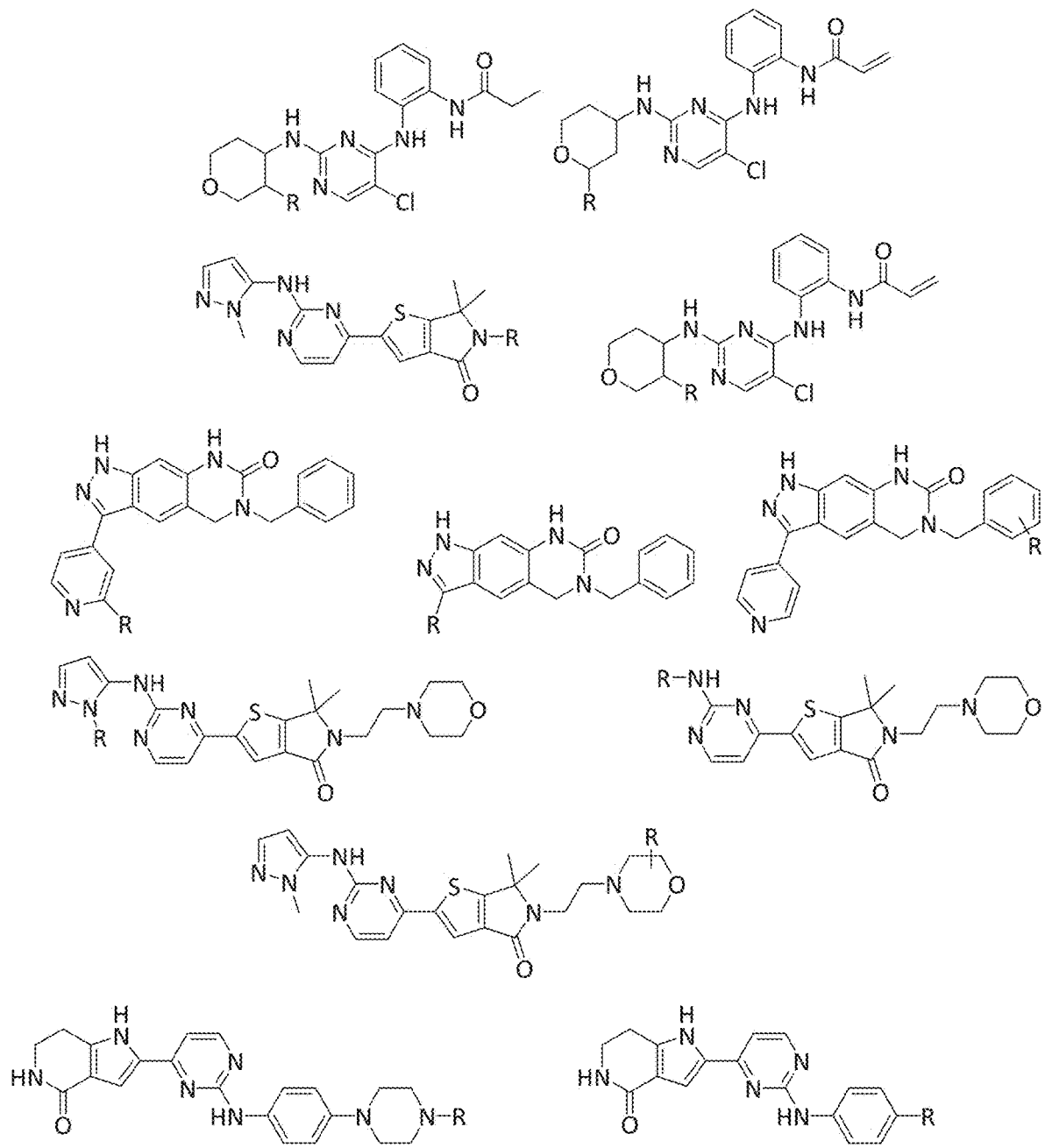

FIG. 8EEE
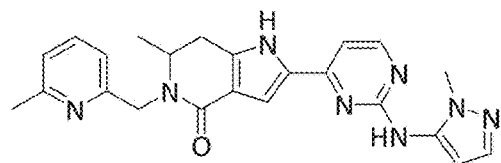
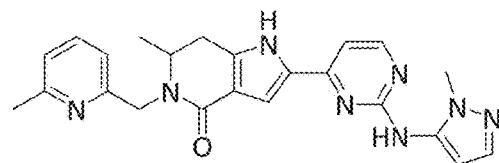
FIG. 8FFF
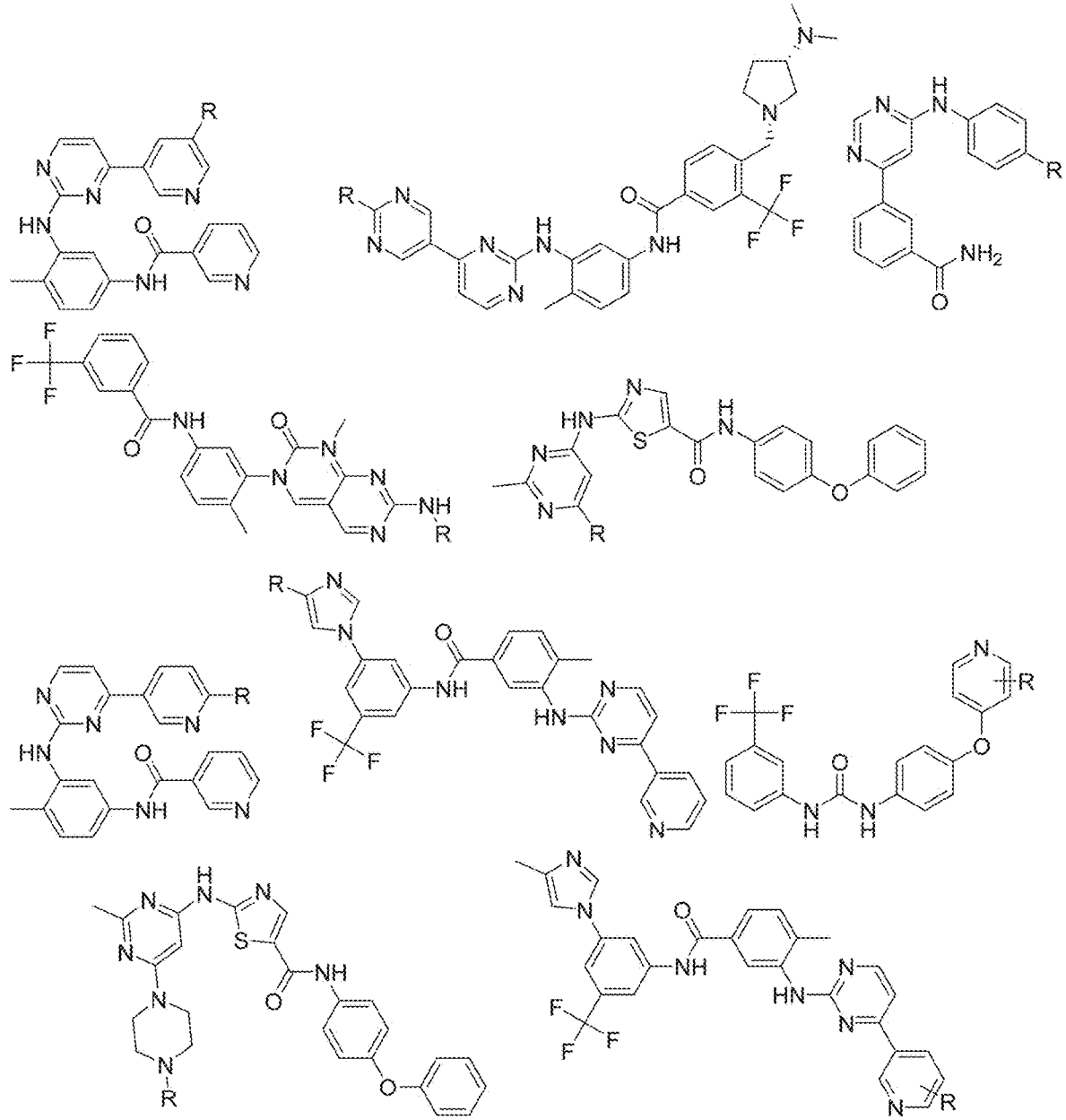

FIG. 8GGG
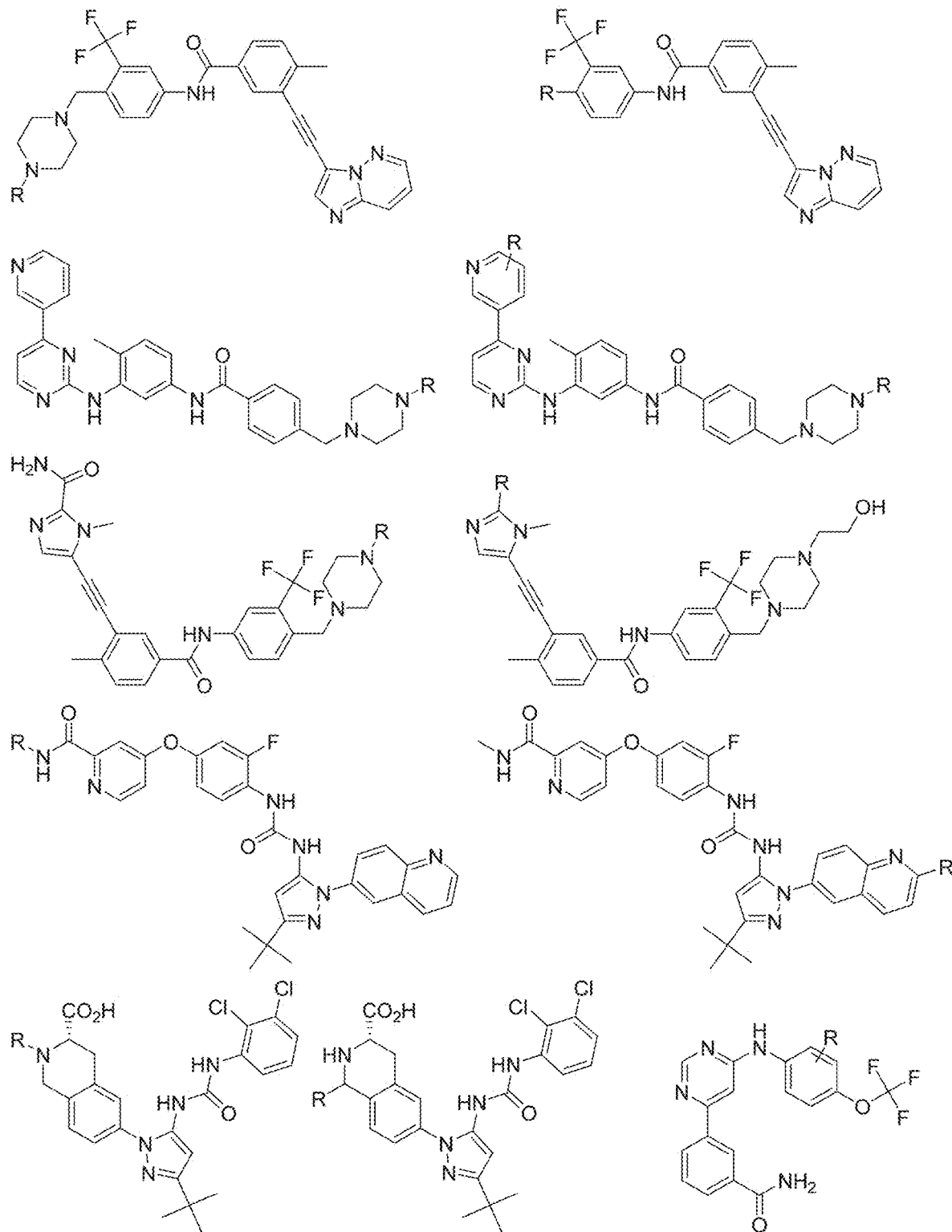

FIG. 8HHH
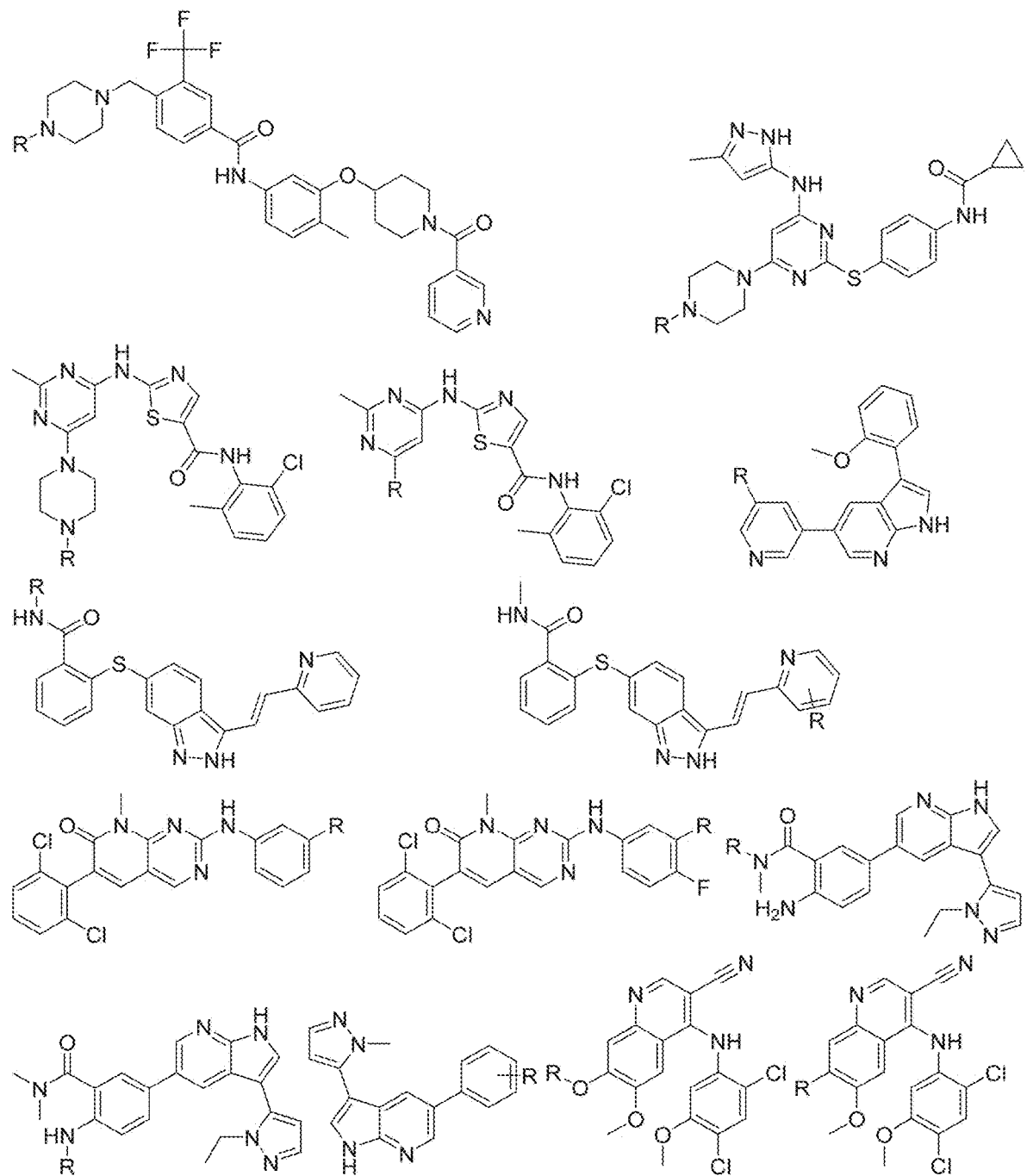

FIG. 8III
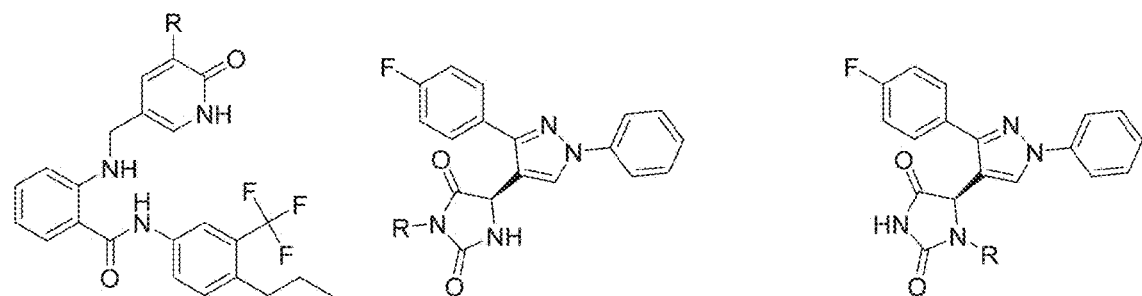
FIG. 8JJJ
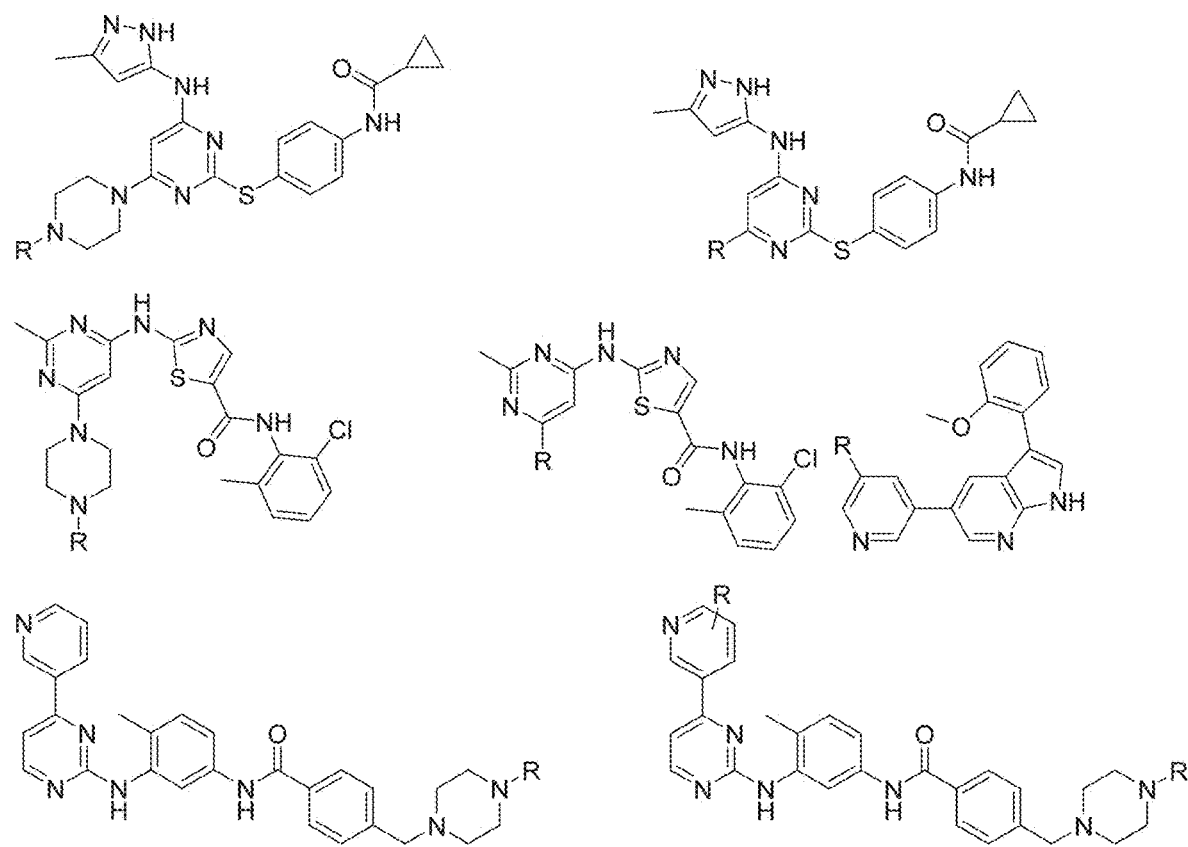

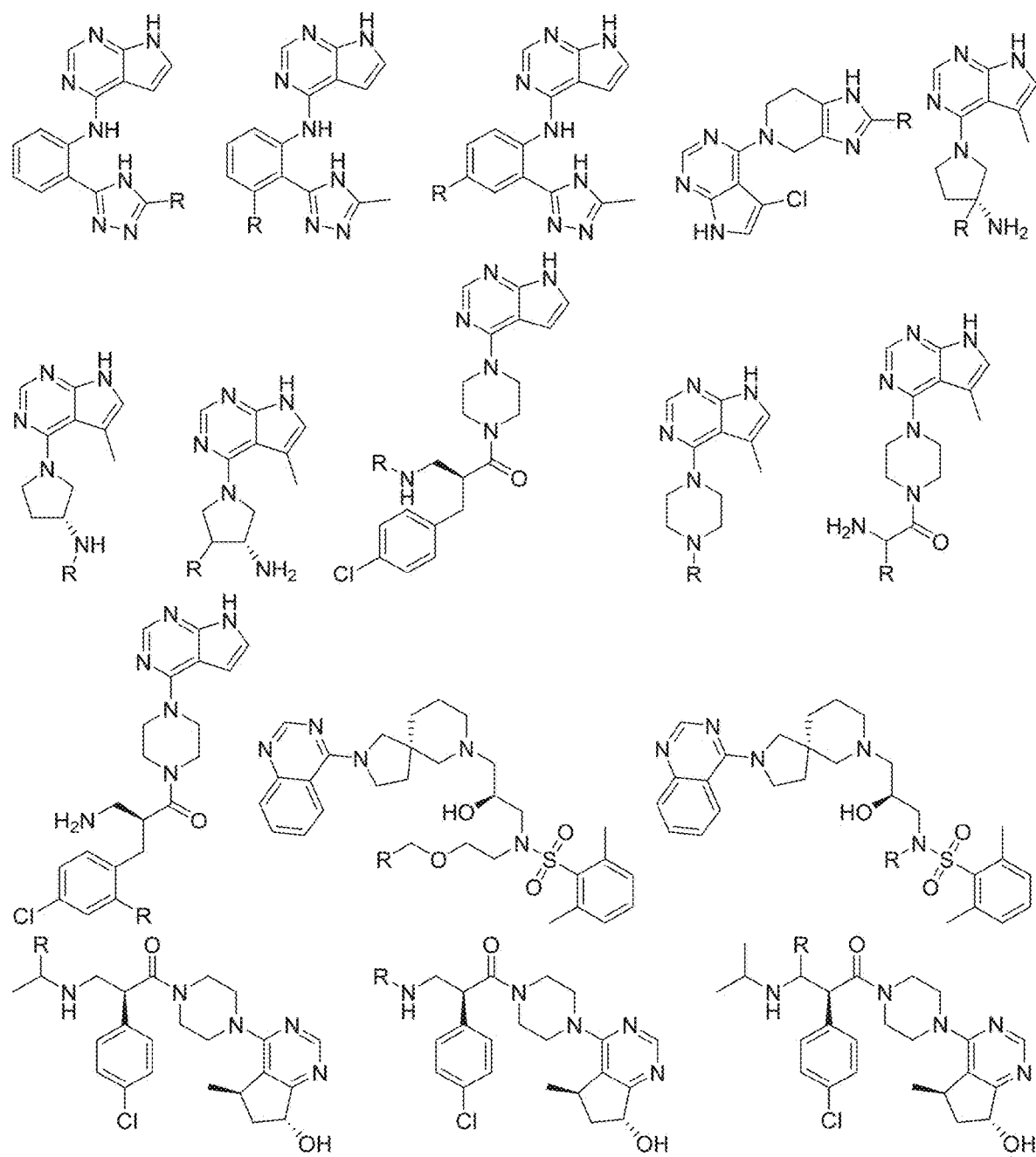
FIG. 8KKK

FIG. 8LLL
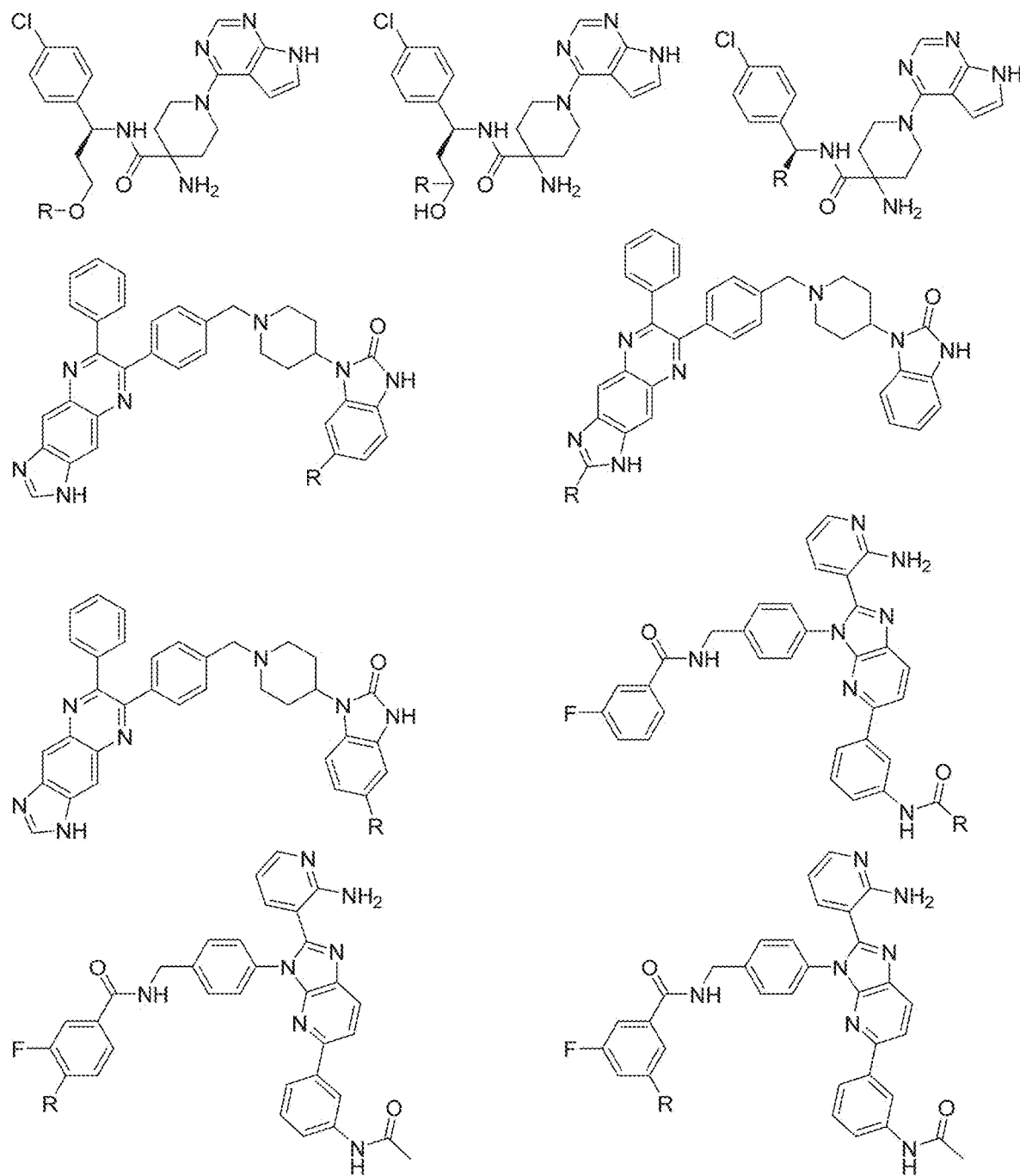

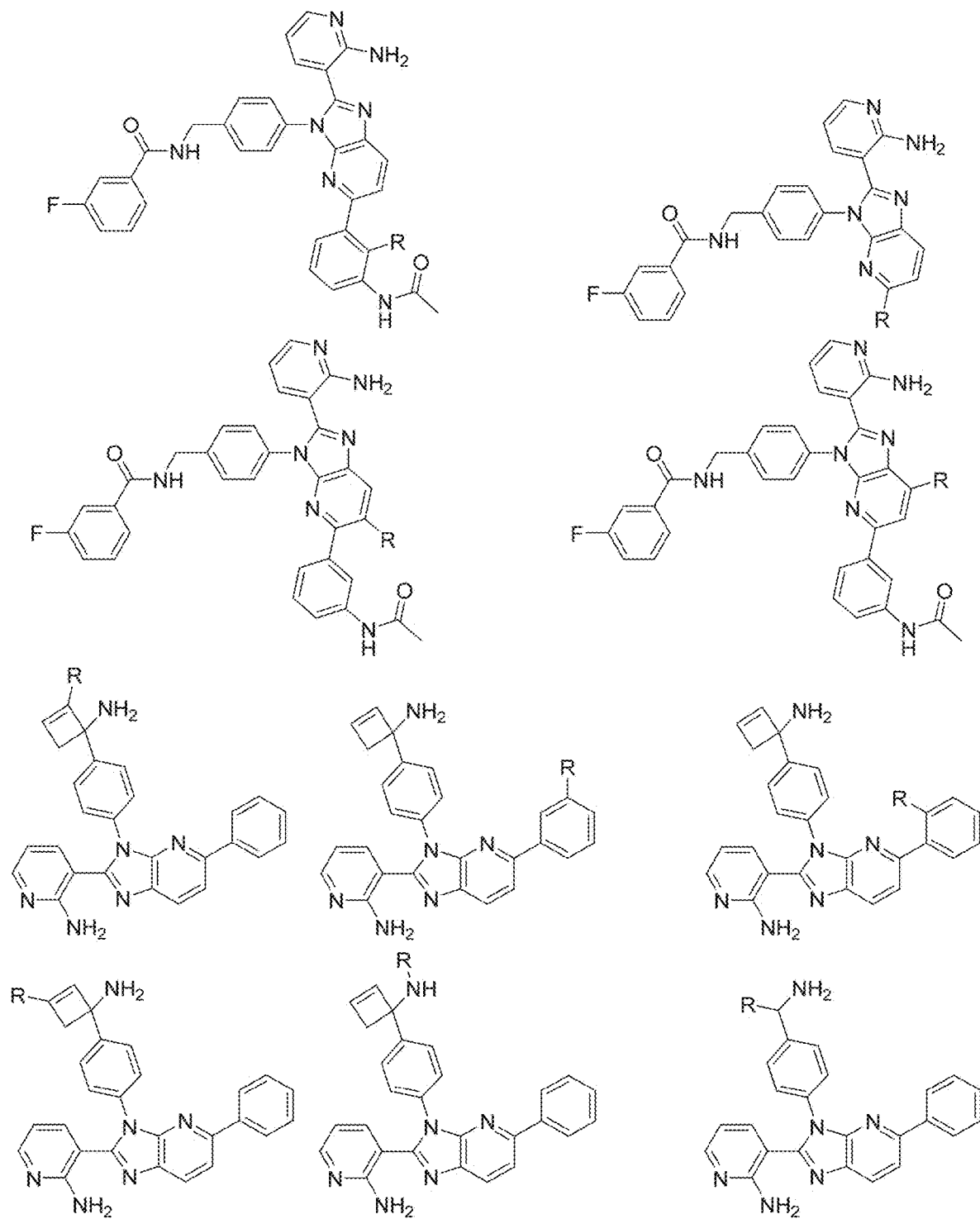
FIG. 8MMM

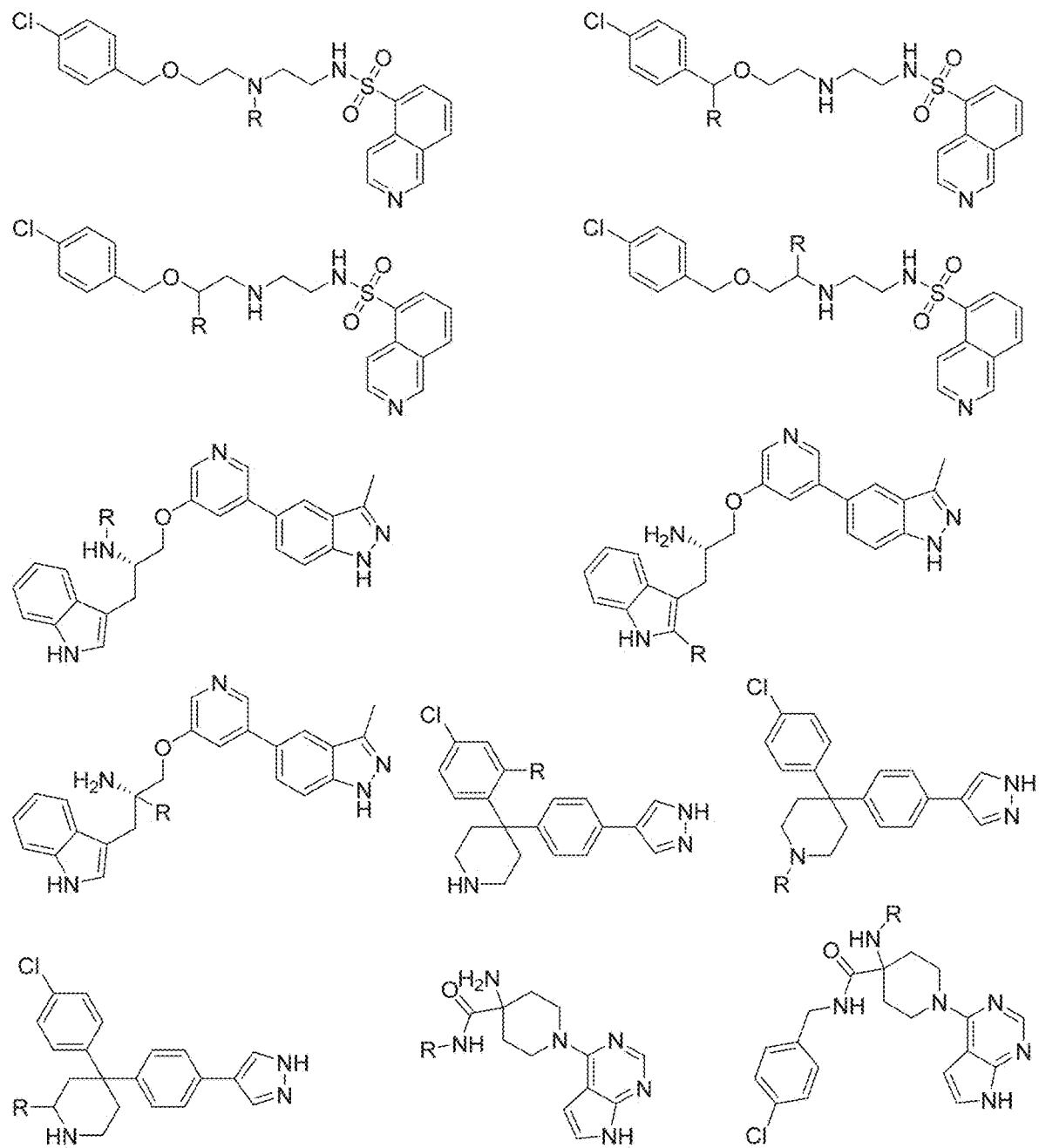
FIG. 8NNN

FIG. 8OOO
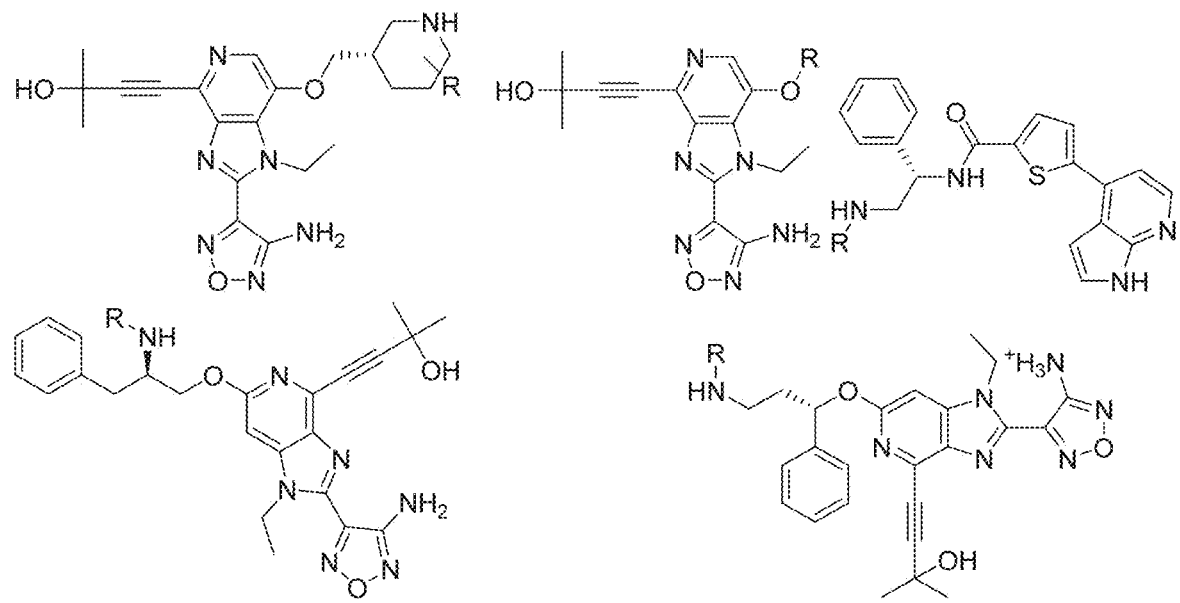
FIG. 8PPP
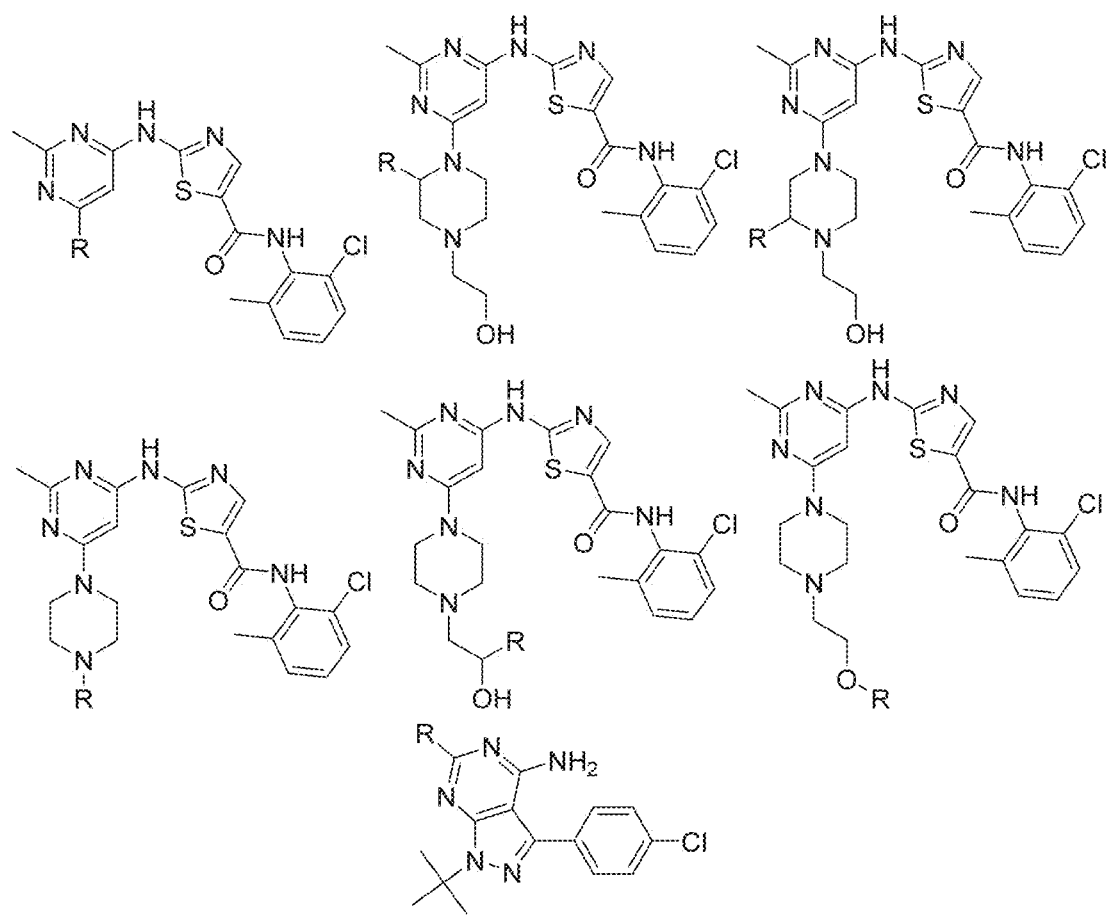

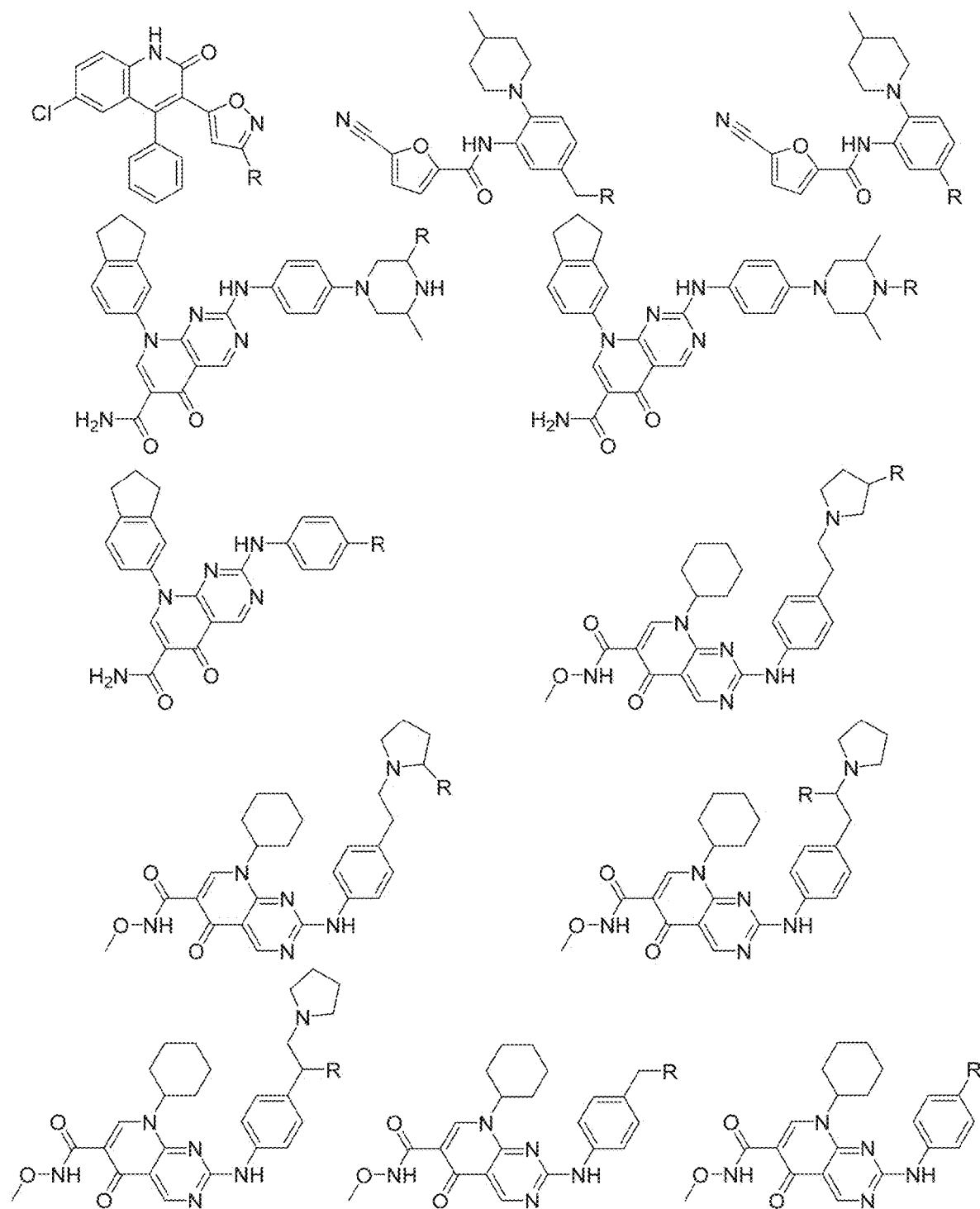
FIG. 8QQQ

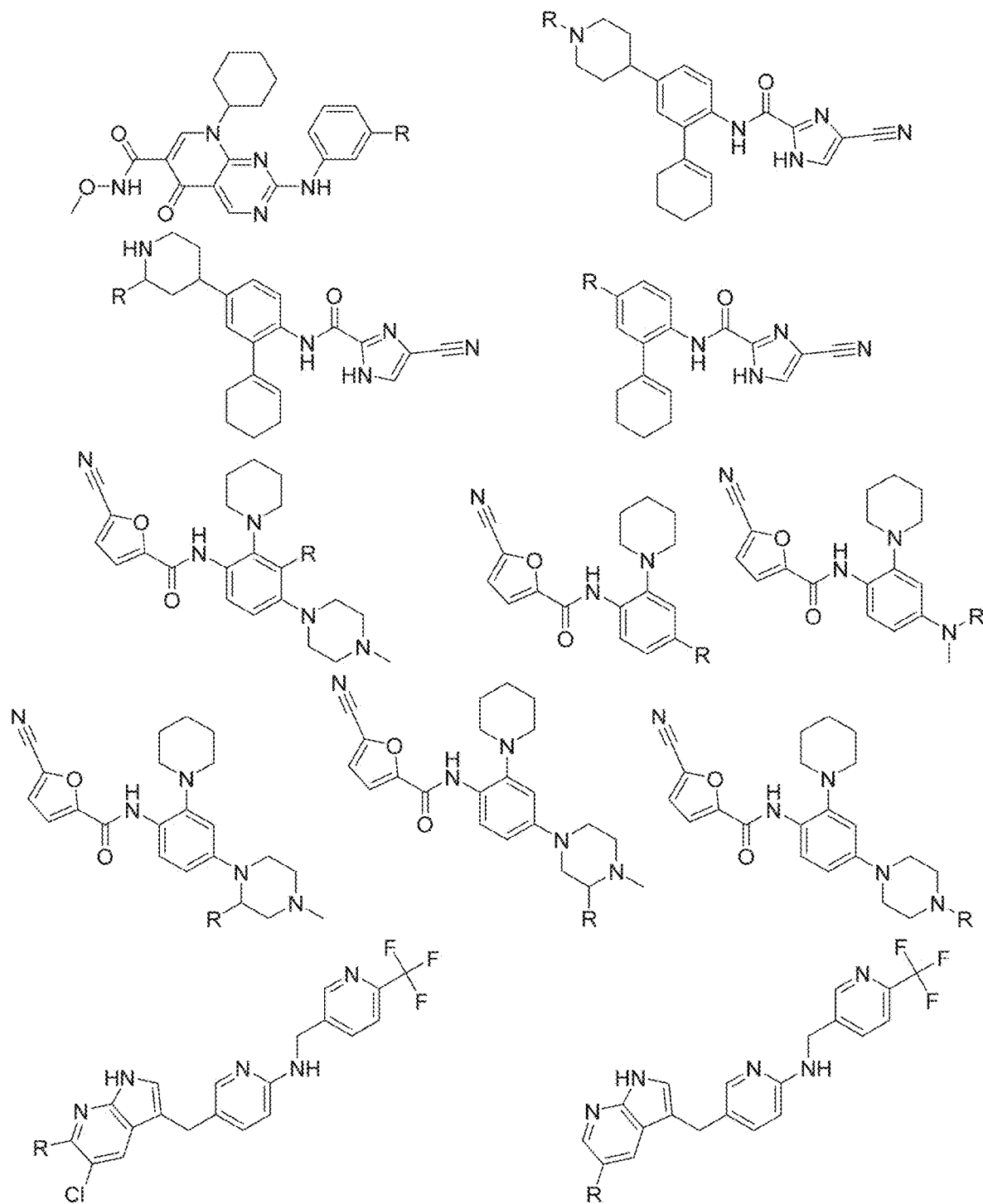
FIG. 8RRR

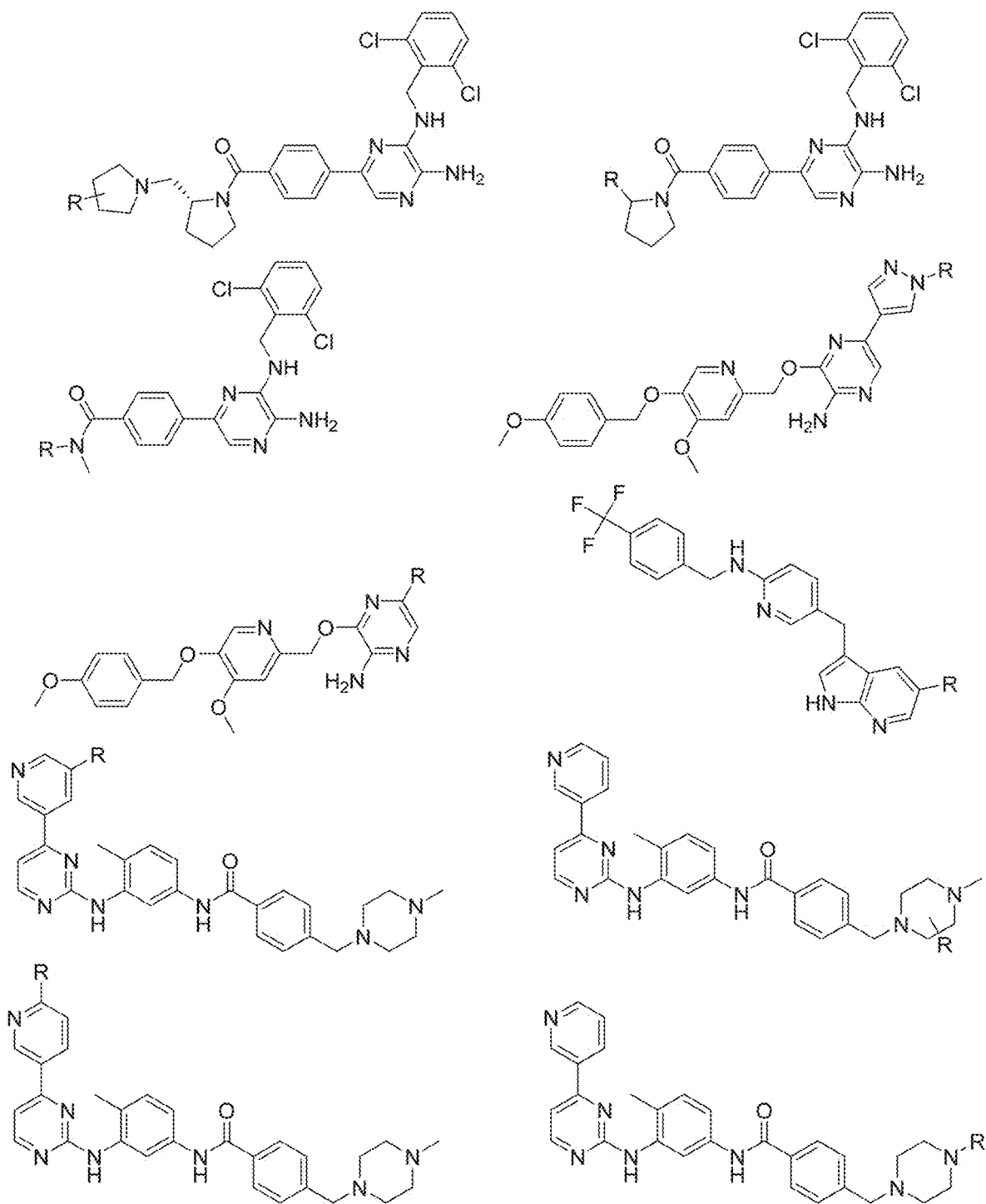
FIG. 8SSS

FIG. 8TTT
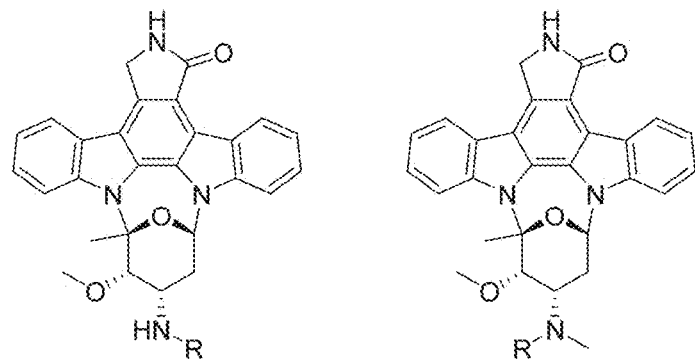
FIG. 8UUU
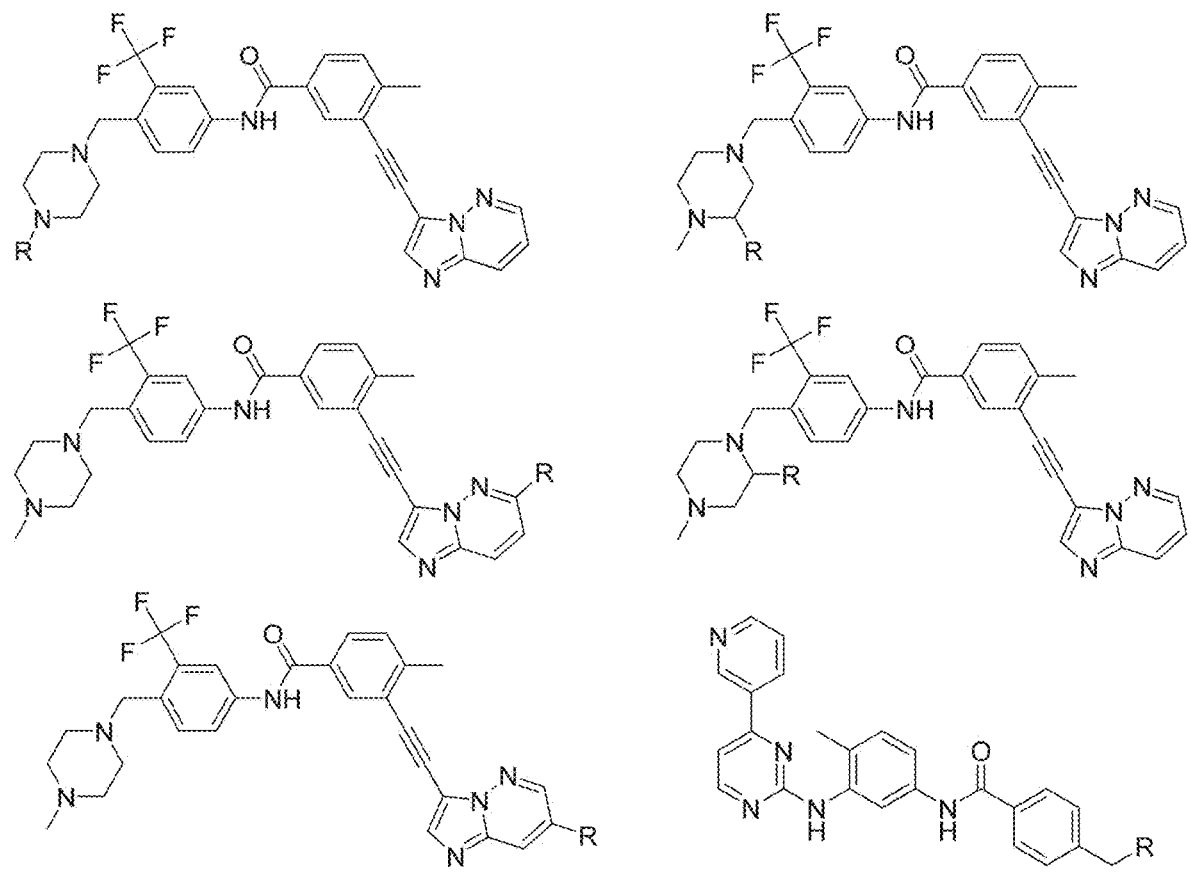

FIG. 8VVV
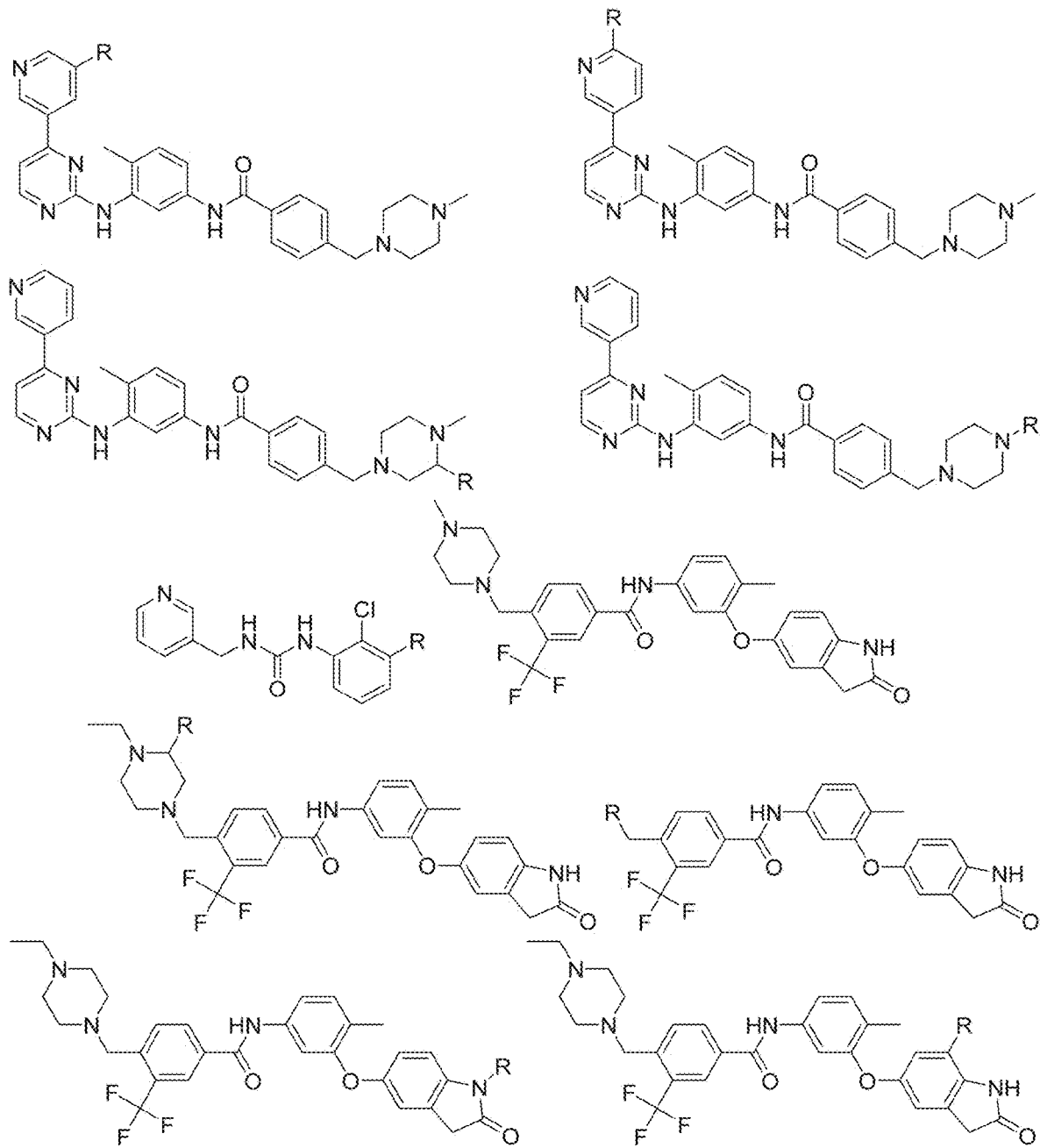

FIG. 8WWW
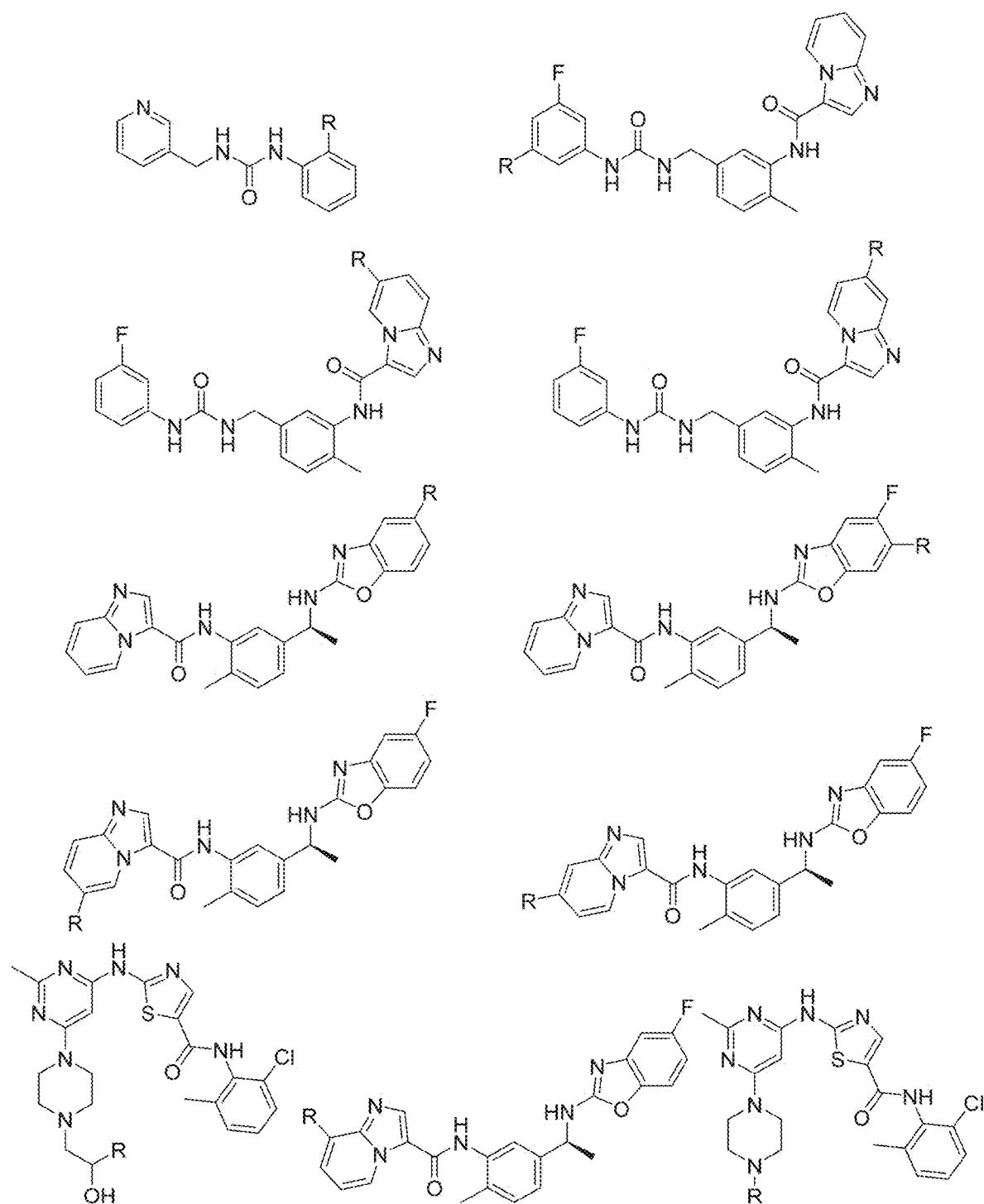

FIG. 8XXX
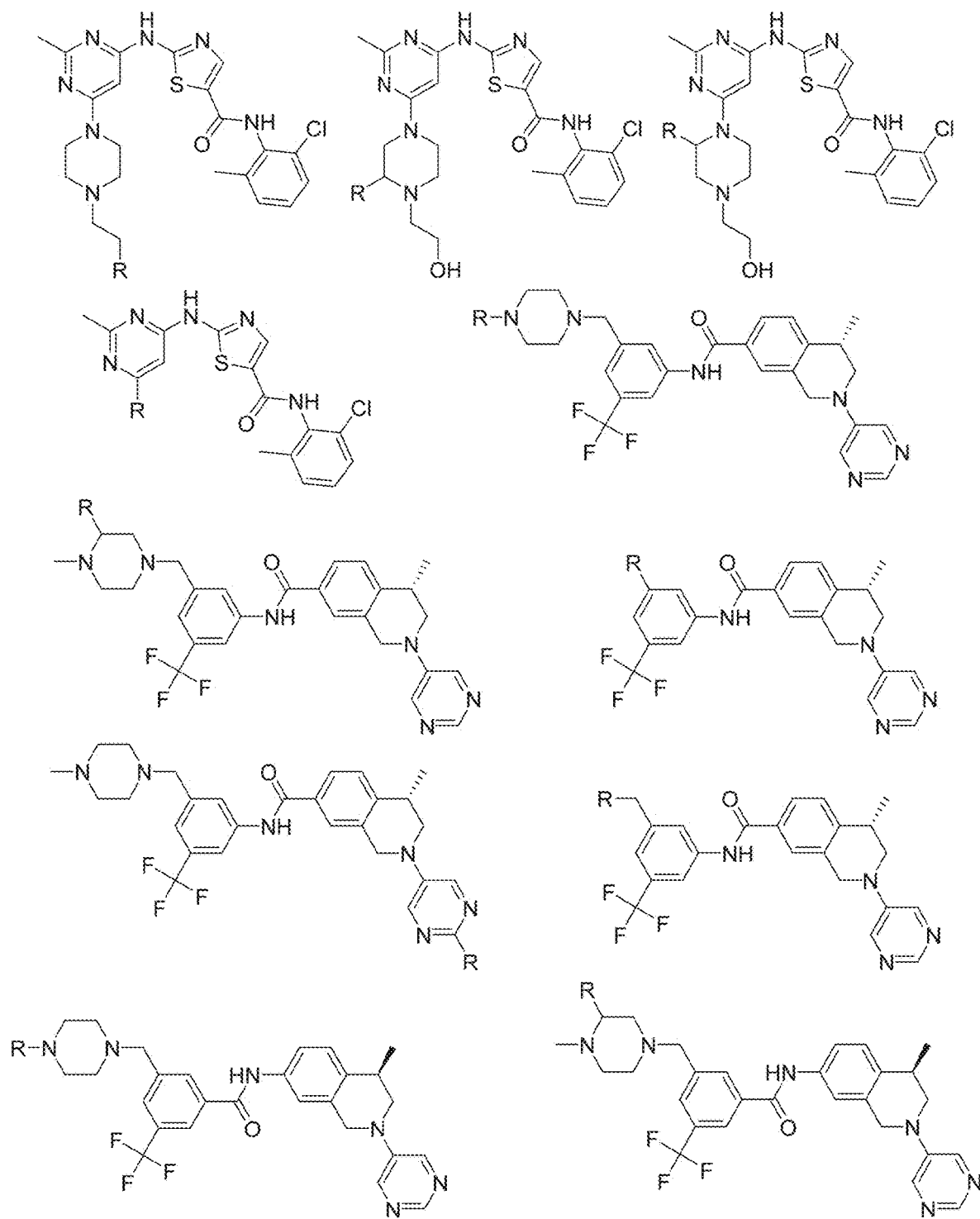

FIG. 8YYY
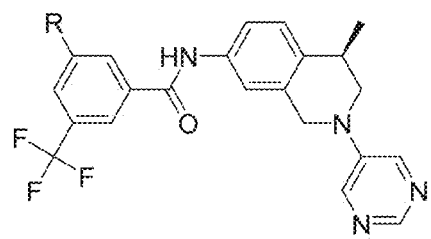
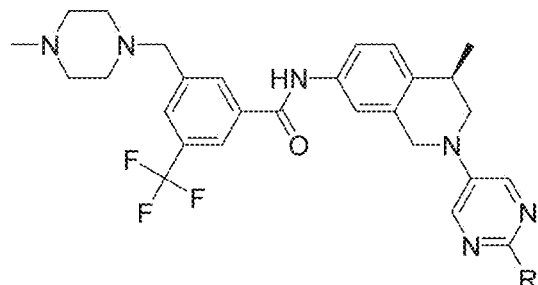
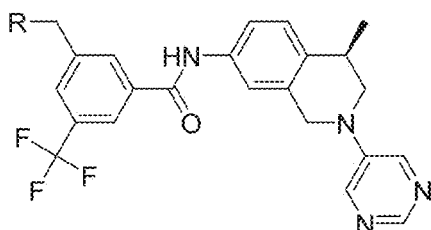
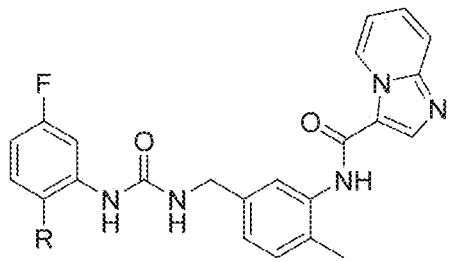
FIG. 8ZZZ
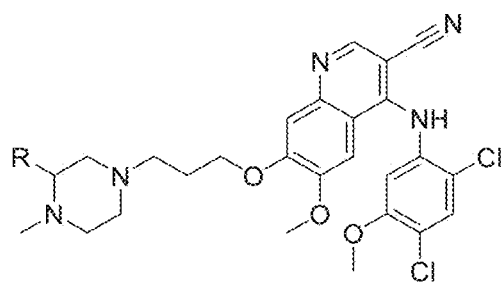
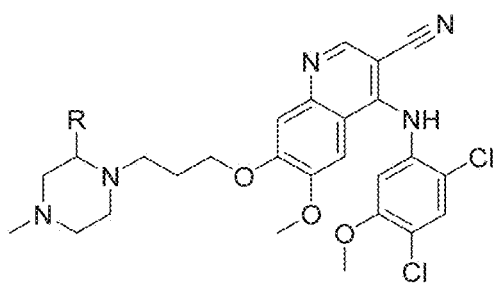
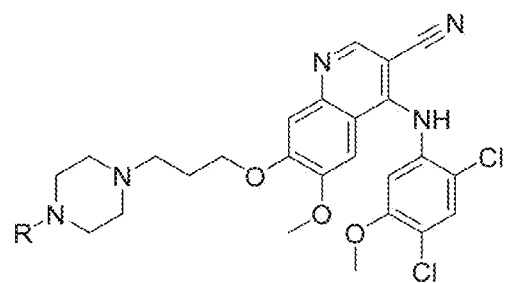
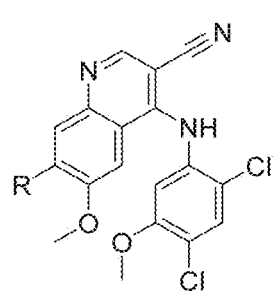
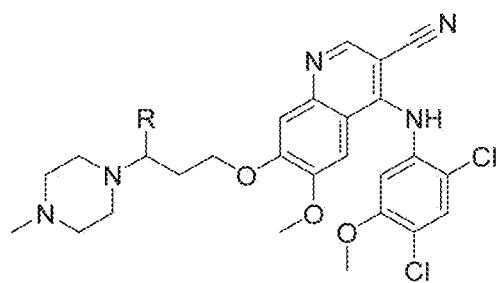
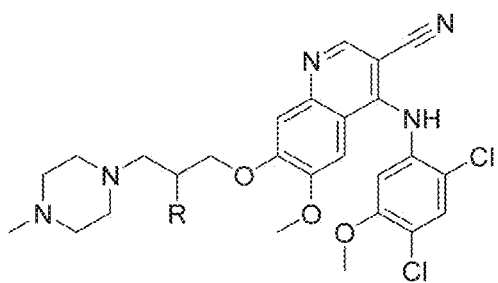

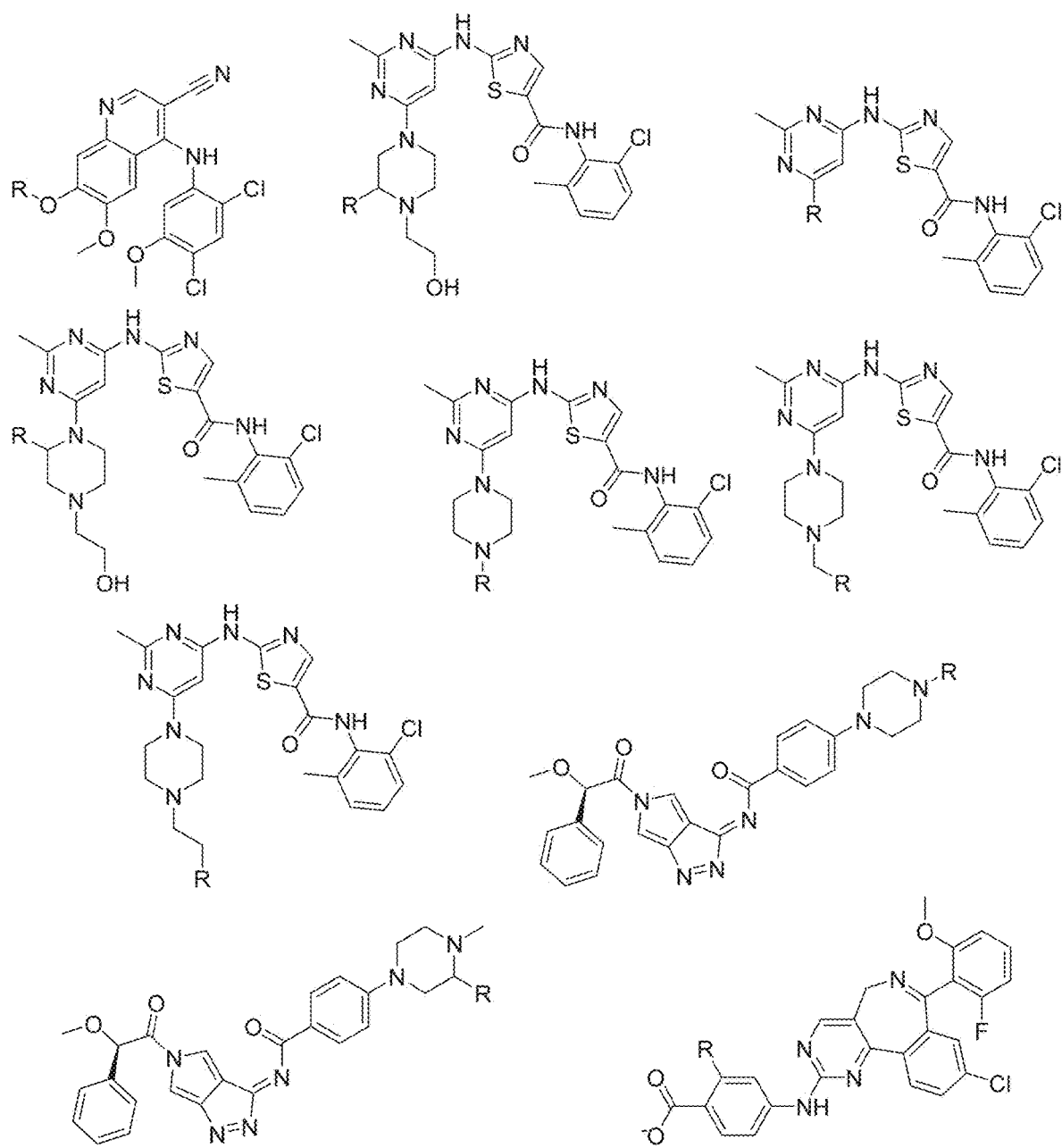
FIG. 8AAAA

FIG. 8BBBB
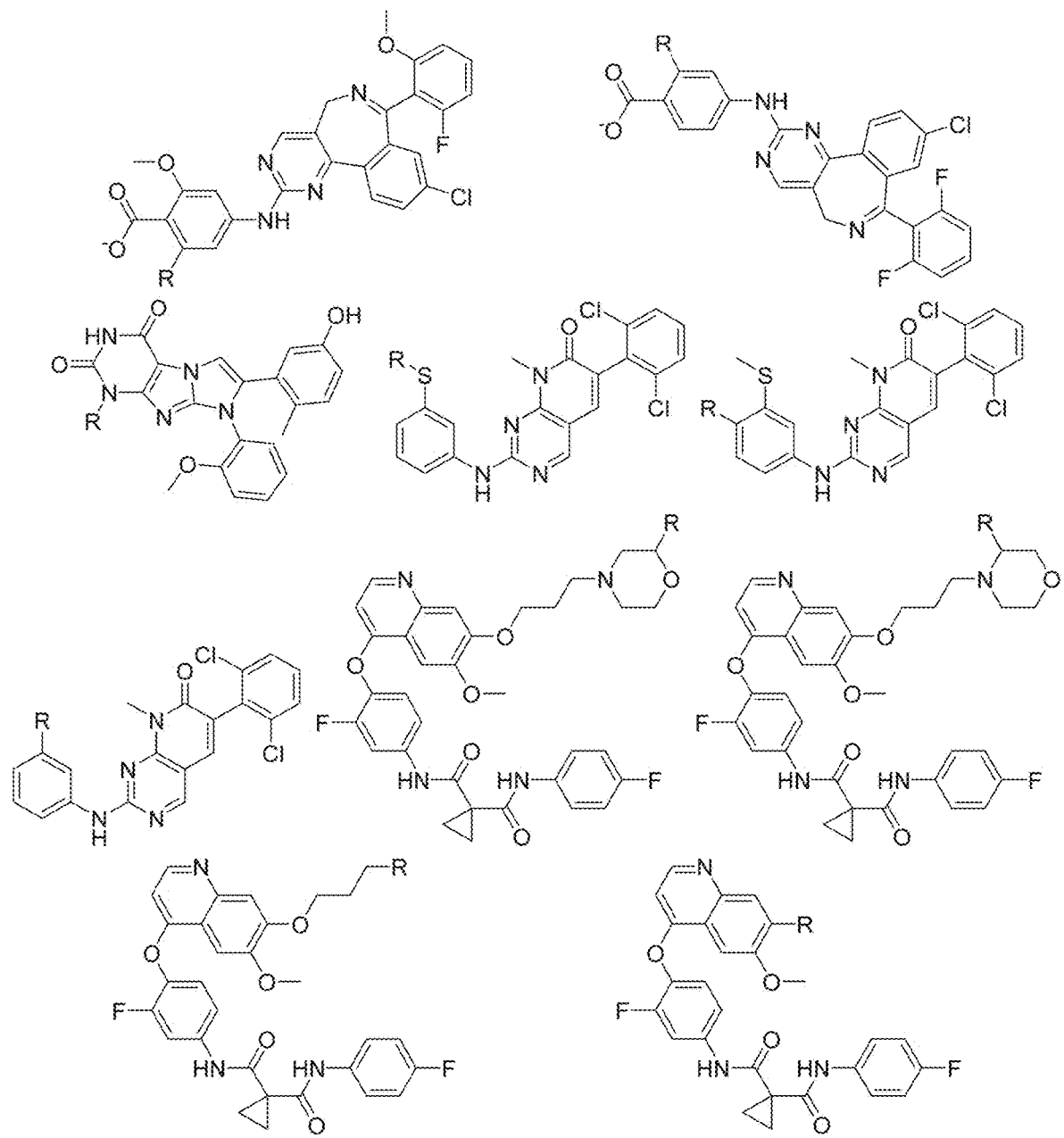

FIG. 8CCCC
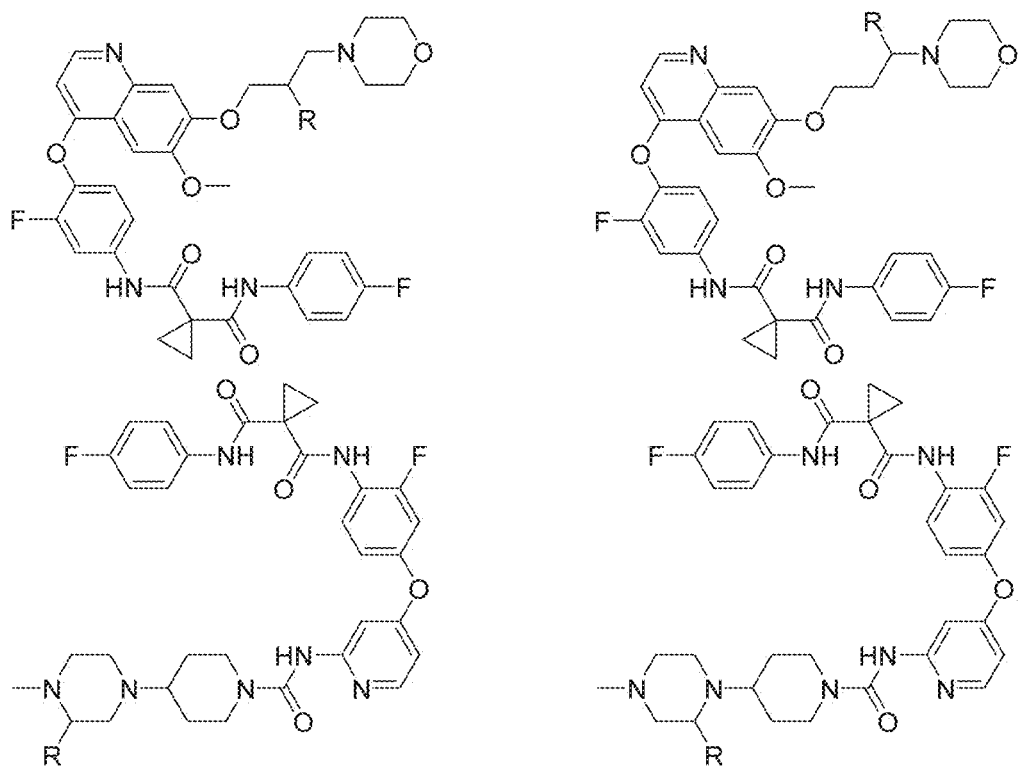
FIG. 8DDDD
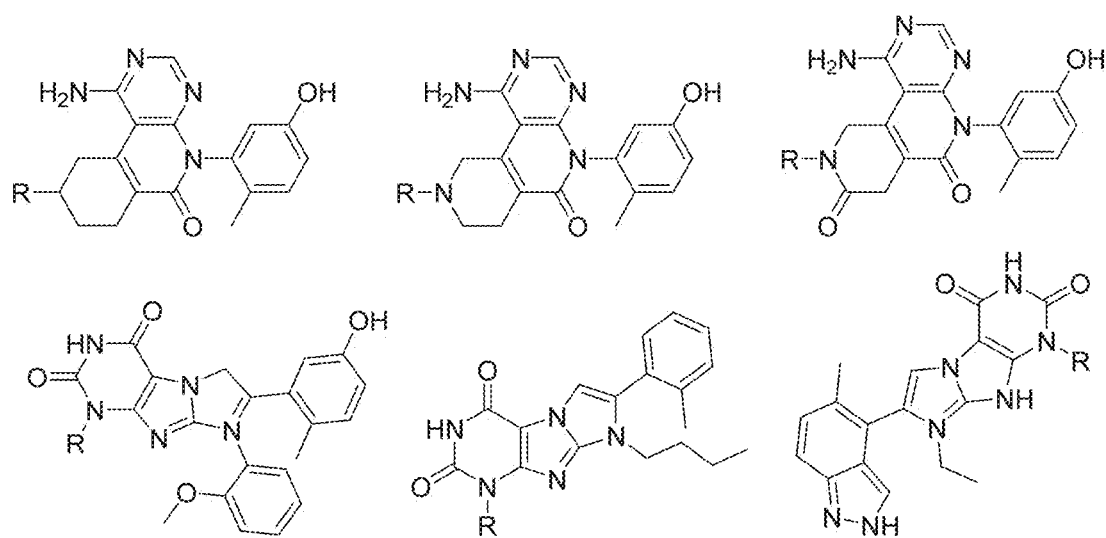

FIG. 8EEEE
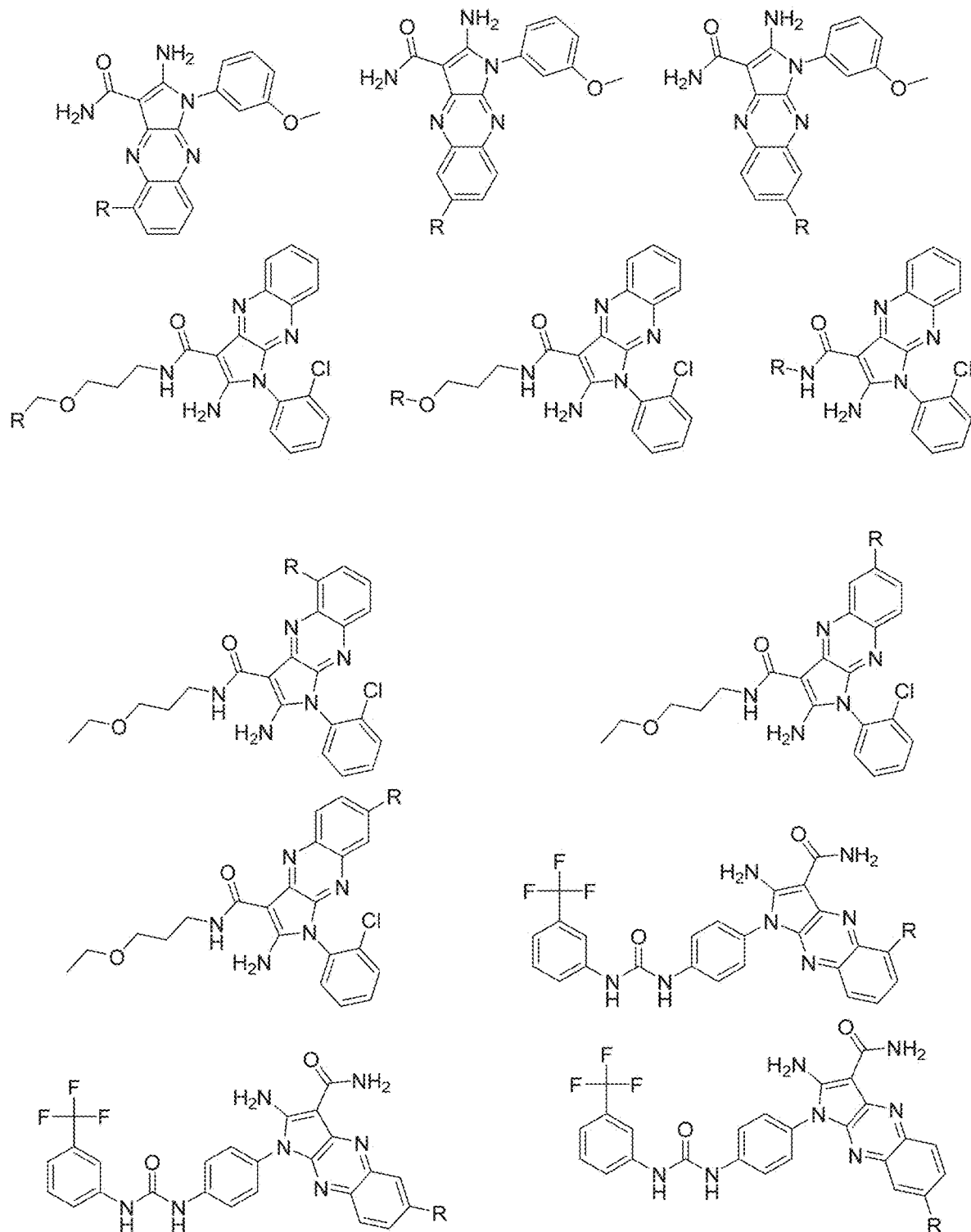

FIG. 8FFFF
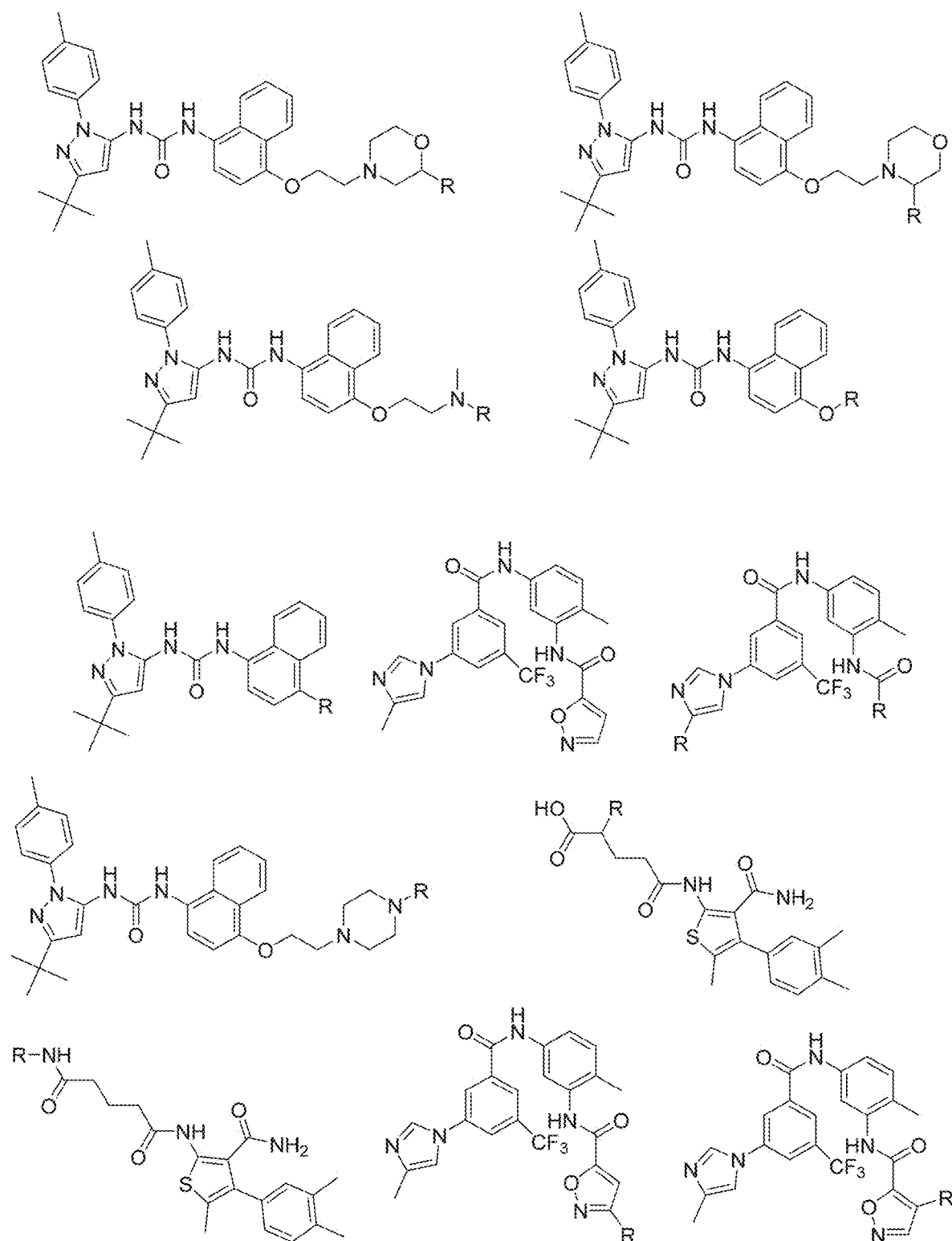

FIG. 8GGGG
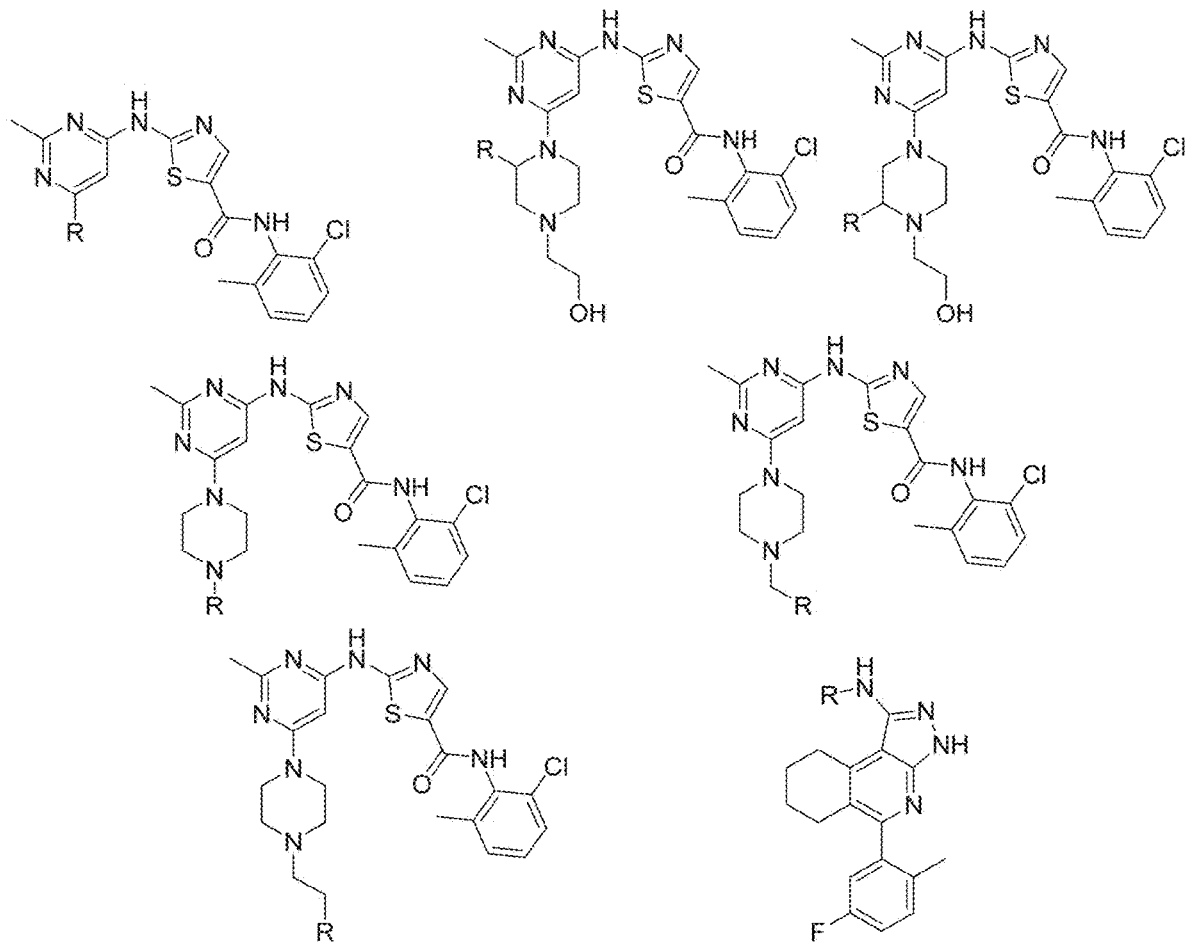
FIG. 8HHHH
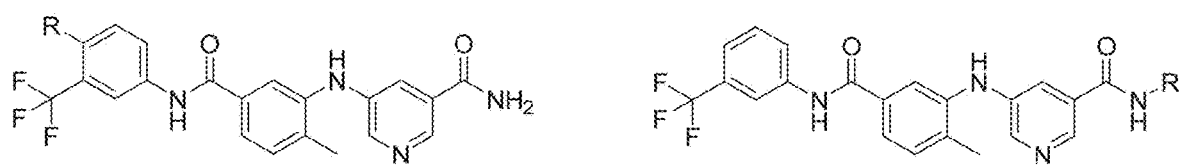
FIG. 8IIII
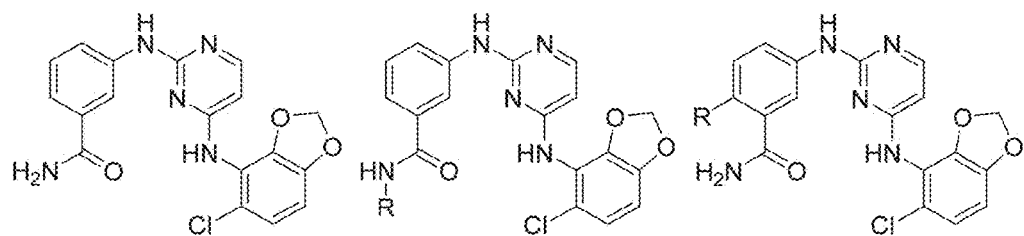

FIG. 8JJJJ
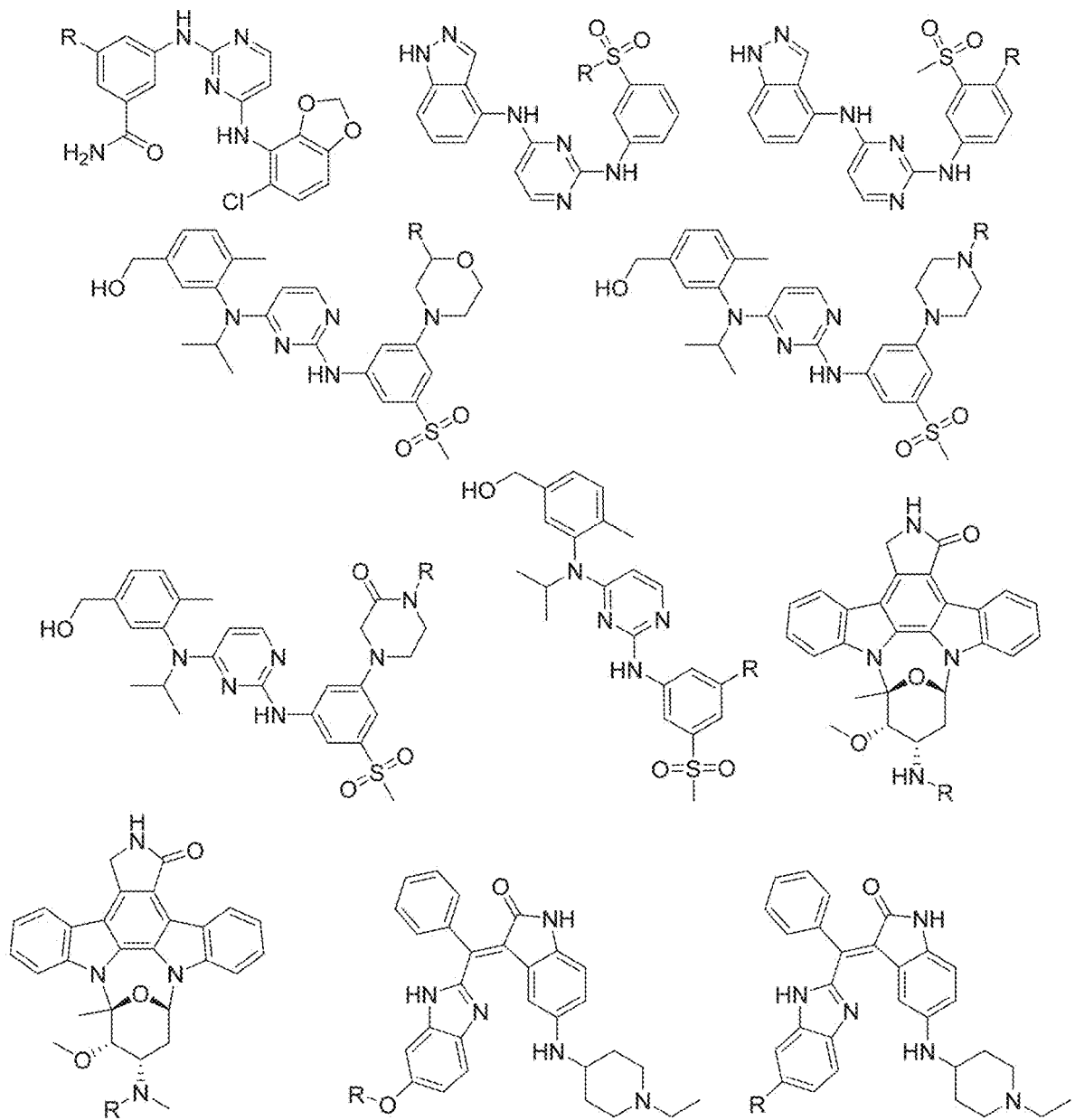

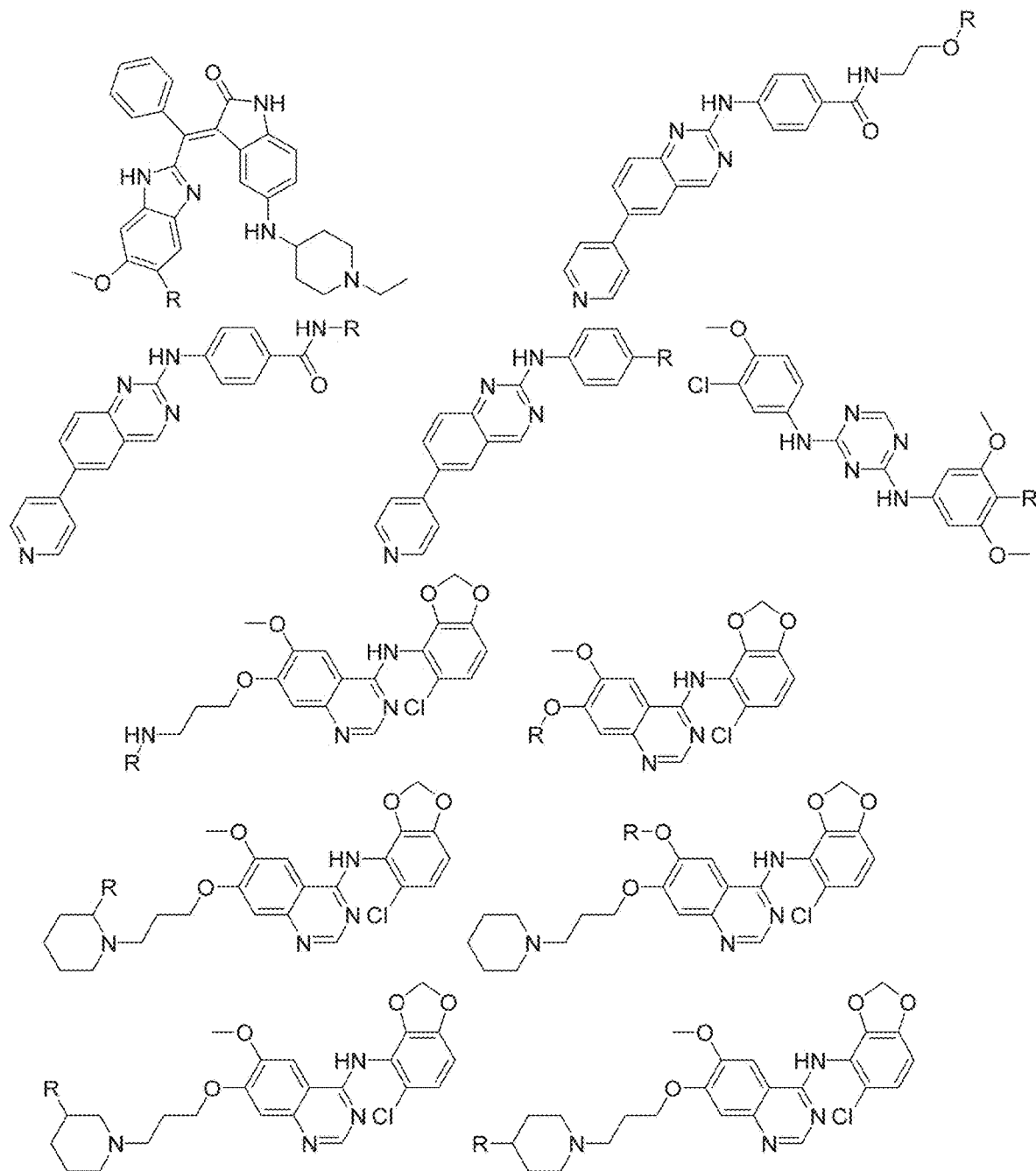
FIG. 8KKKK

FIG. 8LLLL
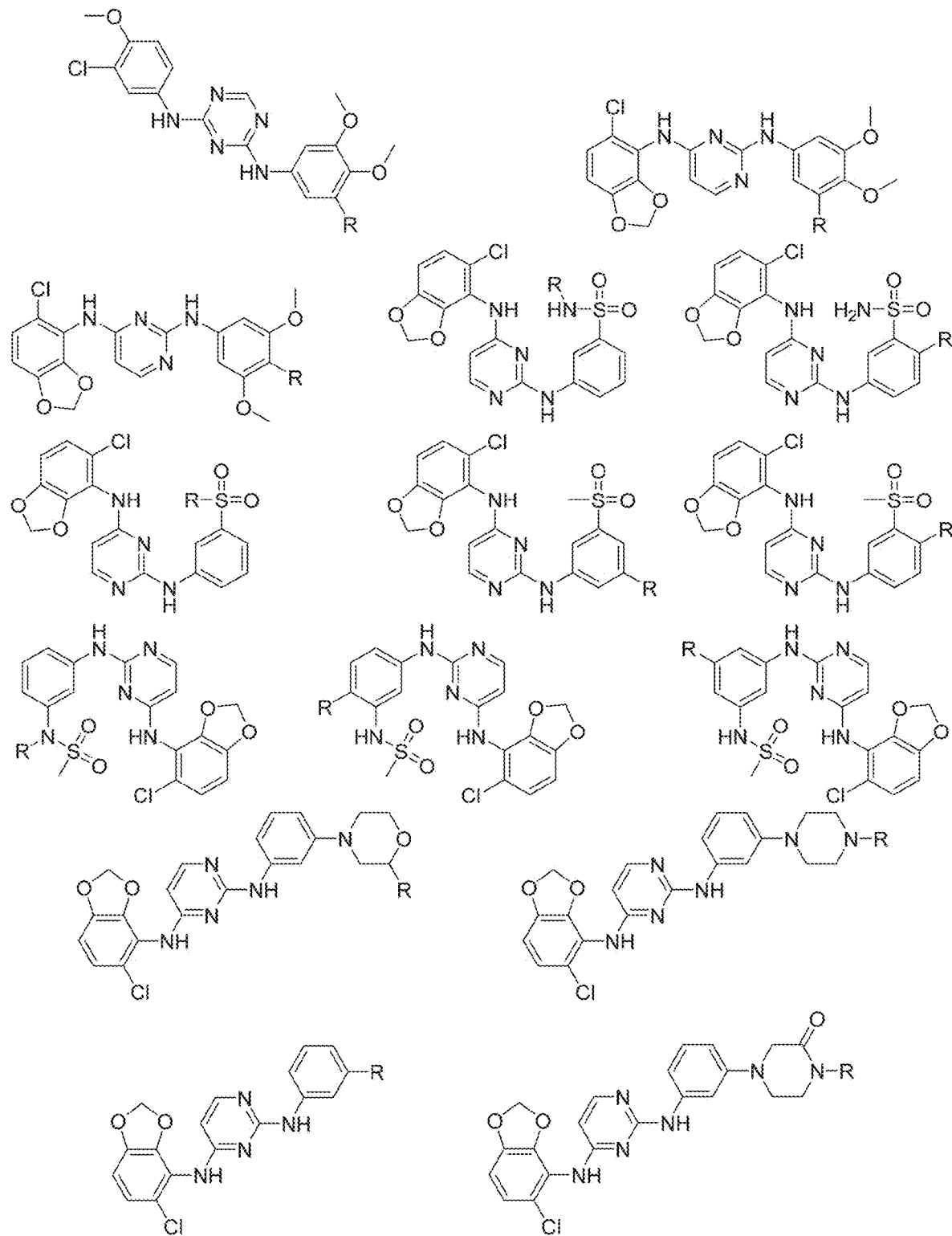

FIG. 8MMMM
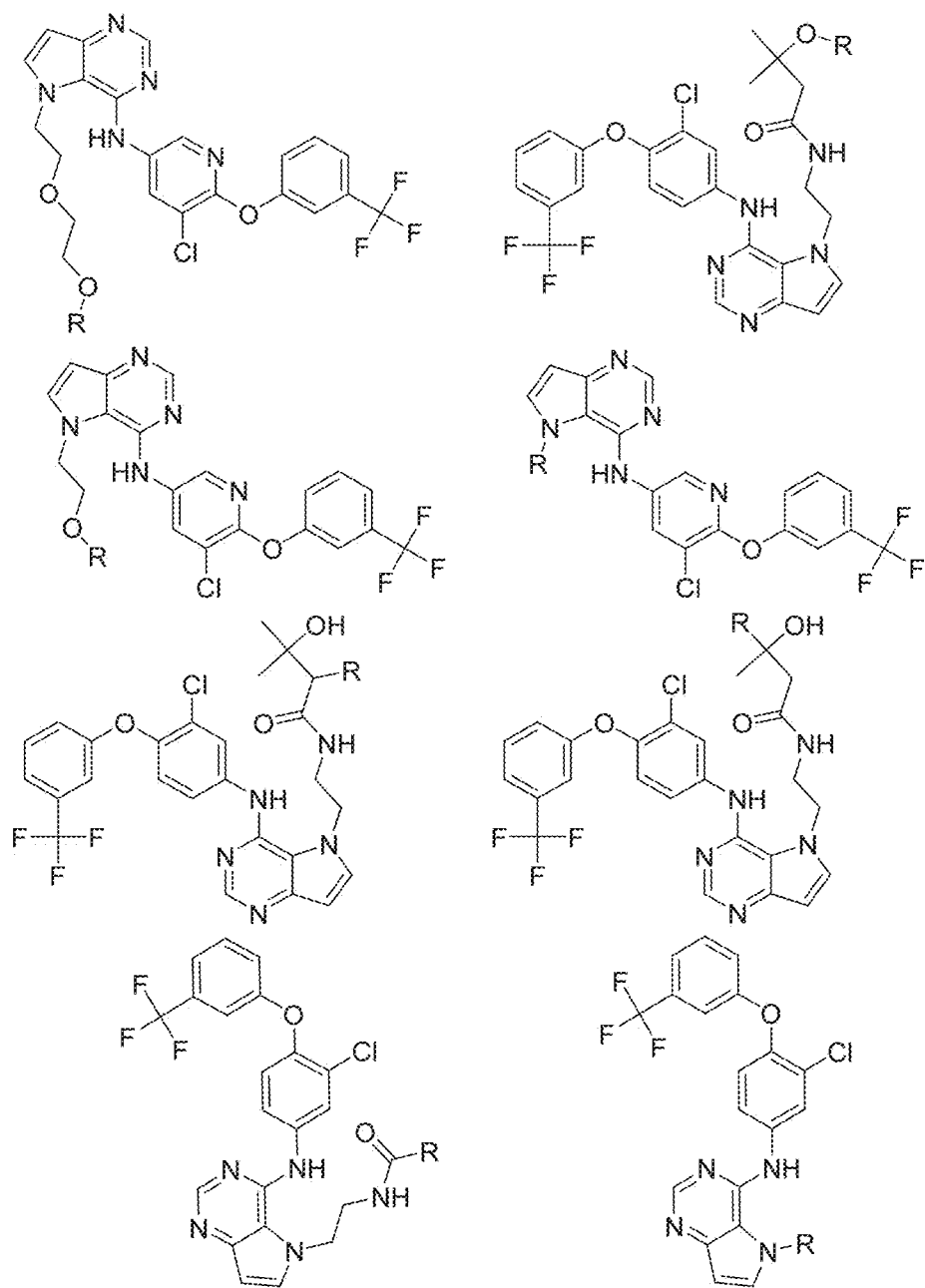

FIG. 8NNNN
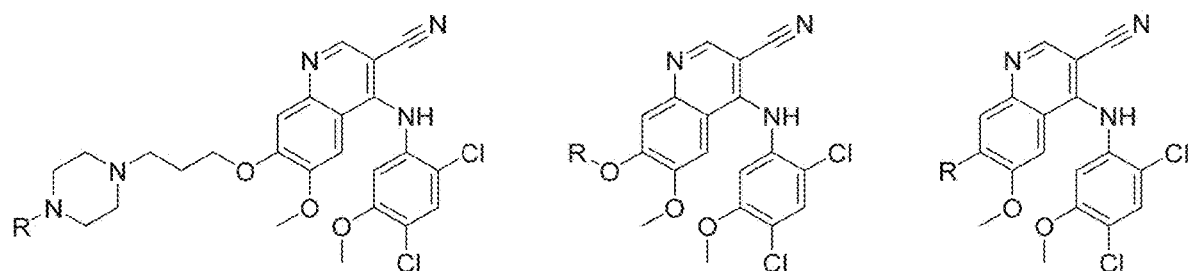
FIG. 8OOOO
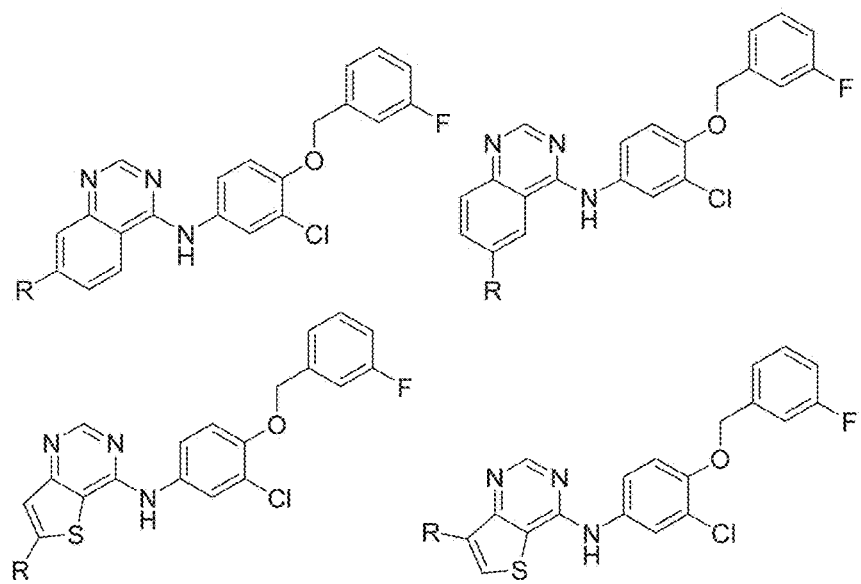
FIG. 8PPPP
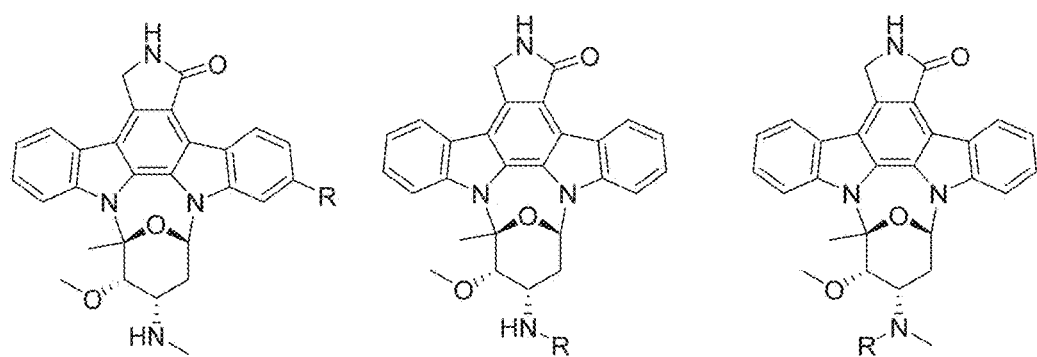

FIG. 8QQQQ
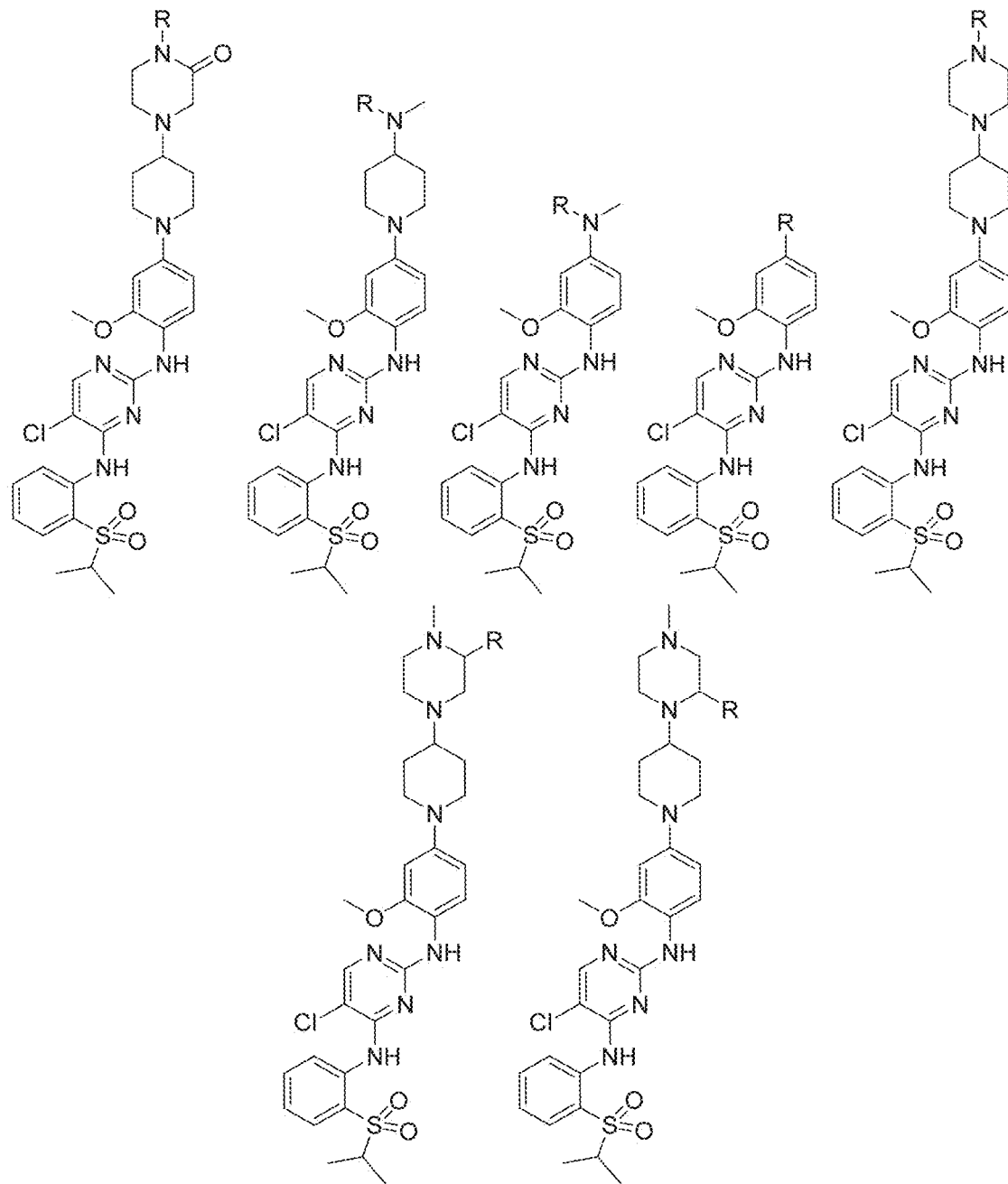

FIG. 8RRRR
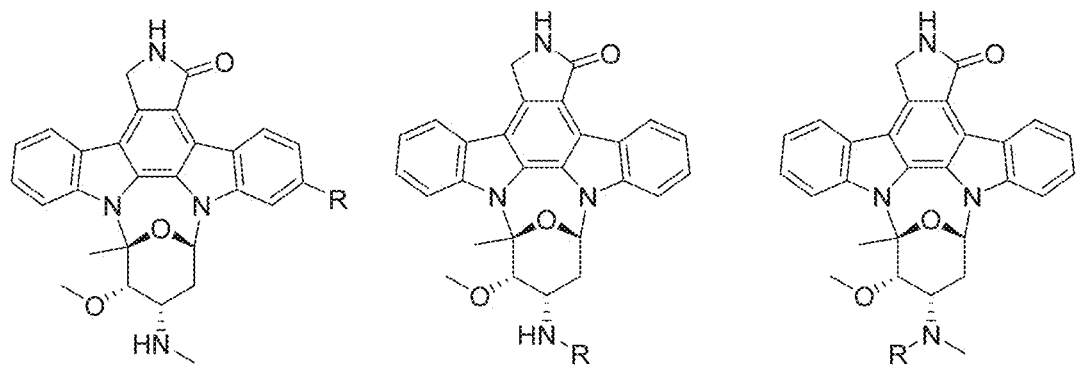
FIG. 8SSSS
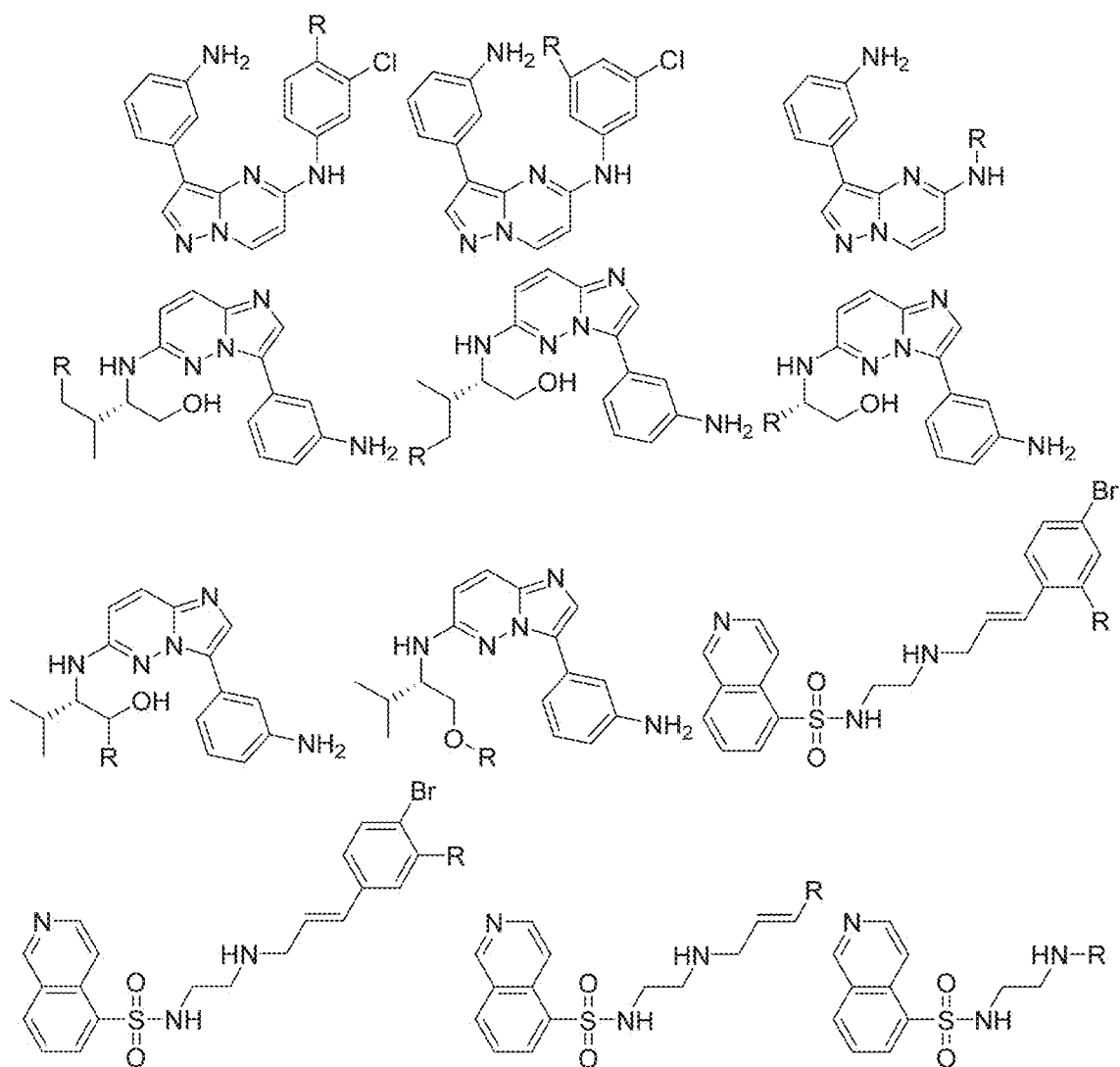

FIG. 8TTTT
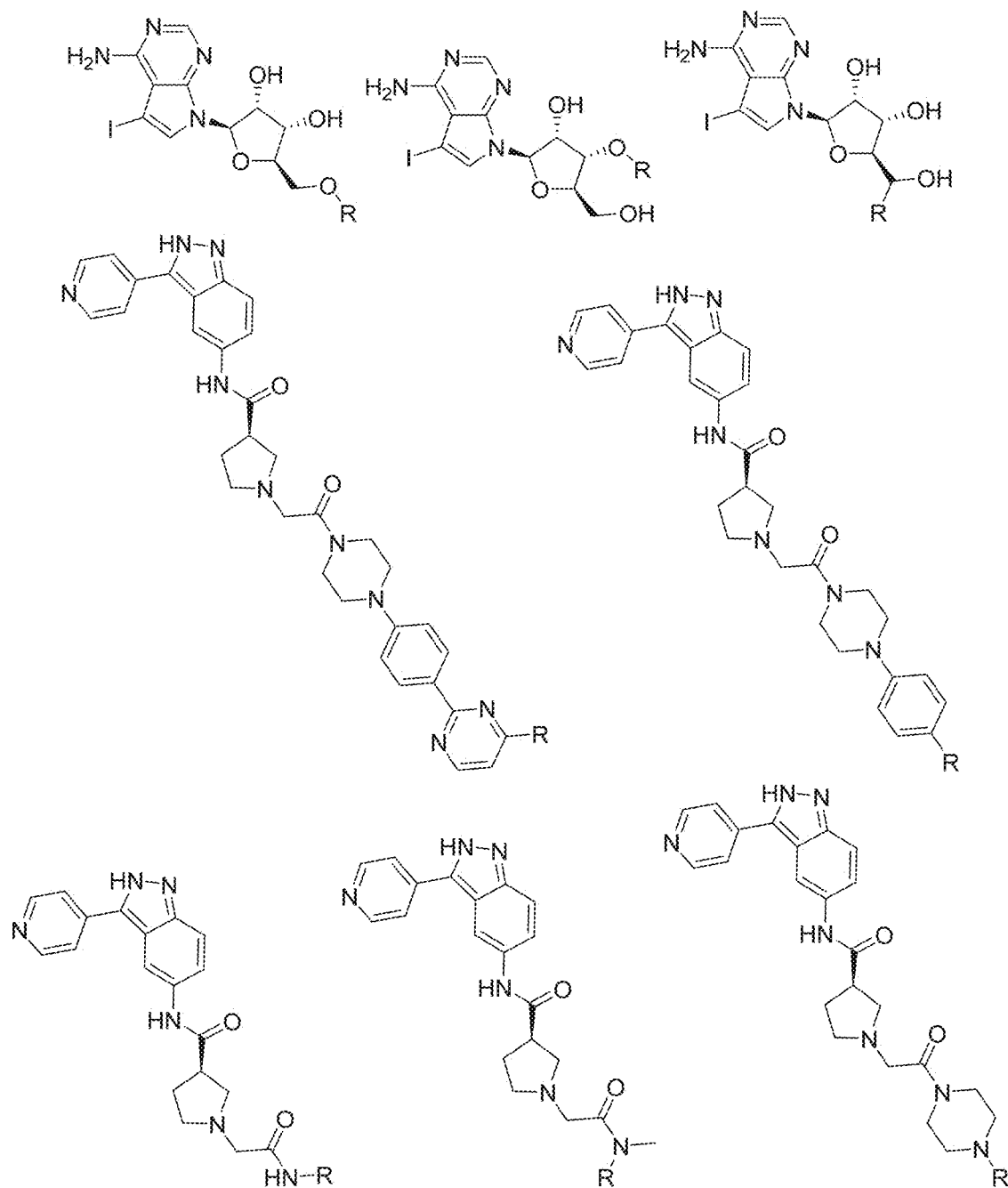

FIG. 8UUUU
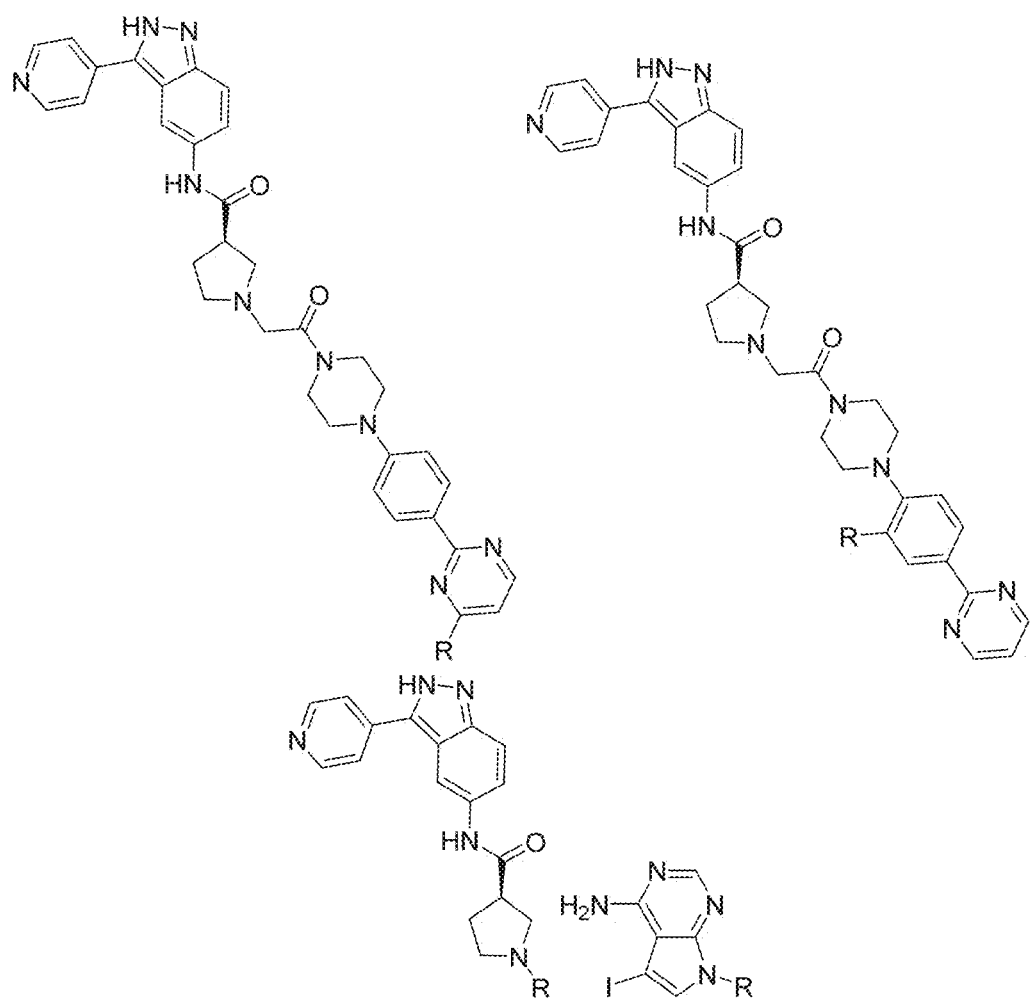

FIG. 8VVVV
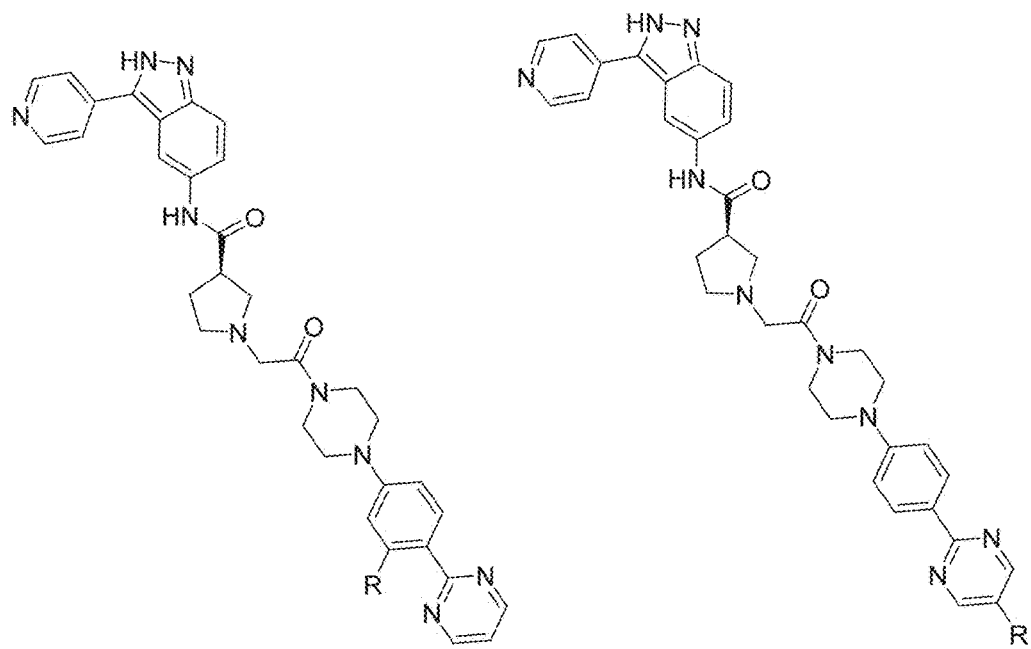
FIG. 8WWWW
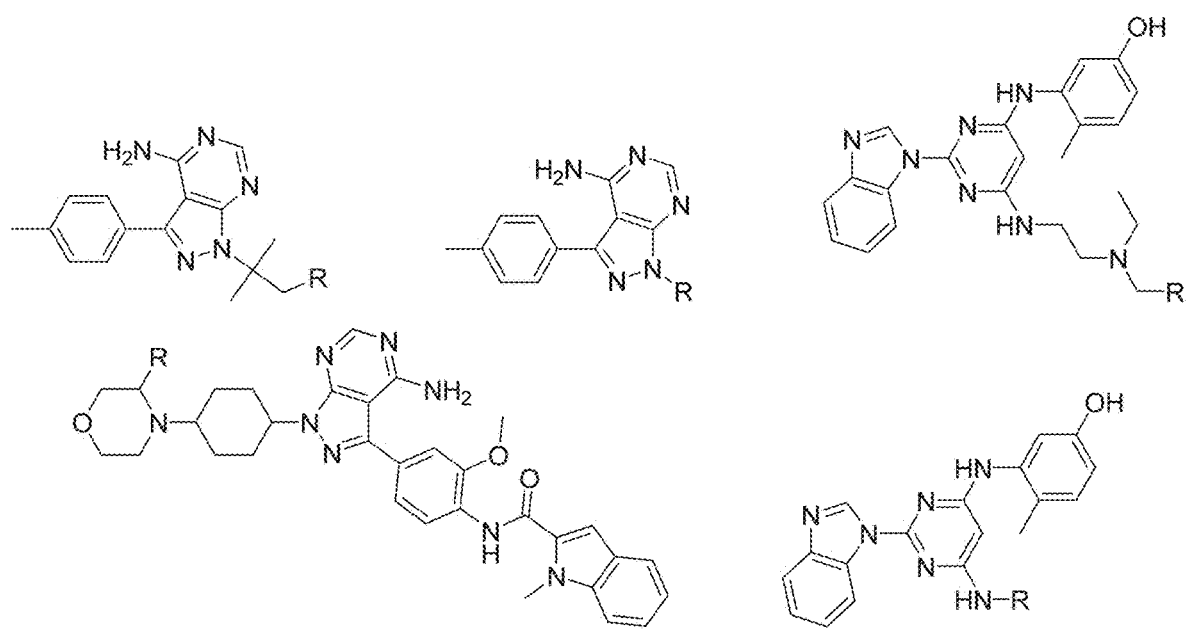

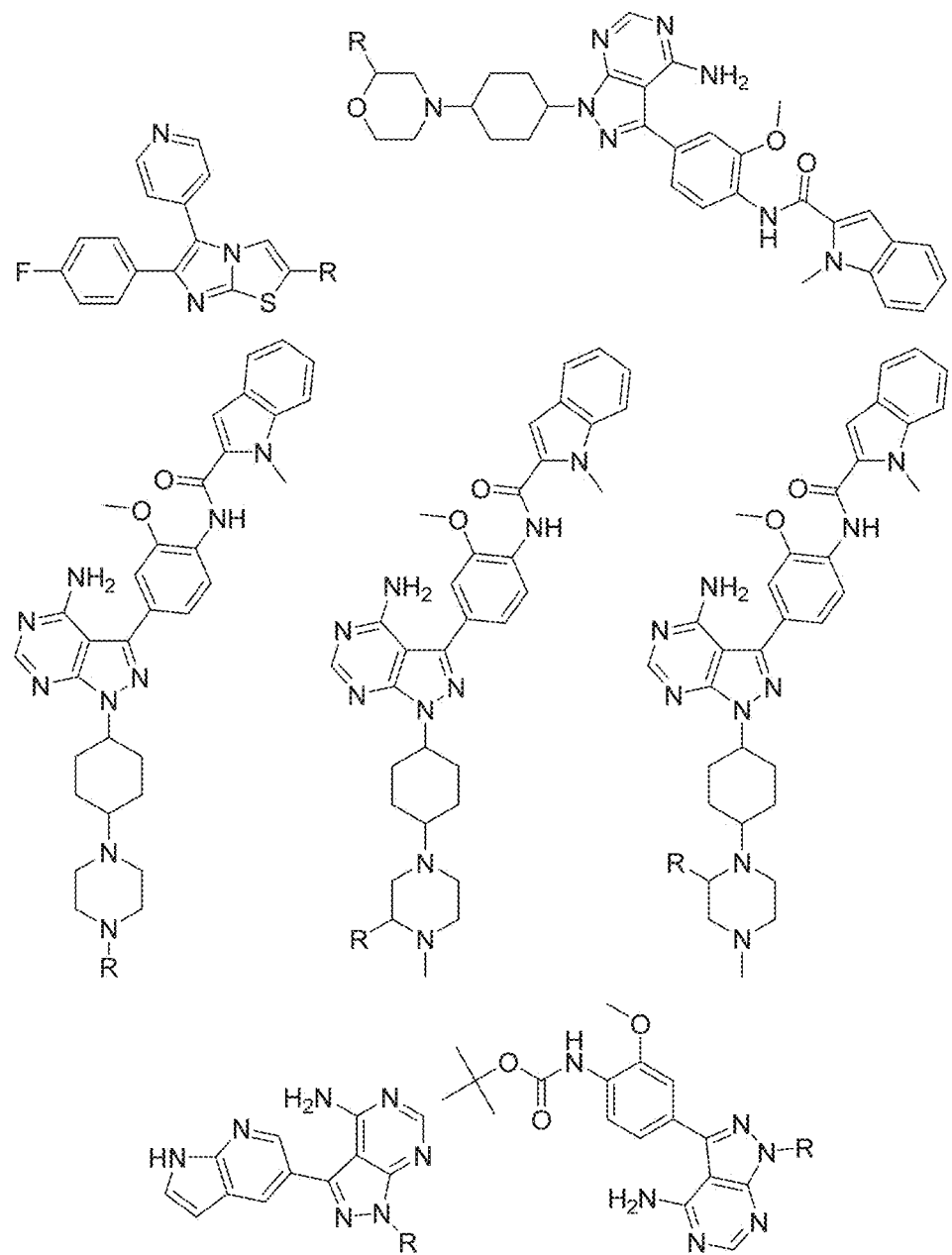
FIG. 8XXXX

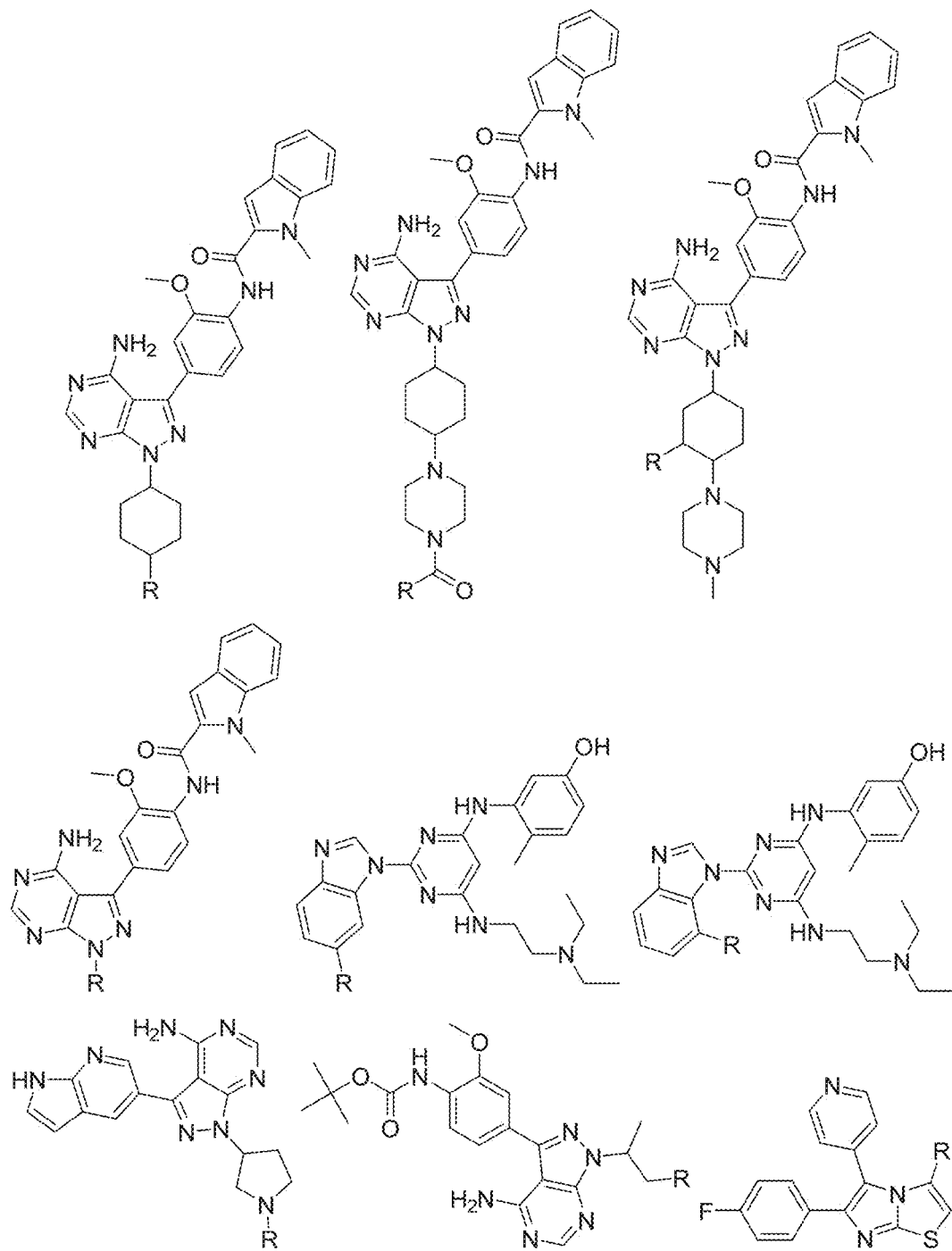
FIG. 8YYYY

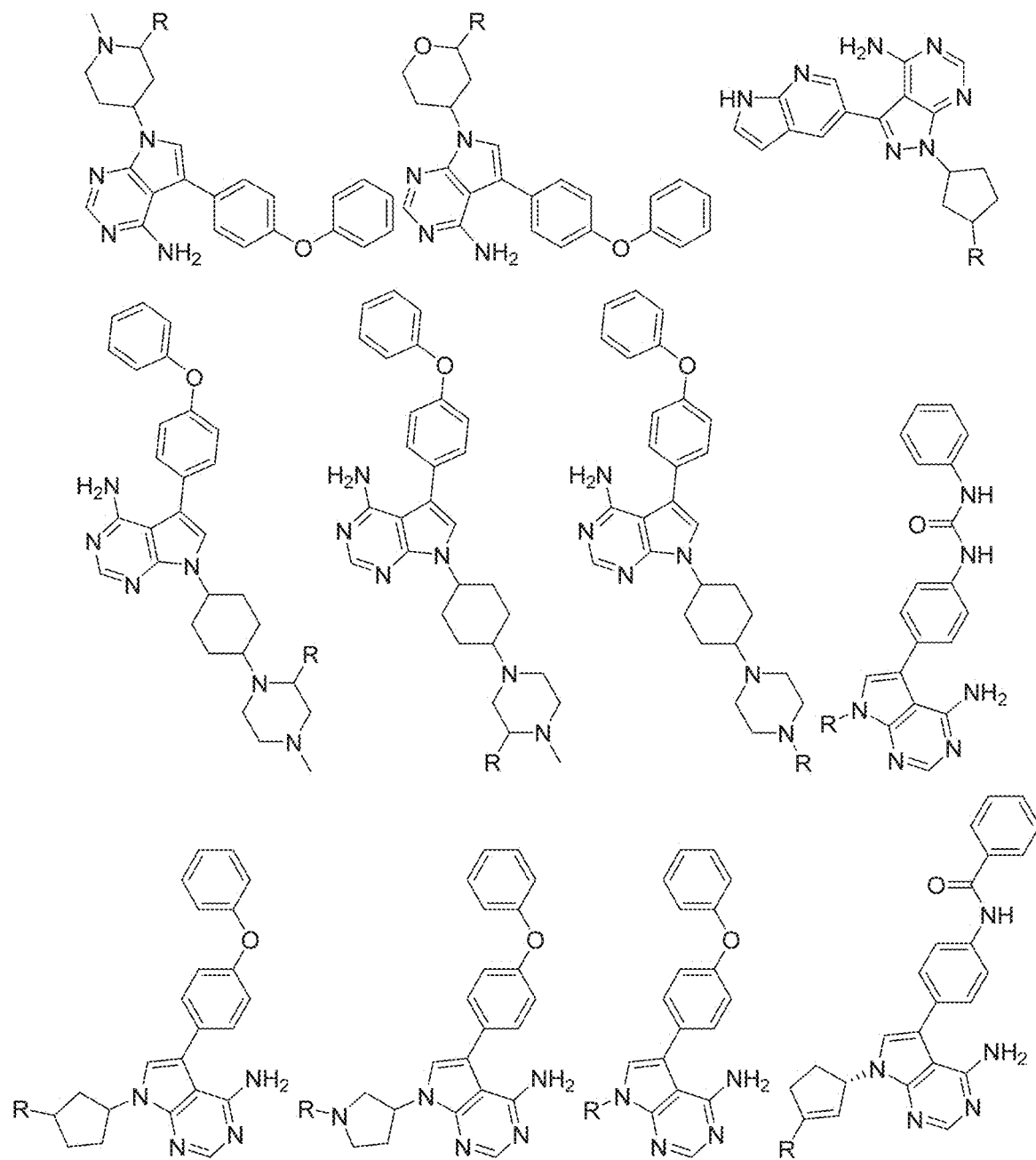
FIG. 8ZZZZ

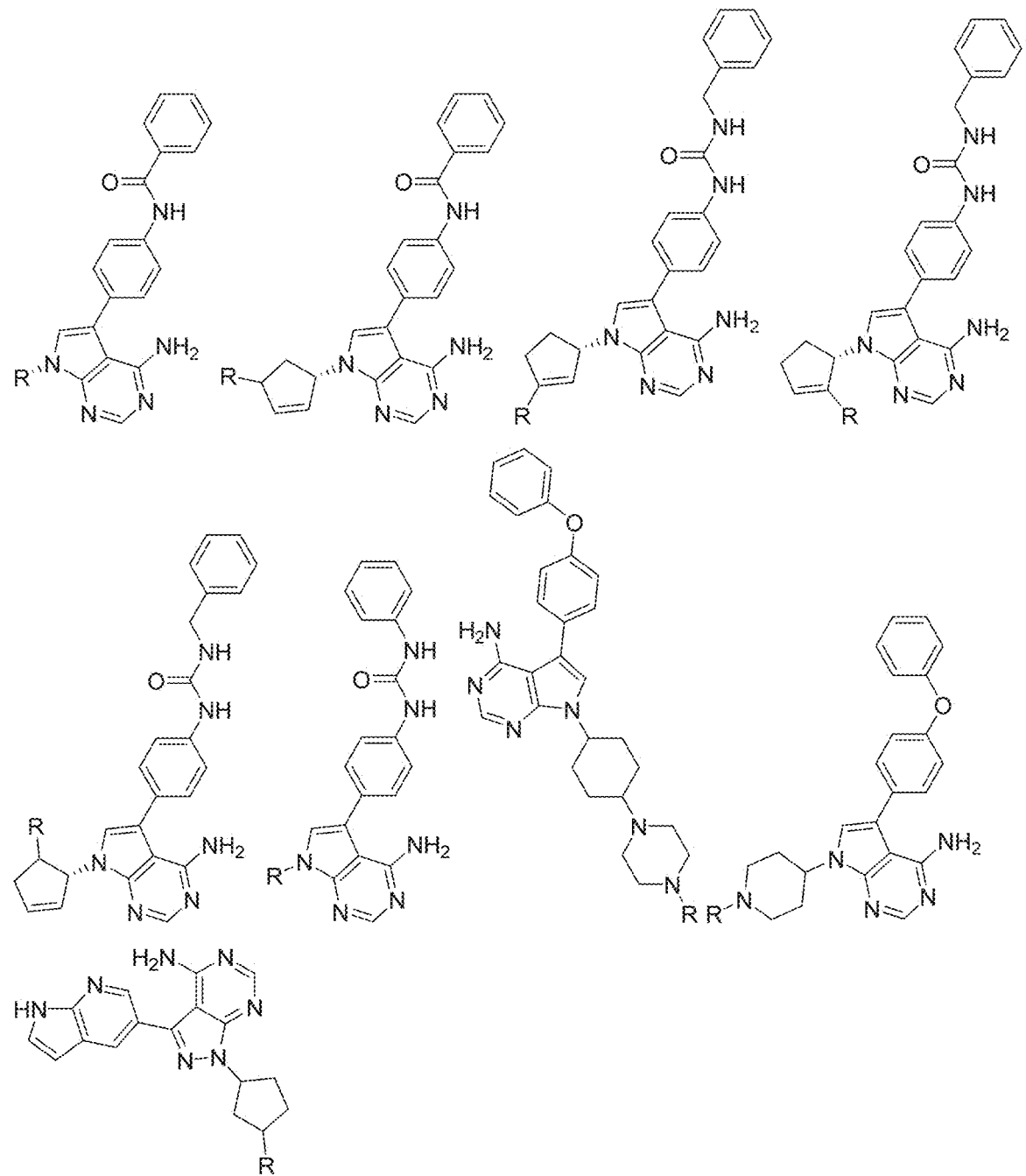
FIG. 8AAAAA

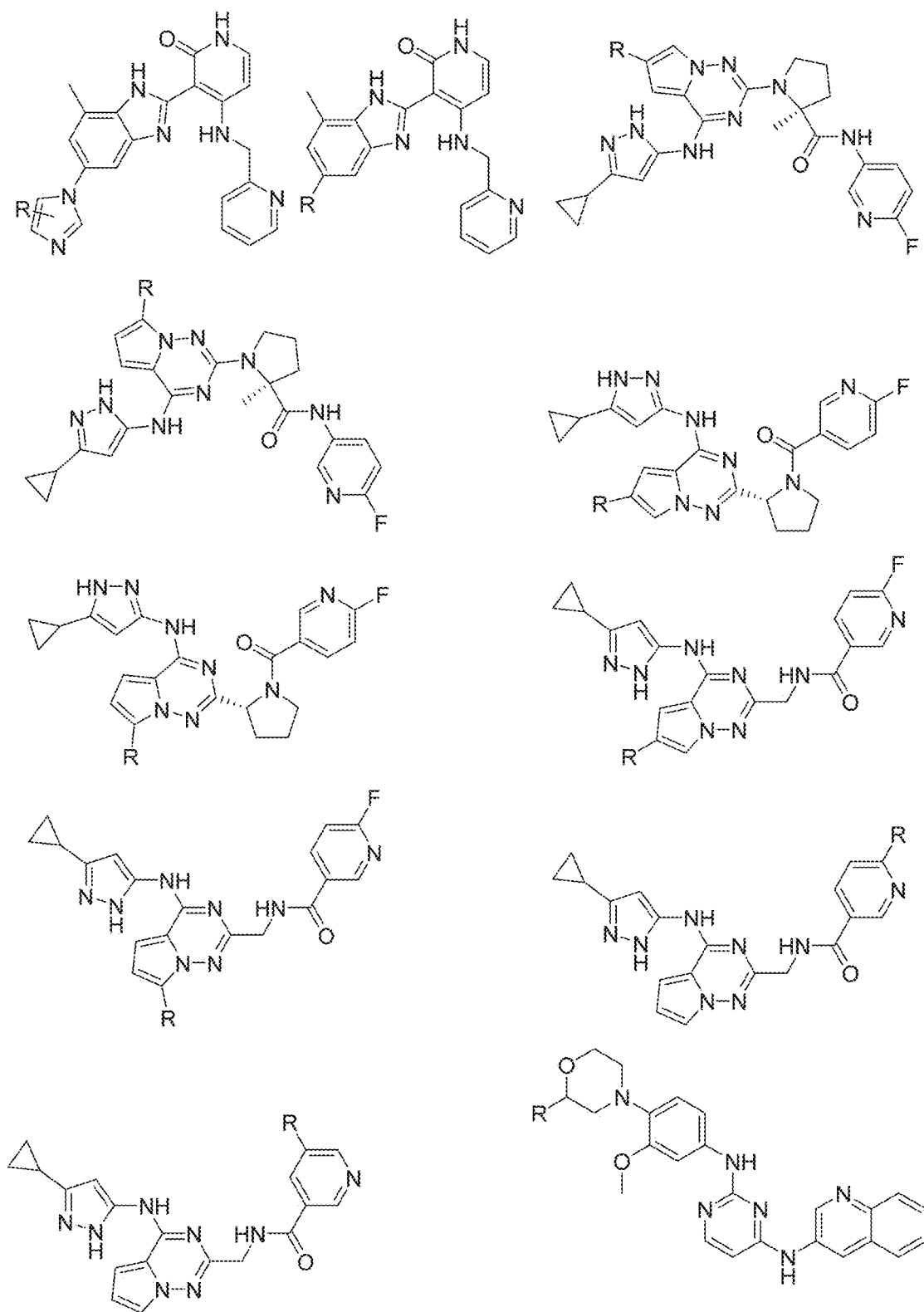
FIG. 8BBBBB

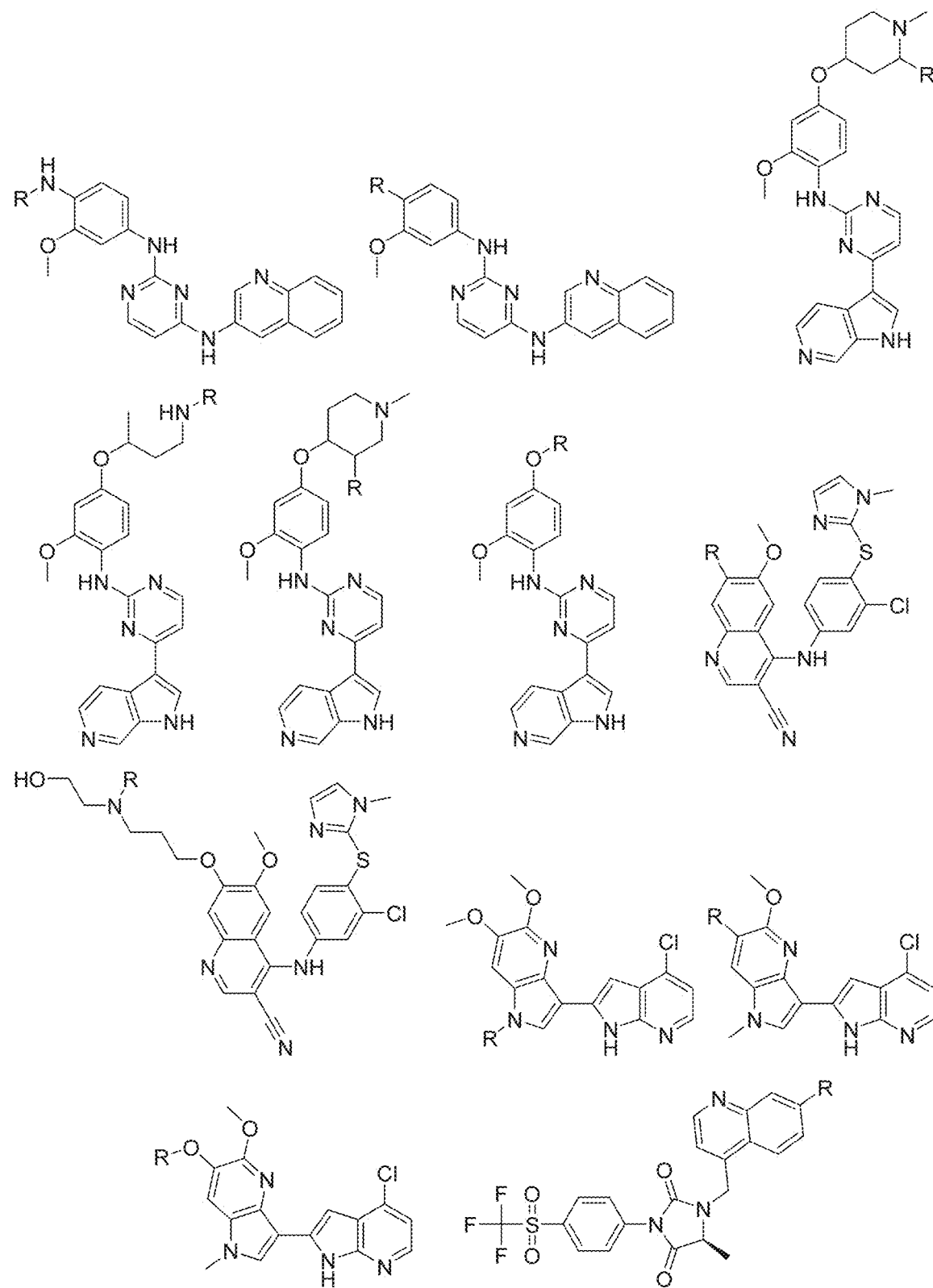
FIG. 8CCCCC

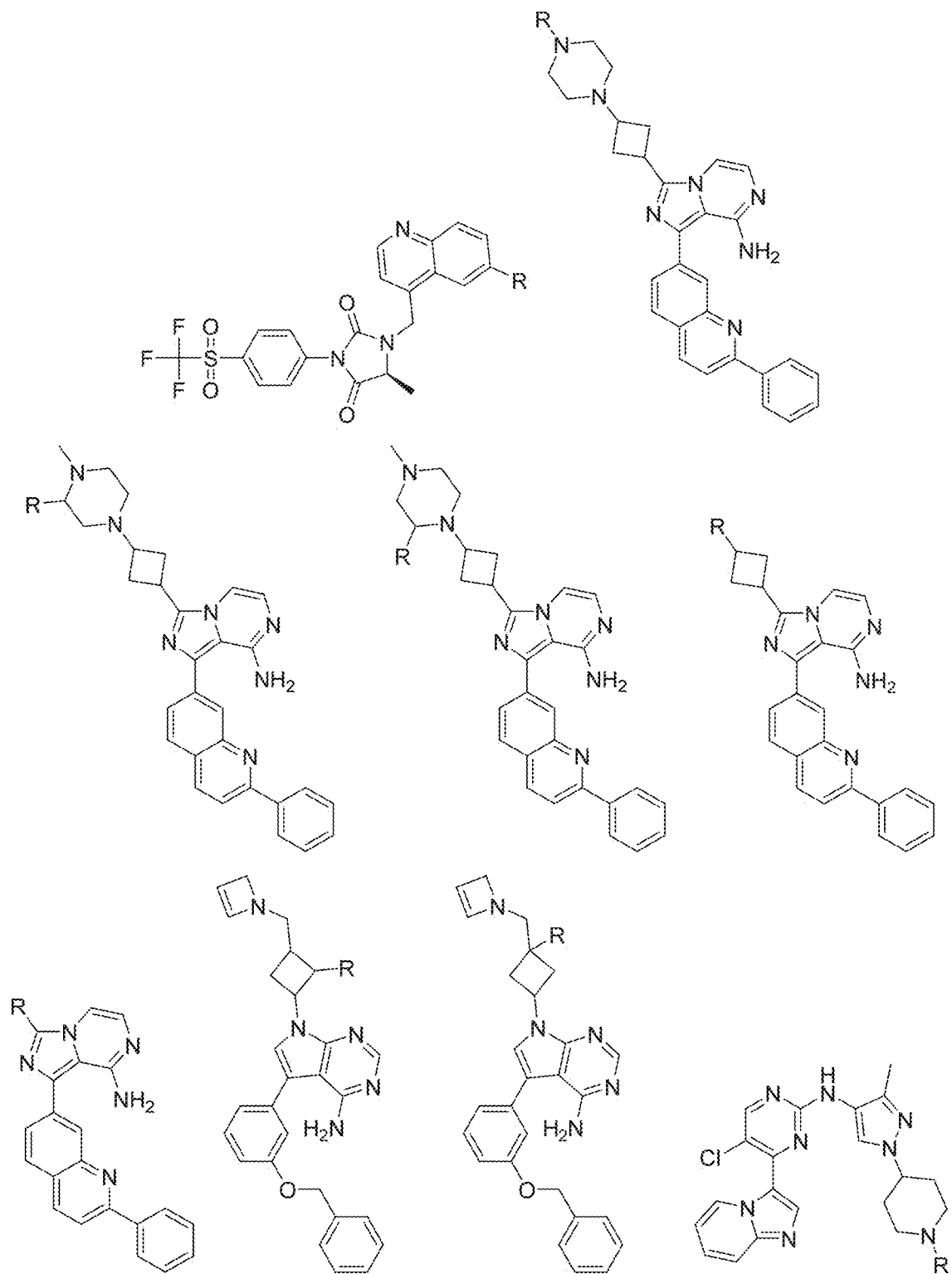
FIG. 8DDDDD

FIG. 8EEEEE

FIG. 8FFFFF
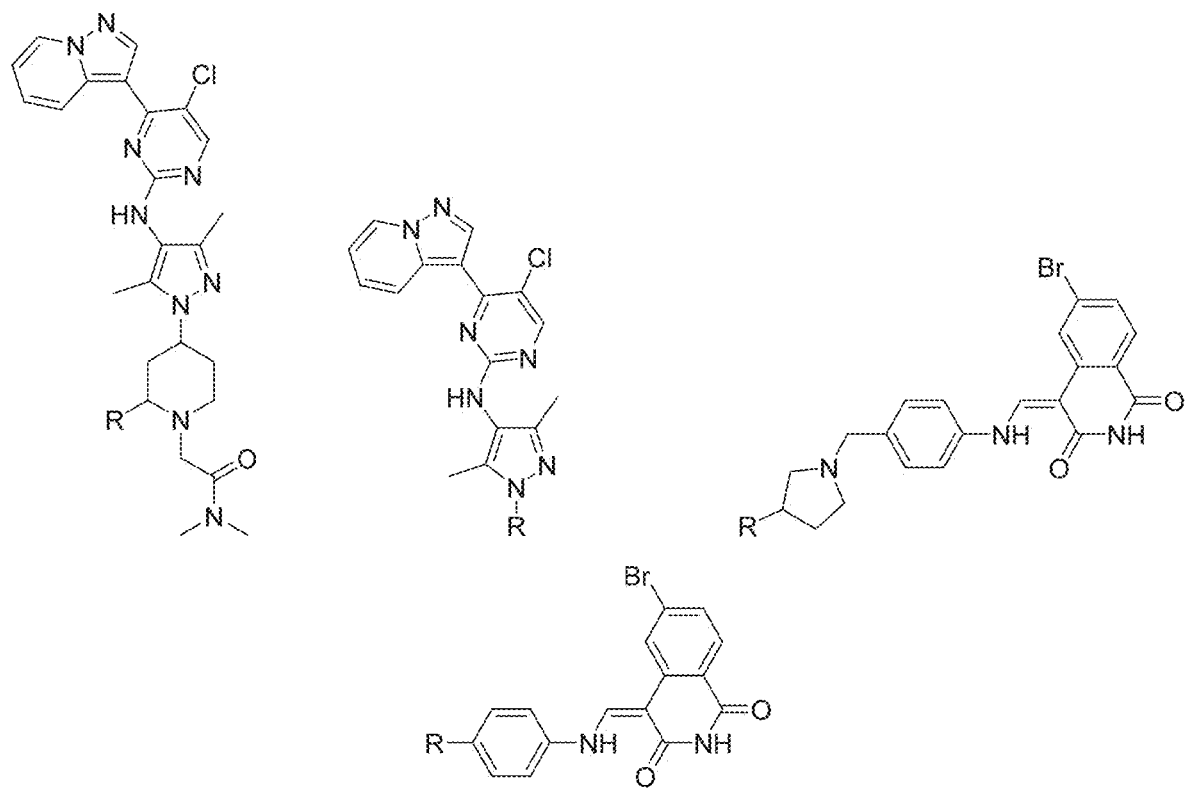
FIG. 8GGGGG
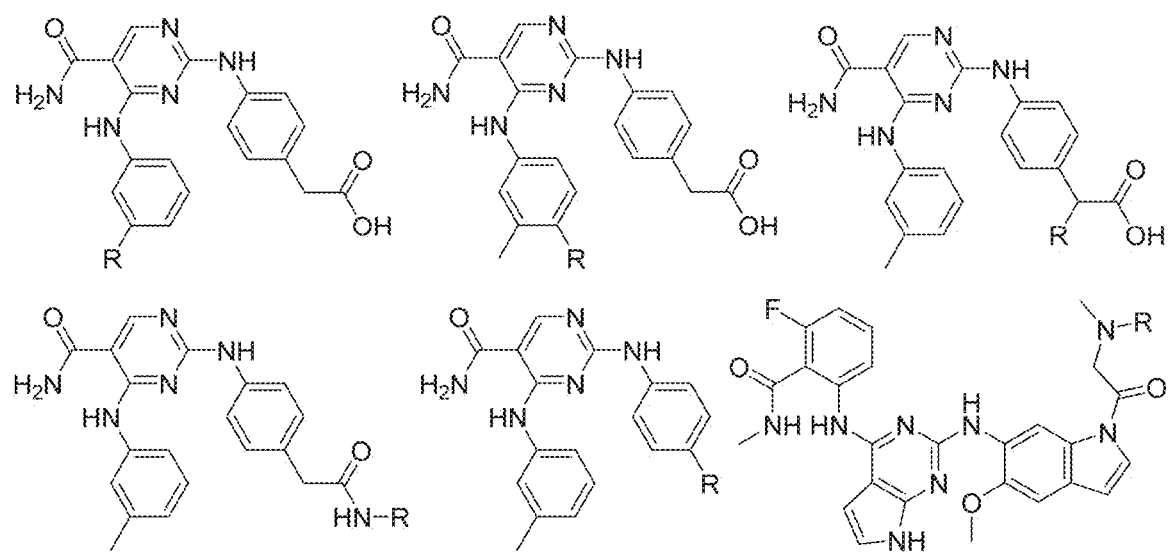

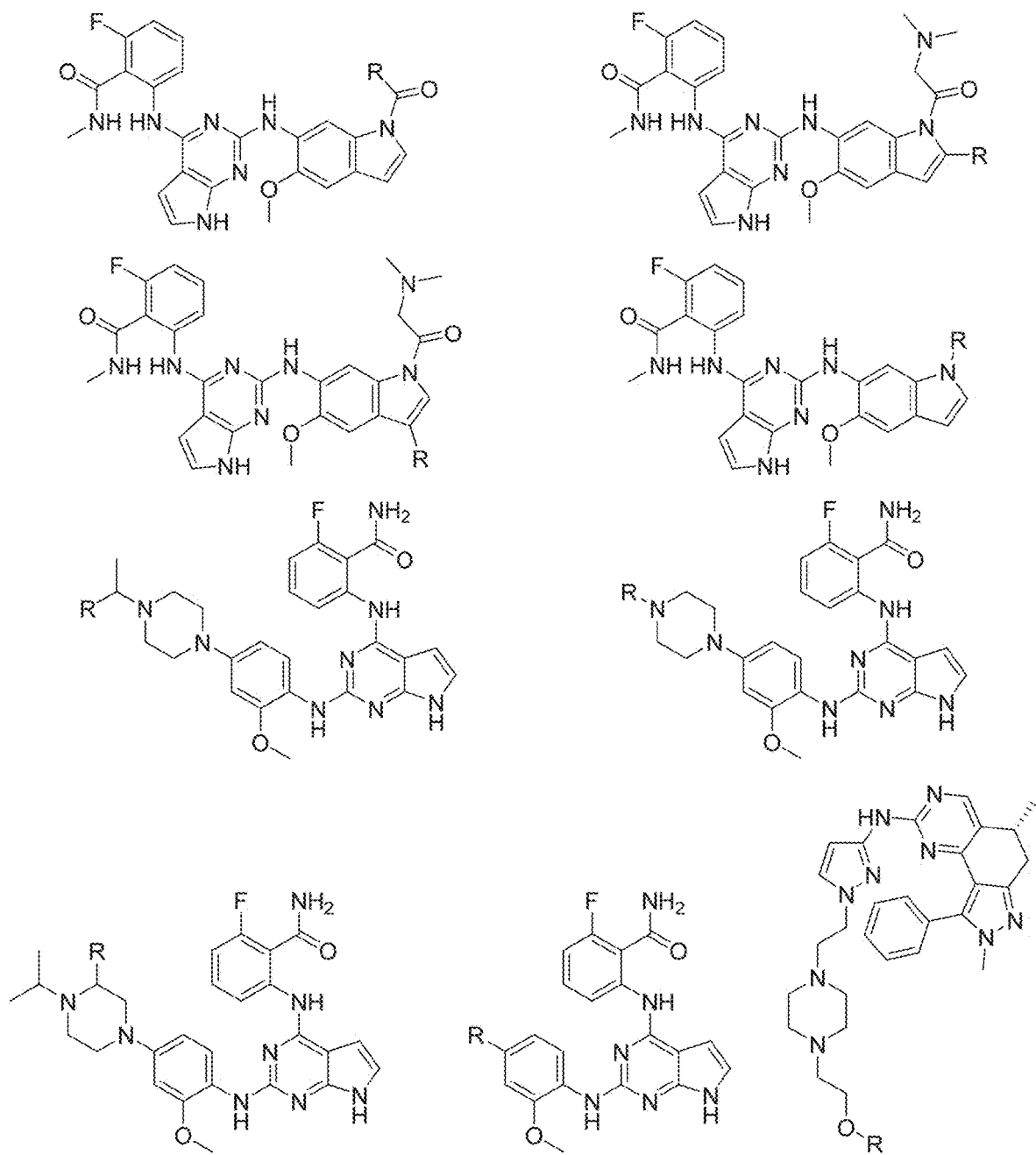
FIG. 8HHHHH

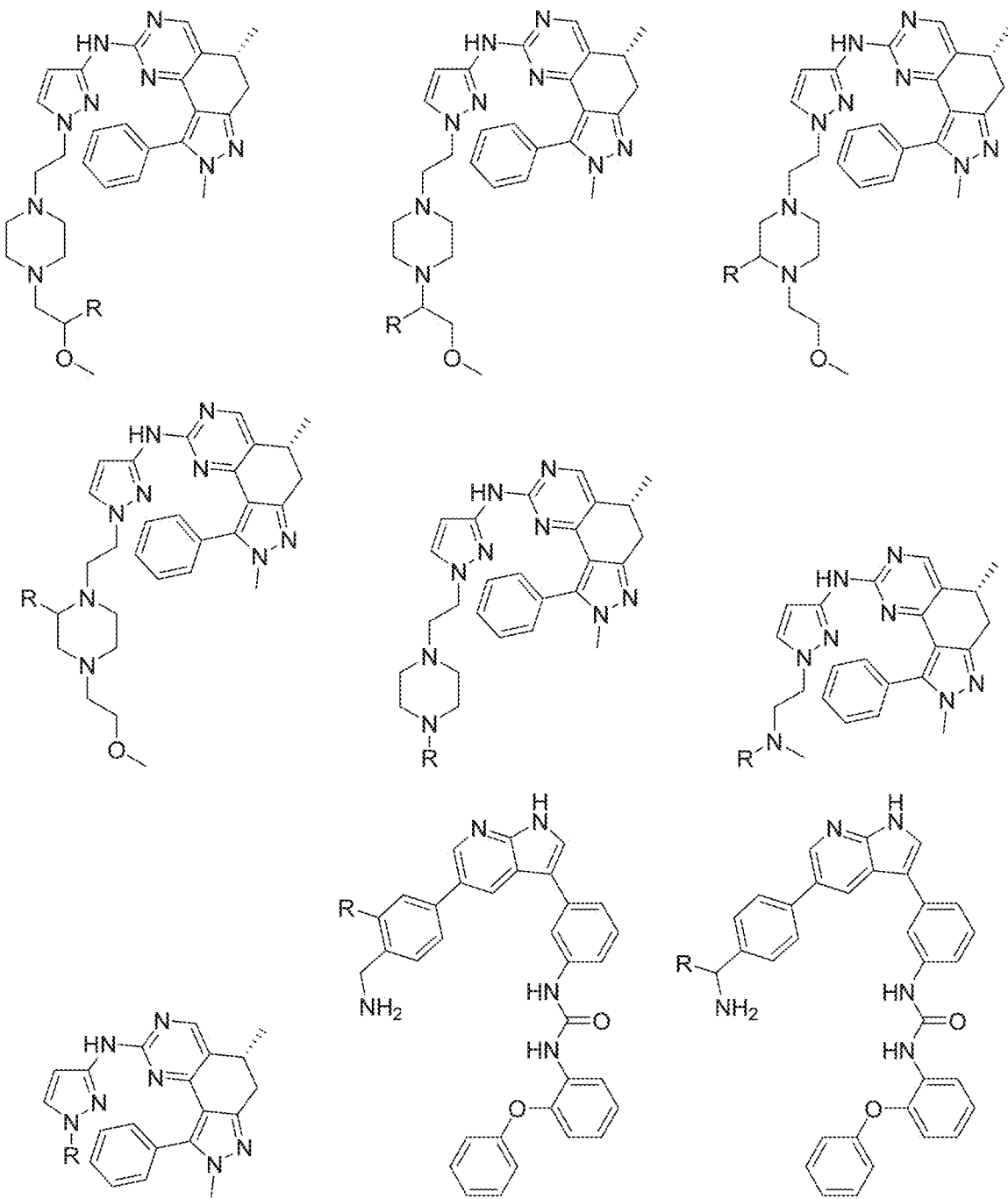
FIG. 8IIIII

FIG. 8JJJJJ
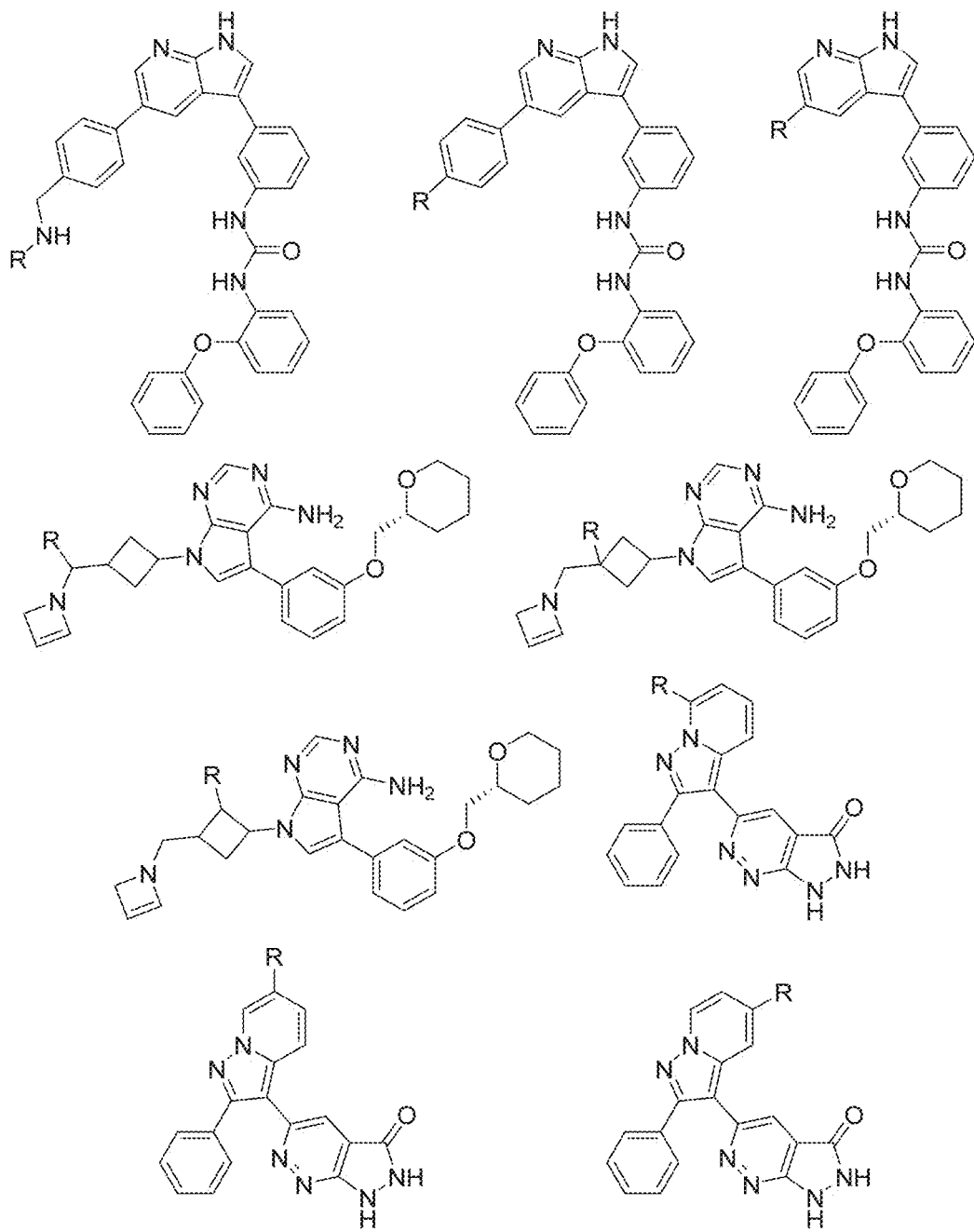

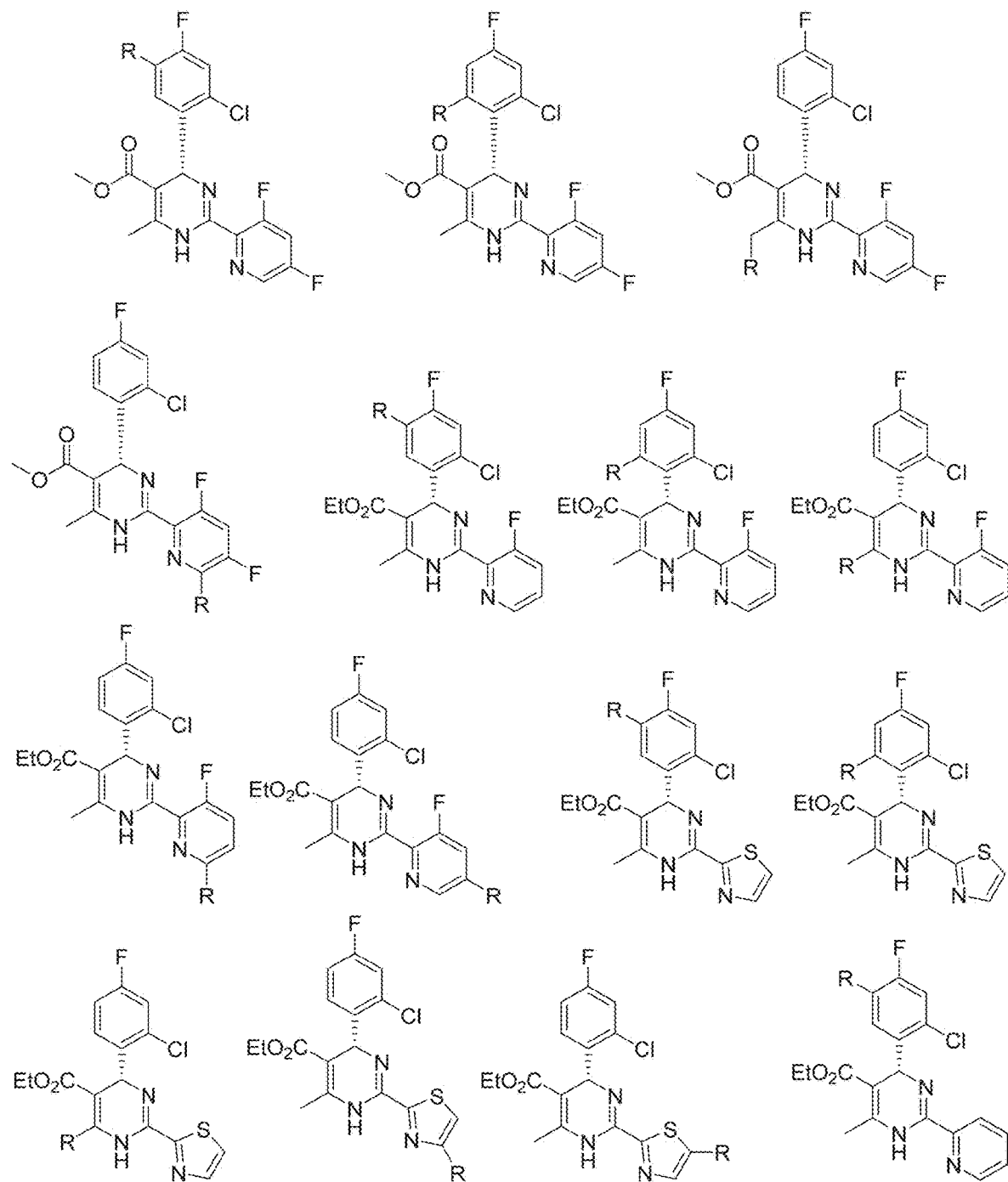
FIG. 8KKKKK

FIG. 8LLLLL
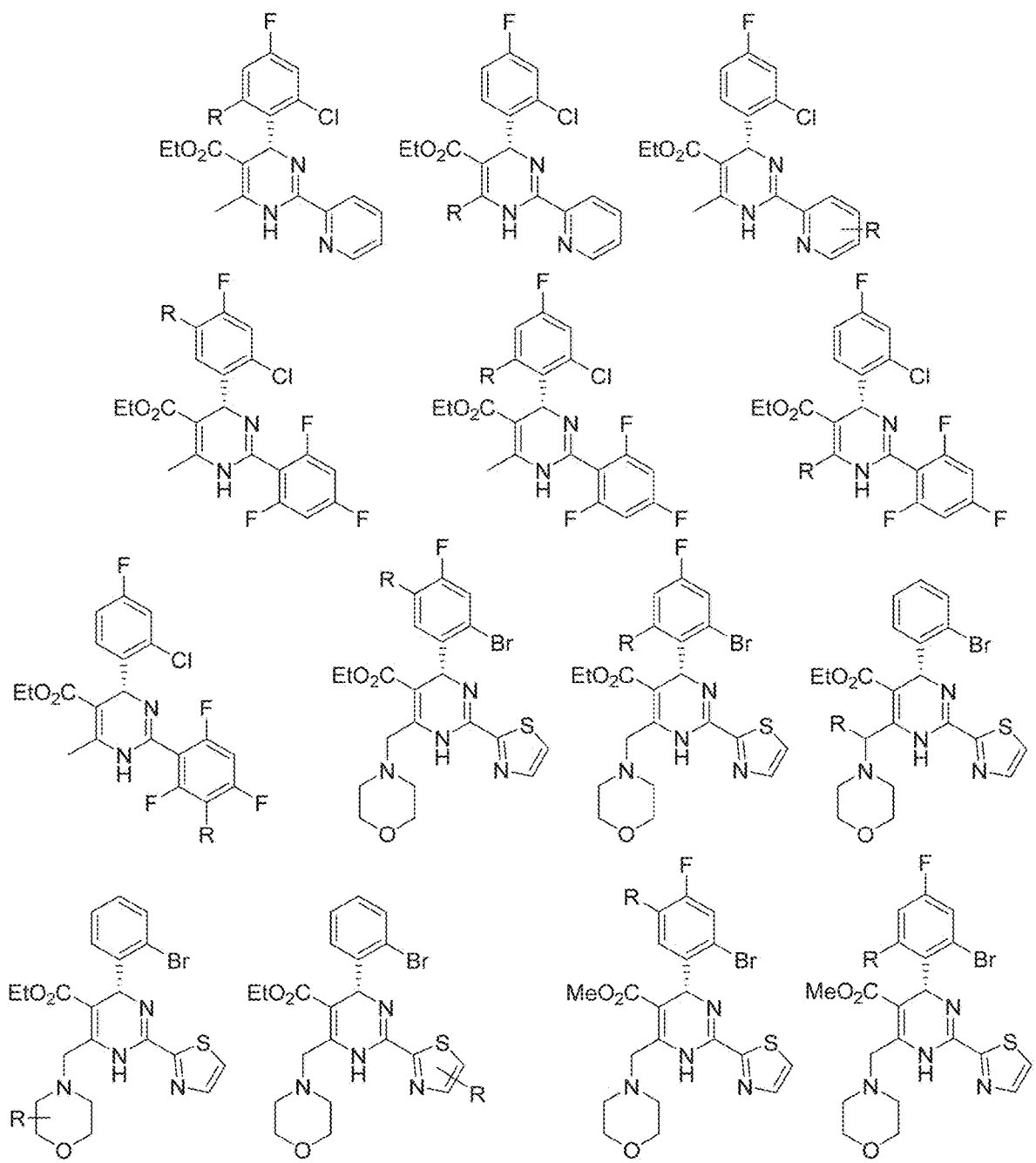

FIG. 8MMMMM
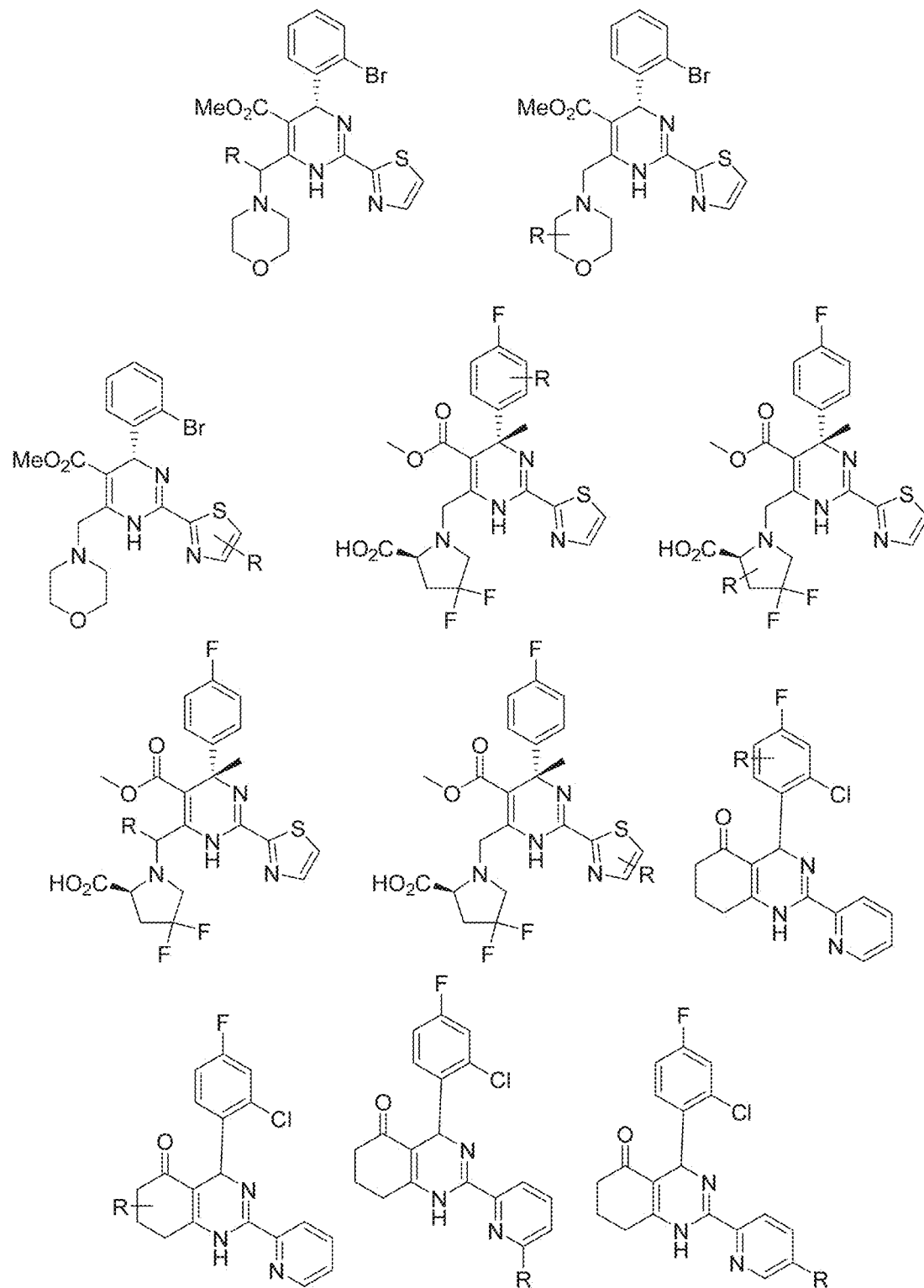

FIG. 8NNNNN
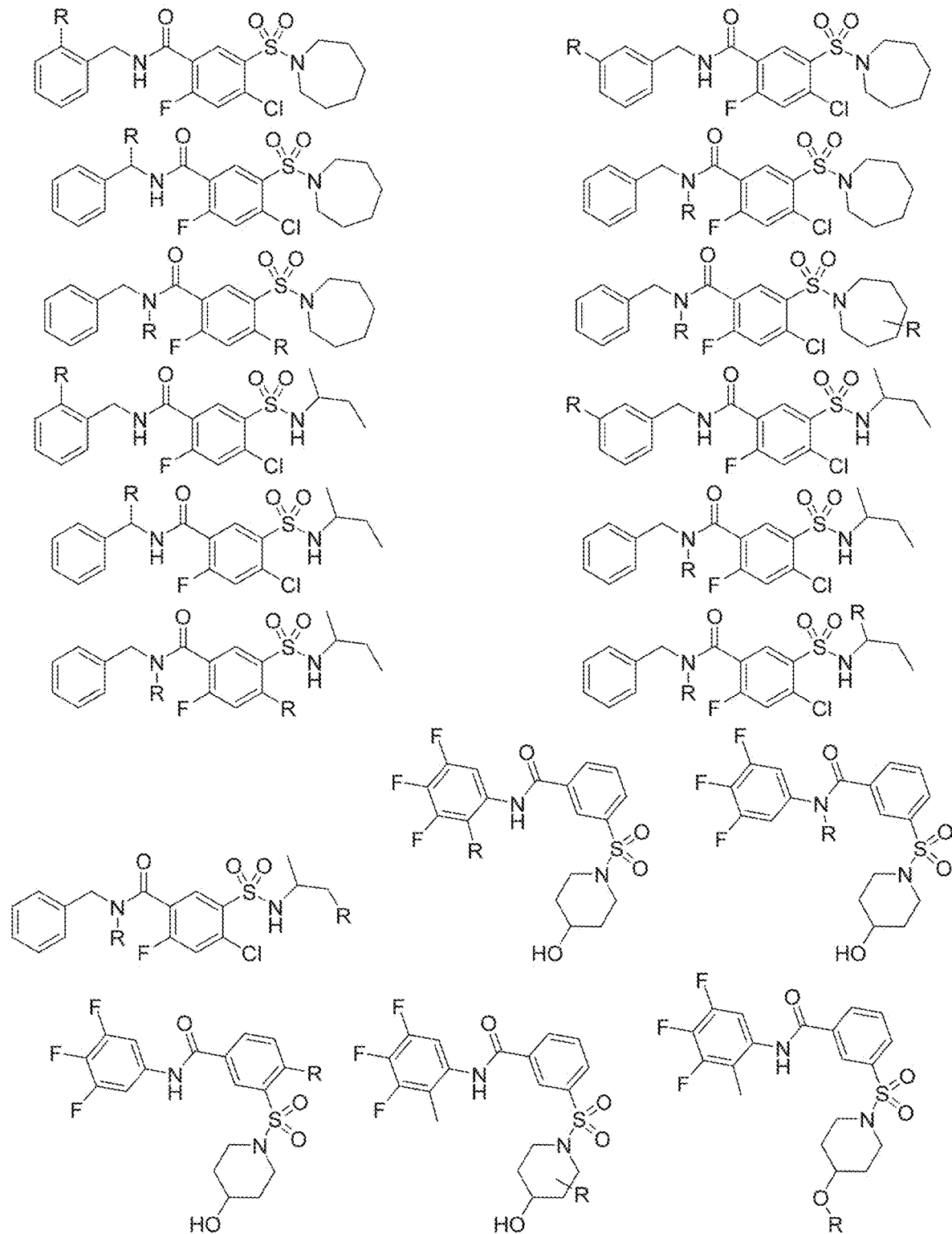

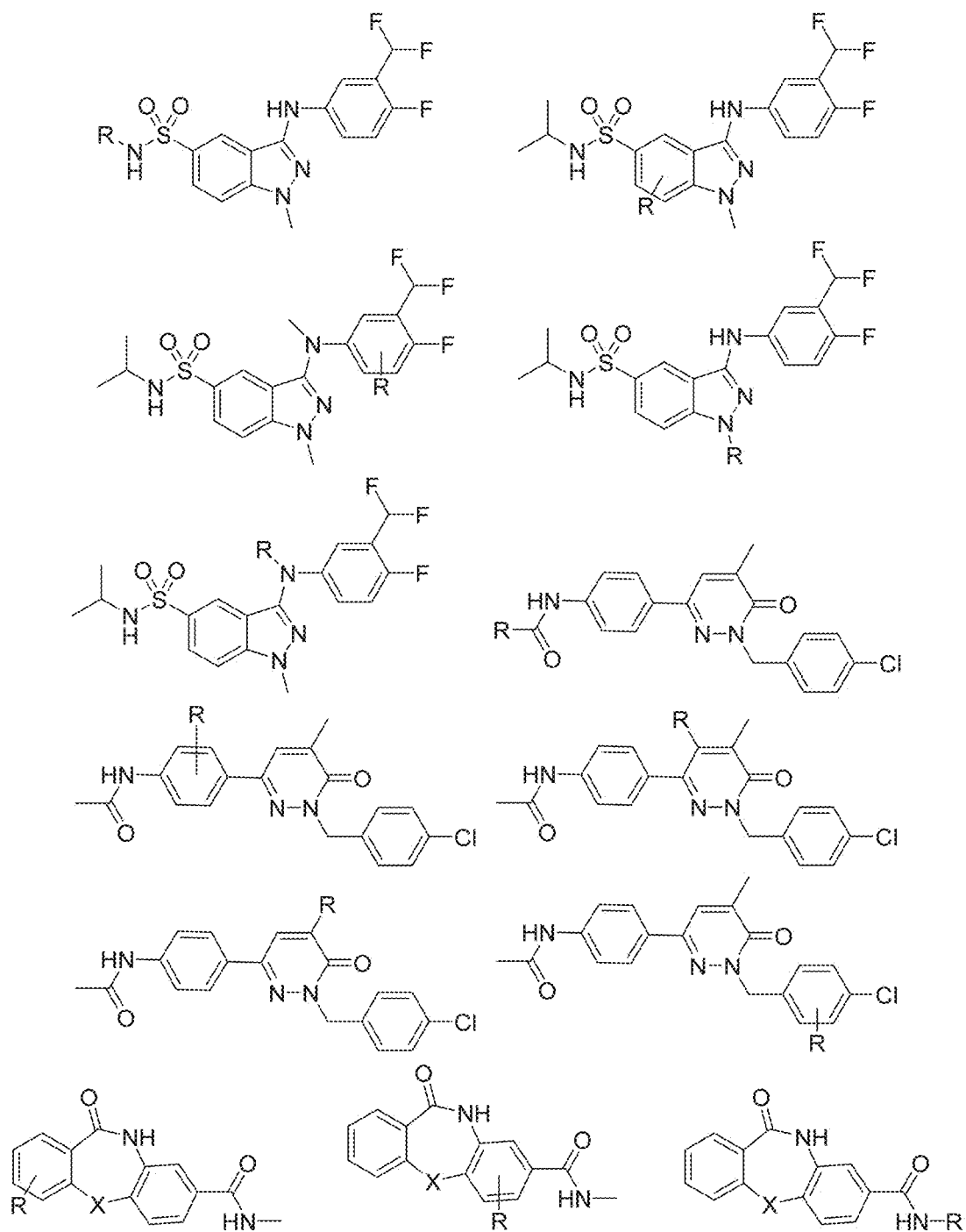
FIG. 800000

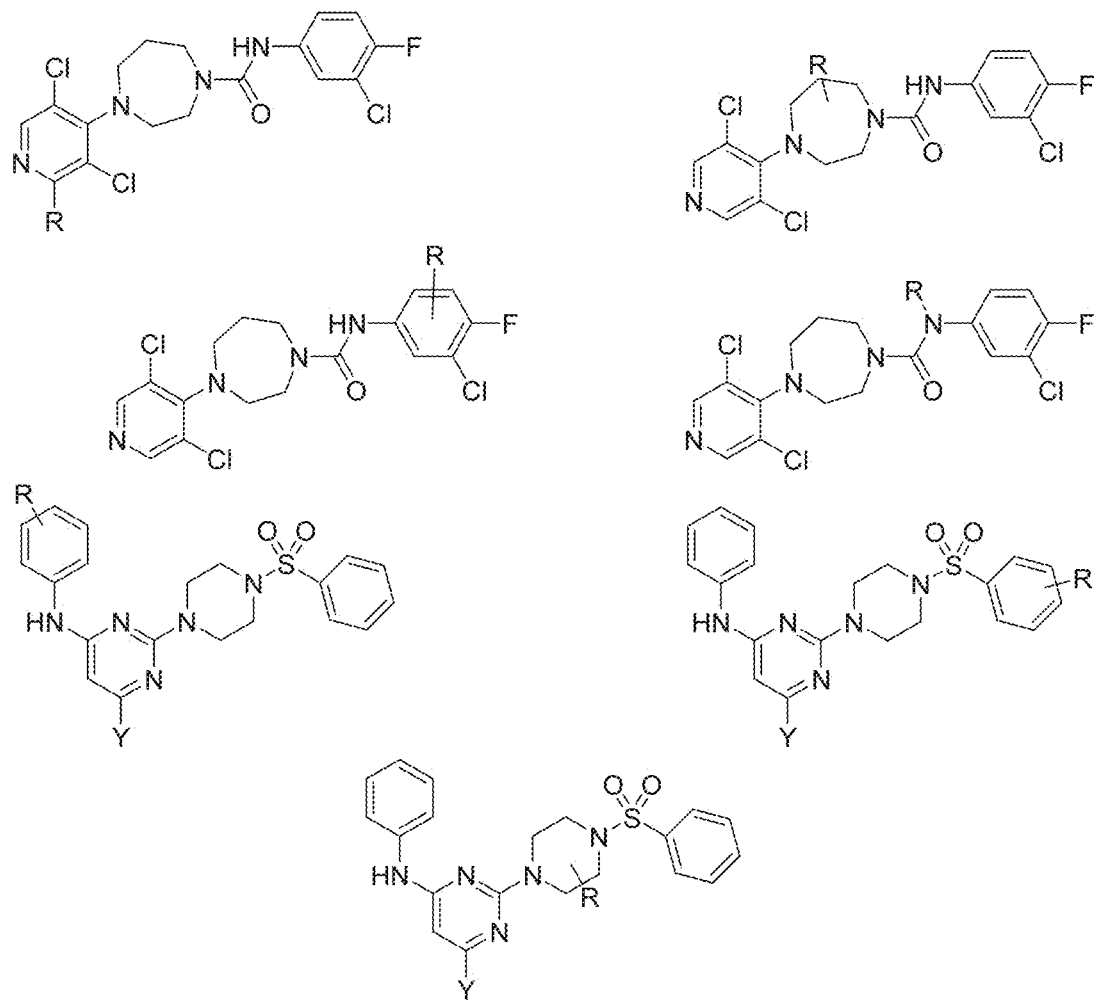
FIG. 8PPPPP

C3-CARBON LINKED GLUTARIMIDE DEGRONIMERS FOR TARGET PROTEIN DEGRADATION

CROSS-REFERENCE TO RELATED APPLICATIONS

This application is a continuation of International Application No. PCT/US2017/032041, filed in the International Patent Cooperation Treaty, U.S. Receiving Office on May 10, 2017, which claims the benefit of priority to U.S. Application No. 62/334,362, filed May 10, 2016. The entirety of these applications are hereby incorporated by reference herein for all purposes.

FIELD OF THE INVENTION

This invention provides Degronimers that have carbon-linked E3 Ubiquitin Ligase targeting moieties (Degrons), which can be linked to a targeting ligand for a protein that has been selected for in vivo degradation, and methods of use and compositions thereof as well as methods for their preparation.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (*PLOS One*, 2008, 3, 1487) titled "Genome-wide and functional annotation of human E3 ubiquitin ligases identifies MULAN, a mitochondrial E3 that regulates the organelle's dynamics and signaling."; Berndsen et al. (*Nat. Struct. Mol. Biol.*, 2014, 21, 301-307) titled "New insights into ubiquitin E3 ligase mechanism"; Deshaies et al. (*Ann. Rev. Biochem.*, 2009, 78, 399-434) titled "RING domain E3 ubiquitin ligases."; Spratt et al. (*Biochem.* 2014, 458, 421-437) titled "RBR E3 ubiquitin ligases: new structures, new insights, new questions."; and Wang et al. (*Nat. Rev. Cancer.*, 2014, 14, 233-347) titled "Roles of F-box proteins in cancer."

In 1995, Gosink et al. (*Proc. Natl. Acad. Sci. USA* 1995, 92, 9117-9121) in a publication titled "Redirecting the Specificity of Ubiquitination by Modifying Ubiquitin-Conjugating Enzymes", provided proof of concept in vitro that engineered peptides can selectively direct ubiquitination of intracellular proteins. The publication by Nawaz et al. (*Proc. Natl. Acad. Sci. U.S.A.* 1999, 96, 1858-1862) titled "Proteasome-Dependent Degradation of the Human Estrogen Receptor" describes ER degradation which takes advantage of the ubiquitin-proteasome pathway.

Proteinex, Inc. filed a patent application in February 1999 that issued as U.S. Pat. No. 6,306,663 claiming a method of generating a compound for activating the ubiquitination of a Target Protein which comprises covalently linking a Target Protein binding element able to bind specifically to the Target Protein via a ubiquitination recognition element. Proteinex described that the invention can be used to control protein levels in eukaryotes. While the '663 patent may have been based on the first patent application to describe the high level concept of how to manipulate the UPP system to degrade selected proteins in vivo, the patent did not provide sufficient detail to allow persons of skill to easily construct the range of proposed compounds. For example, for the ubiquitination recognition elements, the skilled person was told among other things to use standard methods for drug discovery and screen for appropriate small molecules that would bind to the ligase. Proteinex also emphasized the use of peptides as ubiquitination recognition elements, which can pose significant difficulties for oral drug administration.

Since then, harnessing the ubiquitin-proteasome pathway for therapeutic intervention has received significant interest from the scientific community. The publication by Zhou et al. from Harvard Medical School (*Mol. Cell* 2000, 6, 751-756) titled "Harnessing the Ubiquitination Machinery to Target the Degradation of Specific Cellular Proteins" described an engineered receptor capable of directing ubiquitination in mammalian and yeast cells.

Following from these early publications and others in the mid to late 1990s, the work of Proteinex was confirmed by Craig Crews and coworkers (Yale University) that a molecule that is capable of binding a Target Protein and a ubiquitin ligase may cause the Target Protein to be degraded. Their first description of such compounds was provided in U.S. Pat. No. 7,041,298 filed in September 2000 by Deshaies et al. and granted in May 2006 titled "Proteolysis Targeting Chimeric Pharmaceutical", which described a "PROTAC" consisting of a small molecule binder of MAP-AP-2 linked to a peptide capable of binding the F-box protein □-TRCP. Information in the '298 patent is also presented in the corresponding publication by Sakamoto et al. (*Proc. Natl. Acad. Sci. USA* 2001, 98, 8554-8559) titled "Protacs: Chimeric Molecules That Target Proteins to the Skp1-Cullin-F Box Complex for Ubiquitination and Degradation". The publication by Sakamoto et al. (*Mol. Cell. Proteomics* 2003, 2, 1350-1358) titled "Development of Protacs to Target Cancer-Promoting Proteins for Ubiquitination and Degradation" describes an analogous PROTAC (PROTAC2) that instead of degrading MAP-AP-2 degrades estrogen and androgen receptors.

The first E3 ligase successfully targeted with a small molecule was MDM2, which ubiquitinates the tumor suppressor p53. The targeting ligand was an HDM2/MDM2 inhibitor identified in Vassilev et al. (*Science* 2004, 303, 844-848) titled "In Vivo Activation of the P53 Pathway by Small-Molecule Antagonists of MDM2".

Other examples of direct small molecule-induced recruitment of Target Proteins to the proteasome for degradation on addition to cultured cells were described in 2004 (Schneekloth et al. (*J. Am. Chem. Soc.* 2004, 126, 3748-3754) titled "Chemical Genetic Control of Protein Levels: Selective in Vivo Targeted Degradation"). Schneekloth et al. describe a degradation agent (PROTAC3) that targets the FK506 binding protein (FKBP12) and shows that both PROTAC2 and PROTAC3 hit their respective targets with green fluorescent protein (GFP) imaging. The publication by Schneekloth et al. (*Chem Bio Chem* 2005, 6, 40-46) titled "Chemical Approaches to Controlling Intracellular Protein Degradation" described the state of the field at the time.

The publication by Schneekloth et al. (*Bioorg. Med. Chem. Lett.* 2008, 18, 5904-5908) titled "Targeted Intracellular Protein Degradation Induced by a Small Molecule: En Route to Chemical Proteomics" describes a degradation agent that consists of two small molecules linked by PEG that in vivo degrades the androgen receptor by concurrently binding the androgen receptor and ubiquitin E3 ligase.

WO 2013/170147 filed by Crews et al. titled "Compounds Useful for Promoting Protein Degradation and Methods of Using Same" describes compounds comprising a protein degradation moiety covalently bound to a linker, wherein the ClogP of the compound is equal to or higher than 1.5. In particular, the specification discloses protein degrading compounds that incorporate certain small molecules that can bind to an E3 ubiquitin ligase.

In unrelated parallel research, scientists were investigating thalidomide toxicity. Ito et al. (*Science* 2010, 327, 1345-1350) titled "Identification of a Primary Target of Thalidomide Teratogenicity", described that cereblon is a thalidomide binding protein. Cereblon forms part of an E3 ubiquitin ligase protein complex which interacts with damaged DNA binding protein 1, forming an E3 ubiquitin ligase complex with Cullin 4 and the E2-binding protein ROC1 (also known as RBX1) where it functions as a substrate receptor to select proteins for ubiquitination. The study revealed that thalidomide-cereblon binding in vivo may be responsible for thalidomide teratogenicity. After the discovery that thalidomide causes teratogenicity in the mid-1960's, the compound and related structures were notwithstanding found to be useful as anti-inflammatory, anti-angiogenic and anti-cancer agents (see Bartlett et al. (*Nat. Rev. Cancer* 2004, 4, 314-322) titled "The Evolution of Thalidomide and Its Imid Derivatives as Anticancer Agents").

The disclosure that thalidomide binds to the cereblon E3 ubiquitin ligase led to research to investigate incorporating thalidomide and certain derivatives into compounds for the targeted destruction of proteins. Two seminal papers were published in *Science* in 2014: G. Lu et al., The Myeloma Drug Lenalidomide Promotes the Cereblon-Dependent Destruction of Ikaros Proteins, *Science*, 343, 305-309 (2014); and J. Kronke et al., Lenalidomide Causes Selective Degradation of IKZF1 and IKZF3 in Multiple Myeloma Cells, *Science*, 343, 301-305 (2014).

U.S. 2014/0356322 assigned to Yale University, GlaxoSmithKline, and Cambridge Enterprise Limited University of Cambridge titled "Compounds and Methods for the Enhanced Degradation of Target Proteins & Other Polypeptides by an E3 Ubiquitin Ligase" describes protein degrading compounds that bind to the VHL E3 Ubiquitin Ligase. See also Buckley et al. (*J. Am. Chem. Soc.* 2012, 134, 4465-4468) titled "Targeting the Von Hippel-Lindau E3 Ubiquitin Ligase Using Small Molecules to Disrupt the Vhl/Hif-1alpha Interaction".

Additional publications in this area include the following: Lu et al. (*Chem. Biol.* 2015, 22, 755-763) titled "Hijacking the E3 Ubiquitin Ligase Cereblon to Efficiently Target Brd4"; Bondeson et al. (*Nat. Chem. Biol.* 2015, 11, 611-617) titled "Catalytic in Vivo Protein Knockdown by Small-Molecule Protacs"; Gustafson et al. (*Angewandte Chemie, International Edition in English* 2015, 54, 9659-9662) titled "Small-Molecule-Mediated Degradation of the Androgen Receptor through Hydrophobic Tagging"; Lai et al. (*Angewandte Chemie, International Edition in English* 2016, 55, 807-810) titled "Modular Protac Design for the Degradation of Oncogenic Bcr-Abl"; Toure et al. (*Angew. Chem. Int. Ed.* 2016, 55, 1966-1973) titled "Small-Molecule Protacs: New Approaches to Protein Degradation"; and Winter et al. (*Science* 2015, 348, 1376-1381) titled "Drug Development. Phthalimide Conjugation as a Strategy for in Vivo Target Protein Degradation" describes thalidomide based Target Protein degradation technology.

WO 2015/160845 assigned to Arvinas Inc. titled "Imide Based Modulators of Proteolysis and Associated Methods of Use" describes protein degradation compounds that incorporate thalidomide and certain derivatives which bind to a cereblon E3 ligase. Additional patent applications filed by Arvinas Inc. directed to the degradation of a Target Protein using known E3 ligase ligands to direct the Target Protein to the proteasome for degradation include U.S. 2016/0058872 titled "Imide Based Modulators of Proteolysis and Associated Methods of Use"; U.S. 2016/0045607 titled "Estrogen-related Receptor Alpha Based PROTAC Compounds and Associated Methods of Use"; U.S. 2016/0214972 titled "Compounds and Methods for the Targeted Degradation of Androgen Receptor"; U.S. 2016/0272639 titled "Compounds and Methods for the Enhanced Degradation of Target Proteins"; U.S. 2017/0008904 titled "MDM2-Based Modulators of Proteolysis and Associated Methods of Use"; U.S. 2017/0037004 titled "Alanine-Based Modulators of Proteolysis and Associated Methods of Use"; U.S. 2017/0065719 titled "Compounds and Methods for the Targeted Degradation of Bromodomain containing proteins"; WO 2016/036036 titled "Tank Binding Kinase-1 PROTACS and Associated Methods of Use"; and WO 2016/197032 "Imide-Based Modulators and Proteolysis and Associated Methods of Use".

Dana-Farber Cancer Institute has also filed several patent applications directed to the degradation of a Target Protein using known E3 ligase ligands to direct the Target Protein to the proteasome for degradation. These filings include US 2016/0176916 titled "Methods to Induce Target Protein Degradation through Bifunctional Molecules; WO 2017/024318 titled "Target Protein Degradation to Attenuate Adoptive T-Cell Therapy Associated Adverse Inflammatory Responses"; WO 2017/024317 titled "Methods to Induce Target Protein Degradation through Bifunctional Molecules"; and WO 2017/024319 titled "Tunable Endogenous Protein Degradation".

While progress has been made in the area of modulation of the UPP for in vivo protein degradation, it would be useful to have additional compounds and approaches to more fully harness the UPP for therapeutic treatments.

It is an object of the present invention to provide new compounds, methods, compositions, and methods of manufacture that are useful to degrade selected proteins in vivo.

SUMMARY

Compounds and their uses and manufacture are provided that cause degradation of a selected protein via the ubiquitin proteasome pathway (UPP). It has been surprisingly discovered that $C^3$-carbon substituted-glutarimides and analogues thereof described herein (Degrons) bind an E3 ligase (typically the cereblon protein). Degronimers are disclosed of Formulas I, IL, V and VI that include a "Targeting Ligand"

that binds (typically non-covalently) to a selected Target Protein, a "Degron" which binds (typically non-covalently) to an E3 Ligase (typically via cereblon) and optionally a Linker that covalently links the Targeting Ligand to the Degron.

A Degronimer provided herein or its pharmaceutically acceptable salt and/or its pharmaceutically acceptable composition can be used to treat a disorder which is mediated by the selected Target Protein that binds to the Targeting Ligand. Therefore, in some embodiments a method to treat a host with a disorder mediated by the Target Protein is provided that includes administering an effective amount of the Degronimer or its pharmaceutically acceptable salt described herein to the host, typically a human, optionally in a pharmaceutically acceptable composition.

In one embodiment, the selected Target Protein is derived from a gene that has undergone an amplification, translocation, deletion, or inversion event which causes or is caused by a medical disorder. In certain aspects, the selected Target Protein has been post-translationally modified by one, or combinations, of phosphorylation, acetylation, acylation including propionylation and crotylation, N-linked glycosylation, amidation, hydroxylation, methylation, poly-methylation, O-linked glycosylation, pyroglutamoylation, myristoylation, farnesylation, geranylation, ubiquitination, sumoylation, or sulfation which causes or is caused by a medical disorder. In an alternative embodiment, the Target Protein can be covalently modified by a Targeting Ligand that has been functionalized to create a covalent bond with the Target Protein, and the covalently bond can be irreversible or reversible.

In one aspect of the present invention a Degronimer of Formula I or Formula II is provided:

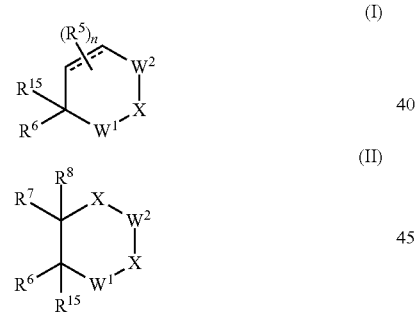

or a pharmaceutically acceptable salt, N-oxide, isotopic derivative, or prodrug thereof, optionally in a pharmaceutically acceptable carrier to form a composition;
wherein:
  $W^1$ is $CR^1R^2$, C=O, C=S, C=CH$_2$, SO$_2$, S(O), P(O)Oalkyl, P(O)NHalkyl, P(O)N(alkyl)$_2$, P(O)alkyl, P(O)OH, P(O)NH$_2$;
  $W^2$ is $CR^3R^4$, C=O, C=S, C=CH$_2$, SO$_2$, S(O), P(O)Oalkyl, P(O)NHalkyl, P(O)N(alkyl)$_2$, P(O)alkyl, P(O)OH, P(O)NH$_2$;
  in a typical embodiment $W^1$ is C=O;
  in another typical embodiment $W^2$ is C=O;
  X is independently selected from NH, NR$^{12}$, CH$_2$, CHR$^{12}$, C(R$^{12}$)$_2$, O, or S;
  n is 0, 1, 2, or 3;
  ==== is a single or double bond;

$R^6$ is selected from:

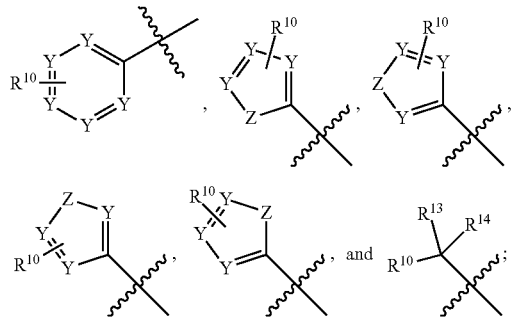

or $R^6$ is selected from:

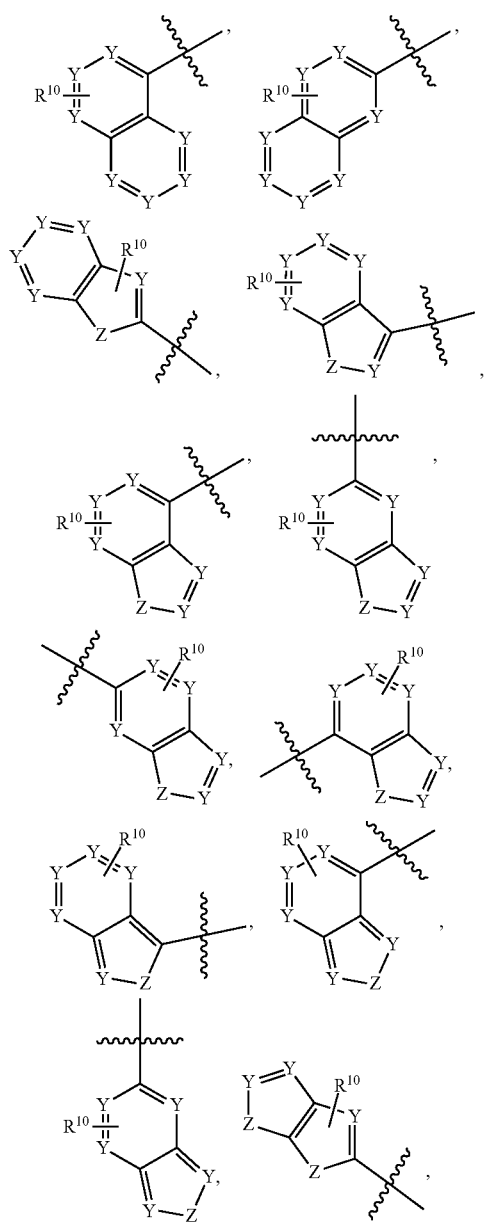

-continued

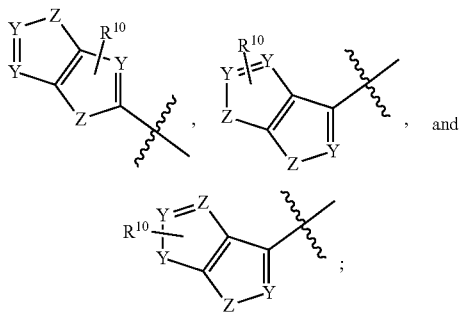
and or R⁶ is selected from:

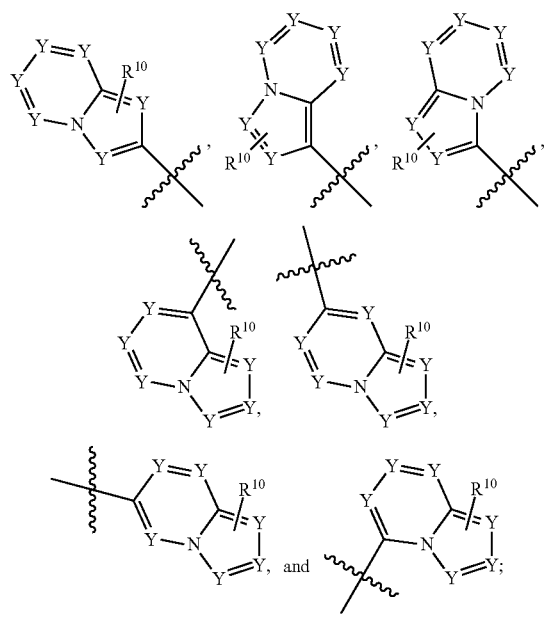

or R⁶ is selected from:

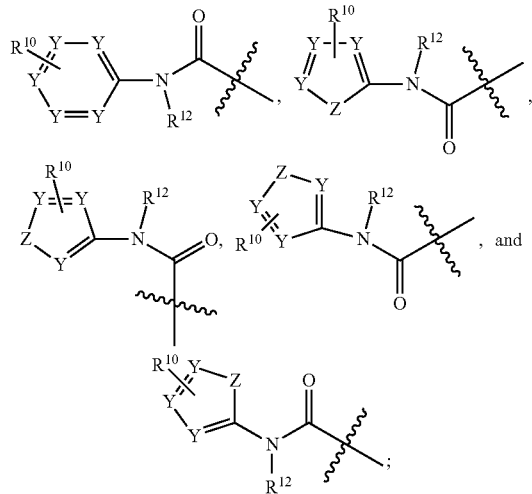

or R⁶ is selected from:

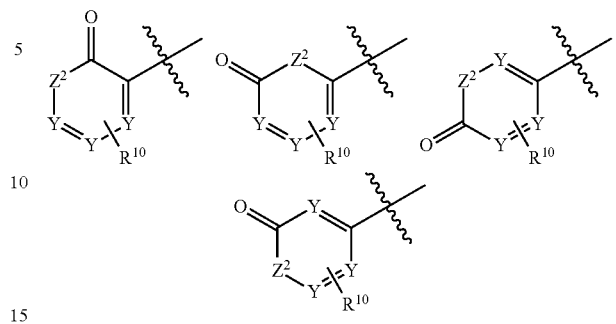

Y is independently selected from N, CH, and $CR^{11}$, wherein 0, 1, 2, 3, or 4 (as context allows) instances of Y are selected to be N and is selected to produce a stable ring and a pharmaceutically acceptable Degronimer. When Y's are in a six-membered ring (unfused or fused), the ring can be, in non-limiting embodiments as allowed by context, a pyridine, diazine, triazine, pyrimidine, pyridazine, pyrazine, triazine or tetrazine.

Z is NH, O, S, or $NR^{12}$;

$Z^2$ is NH or $NR^{12}$;

When Y and/or Y and Z are in a 5-membered ring there is typically not more than 1, 2, 3, or 4 heteroatoms, and non-limiting examples are pyrrole, furan, thiophene, imidazole, pyrazole, oxazole, isoxazole, thiazole, isothiazole, triazole, furazan, oxadiazole, thiadiazole, diazole and tetrazole.

and when $R^{10}$ is bonded to a Y that is carbon, then Y is $CR^{10}$, and when $R^{10}$ is bonded to a Z or $Z^2$ that is nitrogen, then Z or $Z^2$ is $NR^{10}$, etc.

$R^1, R^2, R^3, R^4, R^7, R^8$, and $R^{15}$ are independently selected from hydrogen, alkyl, aliphatic, heteroaliphatic, heterocyclic, carbocyclic, aryl, heteroaryl, hydroxyl, halo, azide, CN—, alkoxy, amine, —NHalkyl, and —Nalkyl$_2$, —NH(aliphatic), and —N(independently aliphatic)$_2$, each of which may be optionally substituted as described in the Definition Section, if desired to achieve the target effect, results in a stable compound that makes chemical sense to the routineer, and the group is not redundant (i.e., as known in the art, alkyl substituted with alkyl is redundant; however for examples, alkoxy substituted with alkoxy is not redundant);

or $R^1$ and $R^2$ together with the carbon to which they are attached form a 3-, 4-, 5-, or 6-membered spiro-carbocycle, or a 4-, 5-, or 6-membered spiro-heterocycle comprising 1 or 2 heteroatoms selected from N and O;

or $R^3$ and $R^4$ together with the carbon to which they are attached form a 3-, 4-, 5-, or 6-membered spiro-carbocycle, or a 4-, 5-, or 6-membered spiro-heterocycle comprising 1 or 2 heteroatoms selected from N and O;

or $R^7$ and $R^8$ together with the carbon to which they are attached form a 3-, 4-, 5-, or 6-membered spiro-carbocycle, or a 4-, 5-, or 6-membered spiro-heterocycle comprising 1 or 2 heteroatoms selected from N and O;

or $R^1$ and $R^3$ form a 1 or 2 carbon bridged ring;
or $R^1$ and $R^7$ form a 1 or 2 carbon bridged ring;
or $R^3$ and $R^7$ form a 1 or 2 carbon bridged ring;
or $R^{15}$ and $R^1$ form a 3, 4, 5, or 6 carbon fused ring;
or $R^{15}$ and $R^7$ form a 3, 4, 5, or 6 carbon fused ring;
or $R^{15}$ and $R^3$ form a 1 or 2 carbon bridged ring;
or $R^{15}$ and $R^5$ form a 3, 4, 5, or 6 carbon fused ring wherein $R^5$ is on the carbon alpha to $R^{15}$ or a 1, 2, 3, or 4 carbon bridged ring wherein $R^5$ is not on the carbon alpha to $R^{15}$;

R[5] is selected at each instance from: alkyl, alkene, alkyne, aliphatic, heteroaliphatic, heterocyclic, aryl, heteroaryl, halogen, hydroxyl, alkoxy, azide, amino, —NH(alkyl or aliphatic), —N(independently alkyl or aliphatic)$_2$, —NHSO$_2$(aliphatic, including alkyl), —N(alkyl or aliphatic)SO$_2$(alkyl or aliphatic), —NHSO$_2$aryl, —N(alkyl or aliphatic)SO$_2$aryl, —NHSO$_2$alkenyl, —N(alkyl or aliphatic)SO$_2$alkenyl, —NHSO$_2$alkynyl, —N(alkyl or aliphatic)SO$_2$alkynyl, and halo(alkyl or aliphatic), each of which is provided to form a stable compound as known to those of skill in the art, and can be optionally substituted as described in the Definition Section, if desired to achieve the target effect, results in a stable compound that makes chemical sense to the routineer, and the group is not redundant (i.e., as known in the art, alkyl substituted with alkyl is redundant; however for examples, alkoxy substituted with alkoxy is not redundant);

or two R[5] substituents together with the carbon atom(s) to which they are bound can form a 3, 4, 5 or 6 membered ring;

R[10] is -Linker-Targeting Ligand;

R[11] is selected at each instance from: hydrogen, alkyl, alkenyl, alkynyl, halogen, hydroxyl, heterocyclic, heteroalkyl, carbocyclic, heteroaliphatic, aliphatic, alkoxy, aryl, heteroaryl, alkylamino, alkylhydroxyl, —NHalkyl, —Nalkyl$_2$, —NH(aliphatic), —N(independently aliphatic)$_2$, amino, cyano, nitro, nitroso, sulfone, sulfoxide, thioalkyl, thiol and haloalkyl, each of which is optionally substituted as described in the Definition Section, if desired to achieve the target effect, results in a stable compound that makes chemical sense to the routineer;

R[12] is selected at each instance from: hydrogen, alkyl, aliphatic, heteroaliphatic, heterocyclic, heteroaryl, aryl, —C(O)H, —C(O)OH, —C(O)alkyl, —C(O)Oalkyl, —C(O)(aliphatic, aryl, heteroaliphatic, aryl or heteroaryl), —C(O)O(aliphatic, aryl, heteroaliphatic, aryl or heteroaryl), alkene, and alkyne, each of which is optionally substituted as described in the Definition Section, if desired to achieve the target effect, results in a stable compound that makes chemical sense to the routineer;

R[13] and R[14] are independently selected from hydrogen, alkyl, alkenyl, alkynyl, alkoxy, haloalkoxy, hydroxy, amino, —NHalkyl, and —N(alkyl)$_2$, each of which is optionally substituted as described in the Definition Section, if desired to achieve the target effect, results in a stable compound that makes chemical sense to the routineer; and or R[13] and R[14] together with the carbon atom to which they are attached, form C(O), C(S), C=CH$_2$, a 3-, 4-, 5-, or 6-membered spirocarbocycle, or a 4-, 5-, or 6-membered spiroheterocycle comprising 1 or 2 heteroatoms selected from N and O.

Formula V provides further Degronimers of the present invention:

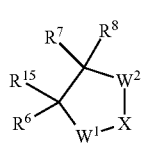

(V)

or a pharmaceutically acceptable salt, N-oxide, isotopic derivative, or prodrug thereof, optionally in a pharmaceutically acceptable carrier to form a composition; wherein the R moieities are as described above.

Formula VII provides additional Degronimers of the present invention:

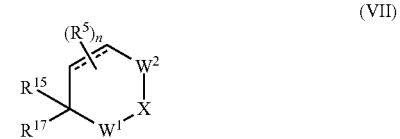

(VII)

wherein:

R[17] is selected from:

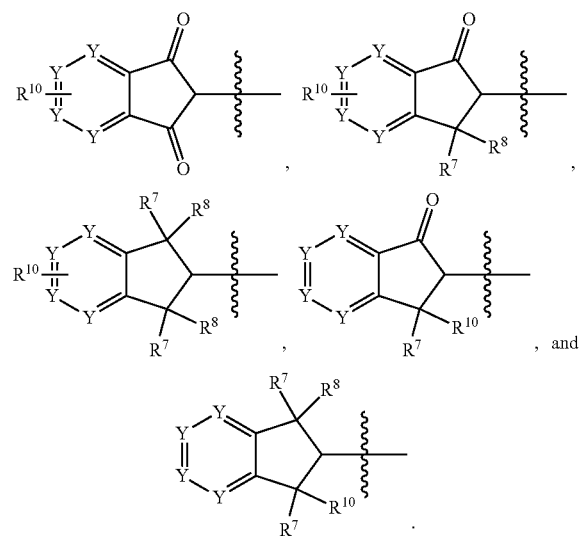

or a pharmaceutically acceptable salt, N-oxide, isotopic derivative, or prodrug thereof, optionally in a pharmaceutically acceptable carrier to form a composition; wherein the R moieties are as described above.

Linker is a chemical group that attaches the Degron to a Targeting Ligand, as described further below.

Targeting Ligand is a small molecule or moiety (for example a peptide, nucleotide, antibody, antibody fragment, aptamer, biomolecule or other chemical structure) that binds to a Target Protein, and wherein the Target Protein is a mediator of disease in a host as described in detail below.

In any of the fused rings that have an R[10], the R[10] can be placed on any available ring atom on either of the fused rings, except when excluded by context (such as where valency precludes), for example, as shown in the formulas:

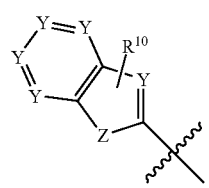

includes compounds of structure

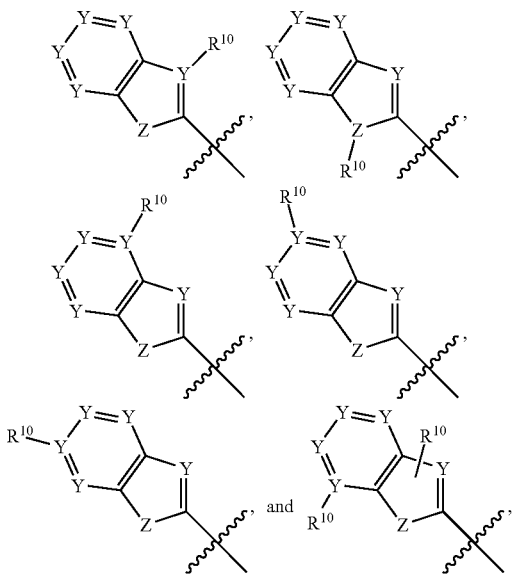

and each is considered specifically and independently described.

The structure of the Degronimer is typically selected such that it is sufficiently stable to sustain a shelf life of at least two, three, four, or five months under ambient conditions. To accomplish this, each of the R groups described herein must be sufficiently stable to sustain the corresponding desired shelf life of at least two, three, four or five months under ambient conditions.

Degronimers of Formula I, II, V and VII are bifunctional with novel carbon-linked E3 Ubiquitin Ligase targeting moieties (Degrons) linked to Targeting Ligands (described in more detail below), which function to recruit Target Proteins to E3 Ubiquitin Ligase, typically through cereblon, for degradation. One non-limiting example of a disorder treatable by such compounds is abnormal cellular proliferation, such as a tumor or cancer, wherein the Target Protein is an oncogenic protein or a signaling mediator of an abnormal cellular proliferative pathway and its degradation decreases abnormal cell growth.

Based on this discovery, compounds and methods are presented for the treatment of a patient with a disorder mediated by a protein that is targeted for selective degradation that includes administering an effective amount of one or a combination of the Degronimers of Formula I, Formula II, Formula V or Formula VII or a pharmaceutically acceptable salt thereof, as described herein to a patient (typically a human) in need thereof, optionally in a pharmaceutically acceptable carrier. In certain embodiments the disorder is selected from a benign growth, neoplasm, tumor, cancer, abnormal cellular proliferation, immune disorder, autoimmune disorder, inflammatory disorder, graft-versus-host rejection, infectious disease, viral infection, bacterial infection, an amyloid-based proteinopathy, a proteinopathy, or fibrotic disorder. In a typical embodiment the patient is a human.

In one embodiment, the present invention provides carbon-linked moieties which are covalently linked to a Targeted Ligand through a Linker which can be of varying length, structure and functionality, as described in more detail below. In one embodiment, the carbon-linked Degron moiety is linked directly to the Targeting Ligand (i.e., the Linker is a bond). In certain embodiments, the Linker can be any chemically stable group that attaches the carbon-linked Degron to the Targeting Ligand.

In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense. Examples of Target Proteins are provided below.

In an alternative embodiment, a carbon-linked $C^3$-glutarimide Degron of Formula III, IV, or VI as described herein can be used alone (i.e., not as part of a Degronimer) as an in vivo binder of cereblon, which can be administered to a host, for example, a human, in need thereof, in an effective amount, optionally as a pharmaceutically acceptable salt, and optionally in a pharmaceutically acceptable composition, for any therapeutic indication which can be treated by modulating the function and or activity of the cereblon-containing E3 Ubiquitin Ligase Protein Complex, including but not limited to uses known for the cereblon binders thalidomide, pomalidomide or lenalidomide. In certain alternative embodiments, the compound of Formula III, IV or VI can activate, decrease or change the natural activity of cereblon. Nonlimiting examples of uses for cereblon binders are multiple myeloma, a hematological disorder such as myelodysplastic syndrome, cancer, tumors, abnormal cellular proliferation, HIV/AIDS, Crohn's disease, sarcoidosis, graft-versus-host disease, rheumatoid arthritis, Behcet's disease, tuberculosis, and myelofibrosis.

Thus, in another aspect of the present invention a Degron of Formula III or Formula IV is provided of the structure:

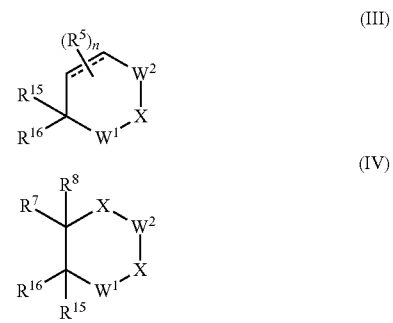

or a pharmaceutically acceptable salt, N-oxide, isotopic derivative, or prodrug thereof, optionally in a pharmaceutically acceptable carrier to form a composition;

wherein the R moieties are as defined above and $R^{16}$ is selected from:

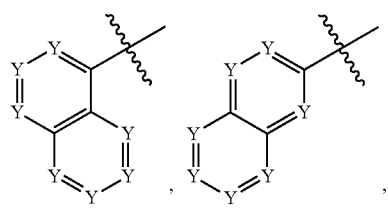

-continued

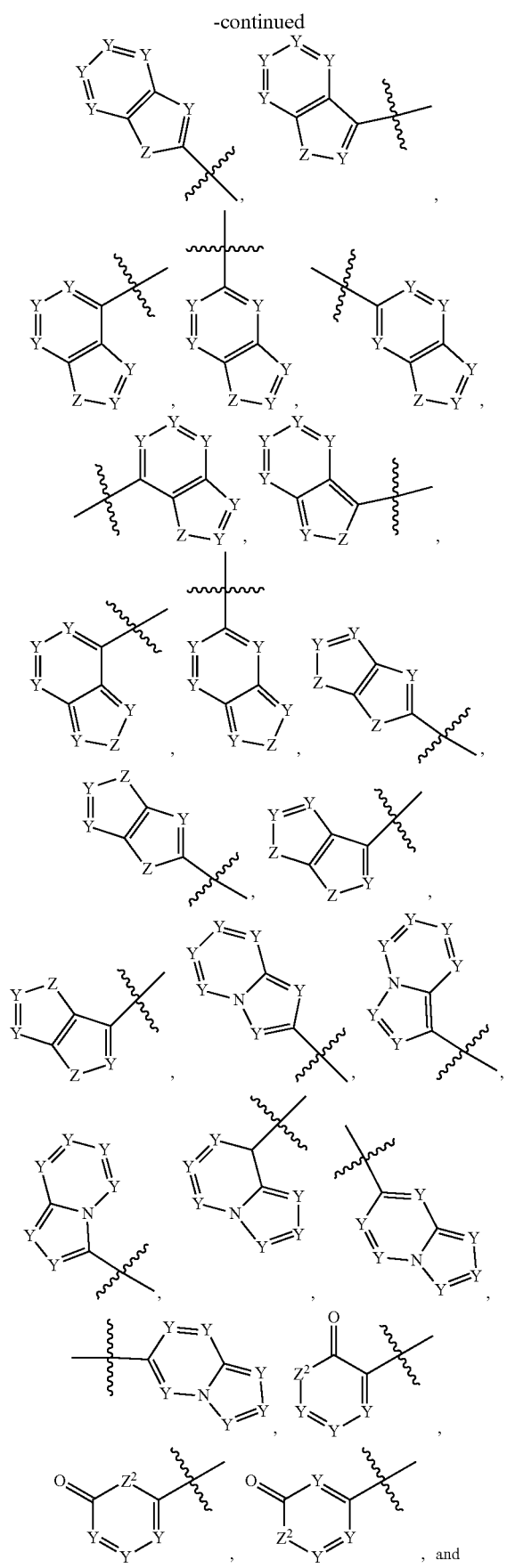

, and

-continued

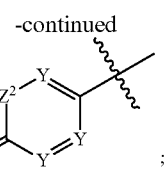

;

In one aspect of the present invention a Degron of Formula VI is provided:

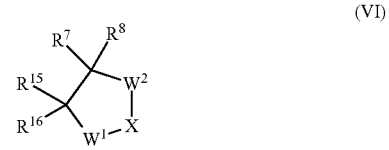

(VI)

or a pharmaceutically acceptable salt, N-oxide, isotopic derivative, or prodrug thereof, optionally in a pharmaceutically acceptable carrier to form a composition, wherein the R moieties are as defined above.

Compounds of the present application may offer important clinical benefits to patients, in particular for the treatment of the disease states and conditions modulated by the proteins of interest.

In certain embodiments, the present invention provides the administration of an effective amount of a compound of Formula I, II, III, IV, V, VI or VII to treat a patient, for example, a human, having an infectious disease, wherein the therapy targets a Target Protein of the infectious agent or a Target Protein of the host (Formula I, II, V or VII), or acts via binding to cereblon or its E3 ligase (Formula III, IV or VI) optionally in combination with another bioactive agent. The disease state or condition may be caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (including but not limited to Gram-negative, Gram-positive, Atypical, *Staphylococcus, Streptococcus, E. Coli, Salmonella, Helicobacter pylori*, meningitis, gonorrhea, Chlamydiaceae, Mycoplasmataceae, etc), fungus, protozoa, helminth, worms, prion, parasite, or other microbe.

In certain embodiments, the compound of Formula I, II, III, IV, V, VI or VII has at least one desired isotopic substitution of an atom, at an amount above the natural abundance of the isotope, i.e., enriched. In one embodiment, the compound of Formula I or Formula II includes a deuterium or multiple deuterium atoms.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the present invention will be apparent from the following detailed description and claims.

The present invention thus includes at least the following features:

(a) A carbon-linked Degronimer of Formula I, II, V or VII as described herein, and pharmaceutically acceptable salts, isotopic derivative (including a deuterated derivative) and prodrugs thereof;

(b) A carbon-linked Degronimer of Formula I, II, V or VII, for the treatment of a disorder that is mediated by a Target Protein, wherein the compound includes a Targeting Ligand for the Target Protein, and wherein the carbon-linked compound is optionally linked to the Targeting Ligand through a Linker;

(c) Use of a Degronimer of Formula I, II, V or VII in an effective amount in the treatment of a patient, including a human, with a disorder mediated by a Target Protein, including abnormal cellular proliferation such as a tumor or cancer, an autoimmune disorder or inflammatory disorder, a cardiac disorder, an infectious disease, or other disorder that responds to such treatment;

(d) Use of a Degronimer of Formula I or Formula II and pharmaceutically acceptable salts, isotopic derivatives and prodrugs thereof in the manufacture of a medicament for the treatment of a medical disorder;

(e) A method for manufacturing a medicament intended for the therapeutic treat a disorder characterized in that a Degronimer of Formula I, II, V or VII as described herein is used in the manufacture;

(f) A Degronimer of Formula I, II, V or VII as described herein, and pharmaceutically acceptable salts, isotopic derivatives and prodrugs thereof that are useful in the treatment of an abnormal cellular proliferation such as cancer, including any of the cancers described herein;

(g) Use of a Degronimer of Formula I, II, V or VII and pharmaceutically acceptable salts, isotopic derivatives and prodrugs thereof in the manufacture of a medicament for the treatment of an abnormal cellular proliferation such as cancer, including any of the cancers described herein;

(h) A method for manufacturing a medicament intended for the therapeutic use of treating an abnormal cellular proliferation such as cancer, including any of the cancers described herein, characterized in that a Degronimer of Formula I, II, V or VII as described herein is used in the manufacture;

(i) A Degronimer of Formula I, II, V or VII as described herein, and pharmaceutically acceptable salts, isotopic derivatives and prodrugs thereof that are useful in the treatment of a tumor, including any of the tumors described herein;

(j) Use of a Degronimer of Formula I, II, V or VII and pharmaceutically acceptable salts, isotopic derivatives and prodrugs thereof in the manufacture of a medicament for the treatment of a tumor, including any of the tumors described herein;

(k) A method for manufacturing a medicament intended for the therapeutic treatment of a tumor, including any of the tumors described herein, characterized in that a Degronimer of Formula I, II, V or VII as described herein is used in the manufacture;

(l) A Degronimer of Formula I, II, V or VII as described herein, and pharmaceutically acceptable salts, isotopic derivatives and prodrugs thereof that are useful in the treatment of an immune, autoimmune or inflammatory disorder;

(m) Use of a Degronimer of Formula I, II V or VII and pharmaceutically acceptable salts and prodrugs thereof in the manufacture of a medicament for the treatment of an immune, autoimmune or inflammatory disorder;

(n) A method for manufacturing a medicament intended for the therapeutic treatment of an immune, autoimmune or inflammatory disorder, characterized in that a Degronimer of Formula I, II, V or VII as described herein is used in the manufacture;

(o) A Degronimer of Formula I, II, V or VII as described herein, and pharmaceutically acceptable salts and prodrugs thereof that are useful in the treatment of a viral infection, including but not limited to HIV, HBV, HCV and RSV;

(p) Use of a Degronimer of Formula I, II, V or VII, and pharmaceutically acceptable salts and prodrugs thereof in the manufacture of a medicament for the treatment of a viral infection, including but not limited to HIV, HBV, HCV and RSV;

(q) A method for manufacturing a medicament intended for the therapeutic treatment of a viral infection including but not limited to HIV, HBV, HCV and RSV, characterized in that a Degronimer of Formula I, II, V or VII as described herein is used in the manufacture;

(r) A pharmaceutical formulation comprising an effective host-treating amount, such as a human-treating amount of the Degronimer of Formula I, II, V or VII or a pharmaceutically acceptable salt or prodrug thereof together with a pharmaceutically acceptable carrier or diluent;

(s) A Degronimer of Formula I, II, V or VII as described herein as a mixture of enantiomers or diastereomers (as relevant), including as a racemate;

(t) A Degronimer of Formula I, II, V or VII as described herein in enantiomerically or diastereomerically (as relevant) enriched form, including as an isolated enantiomer or diastereomer (i.e., greater than 85, 90, 95, 97 or 99% pure);

(u) A process for the preparation of therapeutic products that contain an effective amount of a Degronimer of Formula I, II, V or VII as described herein;

(v) Use of a compound of Formula III, Formula IV, or Formula VI in an effective amount, in the treatment of a patient, including a human, with abnormal cellular proliferation such as a tumor or cancer, an immune or autoimmune disorder or inflammatory disorder, a cardiac disorder, an infectious disease, or other disorder that responds to such treatment;

(w) A method for manufacturing a medicament intended for the therapeutic treat a disorder characterized in that a compound of Formula III, Formula IV, or Formula VI as described herein is used in the manufacture;

(x) A compound of Formula III, Formula IV, or Formula VI as described herein, and pharmaceutically acceptable salts, isotopic derivatives and prodrugs thereof that are useful in the treatment of an abnormal cellular proliferation such as cancer, including any of the cancers described herein;

(y) Use of a compound of Formula III, Formula IV, or Formula VI and pharmaceutically acceptable salts, isotopic derivatives and prodrugs thereof in the manufacture of a medicament for the treatment of an abnormal cellular proliferation such as cancer, including any of the cancers described herein;

(z) A method for manufacturing a medicament intended for the therapeutic use of treating an abnormal cellular proliferation such as cancer, including any of the cancers described herein, characterized in that a compound of Formula III, Formula IV, or Formula VI as described herein is used in the manufacture;

(aa) A compound of Formula III, Formula IV, or Formula VI as described herein, and pharmaceutically acceptable salts, isotopic derivatives and prodrugs thereof that are useful in the treatment of a tumor, including any of the tumors described herein;

(bb) Use of a compound of Formula III, Formula IV, or Formula VI, and pharmaceutically acceptable salts, isotopic derivatives and prodrugs thereof in the manufacture of a medicament for the treatment of a tumor, including any of the tumors described herein;

(cc) A method for manufacturing a medicament intended for the therapeutic treatment of a tumor, including any of the tumors described herein, characterized in that a compound of Formula III, Formula IV, or Formula VI as described herein is used in the manufacture;

(dd) A compound of Formula III, Formula IV, or Formula VI as described herein, and pharmaceutically acceptable salts, isotopic derivatives and prodrugs thereof that are useful in the treatment of an immune, autoimmune or inflammatory disorder;

(ee) Use of a compound of Formula III, Formula IV, or Formula VI and pharmaceutically acceptable salts and prodrugs thereof in the manufacture of a medicament for the treatment of an immune, autoimmune or inflammatory disorder;

(ff) A method for manufacturing a medicament intended for the therapeutic treatment of an immune, autoimmune or inflammatory disorder, characterized in that a compound of Formula III, Formula IV, or Formula VI, as described herein is used in the manufacture;

(gg) A pharmaceutical formulation comprising an effective host-treating amount, such as a human-treating amount of the compound of Formula III, Formula IV, or Formula VI or a pharmaceutically acceptable salt or prodrug thereof together with a pharmaceutically acceptable carrier or diluent;

(hh) A compound of Formula III, Formula IV, or Formula VI as described herein as a mixture of enantiomers or diastereomers (as relevant), including as a racemate;

(ii) A compound of Formula III, Formula IV, or Formula VI as described herein in enantiomerically or diastereomerically (as relevant) enriched form, including as an isolated enantiomer or diastereomer (i.e., greater than 85, 90, 95, 97 or 99% pure); and (jj) A process for the preparation of therapeutic products that contain an effective amount of a compound of Formula III, Formula IV, or Formula VI as described herein.

BRIEF DESCRIPTION OF FIGURES

FIG. 1K-1Q present examples of General Kinase and Phosphatase Targeting Ligands wherein R is the point at which the Linker is attached.

FIG. 1R-1S present examples of Tyrosine Kinase Targeting Ligands wherein R is the point at which the Linker is attached.

FIG. 1T presents examples of Aurora Kinase Targeting Ligands wherein R is the point at which the Linker is attached.

FIG. 1AA presents examples of mTORC1 and/or mTORC2 Targeting Ligands wherein R is the point at which the Linker is attached.

FIG. 1BB-1CC present examples of Mast/stem cell growth factor receptor (SCFR), also known as c-KIT receptor, Targeting Ligands wherein R is the point at which the Linker is attached.

FIG. 1DD presents examples of IGF1R and/or IR Targeting Ligands wherein R is the point at which the Linker is attached.

FIG. 1EE-1FF present examples of HDM2 and/or MDM2 Targeting Ligands wherein R is the point at which the Linker is attached.

FIG. 1GG-1MM present examples of BET Bromodomain-Containing Protein Targeting Ligands wherein R is the point at which the Linker is attached.

FIG. 1NN presents examples of HDAC Targeting Ligands wherein R is the point at which the Linker is attached.

FIG. 1OO presents examples of RAF Receptor Targeting Ligands wherein R is the point at which the Linker is attached.

FIG. 1PP presents examples of FKBP Receptor Targeting Ligands wherein R is the point at which the Linker is attached.

FIG. 1QQ-1TT present examples of Androgen Receptor Targeting Ligands wherein R is the point at which the Linker is attached.

FIG. 1UU presents examples of Estrogen Receptor Targeting Ligands wherein R is the point at which the Linker is attached.

FIG. 1VV-1WW present examples of Thyroid Hormone Receptor Targeting Ligands wherein R is the point at which the Linker is attached.

FIG. 1XX presents examples of HIV Protease Targeting Ligands wherein R is the point at which the Linker is attached.

FIG. 1YY presents examples of HIV Integrase Targeting Ligands wherein R is the point at which the Linker is attached.

FIG. 1ZZ presents examples of HCV Protease Targeting Ligands wherein R is the point at which the Linker is attached.

FIG. 1AAA presents examples of AP1 and/or AP2 Targeting Ligands wherein R is the point at which the Linker is attached.

FIG. 1BBB-1CCC present examples of MCL-1 Targeting Ligands wherein R is the point at which the Linker is attached.

FIG. 1DDD presents examples of IDH1 Targeting Ligands wherein R is the point at which the Linker is attached.

FIG. 1EEE-1FFF present examples of RAS or RASK Targeting Ligands wherein R is the point at which the Linker is attached.

FIG. 1GGG presents examples of MERTK or MER Targeting Ligands wherein R is the point at which the linker is attached.

FIG. 1HHH-1III present examples of EGFR Targeting Ligands wherein R is the point at which the Linker is attached.

FIG. 1JJJ-1KKK present examples of FLT3 Targeting Ligands wherein R is the point at which the Linker is attached.

FIG. 1LLL presents examples of SMRCA2 Targeting Ligands wherein R is the point at which the Linker is attached.

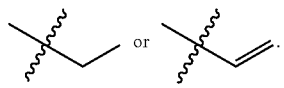

Figure 1A:
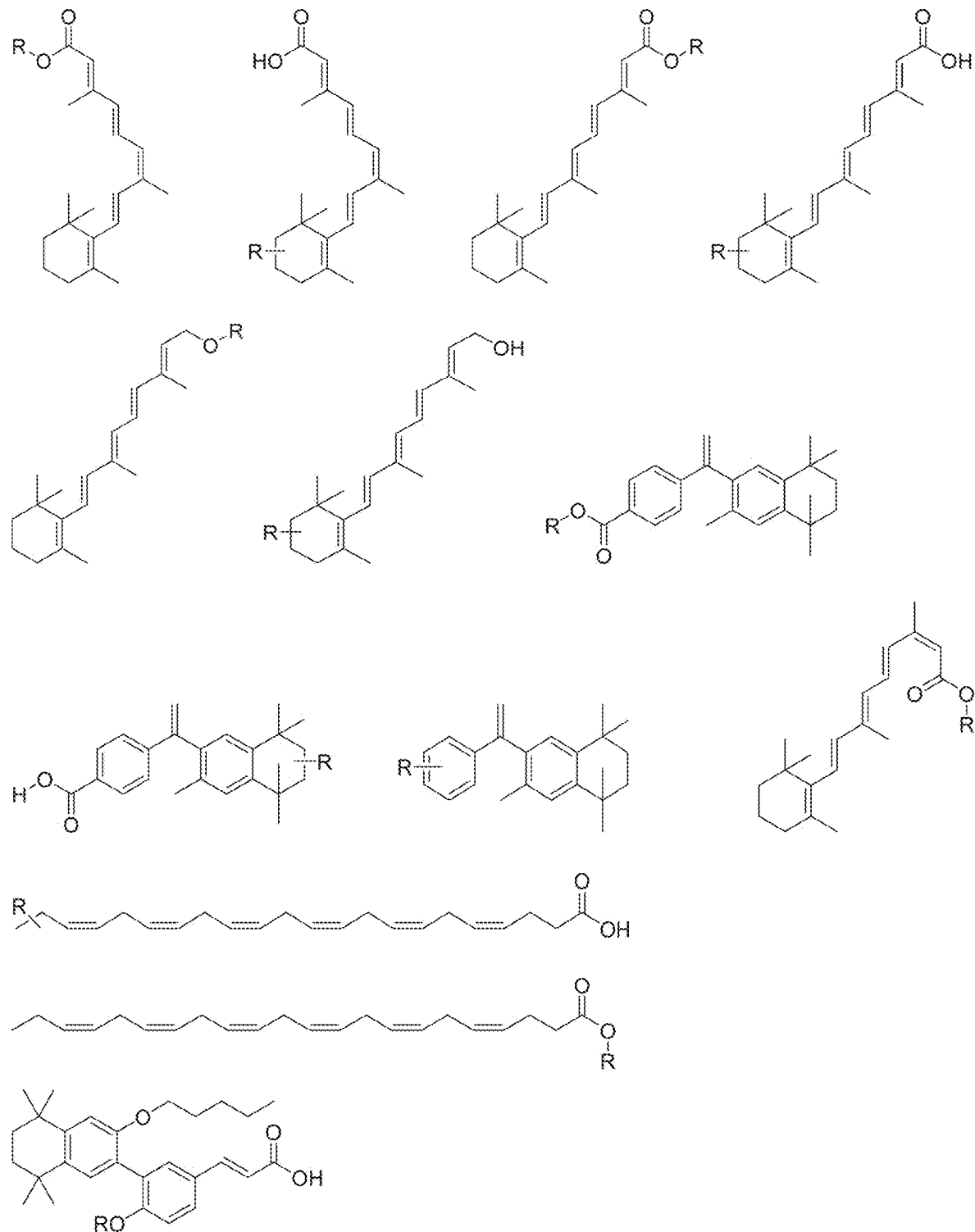
FIG. 1A-1C present examples of Retenoid X Receptor (RXR) Targeting Ligands wherein R is the point at which the Linker is attached.
Figure 1B:
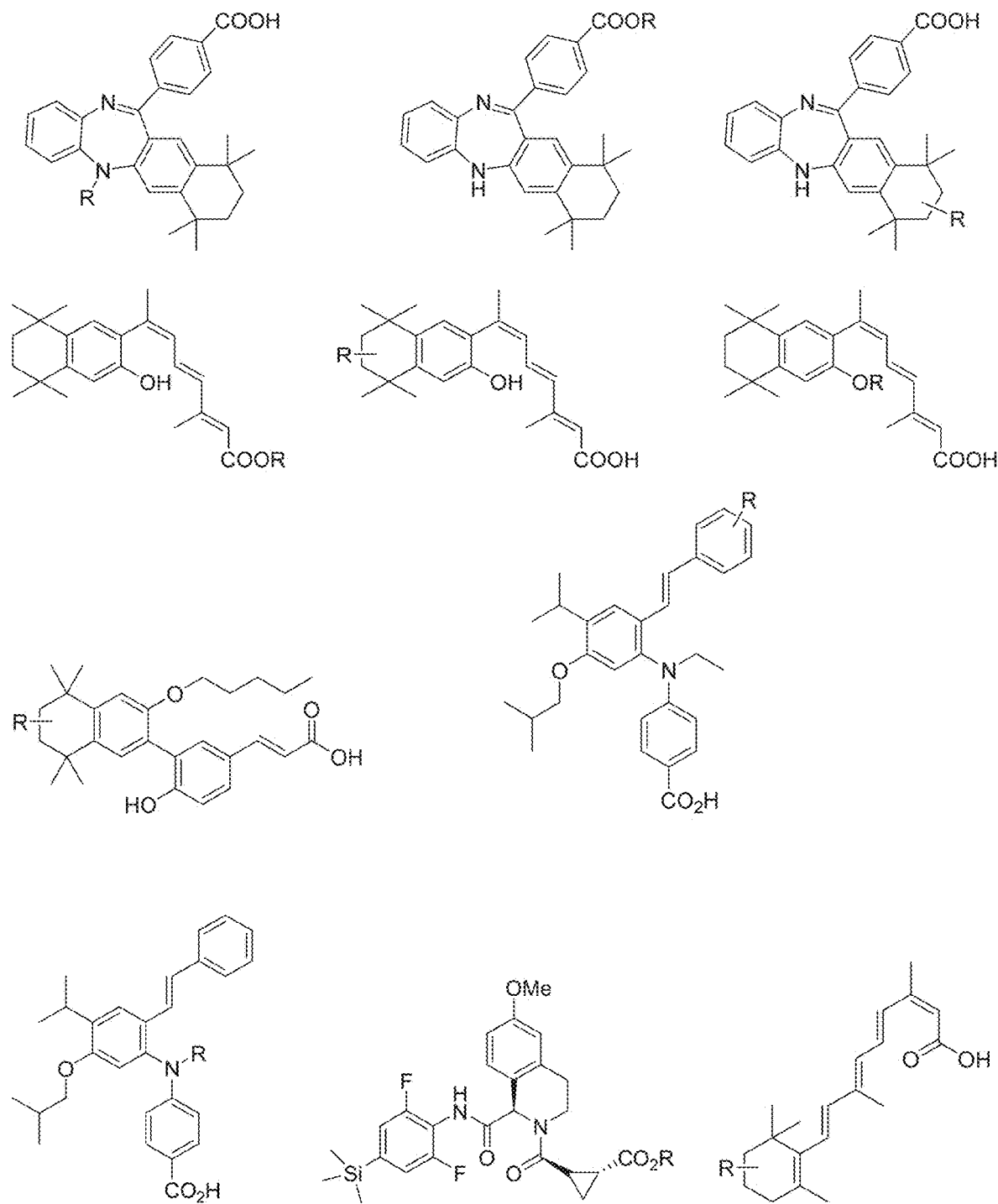
Figure 1C:
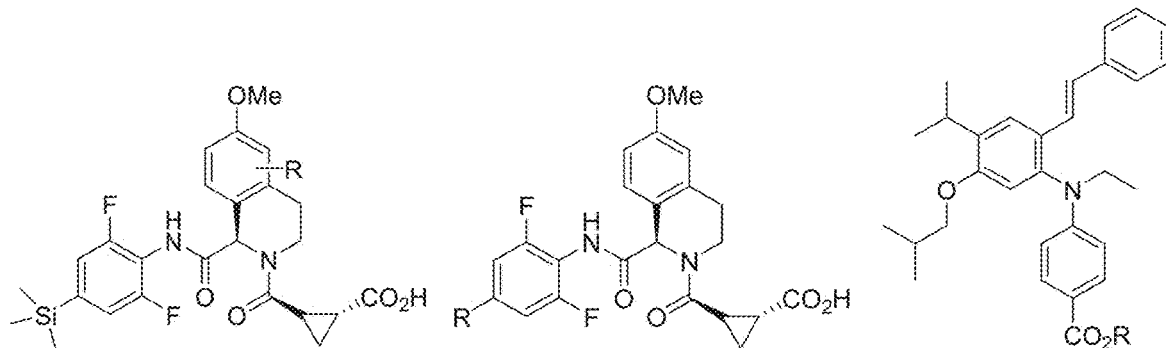
Figure 1D:
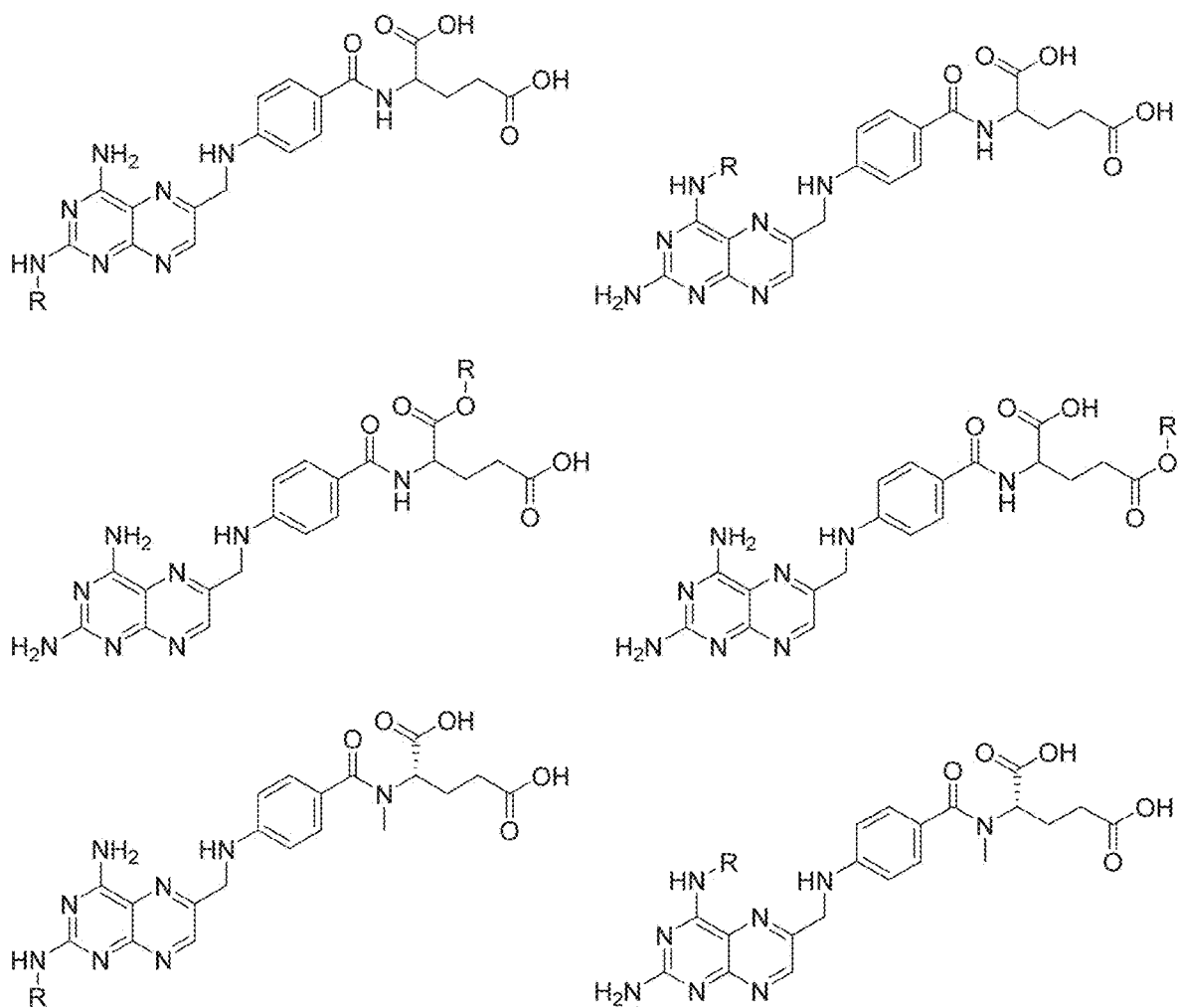
FIG. 1D-1F present examples of general Dihydrofolate reductase (DHFR) Targeting Ligands wherein R is the point at which the Linker is attached.
Figure 1E:
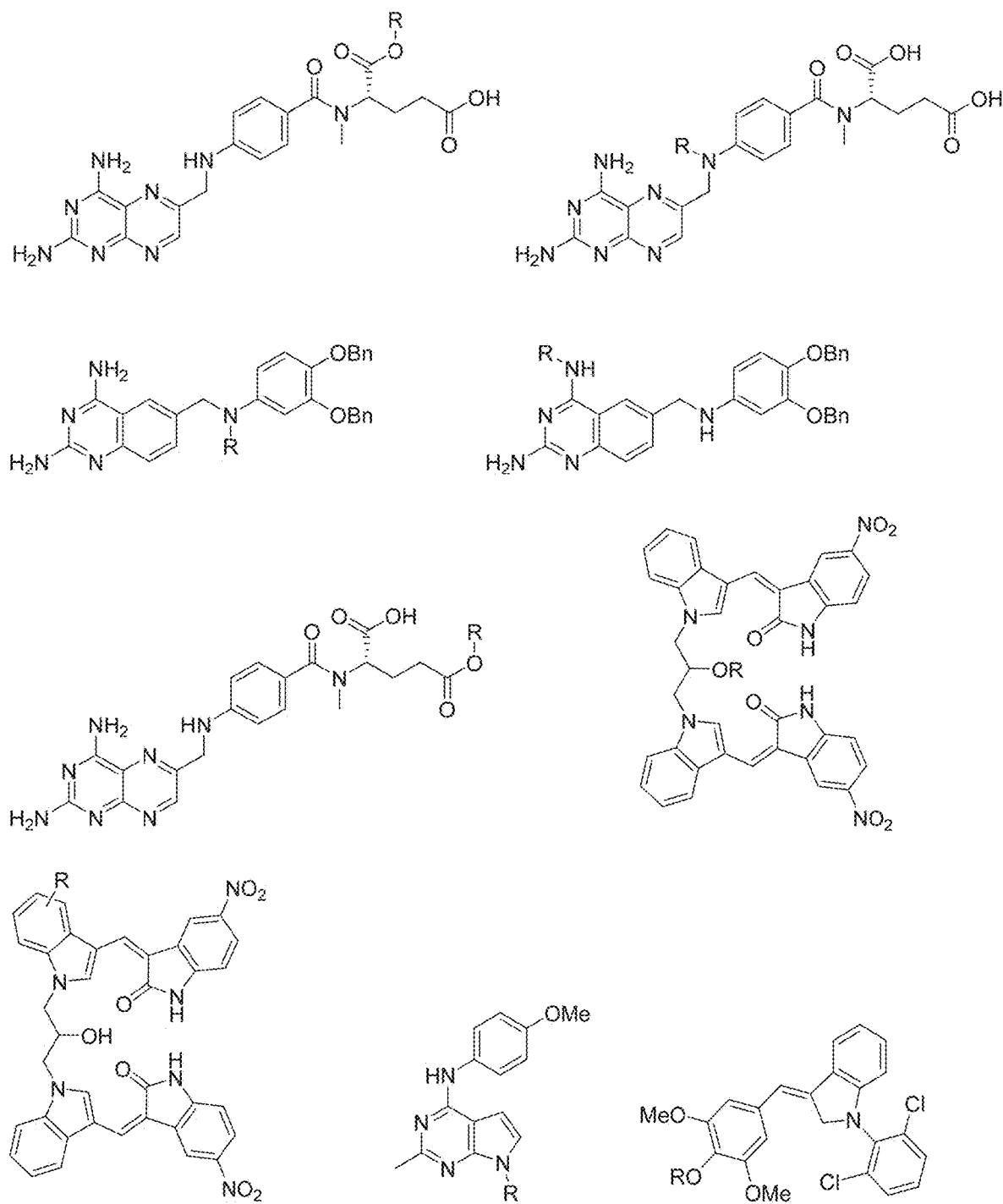
Figure 1F:
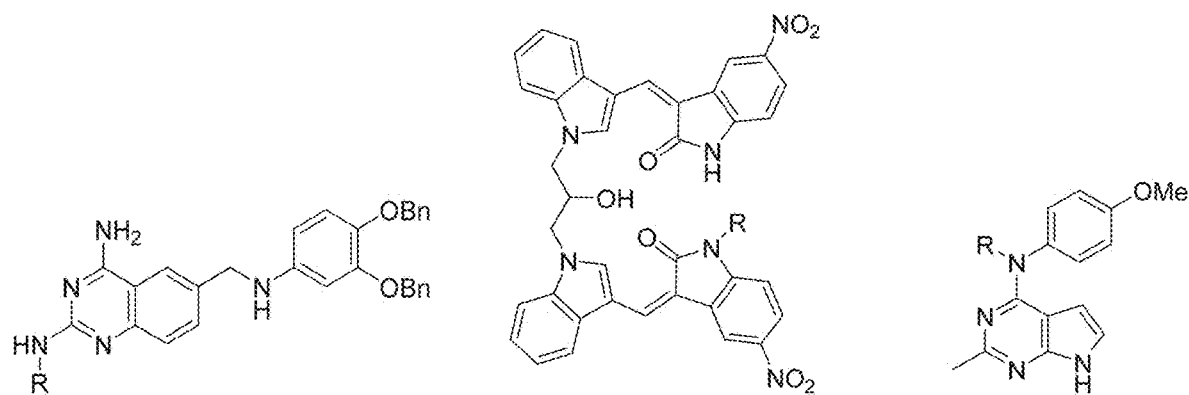
Figure 1G:
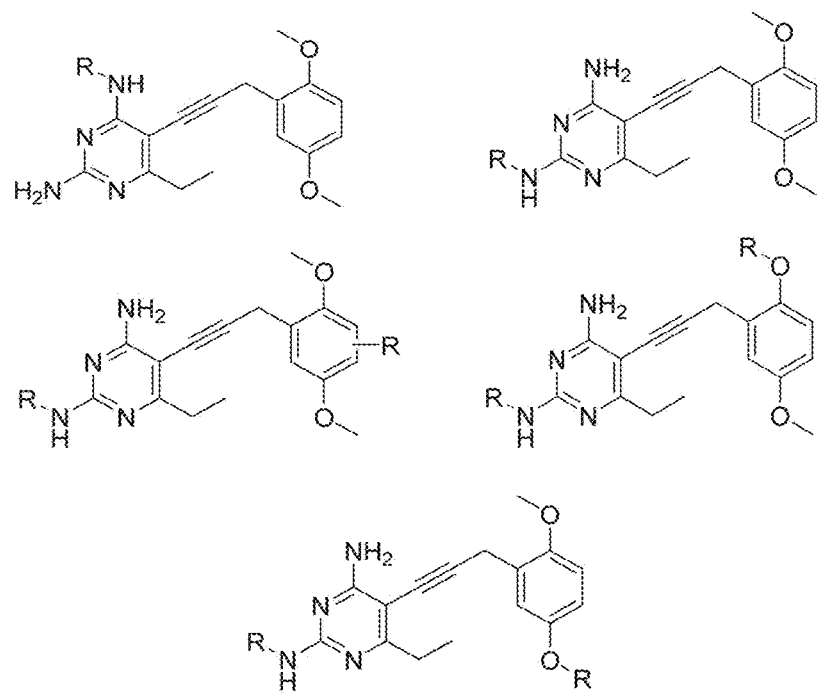
FIG. 1G presents examples of *Bacillus anthracis* Dihydrofolate reductase (BaDHFR) Targeting Ligands wherein R is the point at which the Linker is attached.
Figure 1H:
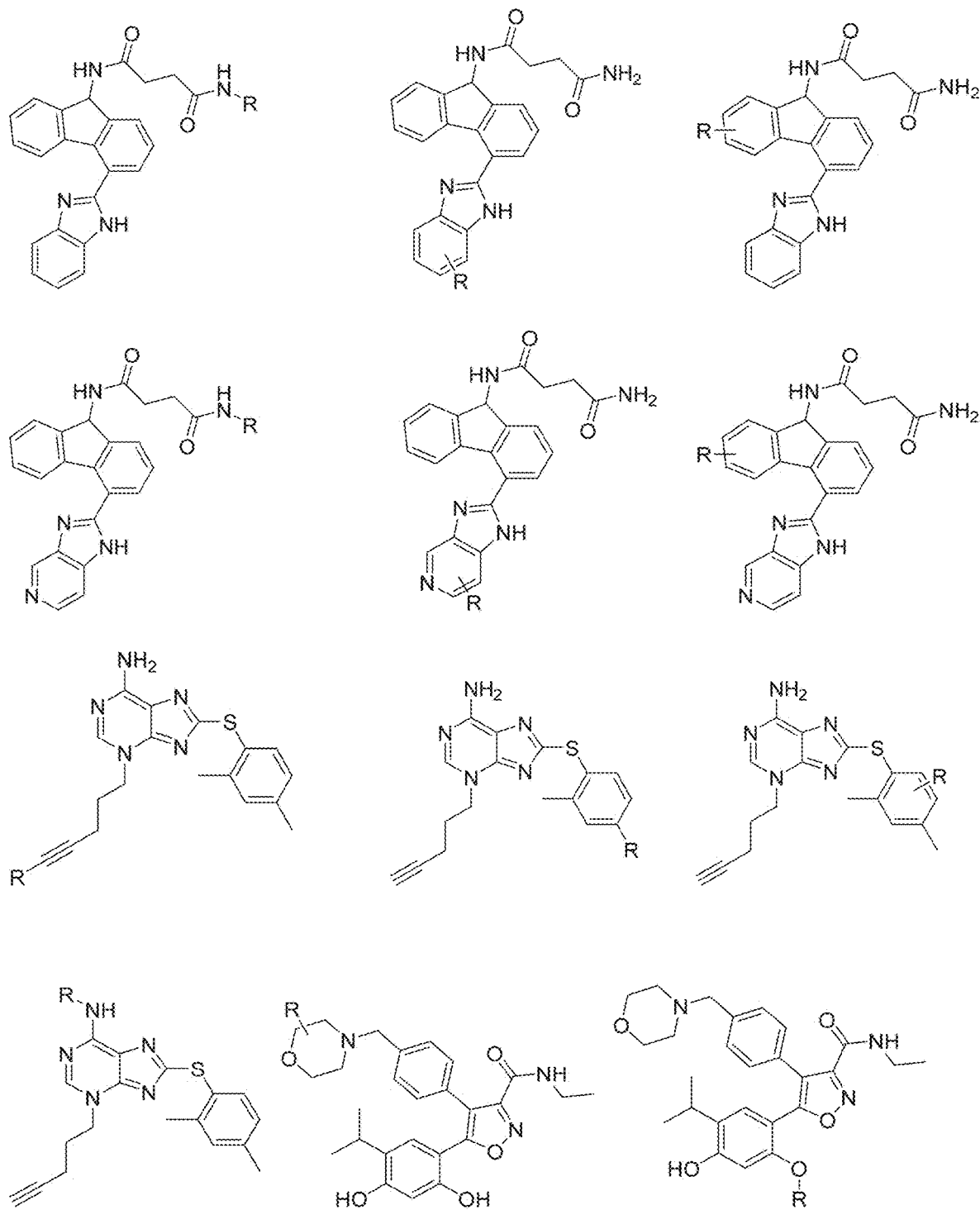
FIG. 1H-1J present examples of Heat Shock Protein 90 (HSP90) Targeting Ligands wherein R is the point at which the Linker is attached.
Figure 1I:
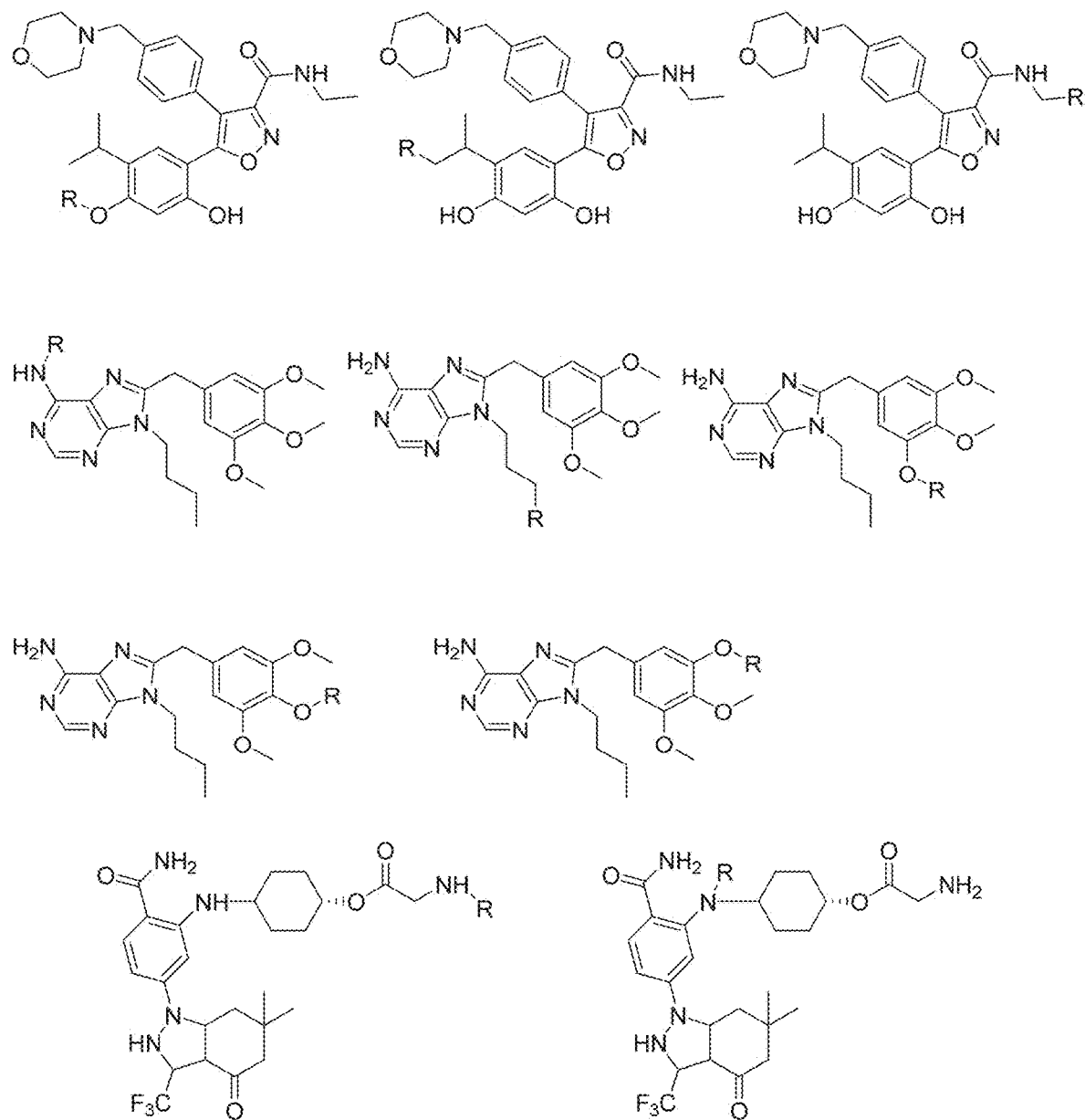
Figure 1J:
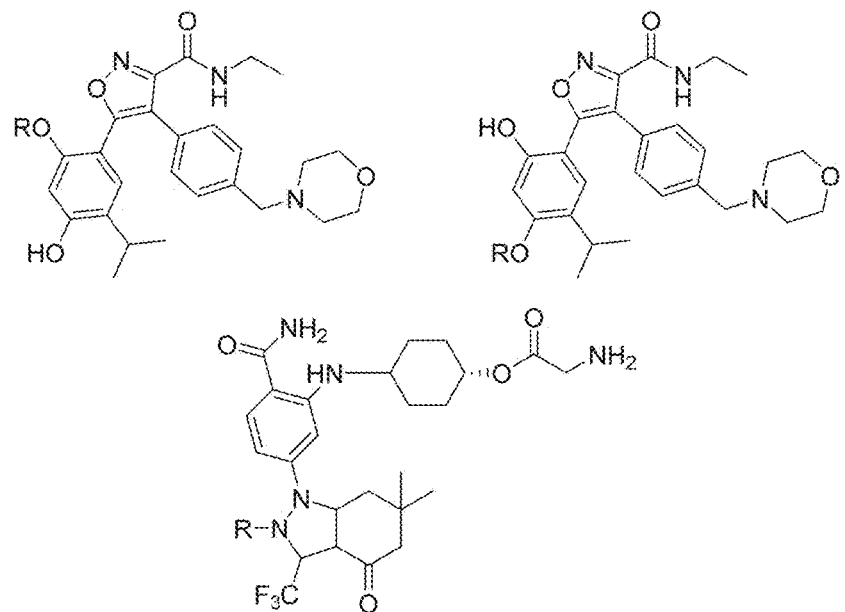
Figure 1K:
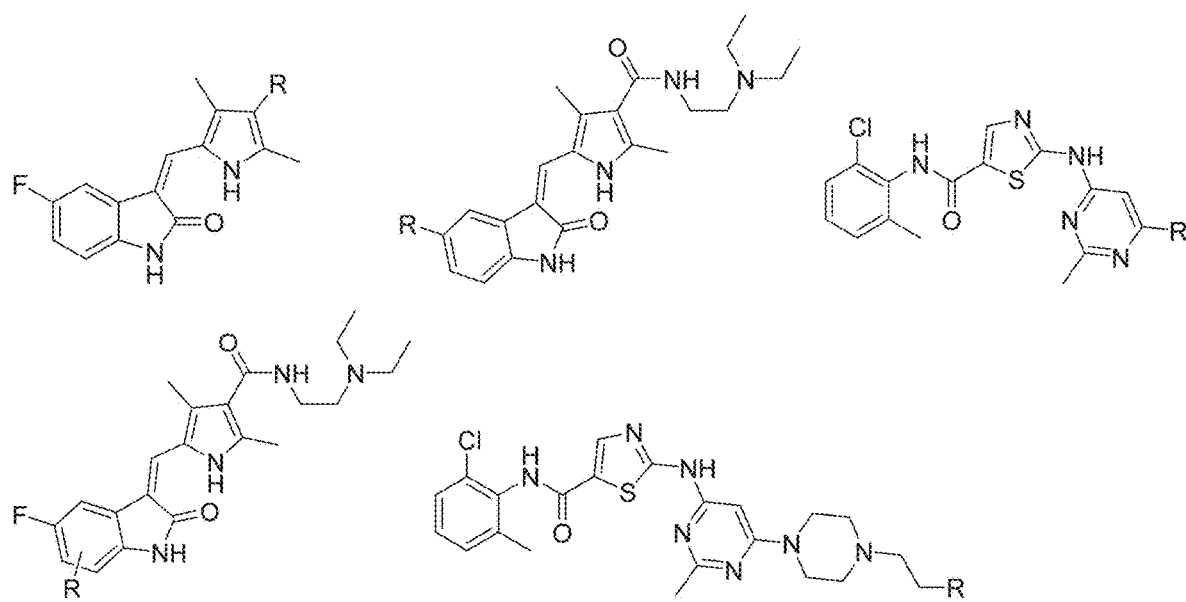
Figure 1L:
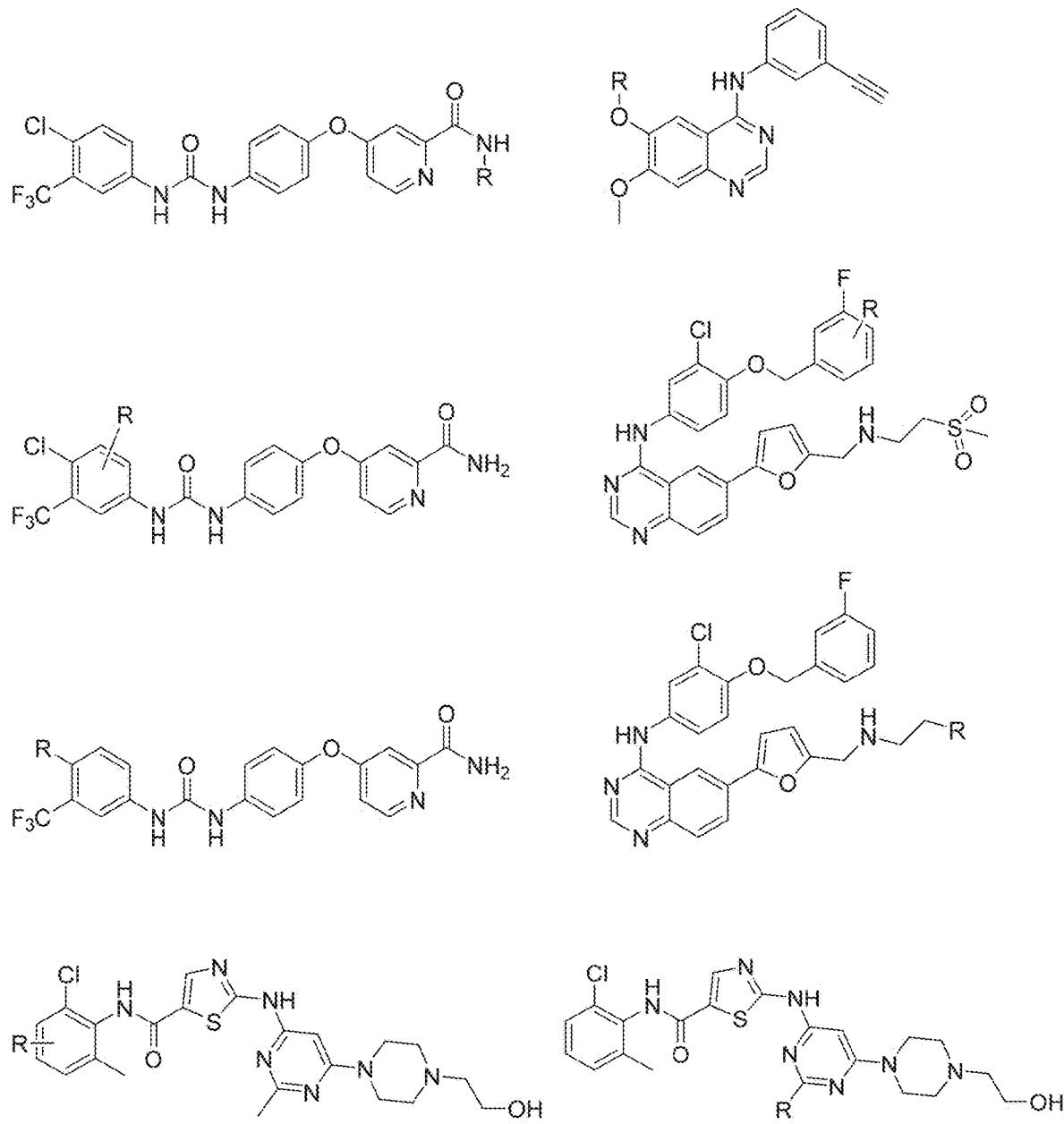
Figure 1M:
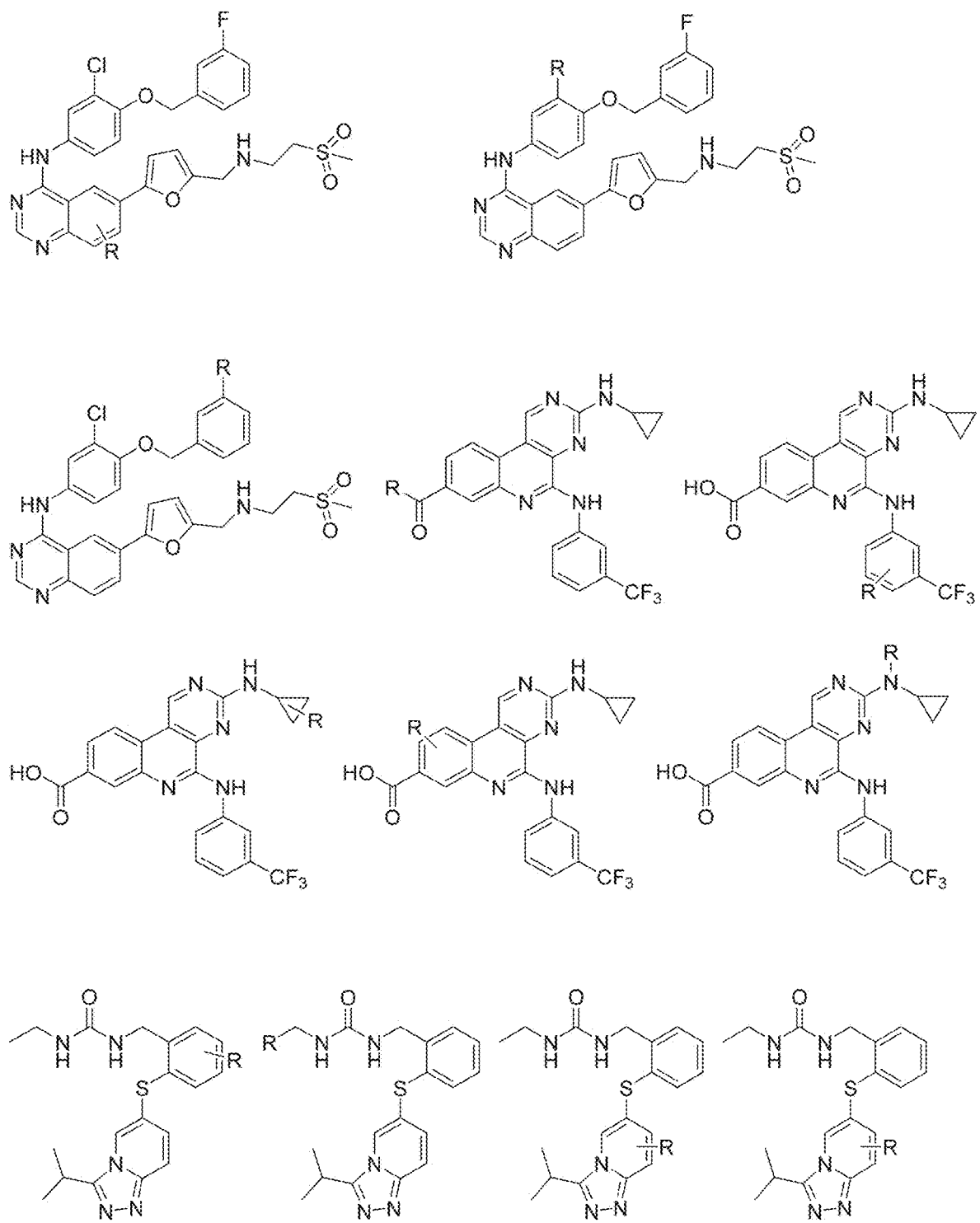
Figure 1N:
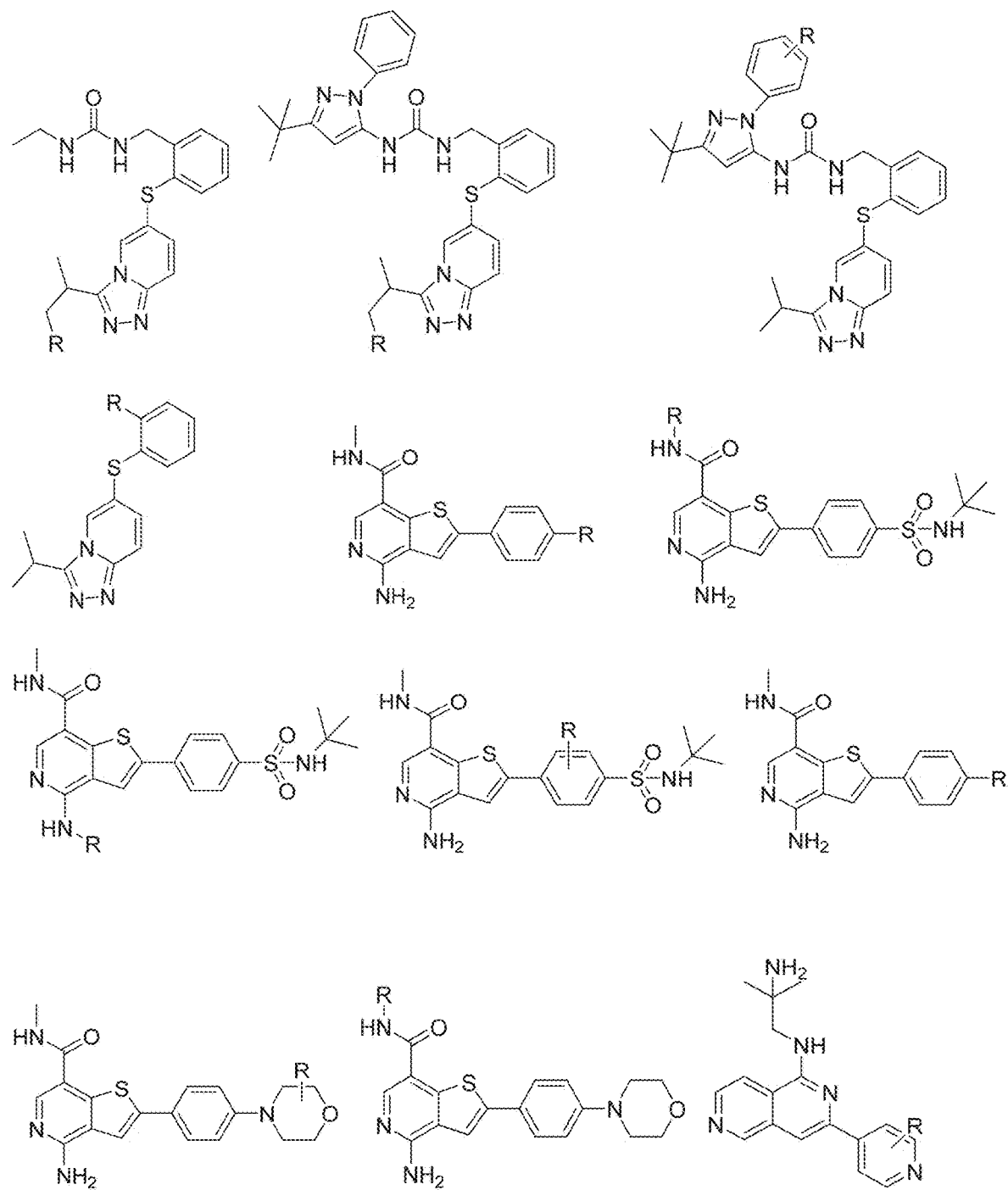
Figure 10:
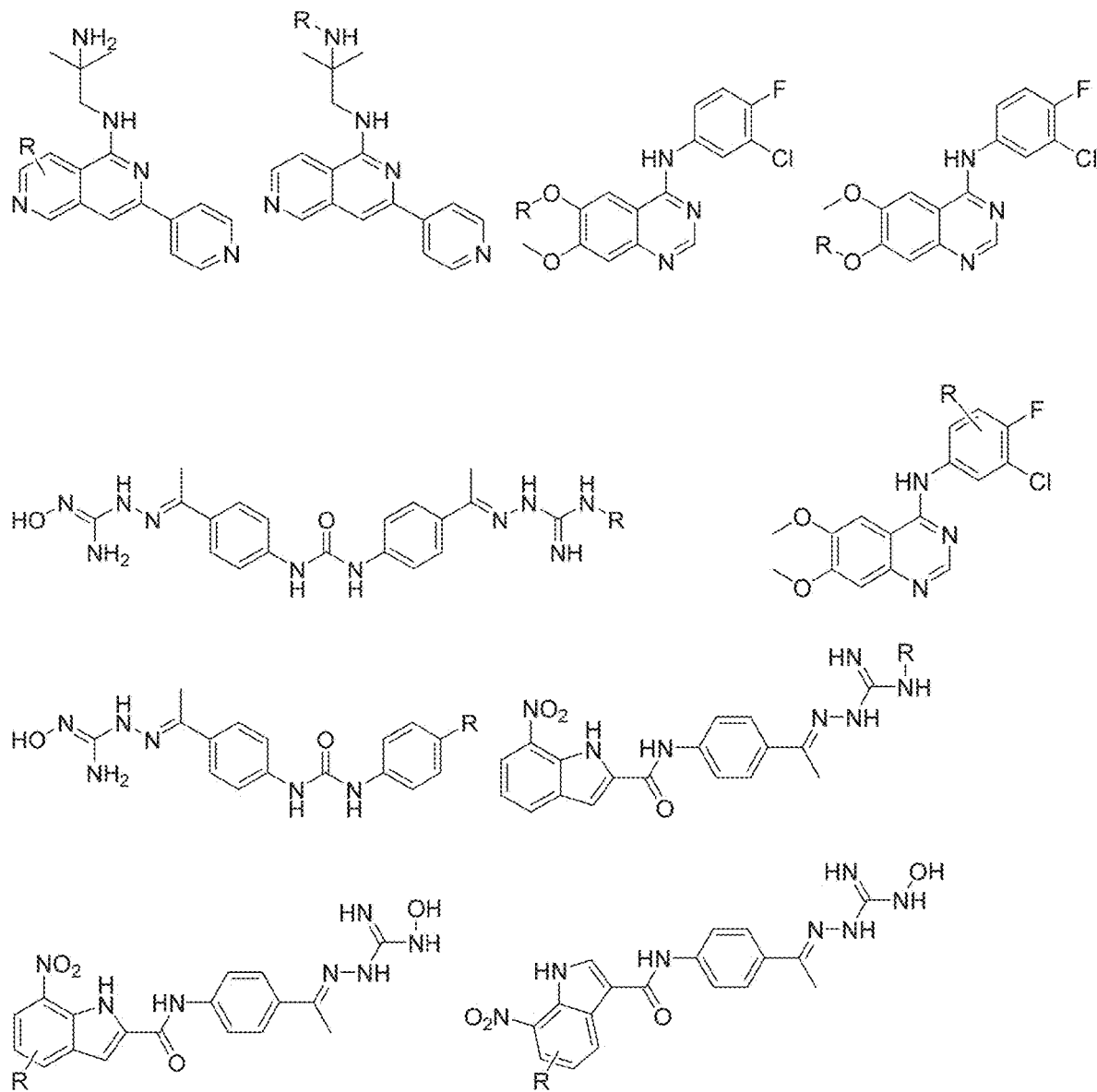
Figure 1P:
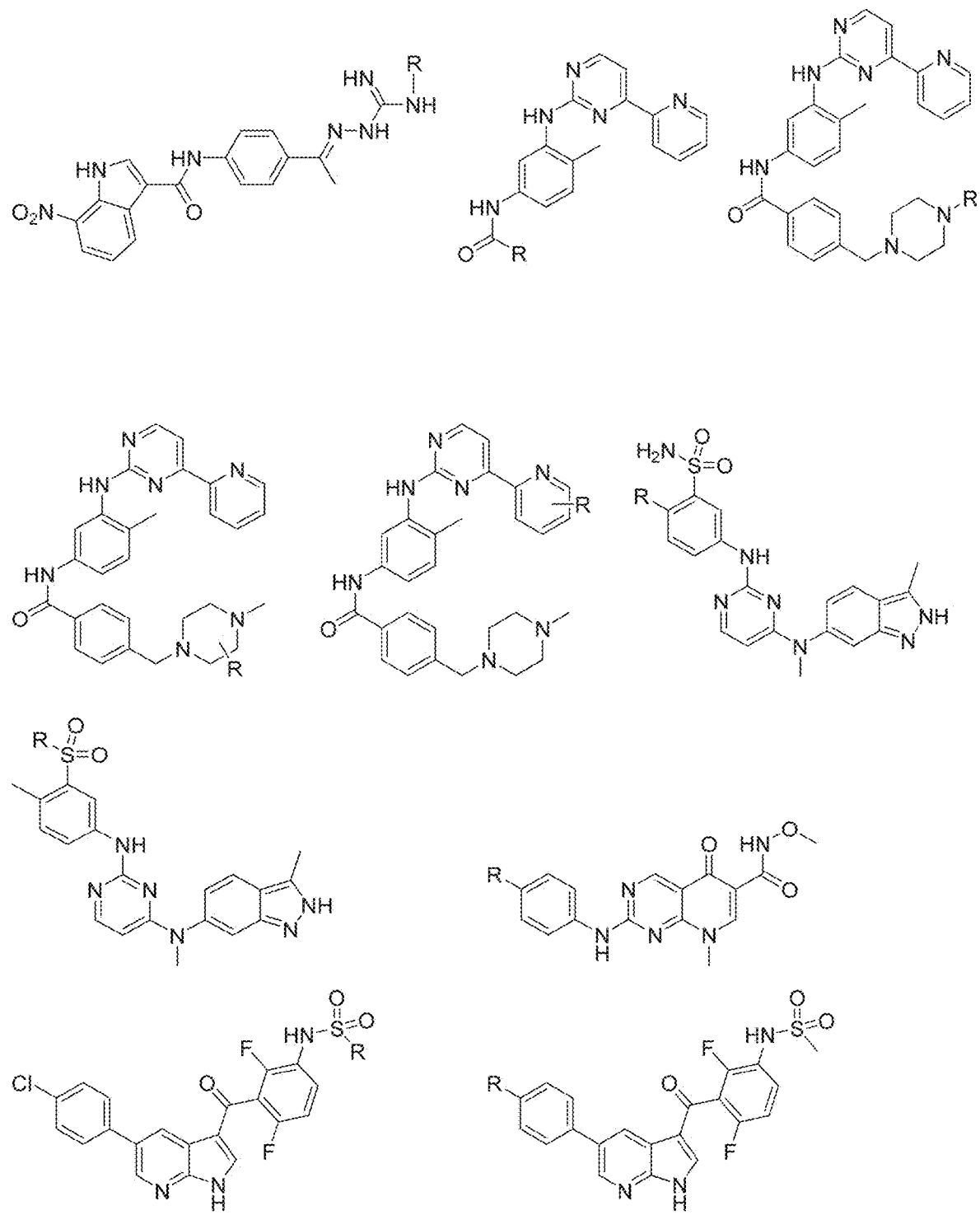
Figure 1U:
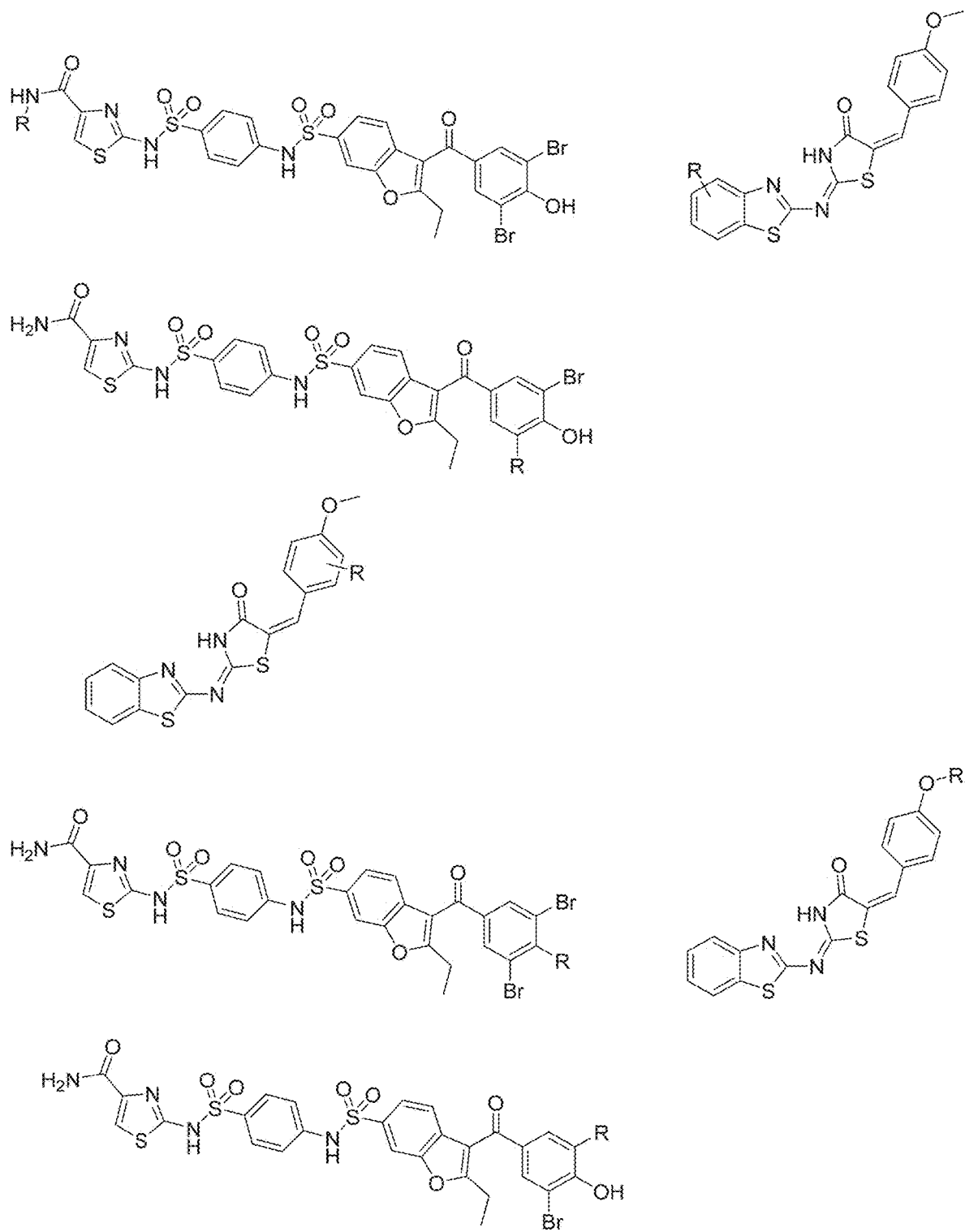
FIG. 1U presents examples of Protein Tyrosine Phosphatase Targeting Ligands wherein R is the point at which the Linker is attached.
Figure 1V:
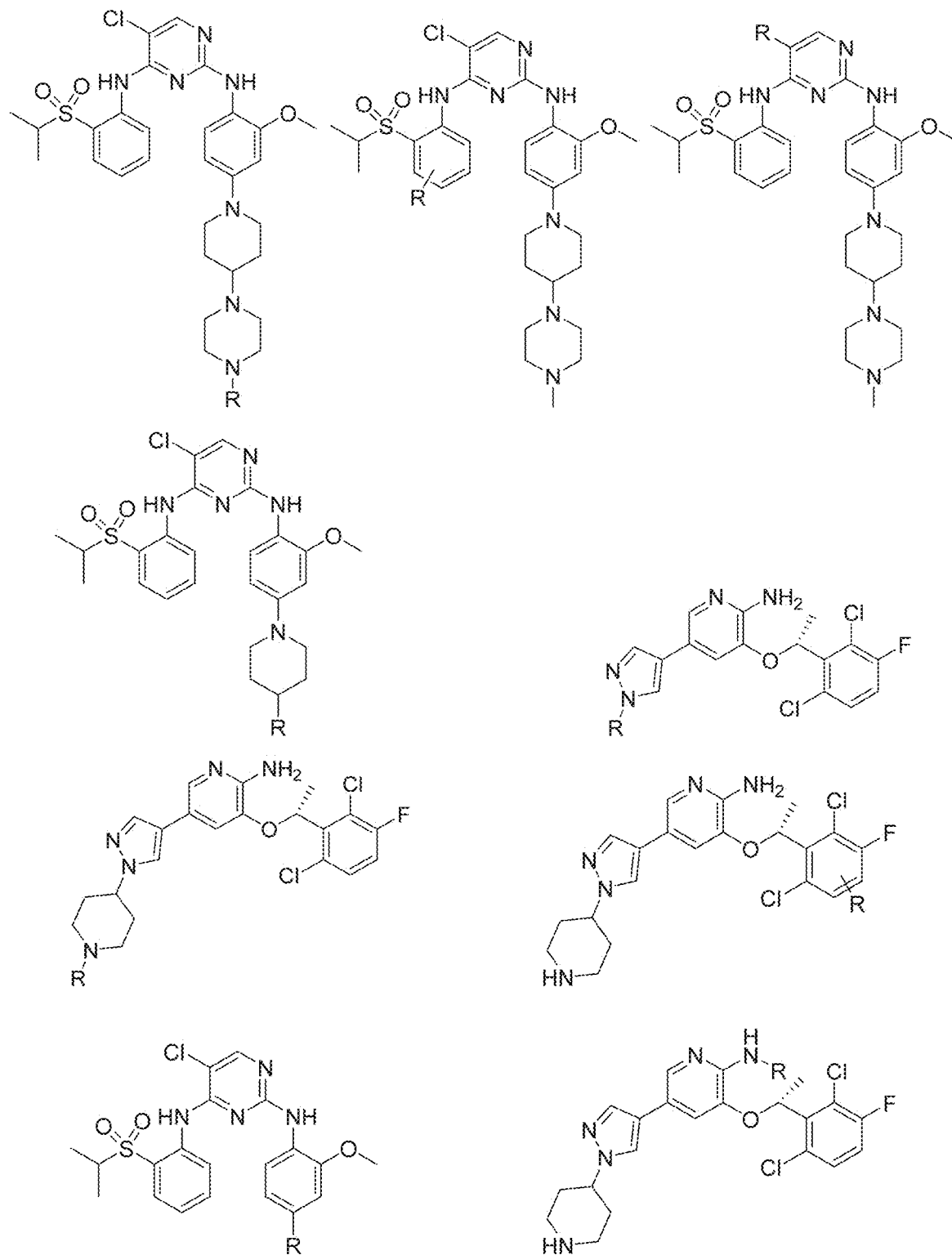
FIG. 1V presents examples of ALK Targeting Ligands wherein R is the point at which the Linker is attached.
Figure 1W:
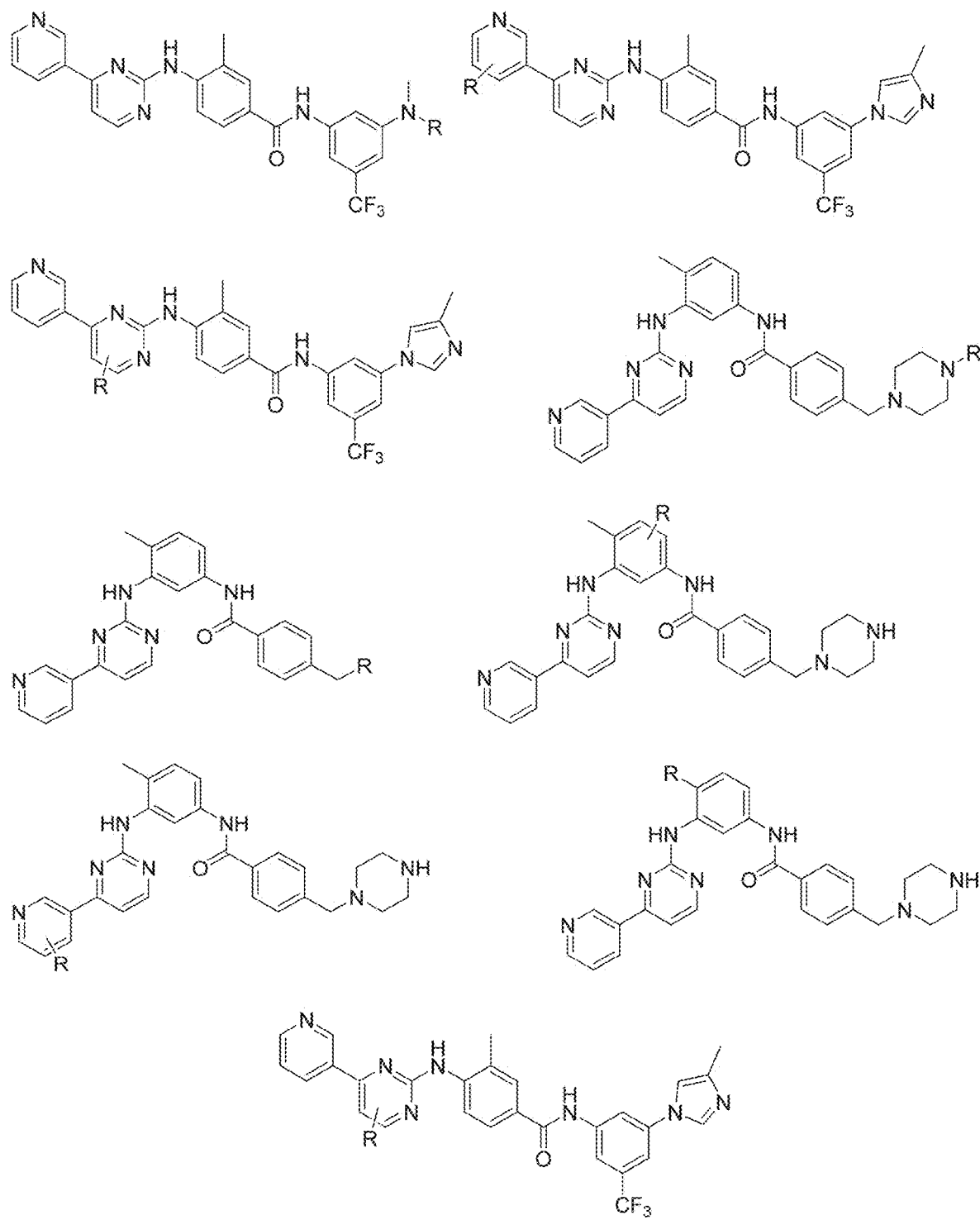
FIG. 1W presents examples of ABL Targeting Ligands wherein R is the point at which the Linker is attached.
Figure 1X:
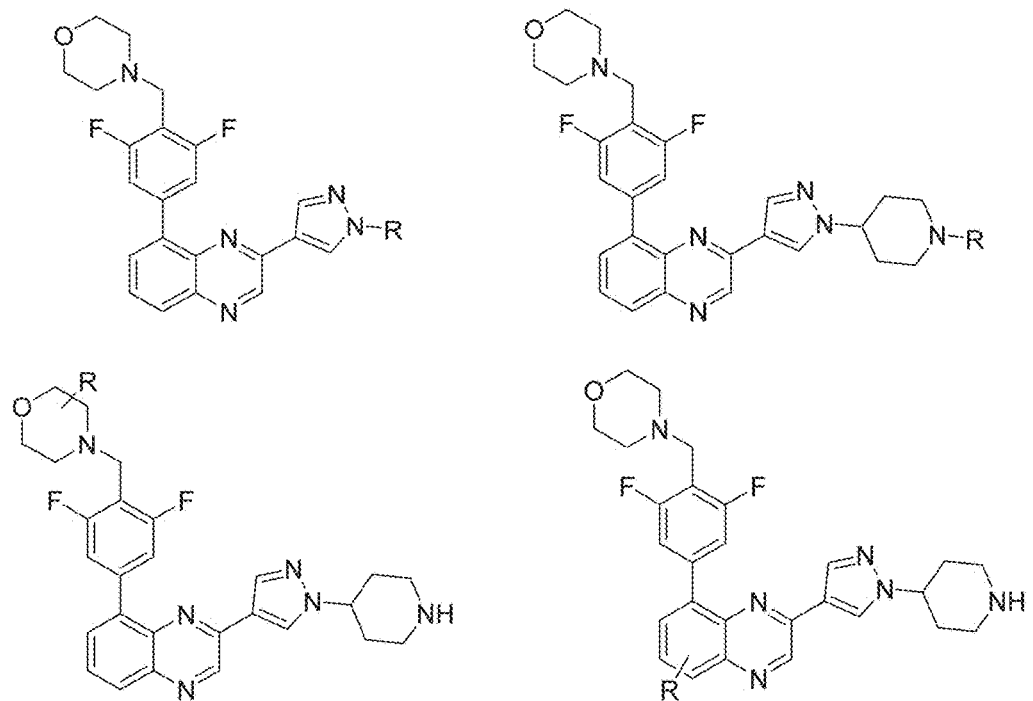
FIG. 1X presents examples of JAK2 Targeting Ligands wherein R is the point at which the Linker is attached.
Figure 1Y:
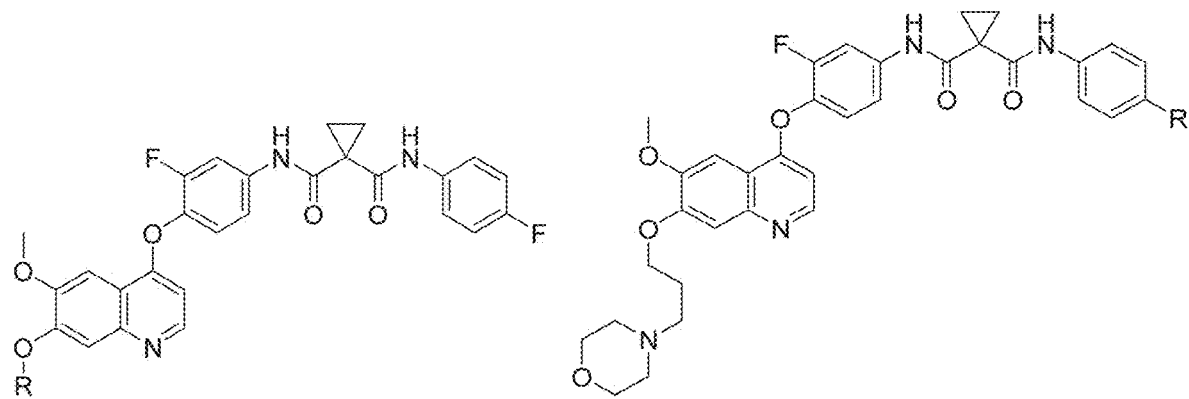
FIG. 1Y-1Z present examples of MET Targeting Ligands wherein R is the point at which the Linker is attached.
Figure 1Z:
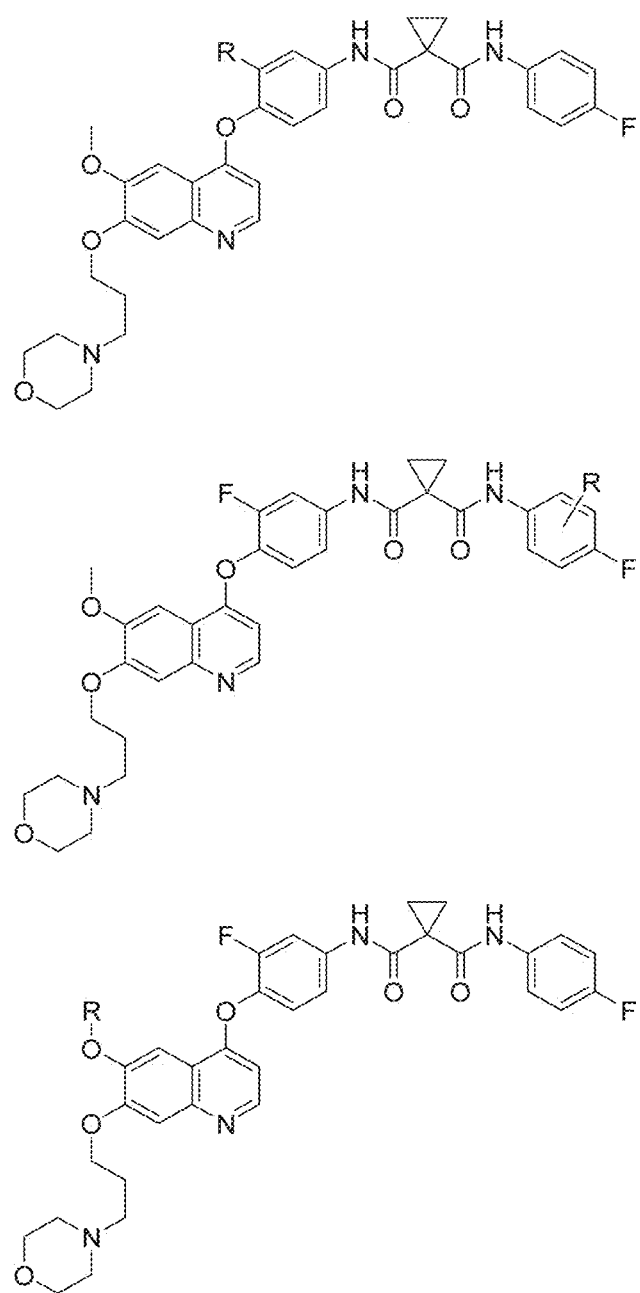
Figure 1A:
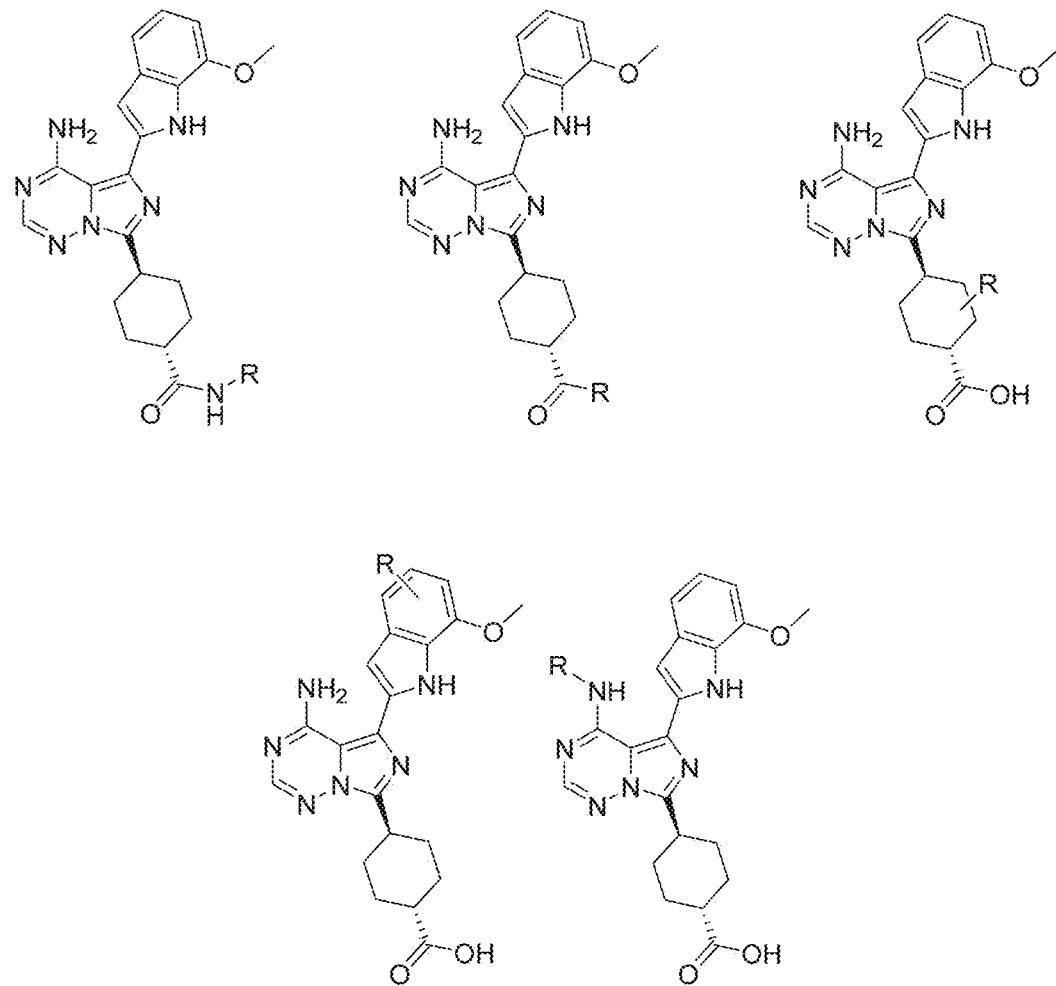
Figure 1B:
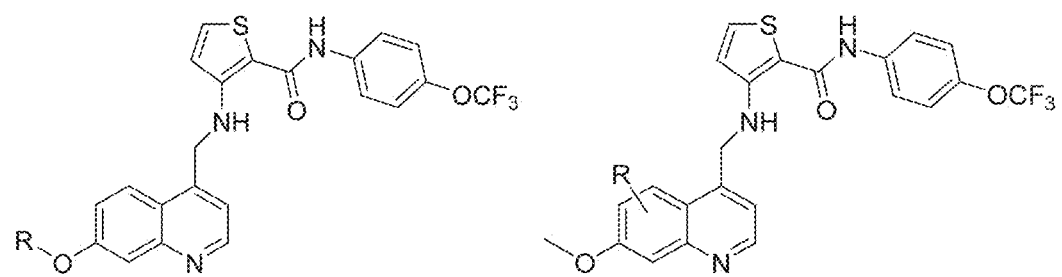
Figure 1C:
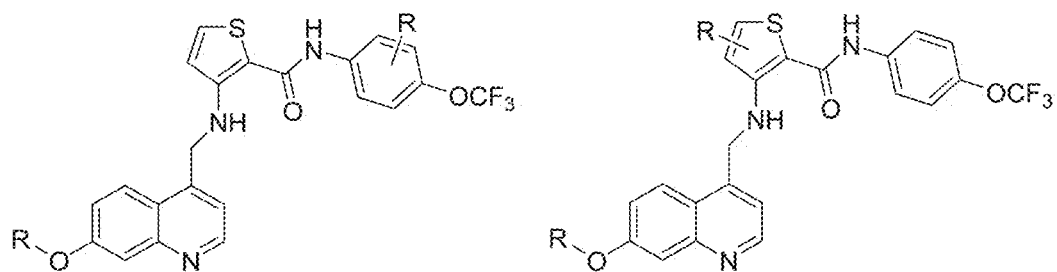
Figure 1D:
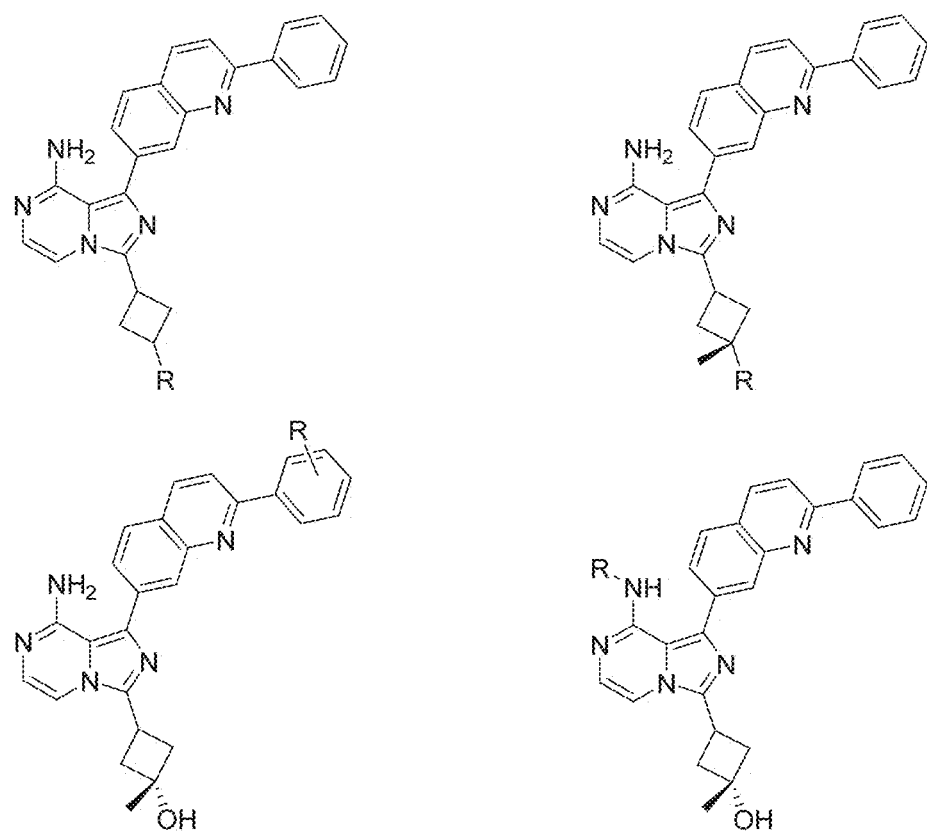
Figure 1F:
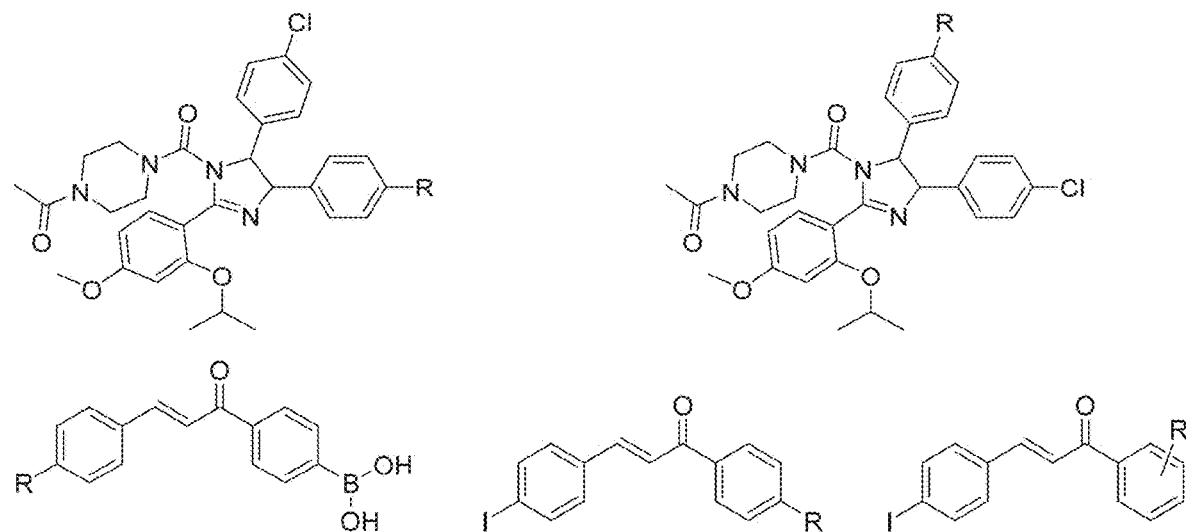
Figure 1G:
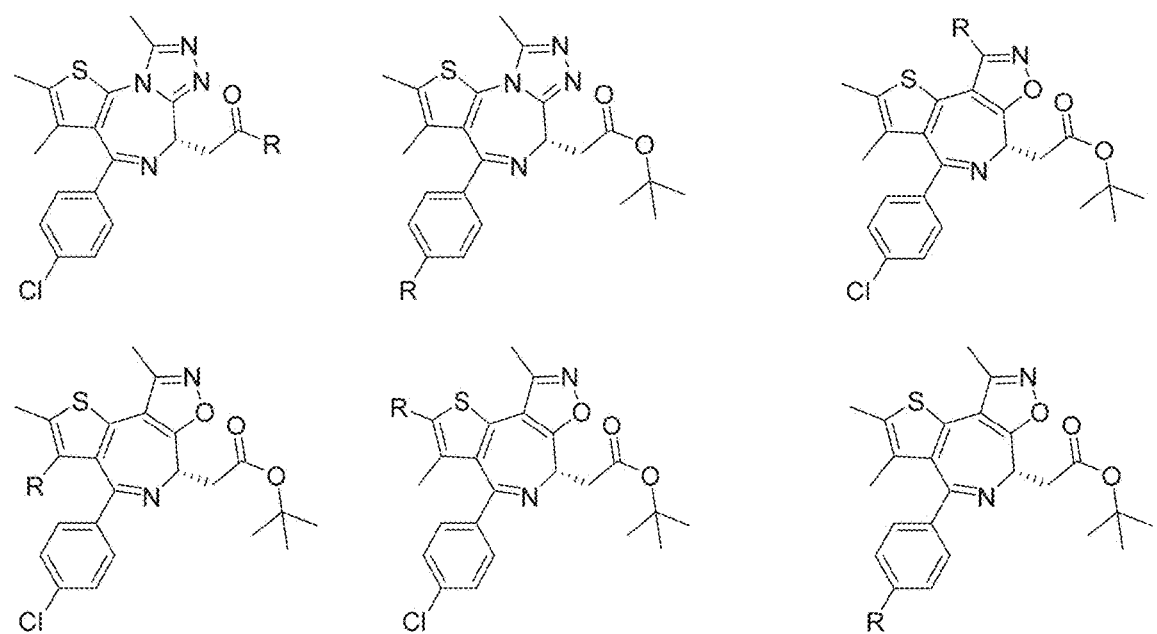
Figure 1H:
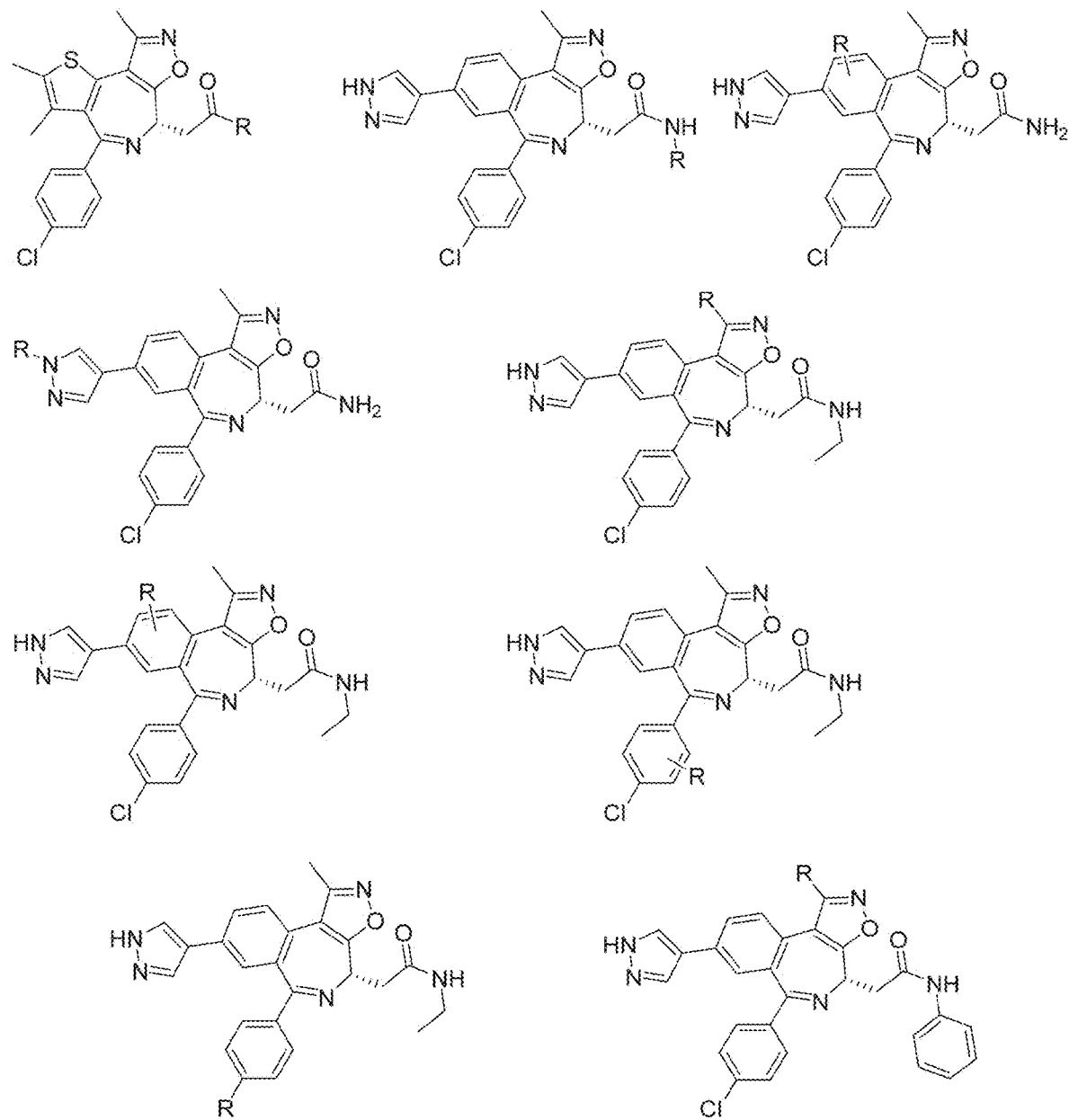
Figure 1J:
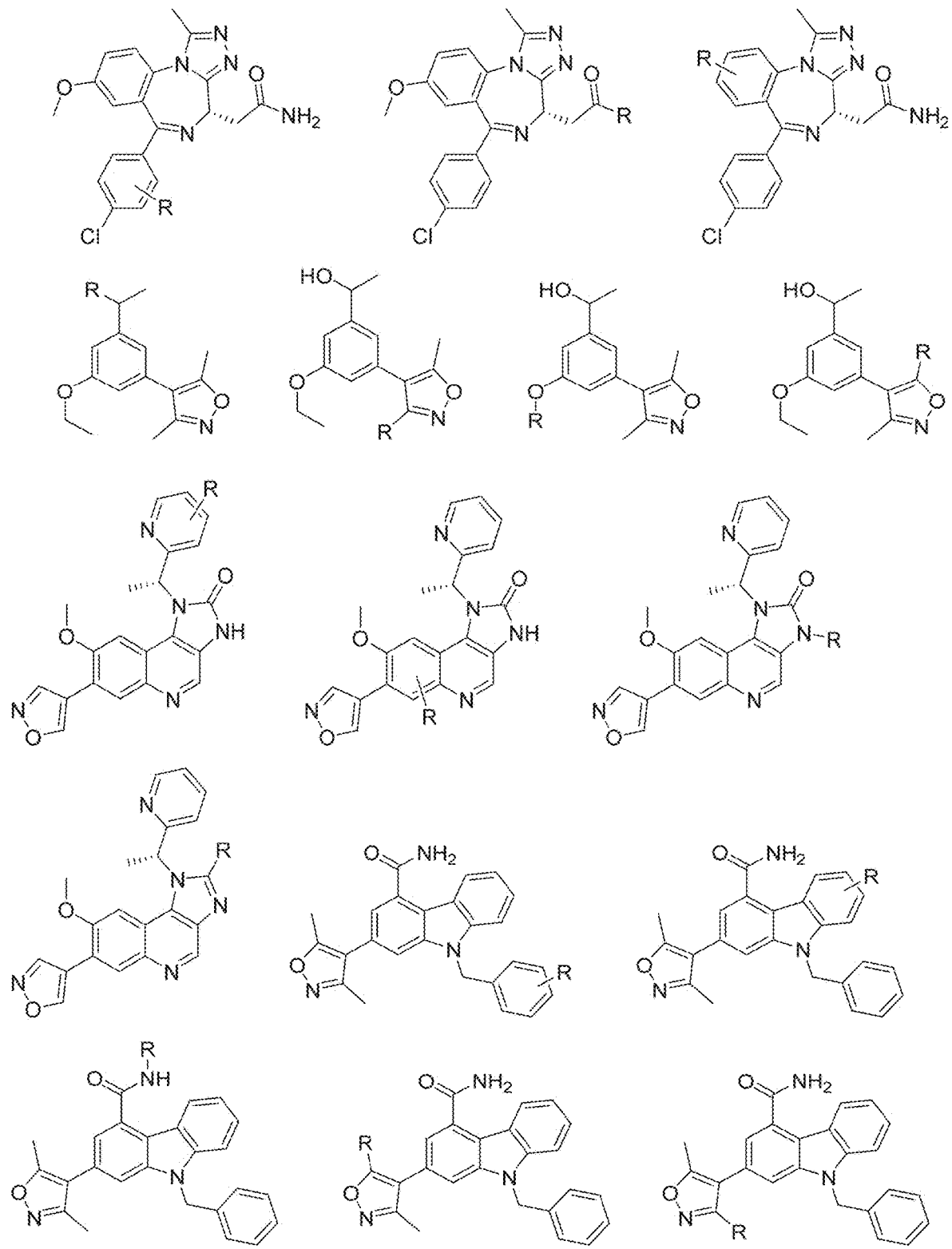
Figure 1K:
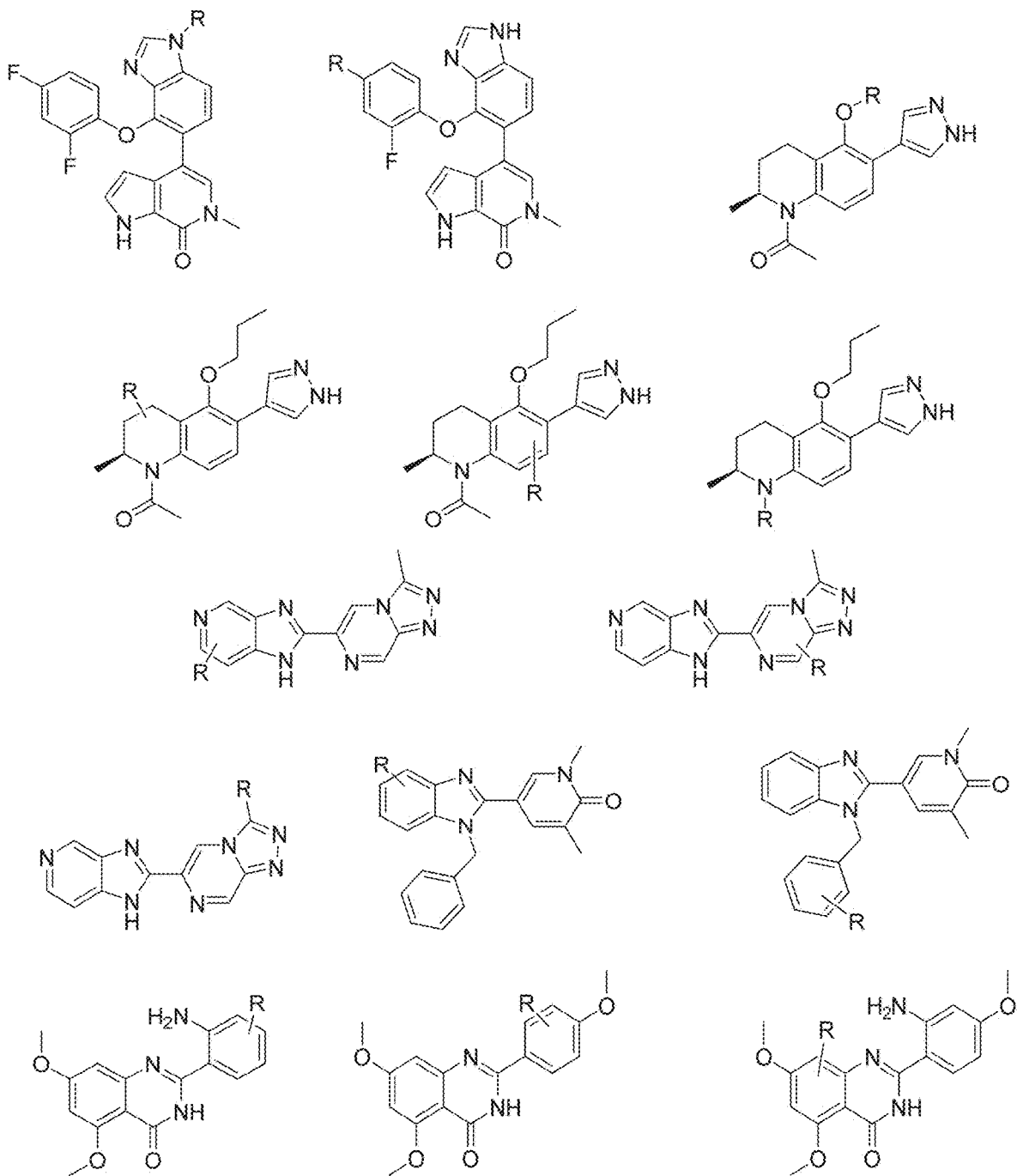
Figure 1L:
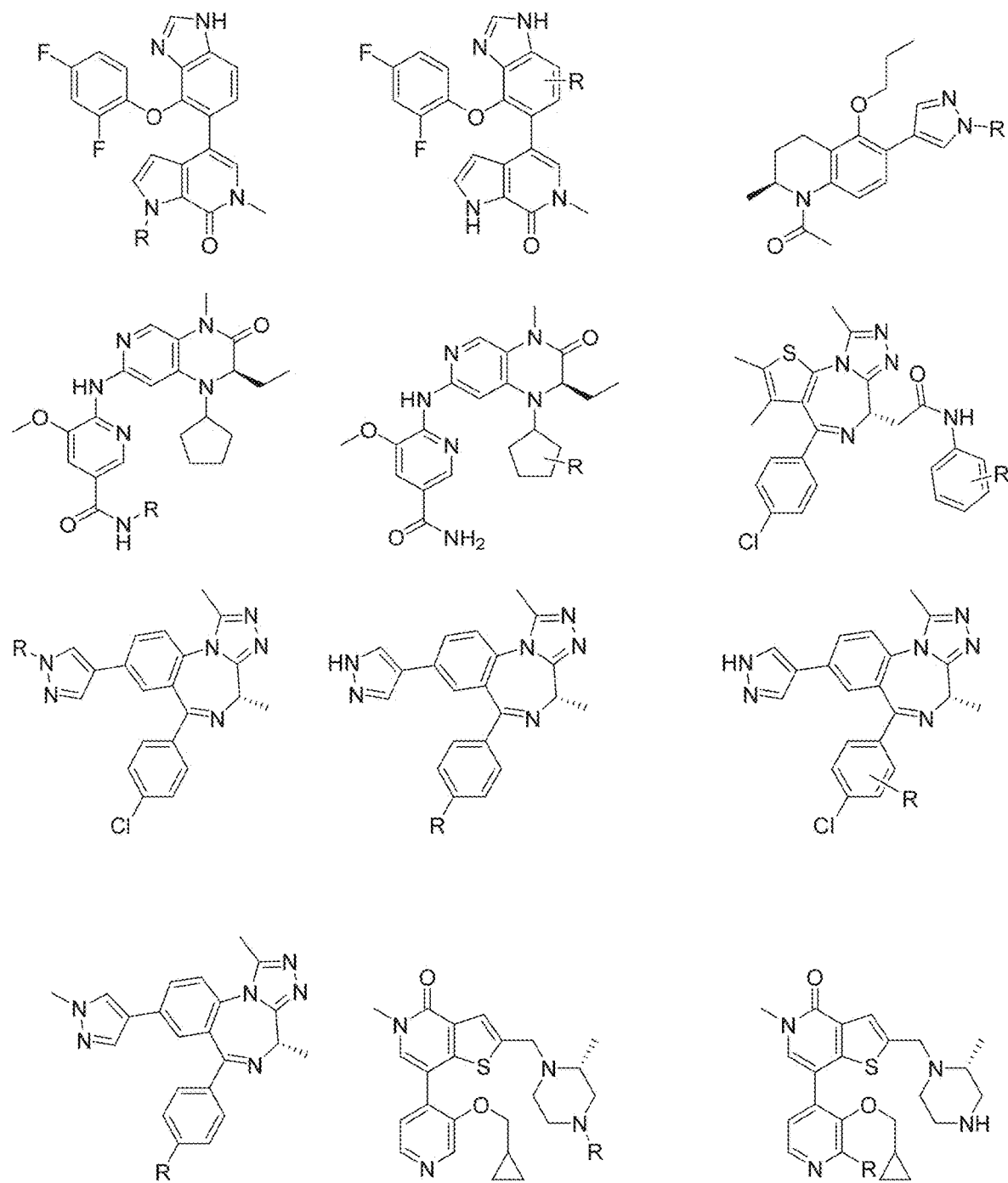
Figure 1M:
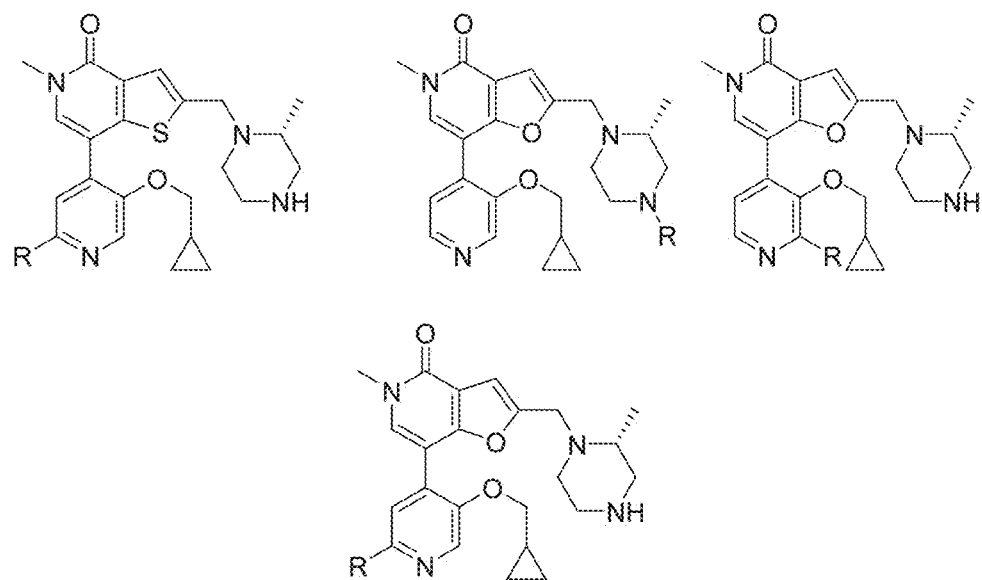
Figure 1N:
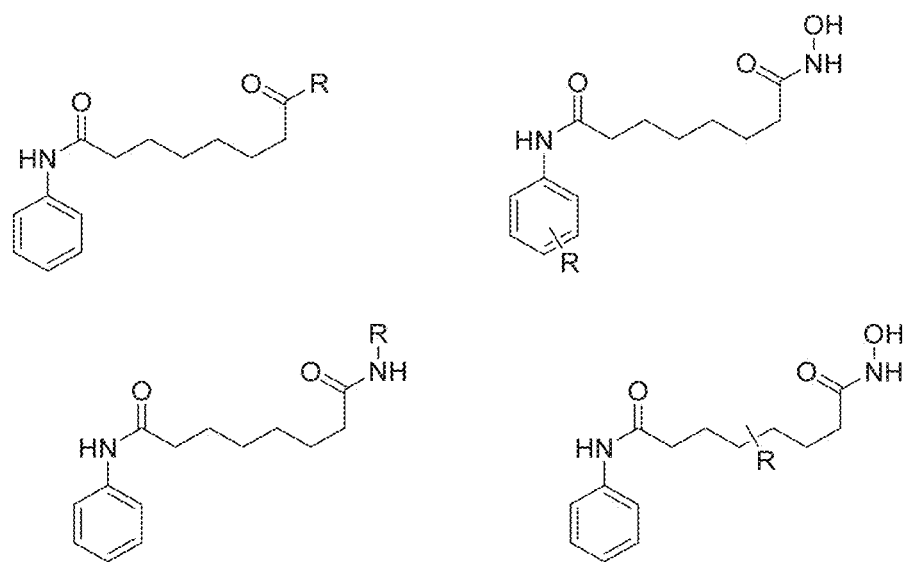
Figure 100:
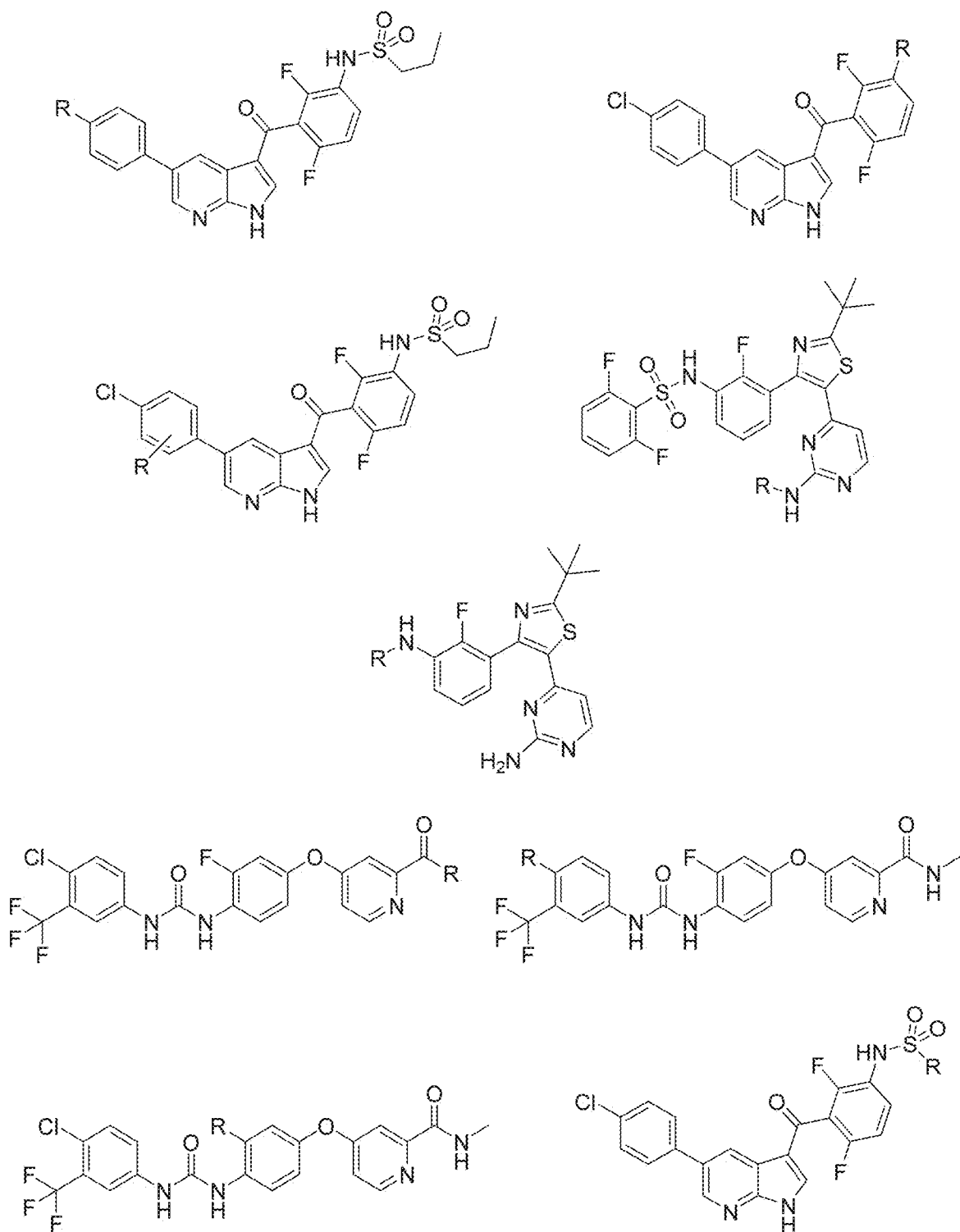
Figure 1S:
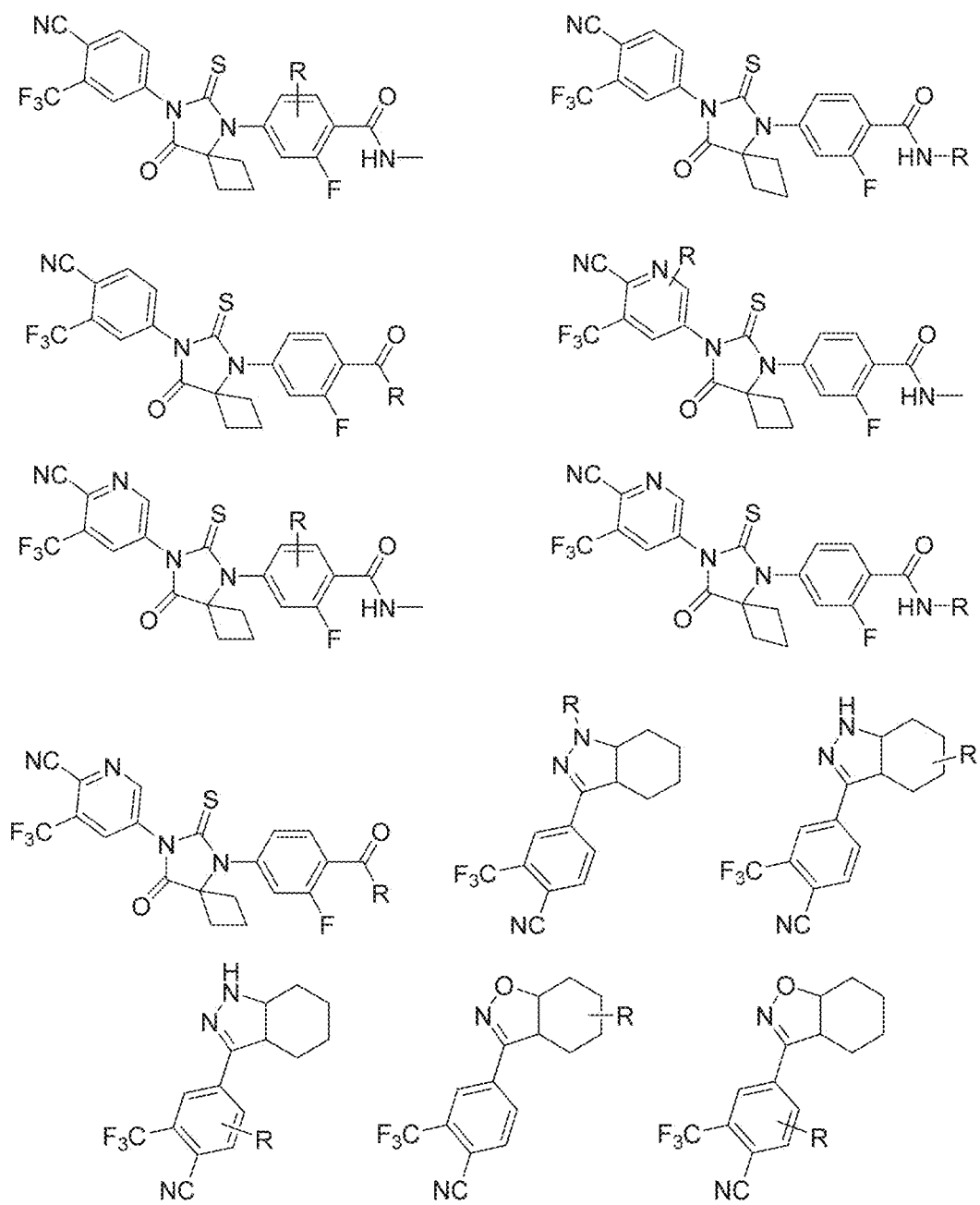
Figure 1Y:
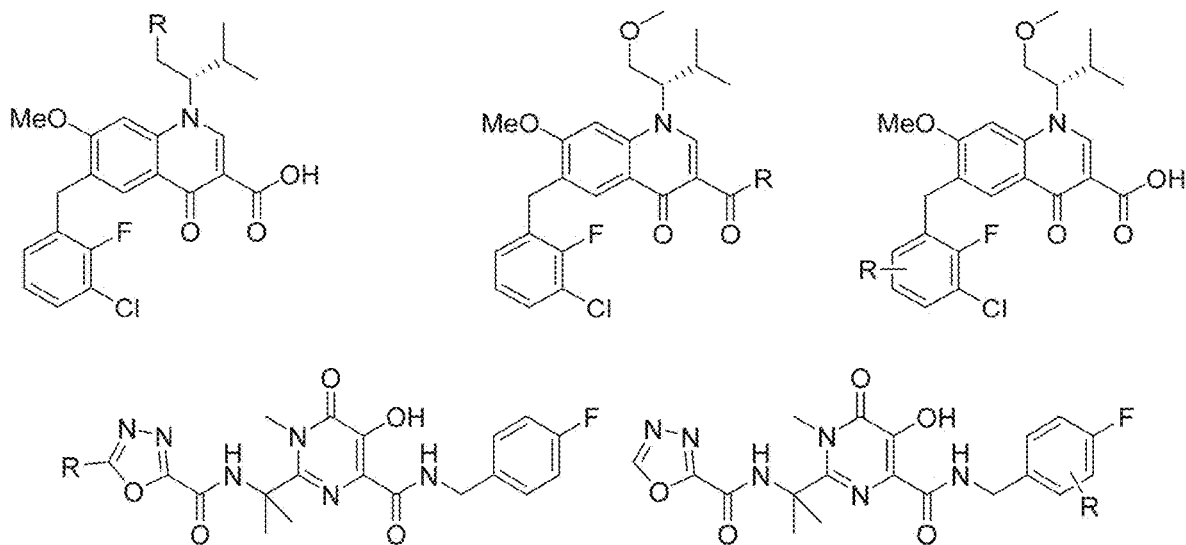
Figure 1Z:
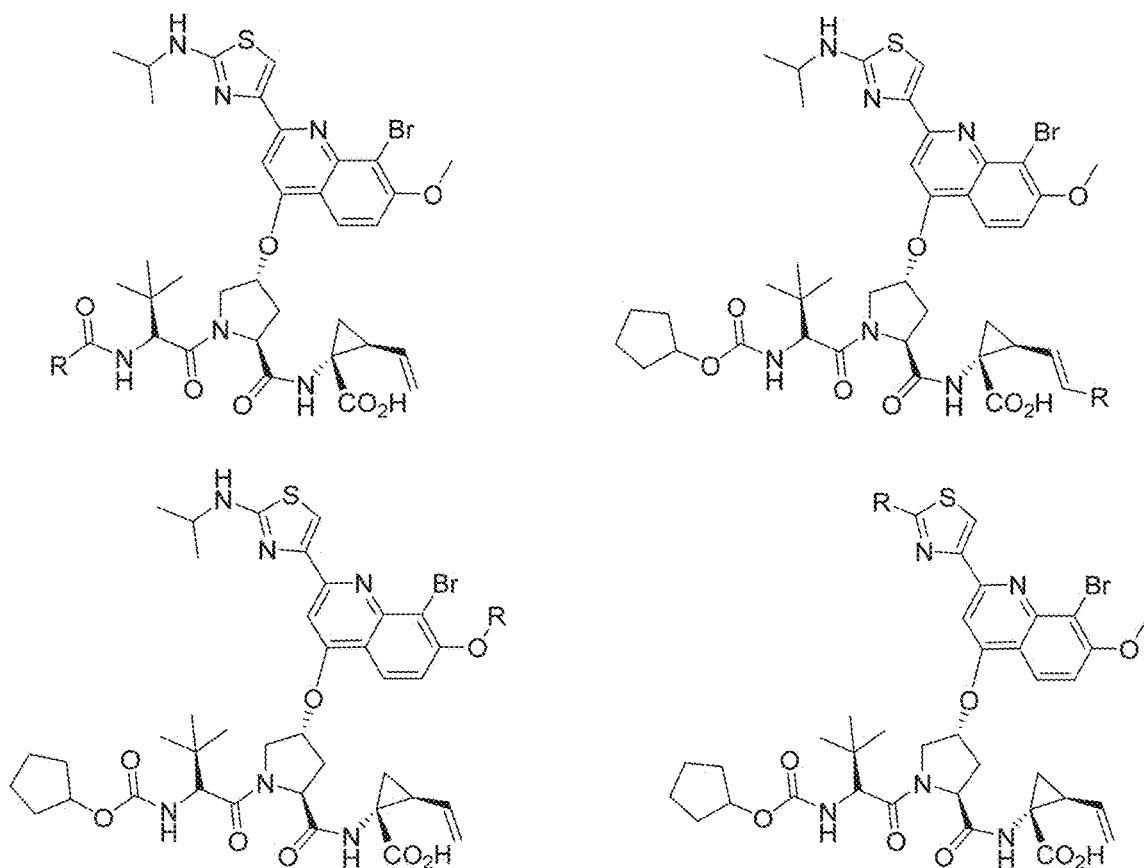
Figure 2A:
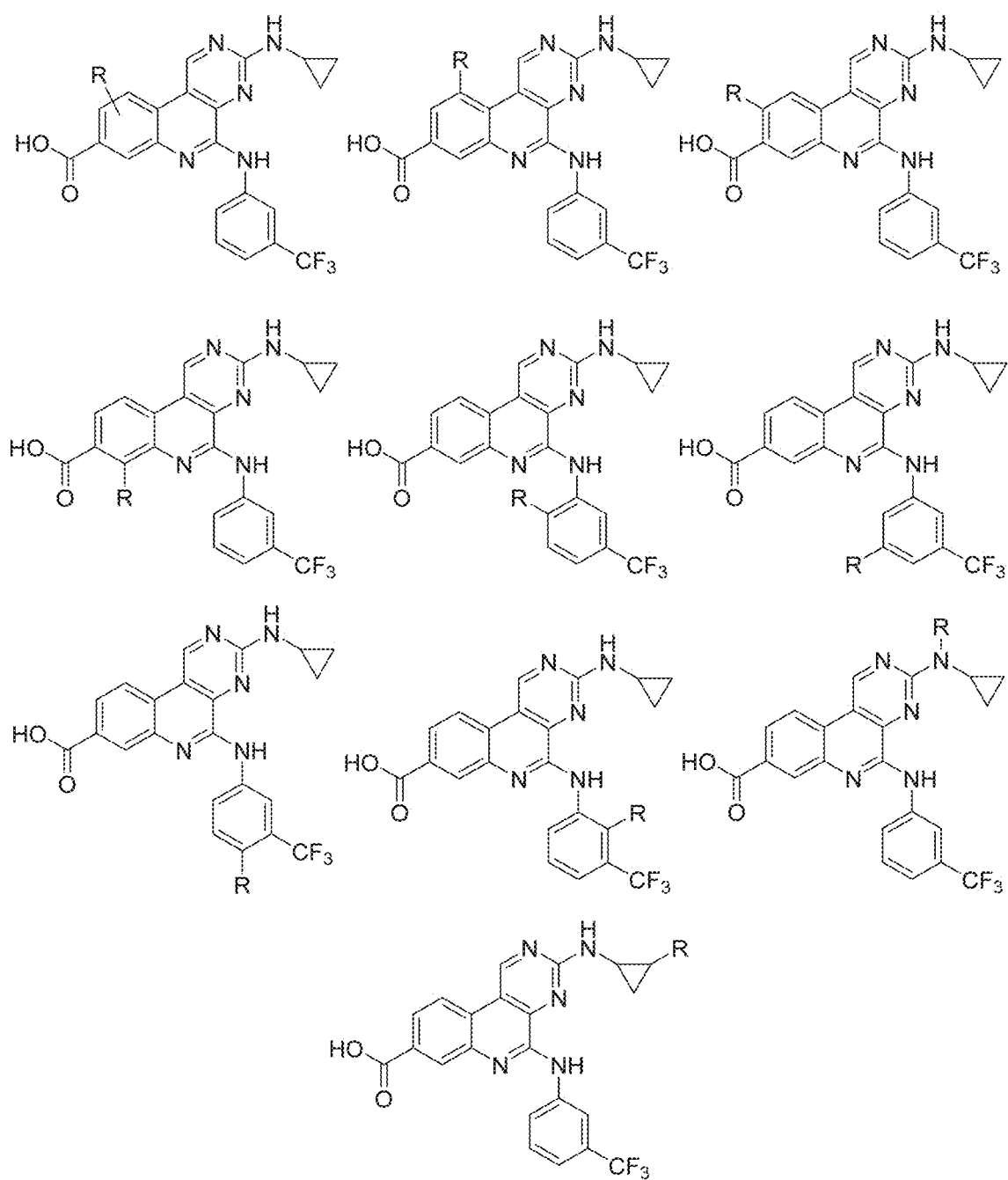
FIG. 2A presents examples of the kinase inhibitor Targeting Ligands U09-CX-5279 (derivatized) wherein R is the point at which the Linker is attached.
Figure 2B:
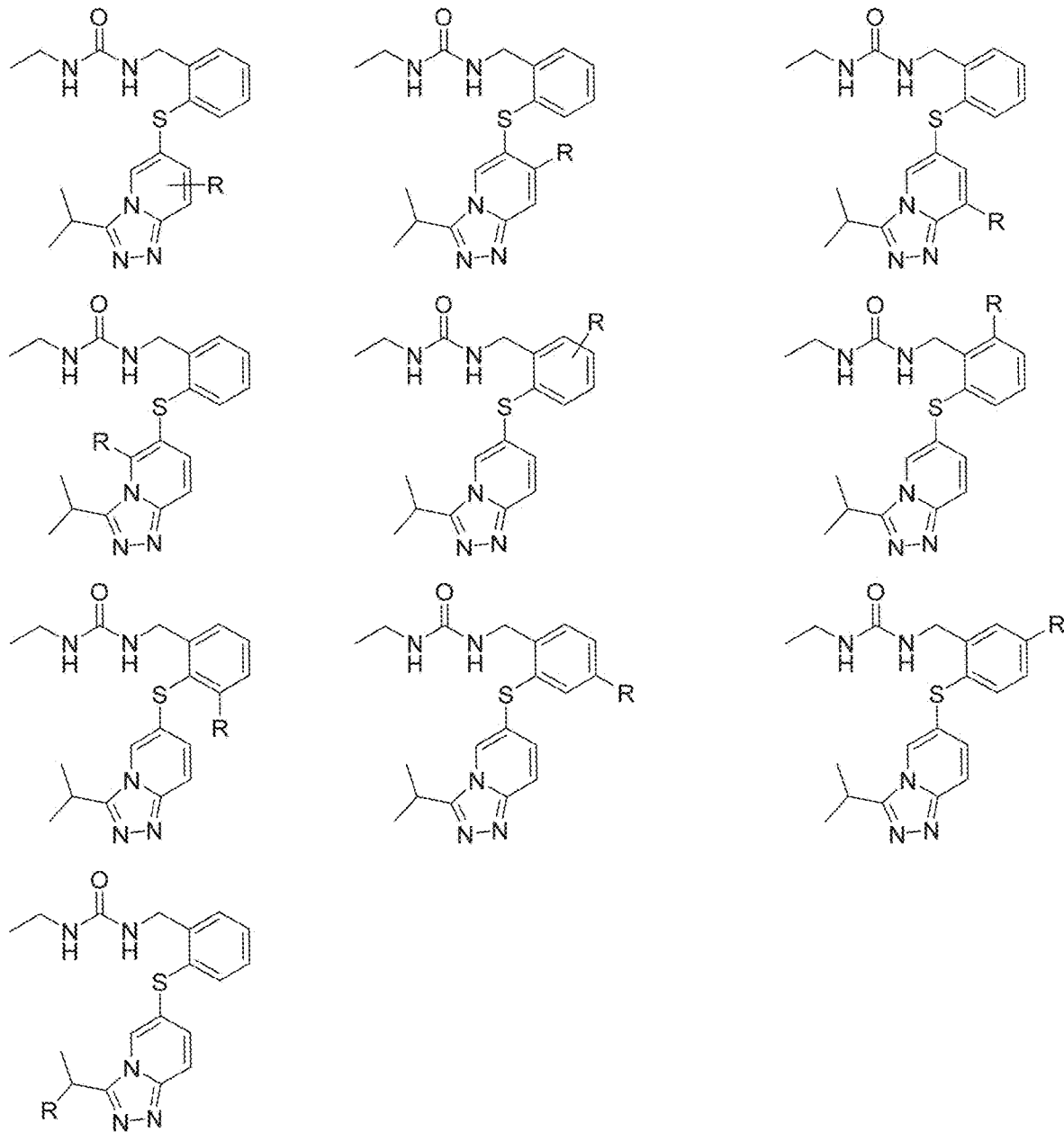
FIG. 2B-2C present examples of kinase inhibitor Targeting Ligands, including the kinase inhibitor compounds Y1W and Y1X (derivatized) wherein R is the point at which the Linker is attached. For additional examples and related ligands, see, the kinase inhibitors identified in Millan et al. "Design and Synthesis of Inhaled P38 Inhibitors for the Treatment of Chronic Obstructive Pulmonary Disease" *J. Med. Chem.*, 54: 7797 (2011).
Figure 2C:
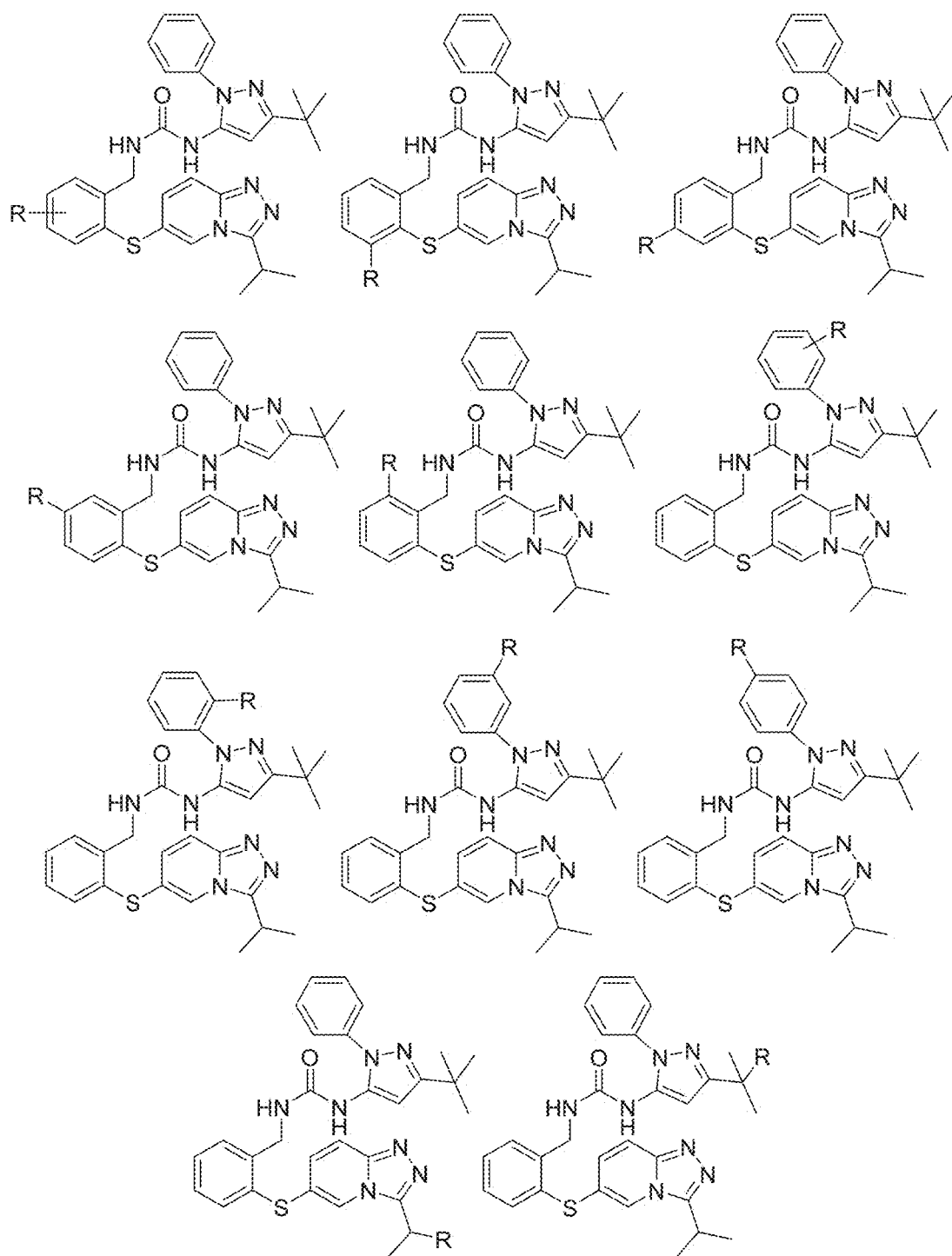
Figure 2D:
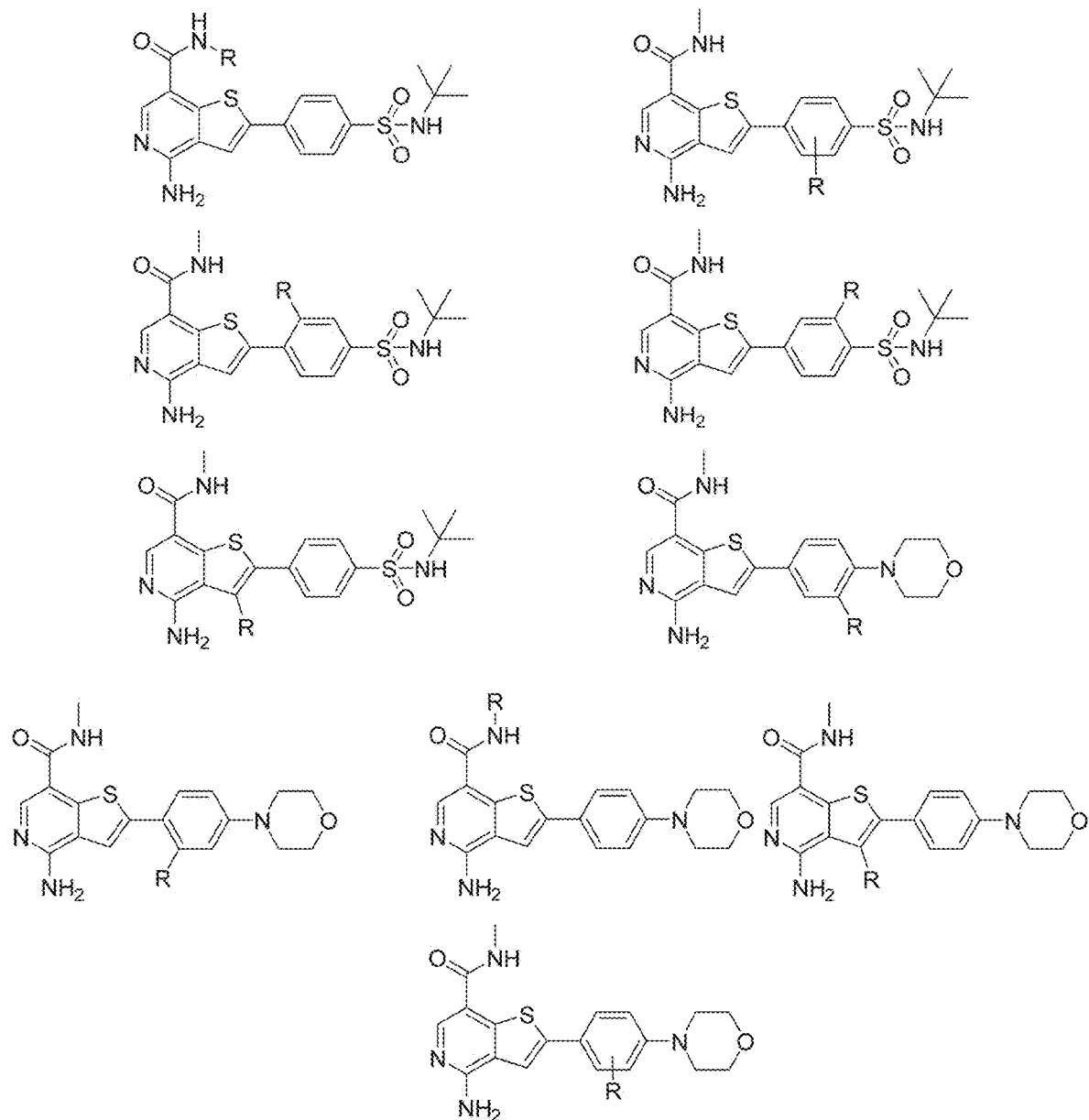
FIG. 2D presents examples of kinase inhibitor Targeting Ligands, including the kinase inhibitor compounds 6TP and 0TP (derivatized) wherein R is the point at which the Linker is attached. For additional examples and related ligands, see, the kinase inhibitors identified in Schenkel et al. "Discovery of Potent and Highly Selective Thienopyridine Janus Kinase 2 Inhibitors" *J. Med. Chem.*, 54 (24): 8440-8450 (2011).
Figure 2E:
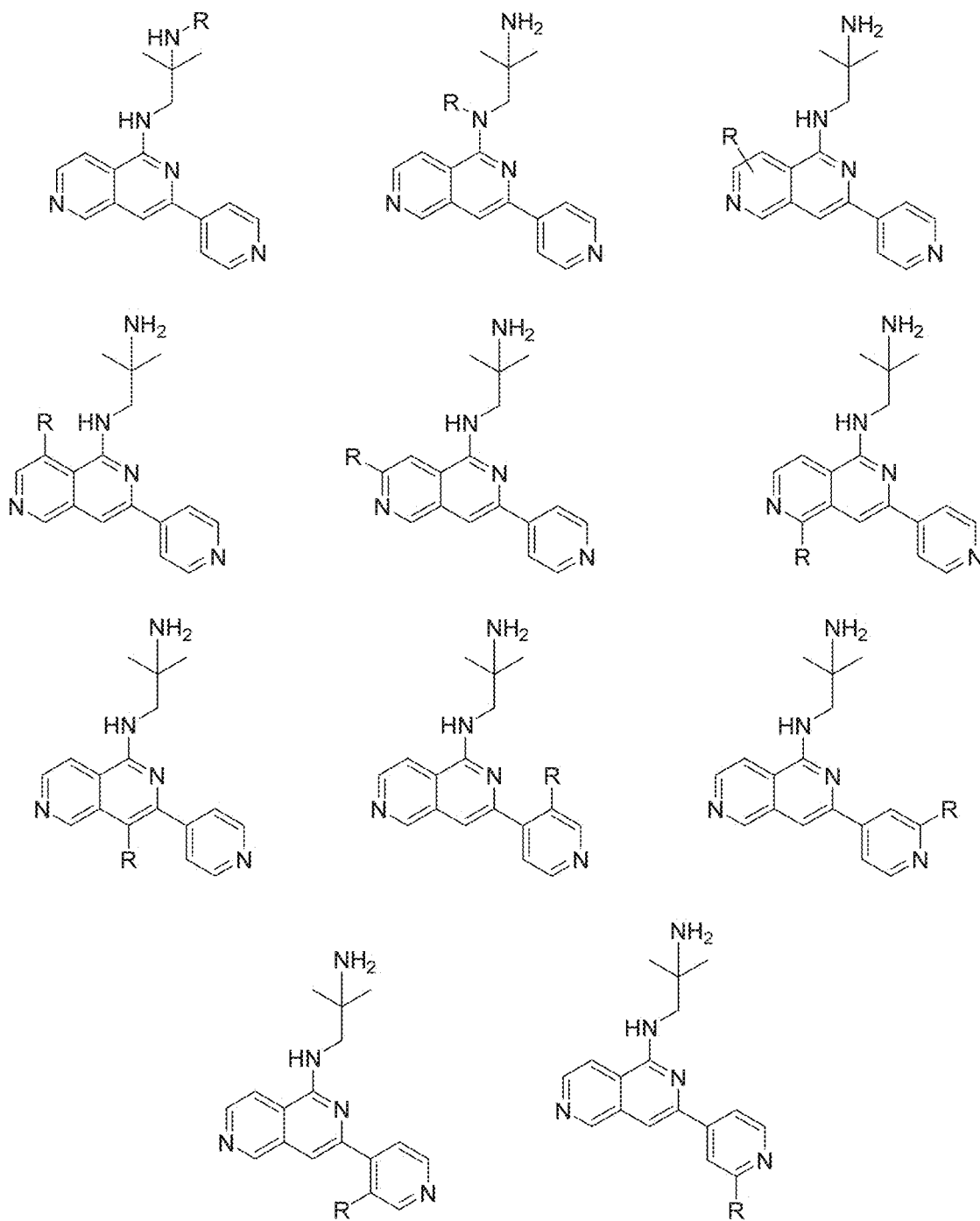
FIG. 2E presents examples of kinase inhibitor Targeting Ligands, including the kinase inhibitor compound 07U wherein R is the point at which the Linker is attached. For additional examples and related ligands, see, the kinase inhibitors identified in Van Eis et al. "2 6-Naphthyridines as potent and selective inhibitors of the novel protein kinase C isozymes" *Biorg. Med. Chem. Lett.*, 21(24): 7367-72 (2011).
Figure 2H:
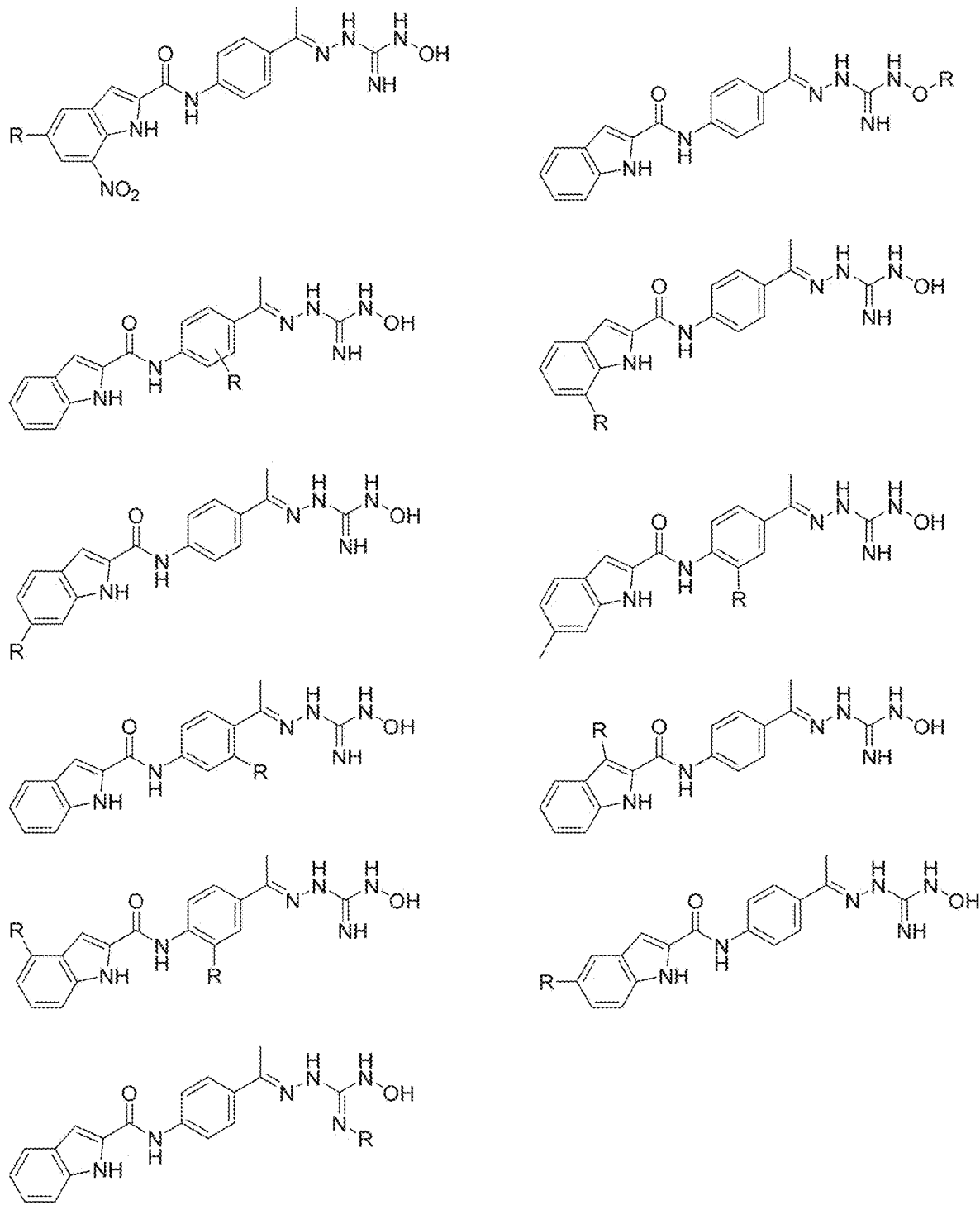
FIG. 2G-2H present examples of kinase inhibitor Targeting Ligands, including the kinase inhibitors XK9 and NXP (derivatized) wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2J:
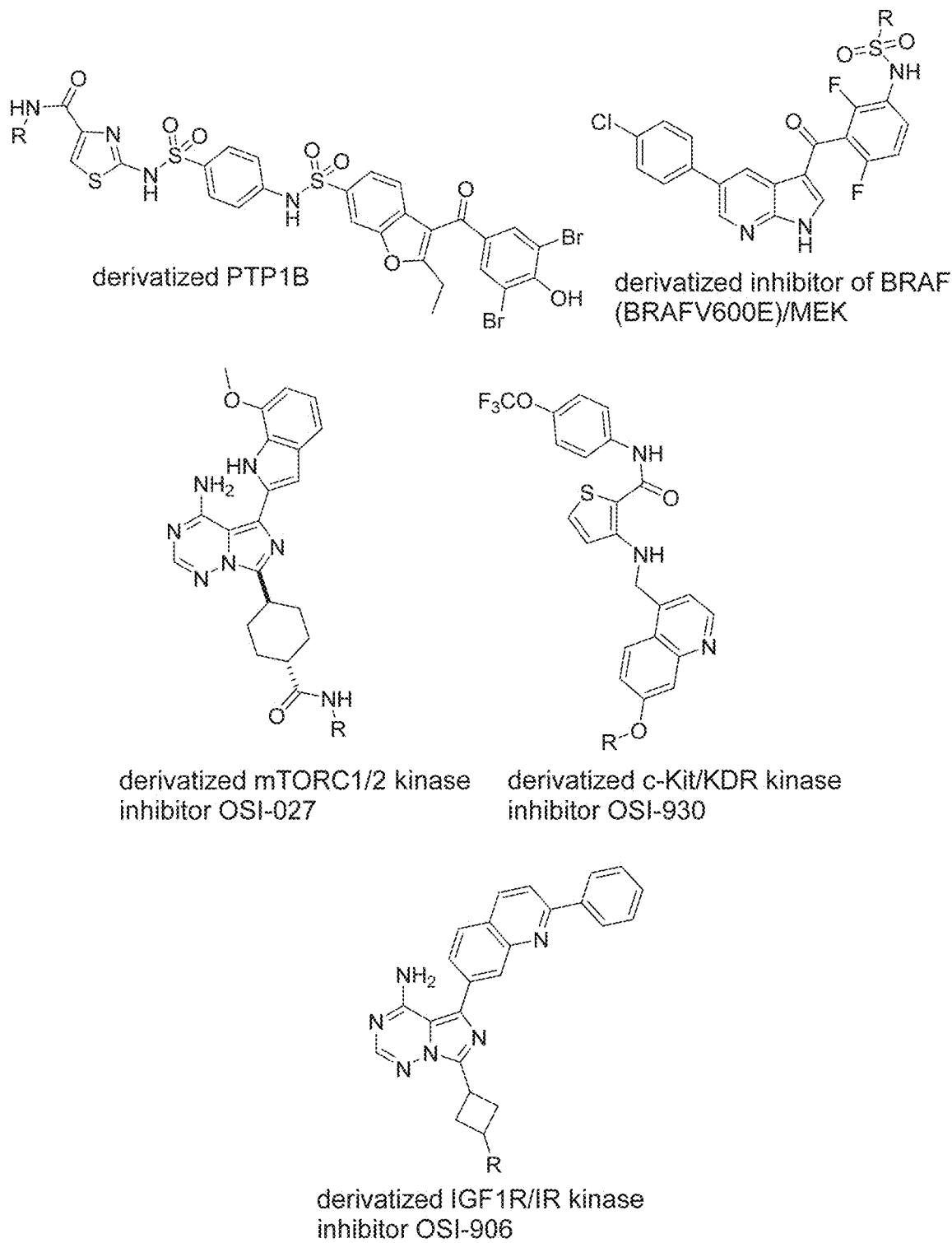
FIG. 2I-2J present examples of kinase inhibitor Targeting Ligands wherein R is the point at which the Linker r is attached.
Figure 2K:
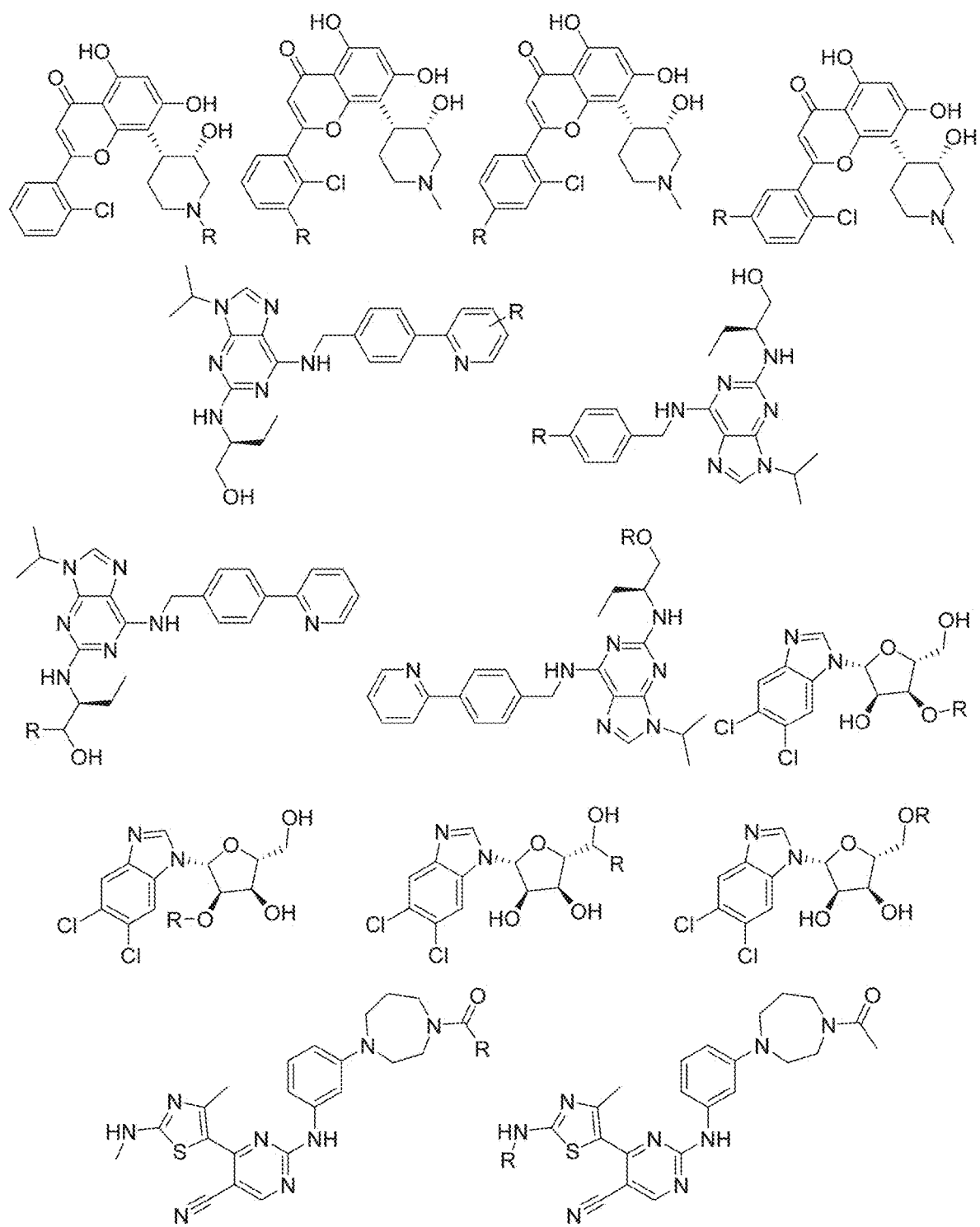
FIG. 2K-2M present examples of Cyclin Dependent Kinase 9 (CDK9) Targeting Ligands wherein R is the point at which the Linker is attached. For additional examples and related ligands, see, Baumli et al. "The structure of P-TEFb (CDK9/cyclin Ti) its complex with flavopiridol and regulation by phosphorylation." *Embo J.*, 27: 1907-1918 (2008); Bettayeb et al. "CDK Inhibitors Roscovitine and CR8 Trigger Mcl-1 Down-Regulation and Apoptotic Cell Death in Neuroblastoma Cells." *Genes Cancer*, 1: 369-380 (2010); Baumli et al. "Halogen bonds form the basis for selective P-TEFb inhibition by DRB." *Chem. Biol.* 17: 931-936 (2010); Hole et al. "Comparative Structural and Functional Studies of 4-(Thiazol-5-Yl)-2-(Phenylamino)Pyrimidine-5-Carbonitrile Cdk9 Inhibitors Suggest the Basis for Isotype Selectivity." *J. Med. Chem.* 56: 660 (2013); Lucking et al. "Identification of the potent and highly selective PTEFb inhibitor BAY 1251152 for the treatment of cancer—From p.o. to i.v. application via scaffold hops." Lücking et al. U. AACR Annual Meeting, Apr. 1-5, 2017 Washington, D.C. USA.
Figure 2L:
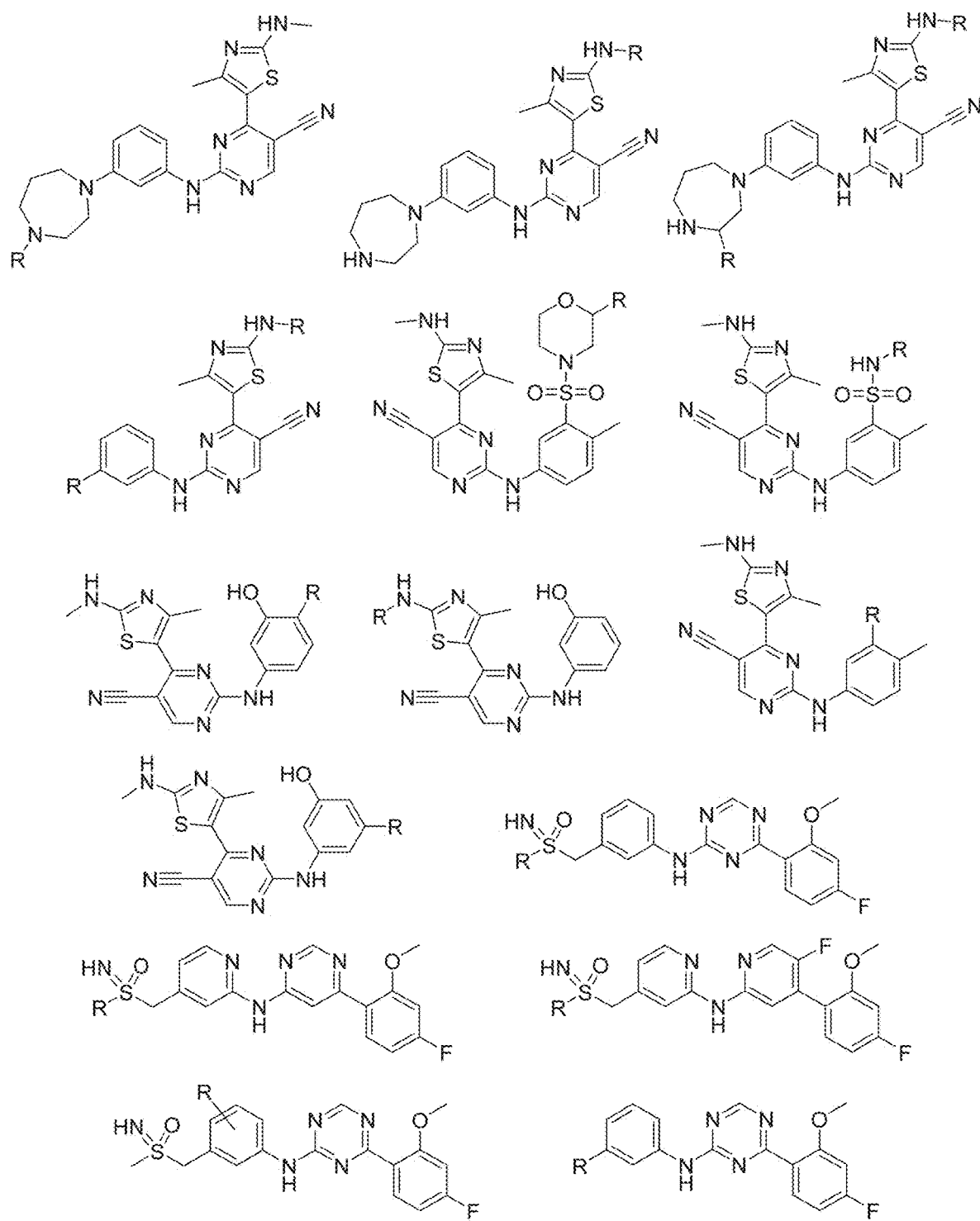
Figure 2M:
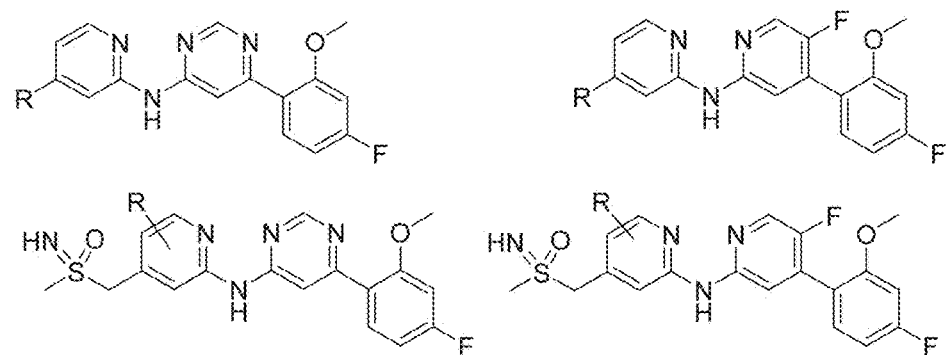
Figure 2N:
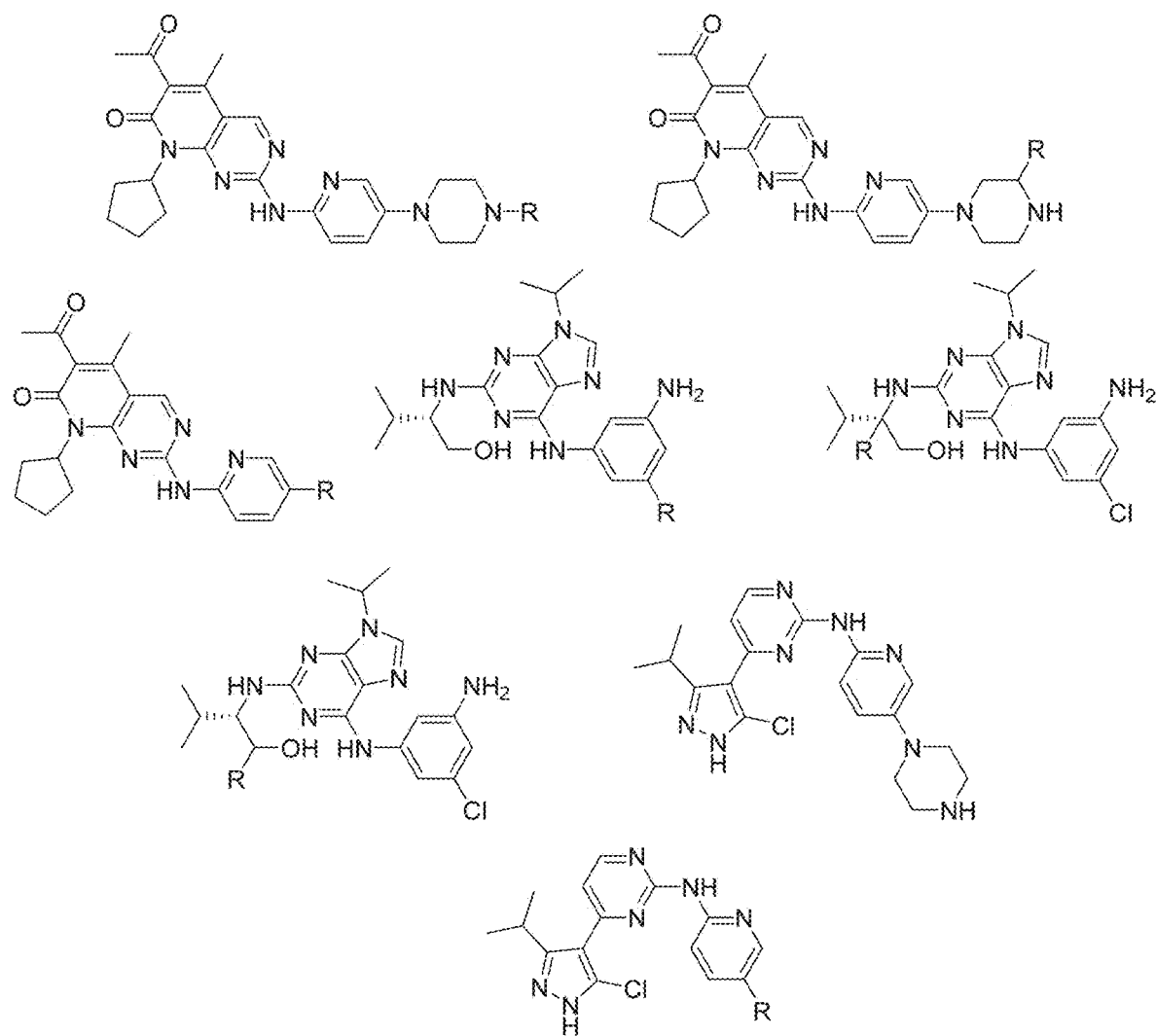
FIG. 2N-2P present examples of Cyclin Dependent Kinase 4/6 (CDK4/6) Targeting Ligands wherein R is the point at which the Linker is attached. For additional examples and related ligands, see, Lu H.; Schulze-Gahmen U.; "Toward understanding the structural basis of cyclin-dependent kinase 6 specific inhibition." *J. Med. Chem.*, 49: 3826-3831 (2006); 4-(Pyrazol-4-yl)-pyrimidines as selective inhibitors of cyclin-dependent kinase 4/6. Cho et al. (2010) J. Med. Chem. 53: 7938-7957; Cho Y. S. et al. "Fragment-Based Discovery of 7-Azabenzimidazoles as Potent Highly Selective and Orally Active CDK4/6 Inhibitors." *ACS Med Chem Lett* 3: 445-449 (2012); Li Z. et al. "Discovery of AMG 925 a FLT3 and CDK4 dual kinase inhibitor with preferential affinity for the activated state of FLT3." *J. Med. Chem.* 57: 3430-3449 (2014); Chen P. et al. "Spectrum and Degree of CDK Drug Interactions Predicts Clinical Performance." *Mol. Cancer Ther.* 15: 2273-2281 (2016).
Figure 2O:
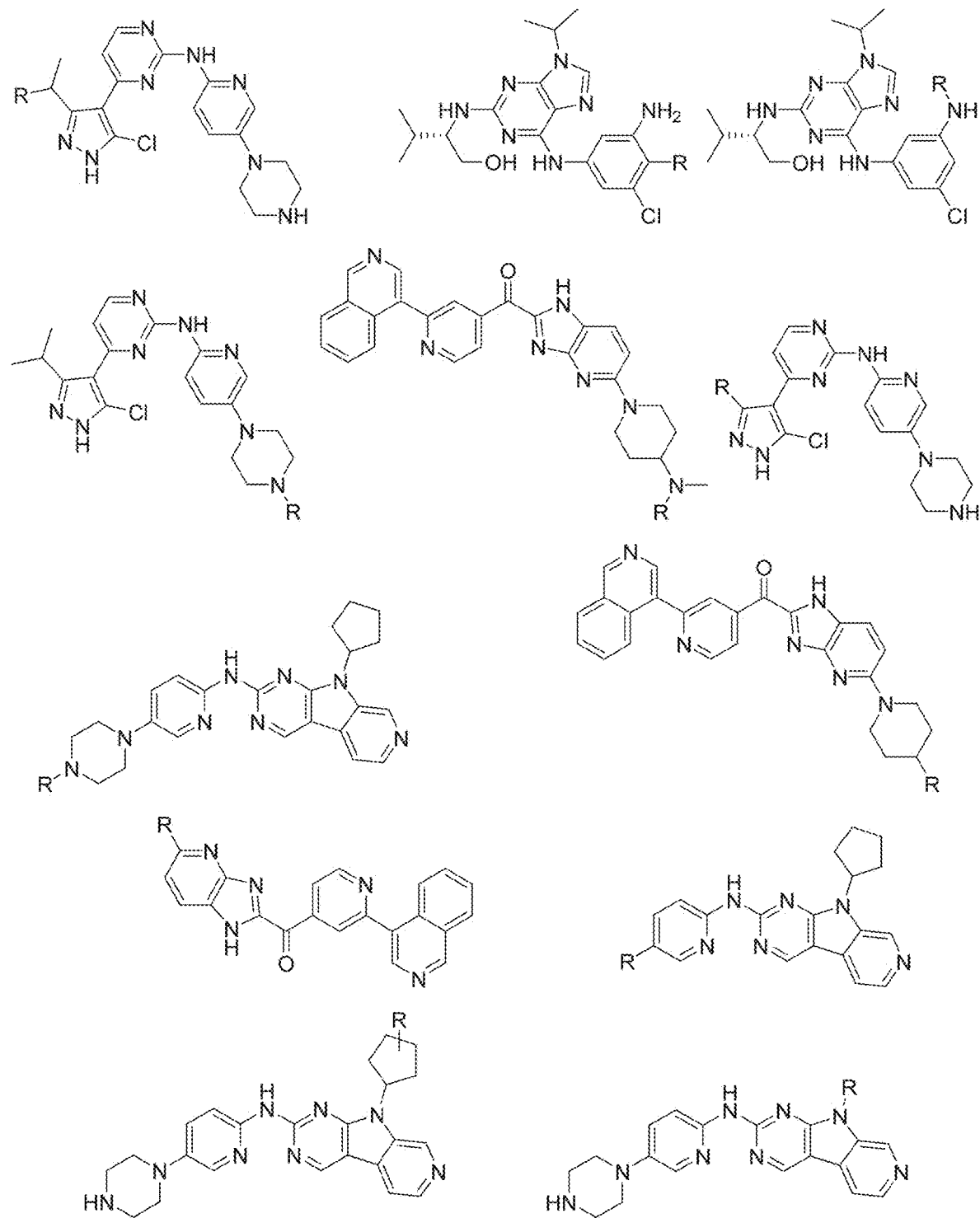
Figure 2P:
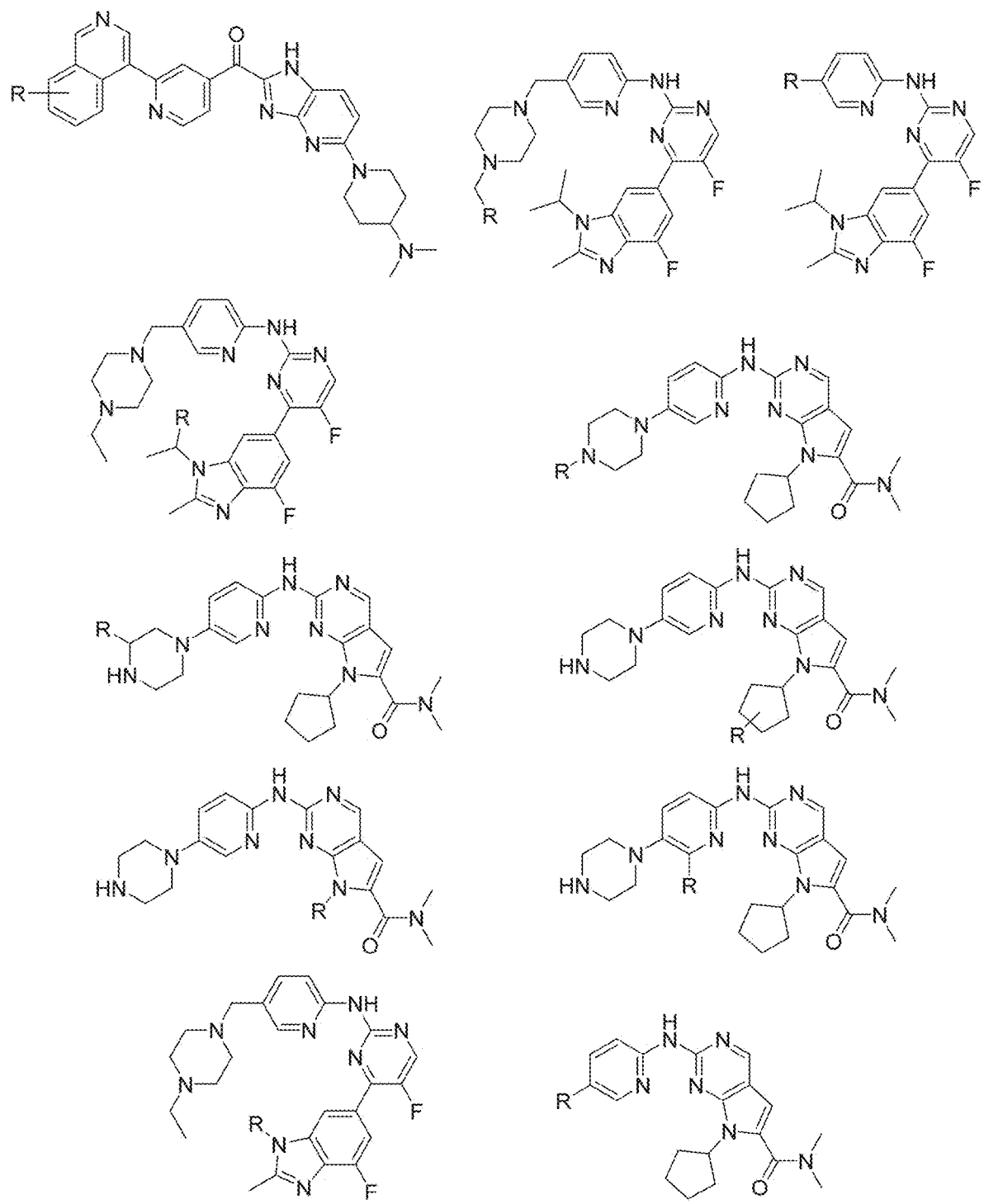
Figure 2Q:
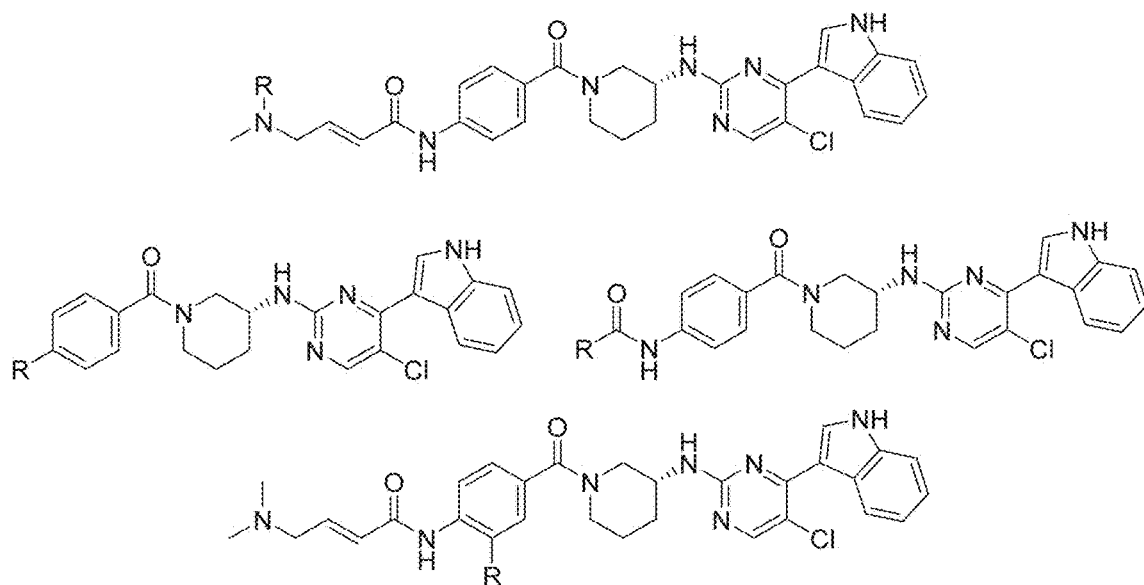
FIG. 2Q presents examples of Cyclin Dependent Kinase 12 and/or Cyclin Dependent Kinase 13 Targeting Ligands wherein R is the point at which the Linker is attached. For additional examples and related ligands, see, Zhang T. et al. "Covalent Targeting of Remote Cysteine Residues to Develop Cdk12 and Cdk13 Inhibitors." *Nat. Chem. Biol.* 12: 876 (2016).
Figure 2R:
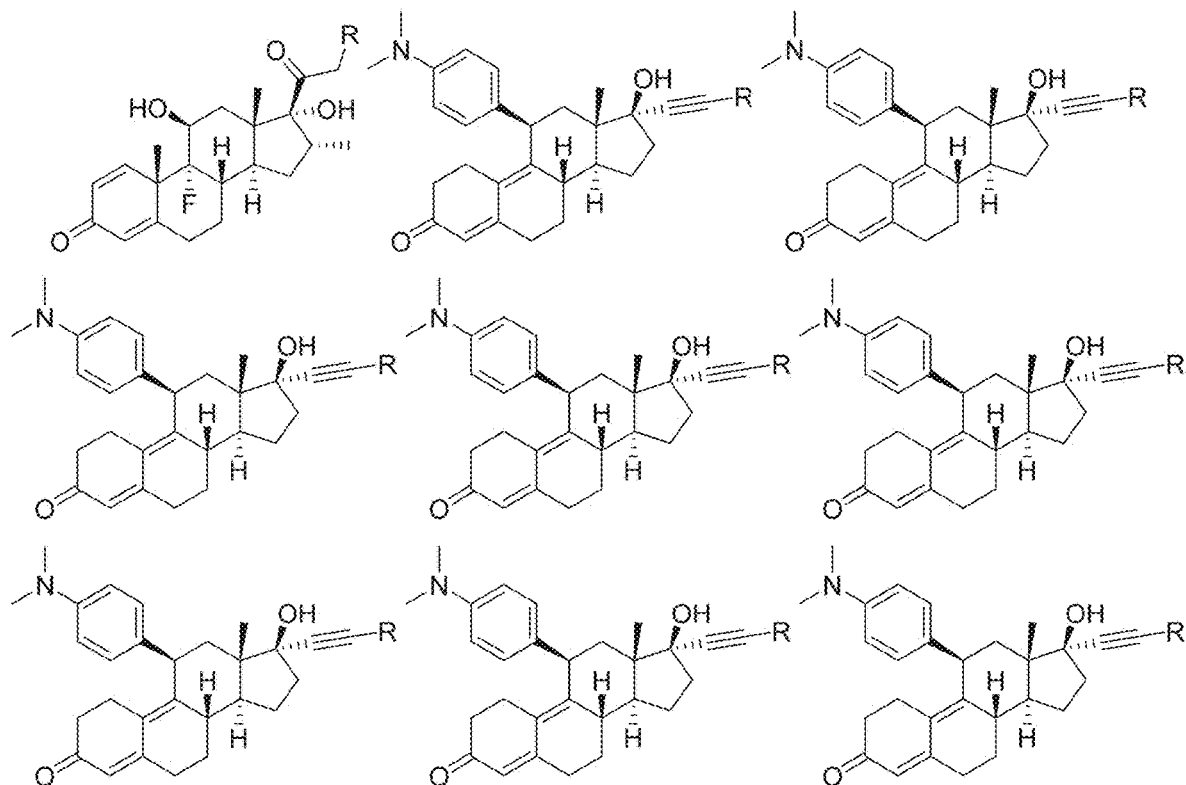
FIG. 2R-2S present examples of Glucocorticoid Receptor Targeting Ligands wherein R is the point at which the Linker is attached.
Figure 2S:
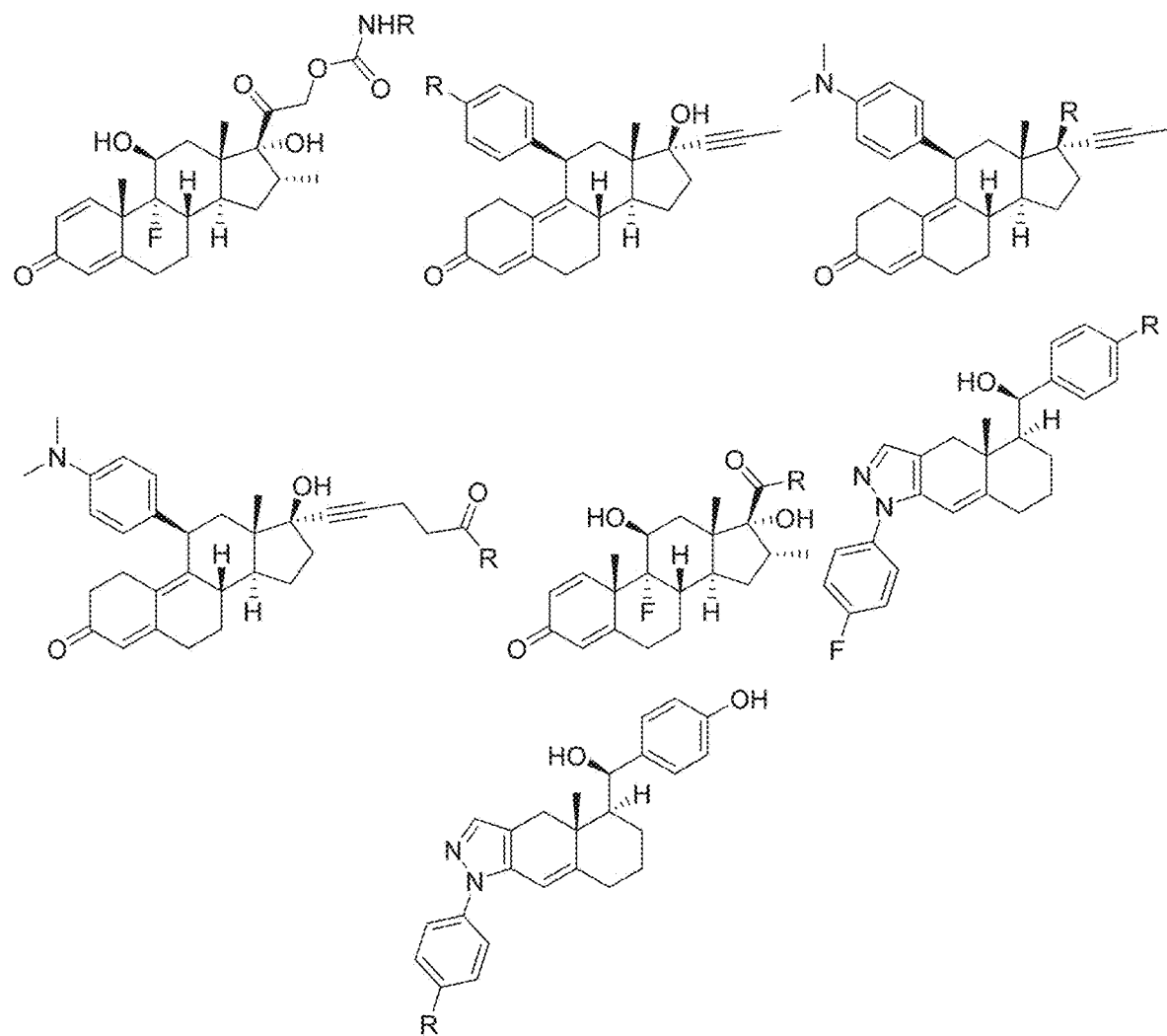
Figure 2T:
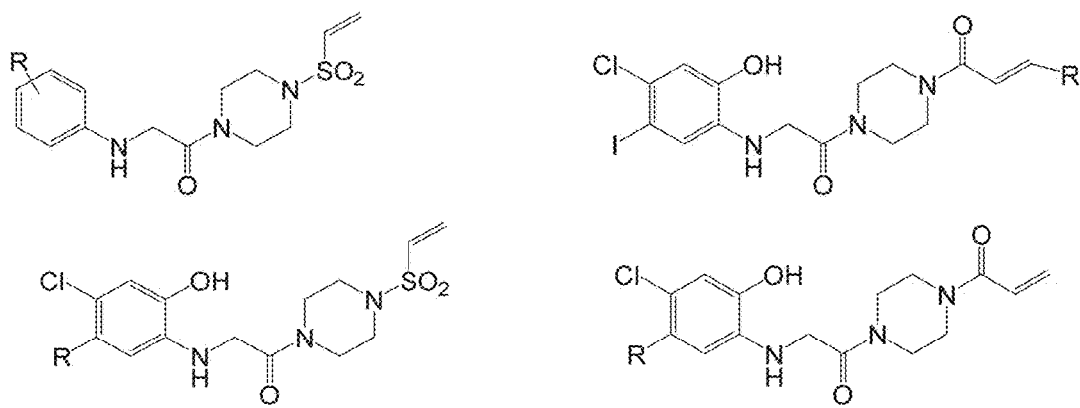
FIG. 2T-2U present examples of RasG12C Targeting Ligands wherein R is the point at which the Linker is attached.
Figure 2U:
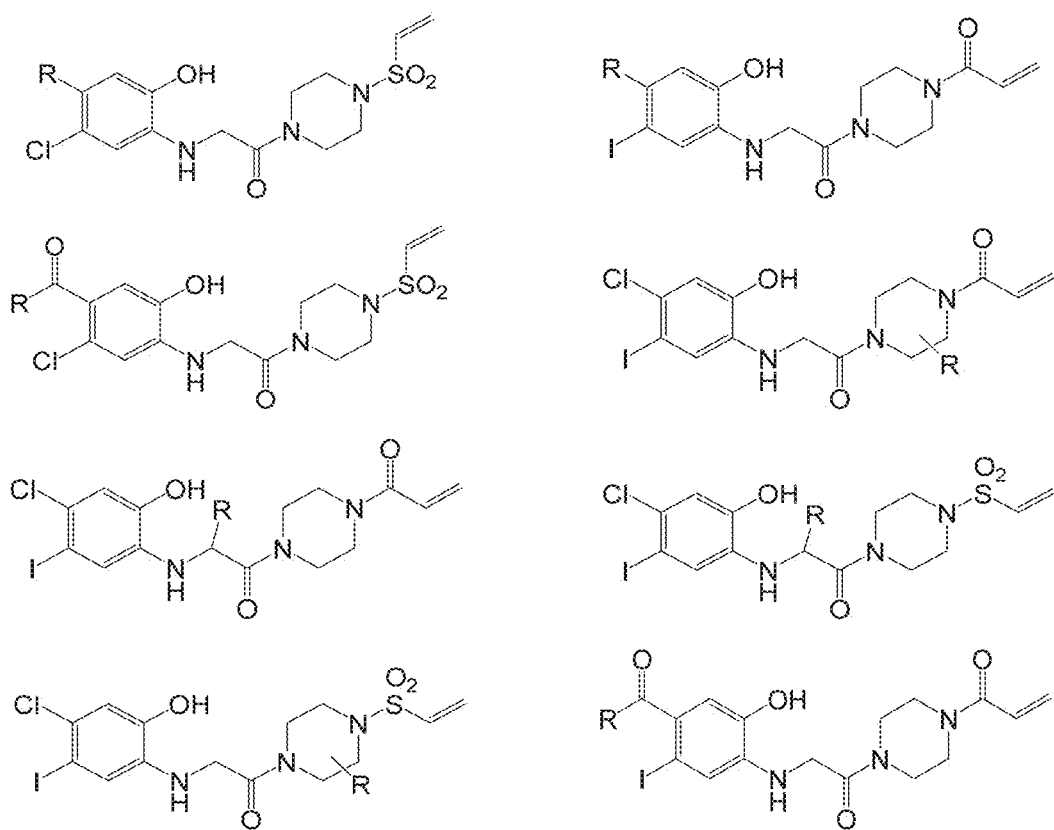
Figure 2V:
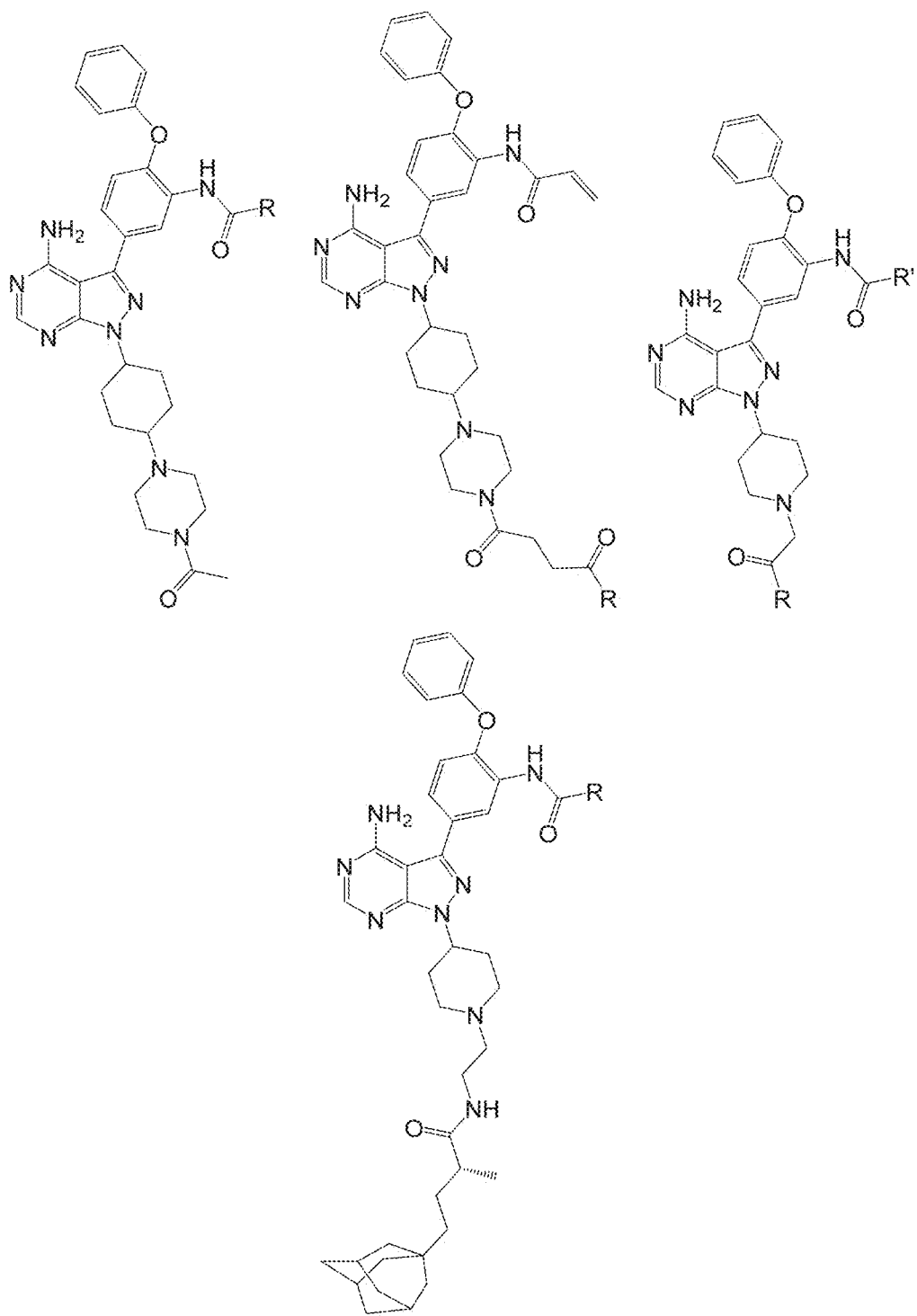
FIG. 2V presents examples of Her3 Targeting Ligands wherein R is the point at which the Linker is attached and R' is
Figure 2Z:
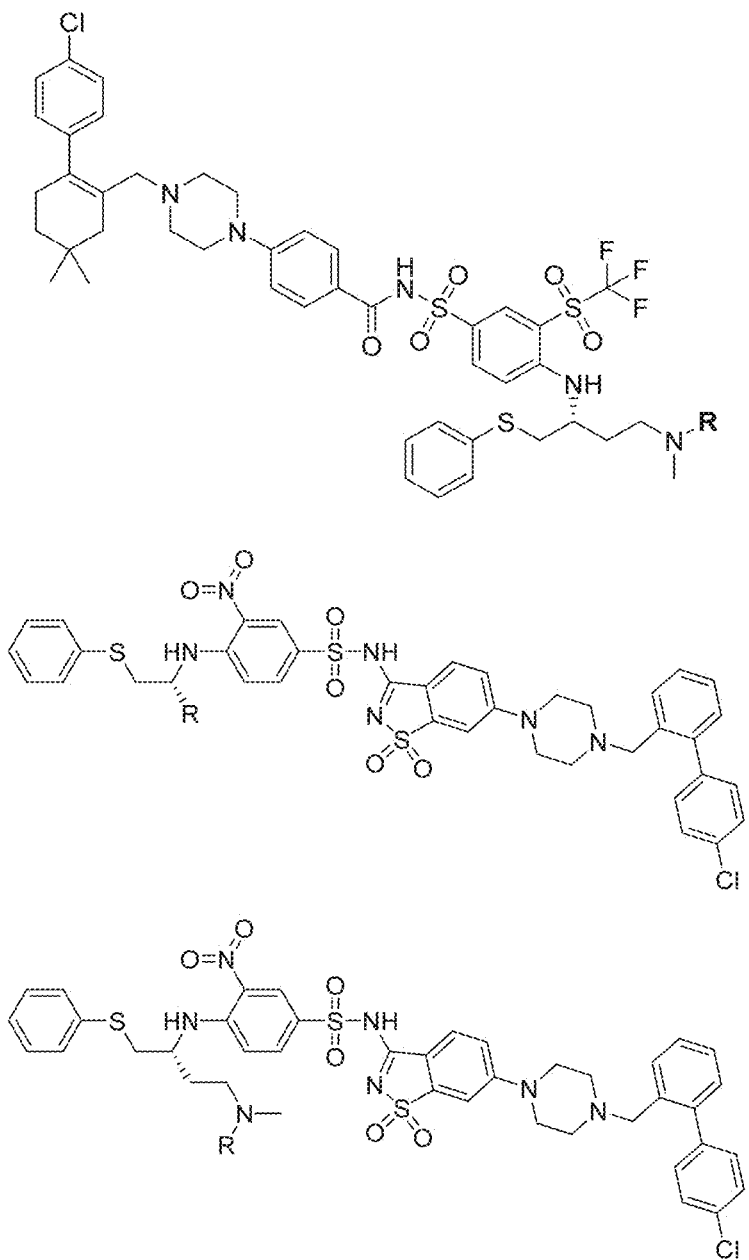
FIG. 2F presents examples of kinase inhibitor Targeting Ligands, including the kinase inhibitor compound YCF, wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2A:
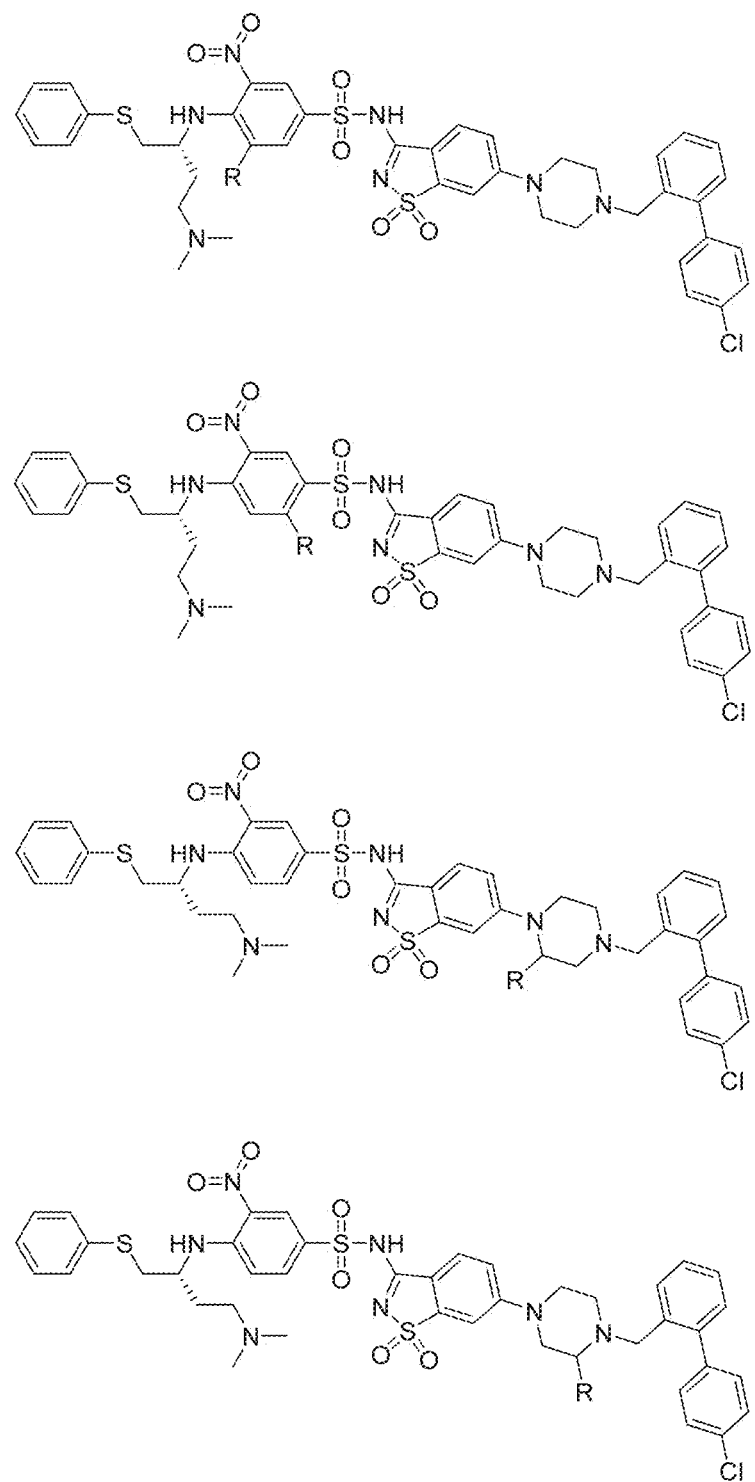
Figure 2B:
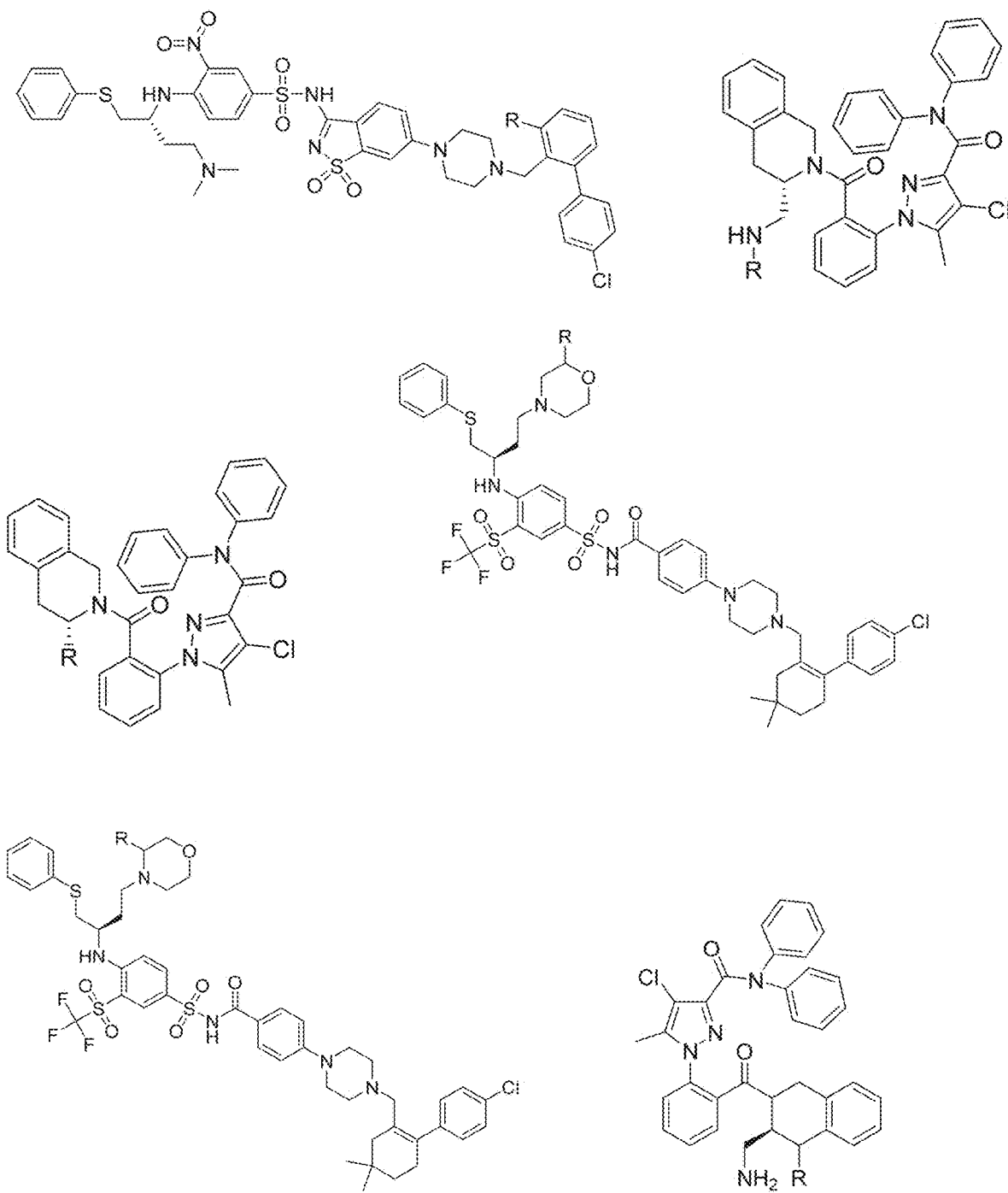
Figure 2C:
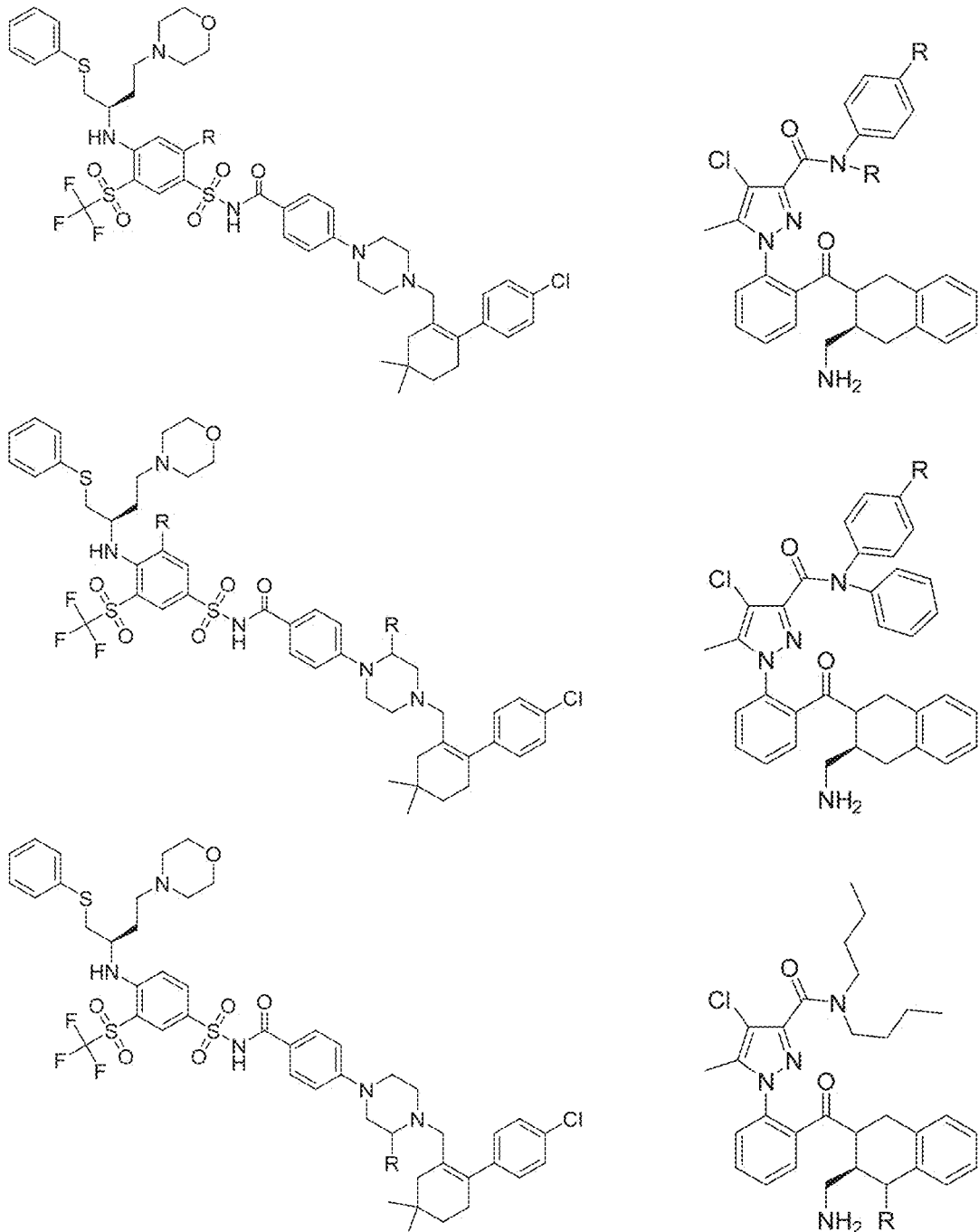
Figure 2D:
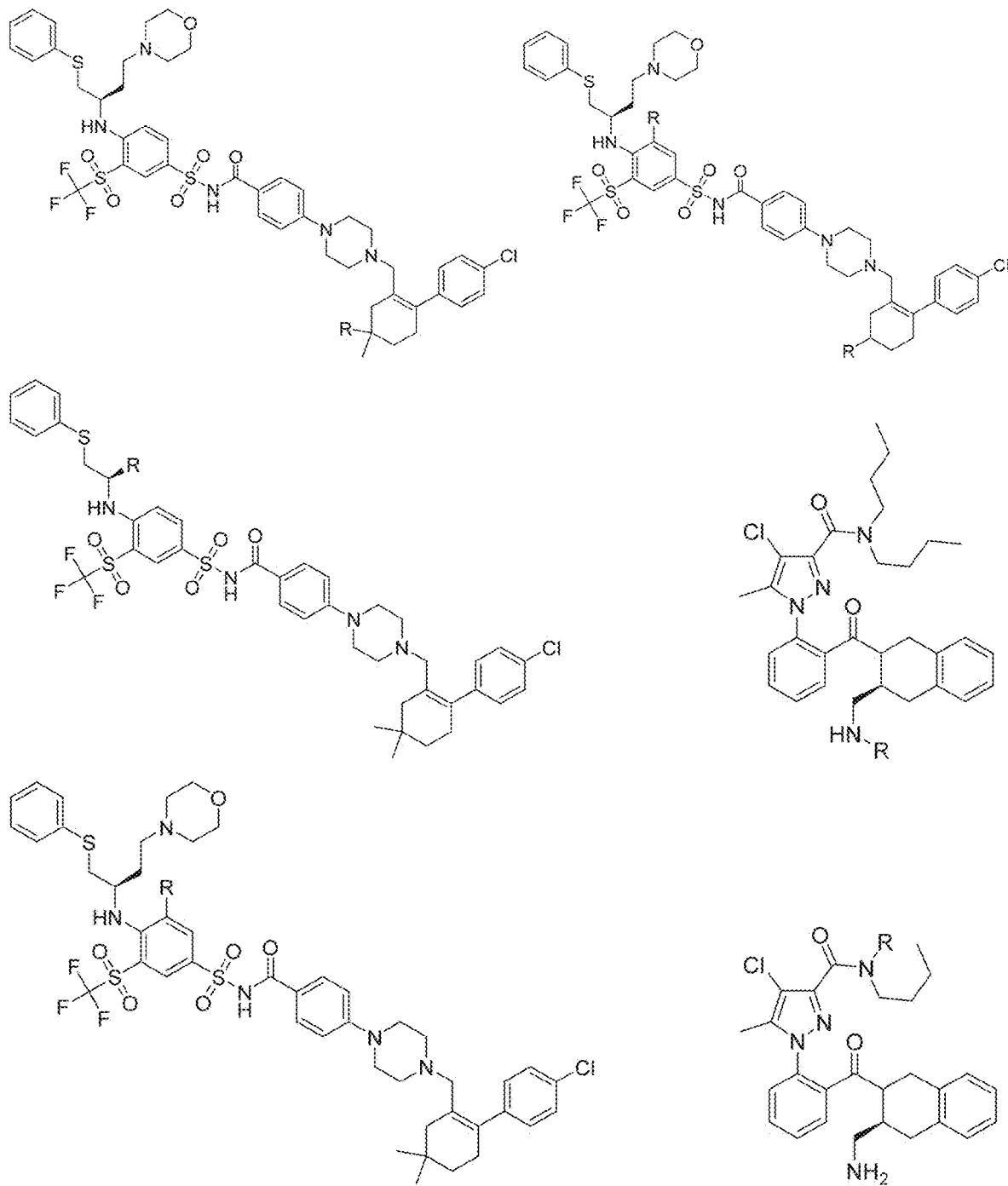
Figure 2E:
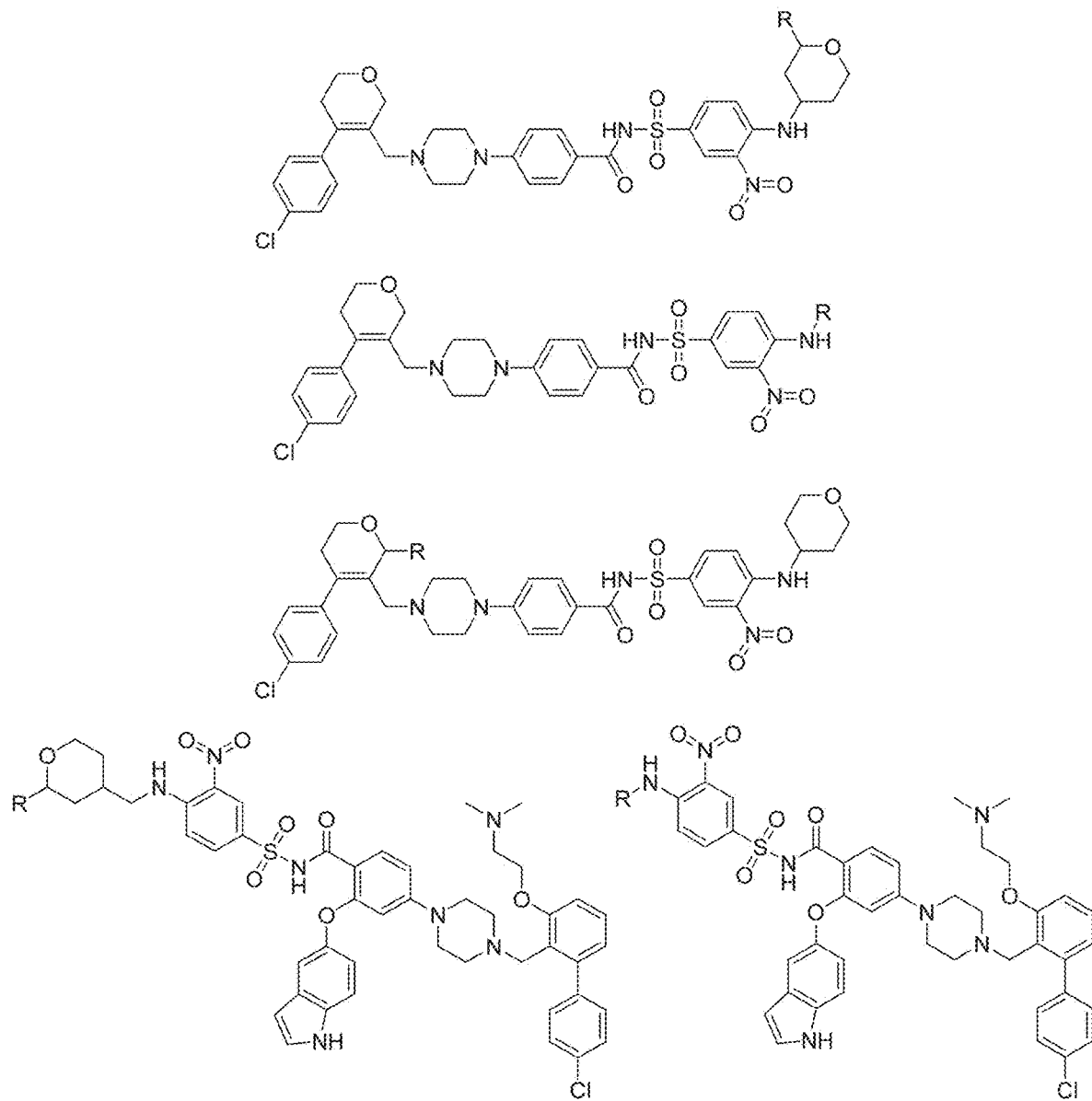
Figure 2F:
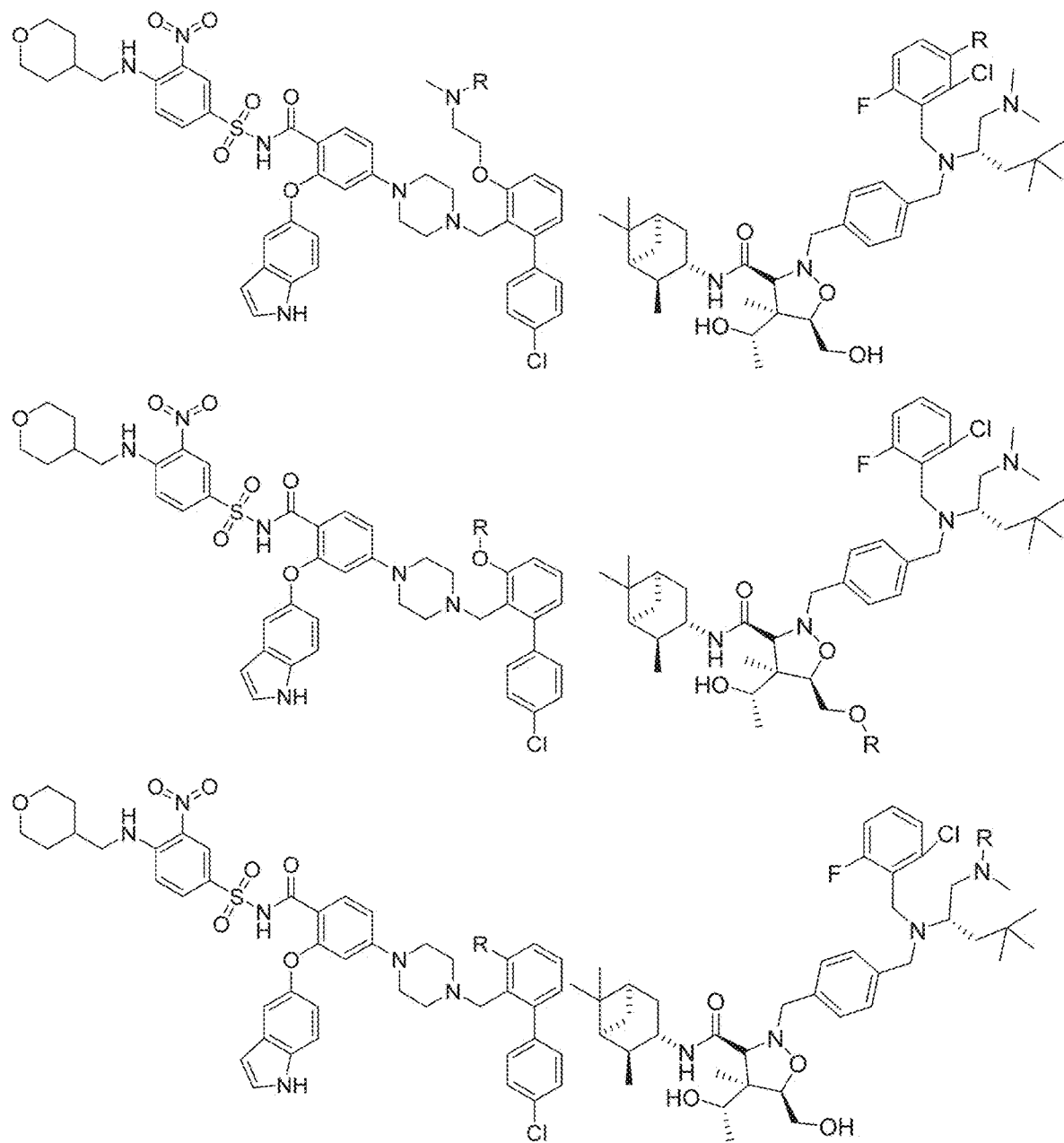
Figure 2G:
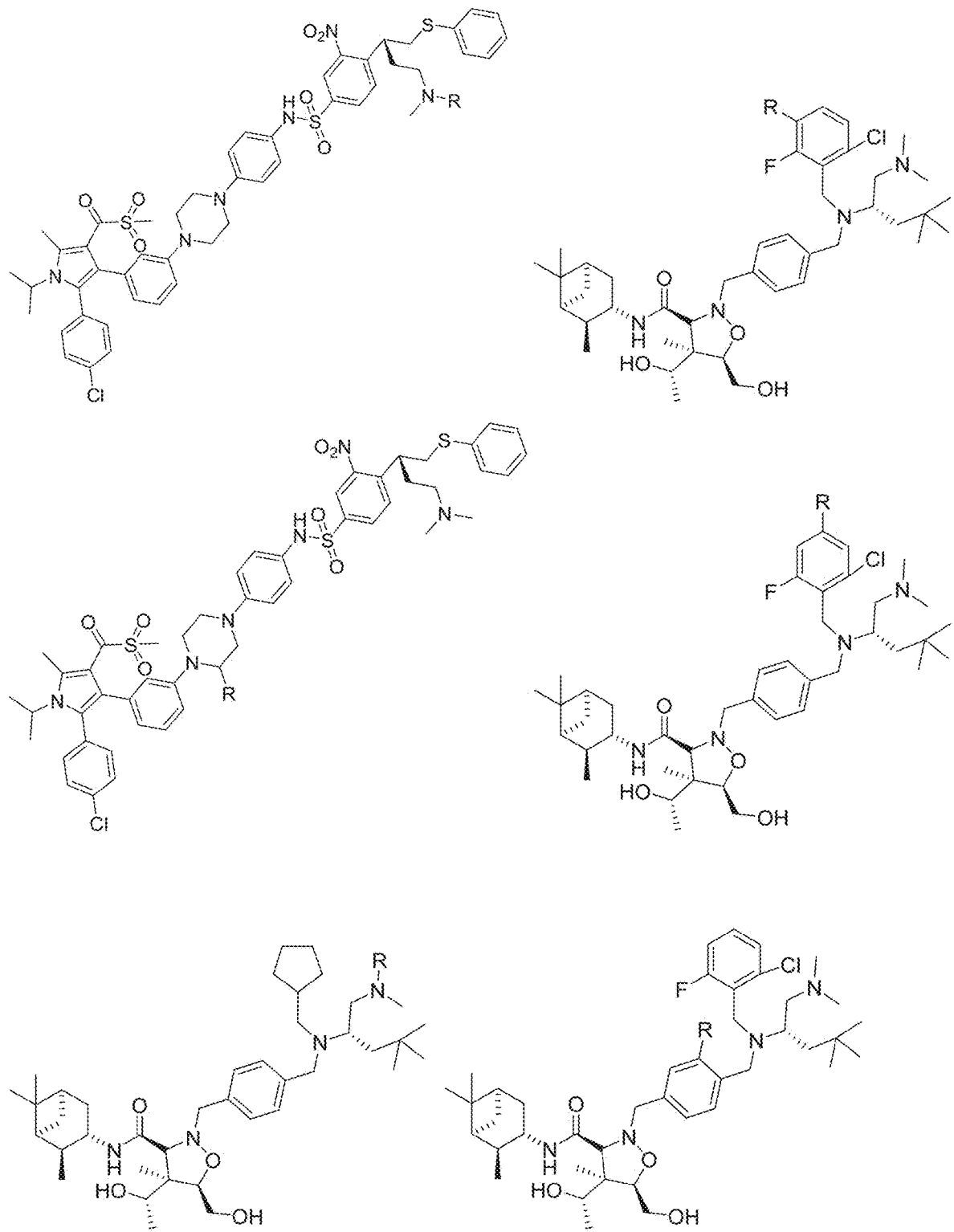
Figure 2H:
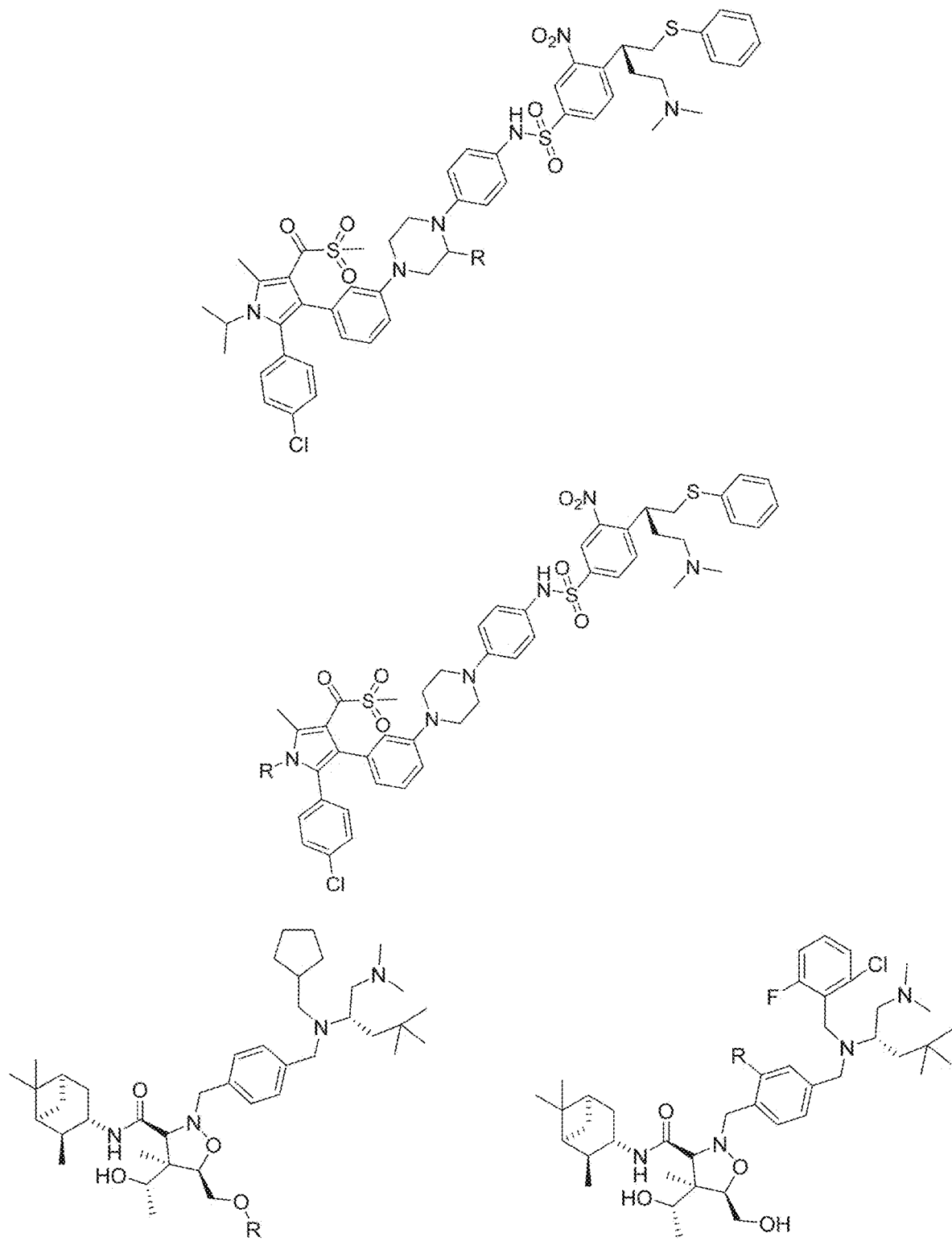
Figure 2I:
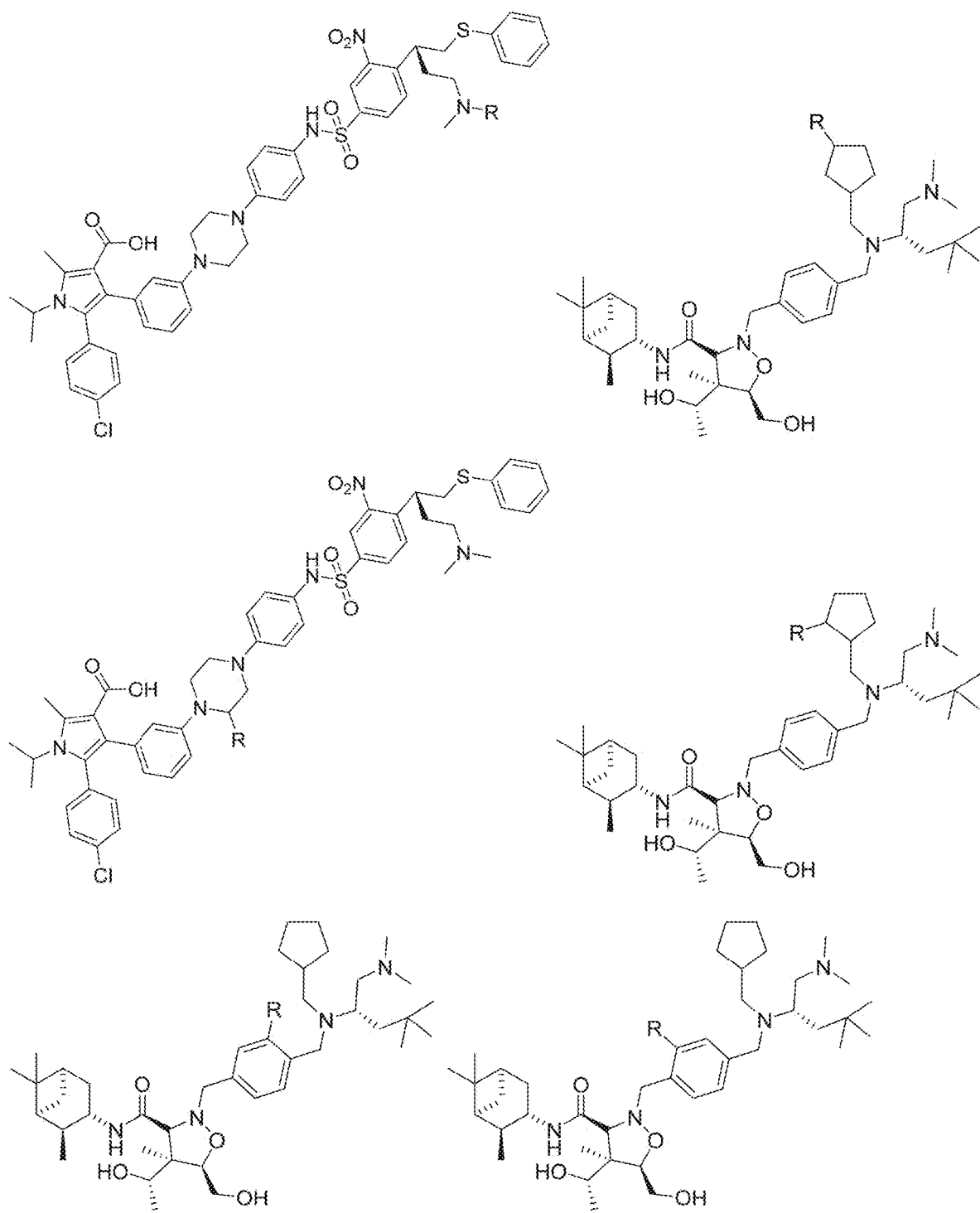
Figure 2J:
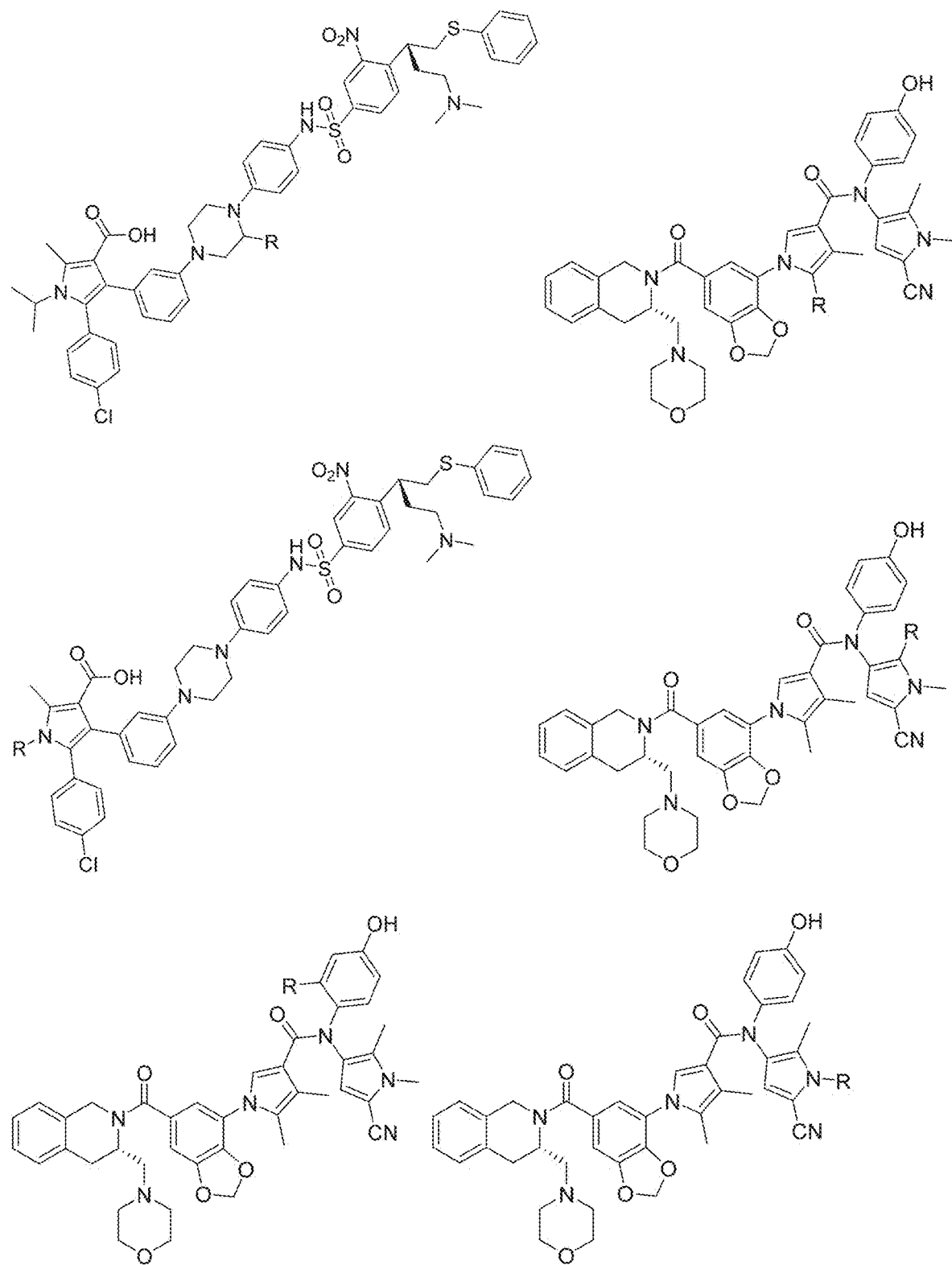
Figure 2K:
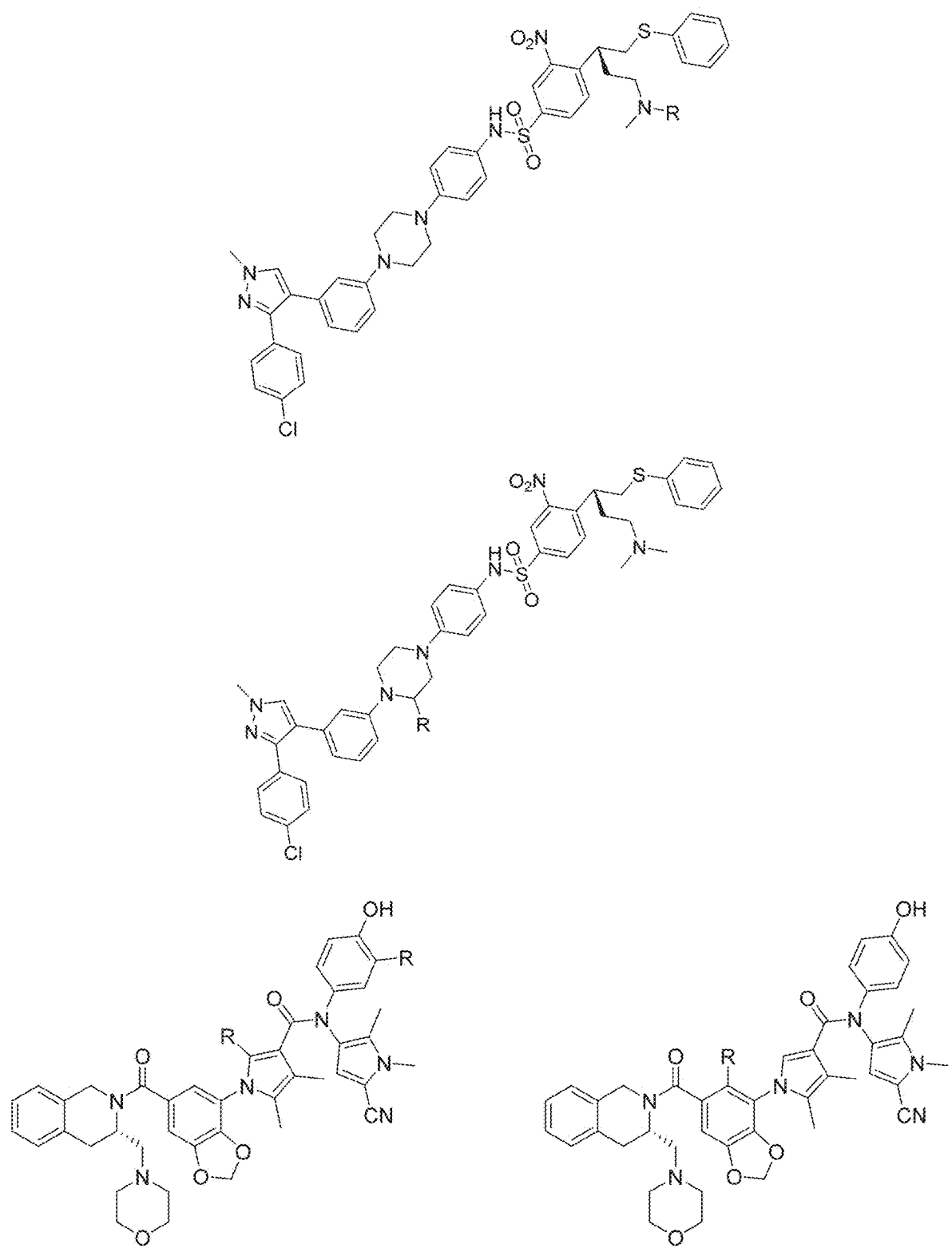
Figure 2L:
Figure 2M:
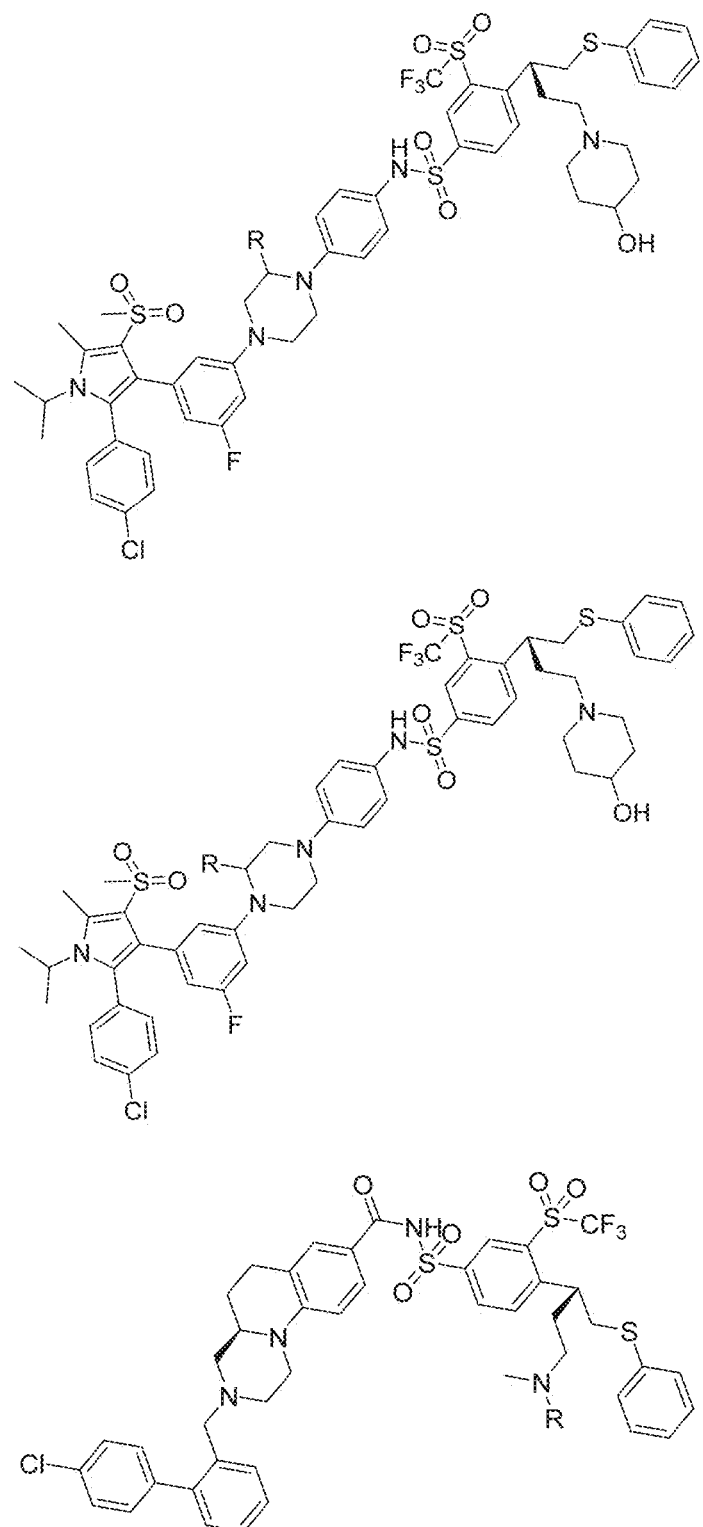
Figure 2N:
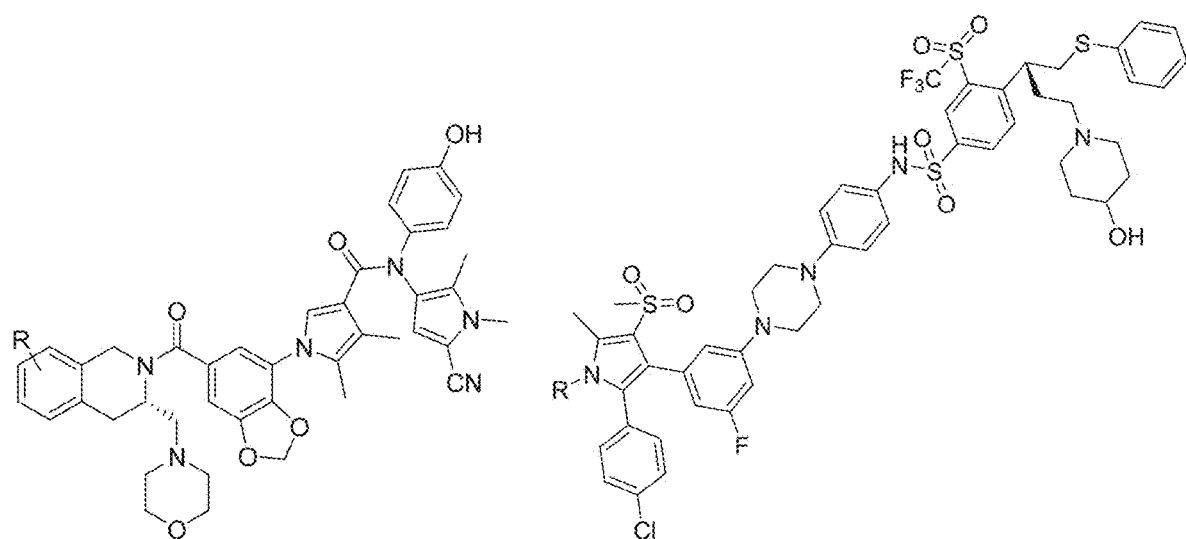
Figure 2O:
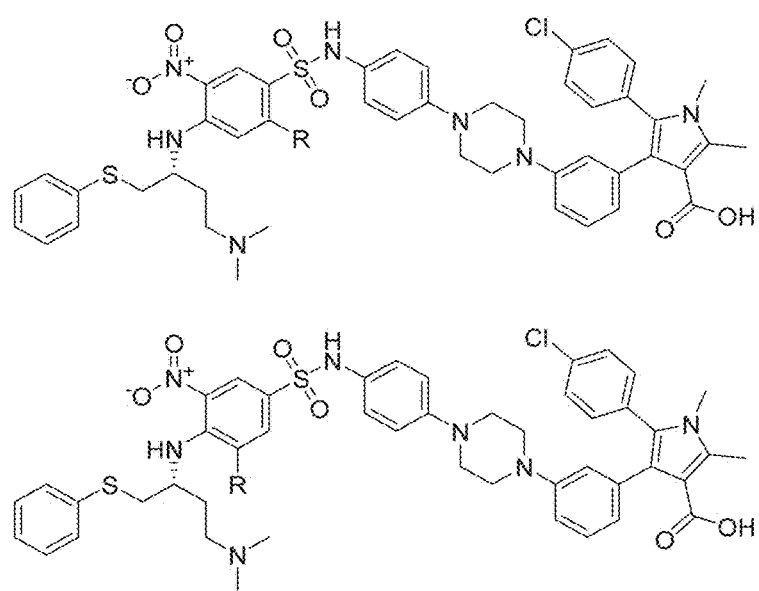
Figure 2P:
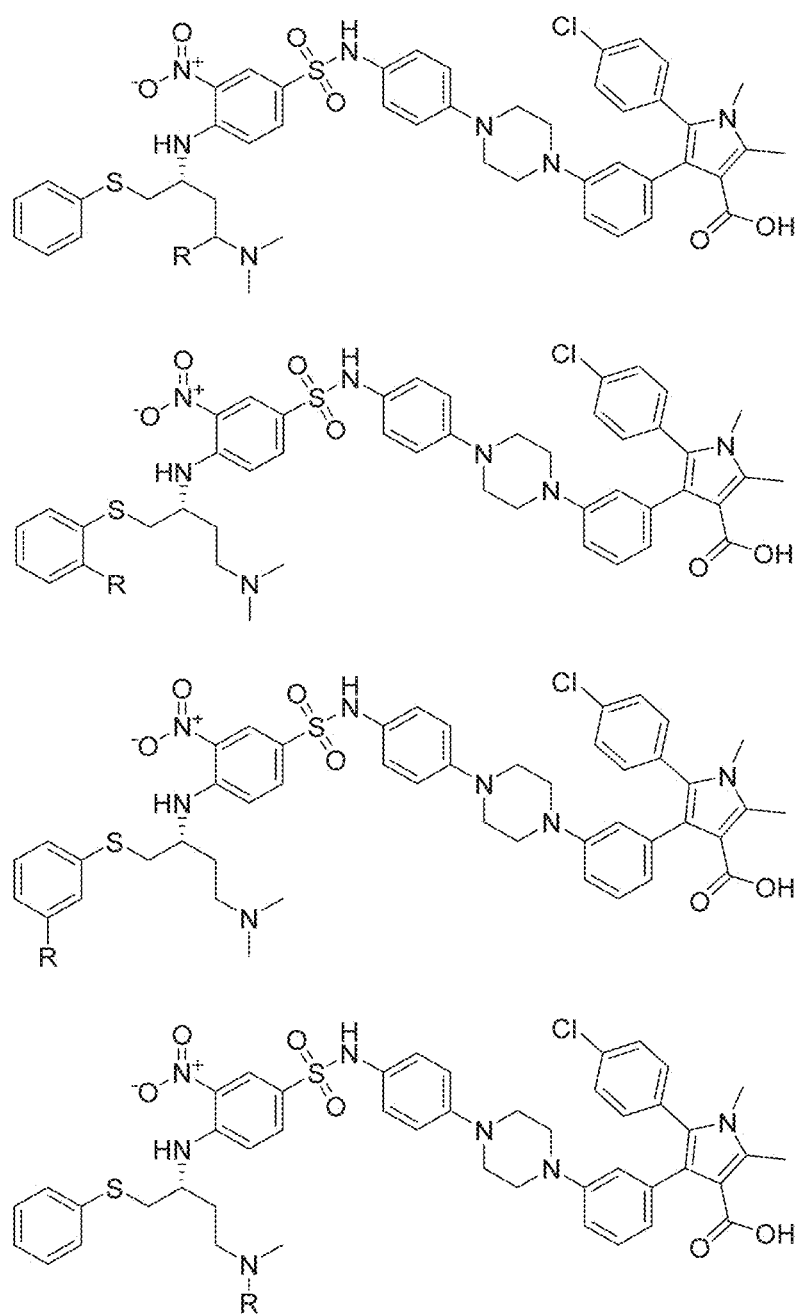
Figure 2Q:
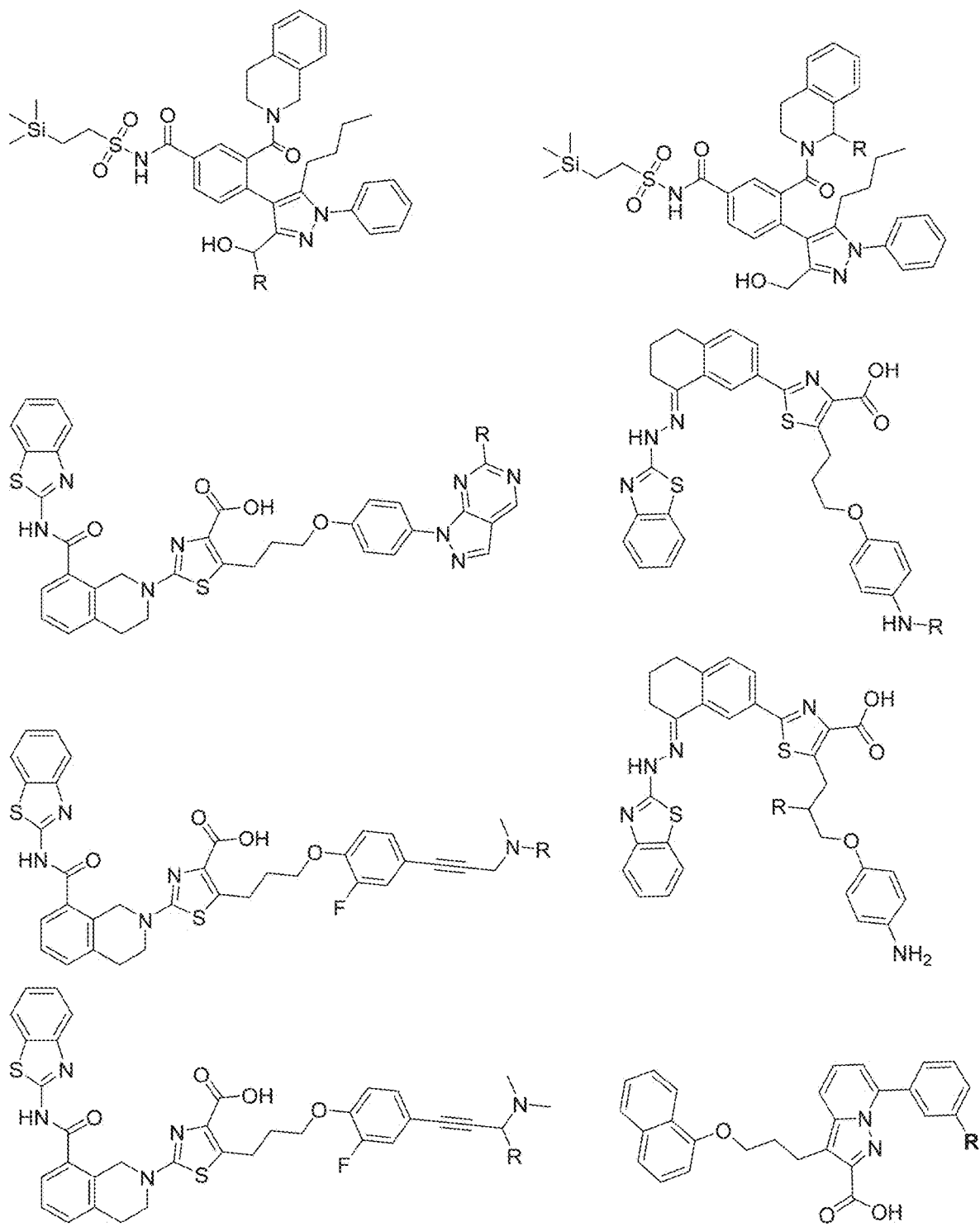
Figure 2R:
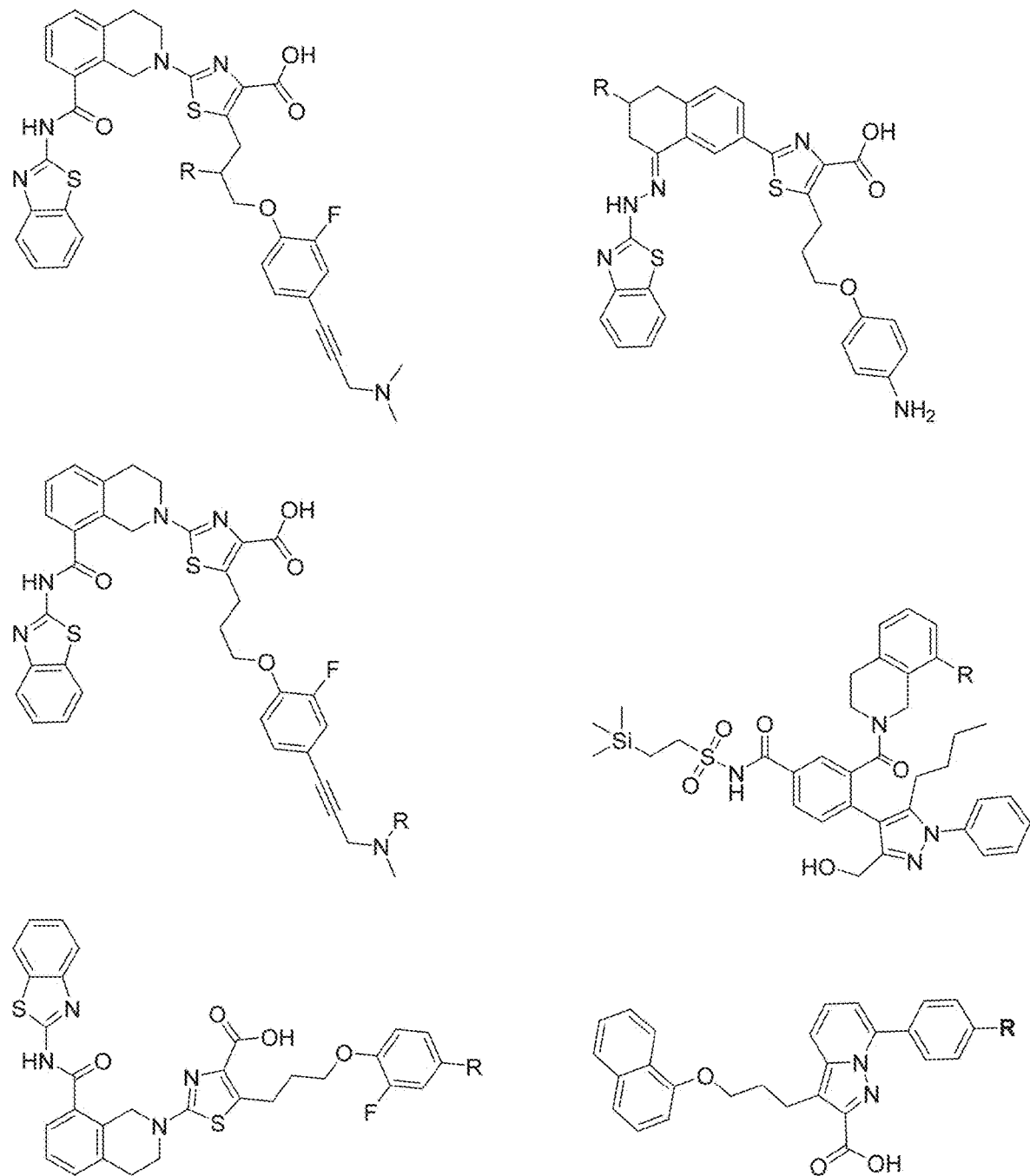
Figure 2S:
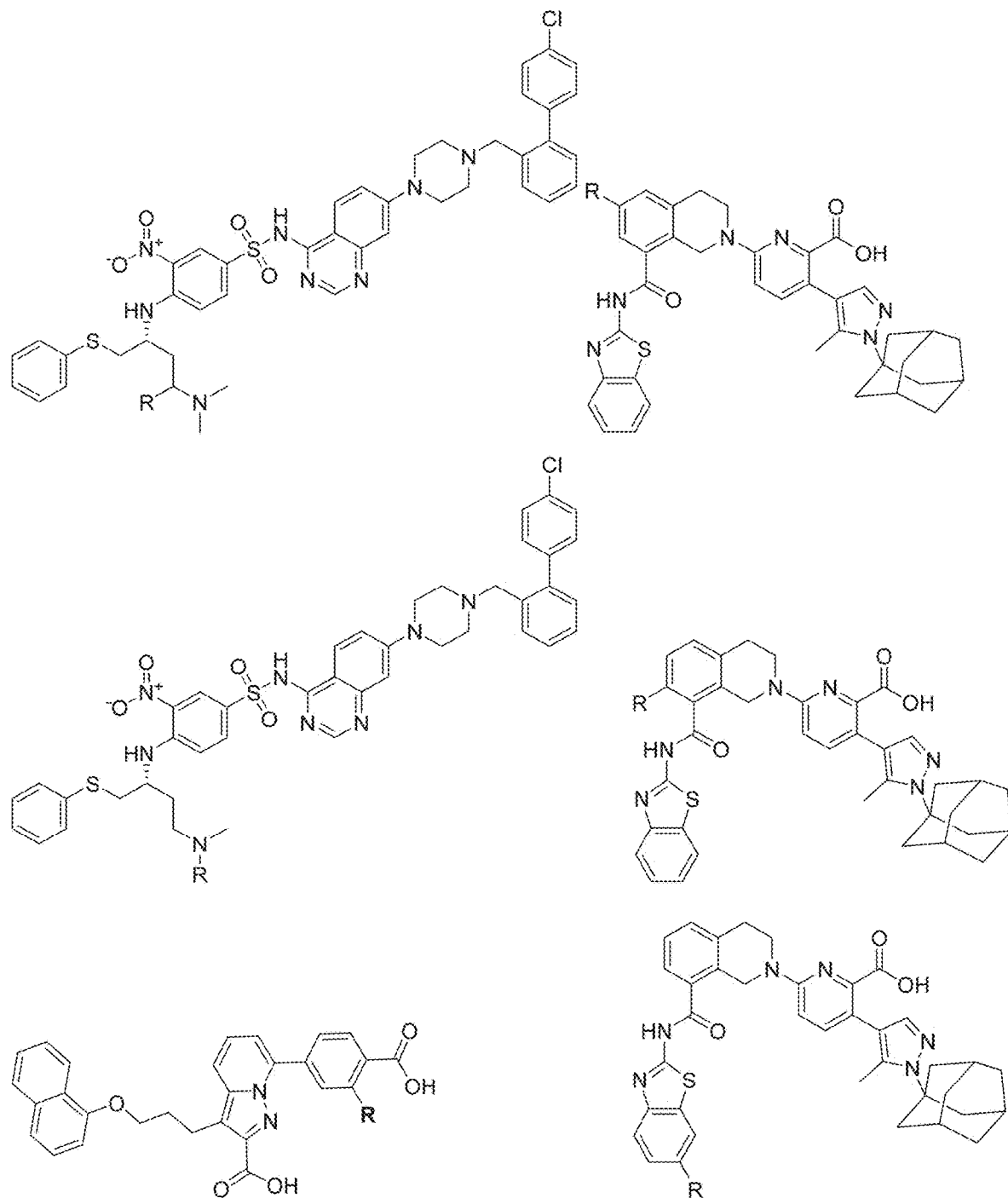
Figure 2T:
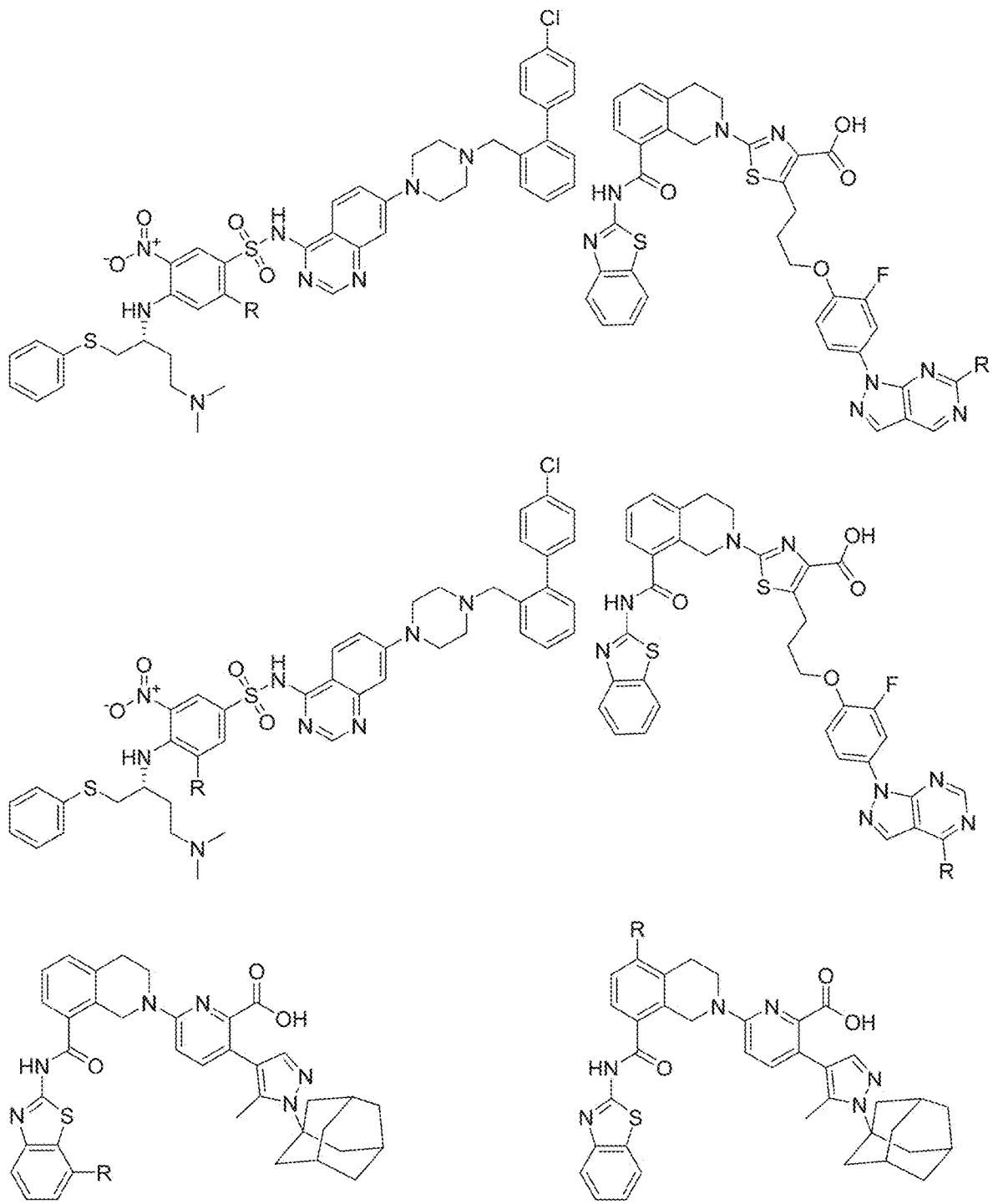
Figure 2W:
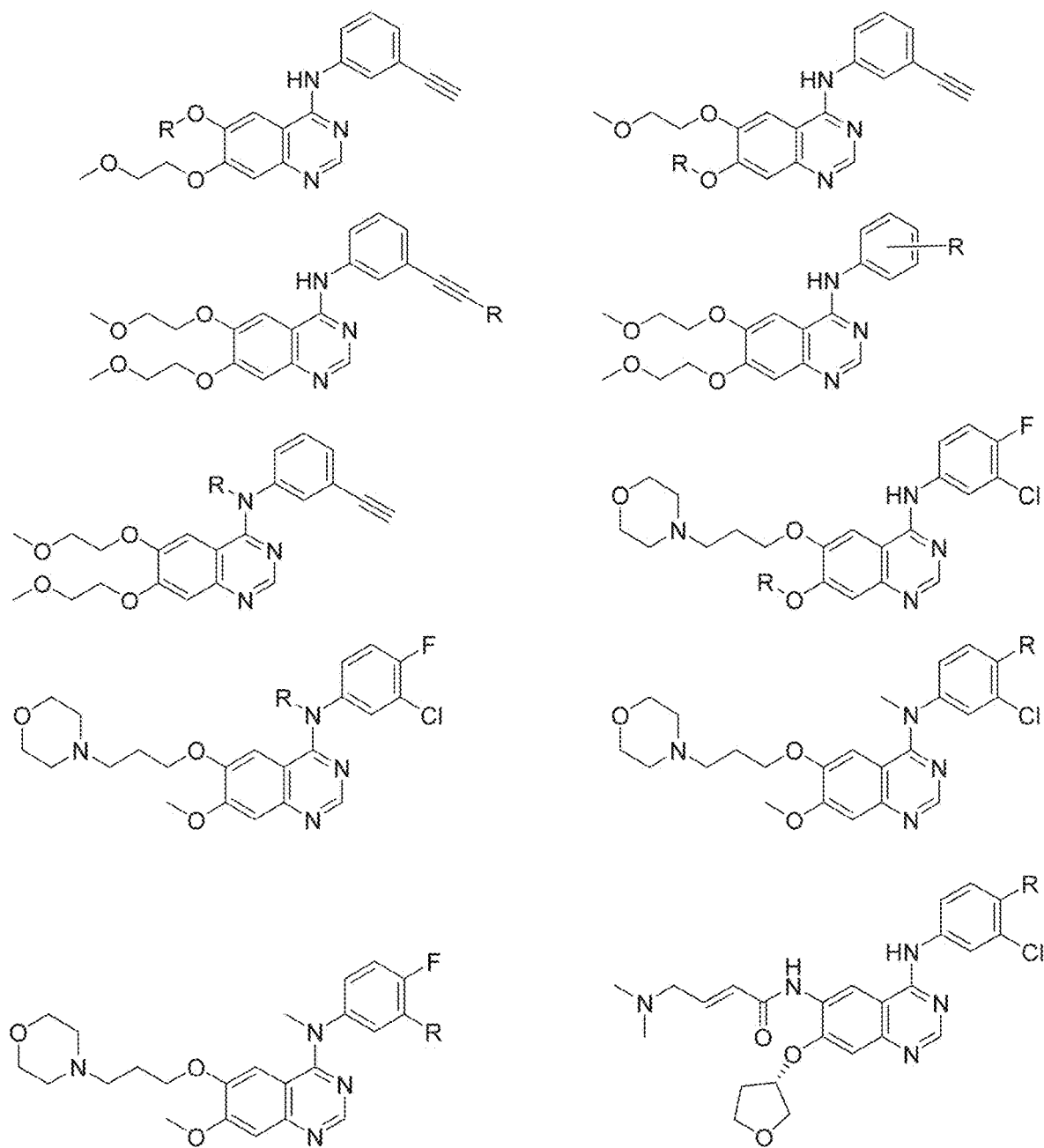

FIG. 2W presents examples of Bcl-2 or Bcl-XL Targeting Ligands wherein R is the point at which the Linker is attached.

Figure 2X:
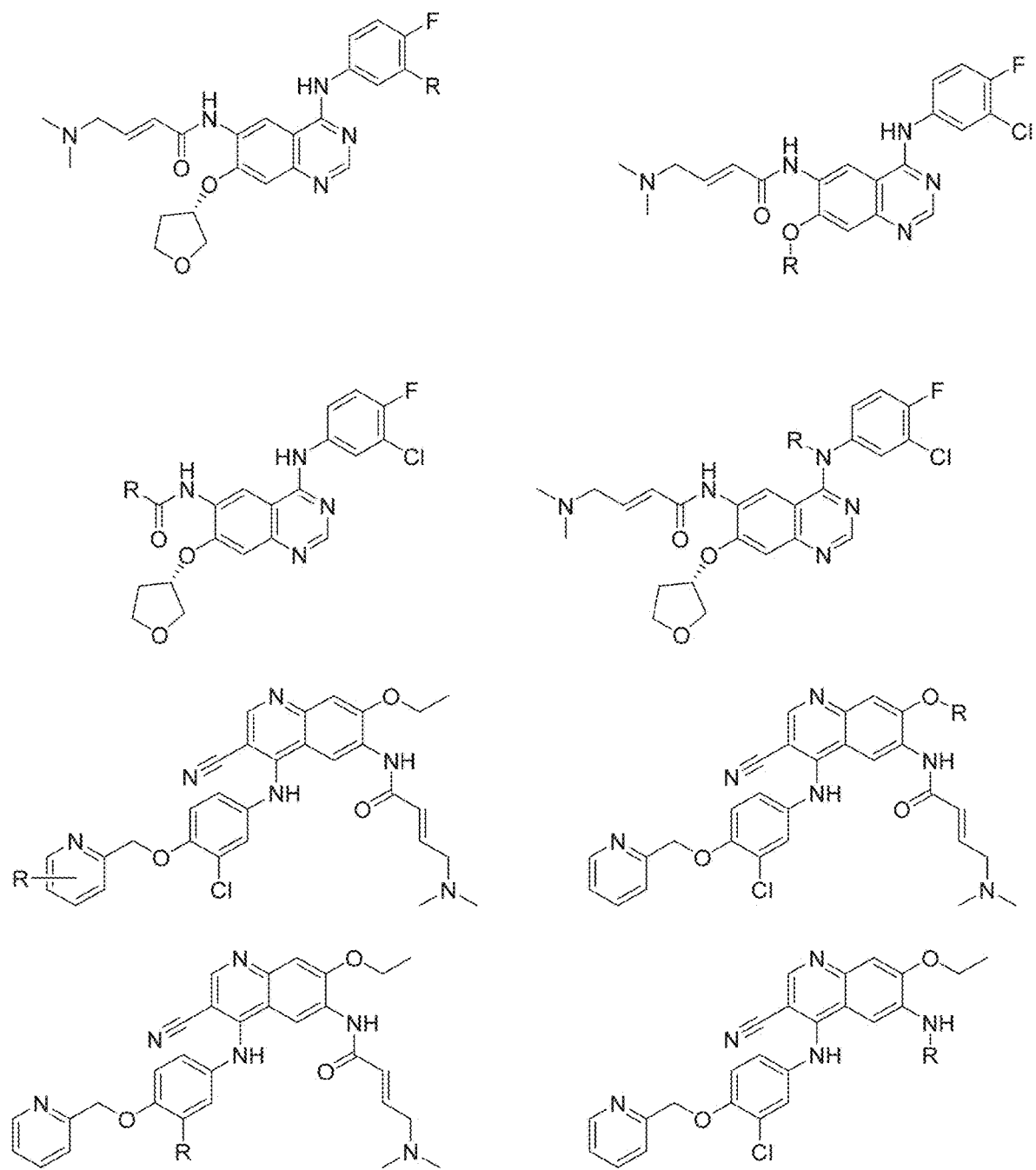

FIG. 2X-2NN present examples of BCL2 Targeting Ligands wherein R is the point at which the Linker is attached. For additional examples and related ligands, see, Toure B. B. et al. "The role of the acidity of N-heteroaryl sulfonamides as inhibitors of bcl-2 family protein-protein interactions." *ACS Med Chem Lett*, 4: 186-190 (2013); Porter J. e.t al. "Tetrahydroisoquinoline Amide Substituted Phenyl Pyrazoles as Selective Bcl-2 Inhibitors" *Bioorg. Med. Chem. Lett.* 19: 230 (2009); Souers A. J. et al. "ABT-199 a potent and selective BCL-2 inhibitor achieves antitumor activity while sparing platelets." *Nature Med.* 19: 202-208 (2013); Angelo Aguilar et al. "A Potent and Highly Efficacious Bcl-2/Bcl-xL Inhibitor" *J Med Chem.* 56(7): 3048-3067 (2013); Longchuan Bai et al. "BM-1197: A Novel and Specific Bcl-2/Bcl-xL Inhibitor Inducing Complete and Long-Lasting Tumor Regression In Vivo" *PLoS ONE* 9(6): e99404; Fariba Ne'matil et al. "Targeting Bcl-2/Bcl-XL Induces Antitumor Activity in Uveal Melanoma Patient-Derived Xenografts" *PLoS ONE* 9(1): e80836; WO2015011396 titled "Novel derivatives of indole and pyrrole method for the production thereof and pharmaceutical compositions containing same"; WO2008060569A1 titled "Compounds and methods for inhibiting the interaction of Bcl proteins with binding partners"; "Inhibitors of the anti-apoptotic Bcl-2 proteins: a patent review" *Expert Opin. Ther. Patents* 22(1):2008 (2012); and, Porter et al. "Tetrahydroisoquinoline amide substituted phenyl pyrazoles as selective Bcl-2 inhibitors" *Bioorg Med Chem Lett.*, 19(1): 230-3 (2009).

FIG. 2OO-2UU present examples of BCL-XL Targeting Ligands wherein R is the point at which the Linker is attached. For additional examples and related ligands, see, Zhi-Fu Tao et al. "Discovery of a Potent and Selective BCL-XL Inhibitor with in Vivo Activity" *ACS Med. Chem. Lett.*, 5: 1088-1093 (2014); Joel D. Leverson et al. "Exploiting selective BCL-2 family inhibitors to dissect cell survival dependencies and define improved strategies for cancer therapy" *Science Translational Medicine*, 7:279ra40 (2015); and, the crystal structure PDB 3ZK6 (Guillaume Lessene et al. "Structure-guided design of a selective BCL-XL inhibitor" *Nature Chemical Biology* 9: 390-397 (2013))

FIG. 2VV presents examples of PPAR-gamma Targeting Ligands wherein R is the point at which the Linker is attached.

FIG. 2WW-2YY present examples of EGFR Targeting Ligands that target the EGFR L858R mutant, including erlotinib, gefitnib, afatinib, neratinib, and dacomitinib, wherein R is the point at which the Linker is attached.

FIG. 2ZZ-2FFF present examples of EGFR Targeting Ligands that target the EGFR T790M mutant, including osimertinib, rociletinib, olmutinib, naquotinib, nazartinib, PF-06747775, Icotinib, Neratinib Avitinib, Tarloxotinib, PF-0645998, Tesevatinib, Transtinib, WZ-3146, WZ8040, and CNX-2006, wherein R is the point at which the Linker is attached.

FIG. 2GGG presents examples of EGFR Targeting Ligands that target the EGFR C797S mutant, including EAI045, wherein R is the point at which the Linker is attached.

FIG. 2HHH presents examples of BCR-ABL Targeting Ligands that target the BCR-ABL T315I mutantm including Nilotinib and Dasatinib, wherein R is the point at which the Linker is attached. See for example, the crystal structure PDB 3CS9.

FIG. 2III presents examples of Targeting Ligands that target BCR-ABL, including Nilotinib, Dasatinib Ponatinib and Bosutinib, wherein R is the point at which the Linker is attached.

FIG. 2JJJ-2KKK present examples of ALK Targeting Ligands that target the ALK L1196M mutant including Ceritinib, wherein R is the point at which the Linker is attached. See for example, the crystal structure PDB 4MKC.

FIG. 2LLL presents examples of JAK2 Targeting Ligands that target the JAK2V617F mutant, including Ruxolitinib, wherein R is the point at which the Linker is attached.

FIG. 2MMM presents examples of BRAF Targeting Ligands that target the BRAF V600E mutant including Vemurafenib, wherein R is the point at which the Linker is attached. For additional examples and related ligands, see, the crystal structure PBD 3OG7.

FIG. 2NNN presents examples of BRAF Targeting Ligands, including Dabrafenib, wherein R is the point at which the Linker is attached.

FIG. 2OOO presents examples of LRRK2 Targeting Ligands that target the LRRK2 R1441C mutant wherein R is the point at which the Linker is attached.

FIG. 2PPP presents examples of LRRK2 Targeting Ligands that target the LRRK2 G2019S mutant wherein R is the point at which the Linker is attached.

FIG. 2QQQ presents examples of LRRK2 Targeting Ligands that target the LRRK2 I2020T mutant wherein R is the point at which the Linker is attached.

FIG. 2RRR-2TTT present examples of PDGFRa Targeting Ligands that target the PDGFRα T674I mutant, including AG-1478, CHEMBL94431, Dovitinib, erlotinib, gefitinib, imatinib, Janex 1, Pazopanib, PD153035, Sorafenib, Sunitinib, and WHI-P180, wherein R is the point at which the Linker is attached.

FIG. 2UUU presents examples of RET Targeting Ligands that target the RET G691S mutant, including tozasertib, wherein R is the point at which the Linker is attached.

FIG. 2VVV presents examples of RET Targeting Ligands that target the RET R749T mutant, including tozasertib, wherein R is the point at which the Linker is attached.

FIG. 2WWW presents examples of RET Targeting Ligands that target the RET E762Q mutant, including tozasertib, wherein R is the point at which the Linker is attached.

FIG. 2XXX presents examples of RET Targeting Ligands that target the RET Y791F mutant, including tozasertib, wherein R is the point at which the Linker is attached.

Figure 2Y:
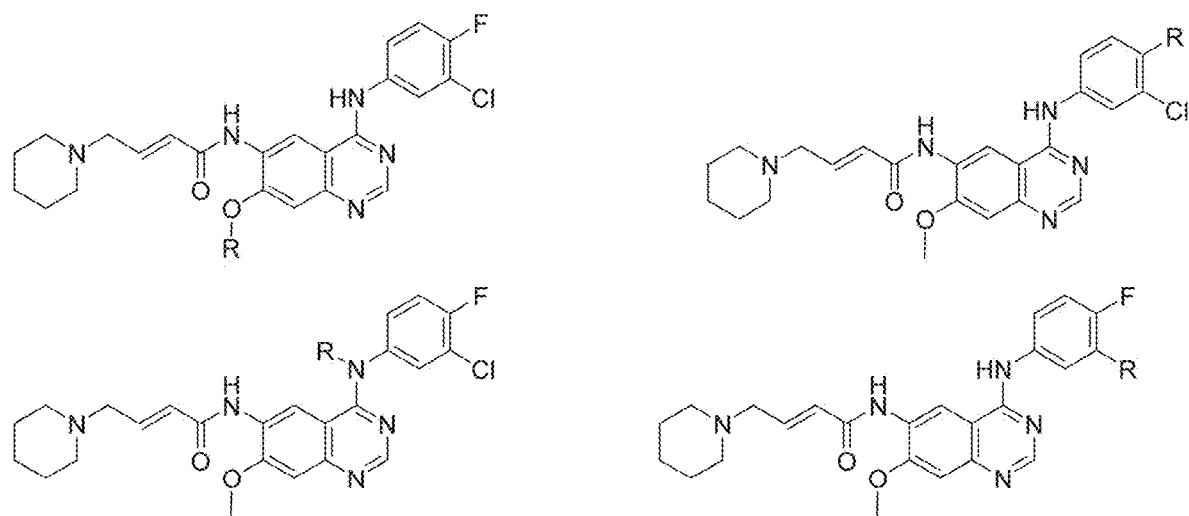
Figure 2Z:
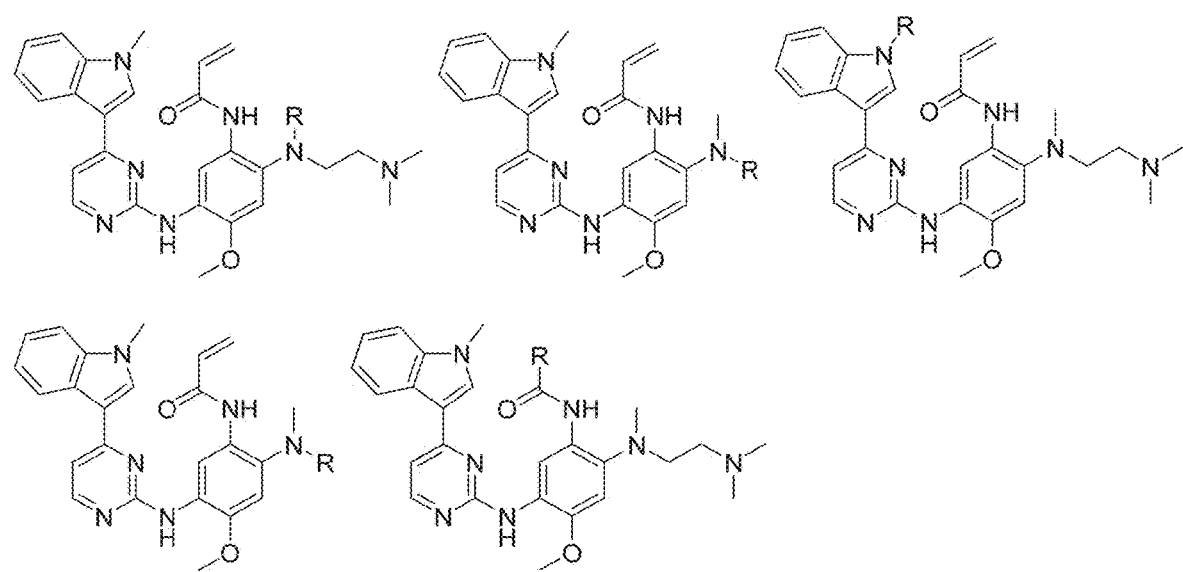

FIG. 2YYY presents examples of RET Targeting Ligands that target the RET V804M mutant, including tozasertib, wherein R is the point at which the Linker is attached.

FIG. 2ZZZ presents examples of RET Targeting Ligands that target the RET M918T mutant, including tozasertib, wherein R is the point at which the Linker is attached.

FIG. 2AAAA presents examples of Fatty Acid Binding Protein Targeting Ligands wherein R is the point at which the Linker is attached.

FIG. 2BBBB presents examples of 5-Lipoxygenase Activating Protein (FLAP) Targeting Ligands wherein R is the point at which the Linker is attached.

FIG. 2CCCC presents examples of Kringle Domain V 4BVV Targeting Ligands wherein R is the point at which the Linker is attached.

FIG. 2DDDD presents examples of Lactoylglutathione Lyase Targeting Ligands wherein R is the point at which the Linker is attached.

FIG. 2EEEE-2FFFF present examples of mPGES-1 Targeting Ligands wherein R is the point at which the Linker is attached.

FIG. 2GGGG-2JJJJ present examples of Factor Xa Targeting Ligands wherein R is the point at which the Linker is attached. For additional examples and related ligands, see, Maignan S. et al. "Crystal structures of human factor Xa complexed with potent inhibitors." *J. Med. Chem.* 43: 3226-3232 (2000); Matsusue T. et al. "Factor Xa Specific Inhibitor that Induces the Novel Binding Model in Complex with Human Fxa." (to be published); the crystal structures PDB liqh, liqi, liqk, and liqm; Adler M. et al. "Crystal Structures of Two Potent Nonamidine Inhibitors Bound to Factor Xa." *Biochemistry* 41: 15514-15523 (2002); Roehrig S. et al. "Discovery of the Novel Antithrombotic Agent 5-Chloro-N-({(5S)-2-Oxo-3-[4-(3-Oxomorpholin-4-Yl)Phenyl]-1 3-Oxazolidin-5-Yl})Methyl)Thiophene-2-Carboxamide (Bay 59-7939): An Oral Direct Factor Xa Inhibitor." *J. Med. Chem.* 48: 5900 (2005); Anselm L. et al. "Discovery of a Factor Xa Inhibitor (3R 4R)-1-(2 2-Difluoro-Ethyl)-Pyrrolidine-3 4-Dicarboxylic Acid 3-[(5-Chloro-Pyridin-2-Yl)-Amide] 4-{[2-Fluoro-4-(2-Oxo-2H-Pyridin-1-Yl)-Phenyl]-Amide} as a Clinical Candidate." *Bioorg. Med. Chem.* 20: 5313 (2010); and, Pinto D. J. et al. "Discovery of 1-(4-Methoxyphenyl)-7-oxo-6-(4-(2-oxopiperidin-1-yl)phenyl)-4 5 6 7-tetrahydro-1H-pyrazolo[3 4-c]pyridine-3-carboxamide (Apixaban BMS-562247) a Highly Potent Selective Efficacious and Orally Bioavailable Inhibitor of Blood Coagulation Factor Xa." *J. Med. Chem.* 50: 5339-5356 (2007).

FIG. 2KKKK presents examples of Kallikrein 7 Targeting Ligands wherein R is the point at which the Linker is attached. For additional examples and related ligands, see, Maibaum J. et al. "Small-molecule factor D inhibitors targeting the alternative complement pathway." *Nat. Chem. Biol.* 12: 1105-1110 (2016).

FIG. 2LLLL-2MMMM present examples of Cathepsin K Targeting Ligands wherein R is the point at which the Linker is attached. For additional examples and related ligands, see, Rankovic Z. et al. "Design and optimization of a series of novel 2-cyano-pyrimidines as cathepsin K inhibitors" *Bioorg. Med. Chem. Lett.* 20: 1524-1527 (2010); and, Cai J. et al. "Trifluoromethylphenyl as P2 for ketoamide-based cathepsin S inhibitors." *Bioorg. Med. Chem. Lett.* 20: 6890-6894 (2010).

FIG. 2NNNN presents examples of Cathepsin L Targeting Ligands wherein R is the point at which the Linker is attached. For additional examples and related ligands, see, Kuhn B. et al. "Prospective Evaluation of Free Energy Calculations for the Prioritization of Cathepsin L Inhibitors." *J. Med. Chem.* 60: 2485-2497 (2017).

FIG. 2OOOO presents examples of Cathepsin S Targeting Ligands wherein R is the point at which the Linker is attached. For additional examples and related ligands, see, Jadhav P. K. et al. "Discovery of Cathepsin S Inhibitor LY3000328 for the Treatment of Abdominal Aortic Aneurysm" *ACS Med. Chem. Lett.* 5: 1138-1142." (2014).

FIG. 2PPPP-2SSSS present examples of MTH1 Targeting Ligands wherein R is the point at which the Linker is attached. For additional examples and related ligands, see, Kettle J. G. et al. "Potent and Selective Inhibitors of Mth1 Probe its Role in Cancer Cell Survival." *J. Med. Chem.* 59: 2346 (2016); Huber K. V. M. et al. "Stereospecific Targeting of Mth1 by (S)-Crizotinib as an Anticancer Strategy." *Nature* 508: 222 (2014); Gad H. et al. "MTH1 inhibition eradicates cancer by preventing sanitation of the dNTP pool." *Nature* 508: 215-221 (2014); Nissink J. W. M. et al. "Mth1 Substrate Recognition—an Example of Specific Promiscuity." *Plos One* 11: 51154 (2016); and, Manuel Ellermann et al. "Novel class of potent and selective inhibitors efface MTH1 as broad-spectrum cancer target." AACR National Meeting Abstract 5226, 2017.

FIG. 2TTTT-2ZZZZ present examples of MDM2 and/or MDM4 Targeting Ligands wherein R is the point at which the Linker is attached. For additional examples and related ligands, see, Popowicz G. M. et al. "Structures of low molecular weight inhibitors bound to MDMX and MDM2 reveal new approaches for p53-MDMX/MDM2 antagonist drug discovery." Cell Cycle, 9 (2010); Miyazaki M. et al. "Synthesis and evaluation of novel orally active p53-MDM2 interaction inhibitors." *Bioorg. Med. Chem.* 21: 4319-4331 (2013); Miyazaki M. et al. "Discovery of DS-5272 as a promising candidate: A potent and orally active p53-MDM2 interaction inhibitor." *Bioorg Med Chem.* 23: 2360-7 (2015); Holzer P. et al. "Discovery of a Dihydroisoquinolinone Derivative (NVP-CGM097): A Highly Potent and Selective MDM2 Inhibitor Undergoing Phase 1 Clinical Trials in p53 wt Tumors." *J. Med. Chem.* 58: 6348-6358 (2015); Gonzalez-Lopez de Turiso F. et al. "Rational Design and Binding Mode Duality of MDM2-p53 Inhibitors." *J. Med. Chem.* 56: 4053-4070 (2013); Gessier F. et al. "Discovery of dihydroisoquinolinone derivatives as novel inhibitors of the p53-MDM2 interaction with a distinct binding mode." *Bioorg. Med. Chem. Lett.* 25: 3621-3625 (2015); Fry D. C. et al. "Deconstruction of a nutlin: dissecting the binding determinants of a potent protein-protein interaction inhibitor." *ACS Med Chem Lett* 4: 660-665 (2013); Ding Q. et al. "Discovery of RG7388 a Potent and Selective p53-MDM2 Inhibitor in Clinical Development." *J. Med. Chem.* 56: 5979-5983 (2013); Wang S. et al. "SAR405838: an optimized inhibitor of MDM2-p53 interaction that induces complete and durable tumor regression." *Cancer Res.* 74: 5855-5865 (2014); Rew Y. et al. "Discovery of AM-7209 a Potent and Selective 4-Amidobenzoic Acid Inhibitor of the MDM2-p53 Interaction." *J. Med. Chem.* 57: 10499-10511 (2014); Bogen S. L. et al. "Discovery of Novel 3 3-Disubstituted Piperidines as Orally Bioavailable Potent and Efficacious HDM2-p53 Inhibitors." *ACS Med. Chem. Lett.* 7: 324-329 (2016); and, Sun D. et al. "Discovery of AMG 232 a Potent Selective and Orally Bioavailable MDM2-p53 Inhibitor in Clinical Development." *J. Med. Chem.* 57: 1454-1472 (2014).

FIG. 2AAAAA-2EEEEE present examples of PARP1, PARP2, and/or PARP3 Targeting Ligands wherein R is the point at which the Linker is attached. For additional examples and related ligands, see, Iwashita A. et al. "Discovery of quinazolinone and quinoxaline derivatives as potent and selective poly(ADP-ribose) polymerase-1/2 inhibitors." *Febs Lett.* 579: 1389-1393 (2005); the crystal structure PDB 2RCW (PARP complexed with A861695, Park C. H.); the crystal structure PDB 2RD6 (PARP complexed with A861696, Park C. H.); the crystal structure PDB 3GN7; Miyashiro J. et al. "Synthesis and SAR of novel tricyclic quinoxalinone inhibitors of poly(ADP-ribose)polymerase-1 (PARP-1)" *Bioorg. Med. Chem. Lett.* 19: 4050-4054 (2009); Gandhi V. B. et al. "Discovery and SAR of substituted 3-oxoisoindoline-4-carboxamides as potent inhibitors of poly(ADP-ribose) polymerase (PARP) for the treatment of cancer." *Bioorg. Med. Chem. Lett.* 20: 1023-1026 (2010); Penning T. D. et al. "Optimization of phenyl-substituted benzimidazole carboxamide poly(ADP-ribose) polymerase inhibitors: identification of (S)-2-(2-fluoro-4-(pyrrolidin-2-yl)phenyl)-1H-benzimidazole-4-carboxamide (A-966492) a highly potent and efficacious inhibitor." *J. Med. Chem.* 53: 3142-3153 (2010); Ye N. et al. "Design, Synthesis, and Biological Evaluation of a Series of Benzo[de][1 7]naphthyridin-7(8H)-ones Bearing a Functionalized Longer Chain Appendage as Novel PARP1 Inhibitors." *J. Med Chem.* 56: 2885-2903 (2013); Patel M. R. et al. "Discovery and Structure-Activity Relationship of Novel 2 3-Dihydrobenzofuran-7-carboxamide and 2 3-Dihydrobenzofuran-3(2H)-one-7-carboxamide Derivatives as Poly (ADP-ribose)polymerase-1 Inhibitors." *J. Med. Chem.* 57: 5579-5601 (2014); Thorsell A. G. et al. "Structural Basis for Potency and Promiscuity in Poly(ADP-ribose) Polymerase (PARP) and Tankyrase Inhibitors." *J. Med. Chem.* 60:1262-1271 (2012); the crystal structure PDB 4RV6 ("Human ARTD1 (PARP1) catalytic domain in complex with inhibitor Rucaparib", Karlberg T. et al.); Papeo G. M. E. et al. "Discovery of 2-[1-(4 4-Difluorocyclohexyl)Piperidin-4-Yl]-6-Fluoro-3-Oxo-2 3-Dihydro-1H-Isoindole-4-Carboxamide (Nms-P118): A Potent Orally Available and Highly Selective Parp-1 Inhibitor for Cancer Therapy." *J. Med. Chem.* 58: 6875 (2015); Kinoshita T. et al. "Inhibitor-induced structural change of the active site of human poly (ADP-ribose) polymerase." *Febs Lett.* 556: 43-46 (2004); and, Gangloff A. R. et al. "Discovery of novel benzo[b][1 4]oxazin-3(4H)-ones as poly(ADP-ribose)polymerase inhibitors." *Bioorg. Med. Chem. Lett.* 23: 4501-4505 (2013).

FIG. 2FFFFF-2GGGGG present examples of PARP14 Targeting Ligands wherein R is the point at which the Linker is attached.

FIG. 2HHHHH presents examples of PARP15 Targeting Ligands wherein R is the point at which the Linker is attached.

FIG. 2IIIII presents examples of PDZ domain Targeting Ligands wherein R is the point at which the Linker(s) are attached.

FIG. 2JJJJJ presents examples of Phospholipase A2 domain Targeting Ligands wherein R is the point at which the Linker is attached.

FIG. 2KKKKK presents examples of Protein S100-A7 2WOS Targeting Ligands wherein R is the point at which the Linker is attached.

FIG. 2LLLLL-2MMMMM present examples of Saposin-B Targeting Ligands wherein R is the point at which the Linker is attached.

FIG. 2NNNNN-2OOOOO present examples of Sec7 Targeting Ligands wherein R is the point at which the Linker is attached.

FIG. 2PPPPP-2QQQQQ present examples of SH2 domain of pp60 Src Targeting Ligands wherein R is the point at which the Linker is attached.

FIG. 2RRRRR presents examples of Tank1 Targeting Ligands wherein R is the point at which the Linker is attached.

FIG. 2SSSSS presents examples of Ubc9 SUMO E2 ligase SF6D Targeting Ligands wherein R is the point at which the Linker is attached.

FIG. 2TTTTT presents examples of Src Targenting Ligands, including AP23464, wherein R is the point at which the Linker is attached.

FIG. 2UUUUU-2XXXXX present examples of Src-AS1 and/or Src AS2 Targeting Ligands wherein R is the point at which the Linker is attached.

FIG. 2YYYYY presents examples of JAK3 Targeting Ligands, including Tofacitinib, wherein R is the point at which the Linker is attached.

FIG. 2ZZZZZ presents examples of ABL Targeting Ligands, including Tofacitinib and Ponatinib, wherein R is the point at which the Linker is attached.

Figure 3B:
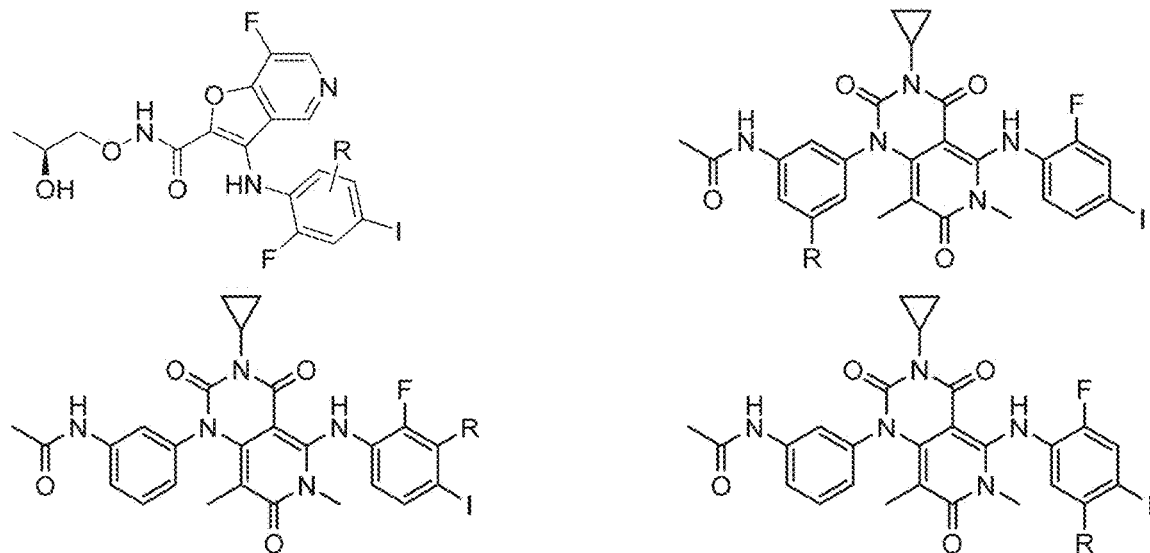
Figure 3C:
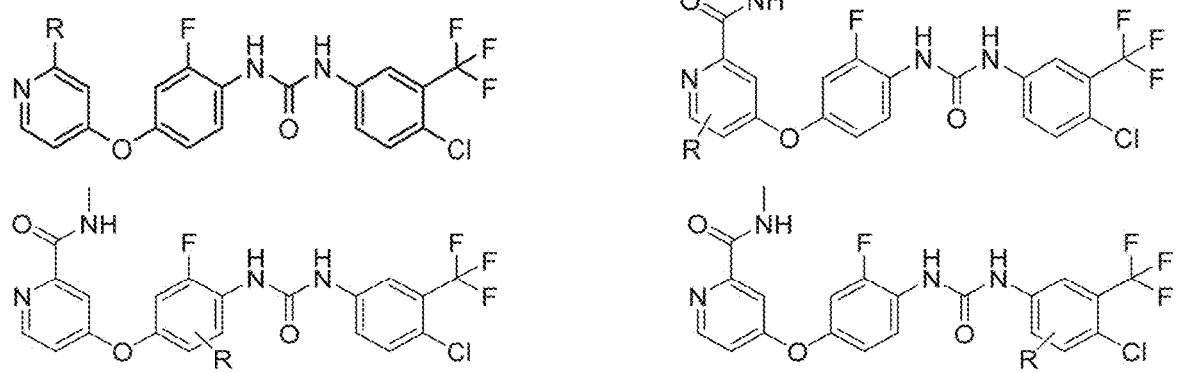
Figure 3D:
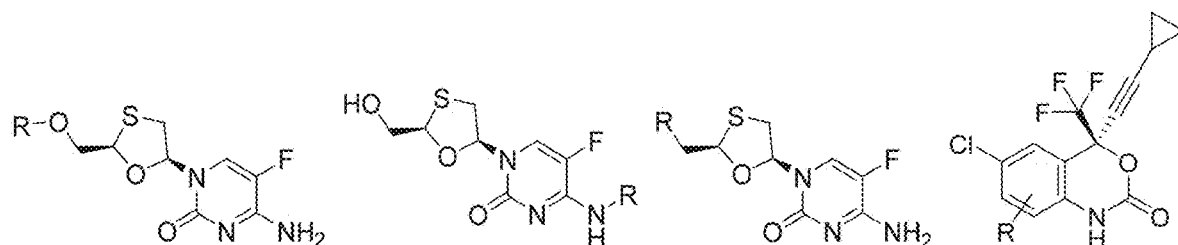
Figure 3E:
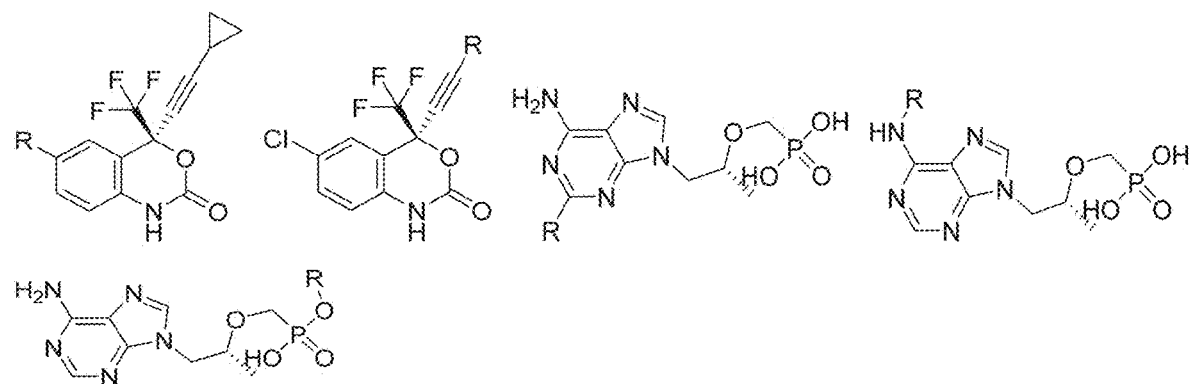
Figure 3F:
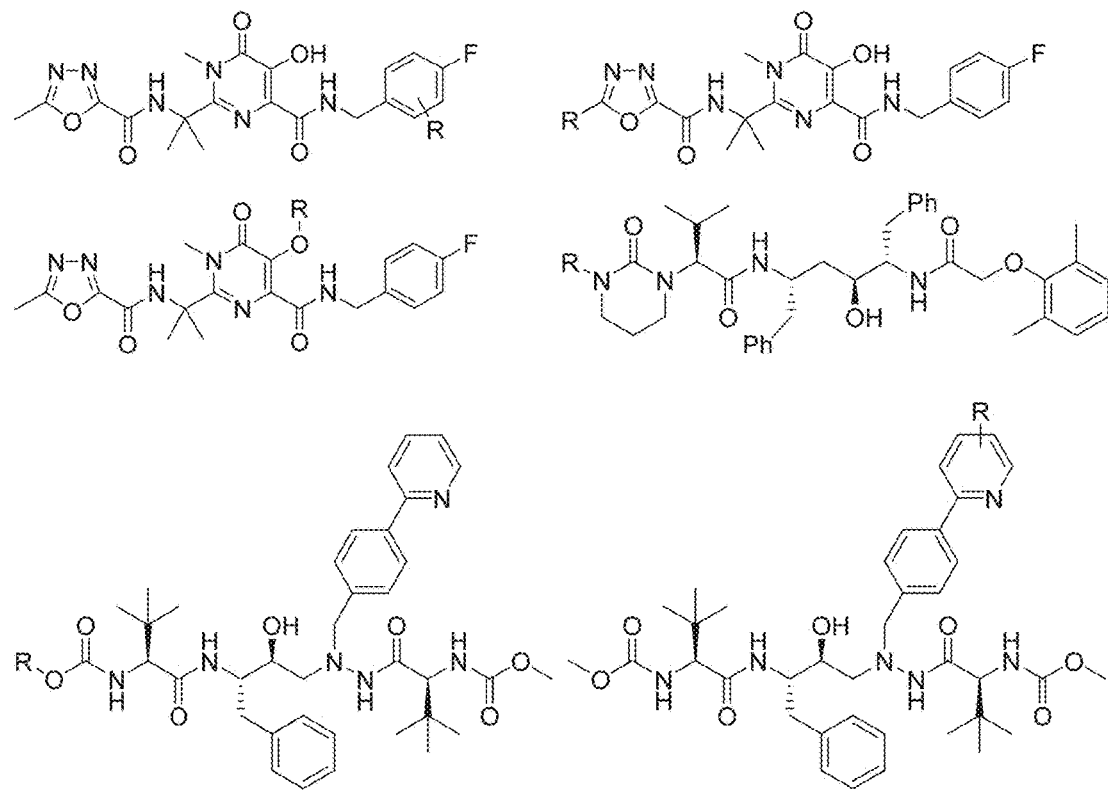
Figure 3G:
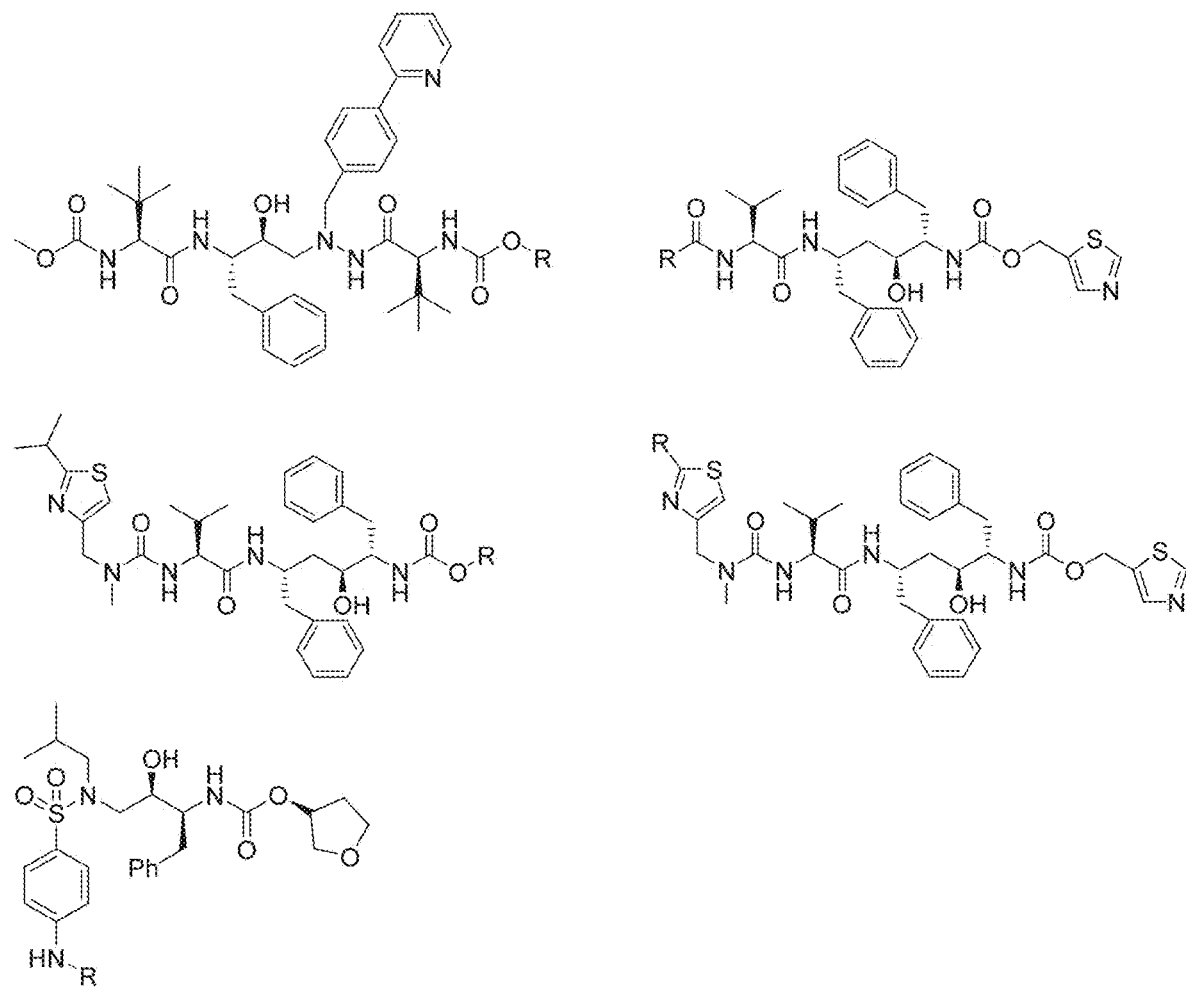
Figure 3H:
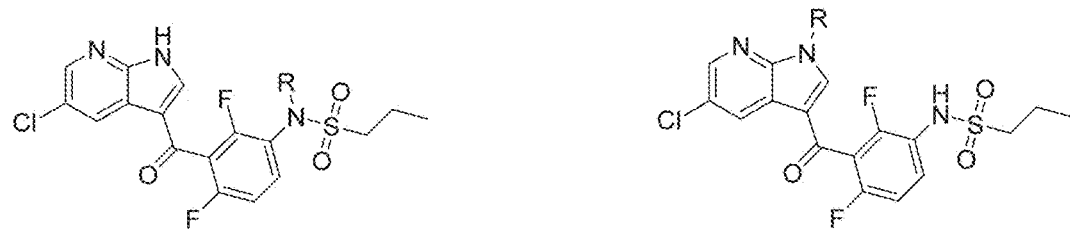
Figure 3K:
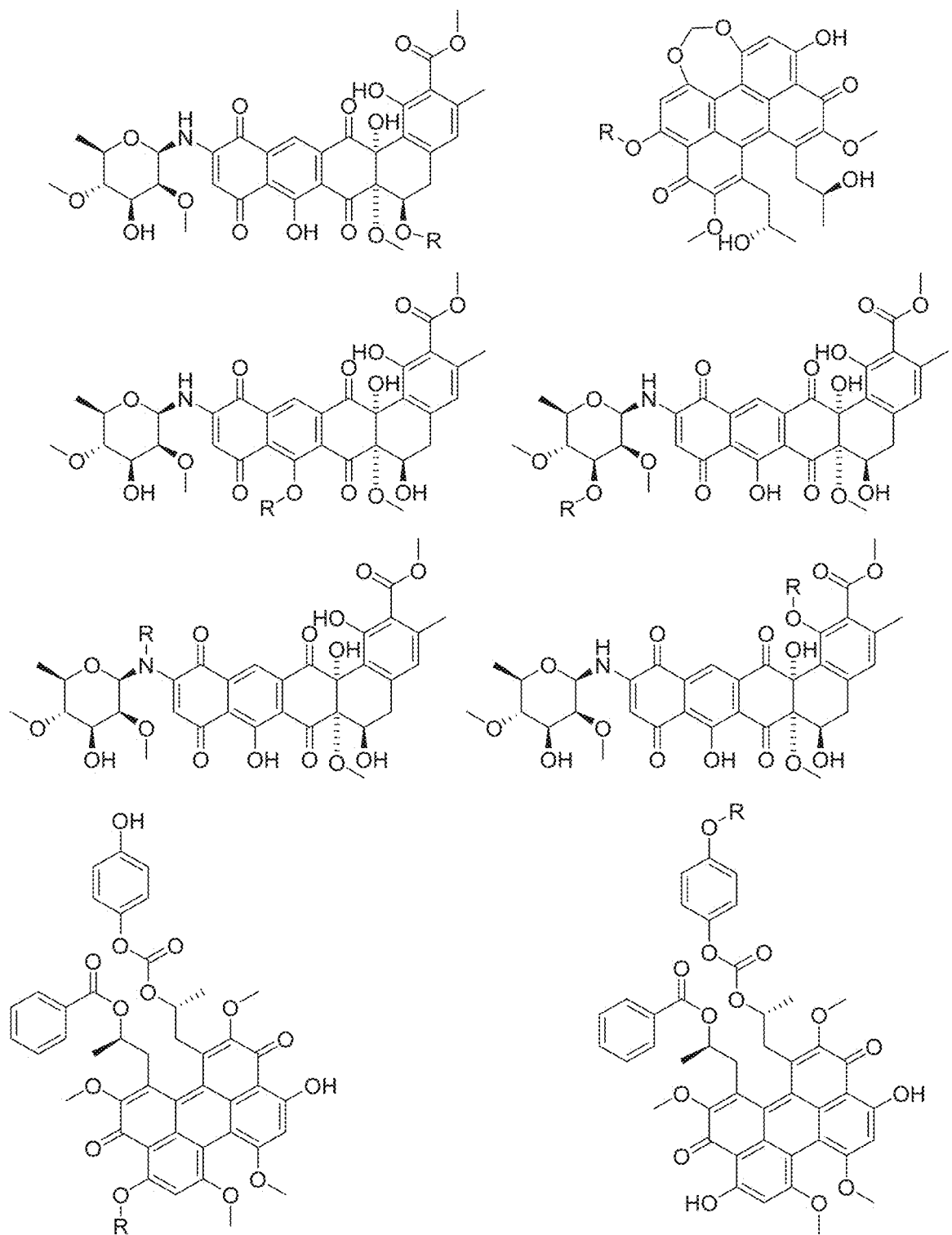
Figure 3L:
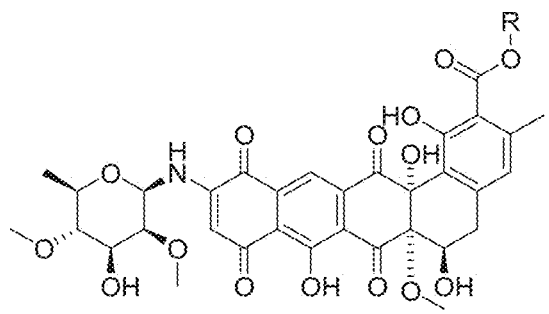
Figure 3M:
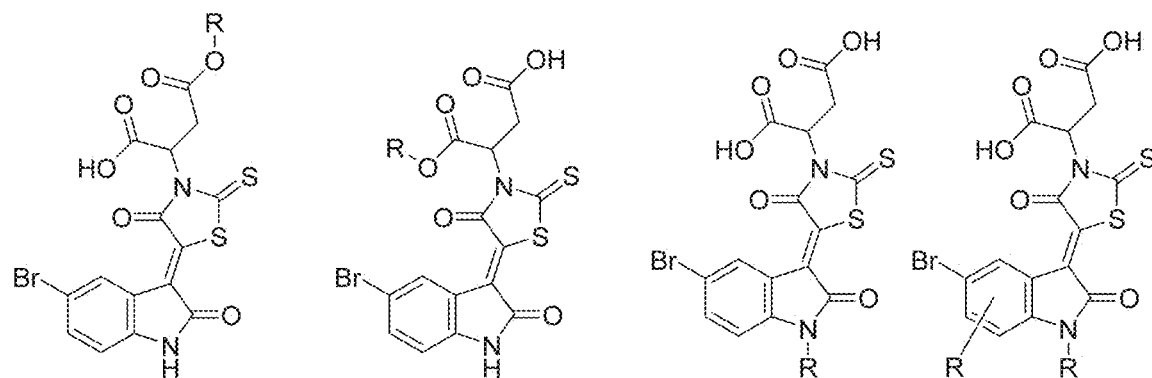
Figure 3N:
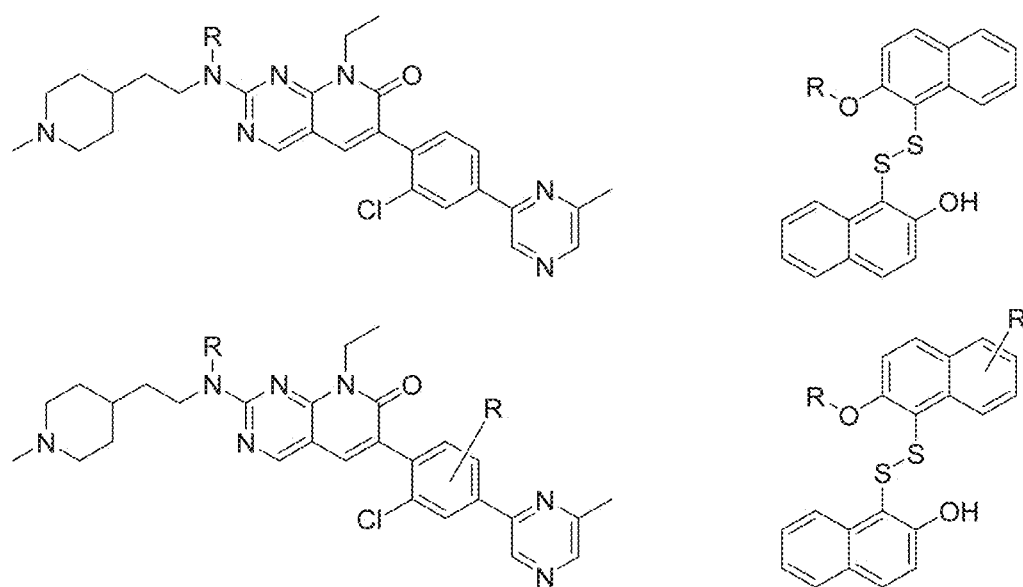
Figure 3O:
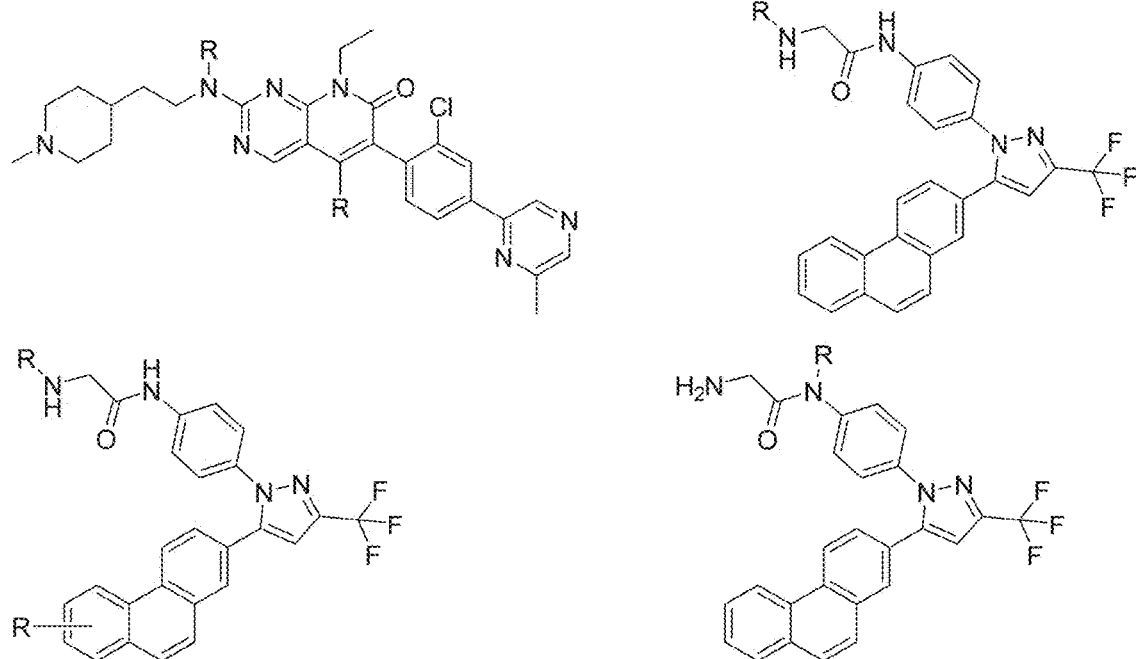
Figure 3P:
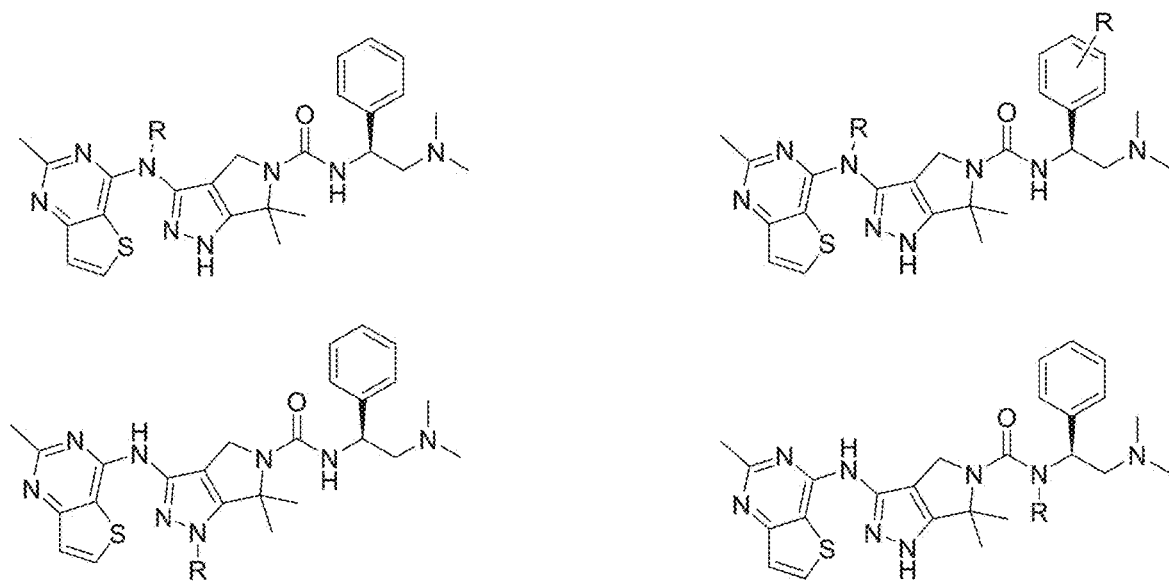
Figure 3Q:
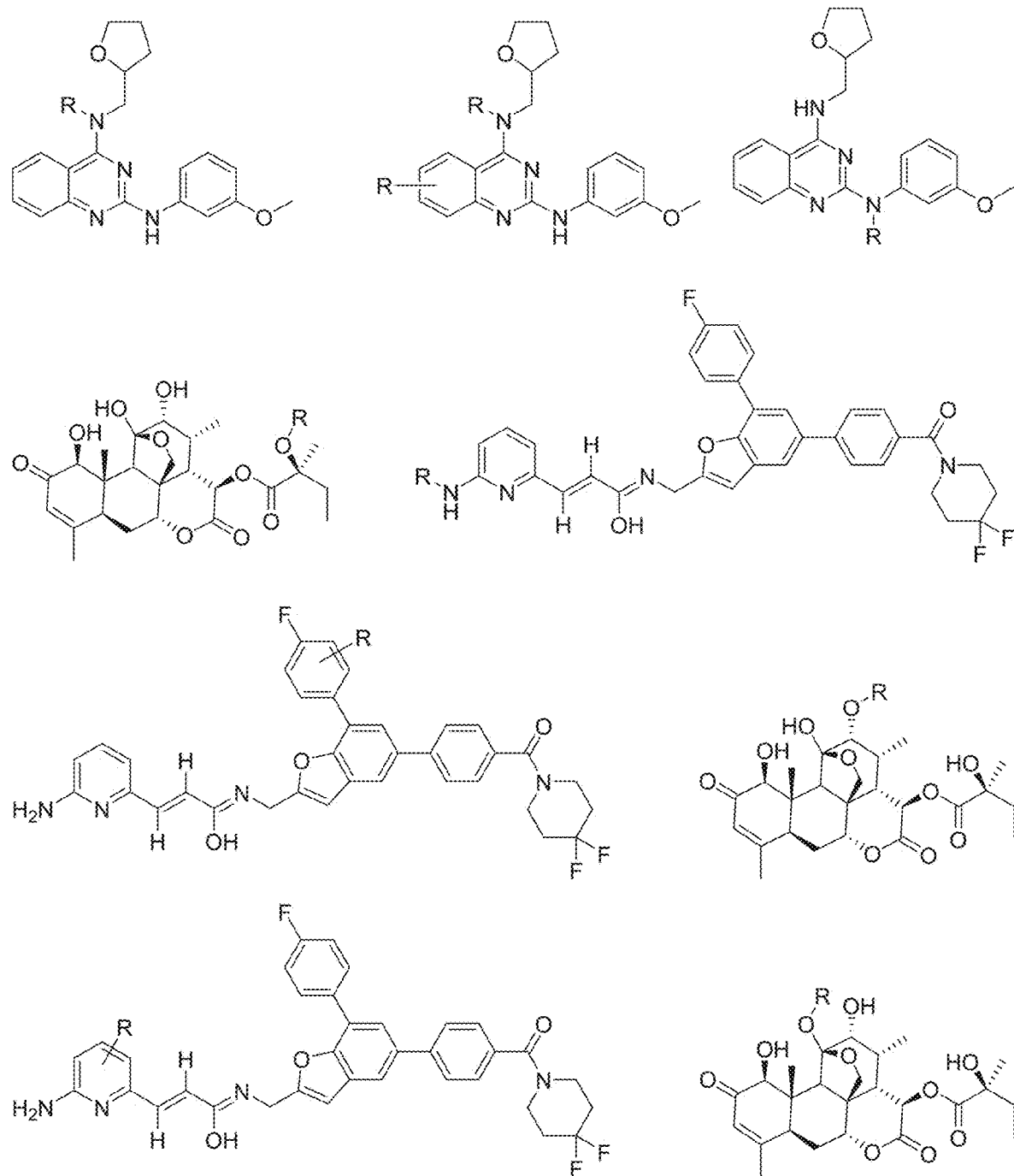
Figure 3R:
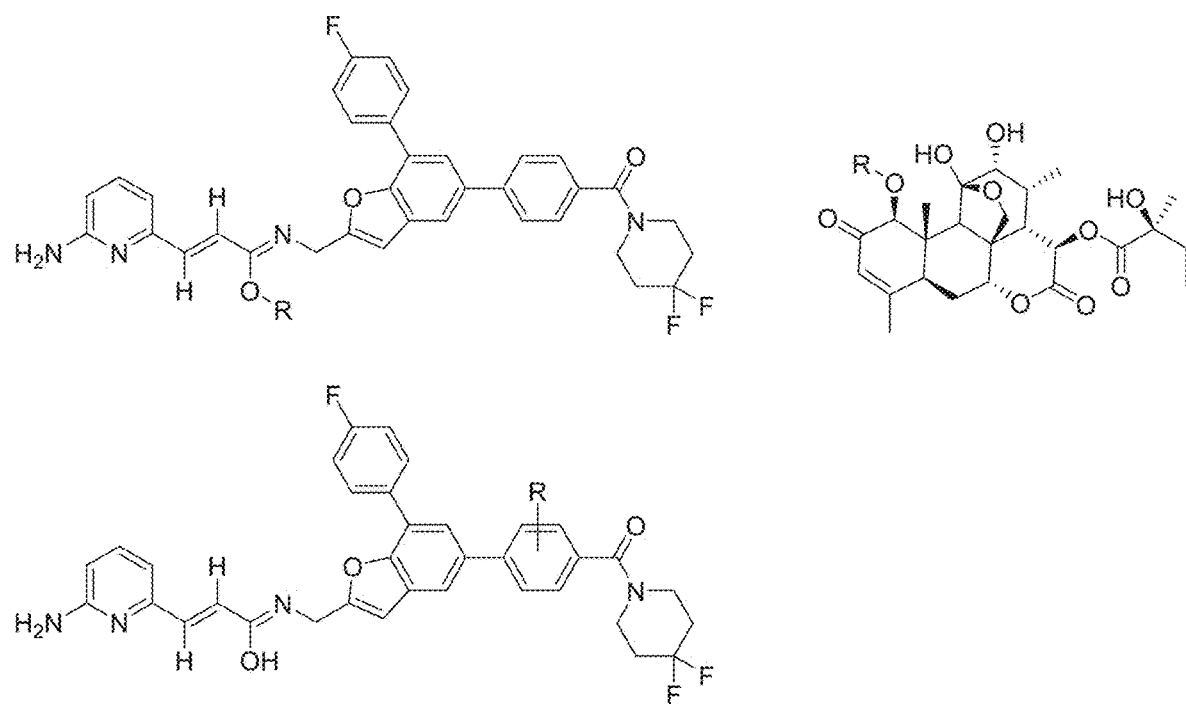
Figure 3S:
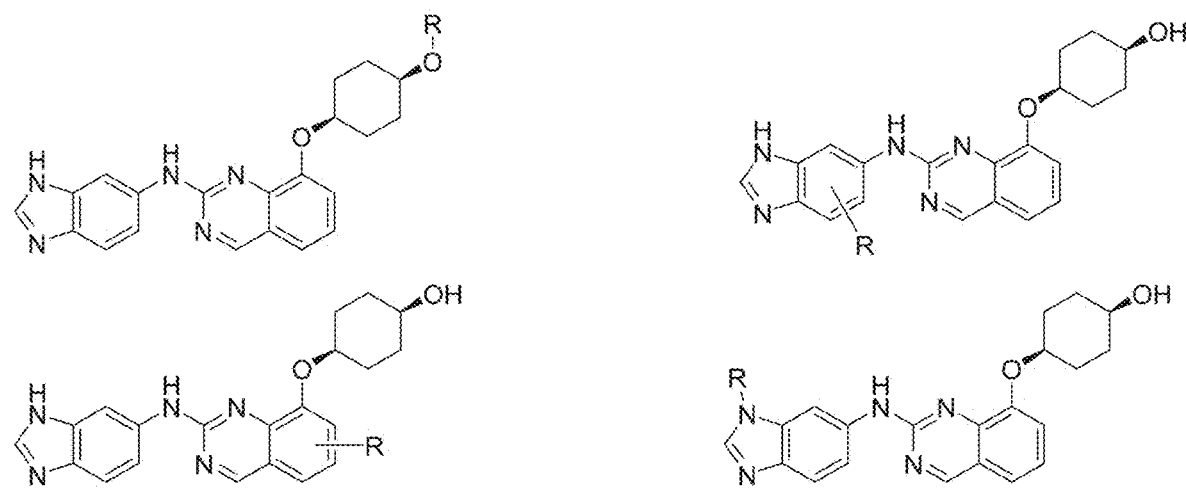
Figure 3T:
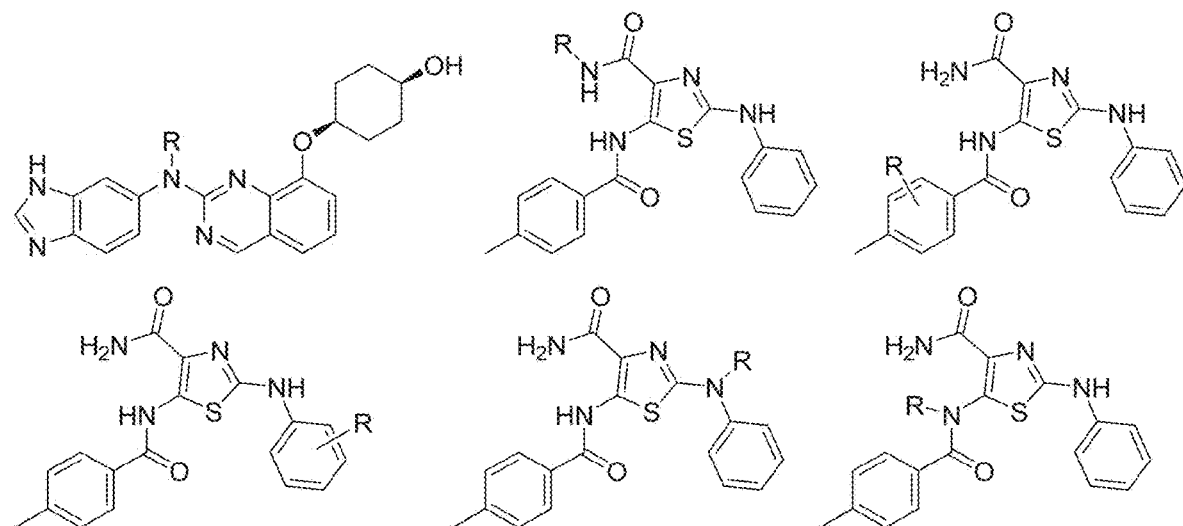
Figure 3U:
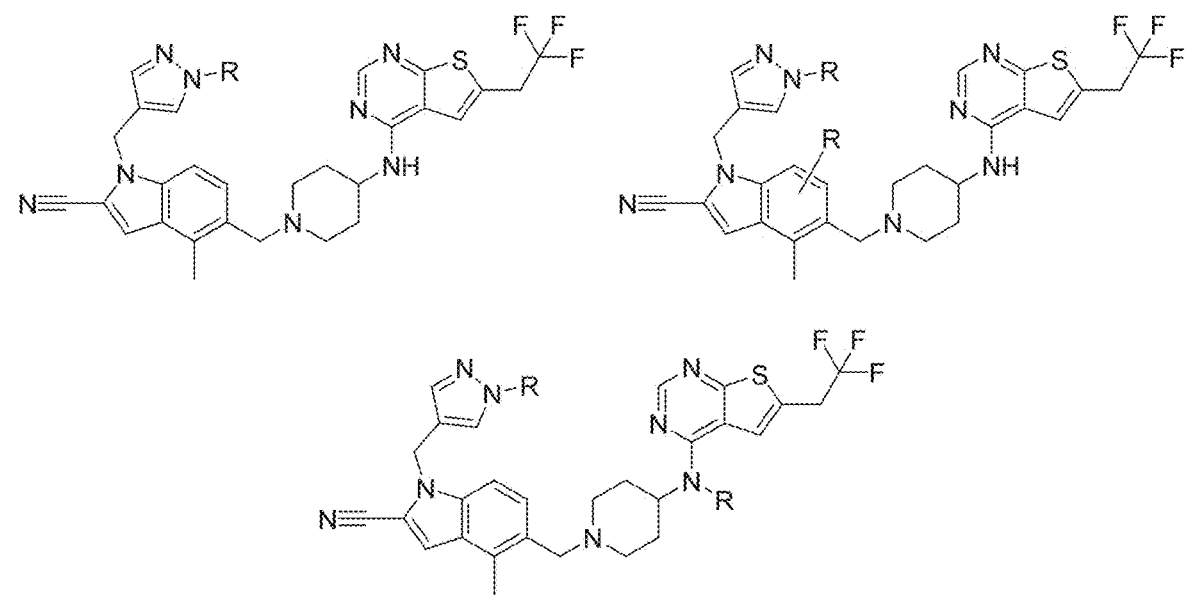
Figure 3V:
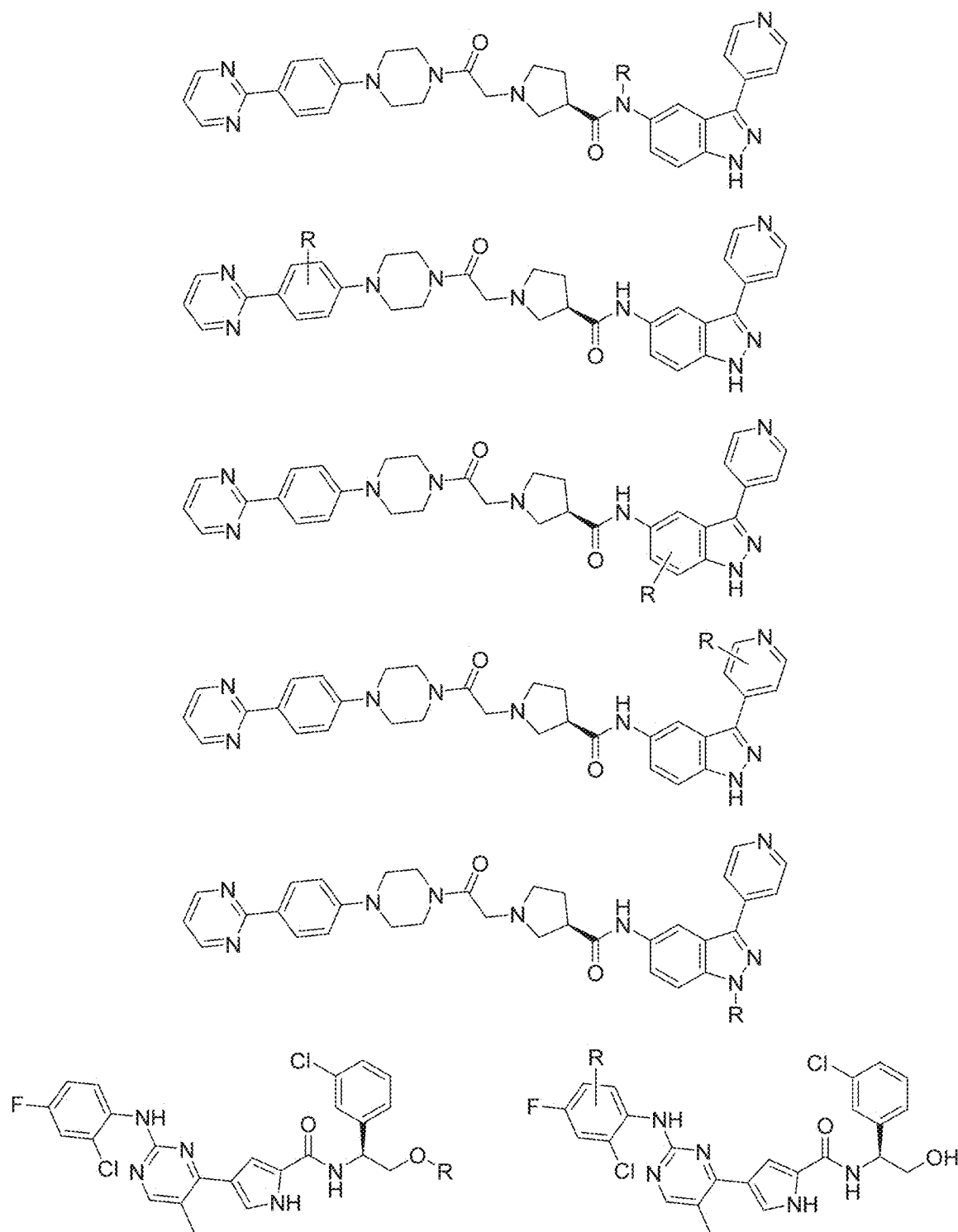
Figure 3W:
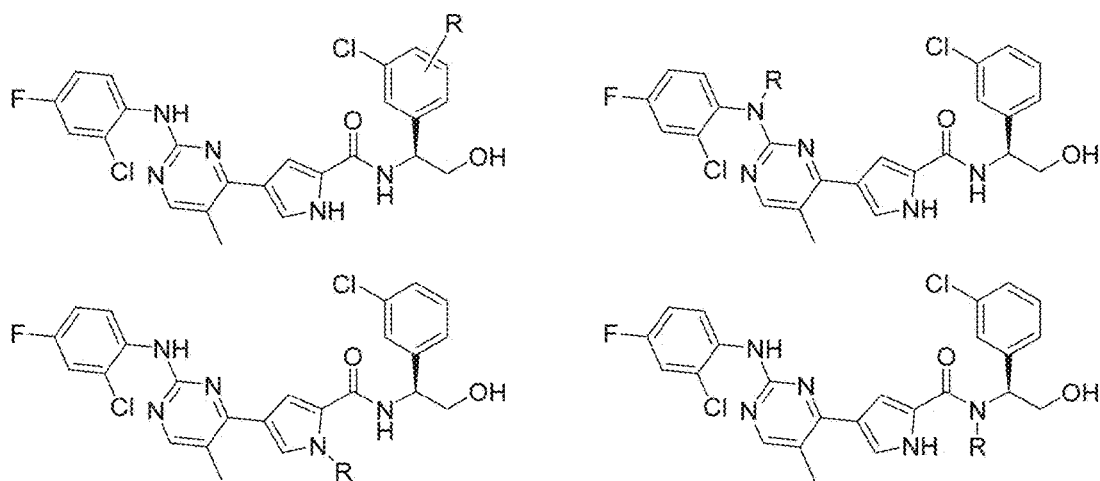
Figure 3X:
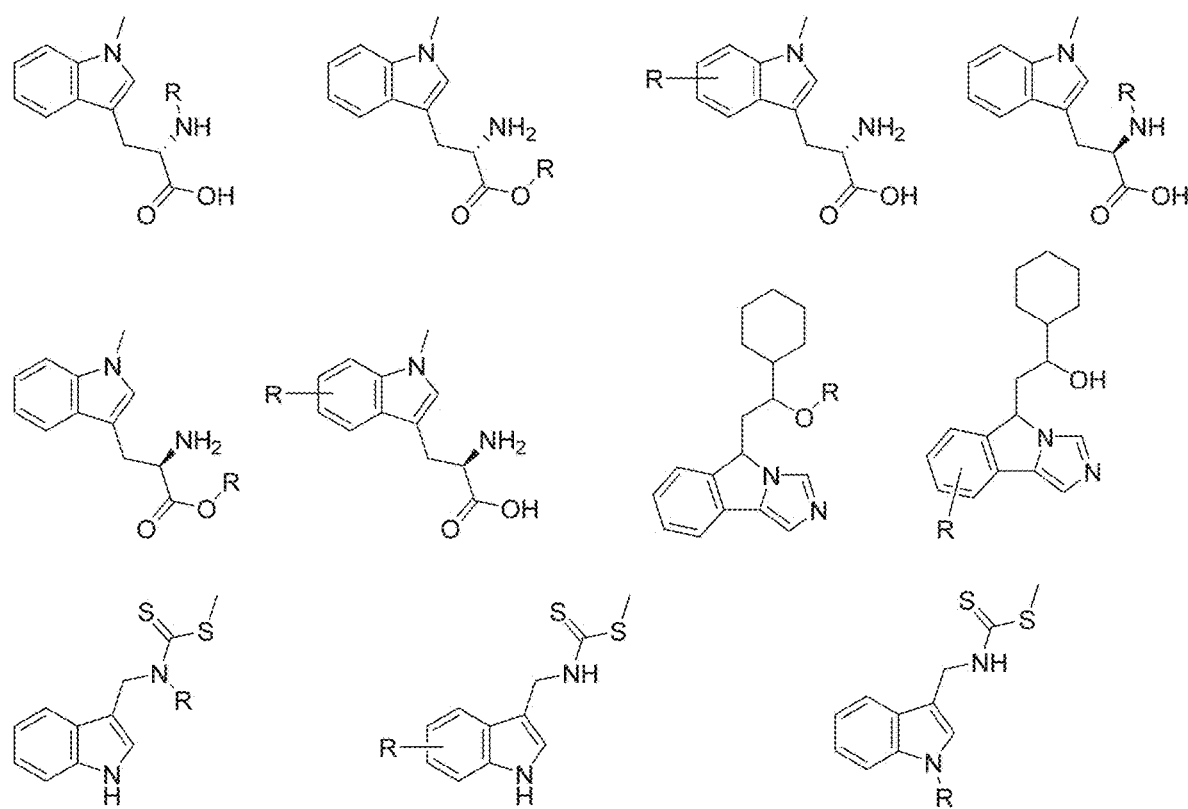
Figure 3Y:
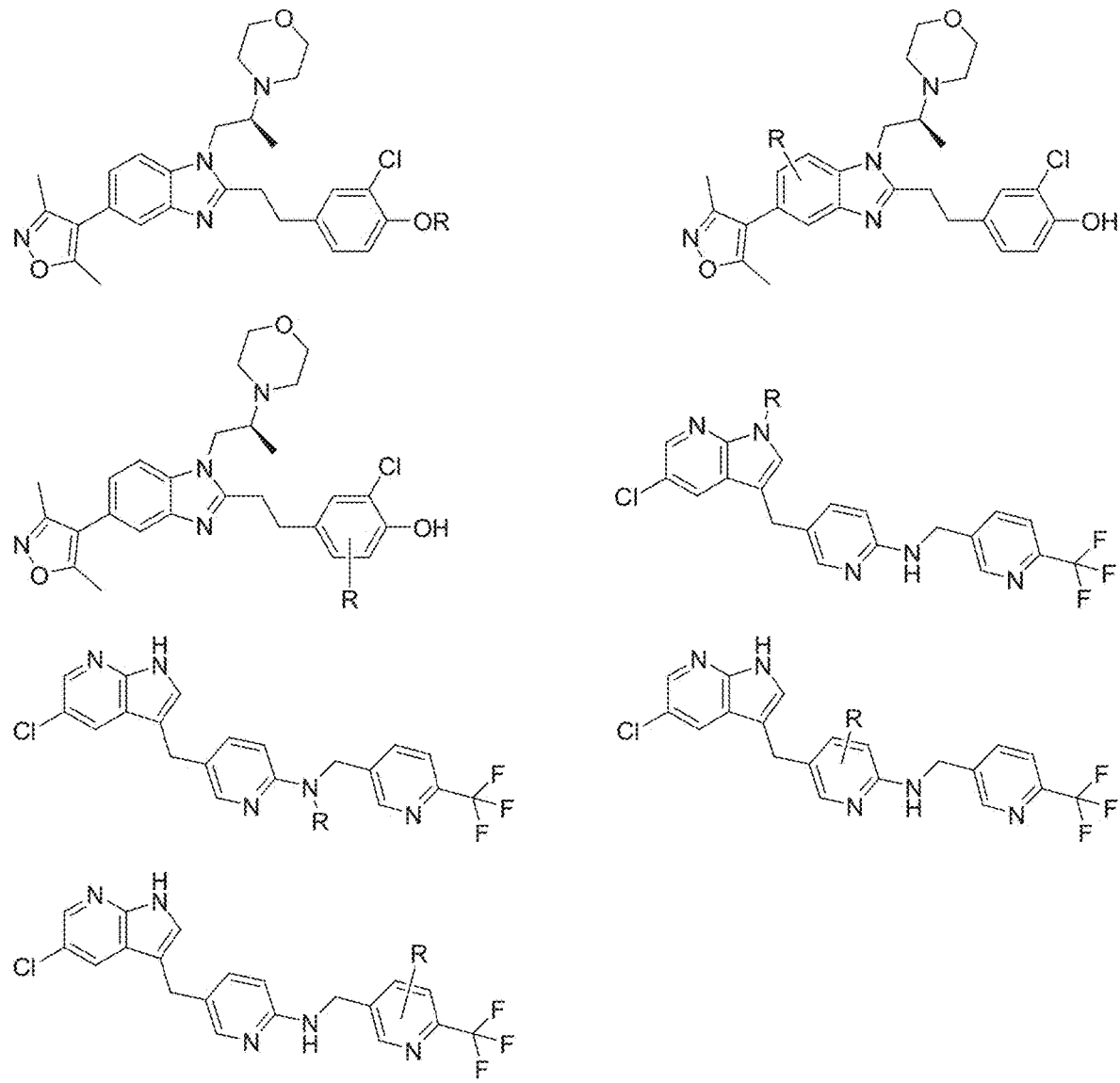
Figure 3Z:
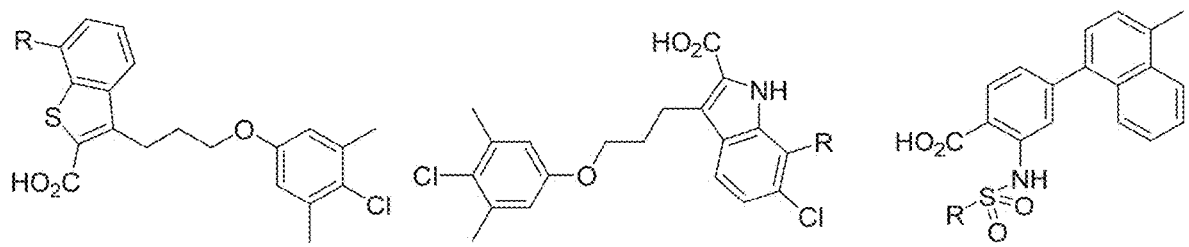
Figure 3A:
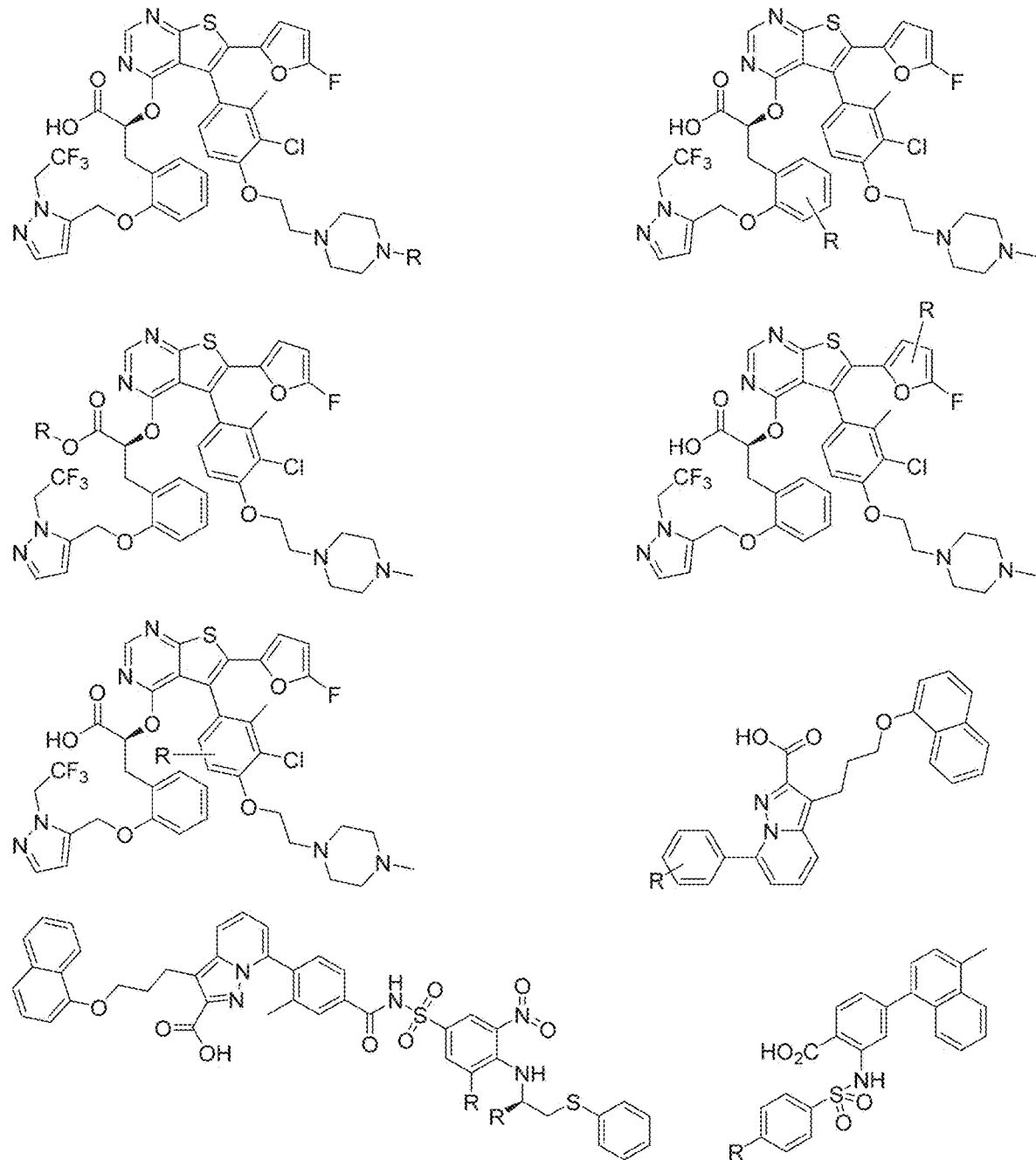
Figure 3B:
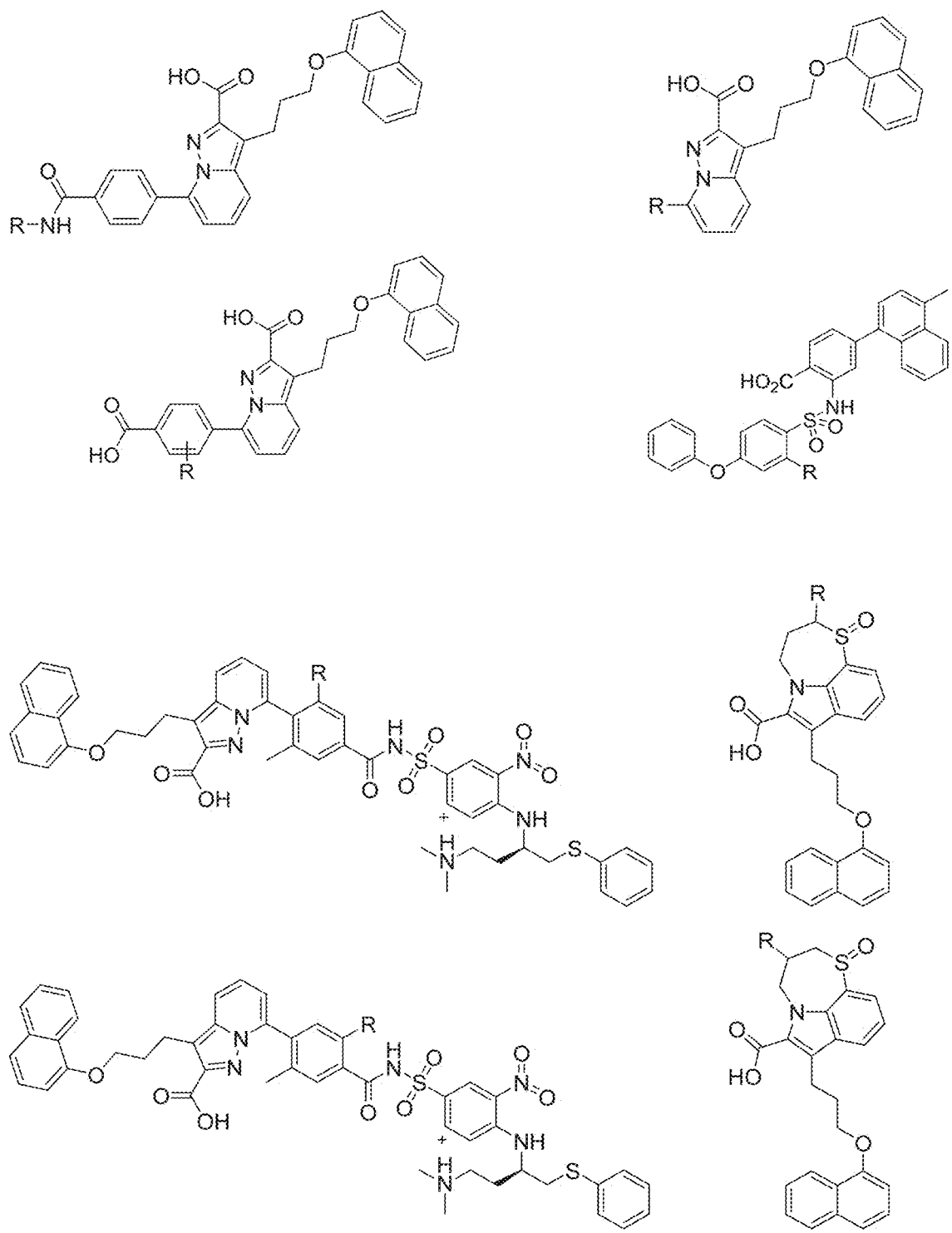
Figure 3D:
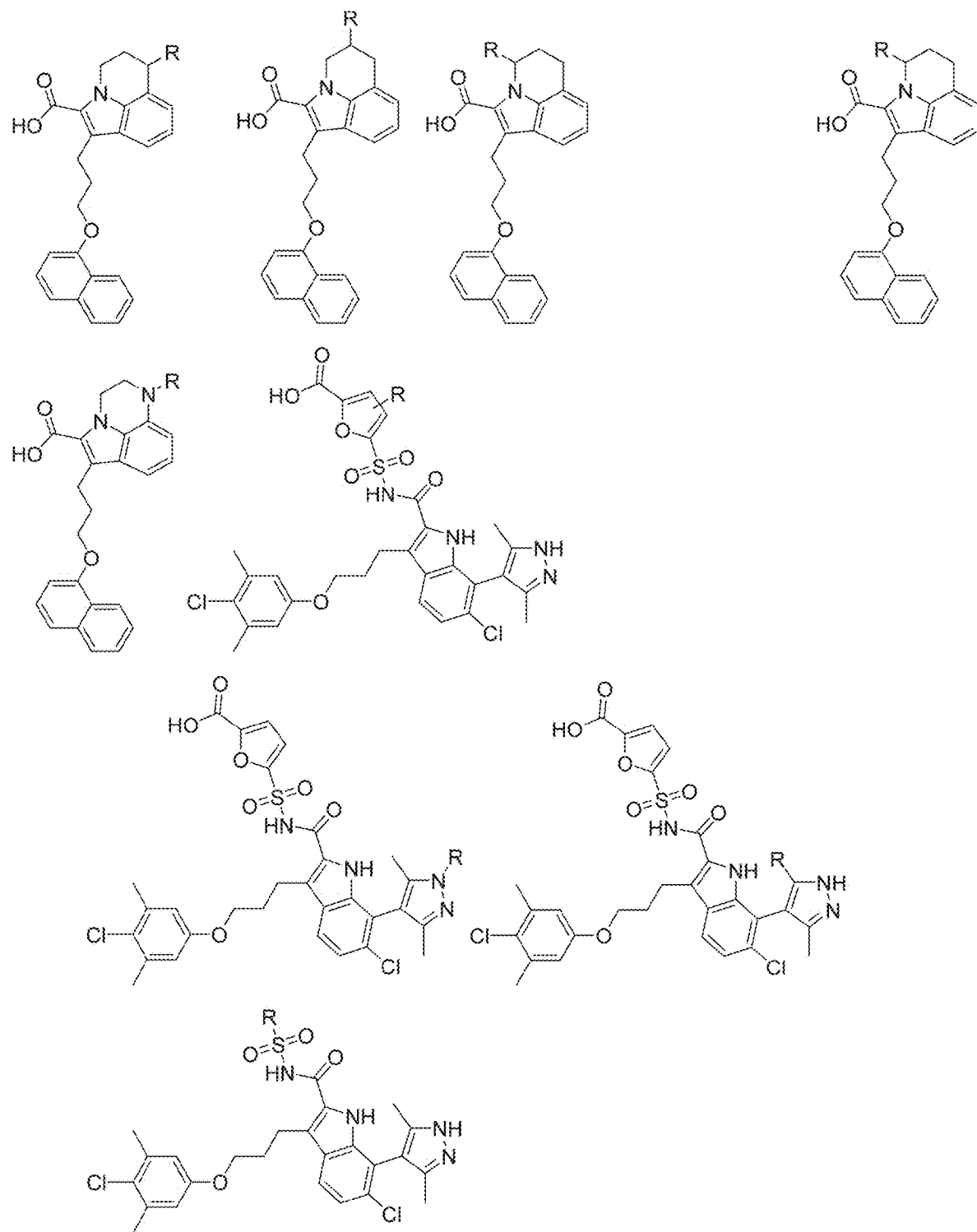
Figure 3E:
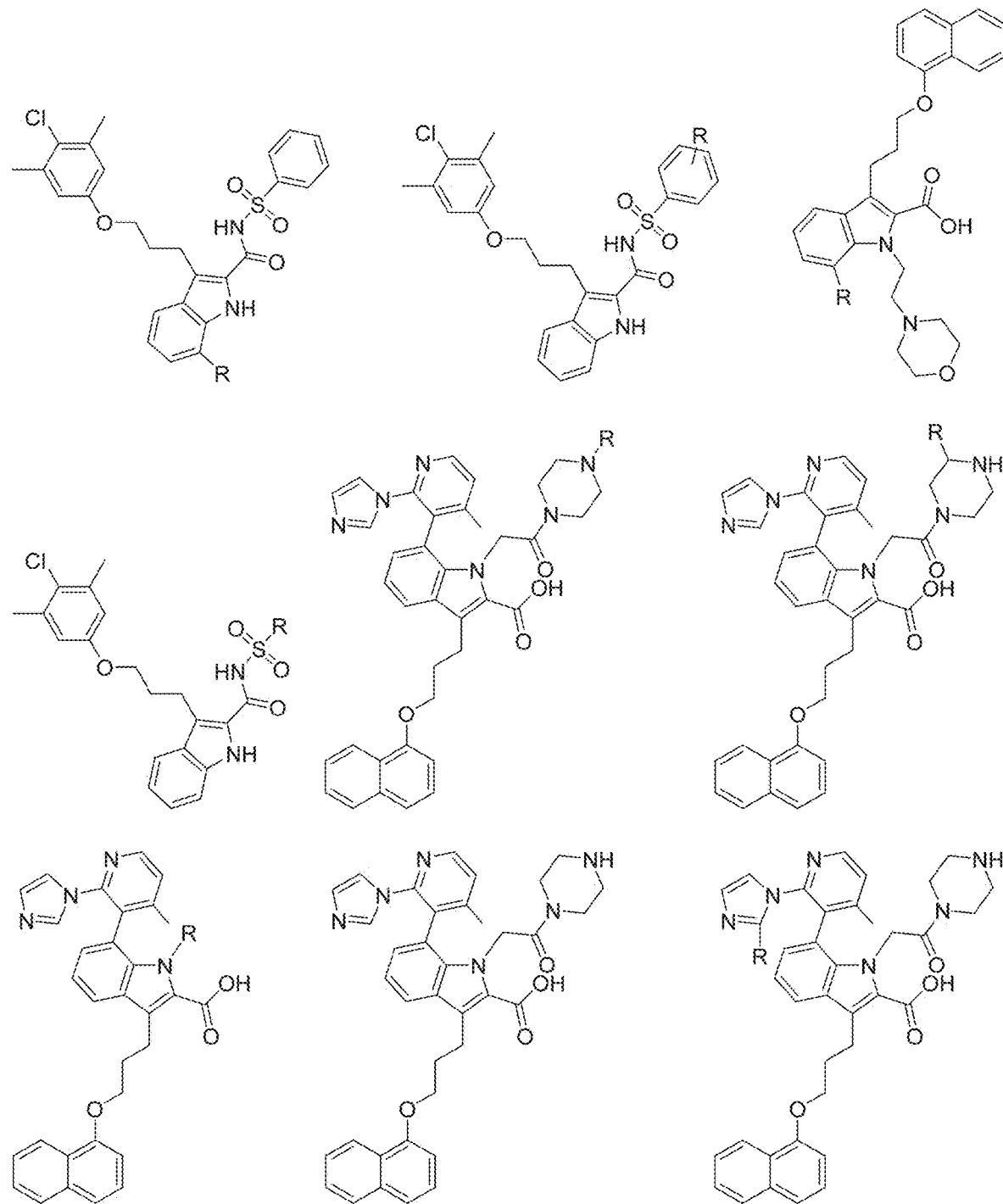
Figure 3H:
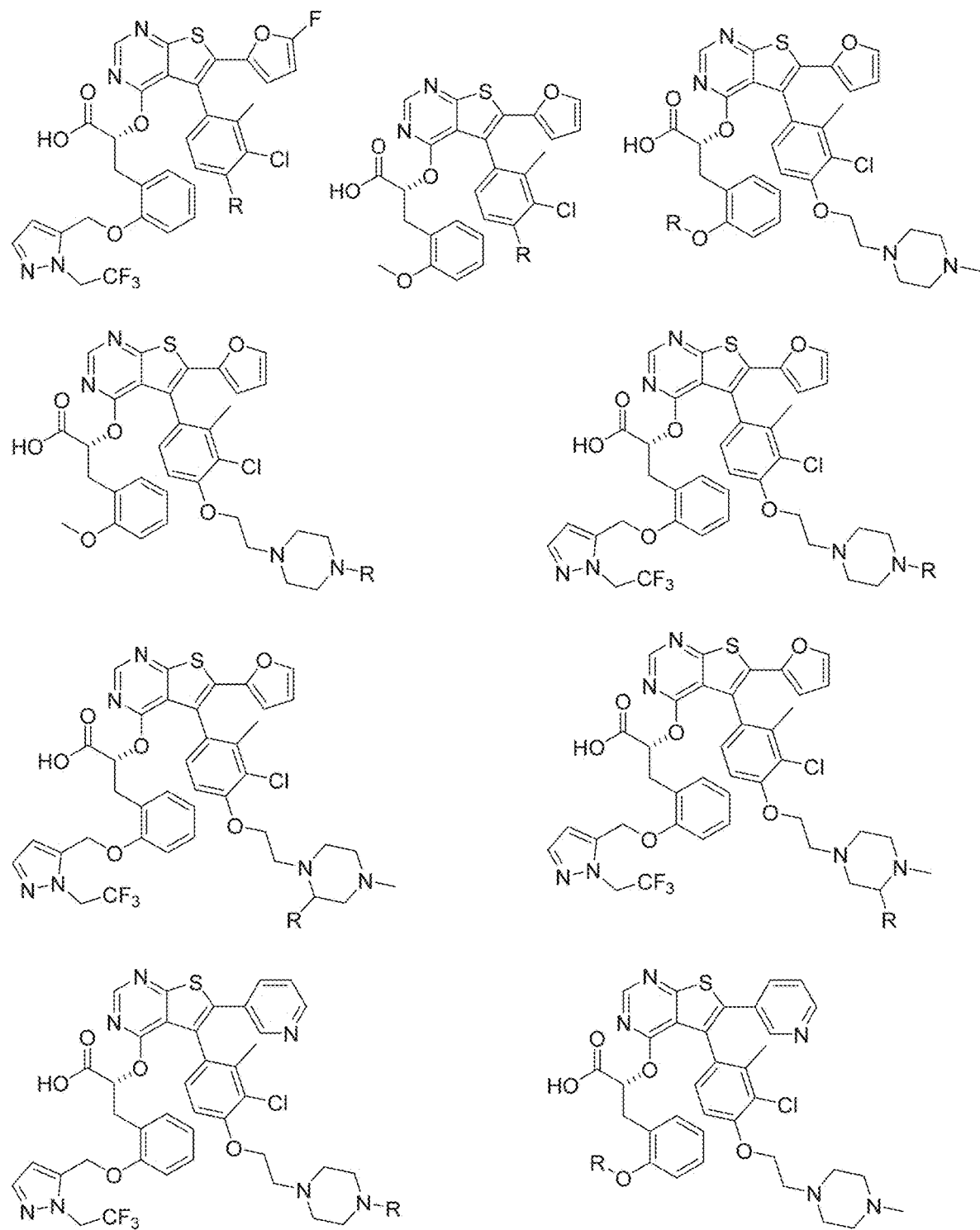

FIG. 3A-3B present examples of MEK1 Targeting Ligands, including PD318088, Trametinib and G-573, wherein R is the point at which the Linker is attached.

FIG. 3C presents examples of KIT Targeting Ligands, including Regorafenib, wherein R is the point at which the Linker is attached.

FIG. 3D-3E present examples of HIV Reverse Transcriptase Targeting Ligands, including Efavirenz, Tenofovir, Emtricitabine, Ritonavir, Raltegravir, and Atazanavir, wherein R is the point at which the Linker is attached.

FIG. 3F-3G present examples of HIV Protease Targeting Ligands, including Ritonavir, Raltegravir, and Atazanavir, wherein R is the point at which the Linker is attached.

Figure 3I:
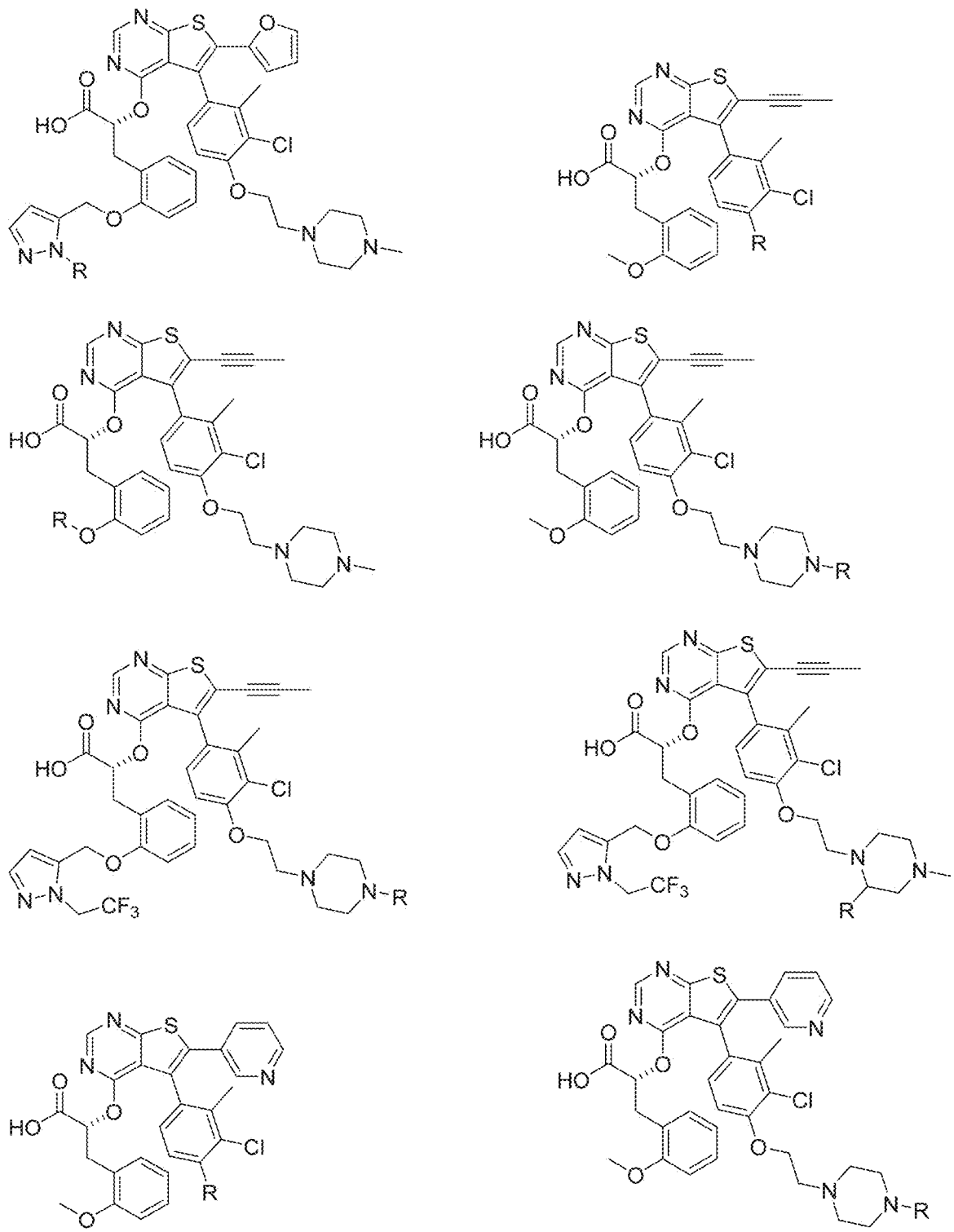
Figure 3L:
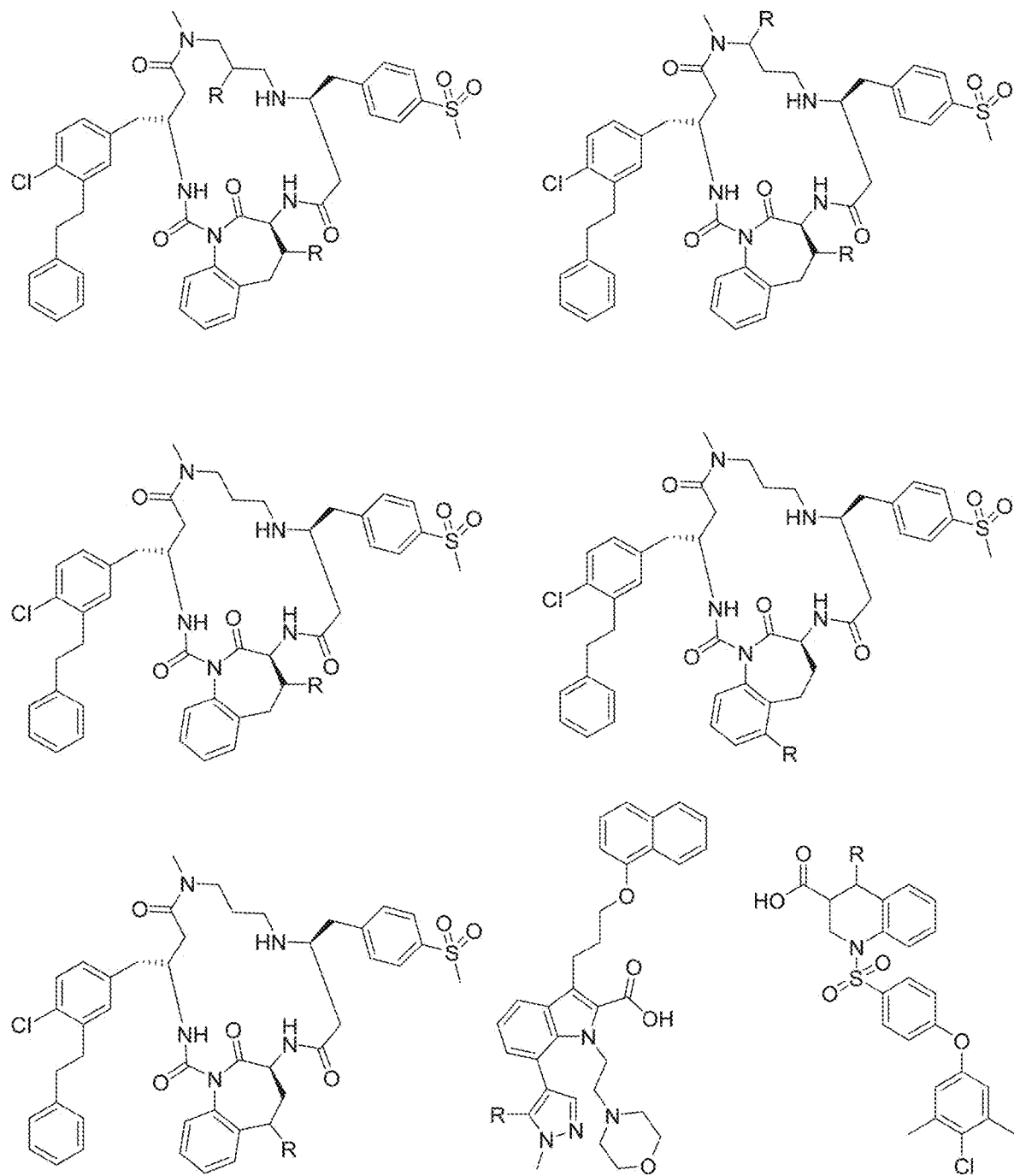
Figure 3M:
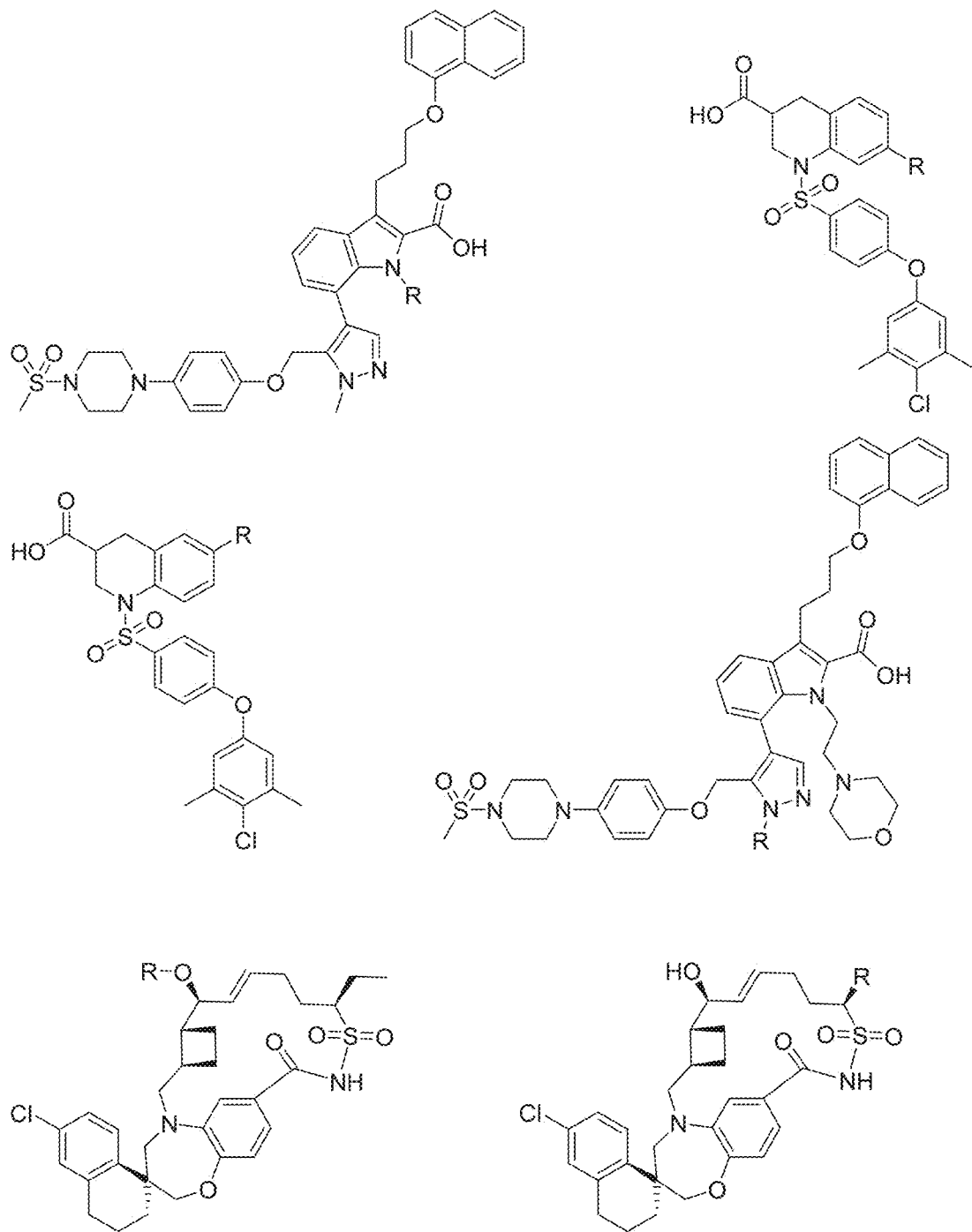
Figure 3O:
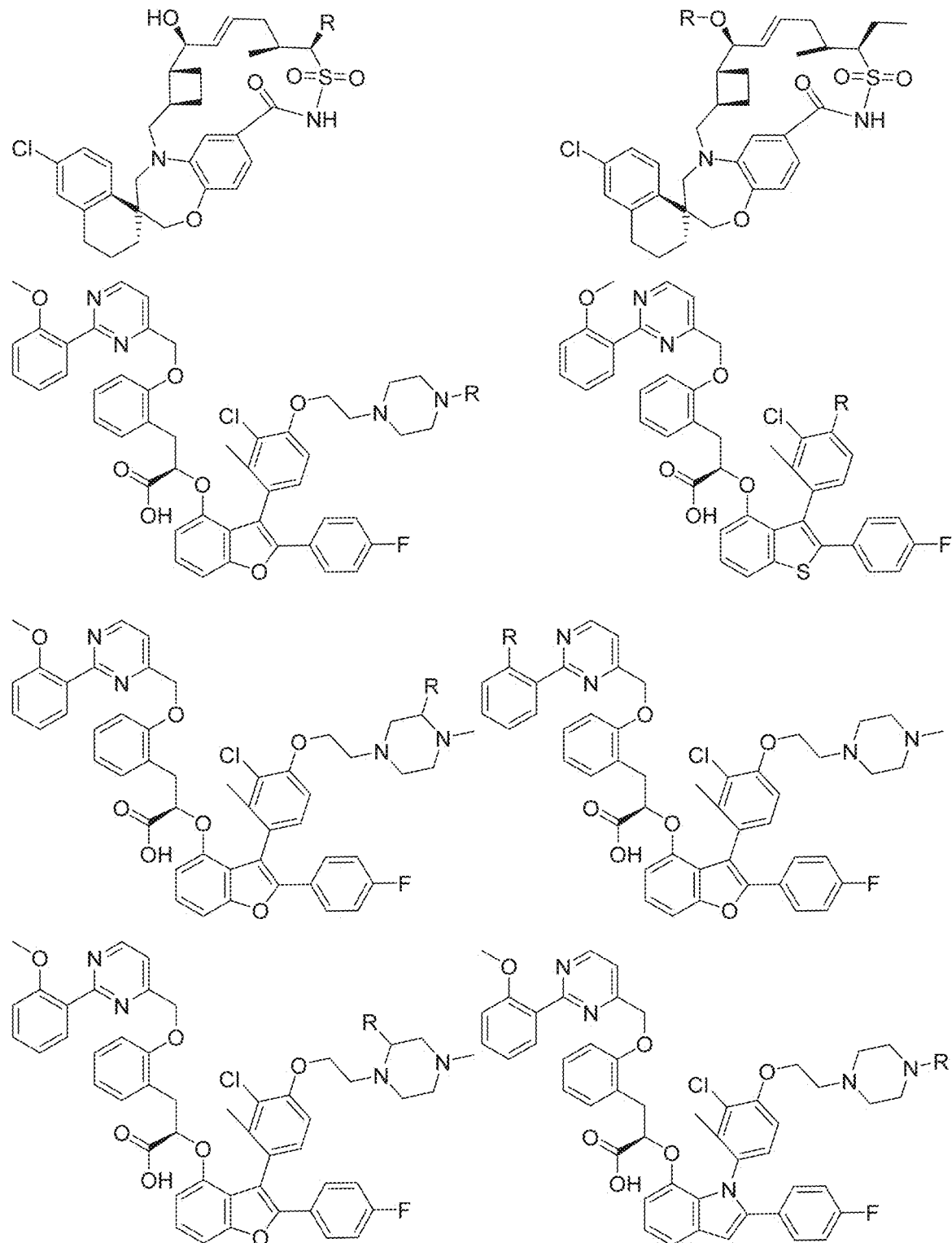
Figure 3P:
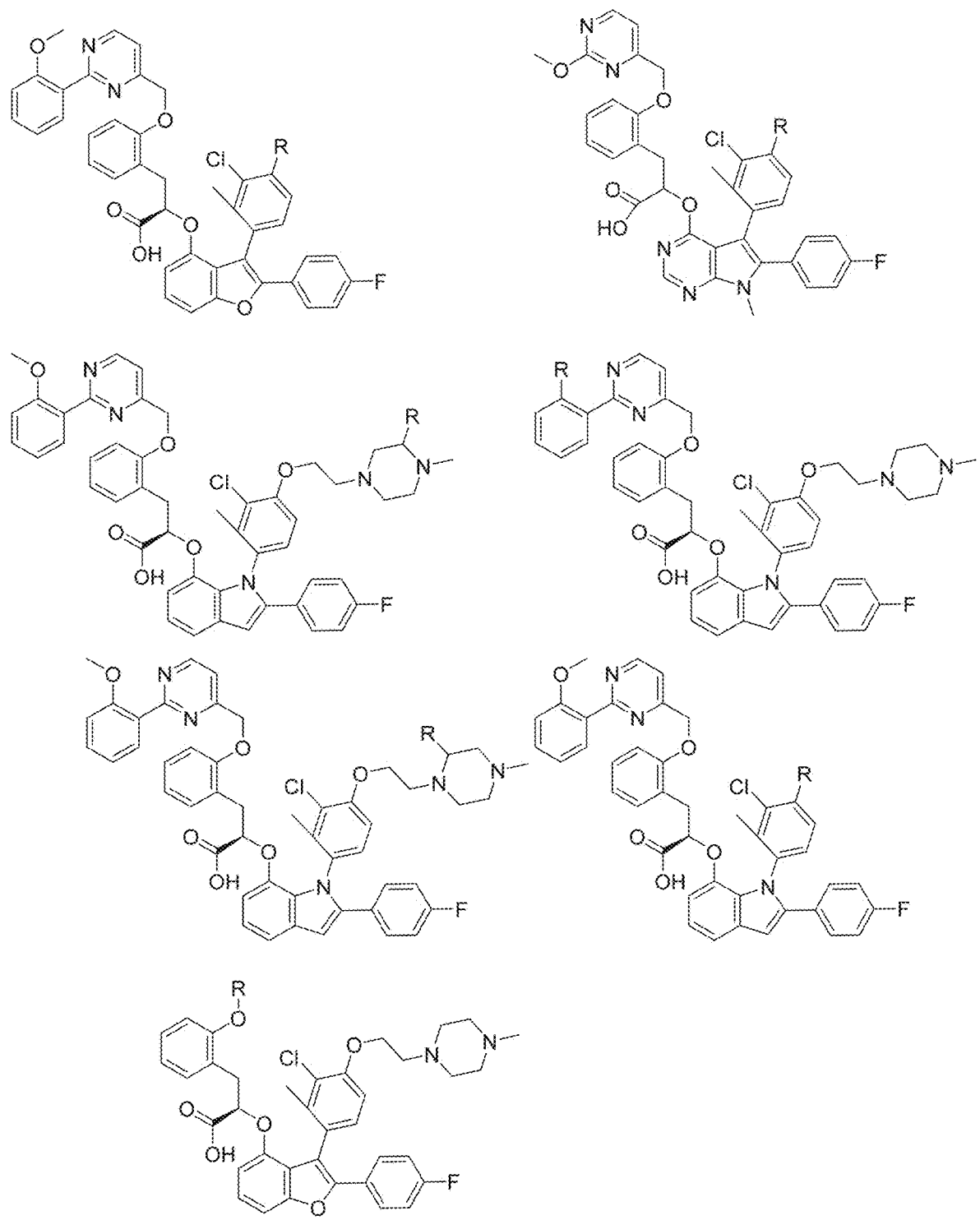
Figure 3Q:
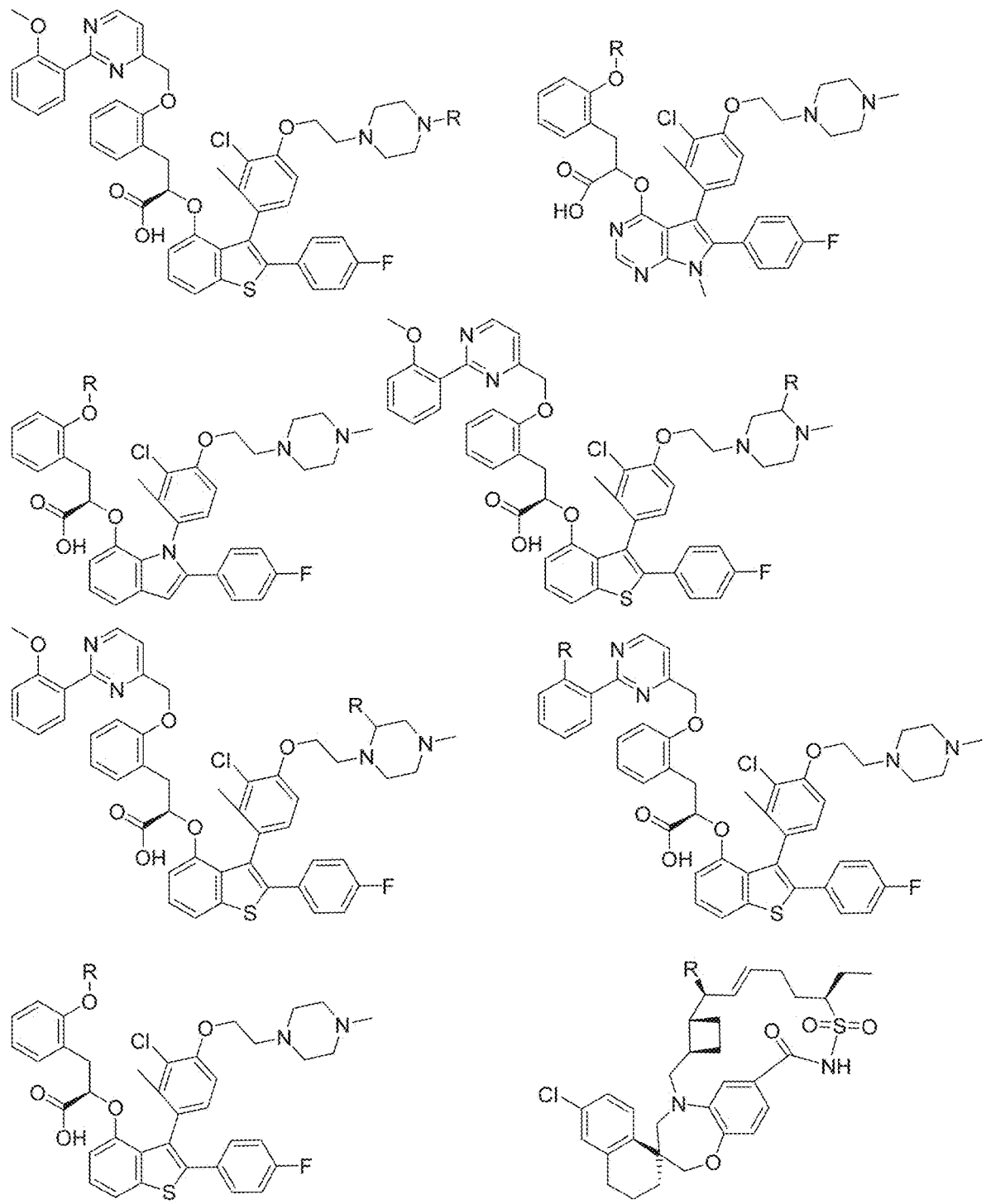
Figure 3R:
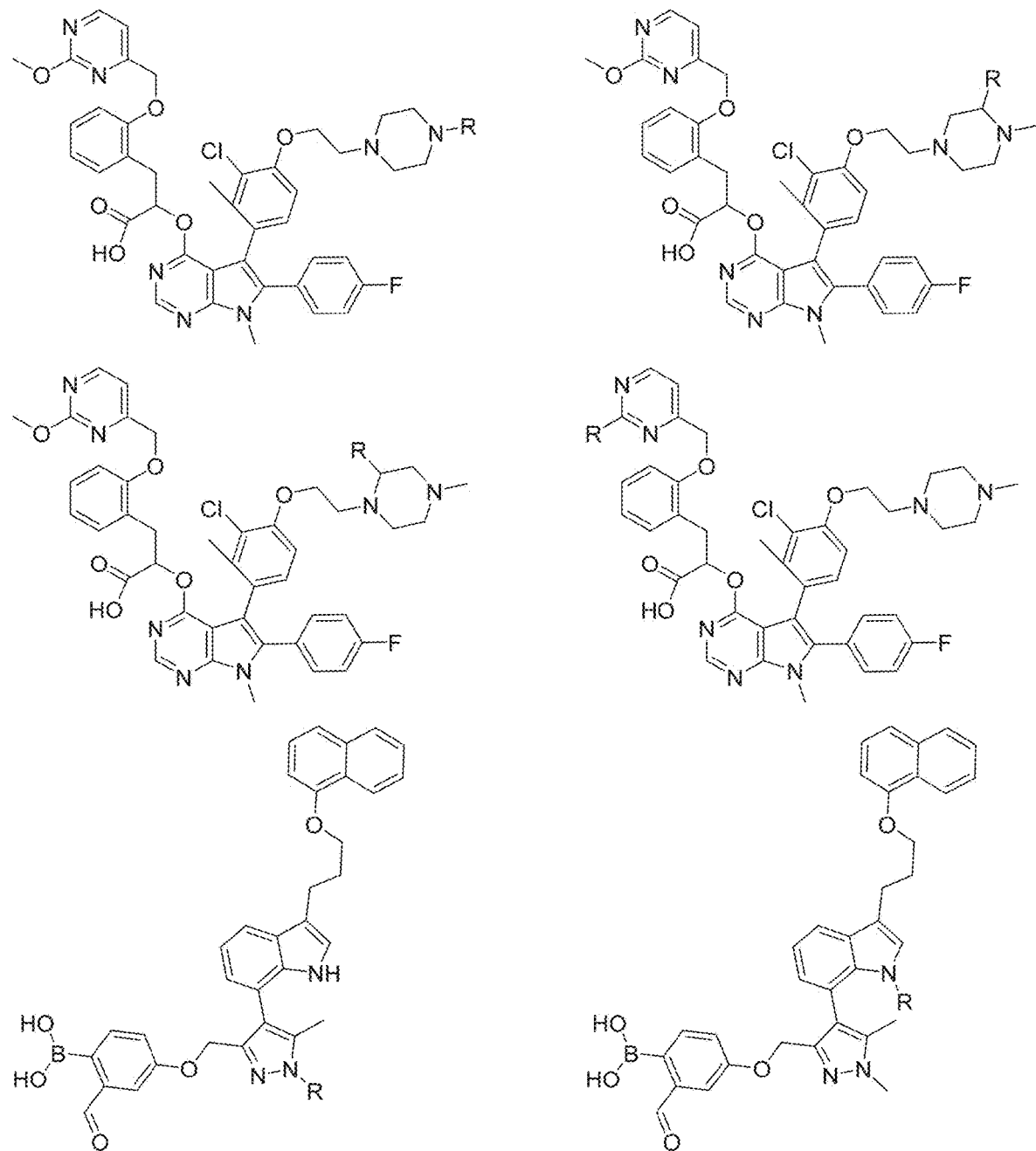
Figure 3S:
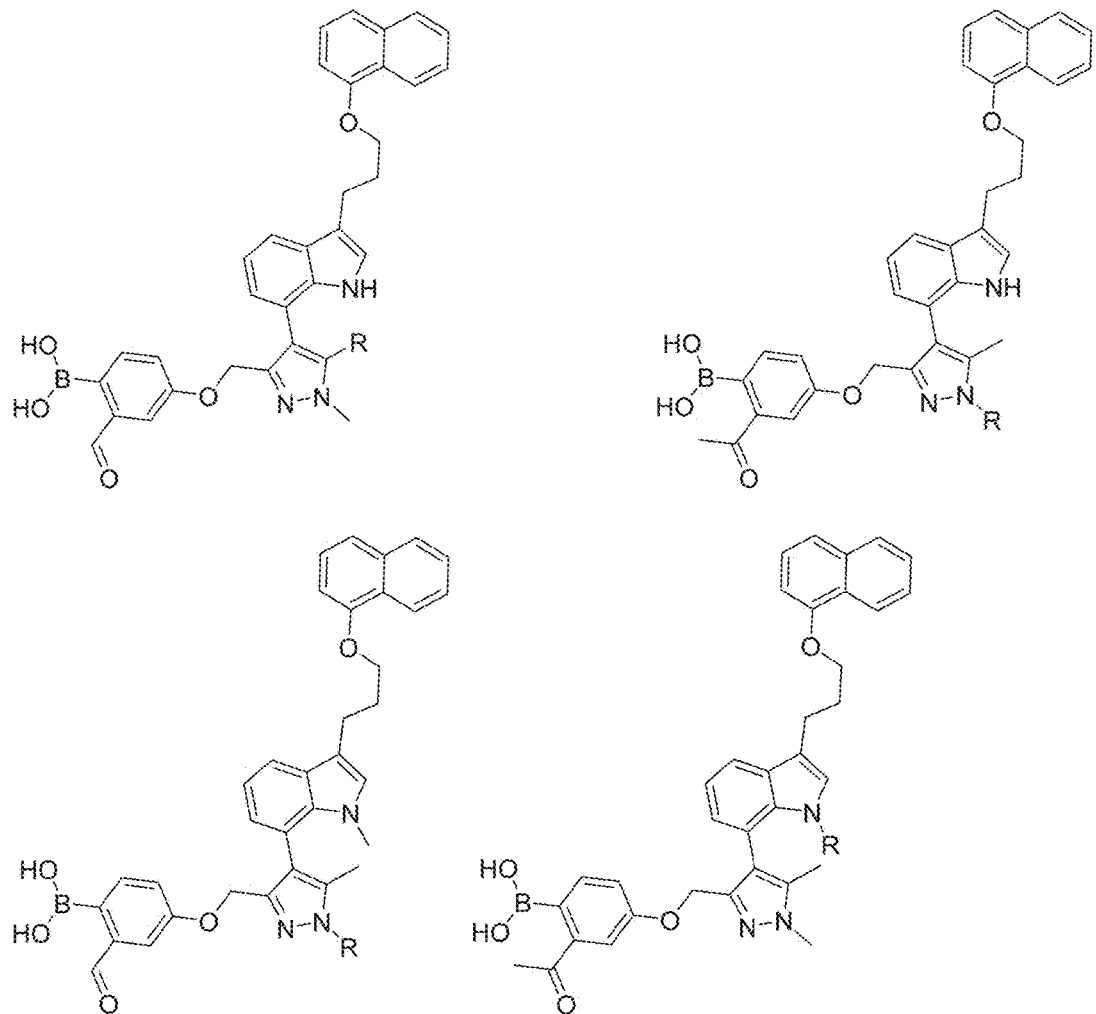
Figure 3T:
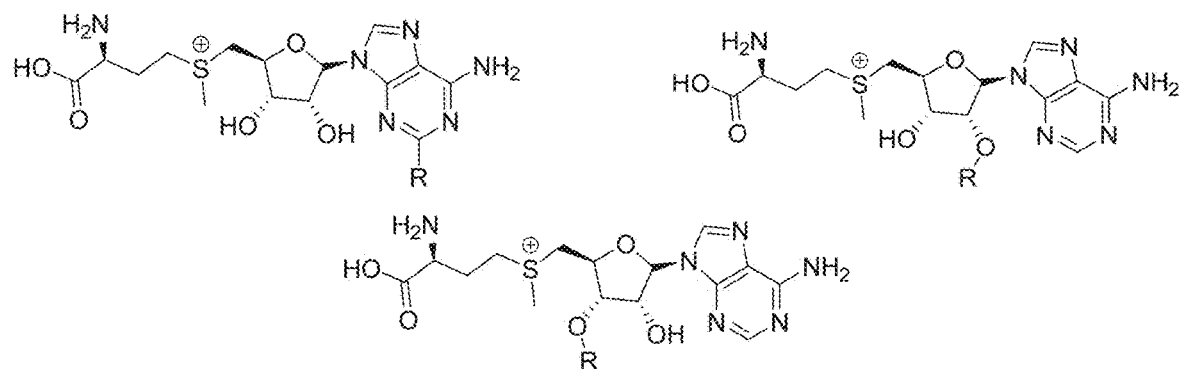
Figure 3U:
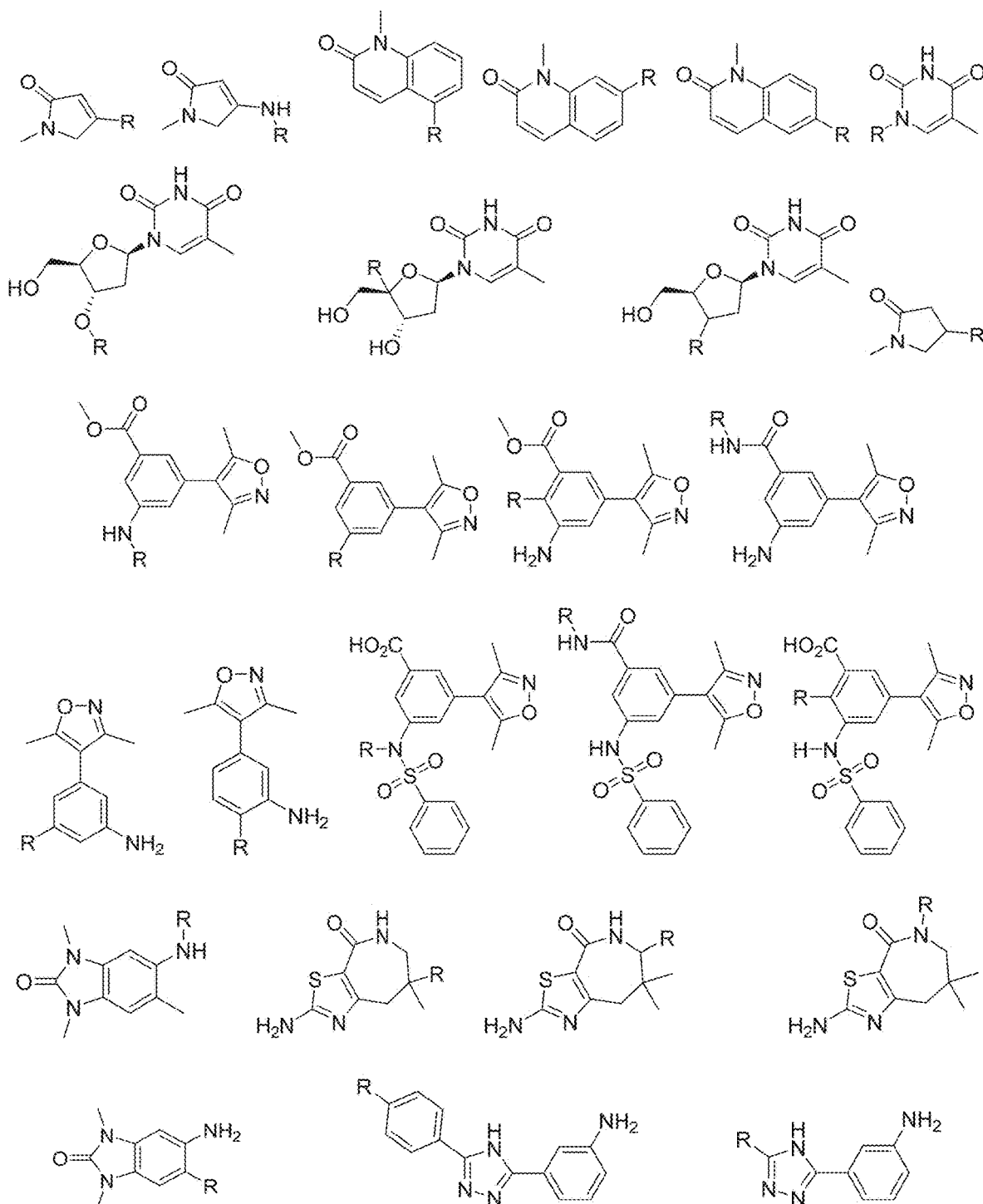
Figure 3V:
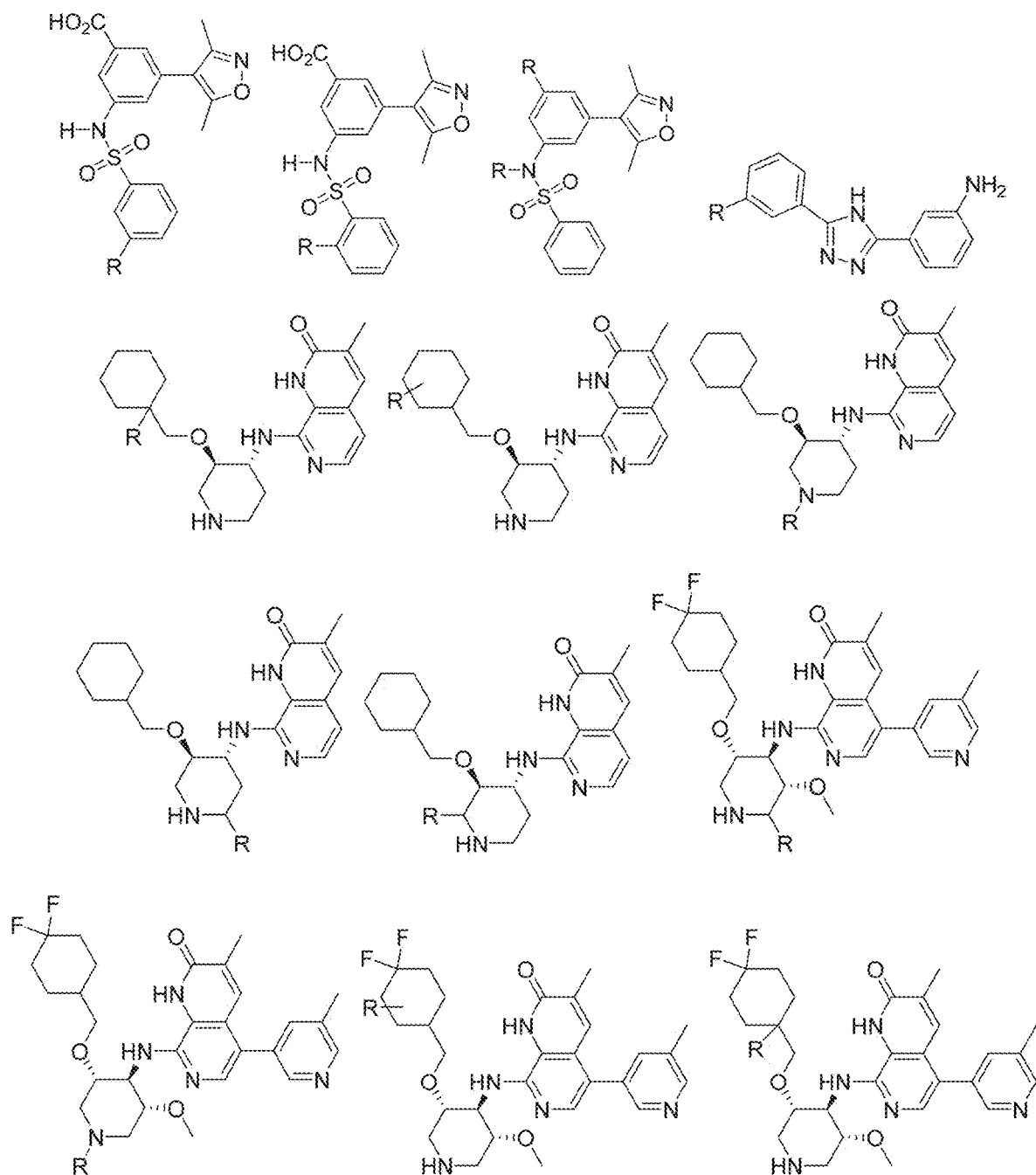
Figure 3W:
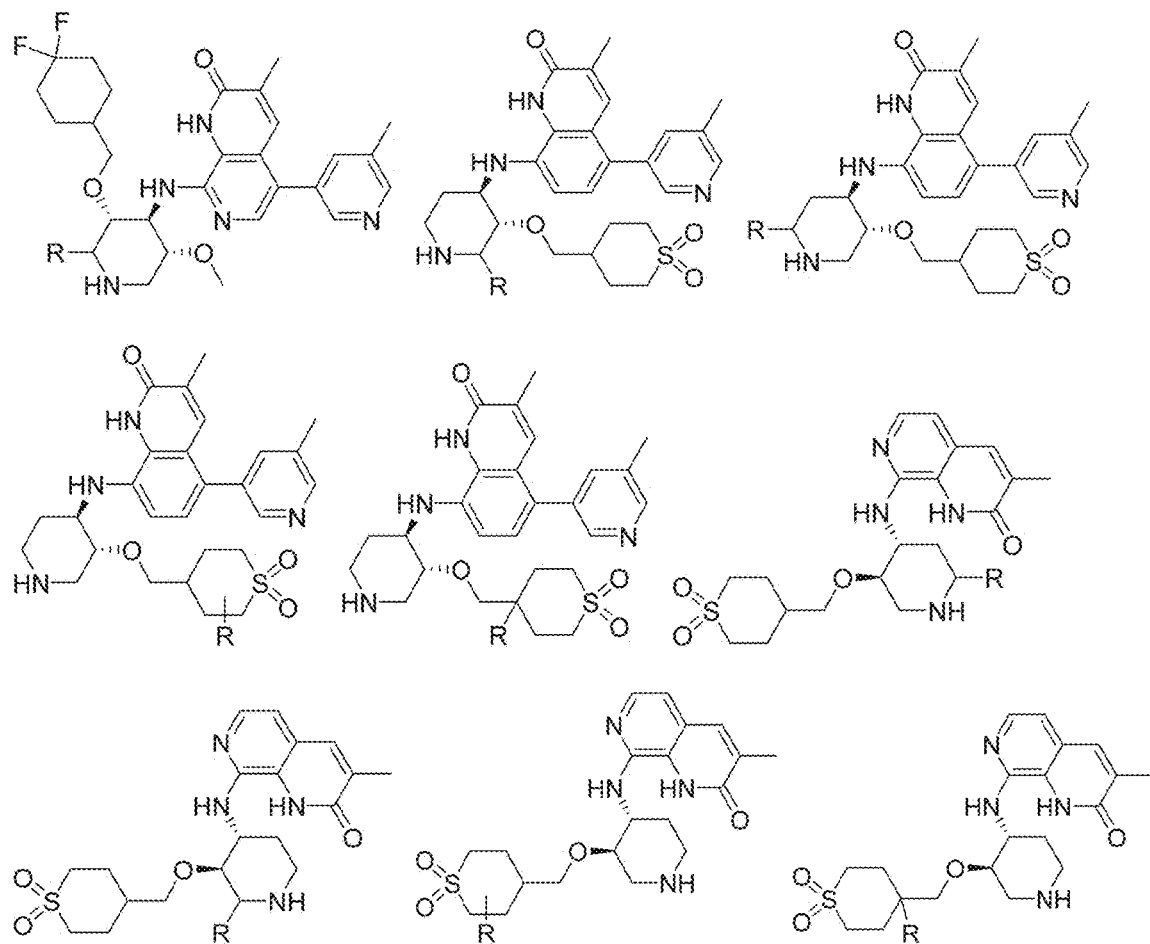
Figure 3X:
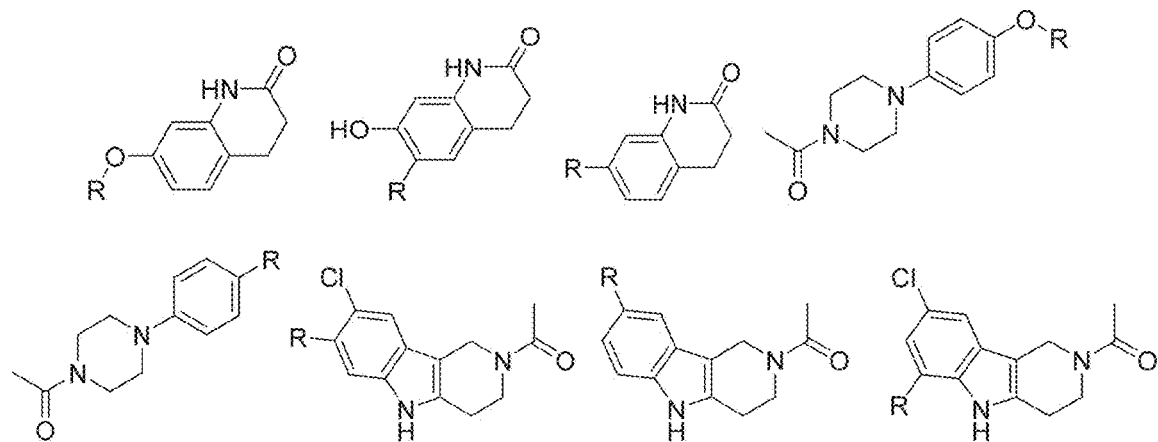
Figure 3Y:
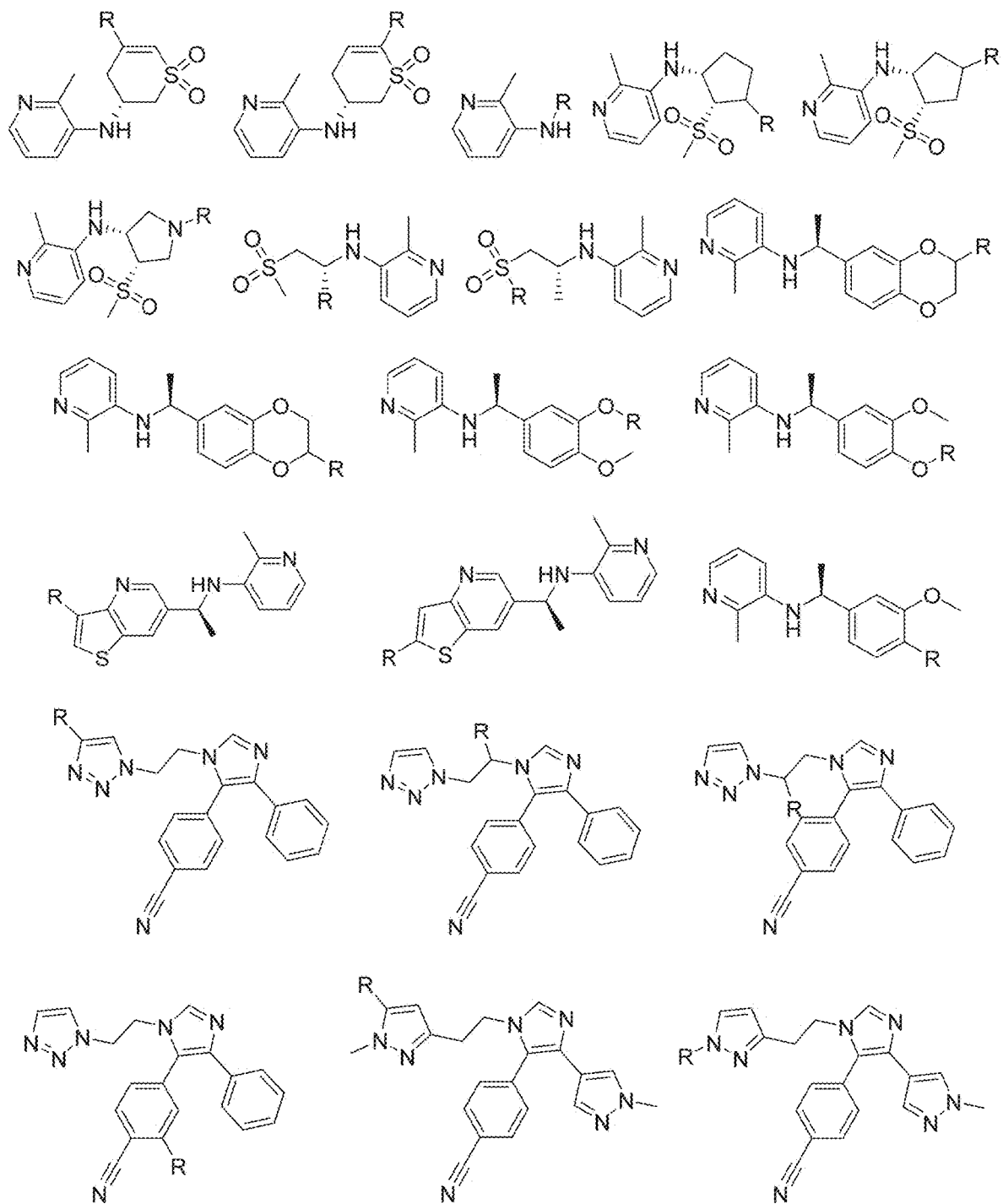
Figure 3Z:
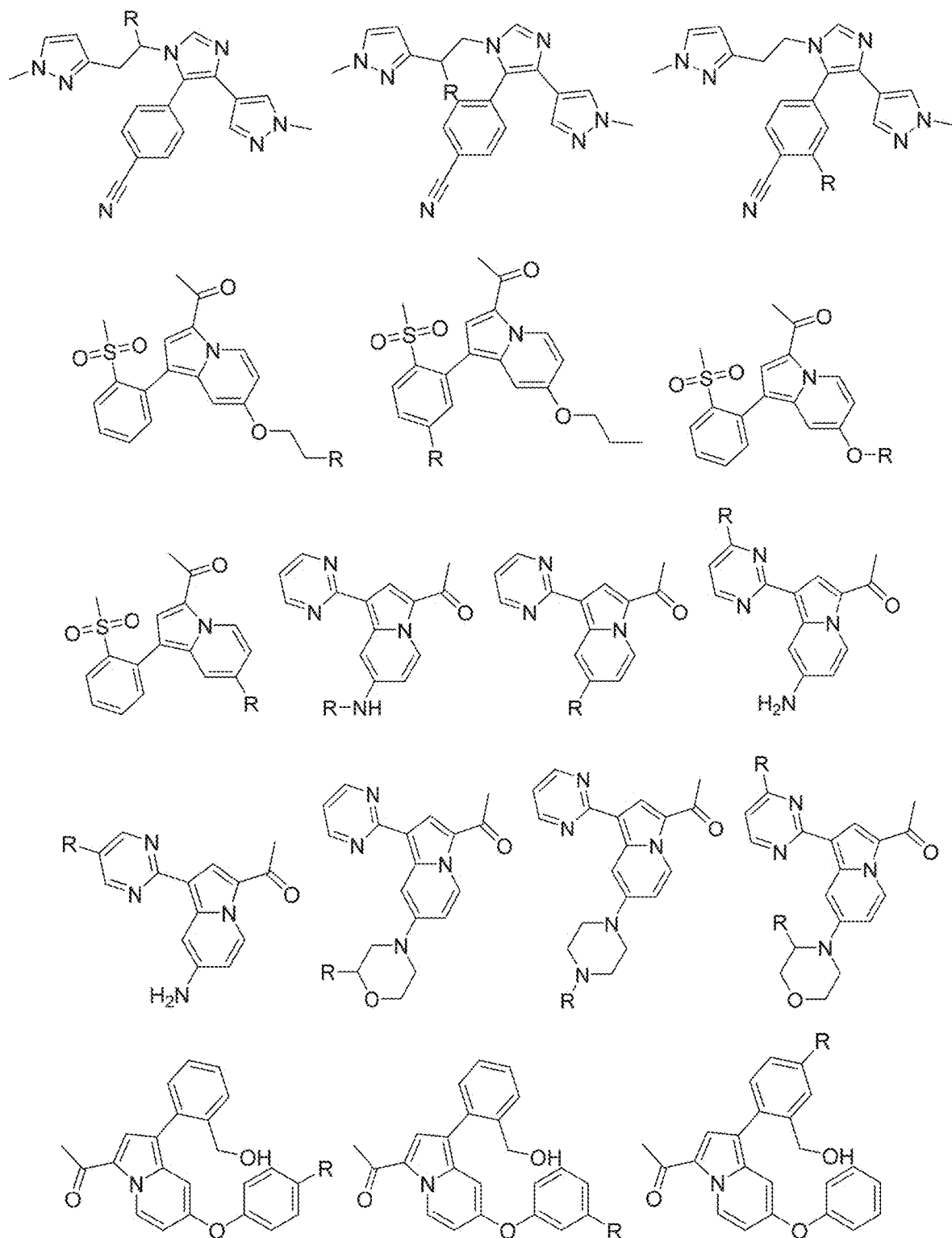

FIG. 3H-3I present examples of KSR1 Targeting Ligands wherein R is the point at which the Linker is attached.

FIG. 3J-3L present examples of CNNTB1 Targeting Ligands wherein R is the point at which the Linker is attached.

FIG. 3M presents examples of BCL6 Targeting Ligands wherein R is the point at which the Linker is attached.

FIG. 3N-3O present examples of PAK1 Targeting Ligands wherein R is the point at which the Linker is attached.

FIG. 3P-3R present examples of PAK4 Targeting Ligands wherein R is the point at which the Linker is attached.

FIG. 3S-3T present examples of TNIK Targeting Ligands wherein R is the point at which the Linker is attached.

FIG. 3U presents examples of MEN1 Targeting Ligands wherein R is the point at which the Linker is attached.

FIG. 3V-3W present examples of ERK1 Targeting Ligands wherein R is the point at which the Linker is attached.

FIG. 3X presents examples of IDO1 Targeting Ligands wherein R is the point at which the Linker is attached.

FIG. 3Y presents examples of CBP Targeting Ligands wherein R is the point at which the Linker is attached.

FIG. 3Z-3SS present examples of MCL1 Targeting Ligands wherein R is the point at which the Linker is attached. For additional examples and related ligands, see, Tanaka Y. et al "Discovery of potent Mcl-1/Bcl-xL dual inhibitors by using a hybridization strategy based on structural analysis of target proteins." *J. Med. Chem.* 56: 9635-9645 (2013); Friberg A. et al. "Discovery of potent myeloid cell leukemia 1 (Mcl-1) inhibitors using fragment-based methods and structure-based design." *J. Med. Chem.* 56: 15-30 (2013); Petros A. M. et al "Fragment-based discovery of potent inhibitors of the anti-apoptotic MCL-1 protein." *Bioorg. Med. Chem. Lett.* 24: 1484-1488 (2014); Burke J. P. et al. "Discovery of tricyclic indoles that potently inhibit mcl-1 using fragment-based methods and structure-based design." *J. Med. Chem.* 58: 3794-3805 (2015); Pelz N. F. et al. "Discovery of 2-Indole-acylsulfonamide Myeloid Cell Leukemia 1 (Mcl-1) Inhibitors Using Fragment-Based Methods." *J. Med. Chem.* 59: 2054-2066 (2016); Clifton M. C. et al. "A Maltose-Binding Protein Fusion Construct Yields a Robust Crystallography Platform for MCL1." *Plos One* 10: e0125010-e0125010 (2015); Kotschy A et al. "The MCL1 inhibitor S63845 is tolerable and effective in diverse cancer models. *Nature* 538:477-482 (2016); EP 2886545 A1 titled "New thienopyrimidine derivatives a process for their preparation and pharmaceutical compositions containing them"; Jeffrey W. Johannes et al. "Structure Based Design of Non-Natural Peptidic Macrocyclic Mcl-1 Inhibitors" *ACS Med. Chem. Lett.* (2017); DOI: 10.1021/acsmedchemlett.6b00464; Bruncko M. et al. "Structure-Guided Design of a Series of MCL-1 Inhibitors with High Affinity and Selectivity." *J. Med. Chem.* 58: 2180-2194 (2015); Taekyu Lee et al. "Discovery and biological characterization of potent myeloid cell leukemia-1 inhibitors." *FEBS Letters* 591: 240-251 (2017); Chen L. et al. "Structure-Based Design of 3-Carboxy-Substituted 1 2 3 4-Tetrahydroquinolines as Inhibitors of Myeloid Cell Leukemia-1 (Mcl-1)." *Org. Biomol Chem.* 14:5505-5510 (2016); US 2016/0068545 titled "Tetrahydronaphthalene derivatives that inhibit mcl-1 protein"; WO 2016207217 A1 titled "Preparation of new bicyclic derivatives as pro-apoptotic agents"; Gizem Akçay et al. "Inhibition of Mcl-1 through covalent modification of a noncatalytic lysine side chain" *Nature Chemical Biology* 12: 931-936 (2016).

FIG. 3TT presents examples of ASH1L Targeting Ligands wherein R is the point at which the Linker is attached. See for example, the crystal structure PDB 4YNM ("Human ASH1L SET domain in complex with S-adenosyl methionine (SAM)" Rogawski D. S. et al.)

FIG. 3UU-3WW present examples of ATAD2 Targeting Ligands wherein R is the point at which the Linker is attached. For additional examples and related ligands, see, Chaikuad A. et al. "Structure-based approaches towards identification of fragments for the low-druggability ATAD2 bromodomain" *Med Chem Comm* 5: 1843-1848 (2014); Poncet-Montange G. et al. "Observed bromodomain flexibility reveals histone peptide- and small molecule ligand-compatible forms of ATAD2." *Biochem. J.* 466: 337-346 (2015); Harner M. J. et al. "Fragment-Based Screening of the Bromodomain of ATAD2." *J. Med. Chem.* 57: 9687-9692 (2014); Demont E. H. et al. "Fragment-Based Discovery of Low-Micromolar Atad2 Bromodomain Inhibitors." *J. Med. Chem.* 58: 5649 (2015); and, Bamborough P. et al. "Structure-Based Optimization of Naphthyridones into Potent Atad2 Bromodomain Inhibitors." *J. Med. Chem.* 58: 6151 (2015).

FIG. 3XX-3AAA present examples of BAZ2A and BAZ2B Targeting Ligands wherein R is the point at which the Linker is attached. For additional examples and related ligands, see, the crystal structure PDB 4CUU ("Human Baz2B in Complex with Fragment-6 N09645" Bradley A. et al.); the crystal structure PDB 5CUA ("Second Bromodomain of Bromodomain Adjacent to Zinc Finger Domain Protein 2B (BAZ2B) in complex with 1-Acetyl-4-(4-hydroxyphenyl)piperazine". Bradley A. et al.); Ferguson F. M. et al. "Targeting low-druggability bromodomains: fragment based screening and inhibitor design against the BAZ2B bromodomain." *J. Med. Chem.* 56: 10183-10187 (2013); Marchand J. R. et al. "Derivatives of 3-Amino-2-methylpyridine as BAZ2B Bromodomain Ligands: In Silico Discovery and in Crystallo Validation." *J. Med. Chem.* 59: 9919-9927 (2016); Drouin L. et al. "Structure Enabled Design of BAZ2-ICR A Chemical Probe Targeting the Bromodomains of BAZ2A and BAZ2B." *J. Med Chem.* 58: 2553-2559 (2015); Chen P. et al. "Discovery and characterization of GSK2801 a selective chemical probe for the bromodomains BAZ2A and BAZ2B." *J. Med. Chem.* 59:1410-1424 (2016).

FIG. 3BBB presents examples of BRD1 Targeting Ligands wherein R is the point at which the Linker is attached. For additional examples and related ligands, see, the crystal structure PDB SAME ("the Crystal Structure of the Bromodomain of Human Surface Epitope Engineered Brd1A in Complex with 3D Consortium Fragment 4-Acetyl-Piperazin-2-One Pearce", N. M. et al.); the crystal structure PDB 5AMF ("Crystal Structure of the Bromodomain of Human Surface Epitope Engineered Brd1A in Complex with 3D Consortium Fragment Ethyl 4 5 6 7-Tetrahydro-1H-Indazole-5-Carboxylate", Pearce N. M. et al.); the crystal structure PDB 5FG6 ("the Crystal structure of the bromodomain of human BRD1 (BRPF2) in complex with OF-1 chemical probe.", Tallant C. et al.); Filippakopoulos P. et al. "Histone recognition and large-scale structural analysis of the human bromodomain family." *Cell*, 149: 214-231 (2012).

FIG. 3CCC-3EEE present examples of BRD2 Bromodomain 1 Targeting Ligands wherein R is the point at which the Linker is attached. For additional examples and related ligands, see, the crystal structure PDB 2ydw; the crystal structure PDB 2yek; the crystal structure PDB 4a9h; the crystal structure PDB 4a9f; the crystal structure PDB 4a9i; the crystal structure PDB 4a9m; the crystal structure PDB 4akn; the crystal structure PDB 4alg, and the crystal structure PDB 4uyf.

FIG. 3FFF-3HHH present examples of BRD2 Bromodomain 2 Targeting Ligands wherein R is the point at which the Linker is attached. For additional examples and related ligands, see, the crystal structure PDB 3oni; Filippakopoulos P. et al. "Selective Inhibition of BET Bromodomains." *Nature* 468: 1067-1073 (2010); the crystal structure PDB 4j1p; McLure K. G. et al. "RVX-208: an Inducer of ApoA-I in Humans is a BET Bromodomain Antagonist." *Plos One* 8: e83190-e83190 (2013); Baud M. G. et al. "Chemical biology. A bump-and-hole approach to engineer controlled selectivity of BET bromodomain chemical probes" *Science* 346: 638-641 (2014); Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016); Gosmini R. et al. "The Discovery of I-Bet726 (Gsk1324726A) a Potent Tetrahydroquinoline Apoal Up-Regulator and Selective Bet Bromodomain Inhibitor" *J. Med. Chem.* 57: 8111 (2014); the crystal structure PDB 5EK9 ("Crystal structure of the second bromodomain of human BRD2 in complex with a hydroquinolinone inhibitor", Tallant C. et al); the crystal structure PDB 5BT5; the crystal structure PDB 5dfd; Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016).

FIG. 3III-3JJJ present examples of BRD4 Bromodomain 1 Targeting Ligands wherein R is the point at which the Linker is attached. For additional examples and related ligands, see, the crystal structure PDB 5WUU and the crystal structure PDB 5F5Z.

FIG. 3KKK-3LLL present examples of BRD4 Bromodomain 2 Targeting Ligands wherein R is the point at which the Linker is attached. For additional examples and related ligands, see, Chung C. W. et al. "Discovery and Characterization of Small Molecule Inhibitors of the Bet Family Bromodomins" *J. Med. Chem.* 54:3827 (2011) and Ran X. et al. "Structure-Based Design of gamma-Carboline Analogues as Potent and Specific BET Bromodomain Inhibitors" *J. Med. Chem.* 58: 4927-4939 (2015).

FIG. 3MMM presents examples of BRDT Targeting Ligands wherein R is the point at which the Linker is attached. For additional examples and related ligands, see, the crystal structure PDB 4flp and the crystal structure PDB 4kcx.

FIG. 3NNN-3QQQ present examples of BRD9 Targeting Ligands wherein R is the point at which the Linker is attached. For additional examples and related ligands, see, the crystal structure PDB 4nqn; the crystal structure PDB 4uit; the crystal structure PDB 4uiu; the crystal structure PDB 4uiv; the crystal structure PDB 4z6h; the crystal structure PDB 4z6i; the crystal structure PDB 5e9v; the crystal structure PDB 5eu1; the crystal structure PDB 5flh; and, the crystal structure PDB 5fp2.

FIG. 3RRR presents examples of SMARCA4 PB1 and/or SMARCA2 Targeting Ligands wherein R is the point at which the Linker is attached, A is N or CH, and m is 0 1 2 3 4 5 6 7 or 8.

FIG. 3SSS-3XXX present examples of additional Bromodomain Targeting Ligands wherein R is the point at which the Linker is attached. For additional examples and related ligands, see, Hewings et al. "3 5-Dimethylisoxazoles Act as Acetyl-lysine Bromodomain Ligands." *J. Med. Chem.* 54 6761-6770 (2011); Dawson et al. "Inhibition of BET Recruitment to Chromatin as an Effective Treatment for MLL-fusion Leukemia." *Nature,* 478, 529-533 (2011); US 2015/0256700; US 2015/0148342; WO 2015/074064; WO 2015/067770; WO 2015/022332; WO 2015/015318; and, WO 2015/011084.

FIG. 3YYY presents examples of PB1 Targeting Ligands wherein R is the point at which the Linker is attached. For additional examples and related ligands, see, the crystal structure PDB 3mb4; the crystal structure PDB 4q0n; and, the crystal structure PDB 5fh6.

FIG. 3ZZZ presents examples of SMARCA4 Targeting Ligands wherein R is the point at which the Linker is attached. For additional examples and related ligands, see, the crystal structure 3uvd and the crystal structure 5dkd.

FIG. 3AAAA presents examples of SMARCA2 Targeting Ligands wherein R is the point at which the Linker is attached. For additional examples and related ligands, see, the crystal structure 5dkc and the crystal structure 5dkh.

FIG. 3BBBB presents examples of TRIM24 (TIF1a) and/or BRPF1 Targeting Ligands wherein R is the point at which the Linker is attached and m is 0 1 2 3 4 5 6 7 or 8.

FIG. 3CCCC presents examples of TRIM24 (TIF1a) Targeting Ligands wherein R is the point at which the Linker is attached. For additional examples and related ligands, see, Palmer W. S. et al. "Structure-Guided Design of IACS-9571: a Selective High-Affinity Dual TRIM24-BRPF1 Bromodomain Inhibitor." *J Med. Chem.* 59: 1440-1454 (2016).

FIG. 3DDDD-3FFFF present examples of BRPF1 Targeting Ligands wherein R is the point at which the Linker is attached. For additional examples and related ligands, see, the crystal structure PDB 4uye; the crystal structure PDB 5c7n; the crystal structure PDB 5c87; the crystal structure PDB 5c89; the crystal structure PDB 5d7x; the crystal structure PDB 5dya; the crystal structure PDB 5epr; the crystal structure PDB 5eq1; the crystal structure PDB 5etb; the crystal structure PDB 5ev9; the crystal structure PDB 5eva; the crystal structure PDB 5ewv; the crystal structure PDB 5eww; the crystal structure PDB 5ffy; the crystal structure PDB 5fg5; and, the crystal structure PDB 5g4r.

FIG. 3GGGG presents examples of CECR2 Targeting Ligands wherein R is the point at which the Linker is attached. For additional examples and related ligands, see, Moustakim M. et al. *Med. Chem. Comm.* 7:2246-2264 (2016) and Crawford T. et al. Journal of *Med. Chem.* 59; 5391-5402 (2016).

FIG. 3HHHH-3OOOO present examples of CREBBP Targeting Ligands wherein R is the point at which the Linker is attached, A is N or CH, and m is 0 1 2 3 4 5 6 7 or 8. For additional examples and related ligands, see, the crystal structure PDB 3p1d; the crystal structure PDB 3svh; the crystal structure PDB 4nr4; the crystal structure PDB 4nr5; the crystal structure PDB 4ts8; the crystal structure PDB 4nr6; the crystal structure PDB 4nr7; the crystal structure PDB 4nyw; the crystal structure PDB 4nyx; the crystal structure PDB 4tqn; the crystal structure PDB 5cgp; the crystal structure PDB 5dbm; the crystal structure PDB 5ep7; the crystal structure PDB 5i83; the crystal structure PDB 5i86; the crystal structure PDB 5i89; the crystal structure PDB 5i8g; the crystal structure PDB 5j0d; the crystal structure PDB 5ktu; the crystal structure PDB 5ktw; the crystal structure PDB 5ktx; the crystal structure PDB 5tb6.

FIG. 3PPPP presents examples of EP300 Targeting Ligands wherein R is the point at which the Linker is attached. For additional examples and related ligands, see, the crystal structure PDB 5BT3.

FIG. 3QQQQ presents examples of PCAF Targeting Ligands wherein R is the point at which the Linker is attached. See for example, M. Ghizzoni et al. *Bioorg. Med. Chem.* 18: 5826-5834 (2010).

FIG. 3RRRR presents examples of PHIP Targeting Ligands wherein R is the point at which the Linker is attached. For additional examples and related ligands, see, *Mol Cancer Ther.* 7(9): 2621-2632 (2008).

FIG. 3SSSS presents examples of TAF1 and TAF1L Targeting Ligands wherein R is the point at which the Linker is attached. For additional examples and related ligands, see, Picaud S. et al. *Sci Adv* 2: e1600760-e1600760 (2016).

FIG. 3TTTT presents examples of Histone Deacetylase 2 (HDAC2) Targeting Ligands wherein R is the point at which the Linker is attached. For additional examples and related ligands, see, Lauffer B. E. *J. Biol. Chem.* 288: 26926-26943 (2013); Wagner F. F. *Bioorg. Med. Chem.* 24: 4008-4015 (2016); Bressi J. C. *Bioorg. Med. Chem. Lett.* 20: 3142-3145 (2010); and, Lauffer B. E. *J. Biol. Chem.* 288: 26926-26943 (2013).

FIG. 3UUUU-3VVVV present examples of Histone Deacetylase 4 (HDAC4) Targeting Ligands wherein R is the point at which the Linker is attached. For additional examples and related ligands, see, Burli R. W. *J. Med. Chem.* 56: 9934 (2013); Luckhurst C. A. *ACS Med. Chem. Lett.* 7: 34 (2016); Bottomley M. J. *J. Biol. Chem.* 283: 26694-26704 (2008).

FIG. 3WWWW presents examples of Histone Deaceytlase 6 Targeting Ligands wherein R is the point at which the Linker is attached. For additional examples and related ligands, see, Harding R. J. (to be published); Hai Y. *Nat. Chem. Biol.* 12: 741-747, (2016); and, Miyake Y. *Nat. Chem. Biol.* 12: 748 (2016).

FIG. 3XXXX-3YYYY presents examples of Histone Deacetylase 7 Targeting Ligands wherein R is the point at which the Linker is attached. For additional examples and related ligands, see, Lobera M. *Nat. Chem. Biol.* 9: 319 (2013) and Schuetz A. *J. Biol. Chem.* 283: 11355-11363 (2008).

FIG. 3ZZZZ-3DDDDD present examples of Histone Deacetylase 8 Targeting Ligands wherein R is the point at which the Linker is attached. For additional examples and related ligands, see, Whitehead L. *Biol. Med. Chem.* 19: 4626-4634 (2011); Tabackman A. A. *J. Struct. Biol.* 195: 373-378 (2016); Dowling D. P. *Biochemistry* 47, 13554-13563 (2008); Somoza J. R. *Biochemistry* 12, 1325-1334 (2004); Decroos C. *Biochemistry* 54: 2126-2135 (2015); Vannini A. *Proc. Natl Acad. Sci.* 101: 15064 (2004); Vannini A. *EMBO Rep.* 8: 879 (2007); the crystal structure PDB 5BWZ; Decroos A. *ACS Chem. Biol.* 9: 2157-2164 (2014); Somoza J. R. *Biochemistry* 12: 1325-1334 (2004); Decroos C. *Biochemistry* 54: 6501-6513 (2015); Decroos A. *ACS Chem. Biol.* 9: 2157-2164 (2014); and, Dowling D. P. *Biochemistry* 47: 13554-13563 (2008).

FIG. 3EEEEE presents examples of Histone Acetyltransferase (KAT2B) Targeting Ligands wherein R is the point at which the Linker is attached. For additional examples and related ligands, see, Chaikuad A. *J. Med. Chem.* 59: 1648-1653 (2016); the crystal structure PDB 1ZS5; and, Zeng L. *J. Am. Chem. Soc.* 127: 2376-2377 (2005).

FIG. 3FFFFF-3GGGGG present examples of Histone Acetyltransferase (KAT2A) Targeting Ligands wherein R is the point at which the Linker is attached. For additional examples and related ligands, see, Ringel A. E. *Acta Crystallogr. D. Struct. Biol.* 72: 841-848 (2016).

FIG. 3HHHHH presents examples of Histone Acetyltransferase Type B Catalytic Unit (HAT1) Targeting Ligands wherein R is the point at which the Linker is attached. For additional examples and related ligands, see, the crystal structure PDB 2POW.

FIG. 3IIIII presents examples of Cyclic AMP-dependent Transcription Factor (ATF2) Targeting Ligands wherein R is the point at which the Linker is attached.

FIG. 3JJJJJ presents examples of Histone Acetyltransferase (KAT5) Targeting Ligands wherein R is the point at which the Linker is attached.

FIG. 3KKKKK-3MMMMM present examples of Lysine-specific histone demethylase 1A (KDM1A) Targeting Ligands wherein R is the point at which the Linker is attached. For additional examples and related ligands, see, Mimasu S. *Biochemistry* 49: 6494-6503 (2010); Sartori L. *J. Med. Chem.* 60:1673-1693 (2017); and, Vianello P. *J. Med. Chem.* 60: 1693-1715 (2017).

FIG. 3NNNNN presents examples of HDAC6 Zn Finger Domain Targeting Ligands wherein R is the point at which the Linker is attached.

FIG. 3OOOOO-3PPPPP present examples of general Lysine Methyltransferase Targeting Ligands wherein R is the point at which the Linker is attached.

FIG. 3QQQQQ-3TTTTT present examples of DOT1L Targeting Ligands wherein R is the point at which the Linker is attached, A is N or CH, and m is 0 1 2 3 4 5 6 7 or 8. For additional examples and related ligands, see, the crystal structure PDB 5MVS ("Dot1L in complex with adenosine and inhibitor CPD1" Be C. et al.); the crystal structure PDB 5MW4 ("Dot1L in complex inhibitor CPD7" Be C. et al.); the crystal structure PDB 5DRT ("Dot1L in complex inhibitor CPD2" Be C. et al.); Be C. et al. *ACS Med. Lett.* 8: 338-343 (2017); the crystal structure PDB 5JUW "(Dot1L in complex with SS148" Yu W. et al. Structural Genomics Consortium).

FIG. 3UUUUU presents examples of EHMT1 Targeting Ligands wherein R is the point at which the Linker is attached. For additional examples and related ligands, see, the crystal structure PDB 5TUZ ("EHMT1 in complex with inhibitor MS0124", Babault N. et al.).

FIG. 3VVVVV presents examples of EHMT2 Targeting Ligands wherein R is the point at which the Linker is attached. For additional examples and related ligands, see, the crystal structure PDB 5TUY ("EHMT2 in complex with inhibitor MS0124", Babault N. et al.); the PDB crystal structure 5TTF ("EHMT2 in complex with inhibitor MS012", Dong A. et al.); the PDB crystal structure 3RJW (Dong A. et al., Structural Genomics Consortium); the PDB crystal structure 3K5K; Liu F. et al. *J. Med. Chem.* 52: 7950-7953 (2009); and, the PDB crystal structure 4NVQ ("EHMT2 in complex with inhibitor A-366" Sweis R. F. et al.).

FIG. 3WWWWW presents examples of SETD2 Targeting Ligands wherein R is the point at which the Linker is attached. For additional examples and related ligands, see, the PDB crystal structure 5LSY ("SETD2 in complex with cyproheptadine", Tisi D. et al.); Tisi D. et al. *ACS Chem. Biol.* 11: 3093-3105 (2016); the crystal structures PDB 5LSS, 5LSX, 5LSZ, 5LT6, 5LT7, and 5LT8; the PDB crystal structure 4FMU; and, Zheng W. et al. *J. Am. Chem. Soc.* 134: 18004-18014 (2012).

FIG. 3XXXXX-3YYYYY present examples of SETD7 Targeting Ligands wherein R is the point at which the Linker is attached. For additional examples and related ligands, see, the PDB crystal structure 5AYF ("SETD7 in complex with cyproheptadine." Niwa H. et al.); the PDB crystal structure 4JLG ("SETD7 in complex with (R)-PFI-2", Dong A. et al.); the PDB crystal structure 4JDS (Dong A. et. al Structural Genomics Consortium); the PDB crystal structure 4E47 (Walker J. R. et al. Structural Genomics Consortium; the PDB crystal structure 3VUZ ("SETD7 in complex with AAM-1." Niwa H. et al.); the PDB crystal structure 3VVO; and, Niwa H et al. *Acta Crystallogr. Sect. D* 69: 595-602 (2013).

FIG. 3ZZZZZ presents examples of SETD8 Targeting Ligands wherein R is the point at which the Linker is attached. For additional examples and related ligands, see, the PDB crystal structure 5TH7 ("SETD8 in complex with MS453", Yu W. et al.) and the PDB crystal structure 5T5G (Yu W et. al.; to be published).

Figure 4B:
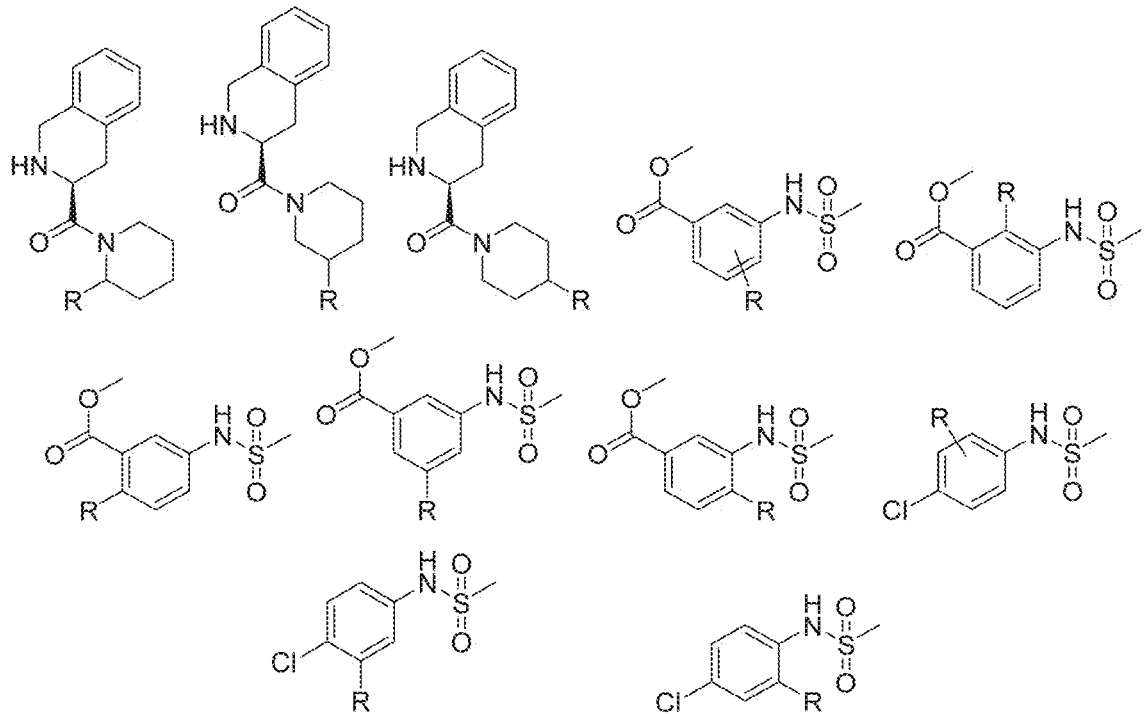
Figure 4C:
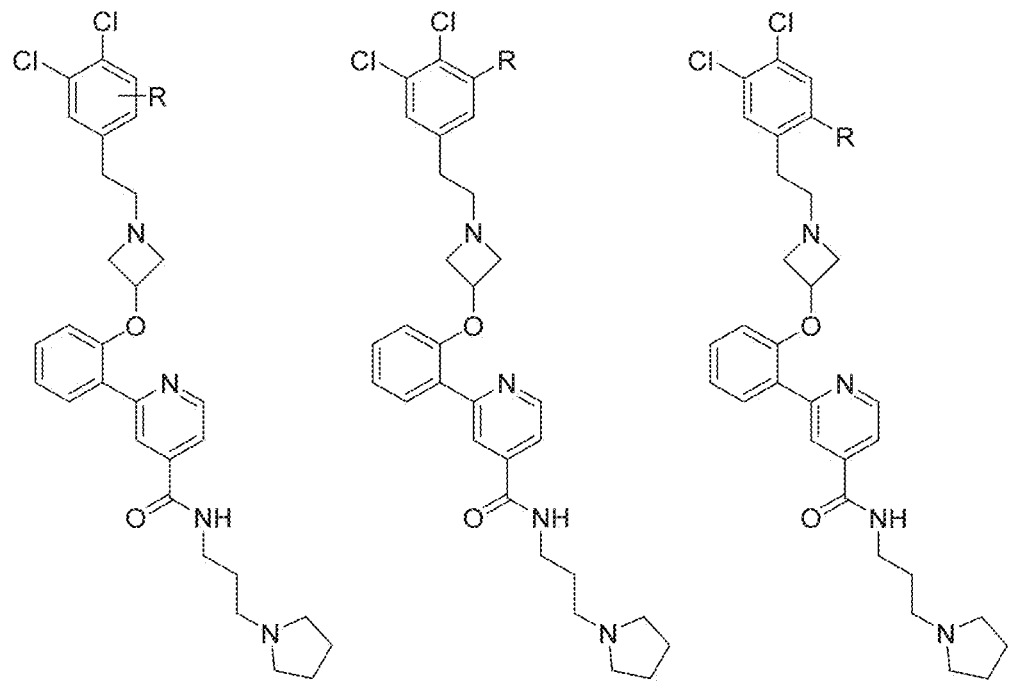
Figure 4D:
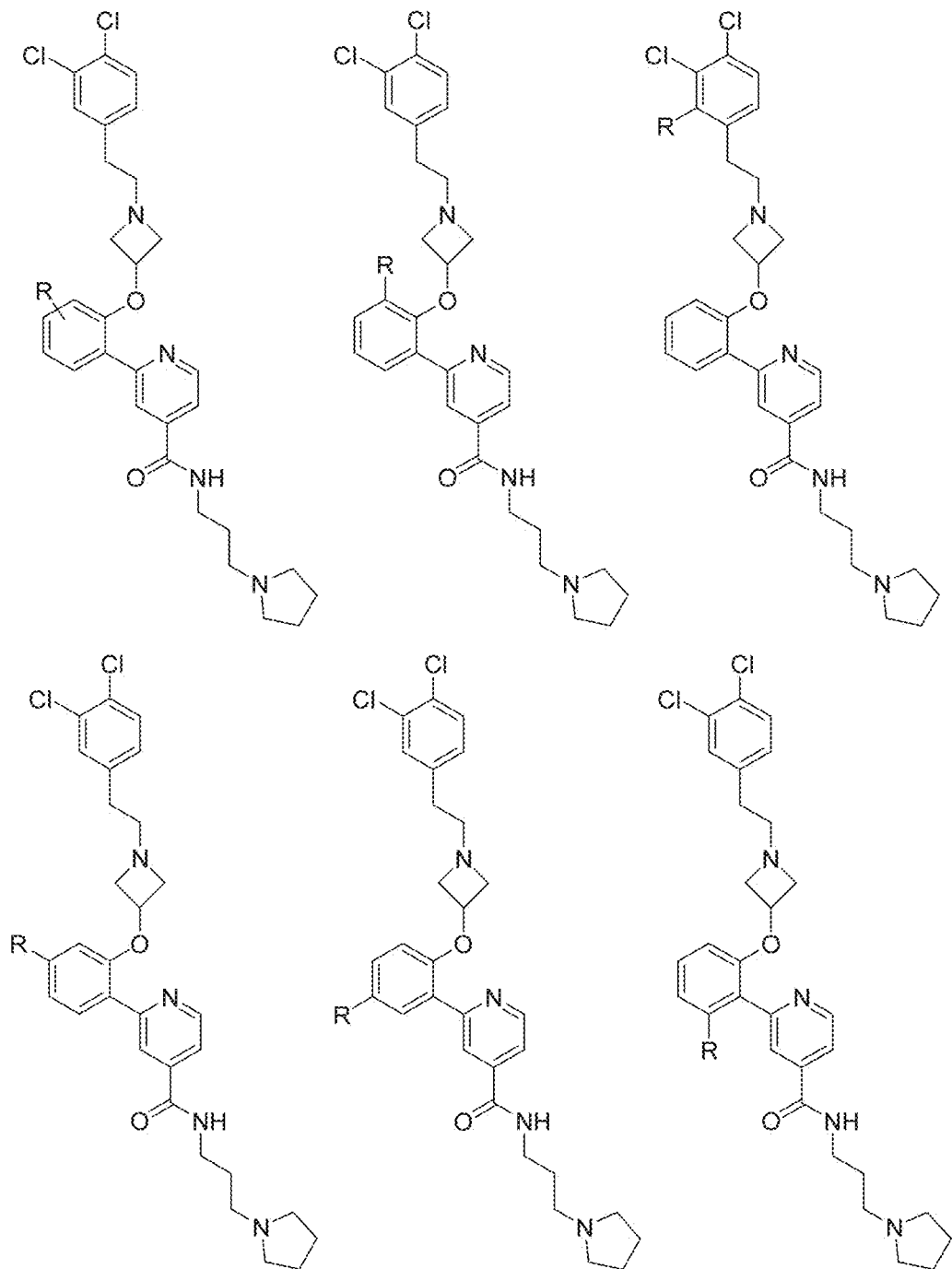
Figure 4E:
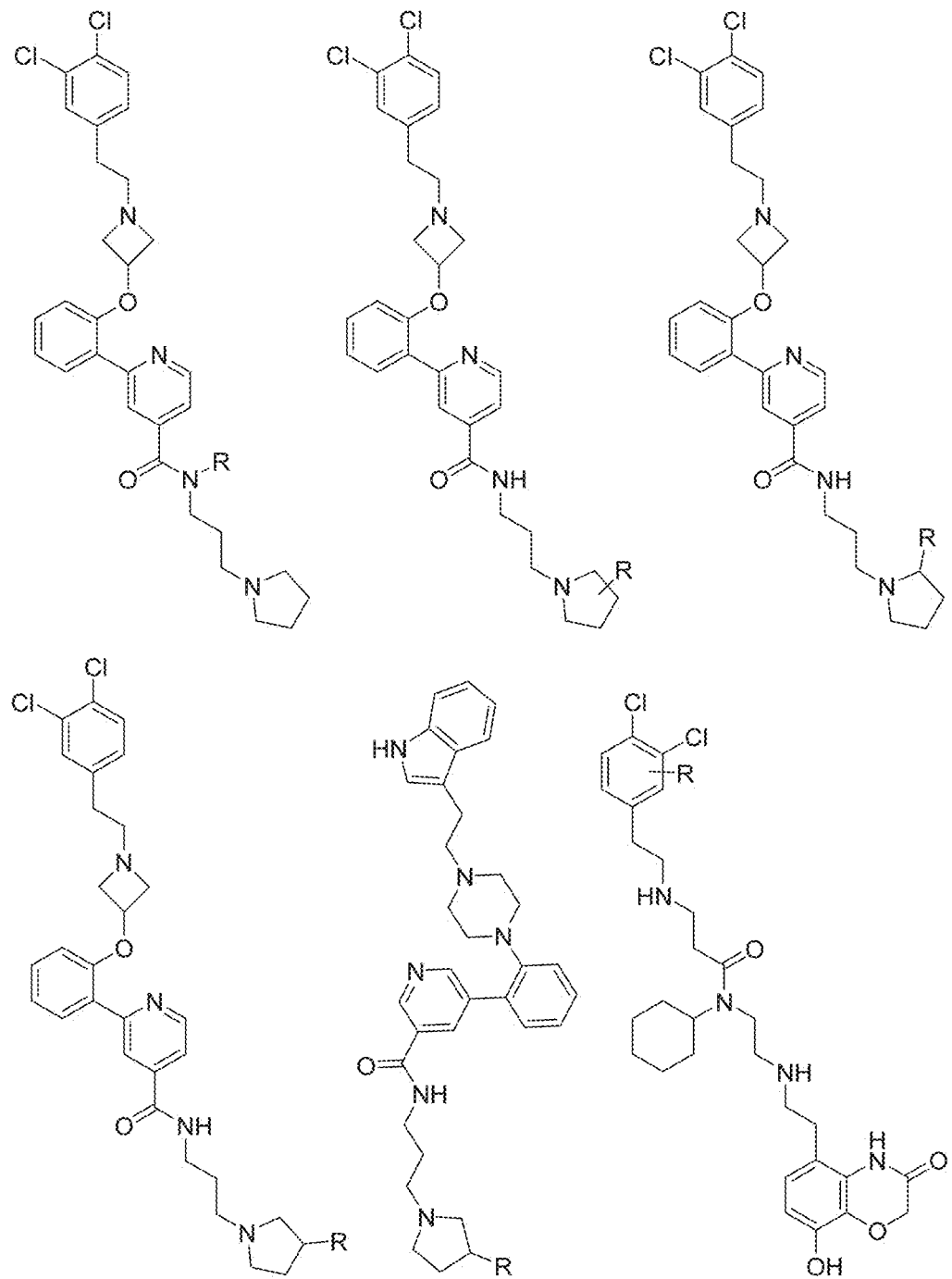
Figure 4F:
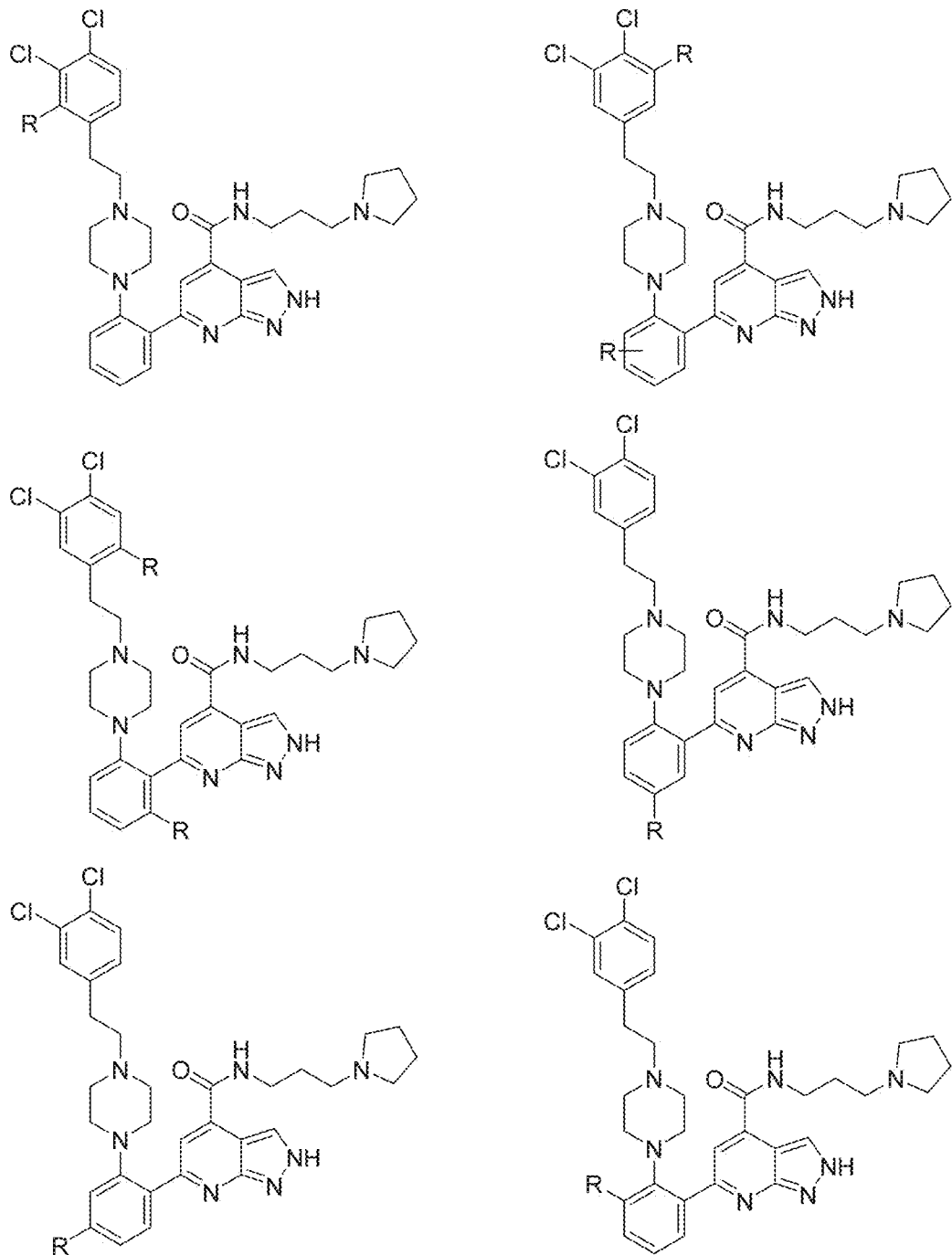
Figure 4G:
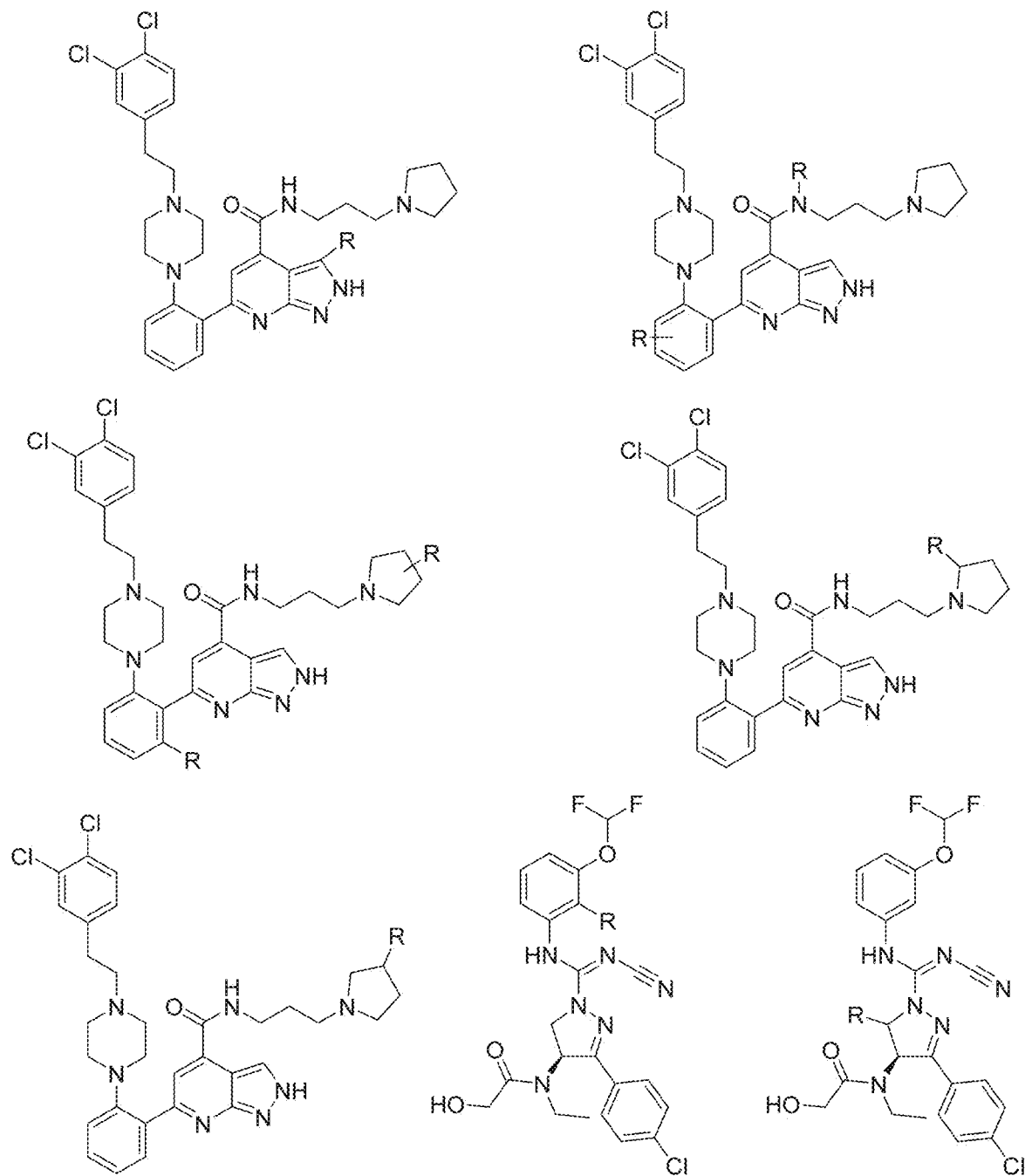
Figure 4H:
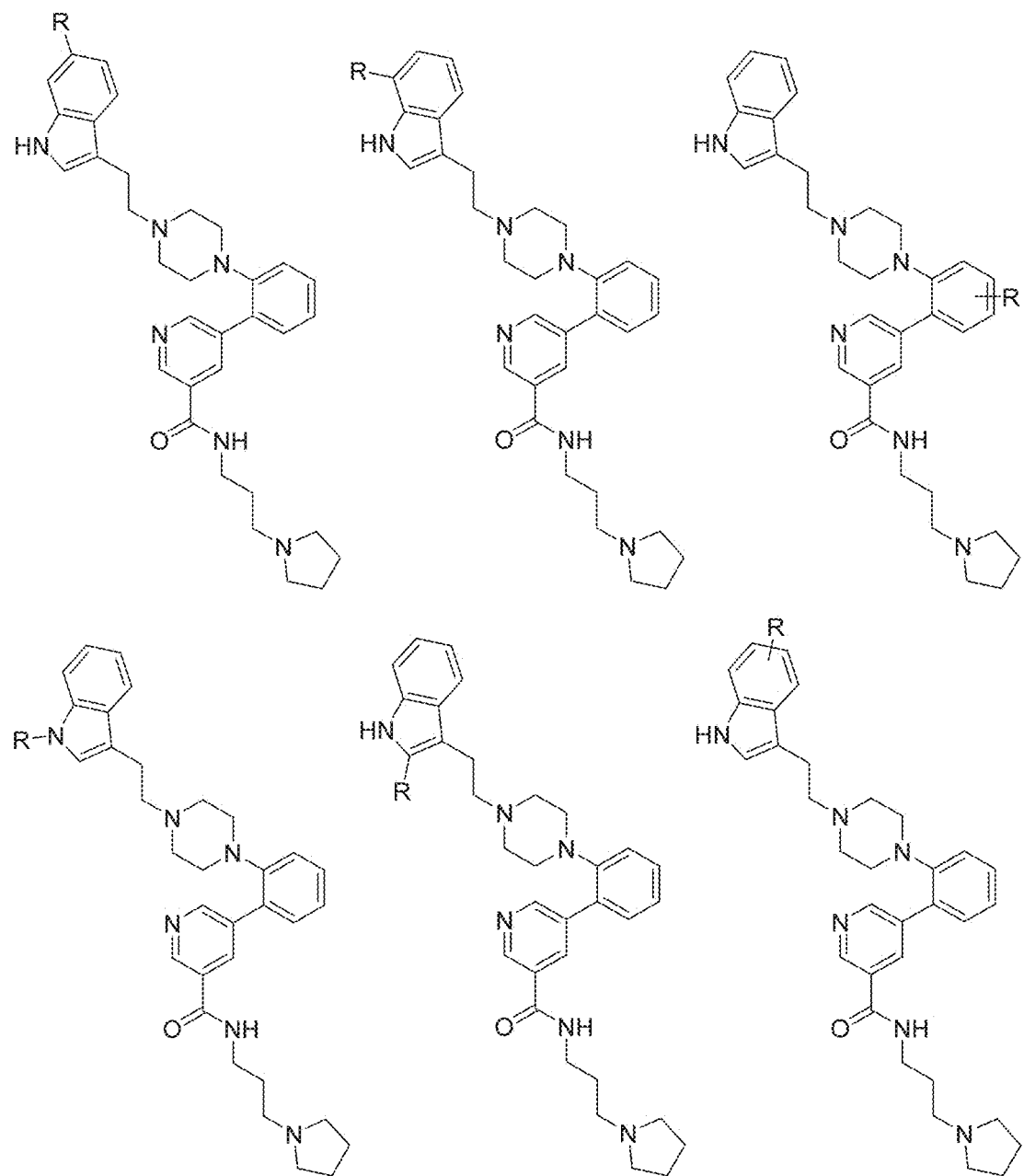
Figure 4I:
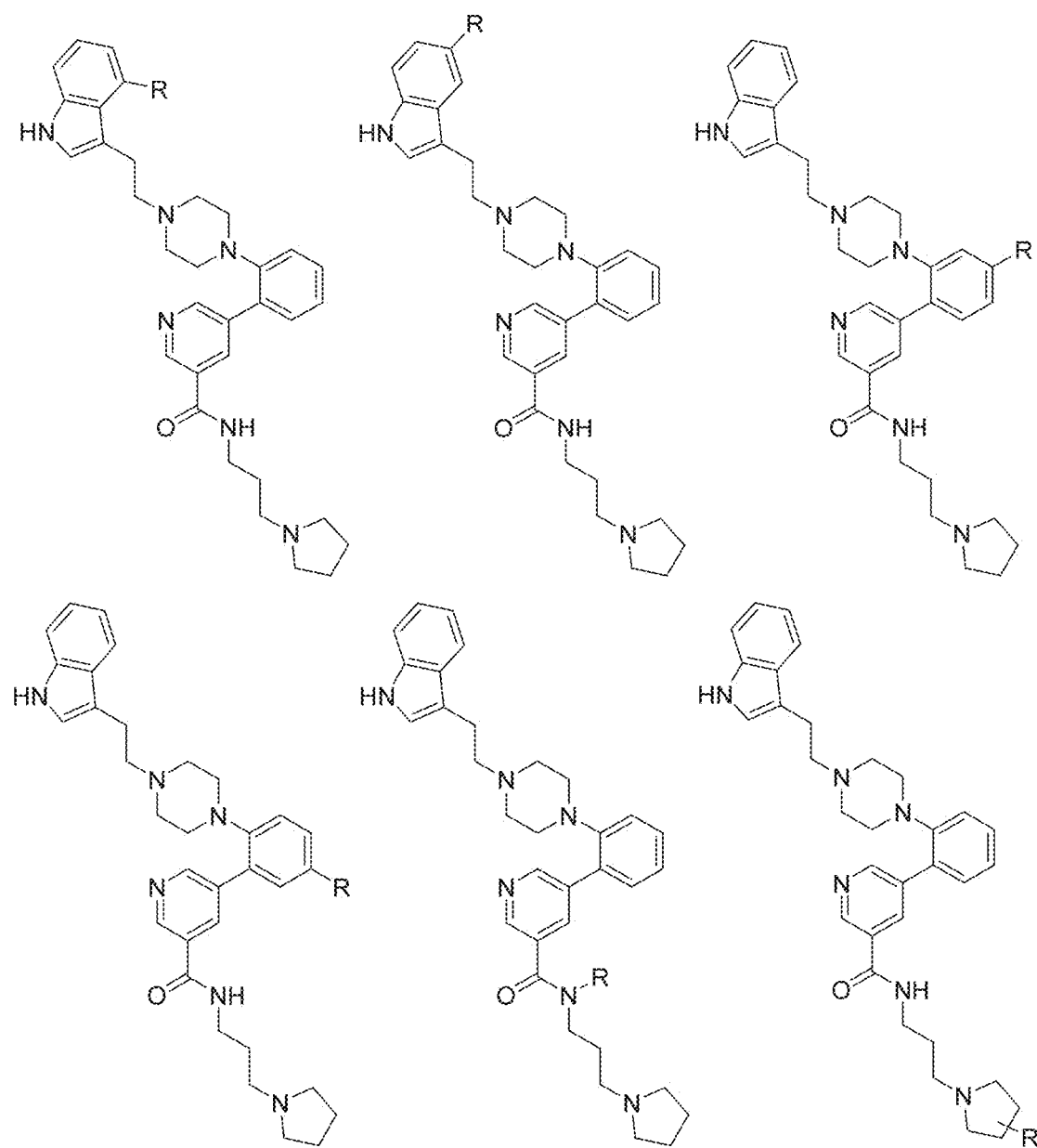
Figure 4J:
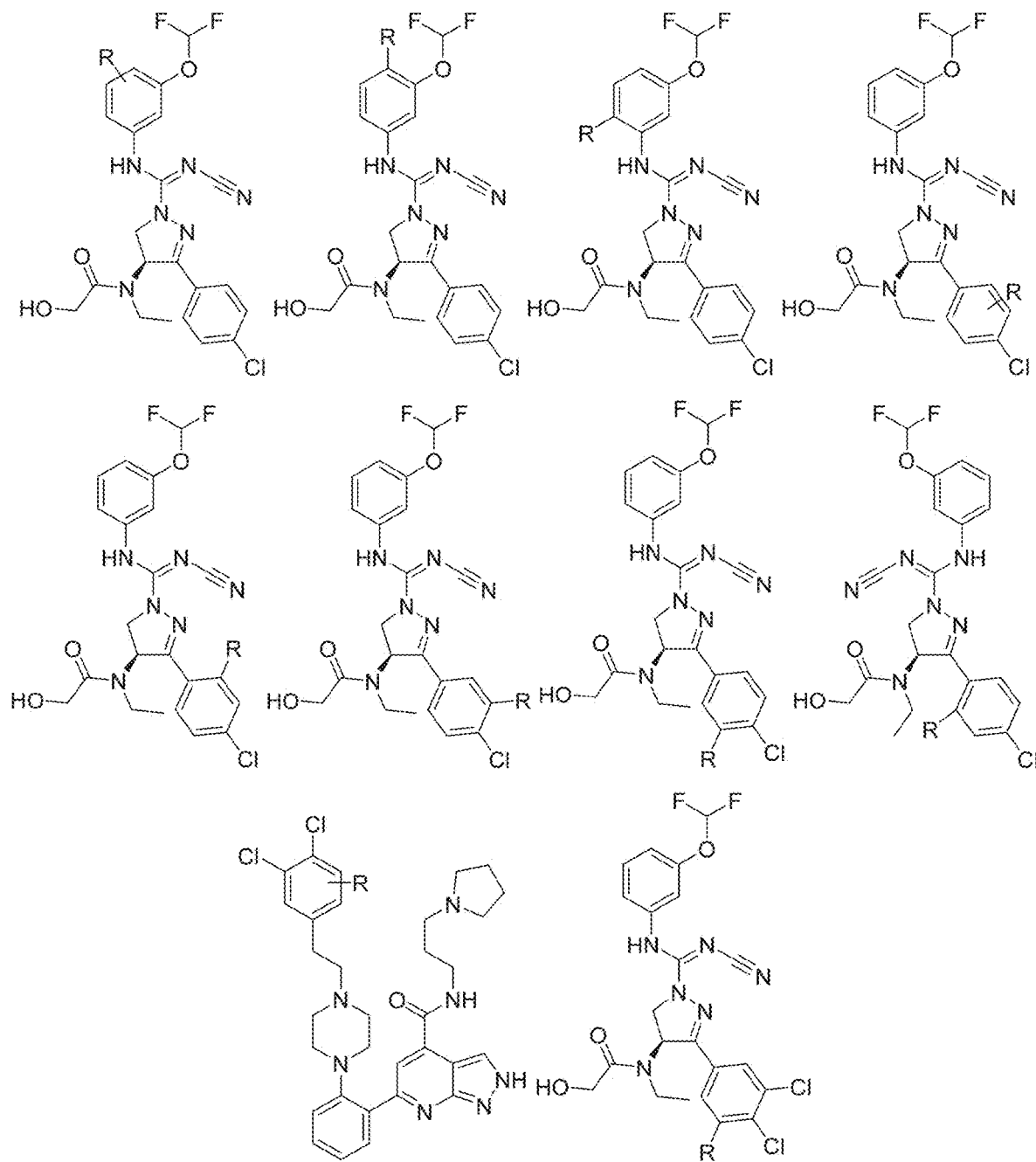
Figure 4K:
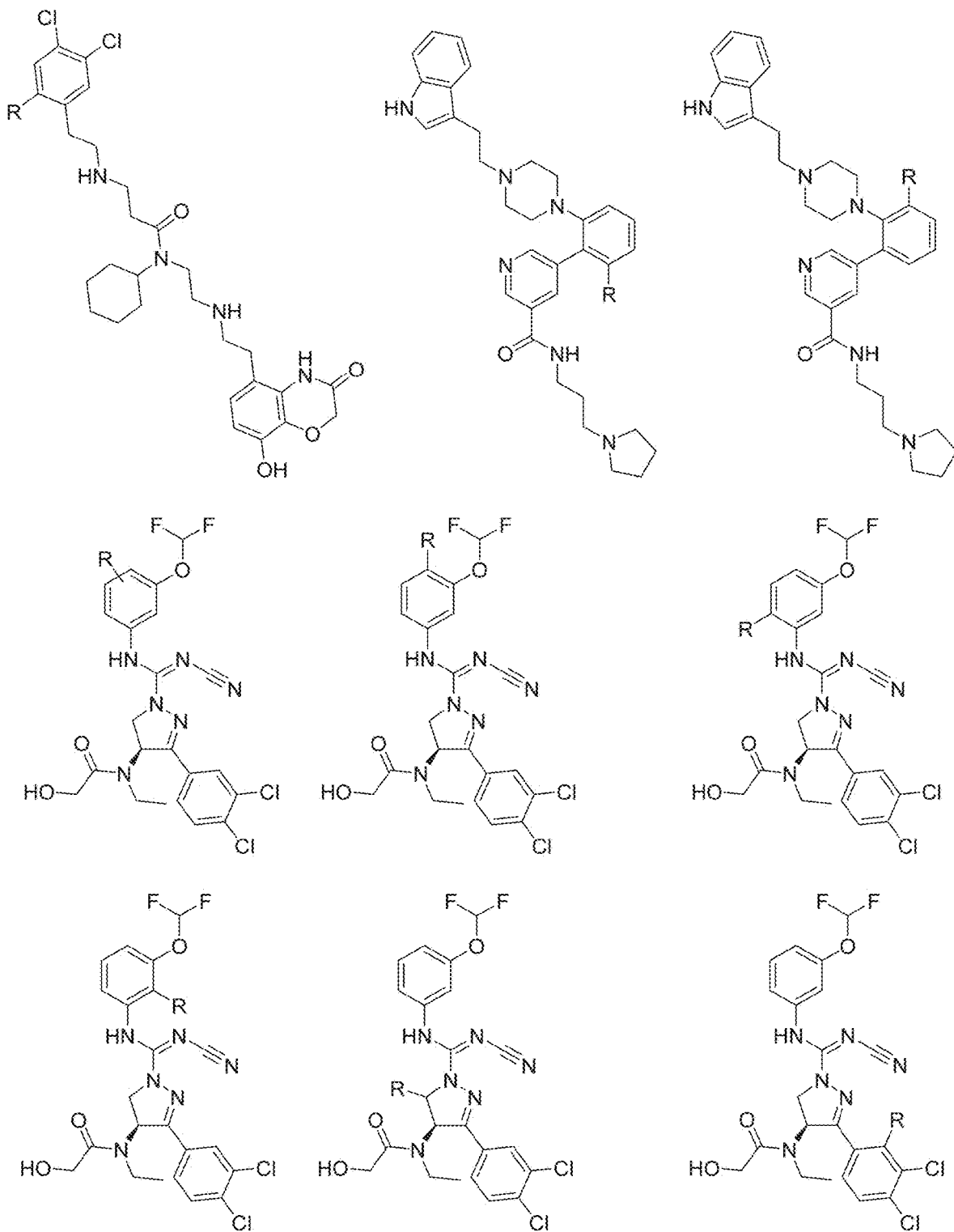
Figure 4L:
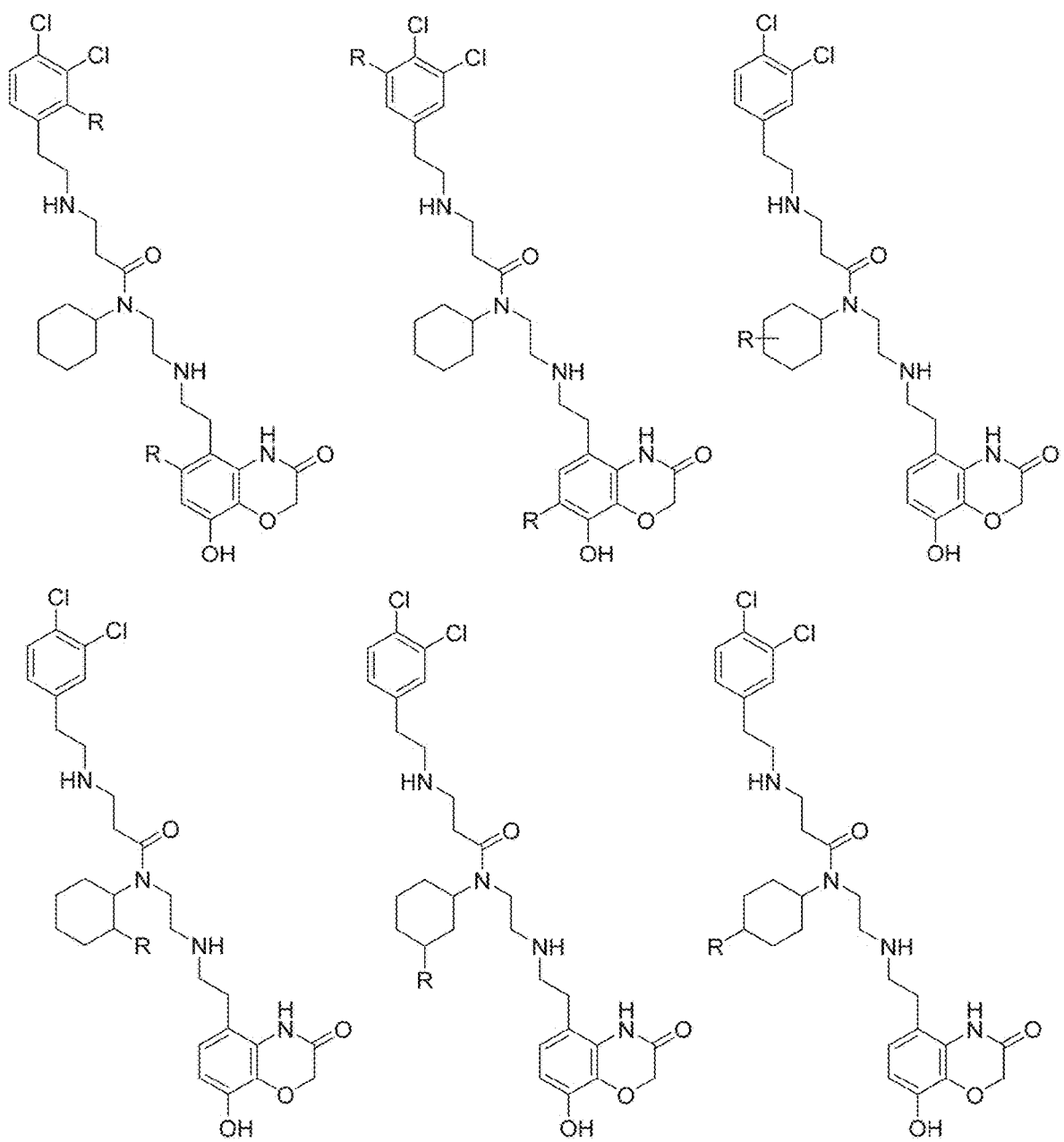
Figure 4M:
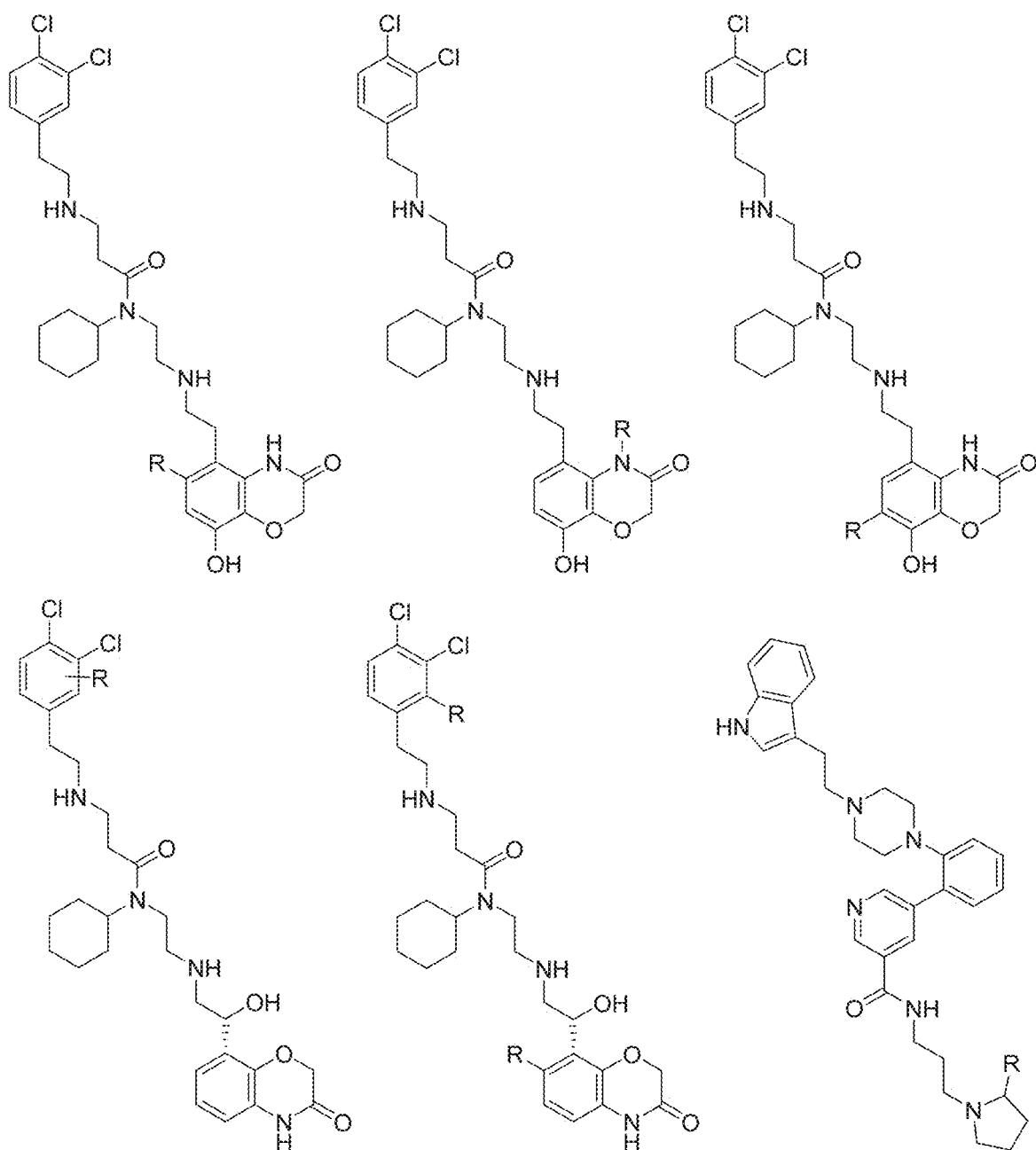
Figure 4N:
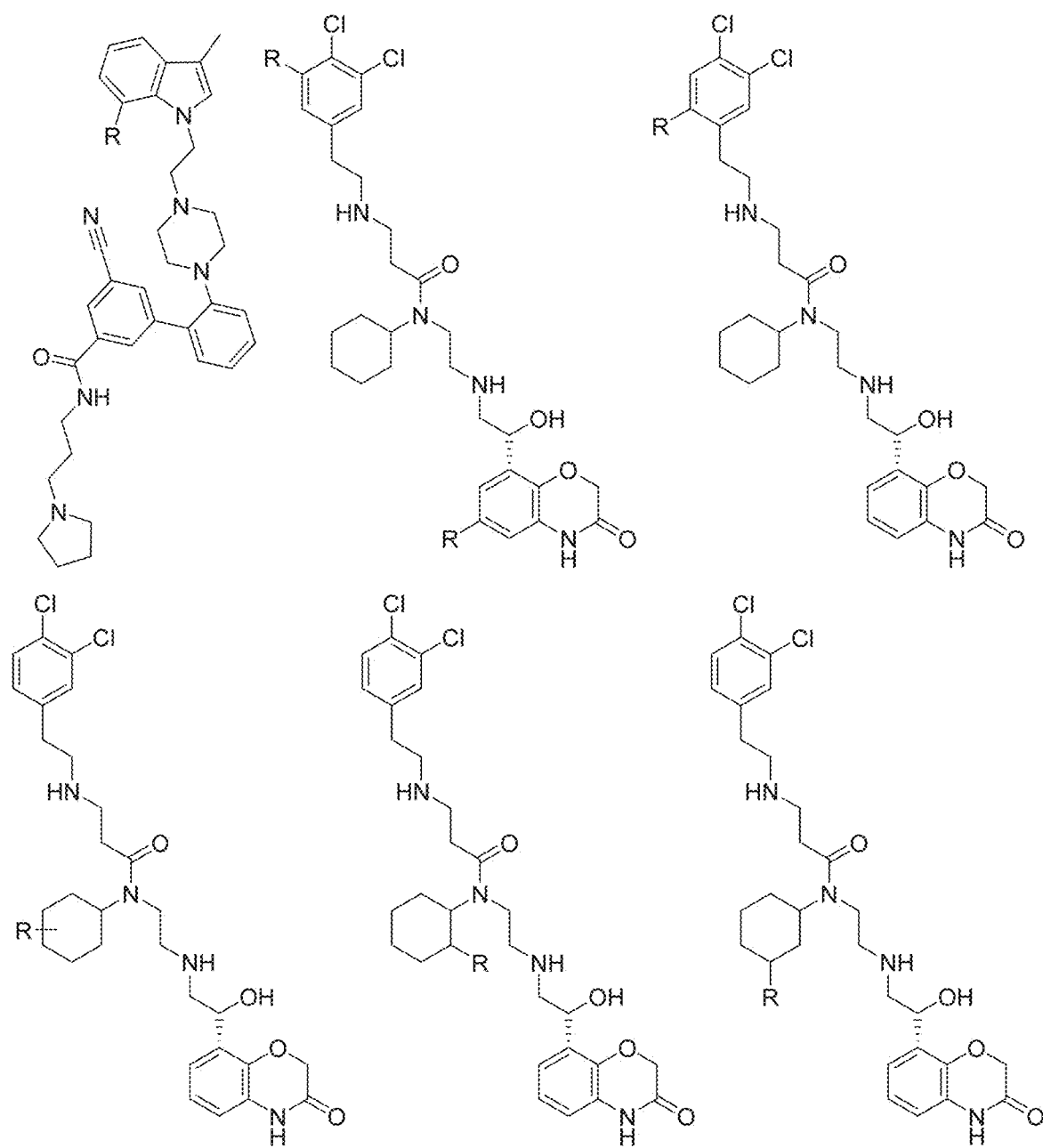
Figure 4O:
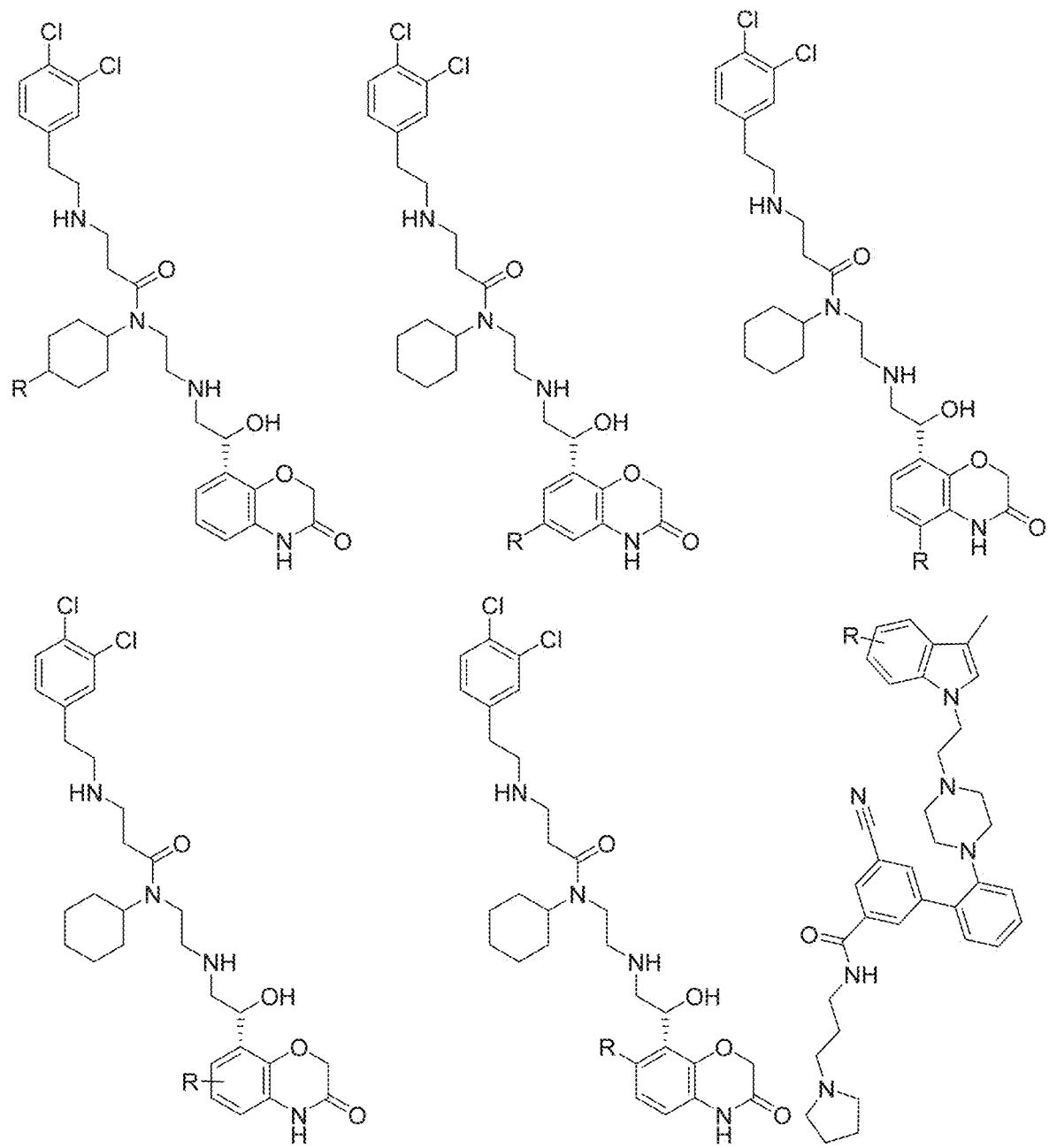
Figure 4P:
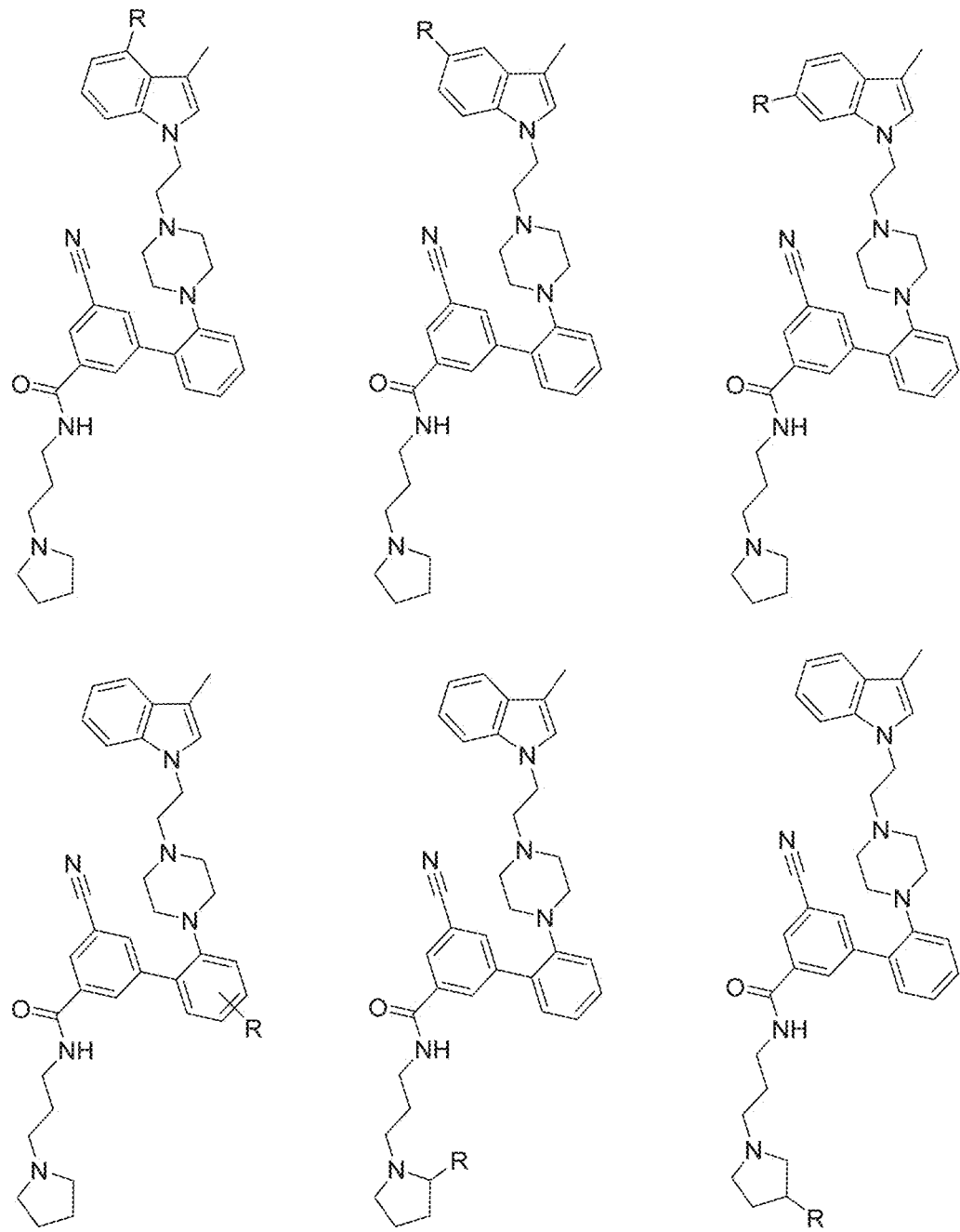
Figure 4Q:
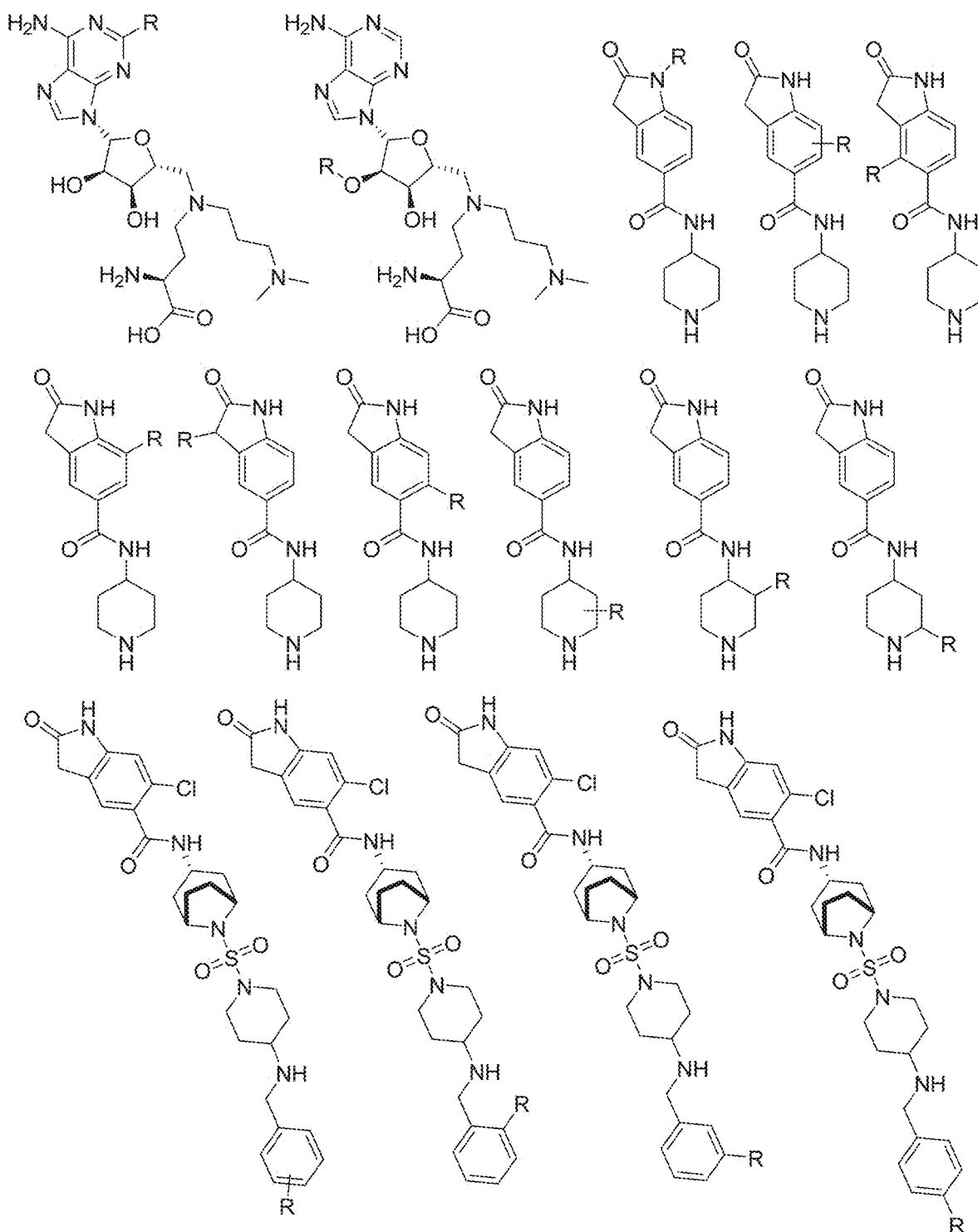
Figure 4R:
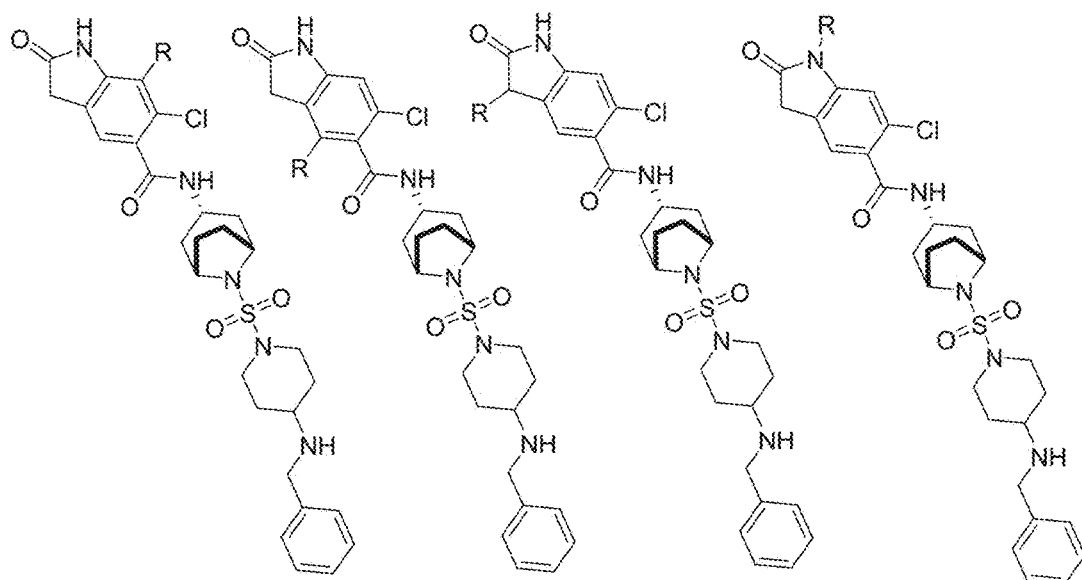
Figure 4S:
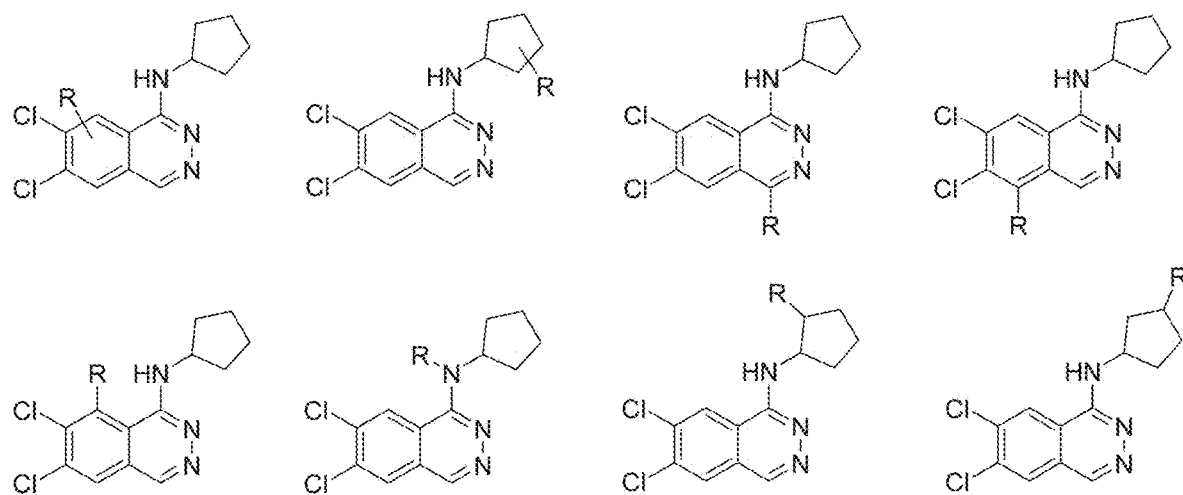
Figure 4T:
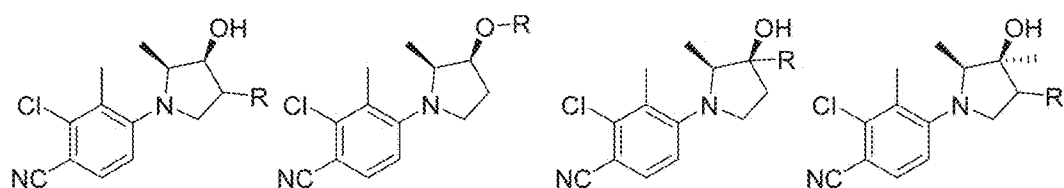
Figure 4U:
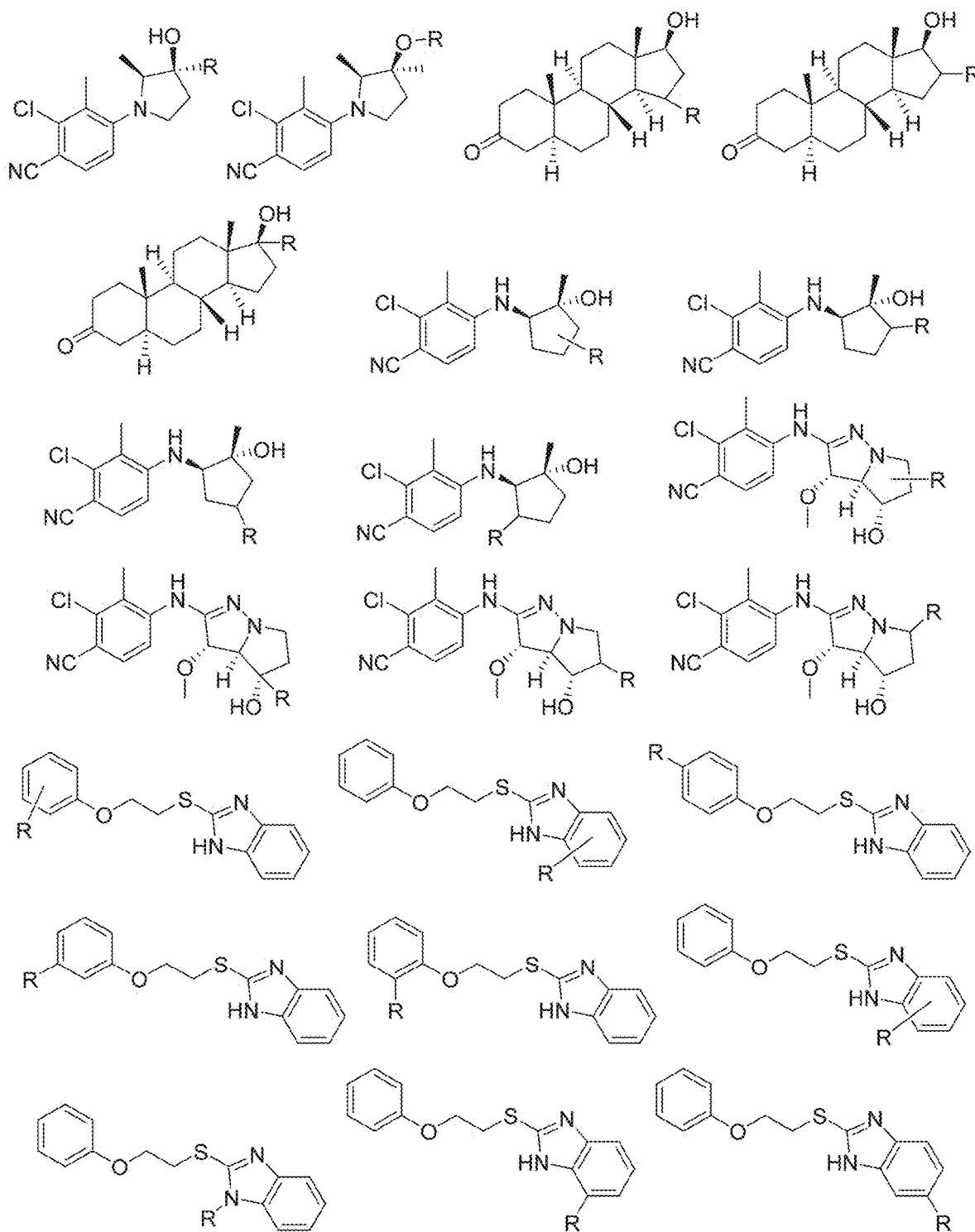
Figure 4V:
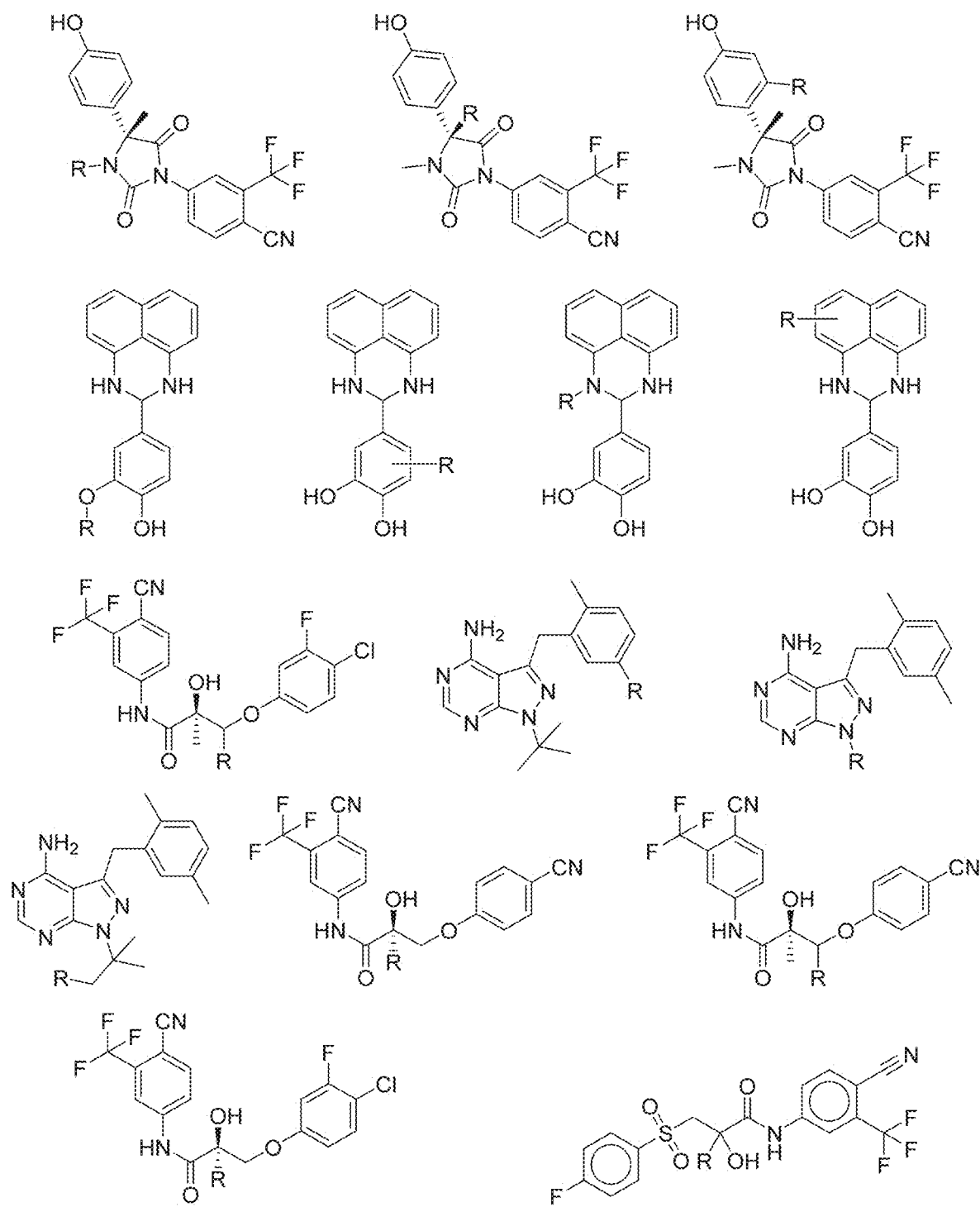
Figure 4W:
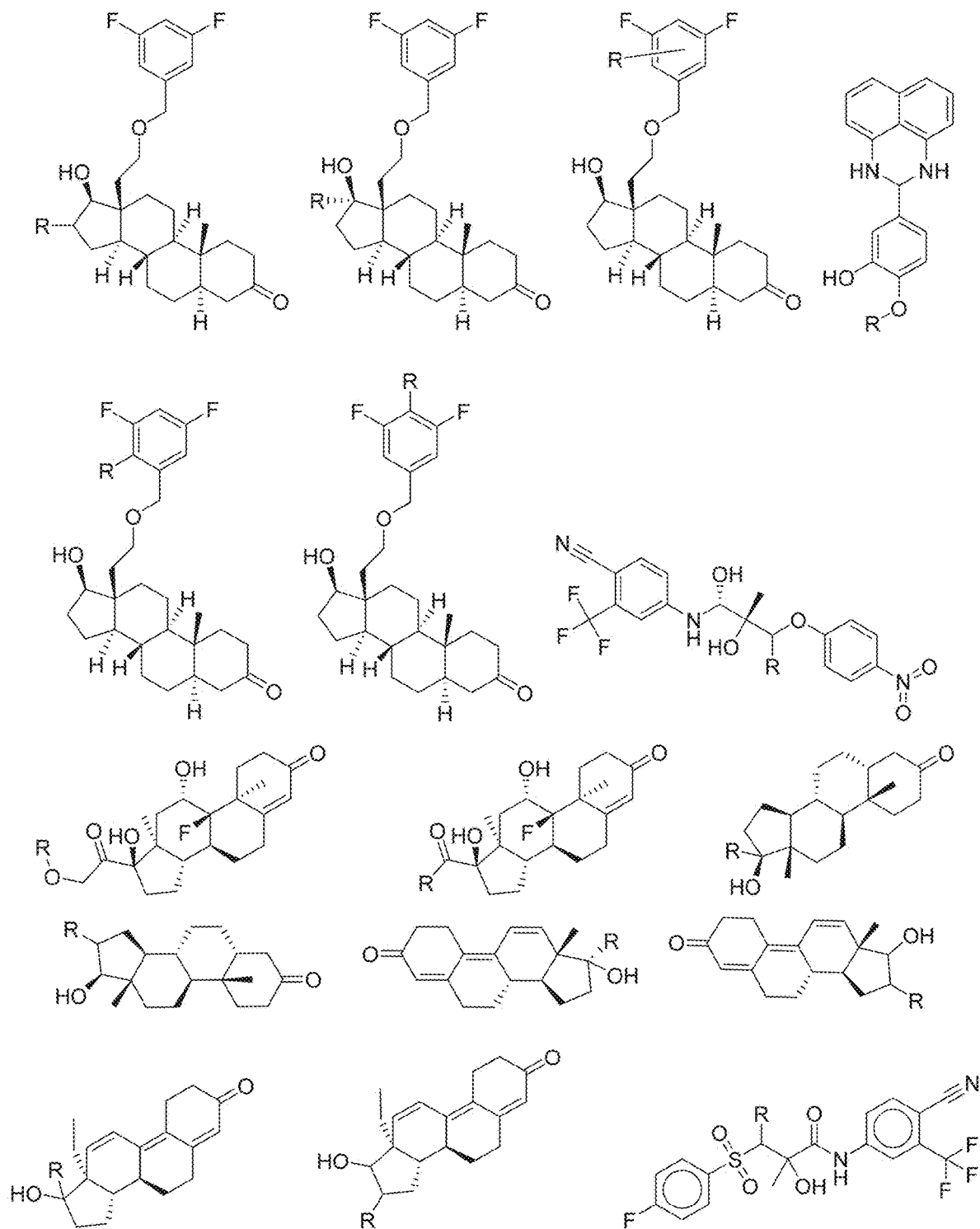
Figure 4X:
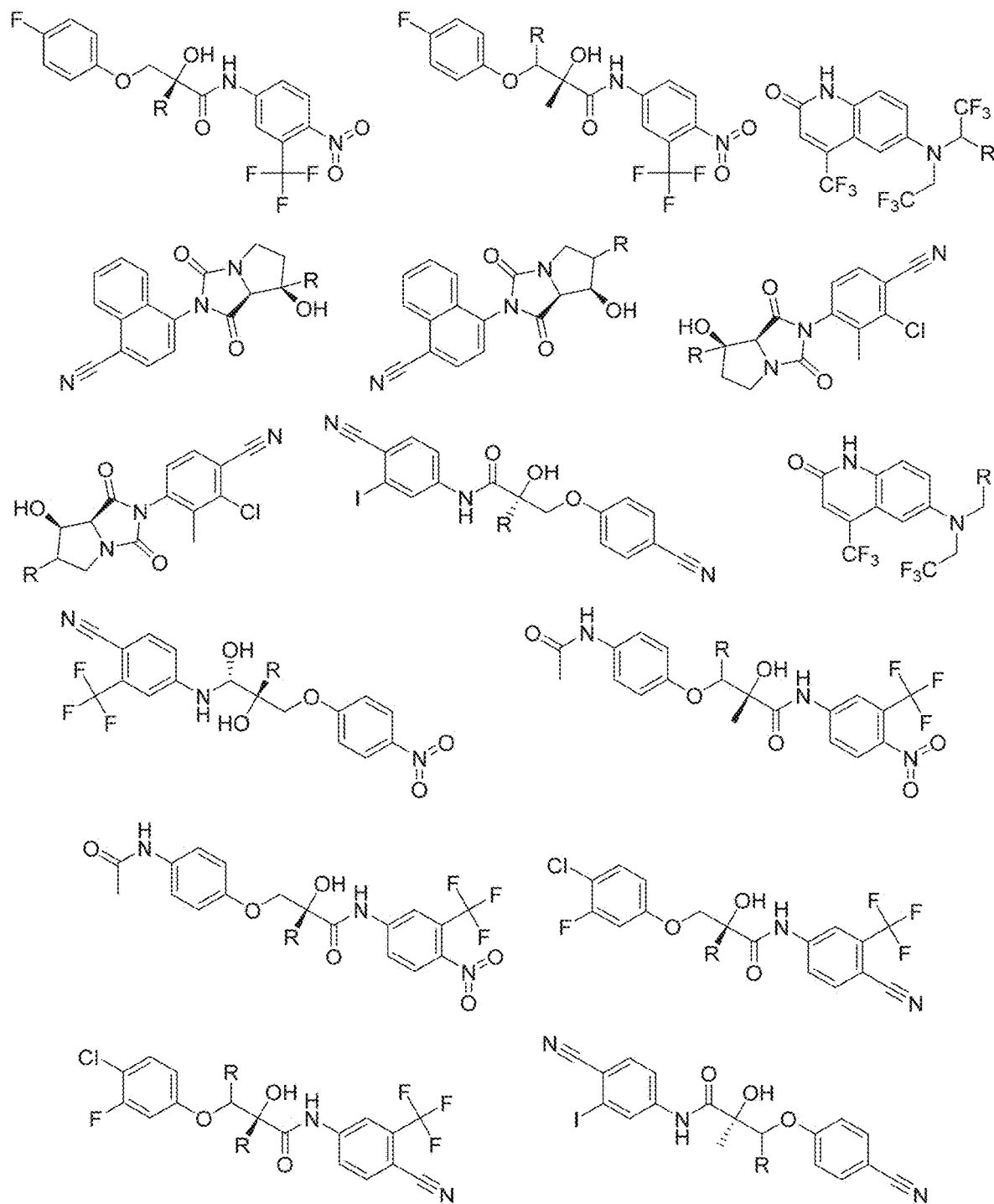
Figure 4Y:
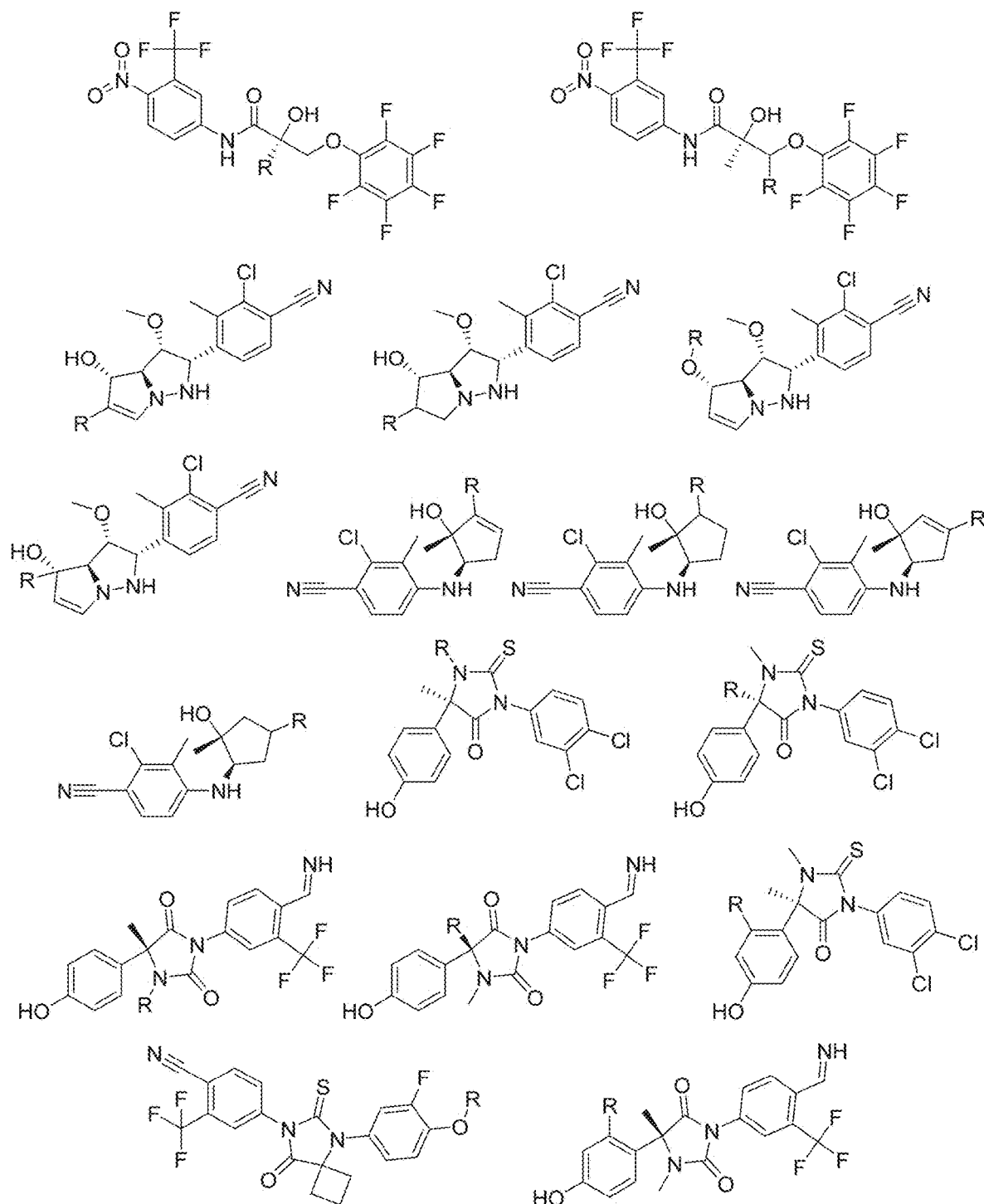
Figure 4Z:
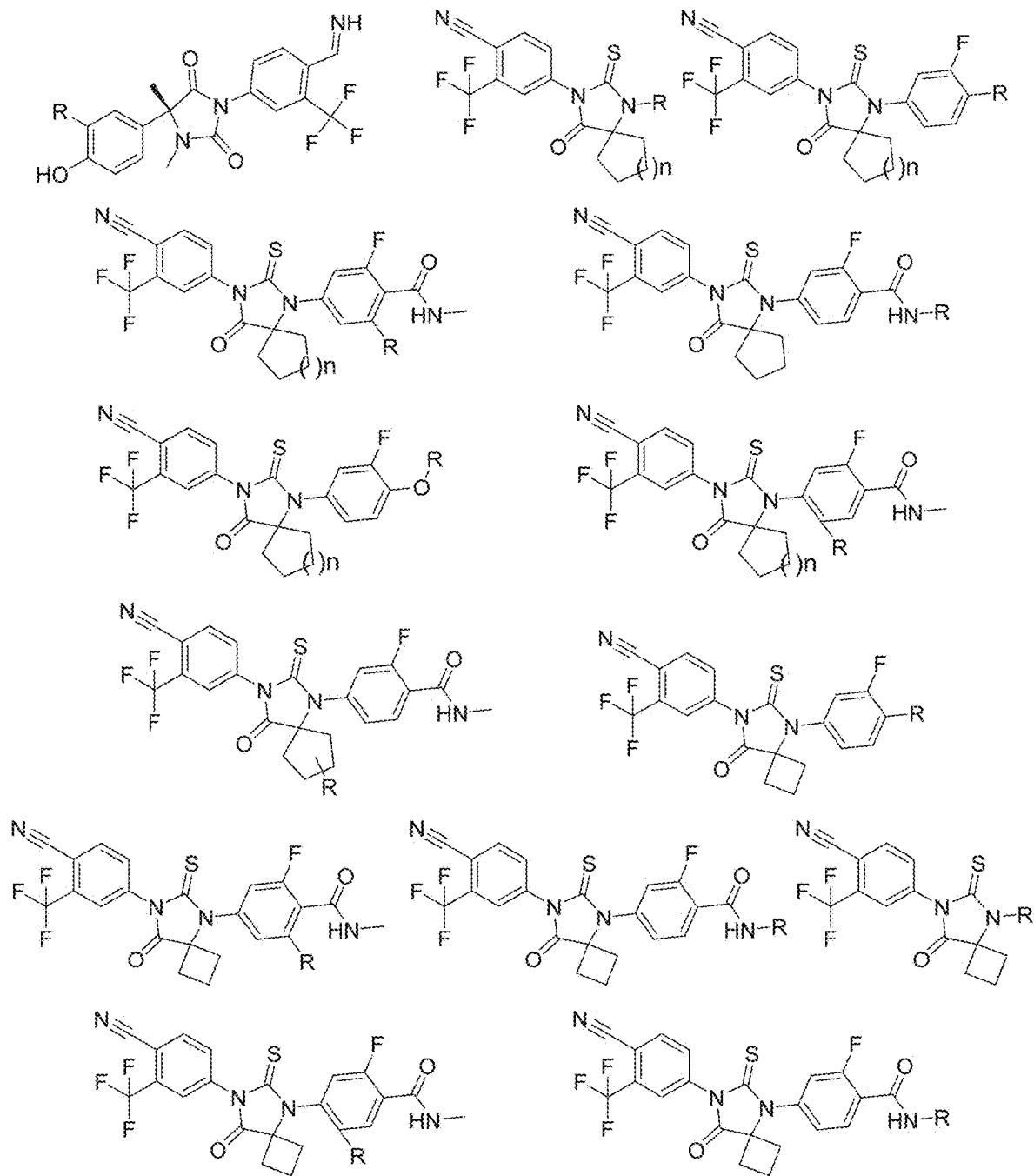
Figure 4A:
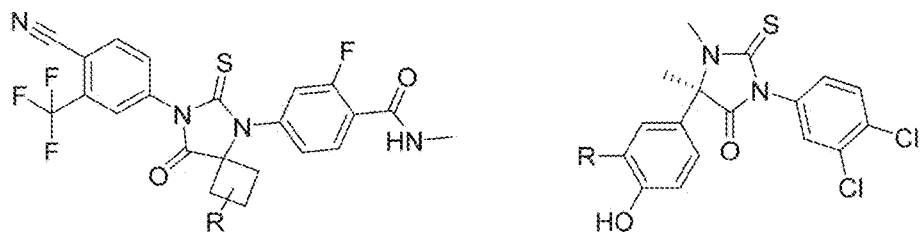
Figure 4B:
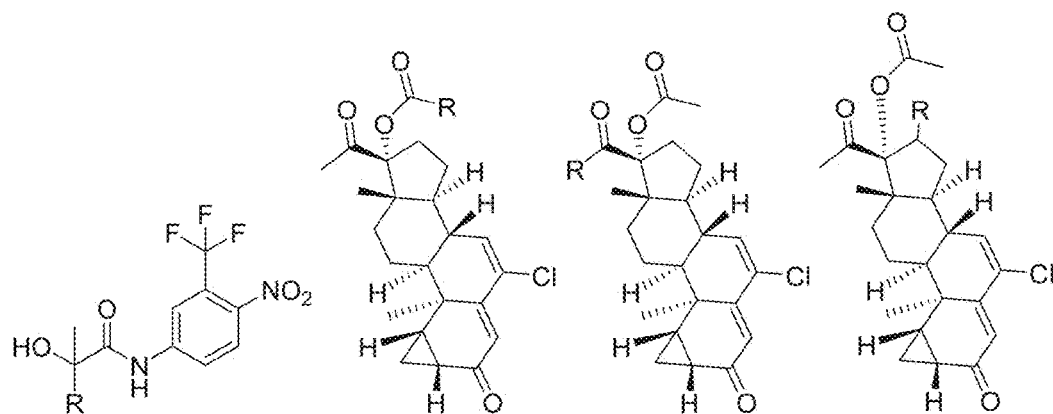
Figure 4C:
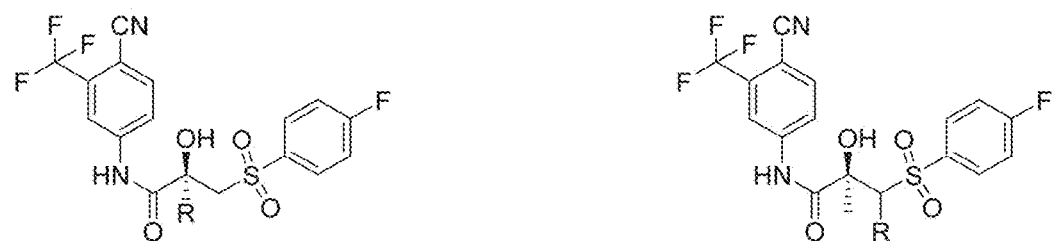
Figure 4D:
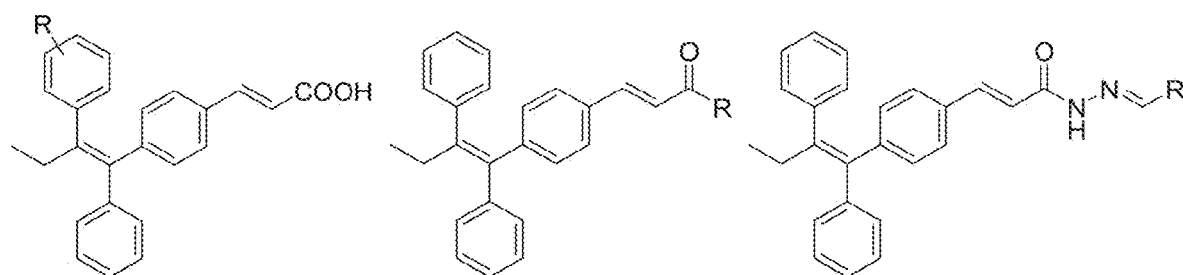
Figure 4E:
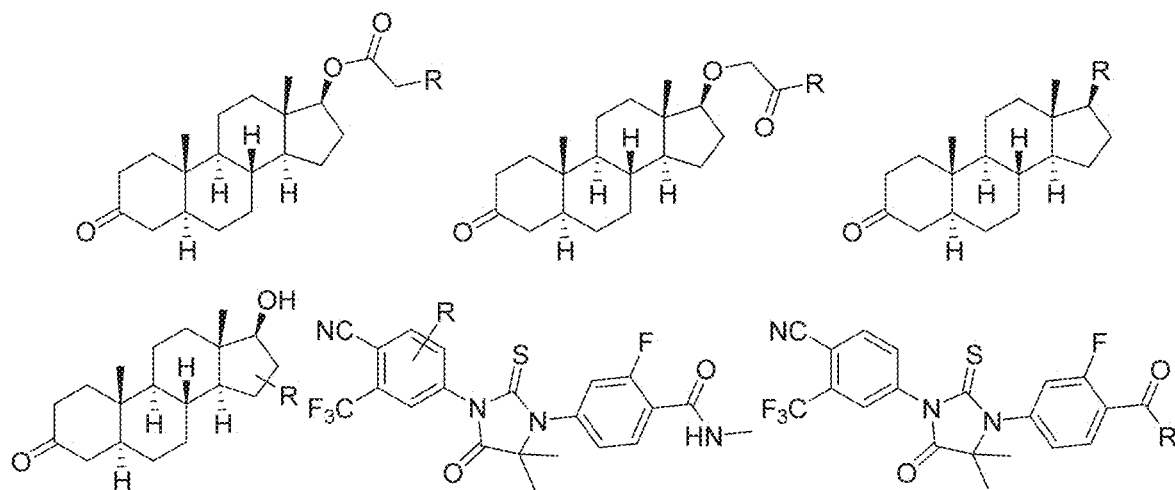

FIG. 4A-4B present examples of SETDB1 Targeting Ligands wherein R is the point at which the Linker is attached. For additional examples and related ligands, see, the PDB crystal structure 5KE2 ("SETDB1 in complex with inhibitor XST06472A", Iqbal A. et al.); the PDB crystal structure 5KE3 ("SETDB1 in complex with fragment MRT0181a", Iqbal A. et al.); the PDB crystal structure 5KH6 ("SETDB1 in complex with fragment methyl 3-(methylsulfonylamino)benzoate", Walker J. R. et al. Structural Genomics Consortium); and, the PDB crystal structure 5KCO ("SETDB 1 in complex with [N]-(4-chlorophenyl)methanesulfonamide", Walker J. R. et al.)

FIG. 4C-4P present examples of SMYD2 Targeting Ligands wherein R is the point at which the Linker is attached. For additional examples and related ligands, see, the PDB crystal structure 5KJK ("SMYD2 in complex with inhibitor AZ13450370", Cowen S. D. et al.); the PDB crystal structure 5KJM ("SMYD2 in complex with AZ931", Cowen S. D. et al.); the PDB crystal structure SKJN ("SMYD2 in complex with AZ506", Cowen S. D. et al.); the PDB crystal structure 5ARF ("SMYD2 in complex with N-[3-(4-chlorophenyl)-1-{N'-cyano-N-[3-(difluoromethoxy)phenyl]carbamimidoyl}-4 5-dihydro-1H-pyrazol-4-YL]-N-ethyl-2-hydroxyacetamide", Eggert E. et al.); the PDB crystal structure 5ARG ("SMYD2 in complex with BAY598", Eggert E. et al.); the PDB crystal structure 4YND ("SMYD2 in complex with A-893", Sweis R. F. et al.); the PDB crystal structure 4WUY ("SMYD2 in complex with LLY-507", Nguyen H. et al.); and, the PDB crystal structure 3S7B ("N-cyclohexyl-N~3~-[2-(3 4-dichlorophenyl)ethyl]-N-(2-{[2-(5-hydroxy-3-oxo-3 4-dihydro-2H-1 4-benzoxazin-8-yl)ethyl] amino}ethyl)-beta-alaninamide", Ferguson A. D. et al.).

FIG. 4Q-4R present examples of SMYD3 Targeting Ligands wherein R is the point at which the Linker is attached. For additional examples and related ligands, see, the crystal structure 5H17 ("SMYD3 in complex with 5'-{ [(3S)-3-amino-3-carboxypropyl][3-(dimethylamino)propyl] amino}-5'-deoxyadenosine", Van Aller G. S. et al.); the crystal structure 5CCL ("SMYD3 in complex with oxindole compound", Mitchell L. H. et al.); and, the crystal structure 5CCM ("Crystal structure of SMYD3 with SAM and EPZ030456").

FIG. 4S presents examples of SUV4-20H1 Targeting Ligands wherein R is the point at which the Linker is attached. For additional examples and related ligands, see, the PDB crystal structure 5CPR ("SUV4-20H1 in complex with inhibitor A-196", Bromberg K. D. et al.).

FIG. 4T-4AA present examples of Wild Type Androgen Receptor Targeting Ligands wherein R is the point at which the Linker is attached. For additional examples and related ligands, see, the PDB crystal structures 5T8E and 5T8J ("Androgen Receptor in complex with 4-(pyrrolidin-1-yl) benzonitrile derivatives", Asano M. et al.); Asano M. et al.

*Bioorg. Med. Chem. Lett.* 27: 1897-1901 (2017); the PDB crystal structure 5JJM ("Androgen Receptor", Nadal M. et al.); the PDB crystal structure 5CJ6 ("Androgen Receptor in complex with 2-Chloro-4-[[(1R 2R)-2-hydroxy-2-methyl-cyclopentyl]amino]-3-methyl-benzonitrile derivatives", Saeed A. et al.); the PDB crystal structure 4QL8 ("Androgen Receptor in complex with 3-alkoxy-pyrrolo[1 2-b]pyrazolines derivatives", Ullrich T. et al.); the PDB crystal structure 4HLW ("Androgen Receptor Binding Function 3 (BF3) Site of the Human Androgen Receptor through Virtual Screening", Munuganti R. S. et al.); the PDB crystal structure 3V49 ("Androgen Receptor lbd with activator peptide and sarm inhibitor 1", Nique F. et al.); Nique F. et al. *J. Med. Chem.* 55: 8225-8235 (2012); the PDB crystal structure 2YHD ("Androgen Receptor in complex with AF2 small molecule inhibitor", Axerio-Cilies P. et al.); the PDB crystal structure 3RLJ ("Androgen Receptor ligand binding domain in complex with SARM S-22", Bohl C. E. et al.); Bohl C. E. et al. *J. Med. Chem.* 54: 3973-3976 (2011); the PDB crystal structure 3B5R ("Androgen Receptor ligand binding domain in complex with SARM C-31", Bohl C. E. et al.); Bohl C. E. et al. *Bioorg. Med. Chem. Lett.* 18: 5567-5570 (2008); the PDB crystal structure 2PIP ("Androgen Receptor ligand binding domain in complex with small molecule", Estebanez-Perpina E. et al.); Estebanez-Perpina. E. *Proc. Natl. Acad. Sci.* 104:16074-16079 (2007); the PDB crystal structure 2PNU ("Androgen Receptor ligand binding domain in complex with EM5744", Cantin L. et al.); and, the PDB crystal structure 2HVC ("Androgen Receptor ligand binding domain in complex with LGD2226", Wang F. et al.). For additional related ligands, see, Matias P. M. et al. "Structural Basis for the Glucocorticoid Response in a Mutant Human Androgen Receptor (Ar(Ccr)) Derived from an Androgen-Independent Prostate Cancer." *J. Med. Chem.* 45: 1439 (2002); Sack J. S. et al. "Crystallographic structures of the ligand-binding domains of the androgen receptor and its T877A mutant complexed with the natural agonist dihydrotestosterone." *Proc. Natl. Acad. Sci.* 98: 4904-4909 (2001); He B. et al. "Structural basis for androgen receptor interdomain and coactivator interactions suggests a transition in nuclear receptor activation function dominance." *Mol. Cell* 16: 425-438 (2004); Pereira de Jesus-Tran K. "Comparison of crystal structures of human androgen receptor ligand-binding domain complexed with various agonists reveals molecular determinants responsible for binding affinity." *Protein Sci.* 15: 987-999 (2006); Bohl C. E. et al. "Structural Basis for Accommodation of Nonsteroidal Ligands in the Androgen Receptor." *Mol Pharmacol.* 63(1): 211-23 (2003); Sun C. et al. "Discovery of potent orally-active and muscle-selective androgen receptor modulators based on an N-aryl-hydroxybicyclohydantoin scaffold." *J. Med. Chem.* 49: 7596-7599 (2006); Nirschl A. A. et al. "N-aryl-oxazolidin-2-imine muscle selective androgen receptor modulators enhance potency through pharmacophore reorientation." *J. Med. Chem.* 52: 2794-2798 (2009); Bohl C. E. et al. "Effect of B-ring substitution pattern on binding mode of propionamide selective androgen receptor modulators." *Bioorg. Med. Chem. Lett.* 18: 5567-5570 (2008); Ullrich T. et al. "3-alkoxy-pyrrolo[1 2-b]pyrazolines as selective androgen receptor modulators with ideal physicochemical properties for transdermal administration." *J. Med. Chem.* 57: 7396-7411 (2014); Saeed A. et al. "2-Chloro-4-[[(1R 2R)-2-hydroxy-2-methyl-cyclopentyl]amino]-3-methyl-benzonitrile: A Transdermal Selective Androgen Receptor Modulator (SARM) for Muscle Atrophy." *J. Med. Chem.* 59: 750-755 (2016); Nique et al. "Discovery of diarylhydantoins as new selective androgen receptor modulators." *J. Med. Chem.* 55: 8225-8235 (2012); and, Michael E. Jung et al. "Structure-Activity Relationship for Thiohydantoin Androgen Receptor Antagonists for Castration-Resistant Prostate Cancer (CRPC)." *J. Med. Chem.* 53: 2779-2796 (2010).

FIG. 4BB presents examples of Mutant T877A Androgen Receptor Targeting Ligands wherein R is the point at which the Linker is attached. For additional examples and related ligands, see, the PDB crystal structure 4OGH ('Androgen Receptor T877A-AR-LBD", Hsu C. L. et al.) and the PDB crystal structure 2OZ7 ("Androgen Receptor T877A-AR-LBD", Bohl C. E. et al.).

FIG. 4CC presents examples of Mutant W741L Androgen Receptor Targeting Ligands wherein R is the point at which the Linker is attached. For additional examples and related ligands, see, the PDB crystal structure 4OJB ("Androgen Receptor T877A-AR-LBD", Hsu C. L. et al.).

FIG. 4DD-4EE presents examples of Estrogen and/or Androgen Targeting Ligands wherein R is the point at which the Linker is attached.

Figure 5A:
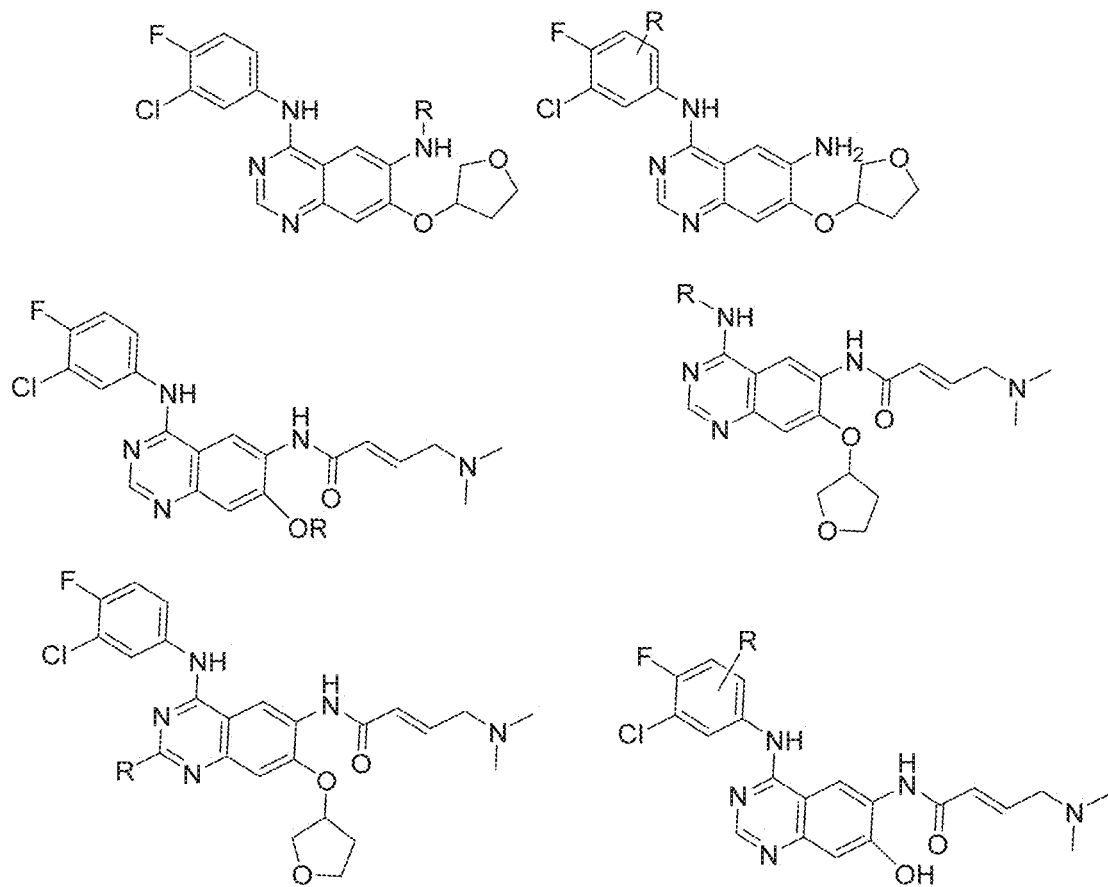

FIG. 5A presents examples of Afatinib, a Targeting Ligands for the EGFR and ErbB2/4 receptors. R is the point at which the Linker is attached.

Figure 5B:
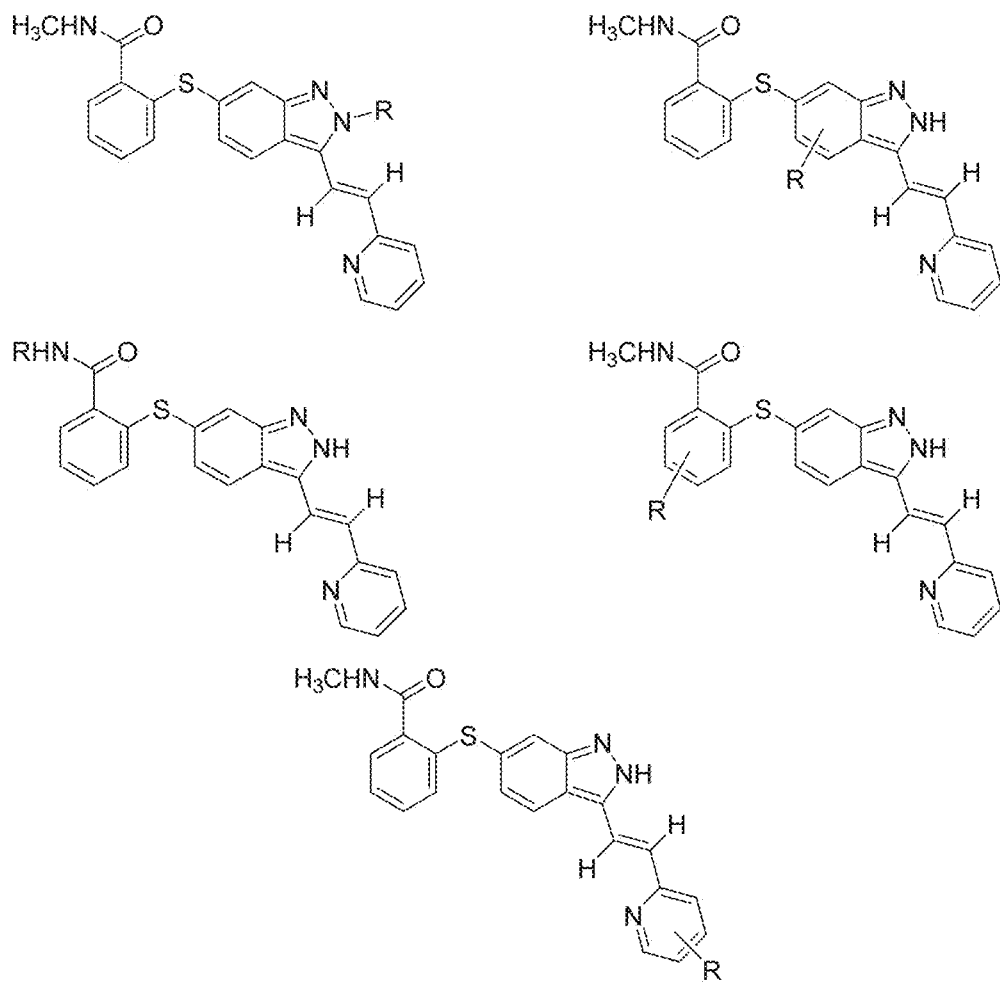

FIG. 5B presents examples of Axitinib, a Targeting Ligands for the VEGFR1/2/3, PDGFRβ, and Kit receptors. R is the point at which the Linker is attached.

Figure 5C:
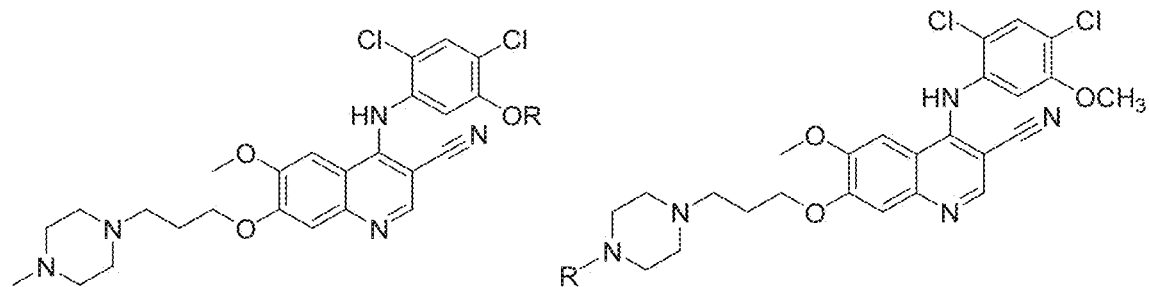
Figure 5D:
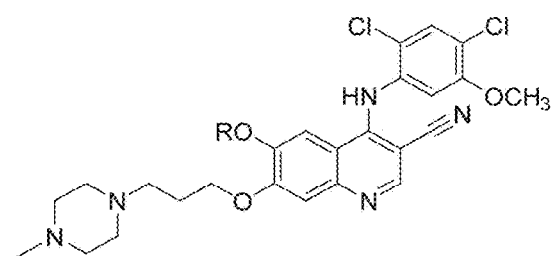

FIG. 5C-5D present examples of Bosutinib, a Targeting Ligands for the BCR-Abl, Src, Lyn and Hck receptors. R is the point at which the Linker is attached.

Figure 5E:
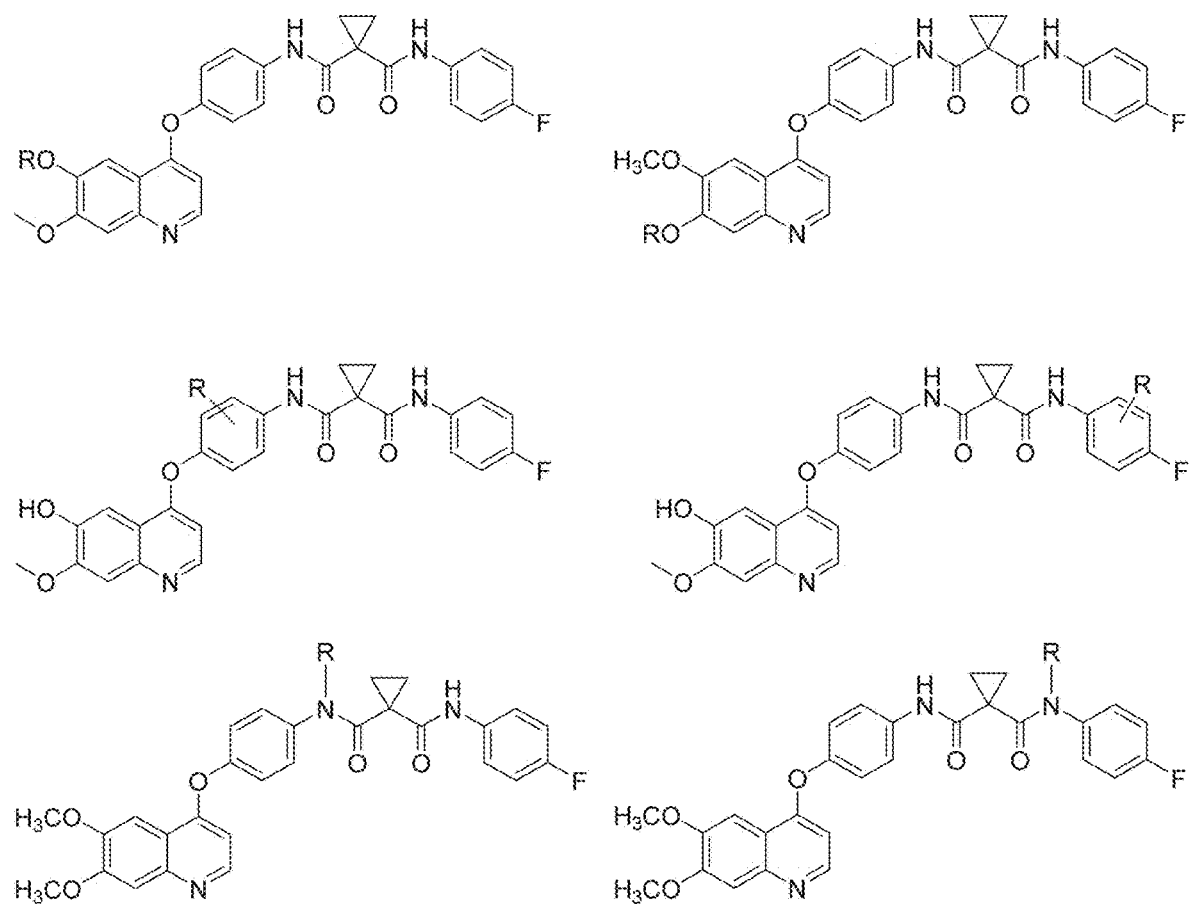

FIG. 5E presents examples of Cabozantinib, a Targeting Ligands for the RET, c-Met, VEGFR1/2/3, Kit, TrkB, Flt3, Axl, and Tie 2 receptors. R is the point at which the Linker is attached.

Figure 5F:
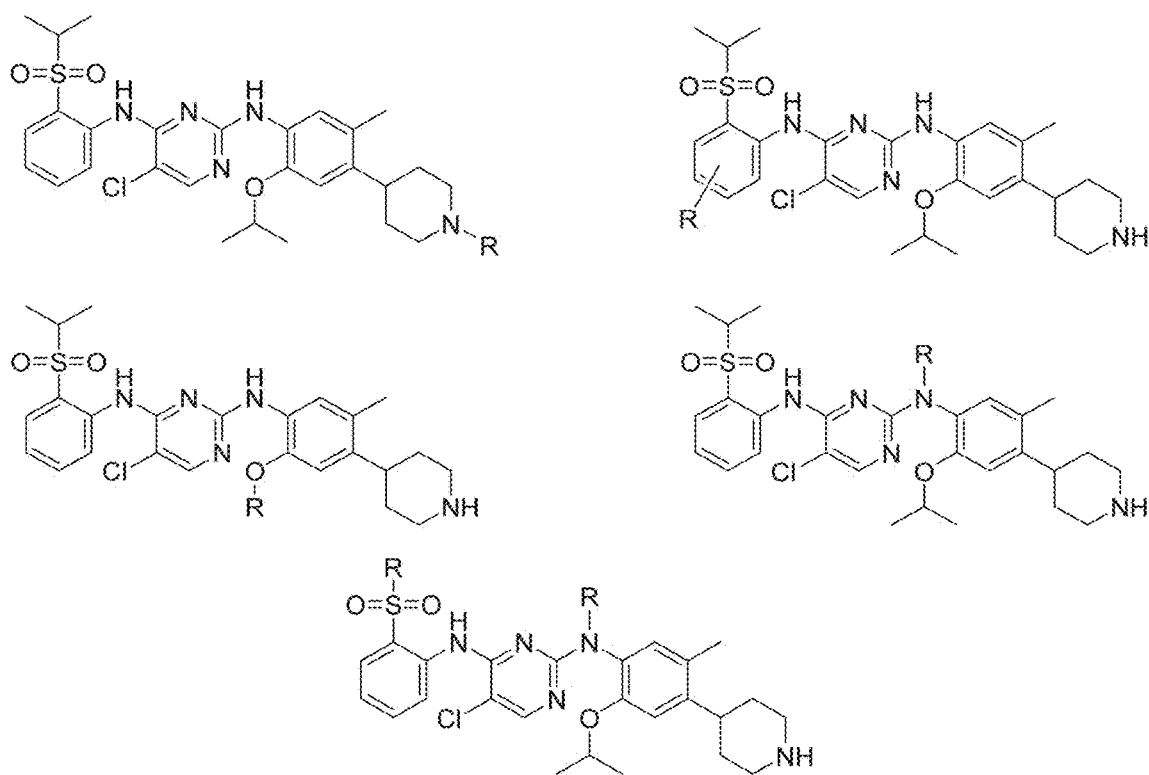

FIG. 5F presents examples of Ceritinib, a Targeting Ligands for the ALK, IGF-1R, InsR, and ROS1 receptors. R is the point at which the Linker is attached.

Figure 5G:
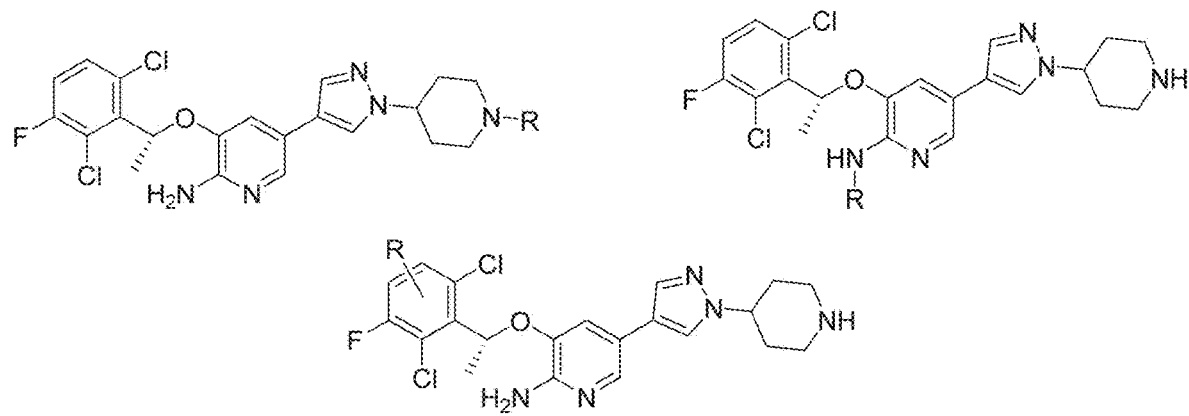

FIG. 5G presents examples of Crizotinib, a Targeting Ligands for the ALK, c-Met, HGFR, ROS1, and MST1R receptors. R is the point at which the Linker is attached.

Figure 5H:
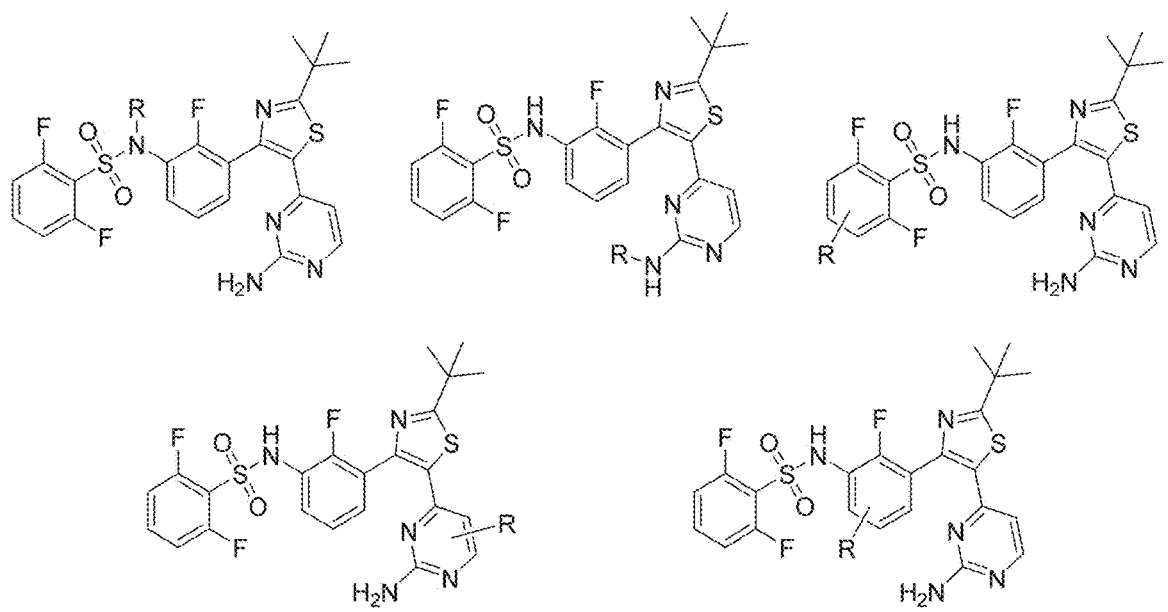

FIG. 5H presents examples of Dabrafenib, a Targeting Ligands for the B-Raf receptor. R is the point at which the Linker is attached.

Figure 5I:
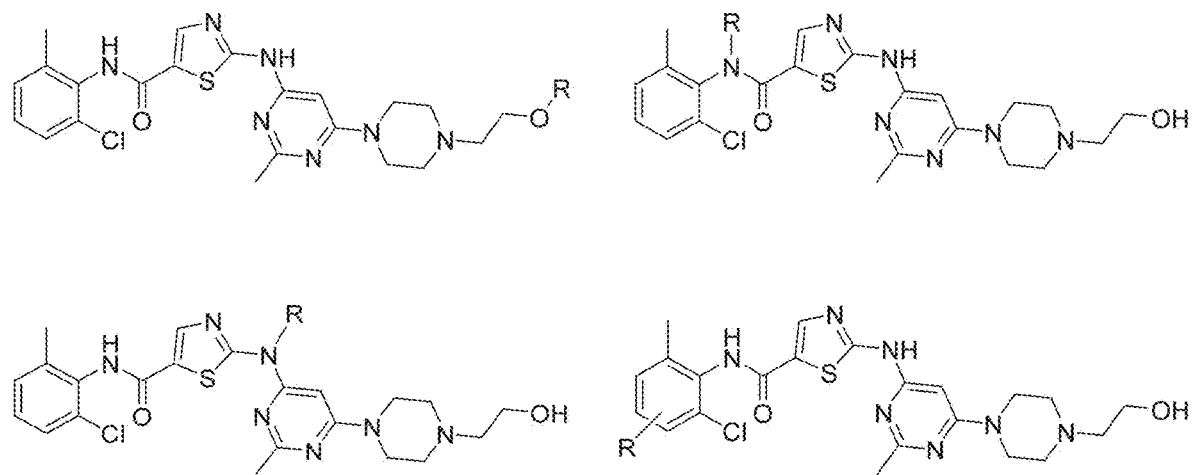

FIG. 5I presents examples of Dasatinib, a Targeting Ligands for the BCR-Abl, Src, Lck, Lyn, Yes, Fyn, Kit, EphA2, and PDGFRβ receptors. R is the point at which the Linker is attached.

Figure 5J:
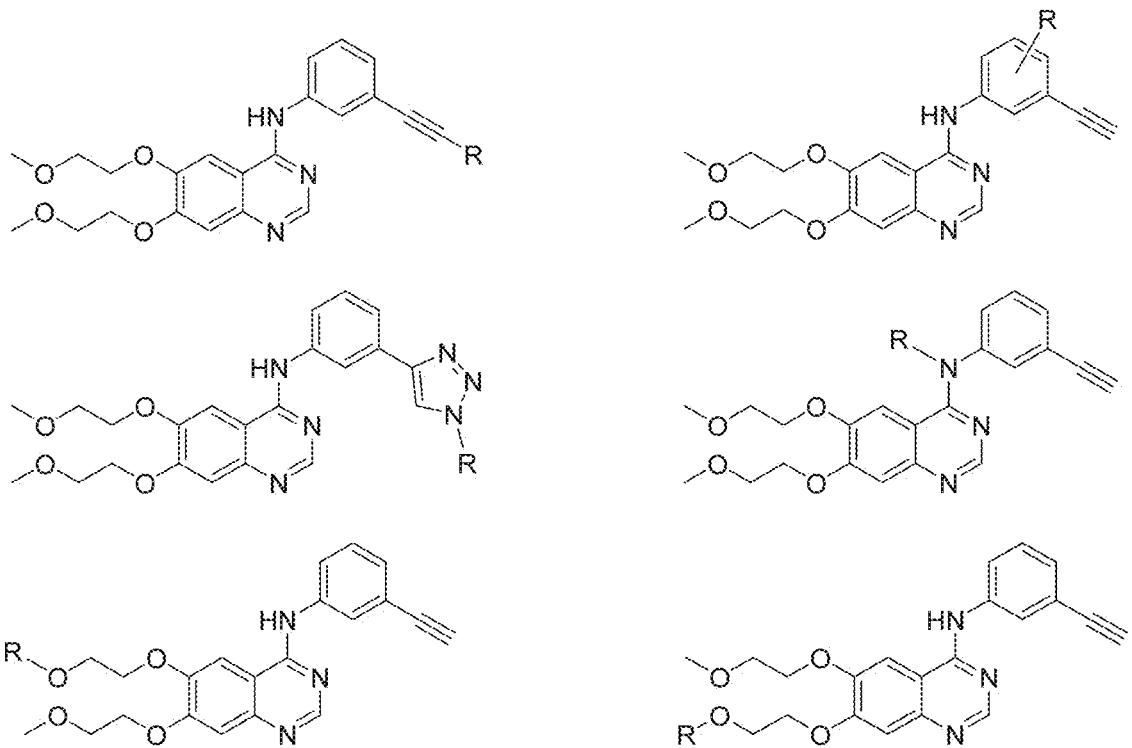

FIG. 5J presents examples of Erlotinib, a Targeting Ligands for the EGFR receptor. R is the point at which the Linker is attached.

Figure 5K:
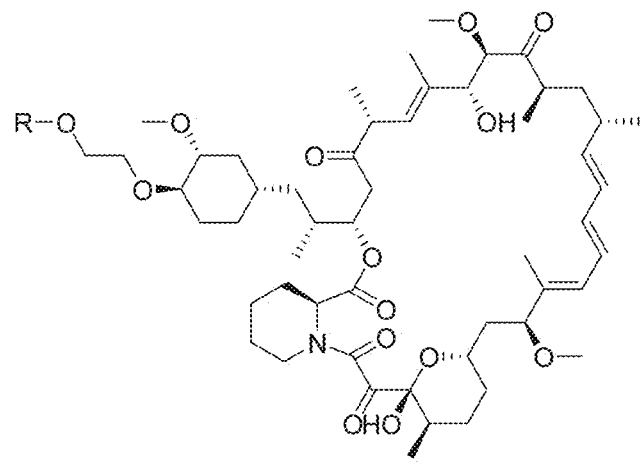
Figure 5M:
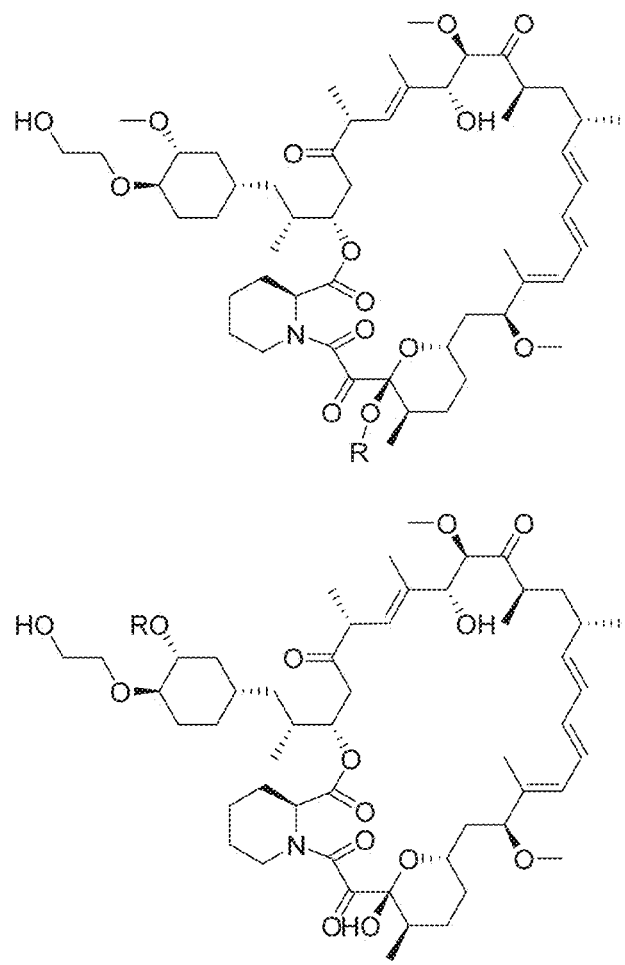
Figure 5N:
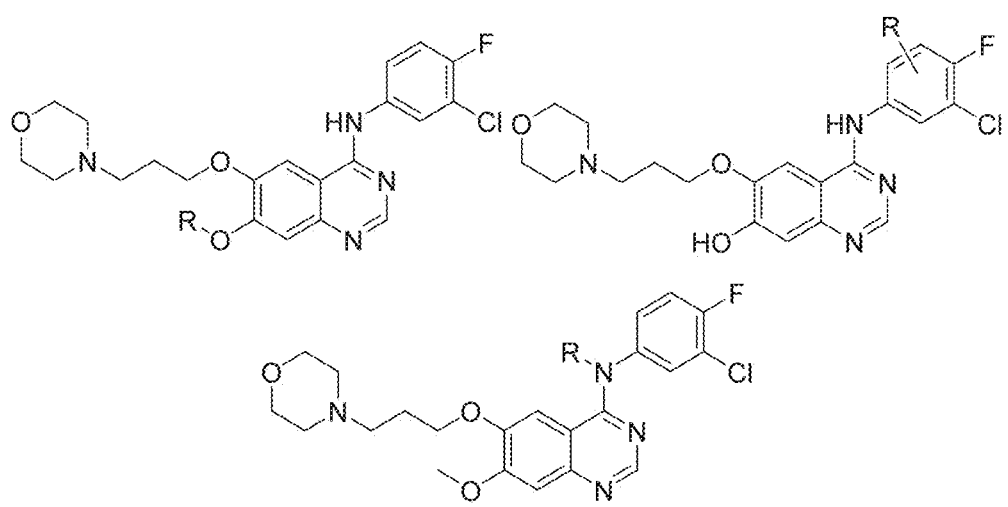
Figure 5O:
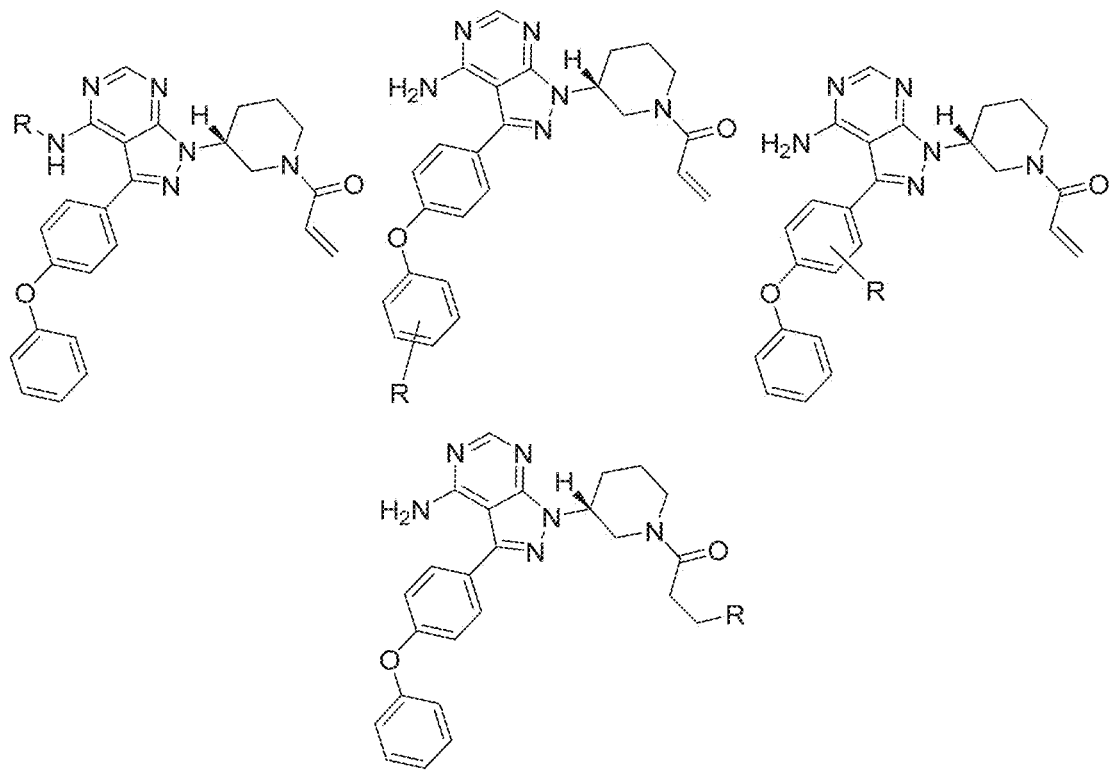
Figure 5P:
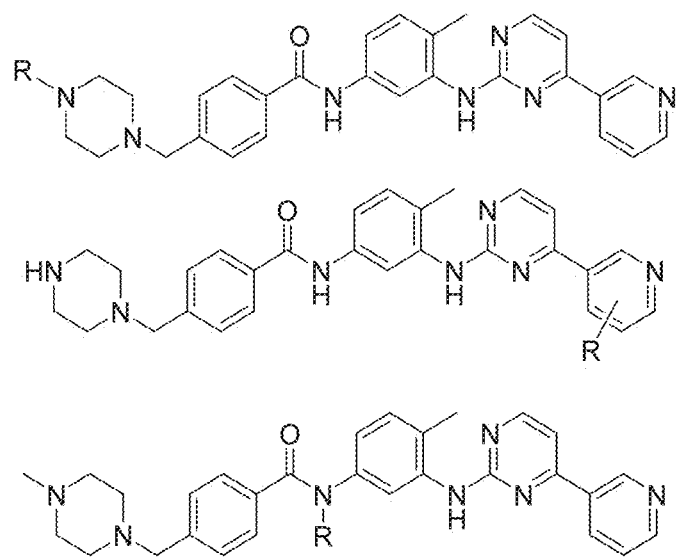
Figure 5Q:
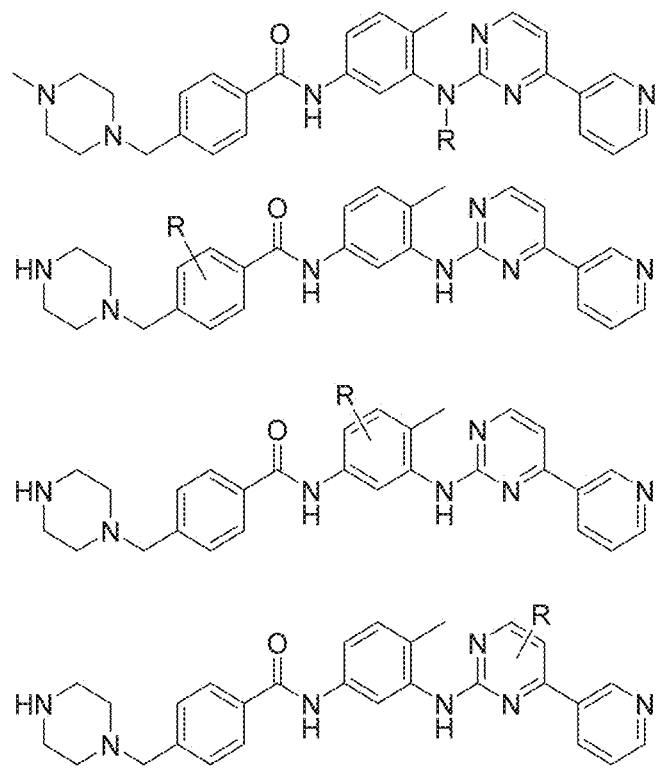
Figure 5R:
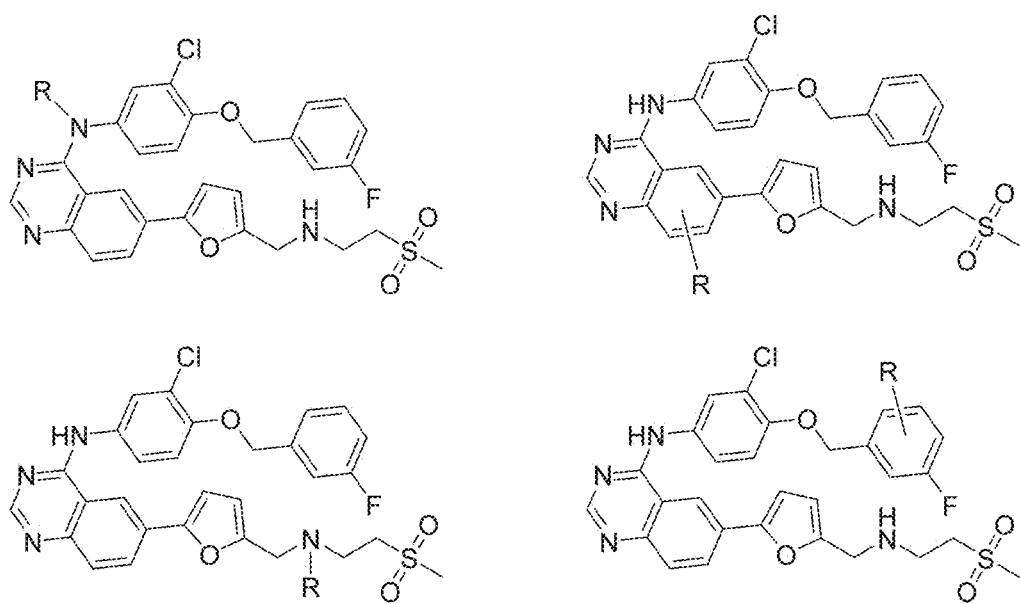
Figure 5S:
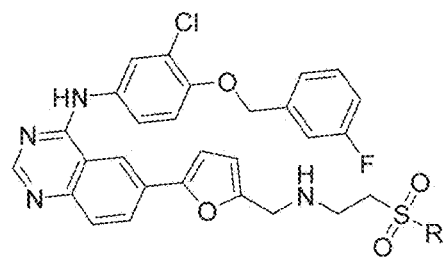
Figure 5T:
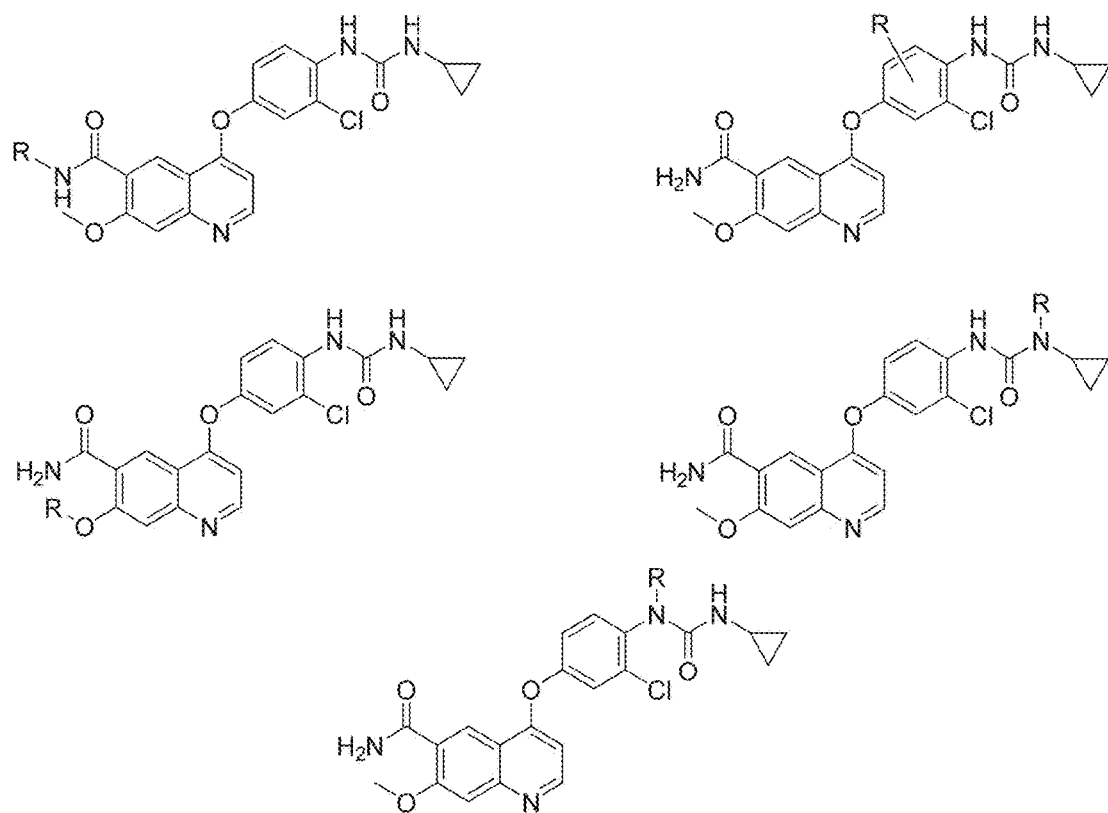
Figure 5U:
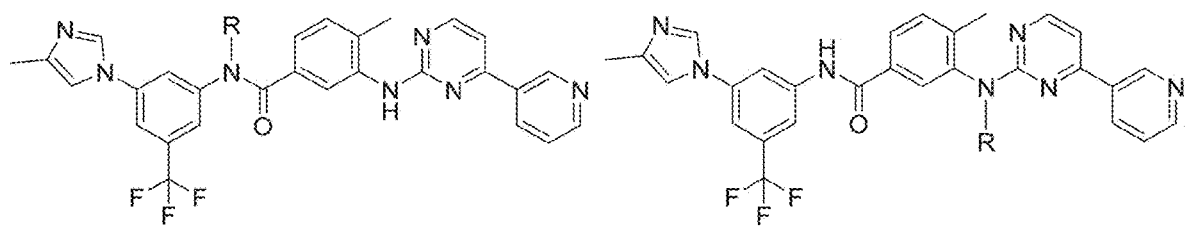
Figure 5V:
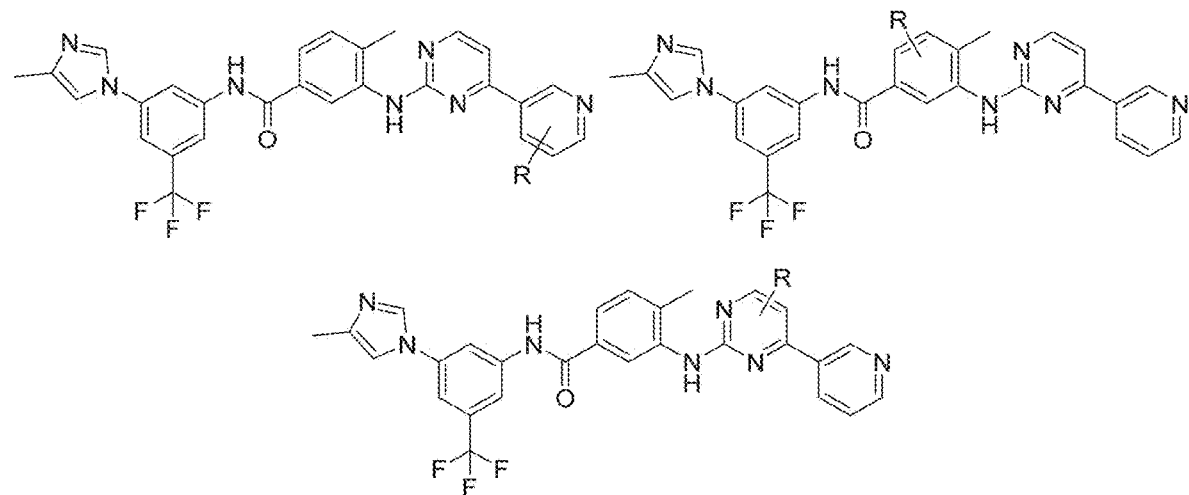
Figure 5W:
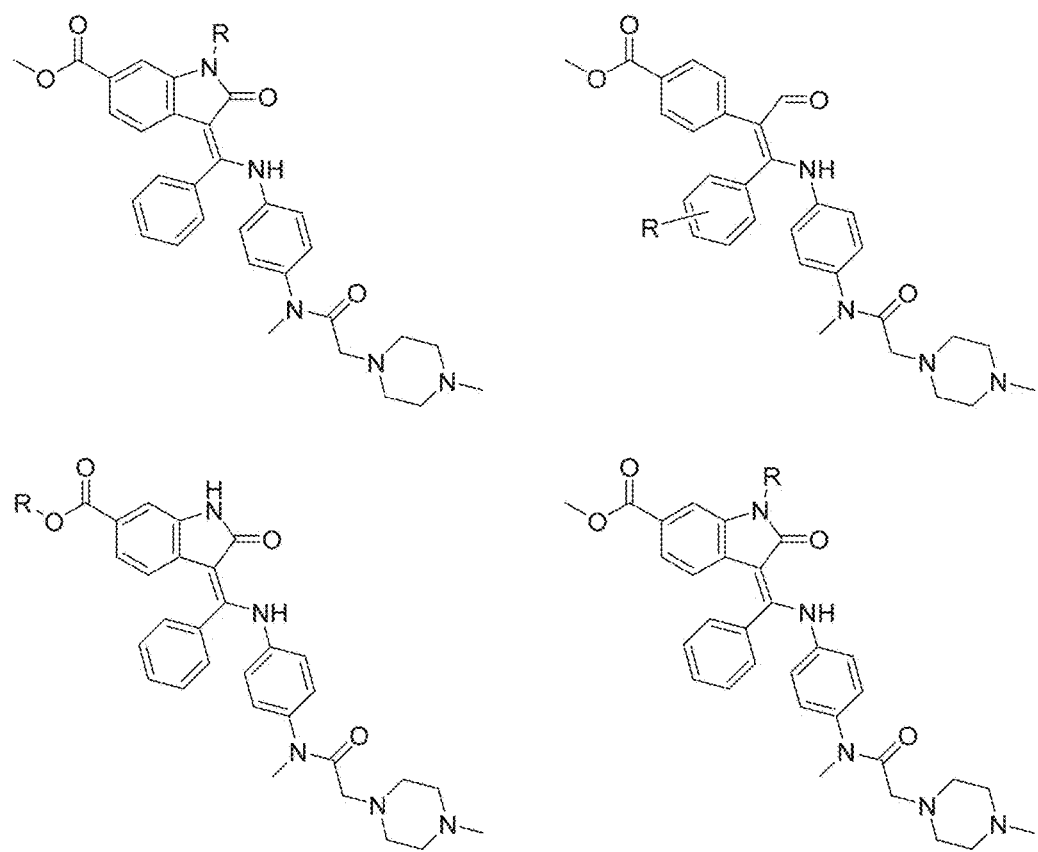
Figure 5X:
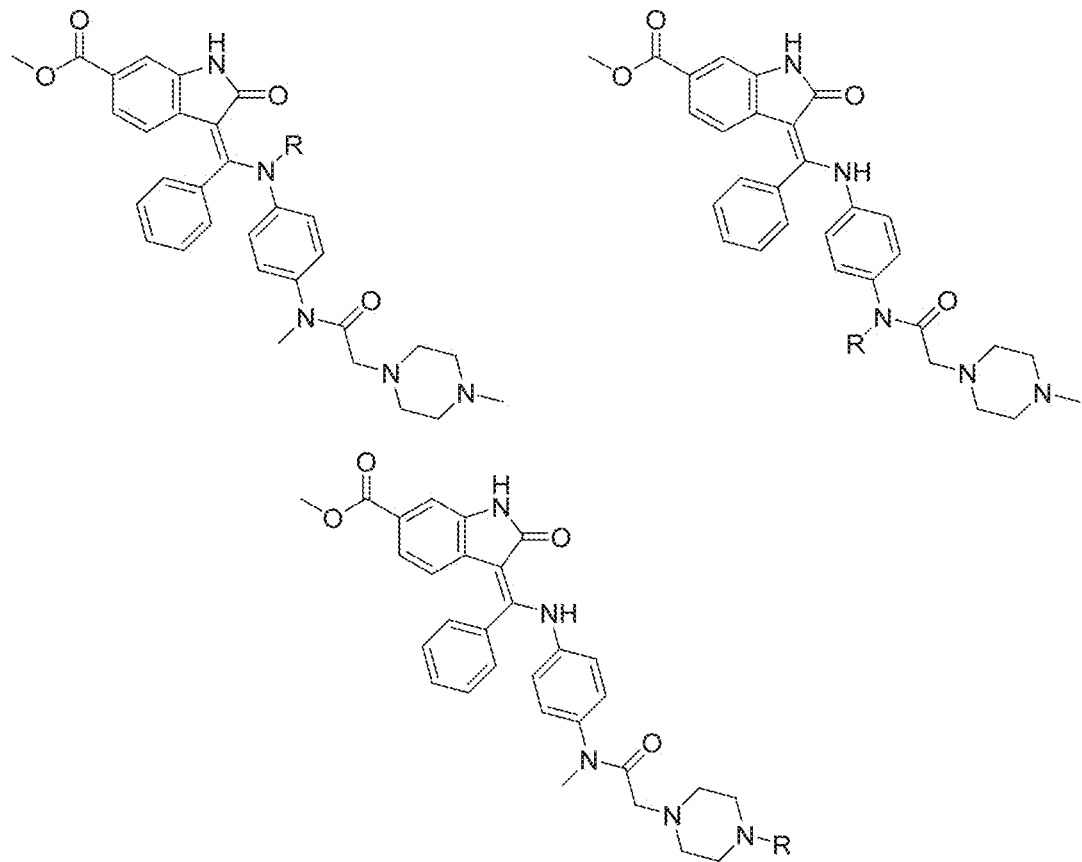
Figure 5Y:
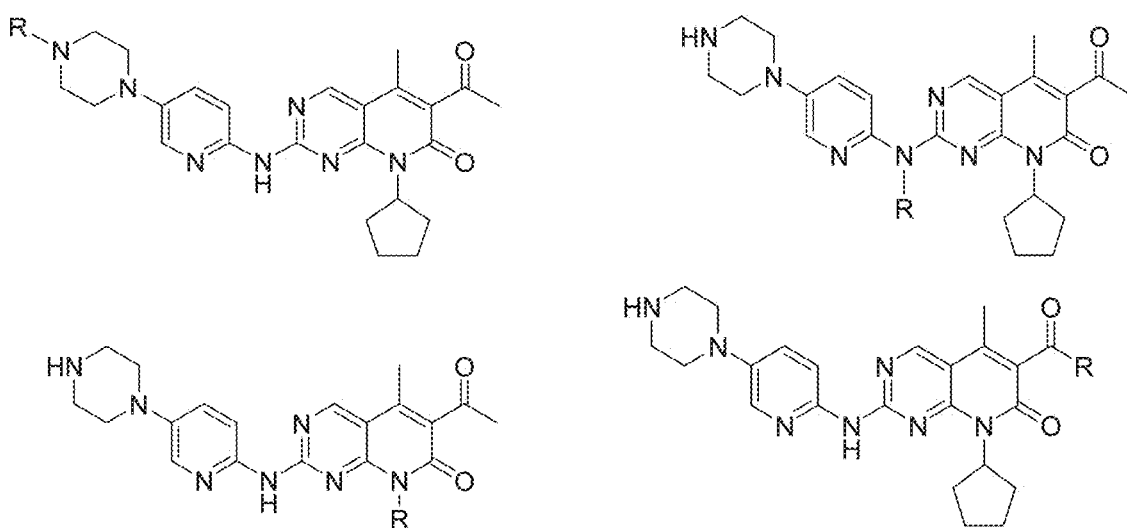
Figure 5C:
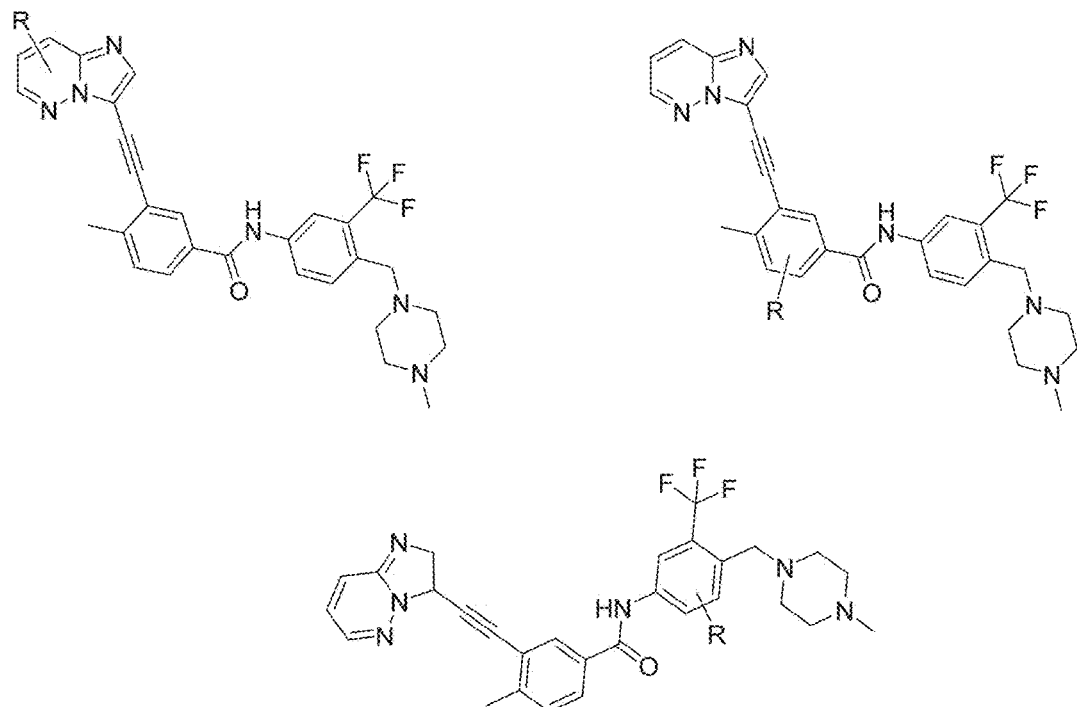
Figure 5D:
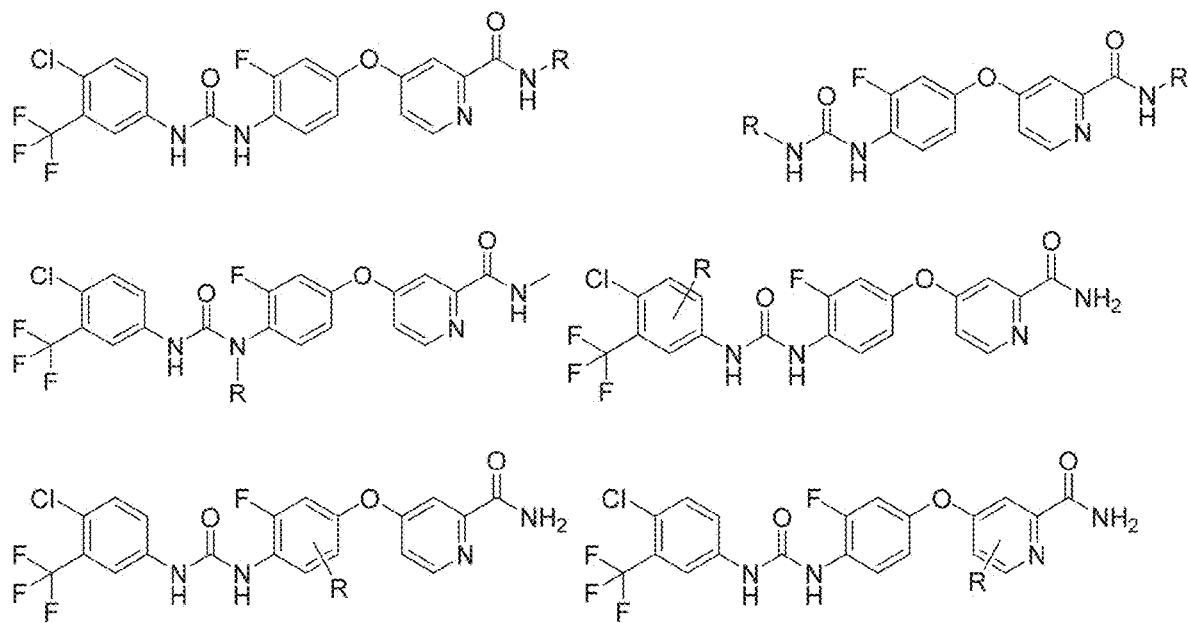
Figure 5E:
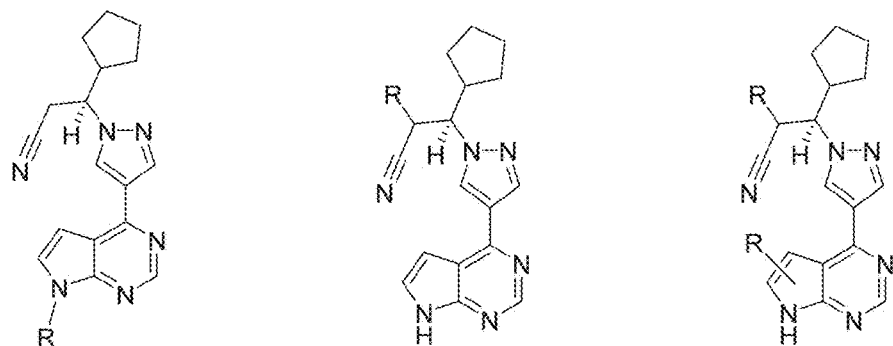
Figure 5F:
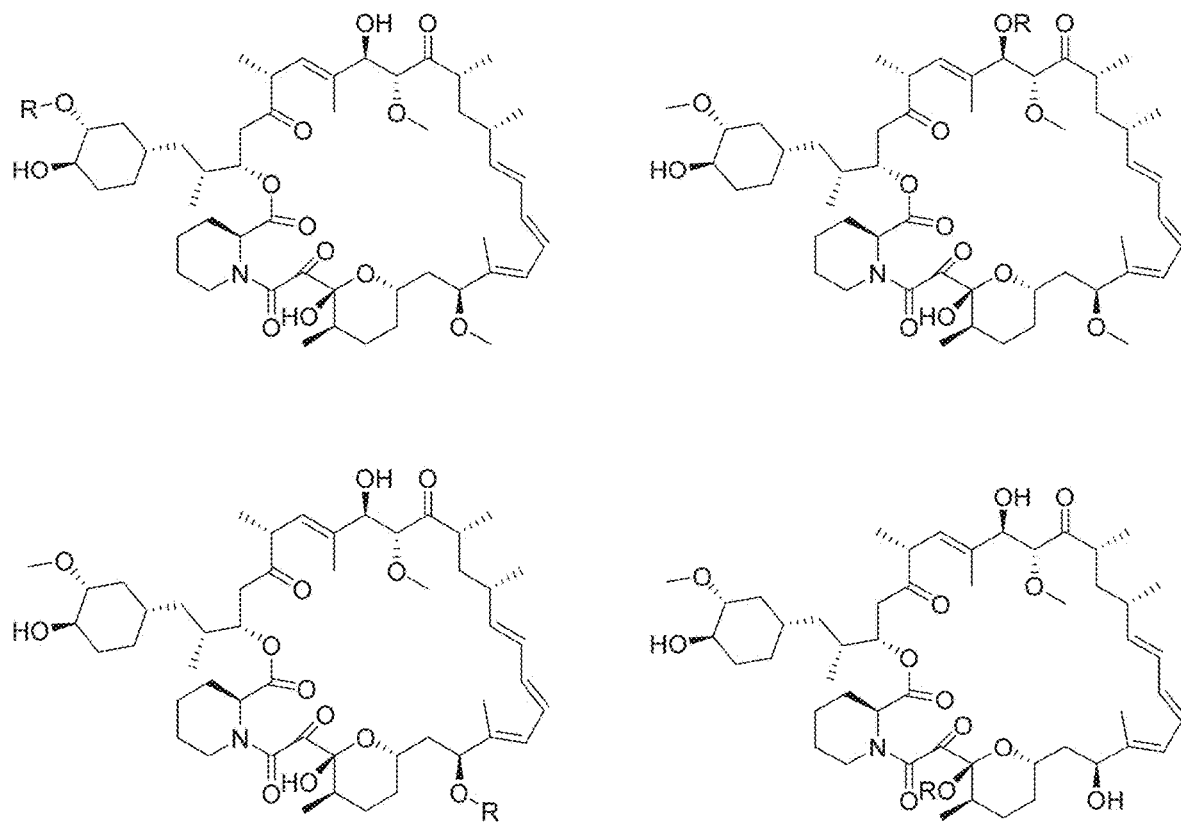
Figure 5G:
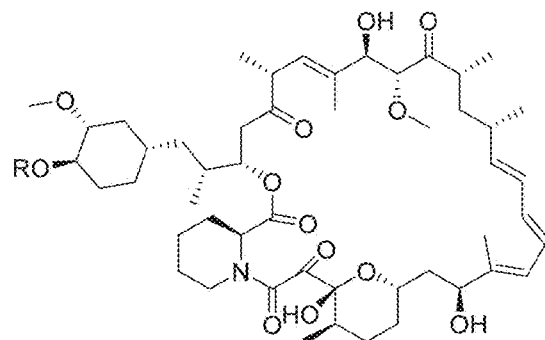
Figure 5H:
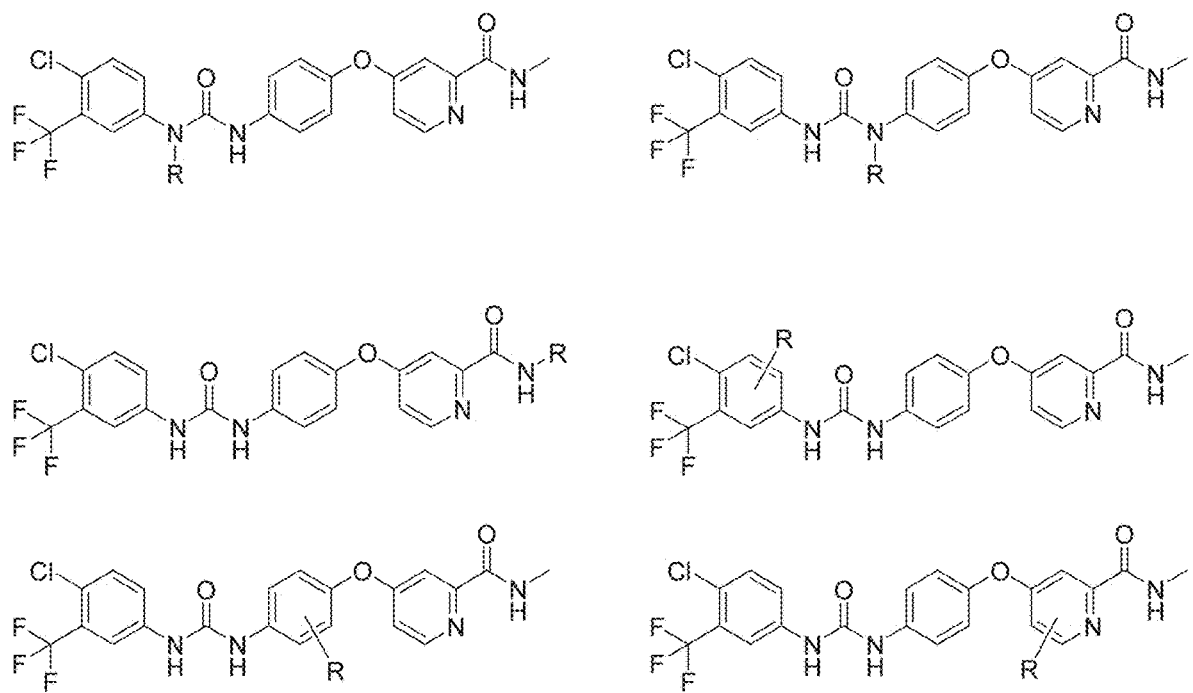
Figure 5I:
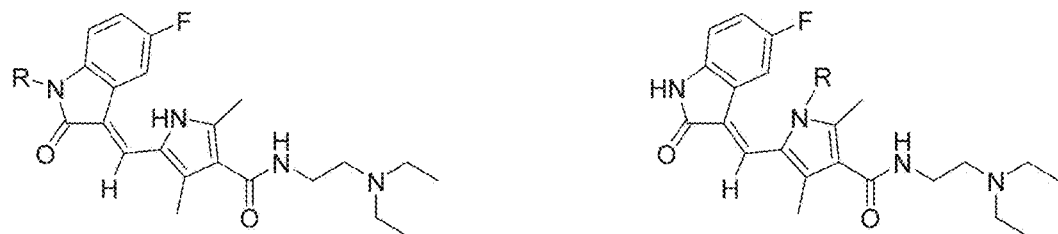
Figure 5L:
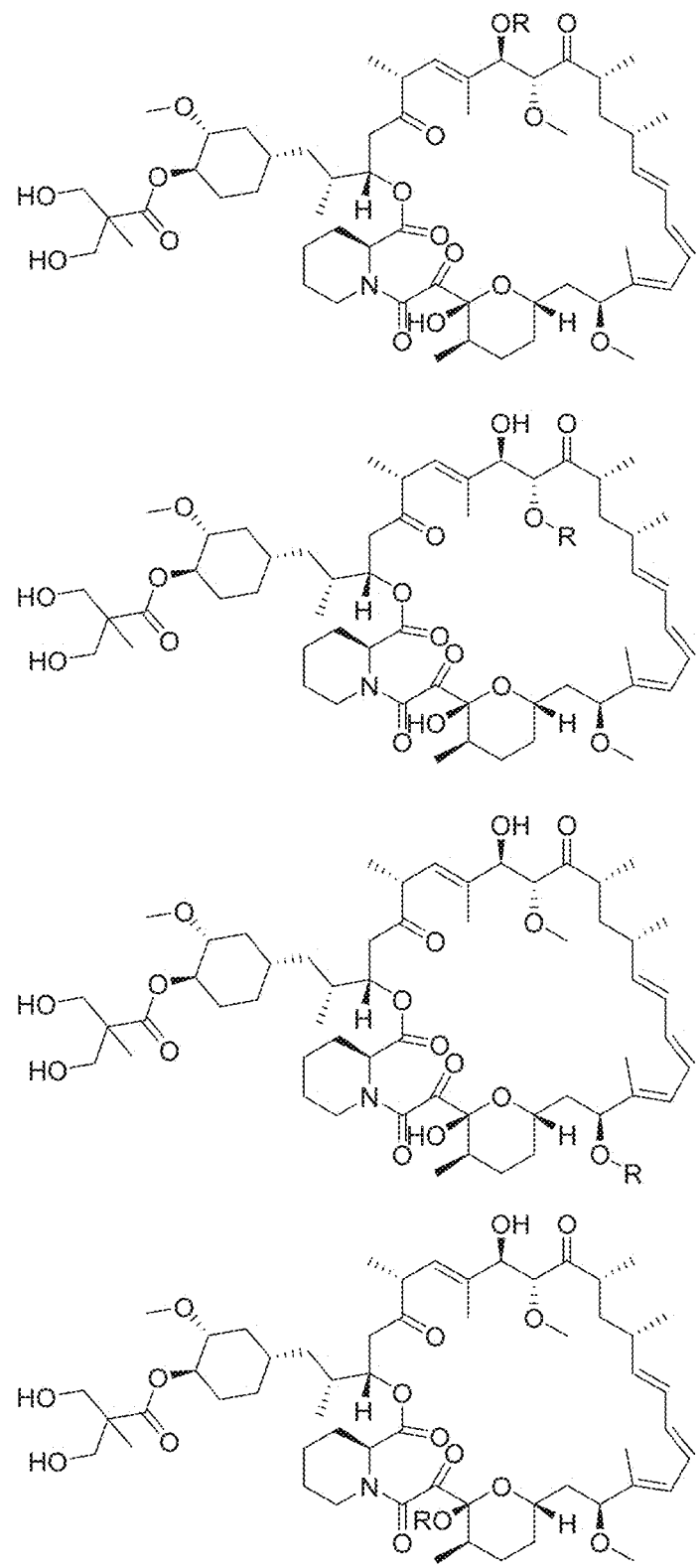
Figure 5M:
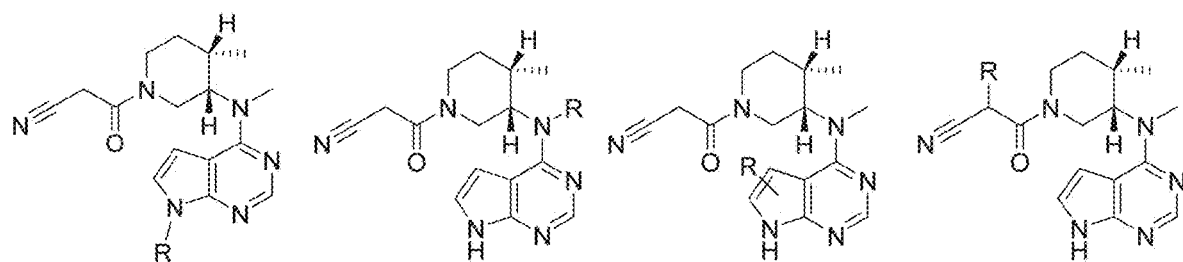
Figure 5N:
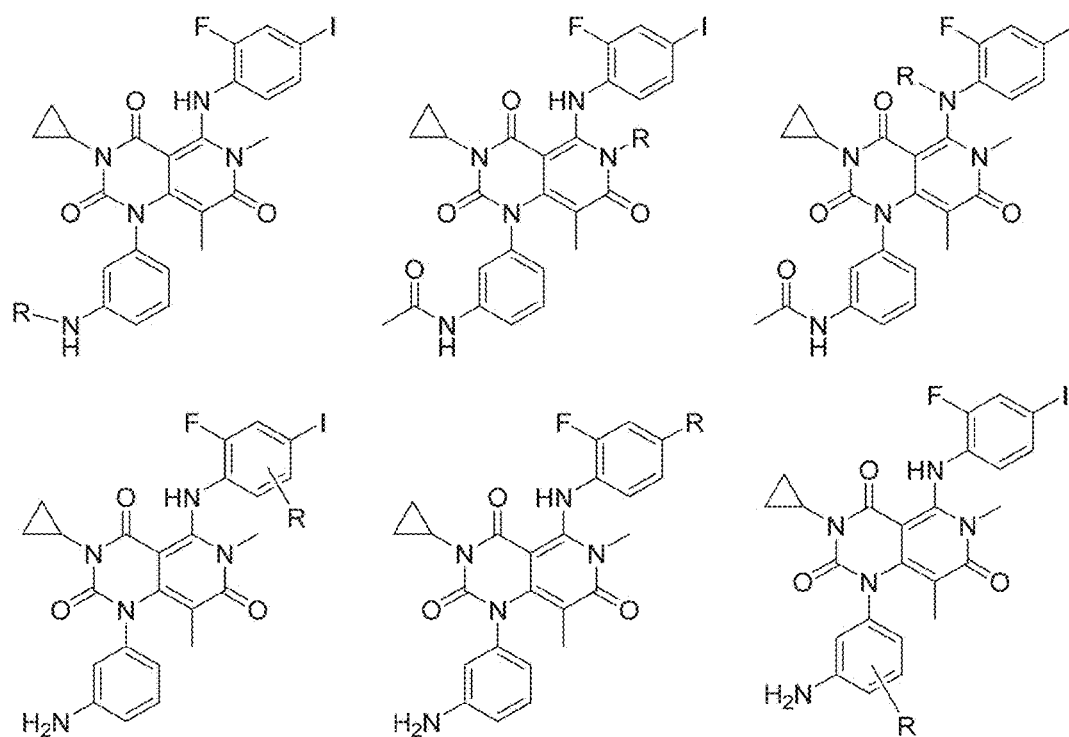
Figure 5O:
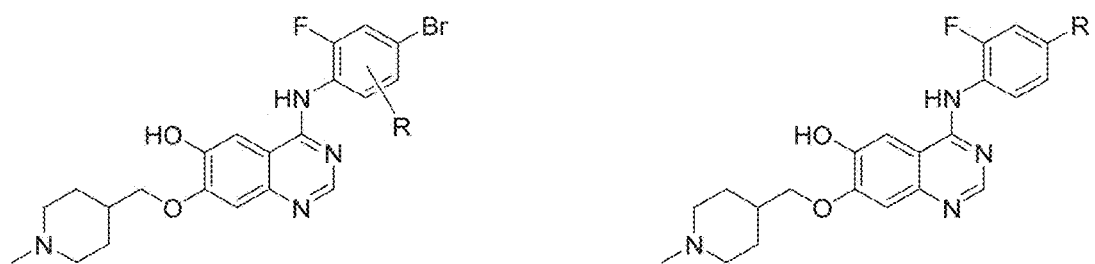
Figure 5P:
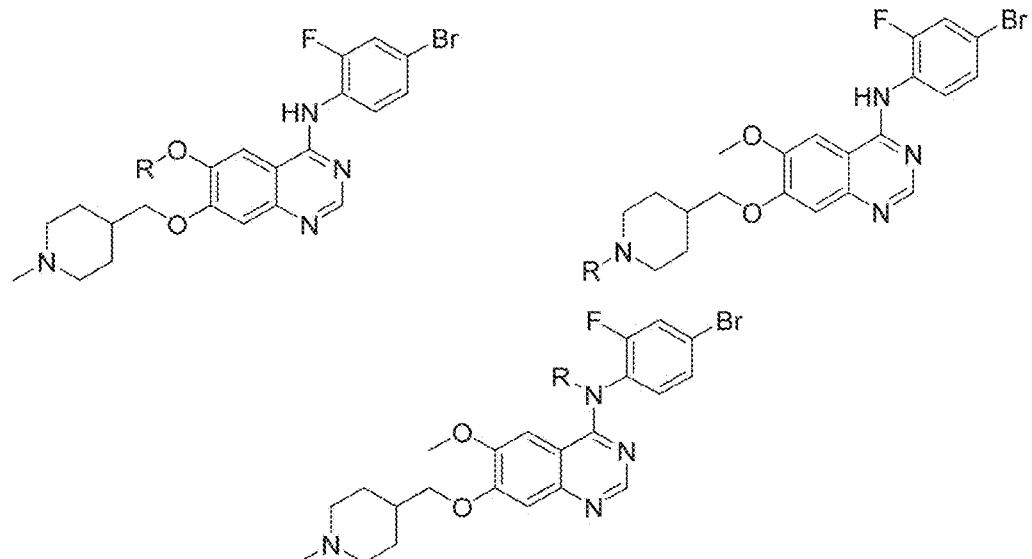
Figure 5Q:
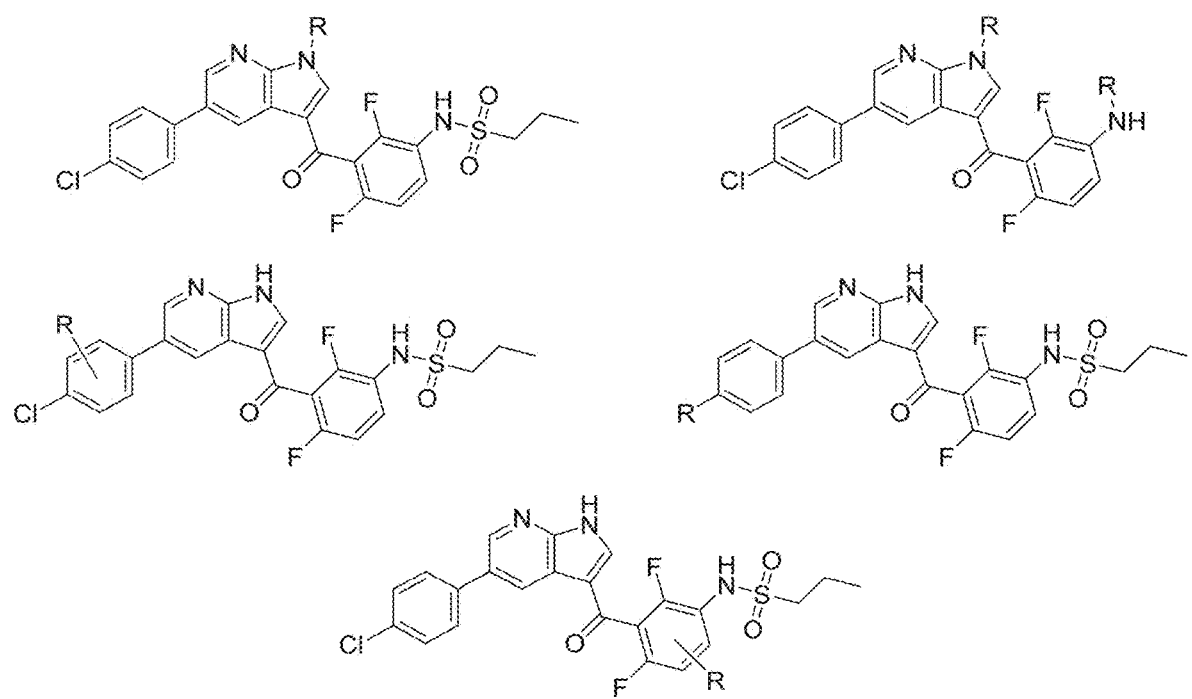
Figure 5R:
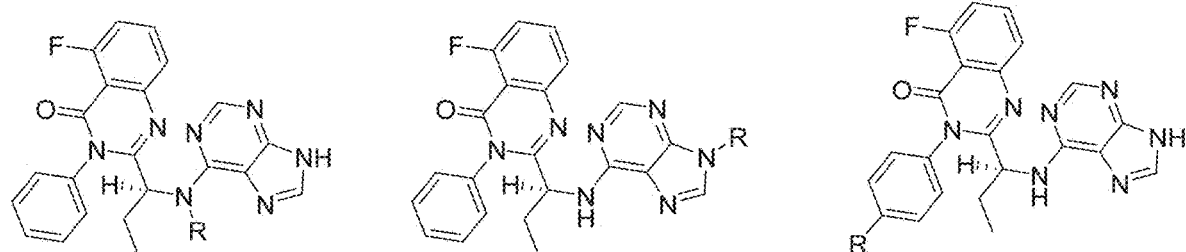
Figure 5S:
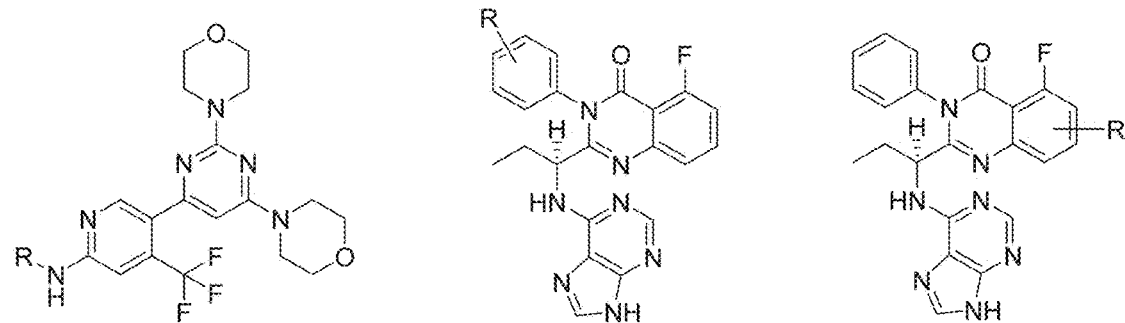
Figure 5T:
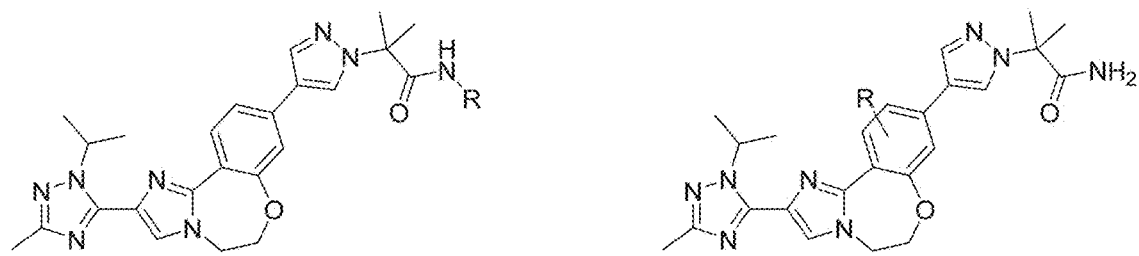
Figure 5U:
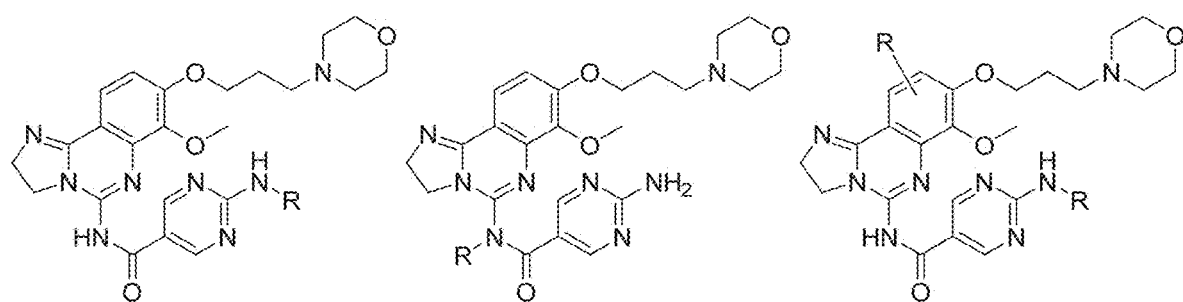
Figure 5V:
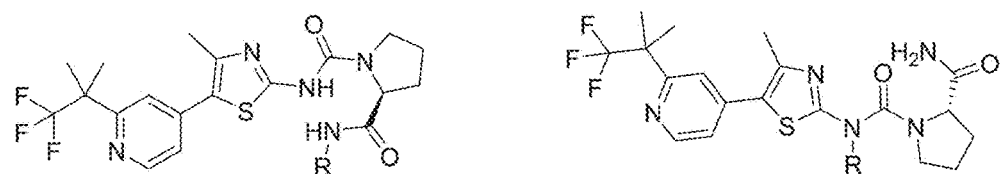
Figure 5W:
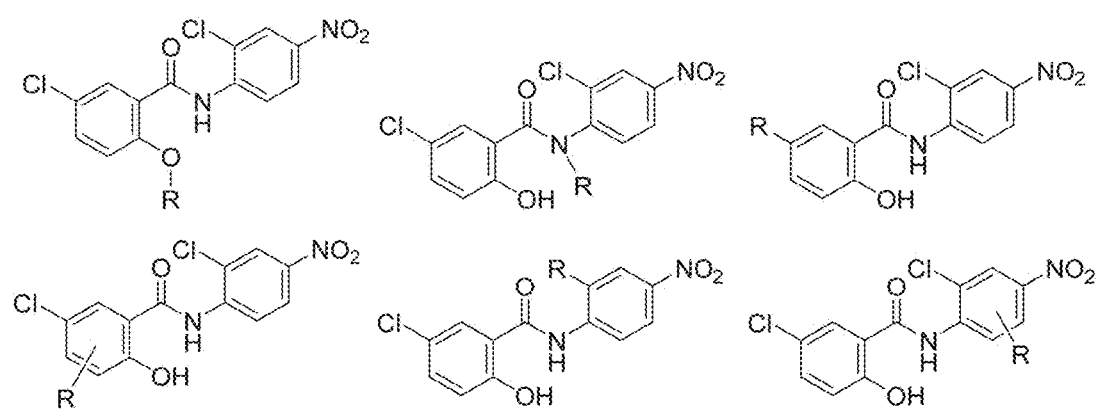

FIG. 5K-5M presents examples of Everolimus, a Targeting Ligands for the HER2 breast cancer receptor, the PNET receptor, the RCC receptors, the RAML receptor, and the SEGA receptor. R is the point at which the Linker is attached.

FIG. 5N presents examples of Gefitinib, a Targeting Ligands for the EGFR and PDGFR receptors. R is the point at which the Linker is attached.

FIG. 5O presents examples of Ibrutinib, a Targeting Ligands for the BTK receptor. R is the point at which the Linker is attached.

FIG. 5P-5Q present examples of Imatinib, a Targeting Ligands for the BCR-Abl, Kit, and PDGFR receptors. R is the point at which the Linker is attached.

FIG. 5R-5S present examples of Lapatinib, a Targeting Ligands for the EGFR and ErbB2 receptors. R is the point at which the Linker is attached.

FIG. 5T presents examples of Lenvatinib, a Targeting Ligands for the VEGFR1/2/3, FGFR1/2/3/4, PDGFRα, Kit, and RET receptors. R is the point at which the Linker is attached.

FIG. 5U-5V a present examples of Nilotinib, a Targeting Ligands for the BCR-Abl, PDGRF, and DDR1 receptors. R is the point at which the Linker is attached.

FIG. 5W-5X present examples of Nintedanib, a Targeting Ligands for the FGFR1/2/3, Flt3, Lck, PDGFRα/β, and VEGFR1/2/3 receptors. R is the point at which the Linker is attached.

FIG. 5Y-5Z present examples of Palbociclib, a Targeting Ligands for the CDK4/6 receptor. R is the point at which the Linker is attached.

FIG. 5AA presents examples of Pazopanib, a Targeting Ligands for the VEGFR1/2/3, PDGFRα/β, FGFR1/3, Kit, Lck, Fms, and Itk receptors. R is the point at which the Linker is attached.

FIG. 5BB-5CC present examples of Ponatinib, a Targeting Ligands for the BCR-Abl, T315I VEGFR, PDGFR, FGFR, EphR, Src family kinases, Kit, RET, Tie2, and Flt3 receptors. R is the point at which the Linker is attached.

FIG. 5DD presents examples of Regorafenib, a Targeting Ligands for the VEGFR1/2/3, BCR-Abl, B-Raf, B-Raf (V600E), Kit, PDGFRα/β, RET, FGFR1/2, Tie2, and Eph2A. R is the point at which the Linker is attached.

FIG. 5EE presents examples of Ruxolitinib, a Targeting Ligands for the JAK1/2 receptors. R is the point at which the Linker is attached.

FIG. 5FF-5GG present examples of Sirolimus, a Targeting Ligands for the FKBP12/mTOR receptors. R is the point at which the Linker is attached.

FIG. 5HH presents examples of Sorafenib, a Targeting Ligands for the B-Raf, CDK8, Kit, Flt3, RET, VEGFR1/2/3, and PDGFR receptors. R is the point at which the Linker is attached.

FIG. 5II-5JJ present examples of Sunitinib, a Targeting Ligands for PDGFRα/β, VEGFR1/2/3, Kit, Flt3, CSF-1R, RET. R is the point at which the Linker is attached.

FIG. 5KK-5LL present examples of Temsirolimus, a Targeting Ligands FKBP12/mTOR. R is the point at which the Linker is attached.

FIG. 5MM presents examples of Tofacitinib, a Targeting Ligands for JAK3 receptors. R is the point at which the Linker is attached.

FIG. 5NN presents examples of Trametinib, a Targeting Ligands for the MEK1/2 receptors. R is the point at which the Linker is attached.

FIG. 5OO-5PP presents examples of Vandetanib, a Targeting Ligands for the EGFR, VEGFR, RET, Tie2, Brk, and EphR. R is the point at which the Linker is attached.

FIG. 5QQ presents examples of Vemurafenib, a Targeting Ligands for the A/B/C-Raf, KSR1, and B-Raf (V600E) receptors. R is the point at which the Linker is attached.

FIG. 5RR presents examples of Idelasib, a Targeting Ligands for the PI3Ka receptor. R is the point at which the Linker is attached.

FIG. 5SS presents examples of Buparlisib, a Targeting Ligands for the PI3Ka receptor. R is the point at which the Linker is attached.

FIG. 5TT presents examples of Taselisib, a Targeting Ligands for the PI3Ka receptor. R is the point at which the Linker is attached.

FIG. 5UU presents examples of Copanlisib, a Targeting Ligands for the PI3Ka. R is the point at which the Linker is attached.

FIG. 5VV presents examples of Alpelisib, a Targeting Ligands for the PI3Ka. R is the point at which the Linker is attached.

FIG. 5WW presents examples of Niclosamide, a Targeting Ligands for the CNNTB1. R is the point at which the Linker is attached.

Figure 6A:
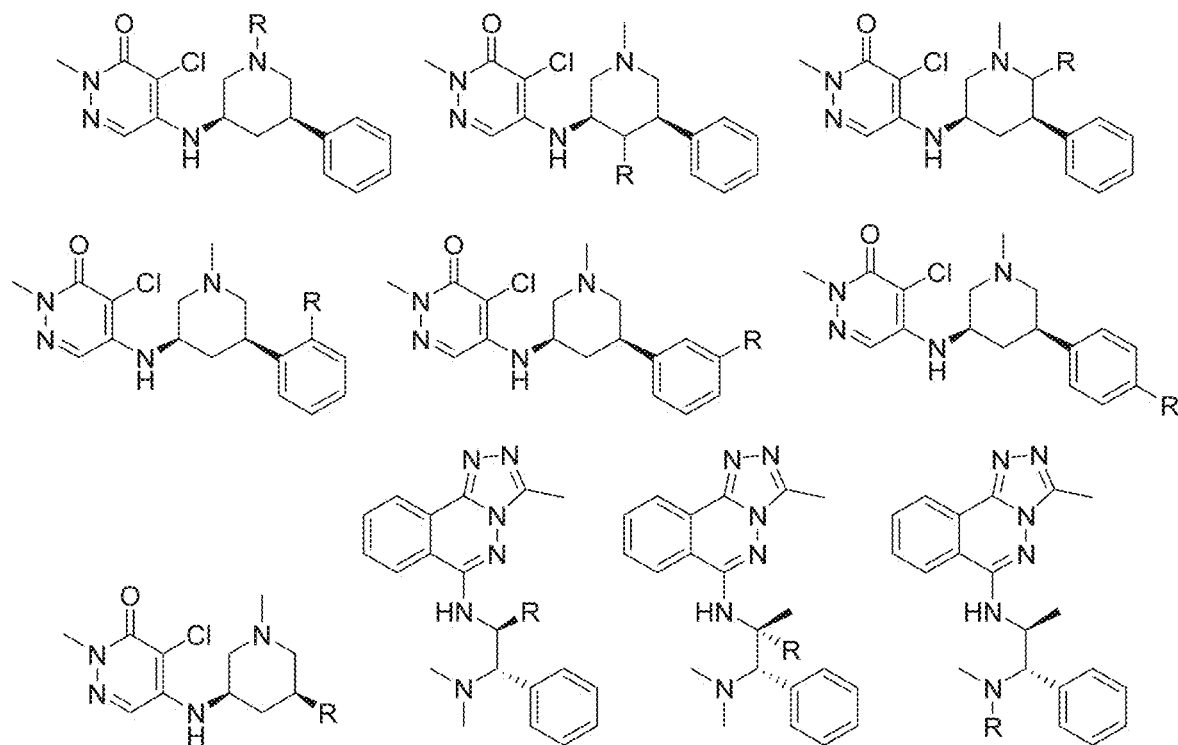
Figure 6B:
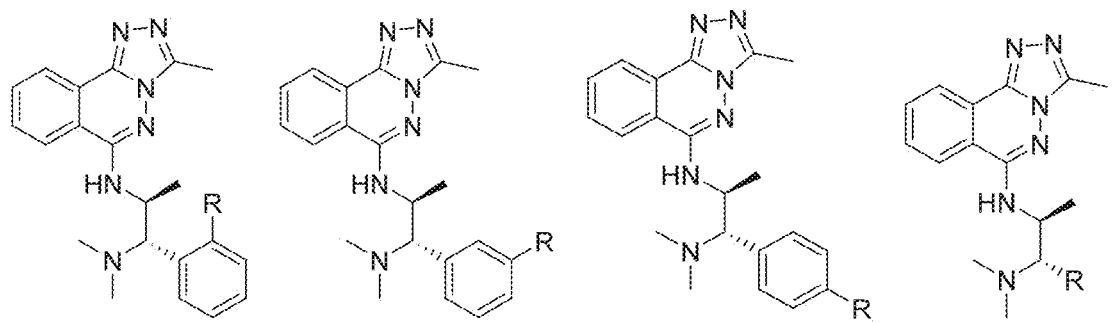

FIG. 6A-6B present examples of the BRD4 Bromodomains of PCAF and GCN5 receptors 1 Targeting Ligands wherein R is the point at which the Linker is attached. For additional examples and related ligands, see, the PDB crystal structure 5tpx ("Discovery of a PCAF Bromodomain Chemical Probe"); Moustakim, M., et al. *Angew. Chem. Int. Ed. Engl.* 56: 827 (2017); the PDB crystal structure 5mlj ("Discovery of a Potent, Cell Penetrant, and Selective p300/CBP-Associated Factor (PCAF)/General Control Nonderepressible 5 (GCN5) Bromodomain Chemical Probe"); and, Humphreys, P. G. et al. *J. Med. Chem.* 60: 695 (2017).

Figure 6C:
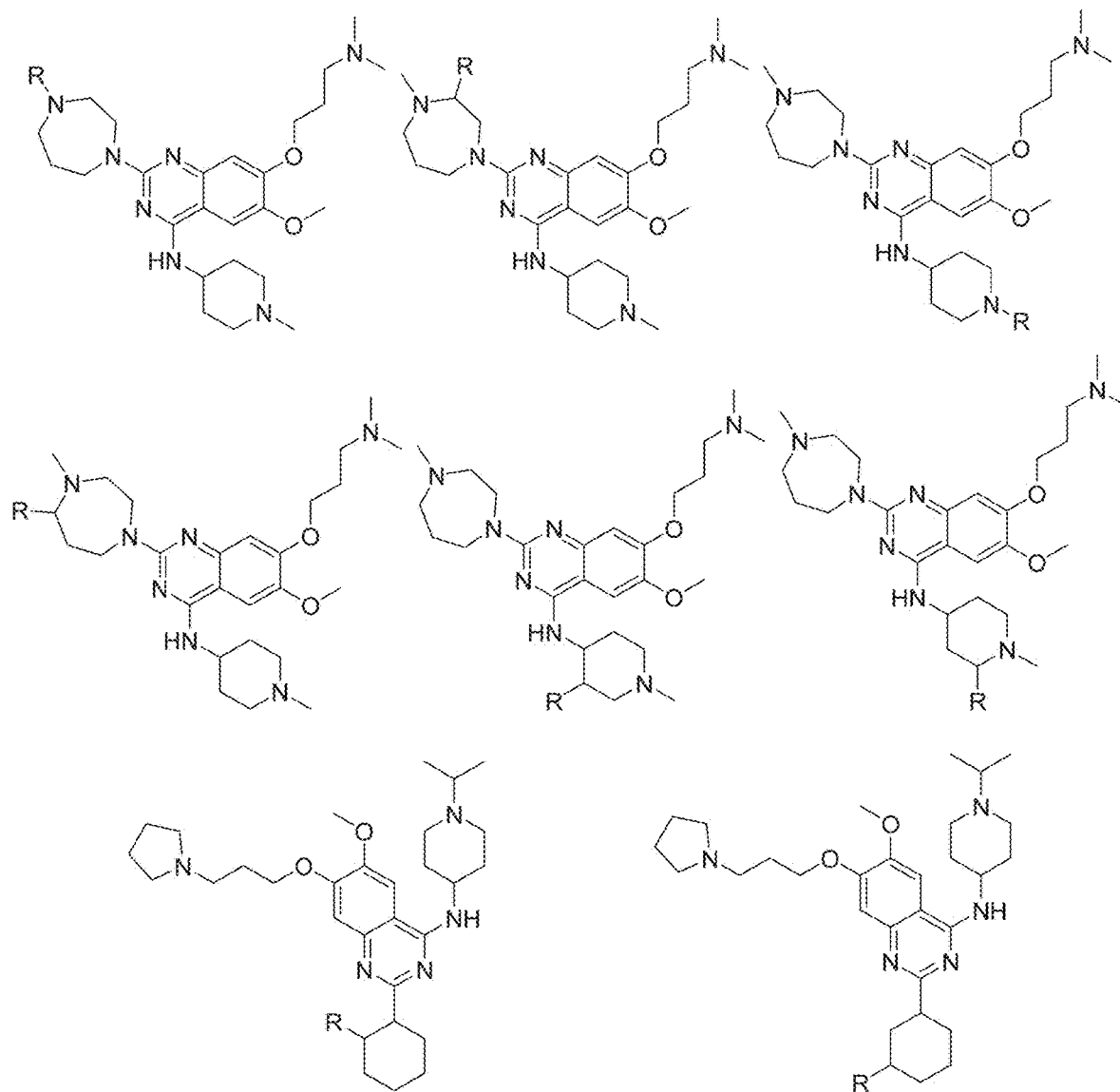
Figures 6D, 6E:

FIG. 6C-6D present examples of G9a (EHMT2) Targeting Ligands wherein R is the point at which the Linker is attached. For additional examples and related ligands, see, the PDB crystal structure 3k5k; ("Discovery of a 2,4-diamino-7-aminoalkoxyquinazoline as a potent and selective inhibitor of histone lysine methyltransferase G9a"); Liu, F. et al. J. Med. Chem. 52: 7950 (2009); the PDB crystal structure 3rjw ("A chemical probe selectively inhibits G9a and GLP methyltransferase activity in cells"); Vedadi, M. et al. *Nat. Chem. Biol.* 7: 566 (2011); the PDB crystal structure 4nvq ("Discovery and development of potent and selective inhibitors of histone methyltransferase g9a"); and, Sweis, R. F. et al. *ACSMed Chem Lett* 5: 205 (2014).

Figure 6F:
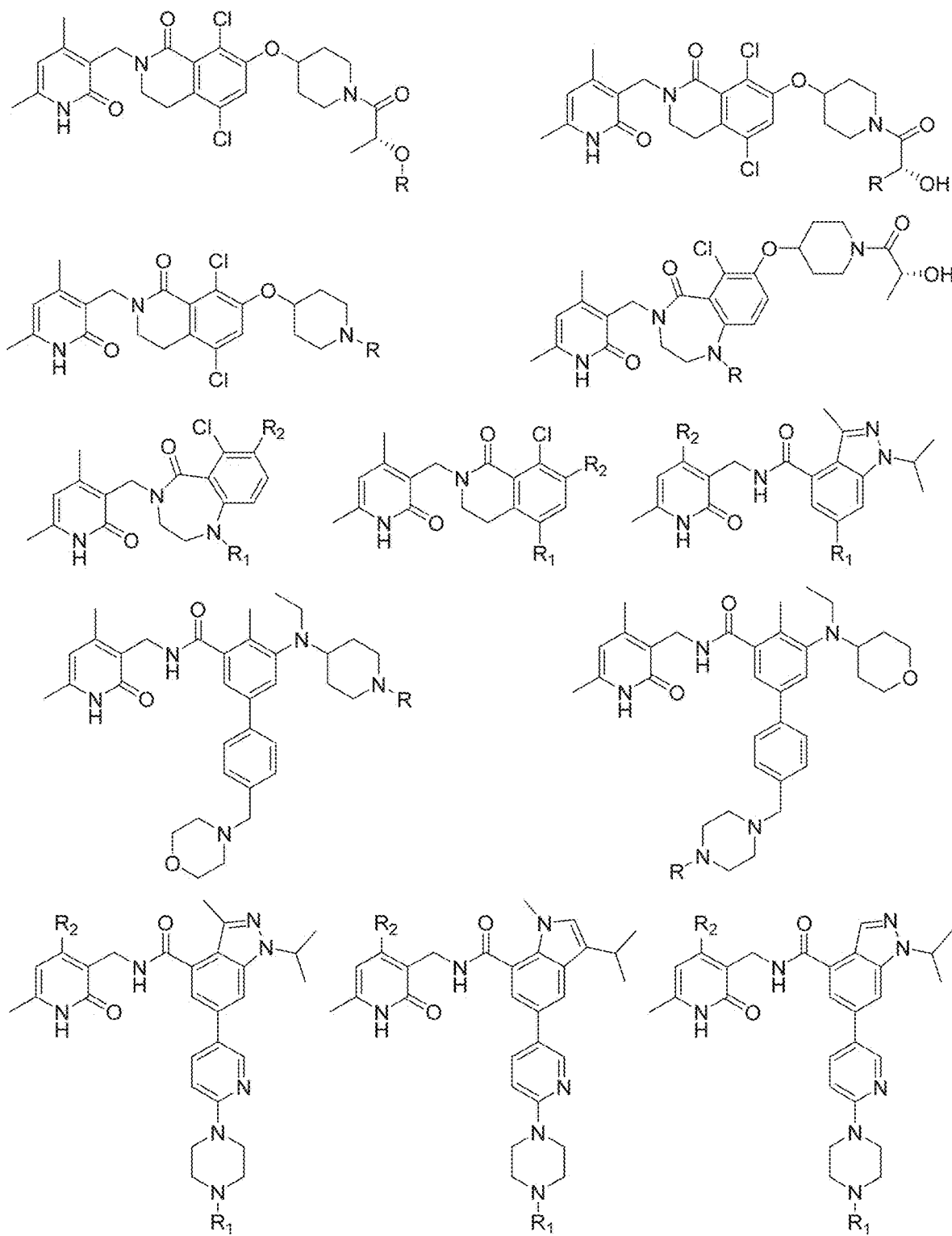
Figure 6G:
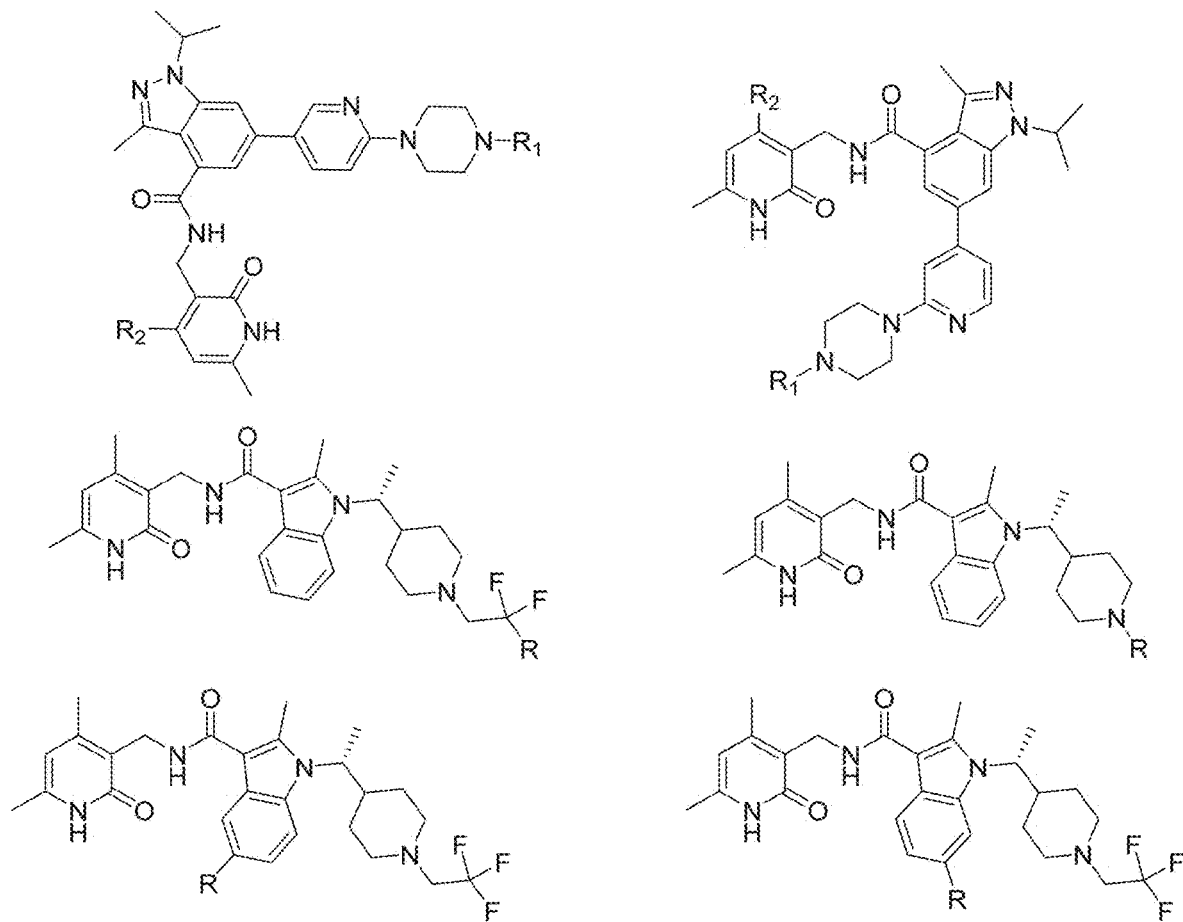

FIG. 6E-6G present examples of EZH2 Targeting Ligands wherein R is the point at which the Linker is attached. For additional examples and related ligands, see, the PDB crystal structure 5ij8 ("Polycomb repressive complex 2 structure with inhibitor reveals a mechanism of activation and drug resistance"); Brooun, A. et al. *Nat Commun* 7: 11384 (2016); the PDB crystal structure 5ls6 ("Identification of (R)—N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas"); Vaswani, R. G. et al. *J. Med Chem.* 59: 9928 (2016); and, the PDB crystal structures 5ij8 and 5ls6.

Figure 6H:
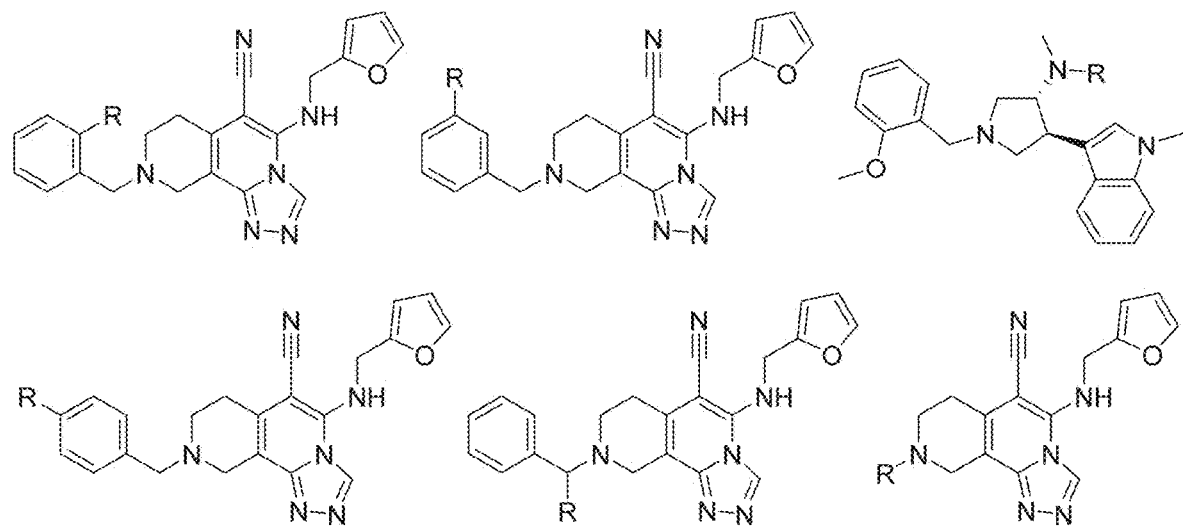
Figure 6I:
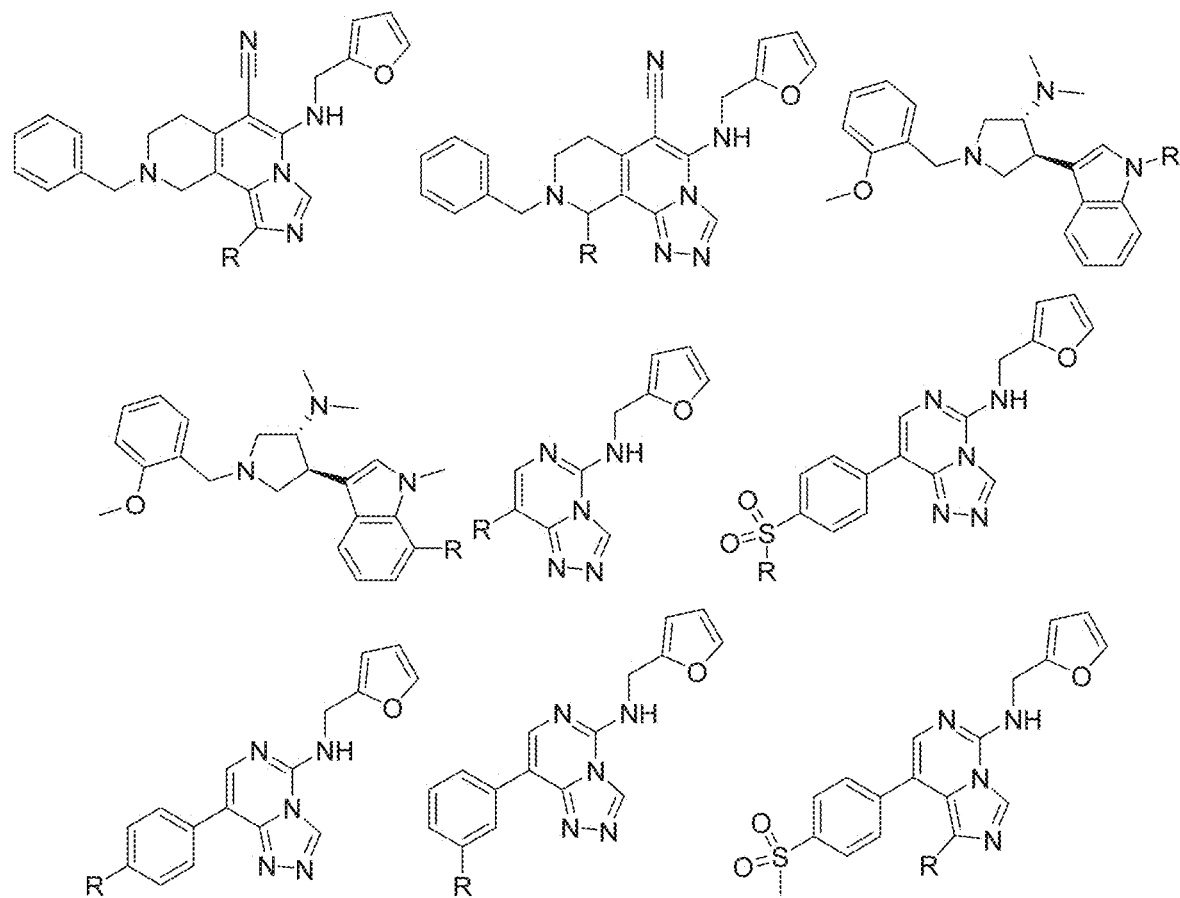

FIG. 6H-6I present examples of EED Targeting Ligands wherein R is the point at which the Linker is attached. For additional examples and related ligands, see, the PDB crystal structures 5h15 and 5h19 ("Discovery and Molecular Basis of a Diverse Set of Polycomb Repressive Complex 2 Inhibitors Recognition by EED"); Li, L. et al. *PLoS ONE* 12: e0169855 (2017); and, the PDB crystal structure 5h19.

Figure 6J:
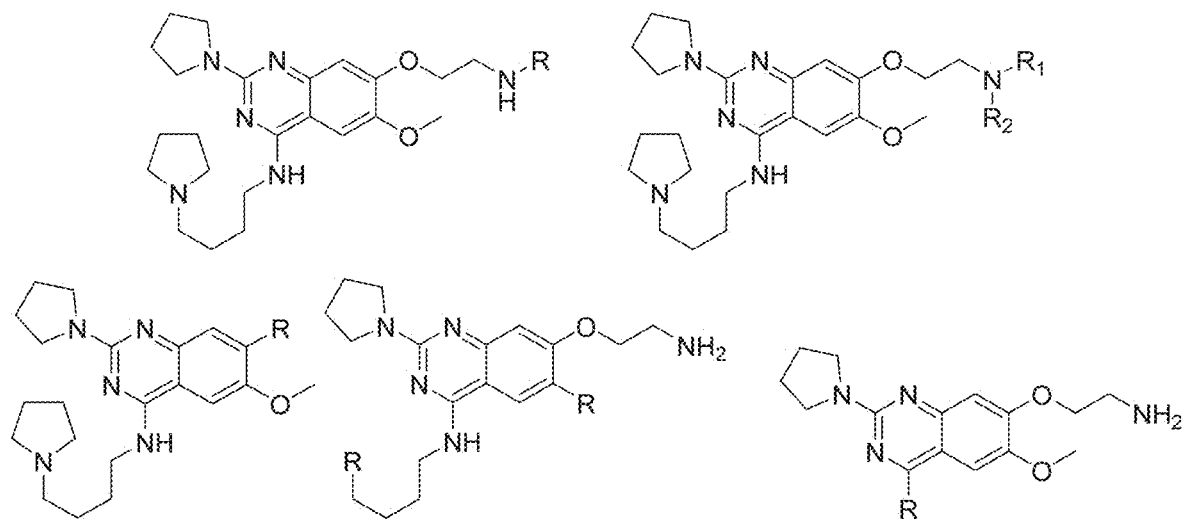

FIG. 6J presents examples of KMT5A (SETD8) Targeting Ligands wherein R is the point at which the Linker is attached. See for example, the PDB crystal structure 5t5g.

Figure 6K:
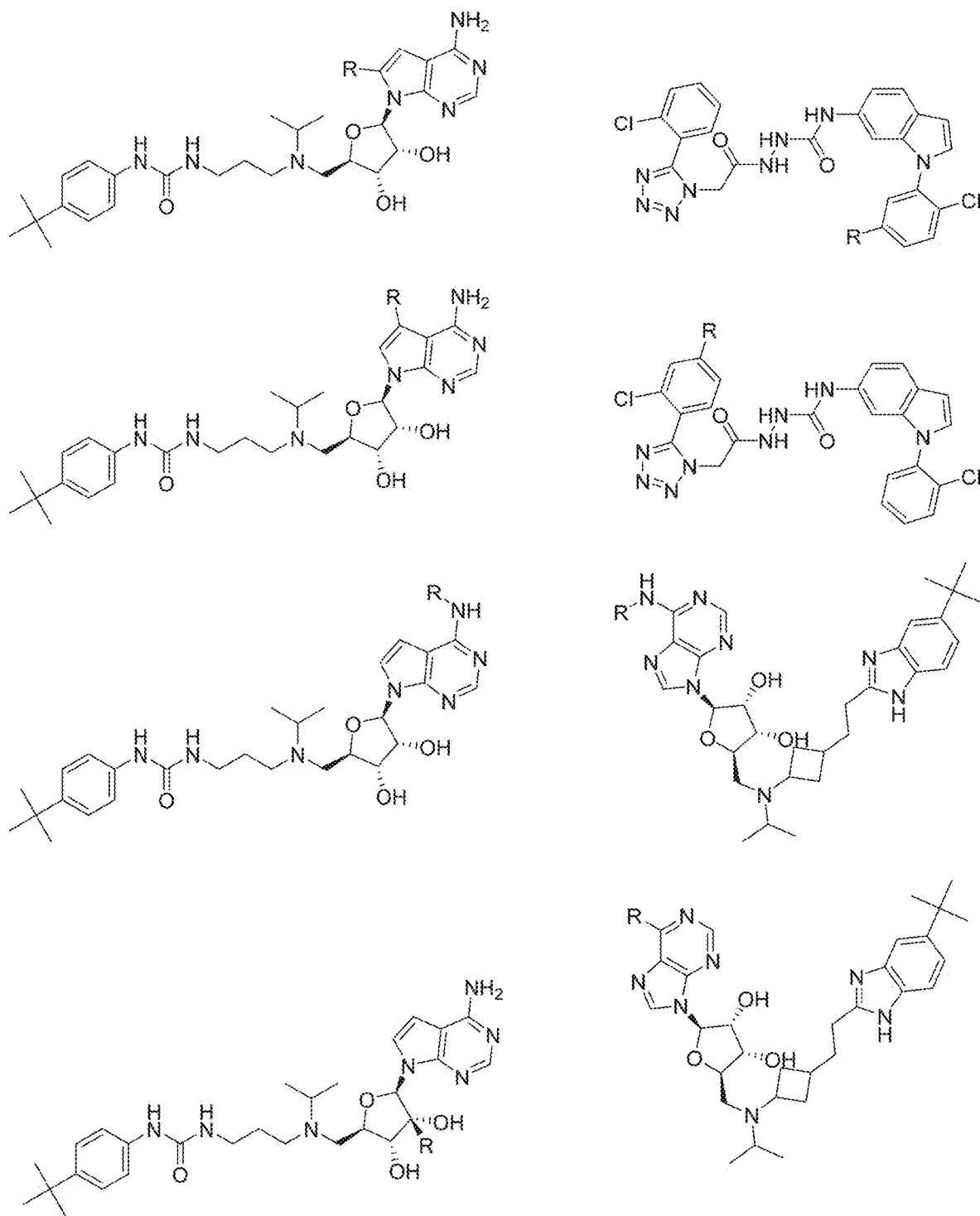
Figure 6L:
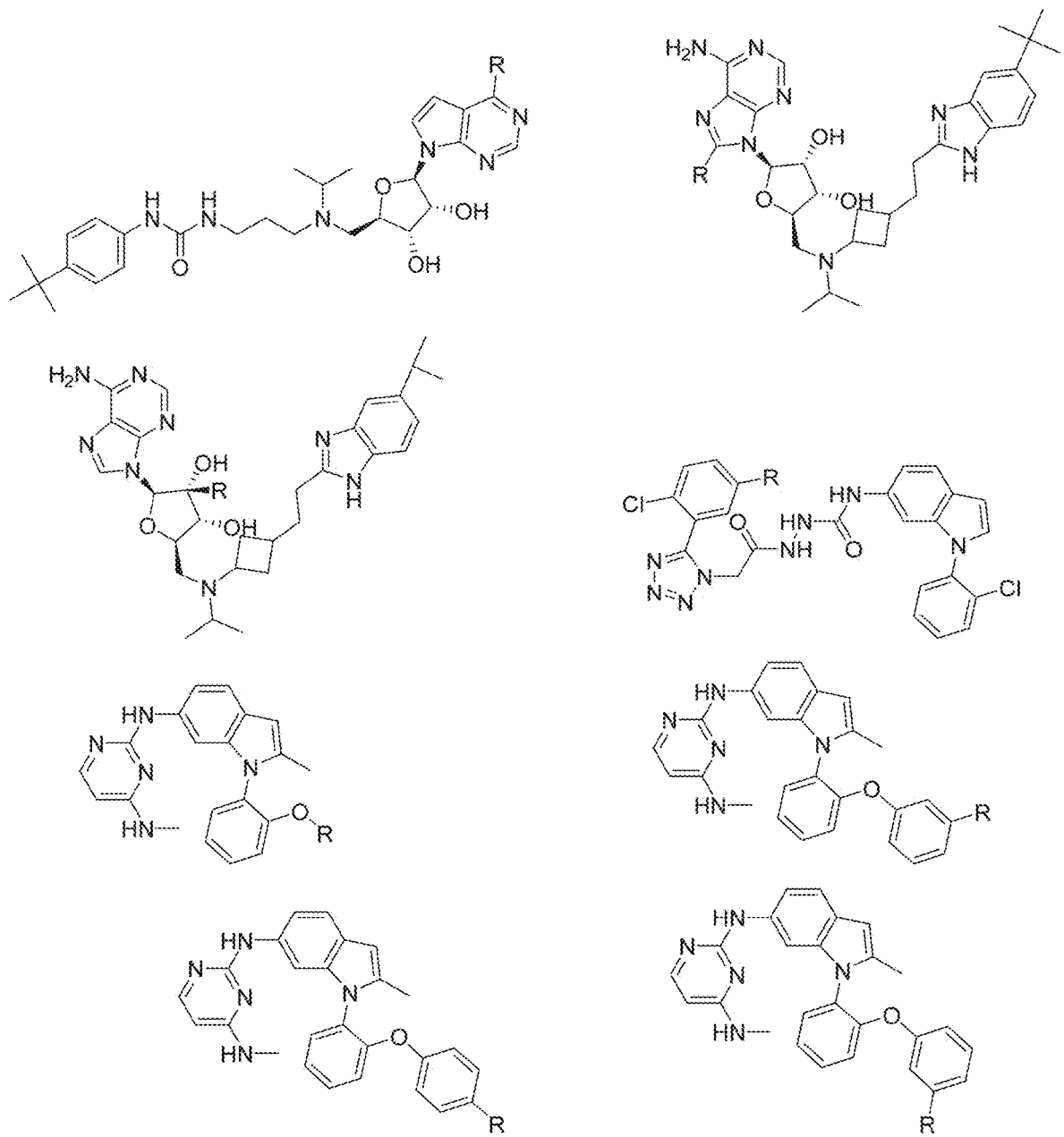

FIG. 6K-6L present examples of DOT1L Targeting Ligands wherein R is the point at which the Linker is attached. For additional examples and related ligands, see, the PDB crystal structure 4eki ("Conformational adaptation drives potent, selective and durable inhibition of the human protein methyltransferase DOT1L"); Basavapathruni, A. et al. *Chem. Biol. Drug Des.* 80: 971 (2012); the PDB crystal structure 4hra ("Potent inhibition of DOT1L as treatment of MLL-fusion leukemia"); Daigle, S. R. et al. *Blood* 122: 1017 (2013); the PDB crystal structure 5dry ("Discovery of Novel Dot1L Inhibitors through a Structure-Based Fragmentation Approach") Chen, C. et al. *ACS Med Chem. Lett.* 7: 735 (2016); the PDB crystal structure 5dt2 ("Discovery of Novel Dot1L Inhibitors through a Structure-Based Fragmentation Approach"); and, Chen, C. et al. *ACS Med Chem. Lett.* 7: 735 (2016).

Figure 6M:
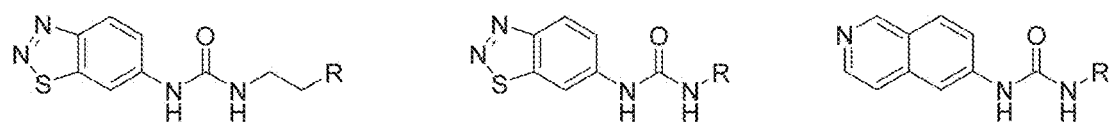
Figure 6N:
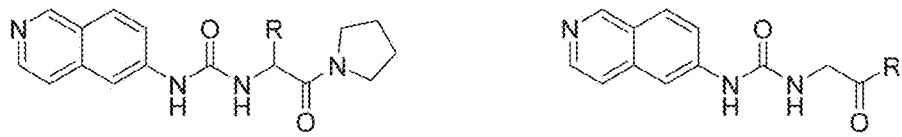

FIG. 6M-6N present examples of PRMT3 Targeting Ligands wherein R is the point at which the Linker is attached. For additional examples and related ligands, see, the PDB crystal structure 3smq ("An allosteric inhibitor of protein arginine methyltransferase 3"); Siarheyeva, A. et al. *Structure* 20: 1425 (2012); PDB crystal structure 4ryl ("A Potent, Selective and Cell-Active Allosteric Inhibitor of Protein Arginine Methyltransferase 3 (PRMT3)"); and Kaniskan, H. U. et al. *Angew. Chem. Int. Ed. Engl.* 54: 5166 (2015).

Figure 6O:
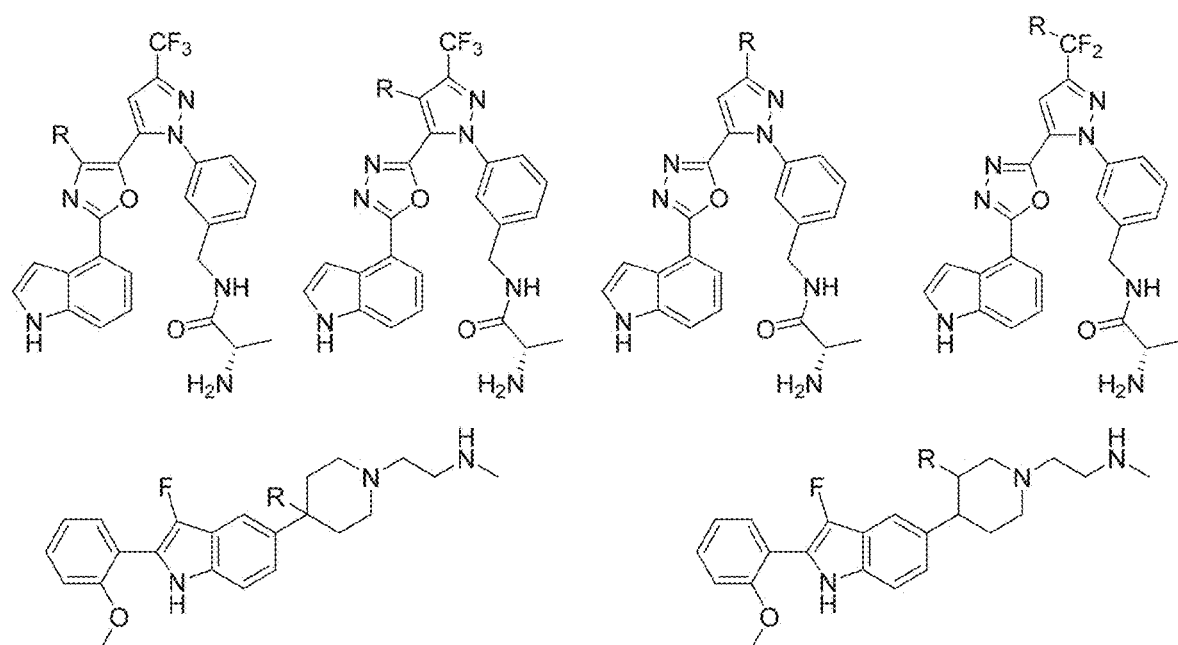

FIG. 6O presents examples of CARM1 (PRMT4) Targeting Ligands wherein R is the point at which the Linker is attached. For additional examples and related ligands, see, the PDB crystal structures 2y1x and 2y1w and related ligands described in "Structural Basis for Carm1 Inhibition by Indole and Pyrazole Inhibitors." Sack, J. S. et al. *Biochem. J.* 436: 331 (2011).

Figure 6P:
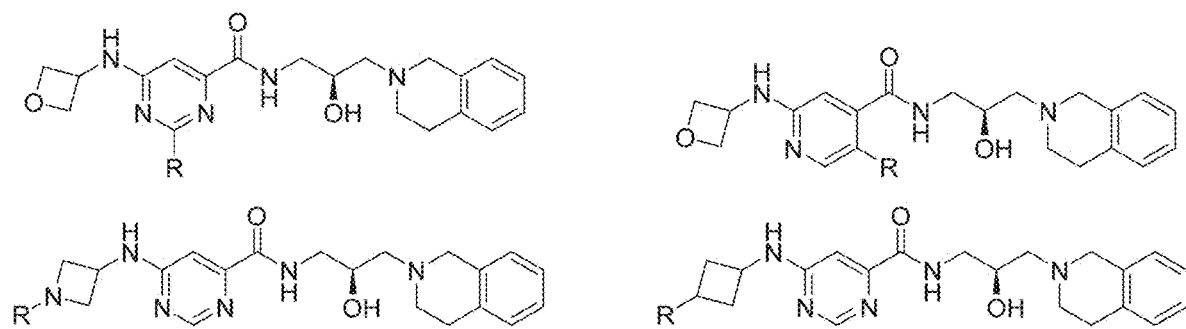

FIG. 6P presents examples of PRMT5 Targeting Ligands wherein R is the point at which the Linker is attached. For additional examples and related ligands, see, the PDB crystal structure 4x61 and related ligands described in "A selective inhibitor of PRMT5 with in vivo and in vitro potency in MCL models". Chan-Penebre, E. *Nat. Chem. Biol.* 11: 432 (2015).

Figure 6Q:
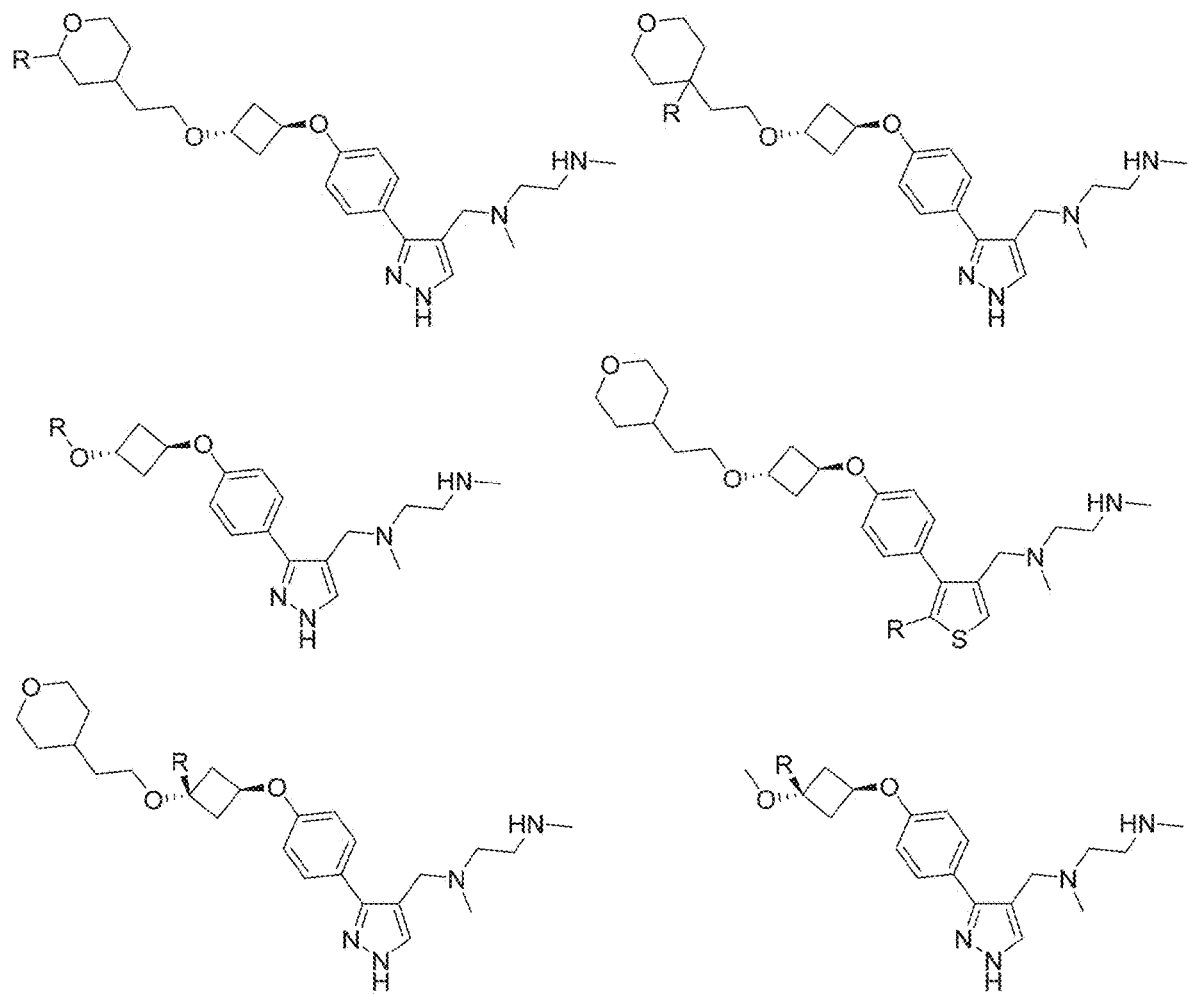

FIG. 6Q presents examples of PRMT6 Targeting Ligands wherein R is the point at which the Linker is attached. For additional examples and related ligands, see, the PDB crystal structure 4y30 and related ligands described in "Aryl Pyrazoles as Potent Inhibitors of Arginine Methyltransferases: Identification of the First PRMT6 Tool Compound". Mitchell, L. H. et al. *ACS Med. Chem. Lett.* 6: 655 (2015).

Figure 6R:
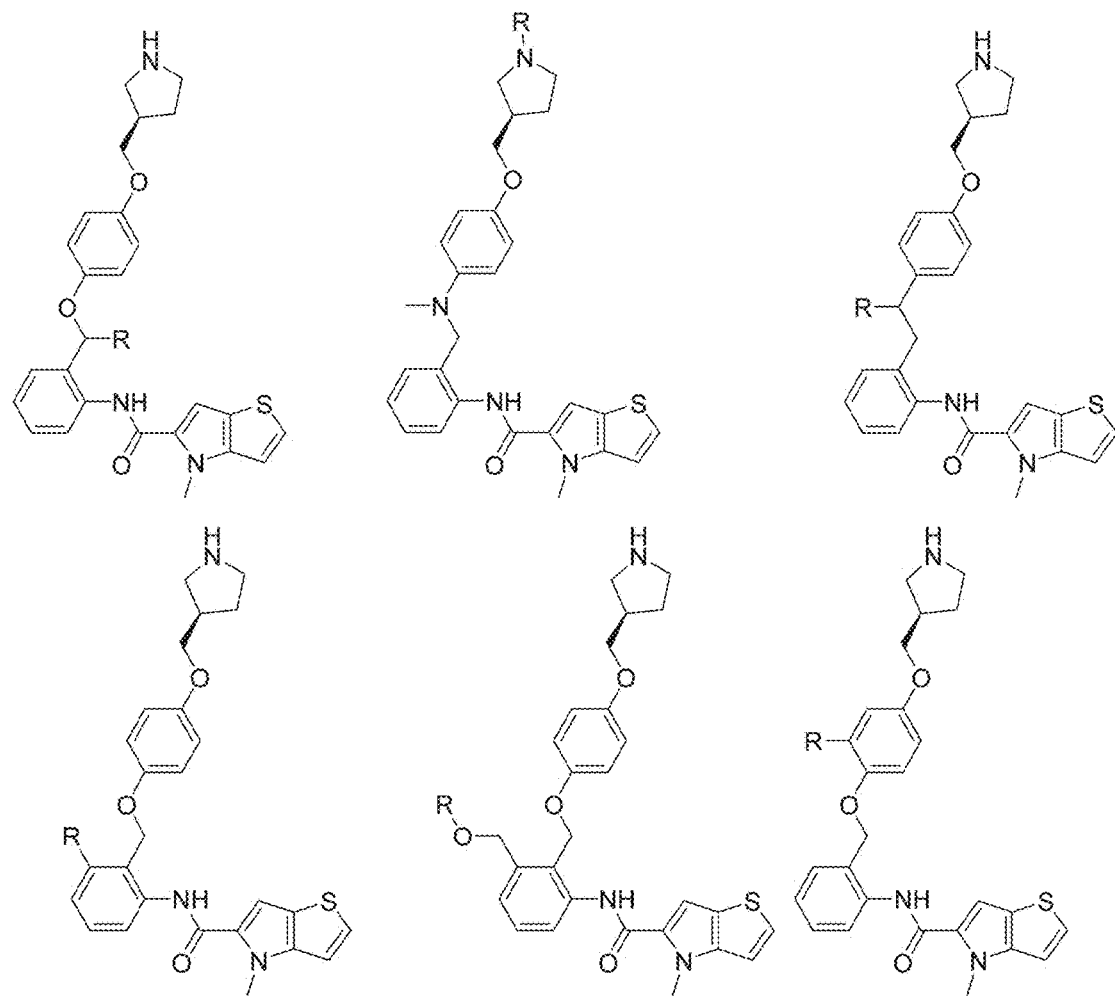

FIG. 6R presents examples of LSD1 (KDM1A) Targeting Ligands wherein R is the point at which the Linker is attached. For additional examples and related ligands, see, the PDB crystal structure 5lgu and related ligands described in "Thieno[3,2-b]pyrrole-5-carboxamides as New Reversible Inhibitors of Histone Lysine Demethylase KDM1A/LSD1. Part 2: Structure-Based Drug Design and Structure-Activity Relationship". Vianello, P. et al. *J. Med. Chem.* 60: 1693 (2017).

Figure 6S:
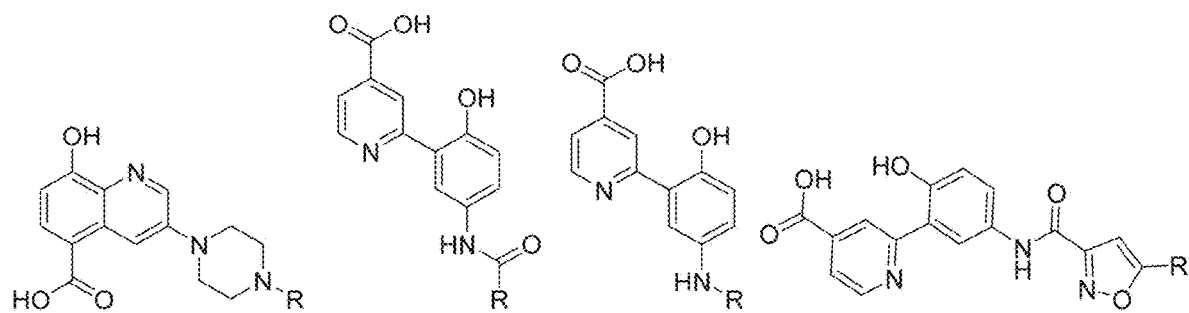
Figure 6T:
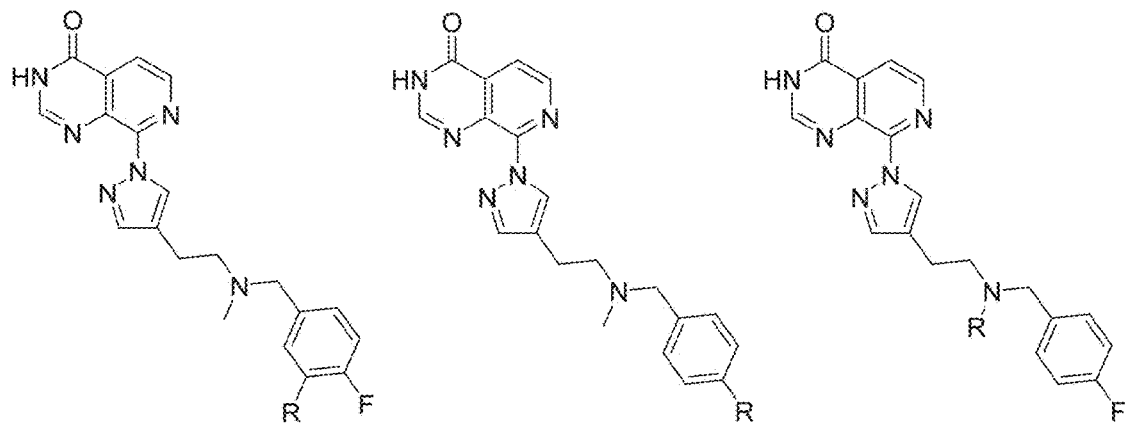

FIG. 6S-6T present examples of KDM4 Targeting Ligands wherein R is the point at which the Linker is attached. For additional examples and related ligands, see, the PDB crystal structure 3rvh; the PDB crystal structure 5a7p and related ligands described in "Docking and Linking of Fragments to Discover Jumonji Histone Demethylase Inhibitors." Korczynska, M., et al. *J. Med. Chem.* 59: 1580 (2016); and, the PDB crystal structure 3f3c and related ligands described in "8-Substituted Pyrido[3,4-d]pyrimidin-4(3H)-one Derivatives As Potent, Cell Permeable, KDM4 (JMJD2) and KDM5 (JARID1) Histone Lysine Demethylase Inhibitors." Bavetsias, V. et al. *J. Med. Chem.* 59: 1388 (2016).

Figure 6U:
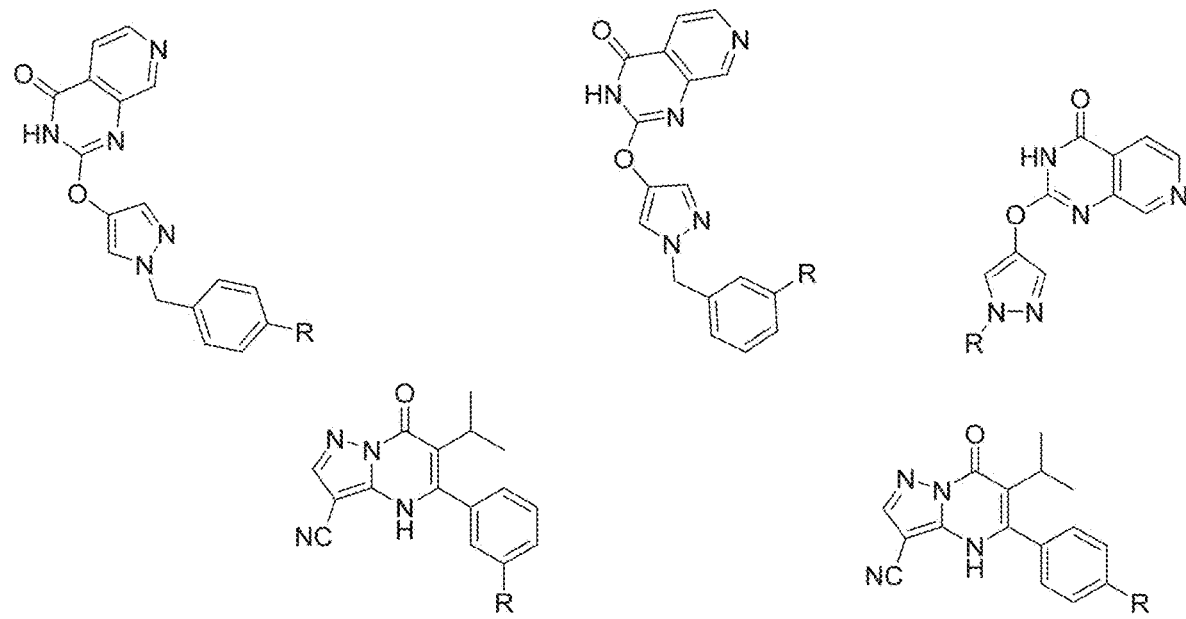

FIG. 6U presents examples of KDM5 Targeting Ligands wherein R is the point at which the Linker is attached. For additional examples and related ligands, see, the PDB crystal structure 3fun and related ligands described in "Structural Analysis of Human Kdm5B Guides Histone Demethylase Inhibitor Development". Johansson, C. et al. *Nat. Chem. Biol.* 12: 539 (2016) and the PDB crystal structure 5ceh and related ligands described in "An inhibitor of KDM5 demethylases reduces survival of drug-tolerant cancer cells". Vinogradova, M. et al. *Nat. Chem. Biol.* 12: 531 (2016).

Figure 6V:
Figure 6W:
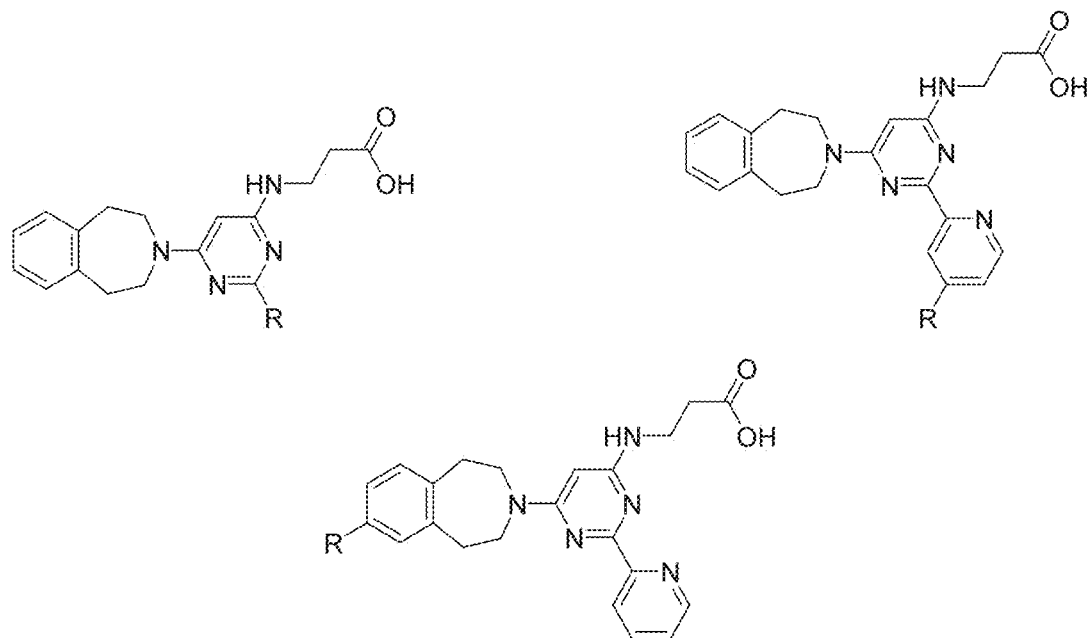

FIG. 6V-6W present examples of KDM6 Targeting Ligands wherein R is the point at which the Linker is attached. For additional examples and related ligands, see, the PDB crystal structure 4ask and related ligands described in "A Selective Jumonji H3K27 Demethylase Inhibitor Modulates the Proinflammatory Macrophage Response". Kruidenier, L. et al. *Nature* 488: 404 (2012).

Figure 6X:
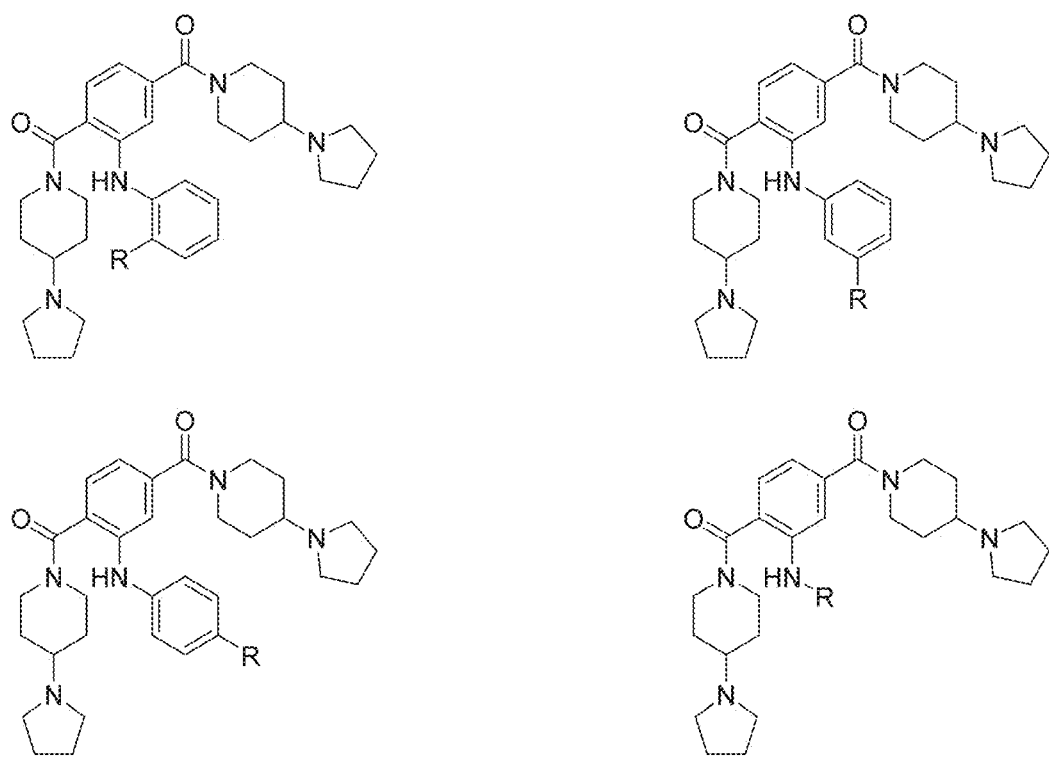

FIG. 6X presents examples of L3MBTL3 targeting ligands wherein R is the point at which the Linker is attached. See for example, the PDB crystal structure 4fl6.

Figure 6Y:
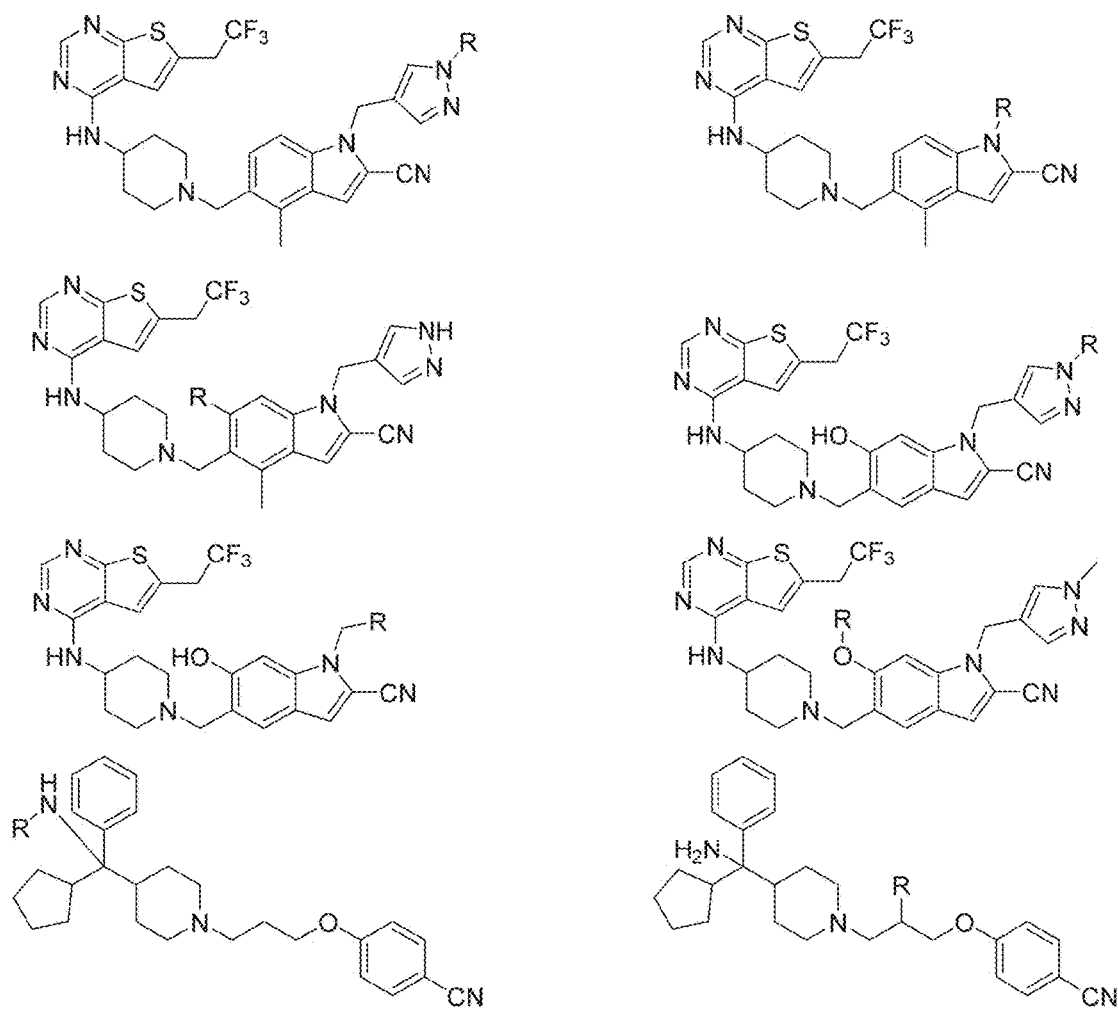

FIG. 6Y presents examples of Menin Targeting Ligands wherein R is the point at which the Linker is attached. For additional examples and related ligands, see, the PDB crystal structure 4x5y and related ligands described in "Pharmacologic Inhibition of the Menin-MLL Interaction Blocks Progression of MLL Leukemia In Vivo" Borkin, D. et al. *Cancer Cell* 27: 589 (2015) and the PDB crystal structure 4og8 and related ligands described in "High-Affinity Small-Molecule Inhibitors of the Menin-Mixed Lineage Leukemia (MLL) Interaction Closely Mimic a Natural Protein-Protein Interaction" He, S. et al. *J. Med. Chem.* 57: 1543 (2014).

Figure 6Z:
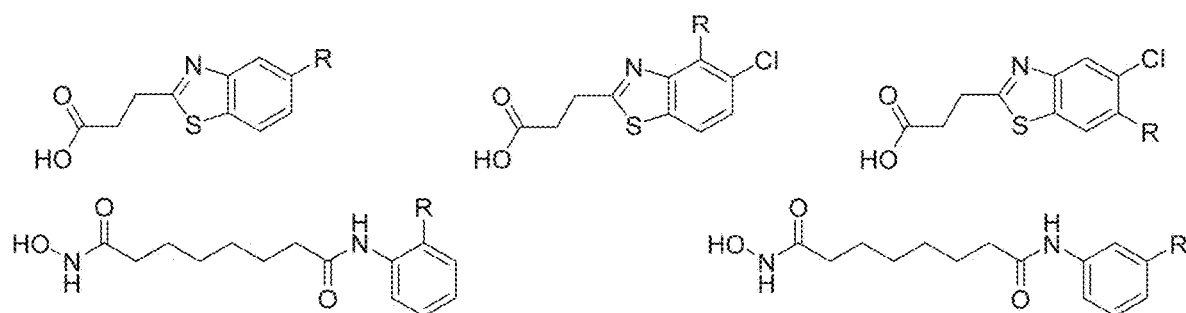

FIG. 6Z-6AA present examples of HDAC6 Targeting Ligands wherein R is the point at which the Linker is attached. See for example, the PDB crystal structures 5kh3 and 5eei.

FIG. 6BB presents examples of HDAC7 Targeting Ligands wherein R is the point at which the Linker is attached. For additional examples and related ligands, see, the PDB crystal structure 3c10 and related ligands described in "Human HDAC7 harbors a class IIa histone deacetylase-specific zinc binding motif and cryptic deacetylase activity." Schuetz, A. et al. *J. Biol. Chem.* 283: 11355 (2008) and the PDB crystal structure PDB 3zns and related ligands described in "Selective Class IIa Histone Deacetylase Inhibition Via a Non-Chelating Zinc Binding Group". Lobera, M. et al. *Nat. Chem. Biol.* 9: 319 (2013).

Figure 7B:
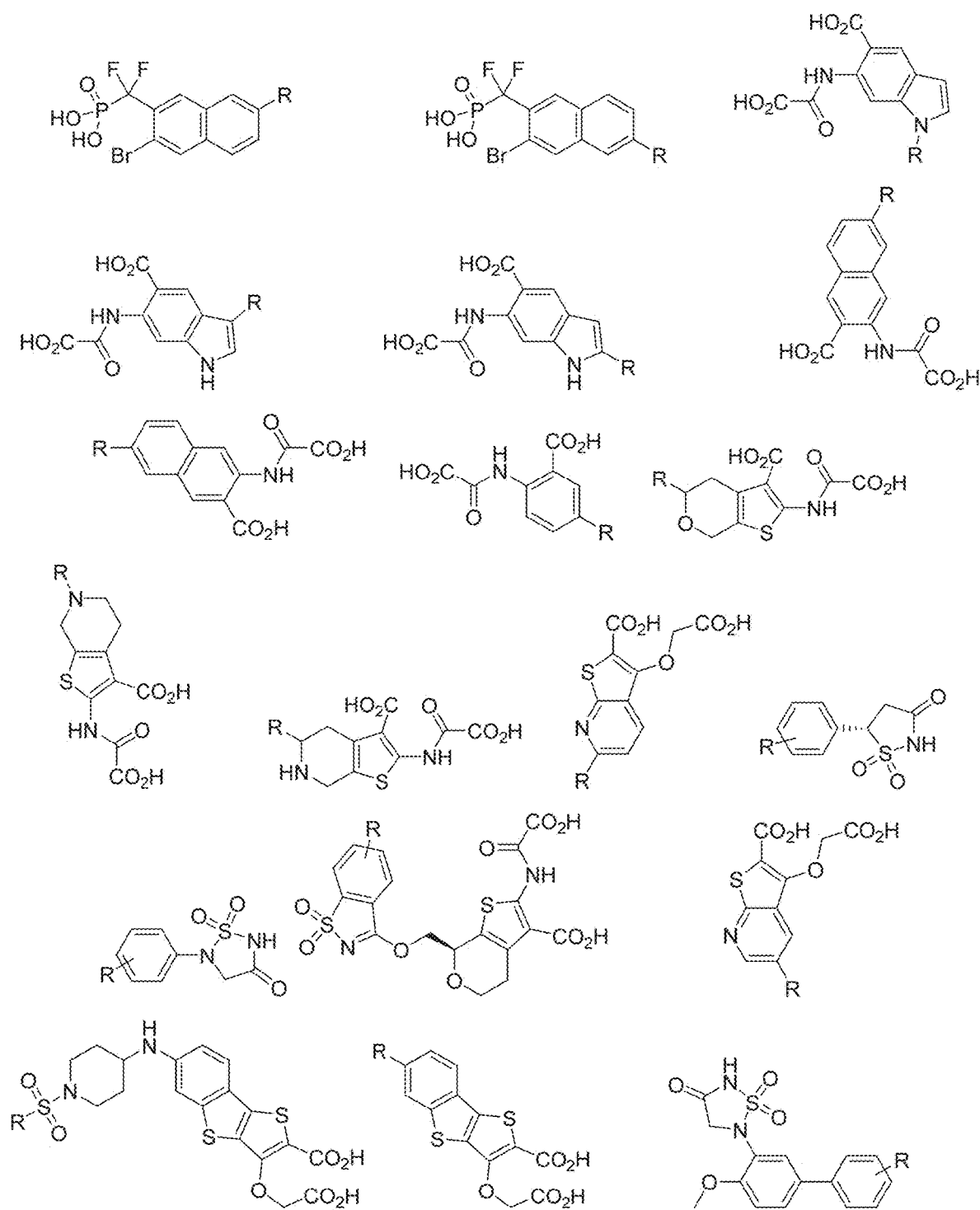
Figure 7C:
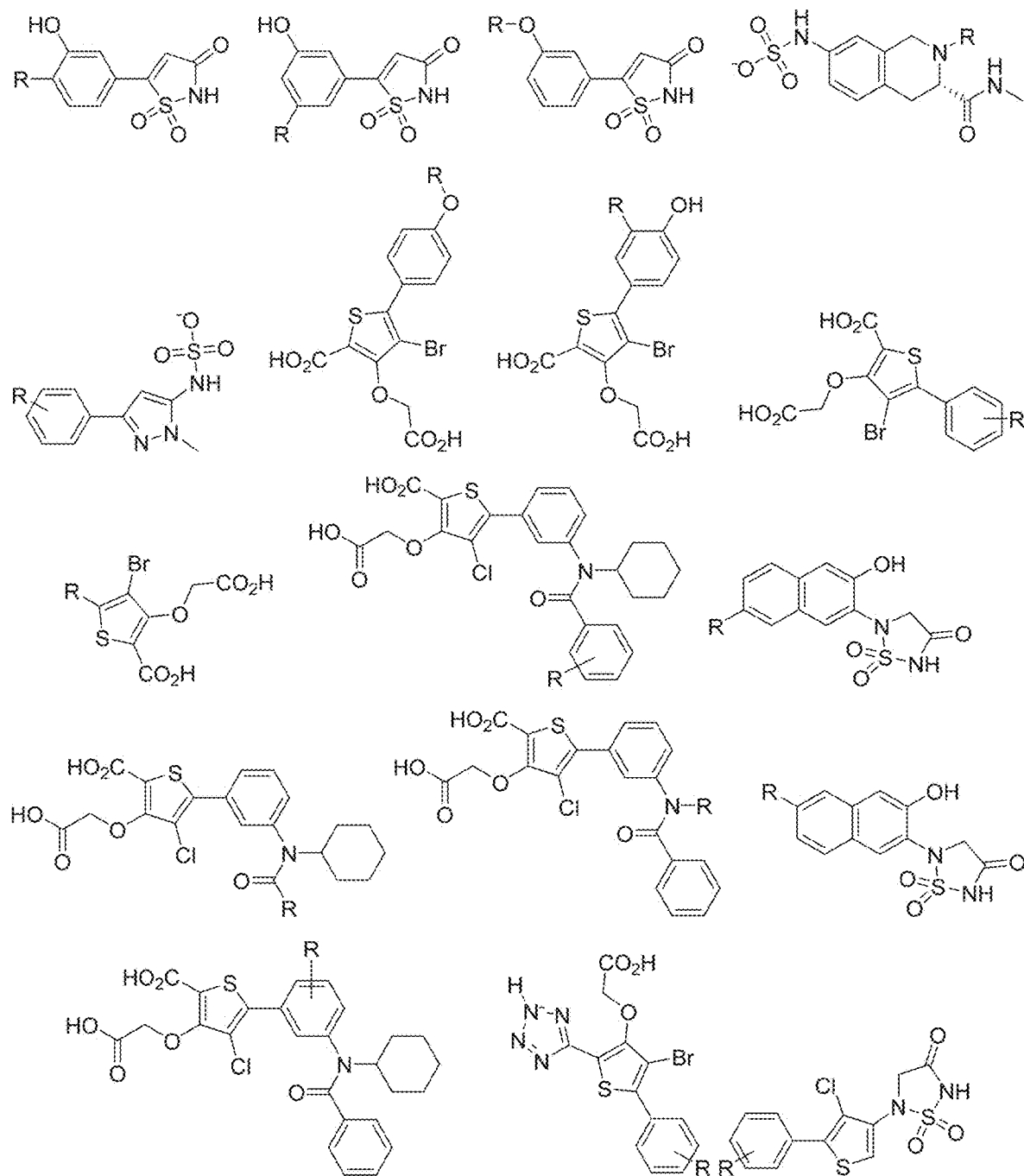

FIG. 7A-7C present examples of Protein Tyrosine Phosphatase, Non-Receptor Type 1, PTP1B Targeting Ligands wherein R is the point at which the Linker is attached. For additional examples and related ligands, see, the PDB crystal structure 1bzj described in "Structural basis for inhibition of the protein tyrosine phosphatase 1B by phosphotyrosine peptide mimetics" Groves, M. R. et al. *Biochemistry* 37: 17773-17783 (1998); the PDB crystal structure 3cwe described in "Discovery of [(3-bromo-7-cyano-2-naphthylXdifluoro)methyl]phosphonic acid, a potent and orally active small molecule PTP1B inhibitor". Han Y, *Bioorg Med Chem Lett.* 18:3200-5 (2008); the PDB crystal structures 2azr and 2b07 described in "Bicyclic and tricyclic thiophenes as protein tyrosine phosphatase 1B inhibitors." Moretto, A. F. et al. *Bioorg. Med. Chem.* 14: 2162-2177 (2006); the PDB crystal structures PDB 2bgd, 2bge, 2cm7, 2cm8, 2cma, 2cmb, 2cmc described in "Structure-Based Design of Protein Tyrosine Phosphatase-1B Inhibitors". Black, E. et al. *Bioorg. Med. Chem. Lett.* 15: 2503 (2005) and "Structural Basis for Inhibition of Protein-Tyrosine Phosphatase 1B by Isothiazolidinone Heterocyclic Phosphonate Mimetics." Ala, P. J. et al. *J. Biol. Chem.* 281: 32784 (2006); the PDB crystal structures 2f6t and 2f6w described in "1,2,3,4-Tetrahydroisoquinolinyl sulfamic acids as phosphatase PTP1B inhibitors". Klopfenstein, S. R. et al. *Bioorg. Med. Chem. Lett.* 16: 1574-1578 (2006); the PDB crystal structures 2h4g, 2h4k, 2hb1 described in "Monocyclic thiophenes as protein tyrosine phosphatase 1B inhibitors: Capturing interactions with Asp48." Wan, Z. K. et al. *Bioorg. Med. Chem. Lett.* 16: 4941-4945 (2006); the PDB crystal structures 2zn7 described in "Structure-based optimization of protein tyrosine phosphatase-1 B inhibitors: capturing interactions with arginine 24". Wan, Z. K. et al. *Chem Med Chem.* 3:1525-9 (2008); the PDB crystal structure 2nt7, 2nta described in "Probing acid replacements of thiophene PTP1B inhibitors." Wan, Z. K. et al. *Bioorg. Med. Chem. Lett.* 17: 2913-2920 (2007); and, WO 2008148744 A1 assigned to Novartis AG titled "Thiadiazole derivatives as antidiabetic agents". See also, the PDB crystal structures 1c84, 1c84, 1c85, 1c86, 1c88, 118g and described in "2-(oxalylamino)-benzoic acid is a general, competitive inhibitor of protein-tyrosine phosphatases". Andersen, H. S. et al. *J. Biol. Chem.* 275: 7101-7108 (2000); "Structure-based design of a low molecular weight, nonphosphorus, nonpeptide, and highly selective inhibitor of protein-tyrosine phosphatase 1B." Iversen, L. F. et al. *J. Biol. Chem.* 275: 10300-10307 (2000); and, "Steric hindrance as a basis for structure-based design of selective inhibitors of protein-tyrosine phosphatases". Iversen, L. F. et al. *Biochemistry* 40: 14812-14820 (2001).

Figure 7D:
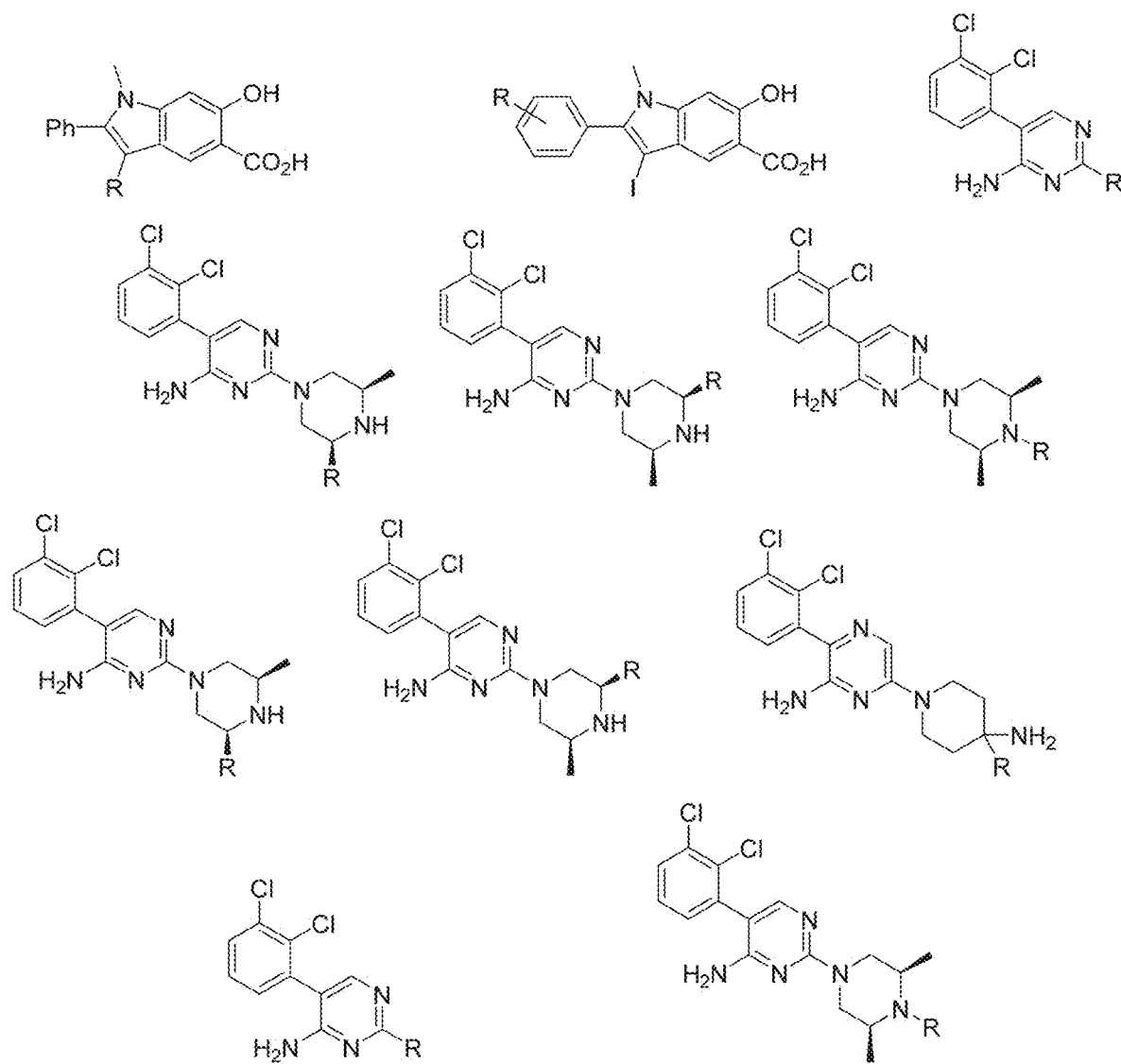

FIG. 7D presents examples of Tyrosine-protein phosphatase non-receptor type 11, SHP2 Targeting Ligands wherein R is the point at which the Linker is attached. For additional examples and related ligands, see, the crystal structures PDB 4pvg and 3o5x and described in "Salicylic acid based small molecule inhibitor for the oncogenic Src homology-2 domain containing protein tyrosine phosphatase-2 (SHP2)." Zhang, X. et al. *J. Med. Chem.* 53: 2482-2493 (2010); and, the crystal structure PDB 5ehr and related ligands described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016). Also, see the crystal structure PDB 5ehr described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016) and "Allosteric inhibition of SHP2 phosphatase inhibits cancers driven by receptor tyrosine kinases." Chen, Y. P. et al. *Nature* 535: 148-152 (2016).

Figure 7E:
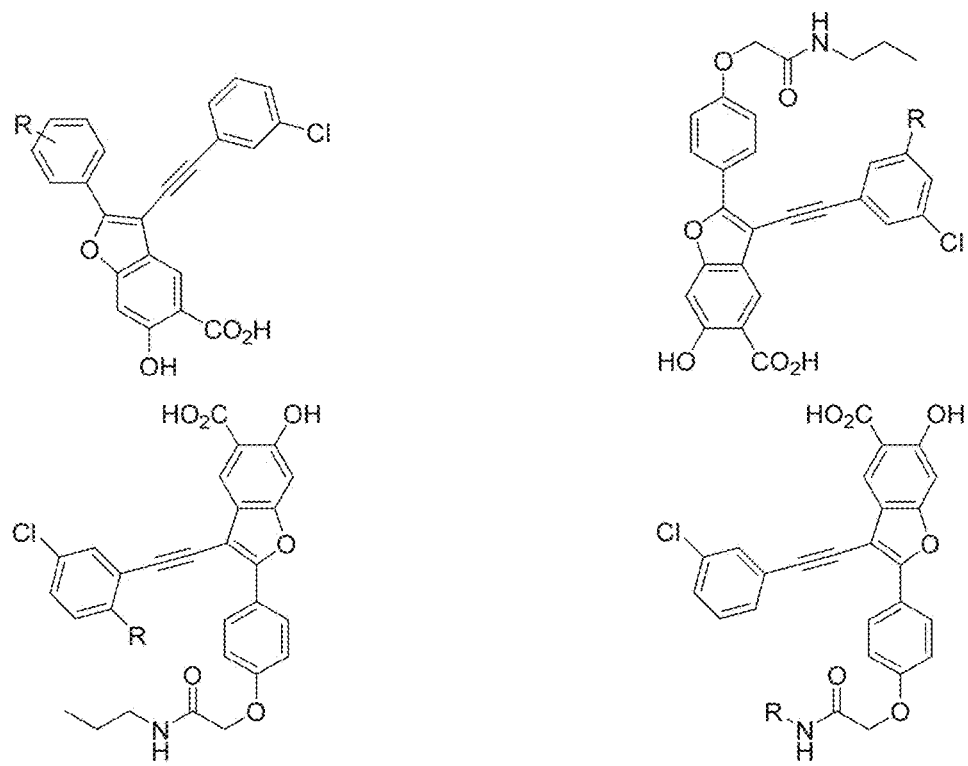

FIG. 7E presents examples of Tyrosine-protein phosphatase non-receptor type 22 Targeting Ligands wherein R is the point at which the Linker is attached. For additional examples and related ligands, see, the crystal structure PDB 4j51 described in "A Potent and Selective Small-Molecule Inhibitor for the Lymphoid-Specific Tyrosine Phosphatase (LYP), a Target Associated with Autoimmune Diseases." He, Y. et al. *J. Med. Chem.* 56: 4990-5008 (2013).

Figure 7F:
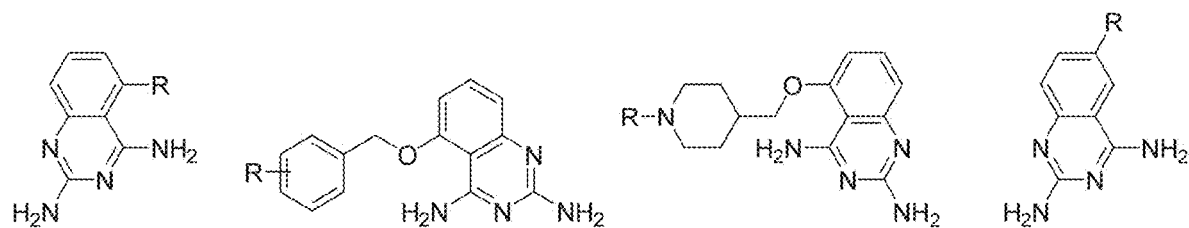

FIG. 7F presents examples of Scavenger mRNA-decapping enzyme DcpS Targeting Ligands wherein R is the point at which the Linker is attached. For additional examples and related ligands, see, the crystal structures PDB 3b17, 3b19, 3bla, 4qde, 4qdv, 4qeb and related ligands described in "DcpS as a therapeutic target for spinal muscular atrophy." Singh, J. et al. *ACS Chem. Biol.* 3: 711-722 (2008).

Figure 8A:
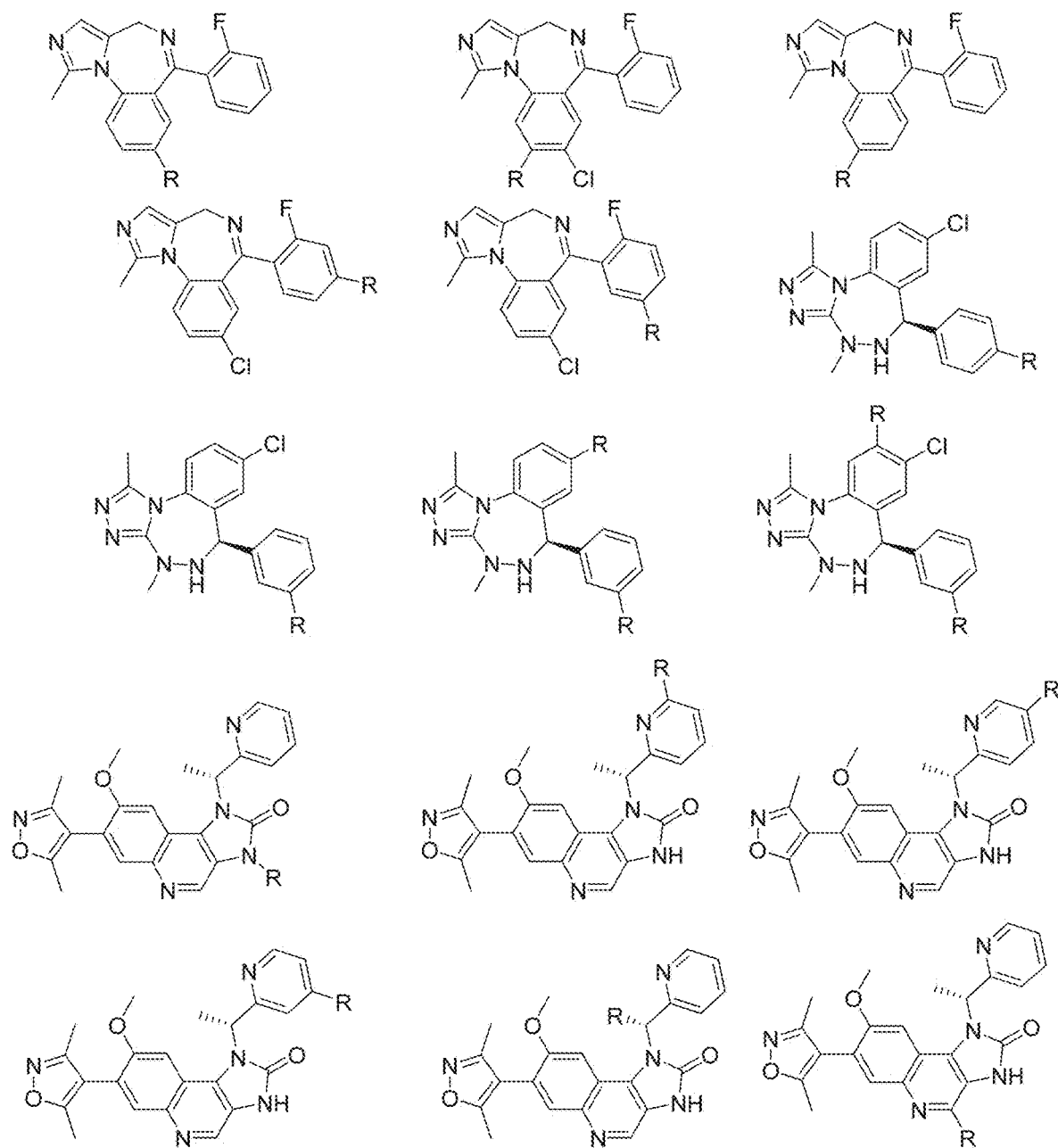
Figure 8B:
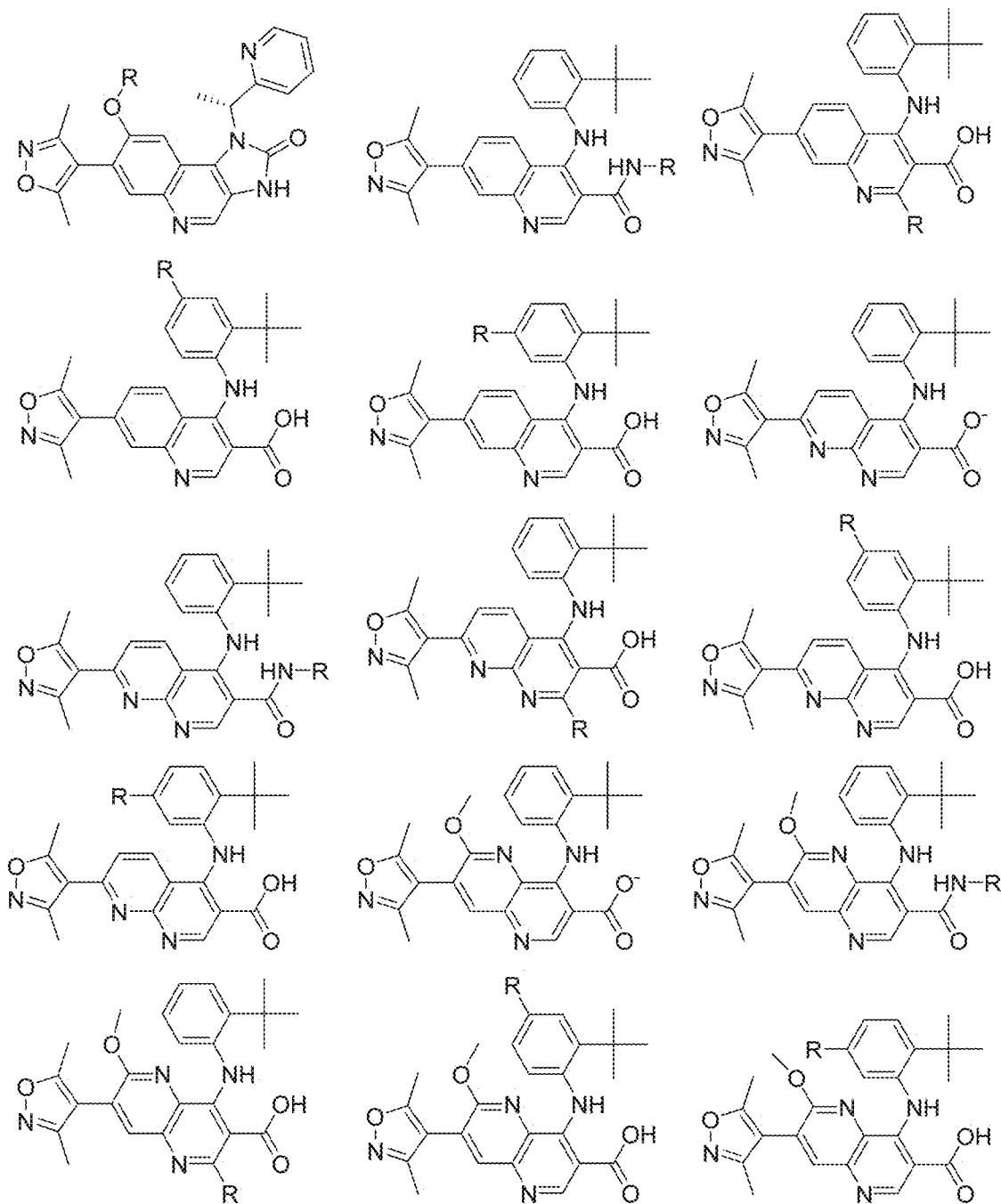
Figure 8C:
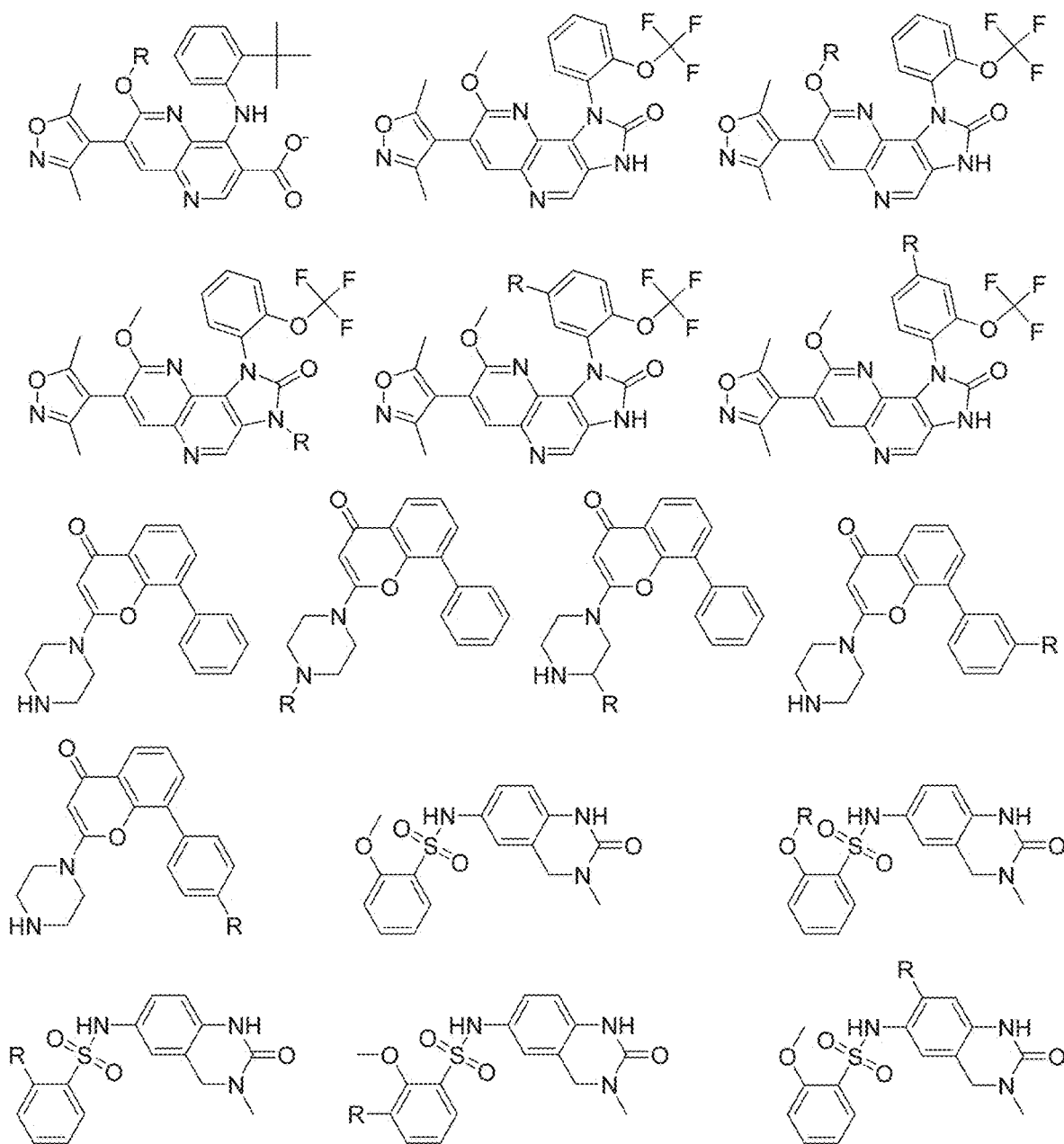
Figure 8D:
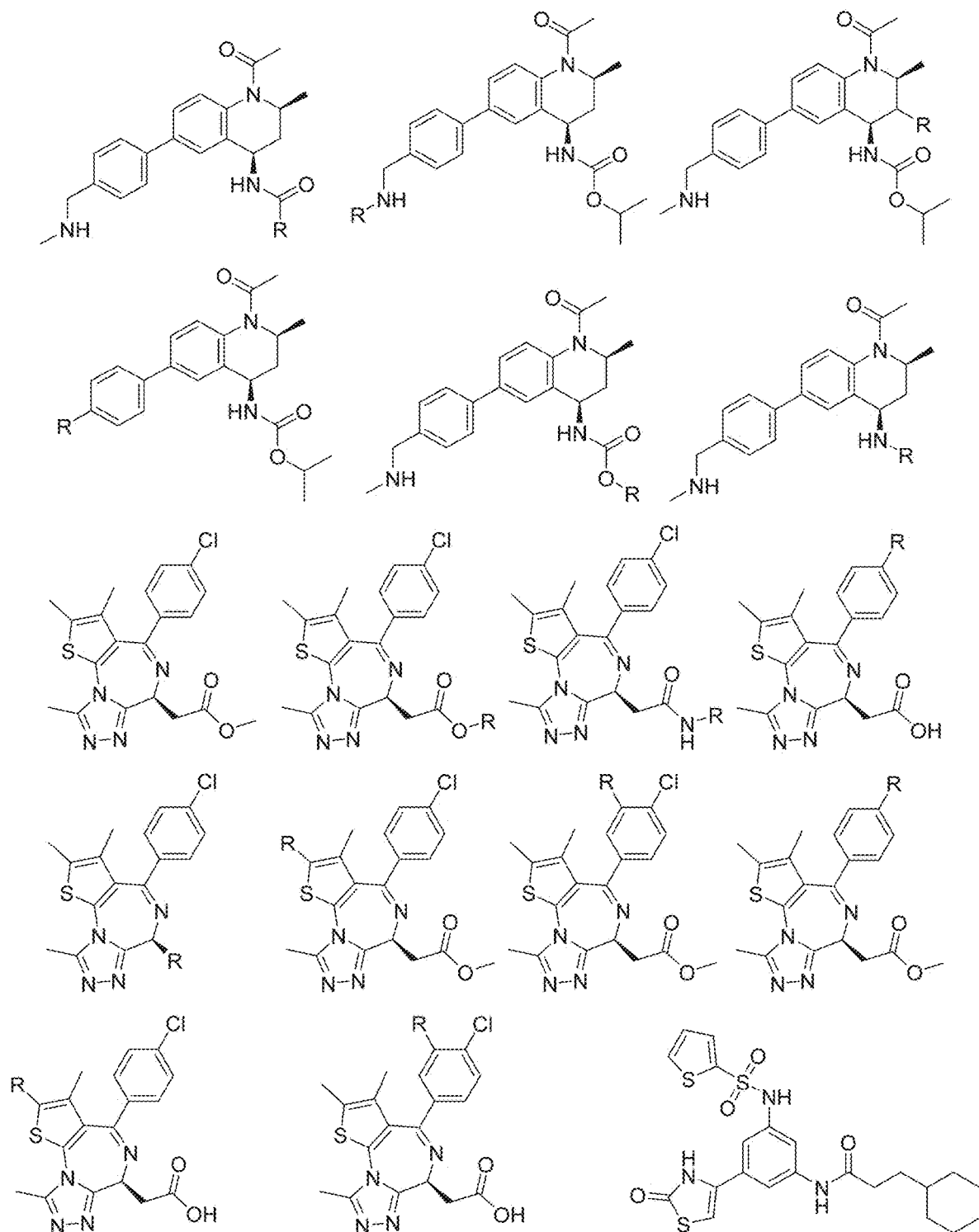
Figure 8E:
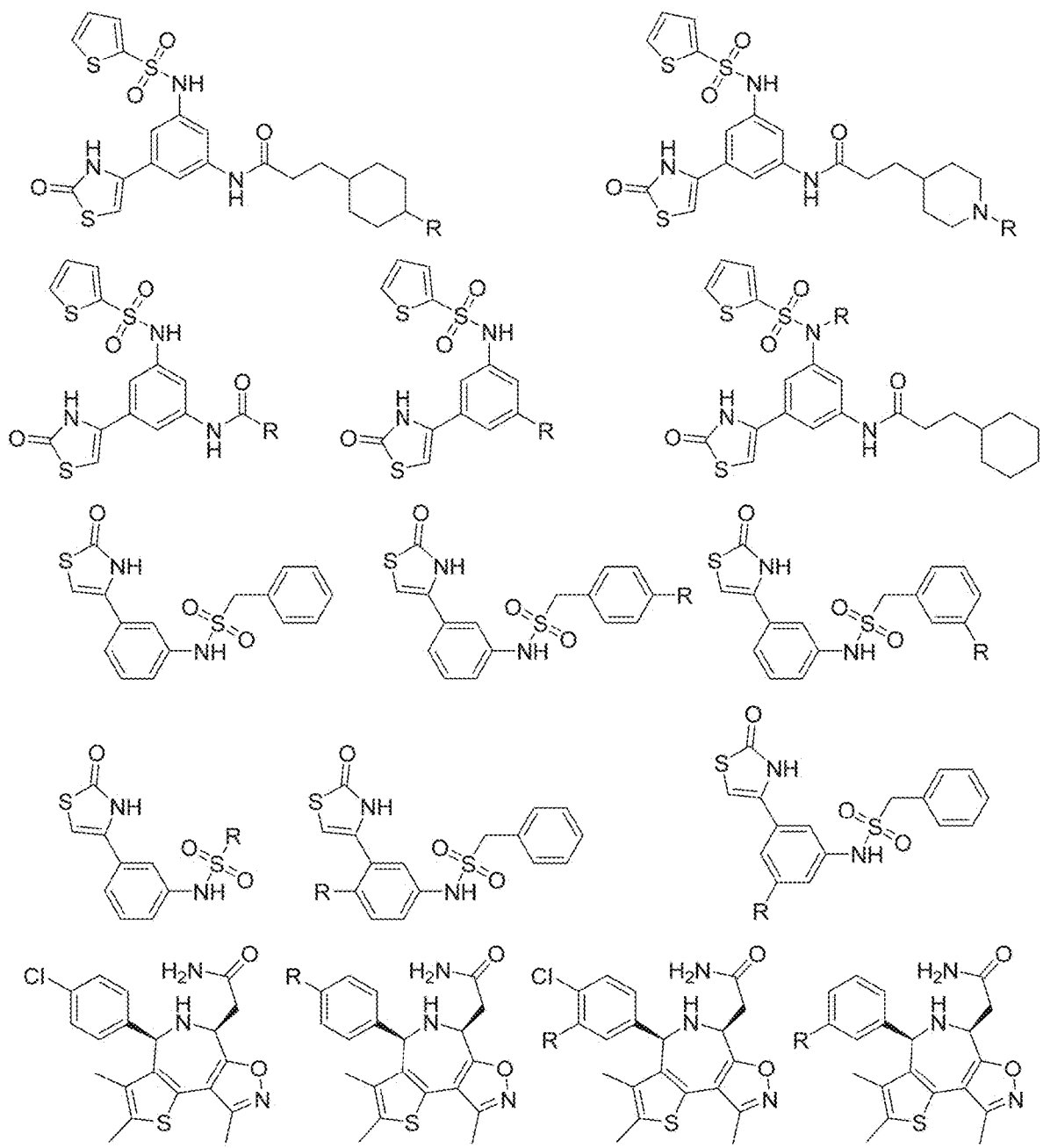
Figure 8F:
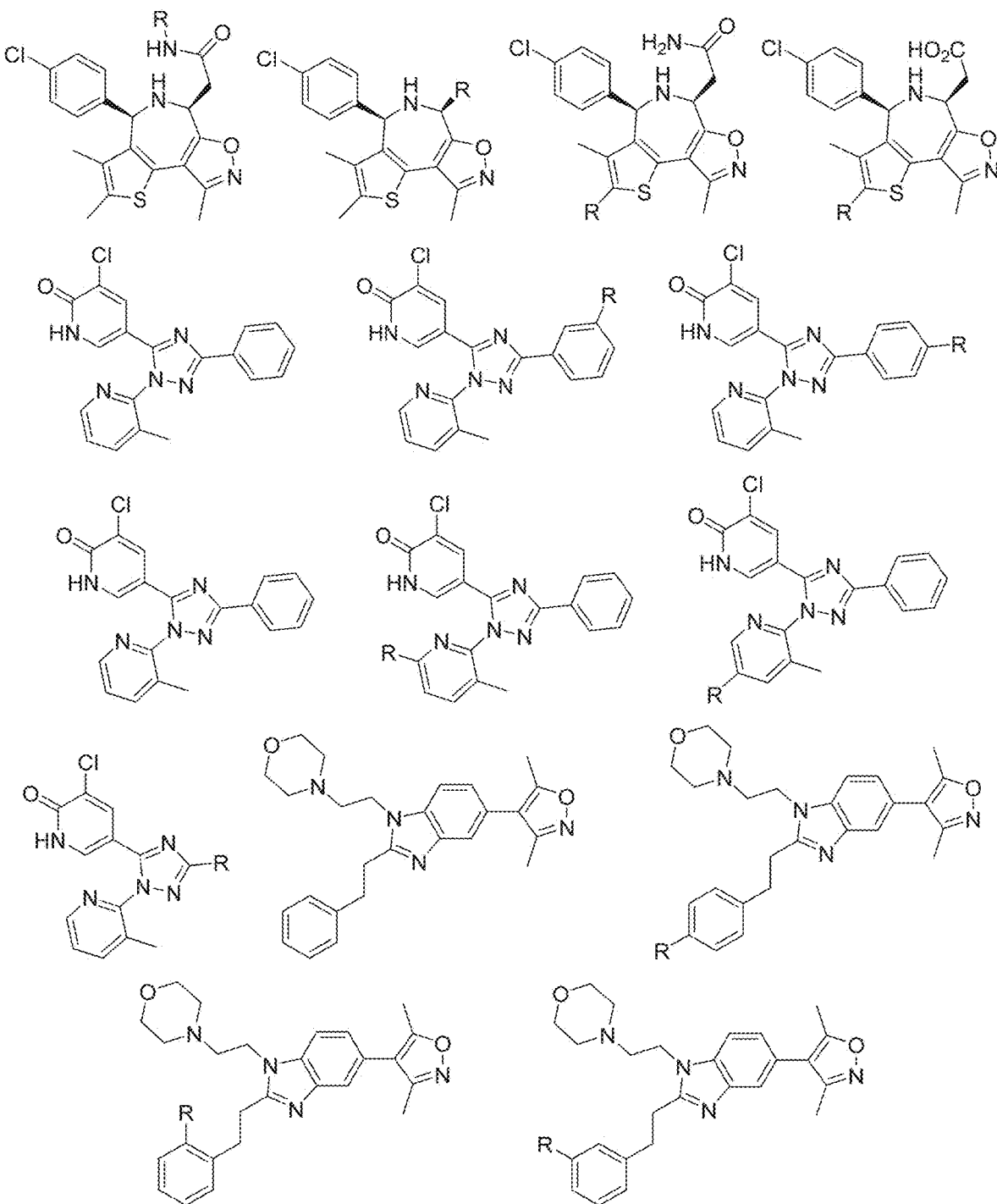
Figure 8G:
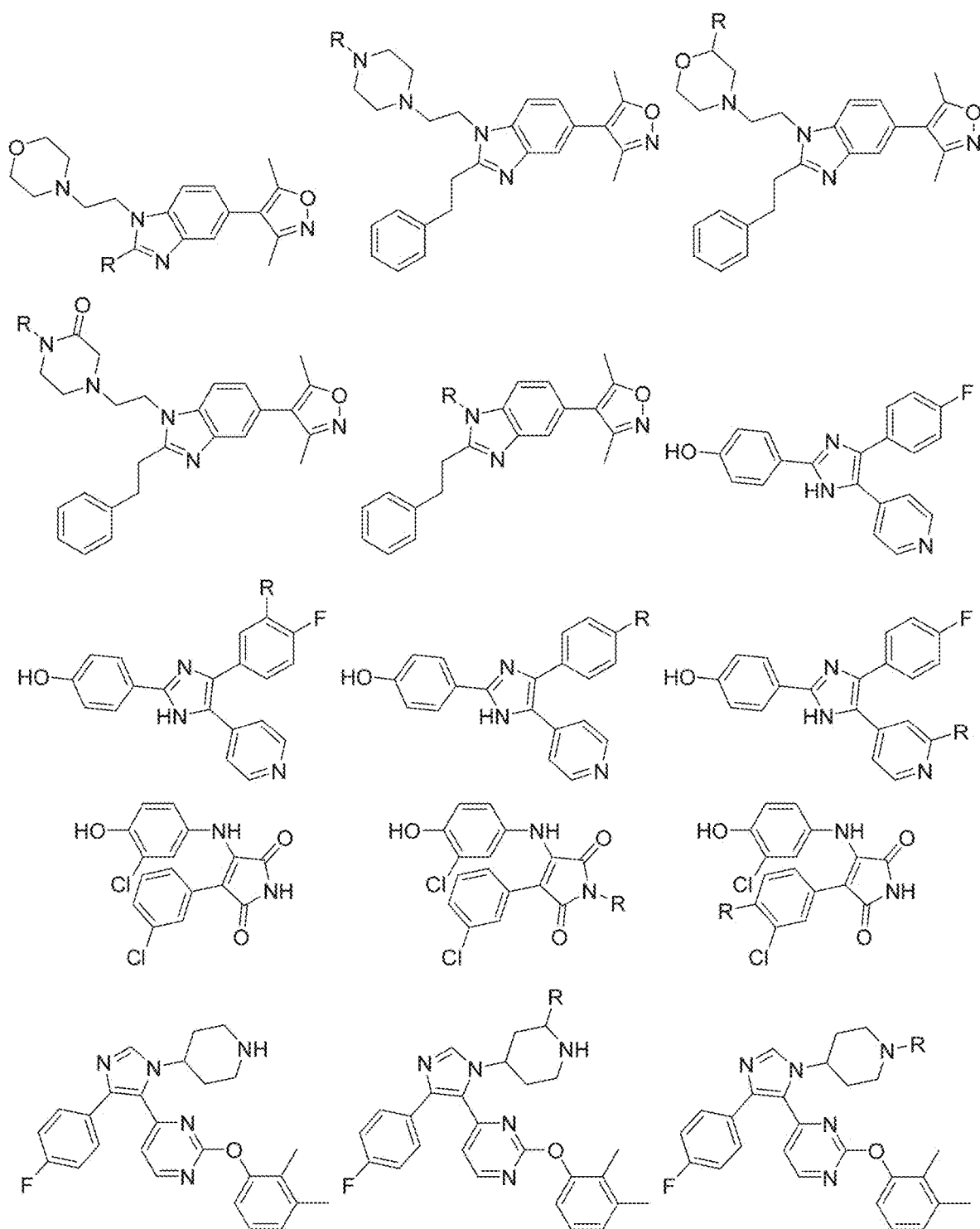
Figure 8H:
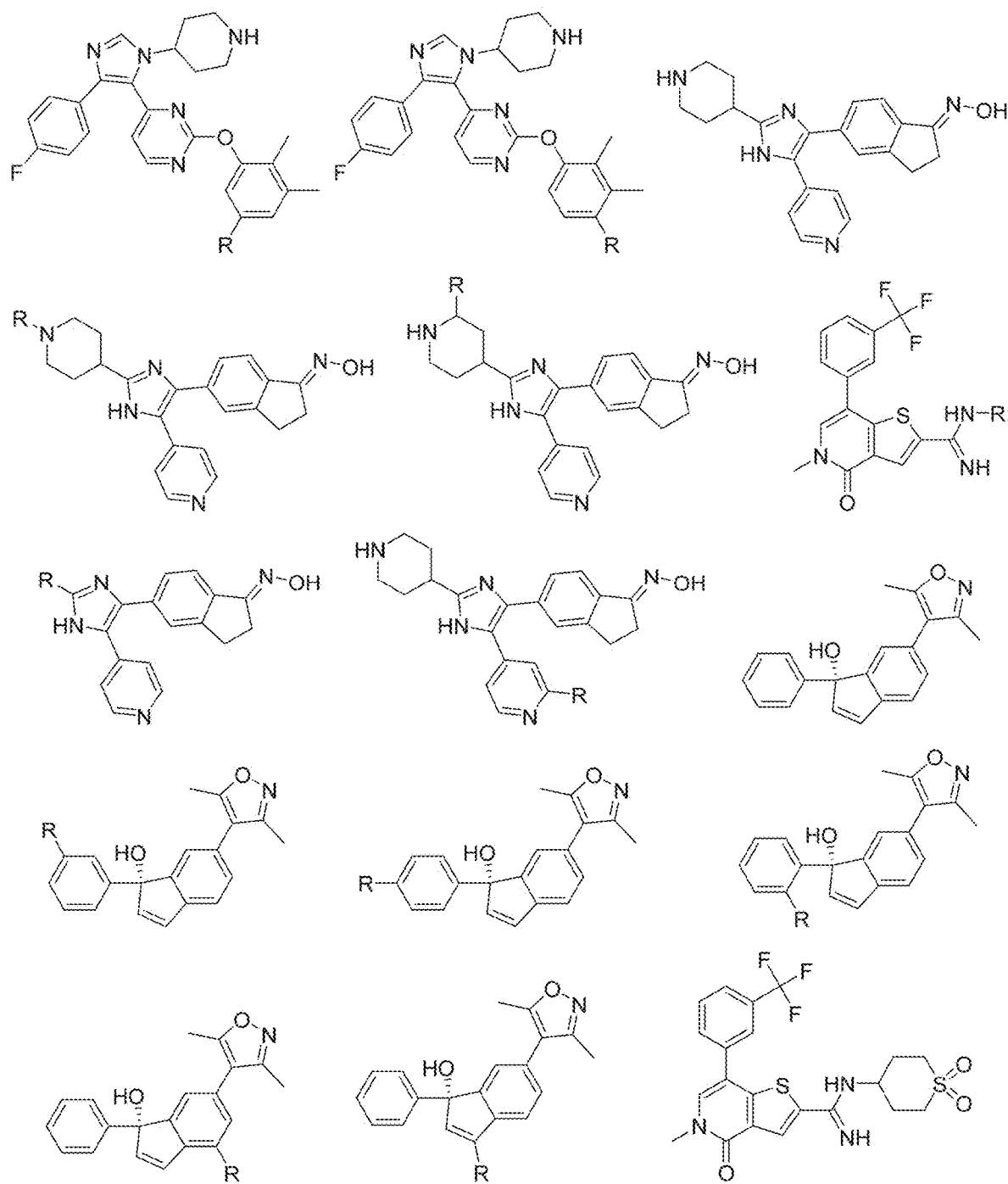
Figure 8I:
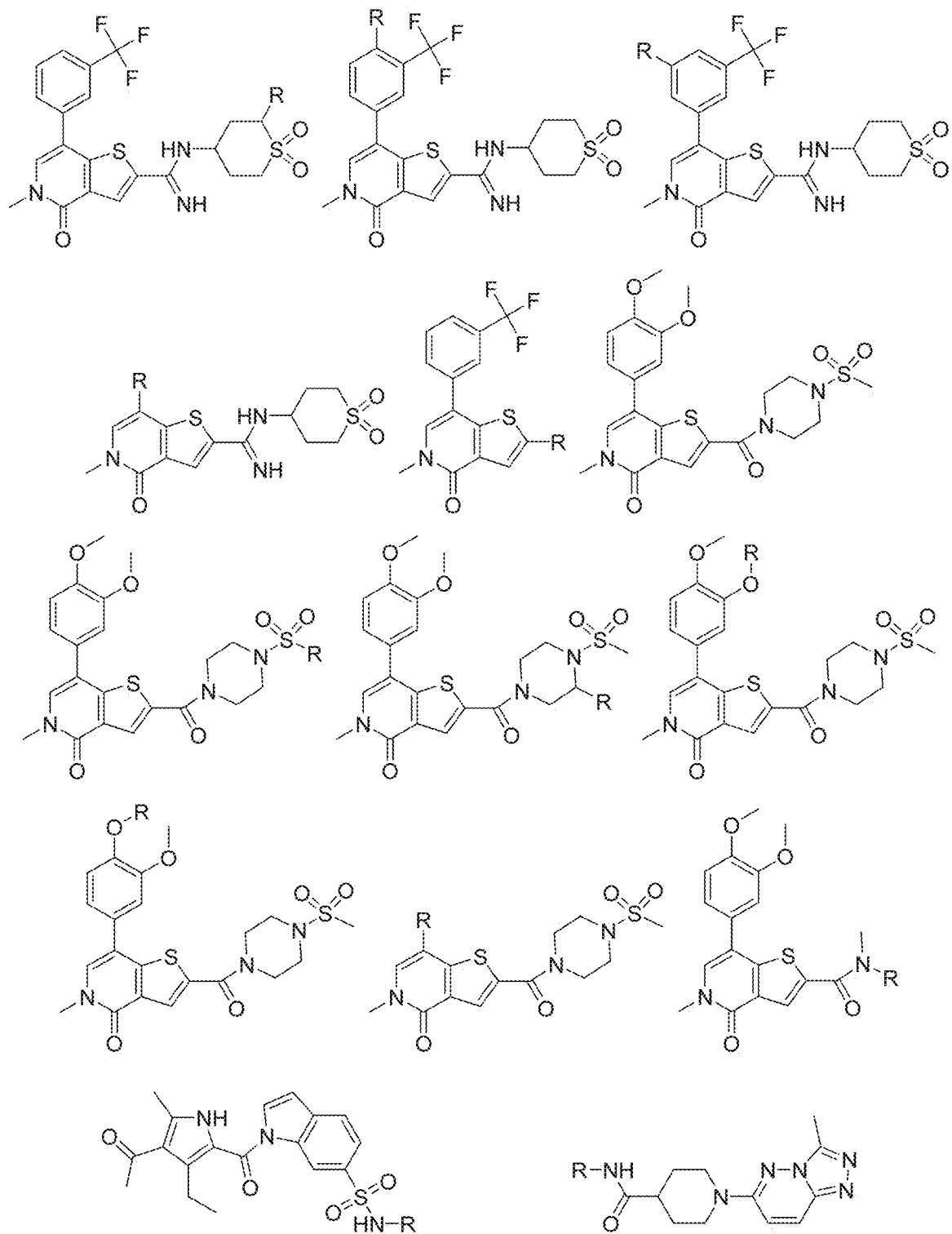
Figure 8J:
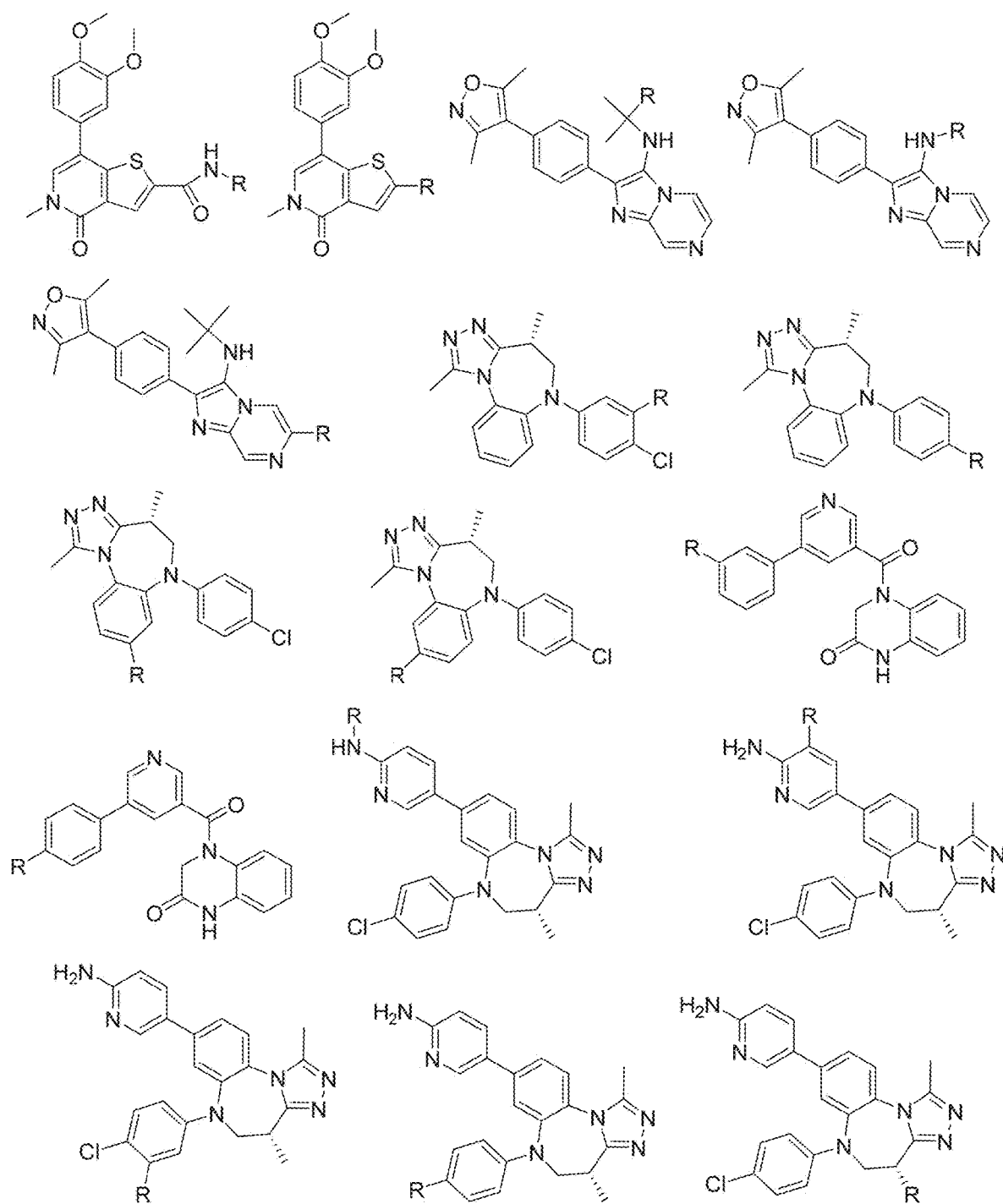
Figure 8K:
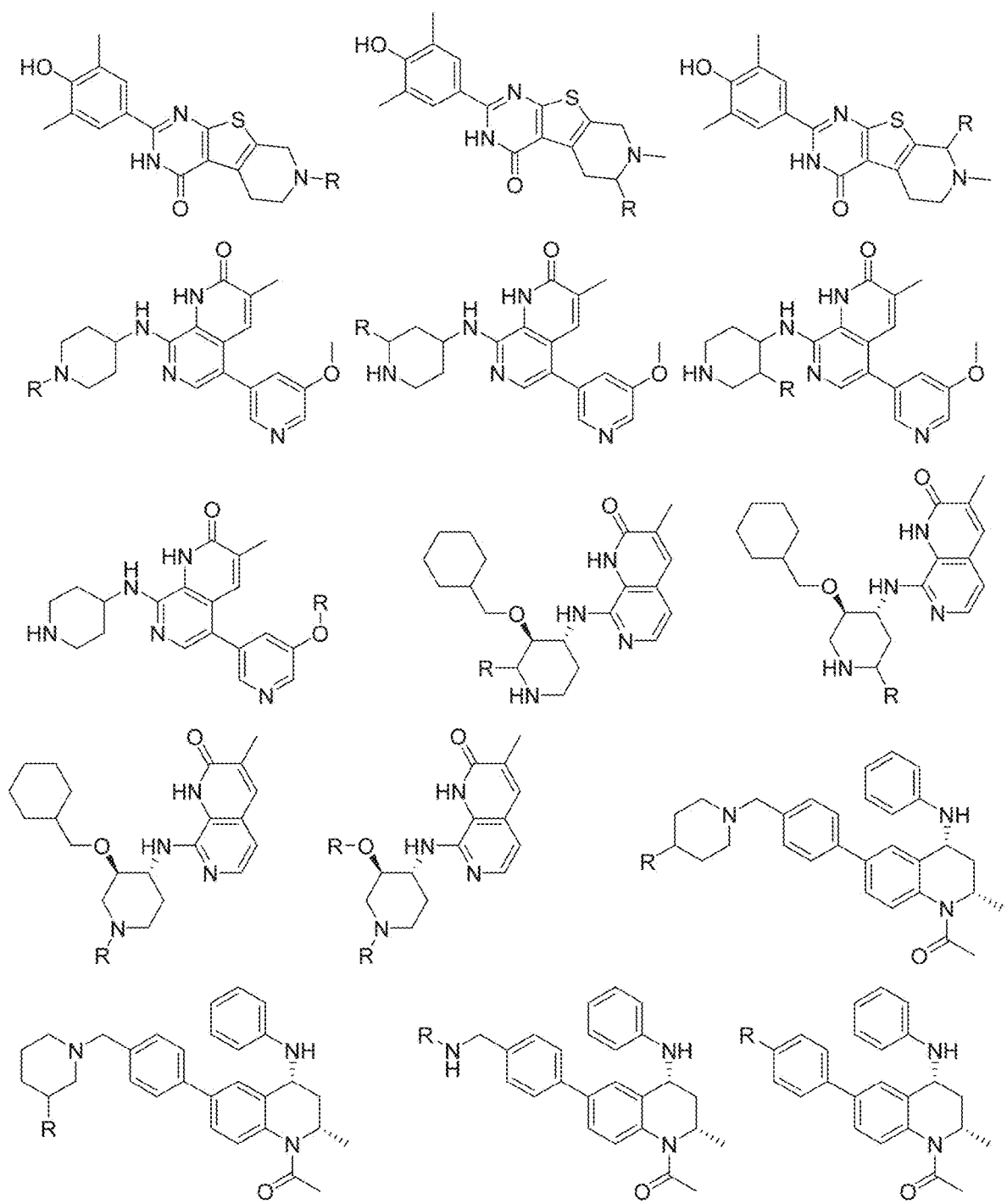
Figure 8L:
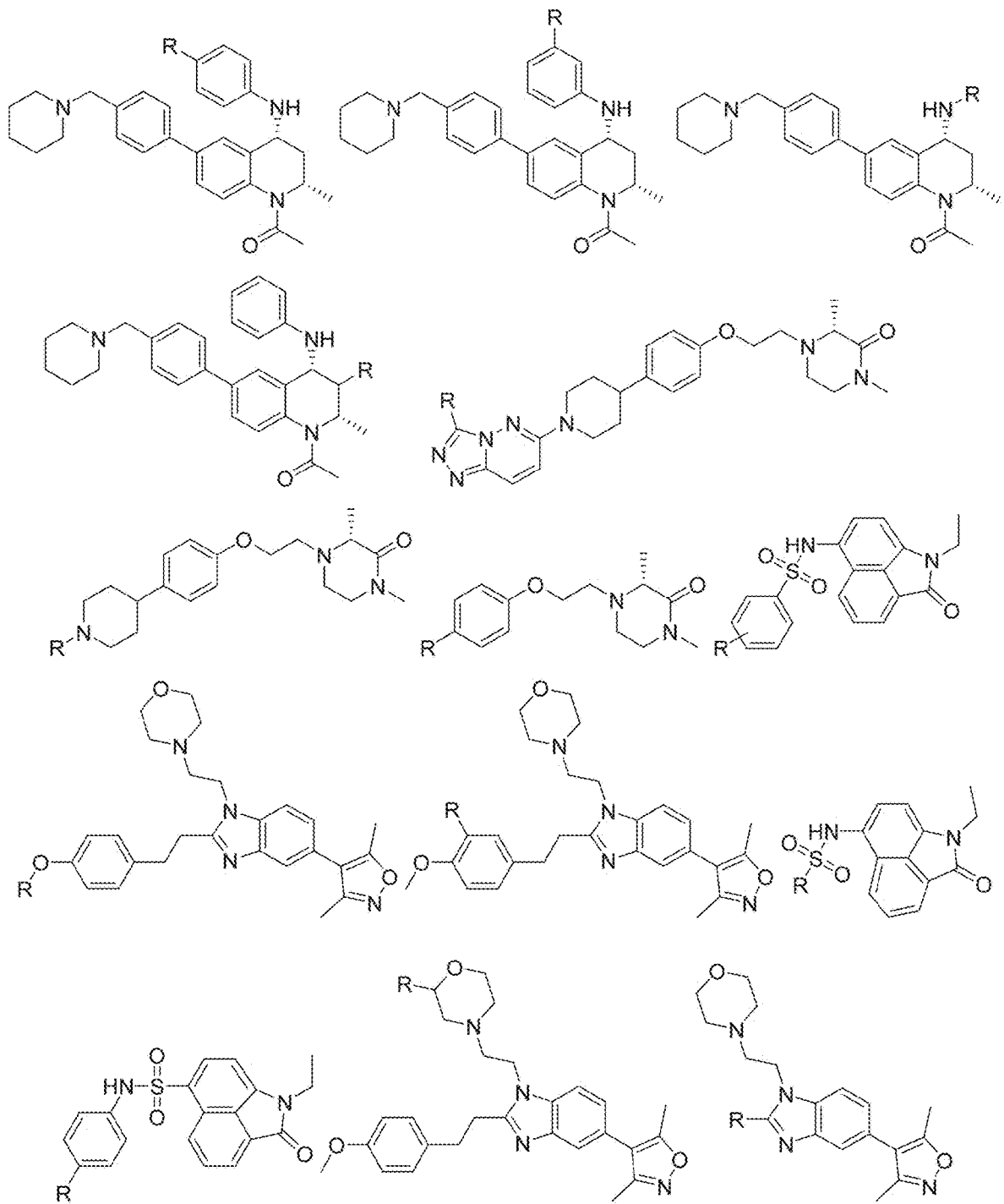
Figure 8M:
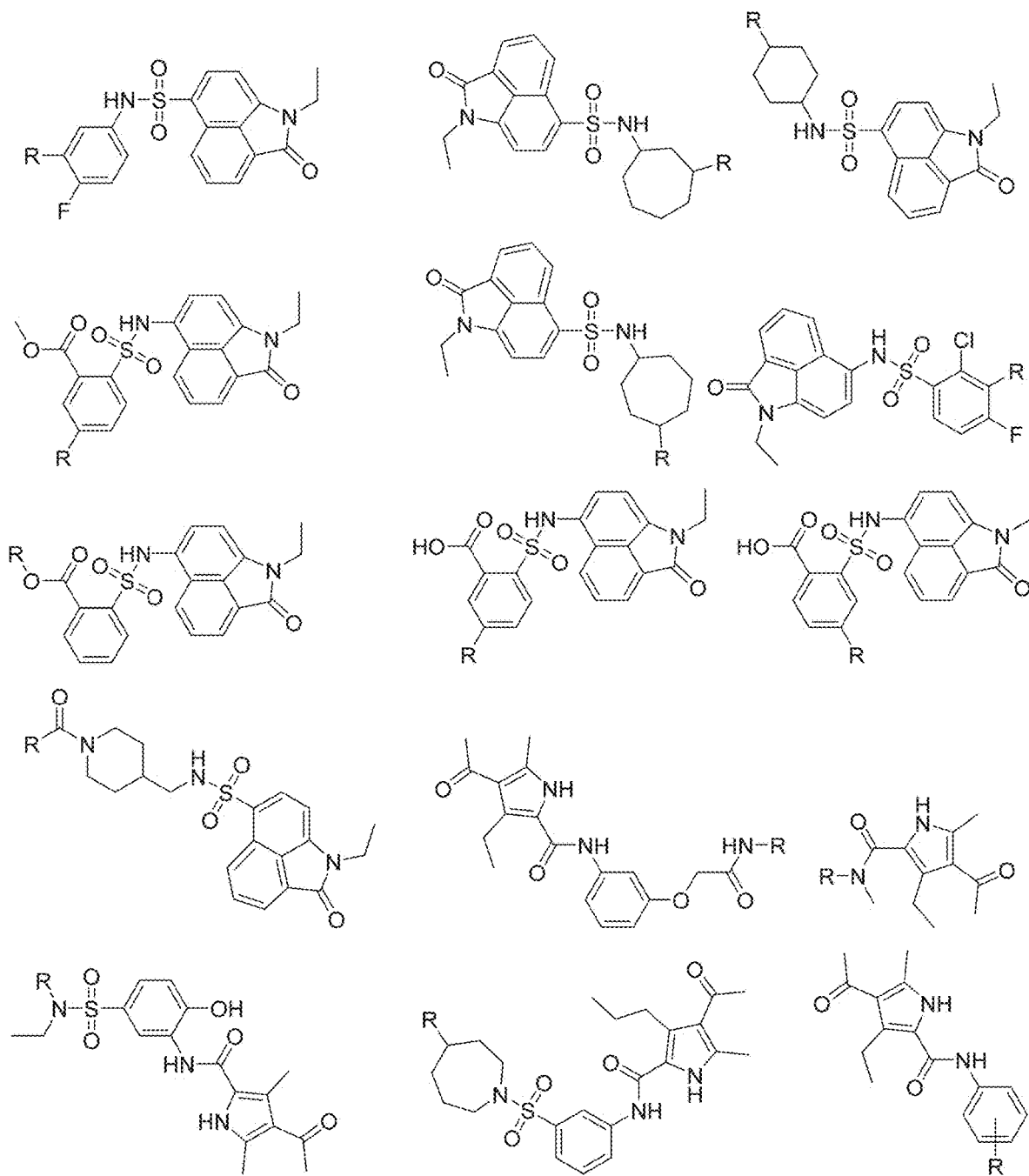
Figure 8N:
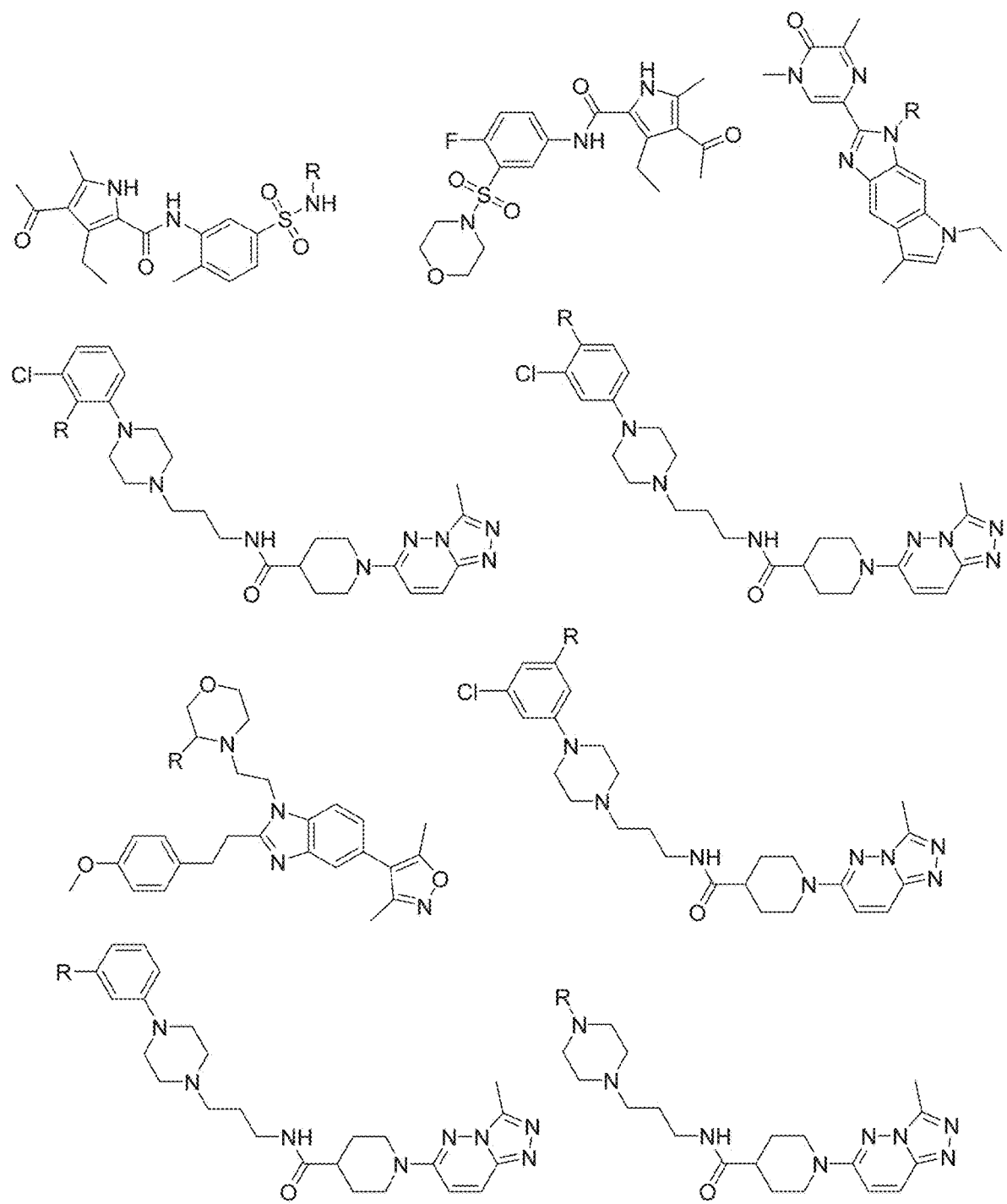
Figure 8O:
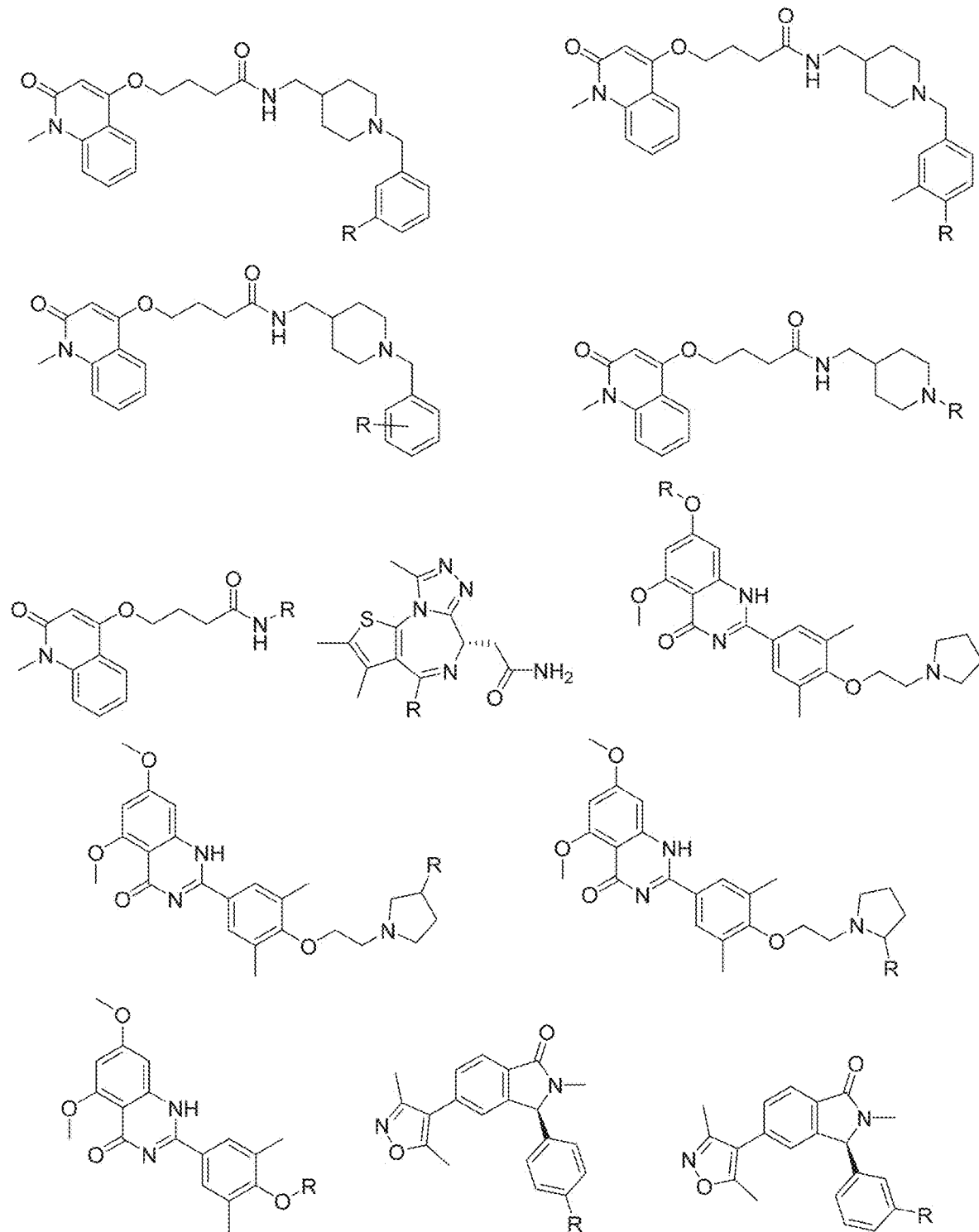
Figure 8P:
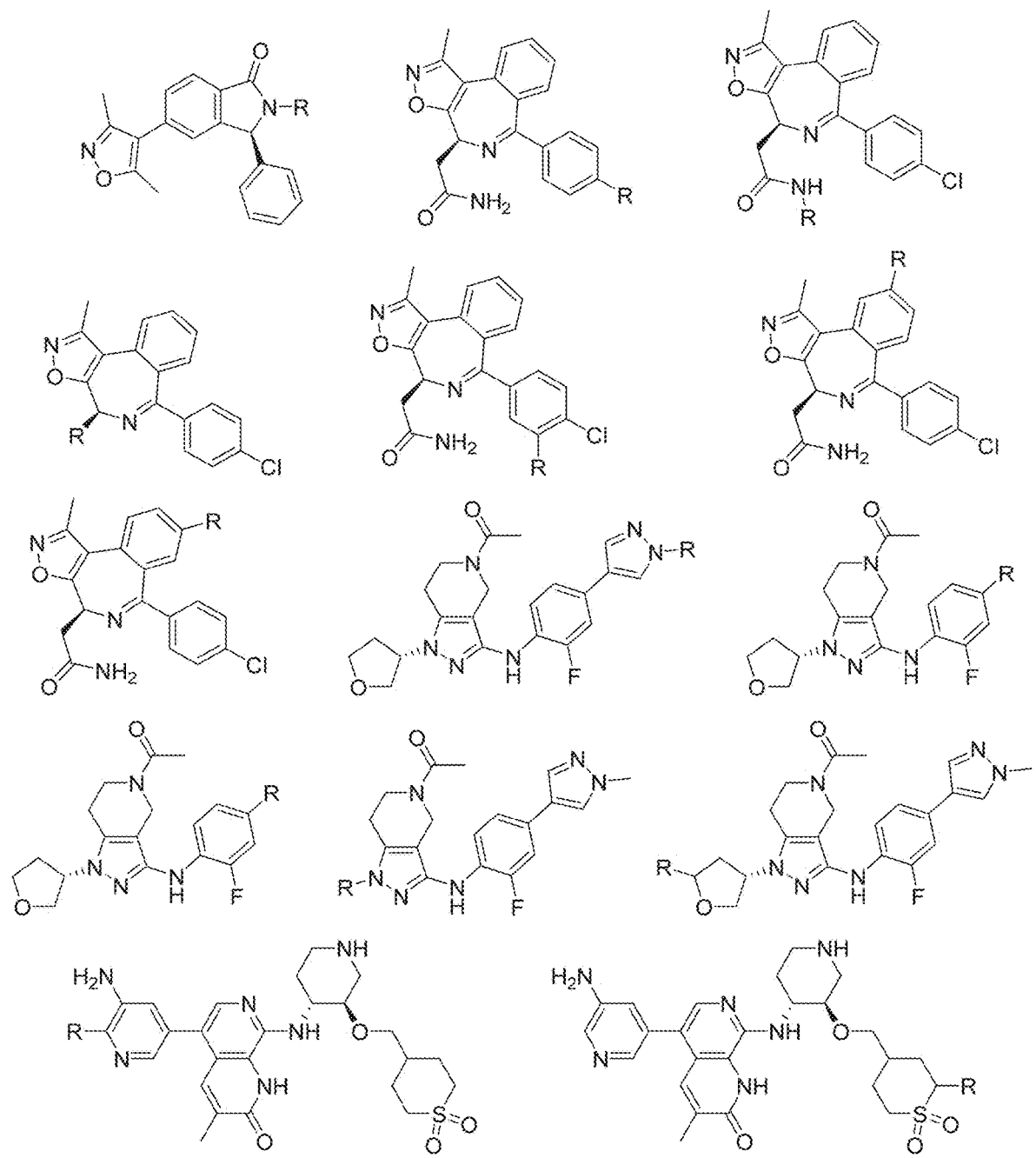
Figure 8Q:
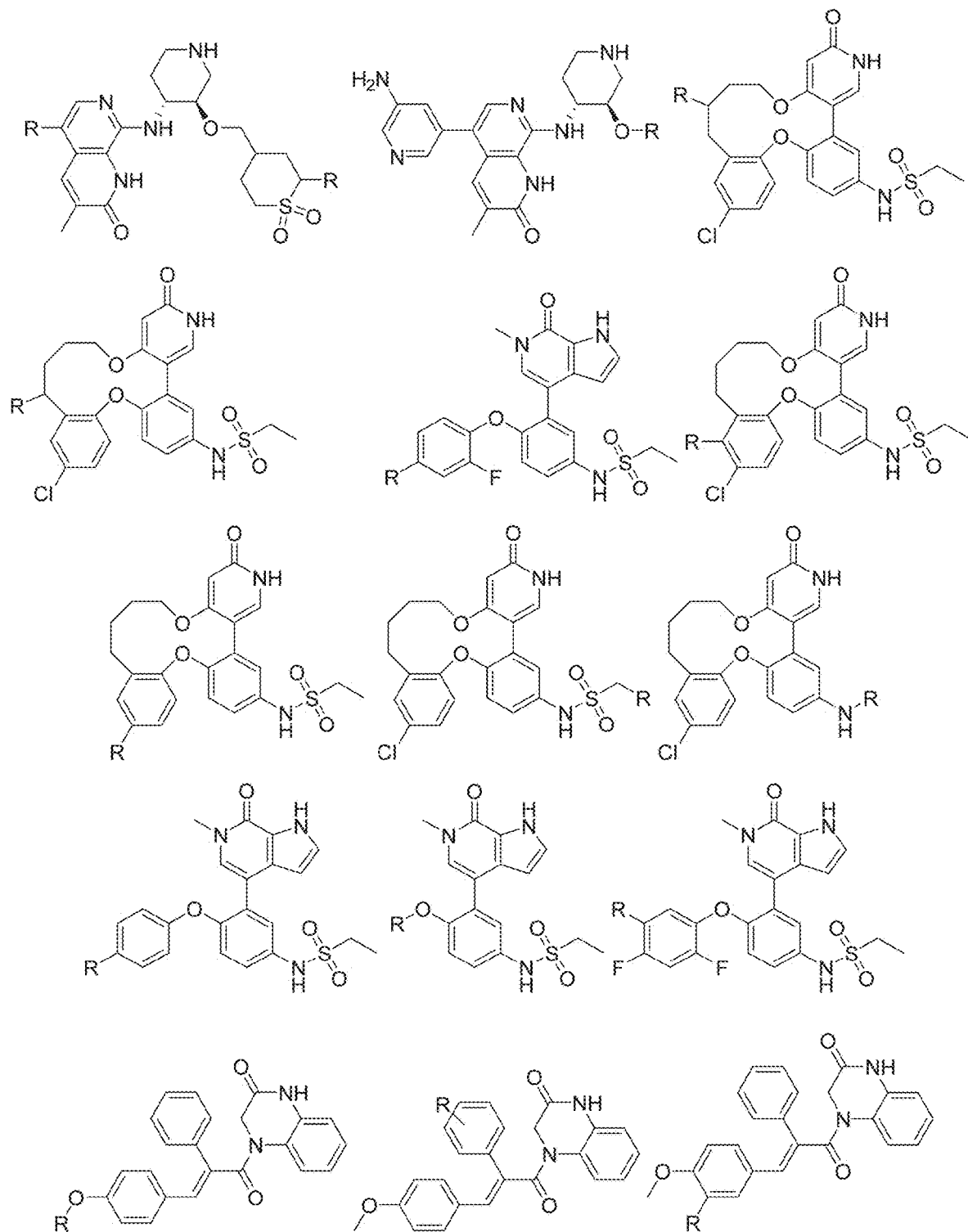
Figure 8R:
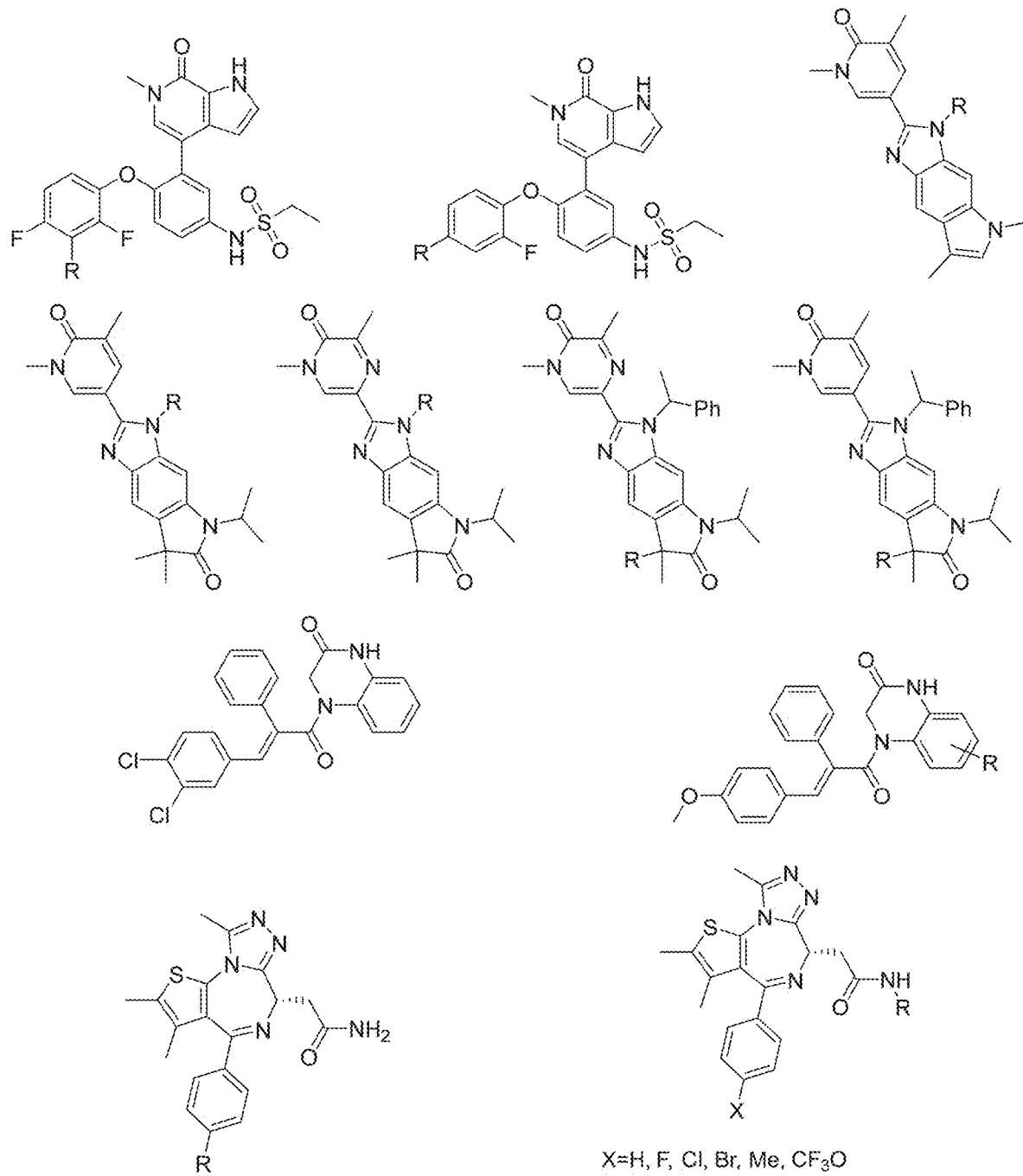
Figure 8U:
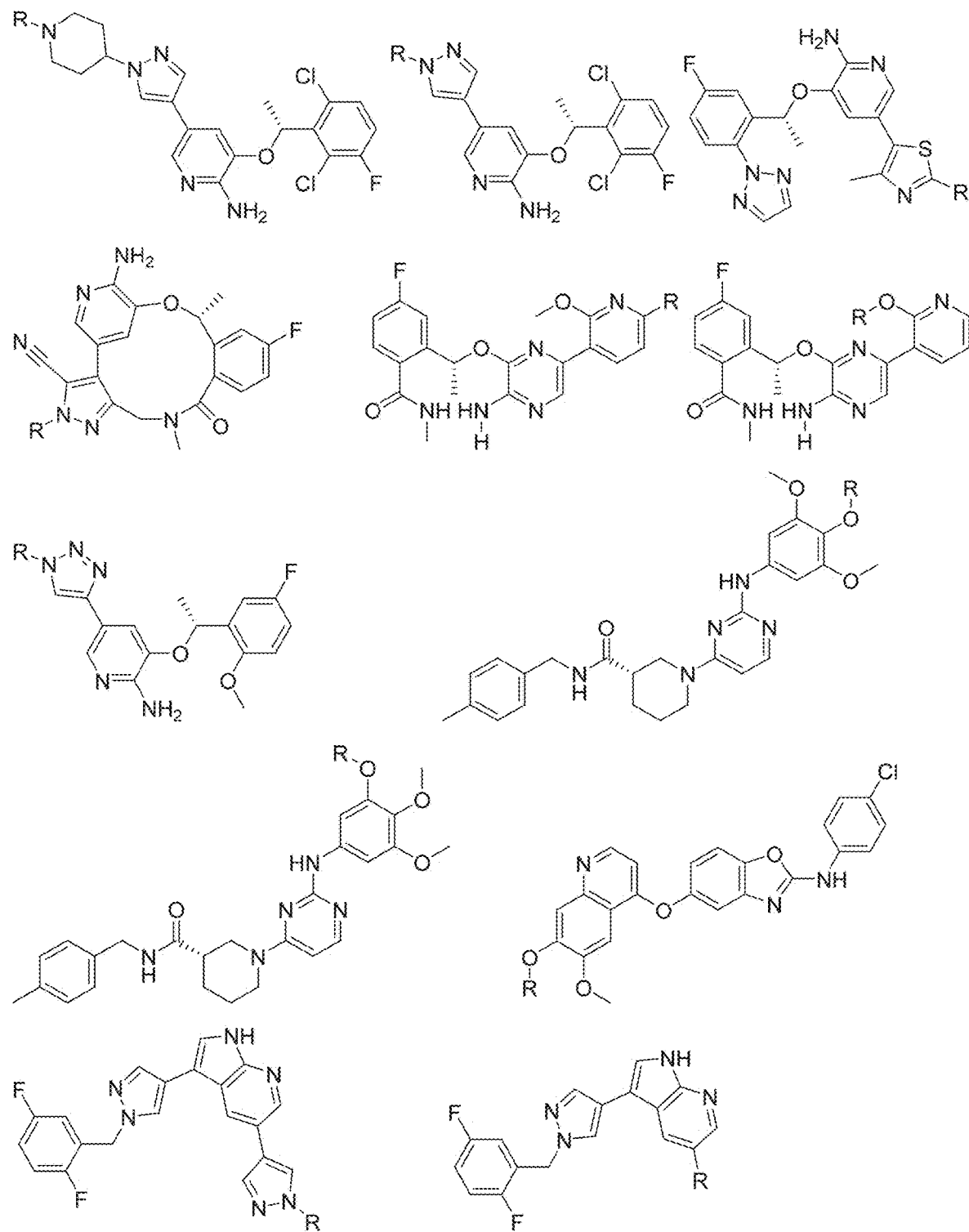
Figure 8V:
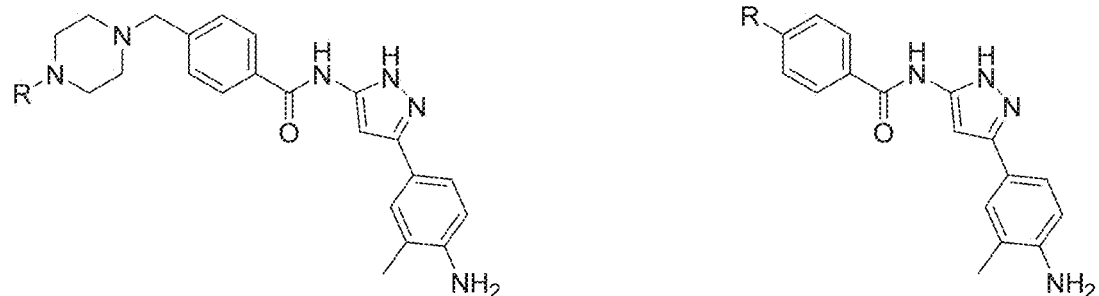
Figure 8W:
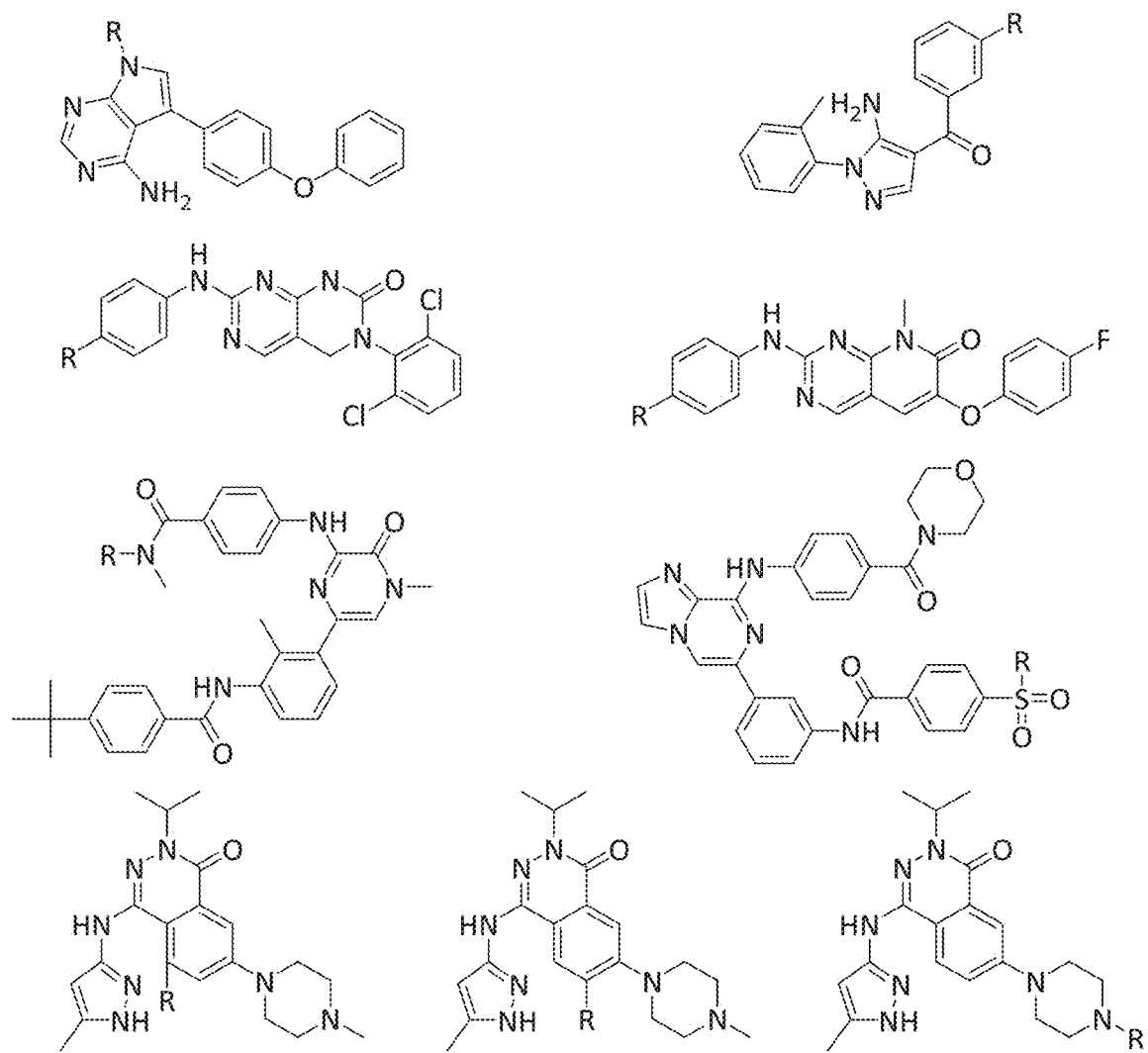
Figure 8X:
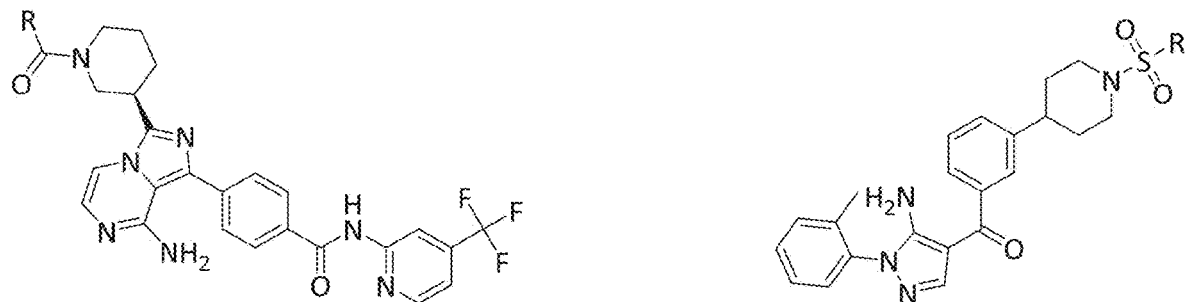
Figure 8Y:
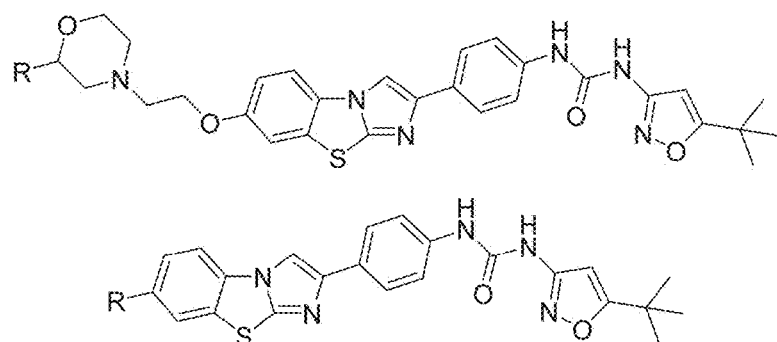
Figure 8Z:
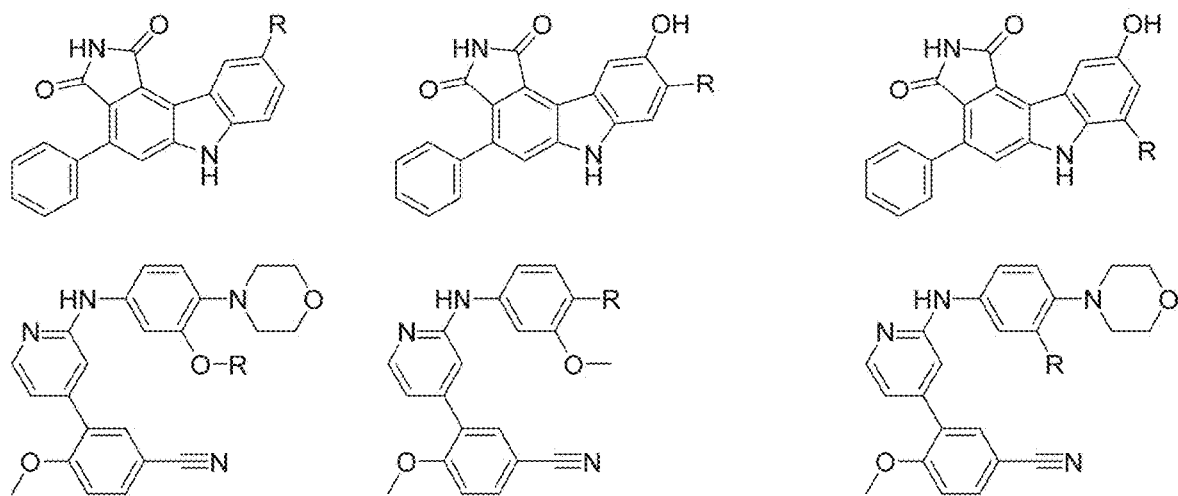
Figure 8A:
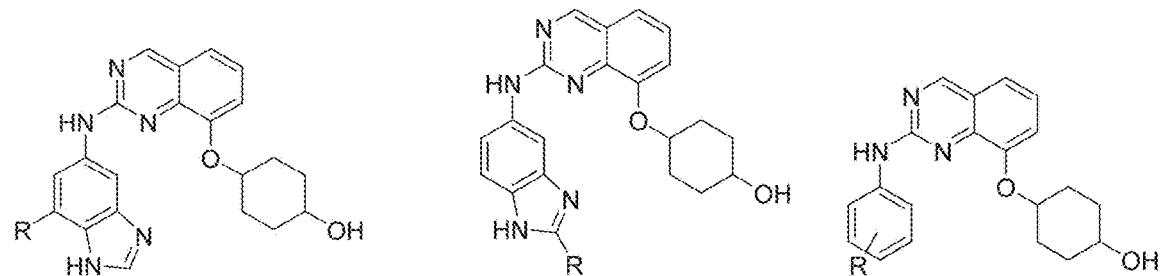
Figure 8B:
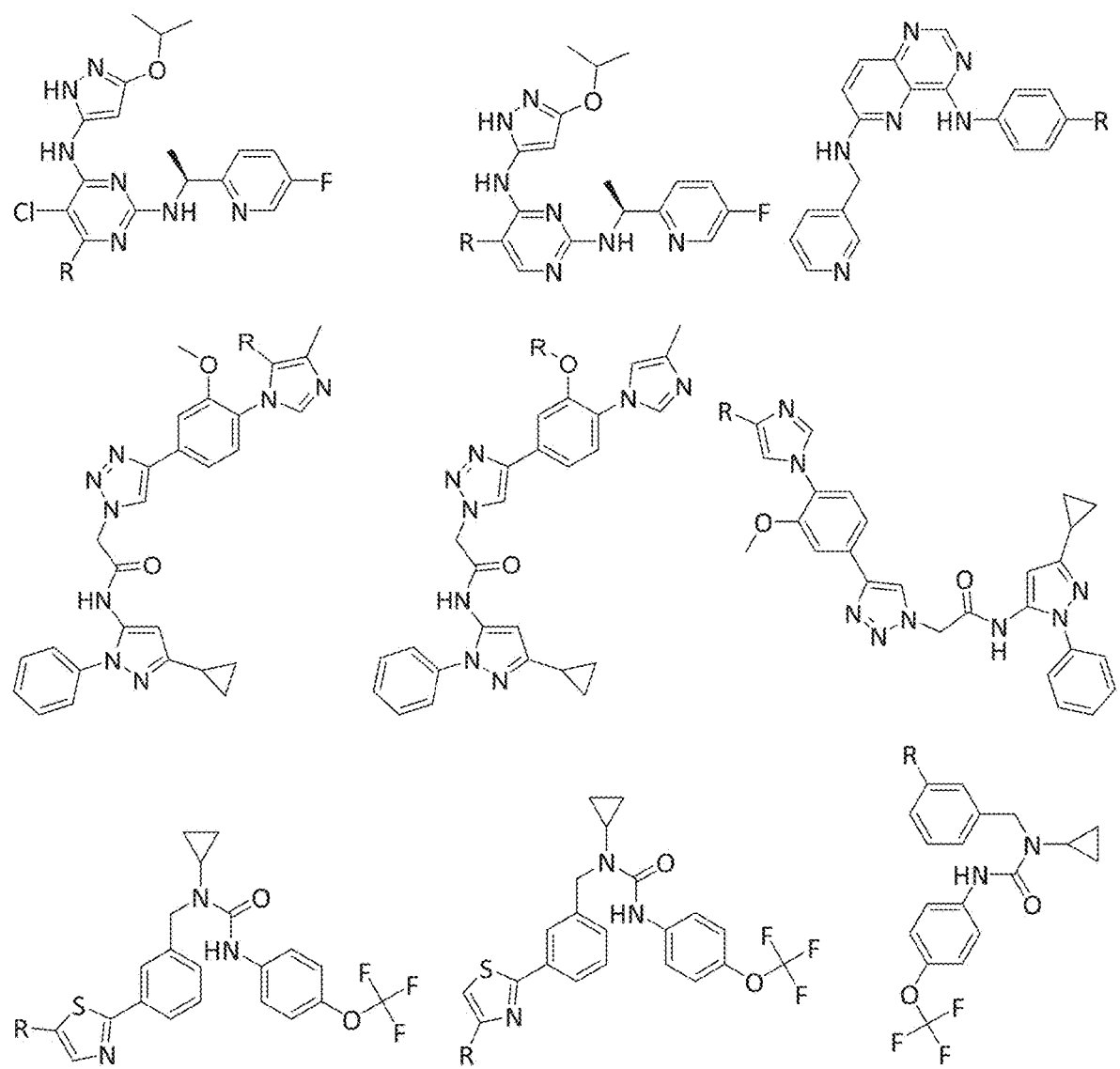
Figure 8C:
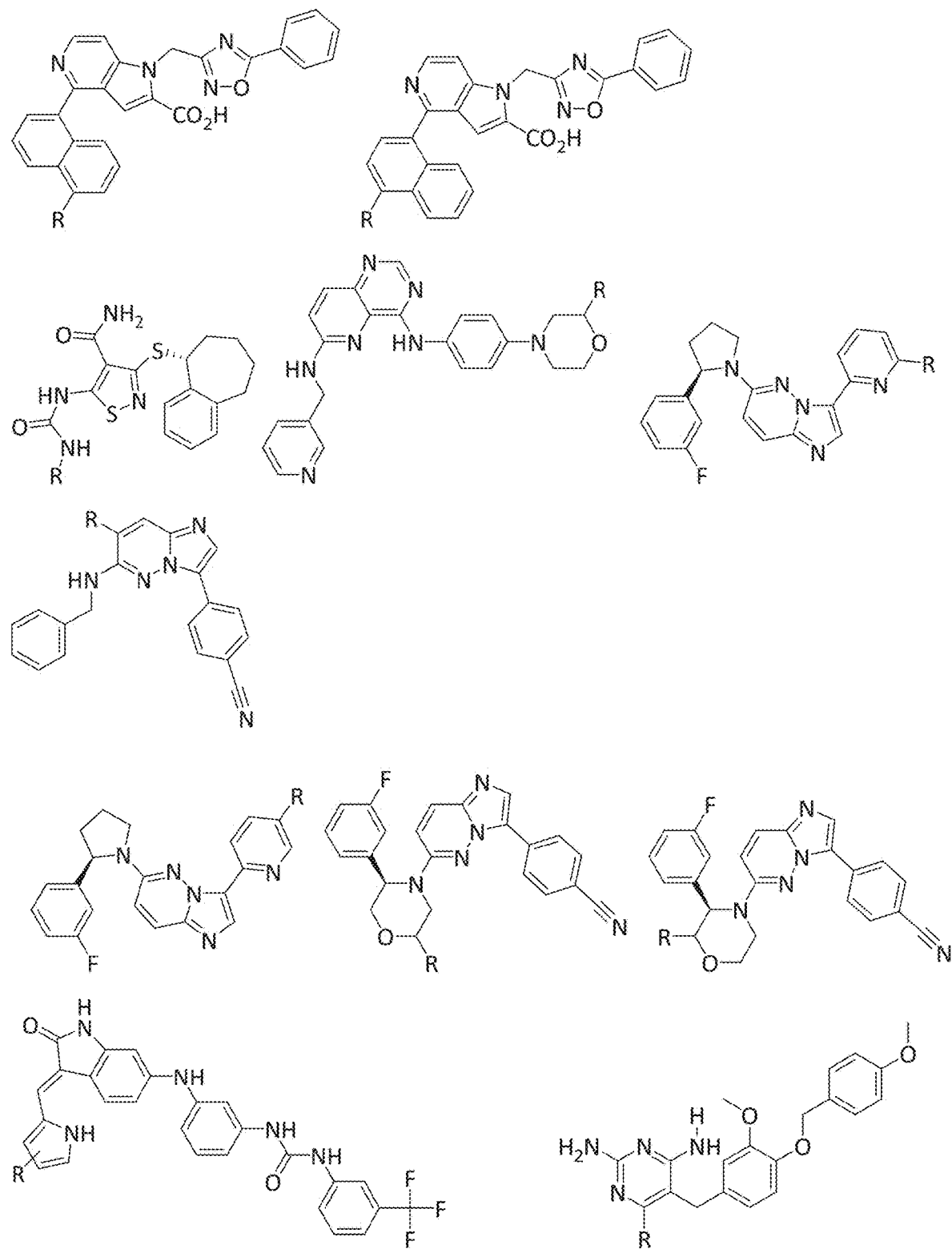
Figure 8D:
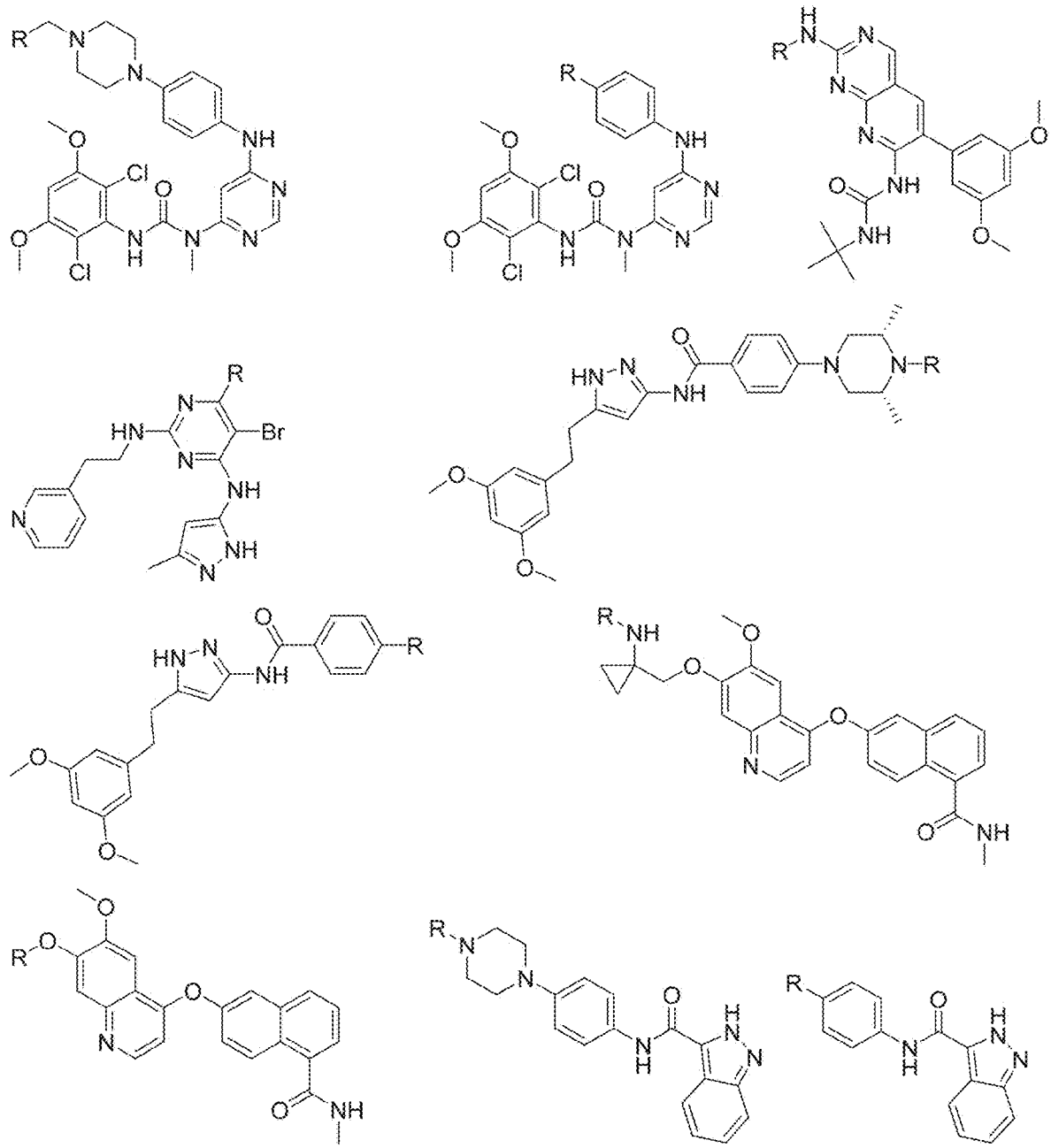
Figure 8E:
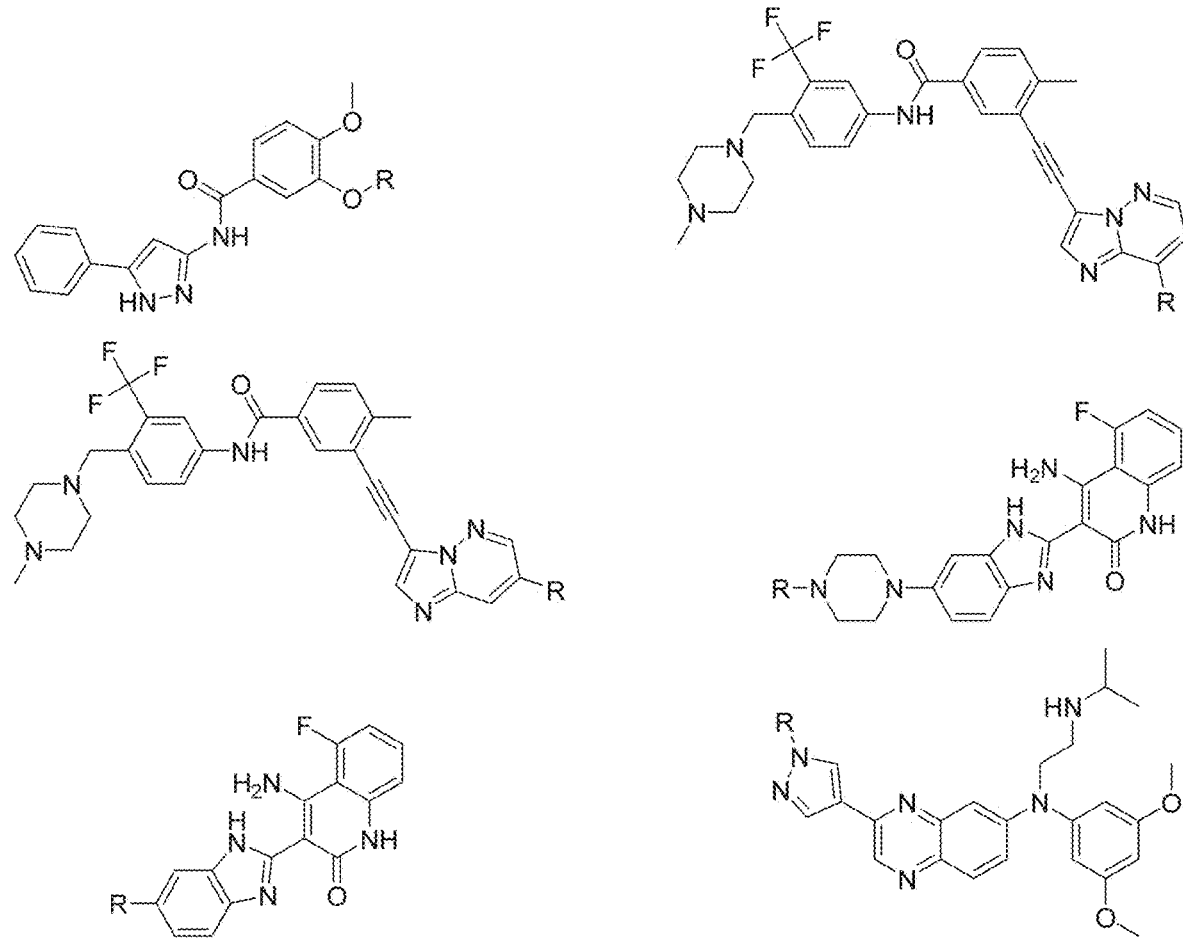
Figure 8F:
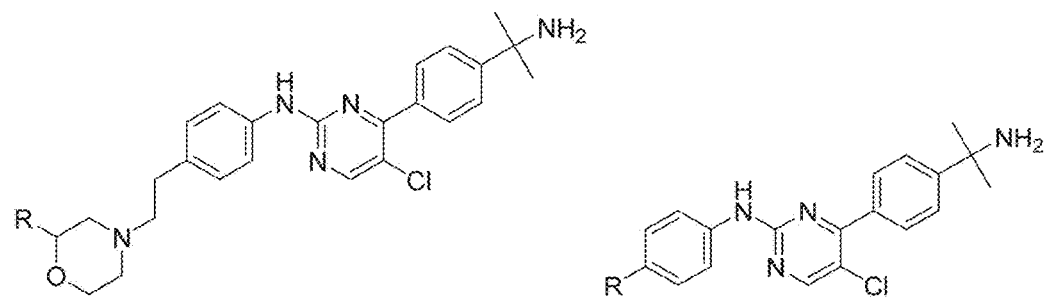
Figure 8G:
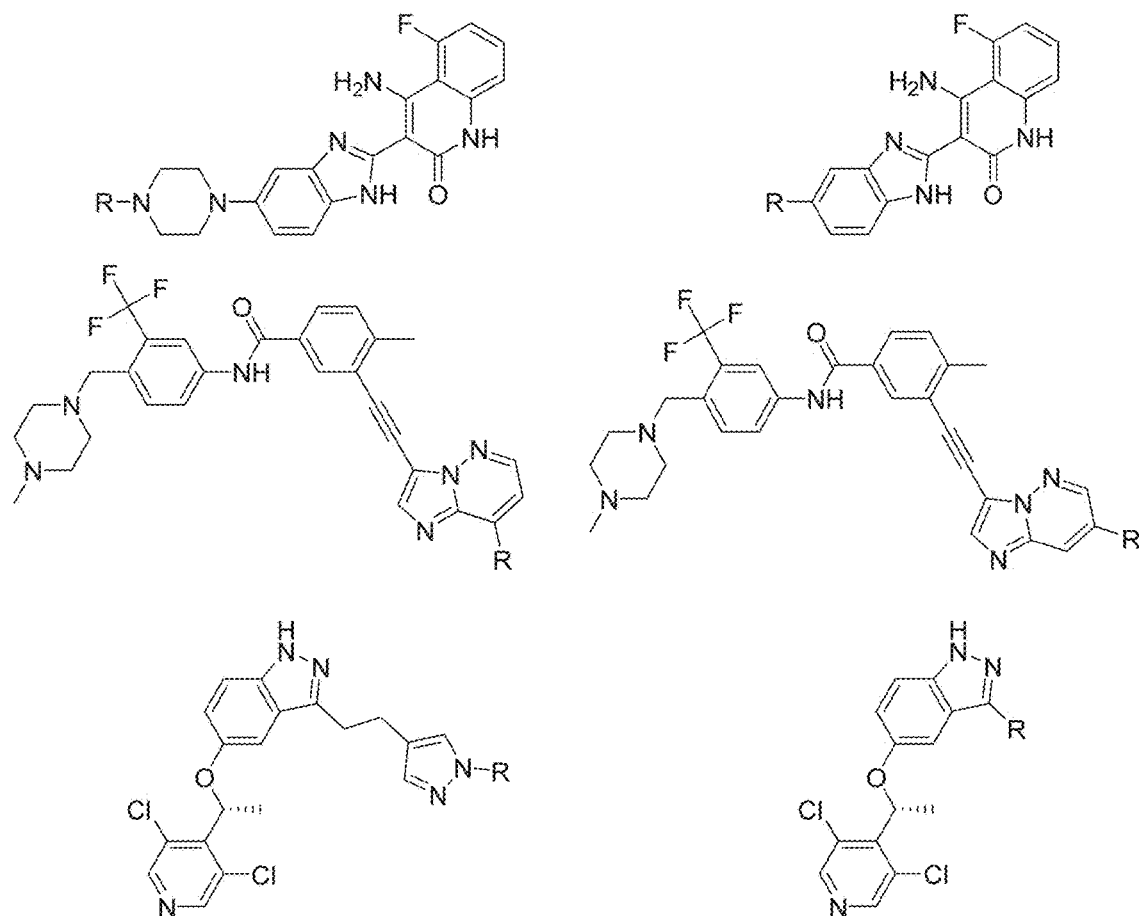
Figure 8H:
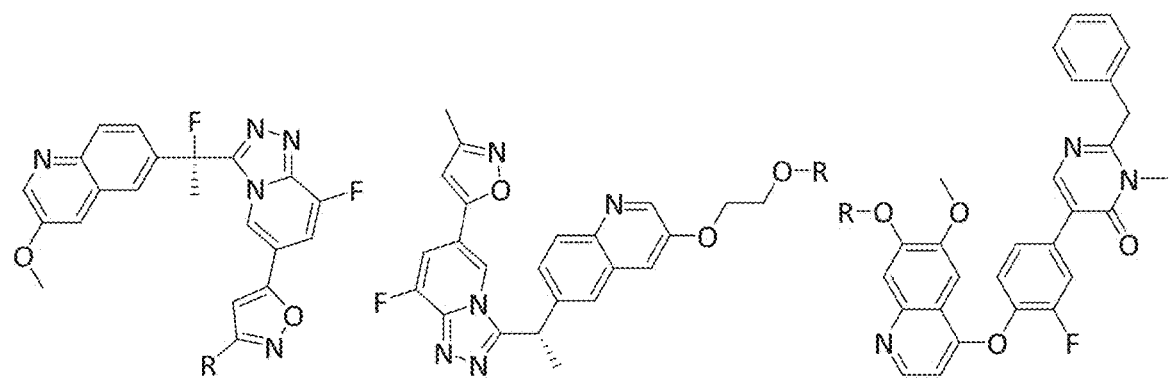
Figure 8I:
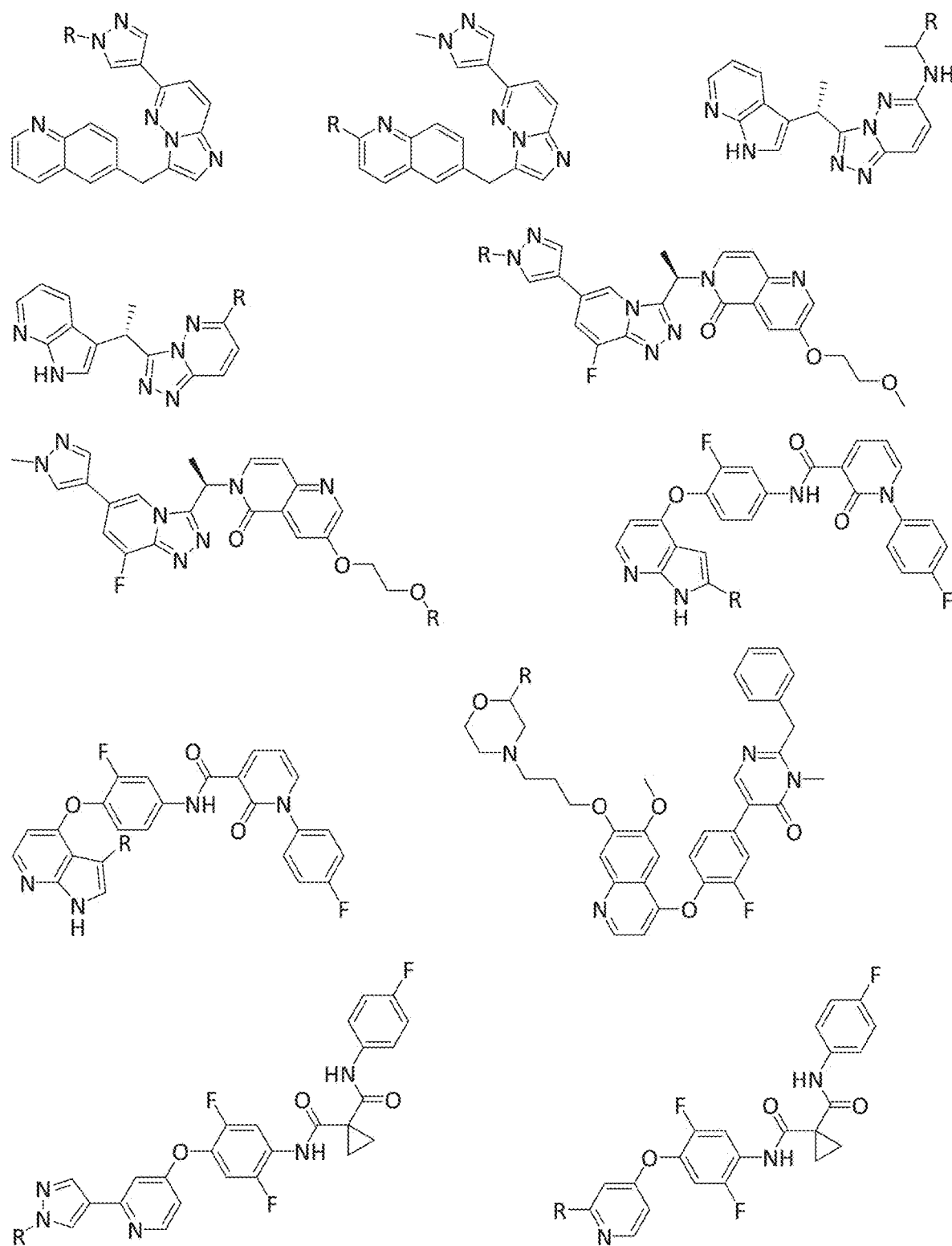
Figure 8J:
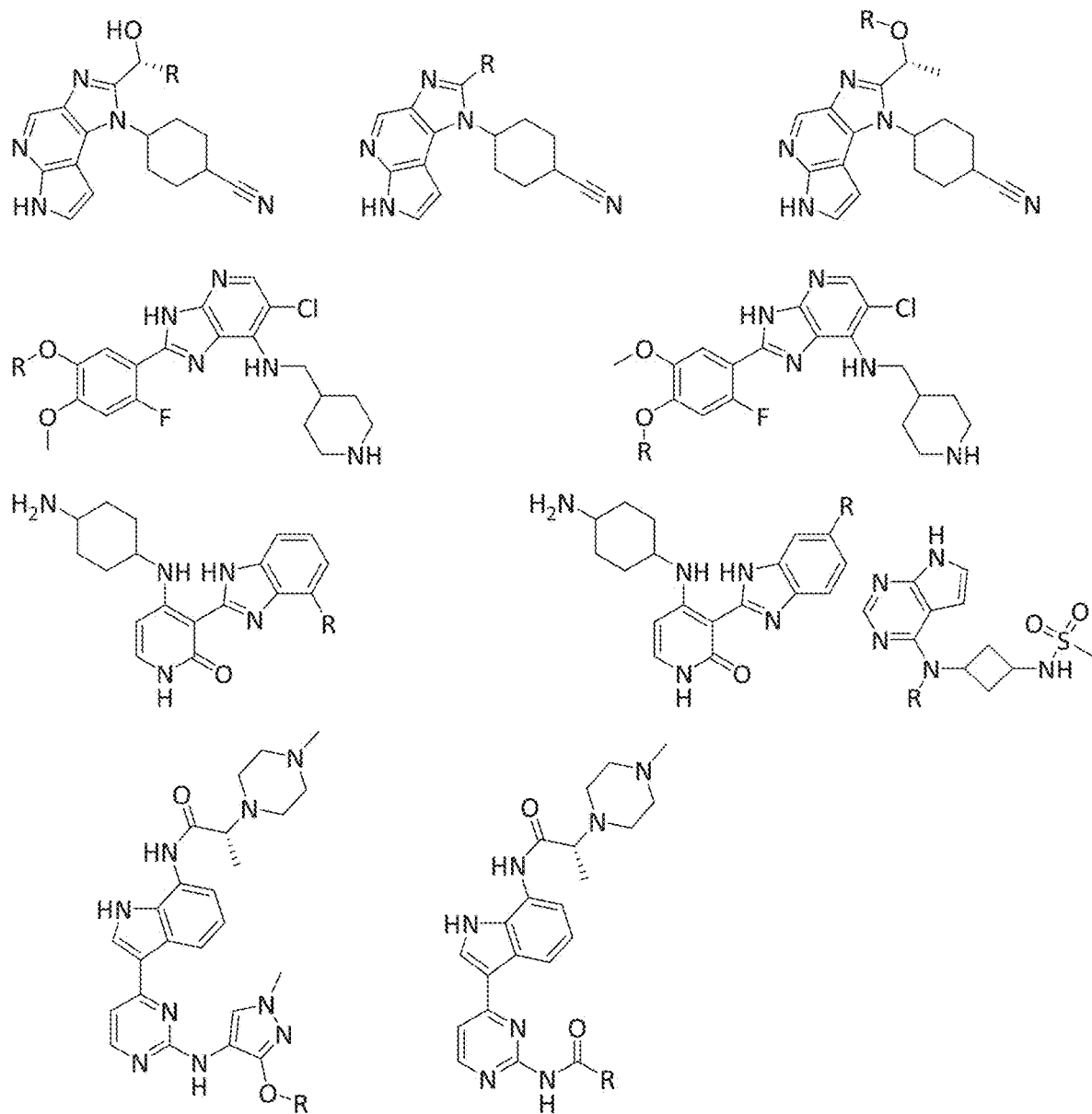
Figure 8K:
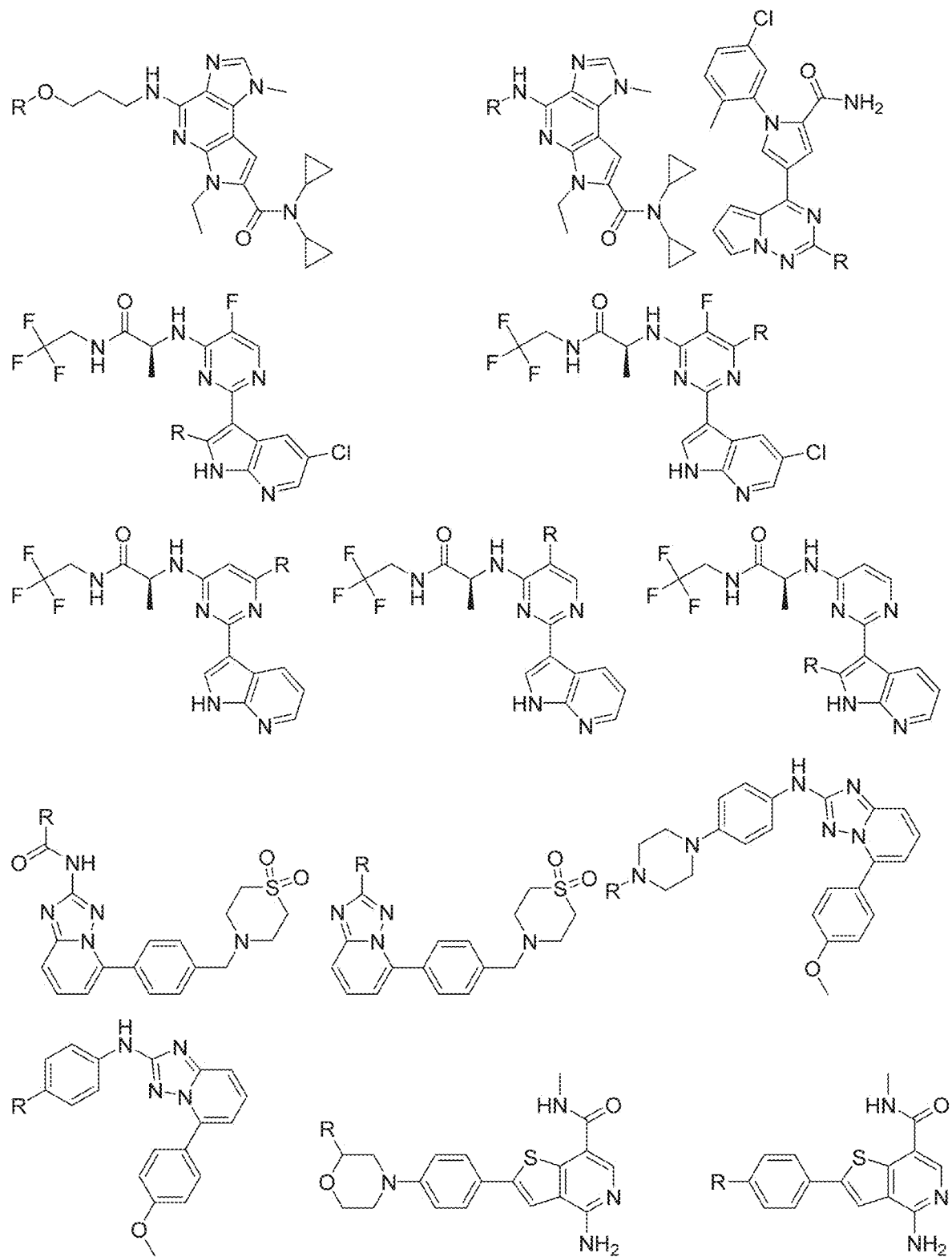
Figure 8L:
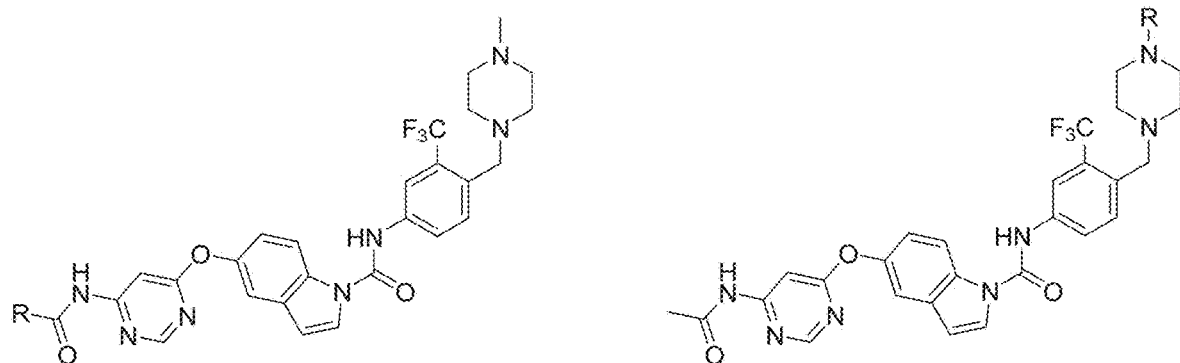
Figure 8M:
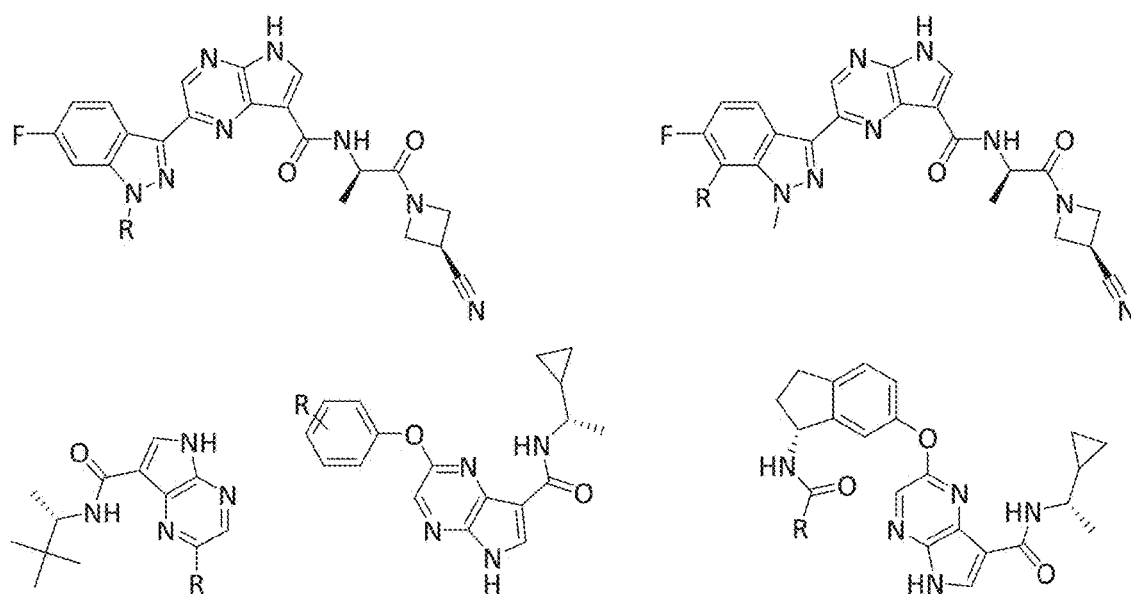
Figure 8N:
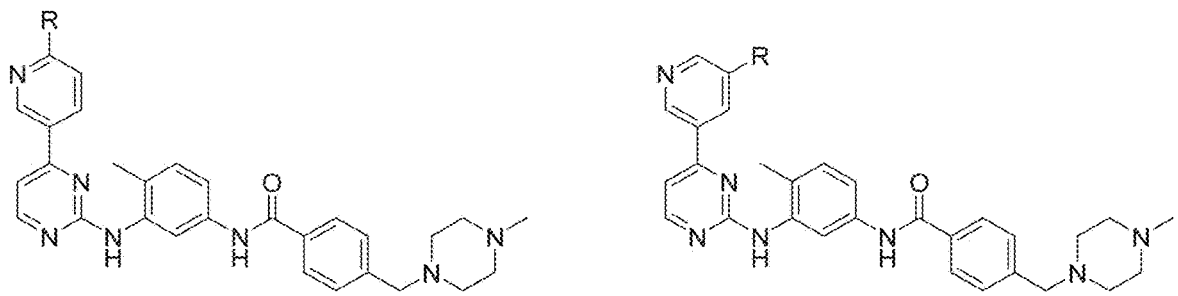
Figure 8O:
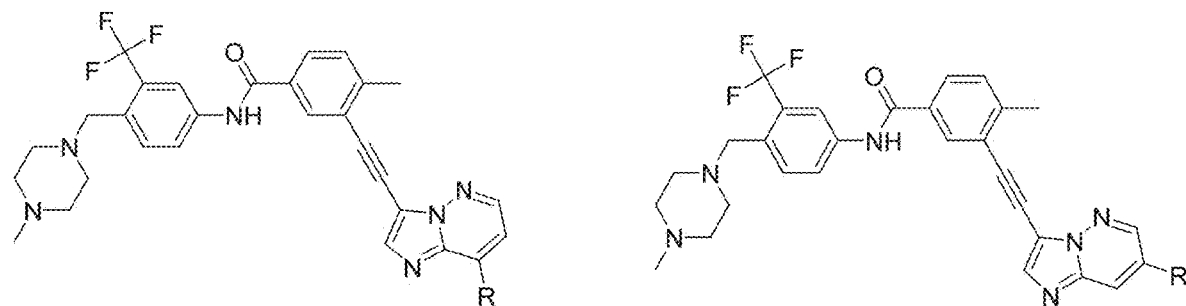
Figure 8P:
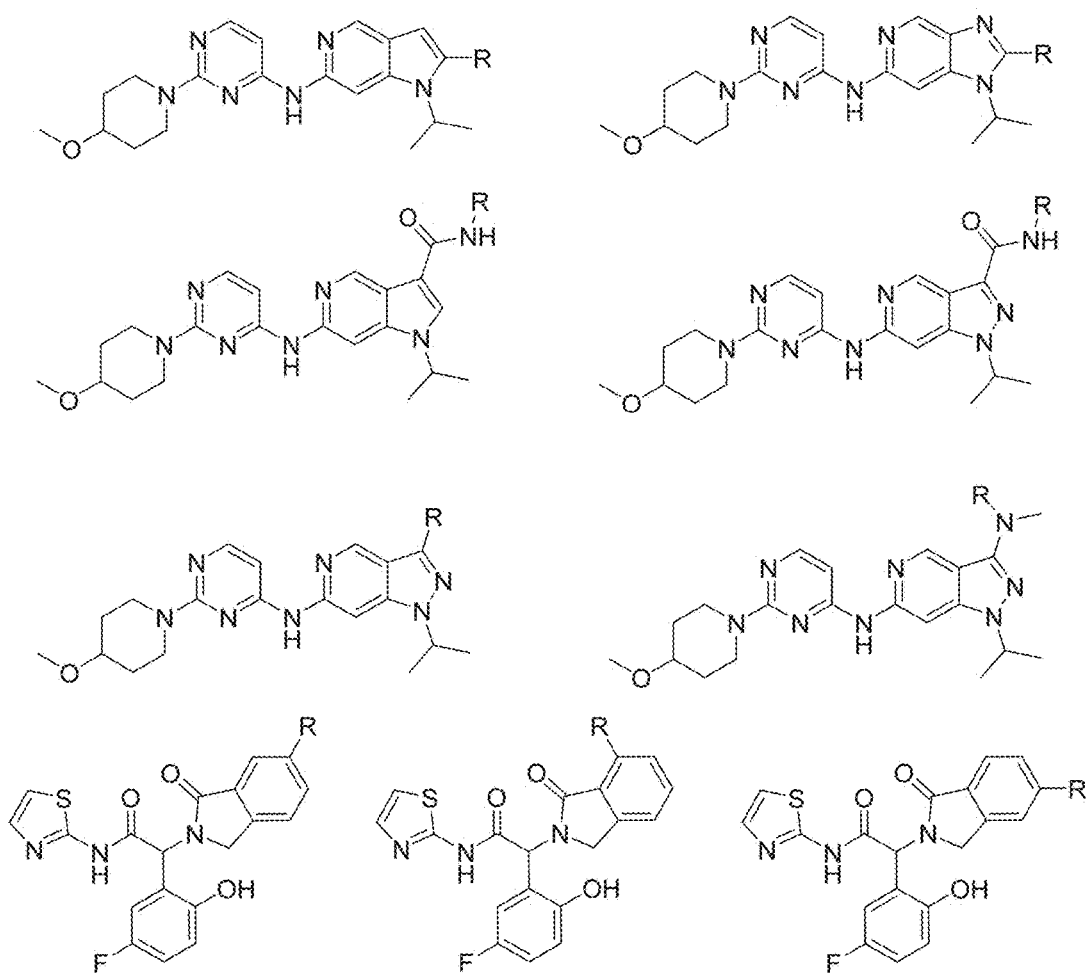
Figure 8Q:
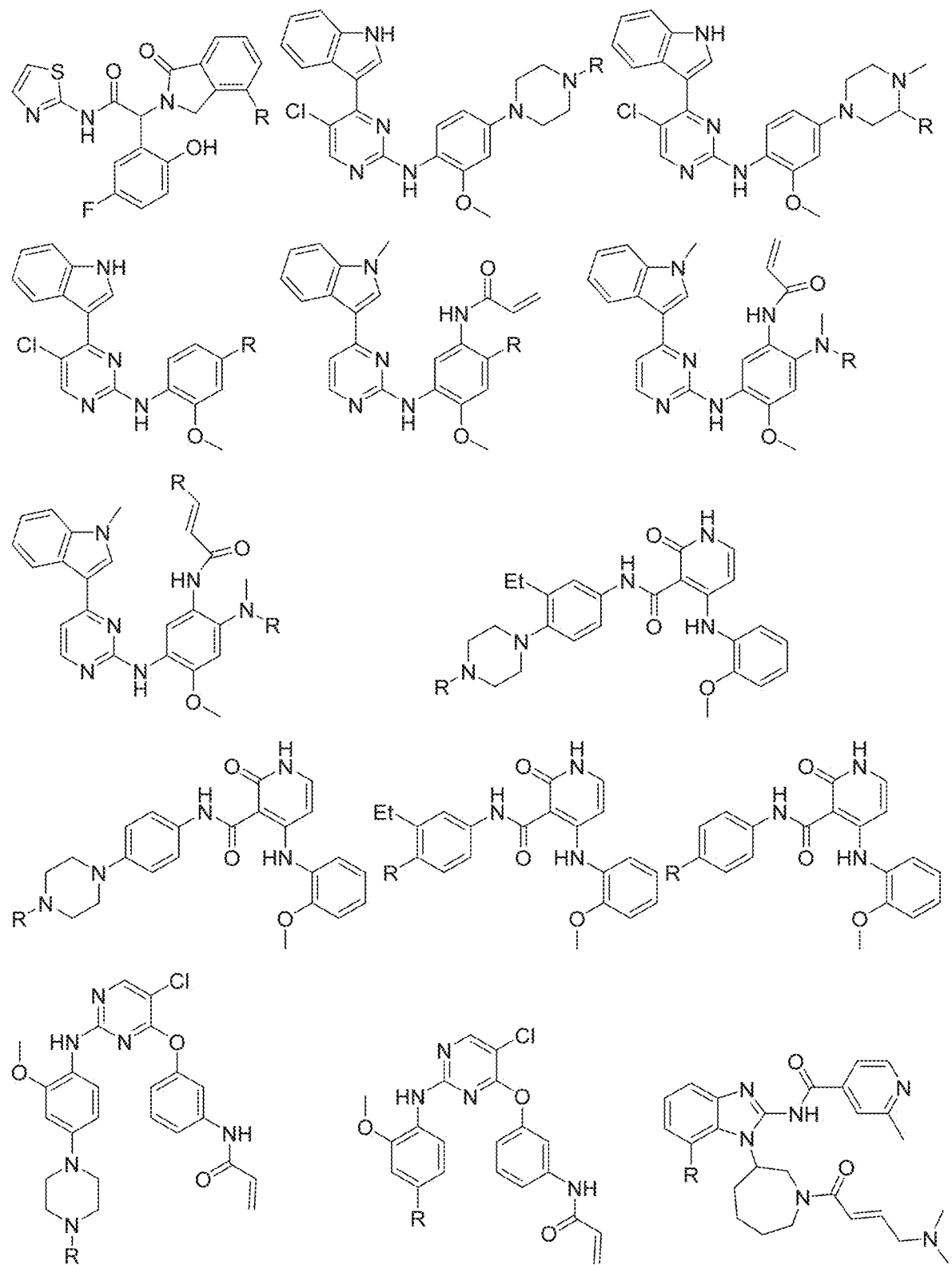
Figure 8R:
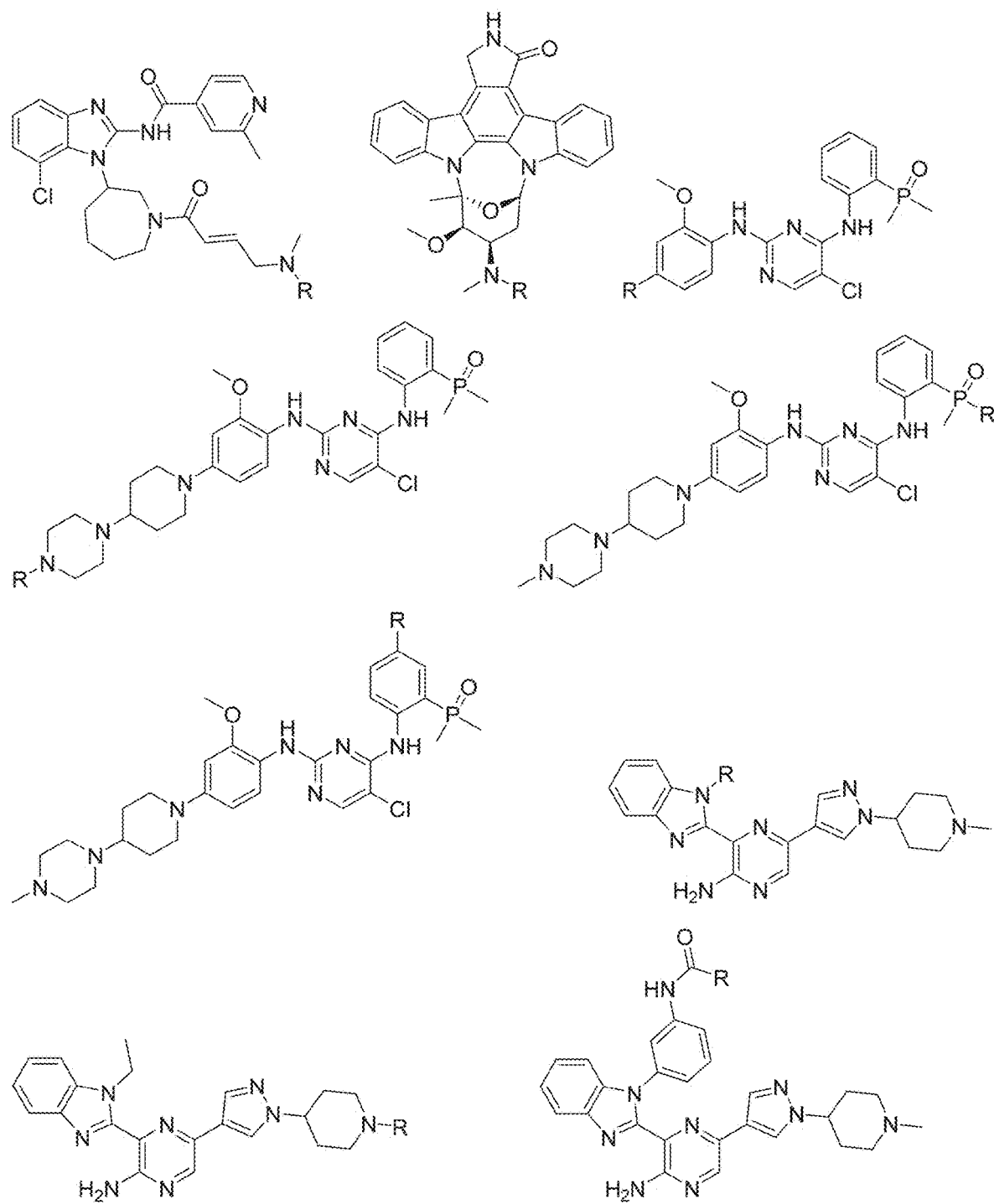
Figure 8S:
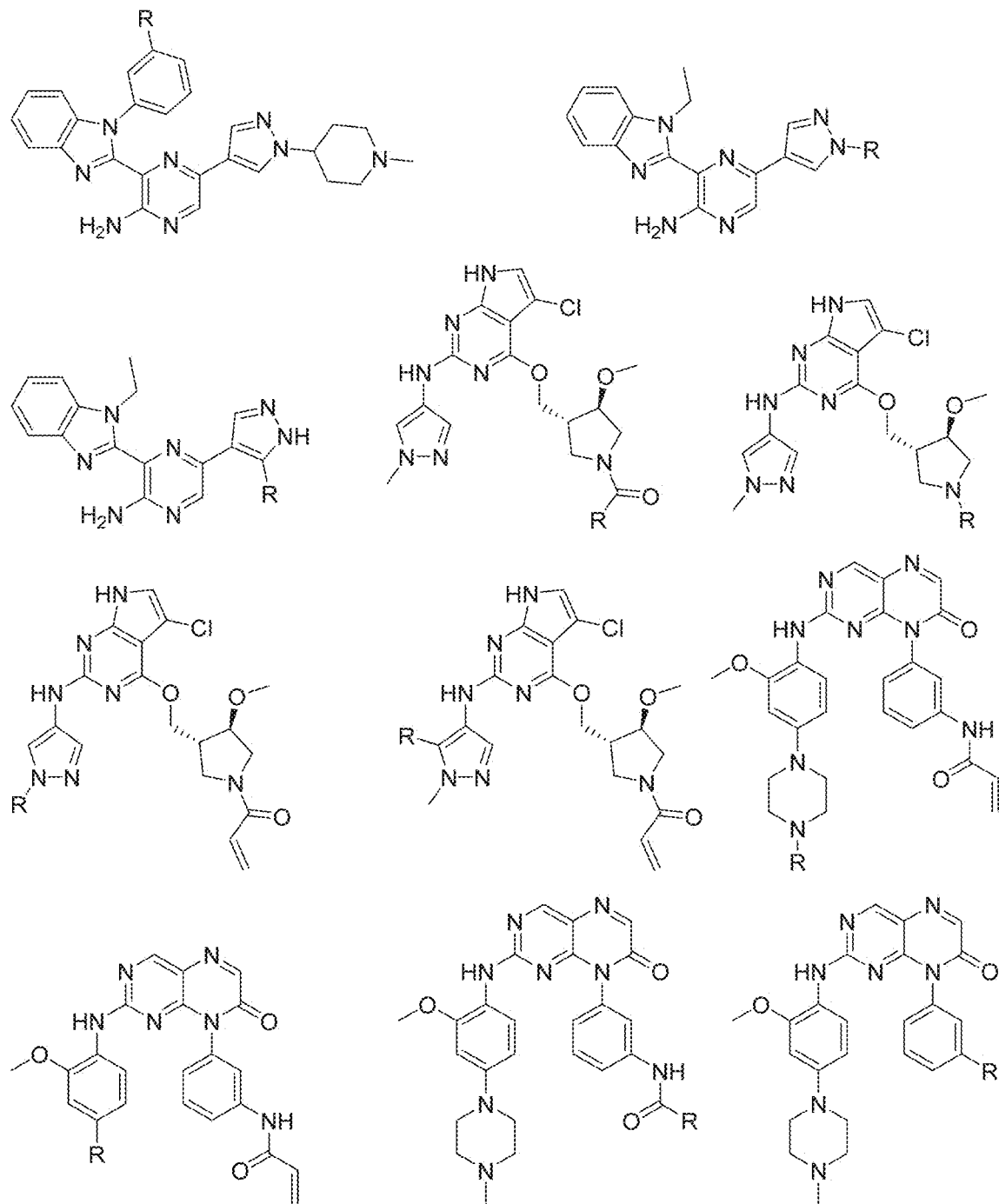

FIG. 8A-8S present examples of BRD4 Bromodomain 1 Targeting Ligands wherein R is the point at which the Linker is attached. For additional examples and related ligands, see, the crystal structures PDB 3u5k and 3u51 and related ligands in Filippakopoulos, P. et al. "Benzodiazepines and benzotriazepines as protein interaction inhibitors targeting bromodomains of the BET family", *Bioorg. Med. Chem.* 20: 1878-1886 (2012); the crystal structure PDB 3u51; the crystal structure PDB 3zyu and related ligands described in Dawson, M. A. et al. "Inhibition of Bet Recruitment to Chromatin as an Effective Treatment for Mll-Fusion Leukaemia." *Nature* 478: 529 (2011); the crystal structure PDB 4bwl and related ligands described in Mirguet, O. et al. "Naphthyridines as Novel Bet Family Bromodomain Inhibitors." *Chemmedchem* 9: 589 (2014); the crystal structure PDB 4cfl and related ligands described in Dittmann, A. et al. "The Commonly Used Pi3-Kinase Probe Ly294002 is an Inhibitor of Bet Bromodomains" *ACS Chem. Biol.* 9: 495 (2014); the crystal structure PDB 4e96 and related ligands described in Fish, P. V. et al. "Identification of a chemical probe for bromo and extra C-terminal bromodomain inhibition through optimization of a fragment-derived hit." *J. Med. Chem.* 55: 9831-9837 (2012); the crystal structure PDB 4clb and related ligands described in Atkinson, S. J. et al. "The Structure Based Design of Dual Hdac/Bet Inhibitors as Novel Epigenetic Probes." *Medchemcomm* 5: 342 (2014); the crystal structure PDB 4f3i and related ligands described in Zhang, G. et al. "Down-regulation of NF-{kappa}B Transcriptional Activity in HIV-associated Kidney Disease by BRD4 Inhibition." *J. Biol. Chem.* 287: 28840-28851 (2012); the crystal structure PDB 4hx1 and related ligands described in Zhao, L. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4hxs and related ligands described in Zhao, L. et al. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4lrg and related ligands described in Gehling, V. S. et al. "Discovery, Design, and Optimization of Isoxazole Azepine BET Inhibitors." *ACS Med Chem Lett* 4: 835-840 (2013); the crystal structure PDB 4mep and related ligands described in Vidler, L. R. "Discovery of Novel Small-Molecule Inhibitors of BRD4 Using Structure-Based Virtual Screening." et al. *J. Med. Chem.* 56: 8073-8088 (2013); the crystal structures PDB 4nr8 and PDB 4c77 and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4o7a and related ligands described in Ember, S. W. et al. "Acetyl-lysine Binding Site of Bromodomain-Containing Protein 4 (BRD4) Interacts with Diverse Kinase Inhibitors." *ACS Chem. Biol.* 9: 1160-1171 (2014); the crystal structure PDB 4o7b and related ligands described in "Acetyl-lysine Binding Site of Bromodomain-Containing Protein 4 (BRD4) Interacts with Diverse Kinase Inhibitors." Ember, S. W. et al. (2014) *ACS Chem. Biol.* 9: 1160-1171; the crystal structure PDB 4o7c and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4gpj; the crystal structure PDB 4uix and related ligands described in Theodoulou, N. H. et al. "The Discovery of I-Brd9, a Selective Cell Active Chemical Probe for Bromodomain Containing Protein 9 Inhibition". *J. Med. Chem.* 59: 1425 (2016); the crystal structure PDB 4uiz and related ligands described in Theodoulou, N. H., et al. "The Discovery of I-Brd9, a Selective Cell Active Chemical Probe for Bromodomain Containing Protein 9 Inhibition". *J. Med. Chem.* 59: 1425 (2016); the crystal structure PDB 4wiv and related ligands described in McKeown, M. R. et al. "Biased multicomponent reactions to develop novel bromodomain inhibitors." *J. Med. Chem.* 57: 9019-9027 (2014); the crystal structure PDB 4x2i and related ligands described in Taylor, A. M. et al. "Discovery of Benzotriazolo[4,3-d][1,4]diazepines as Orally Active Inhibitors of BET Bromodomains." *ACS Med. Chem. Lett.* 7: 145-150 (2016); the crystal structure PDB 4yh3; And related ligands described in Duffy, B. C. "Discovery of a new chemical series of BRD4(1) inhibitors using protein-ligand docking and structure-guided design." *Bioorg. Med. Chem. Lett.* 25: 2818-2823 (2015); the crystal structure PDB 4yh4 and related ligands described in Duffy, B. C. "Discovery of a new chemical series of BRD4(1) inhibitors using protein-ligand docking and structure-guided design." *Bioorg. Med. Chem. Lett.* 25: 2818-2823 (2015); the crystal structure PDB 4z1q and related ligands described in Taylor, A. M. "Discovery of Benzotriazolo[4,3-d][1,4]diazepines as Orally Active Inhibitors of BET Bromodomains." *ACS Med. Chem. Lett.* 7: 145-150 (2016); the crystal structure PDB 4zwl; the crystal structure PDB 5a5s and related ligands described in Demont, E. H. "Fragment-Based Discovery of Low-Micromolar Atad2 Bromodomain Inhibitors. *J. Med. Chem.* 58: 5649 (2015); the crystal structure PDB 5a85 and related ligands described in Bamborough, P. "Structure-Based Optimization of Naphthyridones Into Potent Atad2 Bromodomain Inhibitors" *J. Med. Chem.* 58: 6151 (2015); the crystal structure PDB 5acy and related ligands described in Sullivan, J. M. "Autism-Like Syndrome is Induced by Pharmacological Suppression of Bet Proteins in Young Mice." *J. Exp. Med.* 212: 1771 (2015); the crystal structure PDB 5ad2 and related ligands described in Waring, M. J. et al. "Potent and Selective Bivalent Inhibitors of Bet Bromodomains". *Nat. Chem. Biol.* 12: 1097 (2016); the crystal structure PDB 5cfw and related ligands described in Chekler, E. L. et al. "Transcriptional Profiling of a Selective CREB Binding Protein Bromodomain Inhibitor Highlights Therapeutic Opportunities." *Chem. Biol.* 22: 1588-1596 (2015); the crystal structure PDB 5cqt and related ligands described in Xue, X. et al. "Discovery of Benzo[cd]indol-2(1H)-ones as Potent and Specific BET Bromodomain Inhibitors: Structure-Based Virtual Screening, Optimization, and Biological Evaluation". *J. Med. Chem.* 59: 1565-1579 (2016); the crystal structure PDB 5d3r and related ligands described in Hugle, M. et al. "4-Acyl Pyrrole Derivatives Yield Novel Vectors for Designing Inhibitors of the Acetyl-Lysine Recognition Site of BRD4(1)". *J. Med. Chem.* 59: 1518-1530 (2016); the crystal structure PDB 5dlx and related ligands described in Milhas, S. et al. "Protein-Protein Interaction Inhibition (2P2I)-Oriented Chemical Library Accelerates Hit Discovery." (2016) *ACS Chem. Biol.* 11: 2140-2148; the crystal structure PDB 5dlz and related ligands described in Milhas, S. et al. "Protein-Protein Interaction Inhibition (2P2I)-Oriented Chemical Library Accelerates Hit Discovery." *ACS Chem. Biol.* 11: 2140-2148 (2016); the crystal structure PDB 5dw2 and related ligands described in Kharenko, O. A. et al. "RVX-297—a novel BD2 selective inhibitor of BET bromodomains." *Biochem. Biophys. Res. Commun.* 477: 62-67 (2016); the crystal structure PDB 5dlx; the crystal structure PDB 5his and related ligands described in Albrecht, B. K. et al. "Identification of a Benzoisoxazoloazepine Inhibitor (CPI-0610) of the Bromodomain and Extra-Terminal (BET) Family as a Candidate for Human Clinical Trials." *J. Med. Chem.* 59: 1330-1339 (2016); the crystal structure PDB 5ku3 and related ligands described in Crawford, T. D. et al. "Discovery of a Potent and Selective in Vivo Probe (GNE-272) for the Bromodomains of CBP/EP300 ". *J. Med. Chem.* 59: 10549-10563 (2016); the crystal structure PDB 5lj2 and related ligands described in Bamborough, P. et al. "A Chemical Probe for the ATAD2 Bromodomain." *Angew. Chem. Int. Ed. Engl.* 55: 11382-11386 (2016); the crystal structure PDB 5dlx and related ligands described in Wang, L. "Fragment-based, structure-enabled discovery of novel pyridones and pyridone macrocycles as potent bromodomain and extra-terminal domain (BET) family bromodomain inhibitors". *J. Med. Chem.* 10.1021/acs.jmedchem.7b00017 (2017); WO 2015169962 A1 titled "Benzimidazole derivatives as BRD4 inhibitors and their preparation and use for the treatment of cancer" assigned to Boehringer Ingelheim International GmbH, Germany; and, WO 2011143669 A2 titled "Azolodiazepine derivatives and their preparation, compositions and methods for treating neoplasia, inflammatory disease and other disorders" assigned to Dana-Farber Cancer Institute, Inc, USA.

Figure 8T:
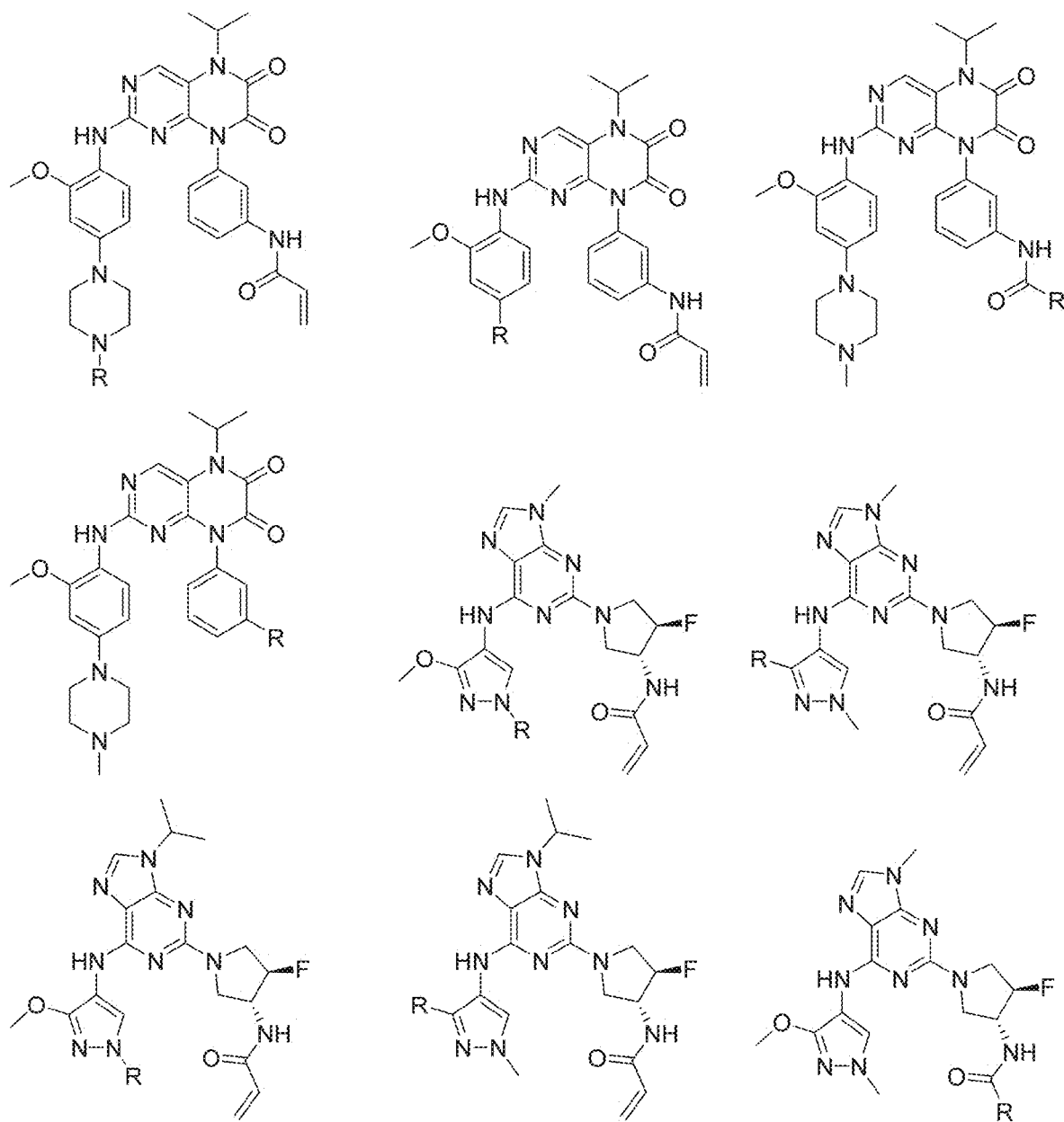
Figure 8U:
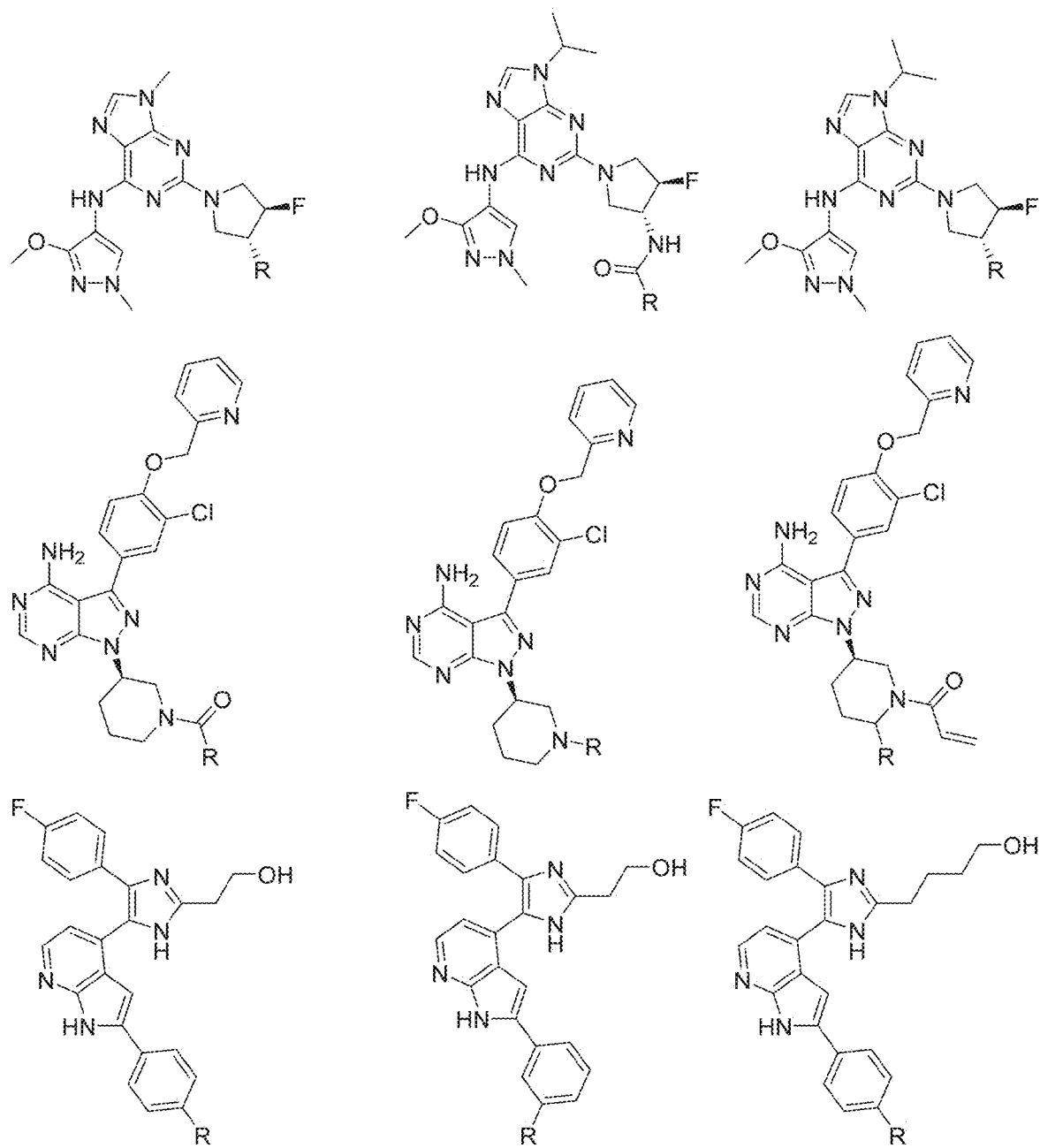
Figure 8V:
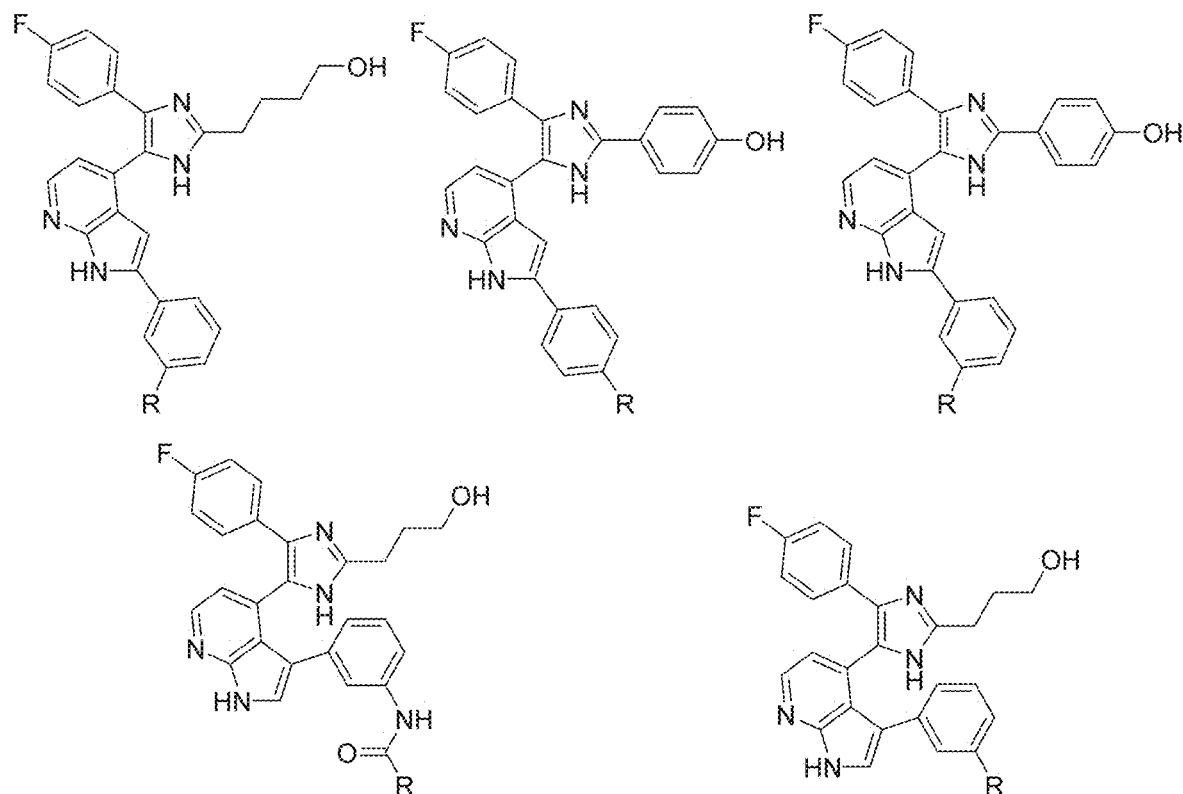
Figure 8W:
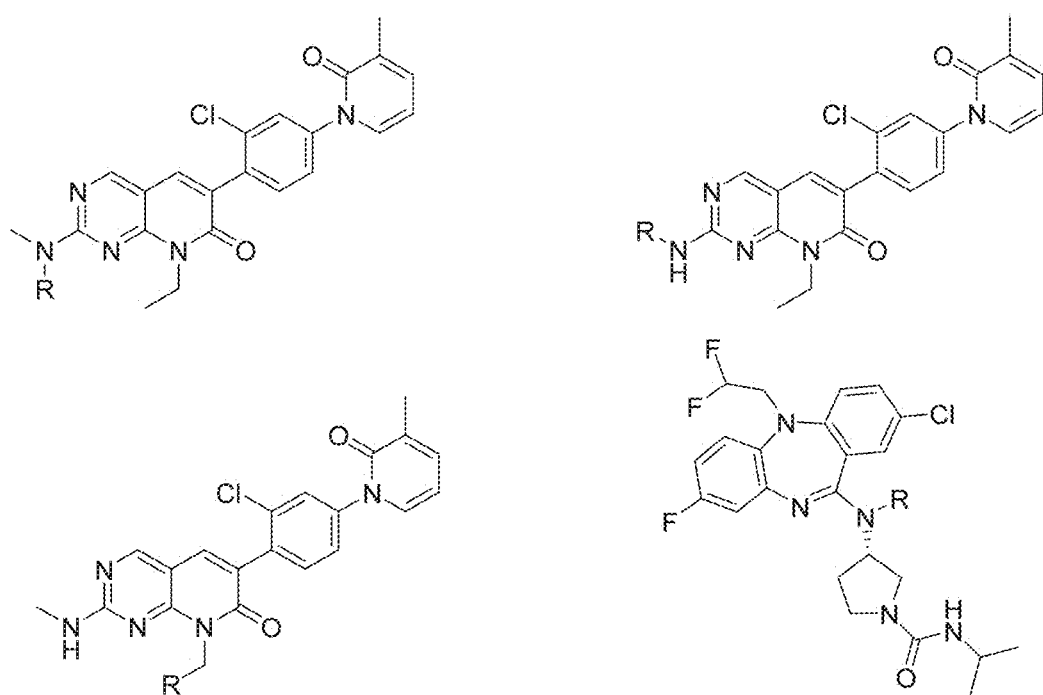
Figure 8X:
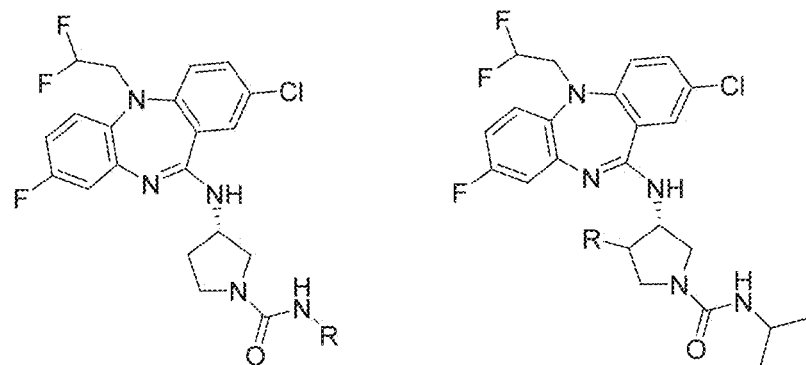
Figure 8Y:
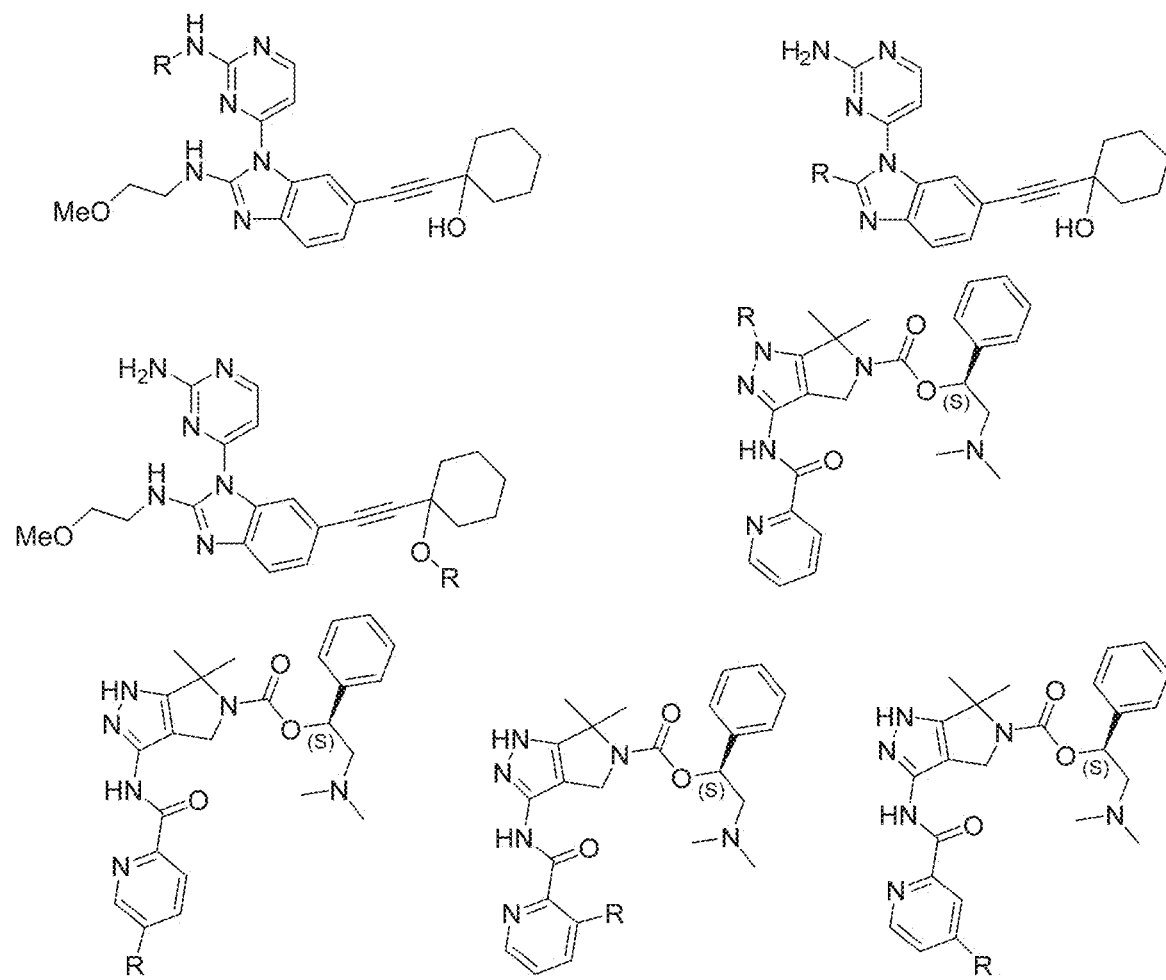
Figure 8Z:
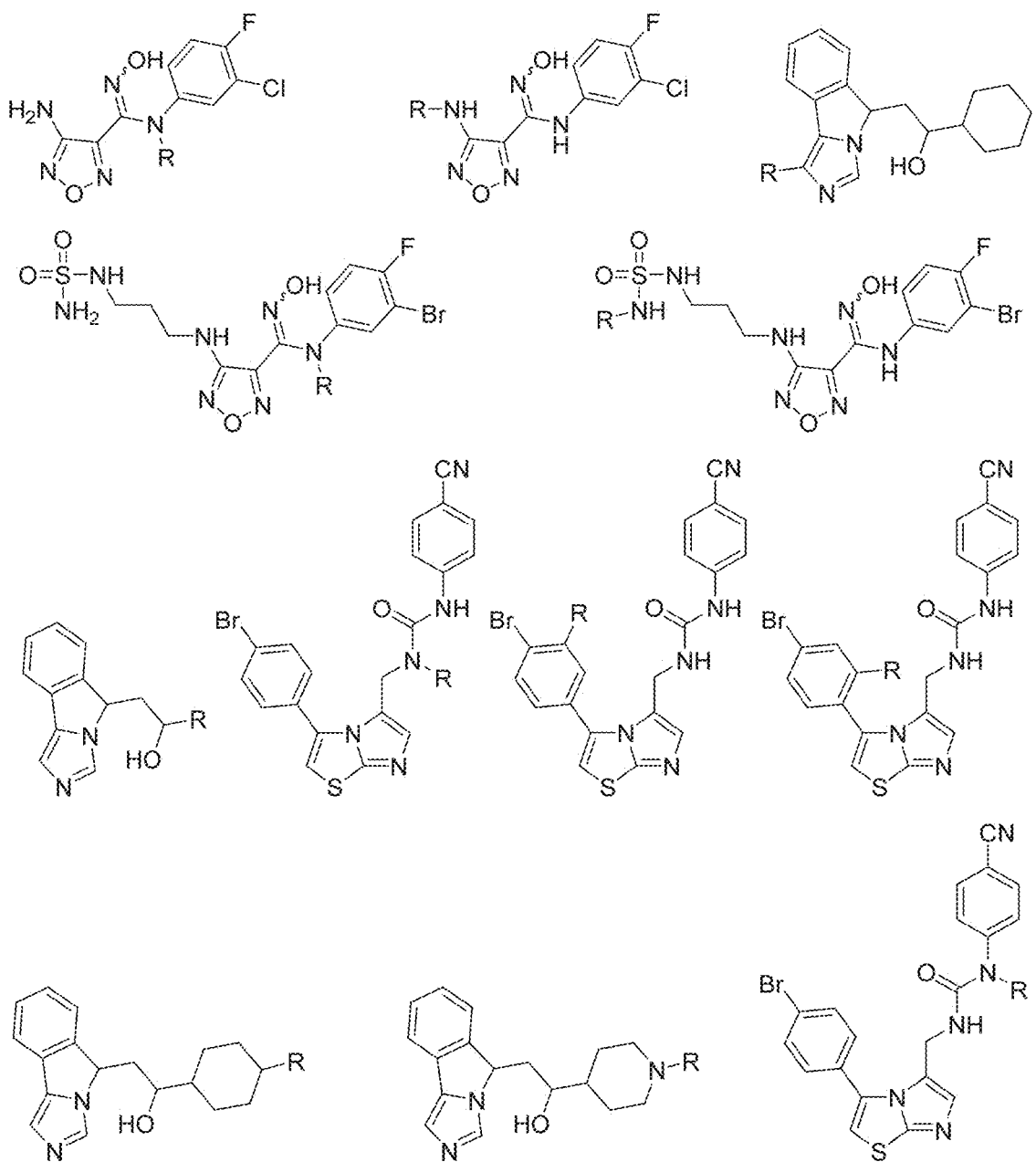

FIG. 8T-8V present examples of ALK Targeting Ligands wherein R is the point at which the Linker is attached. For additional examples and related ligands, see, the crystal structures PDB 2xb7 and 2xba and related ligands described in Bossi, R. T. et al. "Crystal Structures of Anaplastic Lymphoma Kinase in Complex with ATP Competitive Inhibitors" *Biochemistry* 49: 6813-6825 (2010); the crystal structures PDB 2yfx, 4ccb, 4ccu, amd 4cd0 snd related ligands described in Huang, Q. et al. "Design of Potent and Selective Inhibitors to Overcome Clinical Anaplastic Lymphoma Kinase Mutations Resistant to Crizotinib." *J. Med. Chem.* 57: 1170 (2014); the crystal structures PDB, 4cli, 4cmo, and 4cnh and related ligands described in Johnson, T. W. et al. "Discovery of (10R)-7-Amino-12-Fluoro-2,10,16-Trimethyl-15-Oxo-10,15,16,17-Tetrahydro-2H-8,4-(Metheno)Pyrazolo[4,3-H][2,5,11]Benzoxadiazacyclotetradecine-3-Carbonitrile (Pf-06463922), a Macrocyclic Inhibitor of Alk/Ros1 with Pre-Clinical Brain Exposure and Broad Spectrum Potency Against Alk-Resistant Mutations." *J. Med. Chem.* 57: 4720 (2014); the crystal structure PDB 4fny and related ligands described in Epstein, L. F. et al. "The R1275Q Neuroblastoma Mutant and Certain ATP-competitive Inhibitors Stabilize Alternative Activation Loop Conformations of Anaplastic Lymphoma Kinase." *J. Biol. Chem.* 287: 37447-37457 (2012). the crystal structure PDB 4dce and related ligands described in Bryan, M. C. et al "Rapid development of piperidine carboxamides as potent and selective anaplastic lymphoma kinase inhibitors." *J. Med. Chem.* 55: 1698-1705 (2012); the crystal structure PDB 4joa and related ligands described in Gummadi, V. R. et al. "Discovery of 7-azaindole based anaplastic lymphoma kinase (ALK) inhibitors: wild type and mutant (L1196M) active compounds with unique binding mode." (2013) *Bioorg. Med. Chem. Lett.* 23: 4911-4918; and, the crystal structure PDB 5iui and related ligands described in Tu, C. H. et al. "Pyrazolylamine Derivatives Reveal the Conformational Switching between Type I and Type II Binding Modes of Anaplastic Lymphoma Kinase (ALK)." *J. Med Chem.* 59: 3906-3919 (2016).

FIG. 8W-8X present examples of BTK Targeting Ligands wherein R is the point at which the Linker is attached. For additional examples and related ligands, see, the crystal structure PDB 3gen, 3piz and related ligands described in Marcotte, D. J. et al. "Structures of human Bruton's tyrosine kinase in active and inactive conformations suggest a mechanism of activation for TEC family kinases." *Protein Sci.* 19: 429-439 (2010) and Kuglstatter, A. et al. "Insights into the conformational flexibility of Bruton's tyrosine kinase from multiple ligand complex structures" *Protein Sci.* 20: 428-436" (2011); the crystal structure PDB 3ocs, 4ot6 and related ligands described in Lou, Y. et al. "Structure-Based Drug Design of RN486, a Potent and Selective Bruton's Tyrosine Kinase (BTK) Inhibitor, for the Treatment of Rheumatoid Arthritis" *J. Med. Chem.* 58: 512-516 (2015); the crystal structures PDB 5fbn and 5fbo and related ligands described in Liu, J. et al. "Discovery of 8-Amino-imidazo [1,5-a]pyrazines as Reversible BTK Inhibitors for the Treatment of Rheumatoid Arthritis." *ACS Med. Chem. Lett.* 7: 198-203 (2016); the crystal structure PDB 3pix and related ligands described in Kuglstatter, A. et al. "Insights into the conformational flexibility of Bruton's tyrosine kinase from multiple ligand complex structures." *Protein Sci.* 20: 428-436 (2011); and, the crystal structure PDB 3pij and related ligands described in Bujacz, A. et al. "Crystal structures of the apo form of beta-fructofuranosidase from *Bifidobacterium longum* and its complex with fructose." *Febs J.* 278: 1728-1744 (2011).

FIG. 8Y presents examples of FLT3 Targeting Ligands wherein R is the point at which the Linker is attached. For additional examples and related ligands, see, the crystal structures PDB 4xuf and 4rt7 and related ligands described in Zorn, J. A. et al. "Crystal Structure of the FLT3 Kinase Domain Bound to the Inhibitor Quizartinib (AC220)". *Plos One* 10: e0121177-e0121177 (2015).

FIG. 8Z-8AA present examples of TNIK Targeting Ligands wherein R is the point at which the Linker is attached. For additional examples and related ligands, see, the crystal structure PDB 2x7f; the crystal structures PDB 5ax9 and 5d7a; and, related ligands described in Masuda, M. et al. "TNIK inhibition abrogates colorectal cancer stemness." *Nat Commun* 7: 12586-12586 (2016).

FIG. 8BB-8CC present examples of NTRK1, NTRK2, and NTRK3 Targeting Ligands wherein R is the point at which the Linker is attached. For additional examples and related ligands, see, the crystal structure PDB 4aoj and related ligands described in Wang, T. et al. "Discovery of Disubstituted Imidazo[4,5-B]Pyridines and Purines as Potent Trka Inhibitors." *ACS Med. Chem. Lett.* 3: 705 (2012); the crystal structures PDB 4pmm, 4pmp, 4pms and 4pmt and related ligands described in Stachel, S. J. et al. "Maximizing diversity from a kinase screen: identification of novel and selective pan-Trk inhibitors for chronic pain." *J. Med. Chem.* 57: 5800-5816 (2014); the crystal structures PDB 4yps and 4yne snd related ligands described in Choi, H. S. et al. "(R)-2-Phenylpyrrolidine Substituted Imidazopyridazines: A New Class of Potent and Selective Pan-TRK Inhibitors." *ACS Med. Chem. Lett.* 6: 562-567 (2015); the crystal structures PDB 4at5 and 4at3 and related ligands described in Bertrand, T. et al. "The Crystal Structures of Trka and Trkb Suggest Key Regions for Achieving Selective Inhibition." *J. Mol. Biol.* 423: 439 (2012); and, the crystal structures PDB 3v5q and 4ymj and related ligands described in Albaugh, P. et al. "Discovery of GNF-5837, a selective TRK Inhibitor with efficacy in rodent cancer tumor models." *ACS Med. Chem. Lett.* 3: 140-145 (2012) and Choi, H. S. et al. "(R)-2-Phenylpyrrolidine Substitute Imidazopyridazines: a New Class of Potent and Selective Pan-TRK Inhibitors." *ACS Med Chem Lett* 6: 562-567 (2015).

FIG. 8DD-8EE present examples of FGFR1 Targeting Ligands wherein R is the point at which the Linker is attached. For additional examples and related ligands, see, the crystal structures PDB 3tto and 2fgi and related ligands described in Brison, Y. et al. "Functional and structural characterization of alpha-(1-2) branching sucrase derived from DSR-E glucansucrase." *J. Biol. Chem.* 287: 7915-7924 (2012) and Mohammadi, M. et al. "Crystal structure of an angiogenesis inhibitor bound to the FGF receptor tyrosine kinase domain." *EMBO J.* 17: 5896-5904 (1998); the crystal structure PDB 4fb3; the crystal structure PDB 4rwk and related ligands described in Harrison, C. et al. "Polyomavirus large T antigen binds symmetrical repeats at the viral origin in an asymmetrical manner." *J. Virol.* 87: 13751-13759 (2013); the crystal structure PDB 4rwl and related ligands described in Sohl, C. D. et al. "Illuminating the Molecular Mechanisms of Tyrosine Kinase Inhibitor Resistance for the FGFR1 Gatekeeper Mutation: The Achilles' Heel of Targeted Therapy." *ACS Chem. Biol.* 10: 1319-1329 (2015); the crystal structure PDB 4uwc; the crystal structure PDB 4v01 and related ligands described in Tucker, J. A. et al. "Structural Insights Into Fgfr Kinase Isoform Selectivity: Diverse Binding Modes of Azd4547 and Ponatinib in Complex with Fgfr1 and Fgfr4." *Structure* 22: 1764 (2014); the crystal structure PDB 5a46 and related ligands described in Klein, T. et al. "Structural and Dynamic Insights Into the Energetics of Activation Loop Rearrangement in Fgfr1 Kinase." *Nat. Commun.* 6: 7877 (2015); and, the crystal structure PDB Sew8 and related ligands described in Patani, H. et al. "Landscape of activating cancer mutations in FGFR kinases and their differential responses to inhibitors in clinical use." *Oncotarget* 7: 24252-24268 (2016).

FIG. 8FF presents examples of FGFR2 Targeting Ligands wherein R is the point at which the Linker is attached. For additional examples and related ligands, see, the crystal structure PDB 2pvf and related ligands described in Chen, H. et al. "A molecular brake in the kinase hinge region regulates the activity of receptor tyrosine kinases." *Mol. Cell* 27: 717-730 (2007).

FIG. 8GG presents examples of FGFR4 Targeting Ligands wherein R is the point at which the Linker is attached. For additional examples and related ligands, see, the crystal structure PDB 4tyi and related ligands described in Lesca, E. et al. "Structural analysis of the human fibroblast growth factor receptor 4 kinase." *J. Mol. Biol.* 426: 3744-3756 (2014).

FIG. 8HH-8II present examples of MET Targeting Ligands wherein R is the point at which the Linker is attached. For additional examples and related ligands, see, the crystal structures PDB 3qti and 3zcl; the crystal structures PDB 4xmo, 4xyf, and 3zcl and related ligands described in Peterson, E. A. et al. "Discovery of Potent and Selective 8-Fluorotriazolopyridine c-Met Inhibitors." *J. Med. Chem.* 58: 2417-2430 (2015) and Cui, J. J. et al. "Lessons from (S)-6-(1-(6-(1-Methyl-1H-Pyrazol-4-Yl)-[1,2,4]Triazolo[4,3-B]Pyridazin-3-Yl)Ethyl)Quinoline (Pf-04254644), an Inhibitor of Receptor Tyrosine Kinase C-met with High Protein Kinase Selectivity But Broad Phosphodiesterase Family Inhibition Leading to Myocardial Degeneration in Rats." *J. Med. Chem.* 56: 6651 (2013); the crystal structure PDB Seyd and related ligands described in Boezio, A. A. et al. "Discovery of (R)-6-(1-(8-Fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (AMG 337), a Potent and Selective Inhibitor of MET with High Unbound Target Coverage and Robust In Vivo Antitumor Activity." *J. Med. Chem.* 59: 2328-2342 (2016); the crystal structure PDB 3ce3 and related ligands described in Kim, K. S. et al. "Discovery of pyrrolopyridine-pyridone based inhibitors of Met kinase: synthesis, X-ray crystallographic analysis, and biological activities." *J. Med. Chem.* 51: 5330-5341 (2008); the crystal structure PDB 2rfn and related ligands described in Bellon, S. F. et al. "c-Met inhibitors with novel binding mode show activity against several hereditary papillary renal cell carcinoma-related mutations." *J. Biol. Chem.* 283: 2675-2683 (2008); and, the crystal structure PDB 5dg5 and related ligands described in Smith, B. D. et al "Altiratinib Inhibits Tumor Growth, Invasion, Angiogenesis, and Microenvironment-Mediated Drug Resistance via Balanced Inhibition of MET, TIE2, and VEGFR2.". *Mol. Cancer Ther.* 14: 2023-2034 (2015).

FIG. 8JJ presents examples of JAK1 Targeting Ligands wherein R is the point at which the Linker is attached. For additional examples and related ligands, see, the crystal structure PDB 4ivd and related ligands described in Zak, M. et al. "Identification of C-2 Hydroxyethyl Imidazopyrrolopyridines as Potent JAK1 Inhibitors with Favorable Physicochemical Properties and High Selectivity over JAK2." *J. Med. Chem.* 56: 4764-4785 (2013); the crystal structure PDB 5ele and related ligands described in Vasbinder, M. M. et al. "Identification of azabenzimidazoles as potent JAK1 selective inhibitors." *Bioorg. Med. Chem. Lett.* 26: 60-67 (2016); the crystal structure PDB 5hx8 and related ligands described in Simov, V., et al. "Structure-based design and development of (benz)imidazole pyridones as JAK1-selective kinase inhibitors." *Bioorg. Med. Chem. Lett.* 26: 1803-1808 (2016); the crystal structure PDB 5hx8 and related ligands described in Caspers, N. L. et al. "Development of a high-throughput crystal structure-determination platform for JAK1 using a novel metal-chelator soaking system". *Acta Crystallogr.* Sect. F 72: 840-845 (2016); and, Kettle, J. G. "Discovery of the JAK1 selective kinase inhibitor AZD4205", AACR National Meeting, April 2017.

FIG. 8KK-8LL present examples of JAK2 Targeting Ligands wherein R is the point at which the Linker is attached. For additional examples and related ligands, see, the crystal structure PDB 3ugc and related ligands described in Andraos, R. et al. "Modulation of activation-loop phosphorylation by JAK inhibitors is binding mode dependent." *Cancer Discov* 2: 512-523 (2012); the crystal structures PDB 5cf4, 5cf5, 5cf6 and 5cf8 and related ligands described in Hart, A. C. et al. "Structure-Based Design of Selective Janus Kinase 2 Imidazo[4,5-d]pyrrolo[2,3-b]pyridine Inhibitors." *ACS Med. Chem. Lett.* 6: 845-849 (2015); the crystal structure PDB 5aep and related ligands described in Brasca, M. G. et al "Novel Pyrrole Carboxamide Inhibitors of Jak2 as Potential Treatment of Myeloproliferative Disorders" *Bioorg. Med. Chem.* 23: 2387 (2015); the crystal structures PDB 4ytf, 4yth and 4yti and related ligands described in Farmer, L. J. et al. "Discovery of VX-509 (Decernotinib): A Potent and Selective Janus Kinase 3 Inhibitor for the Treatment of Autoimmune Diseases." *J. Med. Chem.* 58: 7195-7216 (2015); the crystal structure PDB 4ytf, 4yth, 4yti and related ligands described in Menet, C. J. et al. "Triazolopyridines as Selective JAK1 Inhibitors: From Hit Identification to GLPG0634." *J. Med. Chem.* 57: 9323-9342 (2014); the crystal structure PDB 4ji9 and related ligands described in Siu, M. et al. "2-Amino-[1,2,4]triazolo [1,5-a]pyridines as JAK2 inhibitors." *Bioorg. Med. Chem. Lett.* 23: 5014-5021 (2013); and, the crystal structures PDB 3io7 and 3iok and related ligands described in Schenkel, L. B. et al. "Discovery of potent and highly selective thienopyridine janus kinase 2 inhibitors." J. Med. Chem. 54: 8440-8450 (2011).

FIG. 8MM presents examples of JAK3 Targeting Ligands wherein R is the point at which the Linker is attached. For additional examples and related ligands, see, the crystal structure PDB 3zc6 and related ligands described in Lynch, S. M. et al. "Strategic Use of Conformational Bias and Structure Based Design to Identify Potent Jak3 Inhibitors with Improved Selectivity Against the Jak Family and the Kinome." *Bioorg. Med. Chem. Lett.* 23: 2793 (2013); and, the crystal structures PDB 4hvd, 4i6q, and 3zep and related ligands described in Soth, M. et al. "3-Amido Pyrrolopyrazine JAK Kinase Inhibitors: Development of a JAK3 vs JAK1 Selective Inhibitor and Evaluation in Cellular and in Vivo Models." *J. Med. Chem.* 56: 345-356 (2013) and Jaime-Figueroa, S. et al. "Discovery of a series of novel 5H-pyrrolo[2,3-b]pyrazine-2-phenyl ethers, as potent JAK3 kinase inhibitors." *Bioorg. Med. Chem. Lett.* 23: 2522-2526 (2013).

FIG. 8NN-8OO present examples of KIT Targeting Ligands wherein R is the point at which the Linker is attached. For additional examples and related ligands, see, the crystal structure PDB 1t46 and related ligands described in Mol, C. D. et al. "Structural basis for the autoinhibition and STI-571 inhibition of c-Kit tyrosine kinase." *J. Biol. Chem.* 279: 31655-31663 (2004); and, the crystal structure PDB 4u0i and related ligands described in Garner, A. P. et al. "Ponatinib Inhibits Polyclonal Drug-Resistant KIT Oncoproteins and Shows Therapeutic Potential in Heavily Pretreated Gastrointestinal Stromal Tumor (GIST) Patients." *Clin. Cancer Res.* 20: 5745-5755 (2014).

FIG. 8PP-8VV present examples of EGFR Targeting Ligands wherein R is the point at which the Linker is attached. For additional examples and related ligands, see, the crystal structures PDB 5hcy, 4rj4, and 5cav; Heald, R., "Noncovalent Mutant Selective Epidermal Growth Factor Receptor Inhibitors: A Lead Optimization Case Study", *J. Med. Chem.* 58, 8877-8895 (2015); Hanano, E. J., "Discovery of Selective and Noncovalent Diaminopyrimidine-Based Inhibitors of Epidermal Growth Factor Receptor Containing the T790M Resistance Mutation." *J. Med. Chem.*, 57, 10176-10191 (2014); Chan, B. K. et al. "Discovery of a Noncovalent, Mutant-Selective Epidermal Growth Factor Receptor Inhibitor" *J Med. Chem.* 59, 9080 (2016); the crystal structure PDB 5d41 and related ligands described in Jia, Y. et al., "Overcoming EGFR(T790M) and EGFR (C797S) resistance with mutant-selective allosteric inhibitors" *Nature* 534, 129 (2016); Ward, R. A. "Structure- and reactivity-based development of covalent inhibitors of the activating and gatekeeper mutant forms of the epidermal growth factor receptor (EGFR)" *J. Med. Chem.* 56, 7025-7048 (2013); the crystal structure PDB 4zau and related ligands described in "Discovery of a Potent and Selective EGFR Inhibitor (AZD9291) of Both Sensitizing and T790M Resistance Mutations That Spares the Wild Type Form of the Receptor" *J. Med. Chem.*, 57 (20), 8249-8267 (2014); the crystal structure PDB 5em7 and related ligands described in Bryan, M. C. et al. "Pyridones as Highly Selective, Noncovalent Inhibitors of T790M Double Mutants of EGFR" *ACS Med. Chem. Lett.*, 7 (1), 100-104 (2016); the crystal structure PDB 3IKA and related ligands described in Zhou, W. et al. "Novel mutant-selective EGFR kinase inhibitors against EGFR T790M" *Nature* 462(7276), 1070-1074 (2009); the crystal structure see PDB 5feq and related ligands described in Lelais, G., J. "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers" *Med. Chem.*, 59 (14), 6671-6689 (2016); Lee, H.-J. "Noncovalent Wild-type-Sparing Inhibitors of EGFR T790M" *Cancer Discov.* 3(2): 168-181 (2013); the crystal structure PDB 5j7h and related ligands described in Huang, W-S. et al. "Discovery of Brigatinib (AP26113), a Phosphine Oxide-Containing, Potent, Orally Active Inhibitor of Anaplastic Lymphoma Kinase." *J. Med. Chem.* 59: 4948-4964 (2016); the crystal structure PDB 4vOg and related ligands described in Hennessy, E. J. et al. "Utilization of Structure-Based Design to Identify Novel, Irreversible Inhibitors of EGFR Harboring the T790M Mutation." *ACS. Med. Chem. Lett.* 7: 514-519 (2016); the crystal structure PDB 5hg7 and related ligands described in Cheng, H. "Discovery of 1-{(3R,4R)-3-[({5-Chloro-2-[(1-methyl-1H-pyrazol-4-yl)amino]-7H-pyrrolo[2,3-d]pyrimidin-4-yl}oxy) methyl]-4-methoxypyrrolidin-1-yl}prop-2-en-1-one (PF-06459988), a Potent, WT Sparing, Irreversible Inhibitor of T790M-Containing EGFR Mutants." *J. Med. Chem.* 59:

2005-2024 (2016); Hao, Y. "Discovery and Structural Optimization of N5-Substituted 6,7-Dioxo-6,7-dihydropteridines as Potent and Selective Epidermal Growth Factor Receptor (EGFR) Inhibitors against L858R/T790M Resistance Mutation." *J. Med. Chem.* 59: 7111-7124 (2016); the crystal structure PDB 5ug8, 5ug9, and 5ugc and related ligands described in Planken, S. "Discovery of N-((3R,4R)-4-Fluoro-1-(6-((3-methoxy-1-methyl-1H-pyrazol-4-yl) amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR." *J. Med. Chem.* 60: 3002-3019 (2017); the crystal structure PDB 5gnk and related ligands described in Wang, A. "Discovery of (R)-1-(3-(4-Amino-3-(3-chloro-4-(pyridin-2-yl-methoxy)phenyl)-1H-pyrazolo[3,4-d]pyrimidin-1-yl)piperidin-1-yl)prop-2-en-1-one (CHMFL-EGFR-202) as a Novel Irreversible EGFR Mutant Kinase Inhibitor with a Distinct Binding Mode." *J. Med. Chem.* 60: 2944-2962 (2017); and, Juchum, M. "Trisubstituted imidazoles with a rigidized hinge binding motif act as single digit nM inhibitors of clinically relevant EGFR L858R/T790M and L858R/T790M/C797S mutants: An example of target hopping." *J. Med. Chem.* DOI: 10.1021/acs.jmedchem.7b00178 (2017).

FIG. 8WW-8XX present examples of PAK1 Targeting Ligands wherein R is the point at which the Linker is attached. For additional examples and related ligands, see, Rudolph, J. et al. "Chemically Diverse Group I p21-Activated Kinase (PAK) Inhibitors Impart Acute Cardiovascular Toxicity with a Narrow Therapeutic Window." *J. Med. Chem.* 59, 5520-5541 (2016) and Karpov A S, et al. *ACS Med Chem Lett.* 22; 6(7):776-81 (2015).

FIG. 8YY presents examples of PAK4 Targeting Ligands wherein R is the point at which the Linker is attached. For additional examples and related ligands, see, Staben S T, et al. *J Med Chem.* 13; 57(3): 1033-45 (2014) and Guo, C. et al. "Discovery of pyrroloaminopyrazoles as novel PAK inhibitors" *J. Med. Chem.* 55, 4728-4739 (2012).

FIG. 8ZZ-8AAA present examples of IDO Targeting Ligands wherein R is the point at which the Linker is attached. For additional examples and related ligands, see, Yue, E. W.; et al. "Discovery of potent competitive inhibitors of indoleamine 2,3-dioxygenase with in vivo pharmacodynamic activity and efficacy in a mouse melanoma model." *J. Med. Chem.* 52, 7364-7367 (2009); Tojo, S.; et al. "Crystal structures and structure, and activity relationships of imidazothiazole derivatives as IDO1 inhibitors." *ACS Med. Chem. Lett.* 5, 1119-1123 (2014); Mautino, M. R. et al. "NLG919, a novel indoleamine-2,3-dioxygenase (IDO)-pathway inhibitor drug candidate for cancer therapy" Abstract 491, AACR 104th Annual Meeting 2013; Apr. 6-10, 2013; Washington, D.C.; and, WO2012142237 titled "Fused imidazole derivatives useful as IDO inhibitors".

FIG. 8BBB-8EEE present examples of ERK1 and ERK2 Targeting Ligands wherein R is the point at which the Linker is attached. For additional examples and related ligands, see, the crystal structures PDB 5K4I and 5K4J and related ligands described in Blake, J. F. et al. "Discovery of (S)-1-(1-(4-Chloro-3-fluorophenyl)-2-hydroxyethyl)-4-(2-((1-methyl-1H-pyrazol-5-yl)amino)pyrimidin-4-yl)pyridin-2 (1H)-one (GDC-0994), an Extracellular Signal-Regulated Kinase 1/2 (ERK1/2) Inhibitor in Early Clinical Development" *J. Med. Chem.* 59: 5650-5660 (2016); the crystal structure PDB 5BVF and related ligands described in Bagdanoff, J. T. et al. "Tetrahydropyrrolo-diazepenones as inhibitors of ERK2 kinase" *Bioorg. Med. Chem. Lett.* 25, 3788-3792 (2015); the crystal structure PDB 4QYY and related ligands described in Deng, Y. et al. "Discovery of Novel, Dual Mechanism ERK Inhibitors by Affinity Selection Screening of an Inactive Kinase" *J. Med. Chem.* 57: 8817-8826 (2014); the crystal structures PDB 5HD4 and 5HD7 and the related ligands described in Jha, S. et al. "Dissecting Therapeutic Resistance to ERK Inhibition" *Mol. Cancer Ther.* 15: 548-559 (2016); the crystal structure PDB 4XJ0 and related ligands described in Ren, L. et al. "Discovery of highly potent, selective, and efficacious small molecule inhibitors of ERK1/2." *J. Med. Chem.* 58: 1976-1991 (2015); the crystal structures PDB 4ZZM, 4ZZN, 4ZZO and related ligands described in Ward, R. A. et al. "Structure-Guided Design of Highly Selective and Potent Covalent Inhibitors of Erk1/2." *J. Med. Chem.* 58: 4790 (2015); Burrows, F. et al. "KO-947, a potent ERK inhibitor with robust preclinical single agent activity in MAPK pathway dysregulated tumors" Poster #5168, AACR National Meeting 2017; Bhagwat, S. V. et al. "Discovery of LY3214996, a selective and novel ERK1/2 inhibitor with potent antitumor activities in cancer models with MAPK pathway alterations." AACR National Meeting 2017; the crystal structures PDB 3FHR and 3FXH and related ligands described in Cheng, R. et al. "High-resolution crystal structure of human Mapkap kinase 3 in complex with a high affinity ligand" *Protein Sci.* 19: 168-173 (2010); the crystal structures PDB 5NGU, 5NHF, 5NHH, 5NHJ, 5NHL, 5NHO, 5NHP, and 5NHV and related ligands described in Ward, R. A. et al. "Structure-Guided Discovery of Potent and Selective Inhibitors of ERK1/2 from a Modestly Active and Promiscuous Chemical Start Point." *J. Med. Chem.* 60, 3438-3450 (2017); and, the crystal structures PDB 3SHE and 3R1N and related ligands described in Oubrie, A. et al. "Novel ATP competitive MK2 inhibitors with potent biochemical and cell-based activity throughout the series." *Bioorg. Med. Chem. Lett.* 22: 613-618 (2012).

FIG. 8FFF-8III present examples of ABL1 Targeting Ligands wherein R is the point at which the Linker is attached. For additional examples and related ligands, see, the crystal structure PDB 1fpu and 2e2b and related ligands described in Schindler, T., et al. "Structural mechanism for STI-571 inhibition of abelson tyrosine kinase", *Science* 289: 1938-1942 (2000); and Horio, T. et al. "Structural factors contributing to the Abl/Lyn dual inhibitory activity of 3-substituted benzamide derivatives", *Bioorg. Med. Chem. Lett.* 17: 2712-2717 (2007); the crystal structures PDB 2hzn and 2hiw and related ligands described in Cowan-Jacob, S. W. et al. "Structural biology contributions to the discovery of drugs to treat chronic myelogenous leukaemia", *Acta Crystallog. Sect. D* 63: 80-93 (2007) and Okram, B. et al. "A general strategy for creating", *Chem. Biol.* 13: 779-786 (2006); the crystal structure PDB 3cs9 and related ligands described in Weisberg, E. et al. "Characterization of AMN107, a selective inhibitor of native and mutant Bcr-Abl", *Cancer Cell* 7: 129-14 (2005); the crystal structure PDB 3ik3 and related ligands described in O'Hare, T. et al. "AP24534, a pan-BCR-ABL inhibitor for chronic myeloid leukemia, potently inhibits the T315I mutant and overcomes mutation-based resistance", *Cancer Cell* 16: 401-412 (2009); the crystal structure PDB 3mss and related ligands described in Jahnke, W. et al. "Binding or bending: distinction of allosteric Abl kinase agonists from antagonists by an NMR-based conformational assay", *J. Am. Chem. Soc.* 132: 7043-7048 (2010); the crystal structure PDB 3oy3 and related ligands described in Zhou, T. et al. "Structural Mechanism of the Pan-BCR-ABL Inhibitor Ponatinib (AP24534): Lessons for Overcoming Kinase Inhibitor Resistance", *Chem. Biol. Drug Des.* 77: 1-11 (2011); the crystal structures PDB 3qri and 3qrk and related ligands described in Chan, W. W. et al. "Conformational Control Inhibition of the BCR-ABL1 Tyrosine Kinase, Including the Gatekeeper T315I Mutant, by the Switch-Control Inhibitor DCC-2036", *Cancer Cell* 19: 556-568 (2011); the crystal structure PDB 5hu9 and 2f4j and related ligands described in Liu, F. et al. "Discovery and characterization of a novel potent type II native and mutant BCR-ABL inhibitor (CHMFL-074) for Chronic Myeloid Leukemia (CML)", *Oncotarget* 7: 45562-45574 (2016) and Young, M. A. et al. "Structure of the kinase domain of an imatinib-resistant Abl mutant in complex with the Aurora kinase inhibitor VX-680", *Cancer Res.* 66: 1007-1014 (2006); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006); and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181 (2007); the crystal structures PDB 3dk3 and 3dk8 and related ligands described in Berkholz, D. S. et al. "Catalytic cycle of human glutathione reductase near 1 A resolution" *J. Mol. Biol.* 382: 371-384 (2008); the crystal structure PDB 3ue4 and related ligands described in Levinson, N. M. et al. "Structural and spectroscopic analysis of the kinase inhibitor bosutinib and an isomer of bosutinib binding to the abl tyrosine kinase domain", *Plos One* 7: e29828-e29828 (2012); the crystal structure PDB 4cy8 and related ligands described in Jensen, C. N. et al. "Structures of the Apo and Fad-Bound Forms of 2-Hydroxybiphenyl 3-Monooxygenase (Hbpa) Locate Activity Hotspots Identified by Using Directed Evolution", *Chembiochem* 16: 968 (2015); the crystal structure PDB 2hz0 and related ligands described in Cowan-Jacob, S. W. et al. "Structural biology contributions to the discovery of drugs to treat chronic myelogenous leukaemia", *Acta Crystallogr D Biol Crystallogr.* 63(Pt 1):80-93 (2007); the crystal structure PDB 3pyy and related ligands described in Yang, J. et al. "Discovery and Characterization of a Cell-Permeable, Small-Molecule c-Abl Kinase Activator that Binds to the Myristoyl Binding Site", *Chem. Biol.* 18: 177-186 (2011); and, the crystal structure PDB 5k5v and related ligands described in Kim, M. K., et al. "Structural basis for dual specificity of yeast N-terminal amidase in the N-end rule pathway", *Proc. Natl. Acad. Sci. U.S.A.* 113: 12438-12443 (2016).

FIG. 8JJJ presents examples of ABL2 Targeting Ligands wherein R is the point at which the Linker is attached. For additional examples and related ligands, see, the crystal structure PDB 2xyn and related ligands described in Salah, E. et al. "Crystal Structures of Abl-Related Gene (Abl2) in Complex with Imatinib, Tozasertib (Vx-680), and a Type I Inhibitor of the Triazole Carbothioamide Class", *J. Med. Chem.* 54: 2359 (2011); the crystal structure PDB 4xli and related ligands described in Ha, B. H. et al. "Structure of the ABL2/ARG kinase in complex with dasatinib" *Acta Crystallogr. Sect. F* 71: 443-448 (2015); and the crystal structure PDB 3gvu and related ligands described in Salah, E. et al. "The crystal structure of human ABL2 in complex with Gleevec", to be published.

FIG. 8KKK-8MMM present examples of AKT1 Targeting Ligands wherein R is the point at which the Linker is attached. For additional examples and related ligands, see, Lippa, B. et al. "Synthesis and structure based optimization of novel Akt inhibitors *Bioorg. Med. Chem. Lett.* 18: 3359-3363 (2008); Freeman-Cook, K. D. et al. "Design of selective, ATP-competitive inhibitors of Akt", *J. Med. Chem.* 53: 4615-4622 (2010); Blake, J. F. et al "Discovery of pyrrolopyrimidine inhibitors of Akt", *Bioorg. Med. Chem. Lett.* 20: 5607-5612 (2010); Kallan, N.C. et al. "Discovery and SAR of spirochromane Akt inhibitors", *Bioorg. Med. Chem. Lett.* 21: 2410-2414 (2011); Lin, K "An ATP-Site On-Off Switch That Restricts Phosphatase Accessibility of Akt", *Sci. Signal.* 5: ra37-ra37 (2012); Addie, M. et al. "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases", *J. Med. Chem.* 56: 2059-2073 (2013); Wu, W. I., et al. "Crystal structure of human AKT1 with an allosteric inhibitor reveals a new mode of kinase inhibition. *Plos One* 5: 12913-12913 (2010); Ashwell, M. A. et al. "Discovery and optimization of a series of 3-(3-phenyl-3H-imidazo[4, 5-b]pyridin-2-yl)pyridin-2-amines: orally bioavailable, selective, and potent ATP-independent Akt inhibitors", *J. Med. Chem.* 55: 5291-5310 (2012); and, Lapierre, J. M. et al. "Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor", *J. Med. Chem.* 59: 6455-6469 (2016).

FIG. 8NNN-8OOO present examples of AKT2 Targeting Ligands wherein R is the point at which the Linker is attached. For additional examples and related ligands, see, the crystal structured PDB 2jdo and 2jdr and related ligands described in Davies, T. G. et al. "A Structural Comparison of Inhibitor Binding to Pkb, Pka and Pka-Pkb Chimera", *J. Mol. Biol.* 367: 882 (2007); the crystal structure PDB 2uw9 and related ligands described in Saxty, G. et al "Identification of Inhibitors of Protein Kinase B Using Fragment-Based Lead Discovery", *J. Med Chem.* 50: 2293-2296 (2007); the crystal structure PDB 2x39 and 2xh5 and related ligands described in Mchardy, T. et al. "Discovery of 4-Amino-1-(7H-Pyrrolo[2,3-D]Pyrimidin-4-Yl)Piperidine-4-Carboxamides as Selective, Orally Active Inhibitors of Protein Kinase B (Akt)", *J. Med. Chem.* 53: 2239d (2010); the crystal structure PDB 3d03 and related ligands described in Hadler, K. S. et al. "Substrate-promoted formation of a catalytically competent binuclear center and regulation of reactivity in a glycerophosphodiesterase from *Enterobacter aerogenes*', *J. Am. Chem. Soc.* 130: 14129-14138 (2008); and, the crystal structures PDB 3e87, 3e8d and 3e88 and related ligands described in Rouse, M. B. et al. "Aminofurazans as potent inhibitors of AKT kinase" *Bioorg. Med. Chem. Lett.* 19: 1508-1511 (2009).

FIG. 8PPP presents examples of BMX Targeting Ligands wherein R is the point at which the Linker is attached. For additional examples and related ligands, see, the crystal structures PDB 3sxr and 3sxr and related ligands described in Muckelbauer, J. et al. "X-ray crystal structure of bone marrow kinase in the x chromosome: a Tec family kinase", *Chem. Biol. Drug Des.* 78: 739-748 (2011).

FIG. 8QQQ-8SSS present examples of CSF1R Targeting Ligands wherein R is the point at which the Linker is attached. For additional examples and related ligands, see, the crystal structures PDB 2i0v and 2i1m and related ligands described in Schubert, C. et al. "Crystal structure of the tyrosine kinase domain of colony-stimulating factor-1 receptor (cFMS) in complex with two inhibitors", *J. Biol. Chem.* 282: 4094-4101 (2007); the crystal structure PDB 3bea and related ligands described in Huang, H. et al. "Design and synthesis of a pyrido[2,3-d]pyrimidin-5-one class of anti-inflammatory FMS inhibitors", *Bioorg. Med. Chem. Lett.* 18: 2355-2361 (2008); the crystal structure PDB 3dpk and related ligands described in M. T., McKay, D. B. Overgaard, "Structure of the Elastase of *Pseudomonas aeruginosa* Complexed with Phosphoramidon", to be published; the crystal structures PDB 3krj and 3krl and related ligands described in Illig, C. R. et al. "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)acetyl]-4-piperidinyl]phenyl]-1H-imidazole-2-carboxamide (JNJ-28312141", *J. Med. Chem.* 54: 7860-7883 (2011); the crystal structure PDB 4r7h and related ligands described in Tap, W. D. et al. "Structure-Guided Blockade of CSF1R Kinase in Tenosynovial Giant-Cell Tumor, *N Engl J Med* 373: 428-437 (2015); the crystal structure PDB 3l cd and 3l coa and related ligands described in Meyers, M. J. et al. "Structure-based drug design enables conversion of a DFG-in binding CSF-1R kinase inhibitor to a DFG-out binding mod", *Bioorg. Med. Chem. Lett.* 20: 1543-1547 (2010); the crystal structure PDB 4hw7 and related ligands described in Zhang, C. et al. "Design and pharmacology of a highly specific dual FMS and KIT kinase inhibitor", *Proc. Natl. Acad. Sci. USA* 110: 5689-5694 (2013); and, the crystal structure PDB 4r7i and related ligands described in Tap, W. D. et al. "Structure-Guided Blockade of CSF1R Kinase in Tenosynovial Giant-Cell Tumor", *N Engl J Med* 373: 428-437 (2015).

FIG. 8TTT presents examples of CSK Targeting Ligands wherein R is the point at which the Linker is attached. For additional examples and related ligands, see, Levinson, N. M. et al. "Structural basis for the recognition of c-Src by its inactivator Csk", *Cell* 134: 124-134 (2008).

FIG. 8UUU-8YYY present examples of DDR1 Targeting Ligands wherein R is the point at which the Linker is attached. For additional examples and related ligands, see, the crystal structures PDB 3zos and 4bkj and related ligands described in Canning, P. et al. "Structural Mechanisms Determining Inhibition of the Collagen Receptor Ddr1 by Selective and Multi-Targeted Type II Kinase Inhibitors", *J. Mol. Biol.* 426: 2457 (2014); the crystal structure PDB 4ckr and related ligands described in Kim, H. et al. "Discovery of a Potent and Selective Ddr1 Receptor Tyrosine Kinase Inhibitor", *ACS Chem. Biol.* 8: 2145 (2013); the crystal structure PDB 5bvk, 5bvn and 5bvw and related ligands described in Murray, C. W et al. "Fragment-Based Discovery of Potent and Selective DDR1/2 Inhibitors", *ACS Med. Chem. Lett.* 6: 798-803 (2015); the crystal structure PDB 5fdp and related ligands described in Wang, Z. et al. "Structure-Based Design of Tetrahydroisoquinoline-7-carboxamides as Selective Discoidin Domain Receptor 1 (DDR1) Inhibitors", *J. Med. Chem.* 59: 5911-5916 (2016); and, the crystal structure PDB 5fdx and related ligands described in Bartual, S. G. et al. "Structure of DDR1 receptor tyrosine kinase in complex with D2164 inhibitor at 2.65 Angstroms resolution", to be published.

FIG. 8ZZZ-8CCCC present examples of EPHA2 Targeting Ligands wherein R is the point at which the Linker is attached. For additional examples and related ligands, see, the crystal structures PDB 5i9x, 5i9y, 5ia0 and 5ia1 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016); the crystal structure PDB 5i9z and related ligands described in Heinzlmeir, S. et al. "Crystal Structure of Ephrin A2 (EphA2) Receptor Protein Kinase with danusertib (PHA739358)", *ACS Chem Biol* 11 3400-3411 (2016); and, the crystal structures PDB 5ia2, 5ia3, 5ia4, and 5ia5 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016).

FIG. 8DDDD-8FFFF present examples of EPHA3 Targeting Ligands wherein R is the point at which the Linker is attached. For additional examples and related ligands, see, the crystal structure PDB 4g2f and related ligands described in Zhao, H. et al. "Discovery of a novel chemotype of tyrosine kinase inhibitors by fragment-based docking and molecular dynamics", *ACS Med. Chem. Lett.* 3: 834-838 (2012); the crystal structure PDB 4gk2 and 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4p4c and 4p5q and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med. Chem.* 57: 6834-6844 (2014); the crystal structure PDB 4p5z and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med. Chem.* 57: 6834-6844 (2014); the crystal structure PDB 4twn and related ligands described in Dong, J. et al. "Structural Analysis of the Binding of Type I, I1/2, and II Inhibitors to Eph Tyrosine Kinases", *ACS Med. Chem. Lett.* 6: 79-83 (2015); the crystal structure PDB 3dzq and related ligands described in Walker, J. R. "Kinase Domain of Human Ephrin Type-A Receptor 3 (Epha3) in Complex with ALW-II-38-3", to be published.

FIG. 8GGGG presents examples of EPHA4 Targeting Ligands wherein R is the point at which the Linker is attached. For additional examples and related ligands, see, the crystal structure PDB 2y60 and related ligands described in Clifton, I. J. et al. "The Crystal Structure of Isopenicillin N Synthase with Delta((L)-Alpha-Aminoadipoyl)-(L)-Cysteinyl-(D)-Methionine Reveals Thioether Coordination to Iron", *Arch. Biochem. Biophys.* 516: 103 (2011) and the crystal structure PDB 2xyu and related ligands described in Van Linden, O. P et al. "Fragment Based Lead Discovery of Small Molecule Inhibitors for the Epha4 Receptor Tyrosine Kinase", *Eur. J. Med. Chem.* 47: 493 (2012).

FIG. 8HHHH presents examples of EPHA7 Targeting Ligands wherein R is the point at which the Linker is attached. For additional examples and related ligands, see, the crystal structure PDB 3dko and related ligands described in Walker, J. R. et al. "Kinase domain of human ephrin type-a receptor 7 (epha7) in complex with ALW-II-49-7", to be published.

FIG. 8IIII-8LLLL presents examples of EPHB4 Targeting Ligands wherein R is the point at which the Linker is attached. For additional examples and related ligands, see, the crystal structure PDB 2vxl and related ligands described in Bardelle, C. et al. "Inhibitors of the Tyrosine Kinase Ephb4. Part 2: Structure-Based Discovery and Optimisation of 3,5-Bis Substituted Anilinopyrimidines", Bioorg. Med. Chem. Lett. 18: 5717 (2008); the crystal structure PDB 2x9f and related ligands described in Bardelle, C. et al. "Inhibitors of the Tyrosine Kinase Ephb4. Part 3: Identification of Non-Benzodioxole-Based Kinase Inhibitors", Bioorg. Med. Chem. Lett. 20: 6242-6245 (2010); the crystal structure PDB 2xvd and related ligands described in Barlaam, B. et al. "Inhibitors of the Tyrosine Kinase Ephb4. Part 4: Discovery and Optimization of a Benzylic Alcohol Series", Bioorg. Med. Chem. Lett. 21: 2207 (2011); the crystal structure PDB 3zew and related ligands described in Overman, R. C. et al. "Completing the Structural Family Portrait of the Human Ephb Tyrosine Kinase Domains", Protein Sci. 23: 627 (2014); the crystal structure PDB 4aw5 and related ligands described in Kim, M. H. et al. "The Design, Synthesis, and Biological Evaluation of Potent Receptor Tyrosine Kinase Inhibitors", Bioorg. Med. Chem. Lett. 22: 4979 (2012); the crystal structure PDB 4bb4 and related ligands described in Vasbinder, M. M. et al. "Discovery and Optimization of a Novel Series of Potent Mutant B-Raf V600E Selective Kinase Inhibitors" J. Med. Chem. 56: 1996.", (2013); the crystal structures PDB 2vwu, 2vwv and 2vww and related ligands described in Bardelle, C. et al "Inhibitors of the Tyrosine Kinase Ephb4. Part 1: Structure-Based Design and Optimization of a Series of 2,4-Bis-Anilinopyrimidines", Bioorg. Med. Chem. Lett. 18: 2776-2780 (2008); the crystal structures PDB 2vwx, 2vwy, and 2vwz and related ligands described in Bardelle, C. et al. "Inhibitors of the Tyrosine Kinase Ephb4. Part 2: Structure-Based Discovery and Optimisation of 3,5-Bis Substituted Anilinopyrimidines", Bioorg. Med. Chem. Lett. 18: 5717 (2008); and, the crystal structure PDB 2vxo and related ligands described in Welin, M. et al. "Substrate Specificity and Oligomerization of Human Gmp Synthetas", J. Mol. Biol. 425: 4323 (2013).

FIG. 8MMMM presents examples of ERBB2 Targeting Ligands wherein R is the point at which the Linker is attached. For additional examples and related ligands, see, the crystal structure and related ligands described in Aertgeerts, K. et al "Structural Analysis of the Mechanism of Inhibition and Allosteric Activation of the Kinase Domain of HER2 Protein", J. Biol. Chem. 286: 18756-18765 (2011) and the crystal structure and related ligands described in Ishikawa, T. et al. "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold" J. Med. Chem. 54: 8030-8050 (2011).

FIG. 8NNNN presents examples of ERBB3 Targeting Ligands wherein R is the point at which the Linker is attached. For additional examples and related ligands, see, Littlefield, P. et al. "An ATP-Competitive Inhibitor Modulates the Allosteric Function of the HER3 Pseudokinase", Chem. Biol. 21: 453-458 (2014).

FIG. 8OOOO presents examples ERBB4 Targeting Ligands wherein R is the point at which the Linker is attached. For additional examples and related ligands, see, Qiu, C. et al. "Mechanism of Activation and Inhibition of the HER4/ErbB4 Kinase", Structure 16: 460-467 (2008) and Wood, E. R. et al. "6-Ethynylthieno[3,2-d]- and 6-ethynylthieno[2,3-d]pyrimidin-4-anilines as tunable covalent modifiers of ErbB kinases", Proc. Natl. Acad. Sci. Usa 105: 2773-2778 (2008).

FIG. 8PPPP-8QQQQ present examples of FES Targeting Ligands wherein R is the point at which the Linker is attached. For additional examples and related ligands, see, Filippakopoulos, P. et al "Structural Coupling of SH2-Kinase Domains Links Fes and Abl Substrate Recognition and Kinase Activation." Cell 134: 793-803 (2008) and Hellwig, S. et al. "Small-Molecule Inhibitors of the c-Fes Protein-Tyrosine Kinase", Chem. Biol. 19: 529-540 (2012).

FIG. 8RRRR presents examples of FYN Targeting Ligands wherein R is the point at which the Linker is attached. For additional examples and related ligands, see, Kinoshita, T. et. al. "Structure of human Fyn kinase domain complexed with staurosporine", Biochem. Biophys. Res. Commun. 346: 840-844 (2006).

FIG. 8SSSS-8VVVV present examples of GSG2 (Haspin) Targeting Ligands wherein R is the point at which the Linker is attached. For additional examples and related ligands, see, the crystal structures PDB 3e7v, PDB 3f2n, 3fmd and related ligands described in Filippakopoulos, P. et al. "Crystal Structure of Human Haspin with a pyrazolo-pyrimidine ligand", to be published; the crystal structure PDB 3iq7 and related ligands described in Eswaran, J. et al. "Structure and functional characterization of the atypical human kinase haspin", Proc. Natl. Acad. Sci. USA 106: 20198-20203 (2009); and, the crystal structure PDB 4qtc and related ligands described in Chaikuad, A. et al. "A unique inhibitor binding site in ERK1/2 is associated with slow binding kinetics", Nat. Chem. Biol. 10: 853-860 (2014).

FIG. 8WWWW-8AAAAA present examples of HCK Targeting Ligands wherein R is the point at which the Linker is attached. For additional examples and related ligands, see, the crystal structure PDB 1qcf and related ligands described in Schindler, T. et al. "Crystal structure of Hck in complex with a Src family-selective tyrosine kinase inhibitor", Mol. Cell 3: 639-648 (1999); the crystal structure PDB 2c0i and 2c0t and related ligands described in Burchat, A. et al. "Discovery of A-770041, a Src-Family Selective Orally Active Lck Inhibitor that Prevents Organ Allograft Rejection", Bioorg. Med. Chem. Lett. 16: 118 (2006); the crystal structure PDB 2hk5 and related ligands described in Sabat, M. et al. "The development of 2-benzimidazole substituted pyrimidine based inhibitors of lymphocyte specific kinase (Lck)", Bioorg. Med. Chem. Lett. 16: 5973-5977 (2006); the crystal structures PDB 3vry, 3vs3, 3vs6, and 3vs7 and related ligands described in Saito, Y. et al. "A Pyrrolo-Pyrimidine Derivative Targets Human Primary AML Stem Cells in Vivo", Sci Transl Med 5: 181ra52-181ra52 (2013); and, the crystal structure PDB 4lud and related ligands described in Parker, L. J. et al "Kinase crystal identification and ATP-competitive inhibitor screening using the fluorescent ligand SKF86002", Acta Crystallogr., Sect. D 70: 392-404 (2014).

FIG. 8BBBBB-8FFFFF present examples of IGF1R Targeting Ligands wherein R is the point at which the Linker is attached. For additional examples and related ligands, see, the crystal structure PDB 2oj9 and related ligands described in Velaparthi, U. et al. "Discovery and initial SAR of 3-(1H-benzo[d]imidazol-2-yl)pyridin-2(1H)-ones as inhibitors of insulin-like growth factor 1-receptor (IGF-1R)", Bioorg. Med. Chem. Lett. 17: 2317-2321 (2007); the crystal structure PDB 3i81 and related ligands described in Wittman, M. D. et al. "Discovery of a 2,4-disubstituted pyrrolo [1,2-f][1,2,4]triazine inhibitor (BMS-754807) of insulin-like growth factor receptor (IGF-1R) kinase in clinical development.", *J. Med. Chem.* 52: 7360-7363 (2009); the crystal structure PDB 3nw5 and related ligands described in Sampognaro, A. J. et al. "Proline isosteres in a series of 2,4-disubstituted pyrrolo[1,2-f][1,2,4]triazine inhibitors of IGF-1R kinase and IR kinase", *Bioorg. Med. Chem. Lett.* 20: 5027-5030 (2010); the crystal structure PDB 3qqu and related ligands described in Buchanan, J. L. et al. "Discovery of 2,4-bis-arylamino-1,3-pyrimidines as insulin-like growth factor-1 receptor (IGF-1R) inhibitors", *Bioorg. Med. Chem. Lett.* 21: 2394-2399 (2011); the crystal structure PDB 4d2r and related ligands described in Kettle, J. G. et al. "Discovery and Optimization of a Novel Series of Dyrk1B Kinase Inhibitors to Explore a Mek Resistance Hypothesis". *J. Med. Chem.* 58: 2834 (2015); the crystal structure PDB 3fxq and related ligands described in Monferrer, D. et al. "Structural studies on the full-length LysR-type regulator TsaR from Comamonas testosteroni T-2 reveal a novel open conformation of the tetrameric LTTR fold", *Mol. Microbiol.* 75: 1199-1214 (2010); the crystal structure PDB 5fxs and related ligands described in Degorce, S. et al. "Discovery of Azd9362, a Potent Selective Orally Bioavailable and Efficacious Novel Inhibitor of Igf-R1", to be published; the crystal structure PDB 2zm3 and related ligands described in Mayer, S. C. et al. "Lead identification to generate isoquinolinedione inhibitors of insulin-like growth factor receptor (IGF-1R) for potential use in cancer treatment", *Bioorg. Med. Chem. Lett.* 18: 3641-3645 (2008); the crystal structure PDB 3f5p and related ligands described in "Lead identification to generate 3-cyanoquinoline inhibitors of insulin-like growth factor receptor (IGF-1R) for potential use in cancer treatment" *Bioorg. Med. Chem. Lett.* 19: 62-66 (2009); the crystal structure PDB 3ivp and related ligands described in Nemecek, C. et al. "Design of Potent IGF1-R Inhibitors Related to Bis-azaindoles" *Chem. Biol. Drug Des.* 76: 100-106 (2010); the crystal structure PDB 3o23 and related ligands described in Lesuisse, D. et al. "Discovery of the first non-ATP competitive IGF-1R kinase inhibitors: Advantages in comparison with competitive inhibitors", *Bioorg. Med. Chem. Lett.* 21: 2224-2228 (2011); the crystal structure PDB 3d94 and related ligands described in Wu, J. et al. "Small-molecule inhibition and activation-loop trans-phosphorylation of the IGF1 receptor", *Embo J.* 27: 1985-1994 (2008); and, the crystal structure PDB 5hzn and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med. Chem. Lett.* 26: 2065-2067 (2016).

FIG. 8GGGGG-8JJJJJ present examples of INSR Targeting Ligands wherein R is the point at which the Linker is attached. For additional examples and related ligands, see, the crystal structure PDB 2z8c and related ligands described in Katayama, N. et al. "Identification of a key element for hydrogen-bonding patterns between protein kinases and their inhibitors", *Proteins* 73: 795-801 (2008); the crystal structure PDB 3ekk and related ligands described in Chamberlain, S. D. et al. "Discovery of 4,6-bis-anilino-1H-pyrrolo[2,3-d]pyrimidines: Potent inhibitors of the IGF-1R receptor tyrosine kinase", (2009) *Bioorg. Med. Chem. Lett.* 19: 469-473; the crystal structure PDB 3ekn and related ligands described in Chamberlain, S. D. et al. "Optimization of 4,6-bis-anilino-1H-pyrrolo[2,3-d]pyrimidine IGF-1R tyrosine kinase inhibitors towards JNK selectivity", *Bioorg. Med. Chem. Lett.* 19: 360-364 (2009); the crystal structure PDB 5els and related ligands described in Sanderson, M. P. et al. "BI 885578, a Novel IGF1R/INSR Tyrosine Kinase Inhibitor with Pharmacokinetic Properties That Dissociate Antitumor Efficacy and Perturbation of Glucose Homeostasis" *Mol. Cancer Ther.* 14: 2762-2772", (2015); the crystal structure PDB 3eta and related ligands described in Patnaik, S. et al. "Discovery of 3,5-disubstituted-1H-pyrrolo[2,3-b]pyridines as potent inhibitors of the insulin-like growth factor-1 receptor (IGF-1R) tyrosine kinase", *Bioorg. Med. Chem. Lett.* 19: 3136-3140 (2009); the crystal structure PDB 5hhw and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med. Chem. Lett.* 26: 2065-2067 (2016); and, the crystal structure PDB 4ibm and related ligands described in Anastassiadis, T. et al. "A highly selective dual insulin receptor (IR)/insulin-like growth factor 1 receptor (IGF-1R) inhibitor derived from an extracellular signal-regulated kinase (ERK) inhibitor", *J. Biol. Chem.* 288: 28068-28077 (2013).

FIG. 8KKKKK-8PPPPP present examples of HBV Targeting Ligands wherein R is the point at which the Linker is attached, Y is methyl or isopropyl, and X is N or C. For additional examples and related ligands, see, Weber, O.; et al. "Inhibition of human hepatitis B virus (HBV) by a novel non-nucleosidic compound in a transgenic mouse model." *Antiviral Res.* 54, 69-78 (2002); Deres, K.; et al. "Inhibition of hepatitis B virus replication by drug-induced depletion of nucleocapsids." *Science,* 299, 893-896 (2003); Stray, S. J.; Zlotnick, A. "BAY 41-4109 has multiple effects on Hepatitis B virus capsid assembly." *J. Mol. Recognit.* 19, 542-548 (2006); Stray, S. J.; et al. "heteroaryldihydropyrimidine activates and can misdirect hepatitis B virus capsid assembly." *Proc. Natl. Acad. Sci. U.S.A,* 102, 8138-8143 (2005); Guan, H.; et al. "The novel compound Z060228 inhibits assembly of the HBV capsid." *Life Sci.* 133, 1-7 (2015); Wang, X. Y.; et al. "In vitro inhibition of HBV replication by a novel compound, GLS4, and its efficacy against adefovir-dipivoxil-resistant HBV mutations." *Antiviral Ther.* 17, 793-803 (2012); Klumpp, K.; et al. "High-resolution crystal structure of a hepatitis B virus replication inhibitor bound to the viral core protein." 112, 15196-15201 (2015); Qiu, Z.; et al. "Design and synthesis of orally bioavailable 4-methyl heteroaryldihydropyrimidine based hepatitis B virus (HBV) capsid inhibitors." *J. Med. Chem.* 59, 7651-7666 (2016); Zhu, X.; et al. "2,4-Diaryl-4,6,7,8-tetrahydroquinazolin-5 (1H)-one derivatives as anti-HBV agents targeting at capsid assembly." *Bioorg. Med. Chem. Lett.* 20, 299-301 (2010); Campagna, M. R.; et al. "Sulfamoylbenzamide derivatives inhibit the assembly of hepatitis B virus nucleocapsids." *J. Virol.* 87, 6931-6942 (2013); Campagna, M. R.; et al. "Sulfamoylbenzamide derivatives inhibit the assembly of hepatitis B virus nucleocapsids." *J. Virol.* 87, 6931-6942 (2013); WO 2013096744 A1 titled "Hepatitis B antivial agents"; WO 2015138895 titled "Hepatitis B core protein allosteric modulators"; Wang, Y. J.; et al. "A novel pyridazinone derivative inhibits hepatitis B virus replication by inducing genome-free capsid formation." *Antimicrob. Agents Chemother.* 59, 7061-7072 (2015); WO 2014033167 titled "Fused bicyclic sulfamoyl derivatives for the treatment of hepatitis"; U.S. 20150132258 titled "Azepane derivatives and methods of treating hepatitis B infections"; and, WO 2015057945 "Hepatitis B viral assembly effector".

Figure 9:
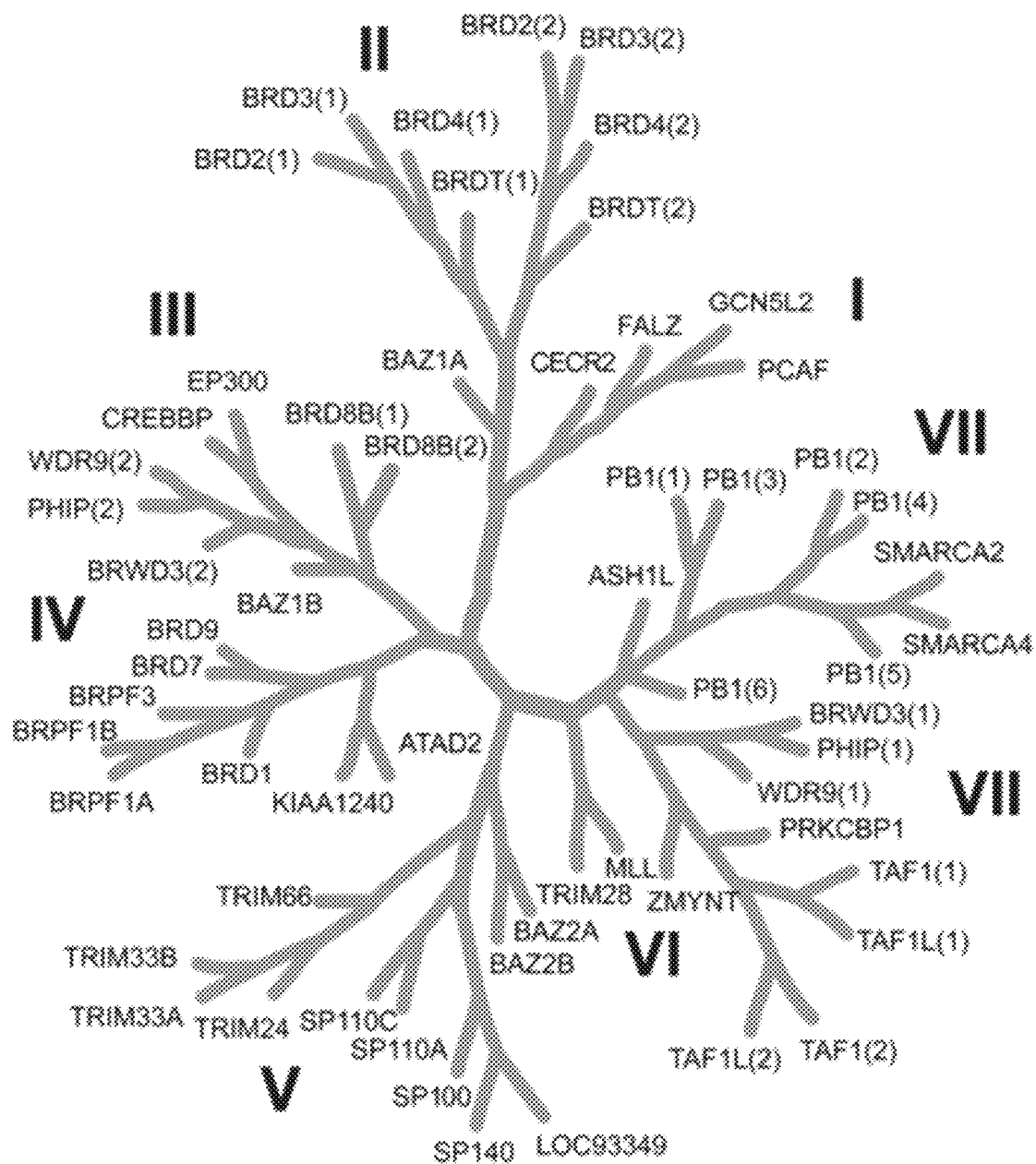

FIG. 9 is a dendrogram of the human bromodomain family of proteins organized into eightsubfamilies, which are involved in epigenetic signaling and chromatin biology. Any of the proteins of the bromodomain family in FIG. 9 can be selected as a Target Protein according to the present invention.

DETAILED DESCRIPTION

I. Definitions

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, and Formula IV with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with, for example $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound of Formula I, Formula II, Formula III, or Formula IV. In one non-limiting embodiment, the substitution of a hydrogen atom for a deuterium atom occurs within one or more groups selected from any of $R^1$, $R^2$, $R^3$, $R^4$, $R^5$, $R^6$, $R^7$, $R^8$, $R^9$, $R^{11}$, $R^{12}$, $R^{13}$, $R^{14}$ $R^{15}$, $R^{20}$, $R^{21}$, $R^{22}$, $R^{23}$, $R^{24}$, $R^{25}$, $R^{26}$, $R^{27}$, $R^{28}$, $R^{101}$, Linker, and Targeting Ligand. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C=O)NH$_2$ is attached through carbon of the carbonyl (C=O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one triple bond.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_6$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Halo" and "Halogen" refers to fluorine, chlorine, bromine or iodine.

"Haloalkyl" is a branched or straight-chain alkyl groups- substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

"Chain" indicates a linear chain to which all other chains, long or short or both, may be regarded as being pendant. Where two or more chains could equally be considered to be the main chain, "chain" refers to the one which leads to the simplest representation of the molecule.

"Haloalkoxy" indicates a haloalkyl group as defined herein attached through an oxygen bridge (oxygen of an alcohol radical).

"Heterocycloalkyl" is an alkyl group as defined herein substituted with a heterocyclo group as defined herein.

"Arylalkyl" is an alkyl group as defined herein substituted with an aryl group as defined herein.

"Heteroarylalkyl" is an alkyl group as defined herein substituted with a heteroaryl group as defined herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 3-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino. Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9, 9a-hexahydro-1H-3-aza-fluorenyl, 5,6,7-trihydro-1,2,4-triazolo[3,4-a]isoquinolyl, 3,4-dihydro-2H-benzo[1,4] oxazinyl, benzo[1,4]dioxanyl, 2,3-dihydro-1H-1λ'-benzo[d] isothiazol-6-yl, dihydropyranyl, dihydrofuryl and dihydrothiazolyl.

Heterocyclo groups also include radicals where heterocyclic radicals are fused/condensed with aryl or heteroaryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including $C_1$-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl ($C_3$-$C_7$cycloalkyl), B(OH)$_2$, phosphate, phosphonate and haloalkoxy including $C_1$-$C_6$haloalkoxy.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of an immunogenic composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

II. Compounds

Formula I and Formula II

In one aspect of the present invention a Degronimer of Formula I or Formula II is provided:

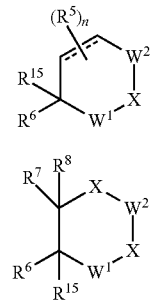

or a pharmaceutically acceptable salt, N-oxide, isotopic derivative, or prodrug thereof, optionally in a pharmaceutically acceptable carrier to form a composition;
wherein:
   the R moieties are as described above;
   Linker is a chemical group that attaches the Degron to a Targeting Ligand;
   Targeting Ligand is a small molecule that binds to a Target Protein, and wherein the Target Protein is a mediator of disease in a host;
   In an additional embodiment, $R^6$ is selected from:

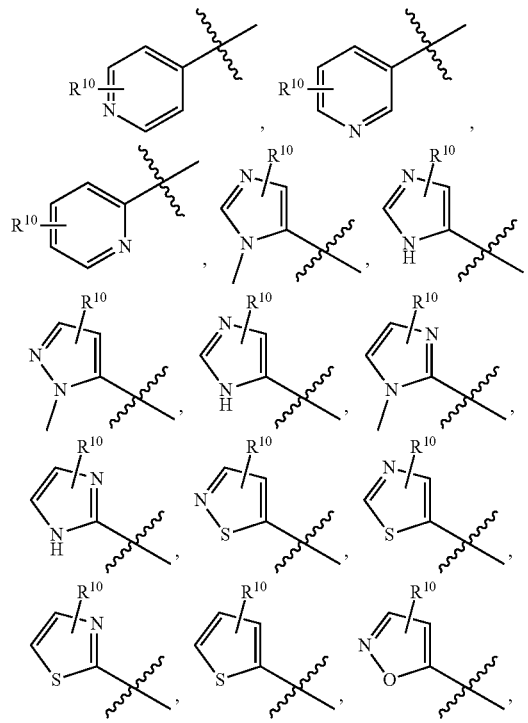

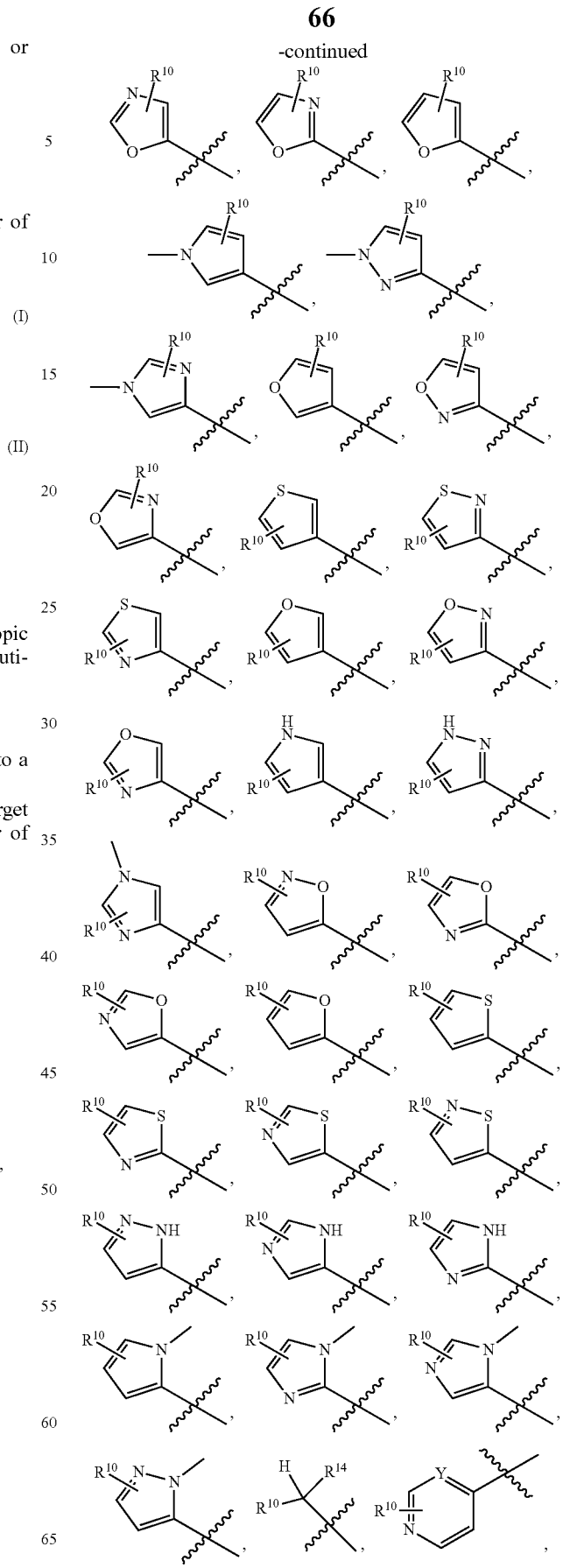

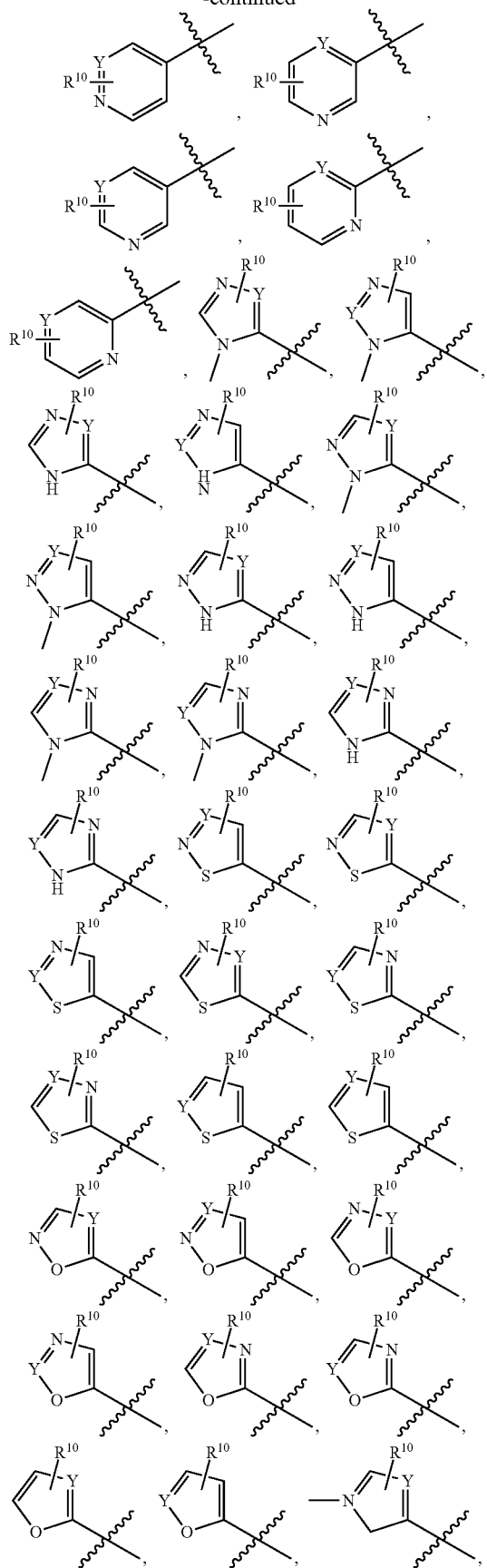
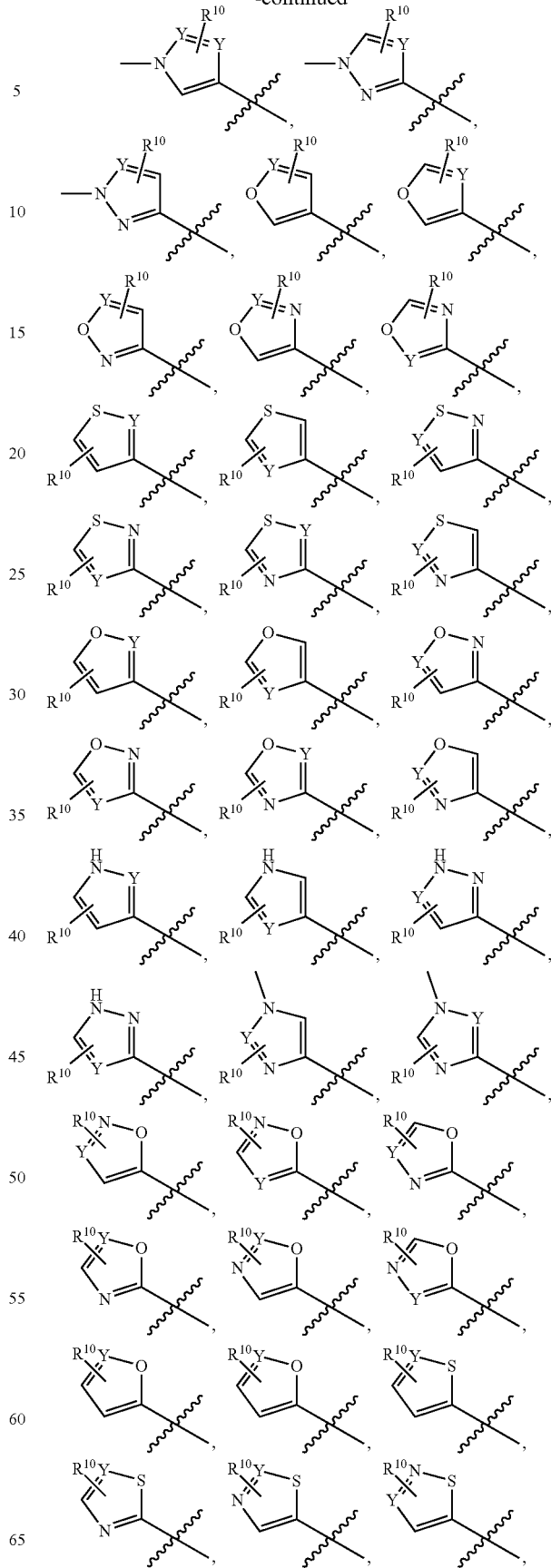

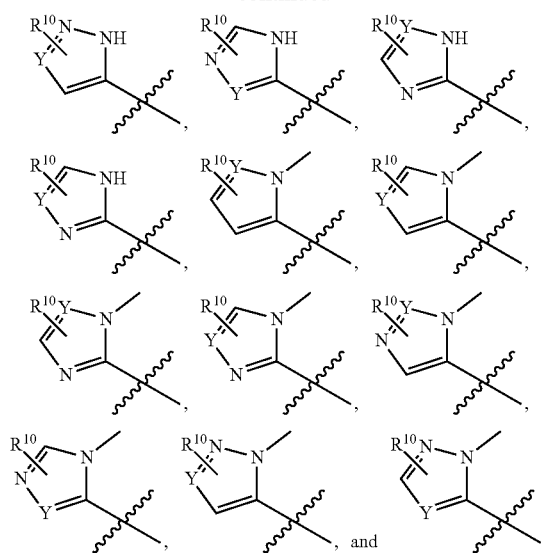
In an additional embodiment, R⁶ is selected from
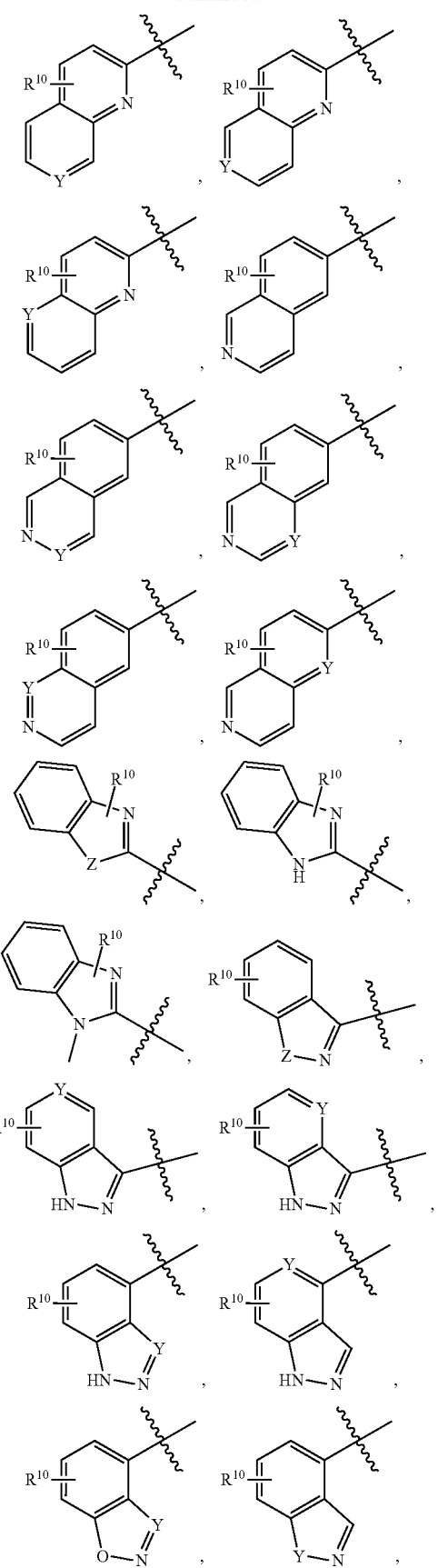

-continued
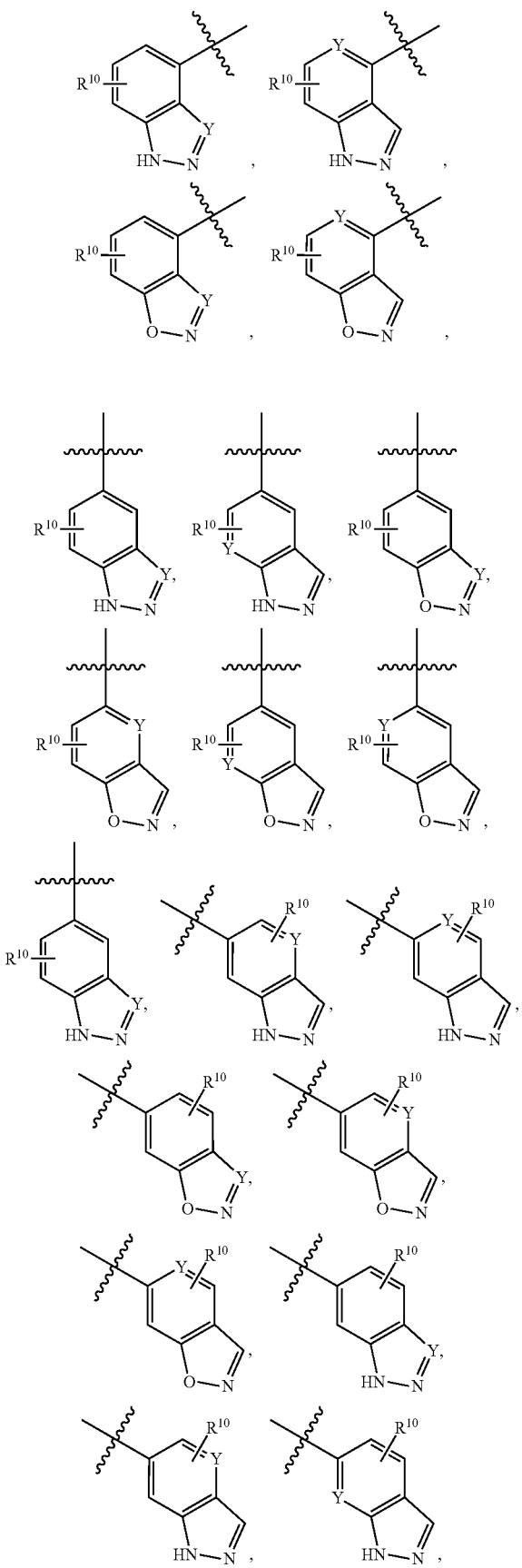
-continued
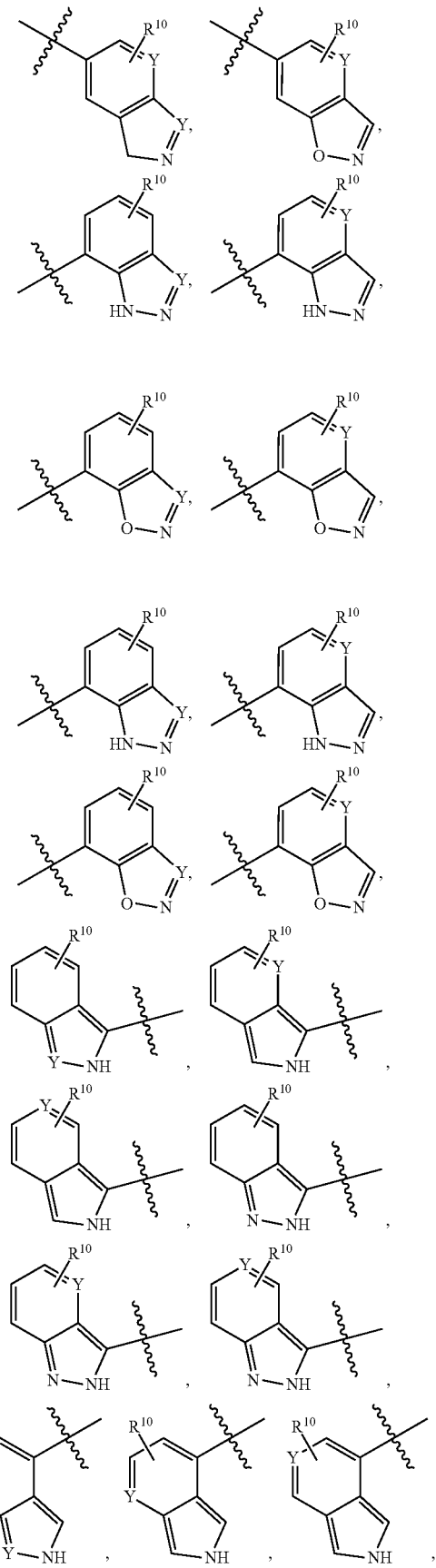

-continued
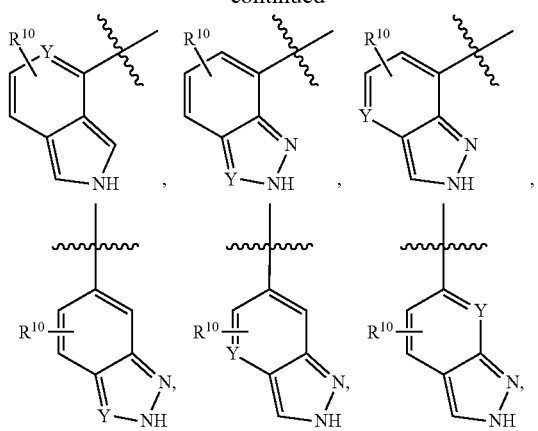
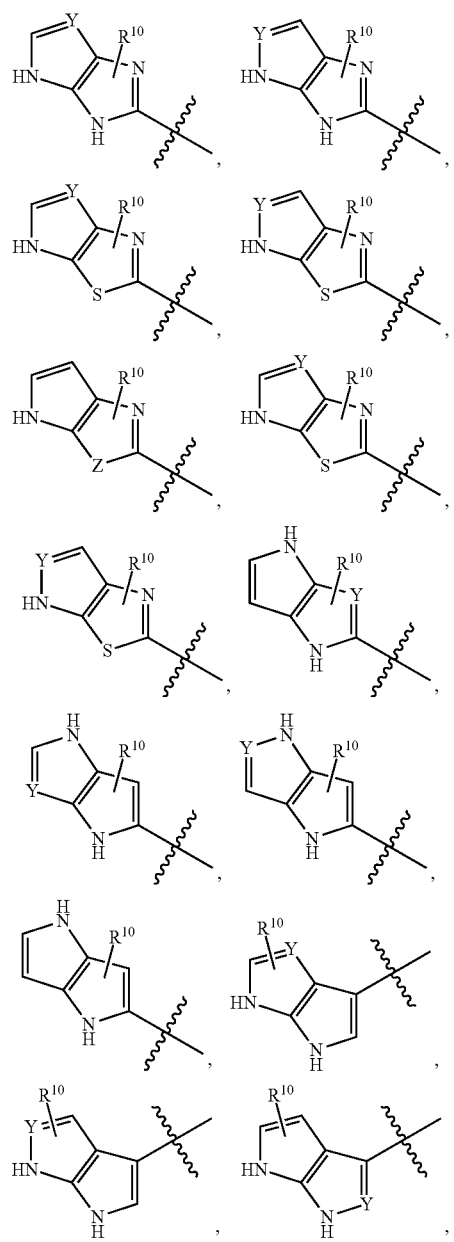
-continued
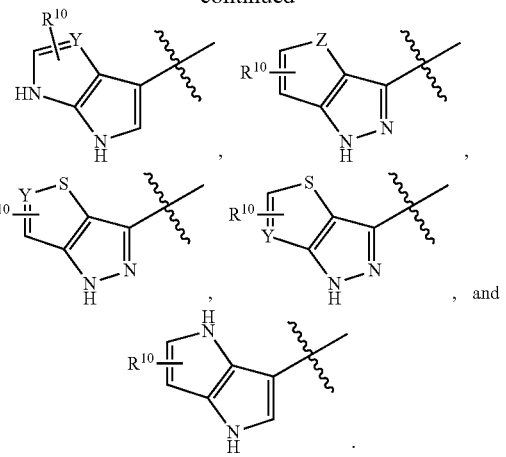
In an additional embodiment, R⁶ is selected from
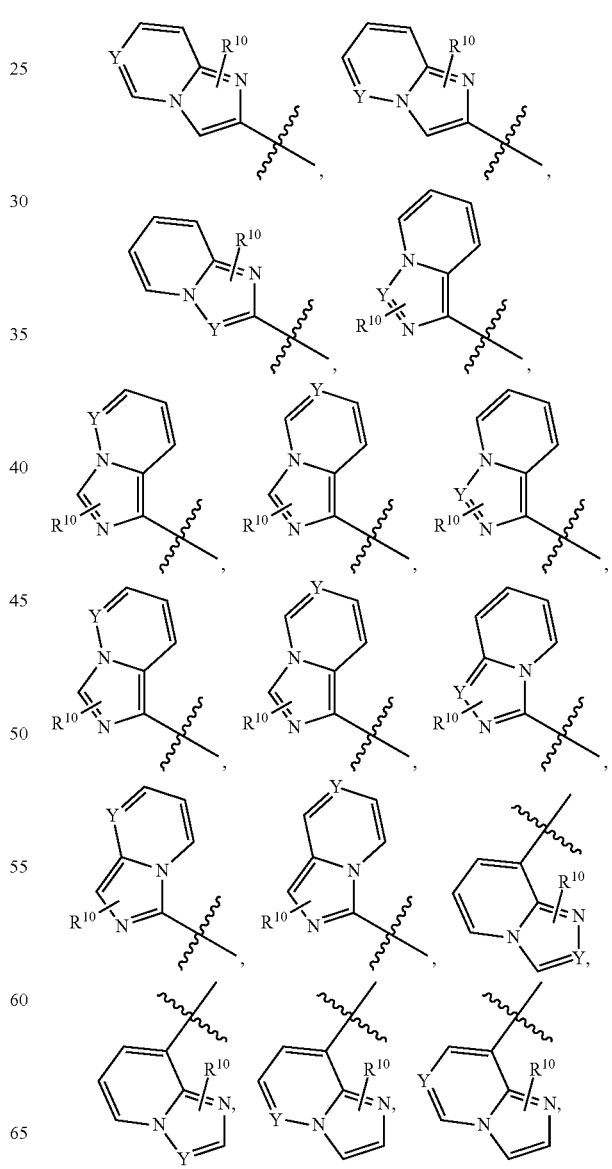

-continued

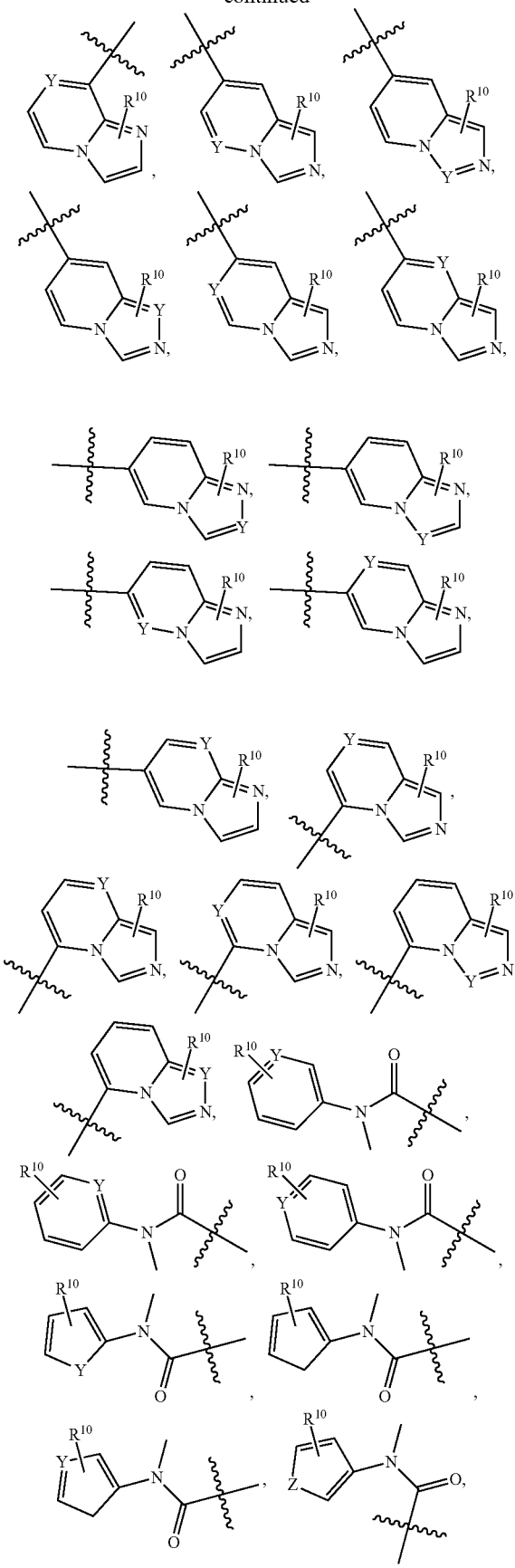

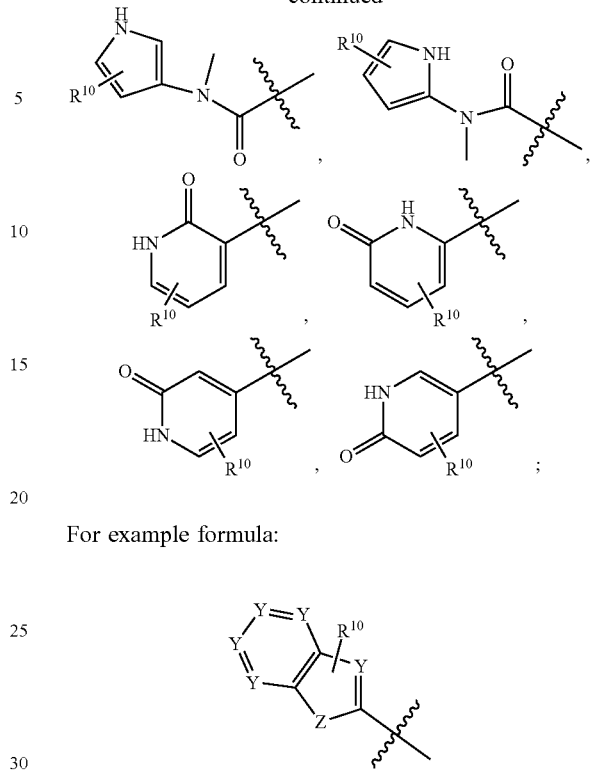

For example formula:

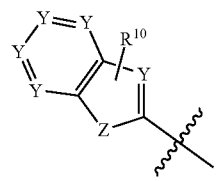

includes compounds of structure

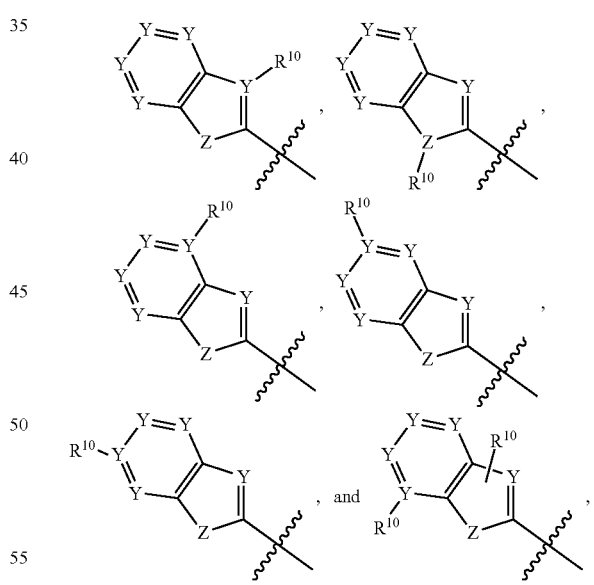

as if each was specifically described.

The Degronimer (Degron, Linker and Targeting Ligand), which includes any of the "R" groups defined herein, may be optionally substituted as described below in Section I. Definitions, if desired to achieve the target effect, results in a stable R moiety and final compound that makes chemical sense to the routineer, and if a final compound for therapy, is pharmaceutically acceptable. Also, all R groups, with or without optional substituents, should be interpreted in a manner that does not include redundancy (i.e., as known in the art, alkyl substituted with alkyl is redundant; however for examples, alkoxy substituted with alkoxy is not redundant). Using this disclosure and teaching, one of ordinary skill in the art will be able to produce the Degronimers of the present invention, and can avoid those moieties that are not stable or are too reactive under the appropriate conditions.

Non-limiting examples of $R^6$ include:

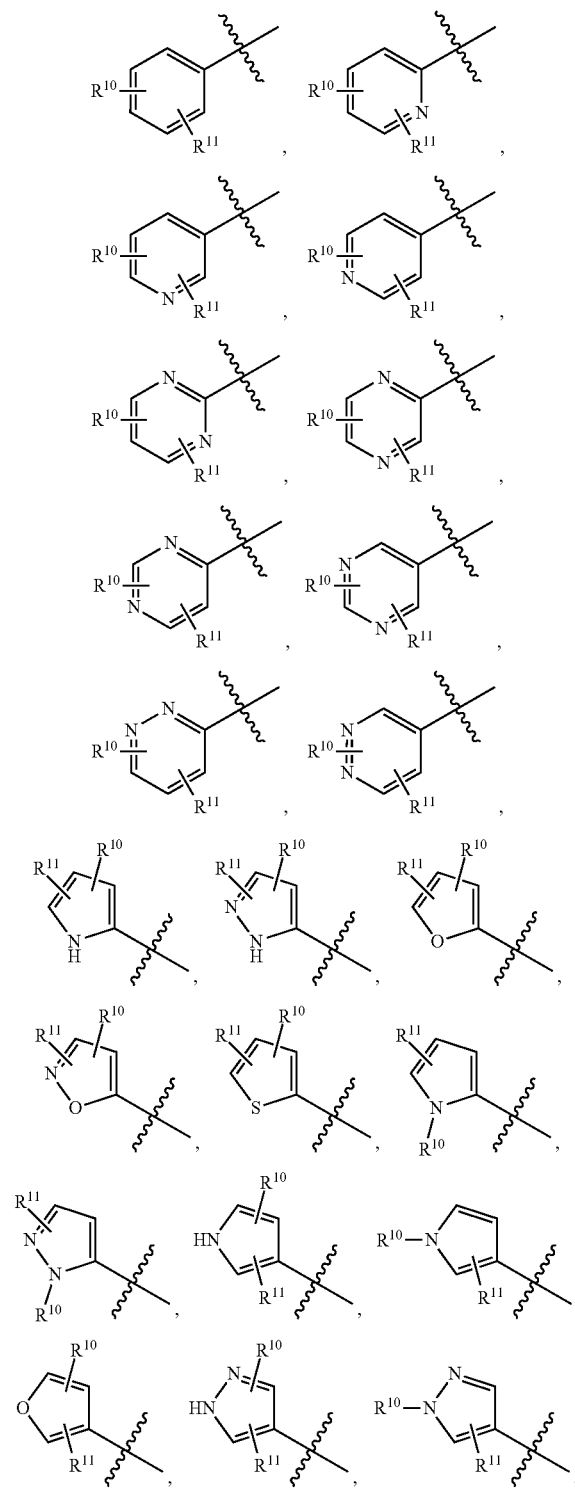

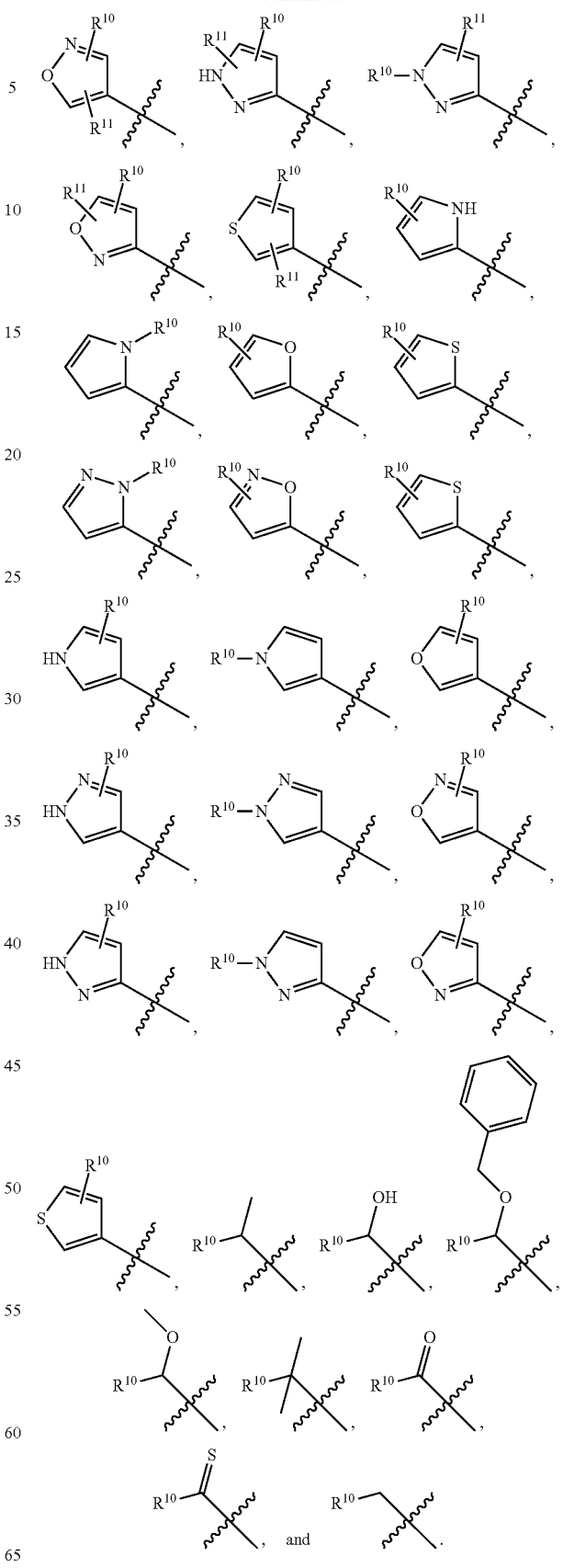

Additional non-limiting examples of $R^6$ include:
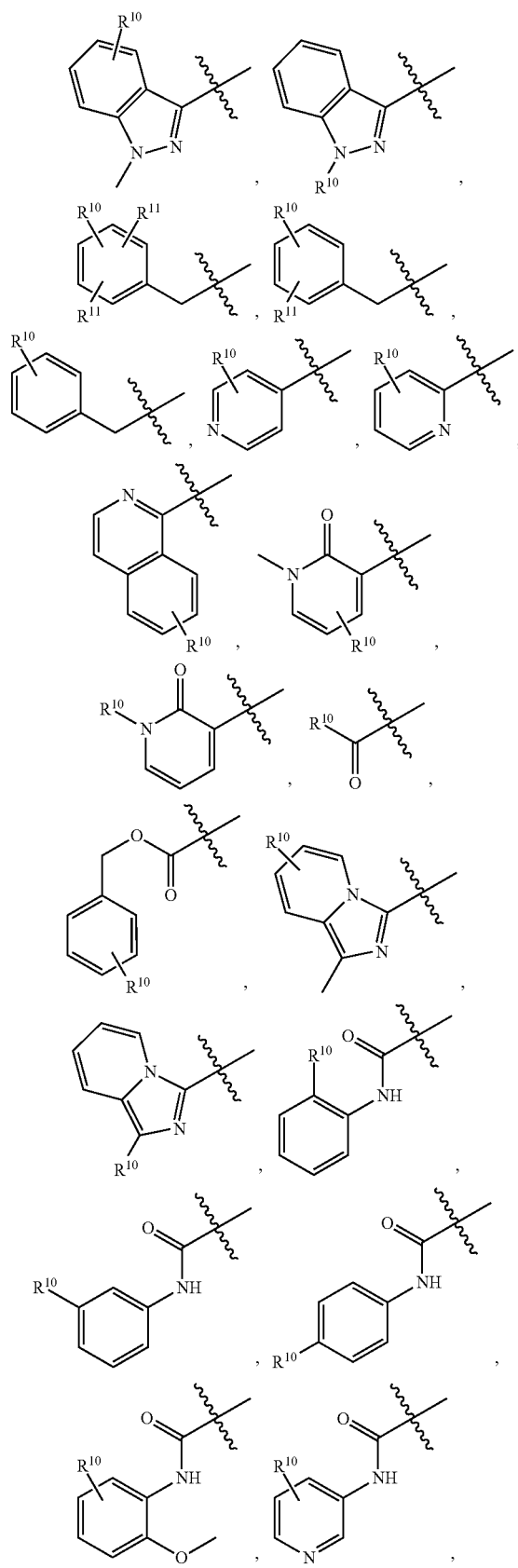
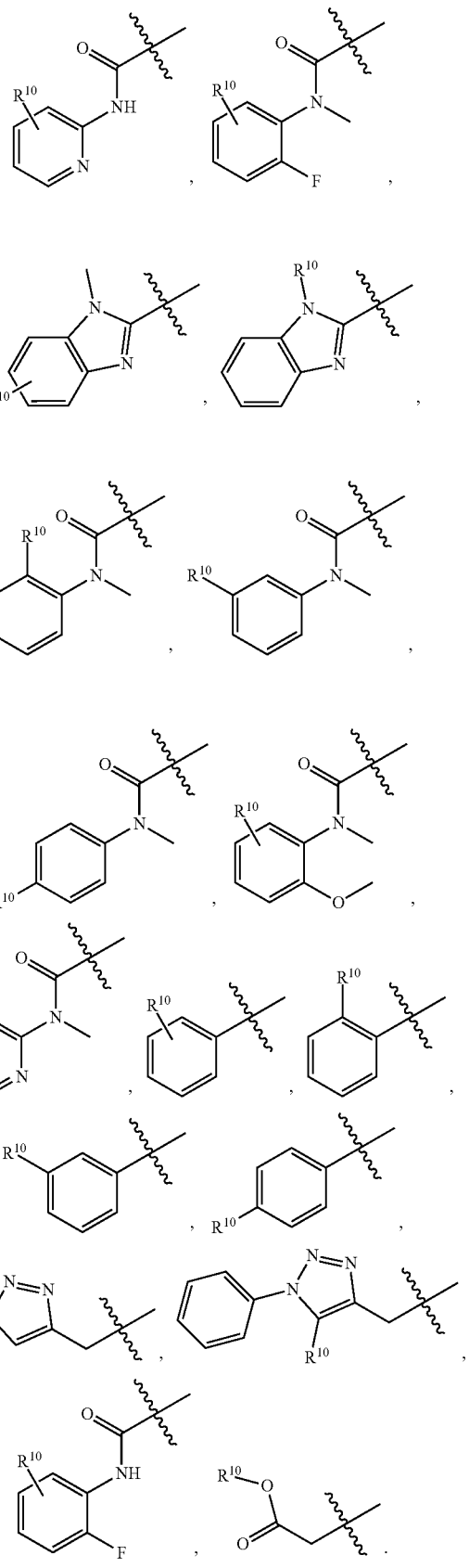

Non-limiting examples of compounds of Formula I include:
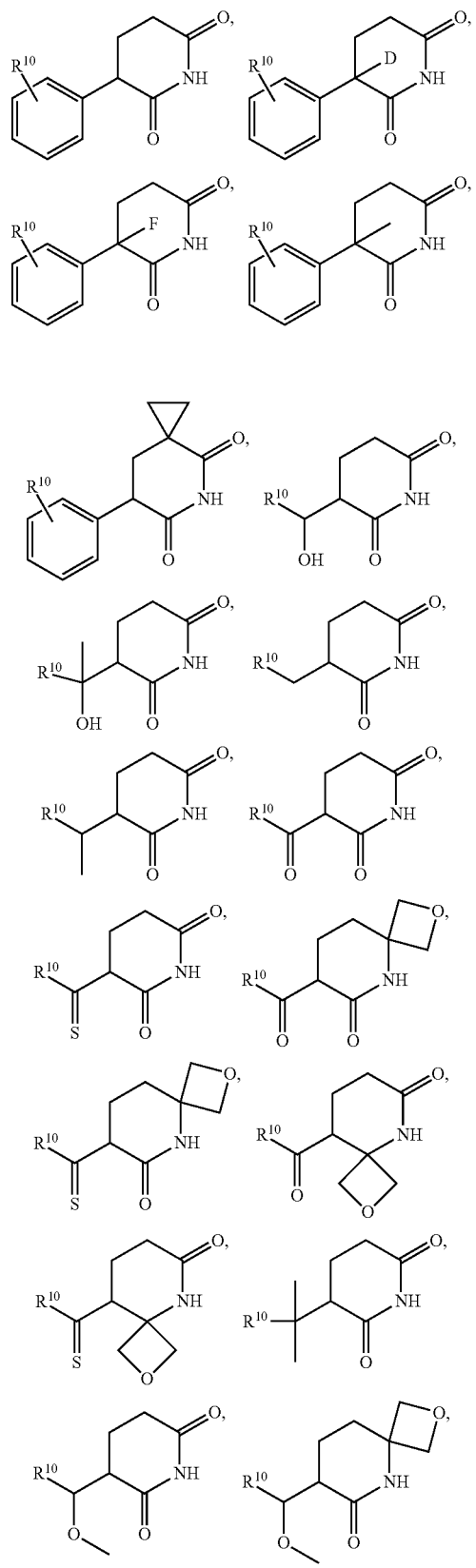
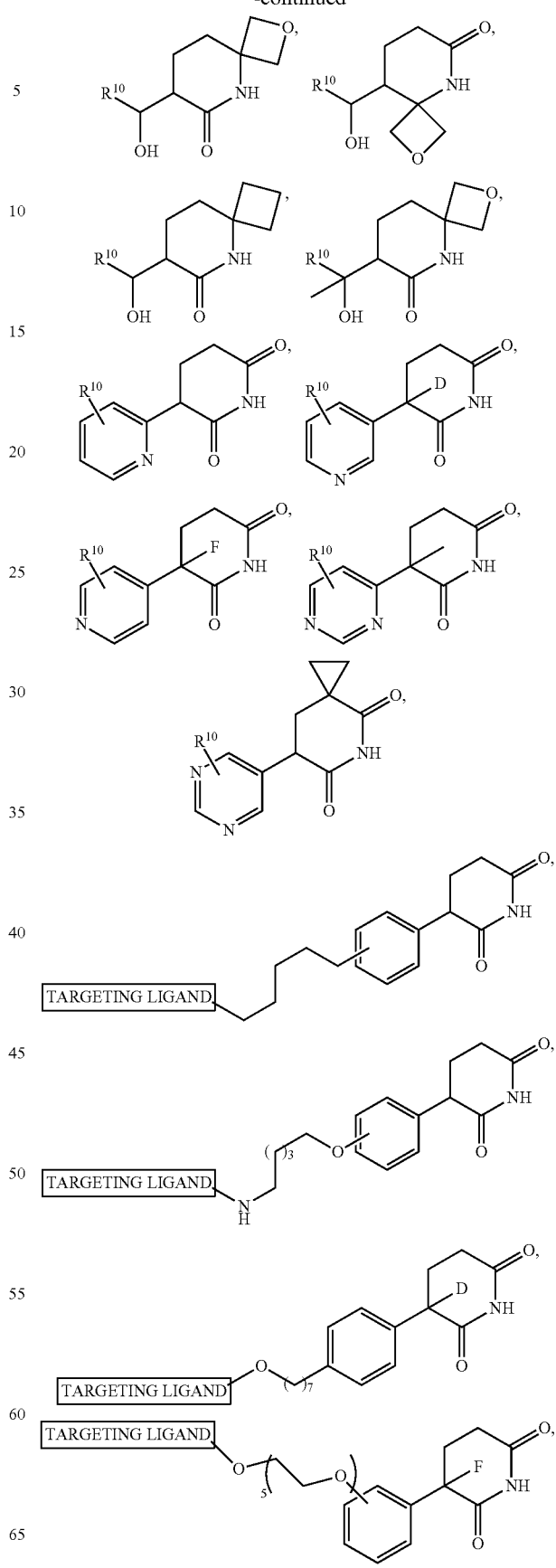

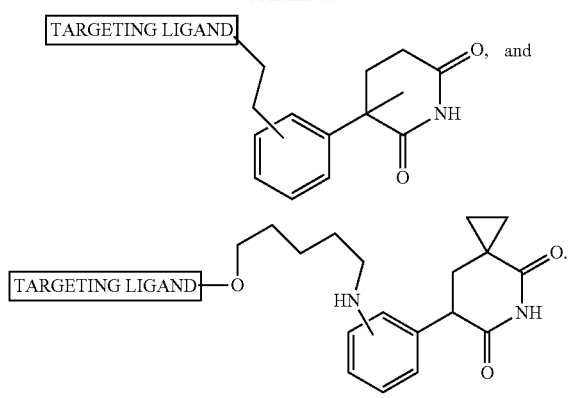
Additional non-limiting examples of compounds of Formula I include:
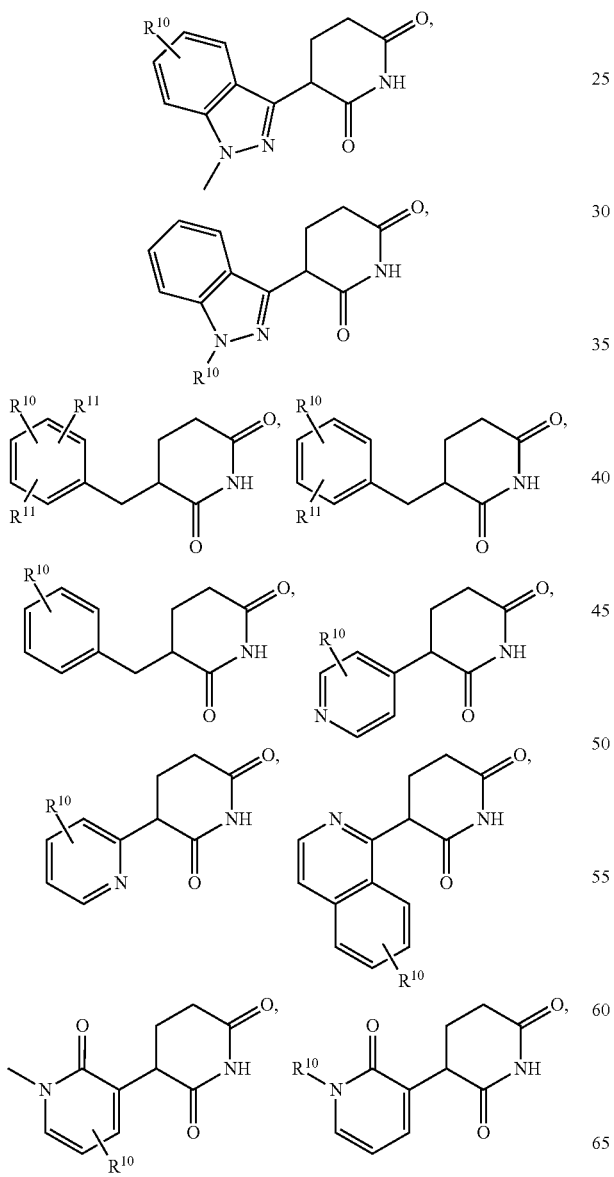
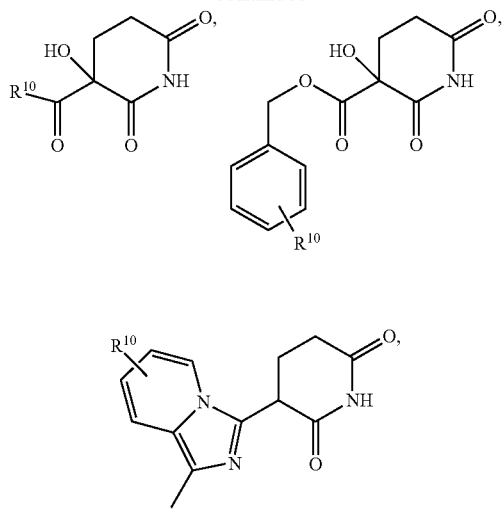
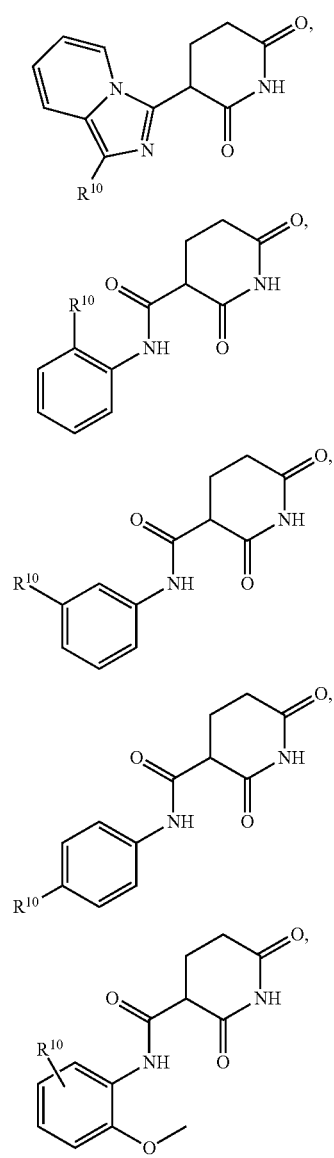

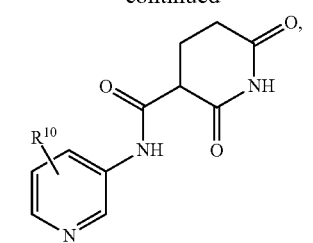
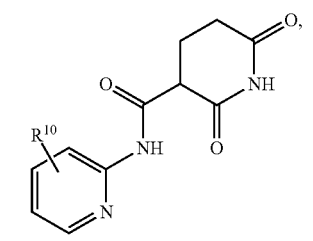
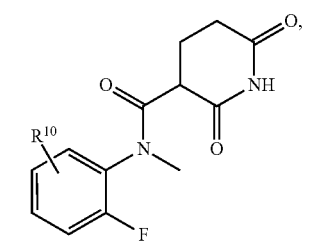
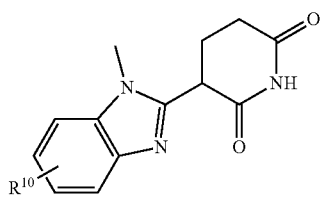
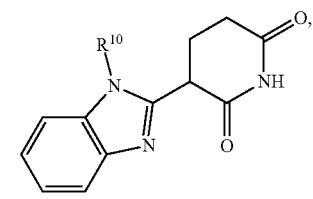
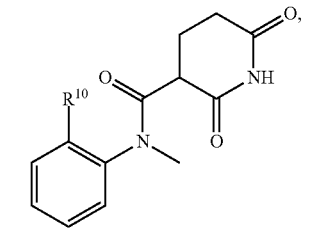
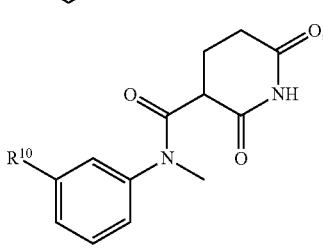
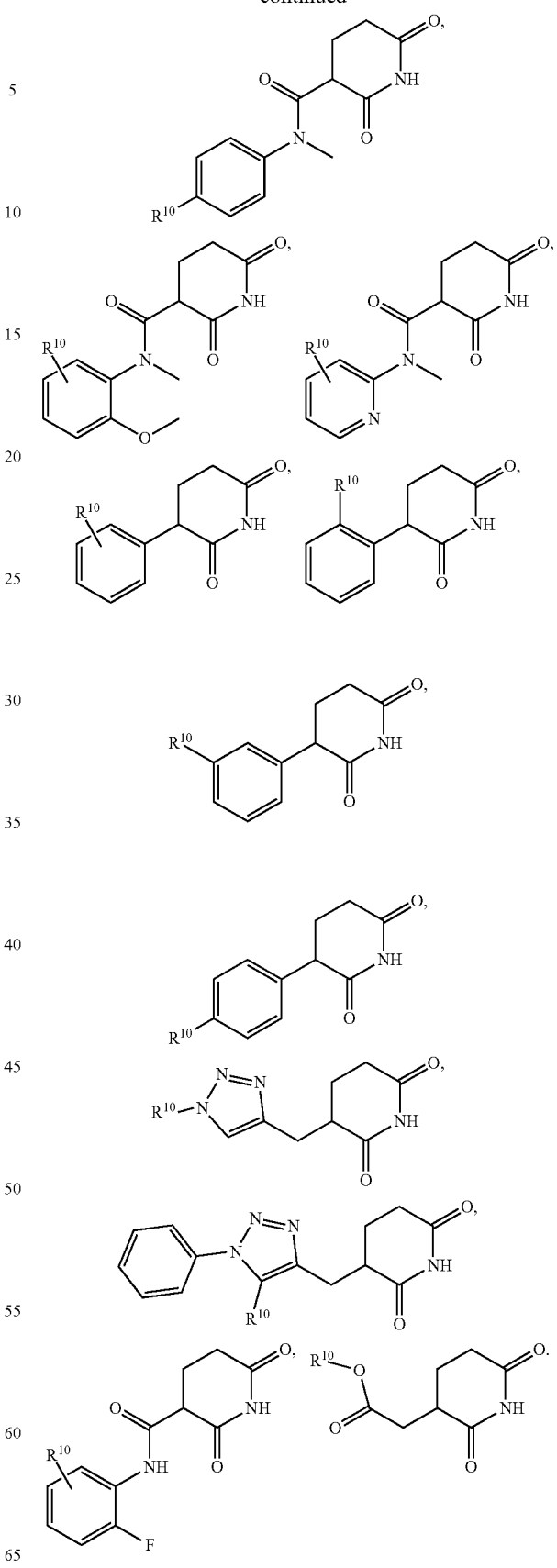

Non-limiting examples of compounds of Formula II include:
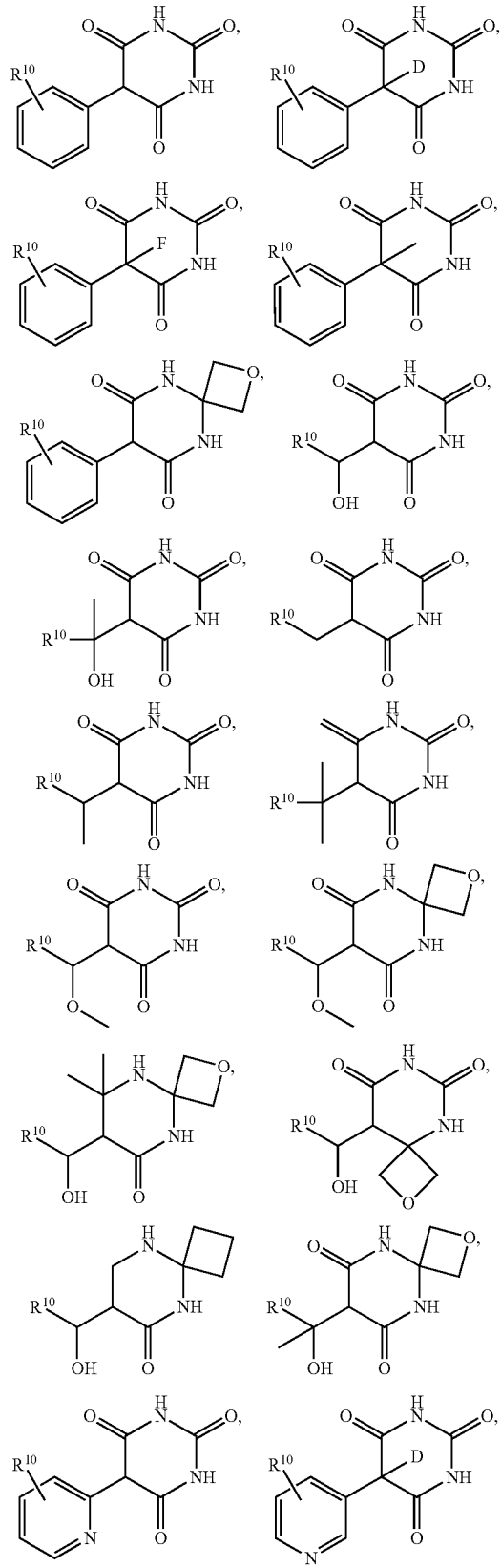
-continued
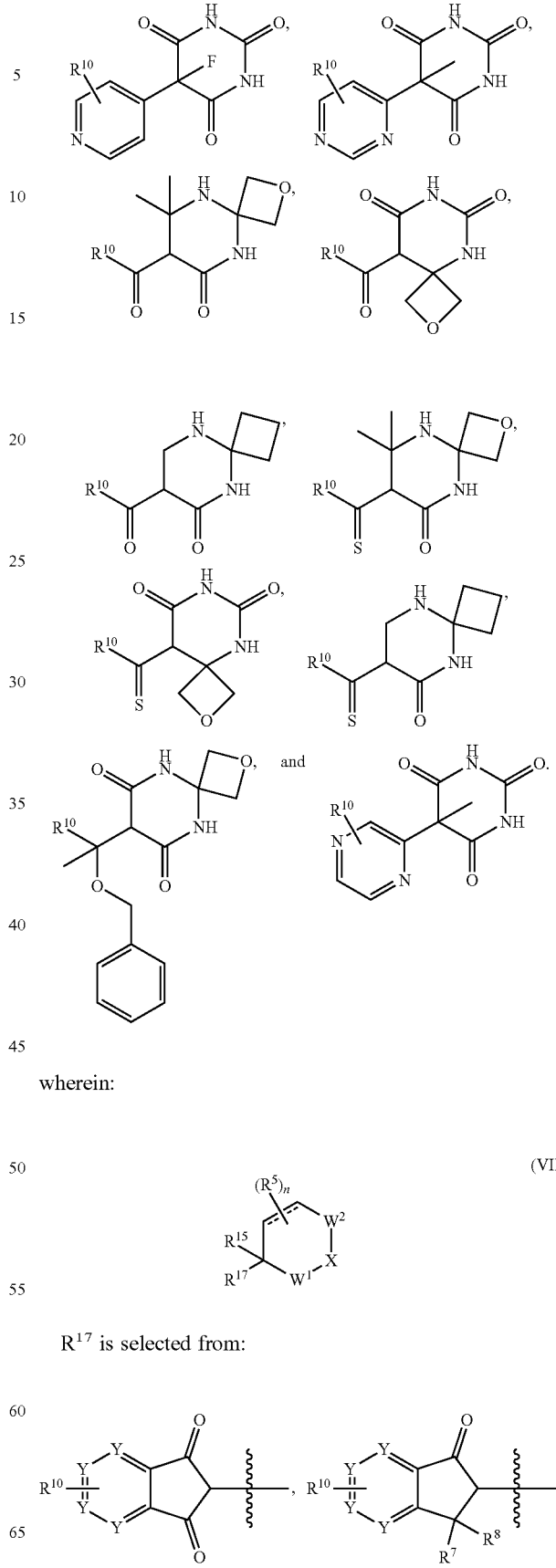
wherein:
$R^{17}$ is selected from:

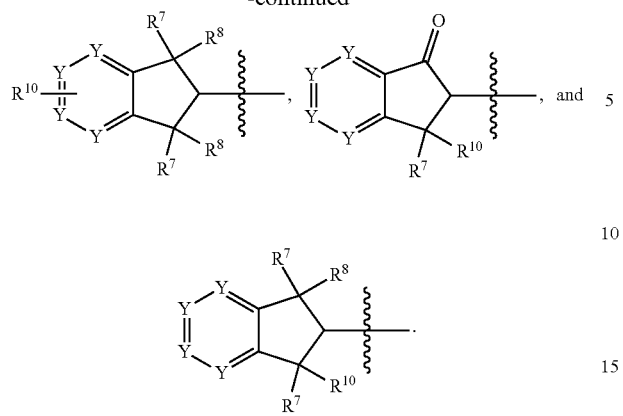
Non-limiting examples of compounds of Formula VII include:
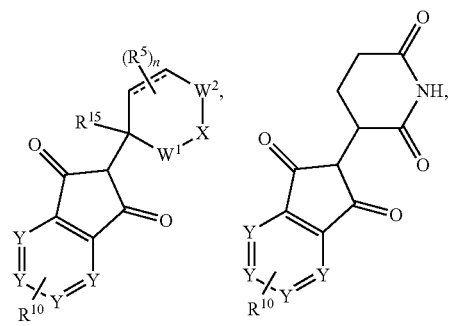
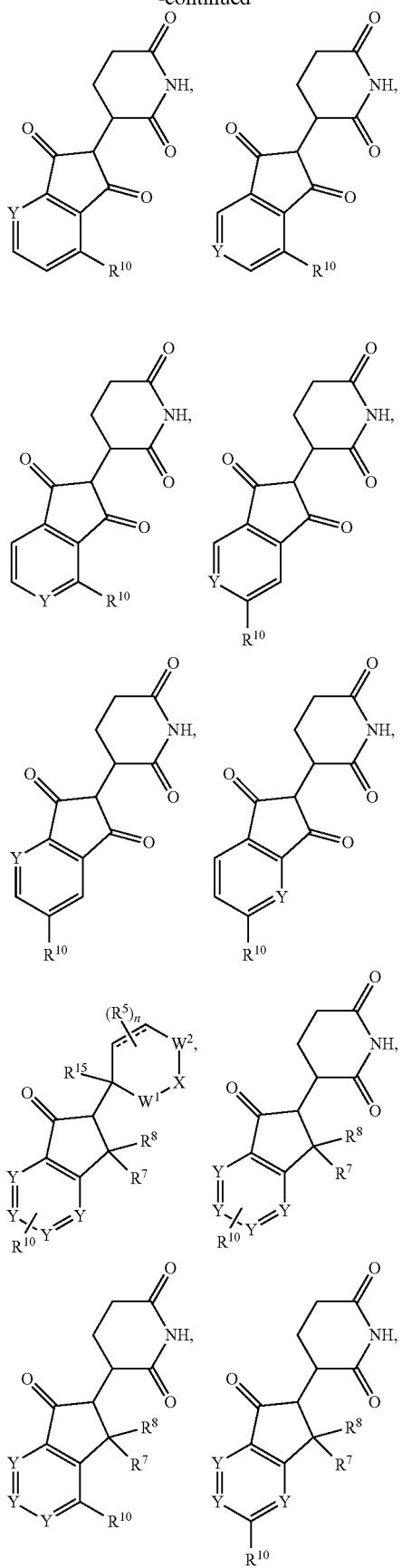

-continued

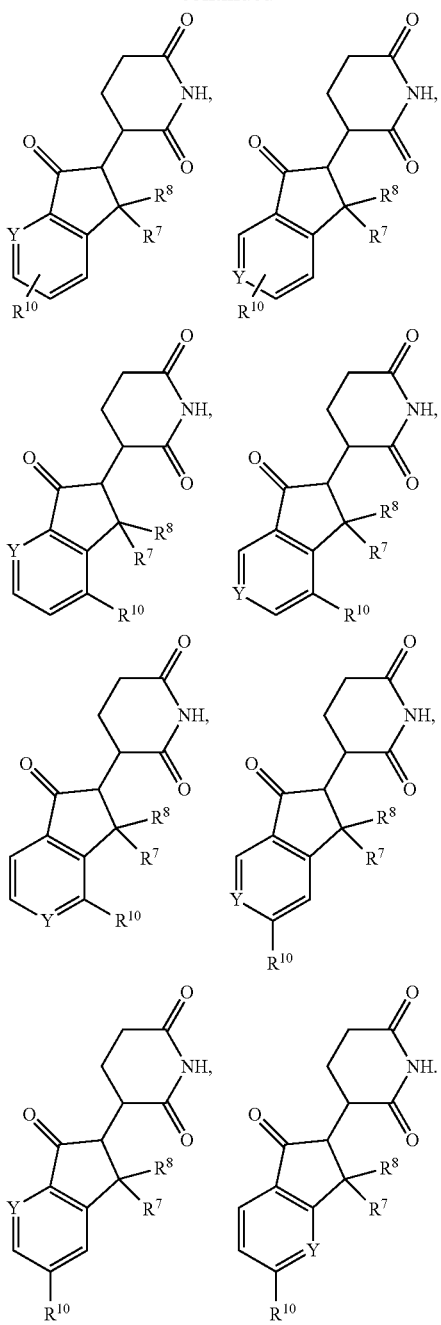

Formula III and Formula IV

In one aspect of the present invention a compound of Formula III or Formula IV is provided:

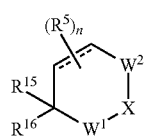
(III)

-continued

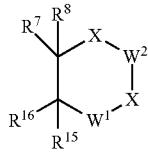
(IV)

or a pharmaceutically acceptable salt, N-oxide, isotopic derivative, or prodrug thereof, optionally in a pharmaceutically acceptable carrier to form a composition;
wherein:

$W^1$ is $CR^1R^2$, C=O, C=S, C=CH$_2$, SO$_2$, S(O), P(O)Oalkyl, P(O)NHalkyl, P(O)N(alkyl)$_2$, P(O)alkyl, P(O)OH, P(O)NH$_2$;

$W^2$ is $CR^3R^4$, C=O, C=S, C=CH$_2$, SO$_2$, S(O), P(O)Oalkyl, P(O)NHalkyl, P(O)N(alkyl)$_2$, P(O)alkyl, P(O)OH, P(O)NH$_2$;

in a typical embodiment $W^1$ is C=O;

in another typical embodiment $W^2$ is C=O;

X is independently selected from NH, $NR^{12}$, CH$_2$, $CHR^{12}$, $C(R^{12})_2$, O, or S;

n is 0, 1, 2, or 3;

⁓⁓⁓ is a single or double bond;

$R^{16}$ is selected from:

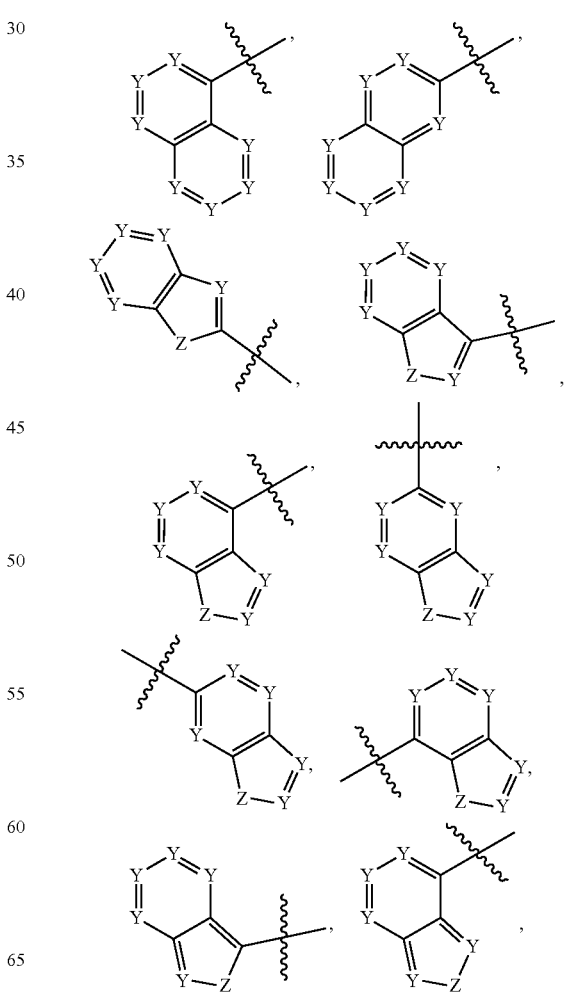

-continued
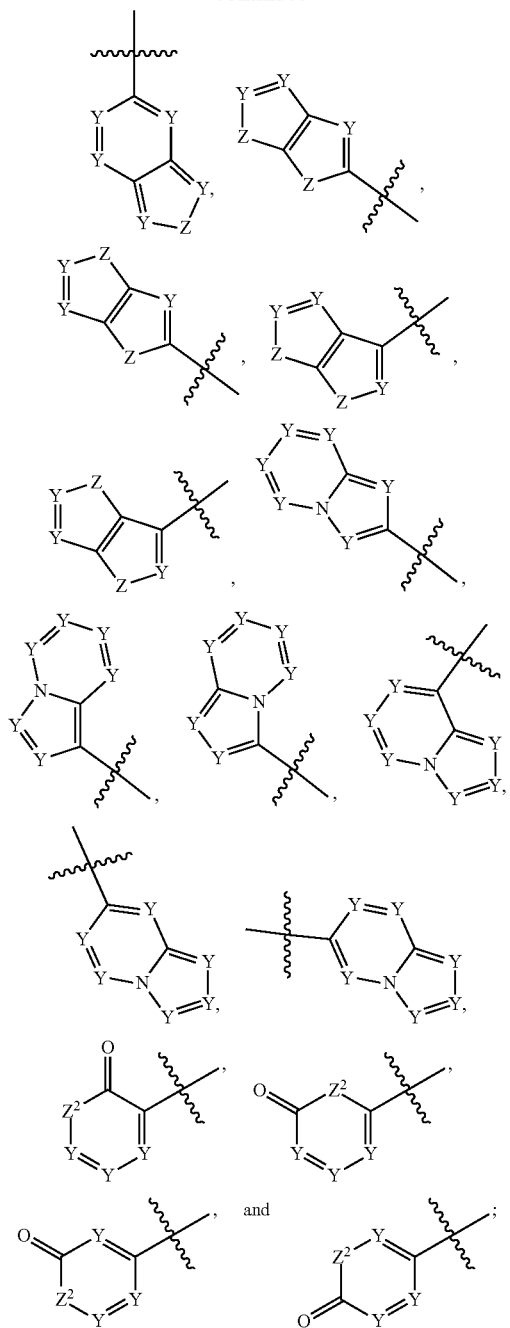
In an additional embodiment, $R^{16}$ is selected from:
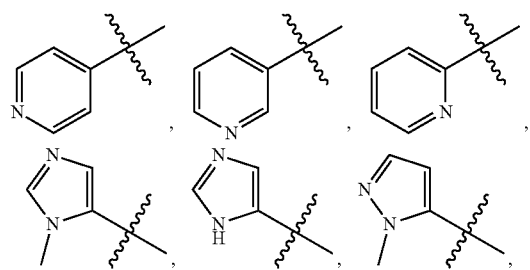
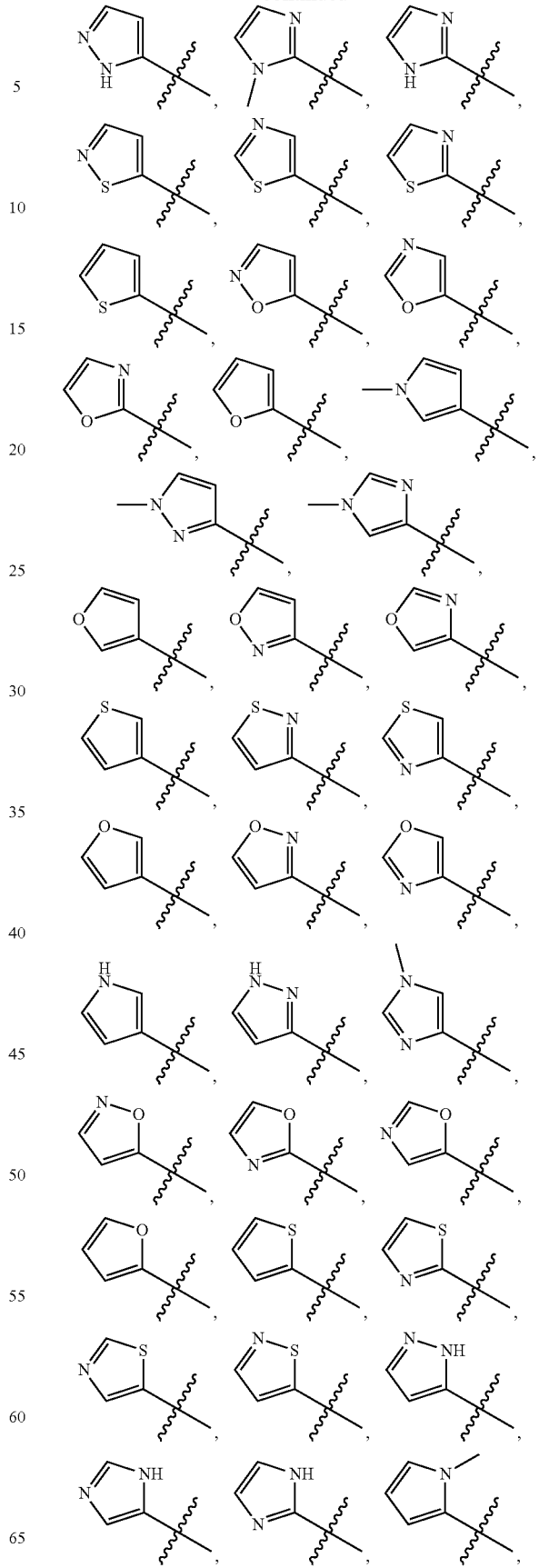

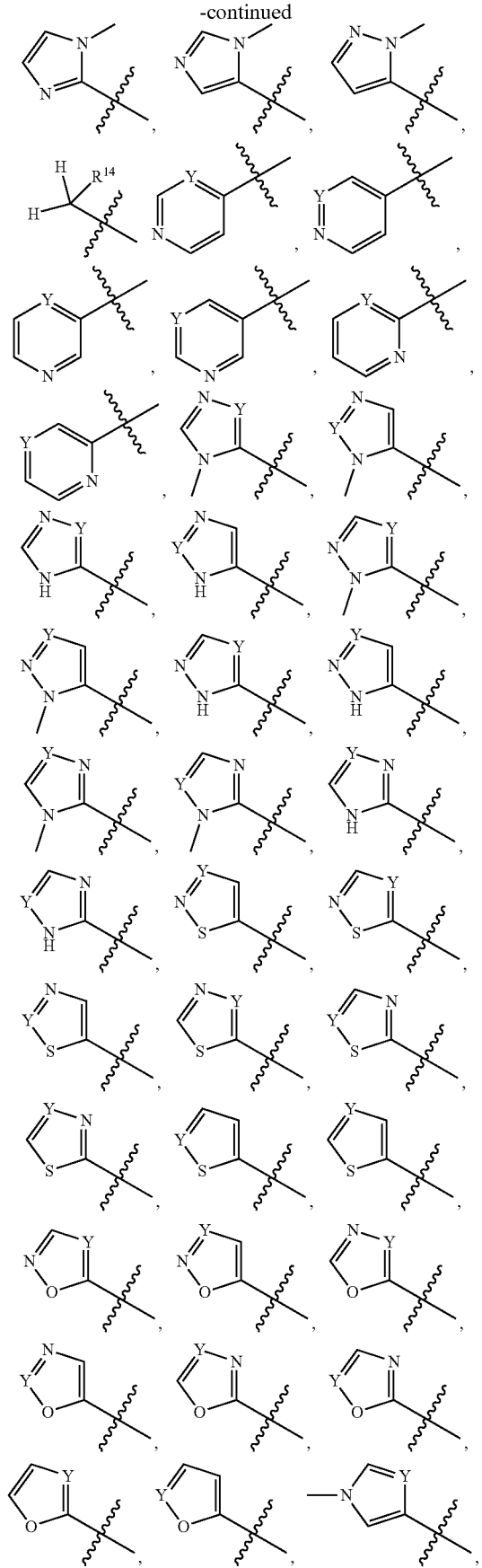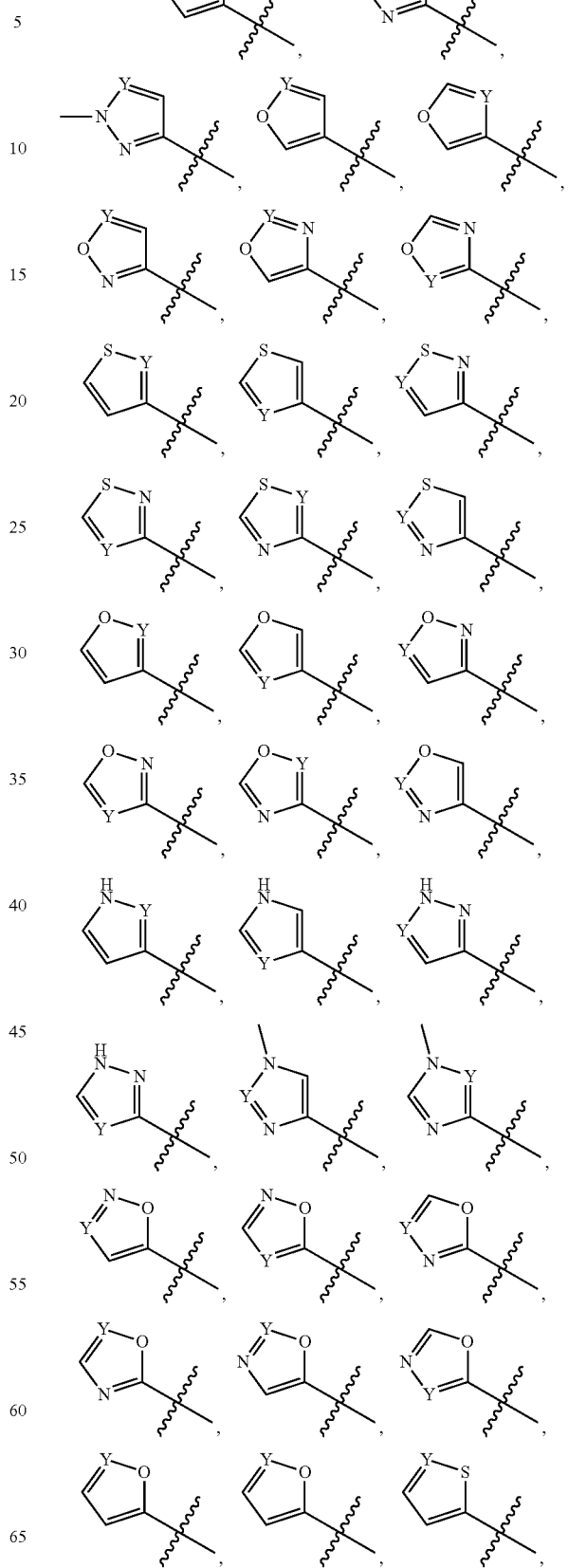

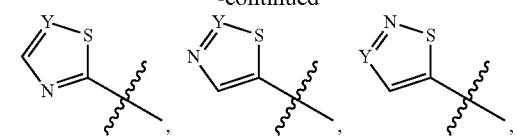
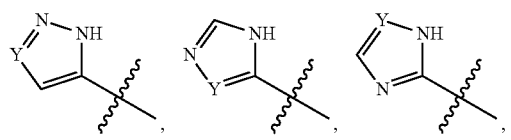
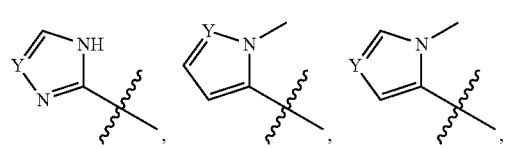
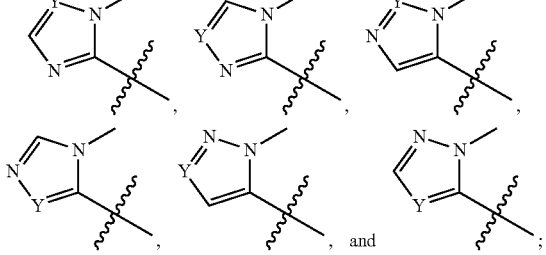
In an additional embodiment, R$^{16}$ is selected from:
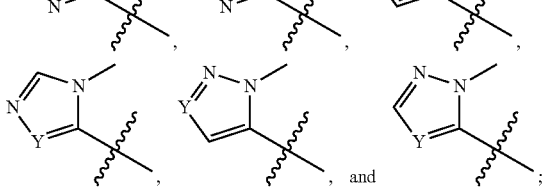
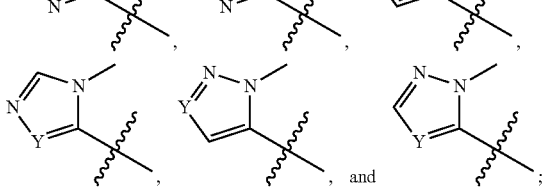
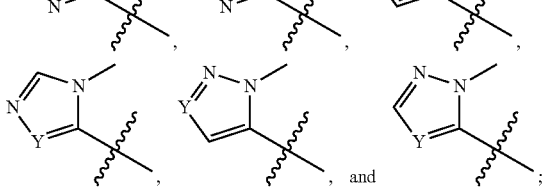
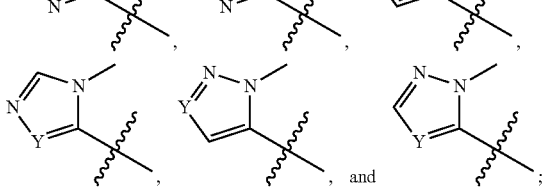
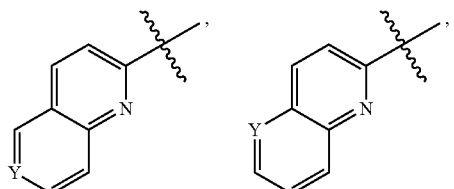
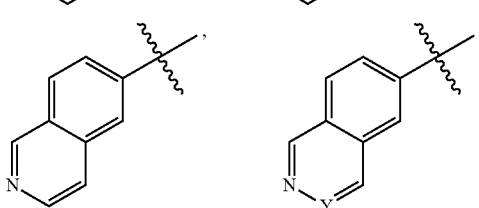
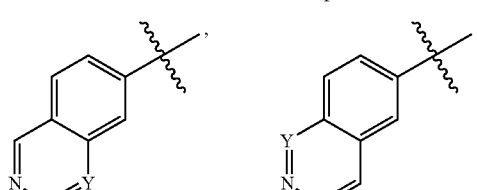
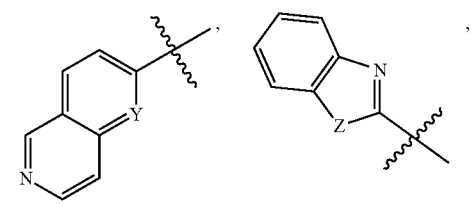
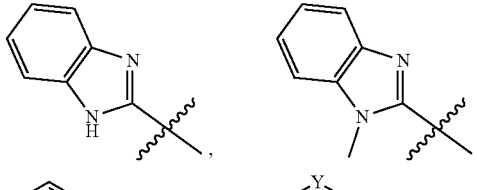
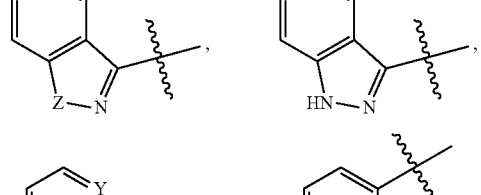
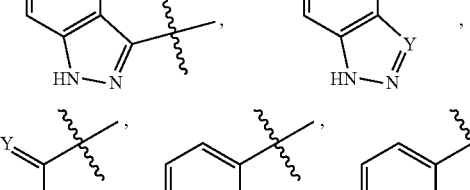
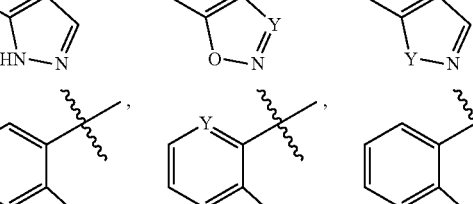
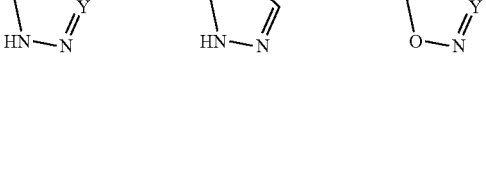
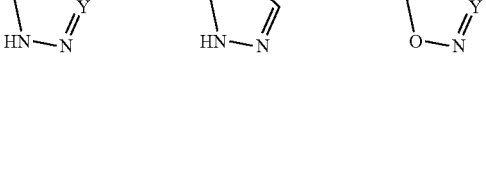
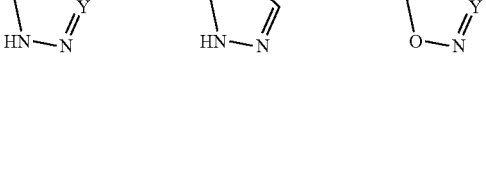
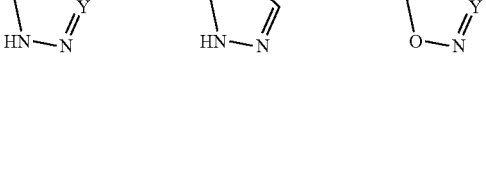
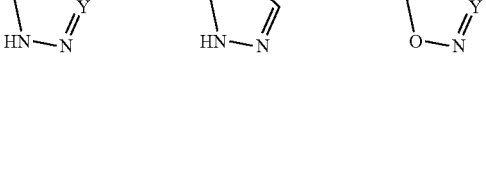
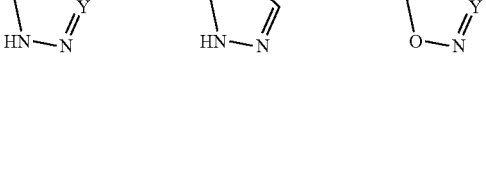

-continued

-continued
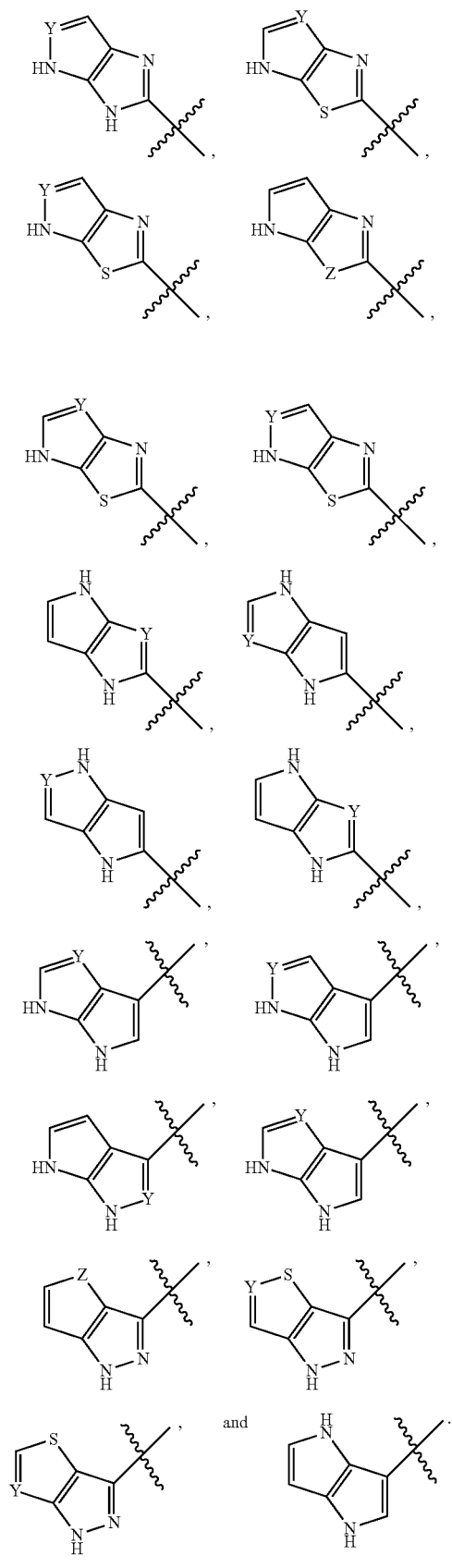
In an additional embodiment, R[16] is selected from
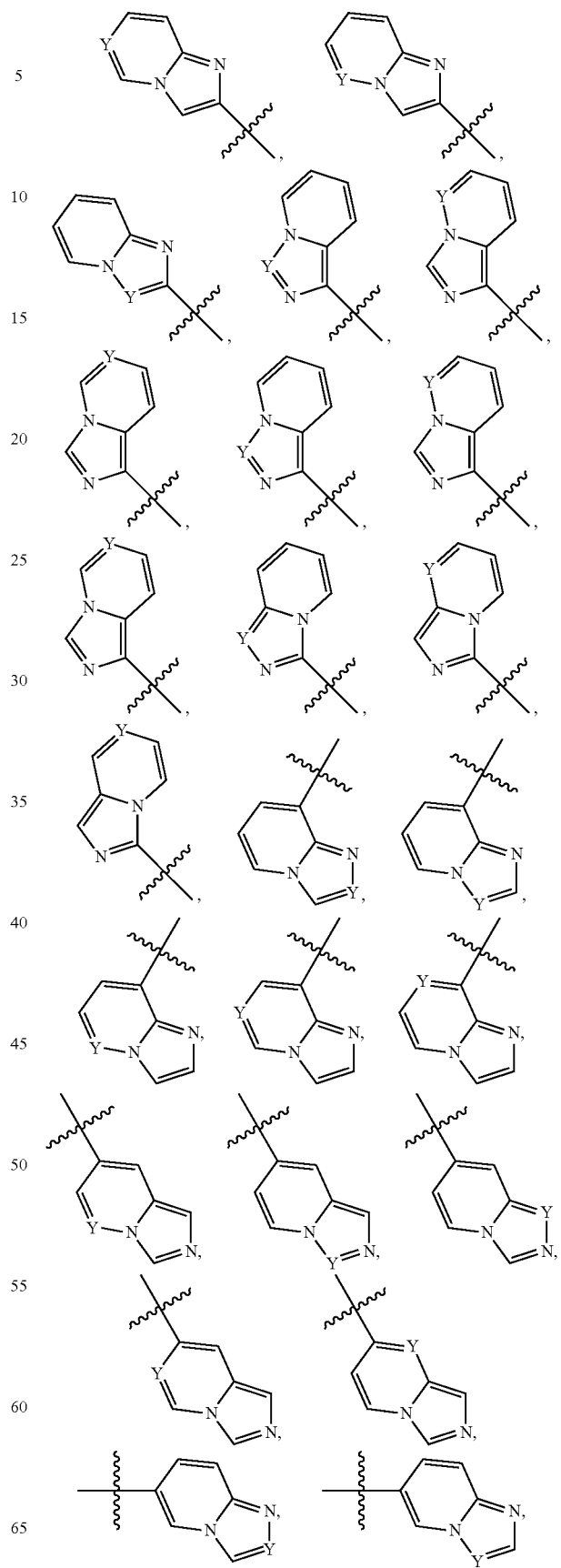

-continued

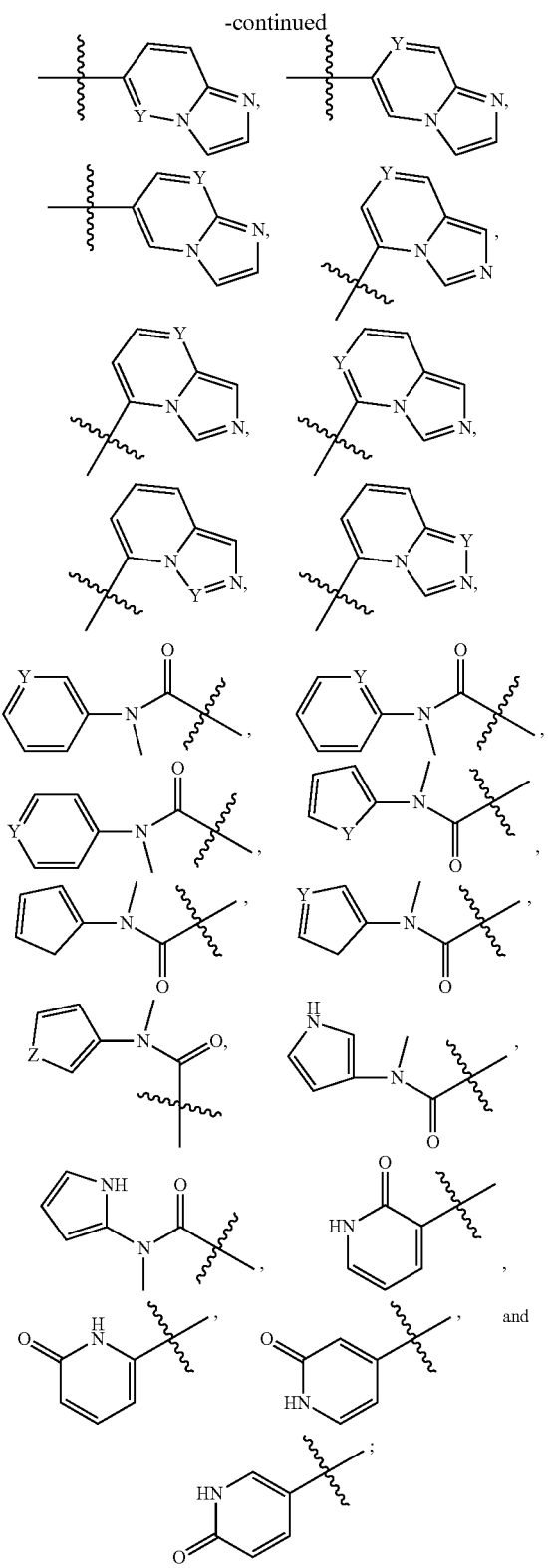

Y is independently selected from N, CH, or CR$^{11}$, wherein 0, 1, or 2 instances of Y are selected to be N;
or 3 instances of Y are selected to be N;
Z is NH, O, S, or NR$^{12}$;
Z$^2$ is NH or NR$^{12}$;

R$^1$, R$^2$, R$^3$, R$^4$, R$^7$, R, and R$^{15}$ are independently selected from hydrogen, alkyl, hydroxyl, alkoxy, amine, —NHalkyl, and —Nalkyl$_2$ each of which is optionally substituted as described in the Definition Section, if desired to achieve the target effect, results in a stable compound that makes chemical sense to the routineer, and the group is not redundant (i.e., as known in the art, alkyl substituted with alkyl is redundant; however for examples, alkoxy substituted with alkoxy is not redundant);
or R$^1$ and R$^2$ together with the carbon to which they are attached form a 3-, 4-, 5-, or 6-membered spirocarbocycle, or a 4-, 5-, or 6-membered spiroheterocycle comprising 1 or 2 heteroatoms selected from N and O;
or R$^3$ and R$^4$ together with the carbon to which they are attached form a 3-, 4-, 5-, or 6-membered spirocarbocycle, or a 4-, 5-, or 6-membered spiroheterocycle comprising 1 or 2 heteroatoms selected from N and O;
or R$^7$ and R$^8$ together with the carbon to which they are attached form a 3-, 4-, 5-, or 6-membered spirocarbocycle, or a 4-, 5-, or 6-membered spiroheterocycle comprising 1 or 2 heteroatoms selected from N and O;
or R$^1$ and R$^3$ form a 1 or 2 carbon bridged ring;
or R$^1$ and R$^7$ form a 1 or 2 carbon bridged ring;
or R$^3$ and R$^7$ form a 1 or 2 carbon bridged ring;
or R$^{15}$ and R$^1$ form a 3, 4, 5, or 6 carbon fused ring;
or R$^{15}$ and R$^7$ form a 3, 4, 5, or 6 carbon fused ring;
or R$^{15}$ and R$^3$ form a 1 or 2 carbon bridged ring;
or R$^{15}$ and R$^5$ form a 3, 4, 5, or 6 carbon fused ring wherein R$^5$ is on the carbon alpha to R$^{15}$ or a 1, 2, 3, or 4 carbon bridged ring wherein R$^5$ is not on the carbon alpha to R$^{15}$;
R$^5$ is selected at each instance from: alkyl, alkene, alkyne, halogen, hydroxyl, alkoxy, azide, amino, —NHalkyl, —N(alkyl)$_2$, —NHSO$_2$alkyl, —N(alkyl)SO$_2$alkyl, —NHSO$_2$aryl, —N(alkyl)SO$_2$aryl, —NHSO$_2$alkenyl, —N(alkyl)SO$_2$alkenyl, —NHSO$_2$alkynyl, —N(alkyl)SO$_2$alkynyl, and haloalkyl, each of which is optionally substituted as described in the Definition Section, if desired to achieve the target effect, results in a stable compound that makes chemical sense to the routineer, and the group is not redundant (i.e., as known in the art, alkyl substituted with alkyl is redundant; however for examples, alkoxy substituted with alkoxy is not redundant);
or two R$^5$ substituents together with the carbon atom(s) to which they are bound can form a 3, 4, 5 or 6 membered ring;
R$^{11}$ is selected at each instance from: hydrogen, alkyl, alkenyl, alkynyl, halogen, hydroxyl, alkoxy, aryl, heteroaryl, alkylamino, alkylhydroxyl, —NHalkyl, —Nalkyl$_2$, amino, cyano, nitro, nitroso, sulfone, sulfoxide, thioalkyl, thiol and haloalkyl, each of which is optionally substituted as described in the Definition Section, if desired to achieve the target effect, results in a stable compound that makes chemical sense to the routineer, and the group is not redundant (i.e., as known in the art, alkyl substituted with alkyl is redundant; however for examples, alkoxy substituted with alkoxy is not redundant);
R$^{12}$ is selected at each instance from: alkyl, —C(O)H, —C(O)OH, —C(O)alkyl, —C(O)Oalkyl, alkene, and alkyne;
R$^{13}$ and R$^{14}$ are independently selected from hydrogen, alkyl, alkenyl, alkynyl, alkoxy, haloalkoxy, hydroxy, amino, —NHalkyl, and —N(alkyl)$_2$;
or R$^{13}$ and R$^{14}$ together with the carbon atom to which they are attached, form C(O), C(S), C=CH2, a 3-, 4-, 5-, or 6-membered spirocarbocycle, or a 4-, 5-, or 6-membered spiroheterocycle comprising 1 or 2 heteroatoms selected from N and O.

Non-limiting examples of compounds of Formula III include:
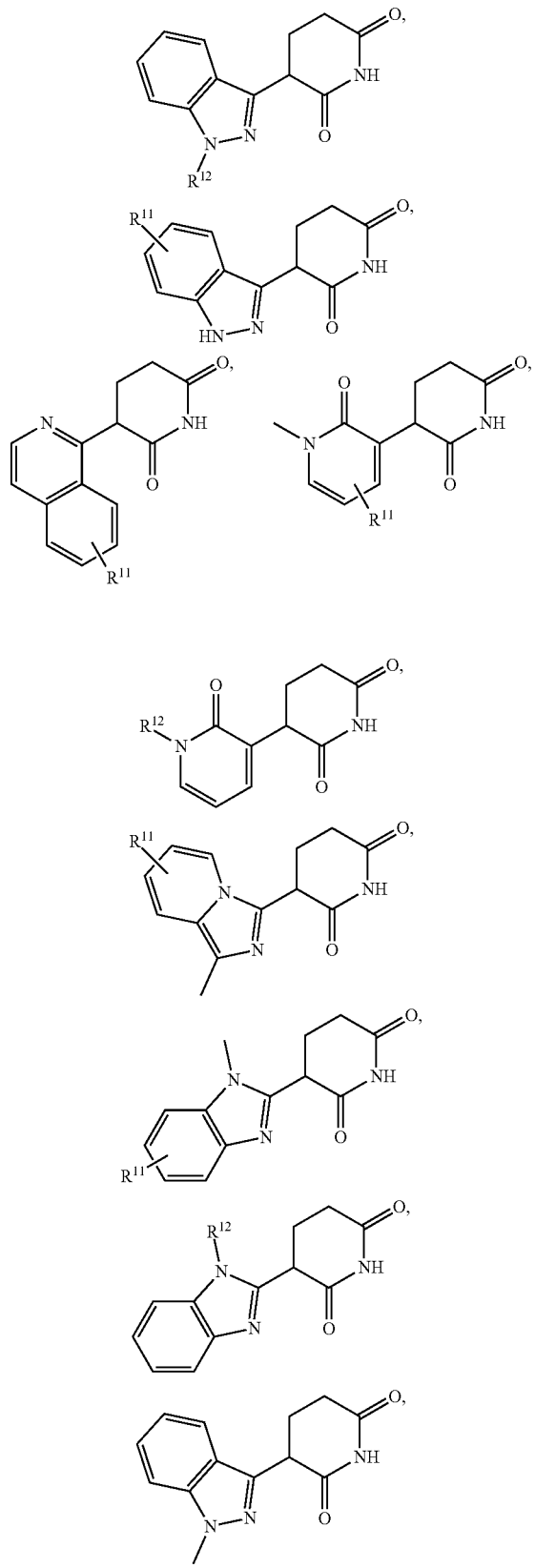
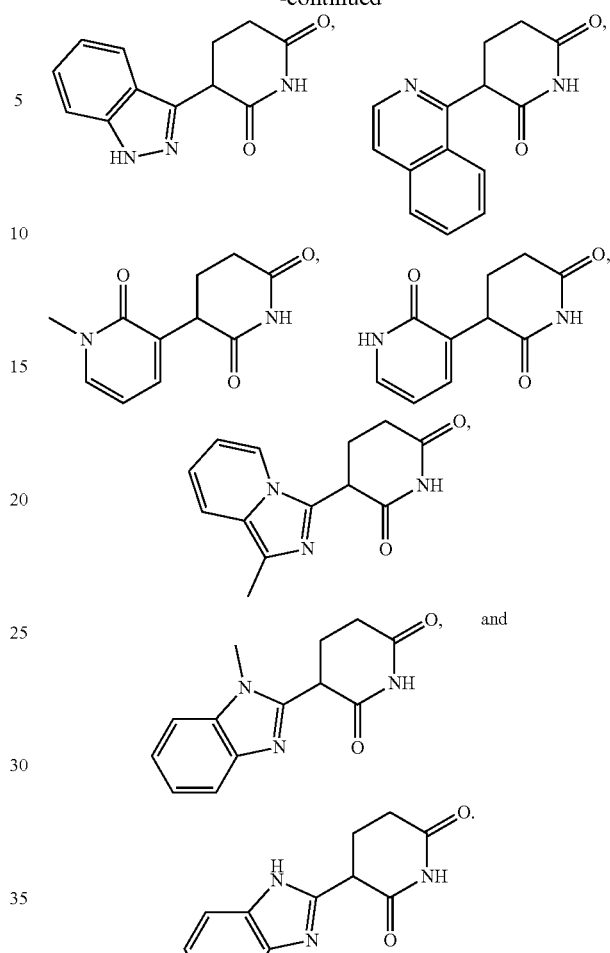
Formula V-A
In one aspect of the present invention a compound of Formula V is provided, wherein the compound of Formula V-A is selected from:
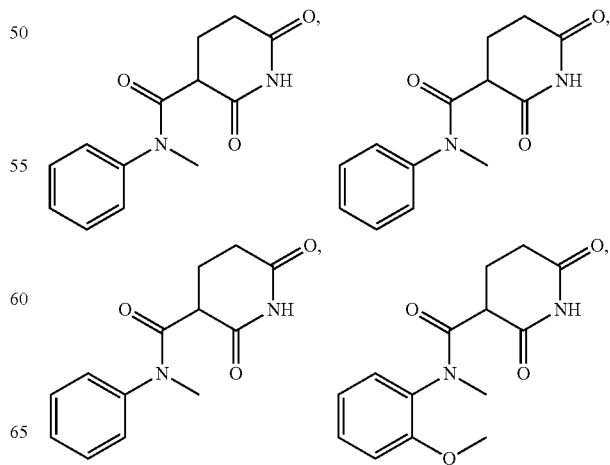

-continued
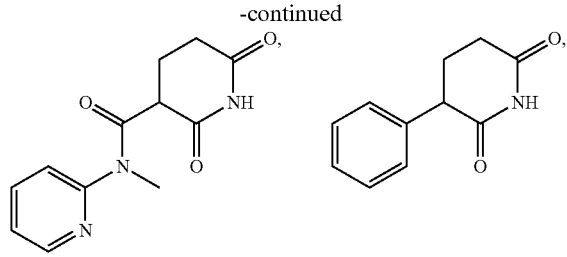
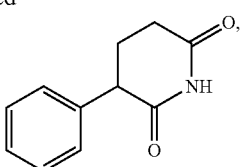
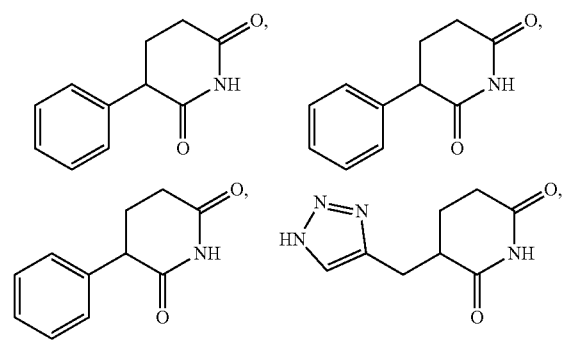
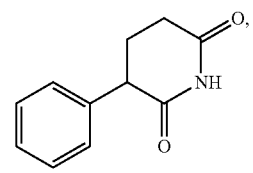
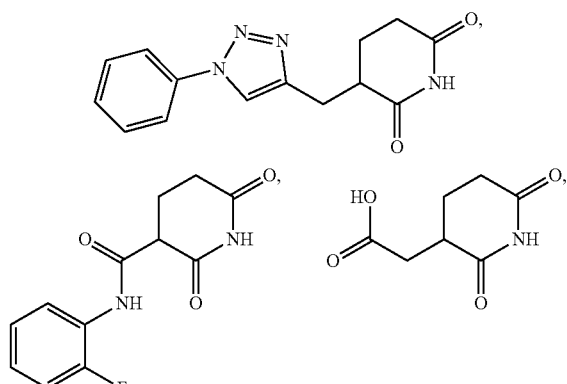
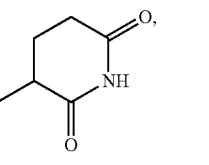
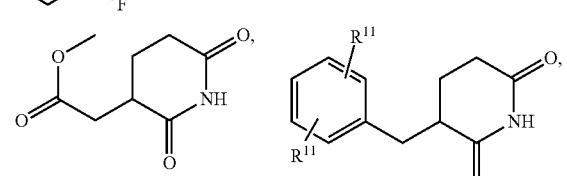
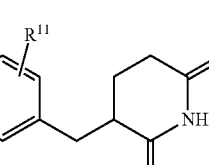
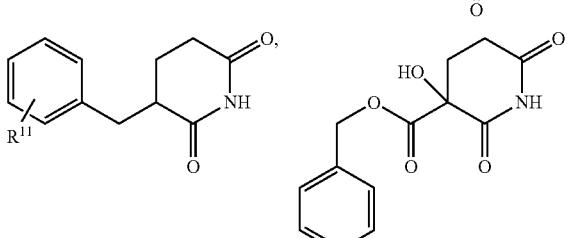
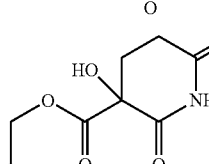
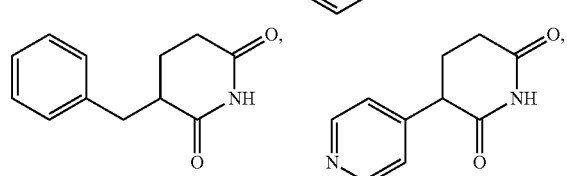
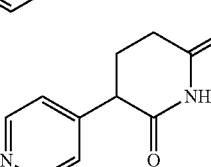
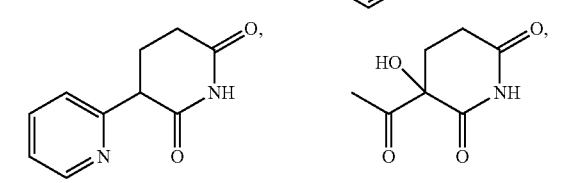
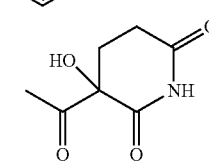
-continued
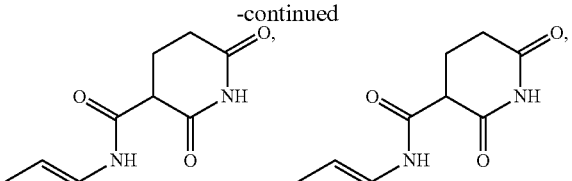
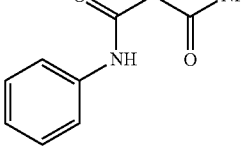
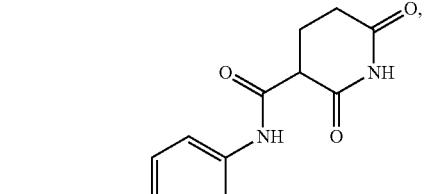
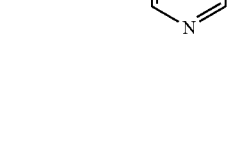
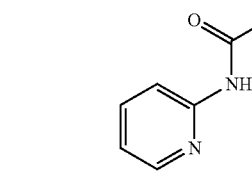
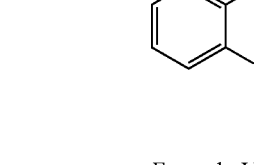
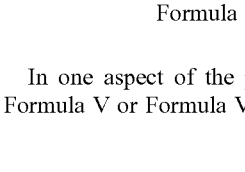
Formula V and Formula VI
In one aspect of the present invention a compound of Formula V or Formula VI is provided:
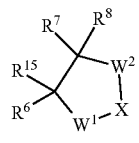
(V)
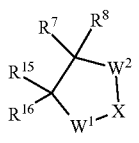
(VI)
or a pharmaceutically acceptable salt, N-oxide, isotopic derivative, or prodrug thereof, optionally in a pharmaceutically acceptable carrier to form a composition;

wherein:

Non-limiting examples of compounds of Formula V include:

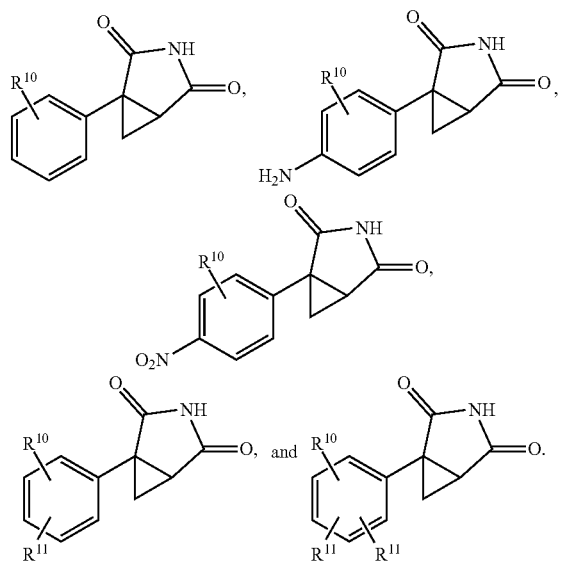

Non-limiting examples of compounds of Formula VI include:

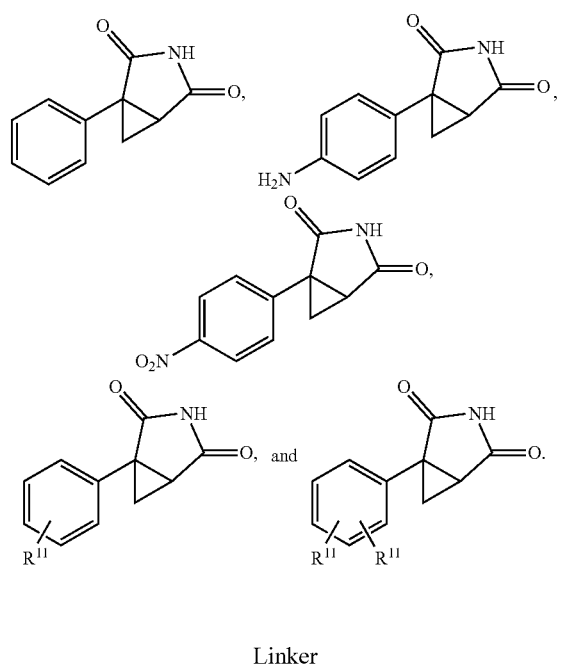

Linker

A Linker is included in the Degronimers of Formula I, II, V and VII. Linker is a bond or a chemically stable group that attaches a Degron to a Targeting Ligand.

Any of the Linkers described herein can be used in either direction, i.e., either the left end is linked to the Degron and the right end is linked to the Target Linker, or the left end is linked to the Target Linker and the right end is linked to the Degron. According to the invention, any desired linker can be used as long as the resulting compound has a stable shelf life for at least 2 months, 3 months, 6 months or 1 year as part of a pharmaceutically acceptable dosage form, and itself is pharmaceutically acceptable.

In a typical embodiment, the Linker has a chain of 2 to 14, 15, 16, 17, 18 or 20 or more carbon atoms of which one or more carbons can be replaced by a heteroatom such as O, N, S, or P. In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units). In certain embodiments the chain has at least 1, 2, 3, 4, 5, 6, 7, or 8 contiguous chains which can have branches which can be independently alkyl, heteroalkyl, aryl, heteroaryl, alkenyl, or alkynyl, aliphatic, heteroaliphatic, cycloalkyl or heterocyclic substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocyclic, cycloalkyl, etc., as desired to achieve the appropriate drug properties.

In one embodiment, the Linker is a moiety selected from Formula LI, Formula LII, Formula LIII, Formula LIV, Formula LV, Formula LVI, and Formula LVII:

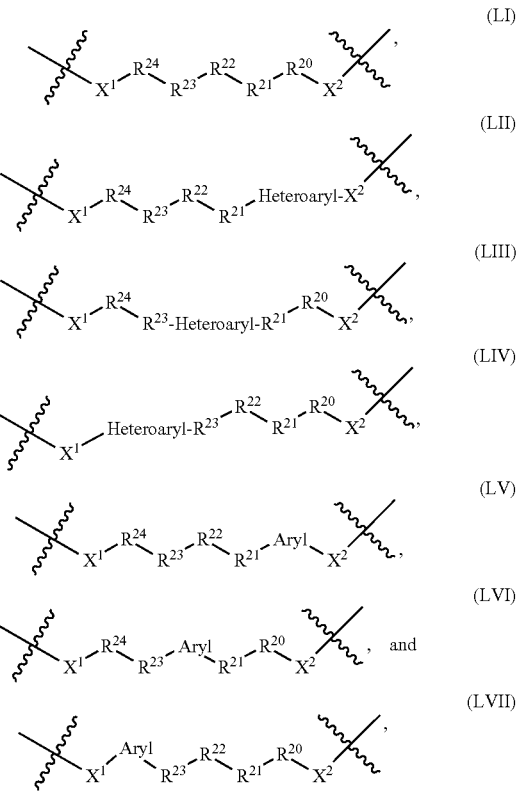

wherein:

$X^1$ and $X^2$ are independently selected from bond, NH, $NR^{25}$, $CH_2$, $CHR^{25}$, $C(R^{25})_2$, O, and S;

$R^{20}$, $R^{21}$, $R^{22}$, $R^{23}$, and $R^{24}$ are independently selected from bond, alkyl, —C(O)— —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—NHR$^{25}$)—, —CH(—NH$_2$)—, —CH(—NR$^{25}_2$)—, —C(—O—R$^{26}$)alkyl-, —C(—NHR$^{25}$)alkyl-, —C(—NH$_2$)alkyl-, —C(—NR$^{25}_2$)alkyl-, —C(R$^4$R$^4$)—, -alkyl(R$^{27}$)-alkyl(R$^{28}$)—, —C(R$^{27}$R$^{28}$)—, —P(O)(OR$^{26}$)O—, —P(O)(OR$^{26}$)—, —NHC(O)NH—, —N(R$^{25}$)C(O)N(R$^{25}$)—, —N(H)C(O)N(R$^{25}$)—, polyethylene glycol, poly(lactic-co-glycolic acid), alkene, haloalkyl, alkoxy, and alkyne;

or $R^{20}$, $R^{21}$, $R^{22}$, $R^{23}$, and $R^{24}$ can in addition to those above be independently selected from heteroarylalkyl, aryl, arylalkyl, heterocycle, aliphatic, heteroaliphatic, heteroaryl, polypropylene glycol, lactic acid, glycolic acid, carbocycle, or —O—(CH$_2$)$_{1-12}$—O—, —NH—(CH$_2$)$_{1-12}$—NH—, —NH—(CH$_2$)$_{1-12}$—O—, or —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, —NH—(CH$_2$)$_{1-12}$—S—, (and wherein the 1-12 can be independently 1, 2, 3, 4, 5, 6, 7, 8, 9, 10, 11 or 12, and wherein one or more of the CH$_2$ or NH can be modified by substitution of a H for a methyl, ethyl, cyclopropyl, F (if on carbon), etc., as described herein), and optionally, a heteroatom, heteroalkyl, aryl, heteroaryl or cycloaliphatic group is interspersed in the chain). Certain nonlimiting examples include —O—CH(CH$_3$)—CH(CH$_3$)CH—O—, —O—CH$_2$—CH(CH$_3$)CH—O—, —O—CH(CH$_3$)—CH$_2$CH—O—, etc.

each of which $R^{20}$, $R^{21}$, $R^{22}$, $R^{23}$, and $R^{24}$ is optionally substituted with one or more substituents selected from $R^{101}$ or alternatively as described in Section 1. Definitions; and $R^{25}$ is selected at each instance from: alkyl, —C(O)H, —C(O)OH, —C(O)alkyl, —C(O)Oalkyl, alkenyl, or alkynyl or alternatively can be aliphatic, heteroaliphatic, aryl, heteroaryl or heterocyclic;

$R^{26}$ is hydrogen, alkyl, silane, arylalkyl, heteroarylalkyl, alkene, and alkyne; or in addition to these can also be selected from aryl, heteroaryl, heterocyclic, aliphatic and heteroaliphatic;

$R^{27}$ and $R^{28}$ are independently selected from hydrogen, alkyl, amine, or together with the carbon atom to which they are attached, form C(O), C(S), C=CH$_2$, a $C_3$-$C_6$ spirocarbocycle, or a 4-, 5-, or 6-membered spiroheterocycle comprising 1 or 2 heteroatoms selected from N and O, or form a 1 or 2 carbon bridged ring;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, heteroaliphatic; and $R^4$ is independently selected from hydrogen, alkyl, hydroxyl, alkoxy, amine, —NHalkyl, and —Nalkyl$_2$ each of which is optionally substituted as described in the Definition Section, if desired to achieve the target effect, results in a stable compound that makes chemical sense to the routineer, and the group is not redundant (i.e., as known in the art, alkyl substituted with alkyl is redundant; however for examples, alkoxy substituted with alkoxy is not redundant).

In an additional embodiment, the Linker is a moiety selected from Formula LVIII, LIX, and LX:

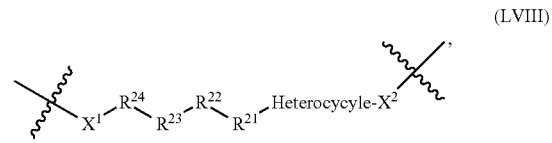

(LVIII)

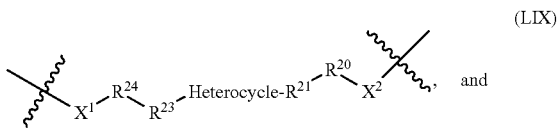

(LIX)

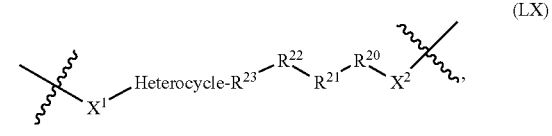

(LX)

wherein each variable is as it is defined in Formula LI. In alternative embodiments of LVIII, LIX and LX, a carbocyclic ring is used in place of the heterocycle.

The following are non-limiting examples of Linkers that can be used in this invention. Based on this elaboration, those of skill in the art will understand how to use the full breadth of Linkers that will accomplish the goal of the invention.

As certain non-limiting examples, Formula LI, Formula LII, Formula LIII, Formula LIV, Formula LV, Formula LVI, or Formula LVII include:

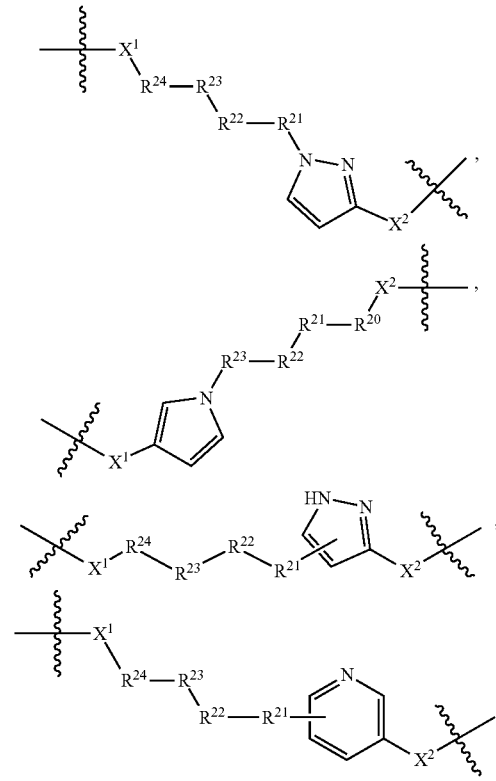

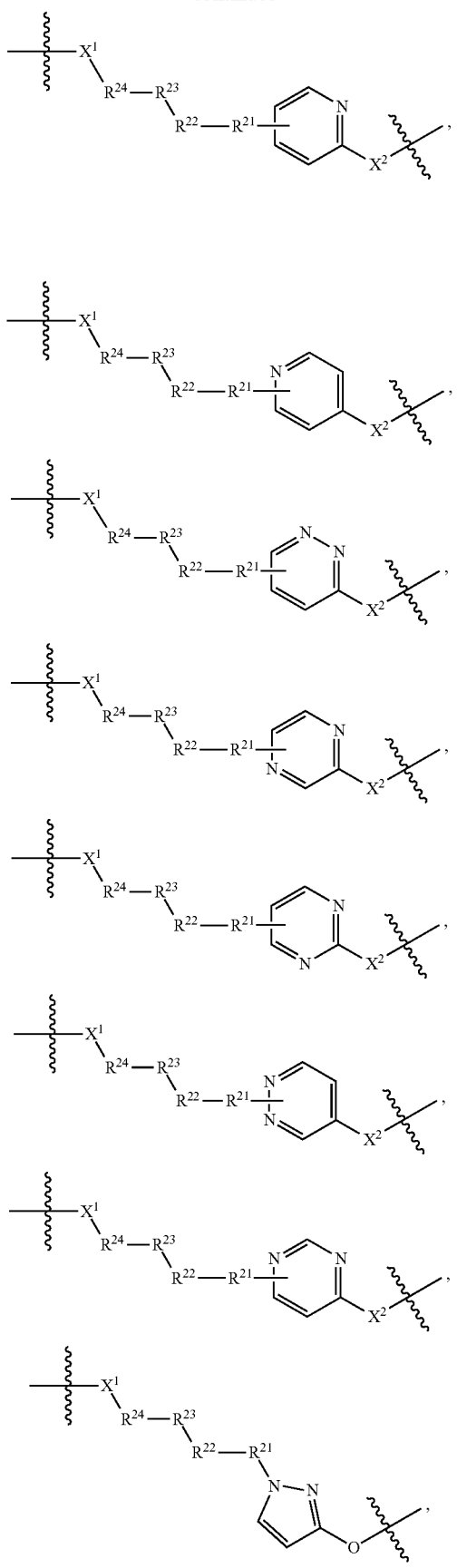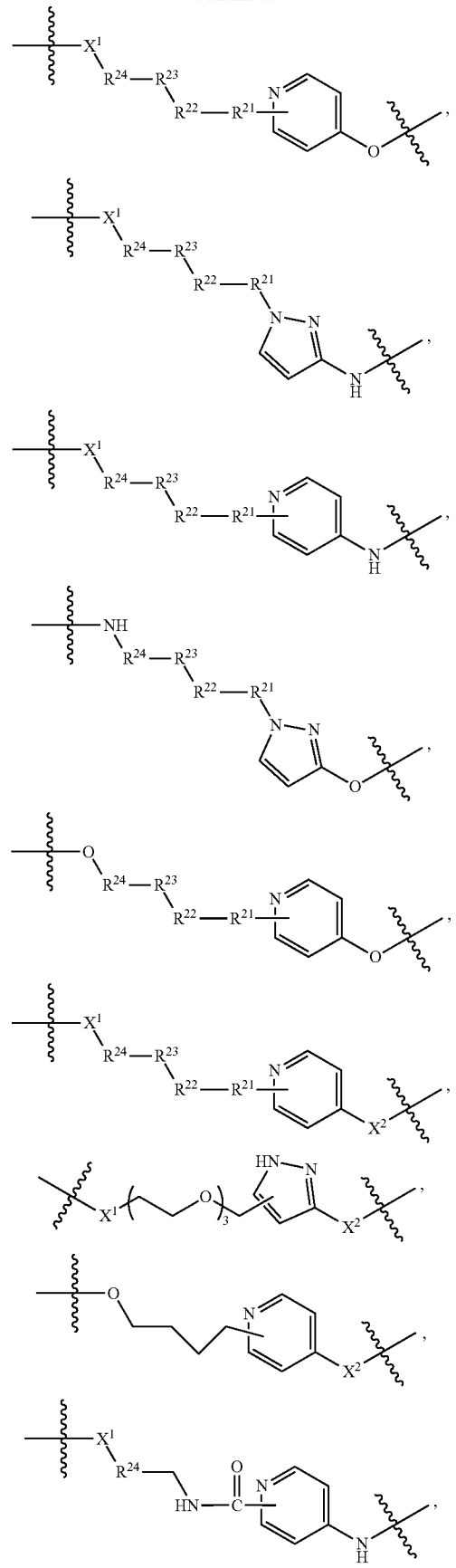

-continued
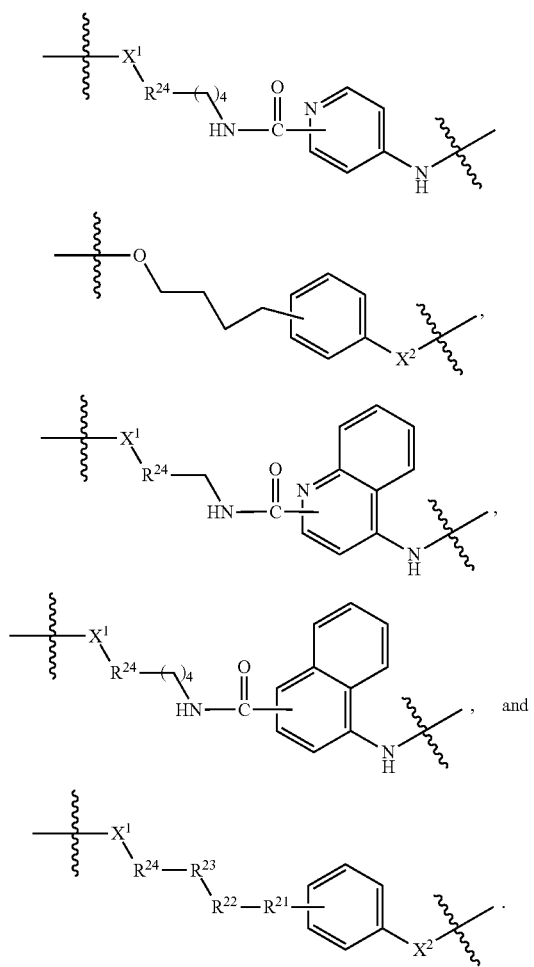
In an additional embodiment Linker is selected from:
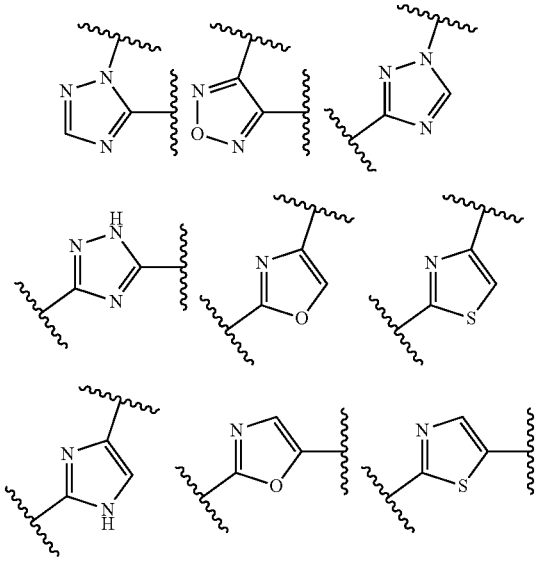
In an additional embodiment Linker is selected from:
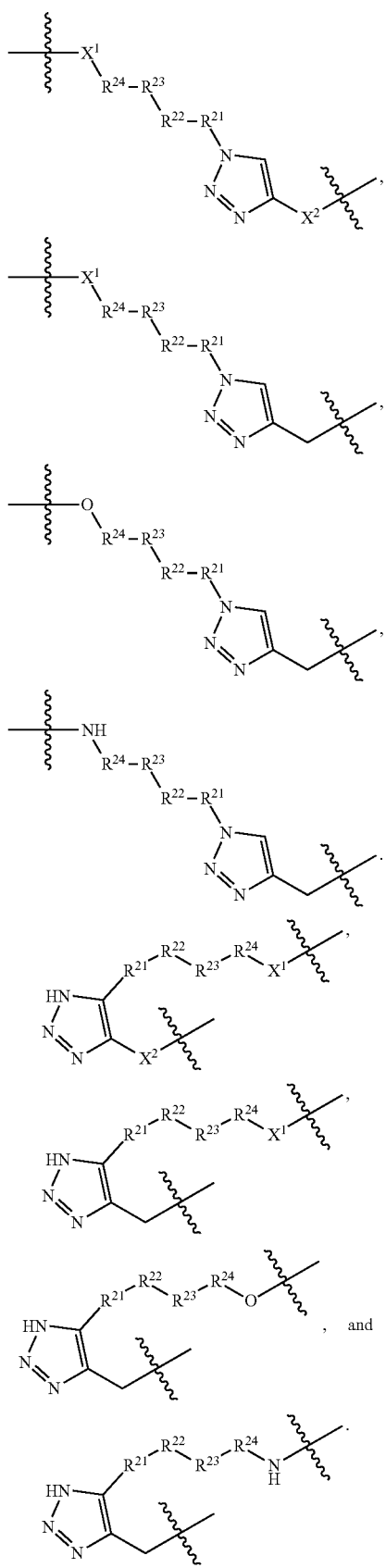

In one embodiment $X^1$ is attached to the Targeting Ligand. In another embodiment $X^2$ is attached to the Targeting Ligand.
Non-limiting examples of moieties of $R^2$, $R^{21}$, $R^{22}$, $R^{23}$, and $R^{24}$ include:
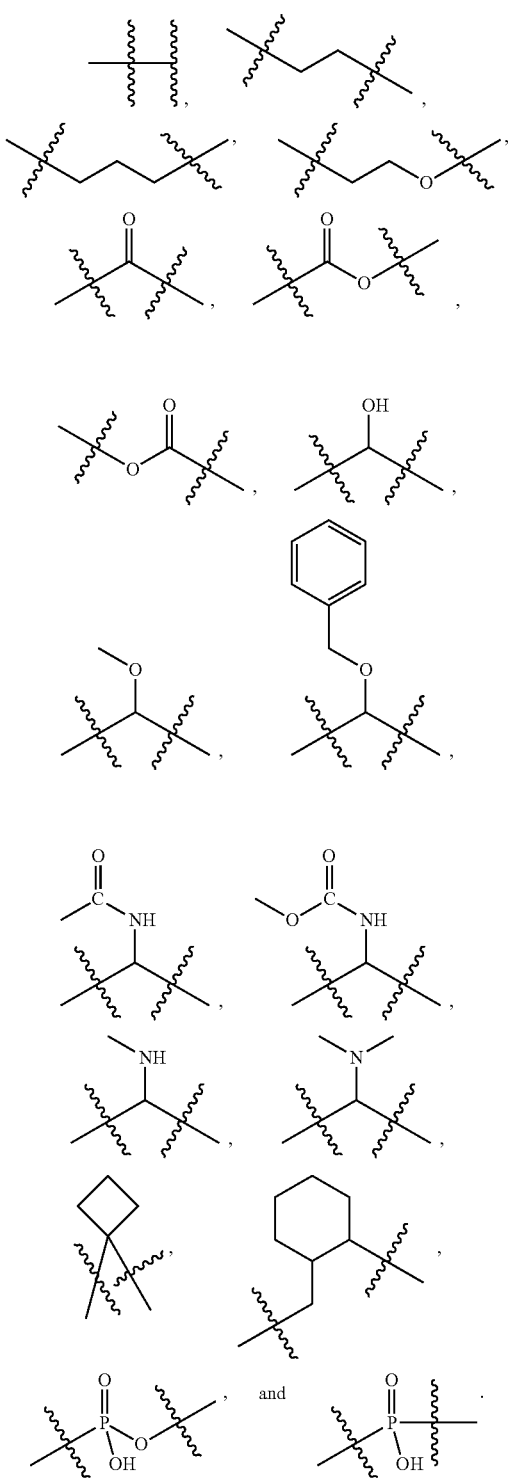
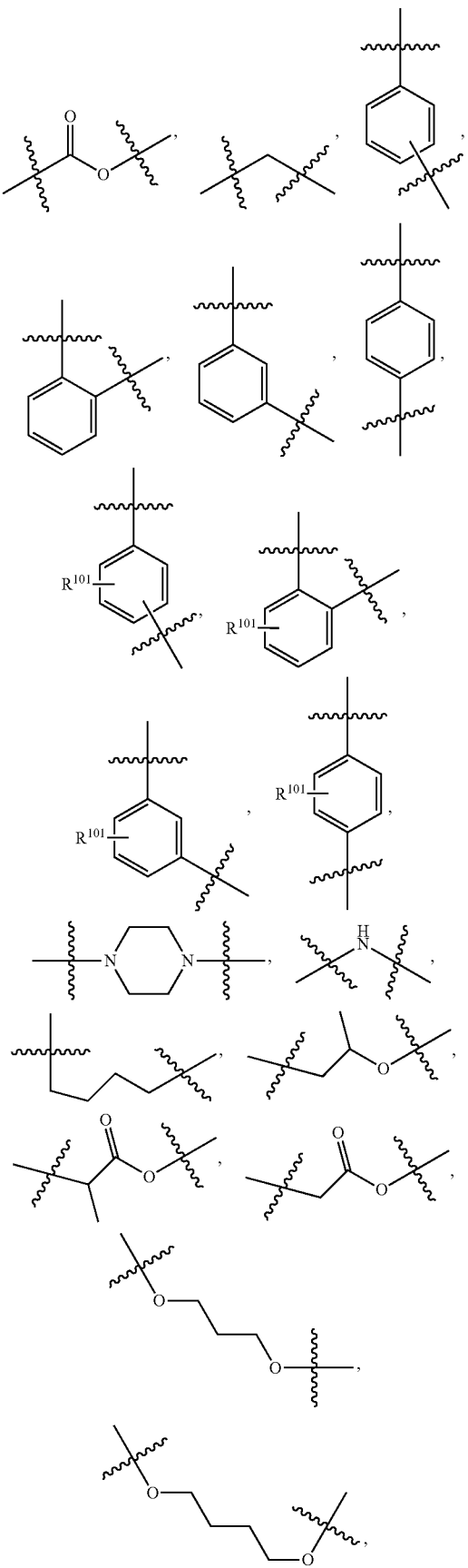
Additional non-limiting examples of moieties of $R^{20}$, $R^{21}$, $R^{22}$, $R^{23}$, and $R^{24}$ include:

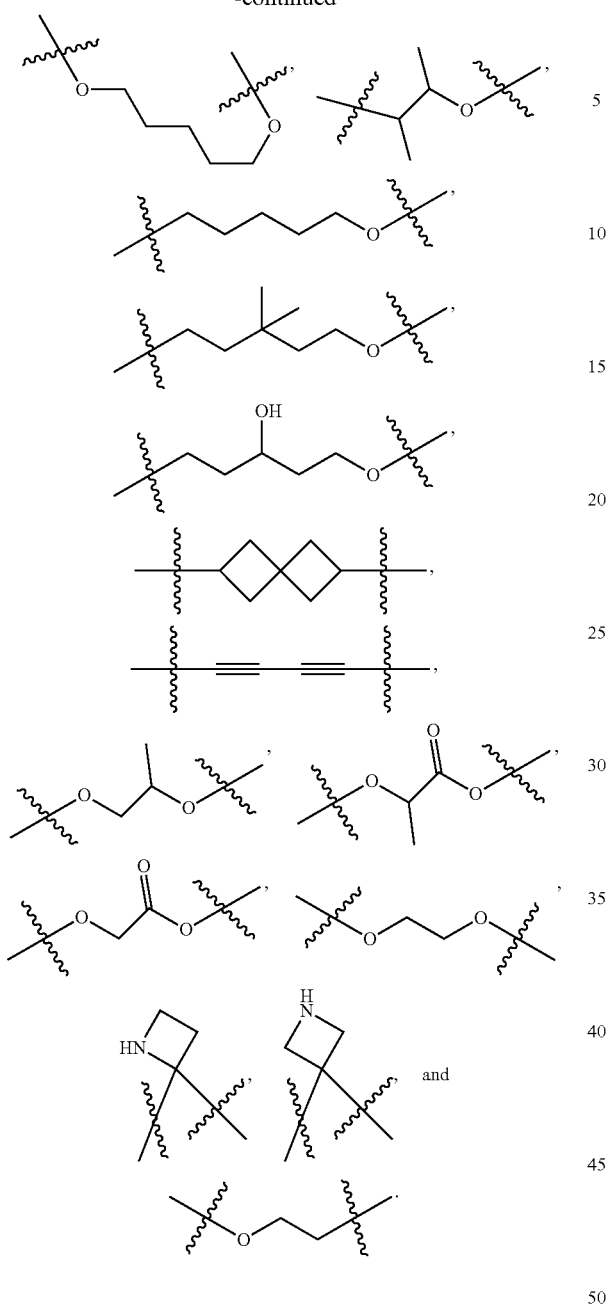
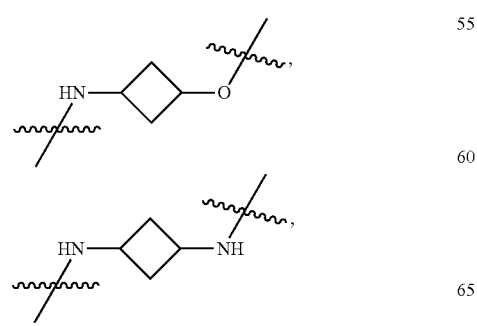
Additional non-limiting examples of moieties of $R^{20}$, $R^{21}$, $R^{22}$, $R^{23}$, and $R^{24}$ include:
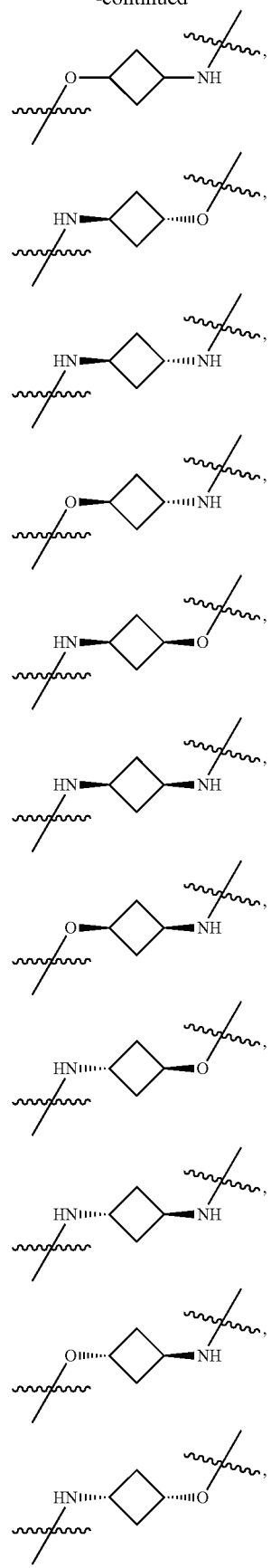

Additional non-limiting examples of moieties of $R^{20}$, $R^{21}$, $R^{22}$, $R^{23}$, and $R^{24}$ include:

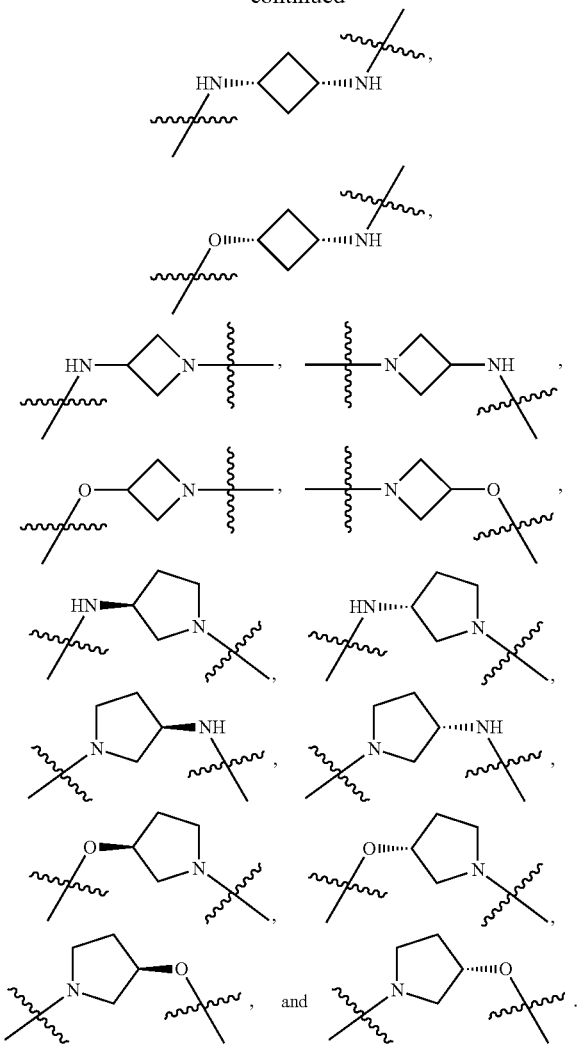

Additional non-limiting examples of moieties of $R^{20}$, $R^{21}$, $R^{22}$, $R^{23}$, and $R^{24}$ include:

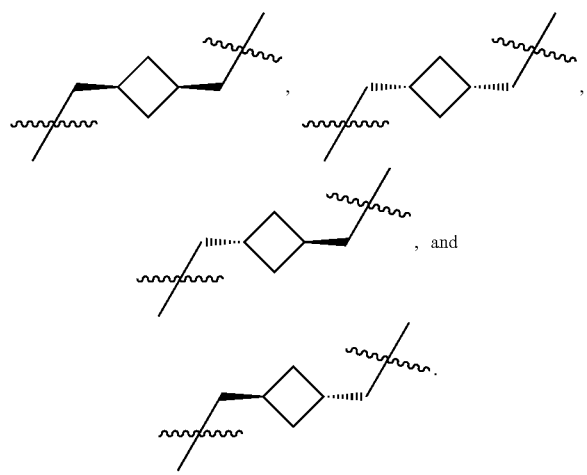

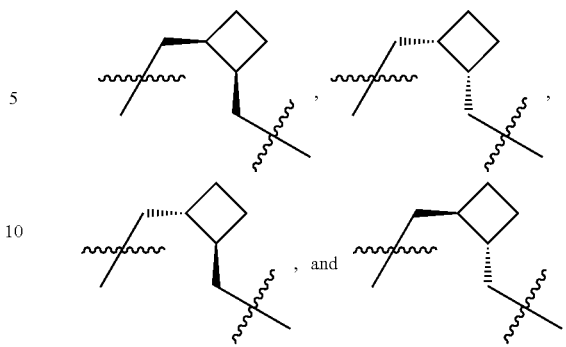

In additional embodiments, the Linker group is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, the Linker is flanked, substituted, or interspersed with an aryl, phenyl, benzyl, alkyl, alkylene, or heterocycle group. In certain embodiments, the Linker may be asymmetric or symmetrical. In some embodiments, the Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, the Linker group may be any suitable moiety as described herein.

In additional embodiments, the Linker is selected from:
—$NR^{61}(CH_2)_{n1}$-(lower alkyl)-, —$NR^{61}(CH_2)_{n1}$-(lower alkoxyl)-,
—$NR^{61}(CH_2)_{n1}$-(lower alkoxyl)-$OCH_2$—, —$NR^{61}(CH_2)_{n1}$-(lower alkoxyl)-(lower alkyl)-$OCH_2$—,
—$NR^{61}(CH_2)_{n1}$-(cycloalkyl)-(lower alkyl)-$OCH_2$—, —$NR^{61}(CH_2)_{n1}$-(heterocycloalkyl)-,
—$NR^{61}(CH_2CH_2O)_{n1}$-(lower alkyl)-O—$CH_2$—, —$NR^{61}(CH_2CH_2O)_{n1}$-(heterocycloalkyl)-O—$CH_2$—,
—$NR^{61}(CH_2CH_2O)_{n1}$-Aryl-O—$CH_2$—, —$NR^{61}(CH_2CH_2O)_{n1}$-(heteroaryl)-O—$CH_2$—,
—$NR^{61}(CH_2CH_2O)_{n1}$-(cycloalkyl)-O-(heteroaryl)-O—$CH_2$—,
—$NR^{61}(CH_2CH_2O)_{n1}$-(cycloalkyl)-O-Aryl-O—$CH_2$—,
—$NR^{61}(CH_2CH_2O)_{n1}$-(lower alkyl)-NH-Aryl-O—$CH_2$—,
—$NR^{61}(CH_2CH_2O)_{n1}$-(lower alkyl)-O-Aryl-$CH_2$,
—$NR^{61}(CH_2CH_2O)_{n1}$-cycloalkyl-O-Aryl-, —$NR^{61}(CH_2CH_2O)_{n1}$-cycloalkyl-O-heteroaryl-,
—$NR^{61}(CH_2CH_2)_{n1}$-(cycloalkyl)-O-(heterocycle)-$CH_2$,
—$NR^{6}(CH_2CH_2)_{n1}$-(heterocycle)-(heterocycle)-$CH_2$, and
—$NR^{61}$-(heterocycle)-$CH_2$;
wherein n1 is 0, 1, 2, 3, 4, 5, 6, 7, 8, 9, or; and $R^{61}$ is H, methyl, or ethyl.

In additional embodiments, the Linker is selected from:
—$N(R^{61})$—$(CH_2)_{m1}$—$O(CH)_{n2}$—$O(CH_2)_{o1}$—$O(CH_2)_{p1}$—$O(CH_2)_{q1}$—$O(CH_2)_{r1}$—$OCH_2$—,
—O—$(CH_2)_{m1}$—$O(CH_2)_{n2}$—$O(CH_2)_{o1}$—$O(CH_2)_{p1}$—O$(CH_2)_{q1}$—$O(CH_2)_{r1}$—$OCH_2$—,
—O—$(CH_2)_{m1}$—$O(CH_2)_{n2}$—$O(CH_2)_{o1}$—$O(CH_2)_{p1}$—O$(CH_2)_{q1}$—$O(CH_2)_{r1}$—O—;
—$N(R^{61})$—$(CH_2)_{m1}$—$O(CH)_{n2}$—$O(CH)_{o1}$—$O(CH_2)_{p1}$—O$(CH_2)_{q1}$—$O(CH_2)_{r1}$—O—;

—$(CH_2)_{m1}$—$O(CH_2)_{n2}$—$O(CH_2)_{o1}$—$O(CH_2)_{p1}$—O$(CH_2)_{q1}$—$O(CH_2)_{r1}$—O—;
—$(CH_2)_{m1}$—$O(CH_2)_{n2}$—$O(CH_2)_{o1}$—$O(CH_2)_{p1}$—O$(CH_2)_{q1}$—$O(CH_2)_{r1}$—$OCH_2$—;
—$O(CH_2)_{m1}O(CH_2)_{n2}O(CH_2)_{p1}O(CH_2)_{q1}OCH_2$—;
—$O(CH_2)_{m1}O(CH_2)_{n2}O(CH_2)_{p1}O(CH_2)_{q1}OCH_2$—;
wherein
m1, n2, o1, p1, q1, and r1 are independently 1, 2, 3, 4, or 5; and
$R^{61}$ is H, methyl, or ethyl.
In additional embodiments, the Linker is selected from:
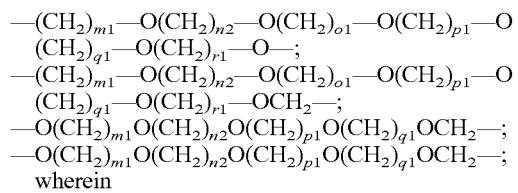
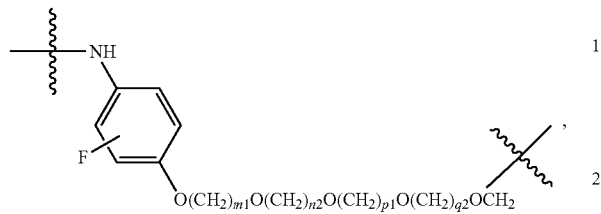
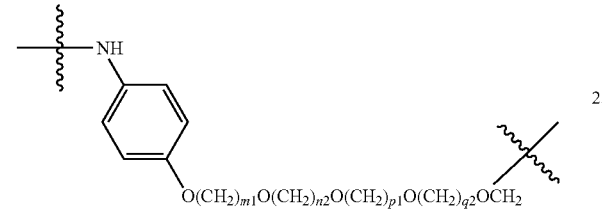
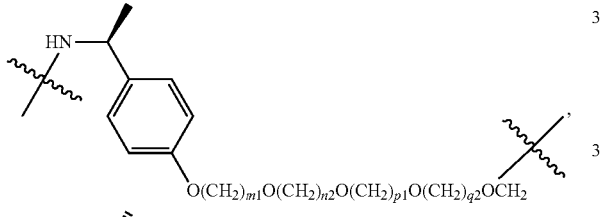
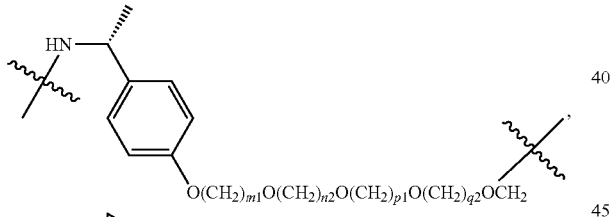
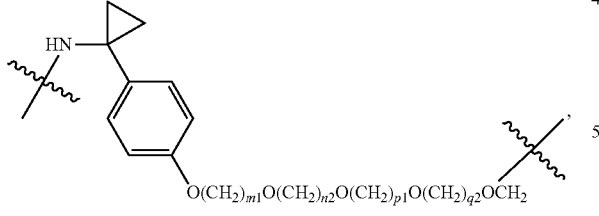
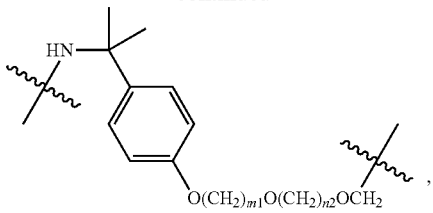
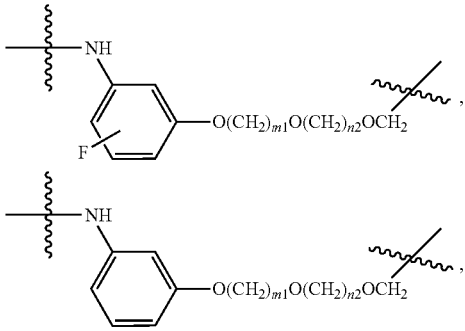
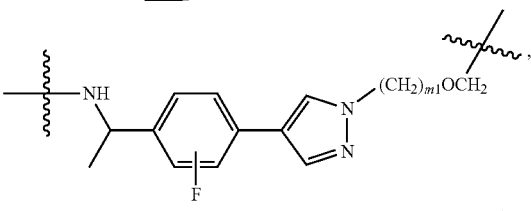
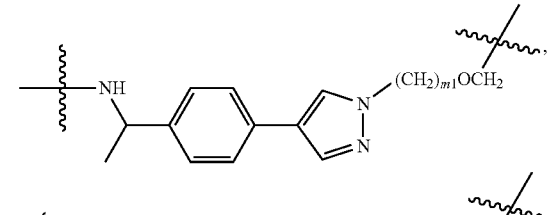
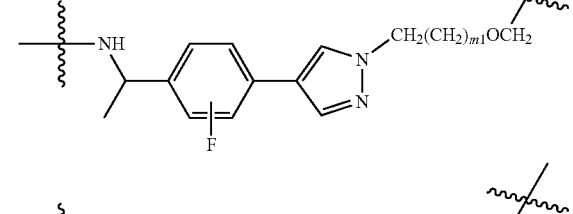
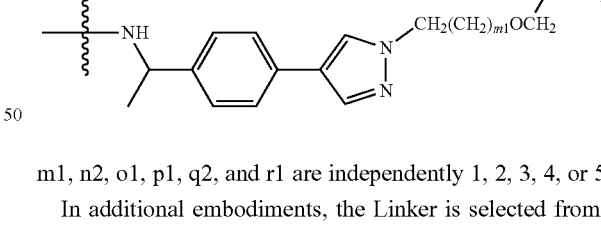
m1, n2, o1, p1, q2, and r1 are independently 1, 2, 3, 4, or 5.
In additional embodiments, the Linker is selected from:
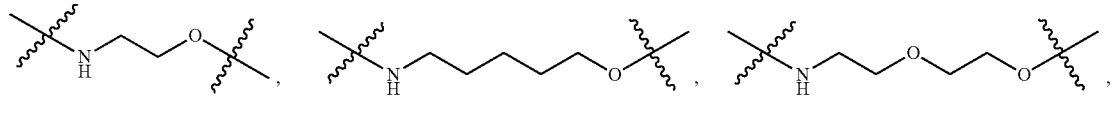
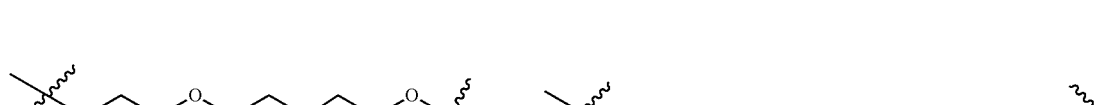

-continued
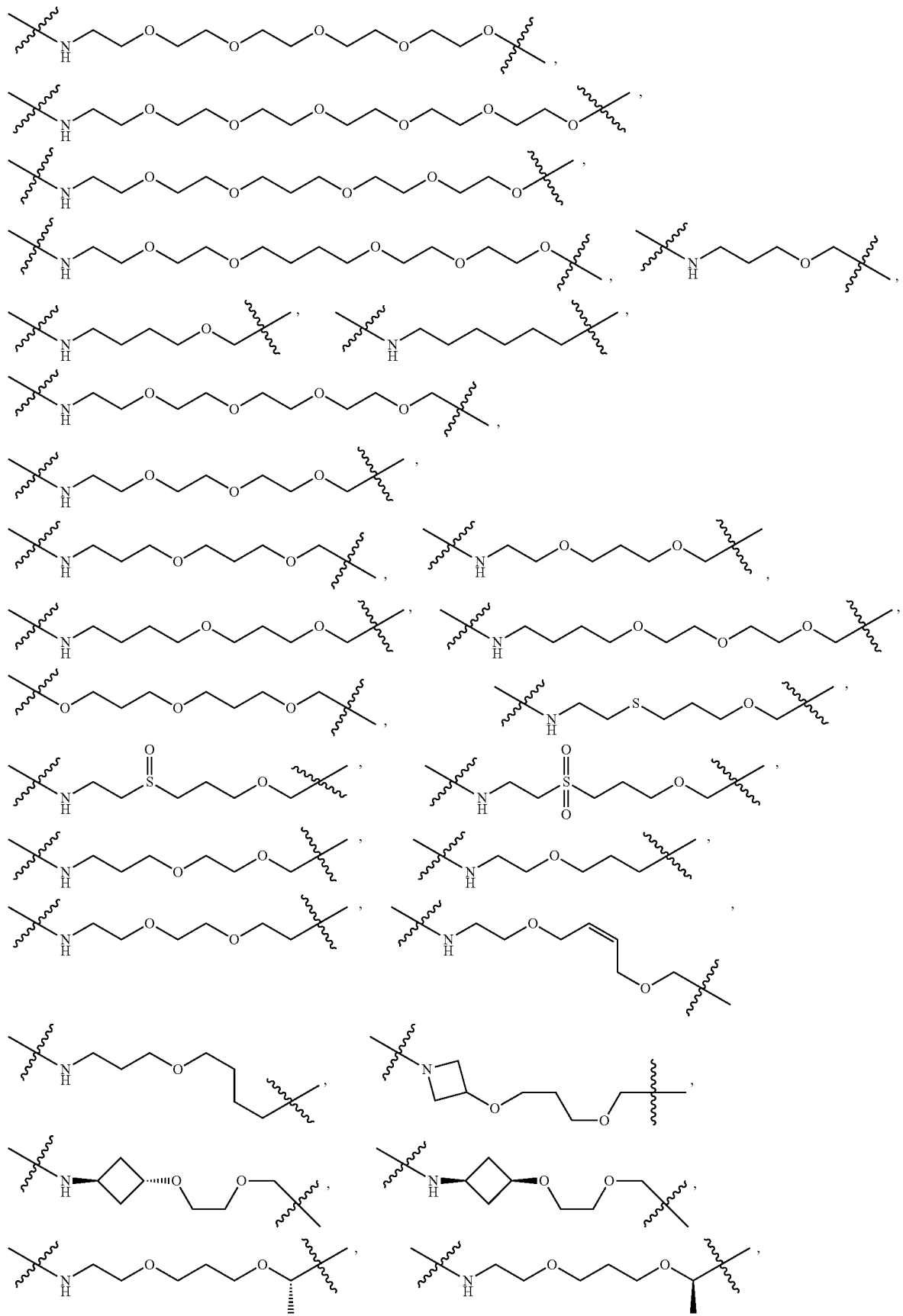

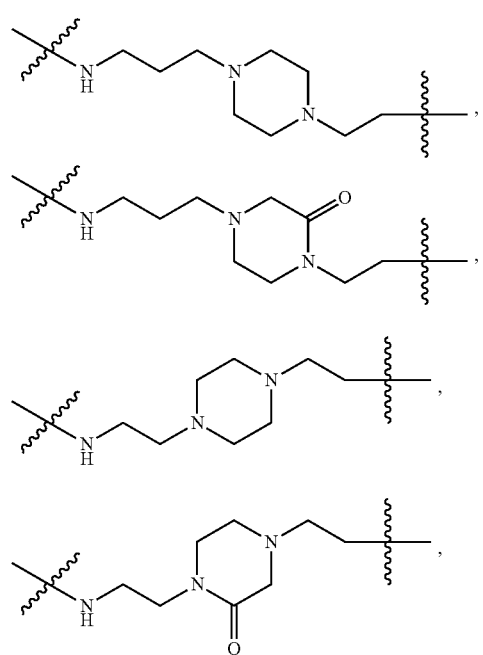
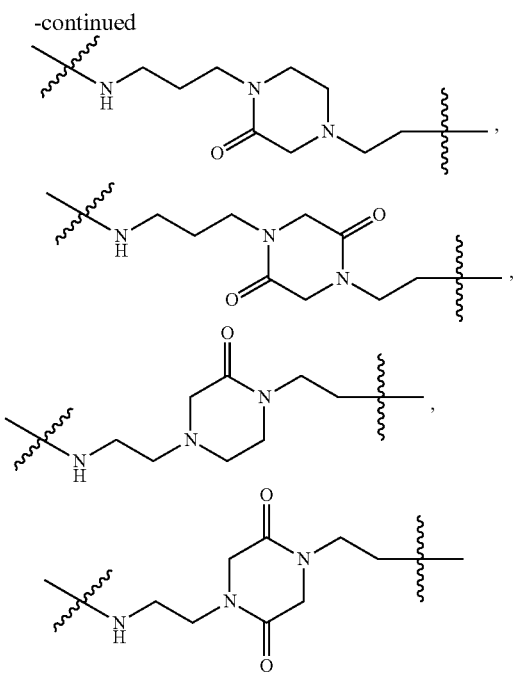
In additional embodiments, the Linker is selected from:
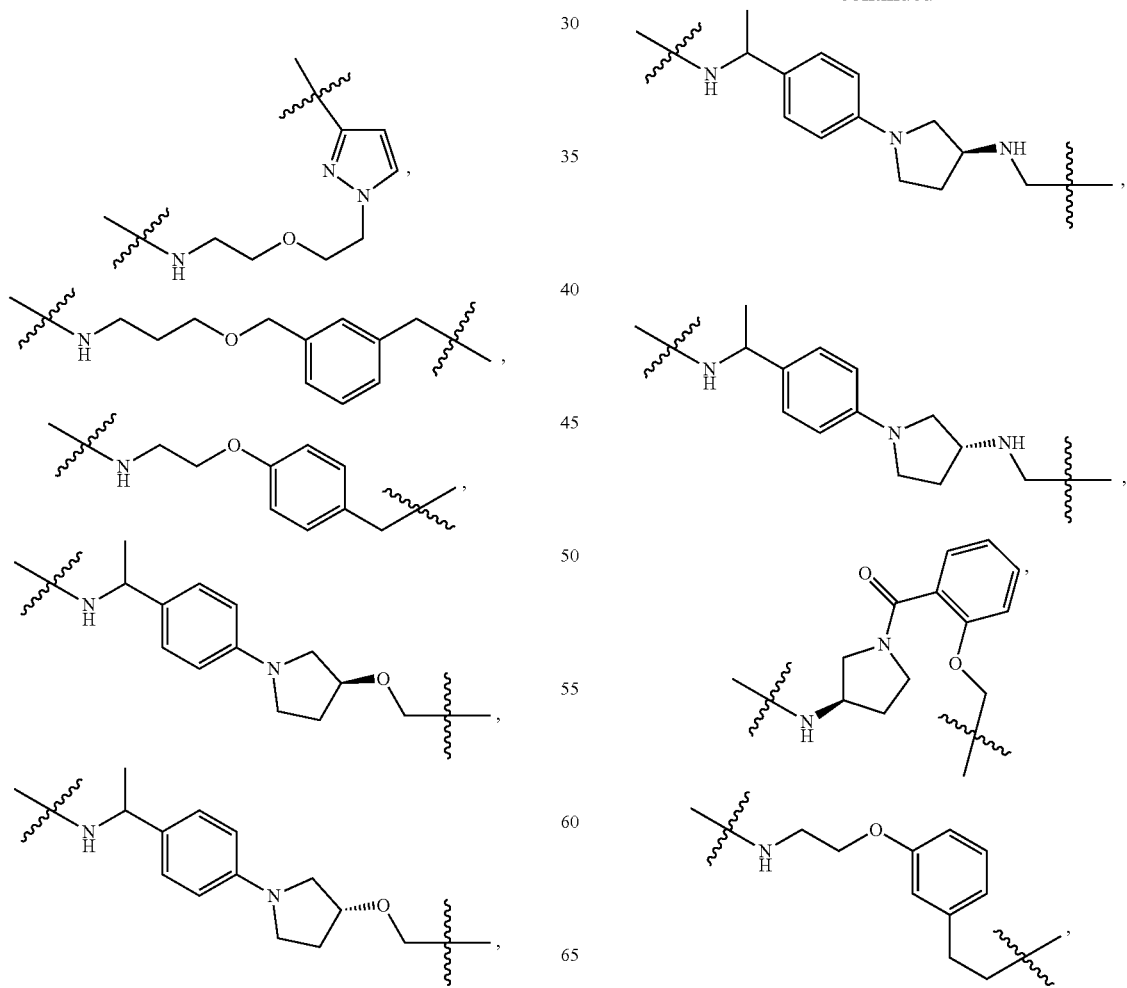

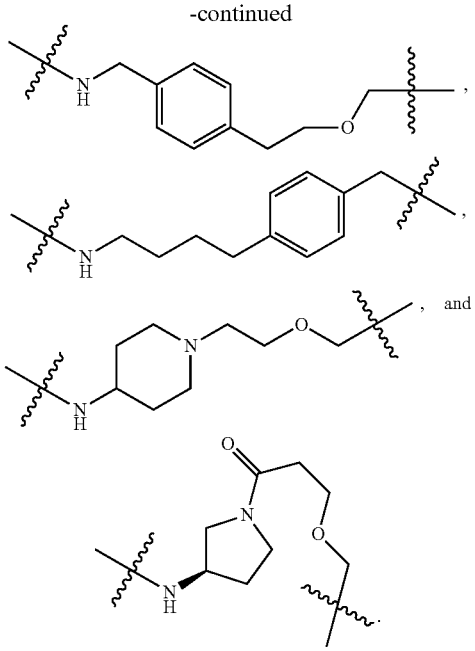
In additional embodiments, the Linker is selected from:
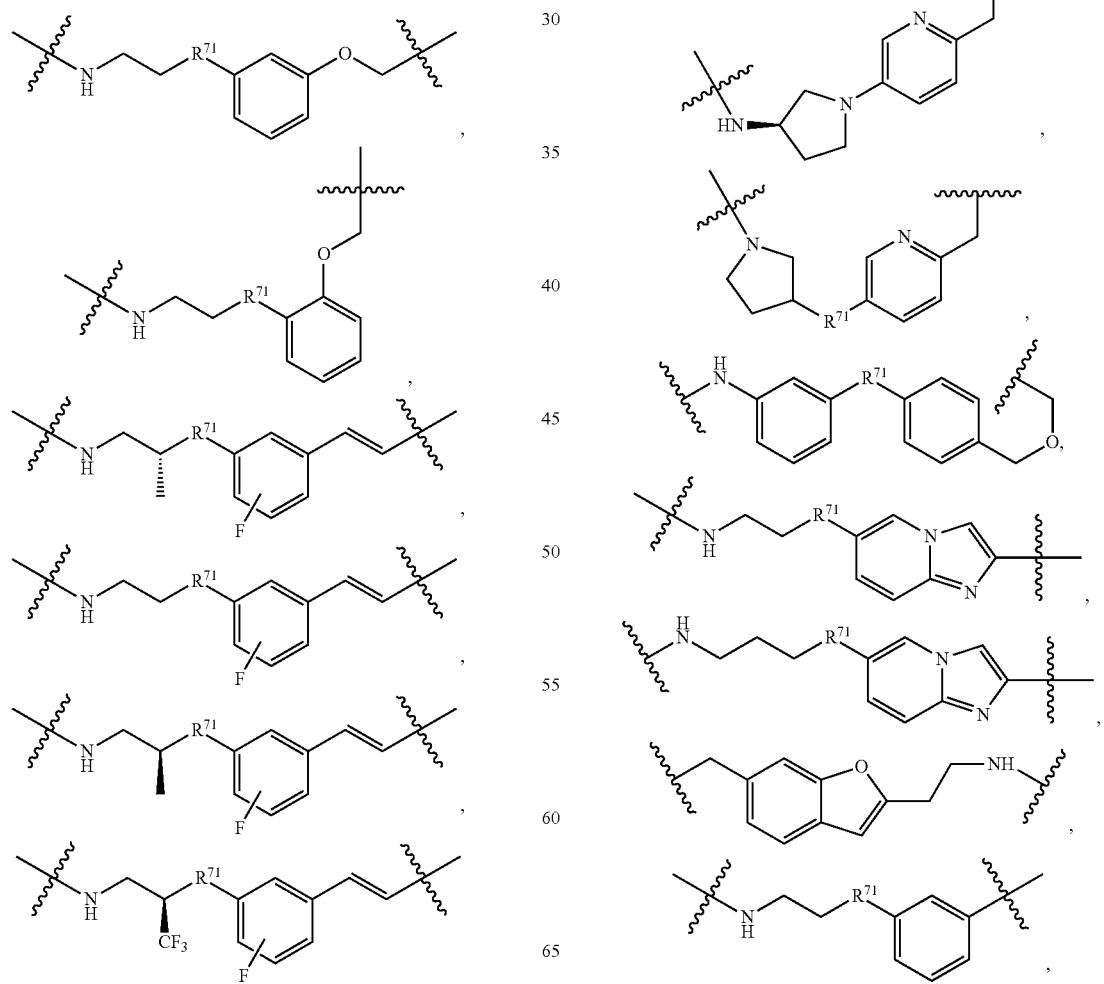

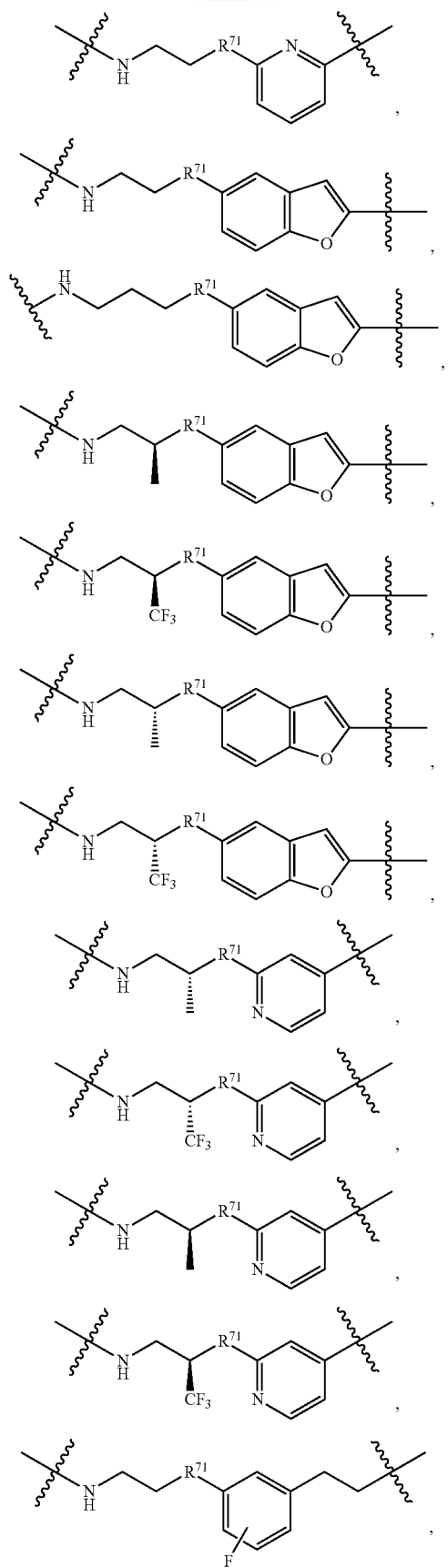
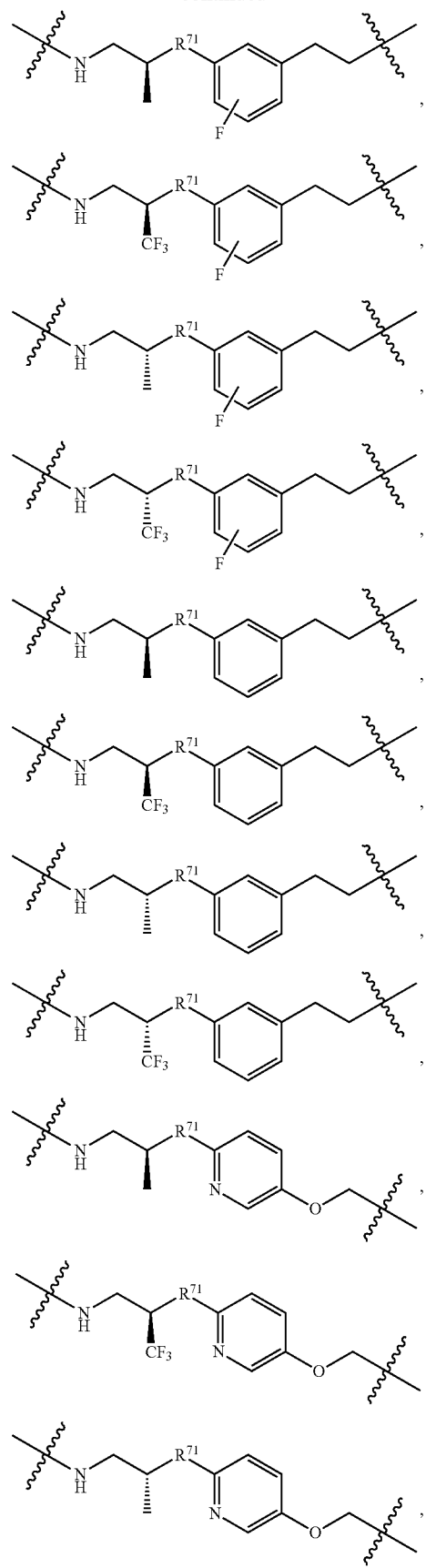

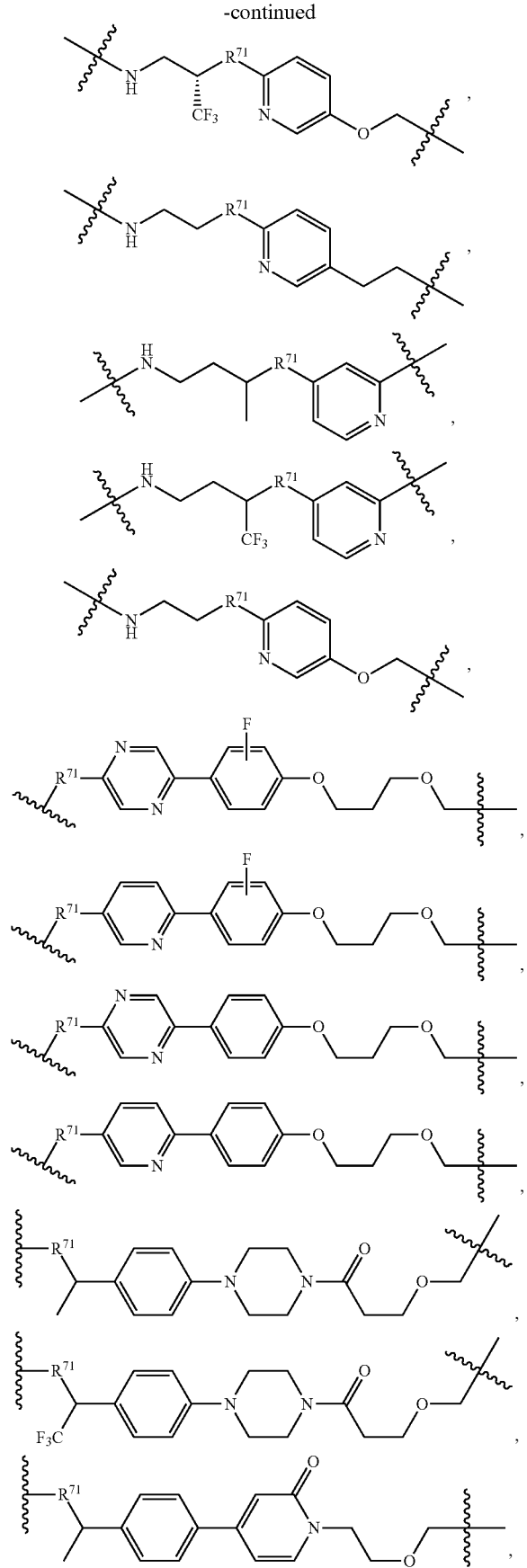
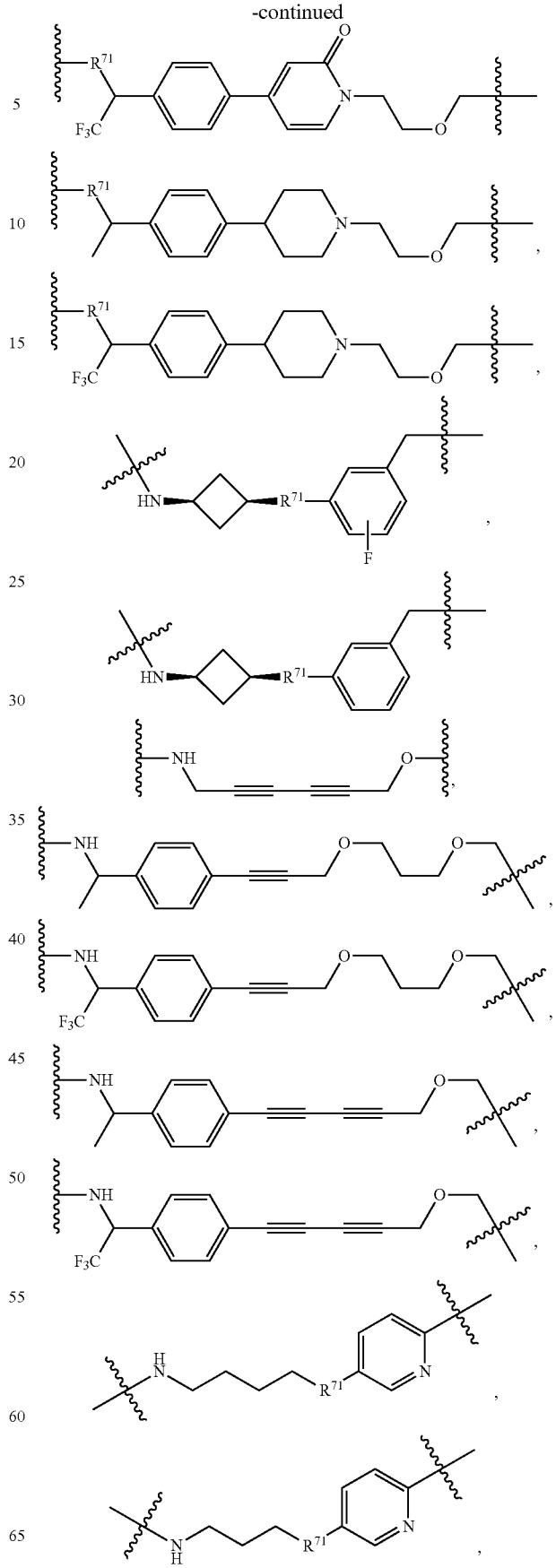

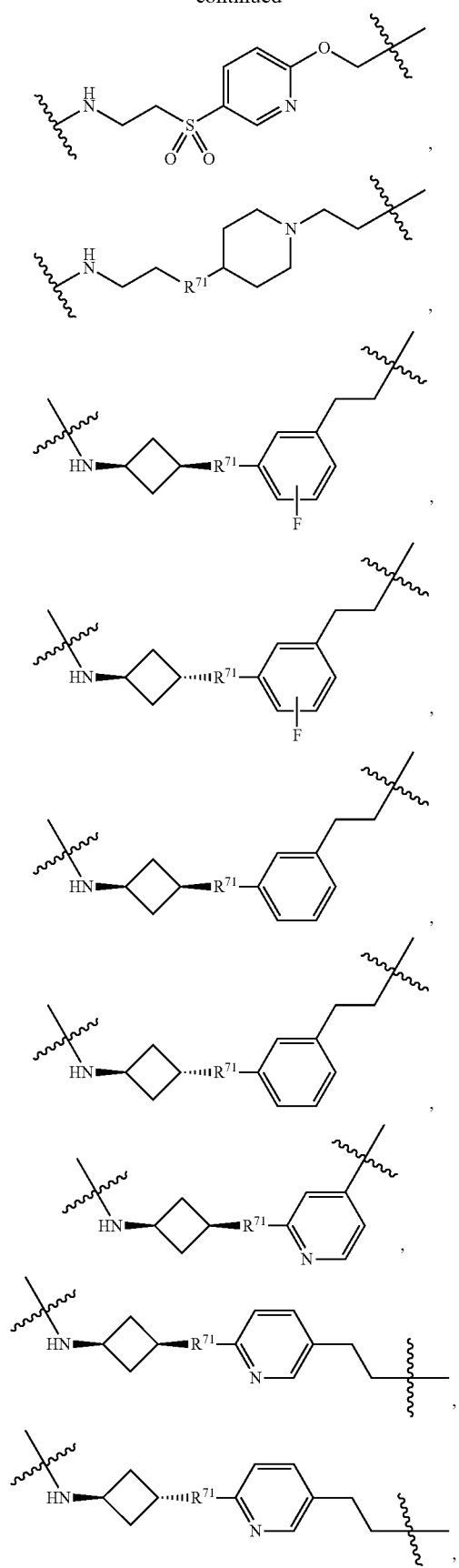
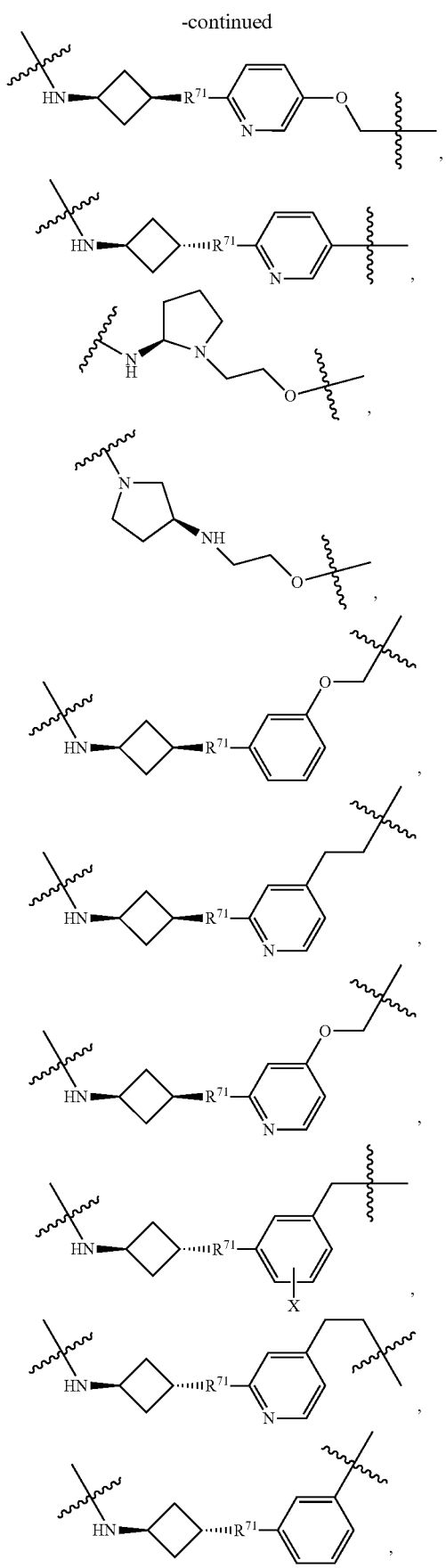

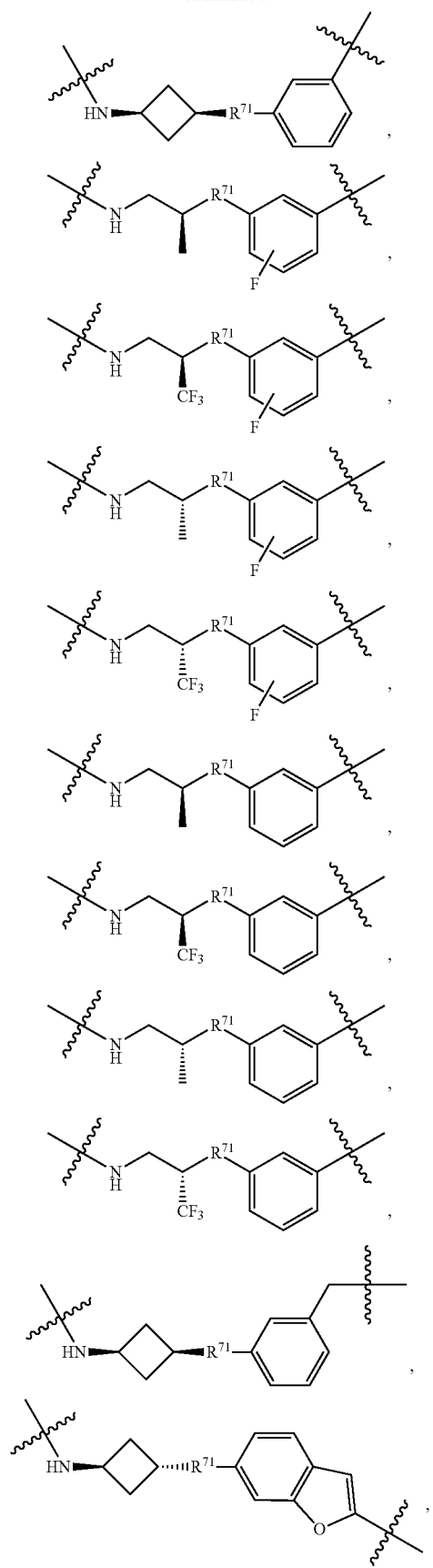
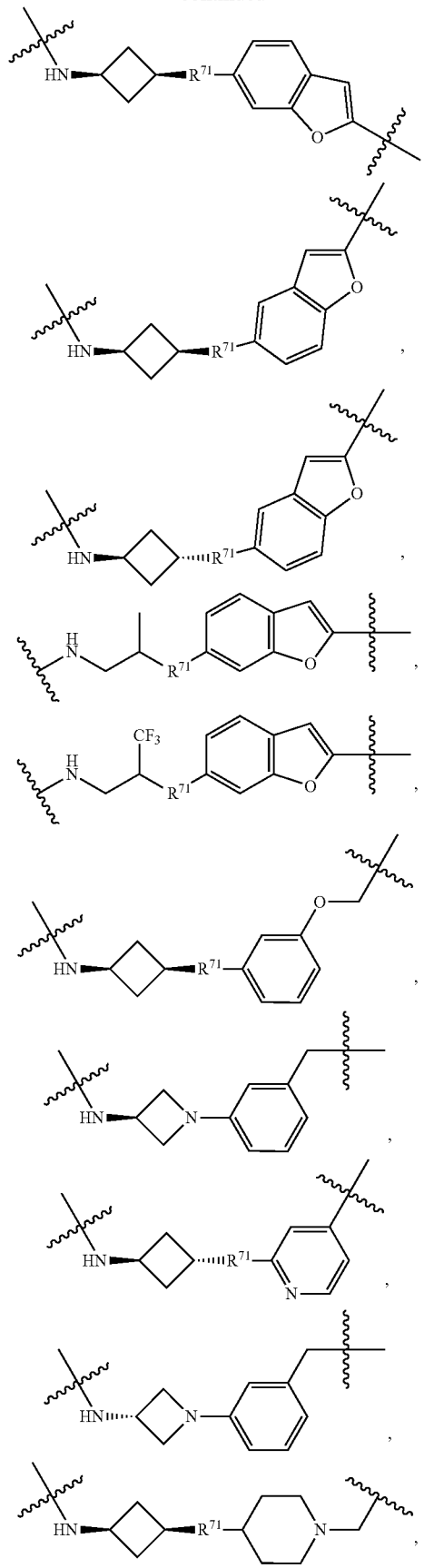

-continued
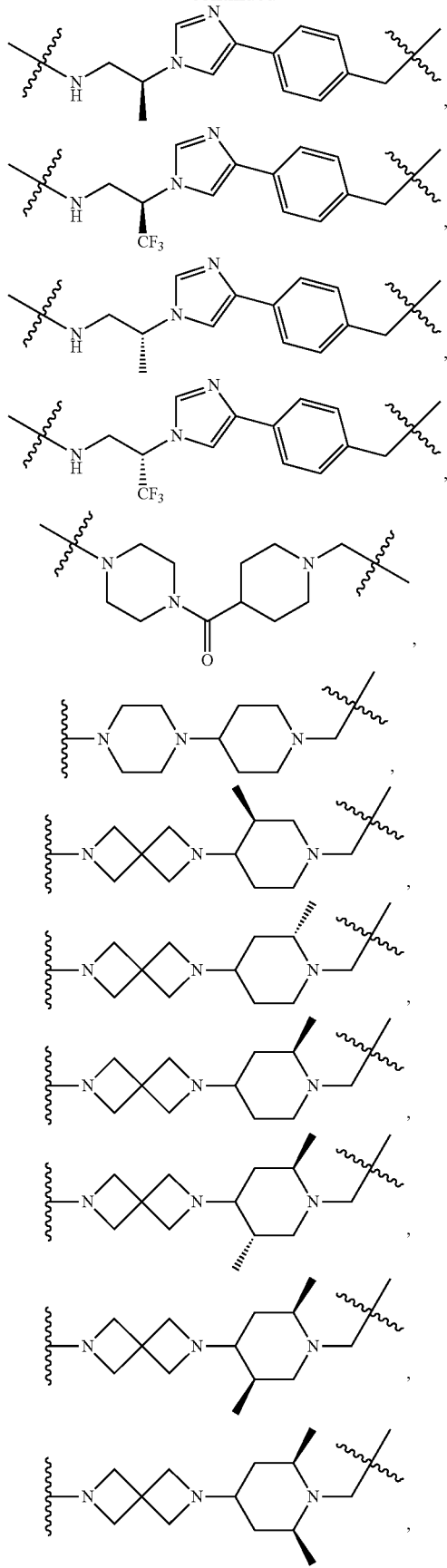
-continued
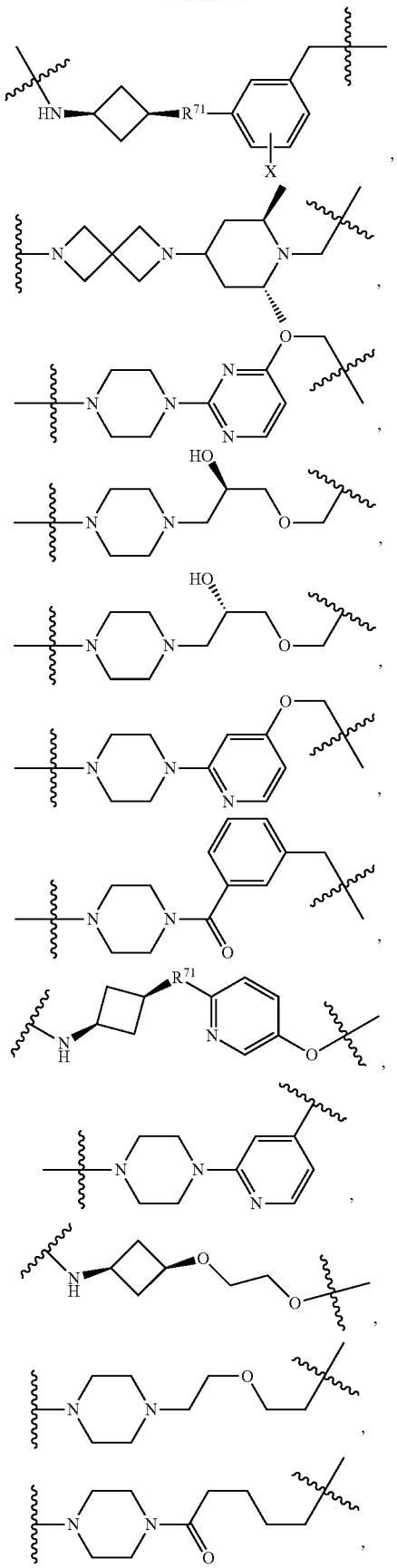

141
-continued
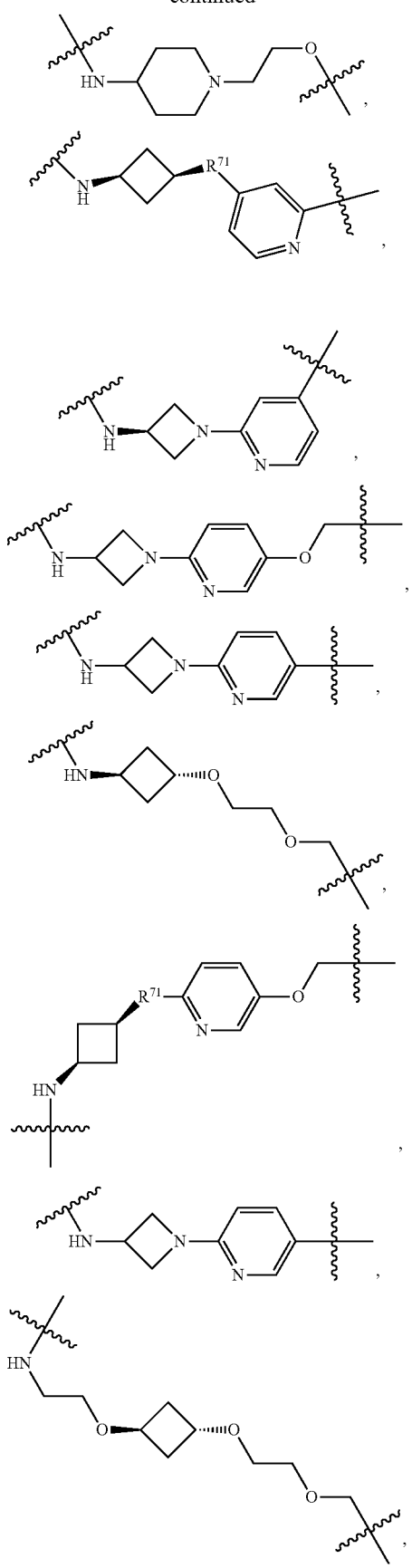
142
-continued
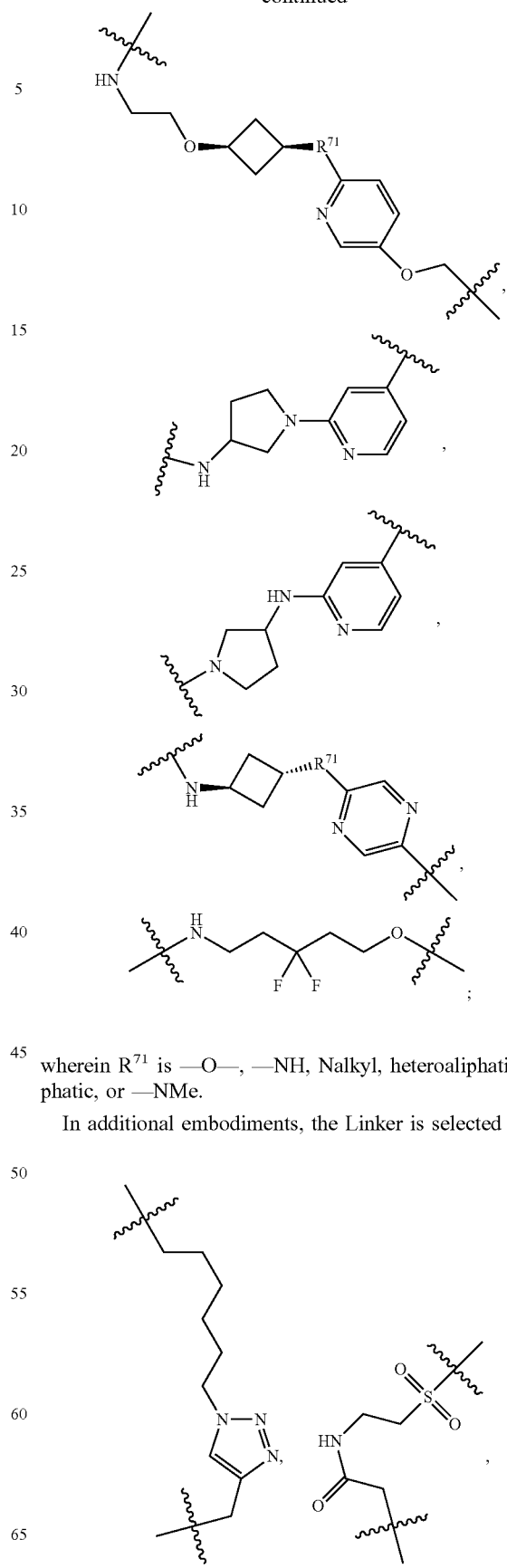
wherein $R^{71}$ is —O—, —NH, Nalkyl, heteroaliphatic, aliphatic, or —NMe.
In additional embodiments, the Linker is selected from:
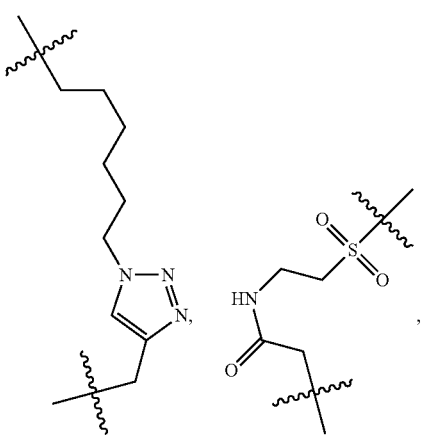

US 10,849,982 B2
143
-continued
144
-continued
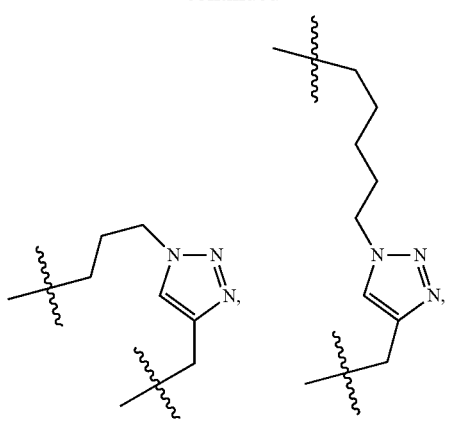
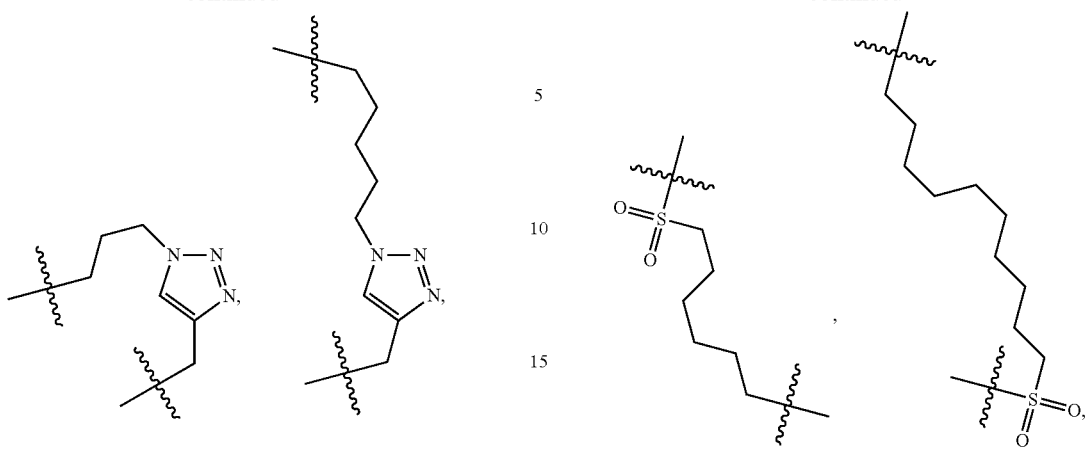
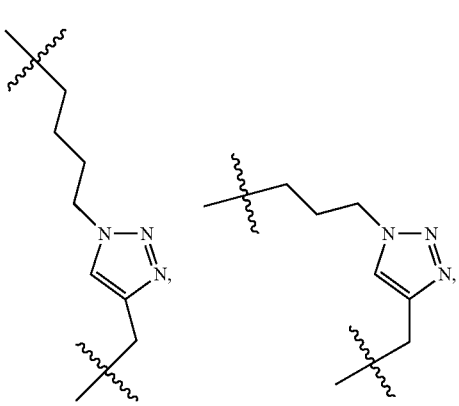
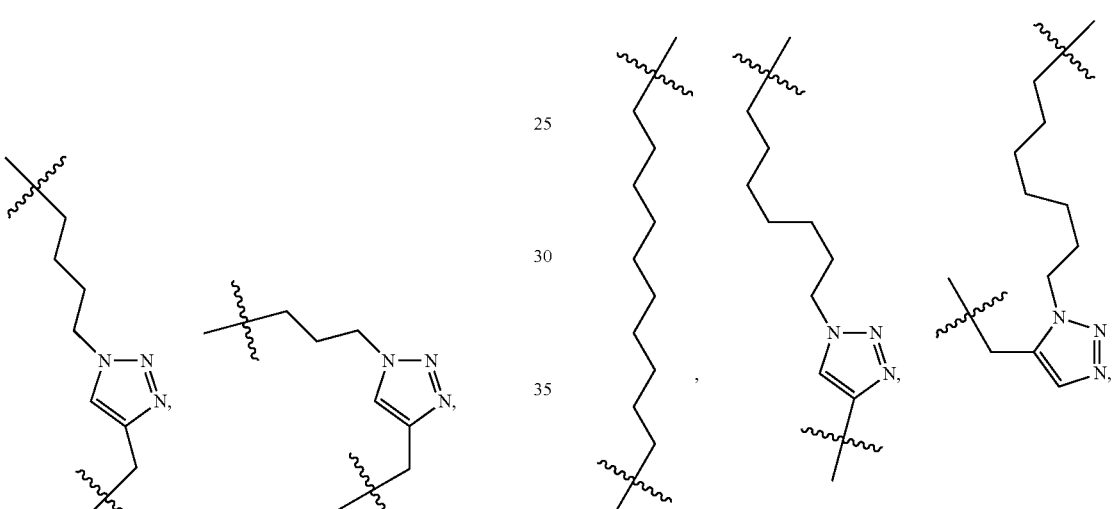
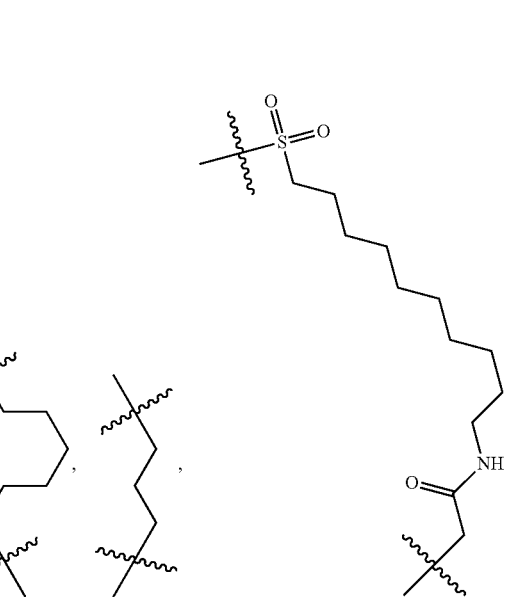
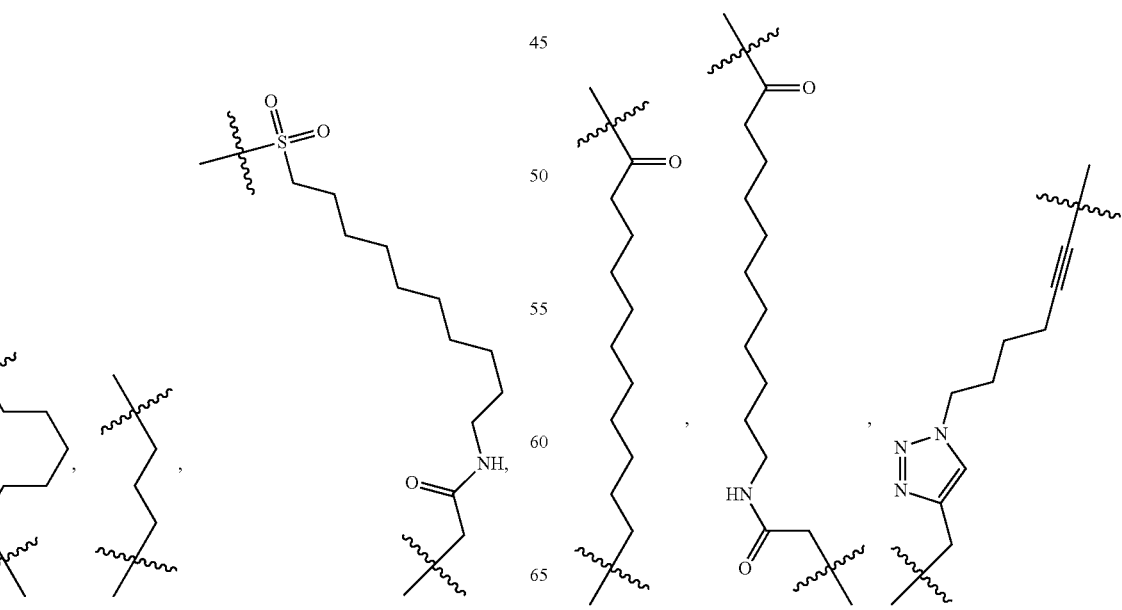

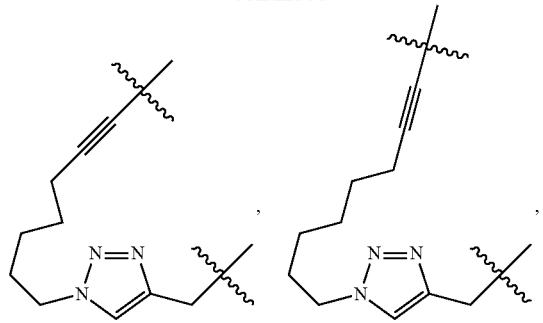
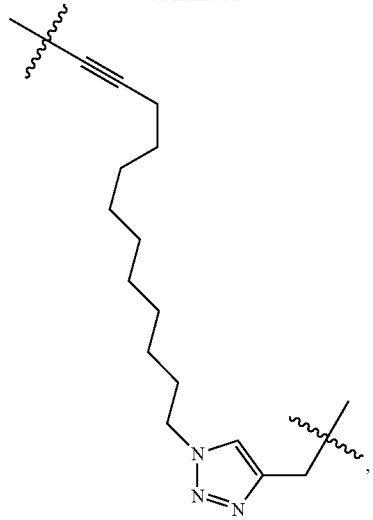
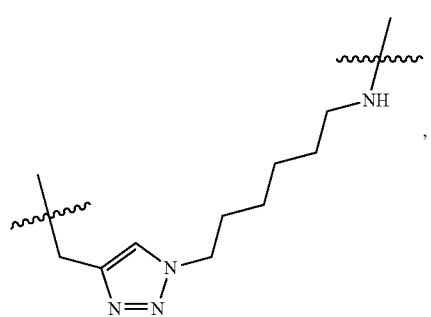
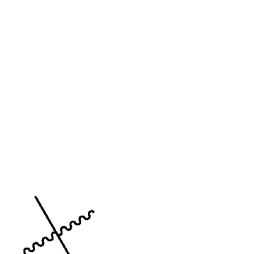
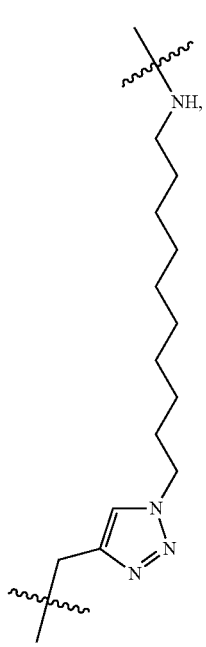

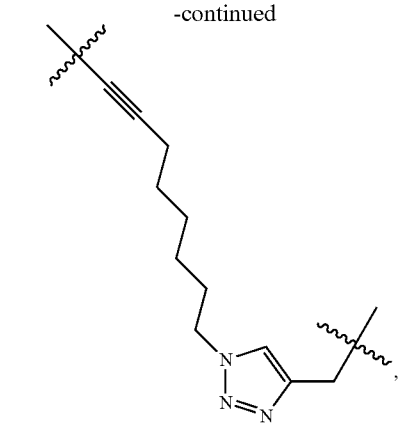
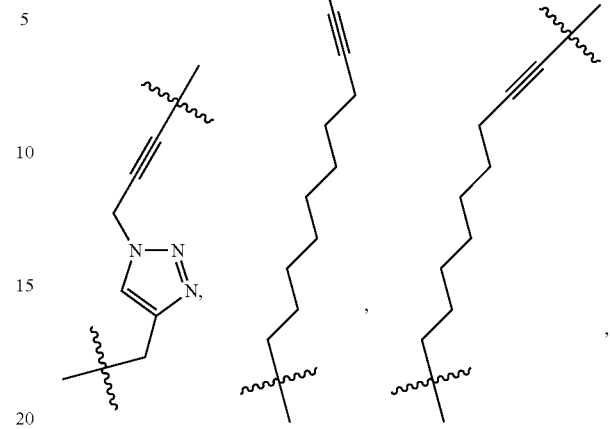
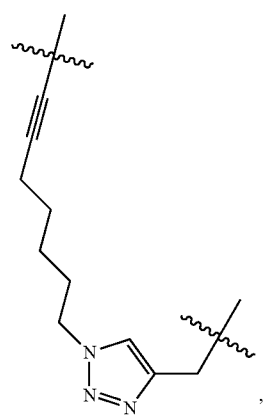
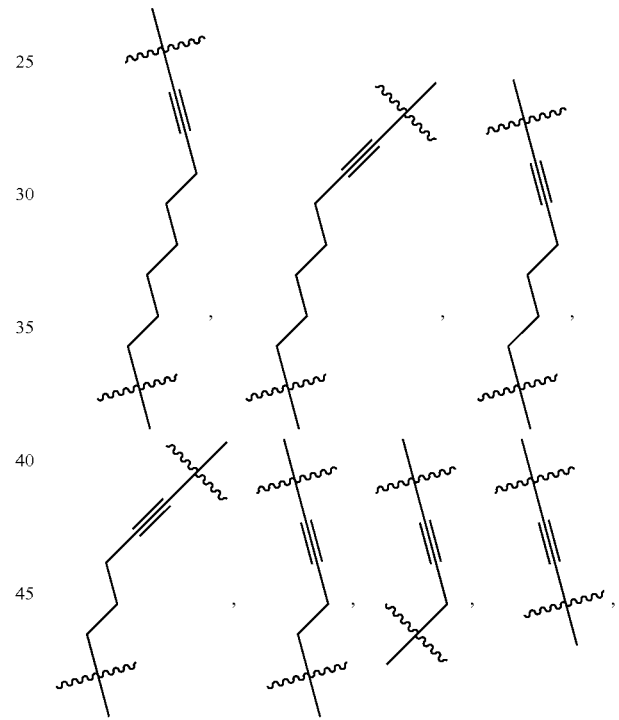
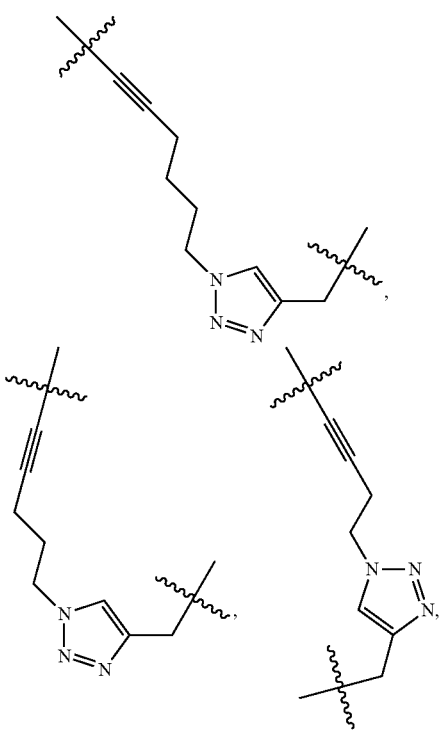
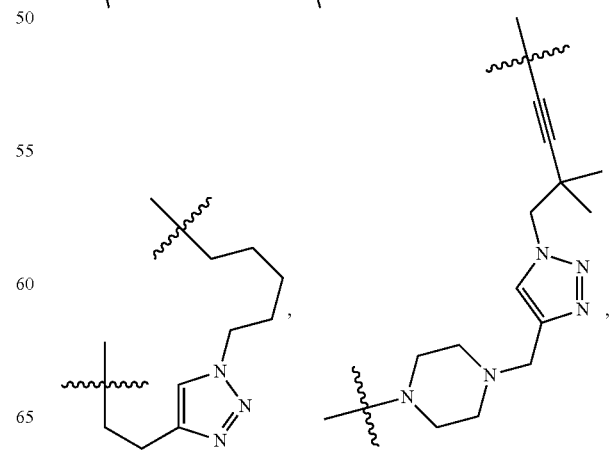

149
-continued
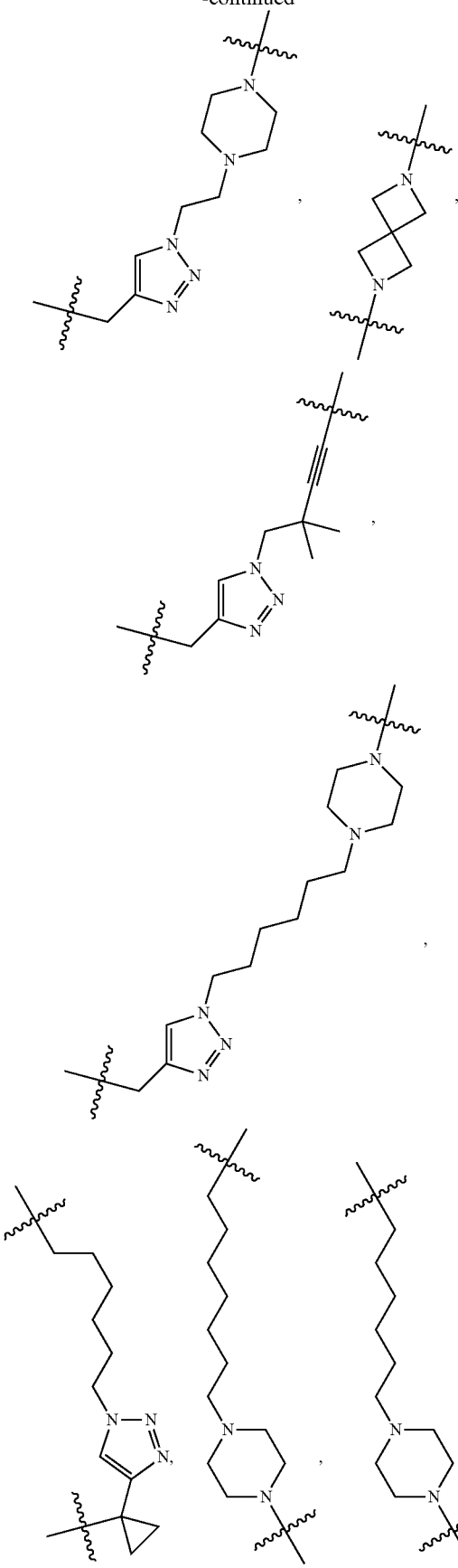
150
-continued
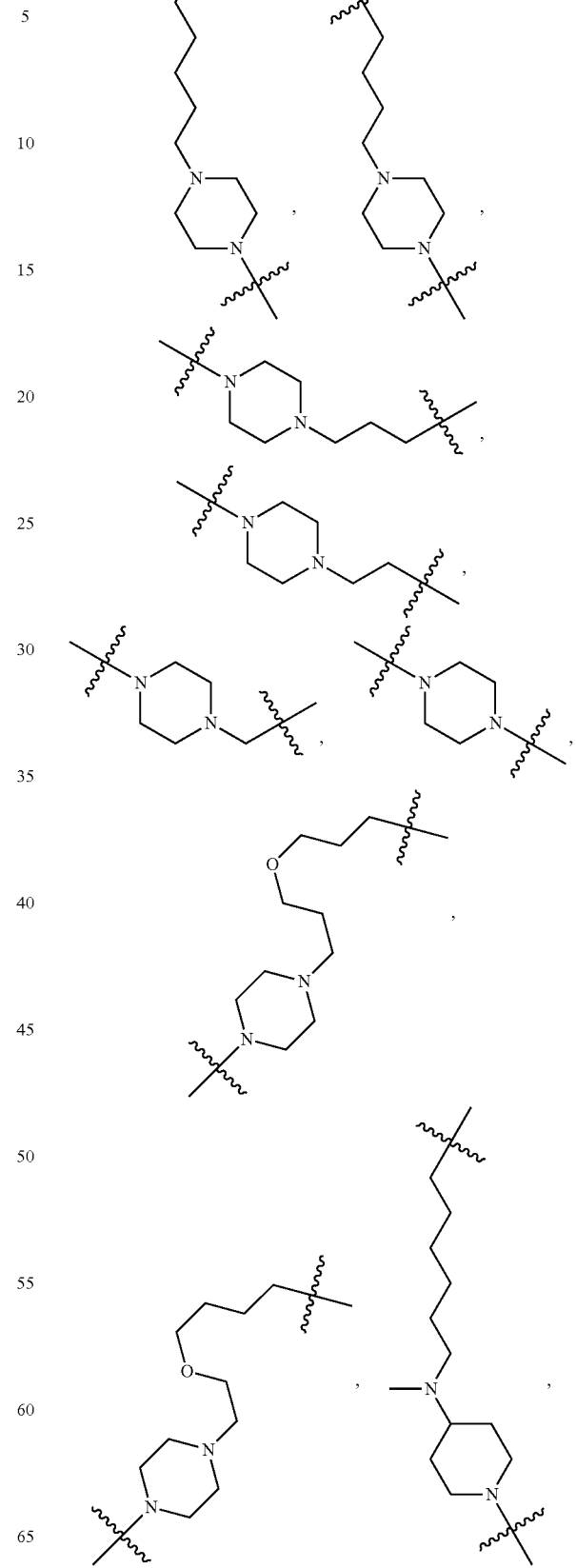

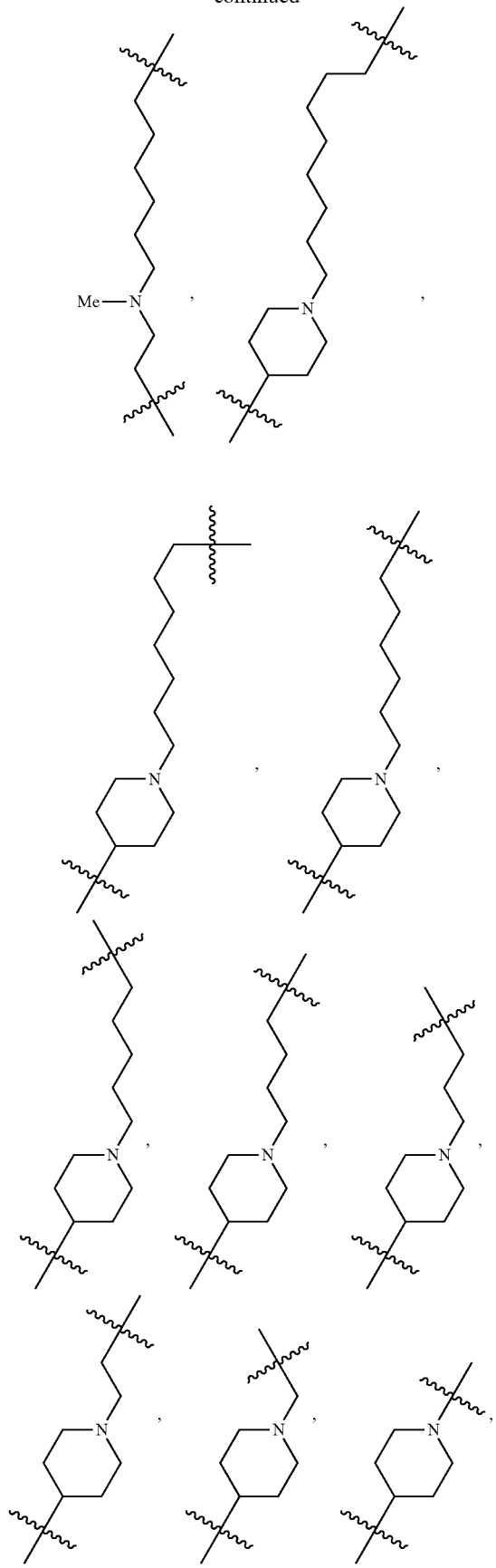
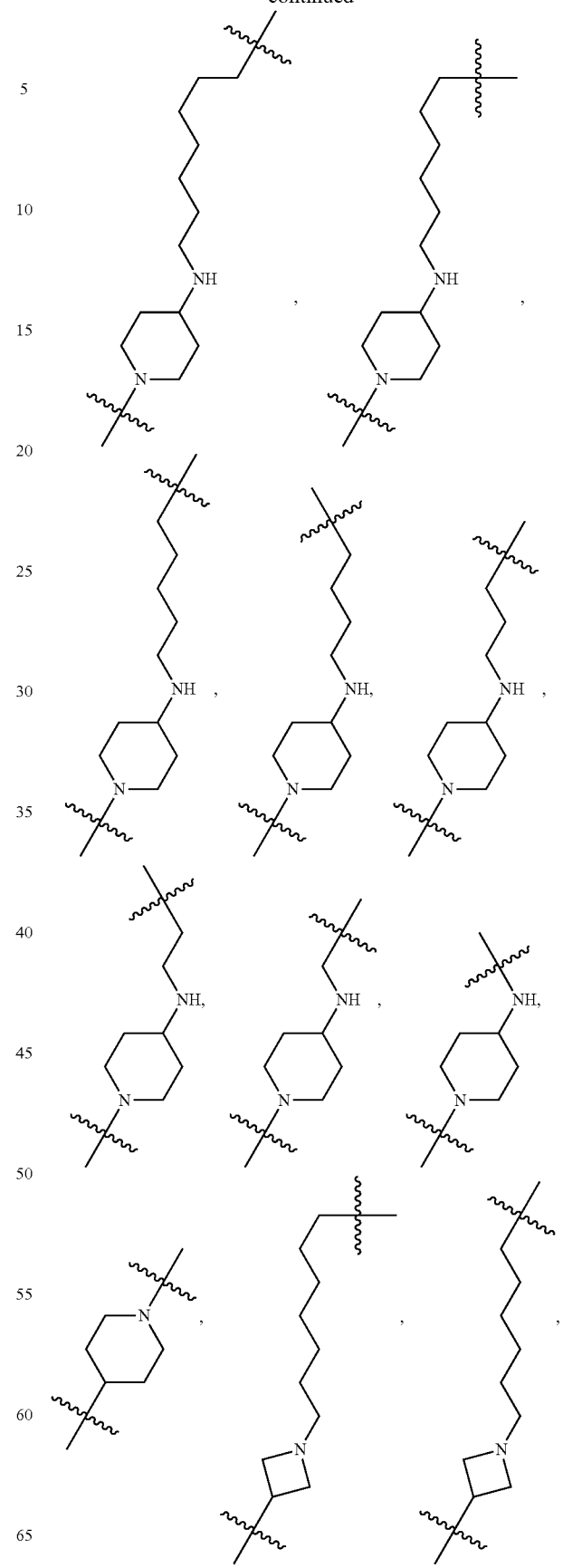

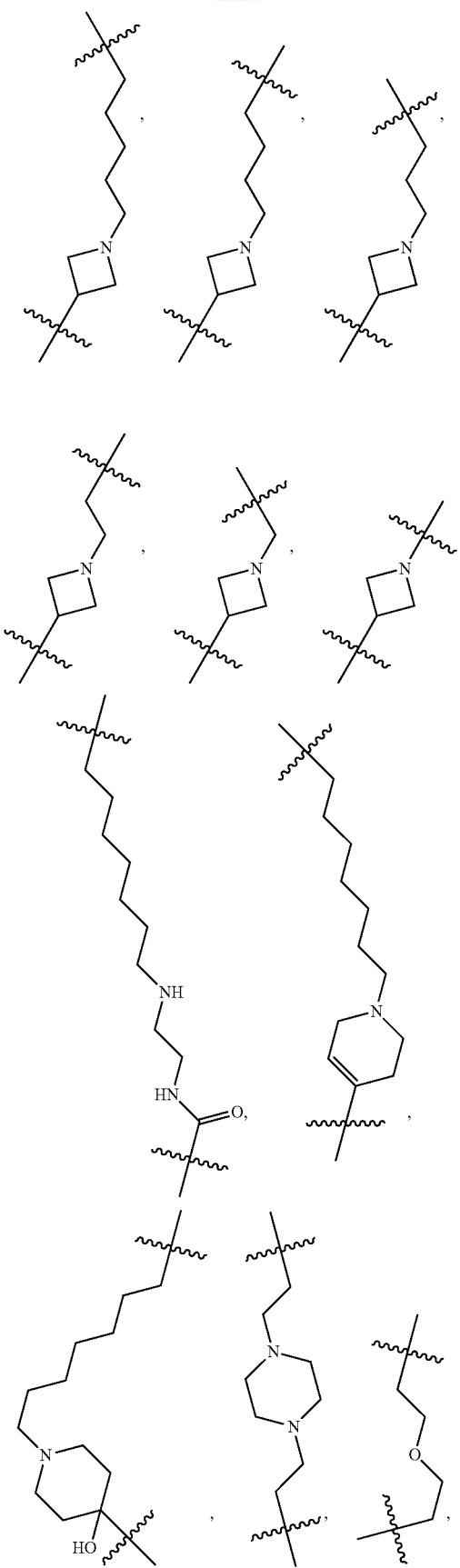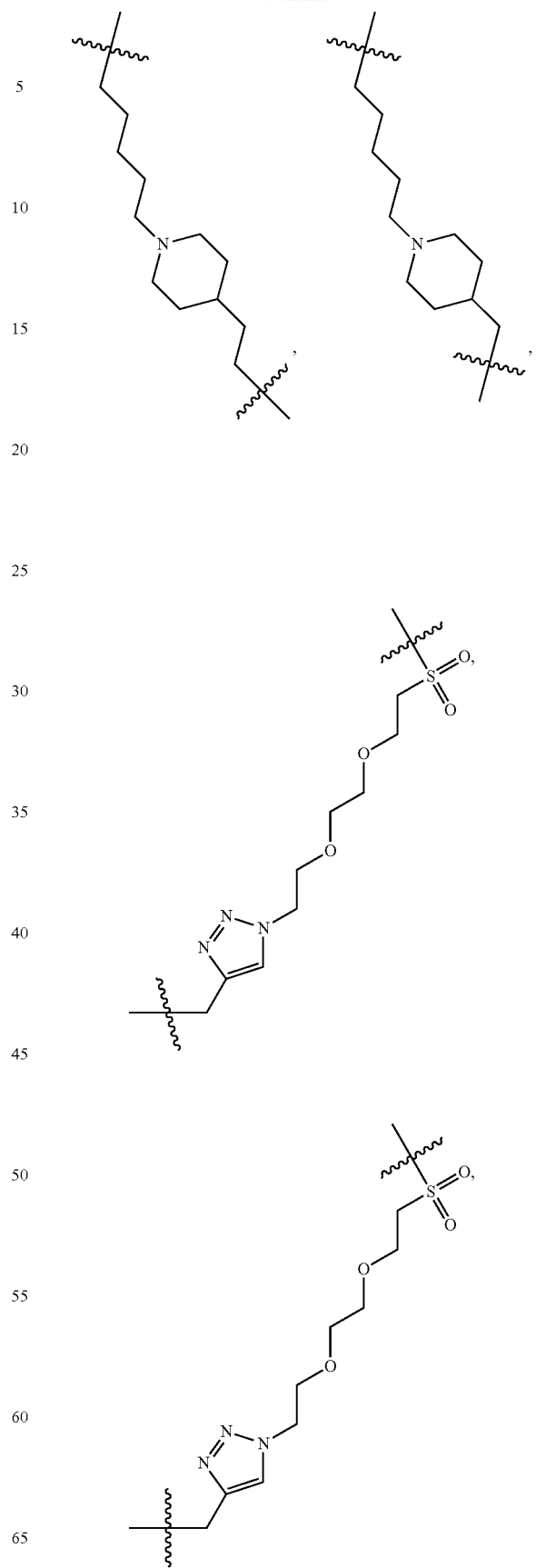

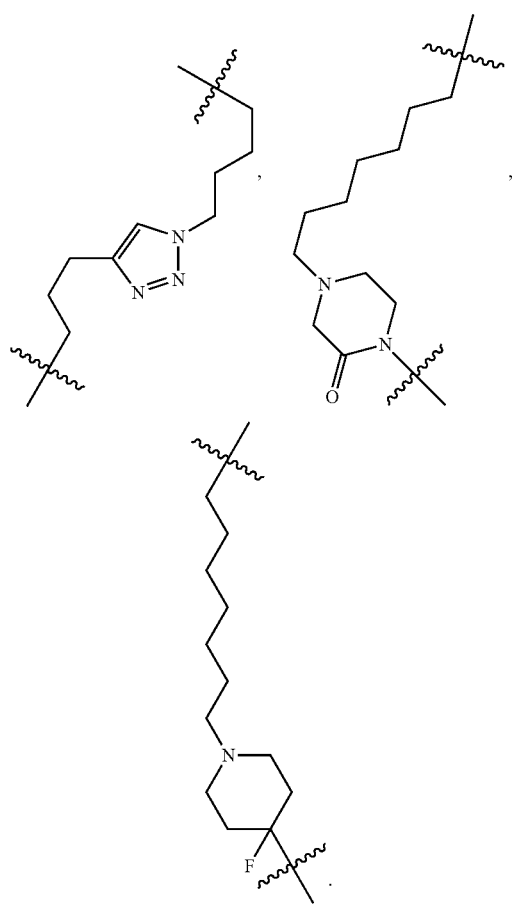
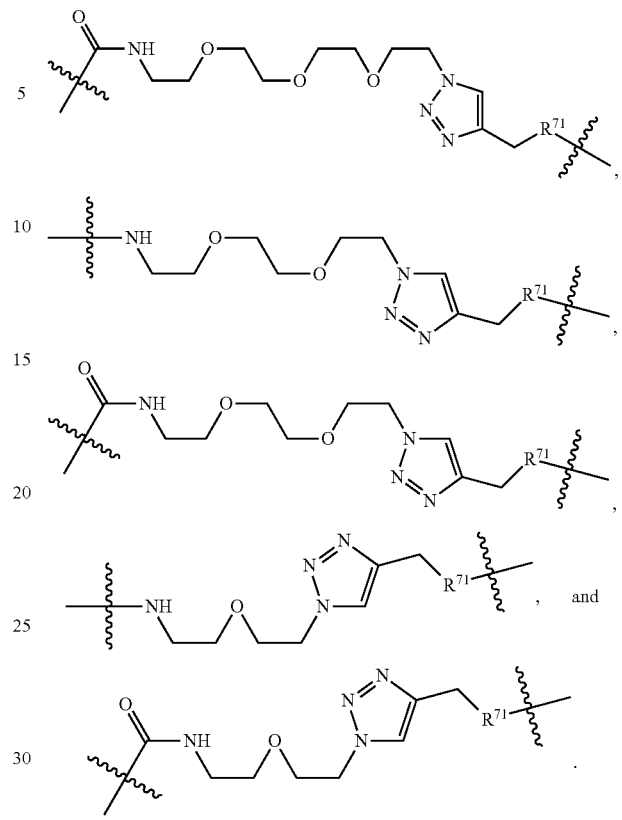
In additional embodiments, the Linker is selected from:
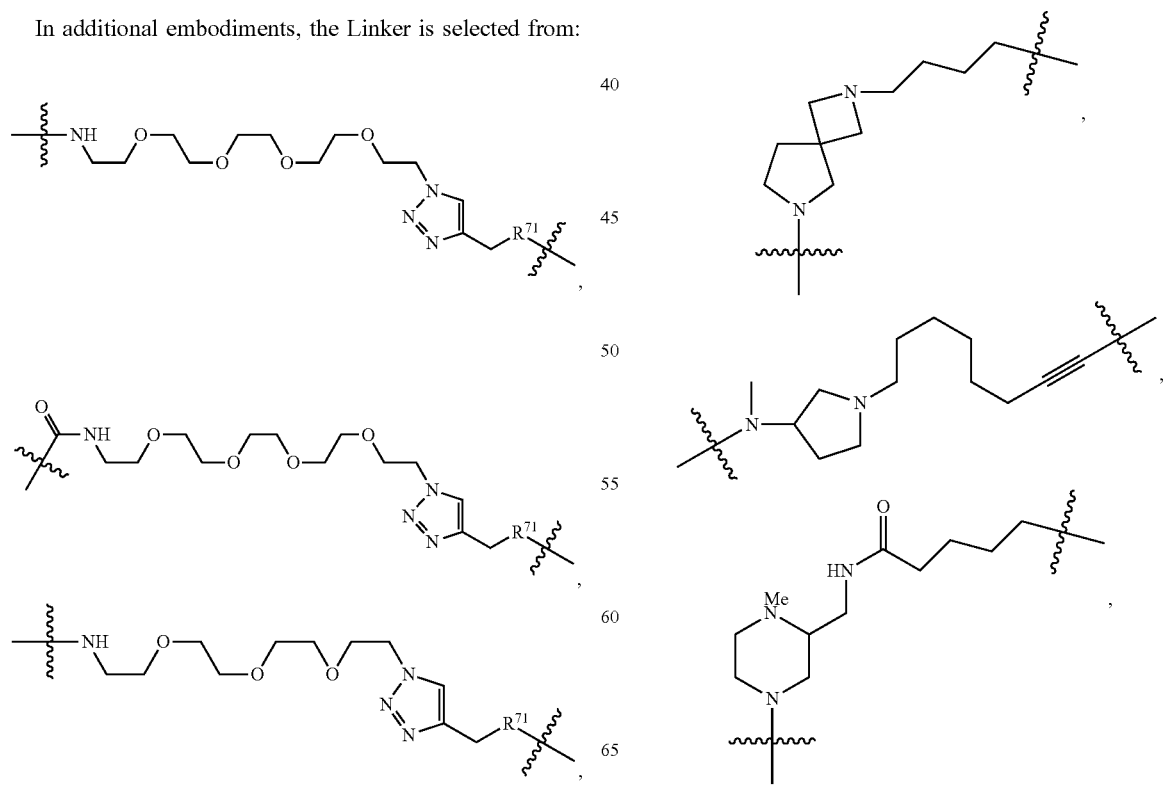

157
-continued
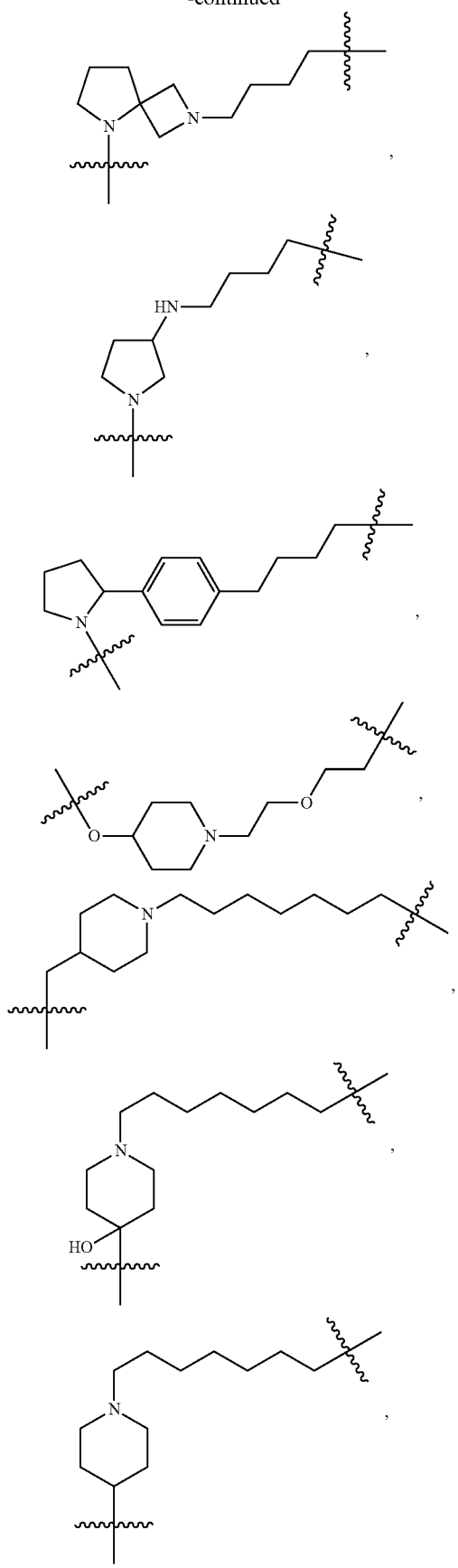
158
-continued
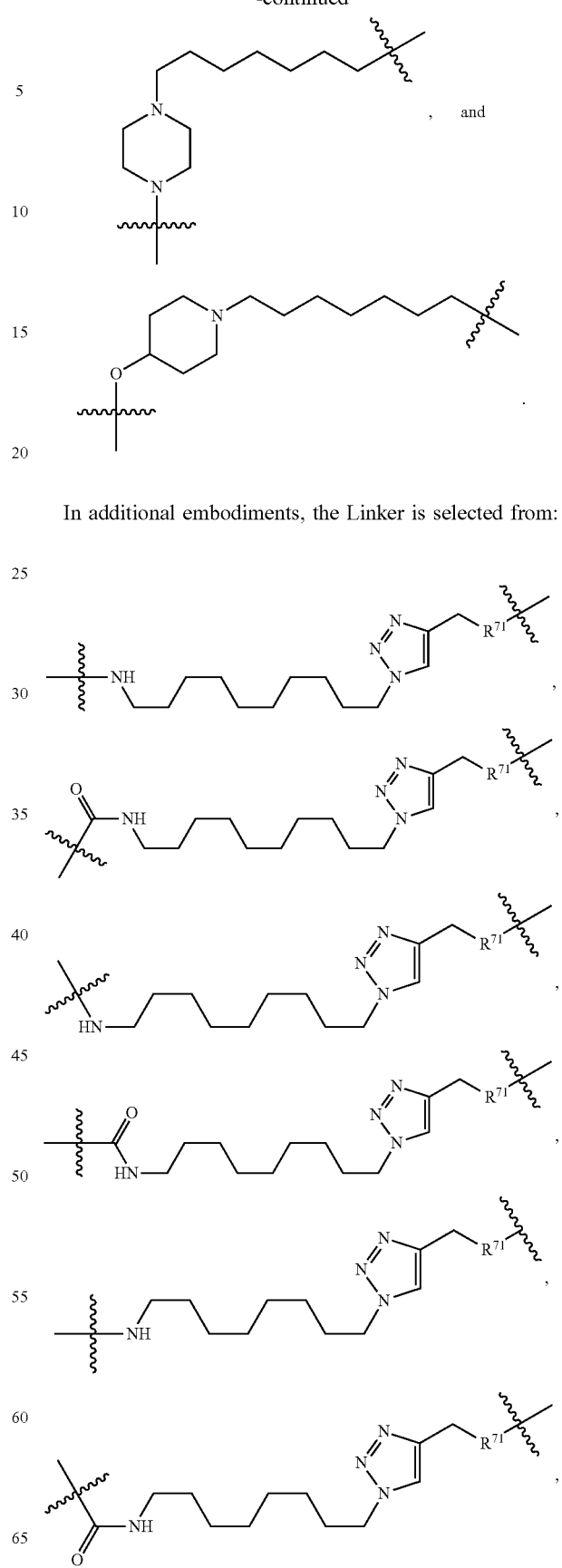
In additional embodiments, the Linker is selected from:

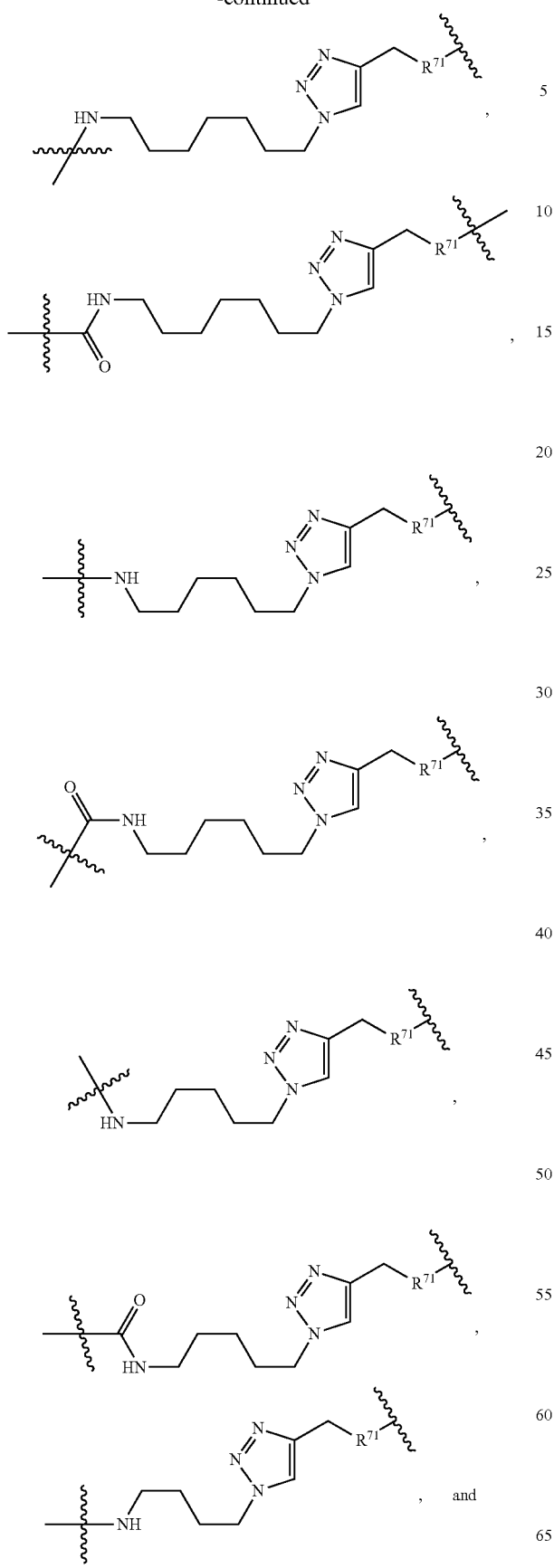
,and
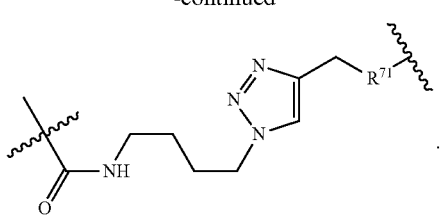
In additional embodiments, the Linker is selected from:
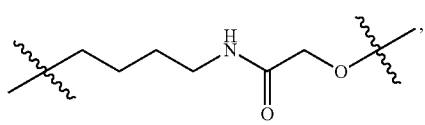
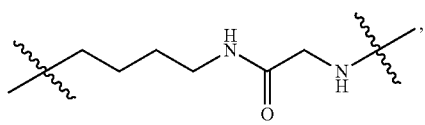
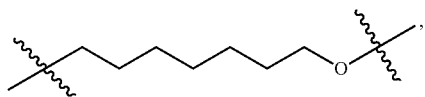
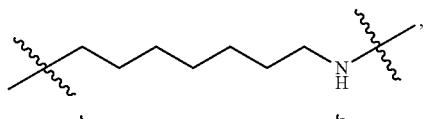
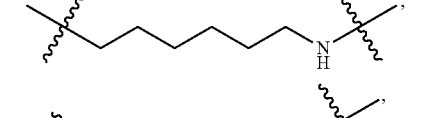
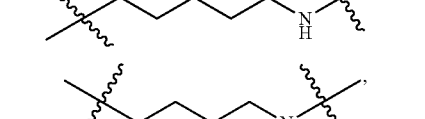
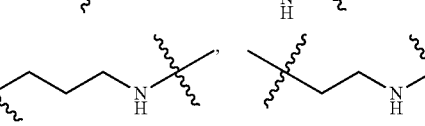
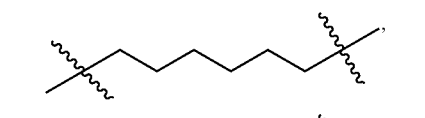
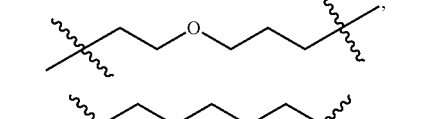
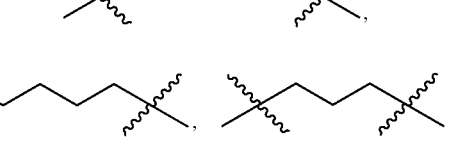
, and In additional embodiments, the Linker is selected from:
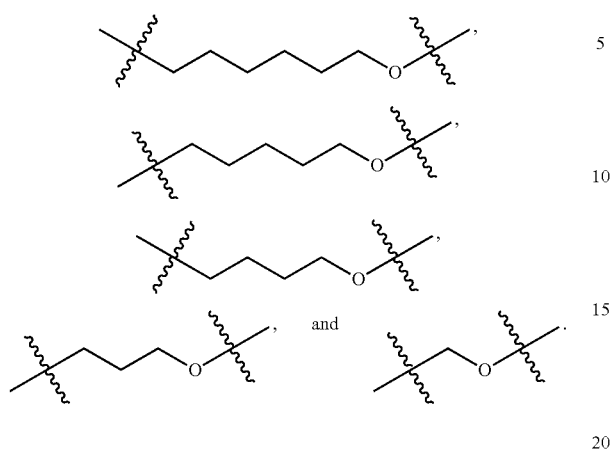
In certain additional embodiments, the Linker is selected from:
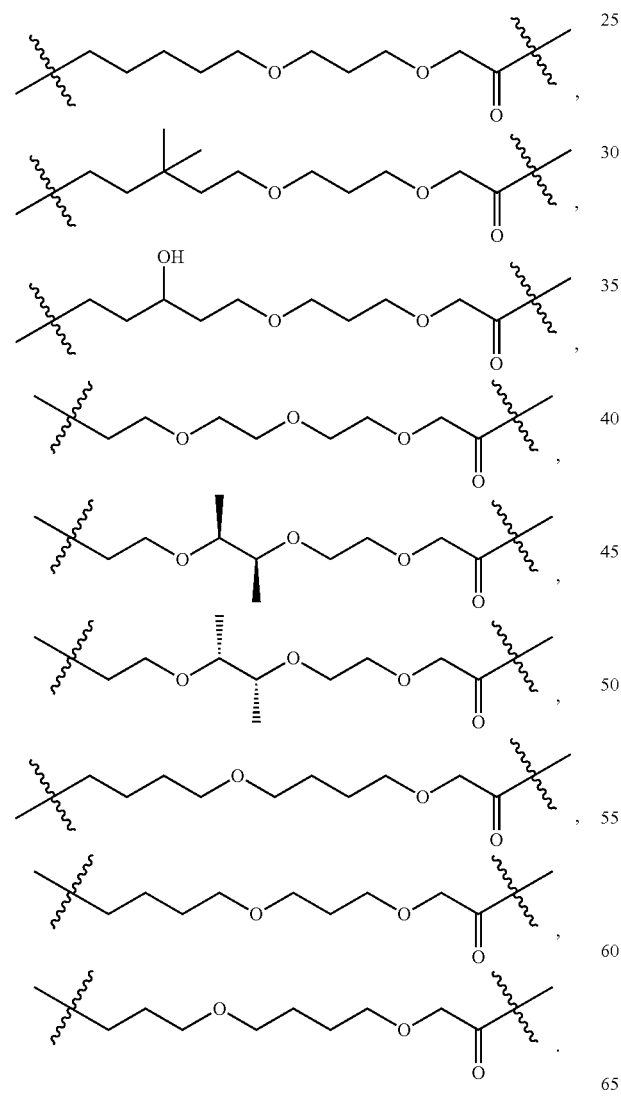
In certain embodiments the Linker is selected from:
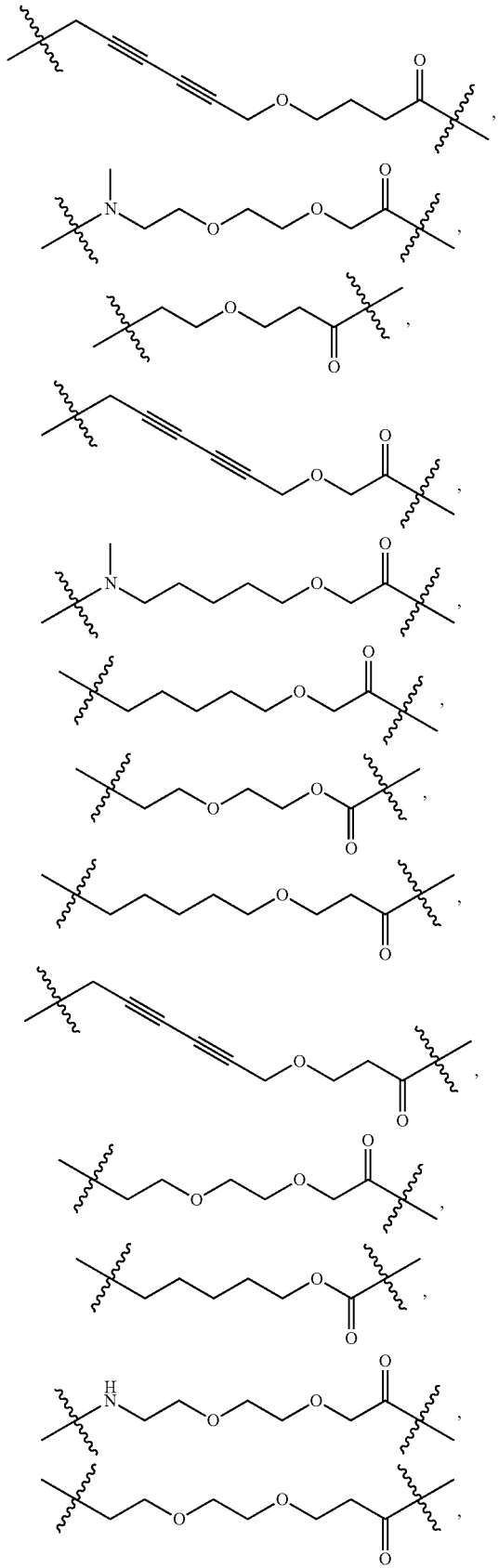

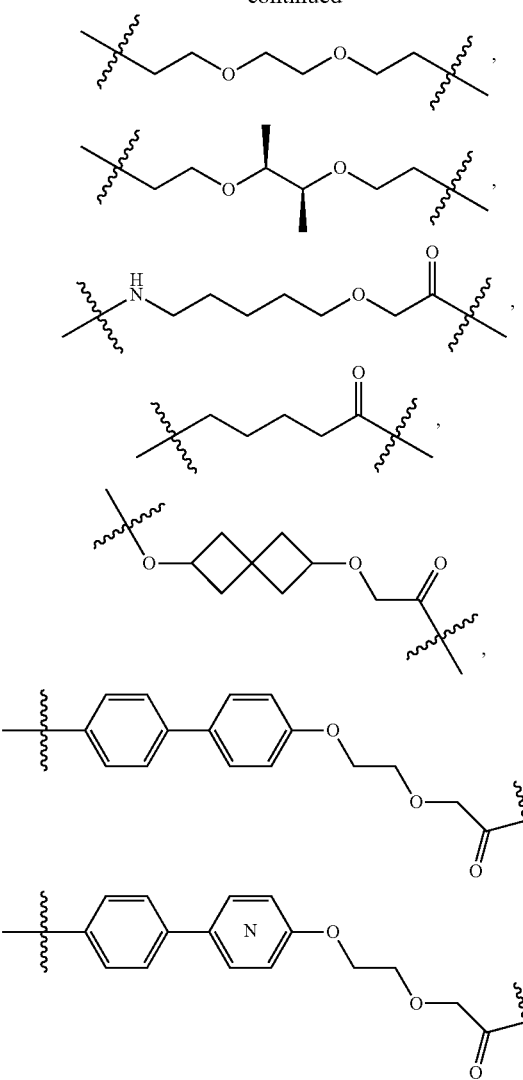
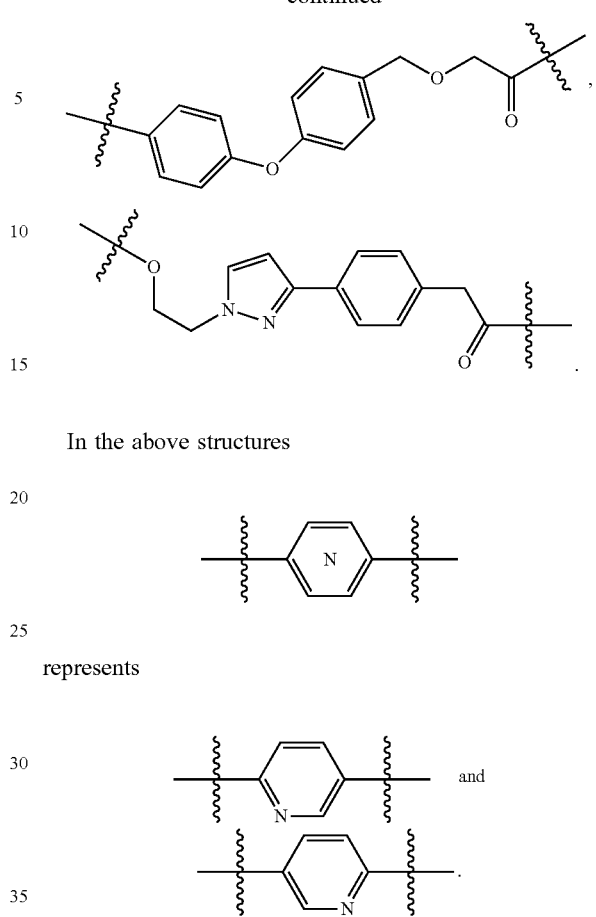
In the above structures
represents
and
.
In certain embodiments, Linker can be a 4-24 carbon atom linear chains, wherein one or more the carbon atoms in the linear chain can be replaced or substituted with oxygen, nitrogen, amide, fluorinated carbon, etc., such as the following:
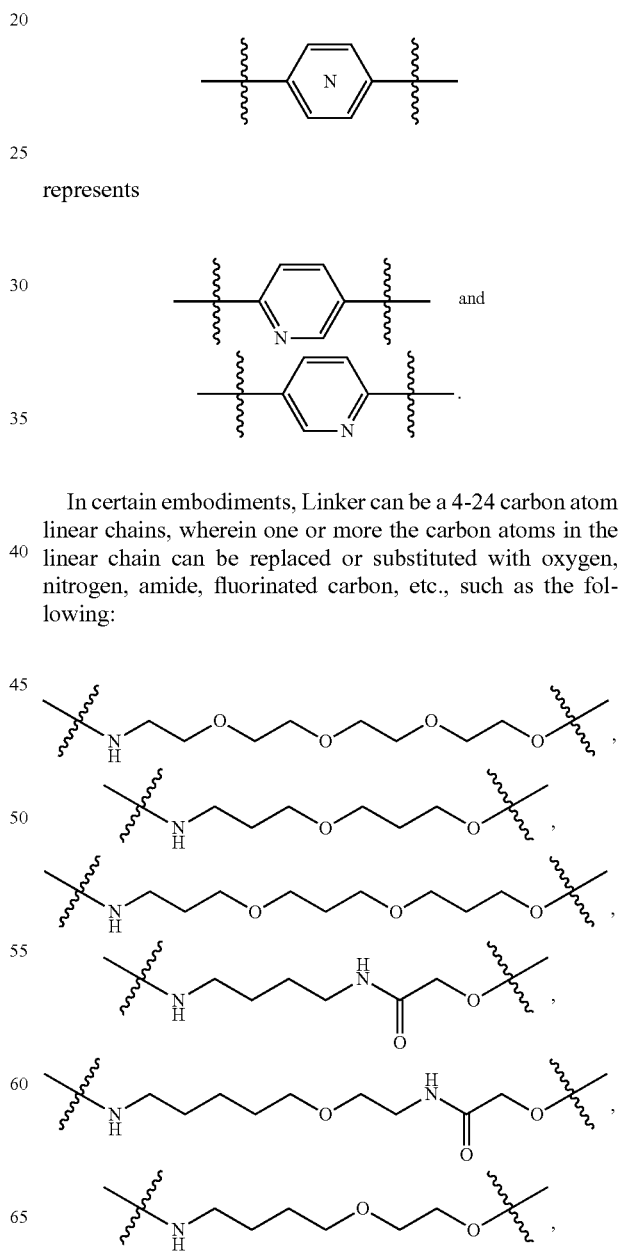

165
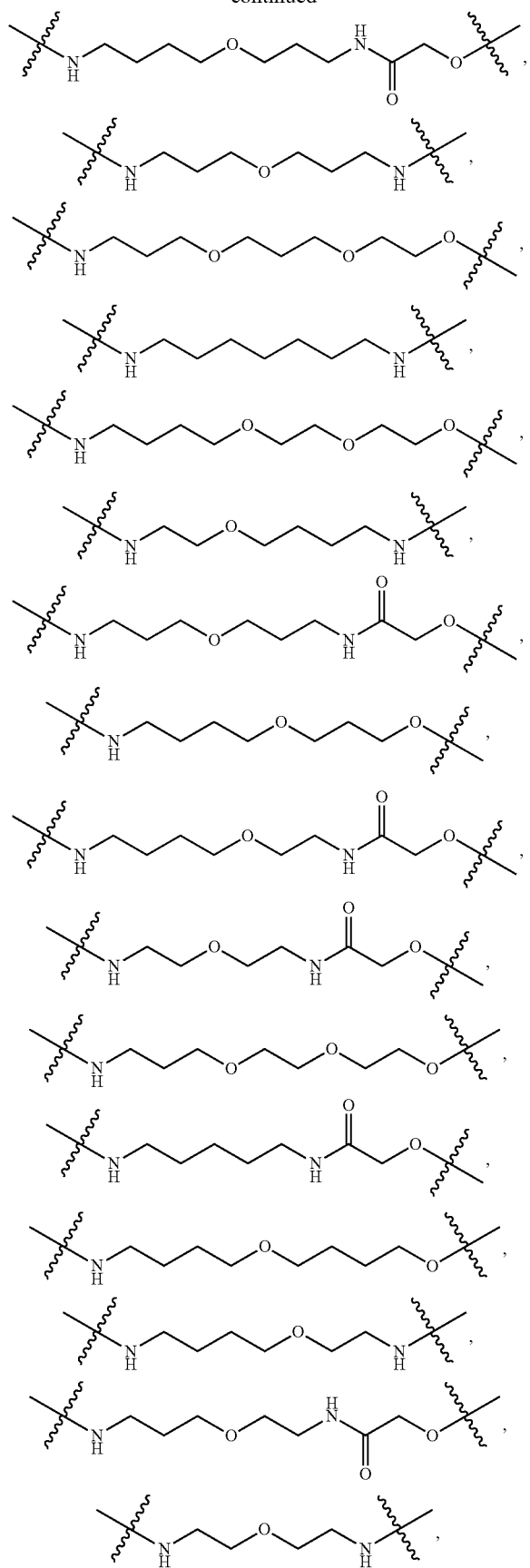
166
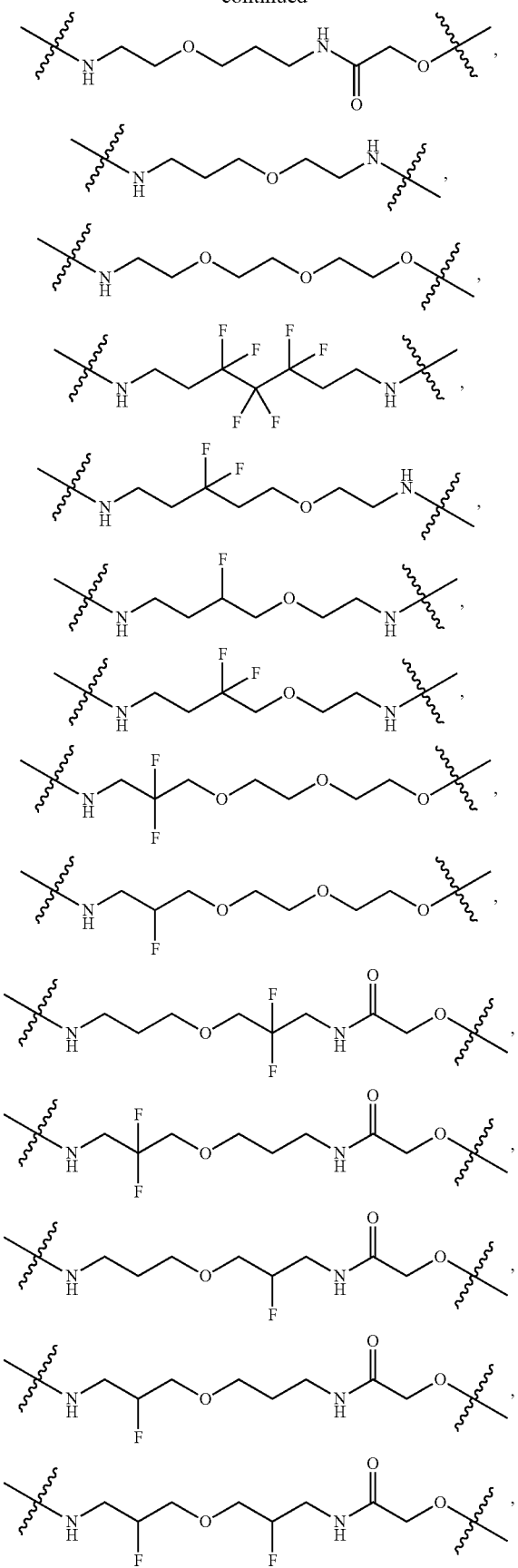

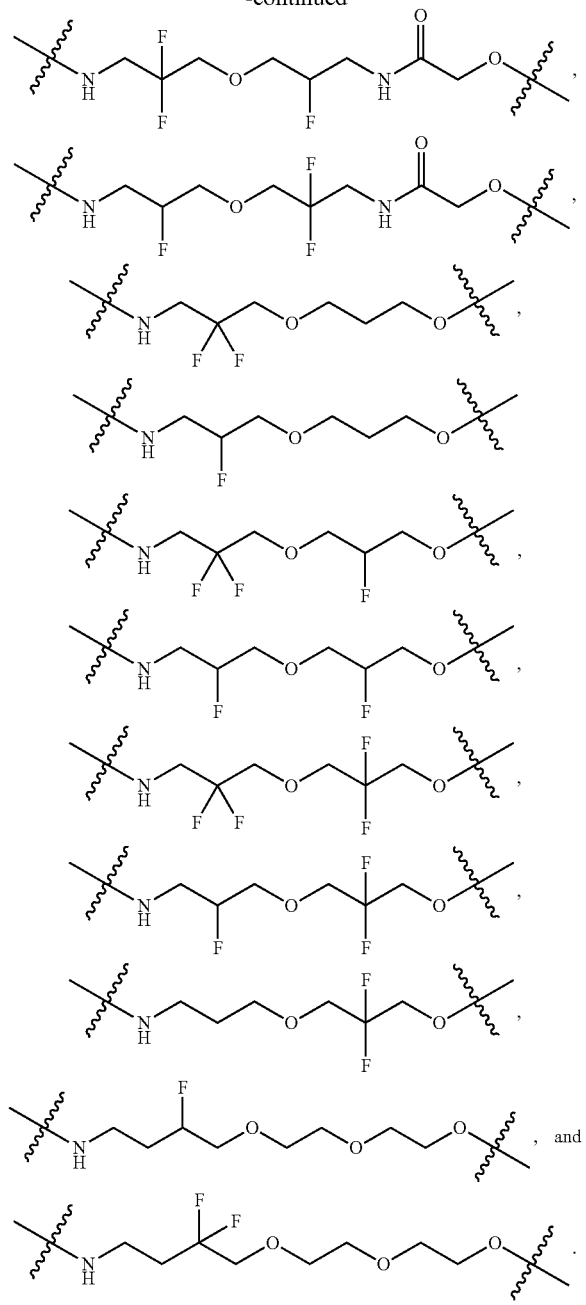

In certain embodiments, Linker can be a nonlinear chain, and can be, or include, aliphatic or aromatic or heteroaromatic cyclic moieties.

In certain embodiments, the Linker may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, the Linker may have 1, 2, 3, 4, 5, 6, 7, 8, 9, 10, 11, 12, 13, 14, or 15 fluorine substituents. In another embodiment the Linker is perfluorinated. In yet another embodiment the Linker is a partially or fully fluorinated poly ether. Nonlimiting examples of fluorinated Linkers include:

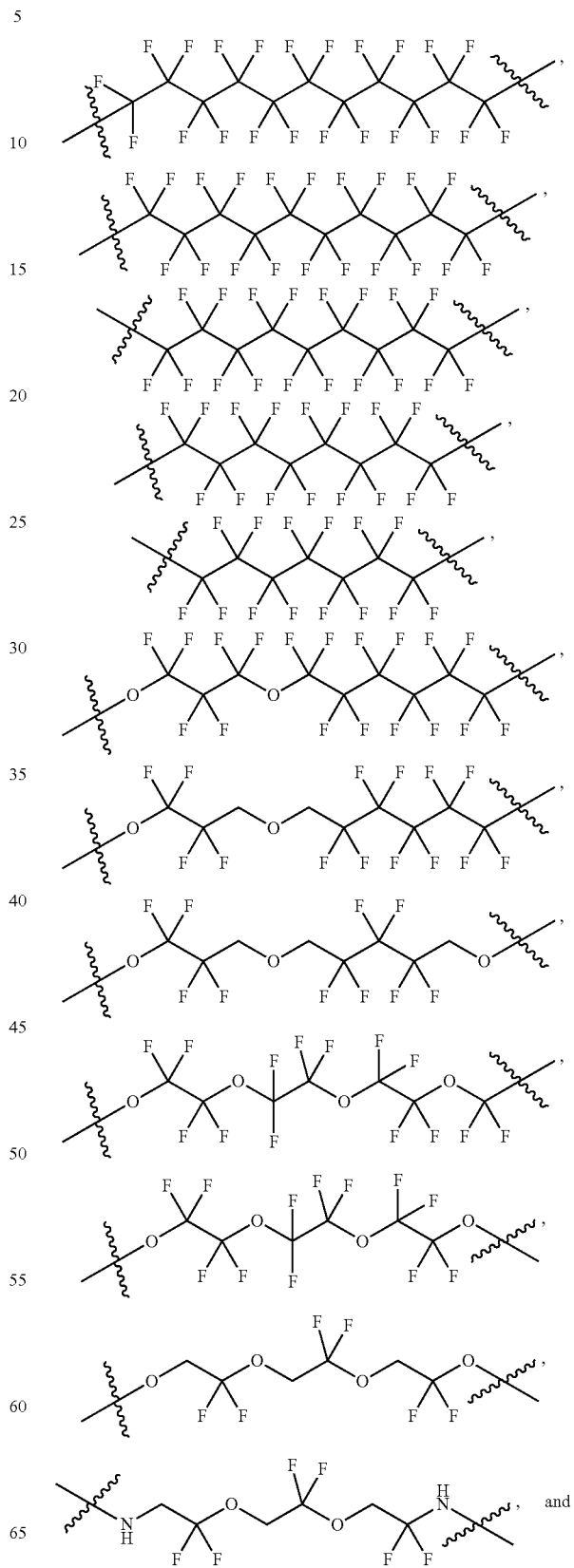

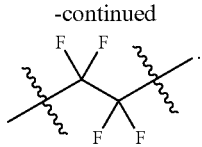

In certain embodiments, where the Target Ligand binds more than one protein (i.e., is not completely selective), selectivity may be enhanced by varying Linker length where the ligand binds some of its targets in different binding pockets, e.g., deeper or shallower binding pockets than others. Therefore, the length can be adjusted as desired.

In certain embodiments, the present application provides Degron-Linker (DL) having the following structure:

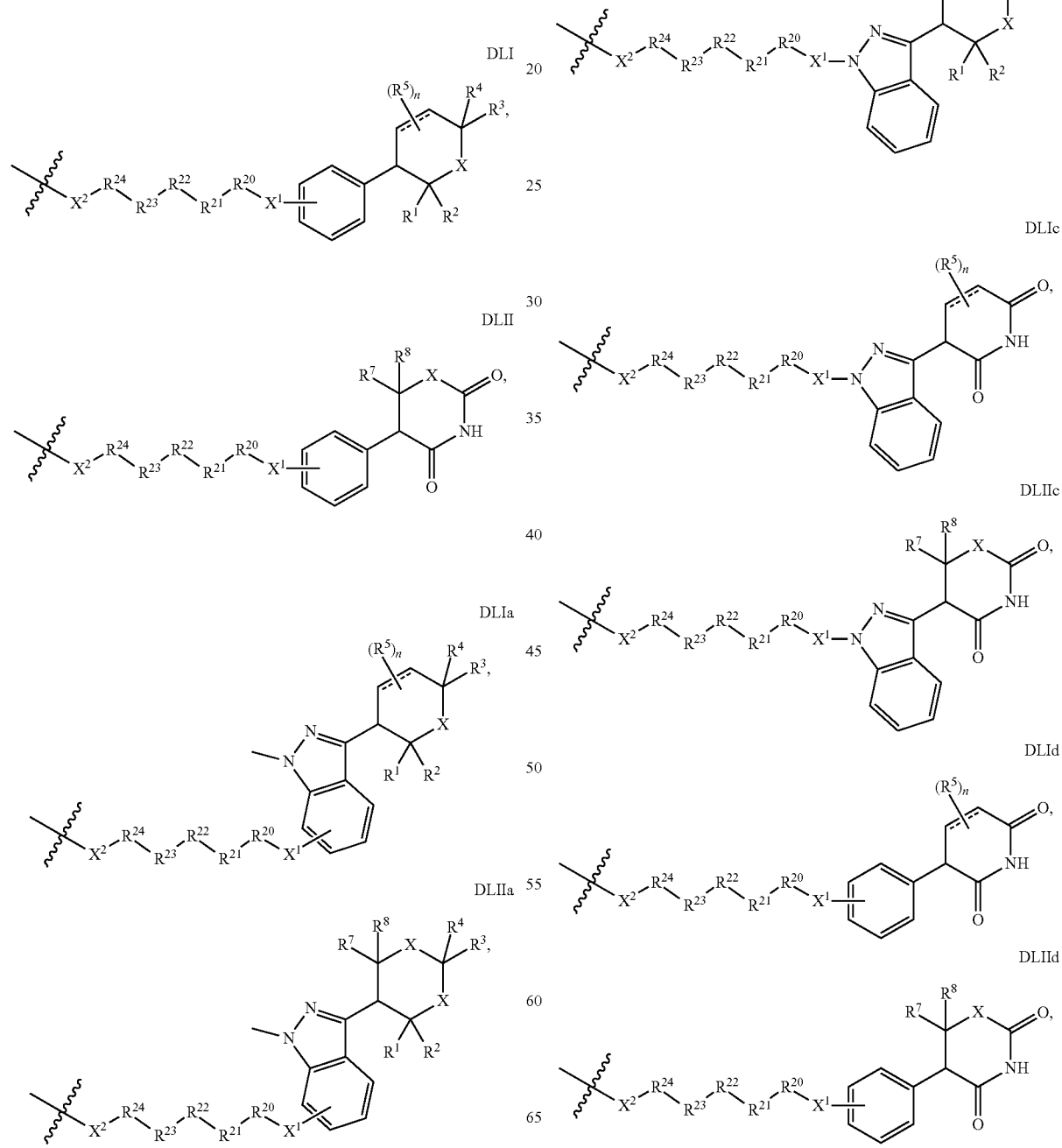

171
-continued
DLIe
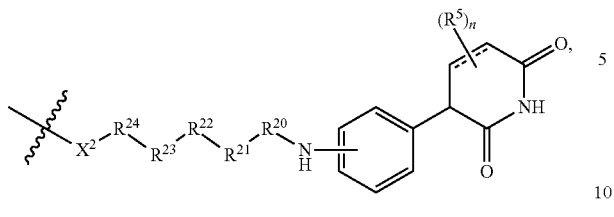
DLIIe
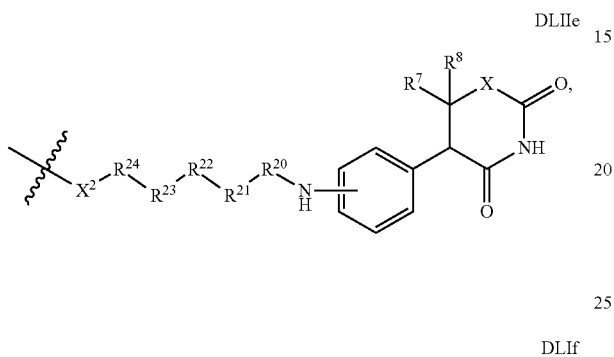
DLIf
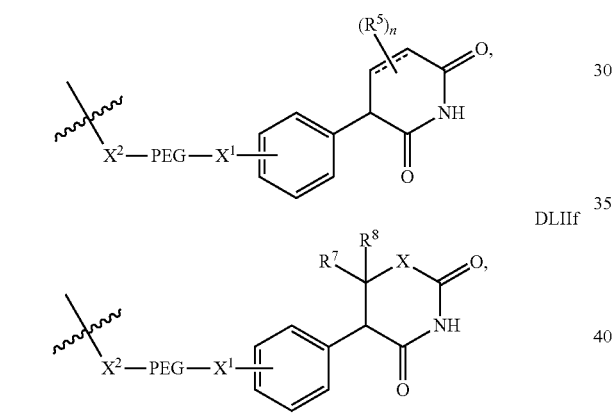
DLIIf
DLIg
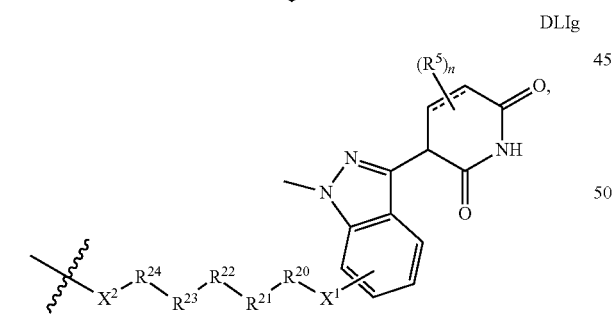
DLIIg
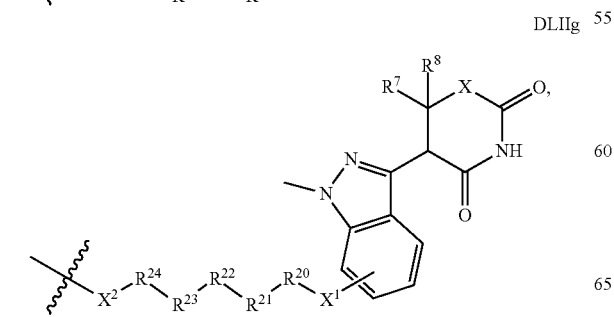
172
-continued
DLIh
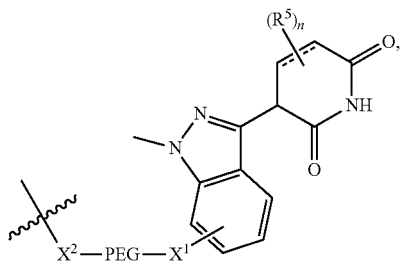
DLIIh
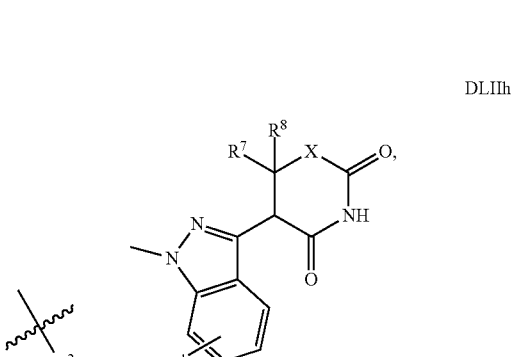
DLIi
DLIIi
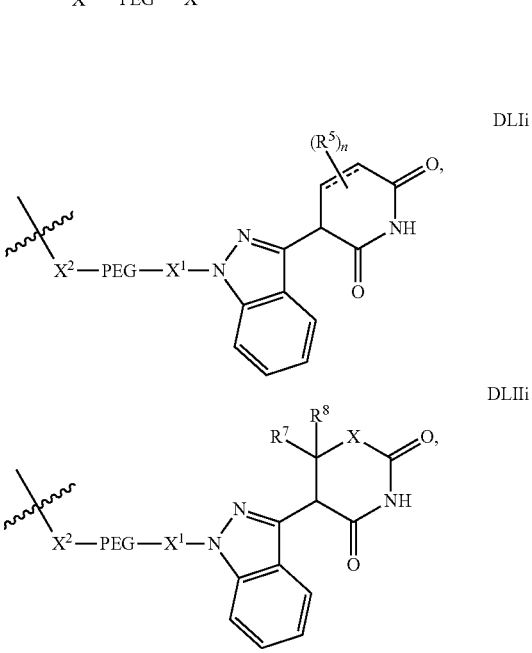
In an alternative embodiment, the present application provides Degron-Linker (DL) having the following structure:
DLIj
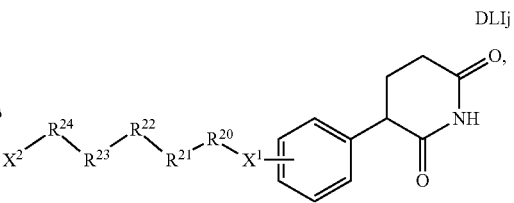

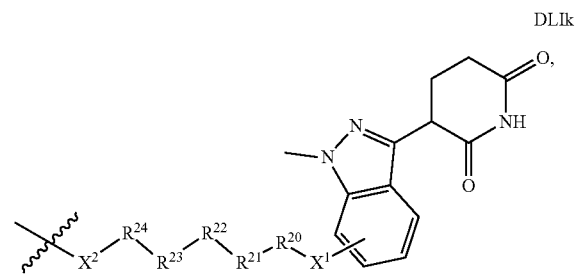
DLIk
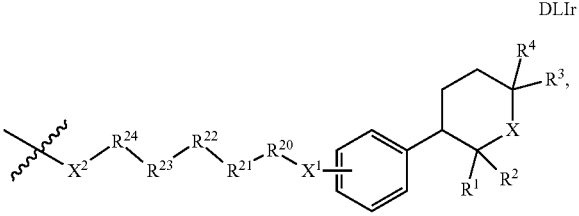
DLIr
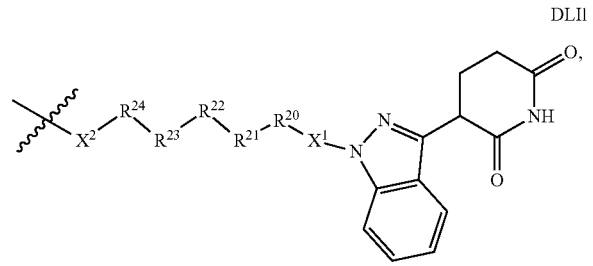
DLIl
DLIs
DLIm
DLIt
DLIn
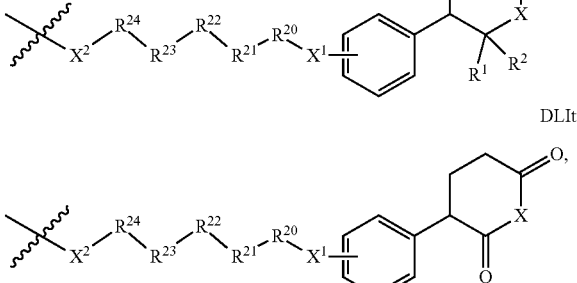
DLIu
DLIo
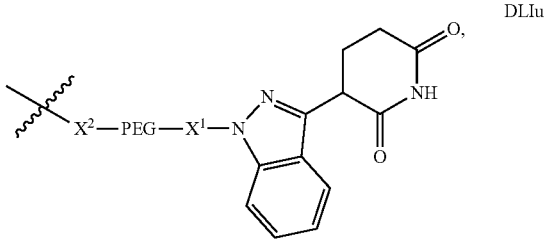
DLIv
DLIp
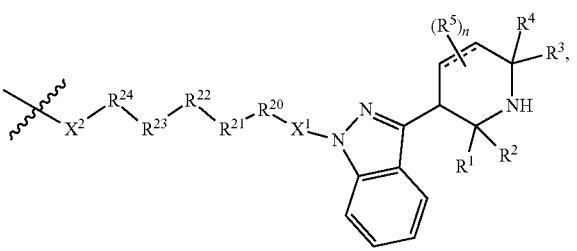
DLIw
DLIq
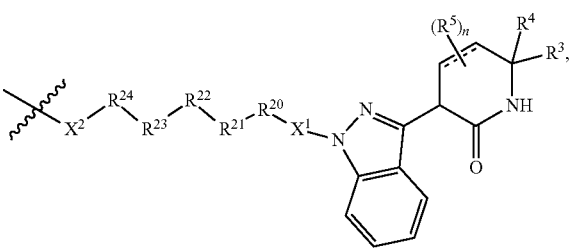
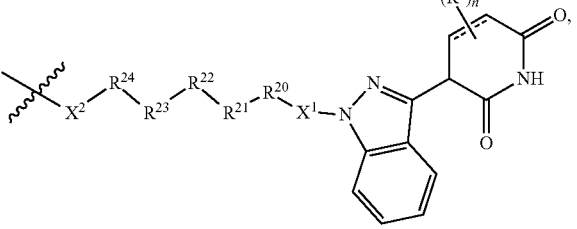
DLIx DLIy
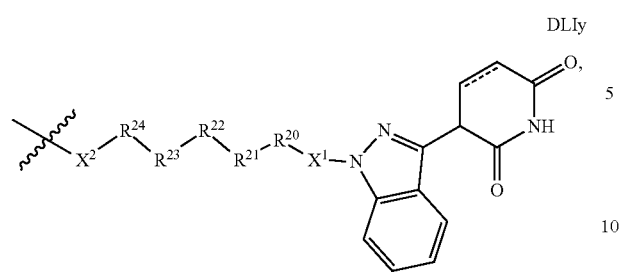
DLIz
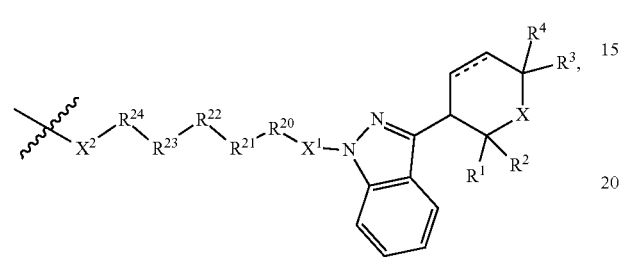
DLIaa
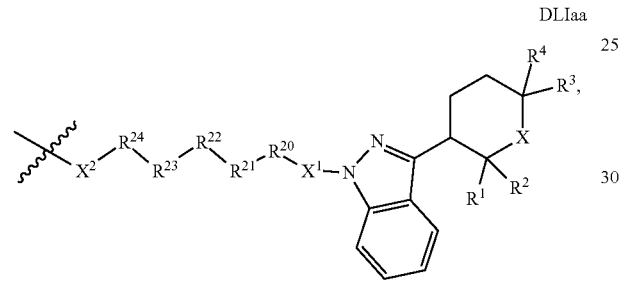
DLIab
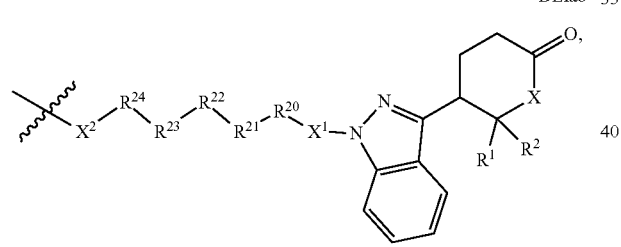
DLIac
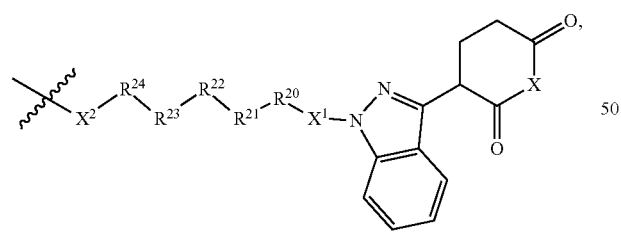
DLIad
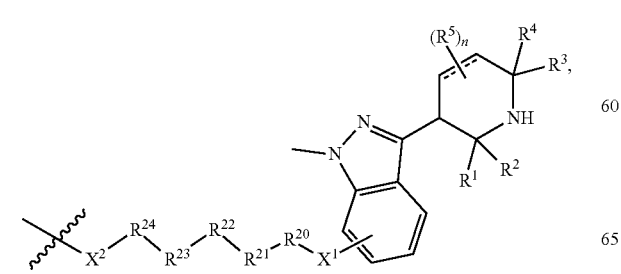
DLIae
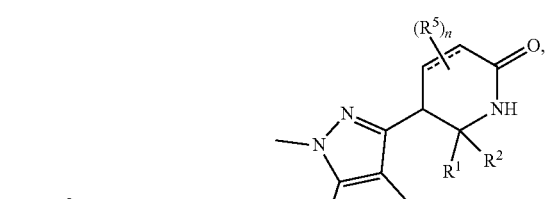
DLIaf
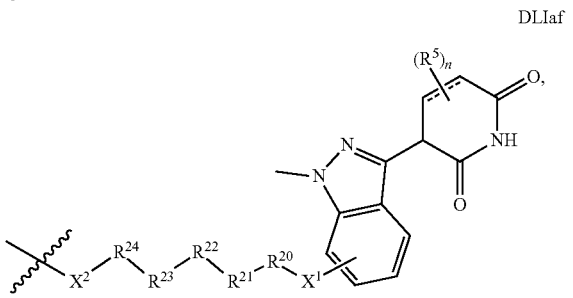
DLIag
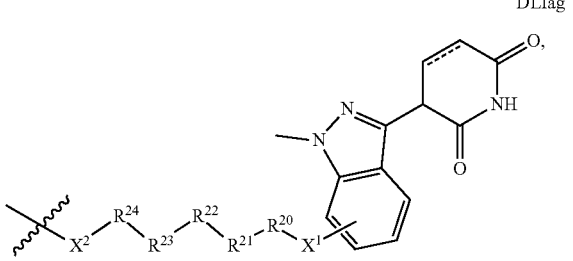
DLIah
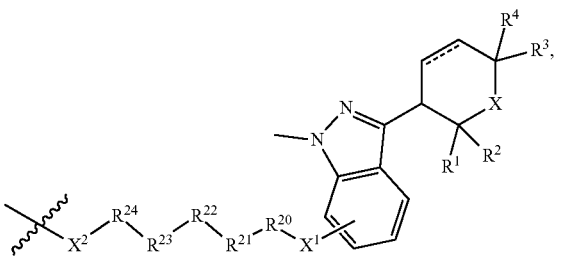
DLIai
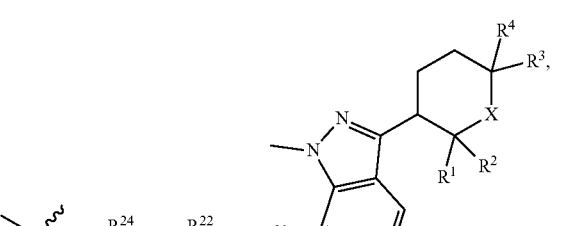
DLIaj
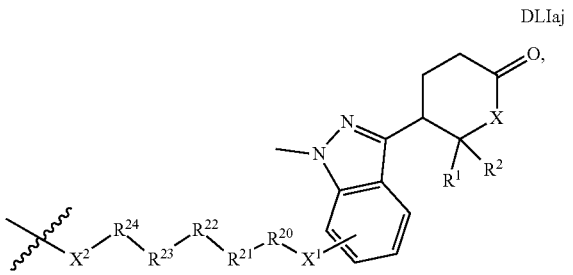

-continued

DLIak

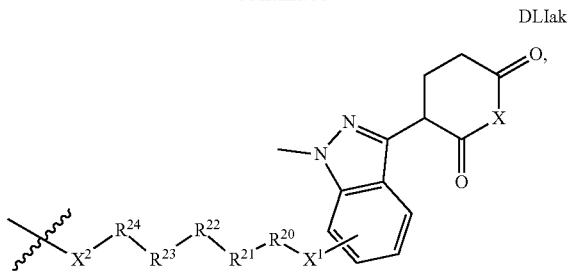

wherein each of the variables is as described above in Formula I and Formula LI; and a Targeting Ligand is covalently bonded to the DL through the

next to $X^2$.

Target Proteins

Degradation of cellular proteins is required for cell homeostasis and normal cell function, such as proliferation, differentiation and cell death. When this system becomes dysfunctional or does not identify and abate abnormal protein behavior in vivo, a disease state can arise in a host, such as a human. A large range of proteins can cause, modulate or amplify diseases in vivo, as well known to those skilled in the art, published in literature and patent filings as well as presented in scientific presentations.

Therefore, in one embodiment, a selected Degronimer of the present invention can be administered in vivo in an effective amount to a host in need thereof to degrade a selected protein that mediates a disorder to be treated. The selected Target Protein may modulate a disorder in a human via a mechanism of action such as modification of a biological pathway, pathogenic signaling or modulation of a signal cascade or cellular entry. In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense, yet for therapeutic purposes, degradation of the protein is preferred to inhibition.

The Target Protein is recruited with a Targeting Ligand for the Target Protein. Typically the Targeting Ligand binds the Target Protein in a non-covalent fashion. In an alternative embodiment, the Target Protein is covalently bound to the Degron in a manner that can be irreversible or reversible.

In one embodiment, the selected Target Protein is expressed from a gene that has undergone an amplification, translocation, deletion, or inversion event which causes or is caused by a medical disorder. In certain aspects, the selected Target Protein has been post-translationally modified by one, or a combination, of phosphorylation, acetylation, acylation including propionylation and crotylation, N-linked glycosylation, amidation, hydroxylation, methylation and polymethylation, O-linked glycosylation, pyrogultamoylation, myristoylation, farnesylation, geranylgeranylation, ubiquitination, sumoylation, or sulfation which causes or is caused by a medical disorder.

As contemplated herein, the present invention includes an Degronimer with a Targeting Ligand that binds to a Target Protein of interest. The Target Protein is any amino acid sequence to which an Degronimer can be bound which by degradation thereof, causes a beneficial therapeutic effect in vivo. In one embodiment, the Target Protein is a non-endogenous peptide such as that from a pathogen or toxin. In another embodiment, the Target Protein can be an endogenous protein that mediates a disorder. The endogenous protein can be either the normal form of the protein or an aberrant form. For example, the Target Protein can be a mutant protein found in cancer cells, or a protein, for example, where a partial, or full, gain-of-function or loss-of-function is encoded by nucleotide polymorphisms. In some embodiments, the Degronimer targets the aberrant form of the protein and not the normal form of the protein. In another embodiment, the Target Protein can mediate an inflammatory disorder or an immune disorder, including an auto-immune disorder.

In one embodiment, the Target Protein is a non-endogenous protein from a virus, as non-limiting examples, HIV, HBV, HCV, RSV, HPV, CMV, flavivirus, pestivirus, coronavirus, noroviridae, etc. In one embodiment, the Target Protein is a non-endogenous protein from a bacteria, which may be for example, a gram positive bacteria, gram negative bacteria or other, and can be a drug-resistant form of bacteria. In one embodiment, the Target Protein is a non-endogenous protein from a fungus. In one embodiment, the Target Protein is a non-endogenous protein from a prion. In one embodiment, the Target Protein is a protein derived from a eukaryotic pathogen, for example a protist, helminth, etc.

In one aspect, the Target Protein mediates chromatin structure and function. The Target Protein may mediate an epigenetic action such as DNA methylation or covalent modification of histones. An example is histone deacetylase (HDAC 1, 2, 3, 4, 5, 6, 7, 8, 9, 10 or 11). Alternatively, the Target Protein may be a bromodomain, which are readers of lysine acetylation (for example, BRD1, 2, 3, 4, 5, 6, 7, 8, 9 and T. FIG. 9 is a dendogram of the proteins of the bromodomain family, which, for example, can act as Target Proteins according to the present invention.

Other nonlimiting examples of Target Proteins are a structural protein, receptor, enzyme, cell surface protein, a protein involved in apoptotic signaling, aromatase, helicase, mediator of a metabolic process (anabolism or catabolism), antioxidant, protease, kinase, oxidoreductase, transferase, hydrolase, lyase, isomerase, ligase, enzyme regulator, signal transducer, structural molecule, binding activity (protein, lipid carbohydrate), cell motility protein, membrane fusion protein, cell communication mediator, regulator of biological processes, behavioral protein, cell adhesion protein, protein involved in cell death, protein involved in transport (including protein transporter activity, nuclear transport, ion transporter, channel transporter, carrier activity, permease, secretase or secretion mediator, electron transporter, chaperone regulator, nucleic acid binding, transcription regulator, extracellular organization and biogenesis regulator, and translation regulator).

In one embodiment, the Target Protein is a modulator of a signaling cascade related to a known disease state. In another embodiment, the Target Protein mediates a disorder by a mechanism different from modulating a signaling cascade. Any protein in a eukaryotic system or a microbial system, including a virus, bacteria or fungus, as otherwise described herein, are targets for proteasomal degradation using the present invention. The Target Protein may be a eukaryotic protein, and in some embodiments, a human protein.

In one embodiment, the Target Protein is RXR, DHFR, Hsp90, a kinase, HDM2, MDM2, BET bromodomain-containing protein, HDAC, IDH1, Mcl-1, human lysine methyltransferase, a nuclear hormone receptor, aryl hydrocarbon receptor (AHR), RAS, RAF, FLT, SMARC, KSR, NF2L, CTNB, CBLB, BCL.

In one embodiment, a bromodomain containing protein has histone acetyl transferase activity.

In one embodiment, the bromodomain containing protein is BRD2, BRD3, BRD4, BRDT or ASH1L.

In one embodiment, the bromodomain containing protein is a non-BET protein.

In one embodiment, the non-BET protein is BRD7 or BRD9.

In one embodiment, the FLT is not FLT 3. In one embodiment, the RAS is not RASK. In one embodiment, the RAF is not RAF1. In one embodiment, the SMARC is not SMARC2. In one embodiment, the KSR is not KSR1. In one embodiment, the NF2L is not NF2L2. In one embodiment, the CTNB is not CTNB1. In one embodiment, the BCL is not BCL6.

In one embodiment, the Target Protein is selected from: EGFR, FLT3, RAF1, SMRCA2, KSR1, NF2L2, CTNB1, CBLB, BCL6, and RASK.

In another embodiment, the Target Protein is not selected from: EGFR, FLT3, RAF1, SMRCA2, KSR1, NF2L2, CTNB1, CBLB, BCL6, and RASK.

In one embodiment, the Targeting Ligand is an EGFR ligand, a FLT3 ligand, a RAF1 ligand, a SMRCA2 ligand, a KSR1 ligand, a NF2L2 ligand, a CTNB1 ligand, a CBLB ligand, a BCL6 ligand, or a RASK ligand.

In one embodiment, the Targeting Ligand is not a EGFR ligand, a FLT3 ligand, a RAF1 ligand, a SMRCA2 ligand, a KSR1 ligand, a NF2L2 ligand, a CTNB1 ligand, a CBLB ligand, a BCL6 ligand, or a RASK ligand.

The present invention may be used to treat a wide range of disease states and/or conditions, including any disease state and/or condition in which a protein is dysregulated and where a patient would benefit from the degradation of proteins.

For example, a Target Protein can be selected that is a known target for a human therapeutic, and the therapeutic can be used as the Targeting Ligand when incorporated into the Degronimer according to the present invention. These include proteins which may be used to restore function in a polygenic disease, including for example B7.1 and B7, TINFR1m, TNFR2, NADPH oxidase, Bcl2/Bax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, e.g., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras/Raf/MER/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, puringergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-2/neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further Target Proteins include Acetyl-CoA carboxylase, adenylosuccinate synthetase, protoporphyrinogen oxidase, and enolpyruvylshikimate-phosphate synthase.

In certain embodiments, the Target Protein is derived from a kinase to which the Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70).

In certain embodiments, the Target Protein is derived from a kinase to which the Targeting Ligand is capable of binding or binds including, but not limited to, a serine/threonine kinase (e.g., casein kinase 2, protein kinase A, protein kinase B, protein kinase C, Raf kinases, CaM kinases, AKT1, AKT2, AKT3, ALK, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK 1, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK, or ULK2).

In certain embodiments, the Target Protein is derived from a kinase to which the Targeting Ligand is capable of binding or binds including, but not limited to a cyclin dependent kinase for example CDK1, CDK2, CDK3, CDK4, CDK5, CDK6, CDK7, CDK8, CDK9, CDK10, CDK11, CDK12, or CDK13.

In certain embodiments, the Target Protein is derived from a kinase to which the Targeting Ligand is capable of binding or binds including, but not limited to a leucine-rich repeat kinase (e.g., LRRK2).

In certain embodiments, the Target Protein is derived from a kinase to which the Targeting Ligand is capable of binding or binds including, but not limited to a lipid kinase (e.g., PIK3CA, PIK3CB) or a sphingosine kinase (e.g. S1P).

In certain embodiments, the Target Protein is derived from a BET bromodomain-containing protein to which the Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the Target Protein is derived from a nuclear protein to which the Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In one embodiment, the Target Protein is a protein, or a precursor, variant (e.g., a splice variant), mutant (e.g., substitution, deletion, duplication, insertion, insertion/deletion, extension, etc.), homolog, chimeric. polymorph, isoform, modification (e.g., post-translationally modified through glycosylation, phosphorylation, proteolysis, etc.), or recombinant thereof.

In certain embodiments, the Target Protein is a member of the Retinoid X Receptor (RXR) family and the disorder treated is a neuropsychiatric or neurodegenerative disorder. In certain embodiments, the Target Protein is a member of the Retinoid X Receptor (RXR) family and the disorder treated is schizophrenia.

In certain embodiments, the Target Protein is dihydrofolate reductase (DHFR) and the disorder treated is cancer. In certain embodiments, the Target Protein is dihydrofolate reductase (DHFR) and the disorder treated is microbial.

In certain embodiments, the Target Protein is dihydrofolate reductase from *Bacillus anthracis* (BaDHFR) and the disorder treated is anthrax.

In certain embodiments, the Target Protein is Heat Shock Protein 90 (HSP90) and the disorder treated is cancer.

In certain embodiments, the Target Protein is a kinase or phosphatase and the disorder treated is cancer.

In certain embodiments, the Target Protein is HDM2 and or MDM2 and the disorder treated is cancer.

In certain embodiments, the Target Protein is a BET bromodomain containing protein and the disorder treated is cancer.

In certain embodiments, the Target Protein is a lysine methyltransferase and the disorder treated is cancer.

In certain embodiments, the Target Protein belongs to the RAF family and the disorder treated is cancer.

In certain embodiments, the Target Protein belongs to the FKBP family and the disorder treated is an autoimmune disorder. In certain embodiments, the Target Protein belongs to the FKBP family and the disorder treated is organ rejection. In certain embodiments, the Target Protein belongs to the FKBP family and the compound is given prophylactically to prevent organ failure.

In certain embodiments, the Target Protein is an androgen receptor and the disorder treated is cancer.

In certain embodiments, the Target Protein is an estrogen receptor and the disorder treated is cancer.

In certain embodiments, the Target Protein is a viral protein and the disorder treated is a viral infection. In certain embodiments, the Target Protein is a viral protein and the disorder treated is HIV, HPV, or HCV.

In certain embodiments, the Target Protein is an AP-1 or AP-2 transcription factor and the disorder treated is cancer.

In certain embodiments, the Target Protein is a HIV protease and the disorder treated is a HIV infection. In certain embodiments, the Target Protein is a HIV integrase and the disorder treated is a HIV infection. In certain embodiments, the Target Protein is a HCV protease and the disorder treated is a HCV infection. In certain embodiments, the treatment is prophylactic and the Target Protein is a viral protein.

In certain embodiments, the Target Protein is a member of the histone deacetylase (HDAC) family and the disorder is a neurodegenerative disorder. In certain embodiments, the Target Protein is a member of the histone deacetylase (HDAC) family and the disorder is Huntingon's, Parkinson's, Kennedy disease, amyotropic lateral sclerosis, Rubinstein-Taybi syndrome, or stroke.

In certain embodiments, the Target Protein as referred to herein is named by the gene that expresses it. The person skilled in the art will recognize that when a gene is referred to as a Target Protein, the protein encoded by the gene is the Target Protein. For example, ligands for the protein SMCA2 which is encoded by SMRCA2 are referred to as SMRCA2 Targeting Ligands.

Targeting Ligands

In certain aspects, the Targeting Ligand is a ligand which covalently or non-covalently binds to a Target Protein which has been selected for proteasomal degradation by the selected Degronimer. FIGS. 1A-8PPPPP describe targeting ligands for a number of proteins wherein R is the point of attachment for the linker. While specific targeting ligands are exemplified in the figures, additional ligands and examples can be found in the references cited in the brief description of figures or are generally known in the art.

In one embodiment, the Targeting Ligand binds to an endogenous protein which has been selected for degradation as a means to achieve a therapeutic effect on the host. Illustrative Targeting Ligands include: RXR ligands, DHFR ligands, Hsp90 inhibitors, kinase inhibitors, HDM2 and MDM2 inhibitors, compounds targeting Human BET bromodomain-containing proteins, HDAC inhibitors, ligands of MerTK, ligands of IDH1, ligands of Mcl-1, ligands of SMRCA2, ligands of EGFR, ligands of RAF, ligands of cRAF, human lysine methyltransferase inhibitors, angiogenesis inhibitors, nuclear hormone receptor compounds, immunosuppressive compounds, and compounds targeting the aryl hydrocarbon receptor (AHR), among numerous others. Targeting Ligands also considered to include their pharmaceutically acceptable salts, prodrugs and isotopic derivatives.

In certain aspects, the Targeting Ligand binds to a dehalogenase enzyme in a patient or subject or in a diagnostic assay and is a haloalkane (preferably a $C_1$-$C_{10}$alkyl group which is substituted with at least one halo group, preferably a halo group at the distal end of the alkyl group (i.e., away from the Linker). In still other embodiments, the Targeting Ligand is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure—$(CH_2)_v$-Halo where v is any integer from 2 to about 12, often about 3 to about 8, more often about 4 to about 6. Halo may be any halogen, but is preferably Cl or Br, more often Cl.

In certain embodiments, the Targeting Ligand is a retinoid X receptor (RXR) agonist or antagonist. Non-limiting examples include retinol, retinoic acid, bexarotene, docosahexenoic acid, compounds disclosed in WO 9929324, the publication by Canan Koch et al. (J. Med. Chem. 1996, 39, 3229-3234) titled "Identification of the First Retinoid X Receptor Homodimer Antagonist", WO 9712853, EP 0947496A1, WO 2016002968, and analogs thereof.

In certain embodiments, the Targeting Ligand is a DHFR agonist or antagonist. Non-limiting examples include folic acid, methotrexate, 8,10-dideazatetrahydrofolate compounds disclosed by Tian et al. (Chem. Biol. Drug Des. 2016, 87, 444-454) titled "Synthesis, Antifolate and Anticancer Activities of N5-Substituted 8,10-Dideazatetrahydrofolate Analogues", compounds prepared by Kaur et al. (Biorg. Med. Chem. Lett. 2016, 26, 1936-1940) titled "Rational Modification of the Lead Molecule: Enhancement in the Anticancer and Dihydrofolate Reductase Inhibitory Activity", WO 2016022890, compounds disclosed by Zhang et al. (Int. J. Antimicrob. Agents 46, 174-182) titled "New Small-Molecule Inhibitors of Dihydrofolate Reductase Inhibit *Streptococcus Mutans*", modified trimethoprim analogs developed by Singh et al. (J. Med. Chem. 2012, 55, 6381-6390) titled "Mechanism Inspired Development of Rationally Designed Dihydrofolate Reductase Inhibitors as Anticancer Agents", WO20111153310, and analogs thereof.

In certain embodiments, the Targeting Ligand derived from estrogen, an estrogen analog, SERM (selective estrogen receptor modulator), a SERD (selective estrogen receptor degrader), a complete estrogen receptor degrader, or another form of partial or complete estrogen antagonist or agonist. Examples are the partial anti-estrogens raloxifene and tamoxifen and the complete antiestrogen fulvestrant. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478,847; 5,393,763; and 5,457, 117, WO2011/156518, U.S. Pat. Nos. 8,455,534 and 8,299, 112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In certain embodiments, the Targeting Ligand is a HSP90 inhibitor identified in Vallee et al. (J. Med. Chem. 2011, 54, 7206-7219) titled "Tricyclic Series of Heat Shock Protein 90 (Hsp90) Inhibitors Part I: Discovery of Tricyclic Imidazo [4,5-C]Pyridines as Potent Inhibitors of the Hsp90 Molecular Chaperone", including YKB (N-[4-(3H-imidazo[4,5-C] Pyridin-2-yl)-9H-Fluoren-9-yl]-succinamide), a HSP90 inhibitors (modified) identified in Brough et al. (J. Med. Chem. 2008, 51, 196-218) titled "4,5-Diarylisoxazole Hsp90 Chaperone Inhibitors: Potential Therapeutic Agents for the Treatment of Cancer", including compound 2GJ (5-[2,4-dihydroxy-5-(1-methylethyl)phenyl]-n-ethyl-4-[4-(morpholin-4-ylmethyl)phenyl]isoxazole-3-carboxamide), the HSP90 inhibitor geldanamycin ((4E,6Z,8S,9S,10E,12S, 13R,14S,16R)-13-hydroxy-8,14,19-trimethoxy-4,10,12,16-tetramethyl-3,20,22-trioxo-2-azabicyclo[16.3.1](derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")), or a HSP90 inhibitor (modified) identified in Wright et al. (Chem. Biol. 2004, 11, 775-785) titled "Structure-Activity Relationships in Purine-Based Inhibitor Binding to Hsp90 Isoforms", including the HSP90 inhibitor PU3. Other non-limiting examples of Hsp90 Targeting Ligands include SNX5422 currently in phase I clinical trials Reddy et al. (Clin. Lymphoma Myeloma Leuk. 2013, 13, 385-391) titled "Phase I Trial of the Hsp90 Inhibitor Pf-04929113 (Snx5422) in Adult Patients with Recurrent, Refractory Hematologic Malignancies", or NVP-AUY922 whose anti-cancer activity was assessed by Jensen et al. (Breast Cancer Research: BCR 2008, 10, R33-R33) titled "Nvp-Auy922: A Small Molecule Hsp90 Inhibitor with Potent Antitumor Activity in Preclinical Breast Cancer Models".

In certain embodiments, the Targeting Ligand is a kinase inhibitor identified in Millan et al. (J. Med. Chem. 2011, 54, 7797-7814) titled "Design and Synthesis of Inhaled P38 Inhibitors for the Treatment of Chronic Obstructive Pulmonary Disease", including the kinase inhibitors Y1W and Y1X, a kinase inhibitor identified in Schenkel et al. (J. Med. Chem. 2011, 54, 8440-8450) titled "Discovery of Potent and Highly Selective Thienopyridine Janus Kinase 2 Inhibitors", including the compounds 6TP and OTP, a kinase inhibitor identified in van Eis et al. (Biorg. Med. Chem. Lett. 2011, 21, 7367-7372) titled "2,6-Naphthyridines as Potent and Selective Inhibitors of the Novel Protein Kinase C Isozymes", including the kinase inhibitors 07U and YCF identified in Lountos et al. (J. Struct. Biol. 2011, 176, 292-301) titled "Structural Characterization of Inhibitor Complexes with Checkpoint Kinase 2 (Chk2), a Drug Target for Cancer Therapy", including the kinase inhibitors XK9 and NXP, afatinib, fostamatinib, gefitinib, lenvatinib, vandetanib, Gleevec, pazopanib, AT-9283, TAE684, nilotanib, NVP-BSK805, crizotinib, JNJ FMS, foretinib, OSI-027, OSI-930, or OSI-906.

In certain embodiments, the Targeting Ligand is a HDM2/MDM2 inhibitor identified in Vassilev et al. (*Science* 2004, 303, 844-848) titled "In Vivo Activation of the P53 Pathway by Small-Molecule Antagonists of Mdm2", and Schneekloth et al. (*Bioorg. Med. Chem. Lett.* 2008, 18, 5904-5908) titled "Targeted Intracellular Protein Degradation Induced by a Small Molecule: En Route to Chemical Proteomics", including the compounds nutlin-3, nutlin-2, and nutlin-1.

In certain embodiments, the Targeting Ligand is a Human BET Bromodomain Targeting Ligand identified in Filippakopoulos et al. (*Nature* 2010, 468, 1067-1073) titled "Selective Inhibition of Bet Bromodomains" such as JQ 1; a ligand identified in Nicodeme et al. (*Nature* 2010, 468, 1119-1123) titled "Suppression of Inflammation by a Synthetic Histone Mimic"; Chung et al. (*J. Med. Chem.* 2011, 54, 3827-3838) titled "Discovery and Characterization of Small Molecule Inhibitors of the Bet Family Bromodomains"; a compound disclosed in Hewings et al. (*J. Med. Chem.* 2011, 54, 6761-6770) titled "3,5-Dimethylisoxazoles Act as Acetyl-Lysine-Mimetic Bromodomain Ligands"; a ligand identified in Dawson et al. (*Nature* 2011, 478, 529-533) titled "Inhibition of Bet Recruitment to Chromatin as an Effective Treatment for MLL-Fusion Leukaemia"; or a ligand identified in the following patent applications US 2015/0256700, US 2015/0148342, WO 2015/074064, WO 2015/067770, WO 2015/022332, WO 2015/015318, and WO 2015/011084.

In certain embodiments, the Targeting Ligand is a HDAC Targeting Ligand identified in Finnin et al. (*Nature* 1999, 401, 188-193) titled "Structures of a Histone Deacetylase Homologue Bound to the Tsa and Saha Inhibitors", or a ligand identified as Formula (I) in PCT WO0222577.

In certain embodiments, the Targeting Ligand is a Human Lysine Methyltransferase ligand identified in Chang et al. (*Nat Struct Mol Biol* 2009, 16, 312-317) titled "Structural Basis for G9a-Like Protein Lysine Methyltransferase Inhibition by Bix-01294", a ligand identified in Liu et al. (*J Med Chem* 2009, 52, 7950-7953) titled "Discovery of a 2,4-Diamino-7-Aminoalkoxyquinazoline as a Potent and Selective Inhibitor of Histone Lysine Methyltransferase G9a", azacitidine, decitabine, or an analog thereof.

In certain embodiments, the Targeting Ligand is an angiogenesis inhibitor. Non-limiting examples of angiogenesis inhibitors include: GA-1, estradiol, testosterone, ovalicin, fumagillin, and analogs thereof.

In certain embodiments, the Targeting Ligand is an immunosuppressive compound. Non-limiting examples of immunosuppressive compounds include: AP21998, hydrocortisone, prednisone, prednisolone, methylprednisolone, beclometasone dipropionate, methotrexate, ciclosporin, tacrolimus, actinomycin, and analogues thereof.

In certain embodiments, the Targeting Ligand is an Aryl Hydrocarbon Receptor (AHR) ligand. Non-limiting examples of AHR ligands include: apigenin, SR1, LGC006, and analogues thereof.

In certain embodiments, the Targeting Ligand is a MerTK or Mer Targeting ligand. Non-limiting examples of MerTK Targeting Ligands are included in WO2013/177168 and WO2014/085225, both titled "Pyrimidine Compounds for the Treatment of Cancer" filed by Wang, et al.

In certain embodiments, the Targeting Ligand is an EGFR ligand. In certain embodiments the Targeting Ligand is an EGRF ligand selected from Afatinib, Dacomitinib, Neratinib, Poziotinib, and Canertinib, or derivatives thereof.

In certain embodiments, the Targeting Ligand is a FLT3 Ligand. In certain embodiments, the Targeting Ligand is a FLT3 ligand selected from Tandutinib, Lestaurtinib, Sorafenib, Midostaurin, Quizartinib, and Crenolanib.

In certain embodiments, the Targeting Ligand is a RAF inhibitor. In certain embodiments the Targeting Ligand is a RAF inhibitor selected from Dabrafenib, Regorafenib, and Vemurafenib. In certain embodiments the Targeting Ligand is a cRAF inhibitor.

In some embodiments, the Targeting Ligand is an Ubc9 SUMO E2 ligase 5F6D Targeting Ligand including but not limited to those described in "Insights Into the Allosteric Inhibition of the SUMO E2 Enzyme Ubc9." by Hewitt, W. M., et. al. (2016) *Angew. Chem. Int. Ed. Engl.* 55: 5703-5707

In another embodiment, the Targeting Ligand is a Tank1 Targeting Ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) *Acta Crystallogr., Sect. F* 68: 115-118; and "Structure-Efficiency Relationship of [1,2,4]Triazol-3-ylamines as Novel Nicotinamide Isosteres that Inhibit Tankyrases." Shultz, M. D., et al. (2013) *J. Med. Chem.* 56: 7049-7059.

In another embodiment, the Targeting Ligand is a SH2 domain of pp60 Src Targeting Ligand including but not limited to those described in "Requirements for Specific Binding of Low Affinity Inhibitor Fragments to the SH2 Domain of pp60Src Are Identical to Those for High Affinity Binding of Full Length Inhibitors," Gudrun Lange, et al., *J. Med. Chem.* 2003, 46, 5184-5195.

In another embodiment, the Targeting Ligand is a Sec7 domain Targeting Ligand including but not limited to those described in "The Lysosomal Protein Saposin B Binds Chloroquine," Huta, B. P., et al., (2016) *Chemmedchem* 11: 277.

In another embodiment, the Targeting Ligand is a Saposin-B Targeting Ligand including but not limited to those described in "The structure of cytomegalovirus immune modulator UL 141 highlights structural Ig-fold versatility for receptor binding" I. Nemcovicova and D. M. Zajonc *Acta Cryst.* (2014). D70, 851-862.

In another embodiment, the Targeting Ligand is a Protein S100-A7 2OWS Targeting Ligand including but not limited to those described in "2WOS STRUCTURE OF HUMAN S100A7 IN COMPLEX WITH 2,6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment, the Targeting Ligand is a Phospholipase A2 Targeting Ligand including but not limited to those described in "Structure-based design of the first potent and selective inhibitor of human non-pancreatic secretory phospholipase A2 "Schevitz, R. W., et al., *Nat. Struct. Biol.* 1995, 2, 458-465.

In another embodiment, the Targeting Ligand is a PHIP Targeting Ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment, the Targeting Ligand is a PDZ Targeting Ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment, the Targeting Ligand is a PARP15 Targeting Ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment, the Targeting Ligand is a PARP14 Targeting Ligand including but not limited to those described in "Discovery of Ligands for ADP-Ribosyltransferases via Docking-Based Virtual Screening." Andersson, C. D., et al., (2012) J. Med. Chem. 55: 7706-7718; "Family-wide chemical profiling and structural analysis of PARP and tankyrase inhibitors."Wahlberg, E., et al. (2012) Nat. Biotechnol. 30: 283-288; "Discovery of Ligands for ADP-Ribosyltransferases via Docking-Based Virtual Screening. "Andersson, C. D., et al. (2012) J. Med. Chem. 55: 7706-7718.

In another embodiment, the Targeting Ligand is a MTH1 Targeting Ligand including but not limited to those described in "MTH1 inhibition eradicates cancer by preventing sanitation of the dNTP pool" Helge Gad, et. al. Nature, 2014, 508, 215-221.

In another embodiment, the Targeting Ligand is a mPGES-1 Targeting Ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment, the Targeting Ligand is a FLAP-5-lipoxygenase-activating protein Targeting Ligand including but not limited to those described in "Crystal structure of inhibitor-bound human 5-lipoxygenase-activating protein," Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) Science 317: 510-512.

In another embodiment, the Targeting Ligand is a FA Binding Protein Targeting Ligand including but not limited to those described in "A Real-World Perspective on Molecular Design." Kuhn, B.; et al. J. Med. Chem. 2016, 59, 4087-4102.

In another embodiment, the Targeting Ligand is a BCL2 Targeting Ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment, the Targeting Ligand is a NF2L2 Targeting Ligand.

In another embodiment, the Targeting Ligand is a CTNNB1 Targeting Ligand.

In another embodiment, the Targeting Ligand is a CBLB Targeting Ligand.

In another embodiment, the Targeting Ligand is a BCL6 Targeting Ligand.

In another embodiment, the Targeting Ligand is a RASK Targeting Ligand.

In another embodiment, the Targeting Ligand is a TNIK Targeting Ligand.

In another embodiment, the Targeting Ligand is a MEN1 Targeting Ligand.

In another embodiment, the Targeting Ligand is a PI3Ka Targeting Ligand.

In another embodiment, the Targeting Ligand is a IDO1 Targeting Ligand.

In another embodiment, the Targeting Ligand is a MCL1 Targeting Ligand.

In another embodiment, the Targeting Ligand is a PTPN2 Targeting Ligand.

In another embodiment, the Targeting Ligand is a HER2 Targeting Ligand.

In another embodiment, the Targeting Ligand is an EGFR Targeting Ligand. In one embodiment the Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR. Non-limiting examples of Linker binding locations are provided in the below tables. In one embodiment, the EGFR Targeting Ligand binds the L858R mutant of EGFR. In another embodiment, the EGFR Targeting Ligand binds the T790M mutant of EGFR. In another embodiment, the EGFR Targeting Ligand binds the C797G or C797S mutant of EGFR. In one embodiment, the EGFR Targeting Ligand is selected from erlotinib, gefitinib, afatinib, neratinib, and dacomitinib and binds the L858R mutant of EGFR. In another embodiment, the EGFR Targeting Ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment, the EGFR Targeting Ligand is EAI045 and binds the C797G or C797S mutant of EGFR.

In one embodiment, the protein target and Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

In one embodiment, the protein target and Targeting Ligand pair are discovered by screening promiscuous kinase binding ligands for context-specific degradation. Non-limiting examples of targeting ligands are shown below and are found in "Optimized Chemical Proteomics Assay for Kinase Inhibitor Profiling" Guillaume Médard, Fiona Pachl, Benjamin Ruprecht, Susan Klaeger, Stephanie Heinzlmeir, Dominic Helm, Huichao Qiao, Xin Ku, Mathias Wilhelm, Thomas Kuehne, Zhixiang Wu, Antje Dittmann, Carsten Hopf, Karl Kramer, and Bernhard Kuster J. Proteome Res., 2015, 14(3), pp 1574-1586:

189 190
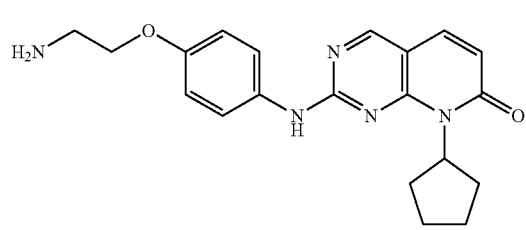
VI16743
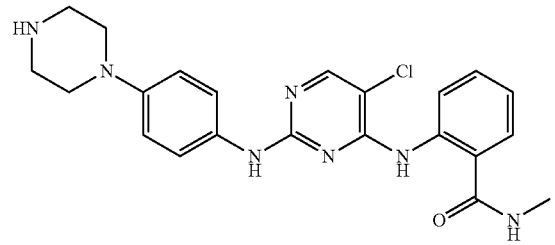
CTx-0294885
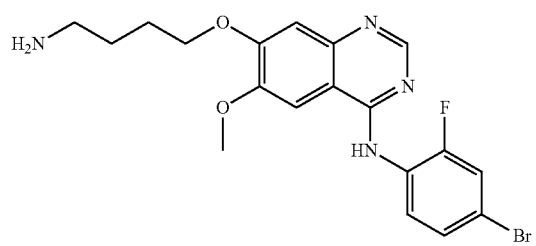
Vandetanib
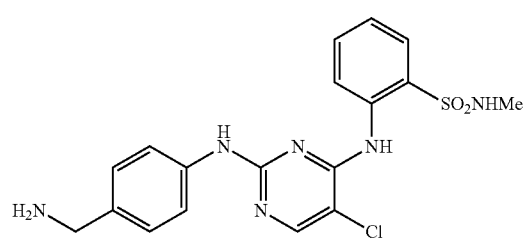
CTx-related
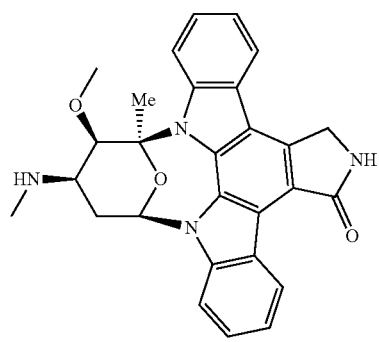
Staurosporine
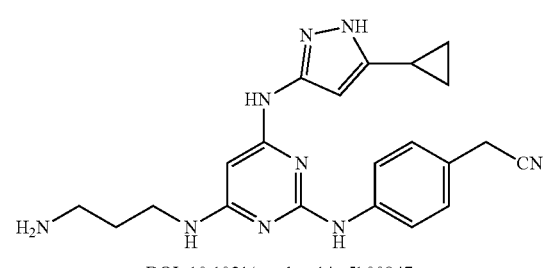
DOI: 10.1021/acschembio.5b00847
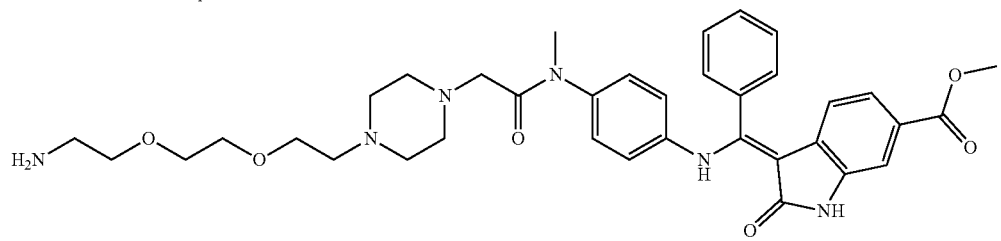
Nintedanib
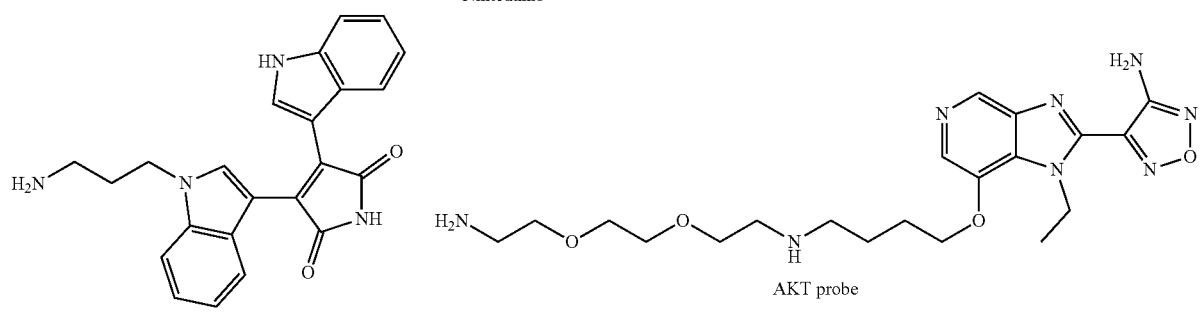
bisindolylmaleimide III
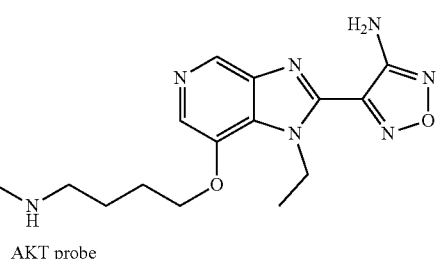
AKT probe -continued
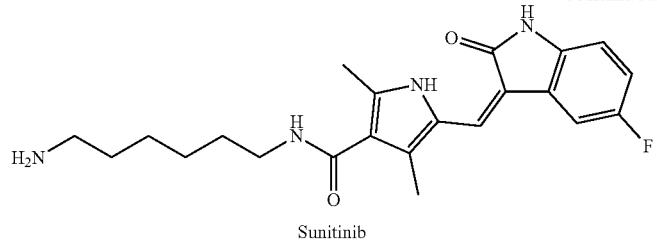
Sunitinib
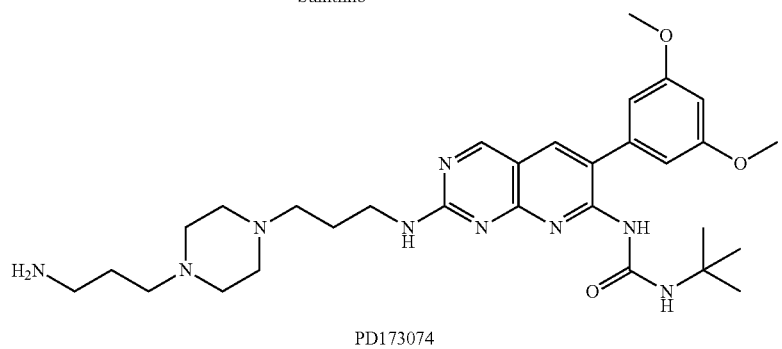
PD173074
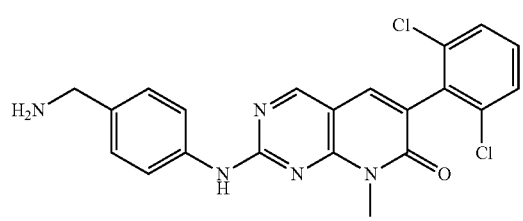
PD173955
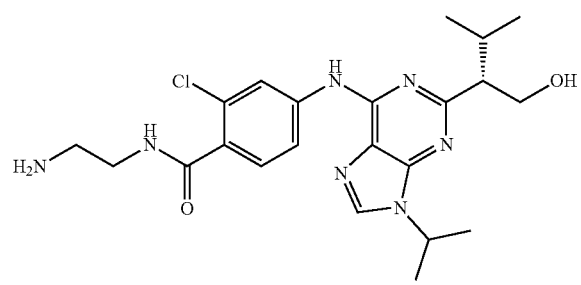
Purvalanol B
CZC8004
These ligands can be attached to linkers as shown below:
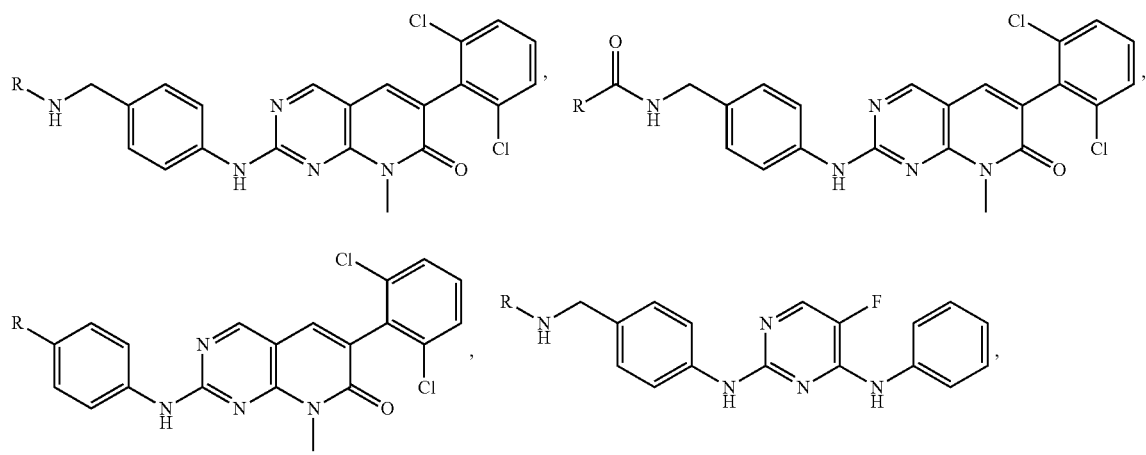

193 194
-continued
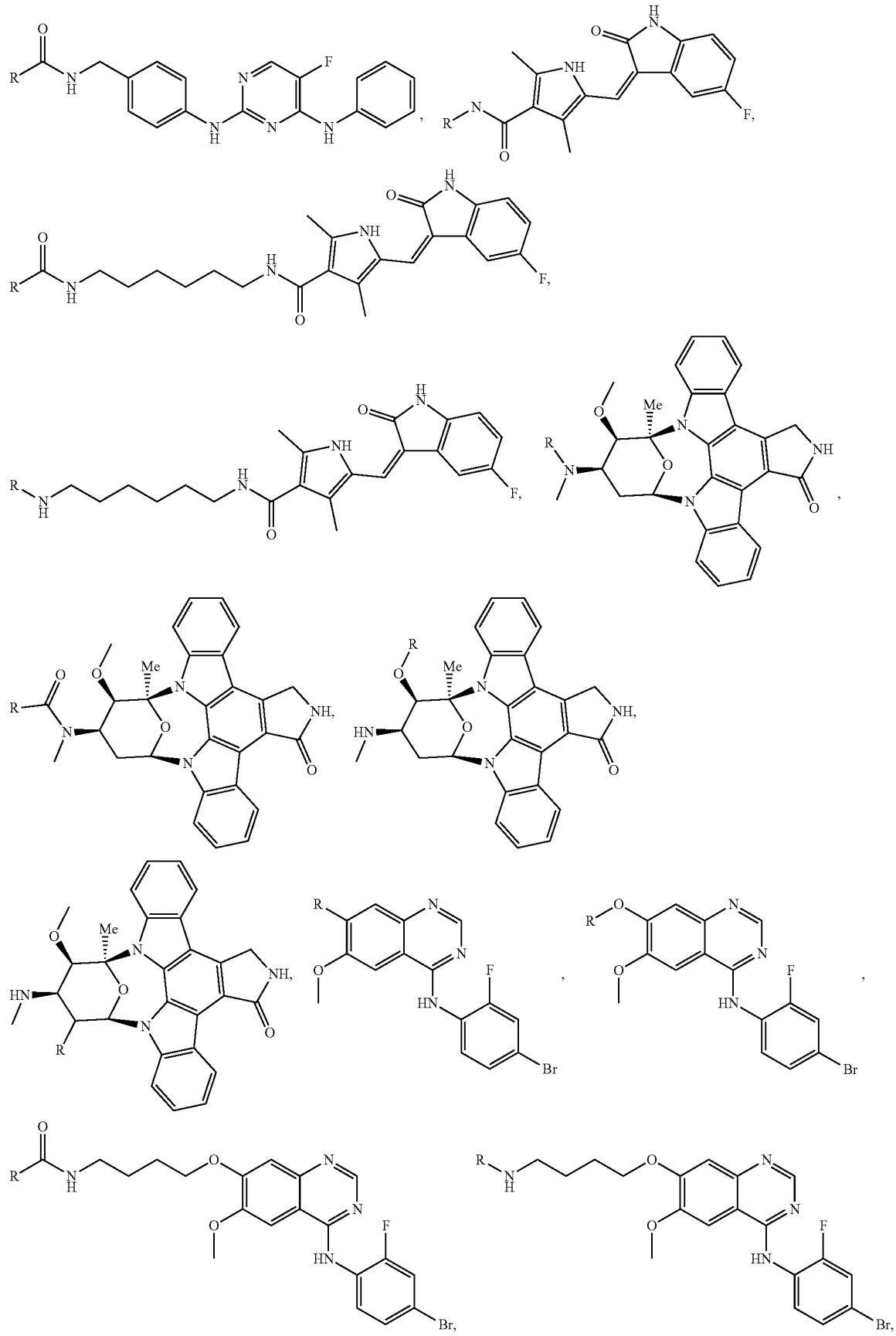

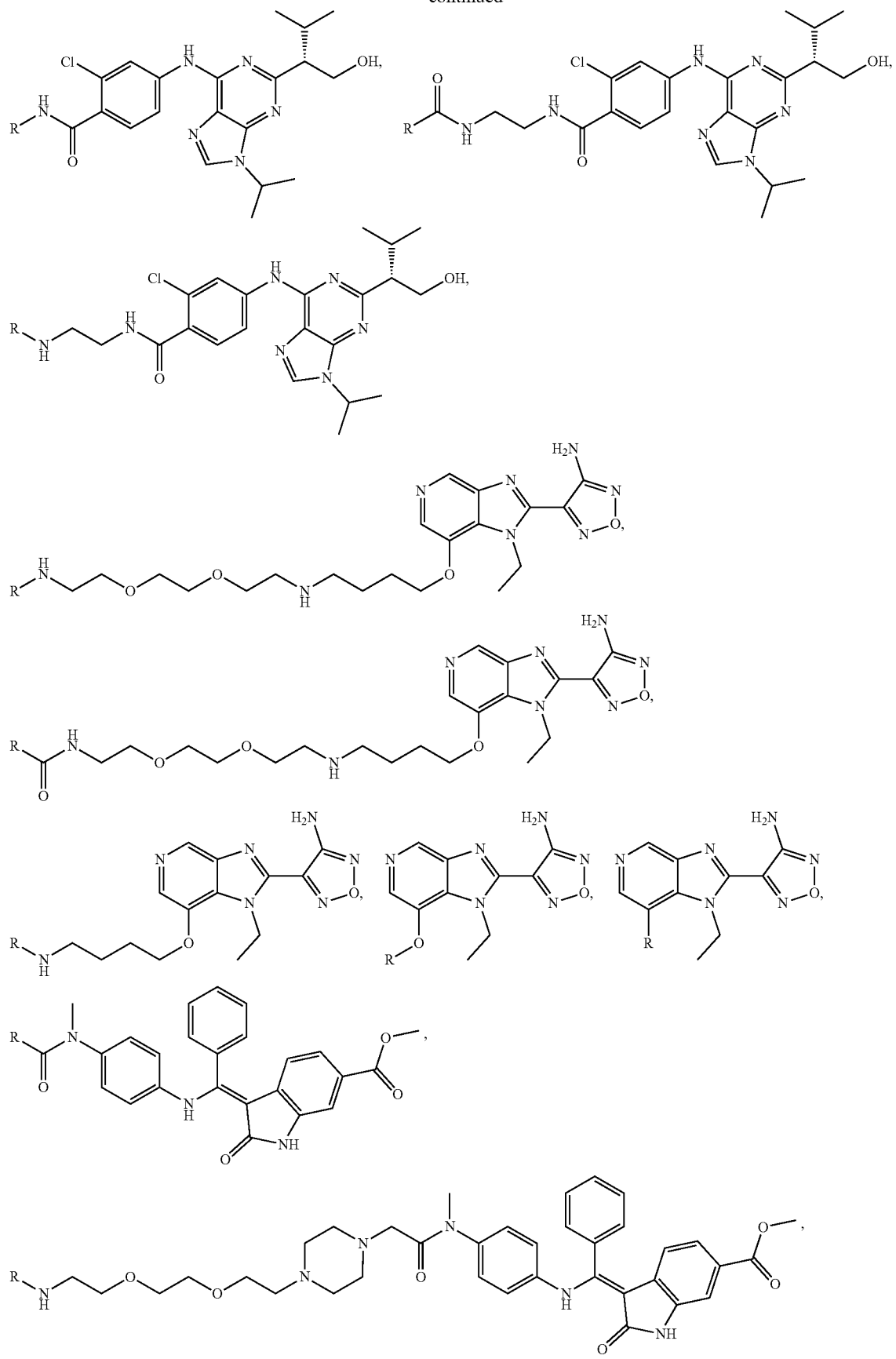

-continued
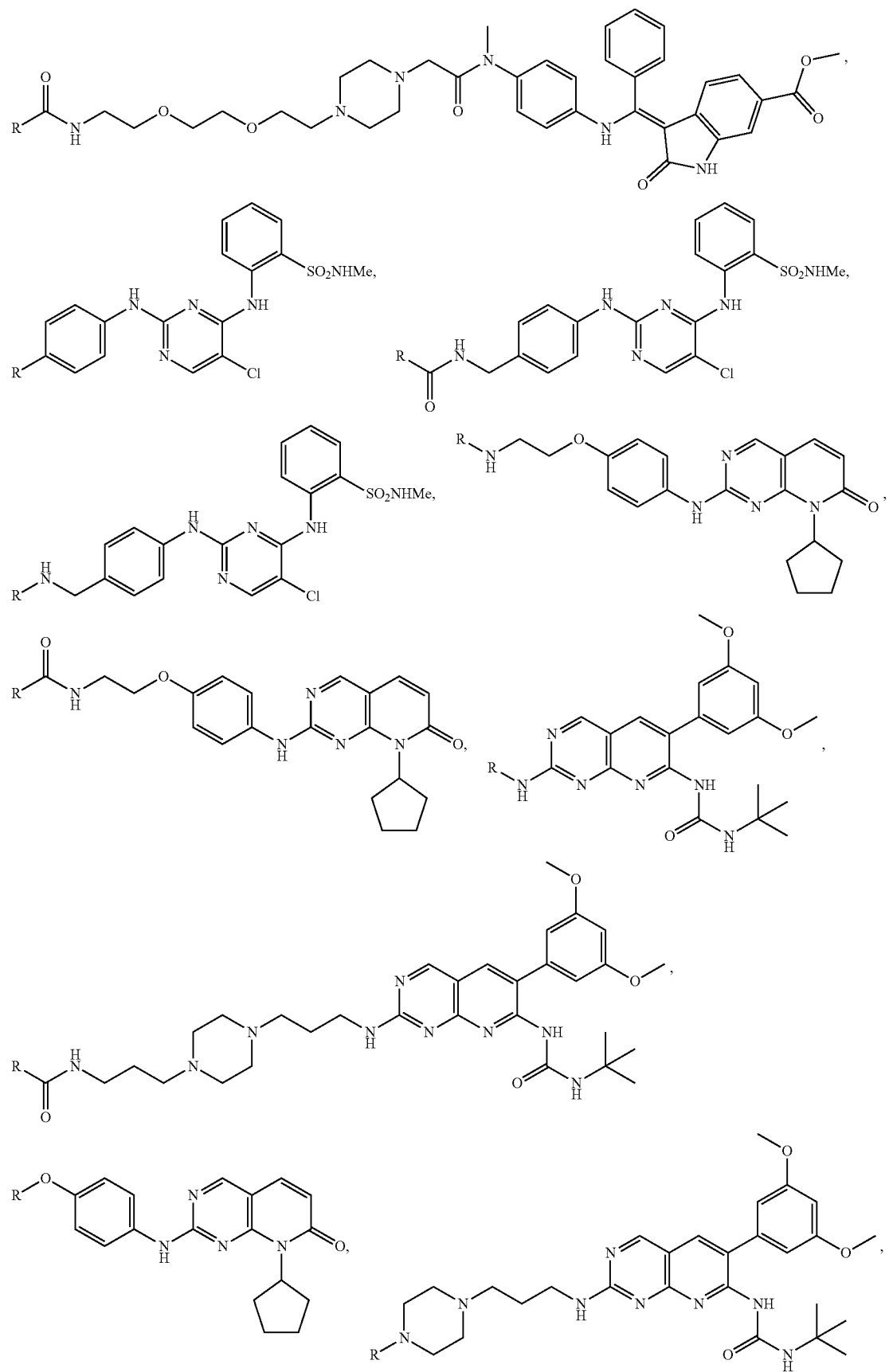

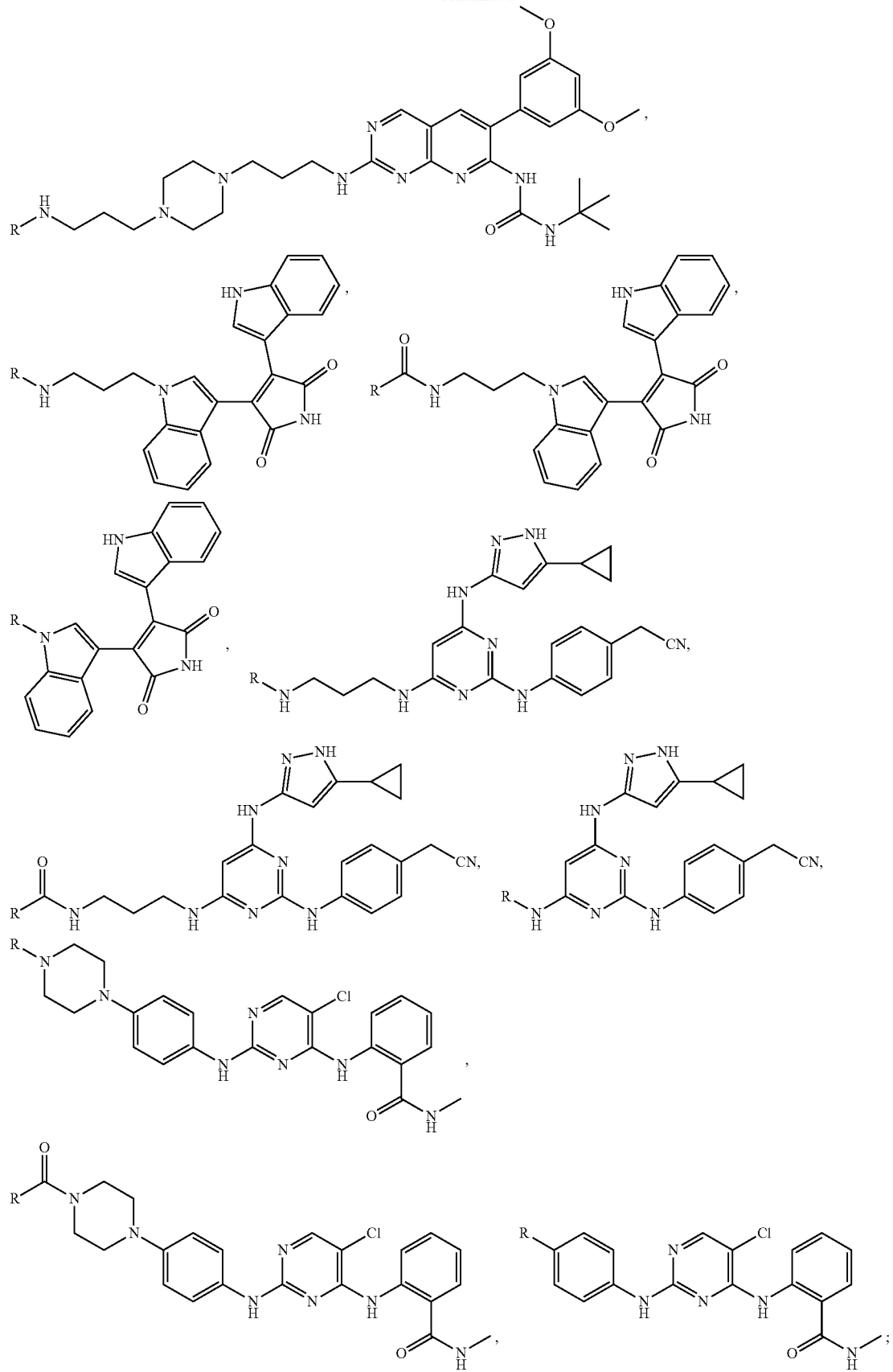

wherein:

R is the point at which the Linker is attached.

According to the present invention, the Targeting Ligand can be covalently bound to the Linker in any manner that achieves the desired results of the Degronimer for therapeutic use. In certain non-limiting embodiments, the Targeting Ligand is bound to the Linker with a functional group that does not adversely affect the binding of the Ligand to the Target Protein. The attachment points below are exemplary in nature and one of ordinary skill in the art would be able to determine different appropriate attachment points.

The non-limiting compounds described below exemplify some of the members of these types of small molecule Targeting Ligands. In the Tables below, R is the point at which the Linker is attached to the Targeting Ligand.

In certain embodiments, the Targeting Ligand is a compound of Formula TL-I:

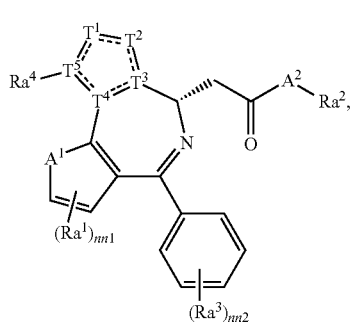

(TL-I)

or a pharmaceutically acceptable salt thereof, wherein:

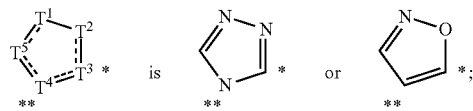

$A^1$ is S or C=C;

$A^2$ is $NRa^5$ or O;

nn1 is 0, 1, or 2;

each $Ra^1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, or R;

$Ra^2$ is H, $C_1$-$C_6$ alkyl, $(CH_2)_{0-3}$-heterocyclyl, $(CH_2)_{0-3}$-phenyl, or R, wherein the heterocyclyl comprises one saturated 5- or 6-membered ring and 1-2 heteroatoms selected from N, O, and S and is optionally substituted with $C_1$-$C_3$ alkyl and wherein the phenyl is optionally substituted with $C_1$-$C_3$ alkyl, CN, halogen, OH, $C_1$-$C_3$ alkoxy;

nn2 is 0, 1, 2, or 3;

each $Ra^3$ is independently $C_1$-$C_3$ alkyl, $(CH_2)_{0-3}$—CN, $(CH_2)_{0-3}$-halogen, or R;

$Ra^4$ is $C_1$-$C_3$ alkyl;

$Ra^5$ is H or $C_1$-$C_3$ alkyl; and

R is the point at which the Linker is attached.

wherein the compound of Formula TL-I is substituted with only one R.

In certain embodiments, the Targeting Ligand is a compound of Formula TL-VIII or Formula TL-IX:

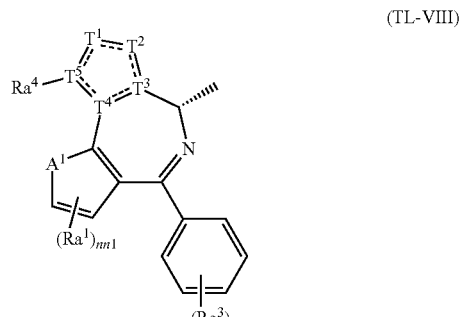

(TL-VIII)

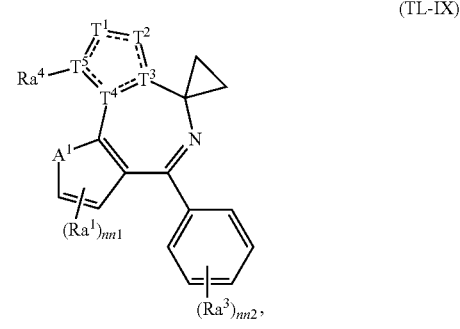

(TL-IX)

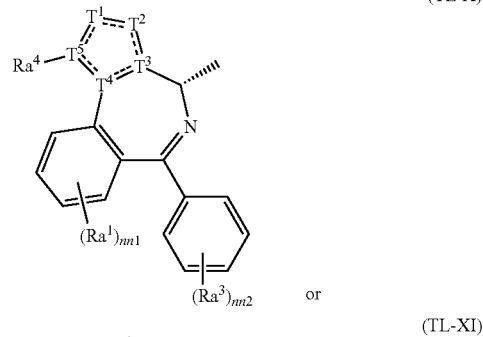

(TL-X)

or

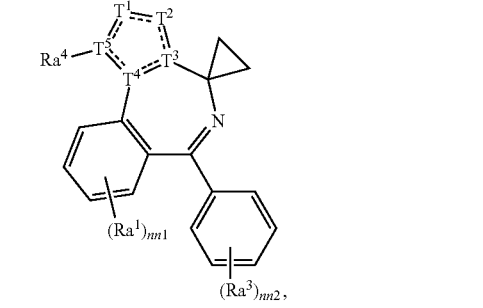

(TL-XI)

wherein the compound of Formula TL-VIII or TL-IX is substituted with only one R.

In certain embodiments,

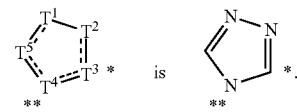

In certain embodiments,

In certain embodiments, $A^1$ is S.
In certain embodiments, $A^1$ is C=C.
In certain embodiments, $A^2$ is $NRa^5$. In further embodiments, $Ra^5$ is H. In other embodiments, $Ra^5$ is $C_1$-$C_3$ alkyl (e.g., methyl, ethyl, propyl, or i-propyl). In further embodiments, $Ra^5$ is methyl.
In certain embodiments, $A^2$ is O.
In certain embodiments, nn1 is 0.
In certain embodiments, nn1 is 1.
In certain embodiments, nn1 is 2.
In certain embodiments, at least one $Ra^1$ is $C_1$-$C_3$ alkyl (e.g., methyl, ethyl, propyl, or i-propyl). In further embodiments, at least one $Ra^1$ is methyl. In further embodiments, two $Ra^1$ are methyl.
In certain embodiments, at least one $Ra^1$ is CN, $(CH_2)$—CN, $(CH_2)_2$—CN, or $(CH_2)_3$—CN. In further embodiments, at least one $Ra^1$ is $(CH_2)$—CN.
In certain embodiments, at least one $Ra^1$ is halogen (e.g., F, $C_1$, or Br), $(CH_2)$-halogen, $(CH_2)_2$-halogen, or $(CH_2)_3$-halogen. In further embodiments, at least one $Ra^1$ is $C_1$, $(CH_2)$—Cl, $(CH_2)_2$—Cl, or $(CH_2)_3$—Cl.
In certain embodiments, at least one $Ra^1$ is OH, $(CH_2)$—OH, $(CH_2)_2$—OH, or $(CH_2)_3$—OH.
In certain embodiments, at least one $Ra^1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^1$ is methoxy.
In further embodiments, $Ra^5$ is H. In other embodiments, $Ra^5$ is $C_1$-$C_3$ alkyl (e.g., methyl, ethyl, propyl, or i-propyl).
In further embodiments, $Ra^5$ is H. In other embodiments, $Ra^5$ is $C_1$-$C_3$ alkyl (e.g., methyl, ethyl, propyl, or i-propyl). In other embodiments, $Ra^5$ is methyl.
In certain embodiments, one $Ra^1$ is R.
In certain embodiments, $Ra^2$ is H.
In certain embodiments, $Ra^2$ is straight-chain $C_1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^2$ is methyl, ethyl, or t-butyl.
In certain embodiments, $Ra^2$ is heterocyclyl, $(CH_2)$-heterocyclyl, $(CH_2)_2$-heterocyclyl, or $(CH_2)_3$-heterocyclyl. In further embodiments, $Ra^2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.
In certain embodiments, the heterocyclyl is substituted with $C_1$-$C_3$ alkyl (e.g., methyl, ethyl, propyl, or i-propyl).
In certain embodiments, $Ra^2$ is phenyl, $(CH_2)$-phenyl, $(CH_2)_2$-phenyl, or $(CH_2)_3$-phenyl. In further embodiments, $Ra^2$ is phenyl.
In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).
In certain embodiments, $Ra^2$ is R.
In certain embodiments, nn2 is 0.
In certain embodiments, nn2 is 1.
In certain embodiments, nn2 is 2.
In certain embodiments, nn2 is 3.
In certain embodiments, at least one $Ra^3$ is $C_1$-$C_3$ alkyl (e.g., methyl, ethyl, propyl, or i-propyl). In further embodiments, at least one $Ra^3$ is methyl.
In certain embodiments, at least one $Ra^3$ is CN, $(CH_2)$—CN, $(CH_2)_2$—CN, or $(CH_2)_3$—CN. In further embodiments, at least one $Ra^3$ is CN.
In certain embodiments, at least one $Ra^3$ is halogen (e.g., F, Cl, or Br), $(CH_2)$-halogen, $(CH_2)_2$-halogen, or $(CH_2)_3$-halogen. In further embodiments, at least one $Ra^3$ is Cl, $(CH_2)$—Cl, $(CH_2)_2$—Cl, or $(CH_2)_3$—Cl. In further embodiments, at least one $Ra^3$ is Cl.
In certain embodiments, one $Ra^3$ is R.
In further embodiments, $Ra^5$ is H. In other embodiments, $Ra^5$ is $C_1$-$C_3$ alkyl (e.g., methyl, ethyl, propyl, or i-propyl).
In certain embodiments, $Ra^4$ is $C_1$-$C_3$ alkyl (e.g., methyl, ethyl, propyl, or i-propyl). In further embodiments, $Ra^4$ is methyl.
In certain embodiments, $Ra^5$ is H.
In certain embodiments, $Ra^5$ is $C_1$-$C_3$ alkyl (e.g., methyl, ethyl, propyl, or i-propyl). In further embodiments, $Ra^5$ is methyl.
In certain embodiments,

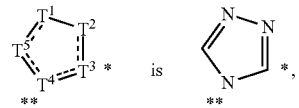

and $A^1$ is S.
In certain embodiments,

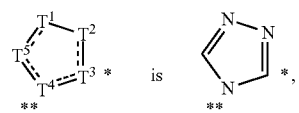

and $A^1$ is C=C.
In certain embodiments,

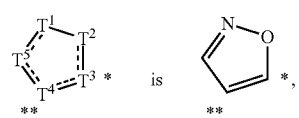

and $A^1$ is C=C.
In certain embodiments, $A^2$ is NH, and $Ra^2$ is $(CH_2)_{0-3}$-heterocyclyl. In further embodiments, $Ra^2$ is $(CH_2)_3$-heterocyclyl.
In certain embodiments, $A^2$ is NH, and $Ra^2$ is $(CH_2)_{0-3}$-phenyl. In further embodiments, $Ra^2$ is phenyl. In further embodiments, the phenyl is substituted with OH.
In certain embodiments, $A^2$ is NH, and $Ra^2$ is R.

In certain embodiments, $A^2$ is NH, and $Ra^2$ is H or $C_1$-$C_6$ alkyl. In further embodiments, $Ra^2$ is $C_1$-$C_4$ alkyl.

In certain embodiments, $A^2$ is O, and $Ra^2$ is H or $C_1$-$C_6$ alkyl. In further embodiments, $Ra^2$ is $C_1$-$C_4$ alkyl.

III. Methods of Treatment

The compound of Formulas I, II, III, IV, V, VI and VII can be used in an effective amount to treat a host with any of the disorders described herein, including a human, in need thereof, optionally in a pharmaceutically acceptable carrier. In certain embodiments, the method comprises administering an effective amount of the active compound or its salt as described herein, optionally including a pharmaceutically acceptable excipient, carrier, adjuvant, i.e., a pharmaceutically acceptable composition, optionally in combination or alternation with another bioactive agent or combination of agents.

The compound of Formula I, II, V or VII or a pharmaceutically acceptable salt thereof as described herein can be used to degrade a Target Protein which is a mediator of the disorder affecting the patient, such as a human. The reduction in the Target Protein level afforded by the Formula I, II, V or VII Degronimers of the present invention provides treatment of the implicated disease state or condition, which is modulated through the Target Protein by lowering the level of that protein in the cell, e.g., cell of a patient. The term "disease state or condition" when used in connection with a Formula I, II, V or VII compound is meant to refer to any disease state or condition wherein protein dysregulation occurs that involves the selected Target Protein and where degradation of such protein in a patient may provide beneficial therapy or relief of symptoms to a patient in need thereof. In certain instances, the disease state or condition may be cured.

The compounds of Formula I, II, V or VII are useful as therapeutic agents when administered in an effective amount to a host, including a human, to treat a tumor, cancer (solid, non-solid, diffuse, hematological, etc), abnormal cellular proliferation, immune disorder, inflammatory disorder, blood disorder, a myelo- or lymphoproliferative disorder such as B- or T-cell lymphomas, multiple myeloma, breast cancer, prostate cancer, AML, ALL, ACL, lung cancer, pancreatic cancer, colon cancer, skin cancer, melanoma, Waldenstrom's macroglobulinemia, Wiskott-Aldrich syndrome, or a post-transplant lymphoproliferative disorder; an autoimmune disorder, for example, Lupus, Crohn's Disease, Addison disease, Celiac disease, dermatomyositis, Graves disease, thyroiditis, multiple sclerosis, pernicious anemia, reactive arthritis, or type I diabetes; a disease of cardiologic malfunction, including hypercholesterolemia; an infectious disease, including a viral and/or bacterial infection; an inflammatory condition, including asthma, chronic peptic ulcers, tuberculosis, rheumatoid arthritis, periodontitis, ulcerative colitis, or hepatitis.

The term "disease state or condition" when used in connection with a Formula III, IV or VI compound, for example, refers to any therapeutic indication which can be treated by decreasing the activity of cereblon or a cereblon-containing E3 Ligase, including but not limited to uses known for the cereblon binders thalidomide, pomalidomide or lenalidomide. Nonlimiting examples of uses for cereblon binders are multiple myeloma, a hematological disorder such as myelodysplastic syndrome, cancer, tumor, abnormal cellular proliferation, breast cancer, prostate cancer, AML, ALL, ACL, lung cancer, pancreatic cancer, colon cancer, skin cancer, melanoma, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders for example as Lupus, Addison disease, Celiac disease, dermatomyositis, Graves disease, thyroiditis, multiple sclerosis, pernicious anemia, arthritis, and in particular rheumatoid arthritis, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides the administration of an effective amount of a compound to treat a patient, for example, a human, having an infectious disease, wherein the therapy targets a Target Protein of the infectious agent or host (Formulas I, II, V or VII), or acts via binding to cereblon or its E3 ligase (Formulas III, IV and VI) optionally in combination with another bioactive agent. The disease state or condition may be caused by a microbial agent or other exogenous agent such as a virus (as nonlimiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (including but not limited to Gram-negative, Gram-positive, Atypical, *Staphylococcus, Streptococcus, E. Coli, Salmonella, Helicobacter pylori*, meningitis, gonorrhea, Chlamydiaceae, Mycoplasmataceae, etc), fungus, protozoa, helminth, worms, prion, parasite, or other microbe.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states which may be treated according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by the disclosed compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by the disclosed compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies).

The term "neoplasia" or "cancer" is used throughout the specification to refer to the pathological process that results in the formation and growth of a cancerous or malignant neoplasm, i.e., abnormal tissue (solid) or cells (non-solid) that grow by cellular proliferation, often more rapidly than normal and continues to grow after the stimuli that initiated the new growth cease. Malignant neoplasms show partial or complete lack of structural organization and functional coordination with the normal tissue and most invade surrounding tissues, can metastasize to several sites, are likely to recur after attempted removal and may cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

IV. Combination Therapy

The disclosed compounds of Formula I, II, III, IV, V, VI or VII can be used in an effective amount alone or in combination with another compound of the present invention or another bioactive agent to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810

(Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478, 847; 5,393,763; and 5,457,117, WO2011/156518, U.S. Pat. Nos. 8,455,534 and 8,299,112, 9,078,871; 8,853,423; 8,703, 810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078634; U.S. Pat. No. 6,821,989; US 2002/0128276; U.S. Pat. No. 6,777,424; US 2002/0016340; U.S. Pat. Nos. 6,326, 392; 6,756,401; US 2002/0013327; U.S. Pat. Nos. 6,512, 002; 6,632,834; US 2001/0056099; U.S. Pat. Nos. 6,583, 170; 6,479,535; WO 1999/024027; U.S. Pat. No. 6,005,102; EP 0802184; U.S. Pat. Nos. 5,998,402; 5,780,497, 5,880, 137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC 137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1- methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)-N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S])-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R, 11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl]acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109 having the formula:

Compound 292

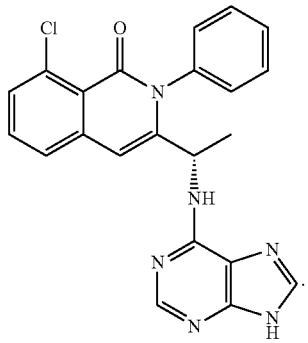

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl] benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3-(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4, 7-trioxo-3,4,6,7-tetrahydropyrido[4,3-d]pyrimidin-(2H-yl}phenyl)acetamide), selumetinob (6-(4-bromo-2-chloroanilino)-7- fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), RO5126766 (3-[[3-Fluoro-2-(methylsulfamoylamino)-4-pyridyl]methyl]-4-methyl-7-pyrimidin-2-yloxychromen-2-one), WX-554, RO4987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR₁ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU1 1248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif)), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®, Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a degronimer disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEEO11), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the invention, the disclosed compound is administered in combination with an anti-infective agent, for example but not limited to an anti-HIV agent, anti-HCV agent, anti-HBV agent, or other anti-viral or anti-bacterial agent. In one embodiment, the anti-HIV agent can be, but is not limited to, for example, a nucleoside reverse transcriptase inhibitor (NRTI), other non-nucloeoside reverse transcriptase inhibitor, protease inhibitor, fusion inhibitor, among others. Nucleoside/Nucleotide Reverse Transcriptase Inhibitors (NRTIs) include, but are not limited to, Abacavir or ABC (Ziagen), Didanosine or ddI (Videx), Emtricitabine or FTC (Emtriva), Lamivudine or 3TC (Epivir), ddC (zalcitabine), Stavudine or d4T (Zerit), Tenofovircor TDF (Viread), D-D4FC (Reverset), and Zidovudine or AZT or ZDV (Retrovir). Non-nucleoside Reverse Transcriptase Inhibitors (NNRTIs) include, but are not limited to, Delavirdine (Rescriptor), Efavirenz (Sustiva), Etravirine (Intelence), Nevirapine (Viramune), and Rilpivirine (Edurant). Anti-HIV Protease Inhibitors (PIs) include, but are not limited to, Atazanavir or ATV (Reyataz), Darunavir or DRV (Prezista), Fosamprenavir or FPV (Lexiva), Indinavir or IDV (Crixivan), Lopinavir+ritonavir, or LPV/r (Kaletra), Nelfinavir or NFV (Viracept), Ritonavir or RTV (Norvir), Saquinavir or SQV (Invirase), Tipranavir, or TPV (Aptivus), Cobicistat (Tybost), Atazanavir+cobicistat, or ATV/COBI (Evotaz), Darunavir+cobicistat, or DRV/COBI (Prezcobix). Anti-HIV Fusion Inhibitors include, but are not limited to, Enfuvirtide or ENF or T-20 (Fuzeon). Anti-HIV also include, but are not limited to, Maraviroc or MVC (Selzentry). Anti-HIV Integrase Inhibitors include, but are not limited to Dolutegravir (Tivicay), Elvitegravir (Vitekta), Raltegravir (Isentress). Anti-HIV combinations agents include Abacavir+Dolutegravir+lamivudine, or ABC/DTG/3TC (Triumeq), Abacavir+lamivudine or ABC/3TC (Epzicom), Abacavir+lamivudine+zidovudine, or ABC/3TC/ZDV (Trizivir), Efavirenz+emtricitabine+tenofovir or EFV/FTC/TDF (Atripla, Tribuss), elvitegravir, cobicistat, emtricitabine, tenofovir alafenamide or EVG/COBI/FTC/TAF or ECF/TAF (Genvoya; (Stribild), emtricitabine+rilpivirine+tenofovir or FTC/RPV/TAF (Odefsey); Emtricitabine+rilpivirine+tenofovir or FTC/RPV/TDF (Complera), Emtricitabine+tenofovir or TAF/FTC (Descovy), emtricitabine and tenofovir disoproxil fumarate (Truvada), and Lamivudine+zidovudine or 3TC/ZDV (Combivir). Other anti-HIV compounds include, but are not limited to Racivir, L-FddC, L-FD4C, SQVM (Saquinavir mesylate), IDV (Indinavir), SQV (Saquinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in co-administration with the disclosed compounds according to the present invention. NNRTIs may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl] piperazine, 1-[3-(Ethylamino)-2-[pyridinyl]-4-[(5-hydroxy-2-indolyl)carbonyl]piperazine, 1-[(6-Formyl-2-indolyl) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4, 7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5 (9bH)-one, Tivirapine (R86183), UC-38 and UC-84, among others.

In one aspect of the invention, the disclosed compound when used to treat an HCV infection can be administered in combination with another anti-HCV agent. Anti-HCV agents are known in the art. To date, a number of fixed dose drug combinations have been approved for the treatment of HCV. Harvoni® (Gilead Sciences, Inc.) contains the NS5A inhibitor ledipasvir and the NS5B inhibitor sofosbuvir. Technivie™ (AbbVie, Inc.) is a fixed-dose combination containing ombitasvir, an NS5A inhibitor; paritaprevir, an NS3/4A protease inhibitor; and ritonavir, a CYP3A inhibitor. Daklinza™ (daclatasvir, Bristol-Myers Squibb) is a HCV NS5A inhibitor indicated for use with sofosbuvir for the treatment of chronic genotype 3 infection. Zepatier™ (Merck & Co.) has recently been approved for the treatment of chronic HCV genotypes 1 and 4. Zepatier™ is a fixed-dose combination product containing elbasvir, an HCV NS5A inhibitor, and grazoprevir, an HCV NS3/4A protease inhibitor. Zepatier™ is indicated with or without ribavirin. Epclusa® (Gilead Sciences, Inc.) is a fixed-dose combination tablet containing sofosbuvir and velpatasvir.

Additional anti-HCV agents and combinations thereof include those described in U.S. Pat. Nos. 9,382,218; 9,321,753; 9,249,176; 9,233,974; 9,221,833; 9,211,315; 9,194,873; 9,186,369; 9,180,193; 9,156,823; 9,138,442; 9,133,170; 9,108,999; 9,090,559; 9,079,887; 9,073,943; 9,073,942; 9,056,090; 9,051,340; 9,034,863; 9,029,413; 9,011,938; 8,987,302; 8,945,584; 8,940,718; 8,927,484; 8,921,341; 8,884,030; 8,841,278; 8,822,430; 8,772,022; 8,765,722; 8,742,101; 8,741,946; 8,674,085; 8,673,288; 8,669,234; 8,663,648; 8,618,275; 8,580,252; 8,575,195; 8,575,135; 8,575,118; 8,569,302; 8,524,764; 8,513,298; 8,501,714; 8,404,651; 8,273,341; 8,257,699; 8,197,861; 8,158,677; 8,105,586; 8,093,353; 8,088,368; 7,897,565; 7,871,607; 7,846,431; 7,829,081; 7,829,077; 7,824,851; 7,572,621; and 7,326,536; Patents assigned to Alios: U.S. Pat. Nos. 9,365,605; 9,346,848; 9,328,119; 9,278,990; 9,249,174; 9,243,022; 9,073,960; 9,012,427; 8,980,865; 8,895,723; 8,877,731; 8,871,737; 8,846,896 and 8,772,474; Achillion U.S. Pat. Nos. 9,273,082; 9,233,136; 9,227,952; 9,133,115; 9,125,904; 9,115,175; 9,085,607; 9,006,423; 8,946,422; 8,835,456; 8,809,313; 8,785,378; 8,614,180; 8,445,430; 8,435,984; 8,183,263; 8,173,636; 8,163,693; 8,138,346; 8,114,888; 8,106,209; 8,088,806; 8,044,204; 7,985,541; 7,906,619; 7,902,365; 7,767,706; 7,741,334; 7,718,671; 7,659,399; 7,476,686; 7,439,374; 7,365,068; 7,199,128; and 7,094,807; Cocrystal Pharma Inc. U.S. Pat. Nos. 9,181,227; 9,173,893; 9,040,479 and 8,771,665; Gilead Sciences U.S. Pat. Nos. 9,353,423; 9,346,841; 9,321,800; 9,296,782; 9,296,777; 9,284,342; 9,238,039; 9,216,996; 9,206,217; 9,161,934; 9,145,441; 9,139,604; 9,090,653; 9,090,642; 9,085,573; 9,062,092; 9,056,860; 9,045,520; 9,045,462; 9,029,534; 8,980,878; 8,969,588; 8,962,652; 8,957,046; 8,957,045; 8,946,238; 8,933,015; 8,927,741; 8,906,880; 8,889,159; 8,871,785; 8,841,275; 8,815,858; 8,809,330; 8,809,267; 8,809,266; 8,779,141; 8,765,710; 8,759,544; 8,759,510; 8,735,569; 8,735,372; 8,729,089; 8,722,677; 8,716,264; 8,716,263; 8,716,262; 8,697,861; 8,664,386; 8,642,756; 8,637,531; 8,633,309; 8,629,263; 8,618,076; 8,592,397; 8,580,765; 8,569,478; 8,563,530; 8,551,973; 8,536,187; 8,513,186; 8,513,184; 8,492,539; 8,486,938; 8,481,713; 8,476,225; 8,420,597; 8,415,322; 8,338,435; 8,334,270; 8,329,926; 8,329,727; 8,324,179; 8,283,442; 8,263,612; 8,232,278; 8,178,491; 8,173,621; 8,163,718; 8,143,394; patents assigned to Idenix, acquired by Merck, include U.S. Pat. Nos. 9,353,100; 9,309,275; 9,296,778; 9,284,307; 9,249,173; 9,243,025; 9,211,300; 9,187,515; 9,187,496, 9,109,001; 8,993,595; 8,951,985; 8,691,788; 8,680,071; 8,637,475; 8,507,460; 8,377,962; 8,362,068; 8,343,937; 8,299,038; 8,193, 372; 8,093,379; 7,951,789; 7,932,240; 7,902,202; 7,662,798; 7,635,689; 7,625,875; 7,608,600; 7,608,597; 7,582,618; 7,547,704; 7,456,155; 7,384,924; 7,365,057; 7,192,936; 7,169,766; 7,163,929; 7,157,441; 7,148,206; 7,138,376; 7,105,493; 6,914,054 and 6,812,219; patents assigned to Merck include U.S. Pat. Nos.

9,364,482; 9,339,541; 9,328,138; 9,265,773; 9,254,292; 9,243,002; 9,242,998; 9,242,988; 9,242,917; 9,238,604; 9,156,872; 9,150,603; 9,139,569; 9,120,818; 9,090,661; 9,073,825; 9,061,041; 8,987,195; 8,980,920; 8,927,569; 8,871,759; 8,828,930; 8,772,505; 8,715,638; 8,697,694; 8,637,449; 8,609,635; 8,557,848; 8,546,420; 8,541,434; 8,481,712; 8,470,834; 8,461,107; 8,404,845; 8,377,874; 8,377,873; 8,354,518; 8,309,540; 8,278,322; 8,216,999; 8,148,349; 8,138,164; 8,080,654; 8,071,568; 7,973,040; 7,935,812; 7,915,400; 7,879,815; 7,879,797; 7,632,821; 7,569,374; 7,534,767; 7,470,664 and 7,329,732; patent application publication US 2013/0029904 to Boehringer Ingelheim GMBH and US 2014/0113958 to Stella Aps.

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

V. Pharmaceutical Compositions

The compounds of Formula I, II, III, VI, V, VI or VII, as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of the disclosed compound or pharmaceutically acceptable salt thereof together with at least one pharmaceutically acceptable carrier for any of the uses described herein. The pharmaceutical composition may contain the disclosed compound or salt as the only active agent, or, in an alternative embodiment, the disclosed compound and at least one additional active agent.

Compounds disclosed herein may be administered by any suitable route desired by the healthcare provider, including orally, topically, systemically, parenterally, by inhalation or spray, sublingually, via implant, including ocular implant, transdermally, via buccal administration, rectally, as an ophthalmic solution, injection, including ocular injection, intraveneous, intra-arterial, intra-aortal, intracranial, subdermal, intraperitioneal, subcutaneous, transnasal, sublingual, or rectal or by other means, in dosage unit formulations containing conventional pharmaceutically acceptable carriers.

In general, the compositions of the disclosure will be administered in a therapeutically effective amount by the desired mode of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

In certain embodiments the pharmaceutical composition is in a dosage form that contains from about 0.1 mg to about 2000 mg, from about 10, 25, 50 or 100 mg to about 1000 mg, from about 100 mg to about 800 mg, or from about 50 to 500, 75 to 500, or 200 mg to about 600 mg of the active compounds and optionally for example from about 0.1 mg to about 2000 mg, from about 10, 25, 50 or 100 mg to about 1000 mg, from about 50 to 500, 75 to 500, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, 750 or 800 mg of active compound, or its salt.

The therapeutically effective dosage of any active compound described herein will be determined by the health care practitioner depending on the condition, size and age of the patient as well as the route of delivery. In one non-limited embodiment, a dosage from about 0.1 to about 200 mg/kg, from about 0.01 mg/kg to about 250 mg/kg body weight, more preferably about 0.1 mg/kg to up to about 1, 2, 3, 4, 5, 6, 7, 8, 9, 10, 20 or 30 mg/kg, in at least one dose. In some embodiments, the dosage may be the amount of compound needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution.

Some dosage forms, such as tablets and capsules, are subdivided into suitably sized unit doses containing appropriate quantities of the active components, e.g., an effective amount to achieve the desired purpose.

"Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id. Carriers include excipients must be of sufficiently high purity and sufficiently low toxicity to render them suitable for administration to the patient being treated. The carrier can be inert or it can possess pharmaceutical benefits of its own. The amount of carrier employed in conjunction with the disclosed compound is sufficient to provide a practical quantity of material for administration per unit dose of the compound, as described in more detail herein.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the disclosed compounds of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Thus, for example, a parenteral composition suitable for administration by injection is prepared by stirring 1.5% by weight of active ingredient in 10% by volume propylene glycol and water. The solution is made isotonic with sodium chloride and sterilized.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drug loading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilic hydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

VI. General Synthesis

The compounds described herein can be prepared by methods known by those skilled in the art. In one non-limiting example the disclosed compounds can be using the schemes.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) simulated moving bed chromatography, is used in one embodiment. A wide variety of chiral stationary phases are commercially available.

General Scheme 1

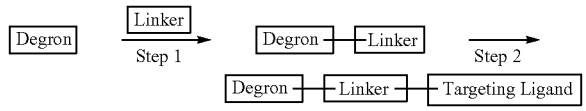

General Scheme 2

233
-continued

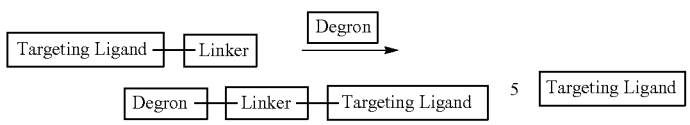

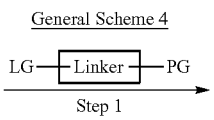

General Scheme 4

As shown in General Scheme 1 compounds for use in the present invention can be prepared by chemically combining a Degron and a Linker followed by subsequent addition of a Targeting Ligand. Similarly, in General Scheme 2 compounds for use in the present invention are prepared by chemically combing a Targeting Ligand and Linker first, followed by subsequent addition of a Degron. As illustrated in the above and following schemes, compounds for use in the present invention can readily be synthesized by one skilled in the art in a variety of methods and chemical reactions.

General Scheme 3

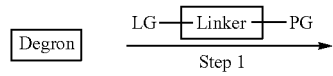

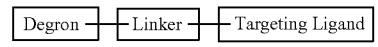

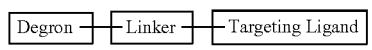

General Scheme 3: In Step 1, a nucleophilic Degron displaces a leaving group on the Linker to make a Degron Linker fragment. In Step 2, the protecting group is removed by methods known in the art to free a nucleophilic site on the Linker. In Step 3, the nucleophilic Degron Linker fragment displaces a leaving group on the Targeting Ligand to form a compound for use in the present invention. In an alternative embodiment Step 1 and/or Step 2 is accomplished by a coupling reaction instead of a nucleophilic attack.

General Scheme 4: In Step 1, a nucleophilic Targeting Ligand displaces a leaving group on the Linker to make a Targeting Ligand Linker fragment. In Step 2, the protecting group is removed by methods known in the art to free a nucleophilic site on the Linker. In Step 3, the nucleophilic Targeting Ligand Linker fragment displaces a leaving group on the Degron to form a compound for use in the present invention. In an alternative embodiment Step 1 and/or Step 2 is accomplished by a coupling reaction instead of a nucleophilic attack.

General Scheme 5

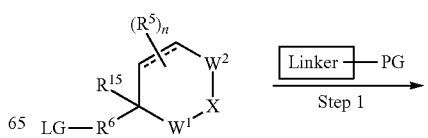

235
-continued

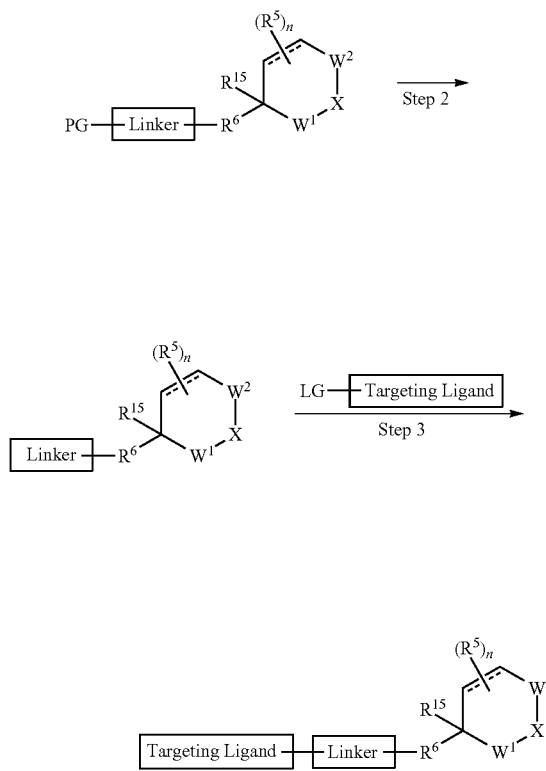

General Scheme 6

236
-continued

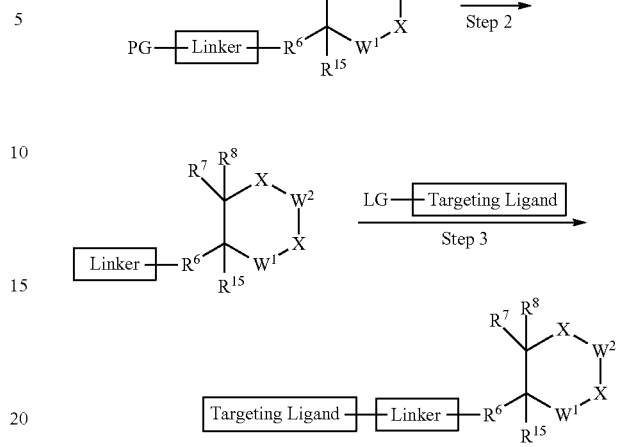

General Scheme 5 and General Scheme 6: In Step 1, a nucleophilic Linker displaces a leaving group on the Degron to make a Degron Linker fragment. In Step 2, the protecting group is removed by methods known in the art to free a nucleophilic site on the Linker. In Step 3, the nucleophilic Degron Linker fragment displaces a leaving group on the Targeting Ligand to form a compound of Formula I or Formula II. In an alternative embodiment Step 1 and/or Step 2 is accomplished by a coupling reaction instead of a nucleophilic attack.

General Scheme 7 and General Scheme 8 show a number of general reactions for the synthesis of functionalized degrons. Following functionalization, the degron can be reacted with the linker or targeting ligand-linker moiety. General Scheme 7 is the functionalization of the 1-methyl-1H indole group on the degron and General Scheme 8 is the functionalization of the 1-methylpyridin-2(1H)-one group on the degron.

General Scheme 7

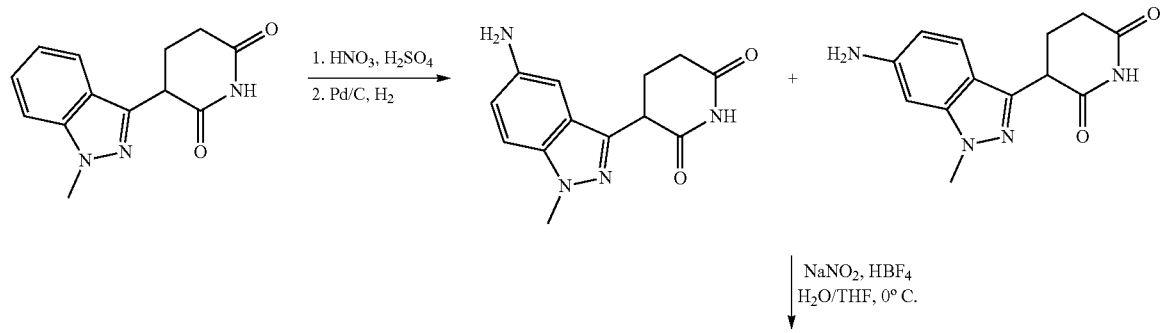

-continued
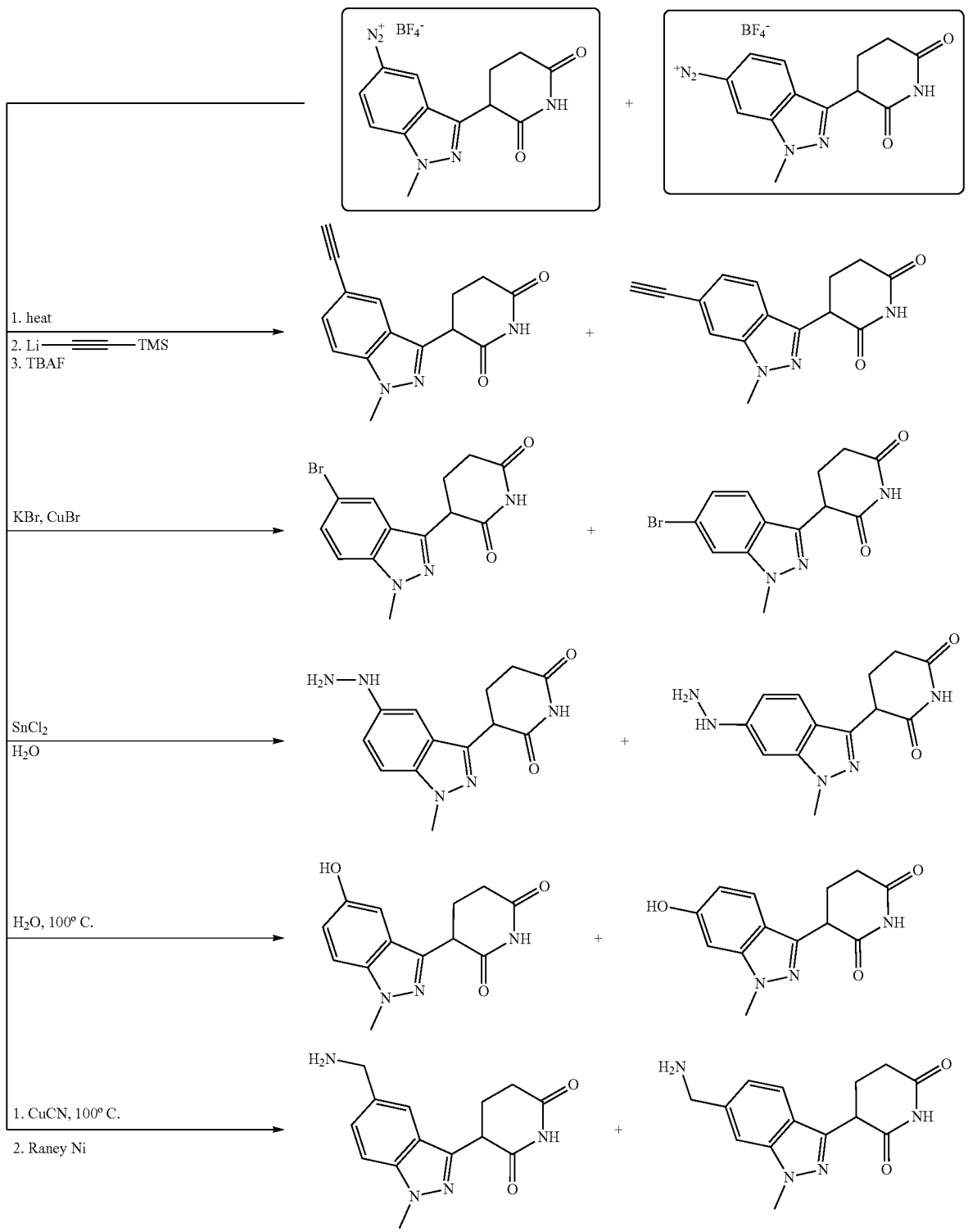

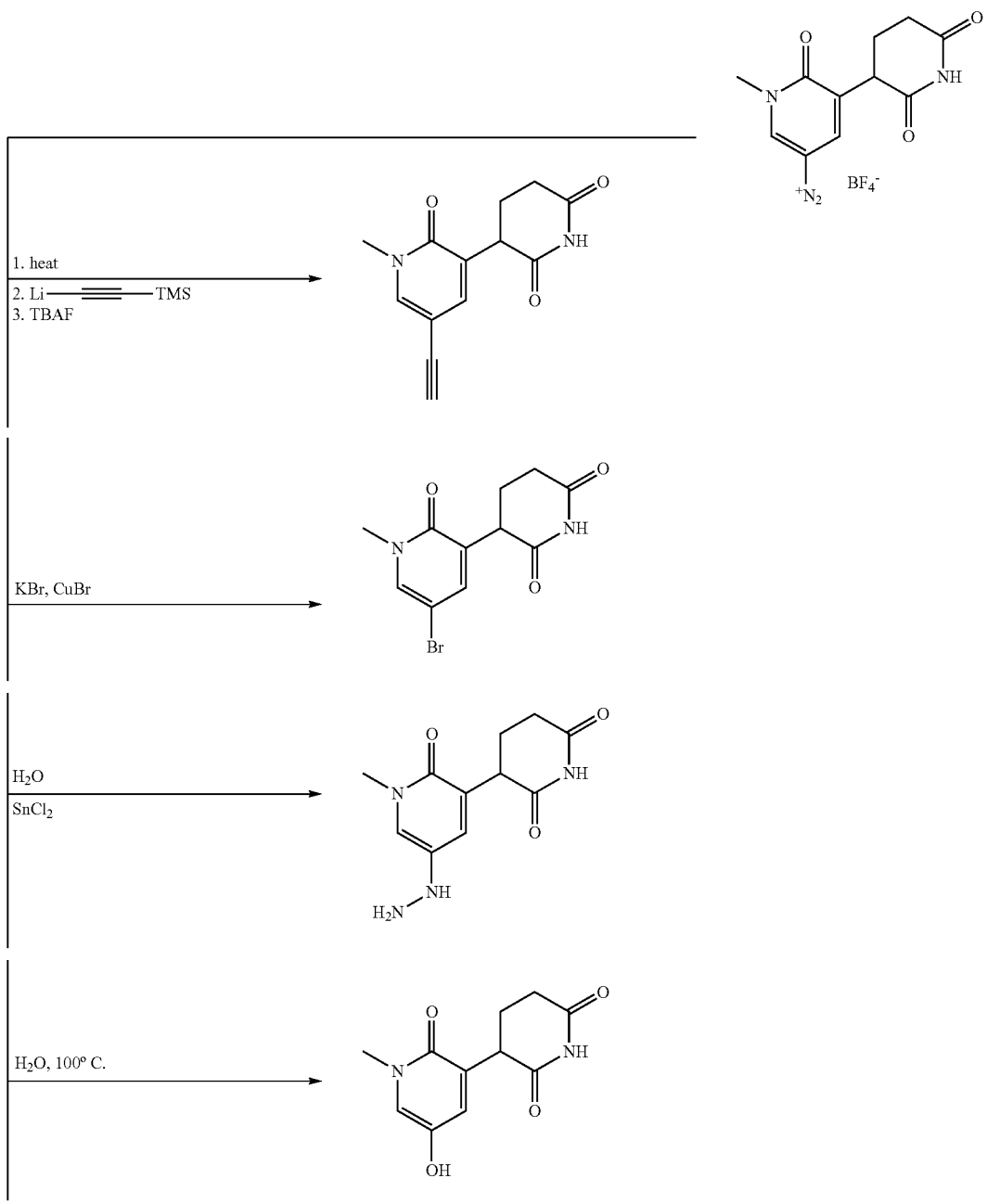
General Scheme 8

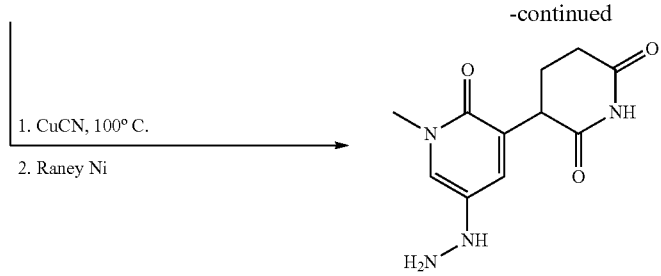
I. Exemplary Methods for Linking Targeting Ligand and Degron Through a Linker
Linking Scheme 1:
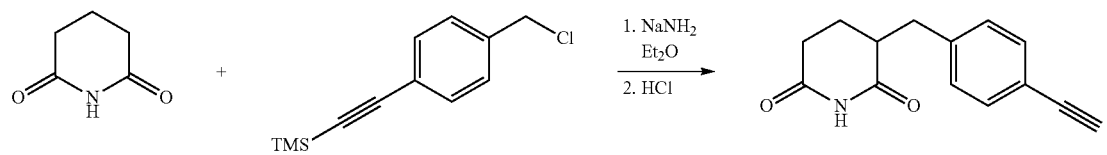
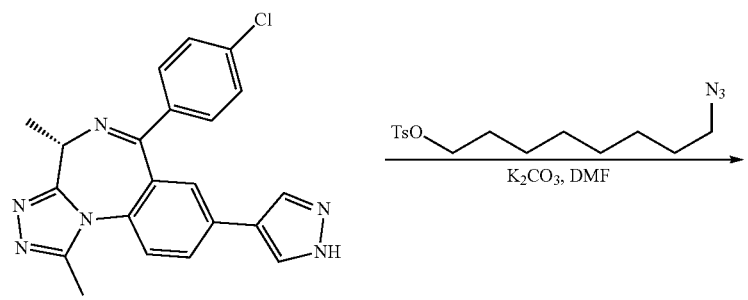
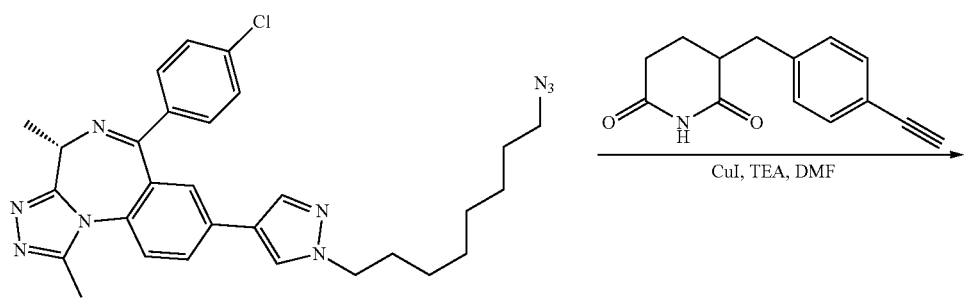

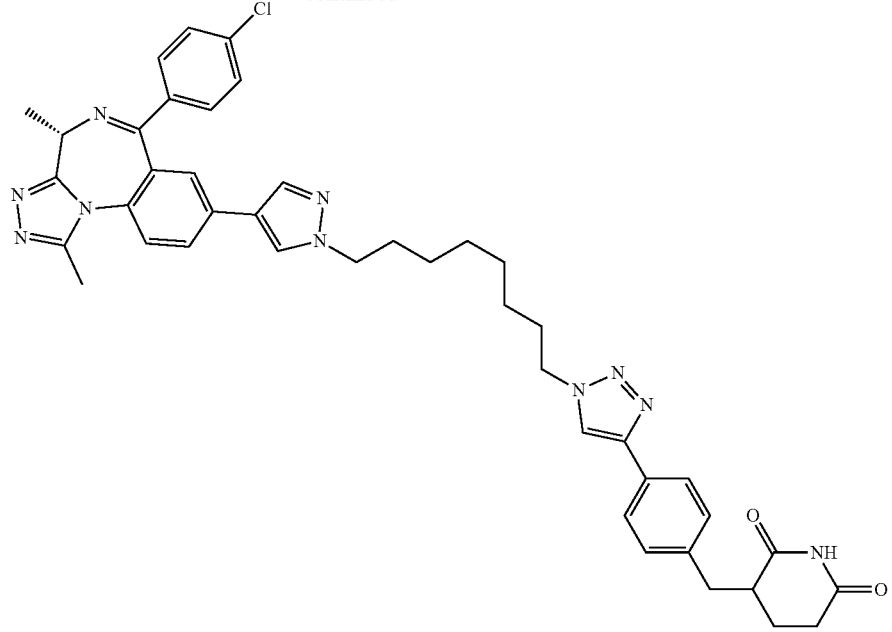
Linking Scheme 2:
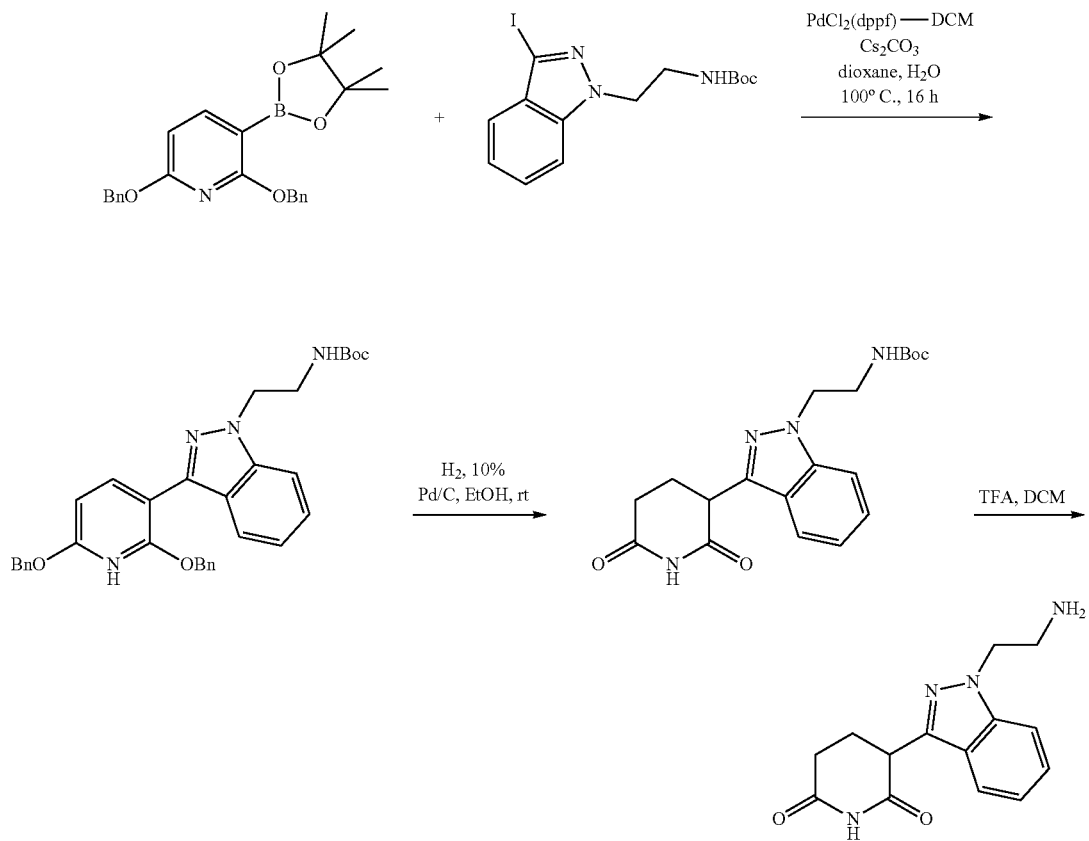

245
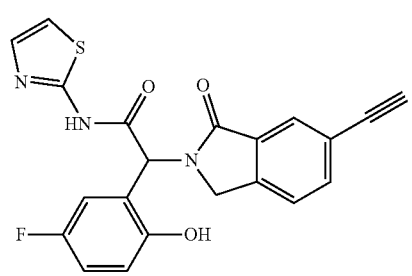
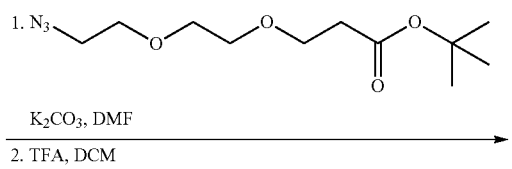
246
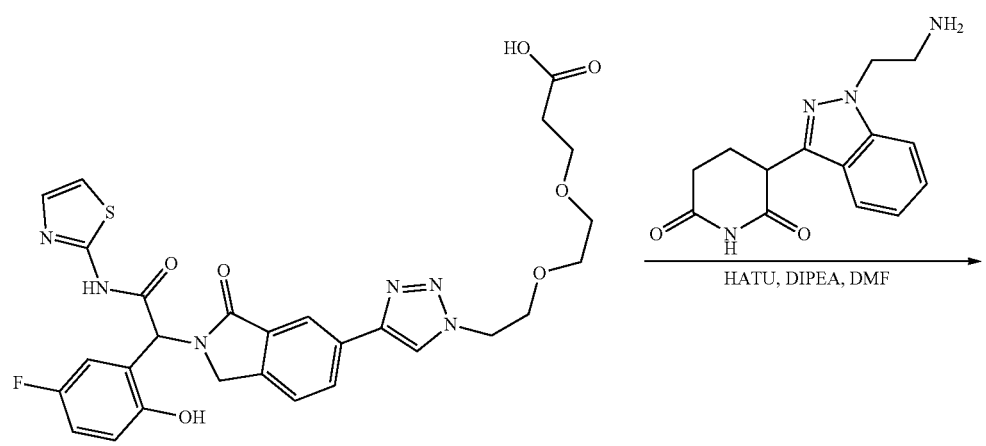
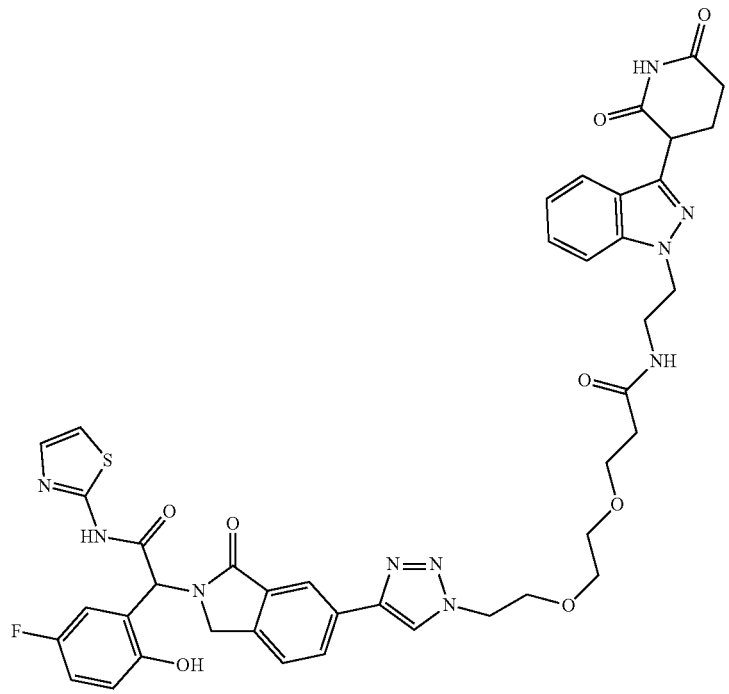 [SMILES: O=C(CCOCCOCCn1cc(-c2ccc3c(c2)C(=O)N(C(C(=O)Nc2nccs2)c2cc(F)ccc2O)C3)nn1)NCCn1nc(C2CCC(=O)NC2=O)c2ccccc21]

Linking Scheme 3:
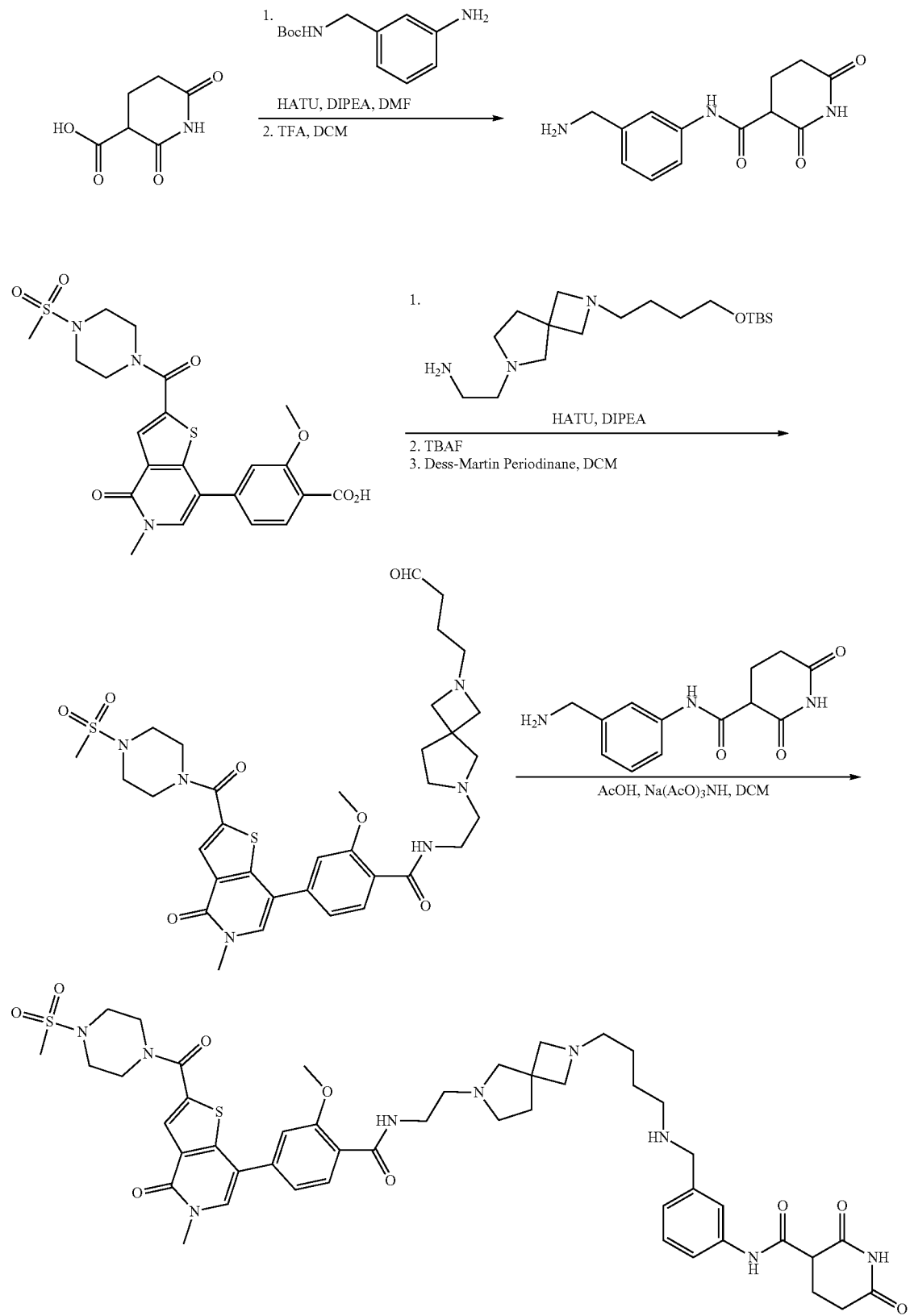

Linking Scheme 4:
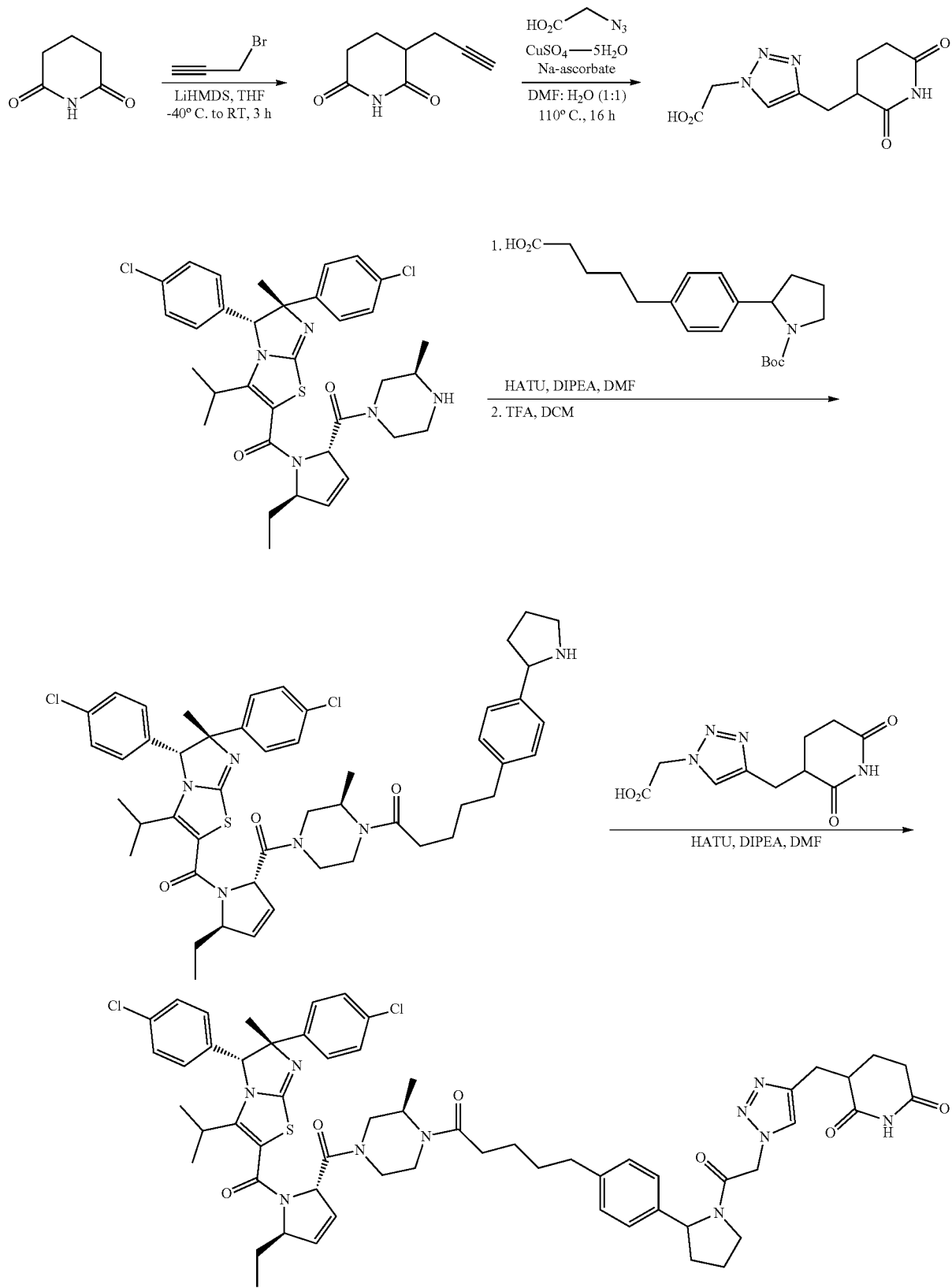

Linking Scheme 5:
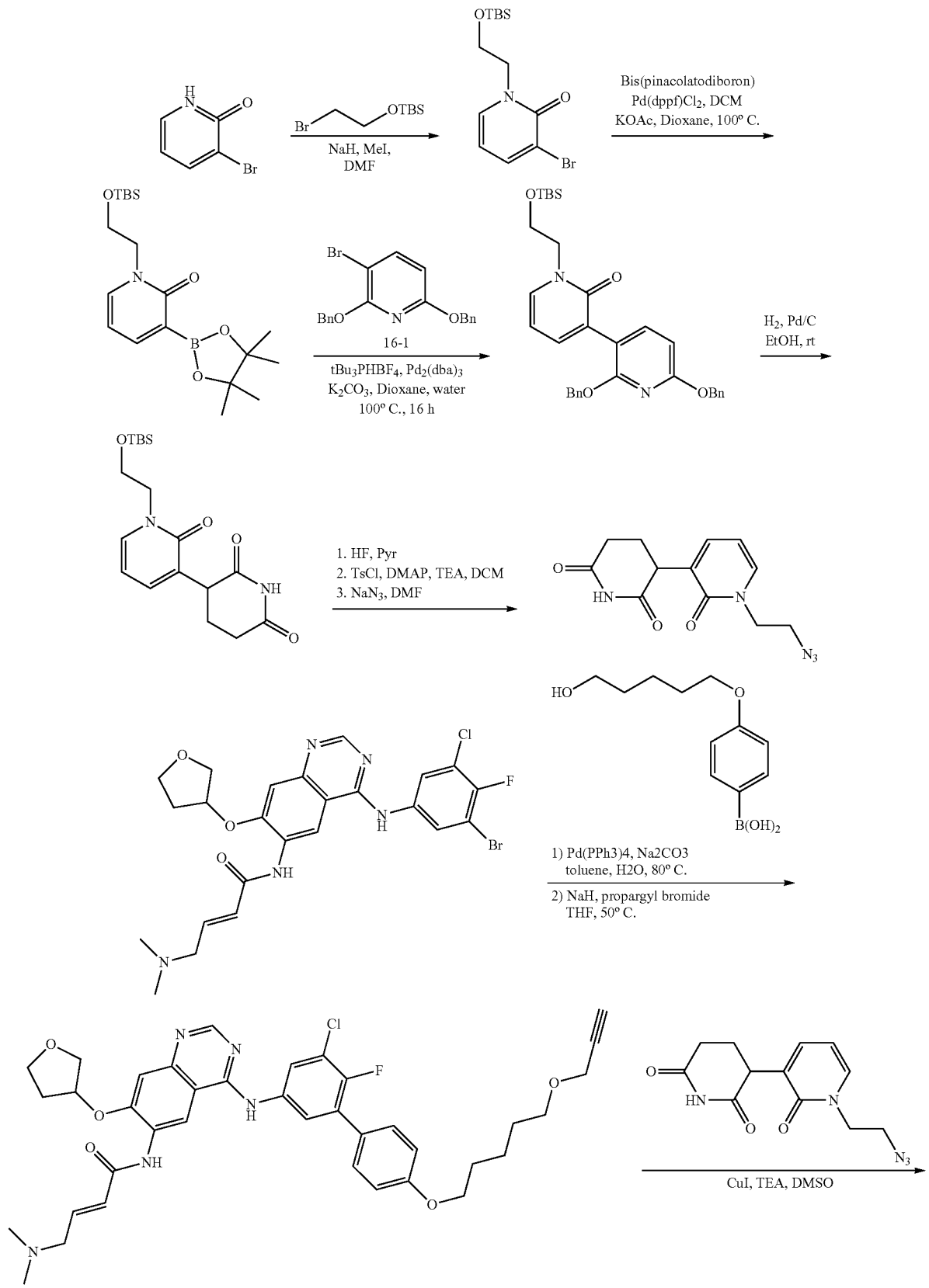

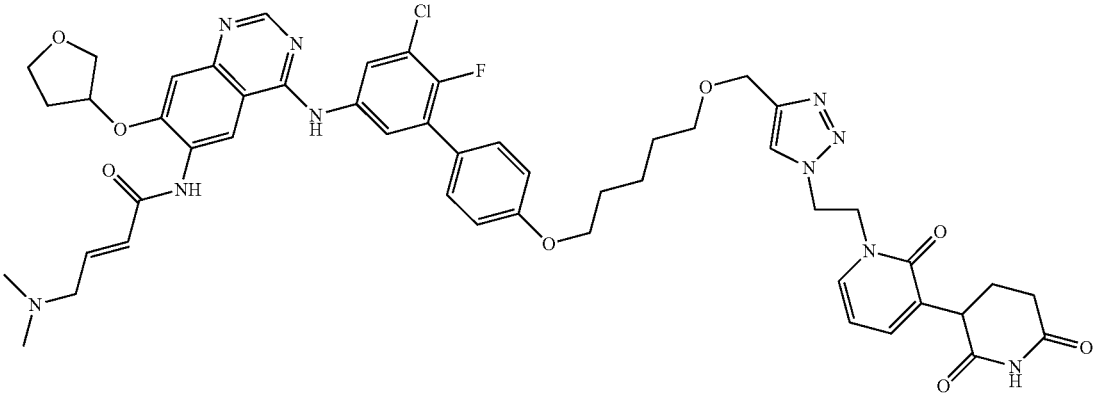 [SMILES: CN(C)C/C=C/C(=O)Nc1cc2c(Nc3cc(Cl)c(F)c(-c4ccc(OCCCCCOCc5cn(CCn6cccc(C7CCC(=O)NC7=O)c6=O)nn5)cc4)c3)ncnc2cc1OC1CCOC1]
Linking Scheme 6:
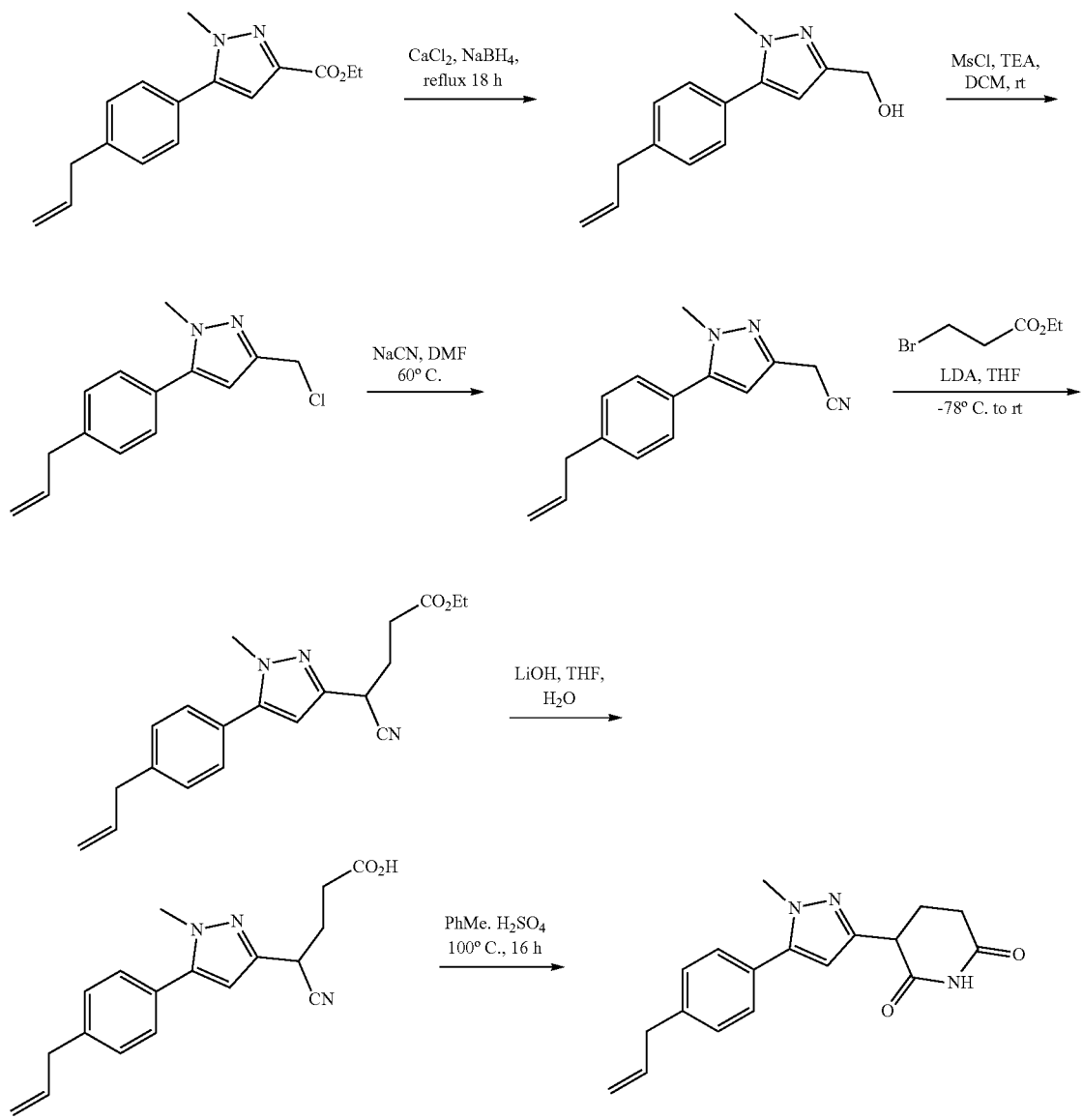

-continued
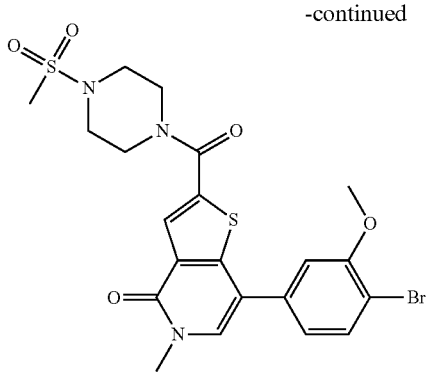
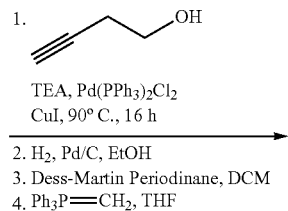
1. 
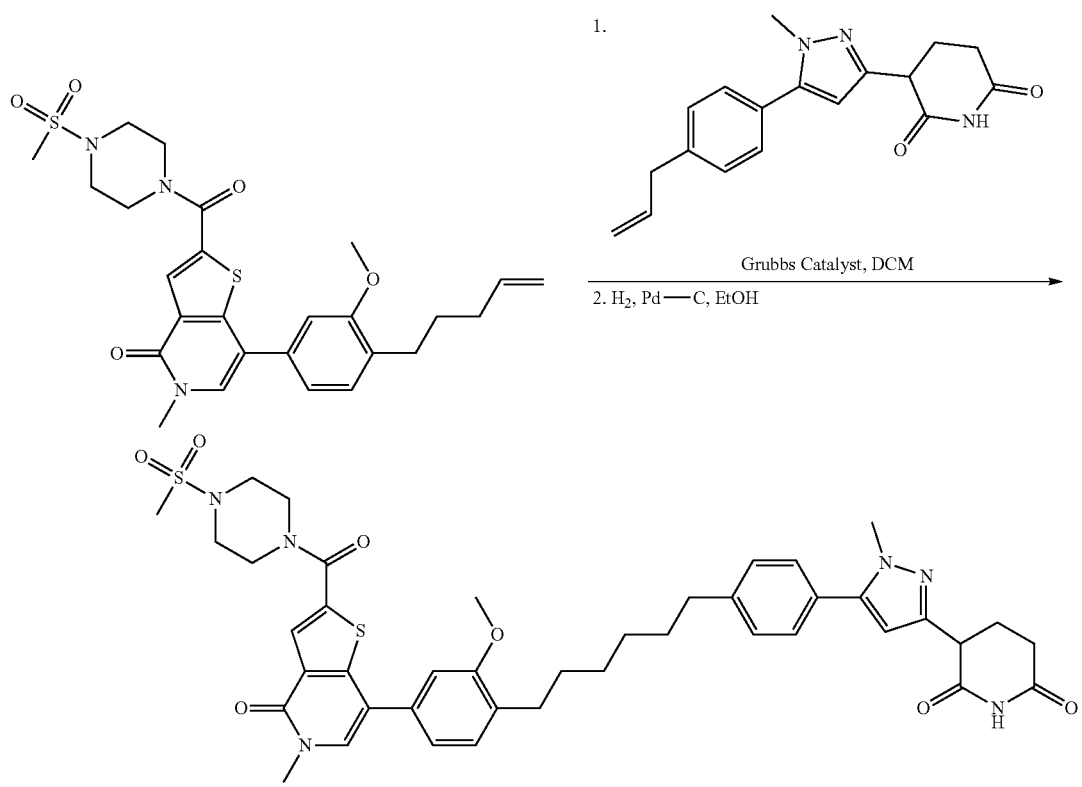
Linking Scheme 7:
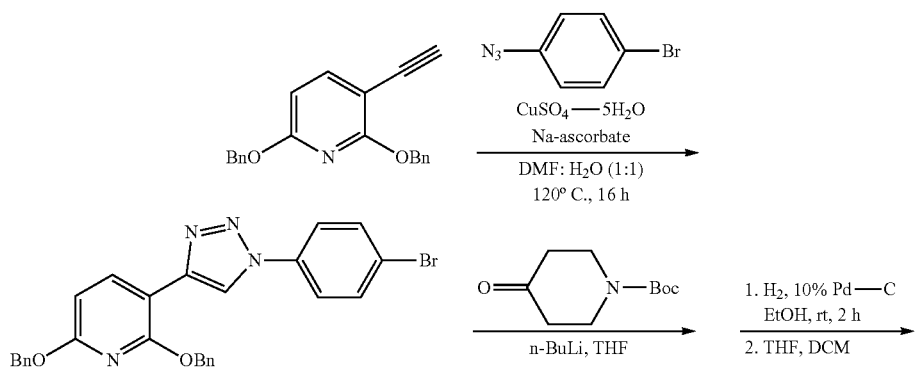

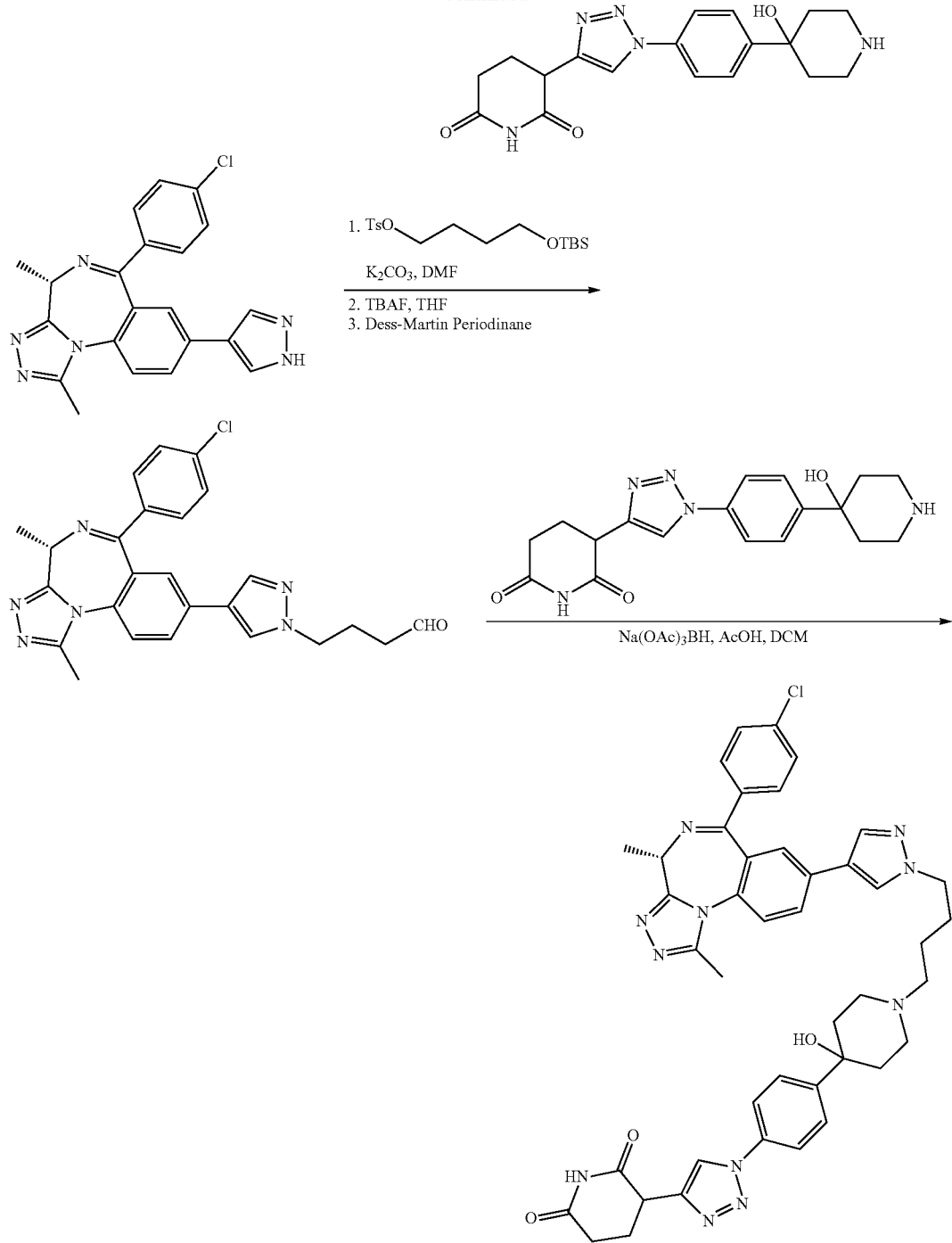
II. Synthesis of Representative Compounds
General Schemes for Glutaramide Synthesis
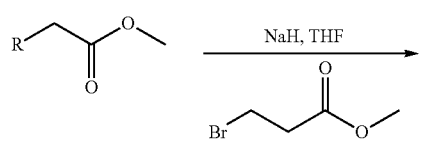
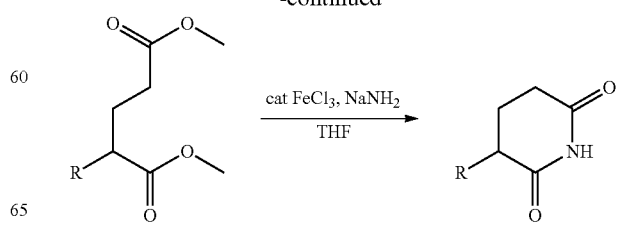

Example 1:
1,3-(4-Bromophenyl)piperidine-2,6-dione

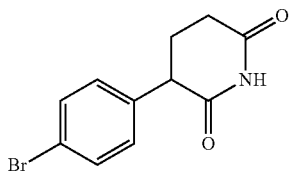 [SMILES: O=C1CCC(c2ccc(Br)cc2)C(=O)N1]

Dimethyl 2-(4-bromophenyl)pentanedioate

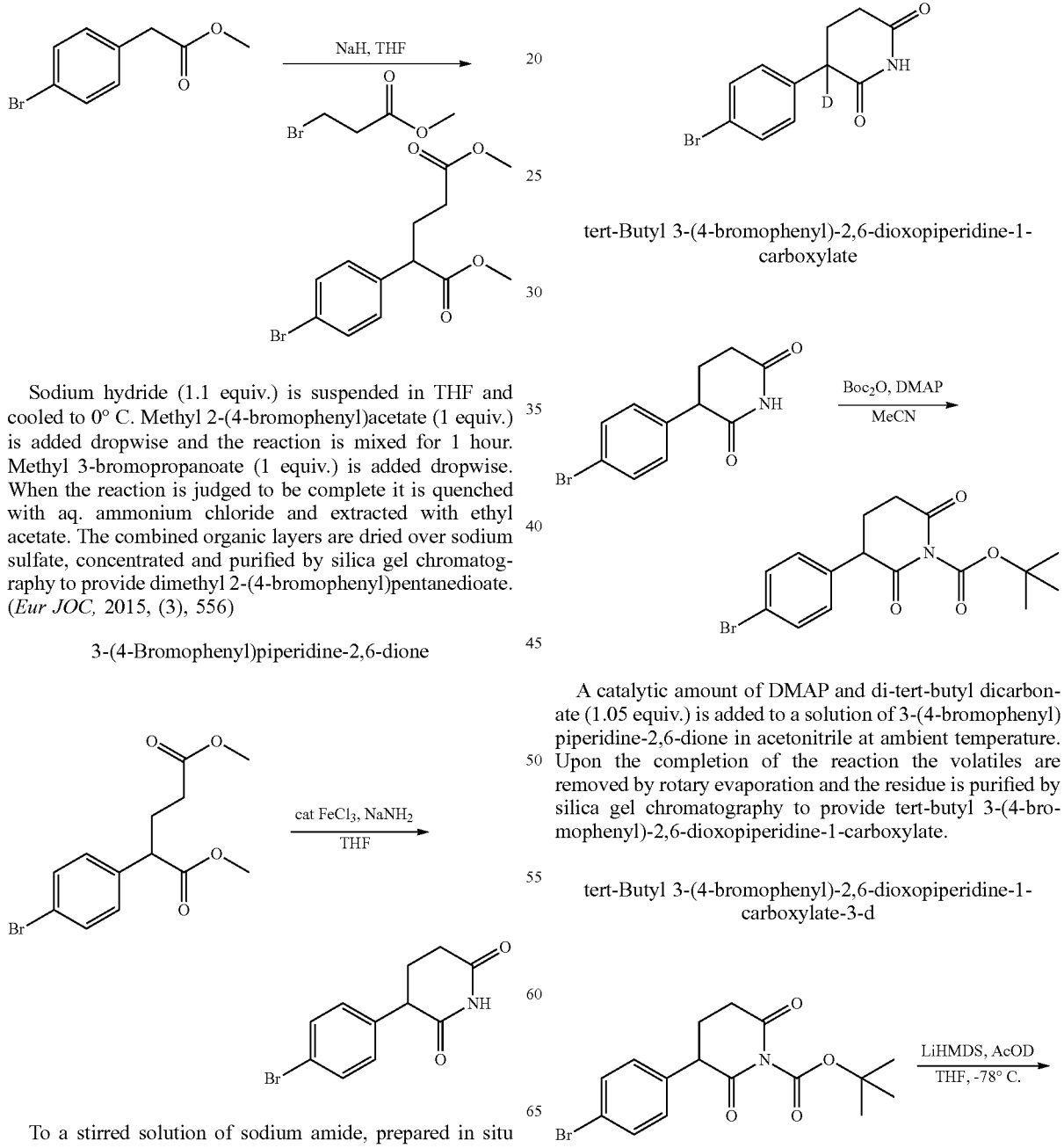

Sodium hydride (1.1 equiv.) is suspended in THF and cooled to 0° C. Methyl 2-(4-bromophenyl)acetate (1 equiv.) is added dropwise and the reaction is mixed for 1 hour. Methyl 3-bromopropanoate (1 equiv.) is added dropwise. When the reaction is judged to be complete it is quenched with aq. ammonium chloride and extracted with ethyl acetate. The combined organic layers are dried over sodium sulfate, concentrated and purified by silica gel chromatography to provide dimethyl 2-(4-bromophenyl)pentanedioate. (*Eur JOC*, 2015, (3), 556)

3-(4-Bromophenyl)piperidine-2,6-dione

To a stirred solution of sodium amide, prepared in situ from sodium metal and ammonia in the presence of a catalytic amount iron(III) chloride in liquid ammonia, is added a solution of the dimethyl 2-(4-bromophenyl)pentanedioate in tetrahydrofuran at −33° C. The reaction is mixed for 3 h, then excess ammonium chloride is added and the ammonia is allowed to evaporate. Water is then added to the residue and the mixture is extracted with chloroform. The combined organic layer is dried over sodium sulfate, concentrated and purified by silica gel chromatography to provide 3-(4-bromophenyl)piperidine-2,6-dione. (*Synthesis*, 1985, (4), 402)

Example 2:
3-(4-Bromophenyl)piperidine-2,6-dione-3-d tert-Butyl 3-(4-bromophenyl)-2,6-dioxopiperidine-1-carboxylate A catalytic amount of DMAP and di-tert-butyl dicarbonate (1.05 equiv.) is added to a solution of 3-(4-bromophenyl) piperidine-2,6-dione in acetonitrile at ambient temperature. Upon the completion of the reaction the volatiles are removed by rotary evaporation and the residue is purified by silica gel chromatography to provide tert-butyl 3-(4-bromophenyl)-2,6-dioxopiperidine-1-carboxylate.

tert-Butyl 3-(4-bromophenyl)-2,6-dioxopiperidine-1-carboxylate-3-d

261

-continued

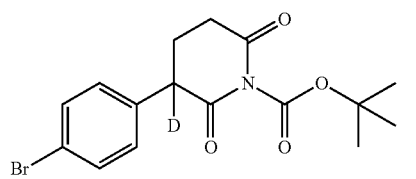

A solution of tert-butyl 3-(4-bromophenyl)-2,6-dioxopiperidine-1-carboxylate in anhydrous THF at −78° C. is treated with lithium bis(trimethylsilyl)amide (1.1 equiv.) for 1 hour. The reaction is quenched with deuterated acetic acid (*Bioorg. Med. Chem. Lett.* 2003, 13, 3415) and warmed to ambient temperature. The crude reaction is diluted with aq. sodium bicarbonate solution and extracted with ethyl acetate. The combined organic layer is dried over sodium sulfate, concentrated and purified by silica gel chromatography to provide tert-butyl 3-(4-bromophenyl)-2,6-dioxopiperidine-1-carboxylate-3-d.

3-(4-Bromophenyl)piperidine-2,6-dione-3-d

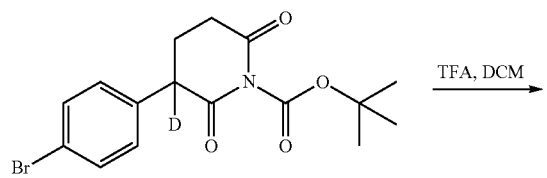

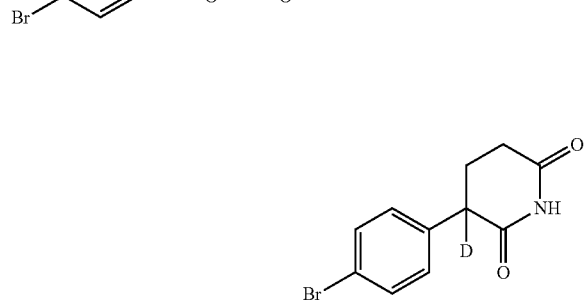

A solution of tert-butyl 3-(4-bromophenyl)-2,6-dioxopiperidine-1-carboxylate-3-d in DCM is treated with TFA (20 equiv.) at ambient temperature. Upon consumption of the starting material, the reaction is concentrated and purified by silica gel chromatography to provide 3-(4-bromophenyl)piperidine-2,6-dione-3-d.

Example 3:
3-(4-Bromophenyl)-3-fluoropiperidine-2,6-dione

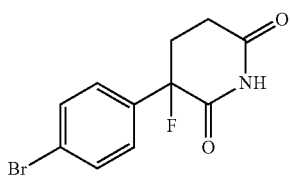 [SMILES: O=C1CCC(F)(c2ccc(Br)cc2)C(=O)N1]

262 tert-Butyl 3-(4-bromophenyl)-3-fluoro-2,6-dioxopiperidine-1-carboxylate

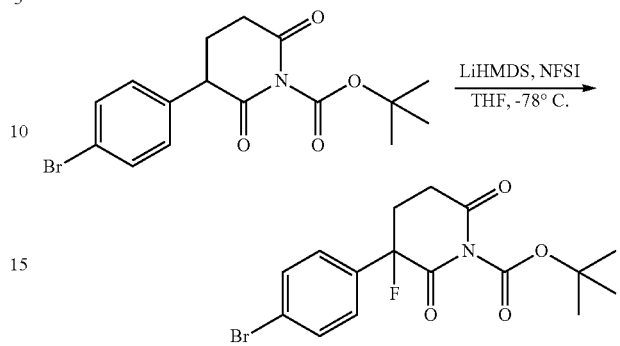

A solution of tert-butyl 3-(4-bromophenyl)-2,6-dioxopiperidine-1-carboxylate in anhydrous THF at −78° C. is treated with lithium bis(trimethylsilyl)amide (1.1 equiv.) for 1 hour. N-fluorobenzenesulfonimide (*Bioorg. Med. Chem. Lett.* 2003, 13, 3415) in a minimal amount of anhydrous THF is added and the reaction is warmed to ambient temperature then quenched. The crude reaction is extracted with ethyl acetate and the combined organic layer is dried over sodium sulfate, concentrated and purified by silica gel chromatography to provide tert-butyl 3-(4-bromophenyl)-3-fluoro-2,6-dioxopiperidine-1-carboxylate.

3-(4-Bromophenyl)-3-fluoropiperidine-2,6-dione

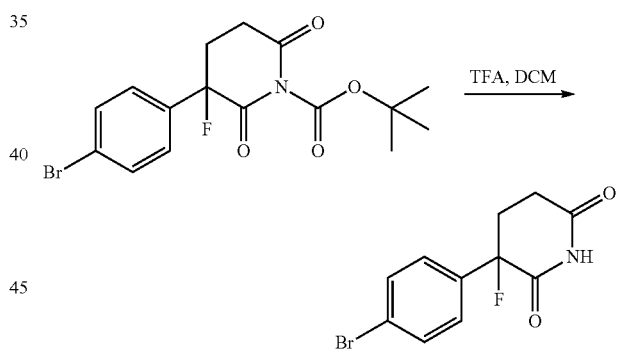

A solution of tert-butyl 3-(4-bromophenyl)-3-fluoro-2,6-dioxopiperidine-1-carboxylate in DCM is treated with TFA (20 equiv.) at ambient temperature. Upon consumption of the starting material, the reaction is concentrated and purified by silica gel chromatography to provide 3-(4-bromophenyl)-3-fluoropiperidine-2,6-dione.

Example 4: 3-Methyl-3-phenylpiperidine-2,6-dione

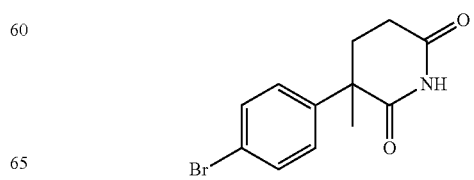

263
tert-Butyl 3-(4-bromophenyl)-3-methyl-2,6-dioxopiperidine-1-carboxylate

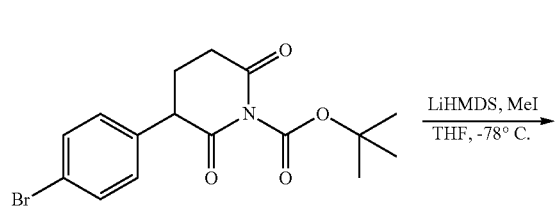

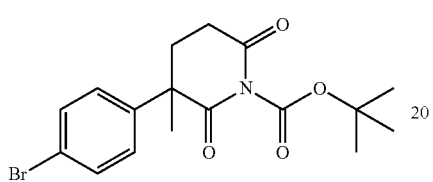

A solution of tert-butyl 3-(4-bromophenyl)-2,6-dioxopiperidine-1-carboxylate in anhydrous THF at −78° C. is treated with lithium bis(trimethylsilyl)amide (1.1 equiv.) for 1 hour. Iodomethane in a minimal amount of anhydrous THF is added and the reaction is warmed to ambient temperature then quenched. The crude reaction is extracted with ethyl acetate and the combined organic layer is dried over sodium sulfate, concentrated and purified by silica gel chromatography to provide tert-butyl 3-(4-bromophenyl)-3-methyl-2,6-dioxopiperidine-1-carboxylate.

3-Methyl-3-phenylpiperidine-2,6-dione

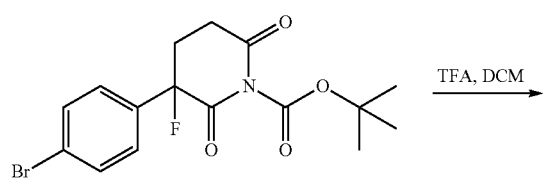

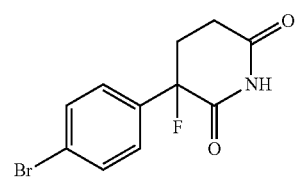

A solution of tert-butyl 3-(4-bromophenyl)-3-methyl-2,6-dioxopiperidine-1-carboxylate in DCM is treated with TFA (20 equiv.) at ambient temperature. Upon consumption of the starting material, the reaction is concentrated and purified by silica gel chromatography to provide 3-methyl-3-phenylpiperidine-2,6-dione.

264
Example 5: 7-(4-Bromophenyl)-5-azaspiro[2.5]octane-4,6-dione

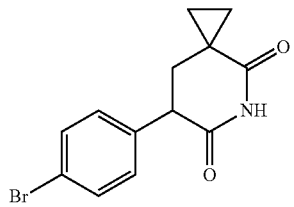 [SMILES: O=C1NC(=O)C2(CC2)CC1c1ccc(Br)cc1]

Methyl 1-(2-(4-bromophenyl)-3-methoxy-3-oxopropyl)cyclopropane-1-carboxylate

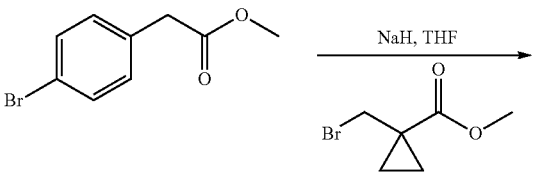

Sodium hydride (1.1 equiv.) is suspended in THF and cooled to 0° C. Methyl 2-(4-bromophenyl)acetate (1 equiv.) is added dropwise and the reaction is mixed for 1 hour. Methyl 1-(bromomethyl)cyclopropane-1-carboxylate (1 equiv.) is added dropwise. When the reaction is judged to be complete it is quenched with aq. ammonium chloride and extracted with ethyl acetate. The combined organic layers are dried over sodium sulfate, concentrated and purified by silica gel chromatography to provide methyl 1-(2-(4-bromophenyl)-3-methoxy-3-oxopropyl)cyclopropane-1-carboxylate. (*Eur JOC*, 2015, (3), 556)

7-(4-Bromophenyl)-5-azaspiro[2.5]octane-4,6-dione

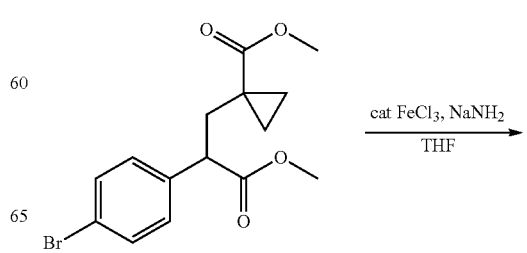

-continued

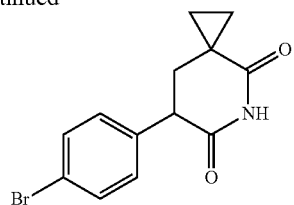

To a stirred solution of sodium amide, prepared in situ from sodium metal and ammonia in the presence of a catalytic amount of iron(III) chloride in liquid ammonia, is added a solution of the methyl 1-(2-(4-bromophenyl)-3-methoxy-3-oxopropyl)cyclopropane-1-carboxylate in tetrahydrofuran at −33° C. The reaction is mixed for 3 h, then excess ammonium chloride is added and the ammonia is allowed to evaporate. Water is then added to the residue and the mixture is extracted with chloroform. The combined organic layer is dried over sodium sulfate, concentrated and purified by silica gel chromatography to provide 7-(4-bromophenyl)-5-azaspiro[2.5]octane-4,6-dione. (Synthesis, 1985, (4), 402)

Example 6: 1-(4-Bromophenyl)-3-azabicyclo[3.1.1]heptane-2,4-dione

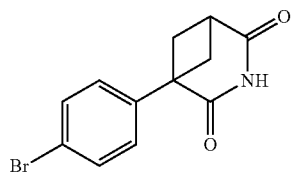 [SMILES: O=C1NC(=O)C2(c3ccc(Br)cc3)CC1C2]

N-(4-Methoxbenzyl)acrylamide

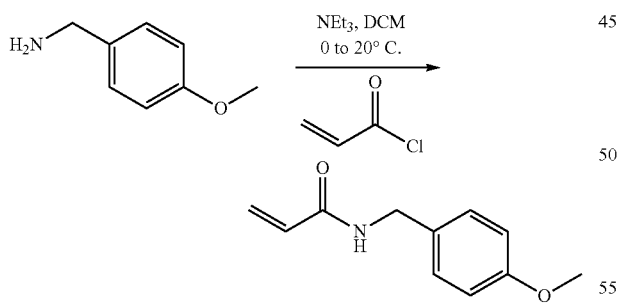

To a 0° C. solution of (4-methoxyphenyl)methanamine (1 equiv.) and trimethylamine (1.5 equiv.) in DCM is added dropwise acryloyl chloride (1.1 equiv.). The reaction is mixed for 1 hour then warmed to ambient temperature. The reaction is quenched with aqueous bicarbonate and mixed for 1 hour then extracted with DCM (3×). The combined organic layers are dried over sodium sulfate, filtered concentrated and purified by silica gel chromatography to provide N-(4-methoxybenzyl)acrylamide. (ChemMed-Chem, 2012, 7(12), 2082)

2-(4-Bromophenyl)Acrylic Acid

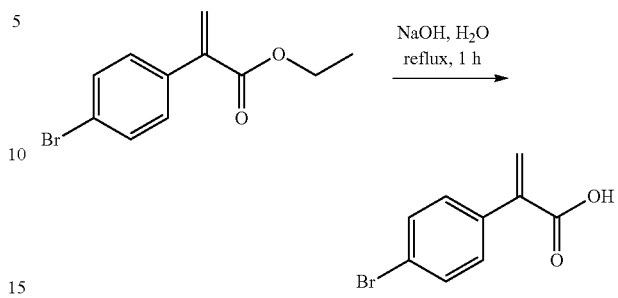

An aqueous solution of 1N sodium hydroxide (10 mL) is added to ethyl 2-(4-bromophenyl)acrylate (5 mmol). The reaction mixture is heated at reflux for 1 hour and cooled to ambient temperature. The resulting mixture is extracted with diethyl ether several times (2×20 mL). The aqueous layer is then acidified with 3N aqueous HCl solutions (pH<1.0 by litmus paper test), and extracted with ethyl ether (3×20 mL). The combined organic extracts are dried over sodium sulfate, filtered and concentrated. Crude 2-(4-bromophenyl)acrylic acid is dried under vacuum and air then used directly in subsequent reactions without further purification. (J. Am. Chem. Soc. 2011, 133(6), 1726)

N-Acryloyl-2-(4-bromophenyl)-N-(4-methoxybenzyl)acrylamide

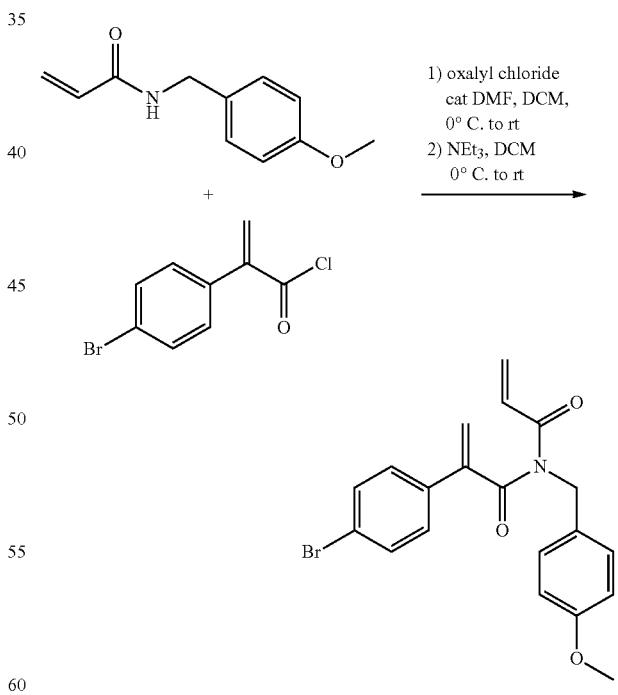

Crude 2-(4-bromophenyl)acrylic acid (1 equiv.) and (2 mol % DMF) are suspended in DCM and cooled to 0° C. Oxalyl chloride (1.5 equiv.) was added dropwise. When the reaction clarifies it is warmed to ambient temperature and mixed for an additional 2 hours. The resultant solution is cooled to 0° C. and triethylamine (2 equiv.) and N-(4- methoxybenzyl)acrylamide (1 equiv.) are added. The reaction is stirred for an additional 1.5 hours then concentrated to dryness and purified by silica gel chromatography to provide N-acryloyl-2-(4-bromophenyl)-N-(4-methoxybenzyl)acrylamide.

1-(4-Bromophenyl)-3-(4-methoxybenzyl)-3-azabicyclo[3.1.1]heptane-2,4-dione

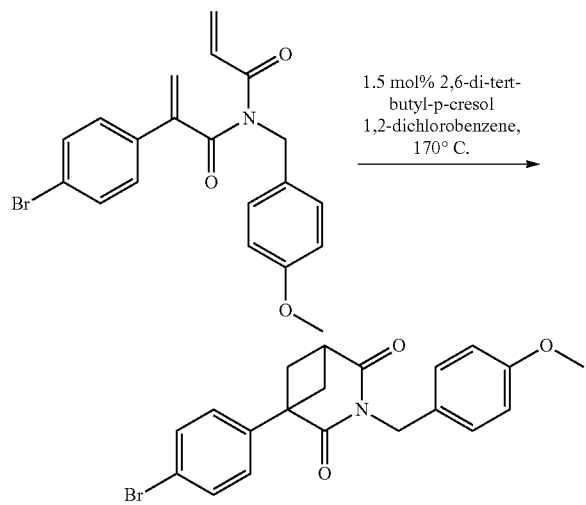

A solution of N-acryloyl-2-(4-bromophenyl)-N-(4-methoxybenzyl)acrylamide (1 equiv.) and 2,6-di-tert-butyl-p-cresol (1.5 mol %) are heated at 170° C. in 1,2-dichlorobenzene for 1.5 hours. The reaction mixture is cooled and the volatiles removed by rotary evaporation and the residue purified by silica gel chromatography to provide 1-(4-bromophenyl)-3-(4-methoxybenzyl)-3-azabicyclo[3.1.1] heptane-2,4-dione. (J. Med. Chem. 1991, 34, 1329)

1-(4-Bromophenyl)-3-azabicyclo[3.1.1]heptane-2,4-dione

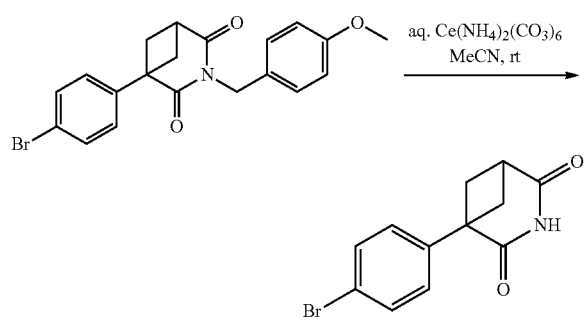

To a solution of 1-(4-bromophenyl)-3-(4-methoxybenzyl)-3-azabicyclo[3.1.1]heptane-2,4-dione (1 equiv.) dissolved in MeCN (0.1M) is added an aqueous solution of cerium(IV)ammonium nitrate (3.75 equiv., 1.3M solution). The reaction is mixed for 4 hours then concentrated to half-volume. This solution is diluted with ethyl acetate and saturated bicarbonate solution and mixed for 0.5 hours. This mixture is filtered through Celite® and the resultant biphasic solution is separated and washed with brine. The combined aqueous layers are saturated with sodium chloride and back-extracted with ethyl acetate. The combined organic layers are dried over sodium sulfate, filtered, concentrated and purified by silica gel chromatography to provide 1-(4-bromophenyl)-3-azabicyclo[3.1.1]heptane-2,4-dione. (J. Med. Chem. 1991, 34, 1329)

3-((4-Bromophenyl)(hydroxy)methyl)piperidine-2,6-dione

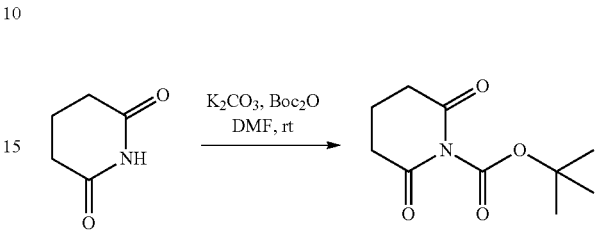

To a stirred solution of piperidine-2,6-dione (1.0 equiv.) in DMF (5 volumes) is added potassium carbonate (2 equiv.) at ambient temperature. The resulting solution is cooled to 5° C. and di-tert-butyl dicarbonate (3 equiv.) is added slowly as a solution in cold dioxane. The resulting mixture is stirred at 0° C. for 1 hour and allowed to warm to ambient temperature overnight. Water (10 volumes) is then added and the aqueous layer extracted with DCM (2×). The combined organic layer is dried over sodium sulfate, filtered and concentrated under vacuum to provide tert-butyl 2,6-dioxopiperidine-1-carboxylate.

tert-Butyl 3-((4-bromophenyl)(hydroxy)methyl)-2,6-dioxopiperidine-1-carboxylate

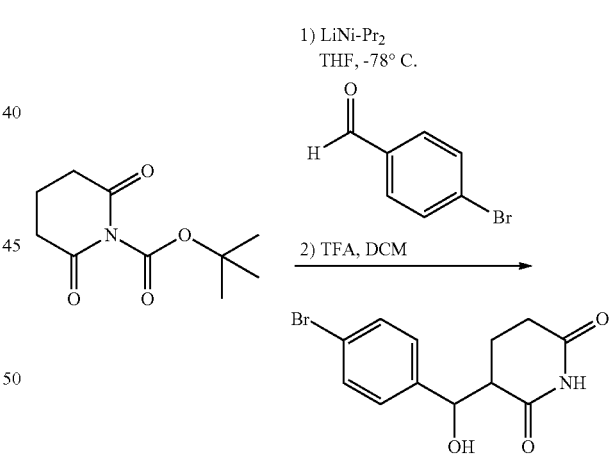

A solution of tert-butyl 2,6-dioxopiperidine-1-carboxylate in anhydrous THF at −78° C. is treated with lithium diisopropylamide (1.1 equiv.) for 1 hour. 4-Bromobenzaldehyde in a minimal amount of anhydrous THF is added and the reaction is warmed to ambient temperature then quenched with aq. ammonium chloride. The crude reaction is extracted with ethyl acetate and the combined organic layer is dried over sodium sulfate, concentrated and purified by silica gel chromatography to provide tert-butyl 3-((4-bromophenyl)(hydroxy)methyl)-2,6-dioxopiperidine-1-carboxylate.

A reaction vessel is charged with tert-butyl 3-((4-bromophenyl)(hydroxy)methyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide 3-((4-bromophenyl)(hydroxy)methyl)piperidine-2,6-dione.

3-(1-(4-Bromophenyl)-1-hydroxyethyl)piperidine-2,6-dione

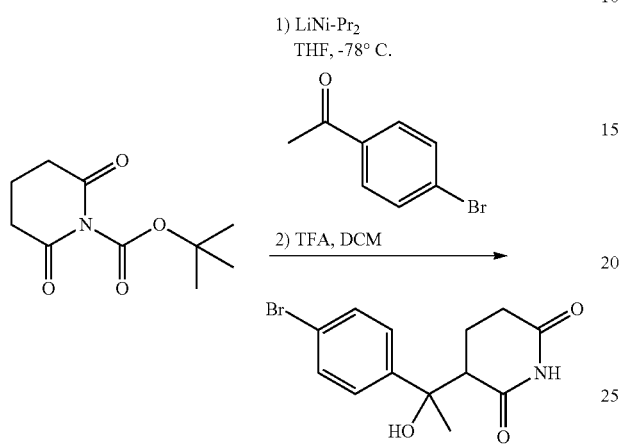

A solution of tert-butyl 2,6-dioxopiperidine-1-carboxylate in anhydrous THF at −78° C. is treated with lithium diisopropylamide (1.1 equiv.) for 1 hour. 1-(4-bromophenyl)ethan-1-one in a minimal amount of anhydrous THF is added and the reaction is warmed to ambient temperature then quenched with aq. ammonium chloride. The crude reaction is extracted with ethyl acetate and the combined organic layer is dried over sodium sulfate, concentrated and purified by silica gel chromatography to provide tert-butyl 3-(1-(4-bromophenyl)-1-hydroxyethyl)-2,6-dioxopiperidine-1-carboxylate.

A reaction vessel is charged with tert-butyl 3-(1-(4-bromophenyl)-1-hydroxyethyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide 3-(1-(4-bromophenyl)-1-hydroxyethyl)piperidine-2,6-dione.

3-(4-Bromobenzyl)piperidine-2,6-dione

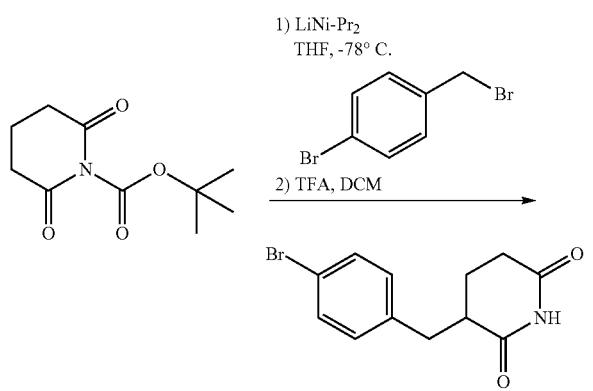

A solution of tert-butyl 2,6-dioxopiperidine-1-carboxylate in anhydrous THF at −78° C. is treated with lithium diisopropylamide (1.1 equiv.) for 1 hour. 1-Bromo-4-(bromomethyl)benzene in a minimal amount of anhydrous THF is added and the reaction is warmed to ambient temperature then quenched with aq. ammonium chloride. The crude reaction is extracted with ethyl acetate and the combined organic layer is dried over sodium sulfate, concentrated and purified by silica gel chromatography to provide tert-butyl 3-(4-bromobenzyl)-2,6-dioxopiperidine-1-carboxylate.

A reaction vessel is charged with tert-butyl 3-(4-bromobenzyl)-2,6-dioxopiperidine-1-carboxylate (1 equiv.) and DCM (0.1 M). TFA (20 equiv.) is added and the reaction is mixed for 1 hour at ambient temperature. The volatiles are removed by rotary evaporation and the residue purified by silica gel chromatography to provide 3-(4-bromobenzyl)piperidine-2,6-dione.

3-(2-(4-Bromophenyl)-2-hydroxypropyl)piperidine-2,6-dione

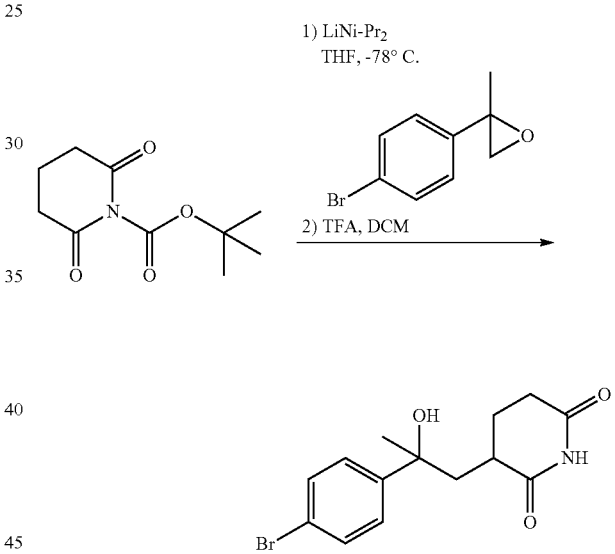

A solution of tert-butyl 2,6-dioxopiperidine-1-carboxylate in anhydrous THF at −78° C. is treated with lithium diisopropylamide (1.1 equiv.) for 1 hour. In a minimal amount of anhydrous THF is added 2-(4-bromophenyl)-2-methyloxirane and the solution is added to the reaction. The reaction is warmed to ambient temperature then quenched with aq. ammonium chloride. The crude reaction is extracted with ethyl acetate and the combined organic layer is dried over sodium sulfate, concentrated and purified by silica gel chromatography to provide tert-butyl 3-(2-(4-bromophenyl)-2-hydroxypropyl)-2,6-dioxopiperidine-1-carboxylate.

A reaction vessel is charged with tert-butyl 3-(2-(4-bromophenyl)-2-hydroxypropyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide 3-(2-(4-bromophenyl)-2-hydroxypropyl)piperidine-2,6-dione.

3-(1-((4-Bromophenyl)amino)ethyl)piperidine-2,6-dione

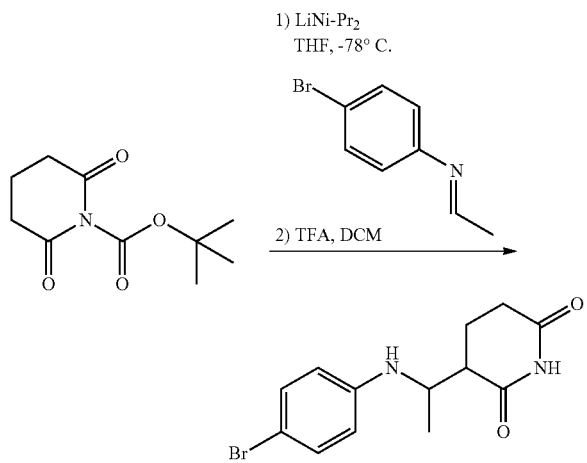

a solution of tert-butyl 2,6-dioxopiperidine-1-carboxylate in anhydrous THF at −78° C. is treated with lithium diisopropylamide (1.1 equiv.) for 1 hour. In a minimal amount of anhydrous THF is added (E)-N-(4-bromophenyl)ethanimine and the solution is added to the reaction. The reaction is warmed to ambient temperature and quenched with aq. ammonium chloride. The crude reaction is extracted with ethyl acetate and the combined organic layer is dried over sodium sulfate, concentrated and purified by silica gel chromatography to provide tert-butyl 3-(1-((4-bromophenyl)amino)ethyl)-2,6-dioxopiperidine-1-carboxylate.

A reaction vessel is charged with tert-butyl 3-(1-((4-bromophenyl)amino)ethyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide 3-(1-((4-bromophenyl)amino)ethyl)piperidine-2,6-dione.

3-(1-((4-Bromophenyl)amino)ethyl)piperidine-2,6-dione

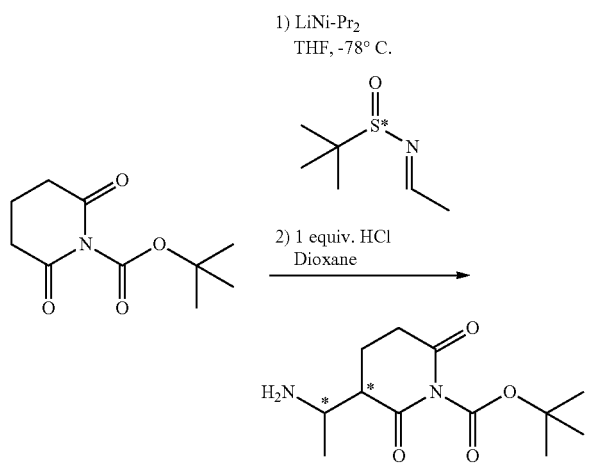

A solution of tert-butyl 2,6-dioxopiperidine-1-carboxylate in anhydrous THF at −78° C. is treated with lithium diisopropylamide (1.1 equiv.) for 1 hour. In a minimal amount of anhydrous THF is added (E)-N-ethylidene-2-methylpropane-2-sulfinamide and the solution is added to the reaction. The reaction is warmed to ambient temperature and quenched with aq. ammonium chloride. The crude reaction is extracted with ethyl acetate and the combined organic layer is dried over sodium sulfate, concentrated and purified by silica gel chromatography to provide tert-butyl 3-(1-((tert-butylsulfinyl)amino)ethyl)-2,6-dioxopiperidine-1-carboxylate.

A reaction vessel is charged with tert-butyl 3-(1-((tert-butylsulfinyl)amino)ethyl)-2,6-dioxopiperidine-1-carboxylate (1 equiv.) and 1,4-dioxane (0.1 M). HCl (4.0 M in dioxane, 1 equiv.) is then added and the reaction is mixed for 1 hour at ambient temperature. The volatiles are removed by rotary evaporation and the residue purified by silica gel chromatography to provide tert-butyl 3-(1-aminoethyl)-2,6-dioxopiperidine-1-carboxylate.

3-(1-((4-Bromophenyl)amino)ethyl)piperidine-2,6-dione

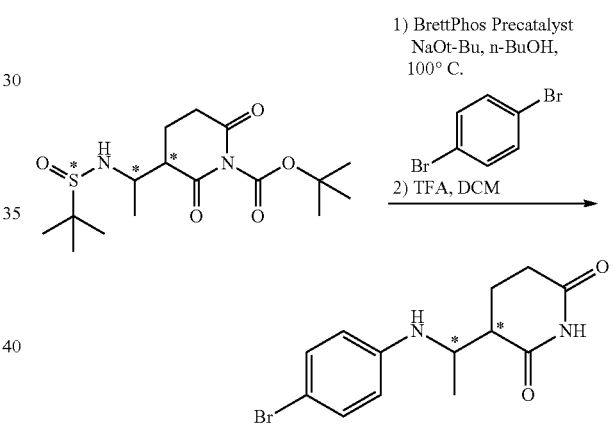

To a reaction vessel is added tert-butyl 3-(1-((tert-butylsulfinyl)amino)ethyl)-2,6-dioxopiperidine-1-carboxylate (1 equiv.), 1,4-dibromobenzene (1 equiv), BretPhos Precatalyst (1 mol %) and sodium tert-butoxide (2 equiv.). The reaction vessel is sealed and the atmosphere cycled between nitrogen and vacuum (3×). n-Butanol (0.5 M) is added and the reaction is heated at 100° C. for 5 hours. The reaction is cooled, diluted with ethyl acetate and filtered through a plug of Celite®. The filtrate is concentrated and purified by silica gel chromatography to provide tert-butyl 3-(1-((4-bromophenyl)(tert-butylsulfinyl)amino)ethyl)-2,6-dioxopiperidine-1-carboxylate (J. Am. Chem. Soc. 2008, 130, 13552).

A reaction vessel is charged with tert-butyl 3-(1-((4-bromophenyl)(tert-butylsulfinyl)amino)ethyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide 3-(1-((4-bromophenyl)amino)ethyl)piperidine-2,6-dione.

Intermediate functionalization in preparation for Linker installation tert-Butyl 3-(4-aminophenyl)-2,6-dioxopiperidine-1-carboxylate

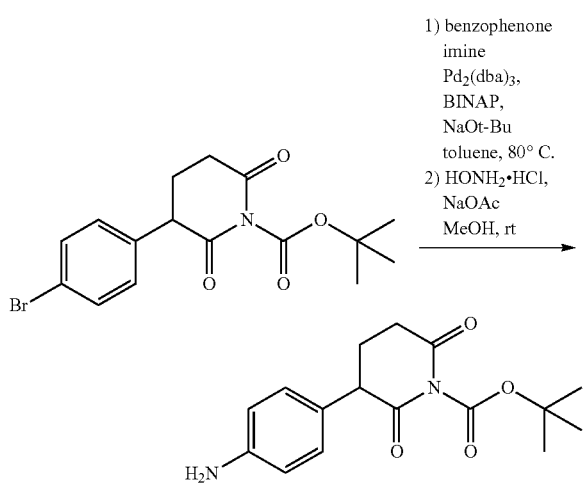

A reaction vessel is charged with tert-butyl 3-(4-bromophenyl)-3-fluoro-2,6-dioxopiperidine-1-carboxylate (1 equiv.), benzophenone imine (1.2 equiv.), tris(dibenzylideneacetone)dipalladium(0) (1 mol %), BINAP (3 mol %) and sodium tert-butoxide and purged by cycling between nitrogen and vacuum 3 times. Toluene is added and the reaction is heated at 80° C. for 18 hours. Ethyl acetate is added and the solids separated by filtration through a plug of Celite®. The filtrate is concentrated and the residue is purified by chromatography to provide tert-butyl 3-(4-((diphenylmethylene)amino)phenyl)-2,6-dioxopiperidine-1-carboxylate.

A reaction vessel is charged with tert-butyl 3-(4-((diphenylmethylene)amino)phenyl)-2,6-dioxopiperidine-1-carboxylate (1 equiv.) and dissolved in MeOH. Hydroxylamine hydrochloride (1.8 equiv.) and sodium acetate (2.4 equiv.) are added and the reaction mixed at ambient temperature for 1 hour. The reaction is quenched by addition of 0.1M aq. NaOH solution and the resultant mixture extracted with ethyl acetate. The combined organic layer is washed with brine, dried over sodium sulfate, filtered, and concentrated. The crude residue is purified by silica gel chromatography to provide tert-butyl 3-(4-aminophenyl)-2,6-dioxopiperidine-1-carboxylate. (PCT Int. Appl., 2015002230, 8 Jan. 2015)

tert-Butyl 3-(4-ethynylphenyl)-2,6-dioxopiperidine-1-carboxylate

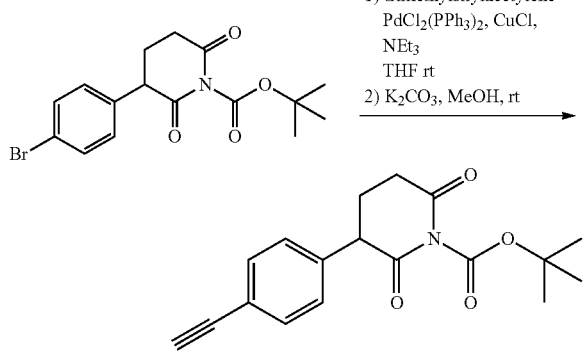

A reaction vessel is charged with bis(triphenylphosphine)palladium(II) chloride (2 mol %), copper(I) iodide (4 mol %) and tert-butyl 3-(4-bromophenyl)-3-fluoro-2,6-dioxopiperidine-1-carboxylate (1 equiv.). The reaction atmosphere is cycled between nitrogen and vacuum 3 times then triethylamine (1.55 equiv.) and trimethylsilylacetylene (1.25 equiv.) are added and the reaction is mixed for 24 hours. When the starting materials are consumed, the reaction is diluted with ethyl acetate and filtered through a plug of Celite®. The filtrate is concentrated and the residue is purified by silica gel chromatography to provide tert-butyl 2,6-dioxo-3-(4-((trimethylsilyl)ethynyl)phenyl)piperidine-1-carboxylate. (Org. Lett. 2014, 16(24), 6302).

A reaction vessel is charged with tert-butyl 2,6-dioxo-3-(4-((trimethylsilyl)ethynyl)phenyl)piperidine-1-carboxylate (1 equiv.), potassium carbonate (4 equiv.) and MeOH. The reaction is mixed at ambient temperature for 8 hours then concentrated. The residue is diluted with water and ethyl acetate. The aqueous layer is extracted with ethyl acetate and the combined organic layer is dried over sodium sulfate, filtered and concentrated. The crude residue is purified by silica gel chromatography to provide tert-butyl 3-(4-ethynylphenyl)-2,6-dioxopiperidine-1-carboxylate.

tert-Butyl 3-(4-hydroxyphenyl)-2,6-dioxopiperidine-1-carboxylate

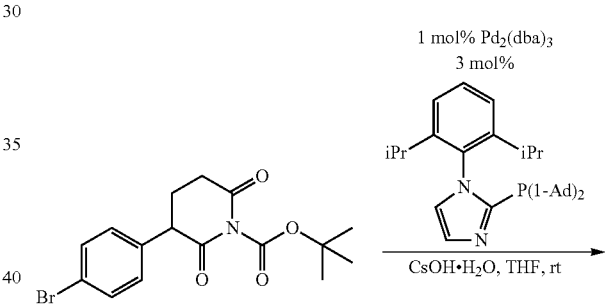

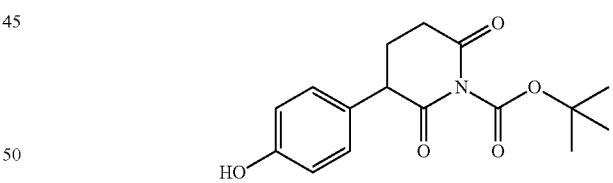

A reaction vial is charged with tris(dibenzylideneacetone)dipalladium(0) (1 mol %), 2-(di-adamantan-1-yl)phosphaneyl)-1-(2,6-diisopropylphenyl)-1H-imidazole (3 mol %), CsOH*H$_2$0 (3 equiv.). The vial is sealed, and the atmosphere is cycled between vacuum and nitrogen three times. Anhydrous THF and tert-butyl 3-(4-bromophenyl)-3-fluoro-2,6-dioxopiperidine-1-carboxylate are added and the reaction is mixed at ambient temperature for 20 hours. The reaction is then diluted with ethyl acetate, filtered through Celite® and concentrated. The crude residue is purified by silica gel chromatography to provide tert-butyl 3-(4-hydroxyphenyl)-2,6-dioxopiperidine-1-carboxylate. (Angew. Chem. Int. Ed. 2009, 48, 7595).

tert-Butyl 2,6-dioxo-3-(4-(prop-2-yn-1-yloxy)phenyl)piperidine-1-carboxylate

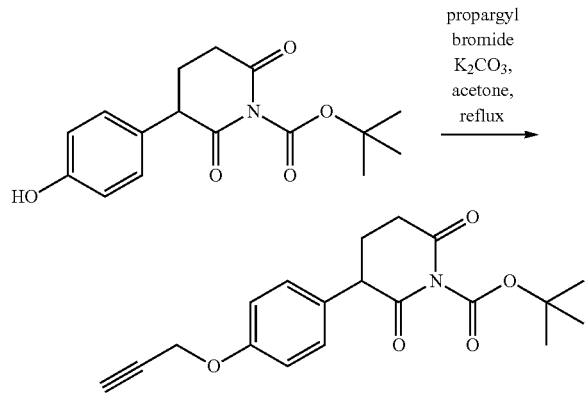

A reaction vessel is charged with tert-butyl 3-(4-hydroxyphenyl)-2,6-dioxopiperidine-1-carboxylate (1 equiv.) and acetone (0.25 M). To this solution is added sequentially potassium carbonate (4 equiv.) and propargyl bromide (1.2 equiv.). The reaction is heated at reflux overnight, cooled to ambient temperature, filtered through a medium frit, and concentrated. The crude residue is purified by silica gel chromatography to provide tert-butyl 2,6-dioxo-3-(4-(prop-2-yn-1-yloxy)phenyl)piperidine-1-carboxylate. (J. Med. Chem. 2013, 56(7), 2828).

4-(1-(tert-Butoxycarbonyl)-2,6-dioxopiperidin-3-yl)benzoic acid

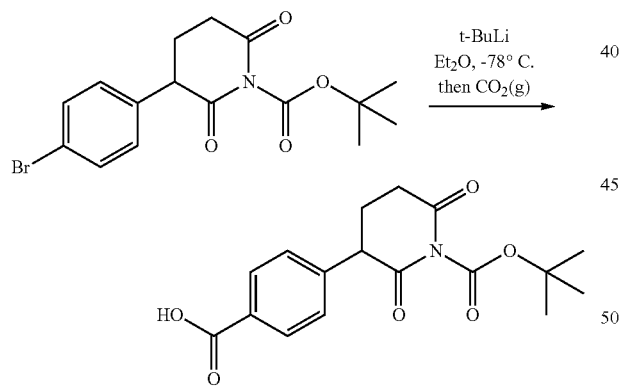

A flame-dried reaction vessel is charged with tert-butyl 3-(4-bromophenyl)-3-fluoro-2,6-dioxopiperidine-1-carboxylate (1 equiv.) and the atmosphere is cycled between nitrogen and vacuum three times. Ether is added and the solution is cooled to −78° C. tert-Butyllithium (2 equiv.) is added dropwise, the reaction is mixed for 15 min then carbon dioxide gas is bubbled through the solution for 15 min. The reaction is warmed to ambient temperature allowing excess carbon dioxide gas to slowly evolve from solution. The reaction is quenched with 1 M aq. NaOH solution and washed with ether (2×). The pH of the aqueous layer is adjusted to pH=3 and the aqueous layer is extracted with ethyl acetate (3×). The combined organic layer is dried over sodium sulfate and concentrated to dryness with toluene (3×) to provide 4-(1-(tert-butoxycarbonyl)-2,6-dioxopiperidin-3-yl)benzoic acid.

tert-Butyl 3-(4-(hydroxymethyl)phenyl)-2,6-dioxopiperidine-1-carboxylate

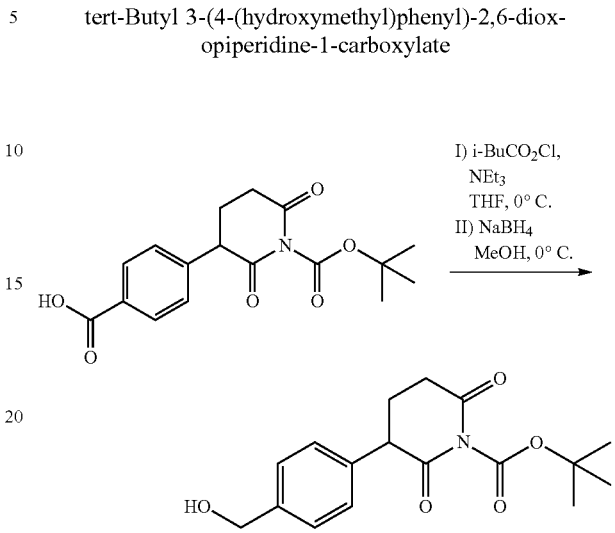

A reaction vessel is charged with 4-(1-(tert-butoxycarbonyl)-2,6-dioxopiperidin-3-yl)benzoic acid (1 equiv.), THF and cool to 0° C. Triethylamine (1.1 equiv.) and isobutylchloroformate (1.1 equiv.) are added and the reaction mixed at ambient temperature for 1 hour. The reaction is filtered through a medium frit and cooled to 0° C. To the solution of mixed anhydride is added a solution of sodium borohydride (2 equiv.) in MeOH. Upon complete reduction to the corresponding benzylic alcohol, the reaction is concentrated then treated with ethyl acetate and 10% aq. HCl. The phases are separated and aqueous solution is extracted with ethyl acetate (3×). The combined organic layer is washed with 5% sodium bicarbonate solution, dried over sodium sulfate, and concentrated. The residue is purified by silica gel chromatography to provide tert-butyl 3-(4-(hydroxymethyl)phenyl)-2,6-dioxopiperidine-1-carboxylate.

tert-Butyl 3-(4-formylphenyl)-2,6-dioxopiperidine-1-carboxylate

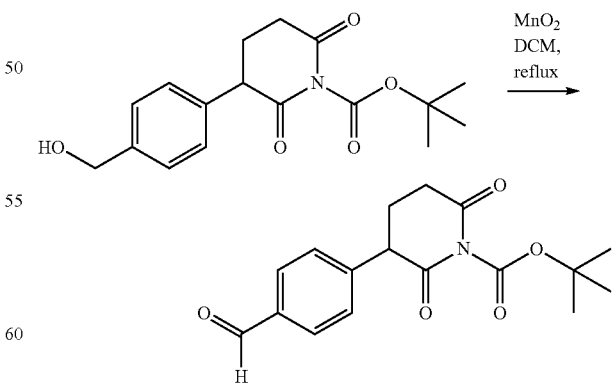

A reaction vessel is charged with tert-butyl 3-(4-(hydroxymethyl)phenyl)-2,6-dioxopiperidine-1-carboxylate (1 equiv.), manganese dioxide (10 equiv.) and DCM. The reaction is heated at reflux overnight then cooled to ambient Linker Installation tert-Butyl 3-(4-((8-hydroxyoctyl)oxy)phenyl)-2,6-dioxopiperidine-1-carboxylate tert-Butyl 3-(4-(bromomethyl)phenyl)-2,6-dioxopiperidine-1-carboxylate

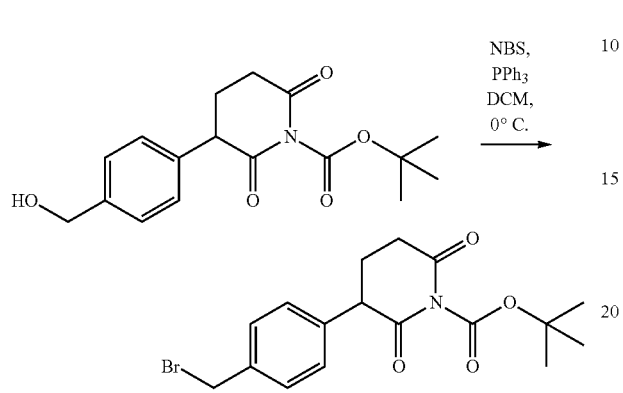

A reaction vessel is charged with tert-butyl 3-(4-(hydroxymethyl)phenyl)-2,6-dioxopiperidine-1-carboxylate (1 equiv.) and DCM. The solution is cooled to 0° C. and N-bromosuccinimide (1.25 equiv.) and triphenylphosphine (1.25 equiv.) are then added. The reaction is mixed for 3 hours then concentrated. The crude residue is purified by silica gel chromatography to provide tert-butyl 3-(4-(bromomethyl)phenyl)-2,6-dioxopiperidine-1-carboxylate. (J. Med. Chem. 2015, 58(3), 1215).

tert-Butyl 3-(4-(azidomethyl)phenyl)-2,6-dioxopiperidine-1-carboxylate

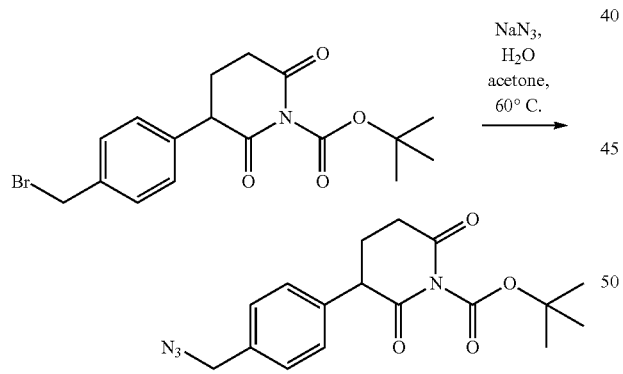

Sodium azide (3 equiv.) is added to a solution of tert-butyl 3-(4-(bromomethyl)phenyl)-2,6-dioxopiperidine-1-carboxylate (1 equiv.) in water and acetone (1:3, 0.25 M). The reaction is heated at 60° C. for 6 hours. The reaction is cooled to ambient temperature and the solvent removed by rotary evaporation. The aqueous layer is extracted with DCM (3×) and the combined organic layer is dried over sodium sulfate and filtered. The filtrate is concentrated and the crude residue is purified by silica gel chromatography to provide tert-butyl 3-(4-(azidomethyl)phenyl)-2,6-dioxopiperidine-1-carboxylate. (Angew. Chem. Int. Ed. 2014, 53(38), 10155).

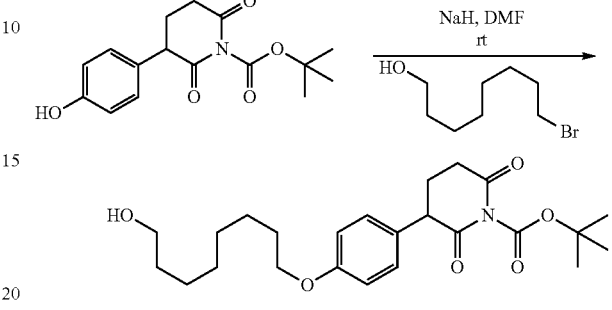

A reaction vessel is charged with tert-butyl 3-(4-hydroxyphenyl)-2,6-dioxopiperidine-1-carboxylate (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then 8-bromooctan-1-ol (1.1 equiv.) is added and the reaction is mixed at ambient temperature overnight. DMF is removed by rotary evaporation and the residue is deposited onto silica gel and purified by silica gel chromatography to provide tert-butyl 3-(4-((8-hydroxyoctyl)oxy)phenyl)-2,6-dioxopiperidine-1-carboxylate.

tert-Butyl 3-(4-(2-(2-(2-hydroxyethoxy)ethoxy)ethoxy)phenyl)-2,6-dioxopiperidine-1-carboxylate

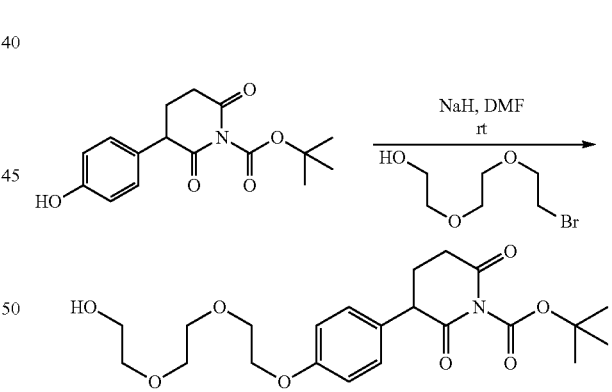

A reaction vessel is charged with tert-butyl 3-(4-hydroxyphenyl)-2,6-dioxopiperidine-1-carboxylate (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then 2-(2-(2-bromoethoxy)ethoxy)ethan-1-ol (1.1 equiv.) is added and the reaction is mixed at ambient temperature overnight. DMF is removed by rotary evaporation and the residue is deposited onto silica gel and purified by silica gel chromatography to provide tert-butyl 3-(4-(2-(2-(2-hydroxyethoxy)ethoxy)ethoxy)phenyl)-2,6-dioxopiperidine-1-carboxylate.

tert-Butyl 3-(4-((1-(3-hydroxypropyl)-1H-1,2,3-triazol-4-yl)methoxy)phenyl)-2,6-dioxopiperidine-1-carboxylate

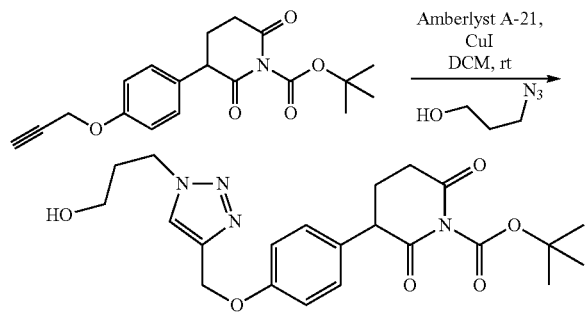

A reaction vessel is charged with the polymer supported catalyst (Amberlyst A-21, 1.23 mmol/g; Cu, 13% mol). The azide (0.5 M in DCM) is added dropwise followed by a solution of the tert-butyl 2,6-dioxo-3-(4-(prop-2-yn-1-yloxy)phenyl)piperidine-1carboxylate (0.5 M in DCM). The suspension is mixed for 12 hours at ambient temperature. The reaction solution is filtered through a frit and the polymer cake is washed with DCM (2×). The combined filtrate is concentrated and the residue purified by silica gel chromatography to provide tert-butyl 3-(4-((1-(3-hydroxypropyl)-1H-1,2,3-triazol-4-yl)methoxy)phenyl)-2,6-dioxopiperidine-1-carboxylate. (Org. Lett. 2006, 8(8), 1689).

tert-Butyl 3-(4-(2-(2,4-dihydroxy-2-methylbutoxy)ethoxy)phenyl)-2,6-dioxopiperidine-1-carboxylate

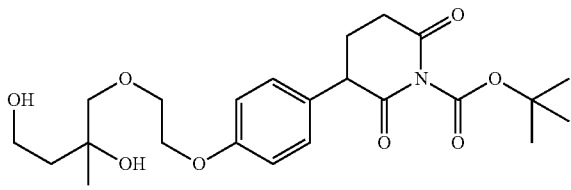 [SMILES: CC(O)(CCO)COCCOc1ccc(C2CCC(=O)N(C(=O)OC(C)(C)C)C2=O)cc1]

tert-Butyl 3-(4-(2-hydroxyethoxy)phenyl)-2,6-dioxopiperidine-1-carboxylate

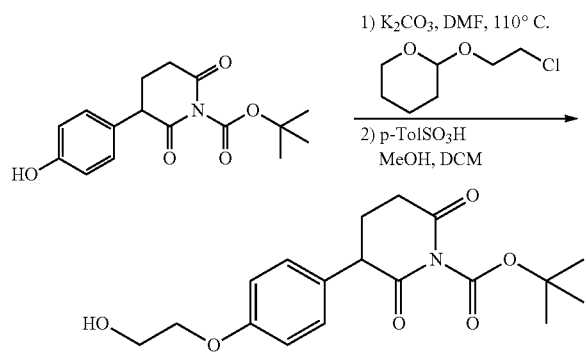

A reaction vessel is charged with tert-butyl 3-(4-hydroxyphenyl)-2,6-dioxopiperidine-1-carboxylate (1 equiv.), potassium carbonate (2 equiv.) and DMF (0.5 M). 2-(2-Chloroethoxy)tetrahydro-2H-pyran (1.1 equiv.) is added and the reaction is heated at 110° C. for 12 hours. The reaction is then cooled to ambient temperature and concentrated. The residue is taken up in water and ethyl acetate and the layers separated. The aqueous layer is extracted with ethyl acetate (2×). The combined organic layer is washed with brine, dried over sodium sulfate, filtered and concentrated. The crude residue is used directly in the following reaction.

A reaction vessel is charged with crude tert-butyl 2,6-dioxo-3-(4-(2-((tetrahydro-2H-pyran-2-yl)oxy)ethoxy)phenyl)piperidine-1-carboxylate (1 equiv.), MeOH and DCM (1:1, 0.2 M). p-Toluenesulfonic acid (0.1 equiv.) is added and the reaction mixed at ambient temperature. Upon completion of the hydrolysis reaction, the volatiles are removed by rotary evaporation and the residue purified by silica gel chromatography to provide tert-butyl 3-(4-(2-hydroxyethoxy)phenyl)-2,6-dioxopiperidine-1-carboxylate.

tert-Butyl 2,6-dioxo-3-(4-(2-(2-oxopropoxy)ethoxy)phenyl)piperidine-1-carboxylate

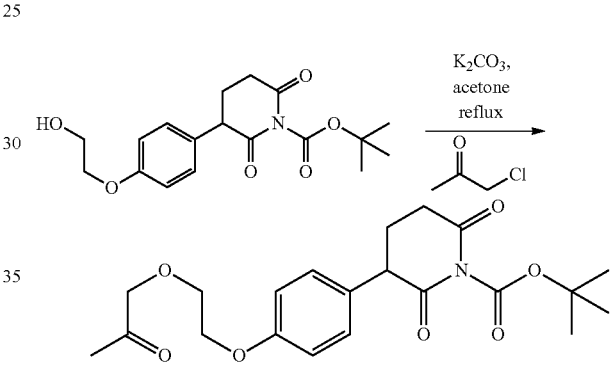

A reaction vessel is charged with tert-butyl 3-(4-(2-hydroxyethoxy)phenyl)-2,6-dioxopiperidine-1-carboxylate (1 equiv.), potassium carbonate (1.2 equiv.) and acetone (0.1 M). Chloroacetone (1.2 equiv.) is then added and the reaction heated at reflux overnight. The reaction is cooled then concentrated and the crude residue partitioned between water and ethyl acetate. The layers are separated and the aqueous layer extracted with ethyl acetate (2×). The combined organic layers are dried over sodium sulfate, filtered and concentrated. The crude residue is purified by column chromatography to provide tert-butyl 2,6-dioxo-3-(4-(2-(2-oxopropoxy)ethoxy)phenyl)piperidine-1-carboxylate. (J. Med. Chem. 2007, 50(18), 4304).

tert-Butyl 3-(4-(2-(2,4-dihydroxy-2-methylbutoxy)ethoxy)phenyl)-2,6-dioxopiperidine-1-carboxylate

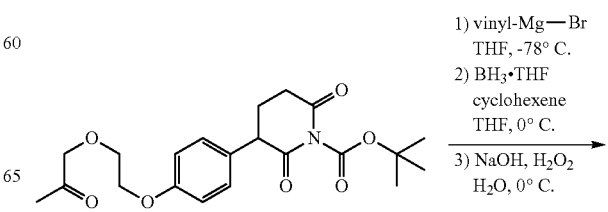

281

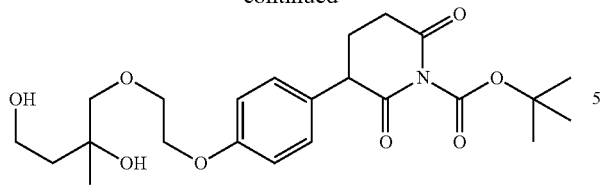

A reaction vessel is charged with tert-butyl 2,6-dioxo-3-(4-(2-(2-oxopropoxy)ethoxy)phenyl)piperidine-1-carboxylate (1 equiv.), and THF (0.2 M), purged with nitrogen and cooled to −78° C. Vinylmagnesium bromide (4 equiv.) is added dropwise and the reaction is warmed to 0° C. over 1 hour. The reaction is quenched with aq. 1% HCl solution and extracted with ethyl acetate (3×). The combined organic layer is washed with brine, dried over sodium sulfate, filtered and concentrated. The crude residue is purified by silica gel chromatography to provide tert-butyl 3-(4-(2-((2-hydroxy-2-methylbut-3-en-1-yl)oxy)ethoxy)phenyl)-2,6-dioxopiperidine-1-carboxylate.

Cyclohexene (4.2 equiv.) was added to a solution of BH$_3$.THF (1 M in THF, 2 equiv.) at 0° C. under argon. After stirring for 1 hour at 0° C., a solution of tert-butyl 3-(4-(2-((2-hydroxy-2-methylbut-3-en-1-yl)oxy)ethoxy)phenyl)-2,6-dioxopiperidine-1-carboxylate (1 equiv.) in THF (0.15 M) was added to the mixture at 0° C. After stirring for 2 hours at 0° C., 3N NaOH (6 equiv.) and 30% H$_2$O$_2$ (33% volume of aq. NaOH solution addition) was added to the mixture. This solution is allowed to mix at ambient temperature for 30 min. The reaction is quenched with saturated aqueous NH$_4$Cl (8 volumes) at 0° C., and the resulting mixture is extracted with ethyl acetate (3×). The combined extracts are washed with brine, dried over sodium sulfate, filtered, and concentrated under reduced pressure. The crude residue is purified by silica gel chromatography to provide tert-butyl 3-(4-(2-(2,4-dihydroxy-2-methylbutoxy)ethoxy)phenyl)-2,6-dioxopiperidine-1-carboxylate. (Org. Lett. 2012, 14(24), 6374).

282 tert-Butyl 3-(4-((7-chloro-4-hydroxy-4-methylhept-2-yn-1-yl)oxy)phenyl)-2,6-dioxopiperidine-1-carboxylate

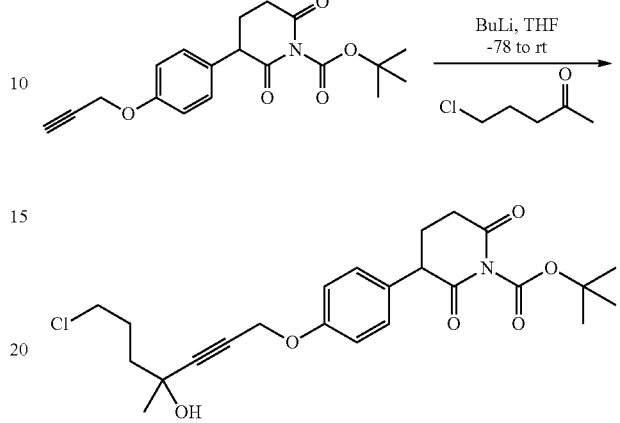

A reaction vessel is charged with tert-butyl 2,6-dioxo-3-(4-(prop-2-yn-1-yloxy)phenyl)piperidine-1-carboxylate (1 equiv.) and the atmosphere cycled between nitrogen and vacuum three times. Anhydrous THF (0.1 M) is added and the reaction cooled to −78° C. Butyllithium (1.05 equiv.) is added and the reaction is mixed for 15 min. 5-Chloro-2-pentanone (1.1 equiv.) in THF (5 volumes) is then added and the reaction is warmed to ambient temperature and quenched with sat. aq. ammonium chloride solution. Ethyl acetate is added and the phases are separated. The aqueous layer is extracted with ethyl acetate (2×). The combined organic layers are washed with brine, dried over sodium sulfate, filtered and concentrated. The crude residue is purified by silica gel chromatography to provide tert-butyl 3-(4-((7-chloro-4-hydroxy-4-methylhept-2-yn-1-yl)oxy)phenyl)-2,6-dioxopiperidine-1-carboxylate.

Examples of Final Compounds d-Bromo

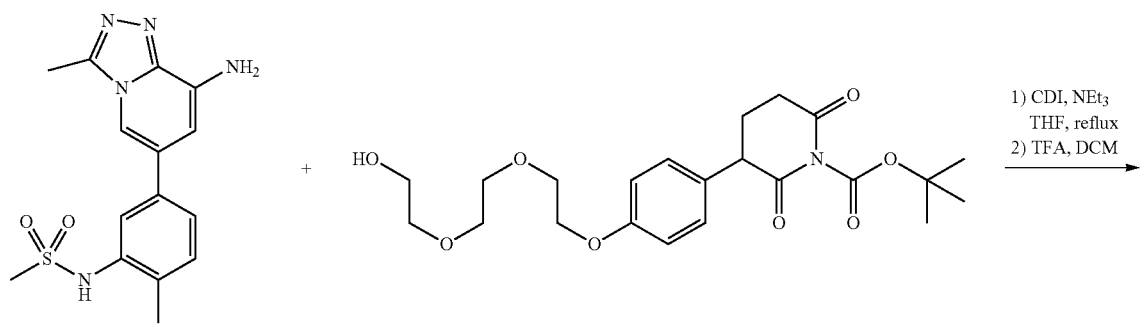

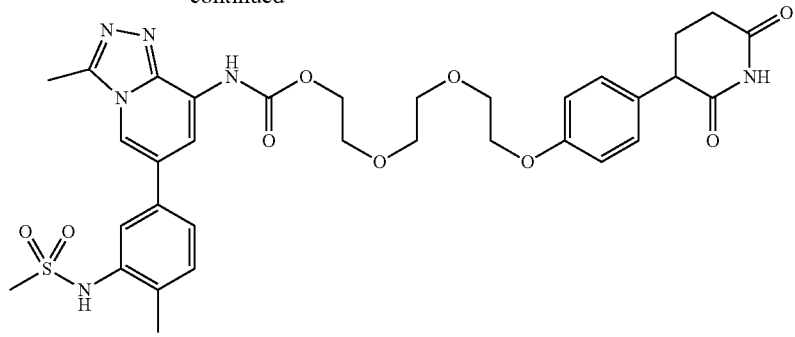

To a reaction vessel is added N-(5-(8-amino-3-methyl-[1,2,4]triazolo[4,3-a]pyridin-6-yl)-2-methylphenyl)methanesulfonamide (1 equiv.), trimethylamine (2 equiv.), THF (0.2 M) and CDI (1.05 equiv.). The reaction is heated at reflux for 2 hours then cooled to ambient temperature. tert-Butyl 3-(4-(2-(2-(2-hydroxyethoxy)ethoxy)ethoxy)phenyl)-2,6-dioxopiperidine-1-carboxylate (1 equiv.) in a minimal amount of THF is added and the reaction mixed overnight. The volatiles are removed by rotary evaporation and the crude residue purified by silica gel chromatography to provide tert-butyl 3-(4-(2-(2-(2-(((3-methyl-6-(4-methyl-3-(methylsulfonamido)phenyl)-[1,2,4]triazolo[4,3-a]pyridin-8-yl)carbamoyl)oxy)ethoxy)ethoxy)-ethoxy)phenyl)-2,6-dioxopiperidine-1-carboxylate.

A reaction vessel is charged with tert-butyl 3-(4-(2-(2-(2-(((3-methyl-6-(4-methyl-3-(methylsulfonamido)phenyl)-[1,2,4]triazolo[4,3-a]pyridin-8-yl)carbamoyl)oxy)ethoxy)-ethoxy)ethoxy)phenyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by reverse phase HPLC to provide d-Bromo.

d-BAZ2A/B

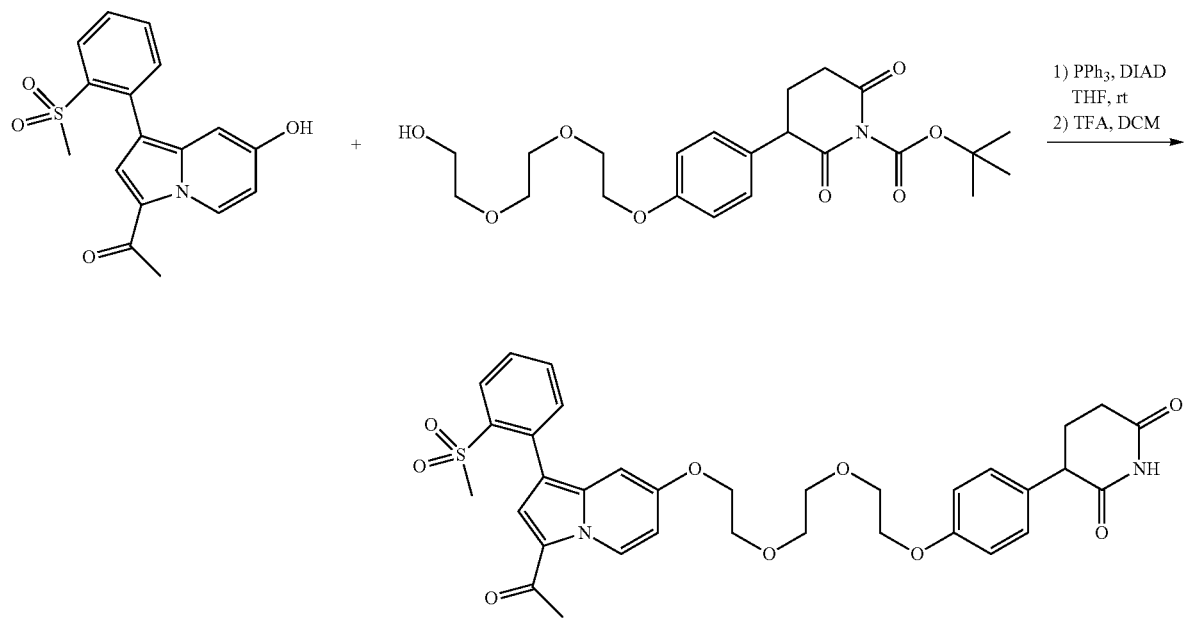

To a flask cooled at 0° C. containing 1-(7-hydroxy-1-(2-(methylsulfonyl)phenyl)indolizin-3-yl)ethan-1-one (1 equiv.), tert-butyl 3-(4-(2-(2-(2-hydroxyethoxy)ethoxy)ethoxy)phenyl)-2,6-dioxopiperidine-1-carboxylate (1 equiv.), triphenylphosphine (2 equiv.) in THF (0.2 M) is added dropwise diisopropyl azodicarboxylate (2 equiv.). The reaction is warmed to ambient temperature and mixed overnight. The volatiles are then removed by rotary evaporation and the crude residue purified by silica gel chromatography to provide tert-butyl 3-(4-(2-(2-(2-((3-acetyl-1-(2-(methylsulfonyl)phenyl)indolizin-7-yl)oxy)ethoxy)ethoxy)ethoxy)phenyl)-2,6-dioxopiperidine-1-carboxylate.

A reaction vessel is charged with tert-butyl 3-(4-(2-(2-(2-((3-acetyl-1-(2-(methylsulfonyl)phenyl)indolizin-7-yl)oxy)ethoxy)ethoxy)ethoxy)phenyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by reverse phase HPLC to provide d-BAZ2A/B.

d-Family VIII Bromo

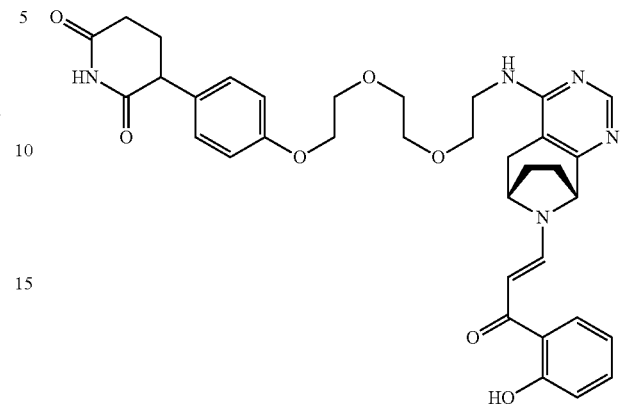

tert-Butyl 2,6-dioxo-3-(4-((3-oxo-1-phenyl-2,7,10-trioxa-4-azadodecan-12-yl)oxy)phenyl)piperidine-1-carboxylate

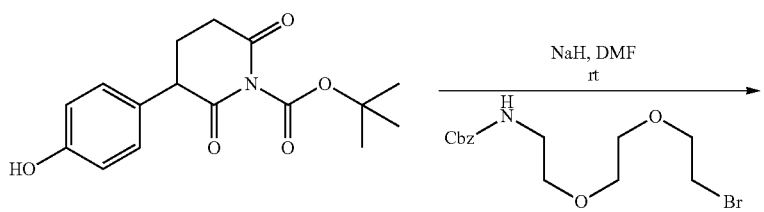

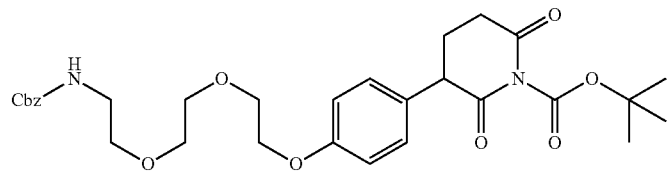

A reaction vessel is charged with tert-butyl 3-(4-hydroxyphenyl)-2,6-dioxopiperidine-1-carboxylate (1 equiv.), DMF (0.3 M) and cooled to 0° C. Sodium hydride (60% dispersion in mineral oil, 1.1 equiv.) is added and the reaction is warmed to ambient temperature and mixed for 1 hour. The reaction is cooled to 0° C. then 8-bromooctan-1-ol (1.1 equiv.) is added and the reaction is mixed at ambient temperature overnight. DMF is removed by rotary evaporation and the residue is deposited onto silica gel and purified by silica gel chromatography to provide tert-butyl 2,6-dioxo-3-(4-((3-oxo-1-phenyl-2,7,10-trioxa-4-azadodecan-12-yl)oxy)phenyl)piperidine-1-carboxylate.

tert-Butyl 2,6-dioxo-3-(4-(2-(2-(2-(((6S,9R)-6,7,8,9-tetrahydro-5H-6,9-epimincyclohepta[d]pyrimidin-4-yl)amino)ethoxy)ethoxy)ethoxy)phenyl)piperidine-1-carboxylate

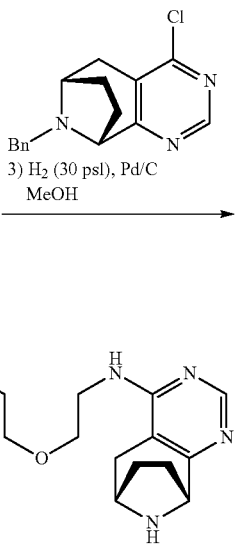

A reaction vessel is charged with tert-butyl 2,6-dioxo-3-(4-((3-oxo-1-phenyl-2,7,10-trioxa-4-azadodecan-12-yl)oxy)phenyl)piperidine-1-carboxylate (1 equiv.) and MeOH (0.2 M). The solution is purged with nitrogen for 5 min (needle in the solution), then Pd/C (10% wt, 10 mol %) is added and the solution is purged for another 2 min. A balloon of hydrogen, fitted with a needle, is added to the flask and the nitrogen atmosphere of the flask is purged with hydrogen. The reaction is mixed at ambient temperature for 2 hours then purged with nitrogen and filtered through a plug of Celite®. The volatiles are removed by rotary evaporation and crude tert-butyl 3-(4-(2-(2-(2-aminoethoxy)ethoxy)ethoxy)phenyl)-2,6-dioxopiperidine-1-carboxylate is used directly in the following reaction.

To a reaction vessel is added tert-butyl 3-(4-(2-(2-(2-aminoethoxy)ethoxy)ethoxy)phenyl)-2,6-dioxopiperidine-1-carboxylat (1 equiv.), (6S,9R)-10-benzyl-4-chloro-6,7,8,9-tetrahydro-5H-6,9-epiminocyclohepta[d]pyrimidine (1 equiv., DOI: 10.1021/acs.jmedchem.6b00012), BretPhos Precatalyst (1 mol %) and sodium tert-butoxide (2 equiv.). The reaction vessel is sealed and the atmosphere cycled between nitrogen and vacuum (3×). Dioxane (0.5 M) is added and the reaction is heated at 100° C. for 5 hours. The reaction is cooled, diluted with ethyl acetate and filtered through a plug of Celite®. The filtrate is concentrated and purified by silica gel chromatography to provide tert-butyl 3-(4-(2-(2-(2-(((6S,9R)-10-benzyl-6,7,8,9-tetrahydro-5H-6,9-epiminocyclohepta[d]pyrimidin-4-yl)amino)ethoxy)ethoxy)ethoxy)phenyl)-2,6-dioxopiperidine-1-carboxylate. (J. Am. Chem. Soc. 2008, 130, 13552).

An appropriate reaction vessel is charged with tert-butyl 3-(4-(2-(2-(2-(((6S,9R)-10-benzyl-6,7,8,9-tetrahydro-5H-6,9-epiminocyclohepta[d]pyrimidin-4-yl)amino)ethoxy)ethoxy)ethoxy)phenyl)-2,6-dioxopiperidine-1-carboxylate (1 equiv.) and MeOH (0.1 M). The solution is purged with nitrogen and Pd/C is added. The solution is purged with nitrogen, the vessel sealed and the atmosphere purged with hydrogen. The reaction is pressurized to 30 psi and mixed for 20 hours at ambient temperature. The hydrogen is purged from the reaction with nitrogen and the solution filtered through a plug of Celite®. The filtrate is concentrated and purified by silica gel chromatography to provide tert-butyl 2,6-dioxo-3-(4-(2-(2-(2-(((6S,9R)-6,7,8,9-tetrahydro-5H-6,9-epiminocyclohepta[d]pyrimidin-4-yl)amino)ethoxy)ethoxy)-phenyl)piperidine-1-carboxylate.

d-Family VIII Bromo

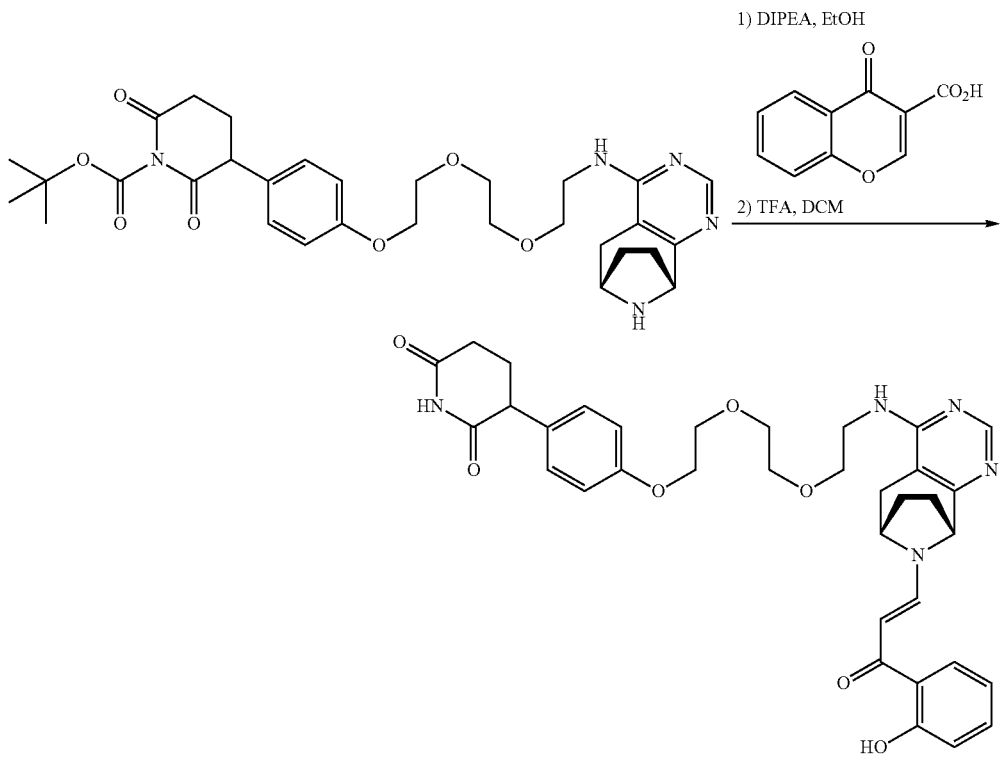

A reaction vessel is charged with tert-butyl 2,6-dioxo-3-(4-(2-(2-(2-(((6S,9R)-6,7,8,9-tetrahydro-5H-6,9-epiminocyclohepta[d]pyrimidin-4-yl)amino)ethoxy)ethoxy)ethoxy)phenyl)piperidine-1-carboxylate (1 equiv.), DIPEA (5 equiv.), chromone-3-carboxylic acid (1.2 equiv.) and ethanol (0.2 M). The reaction is stirred for 4.5 hours at ambient temperature then heated at 50° C. for 5 hours. The reaction is cooled to ambient temperature, concentrated, purified by silica gel chromatography and used directly in the next step.

A reaction vessel is charged with tert-butyl 3-(4-(2-(2-(2-(((6S,9R)-10-((E)-3-(2-hydroxyphenyl)-3-oxoprop-1-en-1-yl)-6,7,8,9-tetrahydro-5H-6,9-epiminocyclohepta[d]pyrimidin-4-yl)amino)ethoxy)ethoxy)ethoxy)phenyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide d-Family VIII Bromo. d-CBP/EP300 tert-Butyl 2,6-dioxo-3-(4-(2-(2-(2-oxoethoxy)ethoxy)ethoxy)phenyl)piperidine-1-carboxylate

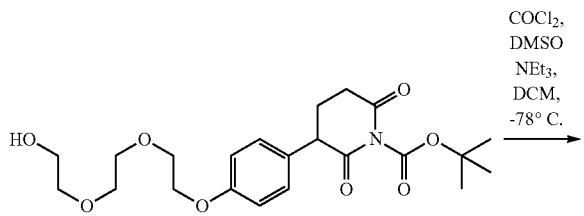

COCl₂, DMSO
NEt₃, DCM,
-78° C.

-continued

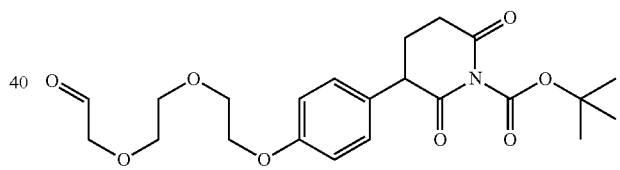

A nitrogen-purged reaction vessel is charged with DMSO (3 equiv.) and DCM (0.1 M). The reaction is cooled to −78° C., oxalyl chloride (2 equiv.) is added dropwise and the reaction is mixed for 0.5 hours. tert-Butyl 3-(4-(2-(2-(2-hydroxyethoxy)ethoxy)ethoxy)phenyl)-2,6-dioxopiperidine-1-carboxylate (1 equiv.) in a minimal amount of DCM is added, the reaction warmed to 0° C. for 5 min then cooled to −78° C. and triethylamine (4 equiv.) is added. The reaction is allowed to warm to ambient temperature slowly overnight and then quenched with water. The biphasic mixture is separated and the aq. layer extracted with DCM (2×). The combined organic layer is washed with brine, dried over sodium sulfate and used directly in the following reaction.

d-CBP/EP300

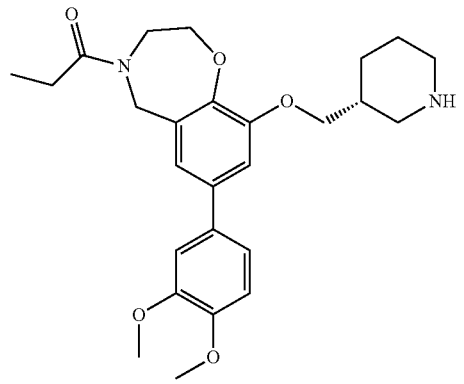

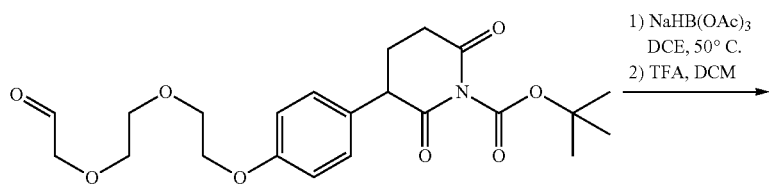

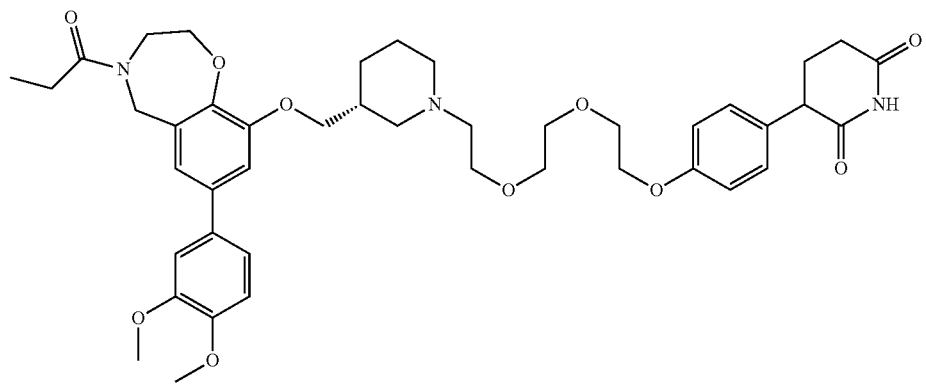

A reaction vessel is charged with tert-butyl 2,6-dioxo-3-(4-(2-(2-(2-oxoethoxy)ethoxy)ethoxy)phenyl)piperidine-1-carboxylate (1 equiv.), (R)-1-(7-(3,4-dimethoxyphenyl)-9-(piperidin-3-ylmethoxy)-2,3-dihydrobenzo[f][1,4]oxazepin-4(5H)-yl)propan-1-one (1 equiv.), sodium triacetoxyborohydride (3 equiv.) and DCE (0.2 M). The reaction is heated at 50° C. for 3 hours then cooled to ambient temperature and concentrated. The crude residue is purified by silica gel chromatography and used directly in the following step.

A reaction vessel is charged with tert-butyl 3-(4-(2-(2-(2-((R)-3-(((7-(3,4-dimethoxyphenyl)-4-propionyl-2,3,4,5-tetrahydrobenzo[f][1,4]oxazepin-9-yl)oxy)methyl)piperidin-1-yl)ethoxy)ethoxy)ethoxy)phenyl)-2,6-dioxopiperidine-1-carboxylate (1 equiv.) and DCM (0.1 M). TFA (20 equiv.) is then added and the reaction is mixed for 1 hour at ambient temperature. The volatiles are removed by rotary evaporation and the residue purified by silica gel chromatography to provide d-CBP/EP300.

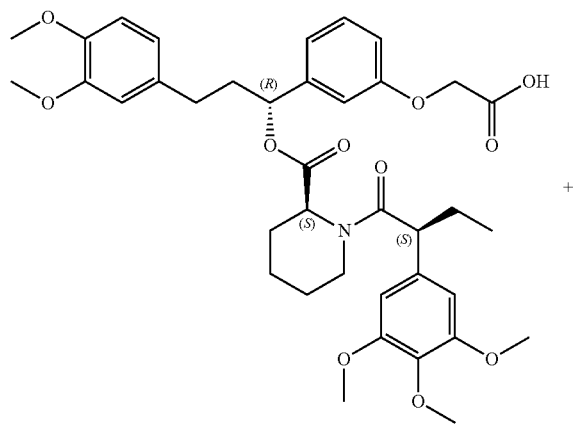

+

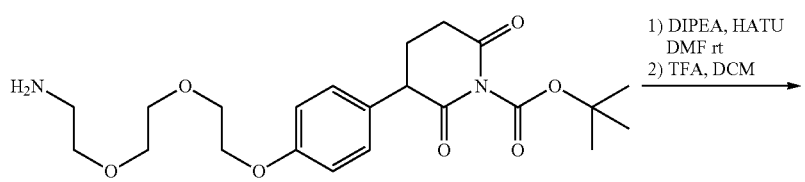

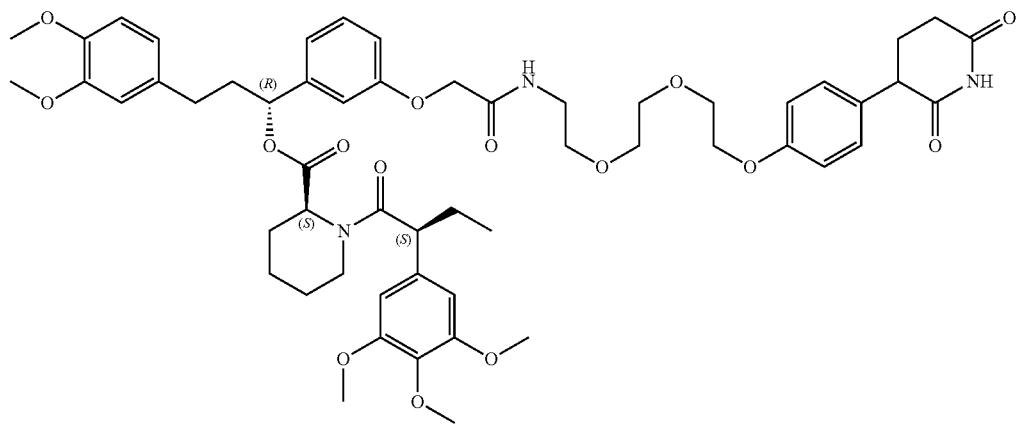

dFKBP* tert-Butyl 3-(4-(2-(2-(2-aminoethoxy)ethoxy)ethoxy)phenyl)-2,6-dioxopiperidine-1-carboxylate (1 equiv.) is added to 2-(3-((R)-3-(3,4-dimethoxyphenyl)-1-(((S)-1-((S)-2-(3,4,5-trimethoxyphenyl)butanoyl) piperidine-2-carbonyl)oxy)propyl)phenoxy)acetic acid (1 equiv.) as a solution in DMF (0.1 M). DIPEA (3 equiv.) and HATU (1 equiv.) are added and the mixture is stirred for 17 hours. The reaction is diluted with EtOAc and washed with saturated sodium bicarbonate, water and brine. The organic layer is then dried over sodium sulfate, filtered and concentrated under reduced pressure. The crude residue is purified by silica gel chromatography to provide tert-butyl 3-(4-(2-(2-(2-(2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetamido)-ethoxy)ethoxy)ethoxy)phenyl)-2,6-dioxopiperidine-1-carboxylate.

A reaction vessel is charged with tert-butyl 3-(4-(2-(2-(2-(2-(3-((R)-3-(3,4-dimethoxyphenyl)-1-(((S)-1-((S)-2-(3,4,5-trimethoxyphenyl)butanoyl)piperidine-2-carbonyl)oxy)propyl)phenoxy)acetamido)ethoxy)ethoxy)ethoxy)phenyl)-2,6-dioxopiperidine-1-carboxylate (1 equiv.) and DCM (0.1 M). TFA (20 equiv.) is added and the reaction is mixed for 1 hour at ambient temperature. The volatiles are removed by rotary evaporation and the residue purified by silica gel chromatography to provide (1R)-3-(3,4-dimethoxyphenyl)-1-(3-(2-((2-(2-(2-(4-(2,6-dioxopiperidin-3-yl)phenoxy)ethoxy)ethyl)amino)-2-oxoethoxy)phenyl)propyl (2S)-1-((S)-2-(3,4,5-trimethoxyphenyl)butanoyl)piperidine-2-carboxylate (d-FKBP*).

Additional Examples
Preparation of Representative Targeting Ligands
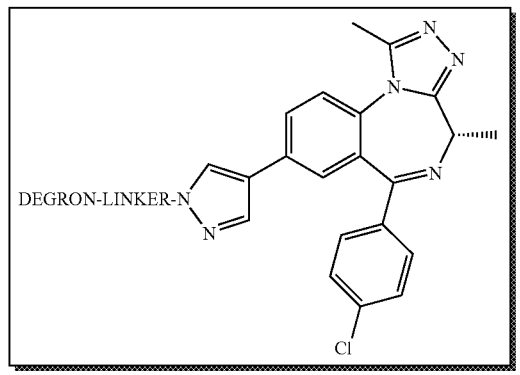
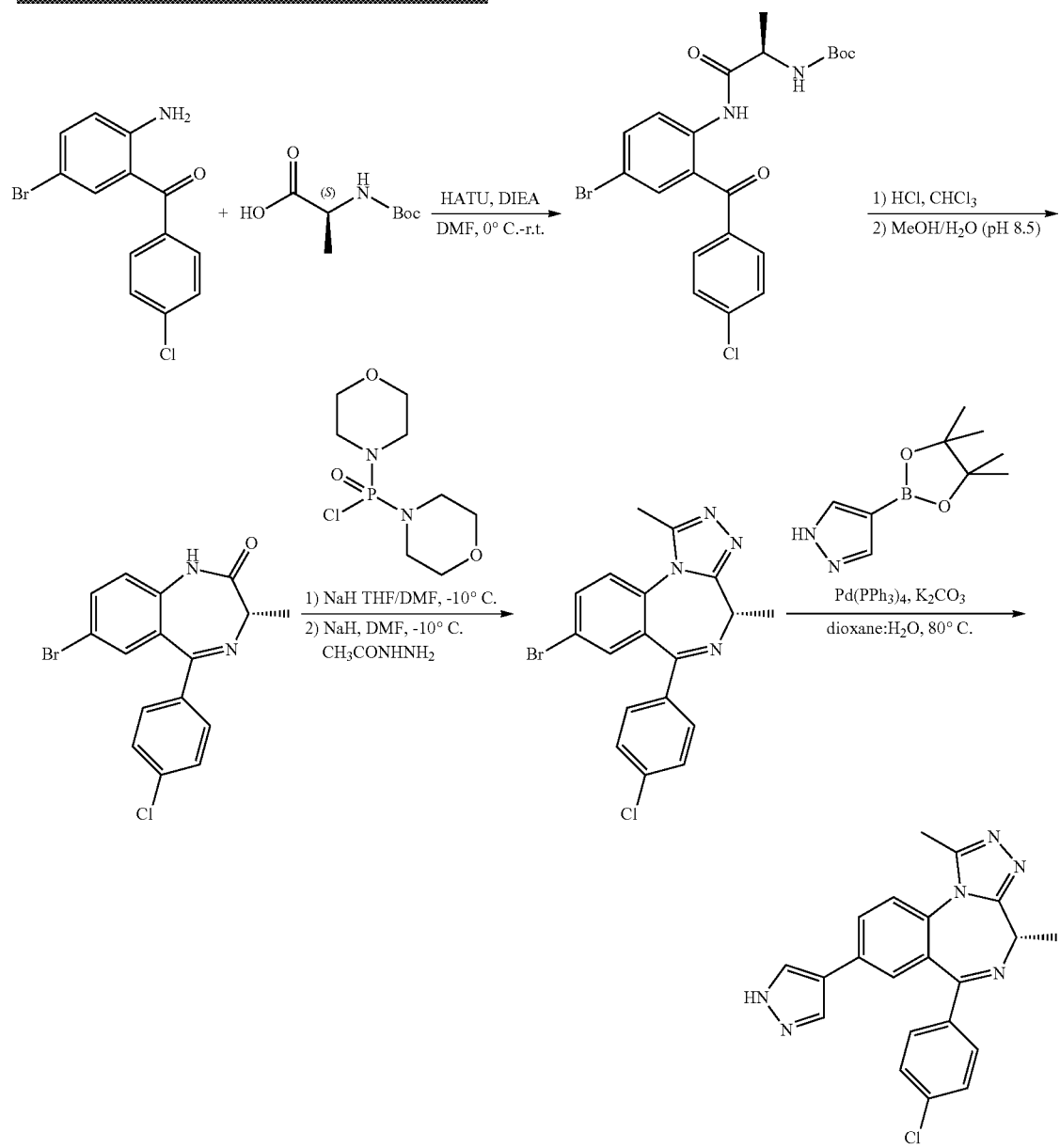

297

(S)-6-(4-Chlorophenyl)-1,4-dimenthyl-8-(1H-pyrazol-4-yl)-4H-benzo[f][1,2,4]triazolo[4,3-a][1,4]diazepine

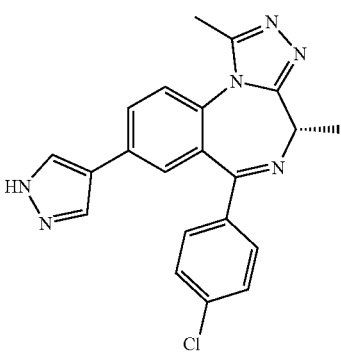 [SMILES: Cc1nnc2n1-c1ccc(-c3cn[nH]c3)cc1C(c1ccc(Cl)cc1)=N[C@H]2C]

tert-Butyl (R)-(1-((4-bromo-2-(4-chlorobenzoyl)phenyl)amino)-1-oxopropan-2-yl)carbamate

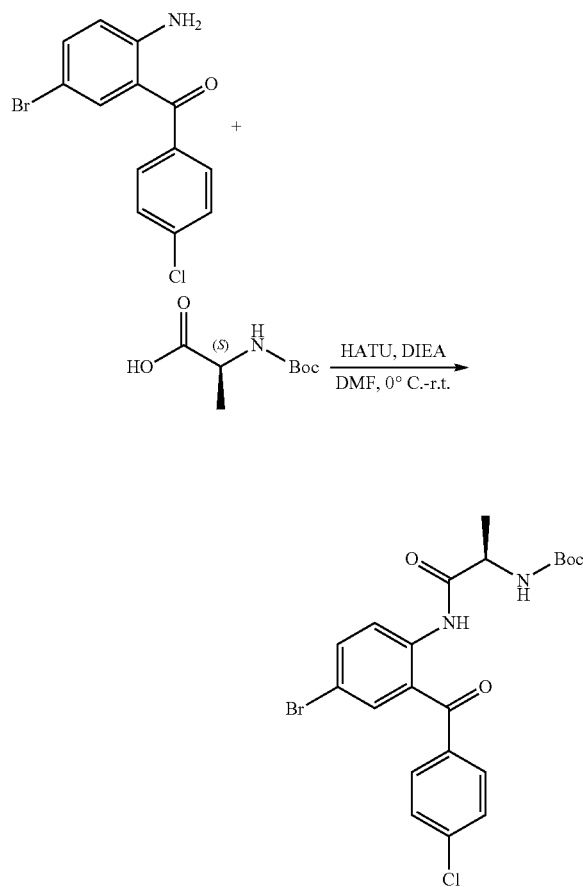

(2-Amino-5-bromophenyl)(4-chlorophenyl)methanone (1.0 equiv.) and Boc-(L)-Ala (1.0 equiv.) are suspended in DMF and cooled to 0° C. DIEA (2.0 equiv.) is added followed by HATU (1.1 equiv.) and the reaction is stirred at

298 reduced temperature for 30 minutes and then warmed to room temperature. When the reaction is judged to be complete it is quenched with aq. ammonium chloride and extracted with ethyl acetate. The combined organic layers are dried over sodium sulfate, concentrated and purified by silica gel chromatography to provide tert-butyl (R)-(1-((4-bromo-2-(4-chlorobenzoyl)phenyl)amino)-1-oxopropan-2-yl)carbamate.

(S)-7-Bromo-5-(4-chlorophenyl)-3-methyl-1,3-dihydro-2H-benzo[e][1,4]diazepin-2-one

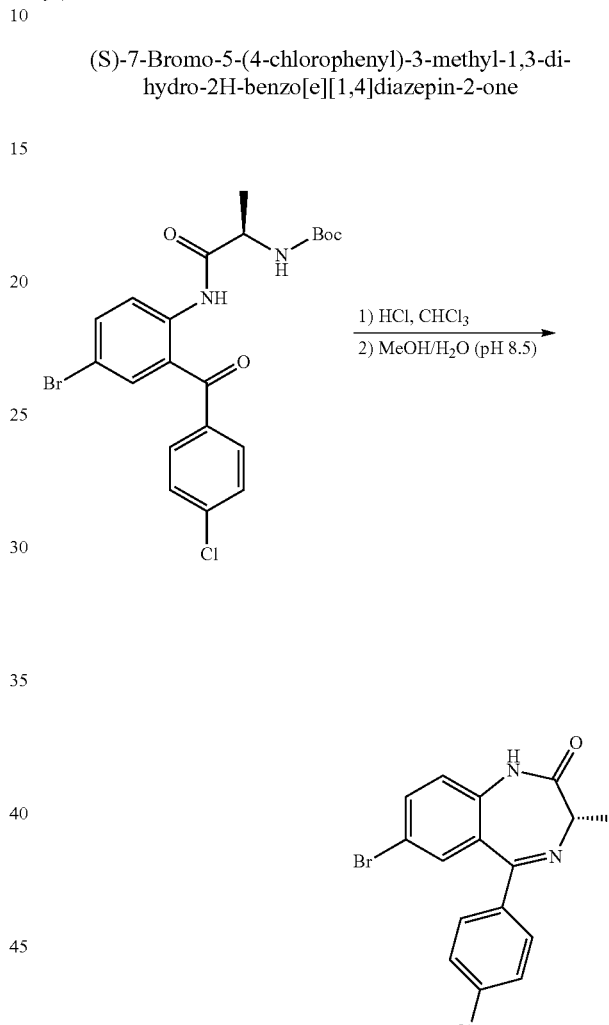

To a stirred solution of Boc protected amine in CHCl₃ at r.t. is slowly added hydrogen chloride gas. After 20 minutes, the addition is stopped and the reaction is stirred at r.t. until deprotection is complete. The reaction mixture is washed with saturated bicarbonate solution (2×) and water (2×). The organic layer is concentrated under reduced pressure. The residue is dissolved in 2:1 methanol:water and the pH is adjusted to 8.5 by the addition of 1N aqueous NaOH. The reaction is then stirred at r.t. until the cyclization is complete. MeOH is then removed under reduced pressure and the solution is extracted with DCM (3×). The combined organic layer is dried over sodium sulfate, concentrated and purified by silica gel chromatography to provide (S)-7-bromo-5-(4-chlorophenyl)-3-methyl-1,3-dihydro-2H-benzo[e][1,4]diazepin-2-one (US 2010 0261711).

299
(S)-8-Bromo-6-(4-chlorophenyl)-1,4-dimethyl-4H-benzo[f][1,2,4]triazolo[4,3-a][1,4]diazepine

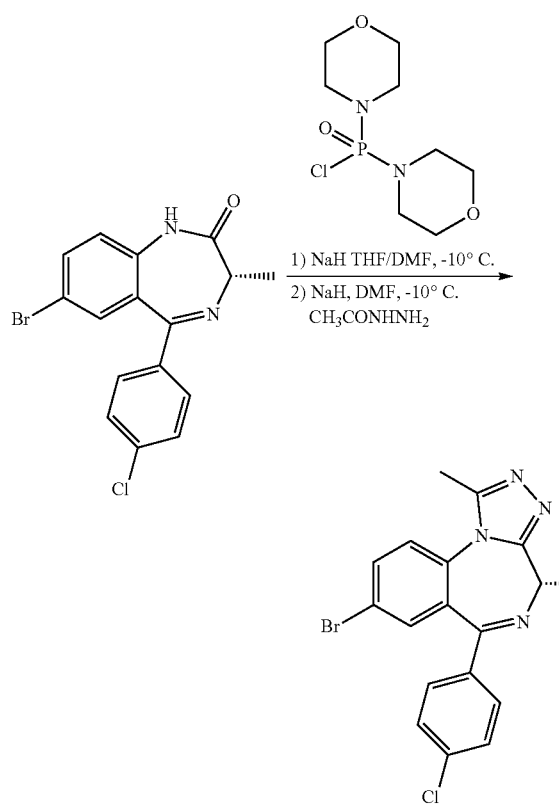

A solution of diazapine (1.0 equiv.) in THF is cooled to −10° C. and NaH (0.85 equiv.) is added in one portion. After an hour at reduced temperature di-4-morphilinylphosphinic chloride (1.07 equiv.) is added at −10° C. and the reaction is allowed to warm to r.t. and stir for 2 hours. To this mixture is added a solution of acetic hydrazide (1.4 equiv.) in n-butanol and stirring is continued for 30 minutes. The solvent is then removed under reduced pressure and the residue dissolved in fresh dry n-butanol before refluxing for the desired time frame. Upon completion of the reaction, the volatiles are removed by rotary evaporation and the residue is partitioned between DCM and brine. The organic layer is dried, concentrated and purified by silica gel chromatography to provide (S)-8-bromo-6-(4-chlorophenyl)-1,4-dimethyl-4H-benzo[f][1,2,4]triazolo[4,3-a][1,4]diazepine (US 2010 0261711).

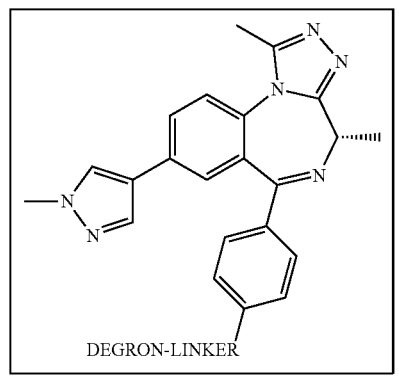

300
(S)-6-(4-Chlorophenyl)-1,4-dimethyl-8-(1H-pyrazol-4-yl)-4H-benzo[f][1,2,4]triazolo[4,3-a][1,4]diazepine

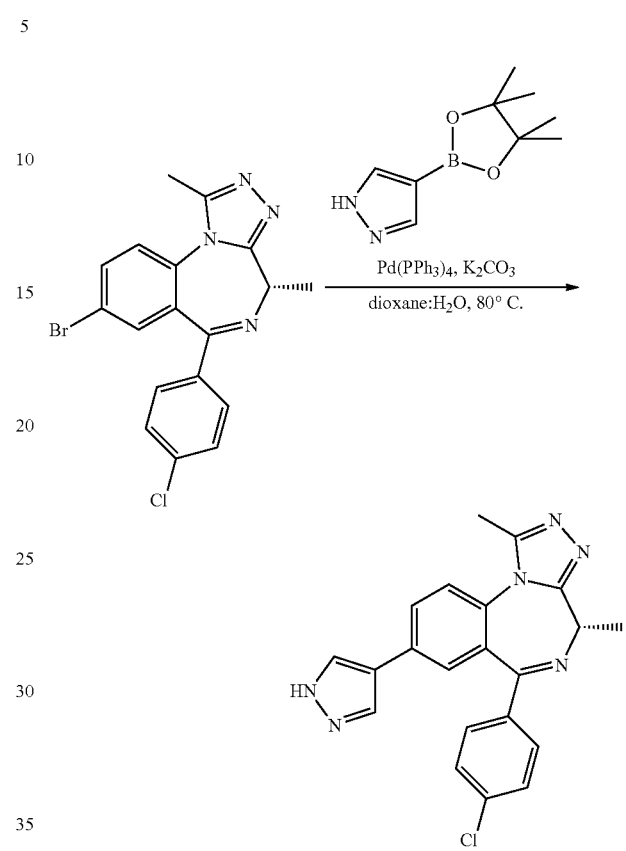

To a vial containing (S)-8-bromo-6-(4-chlorophenyl)-1,4-dimethyl-4H-benzo[f][1,2,4]triazolo[4,3-a][1,4]diazepine (1 equiv.) is added Pd(PPh3)4 (20 mol %), 4-(4,4,5,5-tetramethyl-1,3,2-dioxaborolan-2-yl)-1H-pyrazole (1.5 equiv.), and potassium carbonate (2.5 equiv.). The vial is then evacuated and purged under $N_2$. To the vial is added dioxane:water (2:1). The contents are once again evacuated and purged under $N_2$ and the reaction mixture heated at 80° C. until the SM is converted. The mixture is then cooled to room temperature and filtered over a pad of Celite®. The filter pad is rinsed with EtOAc (3×) and the filtrate is concentrate. The crude material is purified by flash chromatography (WO 2015/156601).

-continued
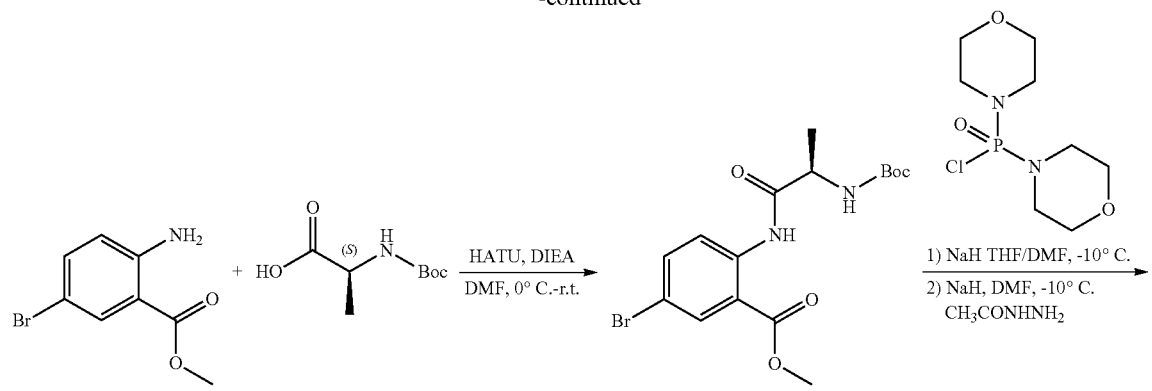
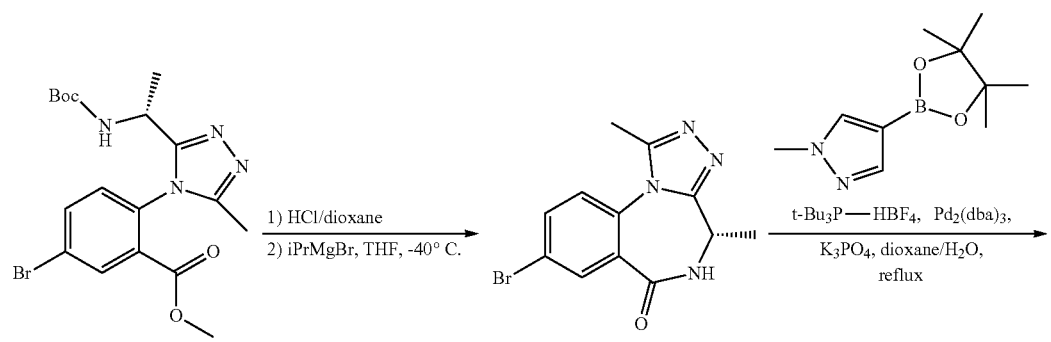
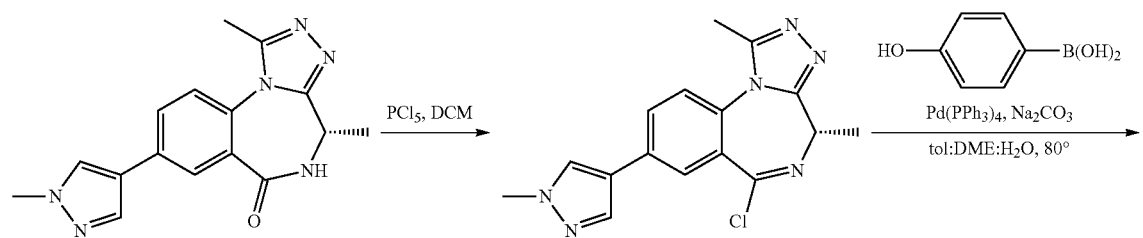
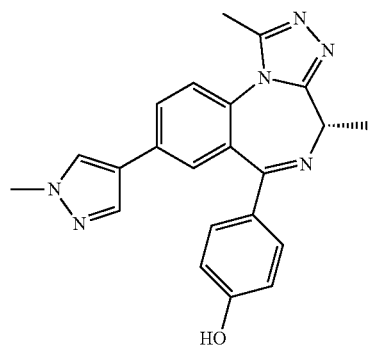

303

(S)-4-(1,4-Dimethyl-8-(1-methyl-1H-pyrazol-4-yl)-
4H-benzo[f][1,2,4]triazolo[4,3-a][1,4]diazepin-6-yl)
phenol

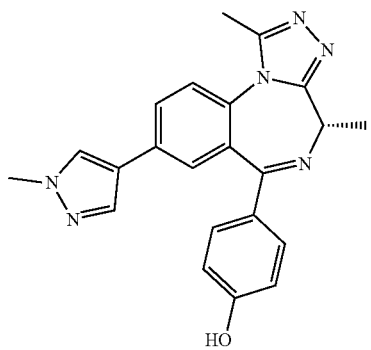

Methyl (R)-5-bromo-2-(2-(tert-butoxycarbonyl)
amino)propanamido)benzoate

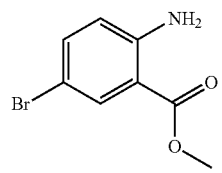

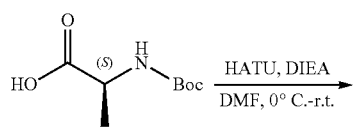

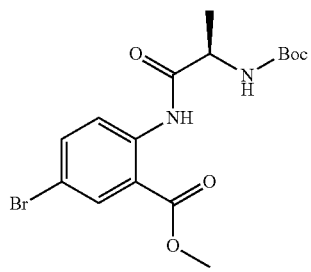

Methyl 2-amino-5-bromobenzoate (1.0 equiv.) and Boc-(L)-Ala (1.0 equiv.) is suspended in DMF and cooled to 0° C. DIEA (2.0 equiv.) is added followed by HATU (1.1 equiv.) and the reaction is stirred at reduced temperature for 30 minutes and then warmed to room temperature. When the reaction is judged to be complete it is quenched with aq. ammonium chloride and extracted with ethyl acetate. The combined organic layers are dried over sodium sulfate, concentrated and purified by silica gel chromatography to provide methyl (R)-5-bromo-2-(2-((tert-butoxycarbonyl)amino)propanamido)benzoate.

304

Methyl 5-bromo-2-(3-((R)-1-((tert-butoxycarbonyl)
amino)ethyl)-5-methyl-4H-1,2,4-triazol-4-yl)benzo-
ate

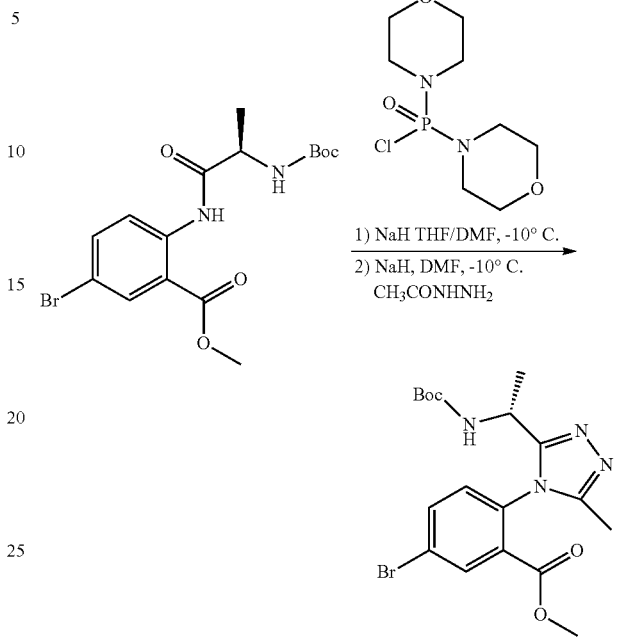

Methyl (R)-5-bromo-2-(2-((tert-butoxycarbonyl)
amino)propanamido)benzoate

A solution of methyl (R)-5-bromo-2-(2-((tert-butoxycarbonyl)amino)propanamido)benzoate (1.0 equiv.) in THF is cooled to −10° C. and NaH (0.85 equiv.) is added in one portion. After an hour at reduced temperature di-4-morpholinylphosphinic chloride (1.07 equiv.) is added at −10° C. and the reaction is allowed to warm to r.t. and stir for 2 hours. To this mixture is added a solution of acetic hydrazide (1.4 equiv.) in n-butanol and stirring is continued for 30 minutes. The solvent is then removed under reduced pressure and the residue dissolved in fresh dry n-butanol before refluxing for the desired time frame. Upon completion of the reaction, the volatiles are removed by rotary evaporation and the residue is partitioned between DCM and brine. The organic layer is dried, concentrated and purified by silica gel chromatography to provide methyl (R)-5-bromo-2-(2-((tert-butoxycarbonyl)amino)propanamido)benzoate (BMCL 2015, 25, 1842-48).

(S)-8-Bromo-1,4-dimethyl-4,5-dihydro-6H-benzo[f]
[1,2,4]triazolo[4,3-a][1,4]diazepin-6-one

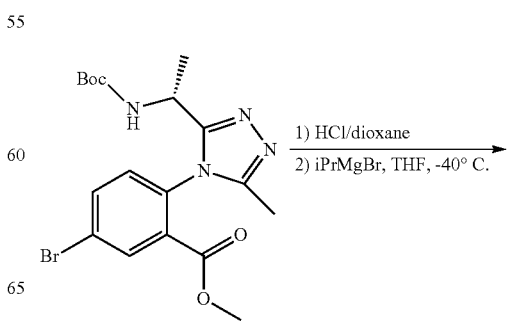

-continued

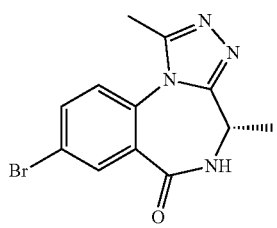

Methyl (R)-5-bromo-2-(2-((tert-butoxycarbonyl)amino)propanamido)benzoate is dissolved in DCM and cooled to 0° C. 4M HCl in dioxane is added and the reaction is warmed to r.t. When deprotection is complete, the reaction is concentrated and then azeotroped from toluene (2×). The crude amine salt is then dissolved in THF, cooled to −40° C., at which time iPrMgBr solution is added dropwise (2.0 equiv.) and the reaction is stirred at reduced temp until complete conversion (BMCL 2015, 25, 1842-48).

(S)-1,4-Dimethyl-8-(1-methyl-1H-pyrazol-4-yl)-4,5-dihydro-6H-benzo[f][1,2,4]triazolo[4,3-a][1,4]diazepin-6-one

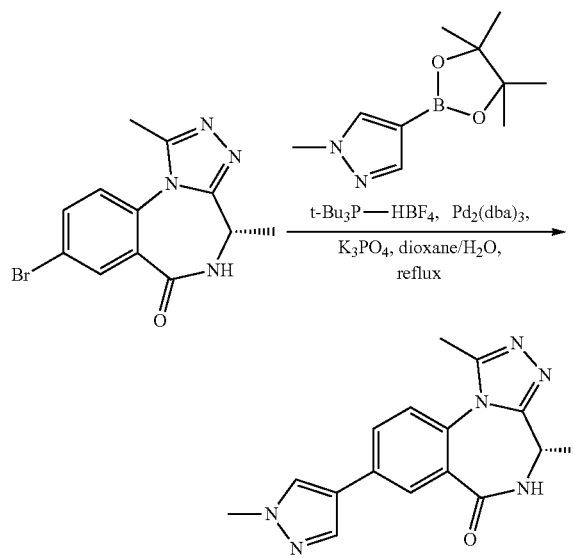

To a vial containing (S)-8-bromo-1,4-dimethyl-4,5-dihydro-6H-benzo[f][1,2,4]triazolo[4,3-a][1,4]diazepin-6-one (1 equiv.) is added Pd$_2$(dba)$_3$ (10 mol %), tri-tert-butylphosphonium tetrafluoroborate (20 mol %), 1-methyl-4-(4,4,5,5-tetramethyl-1,3,2-dioxaborolan-2-yl)-1H-pyrazole (1.5 equiv.), and potassium phosphate tribasic, monohydrate (2.5 equiv.). The vial is then evacuated and purged under N$_2$. To the vial is added 20:1 ratio by volume of dioxane:water. The contents are once again evacuated and purged under N$_2$ (g) and the reaction mixture is heated at 100° C. until the SM is converted. The mixture is then cooled to room temperature and filtered over a pad of Celite®. The filter pad is rinsed with EtOAc (3×) and the filtrate is concentrate. The crude material is purified by flash chromatography.

(S)-6-Chloro-1,4-dimethyl-8-(1-methyl-1H-pyrazol-4-yl)-4H-benzo[f][1,2,4]triazolo[4,3-a][1,4]diazepine

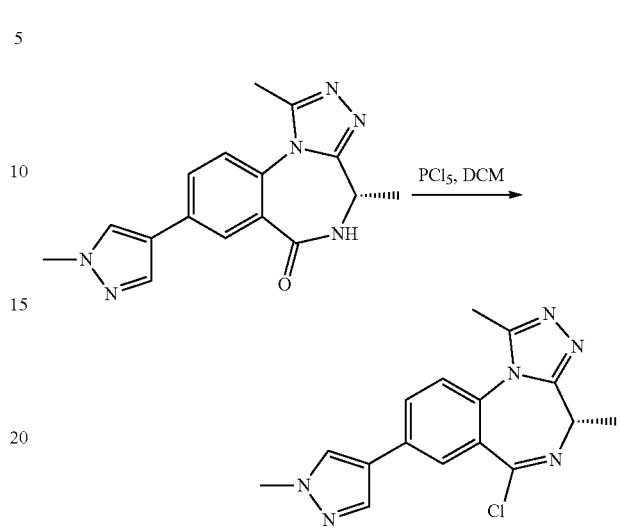

(S)-1,4-dimethyl-8-(1-methyl-1H-pyrazol-4-yl)-4,5-dihydro-6H-benzo[f][1,2,4]triazolo[4,3-a][1,4]diazepin-6-one (1.0 equiv.) is dissolved in DCM and PCl$_5$ (1.7 equiv.) is added in one-portion. After conversion of SM, 2M sodium carbonate is added. The biphasic mixture is subsequently extracted with EtOAc (4×). The combined organic layers are dried over sodium sulfate and concentrated to dryness. The resultant residue is purified by flash chromatography.

(S)-4-(1,4-Dimethyl-8-(1-methyl-1H-pyrazol-4-yl)-4H-benzo[f][1,2,4]triazolo[4,3-a][1,4]diazepin-6-yl)phenol

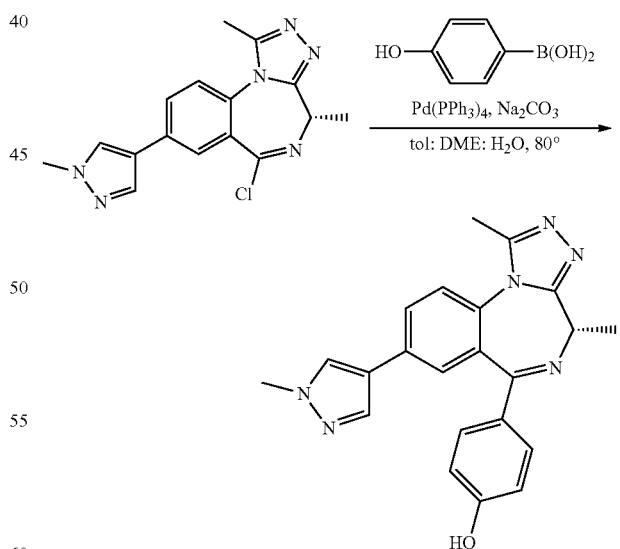

To a vial containing ((S)-6-chloro-1,4-dimethyl-8-(1-methyl-1H-pyrazol-4-yl)-4H-benzo[f][1,2,4]triazolo[4,3-a][1,4]diazepine (1 equiv.) is added Pd(PPh$_3$)$_4$ (20 mol %), 4-hydroxy-phenyl boronic acid (1.5 equiv.), and sodium carbonate (2.5 equiv.). The vial is then evacuated and purged under N$_2$. To the vial is added tol:DME:water (1:1:5). The contents are once again evacuated and purged under N₂ and the reaction mixture is heated at 80° C. until the SM is converted. The mixture is then cooled to room temperature and filtered over a pad of Celite®. The filter pad is rinsed with EtOAc (3×) and the filtrate is concentrate. The crude material is purified by flash chromatography.
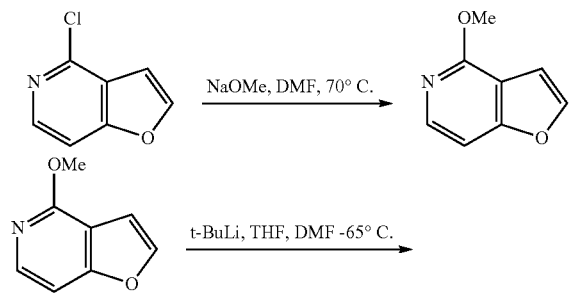
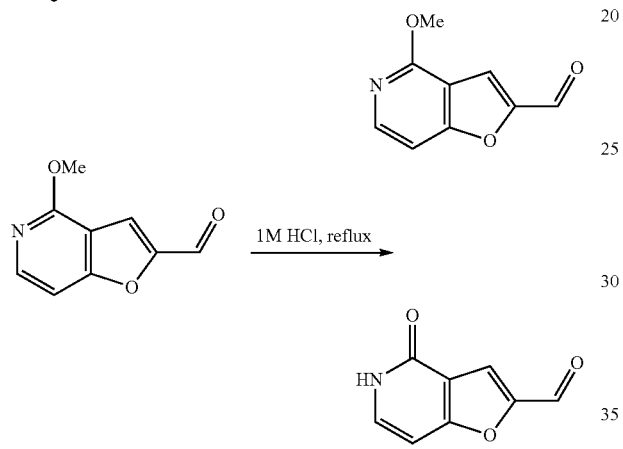
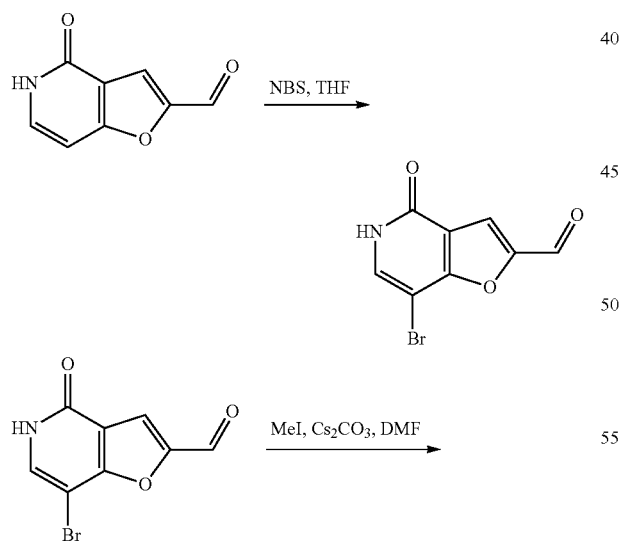
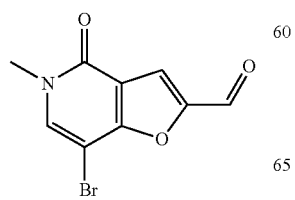
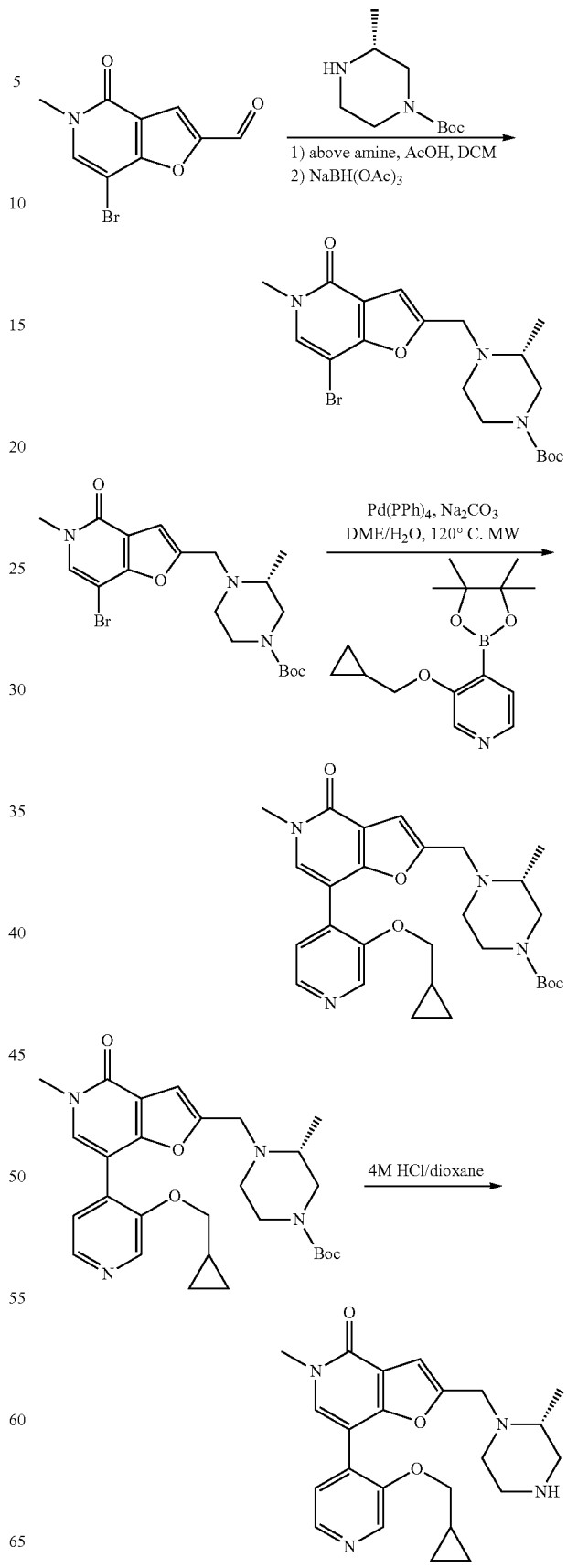

309
-continued
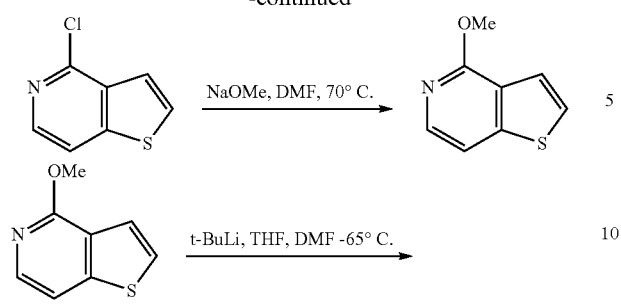
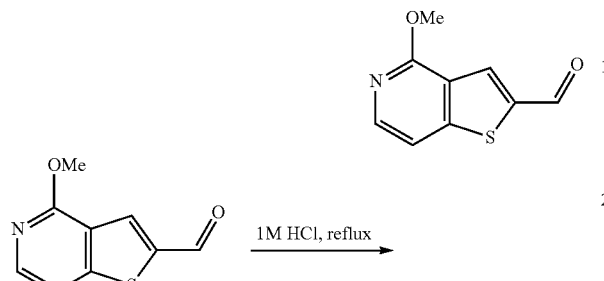
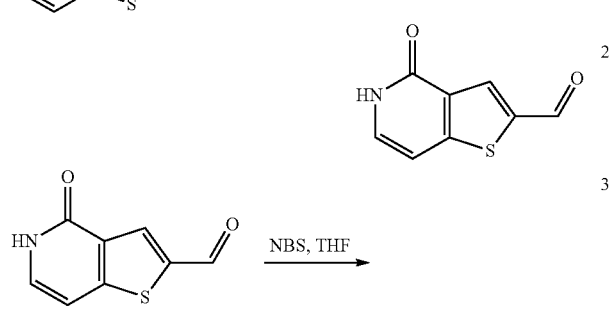
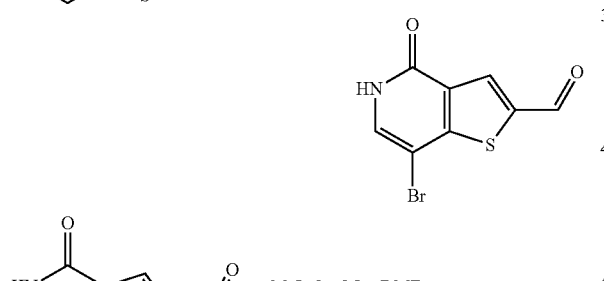
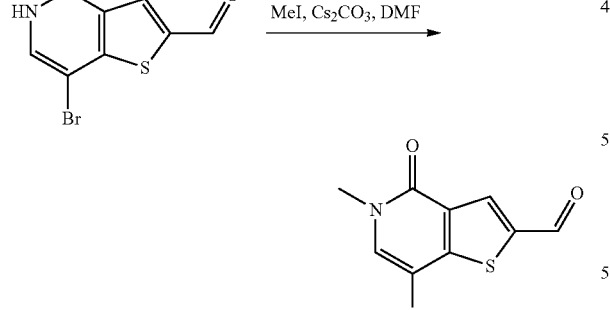
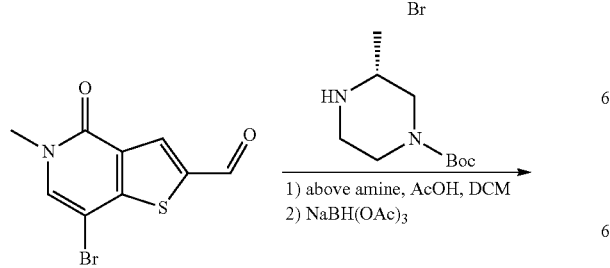
310
-continued
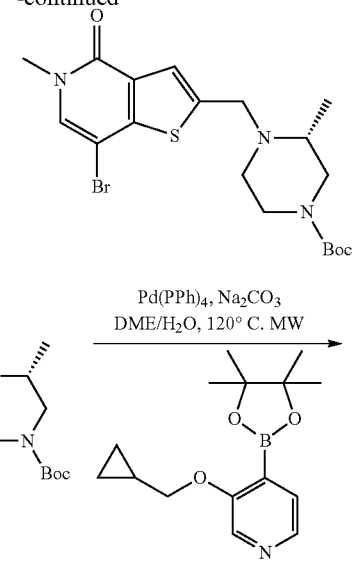
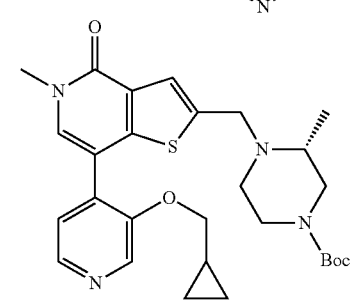
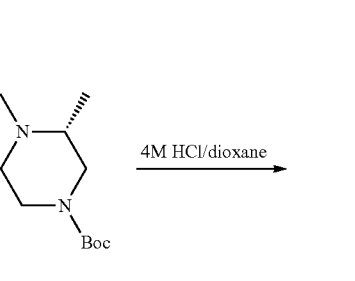
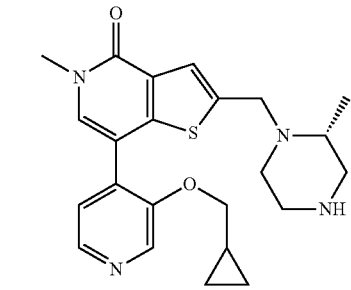
Synthesis of Selected Glutarimides
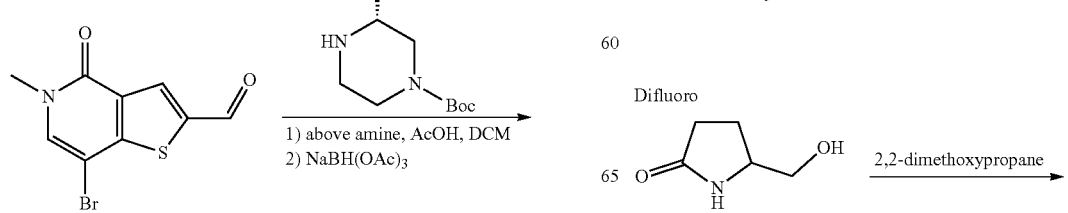

311
-continued
312
-continued
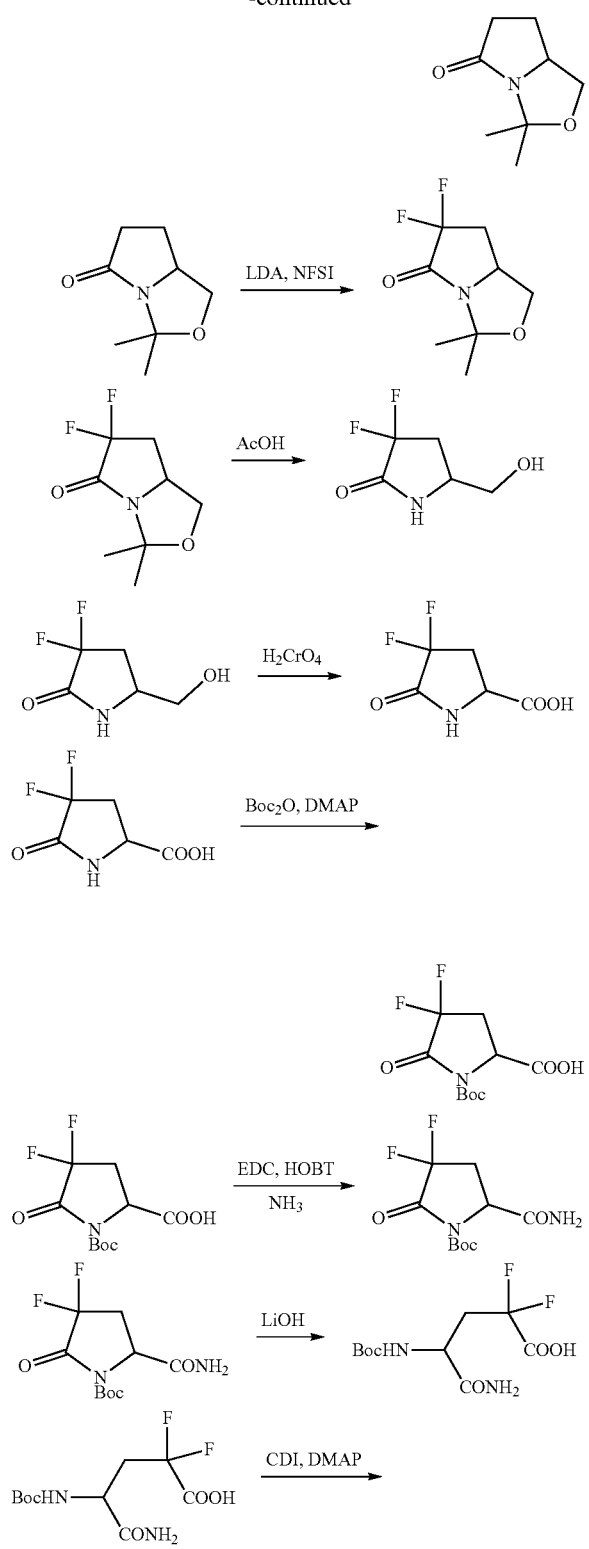
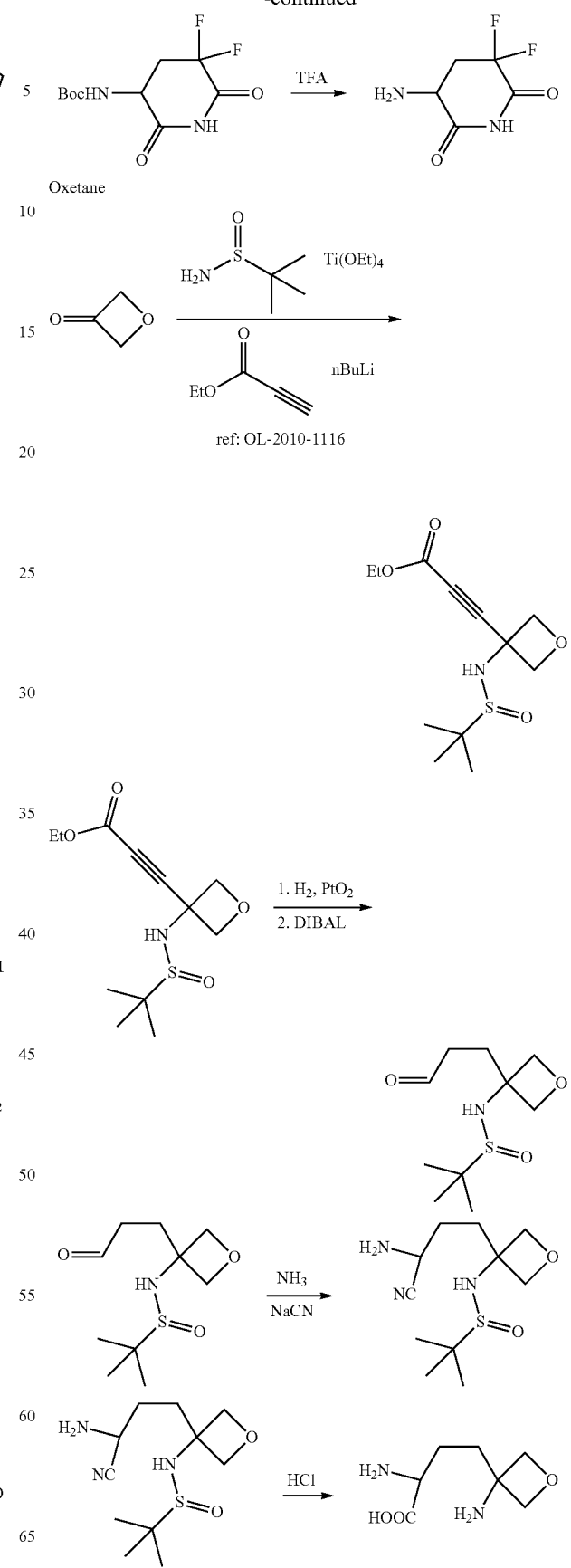

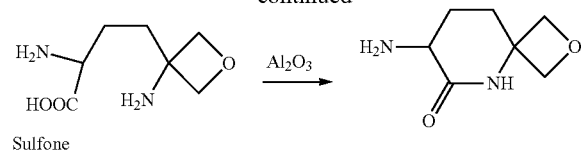
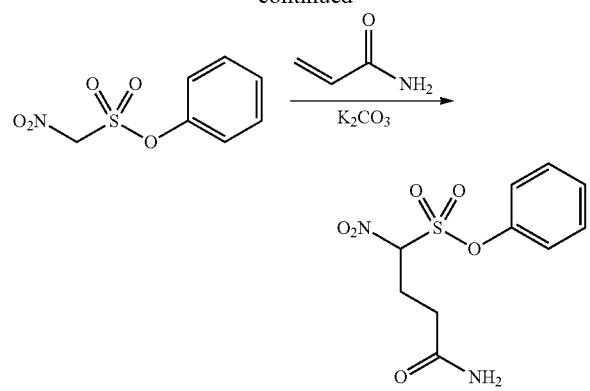
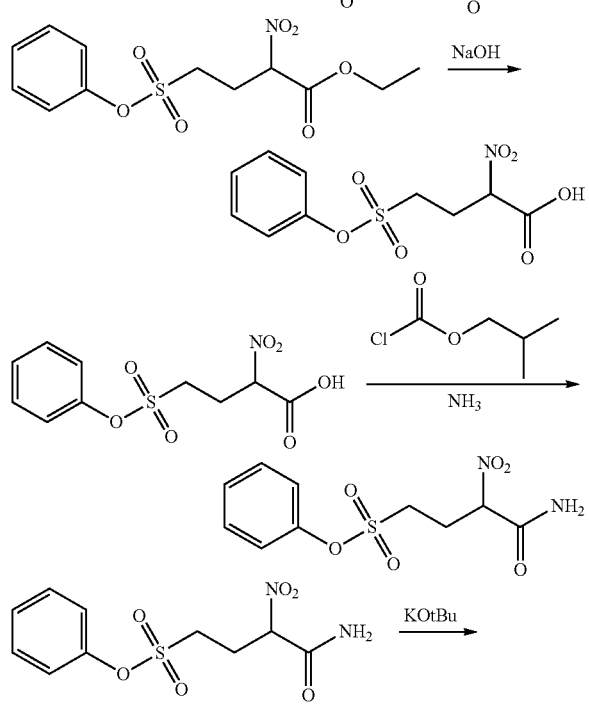
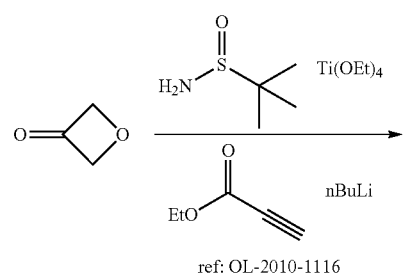

315
-continued

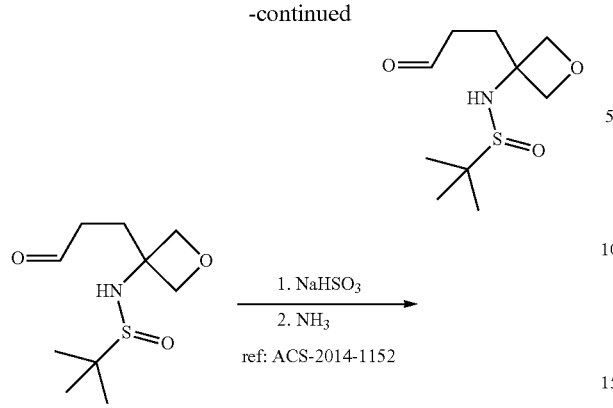

ref: ACS-2014-1152

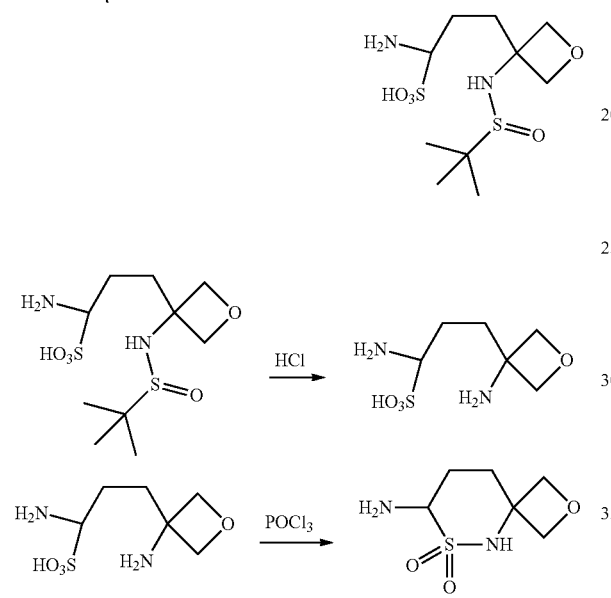

Cyclopropyl

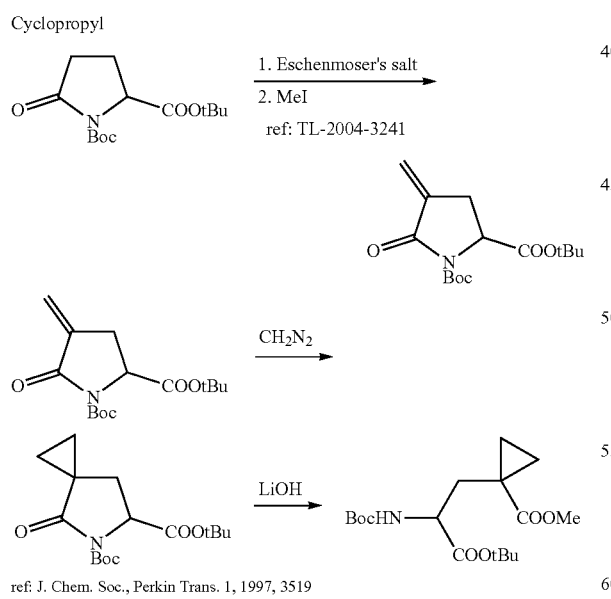

ref: J. Chem. Soc., Perkin Trans. 1, 1997, 3519

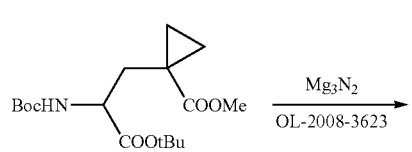

316
-continued

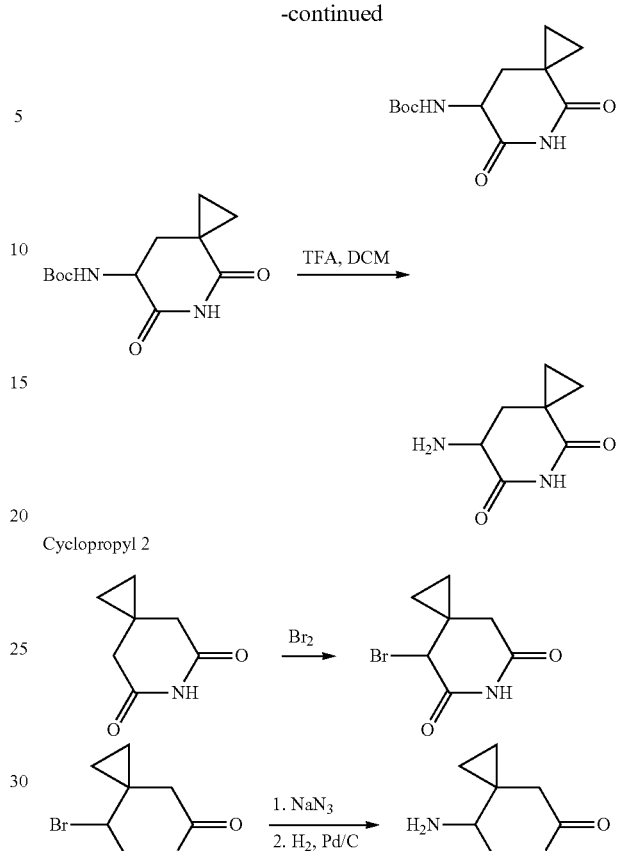

Cyclopropyl 2

C-Linked Experimentals

III. Representative Synthesis of Compounds

Scheme 1
Synthesis of 1-Phenyl-
3-azabicyclo[3.1.0]hexane-2,4-dione (Compound 1)

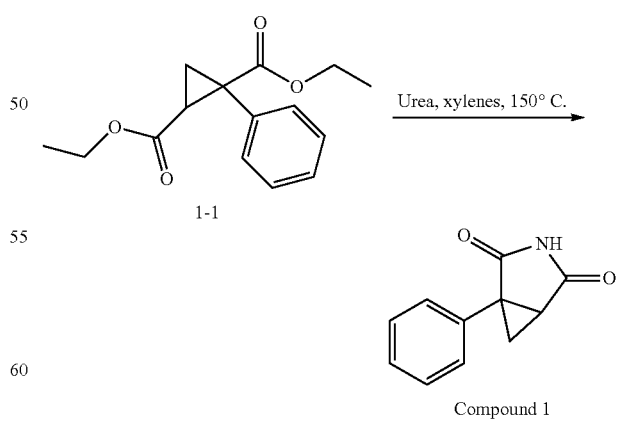

Compound 1

Diethyl 1-phenylcyclopropane-1,2-dicarboxylate (1-1) (200 mg, 0.76 mmol) (prepared according to Epstein, J. W. et al. *J. Med. Chem.* 1981, 24, 481-490.) and urea (91.2 mg, 1.52 mmol) were combined in xylene (10 mL) and stirred at 150° C. for 4 h. The solution was concentrated under high vacuum. The residue was diluted with MTBE (25 mL). The solution was washed with aqueous saturated sodium bicarbonate (10 mL×2), dried ($Na_2SO_4$), and concentrated. The residue was purified by chromatography using EtOAc: hexanes=0:1 to 1:2 to give 1-phenyl-3-azabicyclo[3.1.0]hexane-2,4-dione (Compound 1) (84 mg, 59% yield). $^1$H NMR (400 MHz, Chloroform-d) δ 7.43-7.31 (m, 5H), 2.71 (ddd, J=8.4, 3.6, 1.8 Hz, 1H), 1.99 (dd, J=4.7, 3.6 Hz, 1H), 1.88 (dd, J=8.4, 4.7 Hz, 1H). MS (observed) 188.1

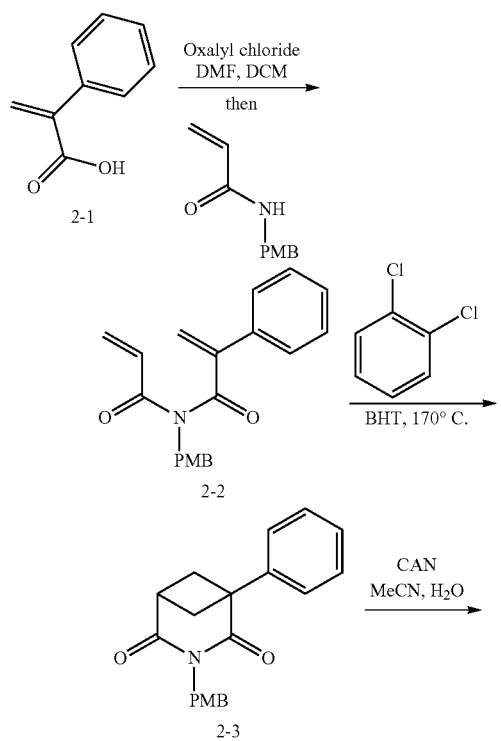

Synthesis of 3-(4-Methoxybenzyl)-1-phenyl-3-azabicyclo[3.1.1]heptane-2,4-dione (2-2)

To a solution of 2-phenylacrylic acid (2-1) (3.7 g, 24.9 mmol) in DMF (77 uL, 1.0 mmol) and DCM (40 ml) was added oxalyl chloride (2.55 mL, 29.8 mmol) over 60 min at room temperature. The mixture was stirred for 4 h, concentrated under reduced pressure, and dried under high vacuum. The residue was dissolved in DCM (20 mL) and slowly added into a solution of N-(4-methoxybenzyl)acrylamide (3.80 g, 19.9 mmol) and $Et_3N$ (7.62 mL, 54.7 mmol) in DCM (20 mL) at −5° C. The mixture was stirred at 0° C. for 1 h and then 35° C. for 3 h. The solution was cooled to room temperature, washed with aqueous saturated sodium bicarbonate (40 ml×3), dried ($Na_2SO_4$), and concentrated. The residue was purified by chromatography using EtOAc: hexanes=0:1 to 15:85 to give 3-(4-methoxybenzyl)-1-phenyl-3-azabicyclo[3.1.1]heptane-2,4-dione (2-2) 2.84 g in 35.5% yield. MS (observed) 322.2

Synthesis of 3-(4-Methoxybenzyl)-1-phenyl-3-azabicyclo[3.1.1]heptane-2,4-dione (2-3)

3-(4-Methoxybenzyl)-1-phenyl-3-azabicyclo[3.1.1]heptane-2,4-dione (2-2) (3.04 g, 9.45 mmol) and BHT (41.6 mg, 0.19 mmol) were combined in 1,2-dichlorobenzene (60 mL) and stirred at 170° C. for 4 h. The solution was concentrated. The residue was purified by chromatography using EtOAc: hexanes=0:1 to 15:85 to 35:65 to give 3-(4-methoxybenzyl)-1-phenyl-3-azabicyclo[3.1.1]heptane-2,4-dione (2-3) 2.21 g in 72.9% yield. MS (observed) 322.3

Synthesis of 1-Phenyl-3-azabicyclo[3.1.1]heptane-2,4-dione (Compound 2)

To 3-(4-methoxybenzyl)-1-phenyl-3-azabicyclo[3.1.1]heptane-2,4-dione (597 mg, 1.86 mmol) in MeCN (4.5 mL) was added CAN (1.01 g, 1.86 mmol) and water (3 ml) at 0° C. The mixture was slowly warmed up to room temperature, stirred for 4 h at room temperature, and concentrated under reduced pressure. MTBE (40 mL) was added. The solution was washed with aqueous saturated ammonium chloride (10 ml×2), dried ($Na_2SO_4$), and concentrated. The residue was purified by chromatography using EtOAc:hexanes=0:1 to 1:1 to give the crude product, which was further purified by Prep-HPLC to give provide 1-phenyl-3-azabicyclo[3.1.1]heptane-2,4-dione (Compound 2), 21.9 mg in 5.9% yield. $^1$H NMR (400 MHz, Chloroform-d) δ 7.76-7.27 (m, 4H), 7.10 (d, J=7.5 Hz, 2H), 3.19 (dt, J=7.1, 3.5 Hz, 1H), 2.80 (ddt, J=14.2, 7.1, 4.2 Hz, 4H). MS (observed) 202.1

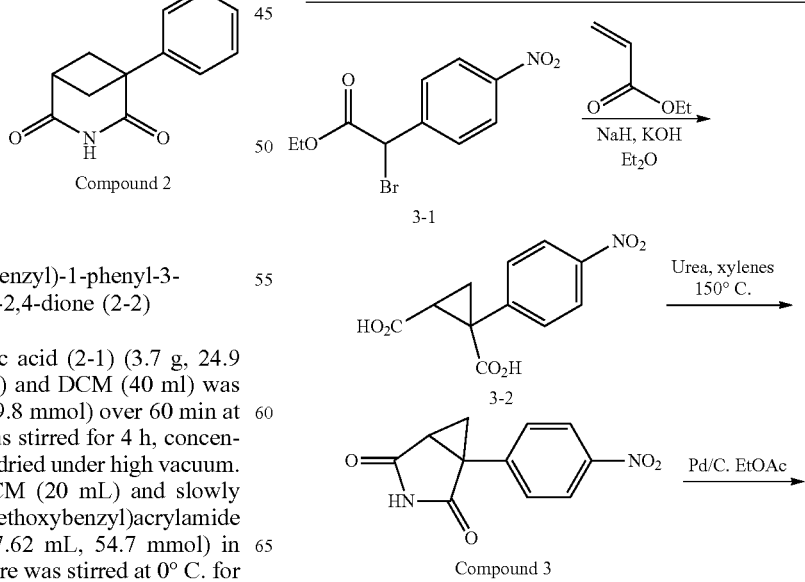

-continued

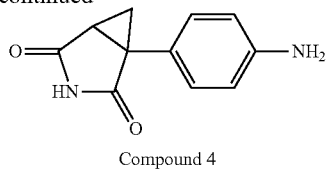

Compound 4

Synthesis of 1-(4-Nitrophenyl)cyclopropane-1,2-dicarboxylic acid (3-2)

EtOH (0.03 mL) was added to a solution of NaH (152 mg, 3.81 mmol, 60% wt) in Et$_2$O (10 mL) at room temperature. A solution of ethyl 2-bromo-2-(4-nitrophenyl)acetate (3-1) (1 g, 3.47 mmol), ethyl acrylate (0.74 mL, 6.94 mmol), and EtOH (0.20 mL) in Et$_2$O (5 mL) was added over 2 h. The resulting solution was stirred at RT overnight and then quenched with saturated ammonium chloride (2 mL). MTBE (50 mL) was added. The mixture was washed with saturated ammonium chloride (10 mL×2) and concentrated. The residue was purified by chromatography using EtOAc:hexanes=0:1 to 15:85 to give the diester (556 mg) in 52% yield. To the Diester (556 mg, 1.8 mmol) in EtOH/Water (1:1, 10 mL) was added KOH (302 mg, 5.4 mmol) at room temperature. The mixture was stirred at 70° C. overnight. The solution was concentrated. The residue was diluted with hydrochloric acid (2 N, 18 mL). After extraction with EtOAc (20 mL×3), the organic solution was dried (Na$_2$SO$_4$) and concentrated to provide 1-(4-nitrophenyl)cyclopropane-1,2-dicarboxylic acid (3-2), which was used directly in the following reaction. MS (observed) 252.1

Synthesis of 1-(4-Nitrophenyl)-3-azabicyclo[3.1.0]hexane-2,4-dione (Compound 3)

To a rbf containing 1-(4-nitrophenyl)cyclopropane-1,2-dicarboxylic acid 3-2 (452 mg, 1.8 mmol) and urea (216 mg, 3.6 mmol) was added xylene (12 ml). The mixture was stirred at 150° C. for 4 h and concentrated under high vacuum. The residue was diluted with MTBE (25 mL). The resulting solution was washed with aqueous saturated sodium bicarbonate (10 mL×2), dried (Na$_2$SO$_4$), and concentrated. The residue was purified by chromatography using EtOAc:hexanes=0:1 to 1:2 to give 1-(4-nitrophenyl)-3-azabicyclo[3.1.0]hexane-2,4-dione (Compound 3) 304 mg in 73% yield. $^1$H NMR (400 MHz, DMSO-d6) δ 10.85 (s, 1H), 8.22 (d, J=8.8 Hz, 2H), 7.78 (dd, J=171.1, 8.8 Hz, 2H), 3.06 (dd, J=8.4, 3.9 Hz, 1H), 2.16 (t, J=4.3 Hz, 1H), 2.00 (dd, J=8.4, 4.7 Hz, 1H). MS (observed) 233.1

Synthesis of 1-(4-Aminophenyl)-3-azabicyclo[3.1.0]hexane-2,4-dione (Compound 4)

To a rbf containing 1-(4-nitrophenyl)-3-azabicyclo[3.1.0]hexane-2,4-dione (Compound 3) (50 mg, 0.22 mmol) and Pd/C (13 mg, 0.01 mmol, 10% wt) was added EtOAc (3 mL). The mixture was purged with hydrogen for 3 times and stirred under hydrogen for 3 hr. Pd/C was filtered with celite, and the solution was concentrated. The residue was purified by chromatography using EtOAc:hexanes=0:1 to 4:1 to give crude product 30 mg with some impurities. The residue was purified by Prep-HPLC to give 1-(4-aminophenyl)-3-azabicyclo[3.1.0]hexane-2,4-dione (Compound 4) as a TFA salt 25.9 mg in 60% yield. $^1$H NMR (400 MHz, DMSO-d6) δ 10.64 (s, 1H), 7.38-7.29 (m, 2H), 7.01-6.88 (m, 2H), 2.75 (ddd, J=8.3, 3.7, 1.7 Hz, 1H), 1.95 (t, J=4.2 Hz, 1H), 1.82 (dd, J=8.3, 4.2 Hz, 1H). MS (observed) 203.2

Scheme 4
Synthesis of 2-(Dimethylamino)-N-(4-(2,4-dioxo-3-azabicyclo[3.1.0]hexan-1-yl)phenyl) acetamide (Compound 5)

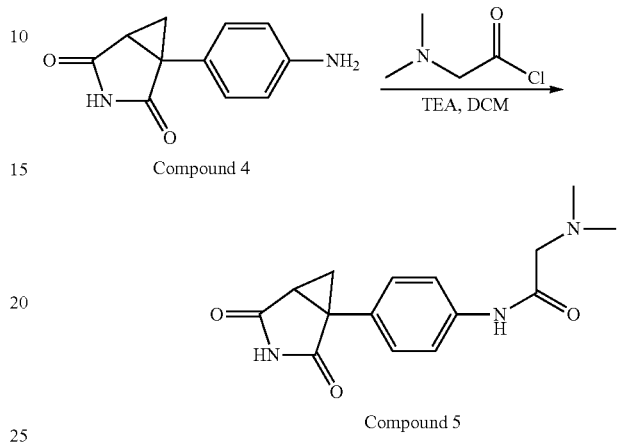

To 1-(4-aminophenyl)-3-azabicyclo[3.1.0]hexane-2,4-dione (Compound 4) (19.8 mg, 0.10 mmol) in CH$_2$Cl$_2$ (2.5 mL) was added Et$_3$N (13.9 uL, 0.21 mmol) at room temperature. The mixture was cooled to 0° C. Dimethylaminoacetyl chloride hydrochloride (17.0 mg, 0.11 mmol) was added. The mixture was slowly warmed to room temperature and stirred overnight. Additional Et$_3$N (13.9 uL, 0.21 mmol) and dimethylaminoacetyl chloride hydrochloride (17.0 mg, 0.11 mmol) were added and the mixture was stirred for 4 h. CH$_2$Cl$_2$ (5 mL) was added. The mixture was washed with water (2 ml×2), dried (Na$_2$SO$_4$), and concentrated. The residue was purified by Prep-HPLC to give 2-(dimethylamino)-N-(4-(2,4-dioxo-3-azabicyclo[3.1.0]hexan-1-yl)phenyl)acetamide (Compound 5) as TFA salt 17.6 mg in 63% yield. $^1$H NMR (400 MHz, DMSO-d$_6$) δ 10.70 (s, 1H), 10.62 (s, 1H), 9.80 (s, 1H), 7.61-7.51 (m, 2H), 7.50-7.39 (m, 2H), 4.14 (s, 2H), 2.88 (s, 6H), 2.82 (ddd, J=8.4, 3.7, 1.6 Hz, 1H), 2.01 (t, J=4.3 Hz, 1H), 1.86 (dd, J=8.4, 4.3 Hz, 1H). MS (observed) 288.2

Scheme 5
Synthesis of N-(4-(2,4-Dioxo-3-azabicyclo[3.1.0]hexan-1-yl)phenyl) acetamide (Compound 6)

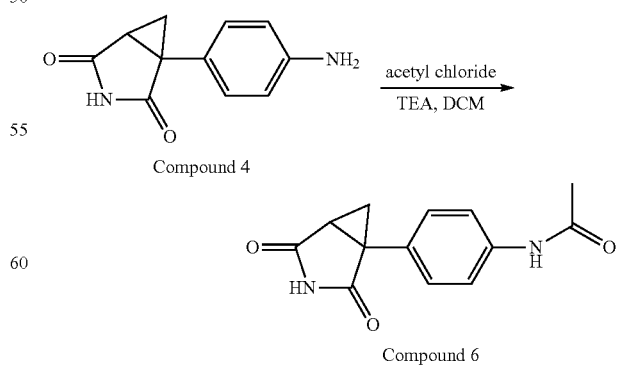

To 1-(4-aminophenyl)-3-azabicyclo[3.1.0]hexane-2,4-dione (Compound 4) (20 mg, 0.10 mmol) in CH$_2$Cl$_2$ (2.5 mL)

was added Et₃N (6.7 uL, 0.10 mmol) at room temperature. The mixture was cooled to 0° C. Acetyl chloride (7.0 uL, 0.10 mmol) was added. The mixture was slowly warmed up to room temperature and stirred overnight. CH₂Cl₂ (5 mL) was added. The mixture was washed with water (2 mL×2), dried (Na₂SO₄), and concentrated. The residue was purified by Prep-HPLC to give N-(4-(2,4-dioxo-3-azabicyclo[3.1.0]hexan-1-yl)phenyl)acetamide (Compound 6), 5.1 mg in 21% yield. ¹H NMR (400 MHz, DMSO-d₆) δ 10.66 (s, 1H), 9.98 (s, 1H), 7.55 (d, J=8.7 Hz, 2H), 7.38-7.33 (m, 2H), 2.78 (ddd, J=8.4, 3.7, 1.7 Hz, 1H), 1.97 (dd, J=4.4, 3.7 Hz, 1H), 1.84 (dd, J=8.4, 4.4 Hz, 1H). MS (observed) 245.1

Scheme 6
Synthesis of N-(4-(2,4-Dioxo-3-azabicyclo[3.1.0]hexan-1-yl)phenyl) methanesulfoamide (Compound 7)

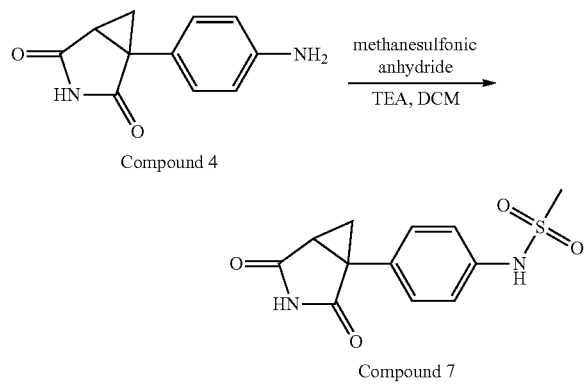

Compound 4

Compound 7

To 1-(4-aminophenyl)-3-azabicyclo[3.1.0]hexane-2,4-dione (Compound 4) (19.8 mg, 0.10 mmol) in CH₂Cl₂ (1 mL) was added Et₃N (7.92 uL, 0.12 mmol). The mixture was cooled to 0° C. Methanesulfonic anhydride (18.8 mg, 0.11 mmol) was added. The mixture was slowly warmed to room temperature and stirred overnight. Additional Et₃N (13.9 uL, 0.21 mmol) and methanesulfonic anhydride (18.8 mg, 0.11 mmol) were added. The mixture was stirred for another 4 h, diluted with CH₂Cl₂ 5 mL, washed with water (2 mL×2), and concentrated. The residue was purified by Prep-HPLC to give N-(4-(2,4-dioxo-3-azabicyclo[3.1.0]hexan-1-yl)phenyl)methanesulfonamide (Compound 7), 2.81 mg in 10.2% yield. ¹H NMR (400 MHz, DMSO-d₆) δ 10.68 (s, 1H), 9.81 (s, 1H), 7.41 (d, J=8.6 Hz, 2H), 7.18 (d, J=8.6 Hz, 2H), 2.99 (s, 3H), 2.80 (ddd, J=8.4, 3.7, 1.7 Hz, 1H), 1.99 (t, J=4.3 Hz, 1H), 1.85 (dd, J=8.4, 4.3 Hz, 1H). MS (observed) 281.2

Scheme 7
Synthesis of 3-Methyl-3-phenylpiperidine-2,6-dione (Compound 8)

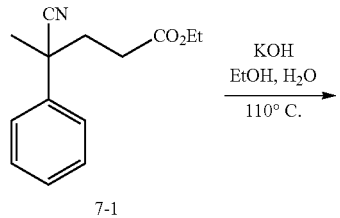

7-1

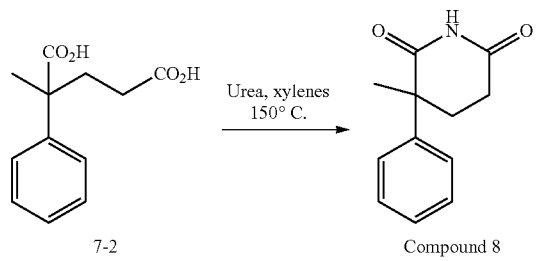

7-2

Compound 8

Synthesis of 2-Methyl-2-phenylpentanedioic acid (7-2)

Ethyl 4-cyano-4-phenylpentanoate 7-1 (Prepared according to Battye, P. J.; Jones, D. W. *J. Chem. Soc., Perkin Trans. 1: Organic and Bio-Organic Chemistry*, 1986, 8, 1479-1489.) (1.17 g, 5.05 mmol), KOH (1.70 g, 30.3 mmol), EtOH (1 mL) and water (12 mL) were stirred at 110° C. overnight. The mixture was cooled to room temperature and acidified (pH=2) with concentrated HCl. The product was extracted with EtOAc (15 mL×3). The organic layers were combined, dried (Na₂SO₄) and concentrated to provide 2-methyl-2-phenylpentanedioic acid 7-2 which was used directly in the next step. MS (observed) 221.1

Synthesis of 3-Methyl-3-phenylpiperidine-2,6-dione (Compound 8)

2-Methyl-2-phenylpentanedioic acid 7-2 (1.12 g, 5.05 mmol) and urea (606 mg, 10.1 mmol) in xylene (24 mL) were stirred at 150° C. overnight. The mixture was concentrated under high vacuum. The residue was diluted with EtOAc (40 mL), washed with brine (15 mL×2), dried (Na₂SO₄), and concentrated. The residue was purified by chromatography using EtOAc:hexanes=0:1 to 1:2 to give 3-methyl-3-phenylpiperidine-2,6-dione (Compound 8), 590 mg in 57% yield. ¹H NMR (500 MHz, Chloroform-d) δ 7.89 (s, 1H), 7.39-7.21 (m, 4H), 2.55 (dddd, J=17.8, 4.4, 3.0, 0.9 Hz, 1H), 2.41 (ddd, J=13.8, 4.9, 3.0 Hz, 1H), 2.31 (ddd, J=17.8, 12.9, 4.9 Hz, 1H), 2.13 (ddd, J=13.8, 12.9, 4.4 Hz, 1H), 1.57 (s, 3H). MS (observed) 204.1

Scheme 8
Synthesis of 3:2 ratio of 3-Methyl-3-(4-nitrophenyl)piperidine-2,6-dione: 3-methyl-3-(2-nitrophenyl)piperidine-2,6-dione (Compound mixture 9 (regioisomers), 3-(4-Aminophenyl)-3-methylpiperidine-2,6-dione (Compound 10), and 3-(2-Aminophenyl)-3-methylpiperidine-2,6-dione (Compound 11)

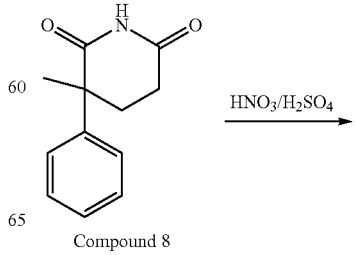

Compound 8

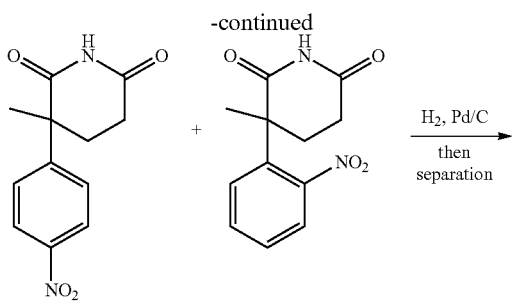

Compound 9 (3:2 mixture of regioisomers)

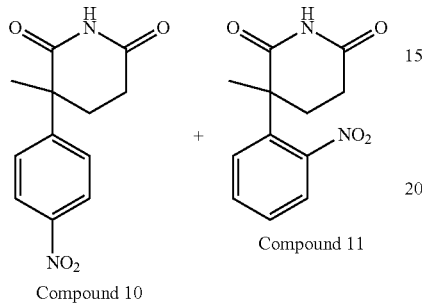

Compound 10                Compound 11

Synthesis of 3:2 ratio of 3-Methyl-3-(4-nitrophenyl) piperidine-2,6-dione: 3-methyl-3-(2-nitrophenyl) piperidine-2,6-dione (Compound mixture 9 (regioisomers)

A solution of H₂SO₄ (3 mL) and HNO₃ (217 mg, 2.35 mmol) were cooled to 0° C. 3-Methyl-3-phenylpiperidine-2,6-dione (Compound 8) (400 mg, 1.96 mmol) was added. The mixture was stirred at 0° C. for 10 min and then reverse quenched into aqueous saturated sodium bicarbonate (30 mL). MTBE 40 mL was added, the mixture was stirred for 30 min, and the organic layer was separated. The aqueous layer was extracted with MTBE (20 ml×2). All organic layers were combined and concentrated. The residue was purified by chromatography using EtOAc:hexanes=0:1 to 3:2. A mixture of regioisomers were obtained in 440 mg, yield 91%—ratio of 3-Methyl-3-(4-nitrophenyl)piperidine-2,6-dione: 3-methyl-3-(2-nitrophenyl)piperidine-2,6-dione=3:2 (Compound mixture 9). ¹H NMR (400 MHz, Chloroform-d) δ 8.34-8.24 (m, 1H), 8.24-8.19 (m, 1H), 8.13 (s, 1H), 7.70-7.57 (m, 1H), 7.57-7.44 (m, 1H), 2.75-2.64 (m, 1H), 2.56-2.46 (m, 1H), 2.36 (dddd, J=17.0, 13.5, 12.1, 4.3 Hz, 1H), 2.29-2.20 (m, 1H), 1.67 (s, 3H). MS (observed) 249.1

Synthesis of 3-(4-Aminophenyl)-3-methylpiperidine-2,6-dione (Compound 10) and 3-(2-aminophenyl)-3-methylpiperidine-2,6-dione (Compound 11)

To a 3:2 mixture of 3-Methyl-3-(4-nitrophenyl)piperidine-2,6-dione and 3-methyl-3-(2-nitrophenyl)piperidine-2,6-dione (Compound mixture 9) (200 mg, 0.81 mmol) and Pd/C (42.6 mg, 0.4 mmol, 10% wt) in a 25 mL round bottom flask was added EtOAc (4 mL). The mixture was purged with H₂ (3 times). The solution was stirred overnight at room temperature. The mixture was filtered with celite, concentrated, and purified by chromatography using EtOAc:hexanes=0:1 to 3:1. Two regioisomers were separated as TFA salts by prep-HPLC to provide 3-(4-aminophenyl)-3-methylpiperidine-2,6-dione (Compound 10), 51 mg and 3-(2-aminophenyl)-3-methylpiperidine-2,6-dione (Compound 11), 25 mg.

Compound 10:

¹H NMR (400 MHz, DMSO-d₆) δ 10.94 (s, 1H), 7.34 (d, J=8.7 Hz, 2H), 7.24 (d, J=8.7 Hz, 2H), 2.50-2.28 (m, 1.5H), 2.16-1.99 (m, 2.5H), 1.44 (s, 4H). MS (observed) 219.2

Compound 11:

¹H NMR (400 MHz, DMSO-d₆) δ 10.94 (s, 1H), 7.31 (t, J=7.9 Hz, 1H), 7.01 (d, J=7.9 Hz, 1H), 6.94 (d, J=8.4 Hz, 1H), 6.91 (d, J=2.1 Hz, 1H), 2.47-2.26 (m, 2H), 2.18-2.00 (m, 2H), 1.43 (s, 3H). MS (observed) 219.2

Scheme 9
Synthesis of 3-(1-Methyl-1H-benzoimidazol-2-ylmethyl)-piperidine-2,6-dione (Compound 12)

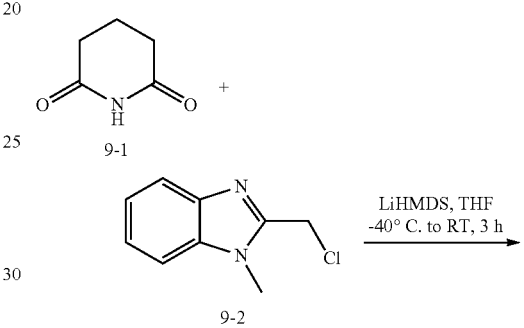

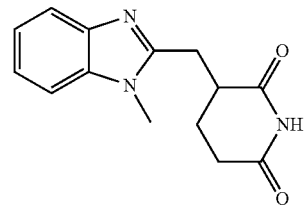 [SMILES: Cn1c(CC2CCC(=O)NC2=O)nc2ccccc21]

Compound 12

To a stirred solution of 9-1 (100.0 mg, 884 μmol) in THF (7 mL) was added LiHMDS (1.94 mL, 1.94 mmol) at −40° C. The solution was stirred at −40° C. for 5-10 minutes followed by the addition of a THF solution (1 mL) of 9-2 (159 mg, 884 μmol). The reaction mixture was stirred at −40° C. for 15 minutes and then it was allowed to warm up to room temperature over 1.5 hours. Aqueous saturated aqueous NH₄Cl solution was added to the reaction and the resulting solution was extracted with Ethyl acetate. The combined Ethyl acetate extracts were washed with water, brine, dried over anhydrous Na₂SO₄ and concentrated under reduced pressure. The crude mass was purified on a preparative TLC plate (eluting with 2% MeOH in DCM) to afford Compound 12 (35.0 mg, 136 μmol, 15%) as an off-white solid. ¹H NMR (400 MHz, DMSO-d₆) δ 10.75 (s, 1H), 7.52 (dd, J=17.4, 7.8 Hz, 2H), 7.17 (dt, J=21.5, 7.4 Hz, 2H), 3.76 (s, 3H), 3.43 (dd, J=16.3, 4.2 Hz, 1H), 3.23-3.15 (m, 1H), 3.00 (dd, J=15.9, 8.4 Hz, 1H), 2.66-2.50 (m, 2H), 2.00 (s, 2H). LC MS: ES+ 258.2.

Scheme 10
Synthesis of 3-(1-Methyl-1H-indazol-3-ylmethyl)-piperidine-2,6-dione (Compound 13)

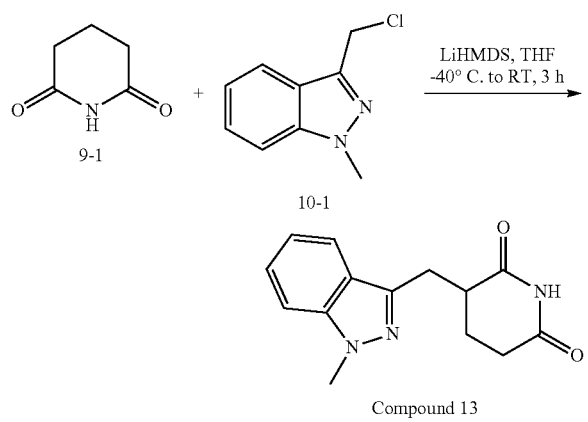

To a stirred solution of 3-(chloromethyl)-1-methyl-1H-indazole 10-1 (135 mg, 751 μmol) in THF (7.0 mL) was added LiHMDS (1.65 mL, 1.65 mmol) at −40° C. and piperidine-2,6-dione 9-1 (85.0 mg, 751 μmol) in THF (3.0 mL) was then added to the reaction mixture after 5 minutes. The reaction mixture was stirred at −40° C. for 15 minutes and then was allowed to warm up to room temperature over 1.5 hour. TLC showed formation of a new spot (Rf-0.3 in 5% MeOH/DCM). The reaction was quenched with saturated aqueous NH$_4$Cl solution and extracted with ethyl acetate. The organics were washed with water, brine, dried over sodium sulfate and concentrated. The crude material was purified on a Prep TLC Plate (eluting with 2% MeOH/DCM) to afford 3-((1-methyl-1H-indazol-3-yl)methyl)piperidine-2,6-dione (Compound 13) (30.0 mg, 116 μmol, 15.5%) as an off-white solid. $^1$H NMR (400 MHz, DMSO-d6) δ 10.71 (s, 1H), 7.74 (d, J=8.0 Hz, 1H), 7.56 (d, J=8.4 Hz, 1H), 7.37 (t, J=7.8 Hz, 1H), 7.10 (t, J=7.5 Hz, 1H), 3.98 (s, 3H), 3.49 (d, J=13.6 Hz, 1H), 3.07-2.96 (m, 2H), 2.50-2.43 (m, 2H), 1.78-1.72 (m, 2H). LC MS: ES+258.3.

Scheme 10
Synthesis of 2,6-Dioxo-piperidine-3-carboxylic acid (11-2)

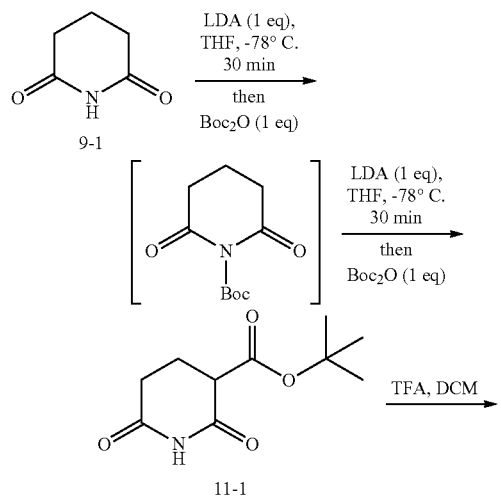

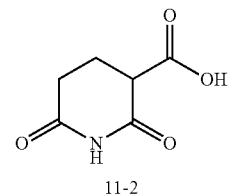

Synthesis of 2,6-Dioxo-piperidine-3-carboxylic acid tert-butyl ester (11-1)

To a stirred solution of 9-1 (3.5 g, 30.9 mmol) in THF (30.0 mL) at −78° C. was added LDA (15.45 mL, 30.9 mmol). After stirring for 10 minutes at the same temperature, (Boc)$_2$O (7.05 mL, 30.9 mmol) was added and the reaction mixture was stirred for another 30 minutes at same temperature. Then again, LDA (15.45 mL, 30.9 mmol) was added to the reaction mixture, followed by (Boc)$_2$O (7.05 mL, 30.9 mmol) after 5 minutes. The temperature of the reaction was allowed to warm to room temperature over 1 hour. The reaction was quenched with saturated aqueous NH$_4$Cl solution and then extracted with ethyl acetate. The organic layer was washed with water, brine, dried over sodium sulfate and concentrated. The crude material was purified by column chromatography using (silica, 100-200, 0%-20% ethyl acetate/hexane) to afford 11-1 (1.50 g, 7.03 mmol, 22.7%) as off white solid. $^1$H NMR (400 MHz, DMSO-d6) δ 10.90 (brs, 1H), 3.55-3.52 (m, 1H), 2.56-2.50 (m, 1H), 2.45-2.38 (m, 1H), 2.11-2.01 (m, 2H), 1.42 (s, 9H).

Synthesis of 2,6-Dioxo-piperidine-3-carboxylic acid (11-2)

To a stirred solution of 11-1 (1.0 g, 4.68 mmol) in DCM (15.0 mL) was added TFA (5.08 mL, 46.8 mmol) and the reaction mixture was stirred at room temperature for 2 hours. The reaction was concentrated under reduced pressure and then triturated with ether to afford 11-2 (650 mg, 4.13 mmol, 88.4%) as an off-white solid. LC MS: ES+ 158.1.

Scheme 12: General amide coupling procedure with intermediate 11-2 as exemplified by the synthesis of 2,6-Dioxo-piperidine-3-carboxylic acid phenylamide (Compound 14):

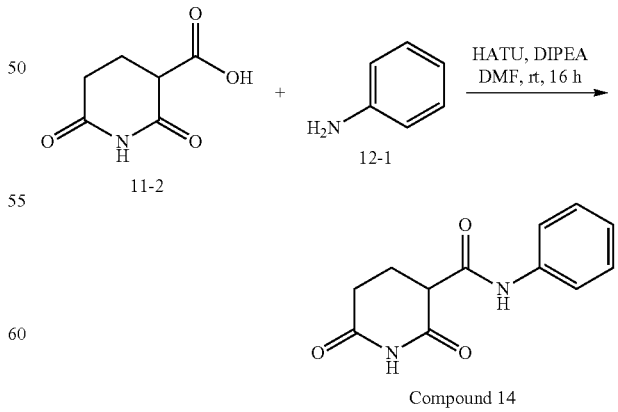

To a stirred solution of 11-2 (50.0 mg, 318 μmol) in DMF (1.0 mL) was added 12-1 (29.0 μL, 318 μmol), DIPEA (234 μL, 1.27 mmol) and HATU (181 mg, 477 μmol). The reaction mixture was then stirred at room temperature for 16 hours. The reaction mixture was diluted with ethyl acetate and the organic layer was washed with saturated aqueous NaHCO₃ solution, water, brine and dried over sodium sulfate. The organics were concentrated and the crude material was purified on a Prep TLC Plate (eluting with 2% Methanol/DCM) to afford Compound 14 (20.0 mg, 86.1 μmol, 27.1%) as white solid. 1H NMR (400 MHz, DMSO-d6) δ 10.95 (s, 1H), 10.26 (s, 1H), 7.63-7.56 (d, J=8.0 Hz, 2H), 7.32 (t, J=8.0 Hz, 2H), 7.07 (td, J=7.4, 1.3 Hz, 1H), 3.62 (dd, J=8.3, 6.2 Hz, 1H), 2.57 (t, J=6.6 Hz, 2H), 2.16 (p, J=6.5, 6.1 Hz, 2H). LC MS: ES+231.45.

The following compounds were synthesized by the general procedure in Scheme 12:

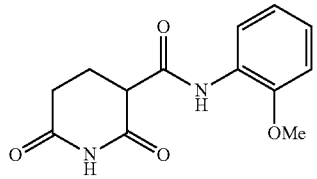 [SMILES: COc1ccccc1NC(=O)C1CCC(=O)NC1=O]

Compound 15

Compound 15: Yield=31%, ¹H NMR (400 MHz, DMSO-d6) δ 10.94 (s, 1H), 9.59 (s, 1H), 8.01 (d, J=8.12 Hz, 1H), 7.04-7.11 (m, 2H), 6.91 (t, J=6.76 Hz, 1H), 3.93 (t, J=6.88 Hz, 1H), 3.84 (s, 3H), 2.52-2.55 (m, 2H), 2.12-2.16 (m, 2H). LC MS: ES+ 263.3

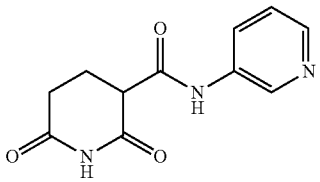 [SMILES: O=C1CCC(C(=O)Nc2cccnc2)C(=O)N1]

Compound 16

Compound 16: Yield=67%, ¹H NMR (400 MHz, DMSO-d6) δ 10.98 (s, 1H), 10.49 (s, 1H), 8.74 (s, 1H), 8.28 (d, J=3.92 Hz, 1H), 8.05 (d, J=8.24 Hz, 1H), 7.35-7.38 (m, 1H), 3.65 (t, J=6.84 Hz, 1H), 2.56-2.58 (m, 2H), 2.14-2.17 (m, 2H). LC MS: ES+ 234.1

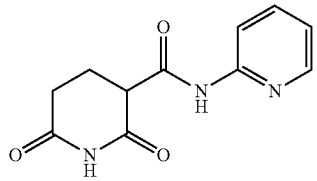 [SMILES: O=C1CCC(C(=O)Nc2ccccn2)C(=O)N1]

Compound 17

Compound 17: Yield=24%, ¹H NMR (400 MHz, DMSO-d6) δ 10.95 (s, 1H), 10.77 (s, 1H), 8.33 (s, 1H), 8.06 (d, J=8.12 Hz, 1H), 7.78-7.80 (m, 1H), 7.13 (brs, 1H), 3.82 (brs, 1H), 2.52-2.54 (m, 2H), 2.13-2.16 (m, 2H). LC MS: ES+ 234.1

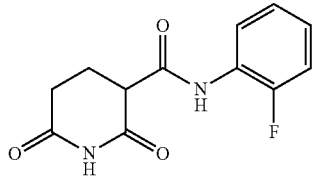 [SMILES: O=C1CCC(C(=O)Nc2ccccc2F)C(=O)N1]

Compound 18

Compound 18: Yield=31%, ¹H NMR (400 MHz, DMSO-d6) δ 10.94 (s, 1H), 10.07 (s, 1H), 7.90-7.94 (m, 1H), 7.24-7.29 (m, 1H), 7.16-7.18 (m, 2H), 3.84 (t, J=7.20 Hz, 1H), 2.54-2.57 (m, 2H), 2.12-2.17 (m, 2H). LC MS: ES+ 251.1

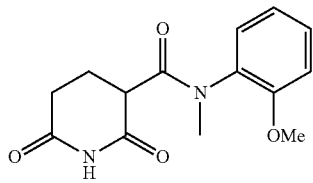 [SMILES: COc1ccccc1N(C)C(=O)C1CCC(=O)NC1=O]

Compound 19

Compound 19: Yield=23%, ¹H NMR (400 MHz, DMSO-d6 at 100° C., rotamers observed at 20° C.) δ 10.38 (br, 1H), 7.30-7.38 (m, 2H), 7.16 (d, J=8.04 Hz, 1H), 7.02 (m, 1H), 3.85 (s, 3H), 3.35 (brs, 1H), 3.11 (s, 3H), 2.40-2.52 (m, 2H), 1.85-2.02 (m, 2H). LC MS: ES+ 277.3

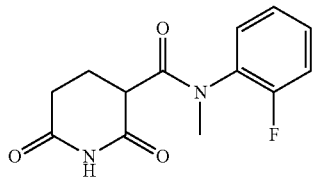 [SMILES: CN(C(=O)C1CCC(=O)NC1=O)c1ccccc1F]

Compound 20

Compound 20: Yield=10%, ¹H NMR (400 MHz, CD3OD) δ 8.50 (d, J=3.60 Hz, 1H), 7.92-7.96 (m, 1H), 7.52 (d, J=8.0 Hz, 1H), 7.37-7.41 (m, 1H), 3.37 (s, 3H), 2.62-2.67 (m, 1H), 2.48-2.52 (m, 1H), 2.23-2.29 (m, 1H), 2.09-2.14 (m, 1H). LC MS: ES+ 248.1

Compound 21

Compound 21: Yield=20%, ¹H NMR (400 MHz, DMSO-d6 at 100° C., rotamers observed at 20° C.) δ 10.47 (br, 1H), 7.29-7.46 (m, 4H), 3.46 (br, 1H), 3.21 (brs, 3H), 2.50-2.66 (m, 2H), 1.95-2.06 (m, 2H). LC MS: ES+ 265.2

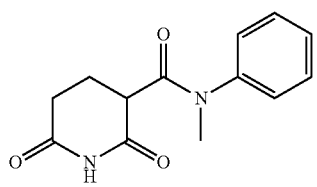

Compound 22

Compound 22: Yield=16%, ¹H NMR (400 MHz, DMSO-d6) δ 10.81 (s, 1H), 7.38-7.48 (m, 5H), 3.44-3.46 (m, 1H), 3.19 (s, 3H), 2.42-2.48 (m, 2H), 2.01-2.05 (m, 1H), 1.88-1.93 (m, 1H); LC MS: ES+ 247.3.

Scheme 13: Synthesis of 2-(2,6-Dioxo-piperidin-3-yl)-N-(2-fluoro-phenyl)-acetamide (Compound 23)

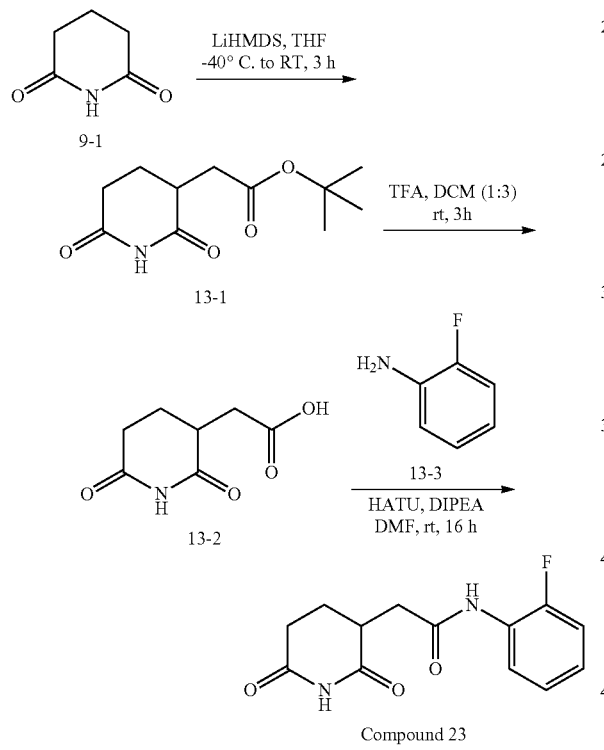

Compound 23

Synthesis of (2,6-Dioxo-piperidin-3-yl)-acetic acid tert-butyl ester (13-1)

At −40° C. a solution of Lithium bis(trimethylsilyl)amide (9.72 mL, 9.72 mmol) was added dropwise to a solution of piperidine-2,6-dione 9-1 (500 mg, 4.42 mmol) in THF (20 mL). After 15 minutes at −40° C., the mixture was allowed to warmed and the mixture was stirred at RT for 4h. TLC (50% ethyl acetate in hexane, Rf=0.5) showed completion of the reaction. It was quenched with a saturated solution of ammonium chloride and the aqueous phase was extracted with dichloromethane (5×50 ml). The combined organic phases were dried over sodium sulfate, filtered and concentrated under reduced pressure. The residue was purified by flash chromatography using ethyl acetate in hexane (30%) to provide tert-butyl 2-(2,6-dioxopiperidin-3-yl)acetate 13-1 (450 mg, 1.98 mmol, 45.0%) as an off-white solid.

¹H NMR (400 MHz, DMSO-d6) δ 10.67 (brs, 1H), 2.83-2.78 (m, 1H), 2.64-2.59 (m, 1H), 2.50-2.43 (m, 3H), 1.84-1.76 (m, 2H), 1.39 (s, 9H)

Synthesis of (2,6-Dioxo-piperidin-3-yl)-acetic acid (13-2)

To a DCM solution (9 mL) of 13-1 (520 mg, 2.28 mmol) at 0° C. was added TFA (3.48 mL, 45.6 mmol) and the resulting solution was warmed to room temperature and stirred for another 3 hours. The reaction mixture was concentrated under reduced pressure and the resultant solid was triturated with Diethyl ether to afford 13-2 (360 mg, 2.10 mmol, 92%) as an off-white solid.

Synthesis of 2-(2,6-Dioxo-piperidin-3-yl)-N-(2-fluoro-phenyl)-acetamide (Compound 23)

To a stirred solution of 13-2 (70.0 mg, 408 μmol) in DMF (1 mL) was added 13-3 (45.3 mg, 408 μmol), DIPEA (300 μL, 1.63 mmol) and HATU (232 mg, 612 μmol). The resulting mixture was stirred at room temperature for 16 hours. The reaction mass was diluted with Ethyl acetate, washed with aqueous saturated NaHCO₃ solution, water and brine. The organic layer was dried over anhydrous Na₂SO₄ and concentrated under reduced pressure. The crude mass was purified over preparative TLC Plate (eluting with 2% MeOH in DCM) to afford Compound 23 (25.0 mg, 94.6 μmol, 23%) as white solid. ¹H NMR (400 MHz, DMSO-d6) δ 10.68 (s, 1H), 9.78 (s, 1H), 7.87 (s, 1H), 7.25-7.23 (m, 1H), 7.18-7.11 (m, 2H), 2.93-7.87 (m, 2H), 2.65-2.50 (m, 2H), 1.93-1.90 (m, 1H), 1.82-1.80 (m, 1H).

Scheme 14
Synthesis of 3-(1-Phenyl-1H-[1,2,3]triazol-4-ylmethyl)-piperidine-2,6-dione (Compound 24)

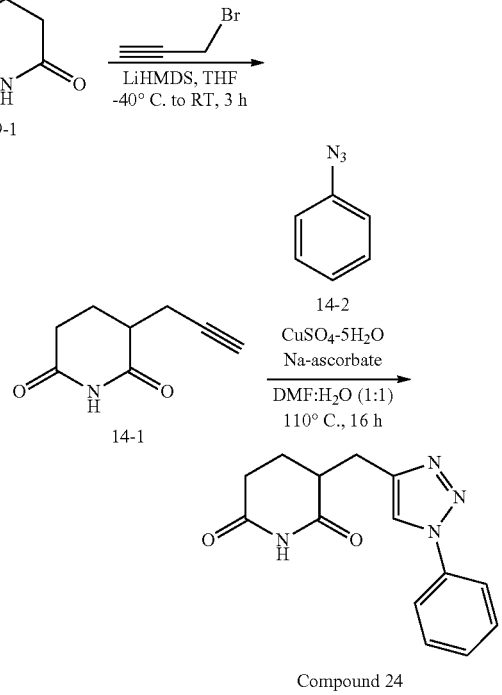

Compound 24

Synthesis of 3-Prop-2-ynyl-piperidine-2,6-dione (14-1)

At −40° C. a solution of Lithium bis(trimethylsilyl)amide (38.7 mL, 38.7 mmol) was added dropwise to a solution of piperidine-2,6-dione 9-1 (200 mg, 17.6 mmol). 3-bromoprop-1-yne (4.70 mL, 52.8 mmol) was then added immediately. After 15 minutes at −40° C., the mixture was allowed to warm to rt and the mixture was stirred for 4h. TLC (50% ethyl acetate in hexane, Rf=0.5) showed completion of the reaction. The reaction was quenched with a saturated solution of ammonium chloride and the aqueous phase was extracted with dichloromethane (5×50 ml). The combined organic phases were dried over sodium sulfate, filtered and concentrated under reduced pressure. The residue was purified by flash chromatography using ethyl acetate in hexane (30%) to provide 3-(prop-2-yn-1-yl)piperidine-2,6-dione 14-1 (910 mg, 6.02 mmol, 34.2%) as an off-white solid. $^1$H NMR (400 MHz, DMSO-d6) δ 10.73 (brs, 1H), 2.86 (s, 1H), 2.68-2.54 (m, 4H), 2.43-2.40 (m, 1H), 2.1-2.00 (m, 1H), 1.82-1.77 (m, 1H)

Synthesis of 3-(1-Phenyl-1H-[1,2,3]triazol-4-ylmethyl)-piperidine-2,6-dione (Compound 24)

14-1 (200.0 mg, 1.32 mmol) and 14-2 (314 mg, 2.64 mmol) were dissolved in DMF-Water (1:1, 10 mL). The resulting solution was degassed with Argon for about 10 minutes and then CuSO$_4$.5H$_2$O (329 mg, 1.32 mmol) and Na-ascorbate (261 mg, 1.32 mmol) were added. The reaction mixture was heated at 110° C. for 16 hours to produce. The reaction was then cooled to room temperature and filtered through a short bed of celite. The filtrate was diluted with Ethyl acetate and washed with water and brine. The organic layer was dried over anhydrous Na$_2$SO$_4$ and then concentrated under reduced pressure. The crude mass was purified over a preparative TLC plate (eluting with 60% Ethyl acetate in Hexane) to afford Compound 24 (34.7 mg, 128 μmol, 10%) as off white solid. $^1$H NMR (400 MHz, DMSO-d6) δ 10.72 (s, 1H), 8.59 (s, 1H), 7.87 (d, J=7.9 Hz, 2H), 7.59 (t, J=7.8 Hz, 2H), 7.47 (t, J=7.4 Hz, 1H), 3.32-3.31 (m, 2H), 2.95-2.79 (m, 2H), 2.59-2.50 (m, 1H), 1.94-1.91 (m, 1H), 1.75-1.72 (m, 1H); LC MS: ES+ 271.3.

Scheme 15
Synthesis of 3-(1-Methyl-1H-[1,2,3]triazol-4-ylmethyl)-piperidine-2,6-dione (Compound 25)

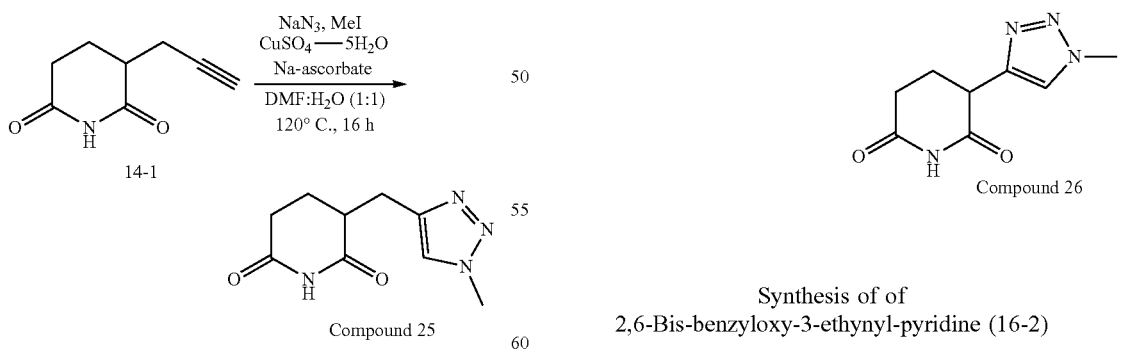

Compound 25

Synthesis of 3-(1-Methyl-1H-[1,2,3]triazol-4-ylmethyl)-piperidine-2,6-dione (Compound 25)

A solution of sodium azide (429 mg, 6.60 mmol), Copper Sulfate (65.9 mg, 264 μmol) and sodium ascorbate (130 mg, 660 μmol) in DMF:H$_2$O (6 mL) was stirred for 5 minutes at room temperature. To this solution was added a solution of 3-(prop-2-yn-1-yl)piperidine-2,6-dione 14-1 (0.2 g, 1.32 mmol) in DMF (1.0 mL) and iodomethane (281 mg, 1.98 mmol). The reaction mixture was heated in sealed tube for 16 hrs at 120° C. TLC showed complete consumption of the starting material and formation of the desired spot at rf=0.3 in 50% ethylacetate-hexane. The solution was cooled and diluted with EtOAc and then washed with water and brine solution. The organic and aqueous fractions were separated. The organic fraction was then dried over anhydrous sodium sulphate and evaporated under reduced pressure. The crude material was purified by flash chromatography to afford 3-((1-methyl-1H-1,2,3-triazol-4-yl)methyl)piperidine-2,6-dione (Compound 25) (8.00 mg, 38.4 μmol, 3.0% yield). $^1$H NMR (400 MHz, DMSO-d6) δ 10.68 (s, 1H), 7.80 (s, 1H), 3.98 (s, 3H), 3.17-3.14 (m, 1H), 2.77-2.72 (m, 2H), 2.42 (m, 1H), 1.84-1.81 (m, 1H), 1.65-1.62 (m, 1H); LC MS: ES+ 209.2.

Scheme 16
Synthesis of 3-(1-Methyl-1H-[1,2,3]triazol-4-yl)-piperidine-2,6-dione (Compound 26):

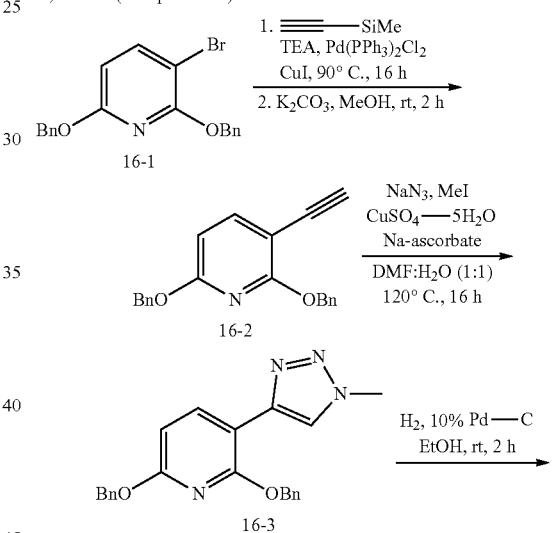

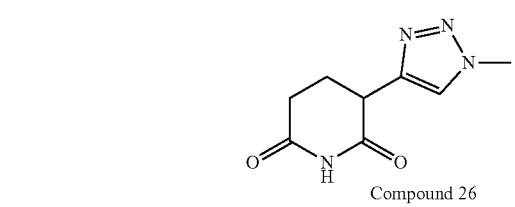

Compound 26

Synthesis of of 2,6-Bis-benzyloxy-3-ethynyl-pyridine (16-2)

A sealed tube was charged with 16-1 (1.0 g, 2.70 mmol), Et$_3$N (4.89 mL, 35.1 mmol) and Ethynyltrimethylsilane (4.85 mL, 35.1 mmol) and the resulting solution was degassed with Argon for about 10 minutes followed by the addition of CuI (514 mg, 2.70 mmol) and PdCl$_2$(PPh3)$_2$ (1.89 g, 2.70 mmol). The reaction tube was sealed and heated at 90° C. for 16 hours. The reaction was then cooled to room temperature and filtered through a short bed of celite. The filtrate was partitioned between heptane and water. The organic layer was separated, dried over anhydrous Na$_2$SO$_4$ and concentrated. The crude mass was dissolved in MeOH (10 mL) and to it was added K$_2$CO$_3$ (713 mg, 5.16 mmol) and the solution was stirred at ambient temperature for 2 hours to produce 16-2. The reaction mass was filtered through a short bed of celite and the filtrate was concentrated under reduced pressure. The crude mass was purified by column chromatography (silica, gradient: 0-10% Ethyl acetate in Hexane) to afford 16-2 (462 mg, 1.46 mmol. 54%) as a white solid. $^1$H NMR (400 MHz, DMSO-d$_6$) δ 7.63 (d, J=8.24 Hz, 1H), 7.43-7.28 (m, 10H), 7.34 (d, J=8.16 Hz, 1H), 5.44 (s, 2H), 5.29 (s, 2H), 3.24 (s, 1H).

Synthesis of 2,6-Bis-benzyloxy-3-(1-methyl-1H-[1,2,3]triazol-4-yl)-pyridine (16-3)

To a stirred mixture of NaN$_3$ (616 mg. 9.48 mmol), CuSO$_4$.5H$_2$O (78.9 mg. 316 μmol) and Na-ascorbate (156 mg. 790 μmol) in DMF-water (1:1, 18 mL) was added 16-2 (500.0 mg, 1.58 mmol) and MeI (156 μL, 2.52 mmol) and the resulting mixture was stirred at 120° C. for 16 hours to produce 16-3. The reaction was then cooled to room temperature, diluted with Ethyl acetate and filtered through a short bed of celite. The filtrate was washed with water, brine, and dried over anhydrous Na$_2$SO$_4$ and concentrated under reduced pressure. The crude mass was purified by column chromatography (silica, gradient: 0-25% Ethyl acetate in Hexane) to afford 16-3 (372 mg, 0.9995 mmol, 63.2%) as a white solid. $^1$H NMR (400 MHz, DMSO-d$_6$) δ 8.53 (d, J=8.20 Hz, 1H), 7.82 (s, 1H), 7.43-7.28 (m, 10H), 6.53 (d, J=8.20 Hz, 1H), 5.48 (s, 2H), 5.35 (s, 2H), 4.06 (s, 3H); LC MS: ES+ 372.8.

Synthesis of 3-(1-Methyl-1H-[1,2,3]triazol-4-yl)-piperidine-2,6-dione (Compound 26)

A 25 mL round bottom flask was charged with 2,6-bis (benzyloxy)-3-(1-methyl-1H-1,2,3-triazol-4-yl)pyridine 16-3 (150 mg, 402 μmol) and ethanol (10.0 mL). The solution was degassed for 15 minutes under argon atmosphere. To the solution was added palladium on carbon (10 wt %, 64.0 mg, 602 μmol) and the reaction was continued for 2 hrs under a hydrogen balloon. TLC showed complete consumption of the starting material and formation of the desired spot at rf=0.2 in ethylacetate. The reaction mixture was filtered over a celite bed and the filtrate was evaporated under reduced pressure. The crude residue which was purified by combiflash chromatography to provide 3-(1-methyl-1H-1,2,3-triazol-4-yl)piperidine-2,6-dione Compound 26 (35.0 mg, 180 μmol, 44.8%) as a white solid. $^1$H NMR (400 MHz, DMSO-d6) δ 10.86 (s, 1H), 7.98 (s, 1H), 3.32 (s, 4H), 2.66 (dt, J=16.4, 7.7 Hz, 1H), 2.56 (d, J=5.0 Hz, 1H), 2.17 (q, J=5.6 Hz, 2H); $^1$H NMR (400 MHz, Chloroform-d) δ 7.86 (s, 1H), 7.63 (s, 1H), 4.10 (s, 3H), 3.98 (dd, J=9.2, 5.2 Hz, 1H), 2.89 (dt, J=17.7, 5.6 Hz, 1H), 2.68 (ddd, J=17.8, 9.8, 5.1 Hz, 1H), 2.60-2.48 (m, 1H), 2.43 (dtd, J=14.1, 9.4, 4.8 Hz, 1H); LC MS: ES+ 195.0.

Scheme 17
Synthesis of 3-(1-Phenyl-1H-[1,2,3]triazol-4-yl)-piperidine-2,6-dione (Compound 27)

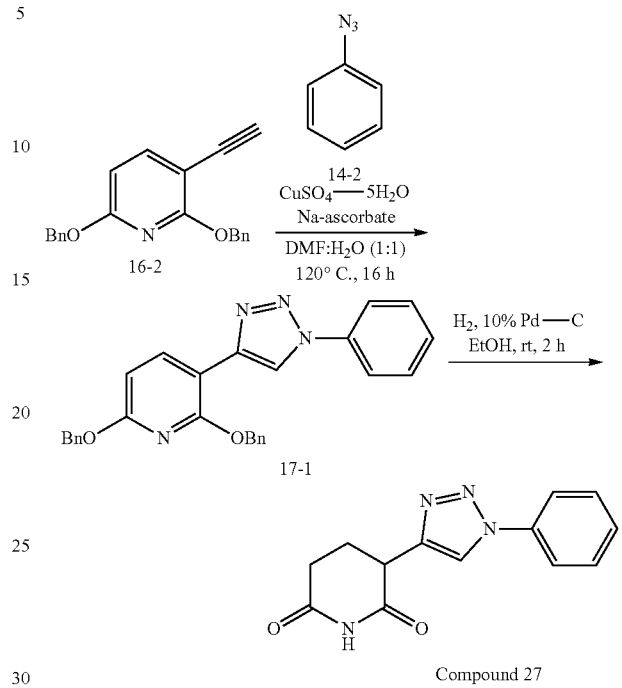

Synthesis of 2,6-Bis-benzyloxy-3-(1-phenyl-1H-[1,2,3]triazol-4-yl)-pyridine (17-1)

To a stirred mixture of Azidobenzene 14-2 (150 mg, 1.26 mmol), CuSO$_4$.5H$_2$O (31.3 mg, 126 μmol) and Na-ascorbate (62.7 mg, 317 μmol) in DMF-water (1.1, 6 mL) was added 16-2 (200 mg, 634 μmol) and the resulting mixture was stirred at 120° C. for 16 h. The reaction was then cooled to room temperature, diluted with Ethyl acetate and filtered through a short bed of celite. The filtrate was washed with water, brine, dried over anhydrous Na$_2$SO$_4$ and concentrated under reduced pressure. The crude mass was purified by column chromatography (silica, gradient: 0-10% Ethyl acetate in Hexane) to afford 17-1 (46.2 mg. 106 μmol, 17%) as a white solid. $^1$H NMR (400 MHz, DMSO-d$_6$) δ 8.60 (d, J=8.24 Hz, 1H), 8.31 (s, 1H), 7.68 (d, J=7.68), 7.51-7.30 (m, 13H), 6.57 (d, J=8.28 Hz, 1H), 5.51 (s, 2H), 5.38 (s, 2H).

Synthesis of 3-(1-Phenyl-1H-[1,2,3]triazol-4-yl)-piperidine-2,6-dione (Compound 27)

A 25 mL rbf was charged with 2,6-bis(benzyloxy)-3-(1-phenyl-1H-1,2,3-triazol-4-yl)pyridine 17-1 (200.0 mg, 460 μmol) and ethanol (10.0 mL) and the solution was degassed for 15 minutes under an argon atmosphere. To the reaction was added palladium on carbon (48.9 mg, 460 μmol) and stirring was continued for 2 hrs in presence of a hydrogen balloon. TLC showed complete consumption of the starting material and the formation of the desired spot at rf=0.2 in 100% ethylacetate. The reaction mixture was filtered over a celite bed and the filtrate was evaporated under reduced pressure to obtain the crude which was purified by combiflash chromatography to obtain the desired compound which was further purified by a preparative TLC (60% ethylacetate-Hexane) to afford 3-(1-phenyl-1H-1,2,3-triazol-4-yl)piperidine-2,6-dione (Compound 27) (8.40 mg, 32.7 μmol, 7.17%) as an off-white solid. $^1$H NMR (400 MHz, DMSO-d6) δ 10.94 (s, 1H), 8.75 (s, 1H), 7.90 (d, J=7.9 Hz, 2H), 7.60 (t, J=7.7 Hz, 2H), 7.49 (t, J=7.3 Hz, 1H), 4.16 (t, J=7.9 Hz, 1H), 2.74-2.59 (m, 2H), 2.33-2.24 (m, 2H); LC MS: ES+ 257.2.

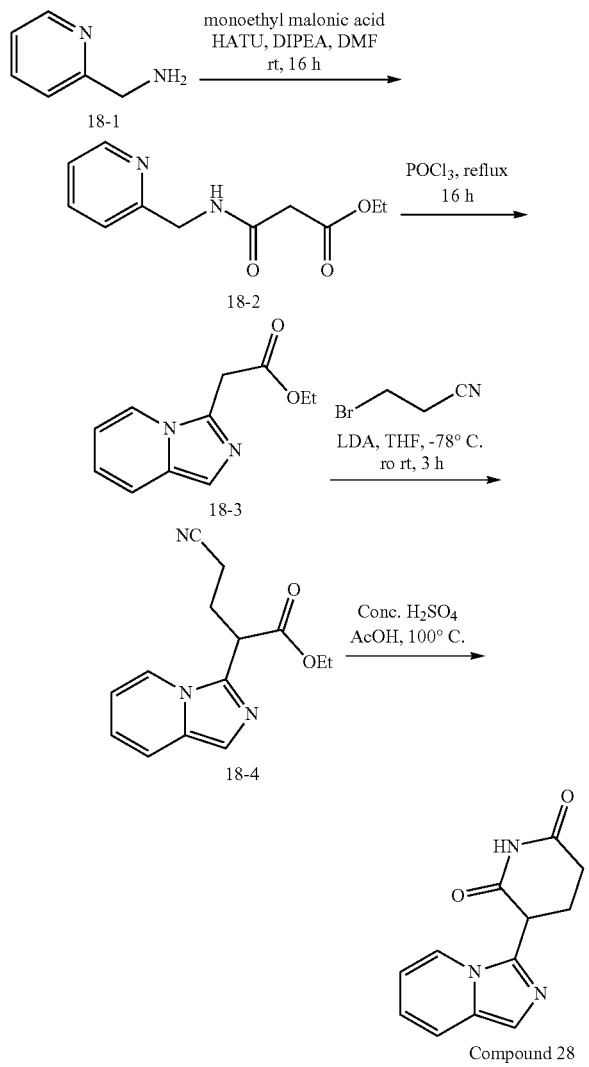

Synthesis of N-Pyridin-2-ylmethyl-malonamic acid ethyl ester (18-2)

To a DMF solution (20 mL) of 18-1 (1 g, 9.24 mmol) was added Monoethyl malonic acid (1.22 g, 9.24 mmol), DIPEA (4.82 mL, 27.7 mmol) and HATU (6.99 g, 18.4 mmol). The resulting solution was stirred at ambient temperature for 16 hours. The reaction mixture was diluted with Ethyl acetate, washed with water and brine. The organic layer was dried over anhydrous Na$_2$SO$_4$ and concentrated under reduced pressure. The crude mass was purified by column chroma-tography (silica, gradient: 0-25% Ethyl acetate in Hexane) to afford 18-2 (540 mg, 2.42 mmol, 26%) as an off-white solid. LC MS: ES+ 223.2.

Synthesis of Imidazo[1,5-a]pyridin-3-yl-acetic acid ethyl ester (18-3)

18-2 (540 mg, 2.42 mmol) was taken up in POCl$_3$ (5 mL) and stirred at reflux for 16 h. The volatiles were removed under reduce pressure and the residue was taken up in aqueous saturated NaHCO$_3$ solution and then extracted with DCM. The combined extracts were dried over anhydrous Na$_2$SO$_4$ and concentrated under reduced pressure. The crude mass was purified by column chromatography (silica, gradient: 0-2% MeOH in DCM) to afford 18-3 (260 mg, 1.27 mmol, 52.6%) as an off-brown gum. LC MS: ES+ 205.2.

Synthesis of 4-Cyano-2-imidazo[1,5-a]pyridin-3-yl-butyric acid ethyl ester (18-4)

Lithium diisopropylamide (1.02 mL, 2.04 mmol) was added dropwise to a THF solution (10 mL) of 18-3 (250 mg, 1.02 mmol) at −78° C. The resulting solution was stirred at 0° C. for 1 hour. The reaction was again cooled to −78° C. and 3-Bromopropionitrile (84.2 μL, 1.02 mmol) was added and stirred was continued for 30 minutes. The reaction was then gradually warmed to room temperature and stirring was continued for another 3 hours. The reaction mixture was quenched with aqueous saturated NH$_4$Cl solution, extracted with Ethyl acetate, dried over anhydrous Na$_2$SO$_4$ and concentrated under reduced pressure to afford 18-4 (175 mg, 680 μmol, 67%) crude as a brown gum. LC MS: ES+ 257.8.

Synthesis of 3-Imidazo[1,5-a]pyridin-3-yl-piperidine-2,6-dione (Compound 28)

18-4 (175 mg, 680 μmol) was taken up into a mixture of conc. H$_2$SO$_4$ (0.5 mL) and Acetic acid (2.5 mL) and the resulting solution was then heated at 110° C. for 6 hours. The reaction mixture was cooled to room temperature, poured onto an ice cold solution of aqueous NaHCO$_3$ and then extracted with Ethyl acetate. The combined extracts were dried over anhydrous Na$_2$SO$_4$ and concentrated under reduced pressure. The crude mass was purified by column chromatography (silica, gradient: 0-50% Ethyl acetate in Hexane) to afford Compound 28 (6.20 mg, 27.0 μmol, 4%) as brown solid. $^1$H NMR (400 MHz, DMSO-d$_6$) δ 10.96 (s, 1H), 8.23 (d, J=7.3 Hz, 1H), 7.54 (d, J=9.1 Hz, 1H), 7.33 (s, 1H), 6.77 (t, J=6.7 Hz, 1H), 6.67 (t, J=6.8 Hz, 1H), 4.63 (dd, J=10.4, 5.0 Hz, 1H), 2.70-2.63 (m, 2H), 2.25-2.17 (m, 2H); LC MS: ES+ 230.2.

Scheme 19
Synthesis of 3-(1-Methyl-1H-indol-3-yl)-piperidine-2,6-dione (Compound 29):

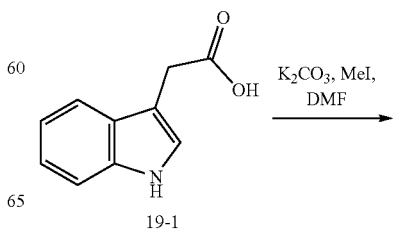

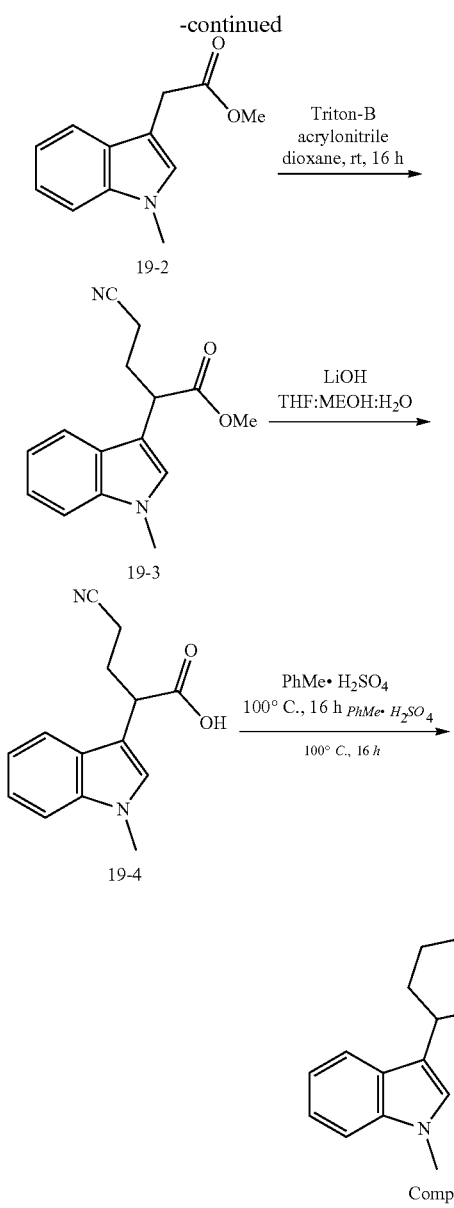

Synthesis of methyl 2-(1-methyl-1H-indol-3-yl) acetate (19-2)

To a stirred solution of 2-(1H-indol-3-yl)acetic acid (19-1) (3.0 g, 17.1 mmol) in DMF (20.0 mL) was added $K_2CO_3$ (7.09 g, 51.3 mmol) and the reaction mixture was stirred for 15 minutes. Methyl iodide (3.19 mL, 51.3 mmol) was then added to the reaction mixture and stirring was continued at room temperature for 16 hours. TLC showed formation of a new spot (Rf-0.5 in 20% ethyl acetate/hexane). The reaction was diluted with water and extracted with ethyl acetate. The organic layer was washed with water, brine, dried over sodium sulfate and concentrated. $^1$HNMR and LCMS showed only the acid group was converted to its methyl ester, N-methylation didn't took place. The residue was again dissolved in THF (15.0 mL) and to it was added NaH (1.0 eq) at 0° C. MeI (1.0 eq) was then added to the reaction mixture and the reaction mixture was stirred at room temperature for 3 hours. TLC showed a new spot formation (Rf-0.6 in 10% ethyl acetate/hexane). The reaction was diluted with cold water and ethyl acetate. The organic layer was separated and washed with water, brine, dried over sodium sulfate, concentrated and the resulting residue was purified by column chromatography (silica 100-200, 0%-2% ethyl acetate/hexane) to afford methyl 2-(1-methyl-1H-indol-3-yl)acetate 19-2 (1.40 g, 6.88 mmol, 40.3%) as a yellow oil. LC MS: ES+ 204.3.

Synthesis of 4-Cyano-2-(1-methyl-1H-indol-3-yl)-butyric acid methyl ester (19-3)

19-2 (500 mg, 2.46 mmol) was dissolved in 1,4-Dioxane (5 mL) and to this solution was added Benzyltrimethylammonium hydroxide (55.6 µL, 123 µmol) and Acrylonitrile (160 µL, 2.46 mmol) at 0° C. The reaction mixture was stirred at room temperature for 16 hours and then diluted with water and extracted with ethyl acetate. The organic layer was washed with water and brine, dried over anhydrous $Na_2SO_4$ and concentrated under reduced pressure. The crude mass was purified by column chromatography (silica, gradient: 0-20% Ethyl acetate in Hexane) to afford 19-3 (145 mg, 565 µmol, 23%) as a brown solid. LC MS: ES+ 310.2.

Synthesis of 4-Cyano-2-(1-methyl-1H-indol-3-yl)-butyric acid (19-4)

19-3 (140 mg, 546 µmol) was dissolved in a mixture of THF (3 mL), water (1 mL) and methanol (0.5 mL) and to this solution was added lithium hydroxide monohydrate (34.3 mg, 818 µmol). The reaction mixture was stirred at room temperature for 4 hours. The solvent was evaporated and the residue was acidified with 1N HCl. The solution was extracted with ethyl acetate and the organic layer was washed with brine, dried $Na_2SO_4$ and evaporated to afford 19-4 (94.0 mg, 387 µmol, 71%) as a gummy solid. LC MS: ES+ 243.1.

Synthesis of 3-(1-Methyl-1H-indol-3-yl)-piperidine-2,6-dione (Compound 29)

To a suspension of 19-4 (90 mg, 371 µmol) in Toluene (1 mL) was added sulfuric acid (3.95 µL, 74.2 µmol) at 0° C. The reaction mixture was stirred at 100° C. for 16 hours. The reaction was then basified with aq. $NaHCO_3$ and extracted with ethyl acetate. The organic layer was washed with brine, dried over $Na_2SO_4$ and evaporated under reduced pressure. The crude residue was purified by preparative TLC (3% methanol-dichloromethane) to afford Compound 29 (45.0 mg, 185 µmol, 50%) as an off-white solid. $^1$H NMR (400 MHz, DMSO-d6) δ 10.79 (s, 1H), 7.49 (d, J=7.9 Hz, 1H), 7.40 (d, J=8.2 Hz, 1H), 7.22-7.10 (m, 2H), 7.01 (t, J=7.4 Hz, 1H), 4.09 (dd, J=10.4, 4.9 Hz, 1H), 3.75 (s, 3H), 2.68 (td, J=11.2, 10.5, 5.6 Hz, 1H), 2.56 (d, J=4.9 Hz, 1H), 2.22 (dd, J=12.5, 8.2 Hz, 1H), 2.11 (dd, J=13.4, 5.7 Hz, 1H); LC MS: ES+ 243.4.

Scheme 20
Synthesis of ethyl 1-methyl-5-phenyl-1H-pyrazole-3-carboxylate (20-2) and ethyl 1-methyl-3-phenyl-1H-pyrazole-5-carboxylate (20-3)

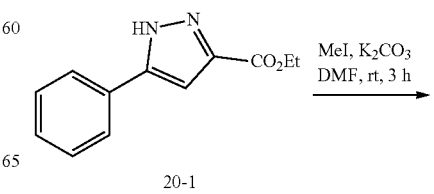

20-1

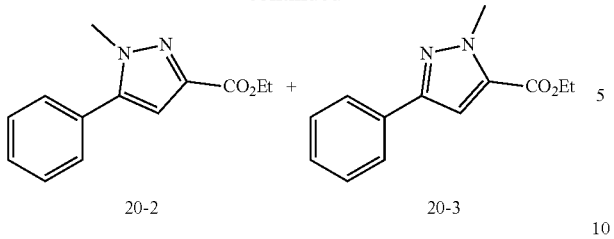

20-2            20-3

To a stirred solution of 20-1 (2.0 g, 9.24 mmol) in DMF (15.0 mL) was added $K_2CO_3$ (2.54 g, 18.4 mmol) and the reaction mixture was stirred at room temperature for 15 minutes. Methyl iodide (855 μL, 13.8 mmol) was added and the reaction mixture was stirred for 4 hours. TLC showed formation of two new spots. The reaction mixture was diluted with ethyl acetate and water. The layers were separated and the organic layer was washed with water, brine, and dried over sodium sulfate. The solution was concentrated and the crude material was purified by column chromatography (silica, 100-200, gradient 0%-30% ethyl acetate/hexane) to afford 20-2 (400 mg, 1.73 mmol, 19%) and 20-3 (1.8 g, 7.81 mmol, 85%) as colorless oils. $^1H$ NMR (20-2, polar fraction) (400 MHz, $CDCl_3$) δ; 7.47-7.39 (m, 5H), 6.84 (s, 1H), 4.42 (q, J=14.04, 7.0 Hz, 2H), 3.94 (s, 3H), 1.40 (t, J=7.08 Hz, 3H). $^1H$ NMR (20-3, non-polar fraction) (400 MHz, $CDCl_3$) δ; 7.78 (d, J=7.4 Hz, 2H), 7.39 (t, J=7.24 Hz, 2H), 7.32-7.29 (m, 1H), 7.11 (s, 1H), 4.36 (q, J=14.16, 7.08 Hz, 2H), 4.22 (s, 3H), 1.39 (t, J=7.0 Hz, 3H)

Scheme 21
Synthesis of 3-(1-methyl-5-phenyl-1H-pyrazol-3-yl)-piperidine-2,6-dione (Compound 30)

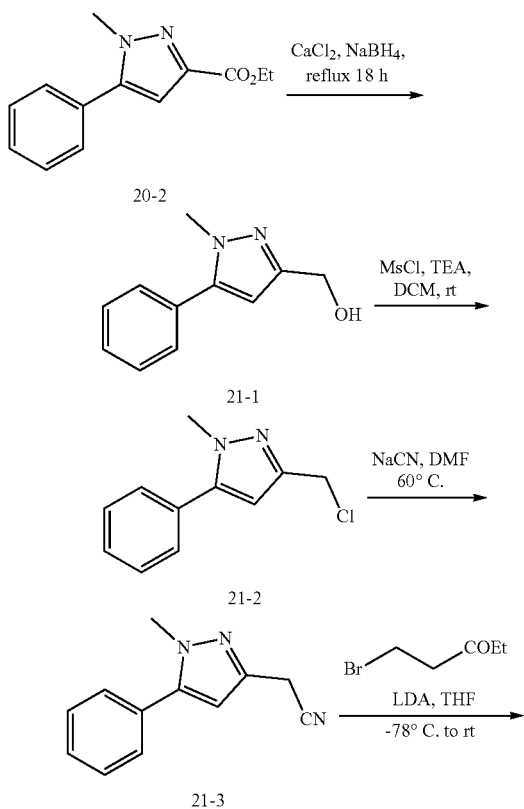

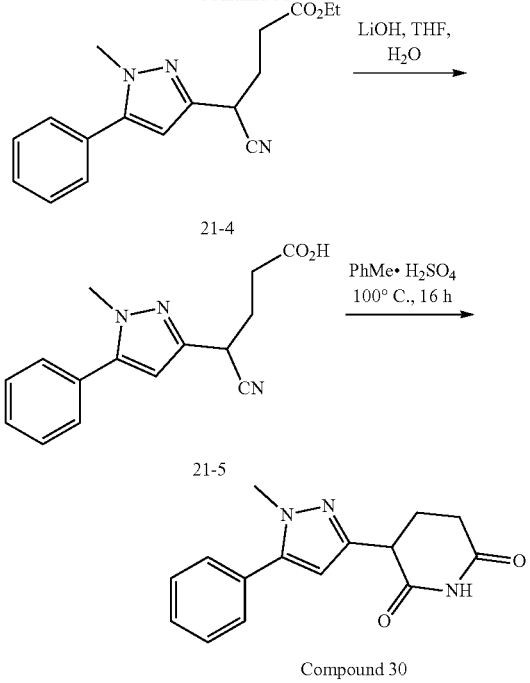

Compound 30

Synthesis of (1-methyl-5-phenyl-1H-pyrazol-3-yl)-methanol (21-1)

To a stirred solution of $CaCl_2$ (116 mg, 1.05 mmol) in THF (5.0 mL) was added $NaBH_4$ (79.8 mg, 2.11 mmol) and the mixture was stirred at room temperature for 1 hour. A solution of 20-2 (325.0 mg, 1.41 mmol) in THF (5.0 mL) was then added to the reaction mixture and the reaction mixture was subjected to reflux for 24 hours. The reaction was cooled and diluted with ice-water and ethyl acetate. The layers were separated and organic layer was washed with water, brine, dried over sodium sulfate, concentrated and the crude material was purified by column chromatography using (silica, 100-200, 0%-25% ethyl acetate/hexane) to afford 21-1 (250 mg, 1.32 mmol, 94%) as a white solid. LC MS: ES+ 189.0.

Synthesis of 3-chloromethyl-1-methyl-5-phenyl-1H-pyrazole (21-2)

To a stirred solution of 21-1 (570.0 mg, 3.02 mmol) in DCM (10.0 mL) was added triethyl amine (848 μL, 6.04 mmol), followed by mesyl chloride (350 μL, 4.53 mmol) at 0° C. The reaction mixture was stirred at room temperature for 16 hours and then diluted with DCM, washed with saturated aqueous $NaHCO_3$ solution, water, brine, dried over sodium sulfate and concentrated to afford 21-2 (624 mg, 3.01 mmol, 100%) as a brown gum. This material was used in the next step without any purification. LC MS: ES+ 206.8.

Synthesis of (1-methyl-5-phenyl-1H-pyrazol-3-yl)-acetonitrile (21-3)

To a stirred solution of 21-2 (624.0 mg, 3.01 mmol) in DMF (5.0 mL) was added NaCN (176 mg, 3.61 mmol) and the reaction mixture was heated at 60° C. for 16 hours. The reaction was diluted with water and ethyl acetate. The organic layer was separated and washed with water, brine, dried over sodium sulfate, concentrated and the crude mass was purified by column chromatography (0-25% ethyl acetate/hexane) to afford 21-3 (500 mg, 2.53 mmol, 84%) as a brown gum. LC MS: ES+ 198.2.

Synthesis of 4-cyano-4-(1-methyl-5-phenyl-1H-pyrazol-3-yl)-butyric acid ethyl ester (21-4)

A 25 ml two-neck round bottom flash was charged with 21-3 (300.0 mg, 1.52 mmol) in Tetrahydrofuran (10 mL) under argon and cooled to −78° C. Lithium diisopropylamide (1.52 mL, 3.04 mmol) was added to the reaction mixture dropwise while allowing the temperature to increase from −78° C. to room temperature over 1h. The reaction was again cooled to −78° C. and ethyl 3-bromopropanoate (194 μL, 1.52 mmol) was added to the reaction mixture. The reaction was gradually warmed to room temperature and stirring was continued for 3 hours. The reaction was quenched with saturated ammonium chloride solution, extracted with ethyl acetate, dried over sodium sulfate and concentrated under reduced pressure to obtain the crude which was purified by column chromatography (silica, gradient: 0-20% Ethyl acetate in Hexane) to afford 21-4 (56.3 mg, 189 μmol, 12%) as a yellow gum. LC MS: ES+ 298.2.

Synthesis of 4-cyano-4-(1-methyl-5-phenyl-1H-pyrazol-3-yl)-butyric acid (21-5)

To a 25 mL round bottom flask was added 21-4 (230.0 mg, 773 μmol) and THF: $H_2O$ (5 mL) and the solution was cooled. To the solution was added lithium hydroxide monohydrate (32.4 mg, 773 μmol) and the reaction was stirred at room temperature for 2.5 hrs. The solvent was first evaporated under reduced pressure, then water and ethyl acetate was added and the organic and aqueous fractions were separated. The aqueous fraction was then acidified with 2N HCl to pH 3 and the desired compound was then extracted with ethyl acetate, washed with water and dried over anhydrous sodium sulfate and evaporated under reduced pressure to obtain 21-5 (46.1 mg, 171 μmol, 22%) as an off white solid. LC MS: ES+ 270.1.

Synthesis of 3-(1-methyl-5-phenyl-1H-pyrazol-3-yl)-piperidine-2,6-dione (Compound 30)

To a 10 mL round bottom flask was added 4-cyano-4-(1-methyl-5-phenyl-1H-pyrazol-3-yl)butanoic acid 21-5 (54.0 mg, 200 μmol) followed by the addition of toluene (2.0 mL) and sulphuric acid (10.6 μL, 200 μmol) and the reaction was refluxed at 110° C. for 7 hrs. TLC showed complete consumption of the starting material and formation of the desired spot at if 0.4 in 5% MeOH-DCM. The reaction mixture was diluted with ethylacetate, washed with sodium bicarbonate solution, water, brine solution and the organic and aqueous fractions were separated. The organic fraction was then dried over anhydrous sodium sulphate and evaporated under reduced pressure to obtain the desired compound which was then washed with ether and pentane to obtain 3-(1-methyl-5-phenyl-1H-pyrazol-3-yl)piperidine-2,6-dione Compound 30 (25.0 mg, 92.8 μmol, 46.4%) as an off-white solid. $^1$H NMR (400 MHz, DMSO-d$_6$) δ 10.79 (s, 1H), 7.56-7.45 (m, 4H), 7.48-7.39 (m, 1H), 6.33 (s, 1H), 3.88 (t, J=6.9 Hz, 1H), 3.81 (s, 3H), 2.58 (td, J=6.4, 6.0, 2.9 Hz, 2H), 2.16 (q, J=6.7 Hz, 2H); LC MS: ES+ 270.3.

Scheme 22
Synthesis of 3-(1-methyl-3-phenyl-1H-pyrazol-5-yl)piperidine-2,6-dione (Compound 31)

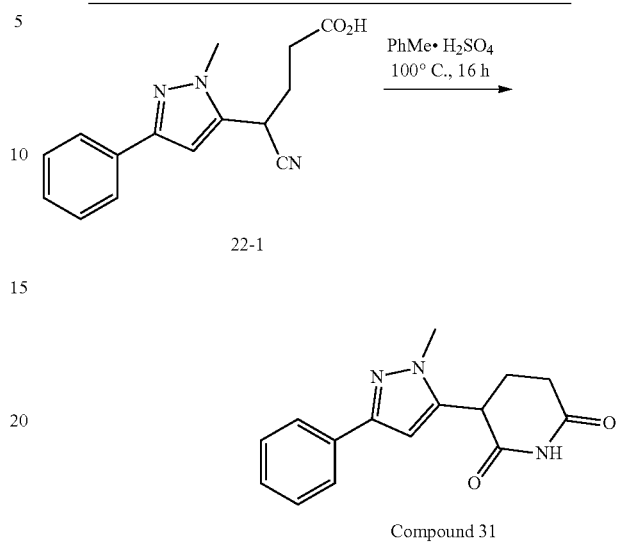

To a stirred solution of 4-cyano-4-(1-methyl-3-phenyl-1H-pyrazol-5-yl)butanoic acid (22-1, prepared from 20-3 by the general procedures in Scheme 21) (35 mg, 129 μmol) in Toluene (2.0 mL) was added $H_2SO_4$ (7.50 μL, 141 μmol) and the reaction mixture was heated at 100° C. for 5 hours. TLC showed formation of a new spot (Rf-0.4 in 5% MeOH/DCM). The reaction was diluted with saturated aqueous $NaHCO_3$ and ethyl acetate. The organic layer was separated and washed with water and brine, dried over sodium sulfate and then concentrated. The resultant solid was triturated with pentane to afford 3-(1-methyl-3-phenyl-1H-pyrazol-5-yl)piperidine-2,6-dione (Compound 31) (15.0 mg, 55.7 μmol, 43.2%) as an off-white solid. $^1$H NMR (400 MHz, DMSO-d6) δ 10.95 (s, 1H), 7.75 (d, J=7.4 Hz, 1H), 7.38 (t, J=7.5 Hz, 2H), 7.32-7.22 (m, 2H), 6.60 (s, 1H), 4.22 (dd, J=12.3, 4.8 Hz, 1H), 3.81 (s, 3H), 2.72 (ddd, J=17.6, 12.4, 5.4 Hz, 1H), 2.61 (dt, J=17.3, 4.1 Hz, 1H), 2.31 (qd, J=12.7, 4.6 Hz, 1H), 2.16 (dt, J=13.0, 4.4 Hz, 1H); LC MS: ES+ 270.3.

Scheme 23
Synthesis of 3-(o-tolyl)piperidine-2,6-dione (Compound 32)

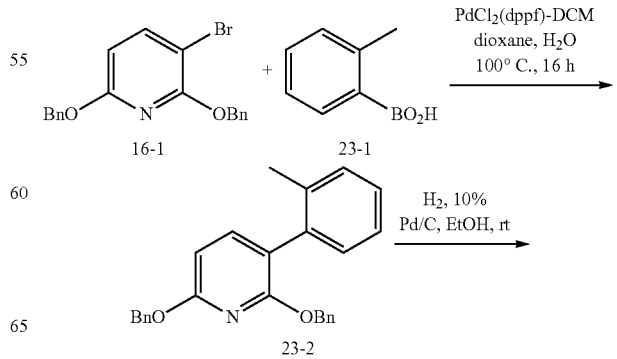

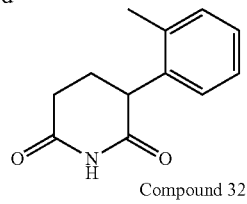

Compound 32

Synthesis of 2,6-bis(benzyloxy)-3-(o-tolyl)pyridine (23-2)

A stirred mixture of 16-1 (170 mg, 459 μmol), 23-1 (124.8 mg 918 μmol) and Potassium phosphate (211 mg, 918 μmol) in Dioxane:water (6:1, 7 mL) was degassed with argon for 10 minutes. PdCl₂dppf.DCM (38 mg, 45.9 μmol) was added and stirred the reaction was stirred at 110° C. for 16 hours, cooled to room temperature and then filtered through a short bed of celite. The filtrate was diluted with Ethyl acetate, washed with water, dried over anhydrous Na₂SO₄ and concentrated under reduced pressure. The crude mass was purified by column chromatography (silica, gradient: 0-5% Ethyl acetate in Hexane) to afford 23-2 (160 mg, 419 μmol, 91%) as a sticky solid. LC MS: ES+ 382.2.

Synthesis of 3-(o-tolyl)piperidine-2,6-dione (Compound 32)

To a solution of 2,6-bis(benzyloxy)-3-(o-tolyl)pyridine (23-2) (200 mg, 524 μmol) in EtOH (10 mL) under inert atmosphere was added Pd/C (60 mg, 563 μmol) and reaction mixture was stirred at room temperature under hydrogen atmosphere overnight. Reaction progress was monitored by TLC and LC-MS. Upon completion, the reaction mixture was filtered through celite bed and the mother liquor was evaporated to dryness. The crude material was submitted for preparative HPLC to yield 3-(o-tolyl)piperidine-2,6-dione (Compound 32) (40.0 mg, 196 μmol, 38%) as a violet solid. ¹H NMR (400 MHz, DMSO-d6) δ 10.83 (s, 1H), 7.93 (d, J=7.9 Hz, 1H), 7.48 (d, J=3.4 Hz, 1H), 7.05 (d, J=8.0 Hz, 1H), 6.45 (d, J=3.5 Hz, 1H), 4.07 (dd, J=9.2, 5.2 Hz, 1H), 3.76 (s, 3H), 2.63 (t, J=6.5 Hz, 2H), 2.41-2.27 (m, 1H), 2.24-2.11 (m, 1H).

Scheme 24
Synthesis of 3-(1-methyl-1H-pyrazol-3-yl)piperidine-2,6-dione (Compound 33)

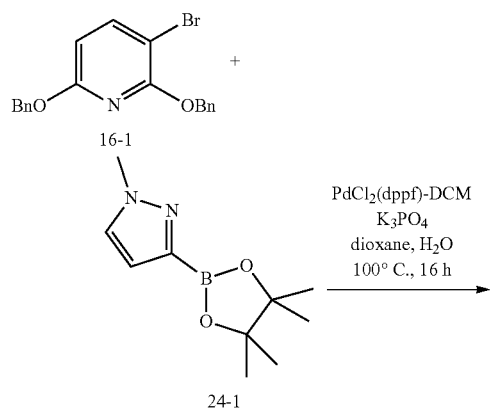

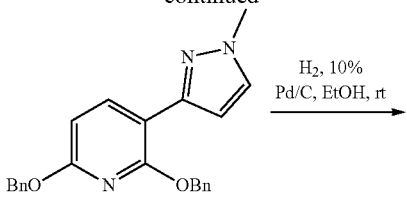

24-2

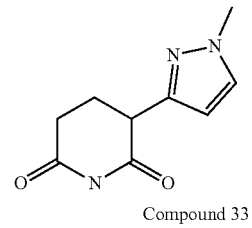

Compound 33

Synthesis of 2,6-bis(benzyloxy)-3-(1-methyl-1H-pyrazol-3-yl)pyridine (24-2)

To a stirred solution of 2,6-bis(benzyloxy)-3-bromopyridine (16-1) (177 mg, 480 μmol), 1-methyl-3-(4,4,5,5-tetramethyl-1,3,2-dioxaborolan-2-yl)-1H-pyrazole 24-1 (100.0 mg, 480 μmol) and potassium phosphate (221 mg, 960 μmol) in water: dioxane (10 mL) was degassed with argon for 10 minute. PdCl₂(dppf)-DCM (39.1 mg, 48.0 μmol) was added to above reaction mixture and the solution was again purged with argon and refluxed for 16 hour at 100° C. After completion of the reaction was observed by TLC (Rf=0.5 in 30% EtOH/Hexane), the reaction mixture was filtered through celite and concentrated. The residue was again dissolved in EtOAc (50 mL), washed with water, brine and evaporated. The crude residue was purified by combi flash chromatography (4 g Isco gold, hexane/EtOAc 70-30%) to give 2,6-bis(benzyloxy)-3-(1-methyl-1H-pyrazol-3-yl)pyridine 24-2 (120 mg, 323 μmol, 67.4%) as a white gummy solid. ¹H NMR (400 MHz, DMSO-d6) δ 8.17 (d, J=8.2 Hz, 1H), 7.65 (d, J=1.9 Hz, 1H), 7.46-7.42 (m, 4H), 7.39-7.33 (m, 4H), 7.33-7.31 (m, 2H), 6.61 (d, J=2.1 Hz, 1H), 6.51-6.49 (m, 1H), 5.46 (s, 2H), 5.37 (s, 2H), 3.85 (s, 3H).

Synthesis of 3-(1-methyl-1H-pyrazol-3-yl)piperidine-2,6-dione (Compound 33)

To a stirred solution of 2,6-bis(benzyloxy)-3-(1-methyl-1H-pyrazol-3-yl)pyridine 24-2 (120 mg, 323 μmol) in ethanol (5 mL) added Pd on C (10 wt %, 342 mg, 1.61 mmol) and the solution was purged with argon for 10 minutes. After that a hydrogen gas balloon was added to the vessel and reaction mixture was stirred at rt for 6 hours. TLC showed an new spot formed (Rf-0.3 in 5% MeOH/DCM) and starting was fully consumed. The reaction mixture was filtered through a celite bed and evaporated. The product was purified by washing with pentane to give 3-(1-methyl-1H-pyrazol-3-yl)piperidine-2,6-dione (Compound 33) (60.0 mg, 310 μmol, 96.1%) as an off-white solid. ¹H NMR (400 MHz, DMSO-d₆) δ 10.75 (s, 1H), 7.60 (d, J=2.2 Hz, 1H), 6.12 (d, J=2.2 Hz, 1H), 3.83-3.80 (m, 1H), 3.78 (s, 3H), 2.56-2.54 (m, 2H), 2.10-2.09 (m, 2H); LC MS: ES+ 194.2.

Scheme 25
Synthesis of 2,6-bis(benzyloxy)-3-(4,4,5,5-tetramethyl-1,3,2-dioxaborolan-2yl) pyridine (25-1)

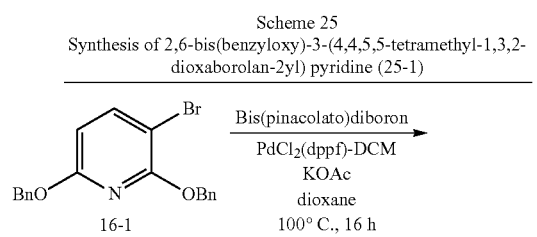

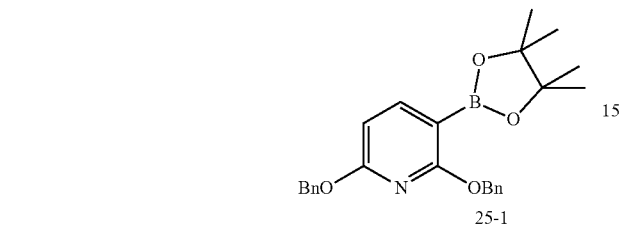

To a stirred solution of 16-1 (5.0 g, 13.5 mmol) in Dioxane (20 mL) was added 4,4,4',4',5,5,5',5'-octamethyl-2,2'-bi(1,3,2-dioxaborolane) (5.12 g, 20.2 mmol) and KOAc (2.64 g, 27.0 mmol). The reaction mixture was degassed with argon for 10 minutes. PdCl2(dppf).DCM (1.10 g, 1.35 mmol) was added and the resulting mixture was stirred at 100° C. for 16 hours. The reaction was then cooled to room temperature and filtered through a short bed of celite. The filtrate was diluted with Ethyl acetate, washed with water, dried over anhydrous $Na_2SO_4$ and concentrated under reduced pressure. The crude mass was purified by column chromatography (silica, gradient: 0-5% Ethyl acetate in Hexane) to afford 25-1 (3.5 g, 62%) as a pale yellow solid.

Scheme 26
Synthesis of 3-(6-methoxypyridin-2-yl)piperidine-2,6-dione (Compound 34)

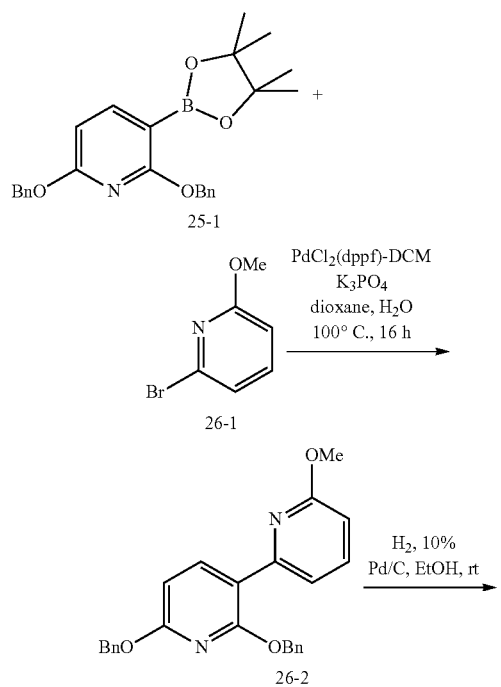

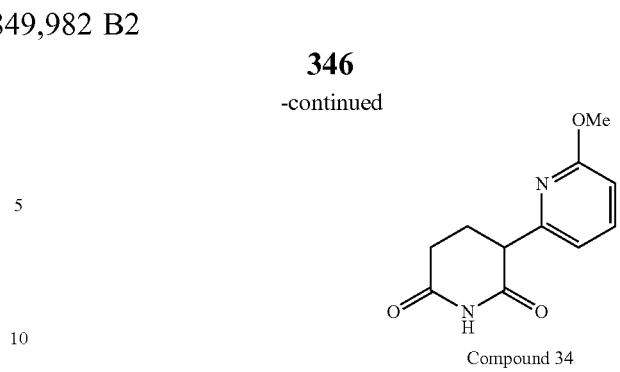

Compound 34

Synthesis of 2',6'-bis(benzyloxy)-6-methoxy-2,3'-bipyridine (26-2)

A stirred solution of 2-bromo-6-methoxypyridine 26-1 (150 mg, 797 µmol), 2,6-bis(benzyloxy)-3-(4,4,5,5-tetramethyl-1,3,2-dioxaborolan-2-yl)pyridine 25-1 (496 mg, 1.19 mmol) and Potassium phosphate (366 mg, 1.59 mmol) in water: dioxane (10 mL) was degassed with argon for 10 minutes. PdCl2dppf.DCM (65.0 mg, 79.7 µmol) was added to above reaction mixture and the solution was again purged with argon and refluxed for 16 hours at 100° C. Upon completion of reaction as monitored by TLC (Rf=0.5 in 20% EtOH/Hexane), the reaction mixture was filtered through celite and the filtrate was evaporated to dryness. The residue was again dissolved in EtOAc (50 mL), washed with water and brine and evaporated. The product was purified by combi flash chromatography (4 g Isco gold, hexane/EtOAc 80-20%) to give 2',6'-bis(benzyloxy)-6-methoxy-2,3'-bipyridine (26-2) (125 mg, 313 µmol, 39.4%) as a white gummy solid. LC MS: ES+ 393.3.

Synthesis of 3-(6-methoxypyridin-2-yl)piperidine-2,6-dione (Compound 34)

To a stirred solution of 2',6'-bis(benzyloxy)-6-methoxy-2,3'-bipyridine (26-2) (120 mg, 301 µmol) in ethanol (7 mL) was added Pd—C (10 wt %, 31.9 mg, 301 µmol) and the reaction was purged with argon for 10 minutes. After that a hydrogen gas balloon was added and reaction mixture stirred at rt for 3 hours. TLC showed that new spots were formed (Rf-0.3 in 5% MeOH/DCM) and the starting material was fully consumed. The reaction mixture was filtered through a celite bed and the filtrate was evaporated. The product was purified by silica gel flash chromatography (4 g Isco gold, DCM/MeOH 0-10%) followed by prep HPLC purification to obtained 3-(6-methoxypyridin-2-yl)piperidine-2,6-dione (Compound 34) (14.0 mg, 63.5 µmol, 21.1%) as a white solid. $^1$H NMR (400 MHz, DMSO-d6) δ 10.85 (s, 1H), 7.68 (t, J=7.8 Hz, 1H), 6.94 (d, J=7.2 Hz, 1H), 6.72 (d, J=8.2 Hz, 1H), 3.93 (dd, J=8.6, 5.3 Hz, 1H), 3.78 (s, 3H), 2.58 (d, J=6.6 Hz, 2H), 2.23-2.11 (m, 2H); LC MS: ES+ 221.2.

Scheme 27
Synthesis of 3-(1-Methyl-1H-pyrrolo[2,3-b]pyridin-6-yl)-piperidine-2,6-dione (Compound 35)

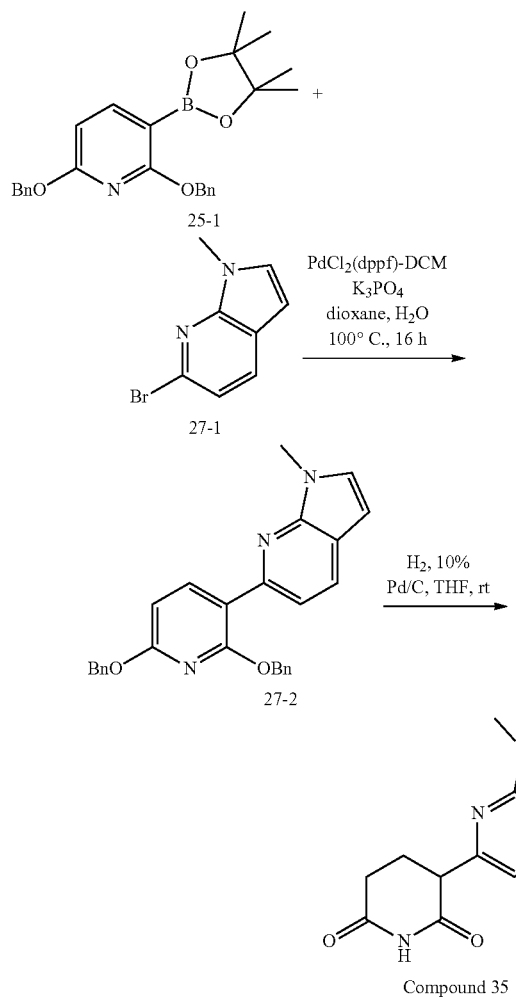

Compound 35

Synthesis of 6-(2,6-Bis-benzyloxy-pyridin-3-yl)-1-methyl-1H-pyrrolo[2,3-b]pyridine (27-2)

To a stirred solution of 6-bromo-1-methyl-1H-pyrrolo[2,3-b]pyridine (27-1) (500.0 mg, 2.36 mmol) and 2,6-bis(benzyloxy)-3-(4,4,5,5-tetramethyl-1,3,2-dioxaborolan-2-yl)pyridine 25-1 (1.18 g, 2.82 mmol) in a sealed tube in dioxane (5 mL) and water (1.5 mL) was added $K_3PO_4$ (1.08 g, 4.69 mmol) and it was degassed for 10 min and then $PdCl_2$(dppf)-DCM (0.2 g, 244 μmol) and again degassed for 5 min. After degassing was complete, the sealed tube was closed with a teflon cap and reaction mixture was stirred at 80° C. for 16 h. After reaction completion as checked by TLC, the reaction mixture was filtered through celite and the organic layer was diluted with ethyl acetate, washed with water and brine, and the organics were dried over anhydrous sodium sulphate, filtered and concentrated under reduced pressure. The crude residue was purified by column chromatography eluted with 0 to 20% ethyl acetate in hexane to provide 6-(2,6-Bis-benzyloxy-pyridin-3-yl)-1-methyl-1H-pyrrolo[2,3-b]pyridine (27-2) (300 mg, 711 umol, 30% yield). $^1$H NMR (400 MHz, DMSO-$d_6$) δ 8.36 (d, J=8.2 Hz, 1H), 7.94 (d, J=8.2 Hz, 1H), 7.74 (d, J=8.2 Hz, 1H), 7.51 (d, J=3.4 Hz, 1H), 7.46-7.44 (m, 4H), 7.40-7.30 (m, 6H), 6.62 (d, J=8.2 Hz, 1H), 6.44 (d, J=3.4 Hz, 1H), 5.50 (s, 2H), 5.41 (s, 2H), 3.84 (s, 3H); LC MS: ES+ 422.4.

Synthesis of 3-(1-Methyl-1H-pyrrolo[2,3-b]pyridin-6-yl)-piperidine-2,6-dione (Compound 35)

To a stirred solution of 6-(2,6-bis(benzyloxy)pyridin-3-yl)-1-methyl-1H-pyrrolo[2,3-b]pyridine (27-2) (0.200 g, 474 μmol) in THF (20 mL) was added Pd/C (0.100 g, 943 μmol). Hydrogen gas was bubbled through this solution at 1 atm, rt for 2 h. After completion of the reaction, as checked by TLC, the reaction mixture was filtered through a celite bed and the organic layer was concentrated under reduced pressure. The crude compound which was purified by prep HPLC to provide 3-(1-methyl-1H-pyrrolo[2,3-b]pyridin-6-yl)piperidine-2,6-dione (Compound 35) (15.0 mg, 61.6 μmol, 13.0%) as a grey solid. $^1$H NMR (400 MHz, DMSO-$d_6$) δ 10.83 (s, 1H), 7.93 (d, J=7.9 Hz, 1H), 7.48 (d, J=3.4 Hz, 1H), 7.05 (d, J=8.0 Hz, 1H), 6.45 (d, J=3.5 Hz, 1H), 4.07 (dd, J=9.2, 5.2 Hz, 1H), 3.76 (s, 3H), 2.63 (t, J=6.5 Hz, 2H), 2.41-2.27 (m, 1H), 2.24-2.11 (m, 1H); LC MS: ES+ 244.1.

Scheme 28
Synthesis of 3-(1-Methyl-1H-pyrrolo[2,3-b]pyridin-6-yl)-piperidine-2,6-dione (Compound 36)

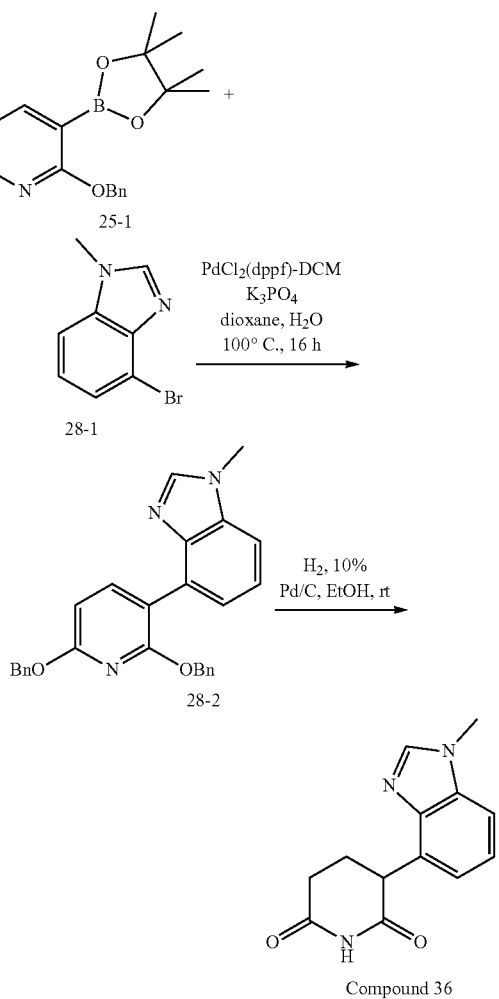

Compound 36

Synthesis of 4-(2,6-Bis-benzyloxy-pyridin-3-yl)-1-methyl-1H-benzoimidazole (28-2)

A stirred solution of 4-bromo-1-methyl-1H-benzo[d]imidazole (28-1) (100 mg, 473 µmol) 2,6-bis(benzyloxy)-3-(4,4,5,5-tetramethyl-1,3,2-dioxaborolan-2-yl)pyridine 25-1 (295 mg, 709 µmol) and Potassium phosphate (217 mg, 946 µmol) in water: dioxane (10 mL) was degassed with argon for 10 minutes. PdCl$_2$(dppf)-DCM (38.6 mg, 47.3 µmol) was added and the solution was again purged with argon and then refluxed for 16 hours at 100° C. After completion of the reaction, as monitored by TLC (Rf=0.5 in 10% EtOH/Hexane), the reaction mixture was filtered through celite and the filtrate was evaporated. The residue was again dissolved in EtOAc (50 mL), washed with water and brine and evaporated to dryness. The crude was purified by combi flash chromatography (12 g Isco gold, hexane/EtOAc 95-5%) to give 4-(2,6-bis(benzyloxy)pyridin-3-yl)-1-methyl-1H-benzo[d]imidazole (28-2) (110 mg, 55.2%) as a white gummy solid. LC MS: ES+ 422.0.

Synthesis of 3-(1-Methyl-1H-pyrrolo[2,3-b]pyridin-6-yl)-piperidine-2,6-dione (Compound 36)

To a stirred solution of 4-(2,6-bis(benzyloxy)pyridin-3-yl)-1-methyl-1H-benzo[d]imidazole (28-2) (110 mg, 260 µmol) in ethanol (5 mL) was added Pd—C (96.3 mg, 909 µmol) and the solution was purged with argon for 10 minutes. After that hydrogen gas (~15 psi) passed through balloon, and reaction mixture stirred at rt for 6 hours. TLC showed a new spot formed (Rf-0.3 in 5% MeOH/DCM) and the starting material was fully consumed. The reaction mixture was filtered through a celite bed and the filtrate was evaporated. The crude product was purified by washing with pentane to give 3-(1-methyl-1H-benzo[d]imidazol-4-yl)piperidine-2,6-dione (Compound 36) (34.0 mg, 139 µmol, 53.7%) as an off-white solid. $^1$H NMR (400 MHz, DMSO-d$_6$) δ 10.82 (s, 1H), 8.13 (s, 1H), 7.48 (d, J=8.1 Hz, 1H), 7.22 (t, J=7.7 Hz, 1H), 7.05 (d, J=7.3 Hz, 1H), 4.24 (d, J=10.2 Hz, 1H), 3.83 (s, 3H), 2.74-2.67 (m, 1H), 2.56-2.50 (m, 2H), 2.04-2.03 (m, 1H). LC MS: ES+ 244.1.

Scheme 29
Synthesis of 3-(1-Methyl-1H-indazol-3-yl)-piperidine-2,6-dione (Compound 37), Compound 38 and Compound 39

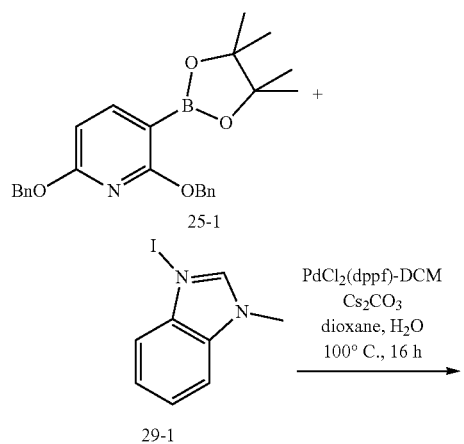

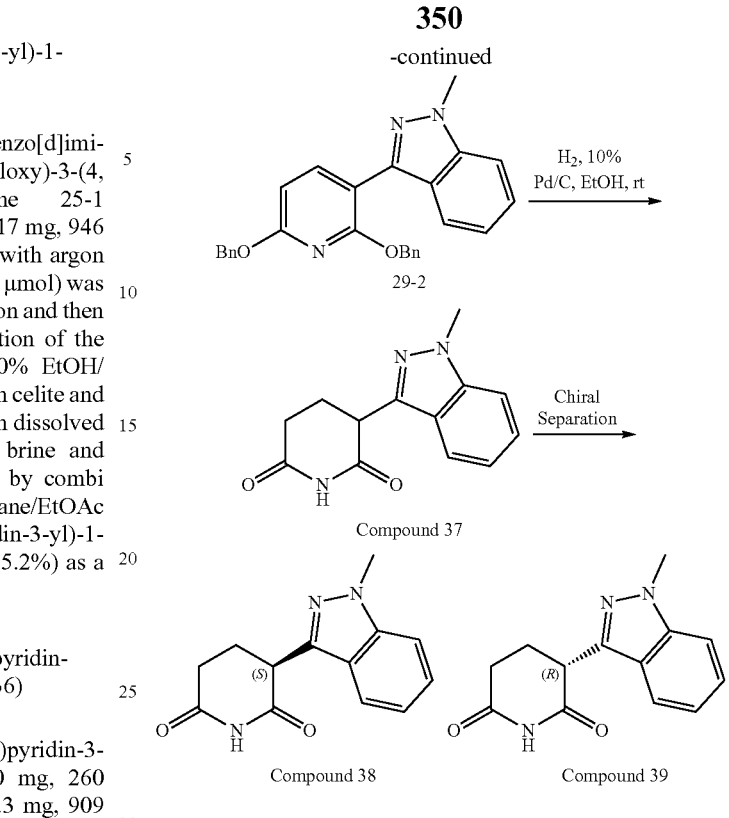

Synthesis of 3-(2,6-Bis-benzyloxy-pyridin-3-yl)-1-methyl-1H-indazole (29-2)

To a stirred solution of 29-1 (160.0 mg, 620 µmol) in dioxane:water (4:1)(10.0 mL) was added 25-1 (388 mg, 930 µmol) and Cs$_2$CO$_3$ (606 mg, 1.86 mmol) and the reaction mixture was degassed for 15 minutes. PdCl$_2$(dppf)-DCM (75.9 mg, 93.0 µmol) was added and the reaction mixture was heated at 100° C. for 16 hours. The reaction was cooled, filtered through a celite bed, washed with ethyl acetate. The organic layer was separated, dried over sodium sulfate and concentrated. The crude material was purified by column chromatography using (silica, gradient: 0-7% Ethyl acetate in Hexane) to afford 29-2 (220 mg, 521 µmol, 84%) as a colorless gum. LC MS: ES+ 422.1.

Synthesis of 3-(1-Methyl-1H-indazol-3-yl)-piperidine-2,6-dione (Compound 37)

A stirred solution of 29-2 (220.0 mg, 521 µmol) in ethanol (10.0 mL) was degassed for 15 minutes. Then 10% Pd—C (55.4 mg, 521 µmol) was added to the reaction mixture and the reaction mixture was subjected to hydrogenation under a hydrogen balloon for 4 hours. The reaction was filtered through a celite bed and the filtrate was concentrated. The crude material was purified by column chromatography using (silica, gradient: 0-1% Methanol in DCM) to afford Compound 37 (65.0 mg, 267 µmol, 52%) as an off-white solid. $^1$H NMR (400 MHz, DMSO-d$_6$) δ 10.90 (s, 1H), 7.72 (d, J=8.2 Hz, 1H), 7.60 (d, J=8.5 Hz, 1H), 7.39 (t, J=7.4 Hz, 1H), 7.12 (t, J=7.5 Hz, 1H), 4.38 (dd, J=9.8, 5.0 Hz, 1H), 4.00 (s, 3H), 2.67-2.55 (m, 2H), 2.38 (ddd, J=13.9, 9.6, 4.9 Hz, 1H), 2.24-2.12 (m, 1H); LC MS: ES+ 244.3.

Chiral Separation of Compound 37 to Provide Compound 38 and Compound 39:

Preparative Chiral HPLC was done using Waters auto purification instrument in normal phase. Column name: Chiralpak ID (250×20 mm, 5μ), Flow rate: 16.0 ml/min, Mobile phase: 100% Acetonitrile, Total runtime: 15 min, Sample diluents: DCM+Acetonitrile. Elution order: Compound 38 and then Compound 39.

Scheme 30: Synthesis of 3-(1-Methyl-2-oxo-1,2-dihydro-quinolin-3-yl)-piperidine-2,6-dione (Compound 40):

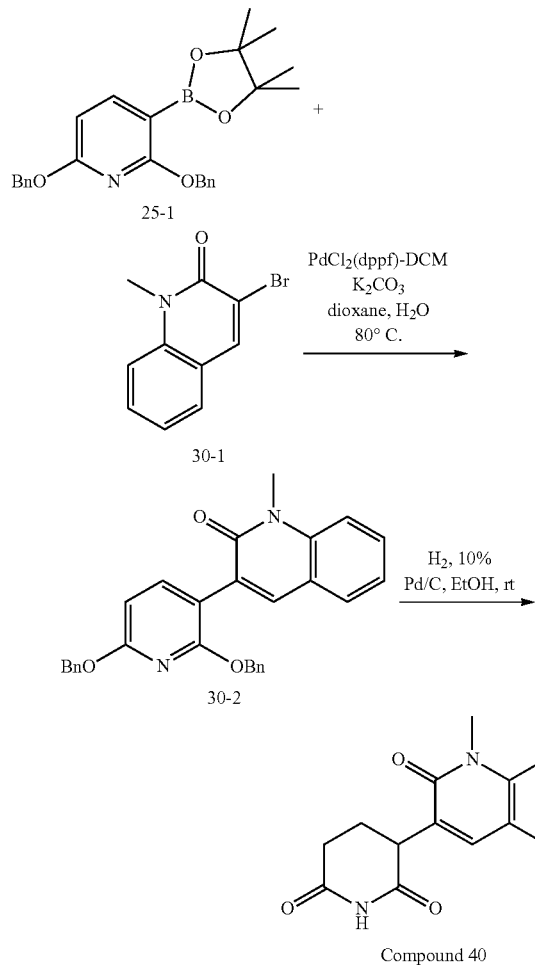

Synthesis of 3-(2,6-Bis-benzyloxy-pyridin-3-yl)-1-methyl-1H-quinolin-2-one (30-2)

A stirred solution of 2,6-bis(benzyloxy)-3-(4,4,5,5-tetramethyl-1,3,2-dioxaborolan-2-yl)pyridine 25-1 (2.19 g, 5.25 mmol) and 3-bromo-1-methylquinolin-2(1H)-one (30-1) (500.0 mg, 2.10 mmol) in dioxane/water (30 mL) in a sealed tube was degassed for 10 minutes under argon atmosphere. PdCl$_2$(dppf)-DCM (153 mg, 210 μmol) was added and the reaction then heated to 80° C. for 10 h. TLC was checked in 30% ethyl acetate/hexane which showed the complete consumption of starting material and formation of the desired spot at rf 0.4 in 30% ethylacetate-hexane. The reaction mixture was diluted with ethyl acetate and washed with water. The layers were separated and the organic layer was concentrated under reduced pressure and purified using combiflash and the desired compound was eluted in 50% ethyl acetate/hexane and concentrated to afford 3-(2,6-bis(benzyloxy)pyridin-3-yl)-1-methylquinolin-2(1H)-one (30-2) (729 mg, 1.62 mmol, 77.4%) as an off-white solid. LC MS: ES+ 448.9.

Synthesis of 3-(1-Methyl-2-oxo-1,2-dihydro-quinolin-3-yl)-piperidine-2,6-dione (Compound 40)

A 50 ml round bottom flask was charged with 3-(2,6-bis(benzyloxy)pyridin-3-yl)-1-methylquinolin-2(1H)-one (30-2) (800.0 mg, 1.78 mmol) and ethanol (10 mL). The solution was degassed for 15 minutes under argon atmosphere, palladium on charcoal (189 mg, 178 μmol) was added and the reaction was continued for 2 hrs in the presence of a hydrogen balloon. TLC was checked, which showed complete consumption of starting material and formation of the desired spot at rf 0.3 in 5% MeOH-DCM. The reaction mixture was filtered through a celite bed and evaporated under reduced pressure. The crude residue was purified by flash chromatography to afford 3-(1-methyl-2-oxo-1,2-dihydroquinolin-3-yl)piperidine-2,6-dione (Compound 40) (14.0 mg, 51.7 μmol, 2.91%) as an off-white solid. $^1$H NMR (400 MHz, DMSO-d6) δ 10.78 (s, 1H), 7.88 (s, 1H), 7.71 (d, J=7.48 Hz, 1H), 7.64-7.60 (m, 1H), 7.53 (d, J=8.44 Hz, 1H), 7.29 (t, J=7.32 Hz, 1H), 3.89 (dd, J=11.84, J$_2$=4.68 Hz, 1H), 3.63 (s, 3H), 2.73-2.66 (m, 1H), 2.49 (m, 1H), 2.39-2.32 (m, 1H), 1.91 (m, 1H), 1.70 (br s, 1H); LC MS: ES+ 271.0.

Scheme 31
Synthesis of 3-(2-Methyl-3-oxo-2,3-dihydro-1H-isoindol-5-yl)-piperidine-2,6-dione (Compound 41)

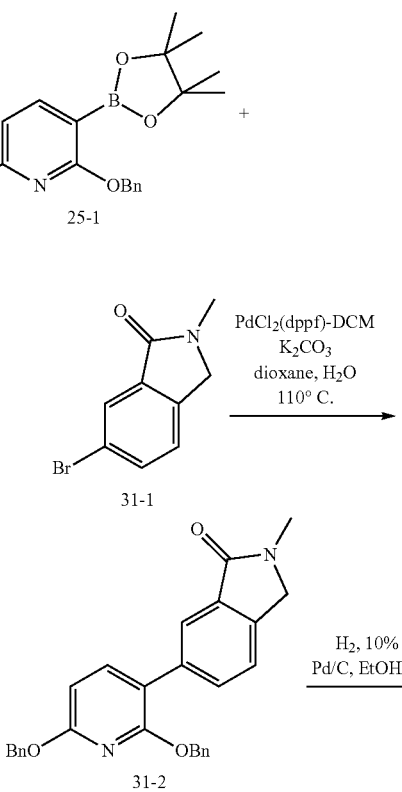

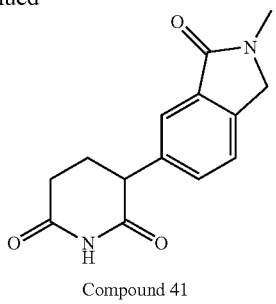

Compound 41

Synthesis of 6-(2,6-Bis-benzyloxy-pyridin-3-yl)-2-methyl-2,3-dihydro-isoindol-1-one (31-1)

A stirred solution of 2,6-bis(benzyloxy)-3-(4,4,5,5-tetramethyl-1,3,2-dioxaborolan-2-yl)pyridine 25-1 (2.19 g, 5.25 mmol) and 6-bromo-2-methylisoindolin-1-one (31-1) (474 mg, 2.10 mmol) in dioxane/water (30 mL), in a sealed tube, was degassed for 10 minutes under an argon atmosphere. $PdCl_2$(dppf)-DCM (153 mg, 210 µmol) was added and the reaction was heated to 80° C. for 10 h. TLC was checked in 30% ethyl acetate/hexane, which showed the complete consumption of starting material and formation of the desired spot at rf 0.4 in 30% ethylacetate-hexane. The reaction mixture was diluted with ethyl acetate, washed with water. The layers were separated and the organic layer was concentrated under reduced pressure. The crude residue was purified using combiflash (50% ethyl acetate/hexane) and concentrated to afford 6-(2,6-Bis-benzyloxy-pyridin-3-yl)-2-methyl-2,3-dihydro-isoindol-1-one (31-1) (725 mg, 1.66 mmol, 79% yield). LC MS: ES+ 437.2.

Synthesis of 3-(2-Methyl-3-oxo-2,3-dihydro-1H-isoindol-5-yl)-piperidine-2,6-dione (Compound 41)

A 50 ml round bottom flask was charged with 6-(2,6-Bis-benzyloxy-pyridin-3-yl)-2-methyl-2,3-dihydro-isoindol-1-one (31-1) (725 mg, 1.66 mmol) and ethanol (10 mL). The resulting solution was degassed for 15 minutes under an argon atmosphere, palladium on charcoal (189 mg, 178 µmol) was added and the reaction was continued for 2 hrs in presence of a hydrogen balloon. TLC was checked, which showed complete consumption of starting material and the formation of the desired spot at rf 0.3 in 5% MeOH-DCM. The reaction mixture was filtered through a celite bed and evaporated under reduced pressure. The crude residue was purified by flash chromatography to afford 3-(2-Methyl-3-oxo-2,3-dihydro-1H-isoindol-5-yl)-piperidine-2,6-dione (Compound 41) (30 mg, 0.116 mmol, 7% yield) as an off-white solid. $^1$H NMR (400 MHz, DMSO-d6) δ 10.87 (s, 1H), 7.54-7.51 (m, 2H), 7.44-7.43 (m, 1H), 4.44 (s, 2H), 4.01-3.99 (m, 2H), 3.07 (s, 3H), 2.72-2.67 (m, 1H), 2.43 (m, 1H), 2.32-2.27 (m, 1H), 2.05 (m, 1H); LC MS: ES+ 259.4.

Scheme 32
Synthesis of 4-(2,6-Dioxo-piperidin-3-yl)-1,3-dihydro-isoindole-2-carboxylic acid tert-butyl ester (Compound 42) and 3-(2,3-Dihydro-1H-isoindol-4-yl)-piperidine-2,6-dione hydrochloride (Compound 43)

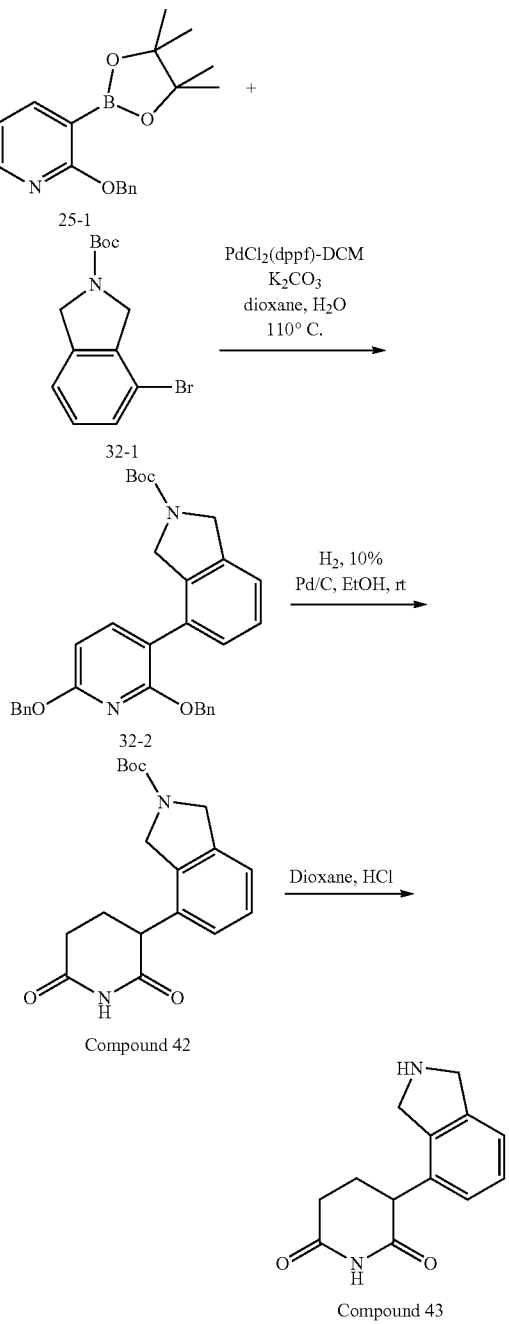

Synthesis of 4-(2,6-bis-benzyloxy-pyridin-3-yl)-1,3-dihydro-isoindole-2-carboxylic acid tert-butyl ester (32-2)

To a stirred solution of tert-butyl 5-bromoisoindoline-2-carboxylate (32-1) (300 mg, 1.00 mmol) in dioxane and water (2.5 ml), was added 2,6-bis(benzyloxy)-3-(4,4,5,5-tetramethyl-1,3,2-dioxaborolan-2-yl)pyridine (25-1) (459 mg, 1.10 mmol) and potassium phosphate (636 mg, 3.00 mmol) at room temperature. The reaction mixture was purged with argon for 5 minutes followed by addition of Pd(dppf)Cl$_2$-DCM (40.8 mg, 50.0 µmol) at room temperature. The reaction mixture was heated to reflux overnight. After completion of reaction (monitored by TLC Rr=0.4 in 20% ea/hexane and LCMS), the reaction mixture was filtered and concentrated. The crude residue was purified by flash column (elution with 15% EtOAc/Hexanes) to afford tert-butyl 5-(2,6-bis(benzyloxy)pyridin-3-yl)isoindoline-2-carboxylate (32-2) (330 mg, 648 µmol, 64.9%) as a gummy liquid. $^1$H NMR (400 MHz, DMSO-d6) δ 7.65-7.63 (m, 1H), 7.45-7.44 (m, 2H), 7.40-7.38 (m, 2H), 7.36-7.21 (m, 7H), 7.19 (m, 1H), 6.54 (m, 1H), 5.37 (br s, 4H), 4.63-4.60 (m, 2H), 4.43 (br s, 2H), 1.44-1.39 (m, 9H).

Synthesis of 4-(2,6-dioxo-piperidin-3-yl)-1,3-dihydro-isoindole-2-carboxylic acid tert-butyl ester (Compound 42)

To a 50 ml round bottom flask was added tert-butyl 5-(2,6-bis(benzyloxy)pyridin-3-yl)isoindoline-2-carboxylate (32-2) (330 mg, 648 µmol) and ethanol (10 mL). The solution was degassed for 15 minutes under an argon atmosphere, palladium on charcoal (189 mg, 178 µmol) was added and the reaction was continued for 2 hrs in presence of a hydrogen balloon. TLC was checked, which showed complete consumption of the starting material and the formation of the desired spot at if 0.3 in 5% MeOH-DCM. The reaction mixture was filtered through a celite bed and evaporated under reduced pressure. The crude residue was purified by flash chromatography to afford 4-(2,6-Dioxo-piperidin-3-yl)-1,3-dihydro-isoindole-2-carboxylic acid tert-butyl ester (Compound 42) (186 mg, 536 µmol, 87% yield) as an off-white solid. $^1$H NMR (400 MHz, DMSO-d6) δ 10.87 (br s, 1H), 7.29-7.25 (m, 2H), 7.11 (d, J=6.6 Hz, 1H), 4.62-4.53 (m, 4H), 3.93-3.87 (m, 1H), 2.73-2.70 (m, 1H), 2.55 (m, 1H), 2.32-2.21 (m, 1H), 2.00 (br s, 1H), 1.45 (s, 9H); LC MS: ES+ 331.4 (−100 and −56 mass fragment were dominant).

Synthesis of 3-(2,3-Dihydro-1H-isoindol-4-yl)-piperidine-2,6-dione hydrochloride (Compound 43)

A 25 ml round bottom flask was charged with 4-(2,6-Dioxo-piperidin-3-yl)-1,3-dihydro-isoindole-2-carboxylic acid tert-butyl ester Compound 42 (122 mg, 369 µmol) and 4M-Dioxane-HCl (5 mL). The reaction was stirred at RT for 3h. The reaction was then concentrated under reduced pressure and the resulting residue was triturated with diethyl ether to afford 3-(2,3-Dihydro-1H-isoindol-4-yl)-piperidine-2,6-dione hydrochloride (Compound 43) (96 mg, 361 µmol, 98%) as an off-white solid. $^1$HNMR (400 MHz, DMSO-d6) δ 10.92 (s, 1H), 9.60 (br s, 2H), 7.38-7.33 (m, 2H), 7.21 (d, J=7.16 Hz, 1H), 4.54 (br s, 2H), 4.46 (br s, 2H), 4.01-3.97 (m, 1H), 2.71-2.67 (m, 1H), 2.58 (m, 1H), 2.32-2.26 (m, 1H), 2.00-1.98 (m, 1H); LC MS: ES+ 231.4

Scheme 33
Synthesis of 4-[2-(2,6-Dioxo-piperidin-3-yl)-acetyl]-piperazine-1-carboxylic acid tert-butyl ester (Compound 44) and 3-(2-Oxo-2-piperazin-1-yl-ethyl)-piperidine-2,6-dione hydrochloride salt (Compound 45)

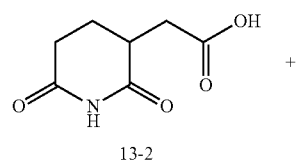

13-2

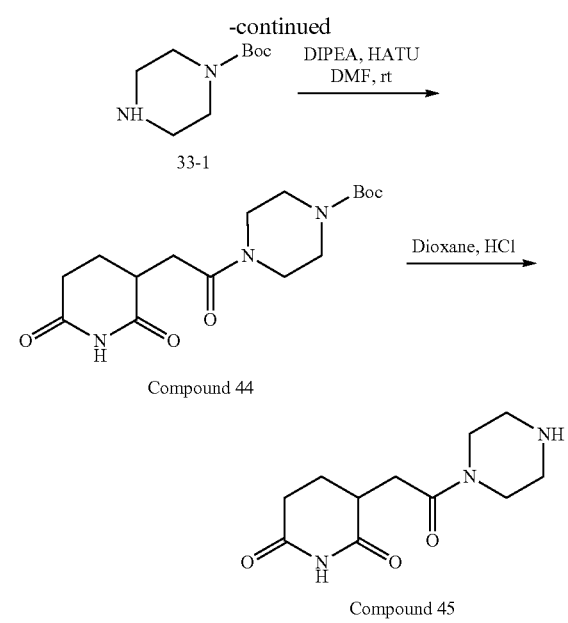

Synthesis of 4-[2-(2,6-Dioxo-piperidin-3-yl)-acetyl]-piperazine-1-carboxylic acid tert-butyl ester (Compound 44)

A 50 ml round bottom flash was charged with 2-(2,6-dioxopiperidin-3-yl)acetic acid (13-2) (200 mg, 1.16 mmol), tert-butyl piperazine-1-carboxylate (258 mg, 1.39 mmol), DIPEA (605 µL, 3.48 mmol) and HATU (882 mg, 2.32 mmol) in Dimethylformamide (20 mL). The reaction was stirred at RT for 16h. The reaction was diluted with ethyl acetate and washed with sat. sodium bicarbonate solution, water and brine. The organic layer was separated, dried over sodium sulfate and concentrated under reduced pressure. The crude residue was purified by column chromatography eluting at 30% ethyl acetate in hexane to afford tert-butyl 4-(2-(2,6-dioxopiperidin-3-yl)acetyl)piperazine-1-carboxylate (Compound 44) (145 mg, 427 µmol, 36.8%) as an off-white solid. $^1$H NMR (400 MHz, DMSO-d6) δ 10.62 (s, 1H), 3.43 (br, 4H), 3.34 (br, 2H), 3.28 (br, 2H), 2.91-2.78 (m, 2H), 3.61-2.53 (m, 2H), 2.46-2.42 (m, 2H), 1.85-1.78 (br m, 2H), 1.41 (s, 9H); LC MS: ES+ 340.1.

Synthesis of 3-(2-Oxo-2-piperazin-1-yl-ethyl)-piperidine-2,6-dione hydrochloride Salt (Compound 45)

A 25 ml round bottom flask was charged with tert-butyl 4-(2-(2,6-dioxopiperidin-3-yl)acetyl)piperazine-1-carboxylate (Compound 44) (122 mg, 359 µmol) and 4M-Dioxane-HCl (5 mL). The reaction was stirred at RT for 3h and then concentrated under reduced pressure and triturated with diethyl ether to afford 3-(2-oxo-2-(piperazin-1-yl)ethyl) piperidine-2,6-dione hydrochloride (Compound 45) (89.2 mg, 323 µmol, 90%) as an off-white solid. $^1$H NMR (400 MHz, DMSO-d6) δ 10.64 (s, 1H), 9.15 (br, 2H), 3.69 (br, 4H), 3.11-3.03 (br, d, 4H), 2.91-2.82 (m, 2H), 2.58 (m, 2H), 1.85-1.78 (m, 2H); LC MS: ES+ 240.

Scheme 34
Synthesis of 3-(2-methyl-1-phenyl-1H-imidazol-4-yl)-piperidine-2,6-dione (Compound 46)

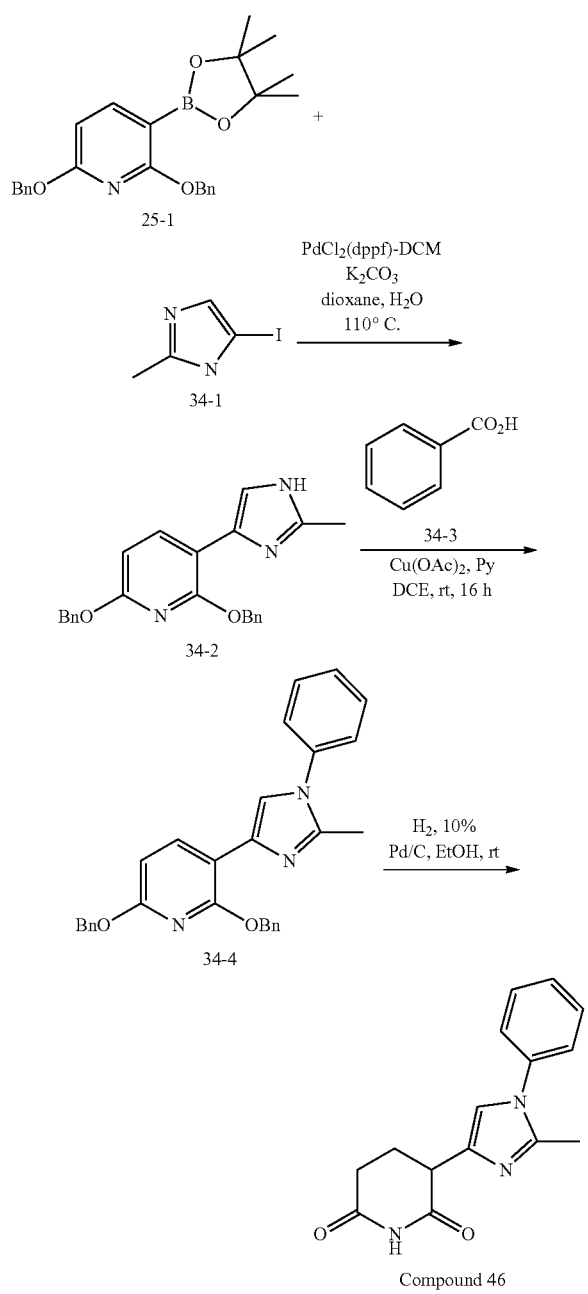

Synthesis of 2,6-bis-benzyloxy-3-(2-methyl-1H-imidazol-4-yl)-pyridine (34-2)

A sealed tube was charge with 5-iodo-2-methyl-1H-imidazole (34-1) (100 mg, 480 μmol), 2,6-bis(benzyloxy)-3-(4,4,5,5-tetramethyl-1,3,2-dioxaborolan-2-yl)pyridine 25-1 (500 mg, 1.20 mmol) and Potassium carbonate (198 mg, 1.44 mmol) in Dioxane:Water (4:1) (5 mL). The solution was degassed with argon for 10 minutes. [1,1'-Bis(diphenylphosphino)ferrocene]dichloropalladium (II), complex with dichloromethane (39.1 mg, 48.0 μmol) was added to the reaction mixture and the solution was heated at 100° C. for 16h. The reaction was cooled to RT, diluted with water, extracted with ethyl acetate, washed with brine, dried over sodium sulfate and concentrated under reduced pressure. The crude residue was purified by silica gel column chromatography eluting at 30% ethyl acetate in hexane to afford 2,6-bis(benzyloxy)-3-(2-methyl-1H-imidazol-5-yl)pyridine (115 mg, 309 μmol, 64.6%) as an off-white solid. LC MS: ES+ 372.0

Synthesis of 2,6-Bis-benzyloxy-3-(2-methyl-1-phenyl-1H-imidazol-4-yl)-pyridine (34-4)

A 25 ml round bottom flask was charged with 2,6-bis(benzyloxy)-3-(2-methyl-1H-imidazol-4-yl)pyridine (34-2) (115 mg, 309 μmol) and phenylboronic acid (34-3) (37.6 mg, 309 μmol) in 1,2-Dichloroethene (5 mL). Pyridine (123 μL, 1.54 mmol) and copper (II) acetate monohydrate (6.16 mg, 30.9 μmol) were added to the reaction mixture and the solution was stirred at RT (keeping mouth of the RB open) for 72h. The reaction was diluted with water, extracted with ethyl acetate, washed with brine, and dried over sodium sulfate and concentrated under reduced pressure. The crude residue was purified by silica gel column chromatography eluting at 20% ethyl acetate in hexane to afford 2,6-bis(benzyloxy)-3-(2-methyl-1-phenyl-1H-imidazol-4-yl)pyridine (34-4) (78.0 mg, 174 μmol, 56.5%) as a gum. LC MS: ES+ 448.0

Synthesis of 3-(2-Methyl-1-phenyl-1H-imidazol-4-yl)-piperidine-2,6-dione (Compound 46)

A 25 ml round bottom flash was charged with 2,6-bis(benzyloxy)-3-(2-methyl-1-phenyl-1H-imidazol-4-yl)pyridine (34-4) (75 mg, 167 μmol) and Ethanol (10 mL). The solution was degassed with argon for 10 minutes. Palladium on carbon (35.4 mg, 33.4 μmol) was added and the reaction mixture was stirred at RT for 16h under a hydrogen balloon, filtered through celite and concentrated under reduced pressure. The crude residue was purified by column chromatography eluting at 1.5% methanol in dichloromethane) to afford 3-(2-methyl-1-phenyl-1H-imidazol-4-yl)piperidine-2,6-dione Compound 46 (8.10 mg, 30.0 μmol, 18.0%) as an off-white sticky solid. $^1$H NMR (400 MHz, DMSO-$d_6$) δ 10.74 (s, 1H), 7.55-7.51 (t, J=7.64 Hz, 2H), 7.45-7.43 (d, Hz, J=7.48 3H), 7.18 (s, 1H), 3.77-3.74 (t, J=7.08 Hz, 1H), 2.66-2.64 (t, 1H), 2.59-2.57 (d, 1H), 2.26 (s, 3H), 2.15-2.11 (br m, 2H); LC MS: ES+ 270.3

Scheme 35
Synthesis of 3-methyl-3-(1-methyl-1H-indazol-3-yl)-piperidine-2,6-dione (Compound 47)

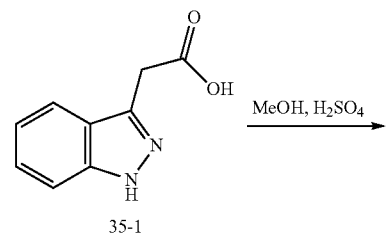

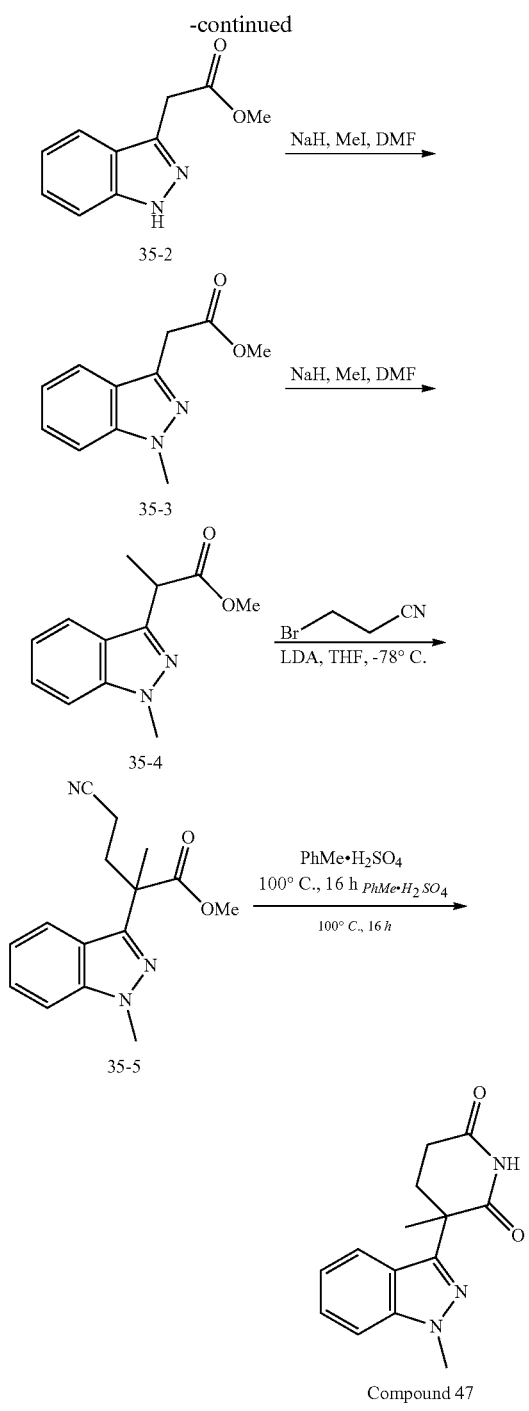

Synthesis of (1H-Indazol-3-yl)-acetic acid methyl ester (35-2)

To a stirred solution of 2-(1H-indazol-3-yl)acetic acid (35-1) (4.86 g, 27.5 mmol) in Methanol (250 mL) was added sulfuric acid (0.543 g, 5.53 mmol) and the reaction was refluxed at 68° C. for 16 h. Reaction progress was monitored by TLC. The MeOH was evaporated to dryness and the residual gum was basified with saturated sodium bicarbonate solution and extracted with ethyl acetate. The organic layer was dried over anhydrous sodium sulphate and evaporated in vacuo to yield methyl 2-(1H-indazol-3-yl)acetate (35-2) (4.90 g, 25.7 mmol, 93%) as a light brown solid.

Synthesis of (1-Methyl-1H-indazol-3-yl)-acetic acid methyl ester (35-3)

To a stirred solution of methyl 2-(1H-indazol-3-yl)acetate (35-2) (2.0 g, 10.5 mmol) in DMF (3.0 mL) was added NaH (503 mg, 12.6 mmol) followed by the addition of MeI (1.30 mL, 21.0 mmol) at 0° C. The reaction mixture was stirred at room temperature for 1 hour, at which time TLC showed formation of two new spots along with very little unreacted SM. The reaction was then diluted with ethyl acetate and water, the layers were separated and the organic layer was washed with water, brine, and dried over sodium sulfate. The organics were concentrated and the crude material was purified by column chromatography using (100-200 silica mesh, 0%-20% ethyl acetate/hexane) to get two fractions. Analysis confirmed the correct regiomeric structure methyl 2-(1-methyl-1H-indazol-3-yl)acetate (35-3) (1.20 g, 5.87 mmol, 56.0%) as a light yellow oil. LC MS: ES+ 205.2

Synthesis of 2-(1-Methyl-1H-indazol-3-yl)-propionic acid methyl ester (35-4)

A stirred solution of methyl 2-(1-methyl-1H-indazol-3-yl)acetate (35-3) (720 mg, 3.52 mmol) in N,N-dimethylformamide (10 mL) was cooled to 0° C. and sodium hydride (168 mg, 4.22 mmol) was added in portions. The reaction mixture was allowed to stir at room temperature for 30 min followed by the addition of Iodomethane (438 µL, 7.04 mmol). The reaction mixture was stirred at room temperature for 16 h. The reaction progress was monitored by TLC. The reaction was quenched with ice cold water and product was extracted with ethyl acetate. The organic layer was washed with ice cold water thrice to remove the DMF from organic layer. The organic layer was dried over anhydrous sodium sulphate and evaporated in vacuo. The product was purified by silica gel flash chromatography (12 g Isco gold, hexane/EtOAc 0-100%) to yield methyl 2-(1-methyl-1H-indazol-3-yl)propanoate (35-4) (500 mg, 2.29 mmol, 65%) as a brown oil. $^1$H NMR (400 MHz, DMSO-$d_6$) δ 7.71 (d, J=8.2 Hz, 1H), 7.58 (d, J=8.5 Hz, 1H), 7.39 (t, J=7.6 Hz, 1H), 7.12 (t, J=7.5 Hz, 1H), 4.27 (dd, J=14.4, 7.2 Hz, 1H), 3.99 (s, 3H), 3.59 (s, 3H), 1.54 (d, J=7.2 Hz, 3H).

Synthesis of 4-cyano-2-methyl-2-(1-methyl-1H-indazol-3-yl)-butyric acid methyl ester (35-5)

A stirred solution of methyl 2-(1-methyl-1H-indazol-3-yl)propanoate (35-4) (200 mg, 916 µmol) in tetrahydrofuran (10 mL) was cooled to −78° C. and Lithiumdiisopropylamide (685 µL, 1.37 mmol) was added dropwise. The reaction mixture was stirred at −78° C. for 45 minutes to generate anion, then 3-bromopropionitrile (135 µL, 1.64 mmol) was added to the reaction mixture at same temperature. The reaction mixture was brought to room temperature and stirred for one hour. Reaction progress was monitored by TLC and LCMS. Reaction was quenched with saturated solution of ammonium chloride and extraction was carried out using ethyl acetate. Organic layer was dried over anhydrous sodium sulphate and evaporated in vacuo. The product was purified by silica gel flash chromatography (Column, hexane/EtOAc 0-100%) to give methyl 4-cyano-2-methyl-2-(1-methyl-1H-indazol-3-yl)butanoate (35-5) (40.0 mg, 147 µmol, 16.1%) as yellow gum. ES+ 272.0

Synthesis of 3-Methyl-3-(1-methyl-1H-indazol-3-yl)-piperidine-2,6-dione (Compound 47)

A stirred solution of methyl 2-(1-methyl-1H-indazol-3-yl)propanoate (35-5) (200 mg, 916 µmol) in Tetrahydrofuran (10 mL) was cooled to −78° C. and Lithiumdiisopropylamide (685 µL, 1.37 mmol) was added dropwise. The reaction mixture was stirred at −78° C. for 45 minutes to generate anion and then 3-bromopropionitrile (135 µL, 1.64 mmol) was added to the reaction mixture at the same temperature. The reaction mixture was brought to room temperature and stirred for one hour. Reaction progress was monitored by TLC and LCMS. The reaction was quenched with saturated solution of ammonium chloride and extraction was carried out using ethyl acetate. The organic layer was dried over anhydrous sodium sulphate and evaporated in vacuo. The product was purified by silica gel flash chromatography (Column, hexane/EtOAc 0-100%) to give methyl 4-cyano-2-methyl-2-(1-methyl-1H-indazol-3-yl)butanoate (Compound 47) (40.0 mg, 147 µmol, 16%) as a yellow gum. $^1$H NMR (400 MHz, DMSO-$d_6$) δ 10.86 (s, 1H), 7.82 (d, J=8.3 Hz, 1H), 7.61 (d, J=8.6 Hz, 1H), 7.39 (t, J=7.6 Hz, 1H), 7.11 (t, J=7.5 Hz, 1H), 3.98 (s, 3H), 2.60-2.50 (m, 2H), 2.43-2.39 (m, 1H), 2.15-2.12 (m, 1H), 1.66 (s, 3H). LC MS: ES+ 258.1

Synthesis of 2-Methyl-5-(4,4,5,5-tetramethyl-[1,3,2] dioxaborolan-2-yl)-benzothiazole (36-2)

To a stirred solution of 5-bromo-2-methylbenzo[d]thiazole (36-1) (0.500 g, 2.19 mmol) and 4,4,4',4',5,5,5',5'-octamethyl-2,2'-bi(1,3,2-dioxaborolane) (0.830 g, 3.26 mmol) in dioxane (10 mL) was added potassium acetate (0.430 g, 4.38 mmol) and the solution was degassed for 10 min in sealed tube. $PdCl_2$(dppf)-DCM (0.170 g, 208 µmol) was added and again the solution was degassed for 5 min and the reaction mixture was stirred at 80° C. for 3 h. After the reaction was deemd complete by TLC, the reaction mixture was diluted with ethyl acetate, washed with water and brine, the organic layer was separated and dried over anhydrous sodium sulphate, filtered and concentrated. The crude residue was purified by column chromatography eluted with 0 to 20% ethyl acetate in hexane to provide 2-Methyl-5-(4,4,5,5-tetramethyl-[1,3,2]dioxaborolan-2-yl)-benzothiazole (36-2) (367 mg, 1.33 mmol, 61% yield). LC MS: ES+ 276.3

Synthesis of 5-(2,6-bis-benzyloxy-pyridin-3-yl)-2-methyl-benzothiazole (36-3)

To a stirred solution of 2-methyl-5-(4,4,5,5-tetramethyl-1,3,2-dioxaborolan-2-yl)benzo[d]thiazole (36-2) (1.1 g, 3.99 mmol) and 2,6-bis(benzyloxy)-3-bromopyridine 25-1 (1.9 g, 5.13 mmol) in a sealed tube, in Dioxane (20 mL) and Water (2 mL), was added $K_3PO_4$ (2.1 g, 9.12 mol) and the solution was degassed for 10 min. $PdCl_2$(dppf)-DCM (0.400 g, 489 µmol) was added and again the solution was degassed for 5 min. After degassing completion, the sealed tube was closed with a teflon cap and the reaction mixture was stirred at 80° C. for 16 h. After reaction completion, as checked by TLC, the reaction mixture was filtered through celite. The organic layer was diluted with ethyl acetate, washed with water and brine, dried over anhydrous sodium sulphate, filtered and concentrated under reduced pressure. The crude material was purified by column chromatography eluted with 5 to 20% ethyl acetate in hexane to provide 5-(2,6-Bis-benzyloxy-pyridin-3-yl)-2-methyl-benzothiazole (36-3) (1.0 g, 2.28 mmol, 57% yield). LC MS: ES+ 439.3.

Synthesis of 3-(2-Methyl-benzothiazol-5-yl)-piperidine-2,6-dione (Compound 48)

To a stirred solution of 5-(2,6-bis(benzyloxy)pyridin-3-yl)-2-methylbenzo[d]thiazole (36-3) (0.180 g, 410 µmol) in a mixture of Ethanol (4 mL) and THF (4 mL) was added Pd/C (10 wt %, 0.100 g, 943 µmol). The solution was sparged with hydrogen gas at 1 atm, RT for 16 h. After reaction completion, the reaction mixture was filtered through celite and concentrated under reduced pressure. The crude material was purified by preparative HPLC to provide 3-(2-Methyl-benzothiazol-5-yl)-piperidine-2,6-dione (Compound 48) (30 mg, 115 µmol, 28% yield). $^1$H NMR (400 MHz, DMSO-$d_6$) δ 10.87 (s, 1H), 7.97 (d, J=8.1 Hz, 1H), 7.77 (s, 1H), 7.26 (d, J=7.4 Hz, 1H), 4.02 (dd, J=4.4, 11.6 Hz, 1H), 2.79 (s, 3H), 2.75-2.68 (m, 1H), 2.55 (m, 1H, merged with residual solvent peak), 2.33-2.28 (m, 1H), 2.10 (m, 1H). LC MS: ES+ 261.2

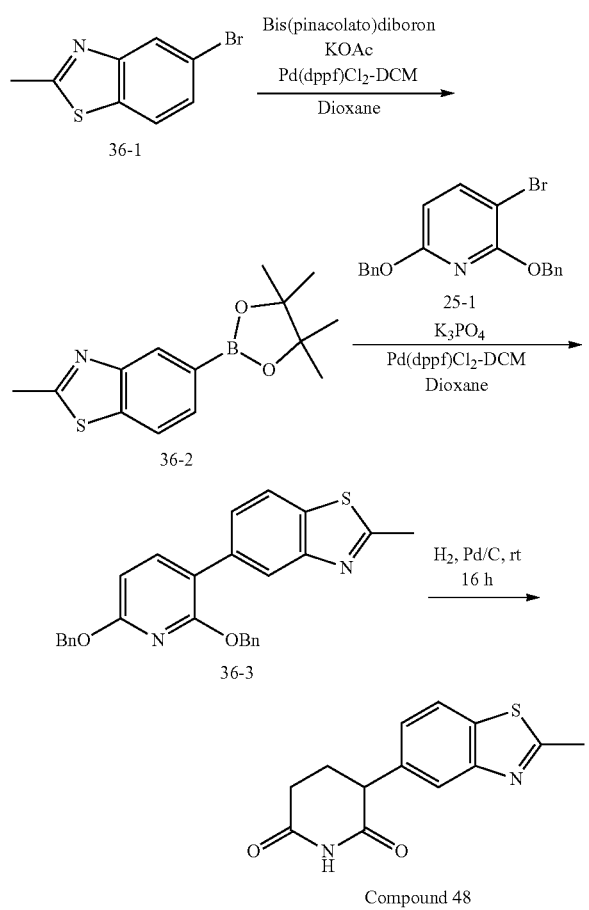

Scheme 36
Synthesis of 3-(2-Methyl-benzothiazol-5-yl)-piperidine-2,6-dione (Compound 48)

Scheme 37
Synthesis of 3-(3-Methyl-2-oxo-2,3-dihydro-benzooxazol-5-yl)-piperidine-2,6-dione (Compound 49)

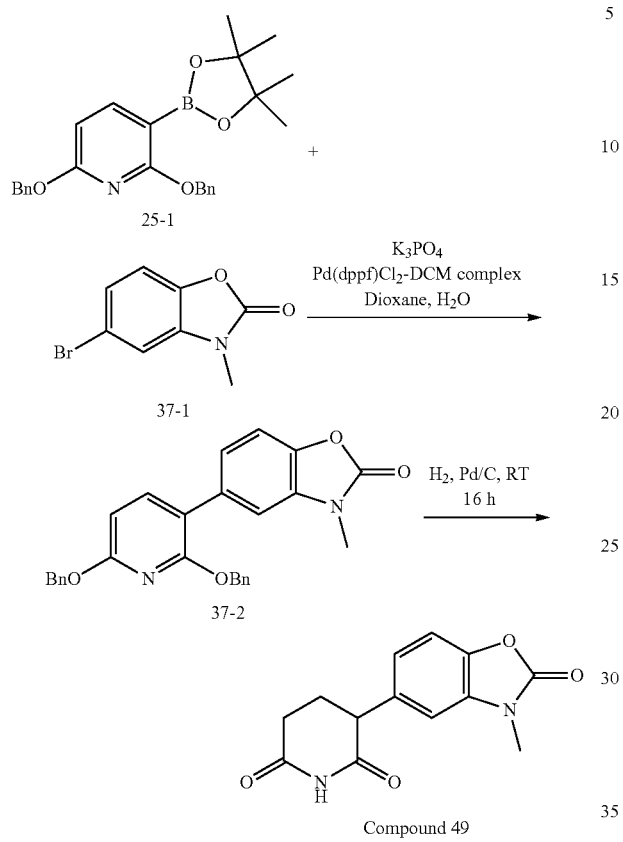

Synthesis of 5-(2,6-Bis-benzyloxy-pyridin-3-yl)-3-methyl-3H-benzooxazol-2-one (37-2)

To a stirred solution of compound 5-bromo-3-methyl-benzo[d]oxazol-2(3H)-one (37-1) (909 mg, 3.99 mmol) and 2,6-bis(benzyloxy)-3-bromopyridine 25-1 (1.9 g, 5.13 mmol), in a sealed tube in Dioxane (20 mL) and Water (2 mL), was added $K_3PO_4$ (2.1 g, 9.14 mmol) and the solution was degassed with argon for 10 min. $PdCl_2$(dppf)-DCM (0.400 g, 489 µmol) was added and again the solution was degassed for 5 min. After degassing completion, the sealed tube was closed with a teflon cap and the reaction mixture stirred at 80° C. for 16 h. After reaction completion as checked by TLC, the reaction mixture was filtered through celite and the organic layer was diluted with ethyl acetate, washed with water followed by brine, and dried over anhydrous sodium sulphate, filtered and concentrated under reduced pressure. The crude residue was purified by column chromatography eluted with 5 to 20% ethyl acetate in hexane to provide 5-(2,6-Bis-benzyloxy-pyridin-3-yl)-3-methyl-3H-benzooxazol-2-one (37-2) (850 mg, 1.39 mmol, 35% yield). LC MS: ES+ 439.3

Synthesis of 3-(3-Methyl-2-oxo-2,3-dihydro-benzo-oxazol-5-yl)-piperidine-2,6-dione (Compound 49)

To a stirred solution of 5-(2,6-Bis-benzyloxy-pyridin-3-yl)-3-methyl-3H-benzooxazol-2-one (37-2) (850 mg, 1.93 mmol) in a mixture of Ethanol (10 mL) and THF (4 mL) was added Pd/C (0.100 g, 943 µmol) and and the solution was sparged with hydrogen gas at 1 atm, RT for 16 h. After reaction completion, the reaction mixture was filtered through celite and concentrated under reduced pressure. The crude residue was purified by preparative HPLC to provide 3-(3-Methyl-2-oxo-2,3-dihydro-benzooxazol-5-yl)-piperidine-2,6-dione (Compound 49) (251 mg, 965 µmol, 50% yield) $^1$H NMR (400 MHz, DMSO-$d_6$) δ 10.83 (s, 1H), 7.25 (s, 1H), 7.19 (d, J=8.0 Hz, 1H), 7.09 (d, J=8.0 Hz, 1H), 3.90 (dd, J=4.7, 11.9 Hz, 1H), 3.40 (s, 3H, merged with residual solvent peak), 2.68-2.64 (m, 2H), 2.27-2.24 (m, 1H), 2.02 (m, 1H). LC MS: ES-259.29

Scheme 38
Synthesis of 3-Benzylpiperidine-2,6-dione (Compound 50)

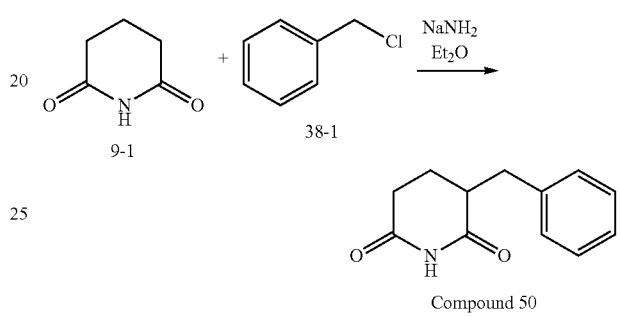

To freshly liquefied ammonia (50 ml) at −78° C. was added potassium metal (402 mg, 10.3 mmol) (N.B. a small piece of the metal was initially added to initiate the reaction, the solution turned deep blue) followed by the addition of catalytic ferric nitrate (a few crystals). The remaining pieces of the metal were thereafter added slowly. The deep blue solution turned light greyish-brown. After stirring for 30 mins, solid powdered piperidine-2,6-dione (9-1) (500 mg, 4.42 mmol) was added at the same temperature and the reaction mass was stirred for 1 hr. A solution of (chloromethyl)benzene (38-1) (615 mg, 4.86 mmol) in dry diethyl ether (3 mL) was prepared and added rapidly to the mixture followed by stirring at −78° C. for an additional 1 hr. A sample of the reaction mixture was syringed out, ether was added, followed by the addition of solid ammonium chloride and a few drops of 6(N) HCl (pH checked to ensure solution acidity) and then ether was added. An aliquot of the ether layer was TLC'd (40% ethyl acetate in Hexane). Consumption of both glutarimide as well as benzyl chloride and appearance of a new spot just above the starting material (glutarimide) was evident. GCMS monitoring showed response of the desired mass (MS 203). The rest of the reaction mixture was quenched and worked up with ether accordingly. (The ether addition was done carefully while the ammonia from the bulk reaction mass was allowed to evaporate.) The organic extract was dried over sodium sulphate, concentrated to afford a crude residue, which was purified by column chromatography (100-200 mesh silica gel, elution with hexane to at 20% EA/hex, compound eluted in 20% EA-hexane) to afford a white solid, whose analysis was found to be consistent with the desired compound, 3-benzylpiperidine-2,6-dione (Compound 50) (120 mg, 13.3%). LC MS: ES+ 204.24, $^1$H NMR (400 MHz, DMSO-$d_6$) δ 10.68 (s, 1H), 7.29 (t, J=7.26 Hz 2H), 7.22 (d, J=7.44 Hz, 3H), 3.21 (dd, J=13.44, 3.76 Hz, 1H), 2.77-2.71 (m, 1H), 2.67-2.59 (m, 1H), 2.49-2.42 (m, 2H), 1.71-1.64 (m, 1H), 1.58-1.48 (m, 1H).

Scheme 39 Synthesis of 3-(6-Amino-1-methyl-1H-indazol-3-yl)piperidine-2,6-dione (Compound 51), tert-Butyl 4-((3-(2,6-dioxopiperidin-3-yl)-1-methyl-1H-indazol-6-yl)amino)piperidine-1-carboxylate (Compound 52), and 3-(1-Methyl-6-(piperidine-4-ylamino)-1H-indazol-3-yl)piperidine-2,6-dione hydrochloride (Compound 53):

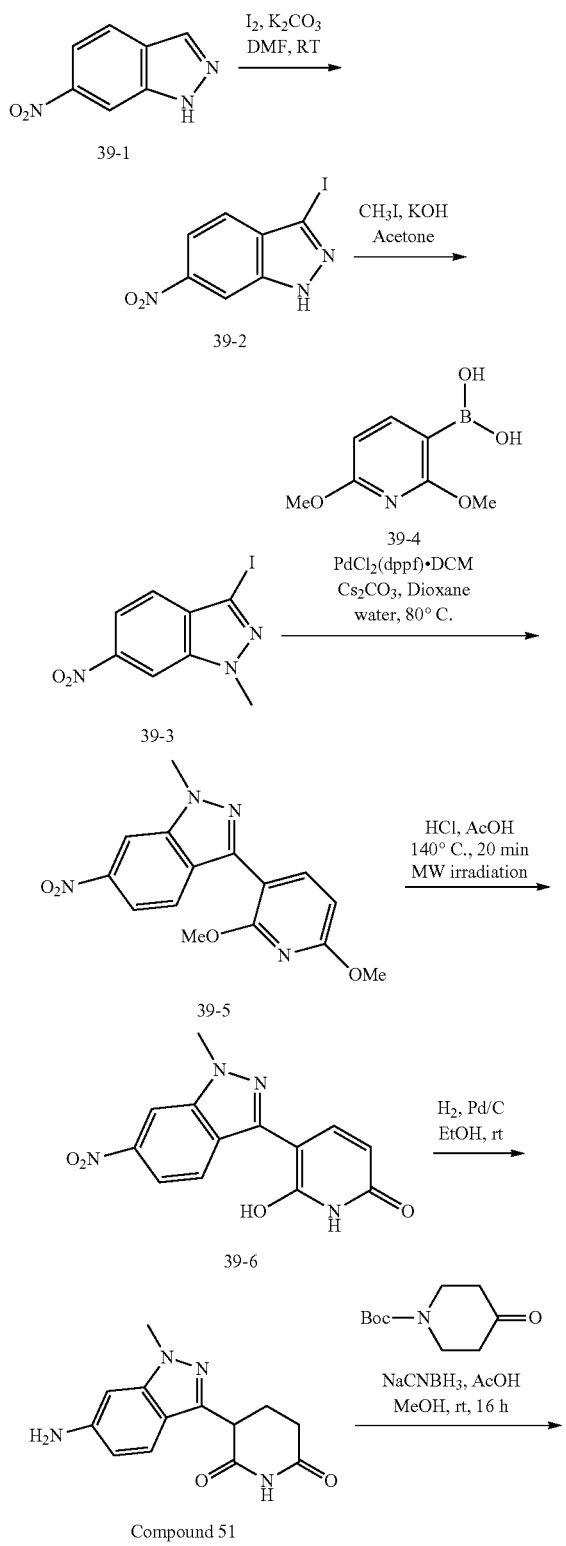

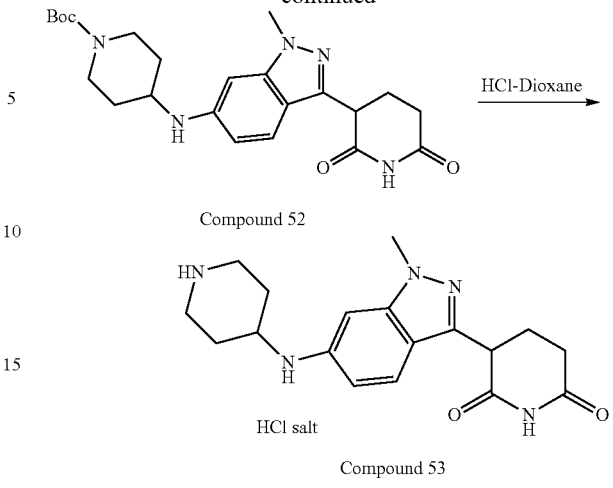

Synthesis of 3-Iodo-6-nitro-1H-indazole (39-2)

A solution of (39-1) (5 g, 30.6 mmol) was treated with a solution of iodine (6.71 g, 52.9 mmol) in DMF (10 mL) and the mixture was stirred in the presence of Potassium carbonate (8.45 g, 61.2 mmol) at room temperature for 2 hours. After consumption of starting material 39-1, as evident from TLC, an aqueous solution of sodium thiosulfate and water (250 mL) was added. The resulting solution was stirred for 15 min, during which time a precipitate formed. The precipitate was filtered, washed with water and dried in vacuo to afford (39-2) (7.00 g, 24.2 mmol, 79%) as a light yellow solid. LCMS: ES− 287.7.

Synthesis of 3-Iodo-1-methyl-6-nitro-1H-indazole (39-3)

A stirred solution of (39-2) (4 g, 13.8 mmol) in acetone (90 mL) at 0° C. containing potassium hydroxide (1.16 g, 20.7 mmol) was treated with a solution of iodomethane (1.02 mL, 16.5 mmol) in acetone (20 mL) dropwise and the mixture was thereafter stirred at room temperature overnight. After consumption of starting materials, as evident from TLC, the reaction mixture was partitioned between ethyl acetate and water (200 mL), and the combined organic extracts were washed with brine, dried over sodium sulphate and concentrated. The crude residue was purified by flash chromatography (elution with 5-10% EtOAc-Hexane) to afford (39-3) (2.40 g, 7.91 mmol, 14.8%) as a light yellow solid. $^1$H NMR (400 MHz, DMSO-d$_6$) δ 8.77 (s, 1H), 8.00-7.99 (d, J=8 Hz, 1H), 7.66 (d, J=8 Hz, 1H), 4.20 (s, 3H).

Synthesis of 3-(2,6-Dimethoxypyridin-3-yl)-1-methyl-6-nitro-1H-indazole (39-5)

A mixture of (39-3) (300 mg, 989 μmol), 39-4 (215 mg, 1.18 mmol) and Cesium carbonate (964 mg, 2.96 mmol) in dioxane (4 mL) and water (0.5 mL) was thoroughly degassed and heated at 80° C. for 12 h in presence of Pd(dppf)Cl$_2$-DCM (48.4 mg, 59.3 μmol). After consumption of 39-3 as evident from TLC, the mixture was filtered through a pad of Celite. The filtrate was partitioned between EtOAc and water, and the combined organic extracts were washed with brine, dried over sodium sulphate, and concentrated. The crude residue was purified by flash chromatography (elution with 10% EtOAc-hexane) to afford (39-5) (200 mg, 636 µmol, 64.5%) as a light yellow solid. LCMS: ES+ 315.1.

Synthesis of 6-Hydroxy-3-(1-methyl-6-nitro-1H-indazol-3-yl)pyridin-2(3H)-one (39-6)

A stirred suspension of (39-5) (300 mg, 954 µmol) in HCl (2 mL) and acetic acid (2 mL) was heated at 140° C. in a microwave for 20 min. After consumption of 39-5 as evident from TLC, the mixture was cooled to RT and evaporated to dryness to afford (39-6) (200 mg, 698 µmol, 73.2%) as a yellow solid. LCMS: ES+ 287.2.

Synthesis of 3-(6-Amino-1-methyl-1H-indazol-3-yl)piperidine-2,6-dione (Compound 51)

A stirred suspension of (39-6) (200 mg, 698 µmol) in ethanol (10 mL) at room temperature was hydrogenated under 1 atm pressure (hydrogen balloon) in presence of palladium on carbon overnight. After formation of the desired product as evident from LCMS, the reaction mixture was filtered. The filtrate was concentrated to afford a crude residue which was purified by Preparative HPLC to afford Compound 51 (35.0 mg, 135 µmol, 31.8%) as a black solid. $^1$H NMR (400 MHz, DMSO-d$_6$) δ 10.81 (brs, 1H), 7.32 (d, J=8.64 Hz, 1H), 6.47 (d, J=8.4 Hz, 1H), 6.41 (s, 1H), 5.34 (s, 2H), 4.19-4.16 (m, 1H), 3.76 (s, 3H), 2.66-2.51 (m, 2H), 2.26-2.22 (m, 1H), 2.16-2.12 (m, 1H); LCMS: ES+ 259.4

Synthesis of tert-Butyl 4-((3-(2,6-dioxopiperidin-3-yl)-1-methyl-1H-indazol-6-yl)amino)piperidine-1-carboxylate (Compound 52)

A solution of Compound 51 (50 mg, 193 µmol) and tert-butyl 4-oxopiperidine-1-carboxylate (46.0 mg, 231 µmol) in dichloroethane (2 mL) was stirred at room temperature overnight in the presence of acetic acid (10.9 µL, 193 µmol). Sodium cyanoborohydide (24.2 mg, 386 µmol) was added and the stirring was continued for another 4 h. After formation of the desired product as evident from LCMS, the mixture was evaporated to dryness, and the residue was partitioned between ethyl acetate and water, the combined organic extracts were washed with brine, dried over sodium sulphate, and concentrated under the reduced pressure. The crude residue was purified by Prep HPLC to afford Compound 52 (15.0 mg, 33.9 µmol, 17.6%) as an off-white solid. $^1$H NMR (400 MHz, DMSO-d6) δ 10.81 (s, 1H), 7.32 (d, J=8.68 Hz, 1H), 6.51 (d, J=9.28 Hz, 1H), 6.42 (s, 1H), 5.79 (d, J=8.2 Hz, 1H), 4.20-4.14 (m, 1H), 3.91-3.85 (m, 1H), 3.81 (s, 3H), 3.55-3.48 (m, 1H), 2.99-2.91 (m, 2H), 2.59-2.51 (m, 2H), 2.22-2.12 (m, 2H, 1.96-1.89 (m, 2H), 1.40 (s, 9H), 1.27-1.24 (m, 2H); LC MS: ES+ 442.2.

Synthesis of 3-(1-Methyl-6-(piperidin-4-ylamino)-1H-indazol-3-yl)piperidine-2,6-dione hydrochloride (Compound 53)

A suspension of Compound 52 (10 mg, 22.6 µmol) in ether (1 ml) was treated with 4 M HCl in ether (0.8 mL) and the mixture was stirred at RT until complete consumption of starting material was evident from LCMS. The reaction mixture was thereafter concentrated and the residue was triturated with ether, dried and finally lyophilized to afford Compound 53 (8.00 mg, 21.1 µmol, 93.7%) as a white solid. 1H NMR (400 MHz, DMSO-d6) δ 10.82 (s, 1H), 8.57 (brs, 1H), 8.47 (brs, 1H), 7.32 (d, J=8.76 Hz, 1H), 6.54 (d, J=8.8 Hz, 1H), 6.46 (s, 1H), 4.19 (dd, J=8.68, 4.8 Hz, 1H), 3.82 (s, 3H), 3.61-3.55 (m, 1H), 3.35-3.30 (m, 2H), 3.08-3.00 (m, 2H), 2.63-2.59 (m, 2H), 2.27-2.22 (m, 1H), 2.16-2.07 (m, 3H), 1.62-1.56 (m, 1H); LC MS: ES+ 342.3.

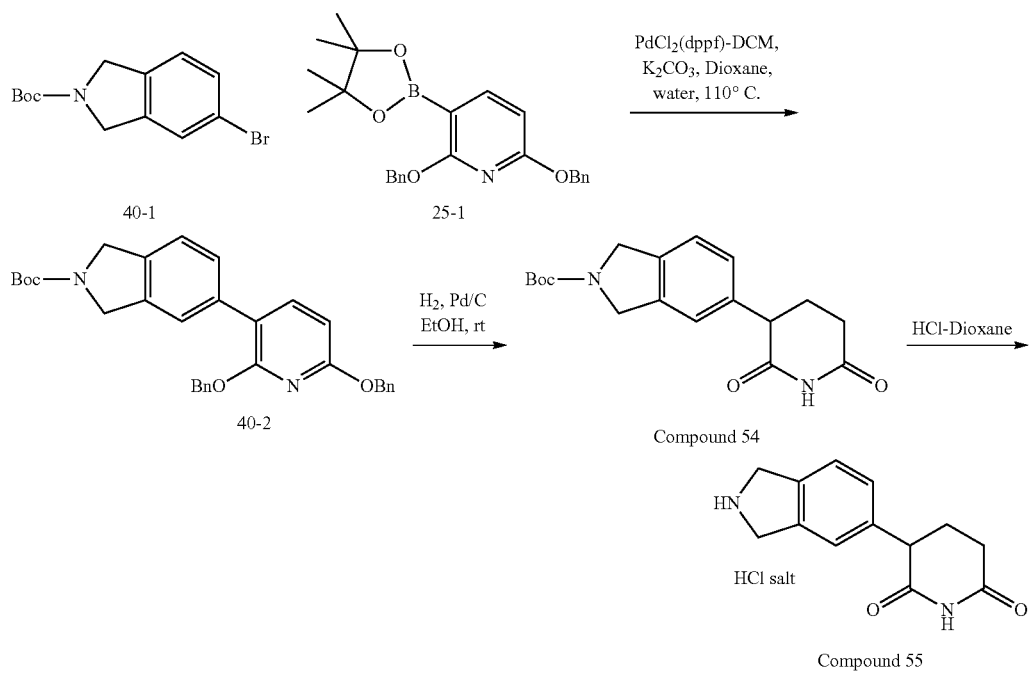

Scheme 40 Synthesis of 5-(2,6-Dioxo-piperidin-3-yl)-1,3-dihydro-isoindole-2-carboxylic acid tert-butyl ester (Compound 54) and 3-(isoindolin-5-yl)piperidine-2,6-dione hydrochloride (Compound 55)

Synthesis of 5-(2,6-Bis-benzyloxy-pyridin-3-yl)-1,3-dihydro-isoindole-2-carboxylic acid tert-butyl ester (40-2)

To a stirred solution of tert-butyl 5-bromoisoindoline-2-carboxylate (40-1) (300 mg, 1.00 mmol) in dioxane and water (2.5 ml), was added 2,6-bis(benzyloxy)-3-(4,4,5,5-tetramethyl-1,3,2-dioxaborolan-2-yl)pyridine 25-1 (459 mg, 1.10 mmol) and potassium phosphate (636 mg, 3.00 mmol) at room temperature. The reaction mixture was purged with argon for 5 minutes followed by addition of Pd(dppf)Cl$_2$-DCM (40.8 mg, 50.0 µmol) at room temperature. The reaction mixture was heating under reflux overnight. After completion of the reaction (monitored by TLC Rr=0.4 in 20% ea/hexane and LCMS), the reaction mixture was filtered and the residual crude residue was purified by a flash column (elution with 15% EtOAc/hexanes) to afford tert-butyl 5-(2,6-bis(benzyloxy)pyridin-3-yl)isoindoline-2-carboxylate (40-2) (330 mg, 648 µmol, 65%) as a gummy liquid. $^1$H NMR (400 MHz, DMSO-d6) δ 7.73-7.69 (m, 1H), 7.48-7.42 (m, 4H), 7.39-7.29 (m, 9H), 6.55 (d, J=8.08 Hz, 1H), 5.40-5.36 (m, 4H), 4.59-4.57 (m, 4H), 1.46 (s, 9H).

Synthesis of 5-(2,6-Dioxo-piperidin-3-yl)-1,3-dihydro-isoindole-2-carboxylic acid tert-butyl ester (Compound 54)

To a stirred solution of tert-butyl 5-(2,6-bis(benzyloxy)pyridin-3-yl)isoindoline-2-carboxylate (40-2) (150 mg, 294 µmol) in ethanol (5 ml) was added Pd/C (31.2 mg, 29.4 µmol), followed by hydrogen balloon pressure and stirring for 4 h at r.t. After TLC analysis (Rf=0.3 in 50% EA/Hex) and LCMS showed product formation, the reaction mass was filtered through a celite bed, washed with methanol and the filtrate was concentrated. The crude residue was purified by prep TLC afforded tert-butyl 5-(2,6-dioxopiperidin-3-yl)isoindoline-2-carboxylate (Compound 54) (30.0 mg, 90.8 µmol, 30.8%) as a white solid. 1HNMR (400 MHz, DMSO-d6) δ 10.83 (s, 1H), 7.29-7.25 (m, 1H), 7.17 (d, J=7.24 Hz, 1H), 7.13 (d, J=7.04 Hz, 1H), 4.56 (d, J=8.64 Hz, 4H), 3.89-3.82 (m, 1H), 2.69-2.61 (m, 1H), 2.22-2.16 (m, 1H), 2.05-2.01 (m, 1H), 1.45 (s, 3H); LC MS: ES− 329.2.

Synthesis of 3-(Isoindolin-5-yl)piperidine-2,6-dione hydrochloride (Compound 55)

A 10 ml round bottom flask was charged with tert-butyl 5-(2,6-dioxopiperidin-3-yl)isoindoline-2-carboxylate (Compound 54) (20 mg, 60 µmol) and 4M-Dioxane-HCl (2 mL). The reaction was stirred at RT for 3h. The reaction was then concentrated under reduced pressure and the residue was triturated with diethyl ether to afford 3-(isoindolin-5-yl)piperidine-2,6-dione hydrochloride (Compound 55) (14 mg, 52 µmol, 86%) as an off-white solid. 1H NMR (400 MHz, DMSO-d6) δ 10.86 (s, 1H), 9.51 (brs, 2H), 7.36 (d, J=7.8 Hz, 1H), 7.26-7.21 (m, 2H), 4.48 (s, 4H), 3.91 (dd, J=11.44, 4.36 Hz, 1H), 2.69-2.65 (m, 1H), 2.48-2.43 (m, 1H), 2.22-2.18 (m, 1H), 2.01-1.99 (m, 1H); LC MS: ES+ 231.14.

Scheme 41
Synthesis of 3-(Pyridin-4-yl)piperidine-2,6-dione (Compound 56)

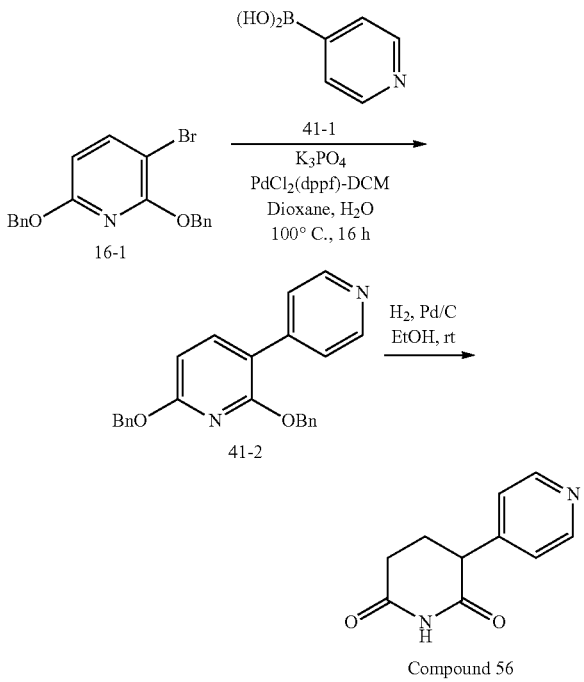

Synthesis of 2,6-Bis-benzyloxy-[3,4']bipyridinyl (41-2)

To the stirred solution of 2,6-bis(benzyloxy)-3-bromopyridine (16-1) (112.0 mg, 302 µmol) in Dioxane and water (7.5 mL) was added Pyridine-4-boronic acid 41-1 (42.1 mg, 453 µmol) and Potassium Phosphate (139 mg, 604 µmol). The reaction was degassed for 10 minutes and PdCl$_2$(dppf)-DCM (24.6 mg, 30.2 µmol) was added. The reaction was refluxed at 90° C. for overnight. Reaction progress was monitored by TLC. Upon completion, the reaction was diluted with water and extracted with ethyl acetate. The organic layer was dried over anhydrous sodium sulphate and evaporated in vacuo. The product was purified by silica gel flash chromatography (4 g Isco gold, hexane/EtOAc 0-100%) to give 2,6-bis(benzyloxy)-3,4'-bipyridine (41-2) (90.0 mg, 244 µmol, 81.0%) as a white solid. MS: ES+ 369.2.

Synthesis of 3-(Pyridin-4-yl)piperidine-2,6-dione (Compound 56)

To a solution of 2,6-bis(benzyloxy)-3,4'-bipyridine 42-2 (90 mg, 244 µmol) in ethanol (5 mL) was added Pd/C (20 mg, 187 µmol) under an inert atmosphere. After stirring for 5 minutes, a hydrogen balloon was attached to the RB flask containing the reaction mixture and the reaction mixture was stirred under a hydrogen atmosphere for 2 h. The reaction progress was monitored by TLC (5% MeOH:DCM (0.5 Rf)). Upon completion, the reaction was filtered through a celite bed. The filtrate was evaporated to dryness. The product was purified by silica gel flash chromatography (4 g Isco gold, DCM/MeOH 0-10%) to give 3-(pyridin-4-yl)piperidine-2,6-dione Compound 56 (25.0 mg, 131 µmol, 54%). LC MS: ES-189.19. $^1$H NMR (400 MHz, DMSO-d6)

δ 11.94 (s, 1H), 8.52 (d, J=4.2 Hz, 2H), 7.28 (d, J=4.2 Hz, 2H), 3.95-3.93 (m, 1H), 2.69-2.64 (m, 1H), 2.56-2.50 (m, 1H), 2.28-2.23 (m, 1H), 2.10-2.02 (m, 1H); LC MS: ES+ 191.4.

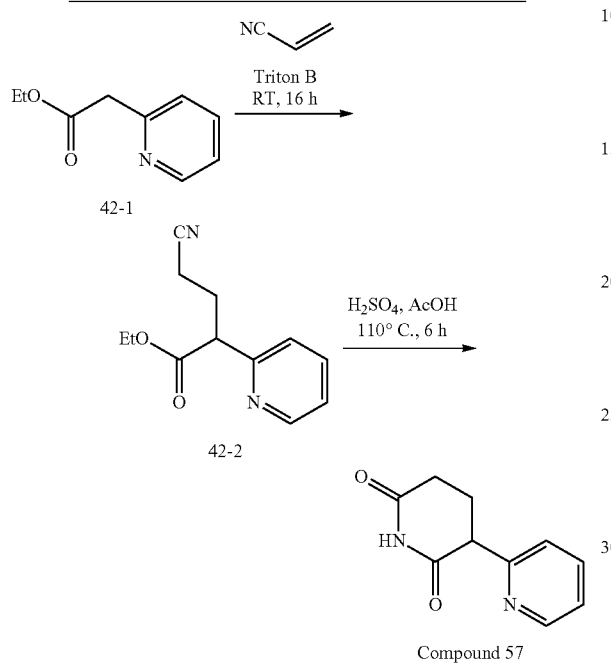

Scheme 42
Synthesis of 4',5'-Dihydro-3'H-[2,3']bipyridinyl-2',6'-dione (Compound 57)

Synthesis of 4-Cyano-2-pyridin-2-yl-butyric acid ethyl ester (42-2)

To a stirred solution of methyl 2-(pyridin-2-yl)acetate (42-1) (0.500 g, 3.30 mmol) in tert-butanol (10 mL) was added benzyl trimethyl ammonium hydroxide (0.110 g, 657 µmol) dropwise in the time span of 10 minutes. After completion of the addition, the reaction mixture was stirred at room temperature for 30 minutes followed by the addition of acrylonitrile (0.105 g, 1.97 mmol). After addition completion, the reaction mixture was stirred at room temperature for 16 hours. The reaction mixture was diluted with water and extracted with ethyl acetate. The organic layer was dried over anhydrous sodium sulfate and concentrated under reduced pressure. The crude compound was purified by column chromatography using (silica, gradient, 0% to 60% ethyl acetate in hexane) to afford (42-2) (200 mg) as a gum. Yield-30%; LC MS: ES+ 205.1.

Synthesis of 4',5'-Dihydro-3'H-[2,3']bipyridinyl-2',6'-dione (Compound 57)

A solution of methyl 4-cyano-2-(pyridin-2-yl)butanoate (42-2) (200 mg, 979 µmol) in Acetic acid (5 mL) and Sulphuric acid (1 mL) was stirred at 110° C. for 4 hours. The reaction mixture was concentrated under reduced pressure. The crude residue was dissolved in water and its pH was adjusted to 8 with sodium bicarbonate and extracted with ethyl acetate. The combined organic layer was washed with brine, dried over anhydrous sodium sulfate and concentrated under reduced pressure. The crude mass was purified by column chromatography using (silica, gradient, 0%-5% Methanol in DCM) to afford Compound 57 (20 mg) as a solid. Yield—11%; $^1$H NMR (400 MHz, DMSO-d6) δ 10.86 (s, 1H), 8.49 (d, J=4.2 Hz, 1H), 7.78 (t, J=7.2 Hz, 1H), 7.36 (d, J=7.8 Hz, 1H), 7.29 (t, J=11.7 Hz, 1H), 4.02-4.00 (m, 1H), 2.67-2.55 (m, 2H), 2.25-2.22 (m, 1H), 2.15-2.12 (m, 1H); LC MS: ES+ 191.1.

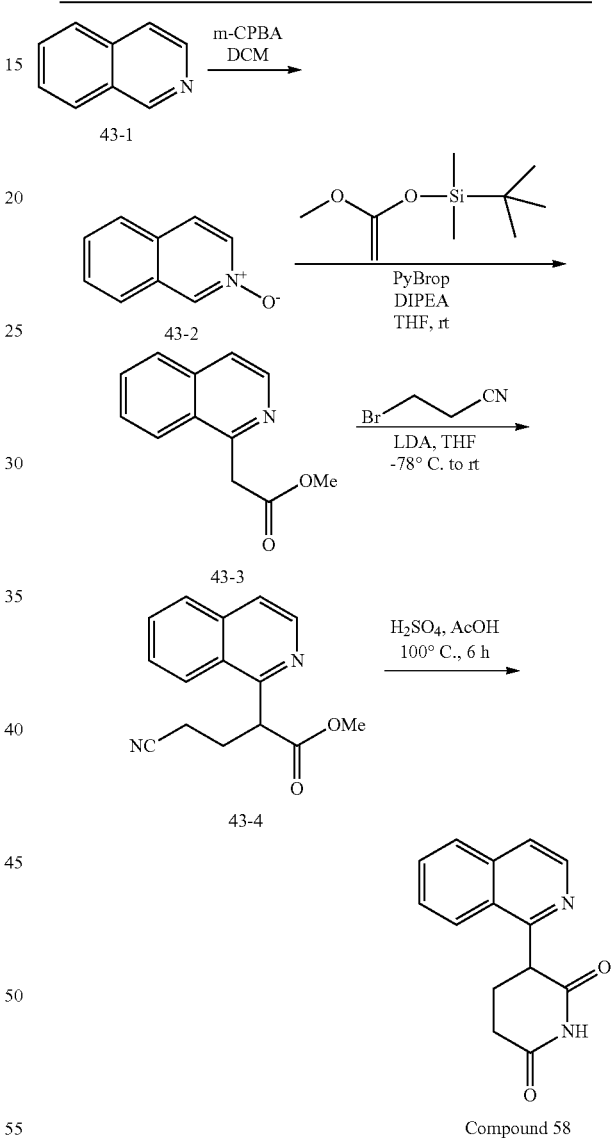

Scheme 43
Synthesis of 3-(Isoquinolin-1-yl)piperidine-2,6-dione (Compound 58)

Synthesis of Isoquinoline 2-oxide (43-2)

To a stirred solution of isoquinoline (43-1) (2 g, 15.4 mmol) in dichloromethane (50 mL) at 0° C., was added mCPBA (3.77 g, 16.9 mmol) portionwise and the reaction mixture was stirred at RT for 18 h. After consumption of starting material as evident from TLC, the reaction mixture was quenched with a saturated solution of sodium sulphite, the organic layer was separated and washed with a saturated solution of sodium carbonate, brine, dried over anhydrous sodium sulphate, and concentrated under reduced pressure to afford isoquinoline 2-oxide (43-2) (2.00 g, 13.7 mmol, 89.6%) as a white gummy solid. $^1$H NMR (400 MHz, DMSO-d6) δ 8.75 (s, 1H), 8.12 (d, J=6 Hz, 1H), 7.85-7.58 (m, 4H).

Synthesis of Methyl 2-(isoquinolin-1-yl)acetate (43-3)

A mixture of isoquinoline 2-oxide (43-2) (200 mg, 1.37 mmol), tert-butyl((1-methoxyvinyl)oxy)dimethylsilane (516 mg, 2.74 mmol) and PyBroP (638 mg, 1.37 mmol) in THF (8 mL) was stirred in the presence of DIPEA (711 μL, 4.11 mmol) at room temperature. After stirring for 2 minutes, a mild exotherm was evident with considerable darkening of the solution. After consumption of starting materials as evident from TLC, the reaction mixture was partitioned between ethyl acetate and water. The combined organic extracts were dried over sodium sulphate and concentrated under reduced pressure. The crude residue was purified by column chromatography (elution with 30-40% EtOAc-Hexane) to afford methyl 2-(isoquinolin-1-yl)acetate (43-3) (60.0 mg, 298 μmol, 21.8%) as a yellow oil. LC MS: ES+ 201.7.

Synthesis of Methyl 4-cyano-2-(isoquinolin-1-yl)butanoate (43-4)

To a stirred solution of methyl 2-(isoquinolin-1-yl)acetate (43-3) (300 mg, 1.49 mmol) in THF (15 ml) was added LDA (319 mg, 2.98 mmol) at −78°. After 1h at 0° C., 3-bromo-propionitrile (199 mg, 1.49 mmol, 3 ml THF) was added to this reaction at 0° C. After 2 hour, TLC ((Rf:0.3. 5.40% ea/hex) and LCMS showed the starting material was consumed and product was formed. The reaction mass was quenched with NH$_4$Cl solution, extracted with ethyl acetate, and the organic layer was dried over sodium sulphate and concentrated. The crude was purified by column chromatography (100-200 mess silica gel) at 20% ea/hex to afford methyl 4-cyano-2-(isoquinolin-1-yl)butanoate (43-4) (240 mg, 943 μmol, 63.4%) as a light yellow liquid. LC MS: ES+ 255.3.

Synthesis of 3-(Isoquinolin-1-yl)piperidine-2,6-dione (Compound 58)

A solution of methyl 4-cyano-2-(isoquinolin-1-yl)butanoate (43-4) (60 mg, 235 μmol) in acetic acid (3 ml) and sulphuric acid (0.5 ml) was heated at 110° C. for 3 h. After 3 hours, TLC showed the product (Rf=0.2 50% ea/hex). The reaction mixture was cooled and concentrated, neutralised with bicarbonate solution, and extracted with ethyl acetate. The organic layer was washed with water, brine and dried over anhydrous sodium sulphate. The crude was purified by column chromatography silica gel (100-200 mesh) eluting with 50% ea/hex to provide the desired product 3-(isoquinolin-1-yl)piperidine-2,6-dione Compound 58 (15.0 mg, 62.4 μmol, 26% yield) as a white solid. $^1$H NMR (400 MHz, DMSO-d6) δ 10.93 (s, 1H), 8.41 (d, J=5.24 Hz, 1H), 8.31 (d, J=7.48 Hz, 1H), 8.00 (d, J=7.72 Hz, 1H), 7.83-7.97 (m, 2H), 7.73-7.69 (m, 1H), 5.02 (brs, 1H), 2.66-2.57 (m, 1H), 2.50-2.36 (m, 2H), 2.27-2.23 (m, 1H); LC MS: ES+ 241.3.

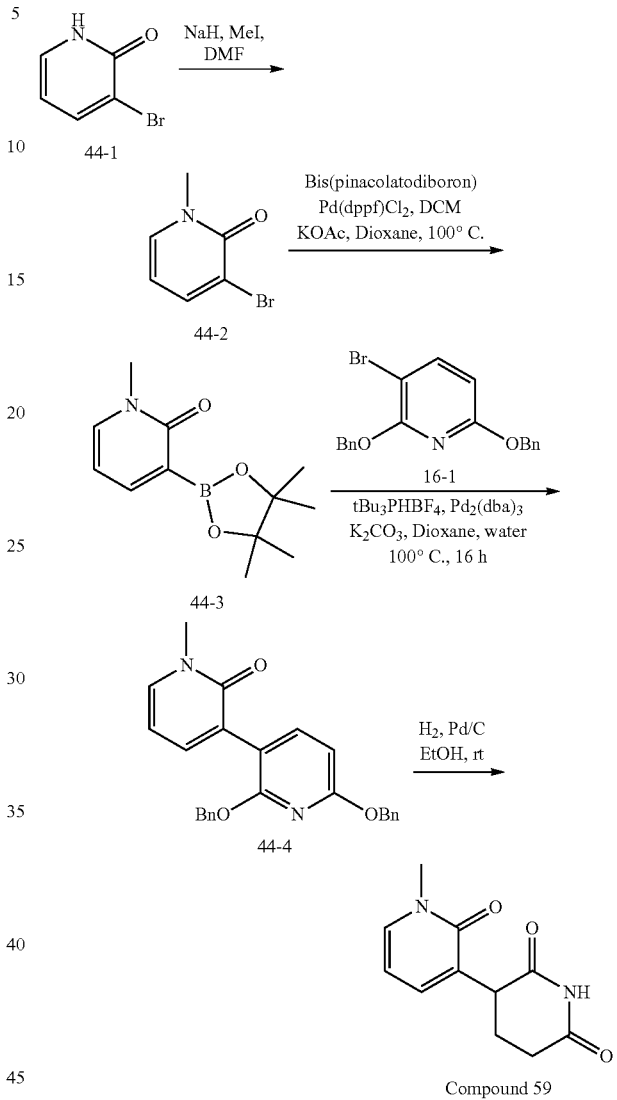

Scheme 44
Synthesis of 3-(1-Methyl-2-oxo-1,2-dihydropyridin-3-yl)-piperidine-2,6-dione (Compound 59)

Synthesis of 3-Bromo-1-methyl-1H-pyridin-2-one (44-2)

To a stirred solution of 3-bromopyridin-2(1H)-one (44-1) (1 g, 5.74 mmol) in dry DMF (4 mL) at 0° C., was added NaH (343 mg, 8.61 mmol) and the mixture was stirred for 30 minutes followed by addition of iodomethane (976 mg, 6.88 mmol) and stirring for another 2 h. After completion of reaction as monitored by TLC, the mixture was partitioned between ethyl acetate and brine. The organic extracts were dried over sodium sulfate, concentrated, and the residue was purified over silica to obtain 3-bromo-1-methylpyridin-2 (1H)-one (44-2) (800 mg, 4.25 mmol, 74.7%) as a solid. LC MS: ES+ 188.0.

Synthesis of 1-Methyl-3-(4,4,5,5-tetramethyl-[1,3,2]dioxaborolan-2-yl)-1H-pyridin-2-one (44-3)

A stirred mixture of 3-bromo-1-methylpyridin-2(1H)-one (42-2) (600 mg, 3.19 mmol), bispinacolatodiboron (1.62 g, 6.38 mmol) and potassium acetate (939 mg, 9.57 mmol) in dioxane (10 mL) was thoroughly degassed under argon followed by addition of Pd(dppf)Cl$_2$-DCM (129 mg, 159 µmol) and heating at 100° C. for 5 hr. The reaction mixture was thereafter filtered over Celite, the filtrate was evaporated and the residual crude purified by column chromatography to obtain 1-methyl-3-(4,4,5,5-tetramethyl-1,3,2-dioxaborolan-2-yl)pyridin-2(1H)-one (44-3) (250 mg, 1.06 mmol, 33.3%) as a sticky mass. LCMS: calculated for [M+H]$^+$ 236; found 154 (corresponding to boronic acid, [M+H]$^+$ 154).

Synthesis of 2',6'-Bis(benzyloxy)-1-methyl-[3,3'-bipyridin]-2(1H)-one (44-4)

A mixture of 1-Methyl-3-(4,4,5,5-tetramethyl-[1,3,2]dioxaborolan-2-yl)-1H-pyridin-2-one 44-3 (200 mg, 1.30 mmol), 2,6-bis(benzyloxy)-3-bromopyridine (16-1) (481 mg, 1.30 mmol) and K$_2$CO$_3$ (539 mg, 3.90 mmol) in dioxane/H$_2$O (2 ml, 4:1, v/v) was thoroughly degassed under argon followed by addition of Pd$_2$(dba)$_3$ (119 mg, 130 µmol) and tri-tertiarybutylphosphine tetrafluoroborate (75.4 mg, 260 µmol) and finally heating at 100° C. overnight. The reaction mixture was filtered over Celite, the filtrate was concentrated and the crude residue was purified by flash column chromatography to afford 2',6'-bis(benzyloxy)-1-methyl-[3,3'-bipyridin]-2(1H)-one (44-4) (120 mg, 301 µmol, 23.2%). LC MS: ES+ 399.2

Synthesis of 3-(1-Methyl-2-oxo-1,2-dihydropyridin-3-yl)piperidine-2,6-dione (Compound 59)

To a stirred solution of 2',6'-bis(benzyloxy)-1-methyl-[3,3'-bipyridin]-2(1H)-one (44-4) (70 mg, 175 µmol) in ethanol (4 ml) was added Pd/C (25 mg) and finally hydrogen balloon pressure. TLC and (Rf=0.3 in 5% MeOH/DCM) LCMS showed product formation. The reaction mass was filtered through a celite bed, which was subsequently washed with methanol. The filtrate was concentrated and the crude was purified by prep TLC to afford 3-(1-methyl-2-oxo-1,2-dihydropyridin-3-yl)piperidine-2,6-dione (compound 59) (15 mg, 38.9%) LCMS: LC MS: ES+221.1.

Scheme 45
Synthesis of 3-Hydroxy-2,6-dioxo-piperidine-3-carboxylic acid benzyl ester (Compound 60)

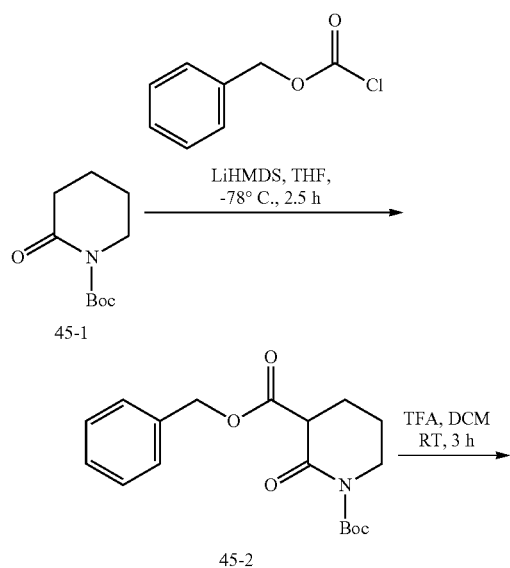

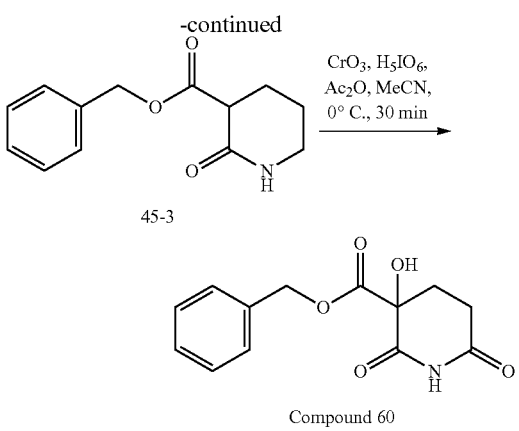

Synthesis of 2-Oxo-piperidine-1,3-dicarboxylic acid 3-benzyl ester 1-tert-butyl ester (45-2)

To a stirred solution of tert-butyl 2-oxopiperidine-1-carboxylate (45-1) (500 mg, 2.50 mmol) in THF (50 mL) was added Lithium bis(trimethylsilyl)amide (5.25 mL, 5.25 mmol) at −78° C. over 30 min. After Benzyl chloroformate (712 µL, 2.50 mmol) was dissolved in THF and added to the reaction mixture at −78° C. stirring was continued for 2 hours. After the reaction mixture was quenched with aqueous saturated NH$_4$Cl solution at −78° C. and extracted with EtOAc (2×100 mL), washed with brine (50 mL), dried (Na$_2$SO$_4$) and evaporated. The crude was purified by column chromatography (silica, gradient, 0%-20% EtOAc in Hexane as eluent) to provide 3-benzyl 1-tert-butyl 2-oxopiperidine-1,3-dicarboxylate (45-2) (605 mg) as a liquid. Yield—90%; LC MS: ES+ 334.3.

Synthesis of 2-Oxo-piperidine-3-carboxylic acid benzyl ester (45-3)

To a stirred solution of 3-benzyl 1-tert-butyl 2-oxopiperidine-1,3-dicarboxylate (45-2) (650 mg, 1.94 mmol) in DCM (10 mL) was added Trifluoroacetic acid (1.5 mL) at 0° C. The reaction mixture was stirred at 0° C. for 3 hours. The reaction mixture was basified with NaHCO$_3$ solution and extracted with EtOAc (2×50 mL), washed with brine (50 mL), dried over Na$_2$SO$_4$ and evaporated. The crude was washed with pentane to provide benzyl 2-oxopiperidine-3-carboxylate (45-3) (440 mg) as a brown semi-solid. Yield-97%; LC MS: ES+ 234.4.

Synthesis of 3-Hydroxy-2,6-dioxo-piperidine-3-carboxylic acid benzyl ester (Compound 60)

A solution of periodic acid (2.55 g, 11.2 mmol) and chromium(VI) oxide (37.5 mg, 376 µmol) in Acetonitrile (40 mL) was stirred at room temperature for 30 minutes. Then, Acetic anhydride (1.14 g, 11.2 mmol) was added. The reaction mixture was cooled to 0° C. and benzyl 2-oxopiperidine-3-carboxylate (45-3) (440 mg, 1.88 mmol) was added in one portion and the reaction mixture was further stirred for 30 min. at room temperature. Ice-water (15-20 mL) was added and the mixture was extracted with ethyl acetate (3×25 mL). The combined organic layer was washed with saturated NaHCO$_3$ and Na$_2$S$_2$O$_3$ solution, and finally with brine. The organic phase was dried over anhydrous Na₂SO₄ and the solvent was removed under reduced pressure. The crude was purified by preparative TLC (3% methanol—EtOAc) to provide benzyl 3-hydroxy-2,6-dioxopiperidine-3-carboxylate (Compound 60) (50.0 mg) as an off-white solid. Yield-10%; ¹H NMR (400 MHz, DMSO-d6) δ 11.05 (s, 1H), 7.37-7.33 (m, 5H), 6.90 (s, 1H), 5.21 (s, 2H), 2.69-2.55 (m, 1H), 2.48-2.40 (m, 1H), 2.32-2.24 (m, 1H), 2.05-2.00 (m, 1H); GC MS: m/z-263.

Scheme 46 Synthesis of 3-(1-Methyl-imidazo[1,5-a]pyridin-3-yl)-piperidine-2,6-dione (Compound 61)

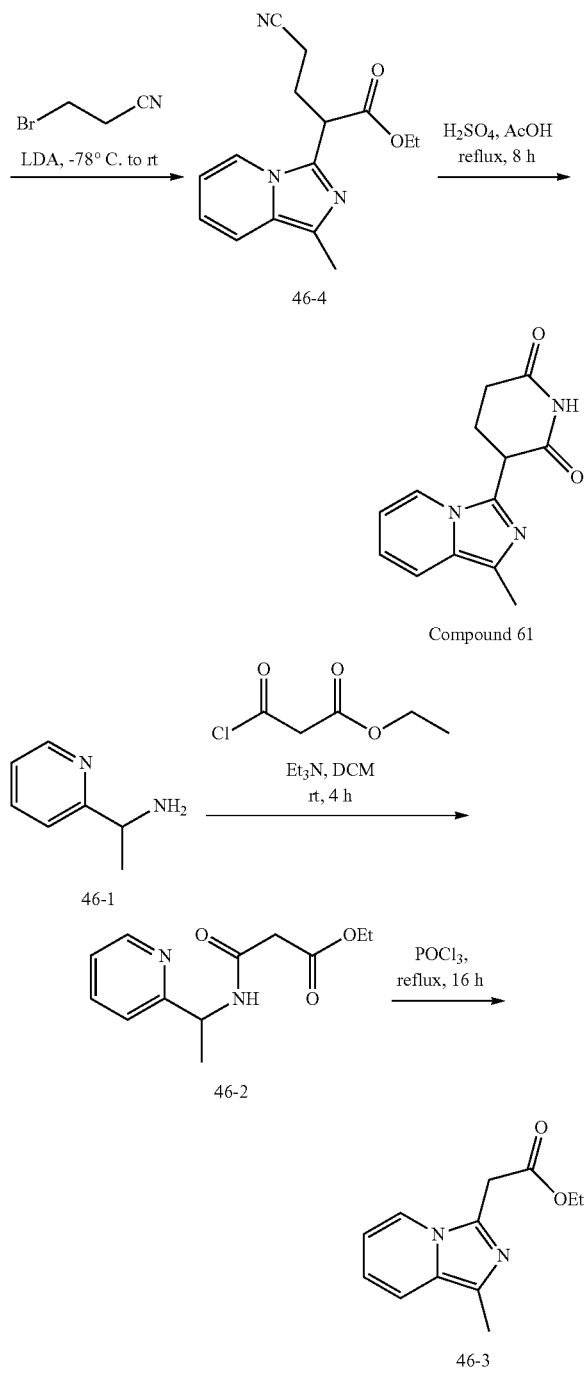

Synthesis of N-(1-Pyridin-2-yl-ethyl)-malonamic acid ethyl ester (46-2)

To a stirred solution of 1-(pyridin-2-yl)ethanamine (46-1) (1 g, 8.18 mmol) in Dichloromethane (20 mL) at 0° C. was added Triethyl amine (1.13 mL, 8.18 mmol) and ethyl 3-chloro-3-oxopropanoate (1.00 mL, 8.18 mmol). The reaction was stirred at room temperature for 4 hours and then diluted with DCM, washed with saturated sodium bicarbonate solution, water, brine and dried over sodium sulfate. The organics were concentrated under reduced pressure and purified by column chromatography using (silica, gradient, 0%-2% methanol in DCM) to afford ethyl 3-oxo-3-((1-(pyridin-2-yl)ethyl)amino)propanoate (46-2) (1 g) as a gum. Yield-52%; LC MS: ES+ 237.3.

Synthesis of (1-Methyl-imidazo[1,5-a]pyridin-3-yl)-acetic acid ethyl ester (46-3)

A stirred solution of ethyl 3-oxo-3-((1-(pyridin-2-yl)ethyl)amino)propanoate (46-2) (600 mg, 2.53 mmol) in Phosphoryl chloride (5 mL) was heated at 100° C. for 16 hours. The reaction was concentrated under reduced pressure, diluted with ice cold water, basified with saturated sodium bicarbonate solution, extracted with dichloromethane. The organics were dried over sodium sulfate, concentrated and purified by column chromatography (silica, gradient, 0%-1.5% methanol in dichloromethane) to provide ethyl 2-(1-methylimidazo[1,5-a]pyridin-3-yl)acetate (46-3) (465 mg) as a brown gum. Yield-84%; LC MS: ES+ 219.1.

Synthesis of 4-Cyano-2-(1-methyl-imidazo[1,5-a]pyridin-3-yl)-butyric acid ethyl ester (46-4)

A stirred solution of ethyl 2-(1-methylimidazo[1,5-a]pyridin-3-yl)acetate (46-3) (250 mg, 1.14 mmol) in Tetrahydrofuran (5 mL) under argon was cooled to −78° C. Lithium diisopropylamide (1.14 mL, 2.28 mmol) was added to the reaction mixture dropwise. The reaction was stirred for 1 hour at 0° C. and then once again cooled to −78° C. 3-Bromopropionitrile (94.1 µL, 1.14 mmol) was added to the reaction mixture and stirring of the mixture was continued for additional 30 minutes at −78° C. The reaction was gradually warmed to room temperature and stirring was continued for 3 hours. The reaction was quenched with saturated ammonium chloride solution and extracted with ethyl acetate. The combined organics were dried over sodium sulfate and concentrated under reduced pressure to afford ethyl 4-cyano-2-(1-methylimidazo[1,5-a]pyridin-3-yl)butanoate (46-4) (180 mg) as a brown gum. Yield-58%; LC MS: ES+ 272.35.

Synthesis of 3-(1-Methyl-imidazo[1,5-a]pyridin-3-yl)-piperidine-2,6-dione (Compound 61)

A 10 mL round bottom flask was charged with ethyl 4-cyano-2-(1-methylimidazo[1,5-a]pyridin-3-yl)butanoate (46-4) (220 mg, 810 mmol), acetic acid (5 mL) and sulfuric acid (1 mL) and the reaction was heated at 110° C. for 6h. The reaction was concentrated under reduced pressure, basified with sat'd sodium bicarbonate solution, extracted with ethyl acetate, dried over sodium sulfate and concentrated under reduced pressure. The residue was purified by column chromatography (35% ethyl acetate in hexane) to provide 3-(1-methylimidazo[1,5-a]pyridin-3-yl)piperidine-2,6-dione (compound 61) (40.0 mg, 164 µmol, 20% yield) as an off-white solid. ¹H NMR (400 MHz, DMSO-d6) δ 10.92

(s, 1H), 8.10 (d, J=7.12 Hz, 1H), 7.48 (d, J=9.08 Hz, 1H), 6.66-6.62 (m, 1H), 6.57 (t, J=6.62 Hz, 1H), 4.57 (dd, J=10.52, 5.0 Hz, 1H), 2.72-2.62 (m, 2H), 2.46-2.36 (m, 1H), 2.22-2.14 (m, 1H); LC MS: ES+ 244.1.

Scheme 47: Synthesis of 3-(1-Methyl-1H-benzoimidazol-2-yl)-piperidine-2,6-dione (Compound 62):

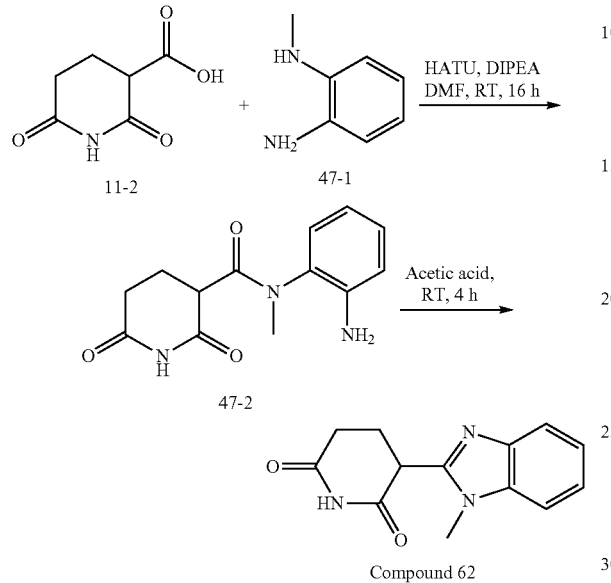

Synthesis of 2,6-Dioxo-piperidine-3-carboxylic acid (2-amino-phenyl)-methyl-amide (47-2)

To a stirred solution of 2,6-dioxopiperidine-3-carboxylic acid (11-2) (220 mg, 1.4 mmol) in DMF (3.0 mL) was added $N^1$-methylbenzene-1,2-diamine 47-1 (310 mg, 1.4 mmol), DIPEA (1 mL) and HATU (692 mg, 1.82 mmol). The reaction mixture was then stirred at room temperature for 16 hours. The reaction was diluted with ethyl acetate and the organic layer was washed with saturated aqueous NaHCO$_3$ solution, water, brine, dried over sodium sulfate. The reaction was concentrated and crude material was purified by Prep TLC Plate (eluting with 2% Methanol/DCM) to afford N-(2-aminophenyl)-N-methyl-2,6-dioxopiperidine-3-carboxamide (47-2) (240 mg, 918 µmol, 65%) as a white solid. LC MS: ES+ 261.9.

Synthesis of 3-(1-Methyl-1H-benzoimidazol-2-yl)-piperidine-2,6-dione (Compound 62)

To a stirred solution of N-(2-aminophenyl)-N-methyl-2,6-dioxopiperidine-3-carboxamide (47-2) (240 mg, 918 µmol) was added acetic acid (3.0 mL) and the reaction was continued for 4 hours. The solvent in the reaction mixture was evaporated under reduced pressure and the desired compound was purified by combiflash and the compound obtained was lyophilized to obtain 3-(1-methyl-1H-benzo[d]imidazol-2-yl)piperidine-2,6-dione (Compound 62) (78.1 mg) as an off-white solid. Yield-35%; $^1$H NMR (400 MHz, DMSO-d6) δ 11.11 (s, 1H), 7.69-7.64 (m, 2H), 7.38-7.35 (m, 2H), 4.64 (m, 1H), 3.86 (s, 3H), 2.69 (m, 2H), 2.52-2.50 (m, 1H), 2.30-2.26 (m, 1H); LC MS: ES+ 244.1.

Scheme 48
Synthesis of 3-Phenyl-piperidine-2,6-dione (Compound 63)

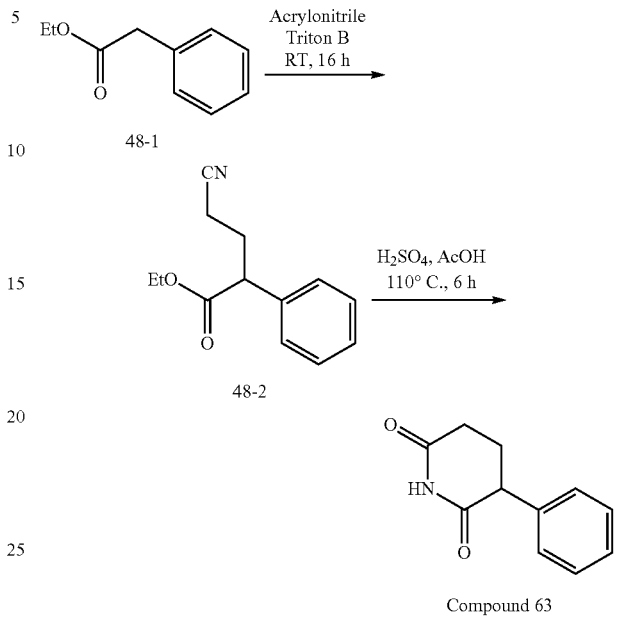

Synthesis of 4-Cyano-2-phenyl-butyric acid ethyl ester (48-2)

To a stirred solution of ethyl 2-phenylacetate (48-1) (1.0 g, 6.09 mmol) in toluene (10.0 mL) was added Triton-B (132 µL, 304 µmol), followed by acrylonitrile (398 µL, 6.09 mmol) and the reaction mixture was stirred at room temperature for 16 hours. TLC showed formation of a new spot (Rf-0.3 in 20% ethyl acetate/hexane). The reaction was diluted with ethyl acetate and the organic layer was washed with water, brine, dried over sodium sulfate and concentrated. The crude material was purified by combiflash chromatography (0%-16% ethyl acetate/hexane) to afford ethyl 4-cyano-2-phenylbutanoate (48-2) (500 mg, 2.30 mmol, 38%) as an off-white solid. ES+ 217.0.

Synthesis of 3-Phenyl-piperidine-2,6-dione (Compound 63)

A 10 mL round bottom flask was charged with ethyl 4-cyano-2-phenylbutanoate (48-2) (200 mg, 920 µmol) and Acetic acid (2 mL). Sulfuric acid (0.5 mL) was added and the reaction mixture was heated at 110° C. for 6h. The reaction was concentrated under reduced pressure, basified with sat'd sodium bicarbonate solution, extracted with ethyl acetate, dried over sodium sulfate and concentrated under reduced pressure. The crude residue was purified by column chromatography (35% ethyl acetate in hexane) to provide 3-phenylpiperidine-2,6-dione (compound 63) (27.0 mg, 142 µmol, 15.5%) as a brown solid. $^1$H NMR (400 MHz, DMSO-d6) δ 10.83 (s, 1H), 7.35-7.28 (m, 2H), 7.26-7.21 (m, 3H), 3.88-3.82 (m, 1H), 2.70-2.60 (m, 1H), 2.50-2.44 (m, 1H), 2.22-2.12 (m, 1H), 2.06-2.01 (m, 1H); GC MS: m/z-189.

Scheme 49 Synthesis of 3-(1-Phenyl-1H-imidazol-4-yl)-piperidine-2,6-dione (Compound 64)

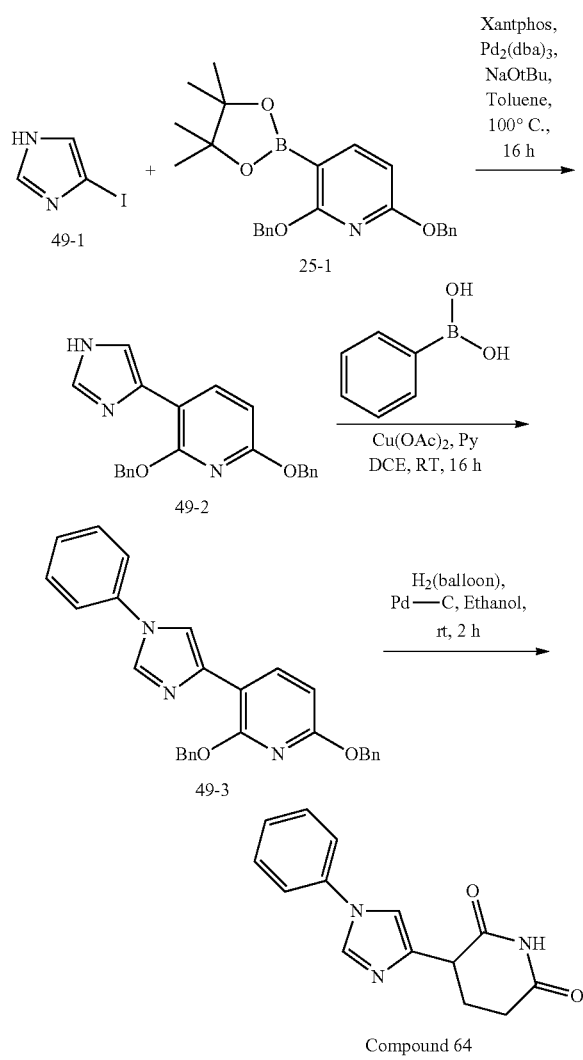

Synthesis of 2,6-Bis-benzyloxy-3-(1H-imidazol-4-yl)-pyridine (49-2)

To a stirred solution of 4-iodo-1H-imidazole (100.0 mg, 515 µmol) in Dioxane:water (4:1) (5.0 mL) was added 2,6-bis(benzyloxy)-3-(4,4,5,5-tetramethyl-1,3,2-dioxaborolan-2-yl)pyridine (534 mg, 1.28 mmol) and $K_2CO_3$ (212 mg, 1.54 mmol). The reaction mixture was degassed for 15 minutes. $PdCl_2$(dppf)-DCM (42.0 mg, 51.5 µmol) was added to the reaction mixture and the reaction mixture was heated at 100° C. for 16 hours. TLC and LCMS showed formation of a new spot (Rf-0.5 in 5% Methanol/DCM). The reaction was cooled to room temperature and filtered through a celite bed. The filtrate was separated and organic layer was dried over sodium sulfate and concentrated. The crude residue was purified by column chromatography using (silica, gradient, 0%-1.5% Methanol in DCM) to afford 2,6-bis(benzyloxy)-3-(1H-imidazol-4-yl)pyridine (49-2) (125 mg, 349 µmol, 67.9%) as an off-white solid. LC MS: ES+ 358.1

Synthesis of 2,6-Bis-benzyloxy-3-(1-phenyl-1H-imidazol-4-yl)-pyridine (49-3)

A 25 ml round bottom flask was charged with 2,6-bis (benzyloxy)-3-(1H-imidazol-4-yl)pyridine (49-2) (125 mg, 349 µmol), phenylboronic acid (42.5 ng, 349 µmol) and 1,2-Dichloroethane (5 mL). Pyridine (139 µL, 1.74 mmol) and Copper(II) acetate monohydrate (6.96 mg, 34.9 µmol) were added to the reaction mixture. The reaction was stirred at RT (keeping mouth of the RB open) for 72h. The reaction was diluted with water, extracted with ethyl acetate, washed with brine and dried over sodium sulfate. The organics were concentrated under reduced pressure and the crude residue was purified by silica gel column chromatography eluting at 20% ethyl acetate in hexane to afford 2,6-bis(benzyloxy)-3-(1-phenyl-1H-imidazol-4-yl)pyridine (49-3) (80.0 mg, 184 µmol, 53%) as a gum. LC MS: ES+ 434.0

Synthesis of 3-(1-Phenyl-1H-imidazol-4-yl)-piperidine-2,6-dione (Compound 64)

A 25 ml round bottom flash was charged with 2,6-bis (benzyloxy)-3-(1-phenyl-1H-imidazol-4-yl)pyridine (49-3) (75 mg, 173 µmol) and Ethanol (10 mL). The solution was degassed with argon for 10 minutes and then Palladium on charcoal (36.8 mg, 34.6 µmol) was added. The reaction was stirred at RT for 16h and then filtered through celite and concentrated under reduced pressure. The crude residue was purified by column chromatography eluting at 1.5% methanol in dichloromethane) to afford 3-(1-phenyl-1H-imidazol-4-yl)piperidine-2,6-dione (Compound 64) (8.90 mg, 34.8 µmol, 20.1%) as brown sticky solid. $^1$H NMR (400 MHz, DMSO-d6) δ 10.79 (s, 1H), 8.21 (s, 1H), 7.66-7.61 (m, 3H), 7.51 (t, J=7.56 Hz, 2H), 7.35 (t, J=6.74 Hz, 1H), 3.85-3.82 (m, 1H), 2.67-2.58 (m, 2H), 2.15 (brs, 2H); LC MS: ES+ 256.4

Scheme 50 Synthesis of (S)-8-(2-(4-(4-Chlorophenyl)-2,3,9-trimethyl-6H-thieno[3,2-f][1,2,4]triazolo[4,3-a][1,4]diazepin-6-yl)acetamido)octanoic acid (50-4)

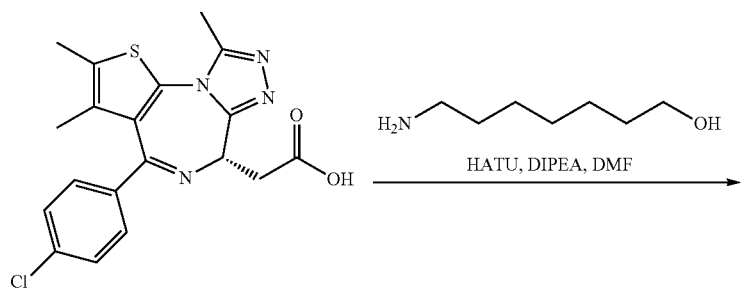

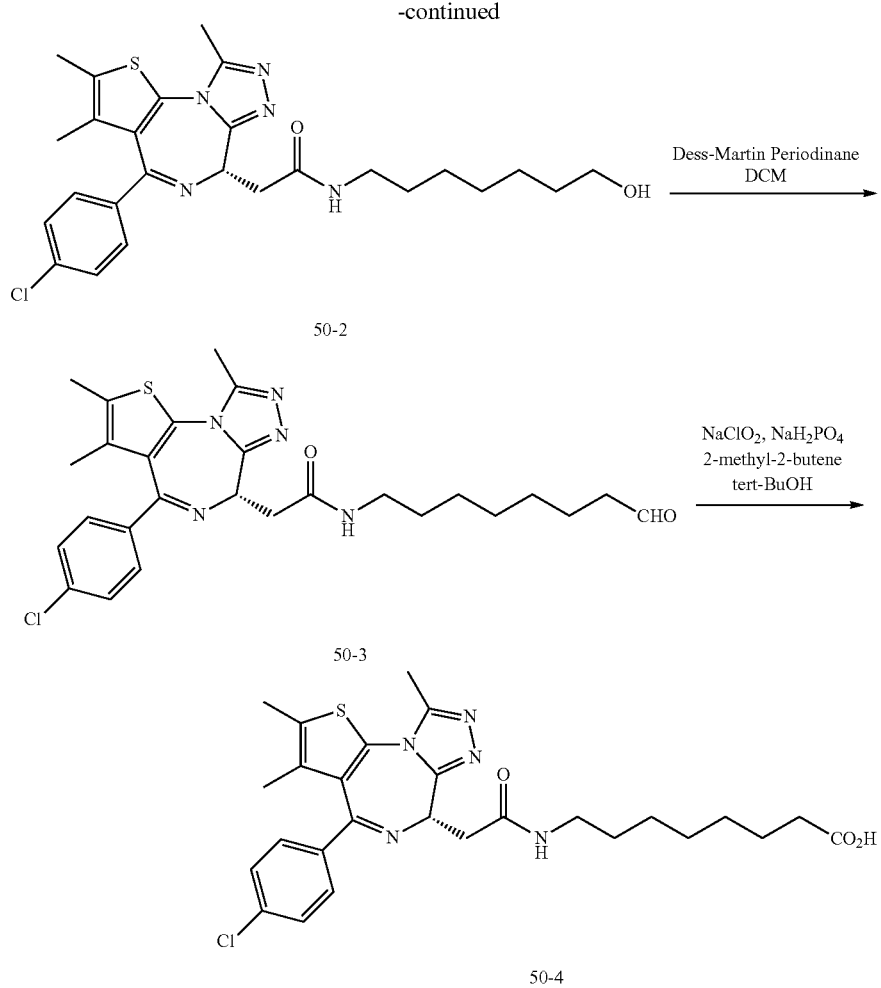

(S)-2-(4-(4-Chlorophenyl)-2,3,9-trimethyl-6H-thieno[3,2-f][1,2,4]triazolo[4,3-a][1,4]diazepin-6-yl)-N-(8-hydroxyoctyl)acetamide (50-2)

To a solution of (S)-2-(4-(4-chlorophenyl)-2,3,9-trimethyl-6H-thieno[3,2-f][1,2,4]triazolo[4,3-a][1,4]diazepin-6-yl)acetic acid (50-1) (450 mg, 1.12 mmol) in DMF (2.80 mL) was added 8-aminooctan-1-ol (244 mg, 1.68 mmol), Diisopropylethylamine (389 µL, 2.24 mmol) and HATU (509 mg, 1.34 mmol), The reaction was stirred for 24 h, at which time the reaction was concentrated and purified by isco (24g column 0-10% MeOH/DCM) to provide (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide (400 mg, 67.6%). LCMS ES+=529.1

Synthesis of (S)-2-(4-(4-Chlorophenyl)-2,3,9-trimethyl-6H-thieno[3,2-f.][1,2,4]triazolo[4,3-a][1,4]diazepin-6-yl)-N-(8-oxooctyl)acetamide (50-3)

A 25 mL rbf was charged with (S)-2-(4-(4-chlorophenyl)-2,3,9-trimethyl-6H-thieno[3,2-f][1,2,4]triazolo[4,3-a][1,4]diazepin-6-yl)-N-(8-hydroxyoctyl)acetamide (50-2) (400 mg, 757 µmol) and dichloromethane (4 mL). Dess-Martin Periodinane (0.3 M in DCM, 3.02 mL, 908 µmol) was added and the reaction was stirred at rt for 1h, then quenched with 0.5 mL isopropanol, sat'd sodium thiosulfate, and sat'd sodium bicarbonate. The reaction was extracted 3×DCM, organics were dried over $Na_2SO_4$, filtered and concentrated to provide (S)-2-(4-(4-chlorophenyl)-2,3,9-trimethyl-6H-thieno[3,2-f][1,2,4]triazolo[4,3-a][1,4]diazepin-6-yl)-N-(8-oxooctyl)acetamide (390 mg, 741 µmol, 98% yield) (50-3), which was used in subsequent reactions without further purification. LCMS ES+ 527.3.

Synthesis of (S)-8-(2-(4-(4-Chlorophenyl)-2,3,9-trimethyl-6H-thieno[3,2-f][1,2,4]triazolo[4,3-a][1,4]diazepin-6-yl)acetamido)octanoic acid (50-4)

A 25 mL rbf was charged with (S)-2-(4-(4-chlorophenyl)-2,3,9-trimethyl-6H-thieno[3,2-f][1,2,4]triazolo[4,3-a][1,4]diazepin-6-yl)-N-(8-oxooctyl)acetamide (50-3) (250 mg, 475 µmol), $NaClO_2$ (128 mg, 1.425 mmol), $NaH_2PO_4$ (202 mg, 1.425 mmol), 2-methyl-2-butene (71 µL, 1.425 mmol) and tert-butanol (5 mL). The reaction was stirred at rt for 18h, acidified with 1N HCl and extracted with ethyl acetate. The combined organics were dried over $Na_2SO_4$, filtered and concentrated. The crude residue was purified by reverse-phase isco (5-100% MeCN/$H_2O$ containing 0.01% TFA) to provide (S)-8-(2-(4-(4-chlorophenyl)-2,3,9-trimethyl-6H-thieno[3,2-f][1,2,4]triazolo[4,3-a][1,4]diazepin-6-yl)acetamido)octanoic acid (50-4) (200 mg, 368 µmol, 77% yield) as a white solid. LCMS ES+=543.3

Scheme 51 Synthesis of (S)-N-(8-Aminooctyl)-2-(4-(4-chlorophenyl)-2,3,9-trimethyl-6H-thieno[3,2-f][1,2,4]triazolo[4,3-a][1,4]diazepin-6-yl)acetamide (51-2)

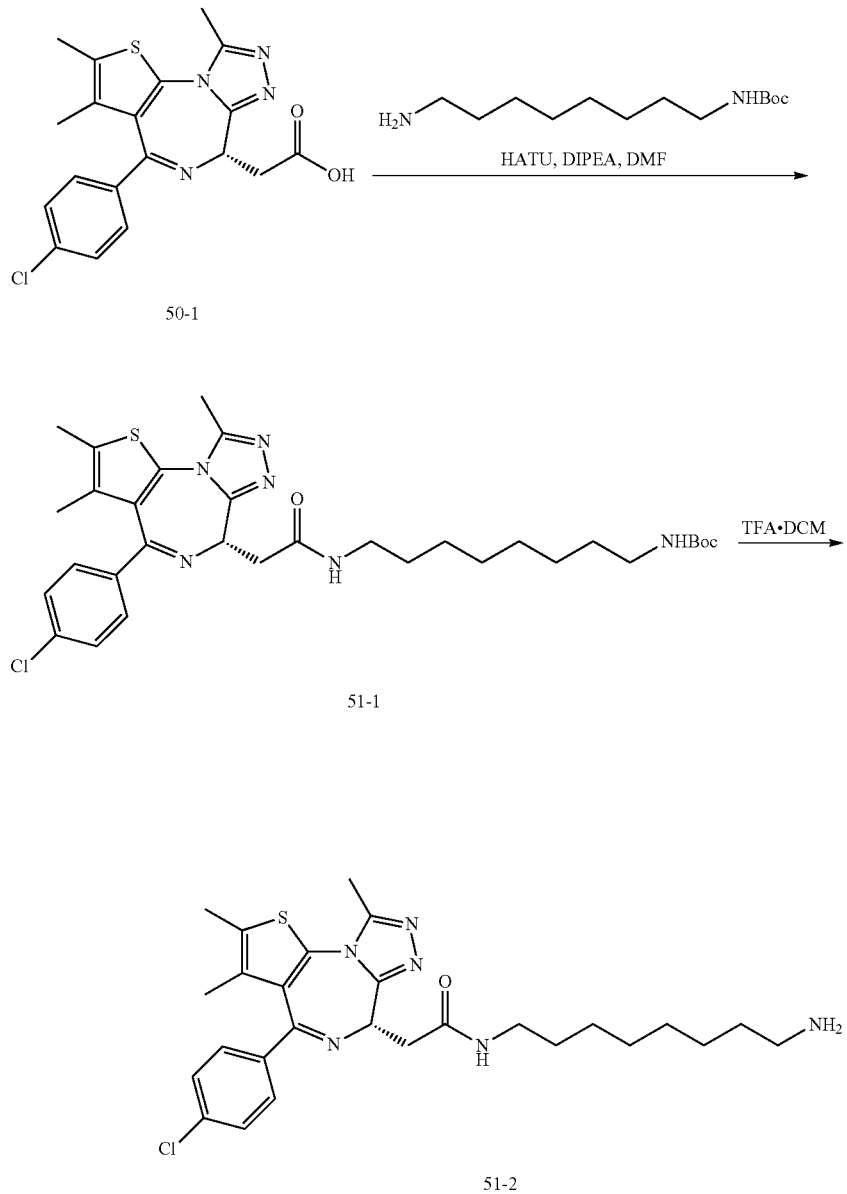

Synthesis of tert-Butyl (S)-(8-(2-(4-(4-chlorophenyl)-2,3,9-trimethyl-6H-thieno[3,2-f][1,2,4]triazolo[4,3-a][1,4]diazepin-6-yl)acetamido)octyl)carbamate (51-1)

To a solution of (S)-2-(4-(4-chlorophenyl)-2,3,9-trimethyl-6H-thieno[3,2-f][1,2,4]triazolo[4,3-a][1,4]diazepin-6-yl)acetic acid (50-1) (150 mg, 374 µmol) in DMF (935 µL) was added tert-butyl (8-aminooctyl)carbamate (118 mg, 486 µmol), Diisopropylethylamine (130 L, 748 µmol) and HATU (170 mg, 448 µmol). The reaction was stirred for 24 h, at which time the reaction was concentrated and purified by isco (24g column 0-10% MeOH/DCM) to provide (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide (51-2) (200 mg, 85.4%).

Synthesis of (S)—N-(8-Aminooctyl)-2-(4-(4-chlorophenyl)-2,3,9-trimethyl-6H-thieno[3,2-f][1,2,4]triazolo[4,3-a][1,4]diazepin-6-yl)acetamide (51-3)

To a solution of (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide (51-1) (200 mg, 85%) in 5 mL DCM was added TFA (3 mL). The reaction was stirred at rt for 1h and then concentrated to provide a TFA salt of (S)—N-(8-aminooctyl)-2-(4-(4-chlorophenyl)-2,3,9-trimethyl-6H-thieno[3,2-f][1,2,4]triazolo[4,3-a][1,4]diazepin-6-yl)acetamide (51-2) (180 mg) which was used in subsequent reactions without further purification.

Scheme 52 Synthesis of 8-(2-((S-)-4-(4-Chlorophenyl)-2,3,9-trimethyl-6H-thieno[3,2-f][1,2,4]triazolo[4,3-a][1,4]diazepin-6-yl)acetamido)-N-(3-(2,6-dioxopiperidin-3-yl)-1-methyl-1H-indazol-6-yl)octanamide (Degronimer 1)

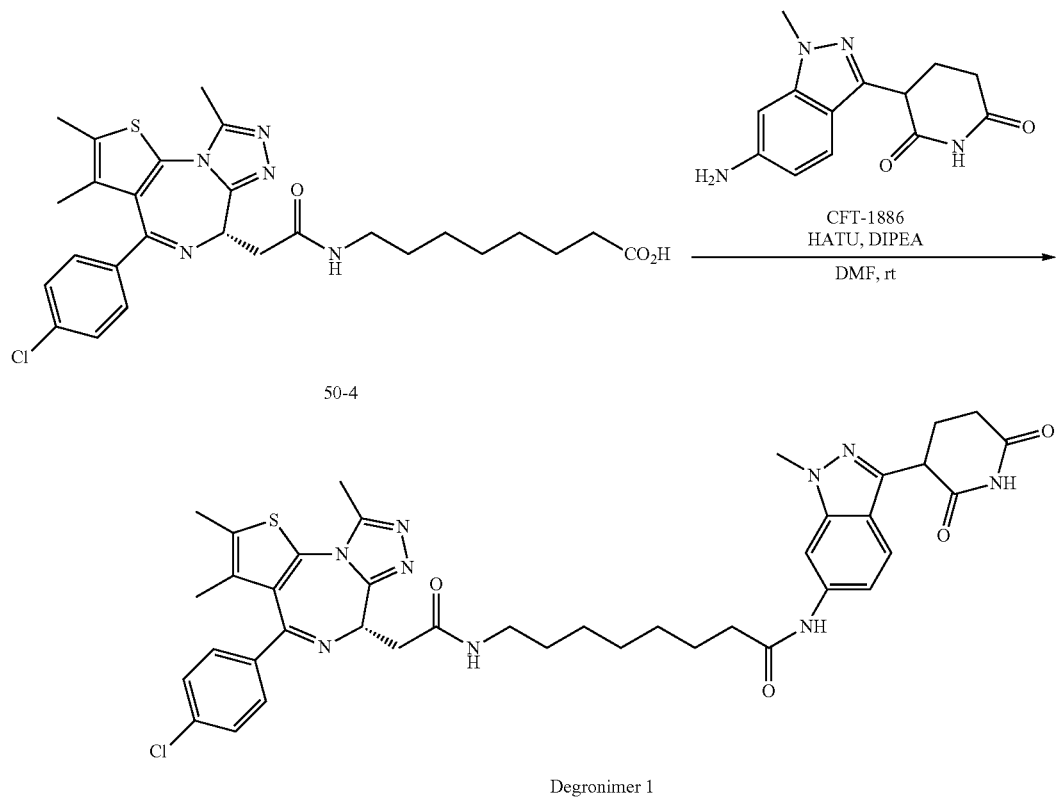

Degronimer 1

(S)-8-(2-(4-(4-chlorophenyl)-2,3,9-trimethyl-6H-thieno[3,2-f][1,2,4]triazolo[4,3-a][1,4]diazepin-6-yl)acetamido)octanoic acid acid (50-4) (30 mg, 55.14 umol) and 3-(6-amino-1-methyl-indazol-3-yl)piperidine-2,6-dione Compound 51 (15.66 mg, 60.65 umol) in DMF (300 uL) were treated with HATU (39.83 mg, 104.76 umol) followed by N,N-Diisopropylethylamine (32.78 mg, 253.63 umol, 44.18 uL). The solution was stirred at rt. Upon completion of the reaction as determined by LCMS, the reaction was purified directly on a reverse-phase C18 column, eluting with 10-100% MeCN in $H_2O$. The product combining fractions were combined, solvent removed and product extracted 3× $CH_2Cl_2$. The organic layers were dried over $Na_2SO_4$, filtered and solvent removed to give 8-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2,6-dioxopiperidin-3-yl)-1-methyl-1H-indazol-6-yl)octanamide Degronimer 1 (12 mg, 15.30 umol, 27.8% yield) as a light brown solid. 1H NMR (400 MHz, DMSO-d6) δ 10.84 (s, 1H), 10.02 (s, 1H), 8.13 (t, J=5.6 Hz, 1H), 8.06 (s, 1H), 7.58 (d, J=8.7 Hz, 1H), 7.46 (d, J=8.5 Hz, 2H), 7.43-7.37 (m, 2H), 4.51-4.44 (m, 1H), 4.29 (dd, J=9.5, 5.1 Hz, 1H), 3.88 (s, 3H), 3.27-3.02 (m, 4H), 2.68-2.60 (m, 2H), 2.57 (s, 2H), 2.37 (s, 2H), 2.35-2.29 (m, 2H), 2.20-2.09 (m, 2H), 1.60 (s, 3H), 1.48-1.40 (m, 2H), 1.30 (s, 4H), 1.22 (s, 5H), 0.91 (t, J=7.4 Hz, 1H), 0.87-0.80 (m, 1H). LC/MS (ES+): m/z 782.2 $(M+H)^+$.

IV. Biological Data

Example 7: CRBN-DDB1 Fluorescence Polarization (FP) Assay

Measuring compound ligand binding to CRBN-DDB1 was carried out using an established sensitive and quantitative in vitro fluorescence polarization (FP) based binding assay. (See, I. J. Enyedy et al, J. Med. Chem., 44: 313-4324 [2001]). Compounds were dispensed from serially diluted DMSO stock into black 384-well compatible fluorescence polarization plates using an Echo acoustic dispenser. Compound binding to CRBN-DDB1 was measured by displacement of either a (−)-Thalidomide-Alexa Fluor® or Pomalidomide-fluorescein conjugated probe dye. A 20 μL mixture containing 400 nM CRBN-DDB 1 and 5 nM probe dye in 50 mM Hepes, pH 7.4, 200 mM NaCl, 1% DMSO and 0.1% pluronic acid-127 acid was added to wells containing compound and incubated at room temperature for 60 min. Matching control wells excluding CRBN-DDB1 were used to correct for background fluorescence. Plates were read on an Envision plate reader with appropriate FP filter sets. The corrected S (perpendicular) and P (parallel) values were used to calculate fluorescence polarization (FP) with the following equation: $FP=1000*(S-G*P)/(S+G*P)$. The fractional amount of bound probe (FB) to CRBN-DDB1 as a function of compound concentration was fitted according to Wang; FEBS Letters 360, (1995), 111-114 to obtain fits for parameter offsets and binding constant ($K_A$) of competitor compound.

Example 8: Cell Viability Analysis

RPMI 1640 medium and fetal bovine serum (FBS) were purchased from Gibco (Grand Island, N.Y., USA). CellTiter-Glo® 2.0 Assay was purchased from Promega (Medison, Wis., USA). MOLT4.1 (WT) cell line was purchased from ATCC (Manassas, Va., USA) and MOLT4.2 (CRBN Knock Out) cell line was generated in house. Cell culture flasks and 384-well microplates were acquired from VWR (Radnor, Pa., USA).

MOLT4.1 and MOLT4.2 cell viability was determined based on quantification of ATP using CellTiter-Glo® 2.0 luminescent Assay kit, which signals the presence of metabolically-active cells. Briefly, MOLT4.1 and MOLT4.2 cells were seeded into 384-well plates at a cell density of 750 cells per well, the plates were kept at 37° C. with 5% CO2 overnight. On the following day, test compounds were added to the cells from a top concentration of 1 μM with 10 points, half log titration in duplicates. The cells treated in the absence of the test compound were the negative control and the cells treated in the absence of CellTiter-Glo® 2.0 were the positive control. At the same day of compound treatment, CellTiter-Glo® 2.0 was added to a plate with cells treated in the absence of the test compound to establish Cytostatic control value (Cro). Cells treated with the test compound were incubated for 72 hr. CellTiter-Glo reagent was then added to the cells and Luminescence was acquired on EnVision™ Multilabel Reader (PerkinElmer, Santa Clara, Calif., USA).

TABLE 1

| Cmpd # | Structure | Kd |
|---|---|---|
| 1 | 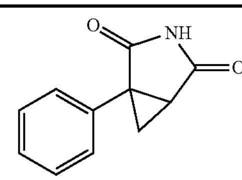 | + |
| 2 | 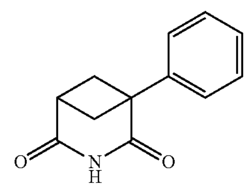 | ++ |
| 3 | 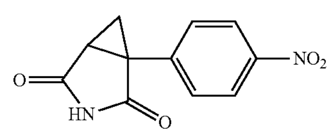 | + |
| 4 | 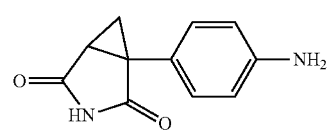 | ++ |
| 5 | 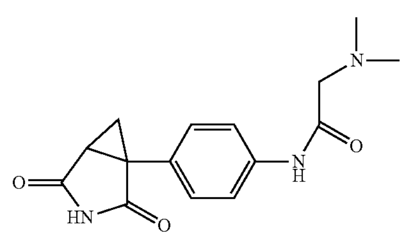 | + |
| 6 | 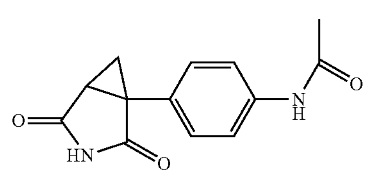 | + |
| 7 | 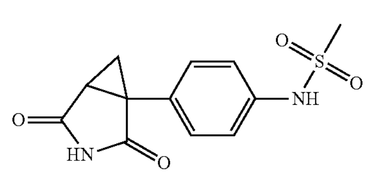 | + |

TABLE 1-continued

| Cmpd # | Structure | Kd |
|---|---|---|
| 8 | (3-methyl-3-phenylpiperidine-2,6-dione) | ++ |
| 9 (3:2 mixture of regioisomers) | (3-methyl-3-(4-nitrophenyl)piperidine-2,6-dione) + (3-methyl-3-(2-nitrophenyl)piperidine-2,6-dione) | ++ |
| 10 | (3-(4-aminophenyl)-3-methylpiperidine-2,6-dione) | ++ |
| 11 | (3-(2-aminophenyl)-3-methylpiperidine-2,6-dione) | ++ |
| 12 | (3-((1-methyl-1H-benzo[d]imidazol-2-yl)methyl)piperidine-2,6-dione) | +++ |
| 13 | (3-((1-methyl-1H-indazol-3-yl)methyl)piperidine-2,6-dione) | + |

TABLE 1-continued

| Cmpd # | Structure | Kd |
|---|---|---|
| 14 | 2,6-dioxopiperidine-3-carboxamide, N-phenyl | +++ |
| 15 | 2,6-dioxopiperidine-3-carboxamide, N-(2-methoxyphenyl) | ++++ |
| 16 | 2,6-dioxopiperidine-3-carboxamide, N-(pyridin-3-yl) | + |
| 17 | 2,6-dioxopiperidine-3-carboxamide, N-(pyridin-2-yl) | + |
| 18 | 2,6-dioxopiperidine-3-carboxamide, N-(2-fluorophenyl) | + |
| 19 | 2,6-dioxopiperidine-3-carboxamide, N-methyl-N-(2-methoxyphenyl) | + |
| 20 | 2,6-dioxopiperidine-3-carboxamide, N-methyl-N-(pyridin-2-yl) | + |
| 21 | 2,6-dioxopiperidine-3-carboxamide, N-methyl-N-(2-fluorophenyl) | +++ |

TABLE 1-continued

| Cmpd # | Structure | Kd |
|---|---|---|
| 22 | 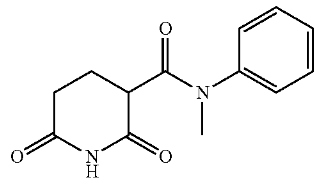 [SMILES: CN(C(=O)C1CCC(=O)NC1=O)c1ccccc1] | + |
| 23 | 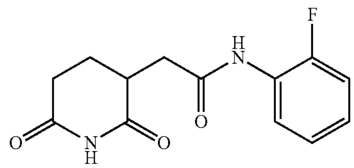 [SMILES: O=C1CCC(CC(=O)Nc2ccccc2F)C(=O)N1] | +++ |
| 24 | 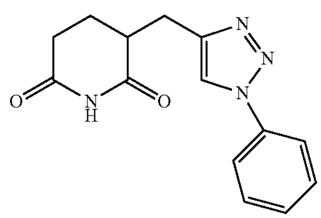 [SMILES: O=C1CCC(Cc2cn(-c3ccccc3)nn2)C(=O)N1] | ++++ |
| 25 | 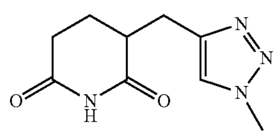 | +++ |
| 26 | 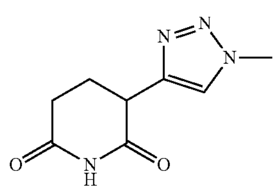 | +++ |
| 27 | 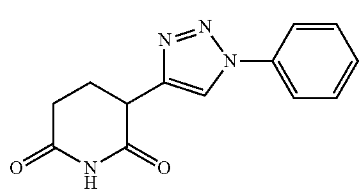 [SMILES: O=C1CCC(c2cn(-c3ccccc3)nn2)C(=O)N1] | ++++ |
| 28 | 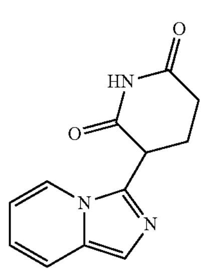 [SMILES: O=C1CCC(c2ncc3ccccn23)C(=O)N1] | +++++ |

TABLE 1-continued

| Cmpd # | Structure | Kd |
|---|---|---|
| 29 | 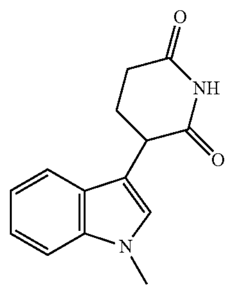 [SMILES: Cn1cc(C2CCC(=O)NC2=O)c2ccccc21] | +++++ |
| 30 | 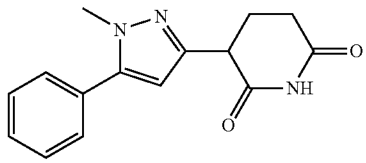 [SMILES: Cn1nc(C2CCC(=O)NC2=O)cc1-c1ccccc1] | +++++ |
| 31 | 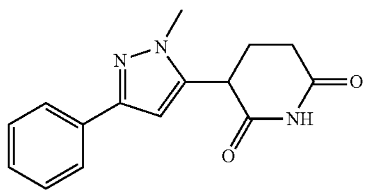 [SMILES: Cn1nc(-c2ccccc2)cc1C1CCC(=O)NC1=O] | +++ |
| 32 | 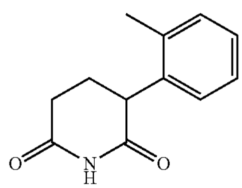 | ++++ |
| 33 | 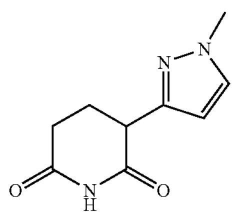 | ++++ |
| 34 | 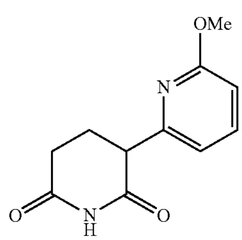 [SMILES: COc1cccc(C2CCC(=O)NC2=O)n1] | ++++ |
| 35 | 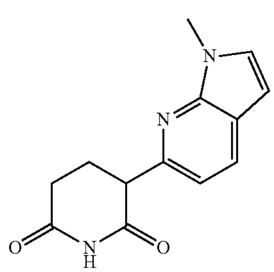 [SMILES: Cn1ccc2ccc(C3CCC(=O)NC3=O)nc21] | ++++ |

TABLE 1-continued

| Cmpd # | Structure | Kd |
|---|---|---|
| 36 | 3-(1-methylbenzimidazol-4-yl)piperidine-2,6-dione | ++++ |
| 37 | 3-(1-methylindazol-3-yl)piperidine-2,6-dione | +++++ |
| 38 | (S)-3-(1-methylindazol-3-yl)piperidine-2,6-dione | +++++ |
| 39 | (R)-3-(1-methylindazol-3-yl)piperidine-2,6-dione | ++++ |
| 40 | 3-(1-methyl-2-oxo-1,2-dihydroquinolin-3-yl)piperidine-2,6-dione | +++++ |
| 41 | 3-(2-methyl-1-oxoisoindolin-5-yl)piperidine-2,6-dione | ++++ |

TABLE 1-continued

| Cmpd # | Structure | Kd |
|---|---|---|
| 42 | [structure: 3-(2-Boc-isoindolin-4-yl)piperidine-2,6-dione] | ++++ |
| 43 | [structure: 3-(isoindolin-4-yl)piperidine-2,6-dione] | |
| 45 | [structure: 3-(2-oxo-2-(piperazin-1-yl)ethyl)piperidine-2,6-dione] | +++ |
| 44 | [structure: 3-(2-(4-Boc-piperazin-1-yl)-2-oxoethyl)piperidine-2,6-dione] | +++ |
| 46 | [structure: 3-(2-methyl-1-phenyl-1H-imidazol-4-yl)piperidine-2,6-dione] | ++++ |
| 47 | [structure: 3-methyl-3-(1-methyl-1H-indazol-3-yl)piperidine-2,6-dione] | ++++ |

TABLE 1-continued

| Cmpd # | Structure | Kd |
|---|---|---|
| 48 | (2-methylbenzothiazol-5-yl glutarimide) | +++++ |
| 49 | (3-methyl-2-oxo-benzoxazol-5-yl glutarimide) | ++++ |
| 50 | (3-benzyl glutarimide) | ++++ |
| 51 | (6-amino-1-methyl-indazol-3-yl glutarimide) | +++ |
| 52 | (6-(N-Boc-piperidin-4-ylamino)-1-methyl-indazol-3-yl glutarimide) | +++++ |
| 53 | (6-(piperidin-4-ylamino)-1-methyl-indazol-3-yl glutarimide), HCl salt | +++++ |
| 54 | (5-(N-Boc-isoindolin-5-yl) glutarimide) | ++++ |
| 55 | (5-(isoindolin-5-yl) glutarimide), HCl salt | +++ |

TABLE 1-continued

| Cmpd # | Structure | Kd |
|---|---|---|
| 56 | 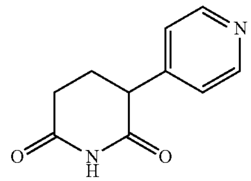 [SMILES: O=C1CCC(c2ccncc2)C(=O)N1] | +++ |
| 57 | 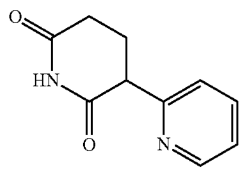 | ++++ |
| 58 | 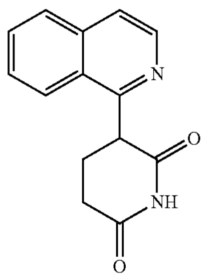 [SMILES: O=C1CCC(c2nccc3ccccc23)C(=O)N1] | ++++ |
| 59 | 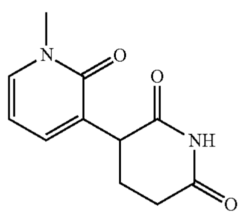 [SMILES: Cn1cccc(C2CCC(=O)NC2=O)c1=O] | +++ |
| 60 | 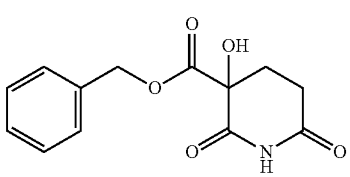 [SMILES: O=C1CCC(O)(C(=O)OCc2ccccc2)C(=O)N1] | ++++ |
| 61 | 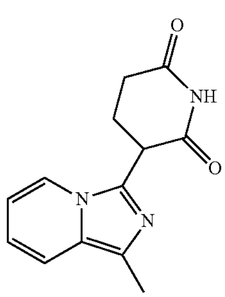 [SMILES: Cc1nc(C2CCC(=O)NC2=O)n2ccccc12] | +++++ |
| 62 | 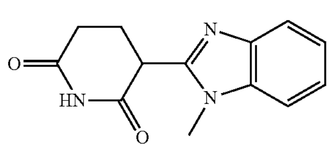 [SMILES: Cn1c(C2CCC(=O)NC2=O)nc2ccccc21] | +++ |

TABLE 1-continued

| Cmpd # | Structure | Kd |
|---|---|---|
| 63 | [2-oxo-3-phenylpiperidin-6-one structure] | ++++ |
| 64 | [3-(1-phenyl-1H-imidazol-4-yl)piperidine-2,6-dione structure] | ++++ |

In Table 2 above >100 μM = +  >30 μM = ++  50-100 μM = +++  10-50 μM = ++++  <10 μM = +++++.

V. Representative Degronimer of the Present Invention

TABLE 2

| Cmpd # | Structure | Kd |
|---|---|---|
| Degronimer 1 | [Degronimer 1 structure: BRD4 binder (triazolo-thienodiazepine with 4-chlorophenyl) linked via acetamide-heptanamide linker to 6-amino-1-methyl-3-(2,6-dioxopiperidin-3-yl)-1H-indazole] | +++++ |

In Table 2 above >100 μM = +  >30 μM = ++  50-100 μM = +++  10-50 μM = ++++  <10 μM = +++++.

TABLE 3

| Cell Line | Sample | Time (hr) | LD50 (nM) | GI50 (nM) | Emax |
|---|---|---|---|---|---|
| MOLT4.1 | Degronimer 1 | 72 | + | ++ | ** |
| MOLT4.2 | Degronimer 1 | 72 | + | + | * |

In Table 3 above for LD50 and GI50 >1 μM = + and 100 nM-1 μM = ++;

for Emax > 50% = * 0-50% =  −50%-0% = * and −100%-0% = ****

TABLE 4

| Modification | Cell Line | Time (hr) | Sample | Emax [%] | DC50 [nM] |
|---|---|---|---|---|---|
| BRD4_BD1 | 293T.29 | 3 | Degronimer 1 | ** | + |

In Table 4 above for DC50 > 0.83 μM = + and for Emax >50% = *

Example 9: CRBN-DDB1 Fluorescence Polarization (FP) Assay

Measuring compound ligand binding to CRBN-DDB1 was carried out using an established sensitive and quantitative in vitro fluorescence polarization (FP) based binding assay. (See, I. J. Enyedy et al, J. Med. Chem., 44: 313-4324 [2001]). Compounds were dispensed from serially diluted DMSO stock into black 384-well compatible fluorescence polarization plates using an Echo acoustic dispenser. Compound binding to CRBN-DDB1 was measured by displacement of either a (−)-Thalidomide-Alexa Fluor® or Pomalidomide-fluorescein conjugated probe dye. A 20 μL mixture containing 400 nM CRBN-DDB 1 and 5 nM probe dye in 50 mM Hepes, pH 7.4, 200 mM NaCl, 1% DMSO and 0.1% pluronic acid-127 acid was added to wells containing compound and incubated at room temperature for 60 min. Matching control wells excluding CRBN-DDB1 were used to correct for background fluorescence. Plates were read on an Envision plate reader with appropriate FP filter sets. The corrected S (perpendicular) and P (parallel) values were used to calculate fluorescence polarization (FP) with the following equation: FP=1000*(S−G*P)/(S+G*P). The fractional amount of bound probe (FB) to CRBN-DDB1 as a function of compound concentration was fitted according to Wang; FEBS Letters 360, (1995), 111-114 to obtain fits for parameter offsets and binding constant ($K_A$) of competitor compound.

Example 10: Cell Viability Analysis

RPMI 1640 medium and fetal bovine serum (FBS) were purchased from Gibco (Grand Island, N.Y., USA). CellTiter-Glo® 2.0 Assay was purchased from Promega (Medison, Wis., USA). MOLT4.1 (WT) cell line was purchased from ATCC (Manassas, Va., USA) and MOLT4.2 (CRBN Knock Out) cell line was generated in house. Cell culture flasks and 384-well microplates were acquired from VWR (Radnor, Pa., USA).

MOLT4.1 and MOLT4.2 cell viability was determined based on quantification of ATP using CellTiter-Glo® 2.0 luminescent Assay kit, which signals the presence of metabolically-active cells. Briefly, MOLT4.1 and MOLT4.2 cells were seeded into 384-well plates at a cell density of 750 cells per well, the plates were kept at 37° C. with 5% CO2 overnight. On the following day, test compounds were added to the cells from a top concentration of 1 µM with 10 points, half log titration in duplicates. The cells treated in the absence of the test compound were the negative control and the cells treated in the absence of CellTiter-Glo® 2.0 were the positive control. At the same day of compound treatment, CellTiter-Glo® 2.0 was added to a plate with cells treated in the absence of the test compound to establish Cytostatic control value (CrT). Cells treated with the test compound were incubated for 72 hr. CellTiter-Glo reagent was then added to the cells and Luminescence was acquired on EnVision™ Multilabel Reader (PerkinElmer, Santa Clara, Calif., USA).

Example 11: HiBit Assay

Materials:

DMEM no-phenol red medium and fetal bovine serum (FBS) were purchased from Gibco (Grand Island, N.Y., USA). Nano-Glo® HiBiT Lytic Assay System was purchased from Promega (Medison, Wis., USA). 293T.29 (HiBiT-BRD4 BD1) cell line was generated in house, ectopically expressing BRD4 BD1 domain with HiBiT fusion tag. Cell culture flasks and 384-well microplates were acquired from VWR (Radnor, Pa., USA).

BRD4 BD1 Degradation Analysis:

BRD4 BD1 degradation was determined based on quantification of luminescent signal using Nano-Glo® HiBiT Lytic Assay kit. Test compounds were added to the 384-well plate from a top concentration of 1 µM with 11 points, half log titration in quadruplicates. 293T.29 cells were added into 384-well plates at a cell density of 15000 cells per well. The plates were kept at 37° C. with 5% CO2 for 3 hours. The cells treated in the absence of the test compound were the negative control and the cells treated with 30 nM of a known BRD4 degrader were the positive control. After 3-hour incubation, Nano-Glo® HiBiT Lytic Assay reagents were added to the cells. Luminescence was acquired on EnVision™ Multilabel Reader (PerkinElmer, Santa Clara, Calif., USA).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

We claim:
1. A compound of Formula:

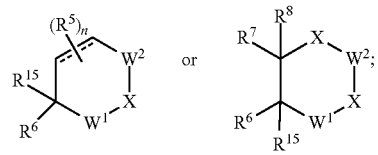

or a pharmaceutically acceptable salt thereof;
wherein:
$W^1$ is C=O;
$W^2$ is C=O;
X is NH;
n is 0, 1, 2, or 3;
≕ is a single or double bond;
$R^6$ is selected from:

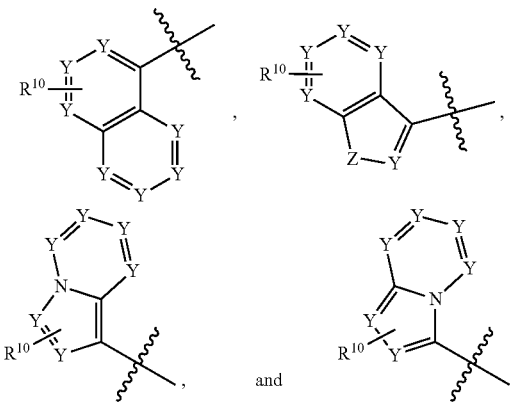

Y is independently selected from N, CH, and $CR^{11}$, wherein 0, 1, or 2 instances of Y are selected to be N;
Z is NH, O, S, or $NR^{12}$;
$R^7$, $R^8$, and $R^{15}$ are independently selected from hydrogen, alkyl, aliphatic, heteroaliphatic, heterocyclic, carbocyclic, aryl, heteroaryl, hydroxyl, halo, azide, CN—, alkoxy, amine, —NHalkyl, —Nalkyl$_2$, —NH(aliphatic), and —N(aliphatic)$_2$;
or $R^7$ and $R^8$ together with the carbon to which they are attached form a 3-, 4-, 5-, or 6-membered spiro-carbocycle, or a 4-, 5-, or 6-membered spiro-heterocycle comprising 1 or 2 heteroatoms selected from N and O;
or $R^{15}$ and $R^7$ form a 3, 4, 5, or 6 carbon fused ring;
or $R^{15}$ and $R^5$ form a 3, 4, 5, or 6 carbon fused ring wherein $R^5$ is on the carbon alpha to $R^{15}$ or a 1, 2, 3, or 4 carbon bridged ring wherein $R^5$ is not on the carbon alpha to $R^{15}$;
$R^5$ is selected at each instance from: alkyl, alkene, alkyne, aliphatic, heteroaliphatic, heterocyclic, aryl, heteroaryl, halogen, hydroxyl, alkoxy, azide, amino, —NH(aliphatic), —N(aliphatic)₂, —NHSO₂(aliphatic), —N(aliphatic)SO₂(aliphatic), —NHSO₂aryl, —N(aliphatic)SO₂aryl, —NHSO₂alkenyl, —N(aliphatic)SO₂alkenyl, —NHSO₂alkynyl, —N(aliphatic)SO₂alkynyl, and halo (aliphatic);

or two $R^5$ substituents together with the carbon atom(s) to which they are bound can form a 3, 4, 5 or 6 membered ring;

$R^{10}$ is a linker-targeting ligand;

linker is selected from:

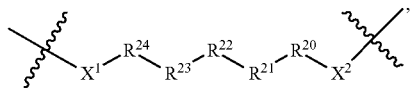

wherein:

$X^1$ and $X^2$ are independently selected from bond, NH, $NR^{25}$, $CH_2$, $CHR^{25}$, $C(R^{25})_2$, O, and S;

$R^{20}$, $R^{21}$, $R^{22}$, $R^{23}$, and $R^{24}$ are independently selected from heteroarylalkyl, aryl, arylalkyl, heterocycle, aliphatic, heteroaliphatic, heteroaryl, polypropylene glycol, lactic acid, glycolic acid, carbocycle, bond, alkyl, —C(O)—, —C(O)O—, —OC(O)—, —C(O)alkyl, —C(O)Oalkyl, —C(S)—, —SO₂—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—$R^{26}$)—, —CH(—NHR²⁵)—, —CH(—NH₂)—, —CH(—NR²⁵₂)—, —C(—O—$R^{26}$)alkyl-, —C(—NHR²⁵)alkyl-, —C(—NH)alkyl-, —C(—NR²⁵)alkyl-, -alkyl($R^{27}$)-alkyl($R^{28}$)—, —C($R^{27}R^{28}$)—, —P(O)(OR²⁶)O—, —P(O)(OR²⁶)—, —NHC(O)NH—, —N(R²⁵)C(O)N(R²⁵)—, —N(H)C(O)N(R²⁵)—, polyethylene glycol, poly(lactic-co-glycolic acid), alkene, haloalkyl, alkoxy, and alkyne;

$R^{25}$ is selected at each instance from alkyl, —C(O)H, —C(O)OH, —C(O)alkyl, —C(O)Oalkyl, alkenyl, and alkynyl;

$R^{26}$ is hydrogen, alkyl, arylalkyl, heteroarylalkyl, alkene, alkyne, aryl, heteroaryl, heterocyclic, aliphatic, or heteroaliphatic;

$R^{27}$ and $R^{28}$ are independently selected from hydrogen, alkyl, and amine, or together with the carbon atom to which they are attached, form C(O), C(S), C=CH₂, a $C_3$-$C_6$ spirocarbocycle, or a 4-, 5-, or 6-membered spiroheterocycle comprising 1 or 2 heteroatoms selected from N and O;

$R^{11}$ is selected at each instance from: hydrogen, alkyl, alkenyl, alkynyl, F, Cl, Br, hydroxyl, heterocyclic, heteroalkyl, carbocyclic, alkoxy, aryl, heteroaryl, alkylamino, alkylhydroxyl, —NHalkyl, —Nalkyl₂, —NH(aliphatic), —N(aliphatic)₂, amino, cyano, nitro, thioalkyl, thiol and haloalkyl;

$R^{12}$ is selected at each instance from: hydrogen, alkyl, aliphatic, heteroaliphatic, heterocyclic, heteroaryl, aryl, —C(O)H, —C(O)OH, —C(O)alkyl, —C(O)Oalkyl, —C(O)(aliphatic, aryl, heteroaliphatic, or heteroaryl), —C(O)O(aliphatic, aryl, heteroaliphatic, or heteroaryl), alkene, and alkyne;

$R^{13}$ and $R^{14}$ are independently selected from hydrogen, alkyl, alkenyl, alkynyl, alkoxy, haloalkoxy, hydroxy, amino, —NHalkyl, and —N(alkyl)₂;

or $R^{13}$ and $R^{14}$ together with the carbon atom to which they are attached, form C(O), C(S), C=CH₂, a 3-, 4-, 5-, or 6-membered spirocarbocycle, or a 4-, 5-, or 6-membered spiroheterocycle comprising 1 or 2 heteroatoms selected from N and O;

targeting ligand binds to a targeted protein selected from the group consisting of AKT1, ALK, AXL, ABL, ABL1, ABL2, AKT2, AP1, AP2, ASH1L, ATAD2, aurora kinase, androgen receptor, ATF2, BMX, BCR-ABL, bromodomain containing protein, Bcl-2, Bcl-XL, BCL6, BAZ2A, BAZ2B, BRD4, BRD9, BRPF1, BMX, CSF1R, CECR2, CBP, CREBBP, CNNTB1, cathepsin, cyclin dependent kinase, DDR1, DOT1L, dihydrofolate reductase, ERBB2, ERBB3, ERBB4, EPHA2, EPHA3, EPHA4, EPHA7, EPHB4, EZH2, EED, EHMT1, EHMT2, ERK1, ERK2, estrogen receptor, FGFR1, FGFR2, FGFR3, FGFR4, FLT3, FES, FYN, FKBP, fatty acid binding protein, factor Xa, FLAP, GSG2, HIV integrase, HIV reverse transcriptase, HIV protease, HCV protease, HDAC6, HDAC7, HDM2, HBV, HCK, histone deacetylase, histone acetyltransferase, heat shock protein, HDAC, Her3, IGF1R, INSR, IDO1, IDH1, ITK, KDM4, KDM5, KDM6, KMT5A, KIT, KSR1, kringle domain V, 4BVV, kallikrein 7, KSR receptor, LRRK2, lactoylglutathione lyase, LSD1, L3MBTL3, lysine-specific histone demethylase, lysine methyltransferase, LCK, LYN, mPGES-1, MERTK, MEK1, MDM2, MDM4, MEN1, MTH1, MCL-1, MER, MET, mast/stem cell growth factor receptor, MST1R, NTRK, NTRK1, NTRK2, NTRK3, PDZ, phospholipase A2 domain, PB1, PCAF, PHIP, protein S100-A7, PAK1, PAK4, PPAR-gamma, PDGFR receptor, PNET, PI3Ka receptor, PIK3CA, ROS1 receptor, RCC receptor, RAML receptor, RET, SETD2, SETD7, SETD8, SETDB1, SMYD2, SMYD3, SUV4-20H1, saposin-B, Sec7, SH2 domain, Src-AS1, Src AS2, SEGA receptor, TNIK, TRIM24, TAF1, TAF1L, mTORC1, mTORC2, TANK1, TRKB, tie 2 receptor, TEC, SF6D, U09-CX-5279, VEGF receptor, WDR5, and YES.

2. A pharmaceutical composition comprising a compound of claim 1 and a pharmaceutically acceptable excipient.

3. The compound of claim 1, wherein n is 0.

4. The compound of claim 1, wherein $R^7$ and $R^8$ are hydrogen.

5. The compound of claim 1, wherein the targeted protein is the estrogen receptor or androgen receptor.

6. The compound of claim 1, wherein the compound is selected from:

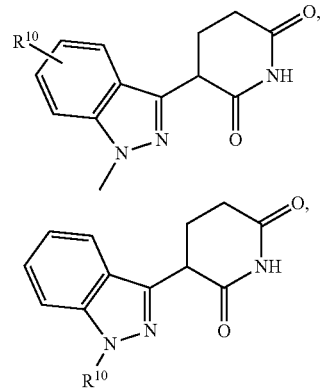

413
-continued
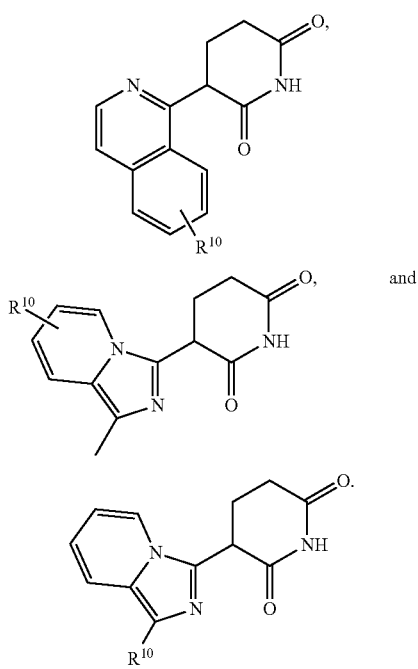
414
-continued
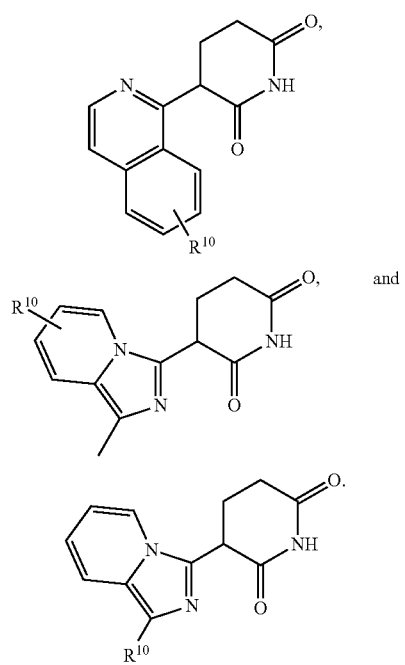
and
7. The compound of claim 1, wherein linker is selected from:
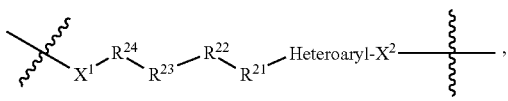
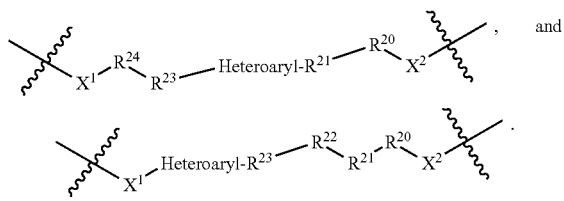
8. The compound of claim 7, wherein the compound is selected from:
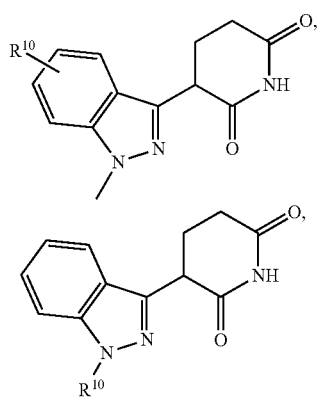
9. The compound of claim 1, wherein the linker is selected from the group consisting of:
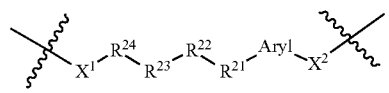
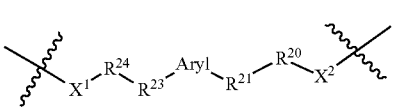
and
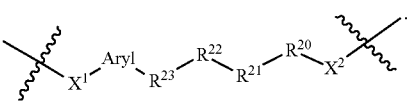
10. The compound of claim 1, wherein the linker is selected from the group consisting of:
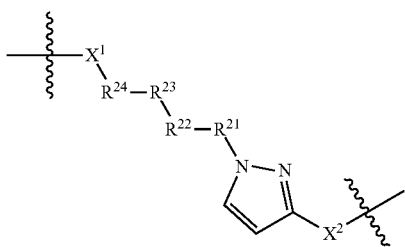

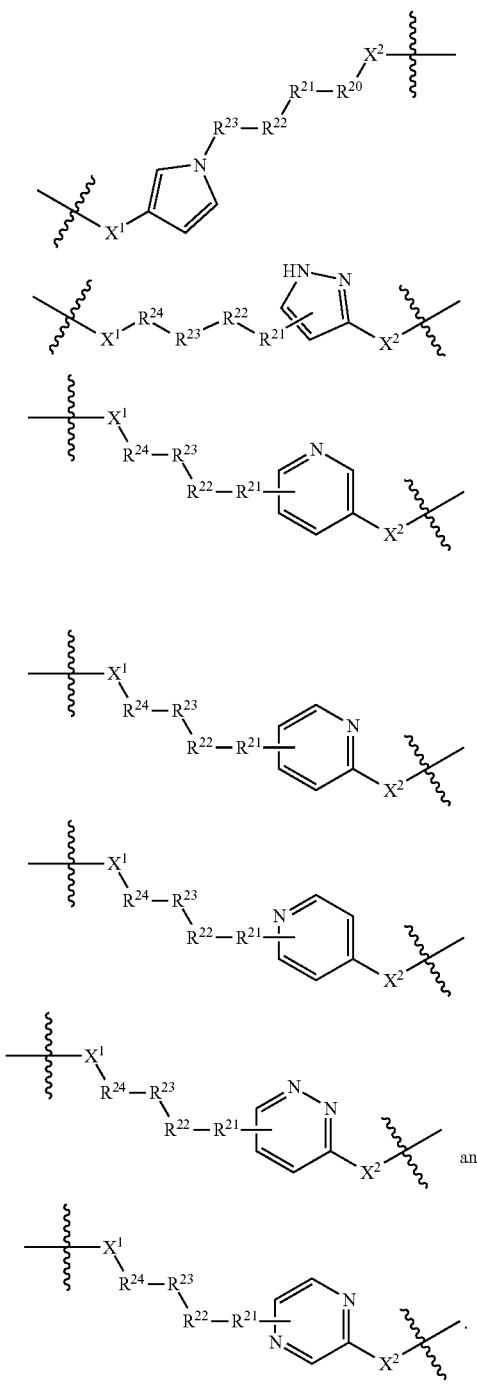
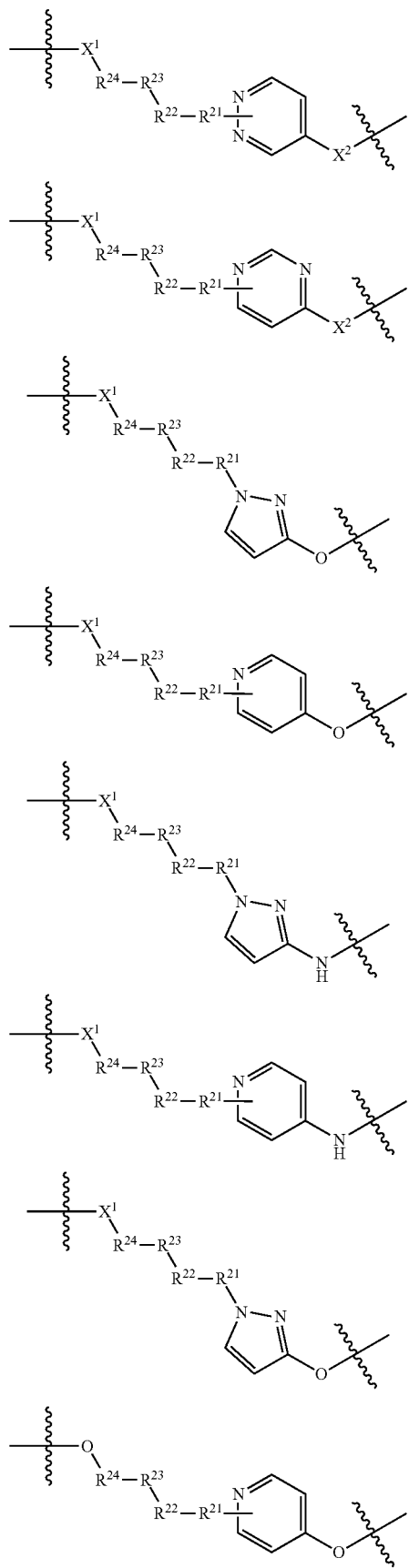
11. The compound of claim 1, wherein the linker is selected from the group consisting of:
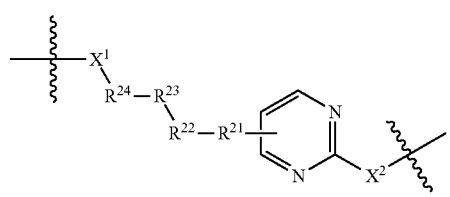

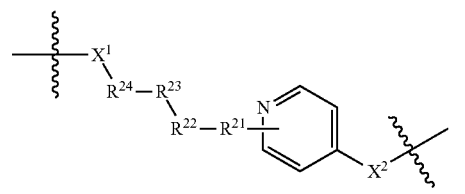
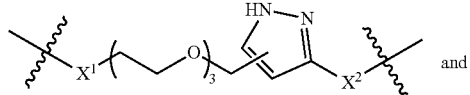
and
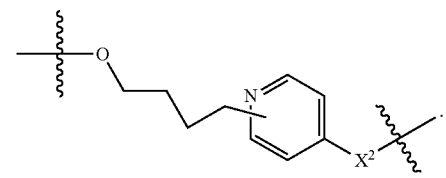
12. The compound of claim 1, wherein the linker is selected from the group consisting of:
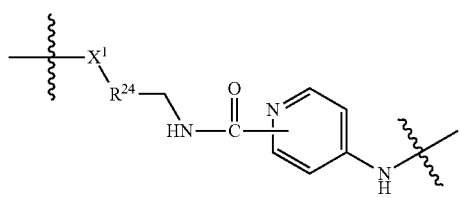
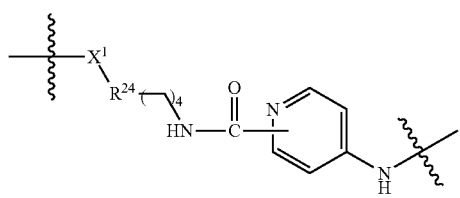
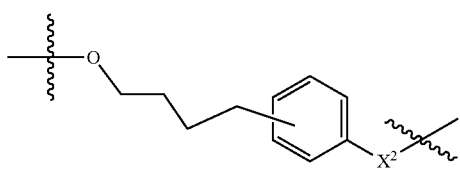
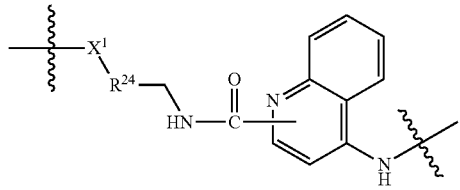
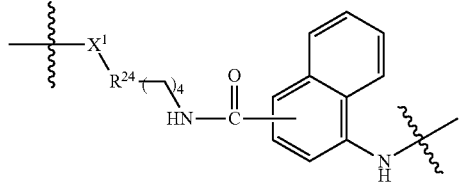
and
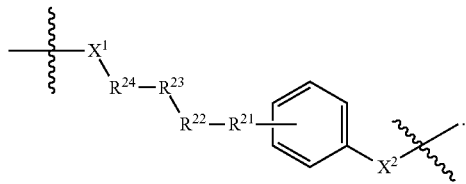
13. The compound of claim 1, wherein the linker is selected from the group consisting of:
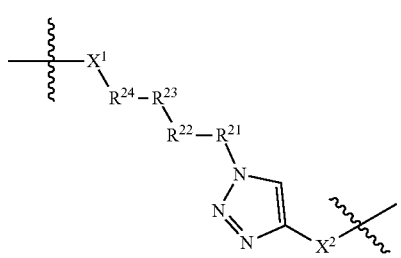
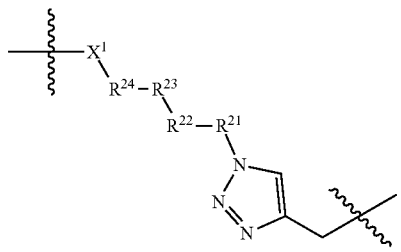
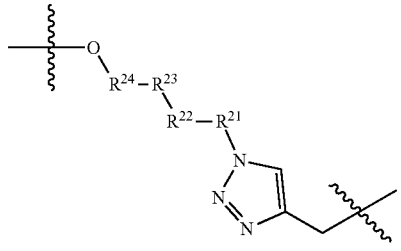
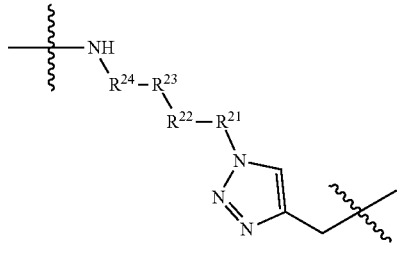
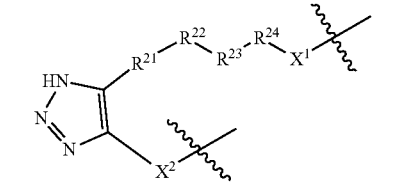
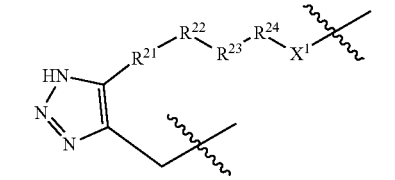

-continued
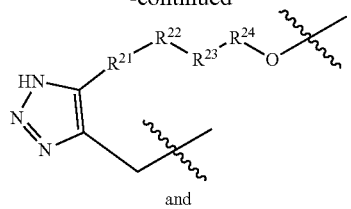
and
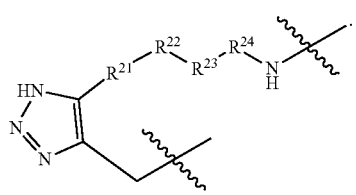
14. The compound of claim 1, wherein the $R^6$ is selected from the group consisting of:
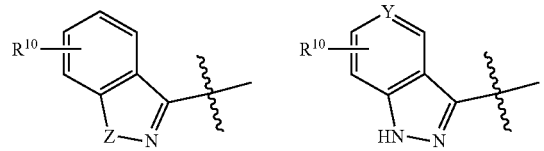
and
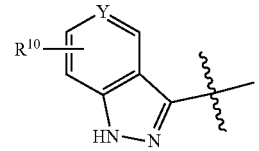
15. The compound of claim 1, wherein the $R^6$ is selected from the group consisting of:
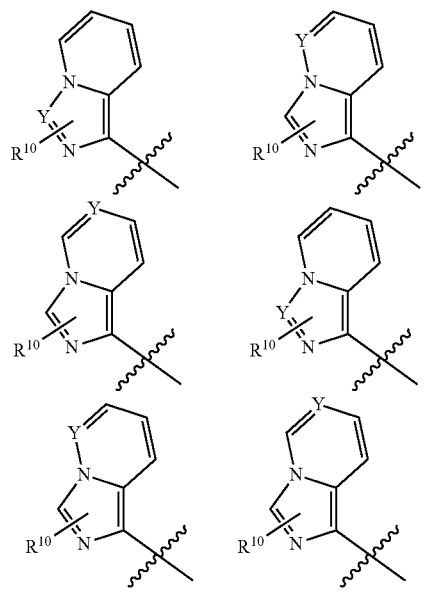
-continued
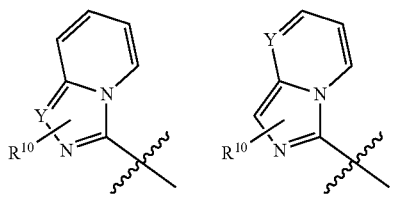
and
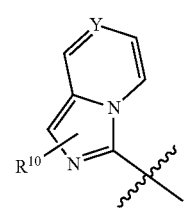
16. The compound of claim 1, wherein the $R^6$ is selected from the group consisting of:
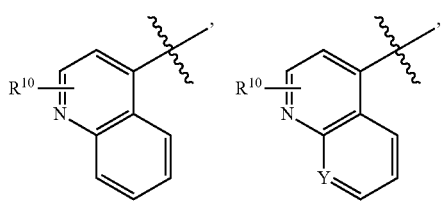
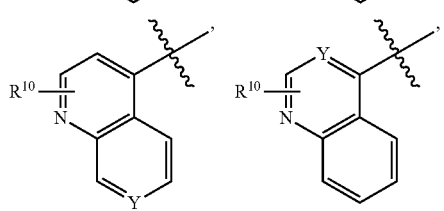
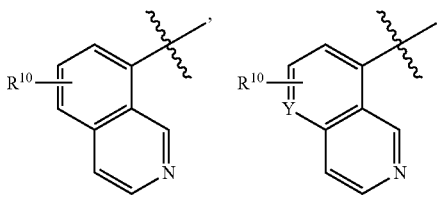
and
17. The compound of claim 1, wherein the targeted protein contains a bromodomain.
\* \* \* \* \*